US011174268B2

(12) United States Patent
Andrez et al.

(10) Patent No.: US 11,174,268 B2
(45) Date of Patent: Nov. 16, 2021

(54) BENZENESULFONAMIDE COMPOUDS AND THEIR USE AS THERAPEUTIC AGENTS

(71) Applicant: Xenon Pharmaceuticals Inc., Burnaby (CA)

(72) Inventors: Jean-Christophe Andrez, Vancouver (CA); David Earl Bogucki, Surrey (CA); Kristen Nicole Burford, Burnaby (CA); Sultan Chowdhury, Surrey (CA); Charles Jay Cohen, Vancouver (CA); Shannon Marie Decker, Burnaby (CA); Christoph Martin Dehnhardt, Burnaby (CA); Robert Joseph Devita, Westfield, NJ (US); James Roy Empfield, Natick, MA (US); Thilo Focken, Burnaby (CA); Michael Edward Grimwood, North Vancouver (CA); Syed Abid Hasan, Vancouver (CA); Qi Jia, Burnaby (CA); James Philip Johnson, Jr., Burnaby (CA); Michael Scott Wilson, Burnaby (CA); Alla Yurevna Zenova, Vancouver (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 16/805,895

(22) Filed: Mar. 2, 2020

(65) Prior Publication Data

US 2021/0171537 A1 Jun. 10, 2021

Related U.S. Application Data

(63) Continuation of application No. 15/600,612, filed on May 19, 2017, now abandoned.

(60) Provisional application No. 62/432,169, filed on Dec. 9, 2016.

(51) Int. Cl.
| | |
|---|---|
| *C07D 491/107* | (2006.01) |
| *C07D 493/10* | (2006.01) |
| *C07D 237/20* | (2006.01) |
| *C07D 213/76* | (2006.01) |
| *C07D 239/69* | (2006.01) |
| *C07D 261/16* | (2006.01) |
| *C07D 263/50* | (2006.01) |
| *C07D 275/03* | (2006.01) |
| *C07D 277/52* | (2006.01) |
| *C07D 285/08* | (2006.01) |
| *C07D 401/12* | (2006.01) |
| *C07D 403/12* | (2006.01) |
| *C07D 413/12* | (2006.01) |
| *C07D 417/12* | (2006.01) |
| *C07D 487/10* | (2006.01) |
| *C07D 417/14* | (2006.01) |
| *C07D 451/06* | (2006.01) |
| *A61K 31/395* | (2006.01) |
| *A61K 31/427* | (2006.01) |

(52) U.S. Cl.
CPC ........ *C07D 491/107* (2013.01); *A61K 31/395* (2013.01); *A61K 31/427* (2013.01); *C07D 213/76* (2013.01); *C07D 237/20* (2013.01); *C07D 239/69* (2013.01); *C07D 261/16* (2013.01); *C07D 263/50* (2013.01); *C07D 275/03* (2013.01); *C07D 277/52* (2013.01); *C07D 285/08* (2013.01); *C07D 401/12* (2013.01); *C07D 403/12* (2013.01); *C07D 413/12* (2013.01); *C07D 417/12* (2013.01); *C07D 417/14* (2013.01); *C07D 451/06* (2013.01); *C07D 487/10* (2013.01); *C07D 493/10* (2013.01)

(58) Field of Classification Search
CPC .............. C07D 491/107; C07D 213/76; C07D 237/20; C07D 239/69; C07D 261/16; C07D 263/50; C07D 275/03; C07D 277/52; C07D 285/08; C07D 401/12; C07D 403/12; C07D 413/12; C07D 417/12; C07D 417/14; C07D 451/06; C07D 487/10; C07D 493/10; A61K 31/427; A61K 31/395
See application file for complete search history.

(56) References Cited

U.S. PATENT DOCUMENTS

| | | | |
|---|---|---|---|
| 3,845,770 | A | 11/1974 | Teeuwes et al. |
| 4,326,525 | A | 4/1982 | Swanson et al. |
| 5,877,193 | A | 3/1999 | Cesura et al. |
| 5,958,910 | A | 9/1999 | Cesura et al. |
| 8,222,281 | B2 | 7/2012 | Toda et al. |
| 9,481,677 | B2 | 11/2016 | Liu et al. |
| 9,630,929 | B2 | 4/2017 | Sun et al. |

(Continued)

FOREIGN PATENT DOCUMENTS

| | | |
|---|---|---|
| CN | 106103415 | 12/2014 |
| EP | 2813491 | 12/2014 |

(Continued)

OTHER PUBLICATIONS

U.S. Appl. No. 16/821,294, Andrez et al., filed Mar. 17, 2020.
U.S. Appl. No. 16/927,178, Burford et al., filed Jul. 13, 2020.
Andrez et al., entitled "Benzenesulfonamide Compounds and Their Use as Therapeutic Agents," Office Action dated Dec. 14, 2017, for U.S. Appl. No. 15/600,490, 16 pages.

(Continued)

*Primary Examiner* — Robert H Havlin
(74) *Attorney, Agent, or Firm* — Fish & Richardson P.C.

(57) ABSTRACT

This invention is directed to benzenesulfonamide compounds, as stereoisomers, enantiomers, tautomers thereof or mixtures thereof; or pharmaceutically acceptable salts, solvates or prodrugs thereof, for the treatment of diseases or conditions associated with voltage-gated sodium channels, such as epilepsy and/or epileptic seizure disorders.

25 Claims, No Drawings

(56) References Cited

U.S. PATENT DOCUMENTS

| | | | |
|---|---|---|---|
| 10,246,453 | B2 | 4/2019 | Andrez et al. |
| 10,745,392 | B2 | 8/2020 | Burford et al. |
| 2009/0023740 | A1 | 1/2009 | Fulp |
| 2010/0267782 | A1 | 10/2010 | Beaudoin et al. |
| 2014/0045862 | A1 | 2/2014 | Shinozuka et al. |
| 2014/0256736 | A1 | 9/2014 | Liu et al. |
| 2014/0315878 | A1 | 10/2014 | Storer et al. |
| 2014/0315933 | A1 | 10/2014 | Owen et al. |
| 2017/0334902 | A1 | 11/2017 | Andrez et al. |
| 2018/0162868 | A1 | 6/2018 | Andrez et al. |
| 2019/0194184 | A1 | 6/2019 | Andrez et al. |
| 2019/0382398 | A1 | 12/2019 | Burford et al. |
| 2020/0071313 | A1 | 3/2020 | Andrez et al. |
| 2020/0157089 | A1 | 5/2020 | Andrez et al. |
| 2020/0361927 | A1 | 11/2020 | Burford et al. |

FOREIGN PATENT DOCUMENTS

| | | |
|---|---|---|
| IN | 201817045857 | 5/2016 |
| WO | WO 1998/50016 | 11/1998 |
| WO | WO 2000/42003 | 7/2000 |
| WO | WO 2001/05393 | 1/2001 |
| WO | WO 2001/40222 | 6/2001 |
| WO | WO 2003/076406 | 9/2003 |
| WO | WO 2004/002481 | 1/2004 |
| WO | WO 2004/092123 | 10/2004 |
| WO | WO 2005/000309 | 1/2005 |
| WO | WO 2005/005421 | 1/2005 |
| WO | WO 2005/013914 | 2/2005 |
| WO | WO 2006/066109 | 6/2006 |
| WO | WO 2006/129199 | 12/2006 |
| WO | WO 2007/039171 | 4/2007 |
| WO | WO 2007 /075895 | 7/2007 |
| WO | WO 2008/019967 | 2/2008 |
| WO | WO 2008/051494 | 5/2008 |
| WO | WO 2009/012242 | 1/2009 |
| WO | WO 2009/013171 | 1/2009 |
| WO | WO 2009/157418 | 12/2009 |
| WO | WO 2010/002956 | 1/2010 |
| WO | WO 2010/029300 | 3/2010 |
| WO | WO 2010/079443 | 7/2010 |
| WO | WO 2012/004743 | 1/2012 |
| WO | WO 2012/022265 | 2/2012 |
| WO | WO 2013/025883 | 2/2013 |
| WO | WO 2013/063459 | 5/2013 |
| WO | WO 2013/064983 | 5/2013 |
| WO | WO 2013/122897 | 8/2013 |
| WO | WO 2013/177224 | 11/2013 |
| WO | WO 2014/061970 | 4/2014 |
| WO | WO 2014/066490 | 5/2014 |
| WO | WO 2014/066491 | 5/2014 |
| WO | WO 2014/170792 | 10/2014 |
| WO | WO 2014/170793 | 10/2014 |
| WO | WO 2014/198849 | 12/2014 |
| WO | WO 2014/201206 | 12/2014 |
| WO | WO 2015/035278 | 3/2015 |
| WO | WO 2015/038533 | 3/2015 |
| WO | WO 2015/077905 | 6/2015 |
| WO | WO 2015/078374 | 6/2015 |
| WO | WO 2015/080988 | 6/2015 |
| WO | WO 2015/099841 | 7/2015 |
| WO | WO 2016/177340 | 11/2016 |
| WO | WO 2017/106409 | 6/2017 |
| WO | WO 2017/165204 | 9/2017 |
| WO | WO 2017/201468 | 11/2017 |
| WO | WO 2018/081384 | 5/2018 |
| WO | WO 2018/093694 | 5/2018 |
| WO | WO 2018/106284 | 6/2018 |

OTHER PUBLICATIONS

Barton et al., "Pharmacological characterization of the 6 Hz psychomotor seizure model of partial epilepsy," Epilepsy Research 47: 217-227, 2001.

Bean et al., "Lidocaine Block of Cardiac Sodium Channels," J Gen. Physiol. 81: 613-642, May 1983.
Boerma et al., "Remarkable Phenytoin Sensitivity in 4 Children with SCN8A-related Epilepsy: A Molecular Neuropharmacological Approach," Neurotherapeutics 13: 192-197, 2016.
Bordwell et al., "The Reduction of Sulfones to Sulfides," JACS 73: 2251-2253, May 1951.
Burgess et al., "Mutation of a new sodium channel gene, Scn8a, in the mouse mutant 'motor endplate disease'," Nature Genetics 10: 461-465, Aug. 1995.
Carroll et al., "Mutation screening of SCN2A in schizophrenia and identification of a novel loss-of-function mutation," Psychiatr. Genet. 26: 60-65, 2016.
Catterall, "Sodium Channels, Inherited Epilepsy, and Antiepileptic Drugs," Annu. Rev. Pharmacol. Toxicol. 54: 317-338, 2014.
Cestele et al., "Molecular mechanisms of neurotoxin action on voltage-gated sodium channels," Biochimie 82: 883-892, 2000.
Cheah et al., "Correlations in timing of sodium channel expression, epilepsy, and sudden death in Dravet syndrome," Channels 7(6): 468-472, Nov./Dec. 2013.
Cojocariu et al., "Sinteza unor N4-(2-hidroxi-4-clmbenzoil)-sulfamide cu activitate antimicotica potentiala," Revista de Chimie 30(12): C-1261, 1979 (3 pages).
Dekovel et al., "Characterization of a de nova SCN8A mutation in a patient with epileptic encephalopathy," Epilepsy Research 108: 1511-1518, 2014.
Dravet et al., Handbook of Clinical Neurology, vol. 111 (3rd series)—Pediatric Neurology Part 1, Elsevier B.V., Amsterdam, Netherlands, 2013, Chapter 65, "Dravet syndrome (severe myoclonic epilepsy in infancy)," pp. 627-633.
Dutton et al., "Preferential inactivation of Scnl a in parvalbumin intemeurons increases seizure susceptibility," Neurobiology of Disease 49: 211-220, 2013.
Estacion et al., "A novel de novo mutation of SCN8A (Navl.6) with enhanced channel activation in a child with epileptic encephalopathy," Neurobiology of Disease 69: 117-123, 2014.
Focken et al., "Discovery of Aryl Sulfonamides as Isoform-Selective Inhibitors of Nav 1.7 with Efficacy in Rodent Pain Models," ACS Med.Chem. Lett. 7: 277-282, 2016.
Fukasa WA et al., "A case of recurrent encephalopathy with SCN2A missense mutation," Brain & Development 37: 631-634, 2015.
Gardner et al., "A Facile Reduction of Sulfones to Sulfides," Can. J Chem. 51: 1419-1421, 1973.
Hadzi et al., "The Role of Hydrogen Bonding in Drug-Receptor Interactions," Journal of Molecular Structure 237: 139-150, 1990.
Hawkins et al., "Hlf is a genetic modifier of epilepsy caused by voltage-gated sodium channel mutations," Epilepsy Research 119: 20-23, 2016.
Hawkins et al., "Neuronal voltage-gated ion channels are genetic modifiers of generalized epilepsy with febrile seizures plus," Neurobiology of Disease 41: 655-660, 2011.
Helbig, "Genetic Causes of Generalized Epilepsies," Semin. Neural. 35: 288-292, 2015.
Hille, "Local Anesthetics: Hydrophilic and Hydrophobic Pathways for the Drug-Receptor Reaction," The Journal of General Physiology 69: 497-515, 1977.
Hitchcock et al., "Perspective: Structure—Brain Exposure Relationships," Journal of Medicinal Chemistry 49(26): 7559-7583, Dec. 28, 2006.
Hossfeld, "Paper Partition Chromatography of Simple Phenols," J Am. Chem. Soc. 73: 852-854, 1951.
Howell et al., "SCN2A encephalopathy: A major cause of epilepsy of infancy with migrating focal seizures," Neurology 85: 958-966, 2015.
Hu et al., "Distinct contributions of NAvl.6 and Navl.2 in action potential initiation and backpropagation," Nature Neuroscience 12(8):996-1002, Aug. 2009 (9 pages).
International Preliminary Report on Patentability, dated Jun. 20, 2019, for PCTAN PCT PCT/US2017 /033666, 21 pages.
International Search Report and Written Opinion, dated Jul. 4, 2017, for PCTAN CT/US2017/033634, 13 pages.
International Search Report and Written Opinion, dated Sep. 25, 2017, for PCTAN PCT/US2017/033666, 30 pages.

(56) References Cited

OTHER PUBLICATIONS

James et al., "A modular, gold-catalyzed approach to the synthesis of lead-like piperazine scaffolds," Org Lett. 15(23): 6094-6097, 2013.
Kearney et al., "A Gain-of-Function Mutation in the Sodium Channel Gene Scn2a Results in Seizures and Behavioral Abnormalities," Neuroscience 102(2): 307-317, 2001.
Kong et al., "SCN8A mutations in Chinese children with early onset epilepsy and intellectual disability," Epilepsia 56(3): 431-438, 2015.
Kuzma et al., "Progress in the Development of Ultra-Long-Acting Local Anesthetics," Regional Anesthesia 22(6): 543-551, 1997.
Larsen et al., "The phenotypic spectrum of SCN8A encephalopathy," Neurology 84: 480-489, 2015.
Leuwer et al., "An improved model for the binding of lidocaine and structurally related local anaesthetics to fast-inactivated voltage-operated sodium channels, showing evidence of cooperativity," British Journal of Pharmacology 141: 47-54, 2004.
Liu et al., "Mutations in Cardiac Sodium Channels: Clinical Implications," Am. J Pharmacogenomics 3(3): 173-179, 2003.
Loscher et al., "Which animal models should be used in the search for new antiepileptic drugs? A proposal based on experimental and clinical considerations," Epilepsy Res. 2: 145-181, 1988.
Luci et al., "Synthesis and Structure—Activity Relationship Studies of 4-((2-Hydroxy-3-methoxybenzyl)amino )benzenesulfonamide Derivatives as Potent and Selective Inhibitors of 12-Lipoxygenase," J Med. Chem. 57: 495-506, 2014.
Makinson et al., "An Scn1a epilepsy mutation in Scn8a alters seizure susceptibility and behavior," Experimental Neurology. 275: 46-58, 2016.
Makinson et al., "Role of the hippocampus in Nav1.6 (Scn8a) mediated seizure resistance," Neurobiology of Disease 68: 16-25, 2014.
Martin et al., "Altered Function of the SCNJA Voltage-gated Sodium Channel Leads toy-Aminobutyric Acid-ergic (GABAergic) Interneuron Abnormalities," The Journal of Biological Chemistry 285(13): 9823-9834, Mar. 26, 2010.
Martin et al., "The voltage-gated sodium channel Scn8a is a genetic modifier of severe myoclonic epilepsy of infancy," Human Molecular Genetics 16(23): 2892-2899, 2007.
Massey et al., "Mechanisms of sudden unexpected death in epilepsy: the pathway to prevention," Nature Reviews Neurology 10: 271-282, May 2014.
Matsukawa et al., "Studies on Chemotherapeutics. XII. Syntheses of p-Hydroxybenezenesulfonamide Derivatives," Yakugaku Zasshi 70(10): 557-561, 1950.
McKusik et al., Epileptic Encephalopathy, Early Infantile 6; EIEE6, Online Mendelian Inheritance in Man: John Hopkins University, 2012, 12 pages, URL=http:omin.org/entry/607208, download date Sep. 6, 2017.
Miller et al., "Mapping genetic modifiers of survival in a mouse model ofDravet syndrome," Genes, Brain and Behavior 13: 163-172, 2014.
Mistry et al., "Strain- and age-dependent hippocampal neuron sodium currents correlate with epilepsy severity in Dravet syndrome mice," Neurobiology of Disease 65: 1-11, 2014.
Norinder et al., "QSAR investigation ofNaV1.7 active compounds using the SVM/Signature approach and the Bioclipse Modeling platform," Bioorganic & Medicinal Chemistry Letters 23:261-263, 2013.
Ogiwara et al., "Nav1.1 Localizes to Axons of Parvalbumin-Positive Inhibitory Interneurons: A Circuit Basis for Epileptic Seizures in Mice Carrying an Scn1 a Gene Mutation," The Journal of Neuroscience 27(22): 5903-5914, May 30, 2007.
Ohba et al., "Early onset epileptic encephalopathy caused by de novo Scn8A mutations," Epilepsia 55(7): 994-1000, 2014.
Patani et al., "Bioisosterism: A Rational Approach in Drug Design," Chem. Rev. 96: 3147-3176, 1996.
Payne et al., "Identification ofKD5 1 70: A novel mercaptoketone-based histone deacetylase inhibitor," Bioorganic & Medicinal Chemistry Letters 18: 6093-6096, 2008.

Piredda et al., "Effect of Stimulus Intensity on the Profile of Anticonvulsant Activity of Phenytoin, Ethosuximide and Valproate," The Journal of Pharmacology and Experimental Therapeutics 232(3): 741-745, 1985.
Prasanthy et al., "Synthesis and Biological Evaluation of 1-Substituted Imidazole Derivatives," Int. J Pharma 1(2): 92-99, 2011.
Raymond et al., "Expression of Alternatively Spliced Sodium Channel a-Subunit Genes," Journal of Biological Chemistry 279(44): 46234-46241, Oct. 29, 2004.
Rogers et al., "Characterization of Endogenous Sodium Channels in the ND7-23 Neuroblastoma Cell Line: Implications for Use as a Heterologous Ion Channel Expression System Suitable for Automated Patch Clamp Screening," Assay and Drug Development Technologies 14(2): 109-130, Mar. 2016.
Royeck et al., "Role of Axonal Nav1.6 Sodium Channels in Action Potential Initiation of Cal Pyramidal Neurons," J Neurophysiol. 100: 2361-2380, 2008.
Saitoh et al., "Missense mutations in sodium channel SCN1A and SCN2A predispose children to encephalopathy with severe febrile seizures," Epilepsy Research 117: 1-6, 2015.
Samanta et al., "De novo R853Q mutation of SCN2A gene and West syndrome," Acta Neural. Bell. 115: 773-776, 2015.
Schwarz et al., "Mutations in the sodium channel gene SCN2A cause neonatal epilepsy with late-onset episodic ataxia," J Neural. 263: 334-343, 2016.
Suzuki et al., "Morphogenetic Effect of Kainate on Adult Hippocampal Neurons Associated with a Prolonged Expression of Brain-derived Neurotrophic Factor," Neuroscience 64(3): 665-674, 1995.
Toman et al., "Properties of Maximal Seizures, and Their Alteration by Anticonvulsant Drugs and Other Agents," J Neurophysiol. 9: 231-239, 1946.
Trudeau et al., "Heterozygosity for a protein truncation mutation of sodium channel SCN8A in a patient with cerebellar atrophy, ataxia, and mental retardation," J Med. Genet. 43: 527-530, 2006.
Tuncer et al., "A clinical variant in SCN1A inherited from a mosaic father cosegregates with a novel variant to cause Dravet syndrome in a consanguineous family," Epilepsy Research 113: 5-10, 2015.
Vaher et al., "De Novo SCN8A Mutation Identified by Whole-Exome Sequencing in a Boy With Neonatal Epileptic Encephalopathy, Multiple Congenital Anomalies, and Movement Disorders," Journal o{Child Neurology 29(12): NP202-NP206, 2014.
Veeramah et al., "De Novo Pathogenic SCN8A Mutation Identified by Whole-Genome Sequencing of a Family Quartet Affected by Infantile Epileptic Encephalopathy and SUDEP," The American Journal of Human Genetics 90: 502-510, Mar. 9, 2012.
Vega et al., "Reduced expression ofNav1.6 sodium channels and compensation of Nav1.2 channels in mice heterozygous for a null mutation in Scn8a," Neuroscience Letters 442: 69-73, 2008.
Wagnon et al., "Convulsive seizures and SUDEP in a mouse model of SCN8A epileptic encephalopathy," Human Molecular Genetics 24(2): 506-515, 2015.
White et al., "The early identification of anticonvulsant activity: role of the maximal electroshock and subcutaneous pentylenetetrazol seizure models," Ital. J Neural. Sci 16: 73-77, 1995.
Wilmshurst et al., Summary of recommendations for the management of infantile seizures: Task Force Report for the ILAE Commission of Pediatrics, Epilepsia 56(8): 1185-1197, 2015.
Wu et al., "Development of New Benzenesulfonamides as Potent and Selective Nav1.7 Inhibitors for the Treatment of Pain," J Med. Chem. 60: 2513-2525, 2017.
Yu et al., "Reduced sodium current in GABAergic interneurons in a mouse model of severe myoclonic epilepsy in infancy," Nature Neuroscience 9(9): 1142-1149, Sep. 2006.
Zerem et al., "Paternal germline mosaicism of a SCN2A mutation results in Ohtahara syndrome in half siblings," European Journal of Paediatric Neurology 18: 567-571, 2014.
Stumpf et al., "Development of an Expedient Process for the Multi-Kilogram Synthesis of Chk1 Inhibitor GDC-0425" Org. Process Res. Dev. 19: 661-672, 2015.
Ward, "Chiral Separations," Anal. Chem. 74: 2863-2872, 2002.

(56) References Cited

OTHER PUBLICATIONS

Rutkauskas et al., "4-Amino-substituted Benzenesulfonamides as Inhibitors of Human Carbonic Anhydrases," Molecules, Nov. 2014, 19(11):17356-17380.

BENZENESULFONAMIDE COMPOUDS AND THEIR USE AS THERAPEUTIC AGENTS

FIELD OF THE INVENTION

The present invention is directed to benzenesulfonamide compounds and pharmaceutical compositions comprising the compounds and methods of using the compounds and the pharmaceutical compositions in treating sodium channel-mediated diseases or conditions, such as epilepsy and/or epileptic seizure disorder, as well as other diseases and conditions associated with the mediation of sodium channels.

BACKGROUND OF THE INVENTION

Voltage gated sodium channels ($Na_V$'s) are critical determinants of cellular excitability in muscle and nerve (Hille, B, *Ion Channels of Excitable Membranes* (2001), Sunderland, Mass., Sinauer Associates, Inc.). Four isoforms in particular, $Na_V1.1$, $Na_V1.2$, $Na_V1.3$, and $Na_V1.6$, account for the majority of sodium current in the neurons of the central nervous system. $Na_V1.3$ is primarily expressed embryonically. Beyond the neonatal stage, $Na_V1.1$, $Na_V1.2$, and $Na_V1.6$ are the critical isoforms that regulate neuronal signaling in the brain (Catterall, W. A., *Annual Review of Pharmacology and Toxicology* (2014), Vol. 54, pp. 317-338).

$Na_V1.5$ is expressed mainly in cardiac myocytes (Raymond, C. K. et al., *J. Biol. Chem.* (2004), Vol. 279, No. 44, pp. 46234-41), including atria, ventricles, the sino-atrial node, atrio-ventricular node and cardiac Purkinje fibers. Mutations in human $Na_V1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., *Am. J. Pharmacogenomics* (2003), Vol. 3, No. 3, pp. 173-9). Sodium channel blocker therapy has been used extensively in treating cardiac arrhythmias.

Epilepsy is a condition characterized by excessive synchronous excitability in the brain that arises when the delicate balance of excitatory and inhibitory signals in the brain fall out of equilibrium. This can happen either due to an excess of excitation, or a deficiency of inhibition. Mutations in the genes encoding $Na_V$ channels have been linked to both types of disequilibrium.

$Na_V1.1$ has been identified as the primary $Na_V$ isoform of inhibitory interneurons (Yu, F. H. et al., *Nat. Neurosci.* (2006), Vol. 9, pp. 1142-1149). These interneurons synapse on many other neurons, including excitatory glutamatergic neurons. Action potentials in the interneurons induce the release of the neurotransmitter GABA onto other neurons, hyperpolarizing them and thus dampening excitation. This results in a negative feedback that enables controlled signaling and prevents local signals from expanding into waves of excitation that spread across large brain regions. Because of this critical role in inhibitory interneurons, mutations that impair $Na_V1.1$ channel function can lead to a failure of those neurons to activate and release GABA (Ogiwara, I. et al., *J. Neurosci.* (2007), Vol. 27, pp. 5903-5914; Martin, M. S. et al., *J. Biol. Chem.* (2010), Vol. 285, pp. 9823-9834; Cheah, C. S. et al., *Channels (Austin)* (2013), Vol. 7, pp. 468-472; and Dutton, S. B., et al., (2013), Vol. 49, pp. 211-220). The result is a loss in the inhibitory tone of the brain and a failure to contain the excitability of the glutamatergic neurons. This failure of the inhibitory interneurons can result in aberrant wide-scale synchronous firing of neurons across regions of the brain (epilepsy).

Mutations in the gene encoding $Na_V1.1$ (SCN1A) fall into two broad classes, those that cause generalized epilepsy with febrile seizures plus (GEFS+) and those that cause severe myoclonic epilepsy of infancy (SMEI), also known as Dravet Syndrome or early infantile epileptic encephalopathy 6 (EIEE6) (McKusik, V. K. et al., A *Epileptic Encephalopathy, Early Infantile 6, EIEE6* (2012), Online Mendelian Inheritance in Man: John Hopkins University). SMEI mutations are heterozygous autosomal dominant mutations and are often caused by a gene deletion or truncation that leads to a channel with little or no function. The mutations arise de novo, or in a few cases have been shown to arise in asymptomatic mosaic parents (Tuncer, F. N. et al., *Epilepsy Research* (2015), Vol. 113, pp. 5-10). Patients are born phenotypically normal and meet developmental milestones until the onset of seizures, typically between the age of 6 months and 1 year. This time of onset is believed to be a consequence of the normal decrease in the expression of the embryonic isoform $Na_V1.3$ and the coincident rise of $Na_V1.1$. When the $Na_V1.1$ channels fail to reach normal levels, the phenotype is revealed (Cheah, C. S. et al., *Channels (Austin)* (2013), Vol. 7, pp. 468-472). The initial seizure is often triggered by a febrile episode and can manifest as status epilepticus. Seizures continue and increase in frequency and severity for the first several years of life and can reach frequencies of over 100 episodes per day. Seizures may be triggered by fever or may arise spontaneously without apparent cause. After seizure onset patients begin to miss developmental milestones and significant cognitive and behavioral deficits accrue (Dravet, C. and Oguni, H., *Handbook of Clinical Neurology* (2013), Vol. 111, pp. 627-633). 80 to 85% of phenotypically diagnosed Dravet syndrome patients are believed to have a responsible mutation in SCN1A, while the other 15-20% of patients have other mutations or are of unknown etiology. There is a high rate of sudden unexplained death in epilepsy (SUDEP) in SMEI patients, with an estimated 37% of patients dying by SUDEP, but the mechanism for this catastrophic outcome remains unclear (Massey, C. A., et al., *Nature Reviews Neurology* (2014), Vol. 10, pp. 271-282). Clinically useful anti-epileptic drugs that target voltage-gated sodium channels non-selectively, like carbamazepine and phenytoin, are contra-indicated for SMEI patients as they can exacerbate seizures in these patients(Wilmshurst, J. M. et al., *Epilepsia* (2015), Vol. 56, pp. 1185-1197). This is presumed to be because patients cannot tolerate further reductions in $Na_V1.1$ function.

GEFS+ is often caused by missense SCN1A mutations that induce relatively mild channel dysfunction, consistent with the relatively milder seizure phenotype. A large and growing number of mutations have been identified, and both the severity and the penetrance of the phenotype varies considerably. Many GEFS+ patients outgrow the seizure phenotype, however not all do, and GEFS+ patients with childhood epilepsy are considerably more prone to have epilepsy as adults than are the general population. Mutations that cause deficits in other genes involved with GABA-ergic signaling, like SCN1B that encodes the sodium channel auxiliary subunit and GABRG2 that encodes a subunit of $GABA_A$ receptors can also give rise to GEFS+ (Helbig, I., Seminars in *Neurology* (2015) Vol. 35, pp. 288-292).

Transgenic mice have been developed that harbor the same mutations identified in SMEI and GEFS+ patients. In both cases the mice replicate the human phenotype well, though the penetrance of the phenotype can be significantly impacted by the genetic background. Some mouse strains tolerate the mutations relatively well, while in other strains the same mutations can cause drastic seizure phenotypes. These differences are presumed to be due to differing levels of expression of other genes that modulate the excitation phenotype (Miller, A. R. et al., *Genes, Brain, and Behavior* (2014), Vol. 13, pp. 163-172; Mistry, A. M. et al., *Neurobiology of Disease* (2014), Vol. 65, pp. 1-11; and Hawkins, N. A. et al., *Epilepsy Research* (2016), Vol. 119, pp. 20-23).

In the brain, $Na_V1.2$ and $Na_V1.6$ are primarily expressed in excitatory glutamatergic neurons. Both channels are especially dense in the action initial segment (AIS), a region of the neuron adjacent to the neuronal soma that acts to integrate inputs and initiates action potential propagation to the soma and the distal dendrites (Royeck, M. et al., *J. Neurophysiol.* (2008), Vol. 100, pp. 2361-2380; Vega, A. V. et al., *Neurosci. Lett.* (2008), Vol. 442, pp. 69-73; and Hu, W. et al., *Nat. Neurosci.* (2009), Vol. 12, pp. 996-1002). $Na_V1.6$ tends to be especially densely localized the early AIS (distal from the soma) where it is thought to act to trigger action potential initiation. $Na_V1.2$ is more highly localized to the segment of the AIS most proximal to the soma. Mutations in both SCN2A ($Na_V1.2$) and SCN8A ($Na_V1.6$) have been linked to epilepsy and cognitive delay. The effects of the mutations are diverse both at the level of the impact on channel function, and on the patient phenotype. Both $Na_V1.2$ and $Na_V1.6$ are also expressed in peripheral neurons. $Na_V1.6$ is especially dense at the nodes of Ranvier of myelinated neurons, where it is critical for maintaining salutatory conduction and high speed neuronal signaling.

Only a handful of $Na_V1.2$ mutations have been described, but they are primarily linked with central nervous system pathologies, especially epilepsy (Kearney, J. A. et al., *Neuroscience* (2001), Vol. 102, pp. 307-317; Zerem, A. et al., *European Journal of Paediatric Neurology: EJPN: Official Journal of the European Paediatric Neurology Society* (2014), Vol. 18, pp. 567-571; Fukasawa, T. et al., *Brain & Development* (2015), Vol. 37, pp. 631-634; Howell, K. B. et al., *Neurology* (2015), Vol. 85, pp. 958-966; Saitoh, M. et al., *Epilepsy Research* (2015), Vol. 117, pp. 1-6; Samanta, D. et al., *Acta Neurologica Belgica* (2015), Vol. 115, pp. 773-776; Carroll, L. S. et al., *Psychiatric Genetics* (2016), Vol. 26, pp. 60-65; and Schwarz, N. et al., *Journal of Neurology* (2016), Vol. 263, pp. 334-343). The epilepsy mutations are presumed to be primarily gain of function mutations, meaning that they lead to an increase in the amount of sodium current and thereby increasing excitability. Establishing the impact on channel function in vivo beyond reasonable doubt is challenging and some of these mutations may yet lead to loss of function phenotypes.

Mutations in SCN8A have likewise been reported to show a range of gain and loss of function effects on the $Na_V1.6$ channel though, for $Na_V1.6$, most mutations examined have been associated with gain of function phenotypes. Mutations in $Na_V1.6$ have been linked with epilepsy and autism spectrum disorders (Trudeau, M. M. et al., *Journal of Medical Genetics* (2006), Vol. 43, pp. 527-530; Veeramah, K. R. et al., *Am. J. Hum. Genet.* (2012), Vol. 90, pp. 502-510; Vaher, U. et al., *Journal of Child Neurology* (2013); de Kovel, C. G. et al., *Epilepsy Research* (2014); Estacion, M. et al., *Neurobiology of Disease* (2014), Vol. 69, pp. 117-123; Ohba, C. et al., *Epilepsia* (2014), Vol. 55, pp. 994-1000; Wagnon, J. L. et al., *Human Molecular Genetics* (2014); Kong, W. et al., *Epilepsia* (2015), Vol. 56, pp. 431-438; and Larsen, J. et al., *Neurology* (2015), Vol. 84, pp. 480-489). The best described SCN8A mutant patients have a syndrome known as early infantile epileptic encephalopathy, 13 (EIEE13). Over 100 EIEE13 patients have been identified. Patients typically present with intractable seizures between birth and 18 months of age. Patients have developmental and cognitive delay, and motor impairment often associated with chronic muscular hypotonia. The most severely impacted patients never gain sufficient motor control to walk. Many are not verbal. Less severe phenotypes learn to walk and talk but are motor-impaired and miss cognitive and social milestones. Most of the identified mutations are missense mutations, and it is assumed that the specific functional impact of the mutation contributes to the variability in the phenotype, though genetic background is also likely involved (Larsen, J. et al., *Neurology* (2015), Vol. 84, pp. 480-489). In contrast to SMEI patients, anecdotal evidence suggests that anti-epileptic drugs that target voltage-gated sodium channels non-selectively can ameliorate symptoms in EIEE13 patients, though no controlled clinical trials have been completed (Boerma, R. S. et al., *Neurotherapeutics: The Journal of the American Society for Experimental Neuro Therapeutics* (2016), Vol. 13, pp. 192-197). While phenytoin does seem to provide efficacy for EIEE13 patients, it does so at a cost. Efficacy is only achieved at very high doses where the significant adverse effects are tolerated only because the patients are in such dire need. Adverse effects commonly associated with phenytoin therapy include hepatic necrosis, hypertrichosis, nervousness, tremor of hands, numbness, dizziness, drowsiness, tremor, depression, confusion, fatigue, constipation, vertigo, ataxia, mental status changes, myasthenia, mood changes, restlessness, irritability, and excitement. It seems likely that a drug that selectively targets $Na_V1.6$ would retain efficacy while reducing its adverse event burden.

Loss of function mutations in SCN8A in mice lead to a phenotype known as motor endplate disease (med) and multiple mutations and phenotypes were linked to the med gene region prior to the identification of the SCN8A gene (Burgess, D. L. et al., *Nat. Genet.* (1995), Vol. 10, pp. 461-465). Mice with $SCN8A^{med}$ mutations have varying degrees of muscle hypotonia, consistent with the degree of dysfunction of the $Na_V1.6$ function. Mice with the $SCN8A^{med/jo}$ have $Na_V1.6$ channels that have a loss of function, but not null, phenotype. $SCN8A^{med}$ and $SCN8A^{med/jo}$ mice are resistant to seizures induced by chemical insult (flurothyl, kainic acid, and picrotoxin) (Martin, M. S. et al., *Human Molecular Genetics* (2007), Vol. 16, pp. 2892-2899; Hawkins, N. A. et al., *Neurobiology of Disease* (2011), Vol. 41, pp. 655-660; and Makinson, C. D. et al., *Neurobiology of Disease* (2014), Vol. 68, pp. 16-25). Curiously, when $SCN8A^{med/jo}$ mice are crossed with $SCN1A^{null}$ mutant mice to produce a mouse that is heterozygous for both the $SCN1A^{null}$ allele and the $SCN8A^{med/jo}$ allele the double mutant mice have a much improved seizure and cognitive phenotype than those with only an $SCN1A^{null}$ mutation (Martin, M. S. et al., *Human Molecular Genetics* (2007), Vol. 16, pp. 2892-2899). Such mice have a spontaneous seizure and death rate similar to wild type mice and their seizure threshold after chemical insult is also increased. A similar result occurs upon crossing mice with missense mutations of SCN1A (a model for GEFS+) and mice with SCN8A loss of function mutations. Having a single allele of $SCN8A^{med/jo}$ protected the GEFS+ model mice from seizures and premature death (Hawkins, N. A. et al., *Neurobiology of Disease* (2011), Vol. 41, pp. 655-660). The ability of SCN8A knock down to improve seizure resistance is not limited to knockouts where the gene is globally absent throughout animal development. Knock down of SCN8A in adult mice either globally or specifically in the hippocampus via a CRE-LOX inducible knockout approach also improved resistance to electrically and chemically induced seizures Makinson, C. D. et al., *Neurobiology of Disease* (2014), Vol. 68, pp. 16-25). These data suggest that the suppression of inhibitory signaling caused by decreased $Na_V1.1$ current can be offset, at least in part, by suppressing excitatory signaling via decreased in $Na_V1.6$ current.

Voltage-gated sodium channel antagonism is the most common mechanism of widely prescribed antiepileptic drugs (AED's) (Ochoa, J. R. et al., *Sodium Channel Blockers. In: Antiepileptic Drugs* (2016), Vol. (Benbadis, S., ed) Medscape News & Perspectives). Carbamazepine, Eslicarbazepine, Oxcarbazepine, Lacosamide, Lamotrigine, Phenytoin, Rufinamide and Zonisamide are all believed to act primarily by blocking that function of $Na_V$ channels. Despite the presumed mechanism of action, these drugs are relatively promiscuous. They block all $Na_V$ channel isoforms indiscriminately, thus block of $Na_V1.1$ would be expected to proconvulsant. Block of $Na_V1.6$, and perhaps $Na_V1.2$, would be anticonvulsant. In addition to sodium channels, these compounds also block other targets, including voltage-gated calcium channels. Selective $Na_V$ antagonists that spare $Na_V1.1$ and other off-target receptors are expected to have both improved efficacy and therapeutic index relative to the currently available $Na_V$ blocking drugs.

There is therefore an unmet medical need to treat epilepsy and other $Na_V1.6$ associated pathological states effectively and without adverse side effects due to the blocking of other sodium channels, such as $Na_V1.1$ and/or $Na_V1.5$. The present invention provides methods to meet these critical needs.

SUMMARY OF THE INVENTION

The present invention is directed to benzenesulfonamide compounds and pharmaceutical compositions comprising the compounds and methods of using the compounds and the pharmaceutical compositions of the invention for the treatment of diseases or conditions associated with the activity of voltage-gated sodium channels, particularly, $Na_V1.6$ activity, such as epilepsy and/or epileptic seizure disorder.

Accordingly, in one aspect, this invention is directed to benzenesulfonamide compounds of formula (I):

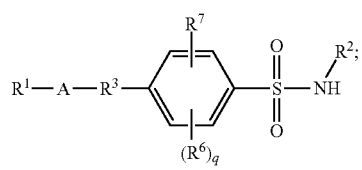

wherein:
A is a direct bond or $-(CH_2)_m-C(R^4)(R^5)-(CH_2)_n-$ where m and n are independently 0, 1, 2, 3 or 4;
q is 1, 2 or 3;
$R^1$ is an optionally substituted cycloalkyl, an optionally substituted aryl, an optionally substituted monocyclic heteroaryl or an optionally substituted bicyclic heteroaryl;
$R^2$ is an optionally substituted 5-membered N-heteroaryl or an optionally substituted 6-membered N-heteroaryl;
$R^3$ is $-O-$, $-N(R^8)-$ or $-S(O)_t-$ (where t is 0, 1 or 2);
$R^4$ and $R^5$ are each independently hydrogen, alkyl, haloalkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl, $-R^9-OR^{10}$ or $-R^9-N(R^{10})R^{11}$;
or $R^4$ and $R^5$, together with the carbon to which they are attached, form an optionally substituted cycloalkyl or an optionally substituted heterocyclyl;
each $R^6$ is independently hydrogen, alkyl, halo, haloalkyl, cyano or $-OR^{12}$;
$R^7$ is alkyl, alkenyl, halo, haloalkyl, cyano or $-OR^{12}$;
each $R^8$, $R^{10}$, $R^{11}$ and $R^{12}$ is independently hydrogen, alkyl, haloalkyl, optionally substituted cycloalkyl, optionally substituted cycloalkylalkyl, optionally substituted heterocyclyl, optionally substituted heterocyclylalkyl; and
each $R^9$ is independently a direct bond or an optionally substituted straight or branched alkylene chain;
as an individual stereoisomer, enantiomer or tautomer thereof or a mixture thereof;
or a pharmaceutically acceptable salt, solvate or prodrug thereof;
provided that:
(a) when A is a direct bond, $R^1$ is not optionally substituted cycloalkyl;
(b) when A is a direct bond and $R^3$ is $-O-$ or $-S(O)_t-$ (where t is 0, 1 or 2), $R^1$ is not optionally substituted phenyl;
(c) when A is a direct bond and $R^3$ is $-N(R^8)-$, $R^1$ is not optionally substituted phenyl or optionally substituted 2,4,5,6-tetrahydrocyclopenta[c]pyrazolyl;
(d) when A is $-(CH_2)_m-C(R^4)(R^5)-(CH_2)_n-$, where m and n are both 0 and $R^4$ and $R^5$ are both hydrogen, and $R^3$ is $-O-$, $R^2$ is not optionally substituted thiadiazolyl; and
(e) when A is direct bond and $R^3$ is $-N(R^8)-$, $R^1$ is not an optionally substituted monocyclic heteroaryl.

The compounds of the invention, which are compounds of formula (I) as described above, as individual stereoisomers, enantiomers or tautomers thereof or mixtures thereof; or as pharmaceutically acceptable salts, solvates or prodrugs thereof, are useful in treating diseases or conditions associated with voltage-gated sodium channels, preferably $Na_V1.6$. Preferably, the compounds of the invention are $Na_V1.6$ inhibitors. More preferably, the compounds of the invention show selectivity of inhibiting $Na_V1.6$ as compared with inhibiting $Na_V1.5$ and/or $Na_V1.1$. Without wishing to be bound by theory, such selectivity is thought to advantageously reduce any side effects which may be associated with the inhibition of $Na_V1.5$ and/or $Na_V1.1$.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of epilepsy and/or epileptic seizure disorder in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of Na$_V$1.6 is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or ameliorating, but not preventing, epilepsy and/or epileptic seizure disorder in a mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed herein.

In another aspect, this invention is directed to methods of selectively inhibiting a first voltage-gated sodium channel in a mammal over a second voltage-gated sodium channel, wherein the method comprises administering to the mammal a inhibitory amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a inhibitory amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of a disease or condition associated with the activity of a voltage-gated sodium channel, preferably Na$_V$1.6, in a mammal and preferably wherein the disease or condition is epilepsy and/or epileptic seizure disorder.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: halo, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)R$^{22}$ (where p is 1 to 2), —S(O)$_p$OR$^{22}$ (where p is 1 to 2), —S(O)$_t$R$^{22}$ (where t is 0 to 2), and —S(O)$_p$N(R$^{20}$)$_2$ (where p is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^2)C(O)R^{22}$, —$N(R^{20})S(O)R^{22}$ (where p is 1 to 2), —$S(O)_pOR^{22}$ (where p is 1 to 2), —$S(O)R^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$N(R^{20})$—$R^{23}$—$OR^{20}$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{22}$, —$R^{21}$—$N(R^{20})C(O)R^{22}$, —$R^{21}$—$N(R^{20})S(O)_pR^{22}$ (where p is 1 to 2), —$R^{21}$—$N$=$C(OR^{20})R^{20}$, —$R^{21}$—$S(O)_pOR^{22}$ (where p is 1 to 2), —$R^{21}$—$S(O)R^{22}$ (where t is 0 to 2), and —$R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted aryl group for $R^1$ herein are alkyl, optionally substituted cycloalkyl, halo, haloalkyl, cyano, optionally substituted heterocyclyl, optionally substituted heterocyclylalkyl, optionally substituted heteroaryl —$R^{21}$—$OR^{20}$ and —$R^{21}$—$N(R^{20})_2$, (where $R^{20}$ and $R^{21}$ are as defined above).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})$—$R^{23}$—$OR^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{22}$, —$R^{21}$—$N(R^{20})C(O)R^{22}$, —$R^{21}$—$N(R^{20})S(O)_pR^{22}$ (where p is 1 to 2), —$R^{21}$—$N$=$C(OR^{20})R^{20}$, —$R^{21}$—$S(O)_pOR^{22}$ (where p is 1 to 2), —$R^{21}$—$S(O)R^{22}$ (where t is 0 to 2), and —$R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"Cycloalkylalkyl" refers to a radical of the formula —$R_bR_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused, bridged and spiro ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, 1-azaspiro[3.3]heptan-1-yl, 5-azaspiro[2.3]hexan-5-yl, 2-oxa-6-azaspiro[3.3]heptan-6-yl, 1-oxa-6-azaspiro[3.4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxothiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})-R^{23}-OR^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group. Preferably the optional substituents on the optionally substituted heterocyclylalkyl group for $R^5$ herein are halo.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})-R^{23}-OR^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical. Preferably the optional substituents on the optionally substituted 5-membered N-heteroaryl group for $R^2$ herein are alkyl and halo. Preferably the optional substituents on the optionally substituted 6-membered N-heteroaryl group for $R^2$ herein are alkyl, halo, and haloalkyl.

"Heteroarylalkyl" refers to a radical of the formula $-R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. In one embodiment of the invention, the compounds of formula (I) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid.

Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, e.g., relieving epilepsy without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 14.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions).

The designations, "R" and "S", for the absolute configuration of an enantiomer of the invention may appear as a prefix or as a suffix in the name of the compound; they may or may not be separated from the enantiomer name by a hyphen; they may or may not be hyphenated; and they may or may not be surrounded by parentheses.

Following the standard chemical literature description practice and as used in this specification, a solid full bond, as illustrated above in Structure (A) and a dashed full bond, as illustrated by the exemplary structure (A) below, means that the substituents are in a trans-configuration with respect to the plane of the ring:

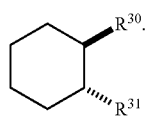

(A)

In the same manner, the bonds in the following exemplary structures (Aa) and (Ab) are in a cis-configuration with respect to the plane of the ring:

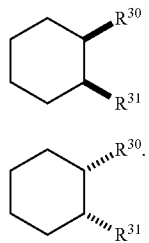

(Aa)

(Ab)

Following the standard chemical literature description practice and as used in this specification, a full wedge bond, as illustrated below in structure (B), means that the substituent bonded to the ring by this bond, in this case the $R^{30}$ substituent, is above the ring plane as illustrated on the page in a two dimensional representation, and a dashed wedge bond, as illustrated below in Structure (B), means that the substituent bonded to the ring by this bond, in this case the $R^{31}$ substituent, is below the ring plane as shown on the page in a two dimensional representation;

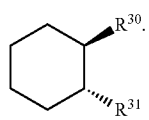

(B)

Following the standard chemical literature description practice and as used in this specification, a wavy bond, as illustrated below in structure (C), indicates that the substituent, in this case the $R^{30}$ substituent, is either below the plane of the ring or above the plane of the ring:

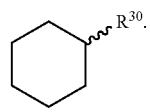

(C)

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, in the following structure (D), the bond attaching the $R^{30}$ substituent can be on any of the carbons, including the carbon to which the $R^{31}$ is attached, provided that the valency allows for such an attachment:

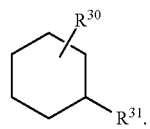

(D)

"Resolution" or "resolving" when used in reference to a racemic compound or a racemic mixture of a compound of the invention refers to the separation of the racemic compound or a racemic mixture into its two enantiomeric forms (i.e., (+) and (−); (R) and (S) forms).

"Enantiomeric excess" or "ee" as used herein refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

The chemical naming protocol and structure diagrams used herein are a modified form of the I.U.P.A.C. nomenclature system, using ChemBioDraw Ultra Version 14.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Accordingly, the (R)-enantiomer of a compound of formula (I), as described above in the Summary of the Invention wherein A is —$(CH_2)_m$—$C(R^4)(R^5)$—$(CH_2)_n$— (where m and n are both 0, $R^4$ is ethyl and $R^5$ is hydrogen); q is 1, $R^1$ is unsubstituted phenyl, $R^2$ is 1,2,4-thiadiazol-5-yl, $R^3$ is —N($R^8$)— where $R^8$ is hydrogen, $R^6$ is hydrogen and $R^7$ is chloro, i.e., the compound of the following structure:

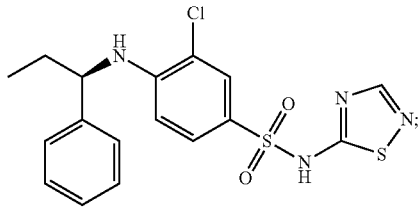 [SMILES: CC[C@@H](Nc1ccc(S(=O)(=O)Nc2ncns2)cc1Cl)c1ccccc1]

is named herein as (R)-3-chloro-4-(1-phenylpropylamino)-N-(1,2,4-thiadiazol-5-yl)benzenesulfonamide.

Embodiments of the Invention

One aspect of the invention are compounds of formula (I), as set forth above in the Summary of the Invention, as an individual stereoisomer, enantiomer or tautomer thereof or a mixture thereof; or a pharmaceutically acceptable salt, solvate or prodrug thereof.

In one embodiment, a compound of formula (I) is a compound of formula (I) wherein $R^3$ is —O—, wherein the compound has the following formula (Ia):

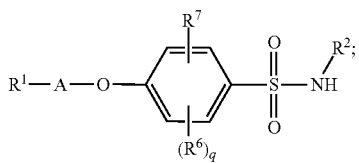

wherein q, A, $R^1$, $R^2$, $R^4$, $R^5$, $R^6$, $R^9$, $R^{11}$, $R^{10}$, $R^{11}$ and $R^{12}$ are each as defined above in the Summary of the Invention;

as an individual stereoisomer, enantiomer or tautomer thereof or mixtures thereof;

or a pharmaceutically acceptable salt, solvate or prodrug thereof.

In another embodiment, a compound of formula (I) is a compound of formula (Ia), as defined above, wherein A is a direct bond, i.e., a compound of formula (Ia1):

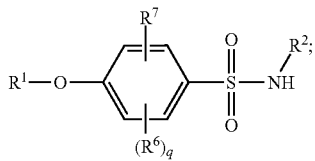

wherein q, $R^1$, $R^2$, $R^6$ and $R^7$ are each as defined above the Summary of the Invention;

as an individual stereoisomer, enantiomer or tautomer thereof or mixtures thereof; or a pharmaceutically acceptable salt, solvate or prodrug thereof.

Of this embodiment, a preferred compound of formula (Ia1) is 5-chloro-2-fluoro-N-(thiazol-4-yl)-4-(4-(trifluoromethyl)-2,3-dihydro-1H-inden-1-yloxy)benzenesulfonamide.

In another embodiment, a compound of formula (I) is a compound of formula (Ia), as defined above, wherein A is —(CH$_2$)$_m$—C($R^4$)($R^5$)—(CH$_2$)$_n$—, i.e., a compound of formula (Ia2):

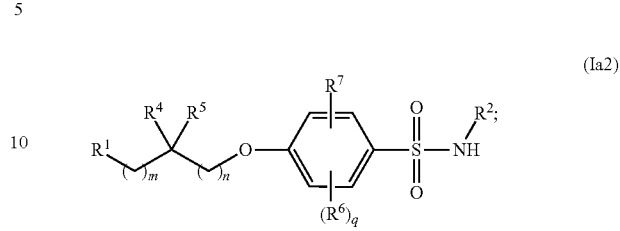

wherein m, n, $R^1$, $R^2$, $R^4$, $R^5$, $R^6$ and $R^7$ are each as defined above in the Summary of the Invention;

as an individual stereoisomer, enantiomer or tautomer thereof or mixtures thereof;

or a pharmaceutically acceptable salt, solvate or prodrug thereof.

Of this embodiment, preferred compounds of formula (Ia2) are selected from:

4-((2-(azetidin-1-ylmethyl)-3,6-difluorobenzyl)oxy)-5-chloro-2-fluoro-N-(thiazol-4-yl)benzenesulfonamide;

(R)-3-chloro-4-(1-phenylethoxy)-N-(1,2,4-thiadiazol-5-yl)benzenesulfonamide;

(S)-3-chloro-4-(1-phenylethoxy)-N-(1,2,4-thiadiazol-5-yl)benzenesulfonamide;

(S)-3-chloro-2-fluoro-4-(1-(2-fluorophenyl)ethoxy)-N-(thiazol-2-yl)benzenesulfonamide;

5-chloro-2-fluoro-4-(isoquinolin-8-ylmethoxy)-N-(thiazol-2-yl)benzenesulfonamide;

(S)-2,5-difluoro-4-(1-(2-fluorophenyl)ethoxy)-N-(thiazol-2-yl)benzenesulfonamide;

(R)-5-chloro-2-fluoro-N-(thiazol-2-yl)-4-(2,2,2-trifluoro-1-phenylethoxy)benzenesulfonamide;

(S)-5-chloro-4-(1-(5-chloro-2-fluorophenyl)ethoxy)-2-fluoro-N-(thiazol-2-yl)benzenesulfonamide;

(S)-5-chloro-2-fluoro-4-(1-(2-fluorophenyl)ethoxy)-N-(thiazol-4-yl)benzenesulfonamide;

(S)-5-chloro-4-(1-(3,4-dichlorophenyl)ethoxy)-2-fluoro-N-(thiazol-2-yl)benzenesulfonamide;

(S)-5-chloro-2-fluoro-4-(1-(3-fluorophenyl)ethoxy)-N-(thiazol-2-yl)benzenesulfonamide;

(S)-5-chloro-2-fluoro-4-(1-phenylethoxy)-N-(thiazol-2-yl)benzenesulfonamide;

(S)-5-chloro-2-fluoro-4-(1-(2-fluorophenyl)ethoxy)-N-(thiazol-2-yl)benzenesulfonamide;

(S)-5-chloro-4-(1-(2-chlorophenyl)ethoxy)-2-fluoro-N-(thiazol-2-yl)benzenesulfonamide;

(S)-5-chloro-2-fluoro-4-(1-(3-fluorophenyl)ethoxy)-N-(thiazol-4-yl)benzenesulfonamide;

(S)-5-chloro-4-(1-(2,6-difluorophenyl)ethoxy)-2-fluoro-N-(thiazol-2-yl)benzenesulfonamide;

(S)-5-chloro-4-(1-(2,6-difluorophenyl)ethoxy)-2-fluoro-N-(thiazol-4-yl)benzenesulfonamide;

(R)-5-chloro-2-fluoro-4-(1-(2-fluorophenyl)ethoxy)-N-(thiazol-2-yl)benzenesulfonamide;

5-chloro-2-fluoro-4-((2-fluorobenzyl)oxy)-N-(thiazol-2-yl)benzenesulfonamide;

(S)-5-chloro-4-(1-(2-chlorophenyl)ethoxy)-2-fluoro-N-(thiazol-4-yl)benzenesulfonamide;

(S)-5-chloro-4-(1-(5-chloro-2-fluorophenyl)ethoxy)-2-fluoro-N-(thiazol-4-yl)benzenesulfonamide;

4-((2-(azetidin-1-ylmethyl)benzyl)oxy)-5-chloro-2-fluoro-N-(thiazol-2-yl)benzenesulfonamide;

(S)-2,6-difluoro-4-(1-(2-fluorophenyl)ethoxy)-N-(thiazol-4-yl)benzenesulfonamide;
5-chloro-2-fluoro-4-(1-phenylcyclopropoxy)-N-(thiazol-4-yl)benzenesulfonamide; and
(S)-5-chloro-2-fluoro-4-(1-(2-fluorophenyl)propoxy)-N-(thiazol-4-yl)benzenesulfonamide.

In another embodiment, a compound of formula (I) is a compound of formula (I) wherein $R^3$ is —N($R^8$)—, wherein the compound has the following formula (Ib):

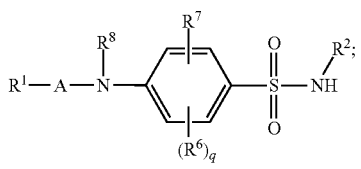

(Ib)

wherein q, A, $R^1$, $R^2$, $R^6$, $R^7$ and $R^8$ are each as defined above in the Summary of the Invention;
as an individual stereoisomer, enantiomer or tautomer thereof or mixtures thereof;
or a pharmaceutically acceptable salt, solvate or prodrug thereof.

In another embodiment, a compound of formula (I) is a compound of formula (Ib), as defined above, wherein A is a direct bond, i.e., a compound of formula (Ib1):

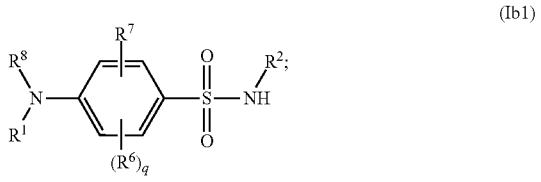

(Ib1)

wherein q, $R^1$, $R^2$, $R^6$, $R^7$ and $R^8$ are each as defined above in the Summary of the Invention;
as an individual stereoisomer, enantiomer or tautomer thereof or mixtures thereof;
or a pharmaceutically acceptable salt, solvate or prodrug thereof.

Of this embodiment, preferred compounds of formula (Ib1) are selected from:
5-chloro-2-fluoro-4-((1-(pyridin-3-yl)propan-2-yl)amino)-N-(thiazol-2-yl)benzenesulfonamide;
(R)-3-chloro-4-(2,3-dihydro-1H-inden-1-ylamino)-N-(1,2,4-thiadiazol-5-yl)benzenesulfonamide;
(S)-3-chloro-4-(2,3-dihydro-1H-inden-1-ylamino)-N-(1,2,4-thiadiazol-5-yl)benzenesulfonamide;
(S)-5-chloro-2-fluoro-4-(1,2,3,4-tetrahydronaphthalen-1-ylamino)-N-(thiazol-2-yl)benzenesulfonamide;
(R)-5-chloro-2-fluoro-4-(1,2,3,4-tetrahydronaphthalen-1-ylamino)-N-(thiazol-2-yl)benzenesulfonamide;
(S)-3-chloro-4-((5,6,7,8-tetrahydroquinolin-8-yl)amino)-N-(thiazol-2-yl)benzenesulfonamide;
5-chloro-2-fluoro-4-((5,6,7,8-tetrahydroisoquinolin-8-yl)amino)-N-(thiazol-2-yl)benzenesulfonamide 2,2,2-trifluoroacetate;
5-chloro-2-fluoro-4-((5,6,7,8-tetrahydroisoquinolin-5-yl)amino)-N-(thiazol-2-yl)benzenesulfonamide 2,2,2-trifluoroacetate;
5-chloro-2-fluoro-4-((5,6,7,8-tetrahydroquinolin-5-yl)amino)-N-(thiazol-2-yl)benzenesulfonamide formic acid salt
4-(((1R,3S)-3-(azetidin-1-yl)-2,3-dihydro-1H-inden-1-yl)amino)-2,6-difluoro-N-(thiazol-4-yl)benzenesulfonamide;
4-(((1R,3S)-3-(azetidin-1-yl)-2,3-dihydro-1H-inden-1-yl)amino)-5-chloro-2-fluoro-N-(thiazol-4-yl)benzenesulfonamide; and
4-(((1S,3S)-3-(azetidin-1-yl)-2,3-dihydro-1H-inden-1-yl)amino)-5-chloro-2-fluoro-N-(thiazol-4-yl)benzenesulfonamide formate.

In another embodiment, a compound of formula (I) is a compound of formula (Ib), as defined above, wherein A is —(CH$_2$)$_m$—C($R^4$)($R^5$)—(CH$_2$)$_n$—, i.e., a compound of formula (Ib2):

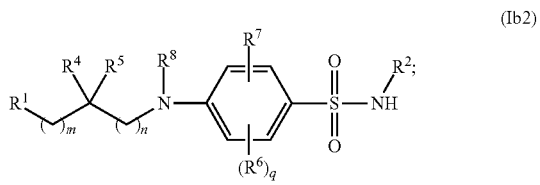

(Ib2)

wherein m, n, $R^1$, $R^2$, $R^4$, $R^5$, $R^6$, $R^7$ and $R^8$ are each as defined above in claim 1;
as an individual stereoisomer, enantiomer or tautomer thereof or mixtures thereof;
or a pharmaceutically acceptable salt, solvate or prodrug thereof.

Of this embodiment, a preferred embodiment are those compounds of formula (Ib2) wherein $R^2$ is an optionally substituted 5-membered N-heteroaryl.

Of this embodiment, a preferred embodiment are those compounds of formula (Ib2) wherein $R^2$ is selected from optionally substituted thiazolyl, optionally substituted thiadiazolyl, optionally substituted isoxazolyl, optionally substituted isothiazolyl or optionally substituted oxazolyl.

Of this embodiment, a preferred embodiment are those compounds of formula (Ib2) wherein:
$R^1$ is optionally substituted cycloalkyl;
or $R^1$ is aryl optionally substituted by one or more substituents selected from halo, alkyl, haloalkyl, optionally substituted cycloalkyl, cyano, —$R^9$—O$R^{12}$, —$R^9$—N($R^{10}$)$R^{11}$, —$R^9$—N($R^{10}$)—$R^{13}$—O$R^{12}$, optionally substituted heterocyclyl and optionally substituted heteroaryl;
$R^2$ is optionally substituted thiazolyl; and
$R^{13}$ is a branched or straight alkylene chain.

Of this embodiment, preferred compounds of formula (Ib2) are selected from:
(S)-5-chloro-4-((1-cyclohexylethyl)amino)-2-fluoro-N-(thiazol-2-yl)benzenesulfonamide;
3-chloro-4-(1-phenylpropylamino)-N-(thiazol-2-yl)benzenesulfonamide;
5-chloro-2-fluoro-4-(1-phenylpropylamino)-N-(thiazol-2-yl)benzenesulfonamide;
(S)-5-chloro-2-fluoro-4-(1-phenylpropylamino)-N-(thiazol-4-yl)benzenesulfonamide;
(R)-5-chloro-2-fluoro-4-(1-phenylpropylamino)-N-(thiazol-2-yl)benzenesulfonamide;
(S)-5-chloro-2-fluoro-4-(1-phenylpropylamino)-N-(thiazol-2-yl)benzenesulfonamide;
5-chloro-2-fluoro-4-(1-(2-fluorophenyl)ethylamino)-N-(thiazol-2-yl)benzenesulfonamide;
5-chloro-4-(2-(dimethylamino)-1-phenylethylamino)-2-fluoro-N-(thiazol-2-yl)benzenesulfonamide;

(R)-5-chloro-2-fluoro-4-(1-phenylethylamino)-N-(thiazol-2-yl)benzenesulfonamide;
(S)-5-chloro-2-fluoro-4-(1-phenylethylamino)-N-(thiazol-2-yl)benzenesulfonamide;
5-chloro-2-fluoro-4-(1-phenylcyclopropylamino)-N-(thiazol-2-yl)benzenesulfonamide;
5-chloro-2-fluoro-N-(thiazol-2-yl)-4-(3,3,3-trifluoro-1-phenylpropylamino)benzenesulfonamide;
(S)-5-bromo-2-fluoro-4-(1-phenylpropylamino)-N-(thiazol-2-yl)benzenesulfonamide;
5-chloro-4-(1-(2-chlorophenyl)ethylamino)-2-fluoro-N-(thiazol-2-yl)benzenesulfonamide;
(S)-5-chloro-2-fluoro-4-(1-(2-fluorophenyl)ethylamino)-N-(thiazol-2-yl)benzenesulfonamide;
(S)-5-chloro-2-fluoro-4-(1-(2-fluorophenyl)propylamino)-N-(thiazol-2-yl)benzenesulfonamide;
3-chloro-4-(cyclopropyl(phenyl)methylamino)-N-(thiazol-2-yl)benzenesulfonamide;
3-chloro-4-(methyl(1-phenylpropyl)amino)-N-(thiazol-2-yl)benzenesulfonamide;
(S)-5-chloro-2-fluoro-4-(1-(4-fluorophenyl)ethylamino)-N-(thiazol-2-yl)benzenesulfonamide;
5-chloro-2-fluoro-4-(2-morpholino-1-phenylethylamino)-N-(thiazol-2-yl)benzenesulfonamide;
(S)-2-fluoro-5-methyl-4-(1-phenylpropylamino)-N-(thiazol-2-yl)benzenesulfonamide;
(S)-3-chloro-4-(1-phenylethylamino)-N-(thiazol-2-yl)benzenesulfonamide;
5-chloro-2-fluoro-4-(1-(5,6,7,8-tetrahydronaphthalen-2-yl)propylamino)-N-(thiazol-2-yl)benzenesulfonamide;
(R)-3-chloro-4-(2-hydroxy-1-phenylethylamino)-N-(thiazol-2-yl)benzenesulfonamide;
(S)-5-chloro-2-fluoro-N-(thiazol-2-yl)-4-(1-o-tolylpropylamino)benzenesulfonamide;
(R)-4-(2-(azetidin-1-yl)-1-phenylethylamino)-5-chloro-2-fluoro-N-(thiazol-2-yl)benzenesulfonamide;
(S)-5-chloro-4-(1-(2-chlorophenyl)ethylamino)-2-fluoro-N-(thiazol-2-yl)benzenesulfonamide;
5-chloro-2-fluoro-4-(1-phenylcyclobutylamino)-N-(thiazol-2-yl)benzenesulfonamide;
5-chloro-2-fluoro-4-(3-methyl-1-phenylbutylamino)-N-(thiazol-2-yl)benzenesulfonamide;
(S)-5-chloro-2-fluoro-4-(2-methoxy-1-phenylethylamino)-N-(thiazol-2-yl)benzenesulfonamide;
(R)-5-chloro-2-fluoro-4-(2-methoxy-1-phenylethylamino)-N-(thiazol-2-yl)benzenesulfonamide;
3-chloro-4-(1-phenylcyclobutylamino)-N-(thiazol-2-yl)benzenesulfonamide;
(S)-5-chloro-2-fluoro-4-(1-phenylethylamino)-N-(thiazol-4-yl)benzenesulfonamide;
3-chloro-4-(3-phenyloxetan-3-ylamino)-N-(thiazol-2-yl)benzenesulfonamide;
(S)-5-chloro-2-fluoro-4-((1-(naphthalen-1-yl)ethyl)amino)-N-(thiazol-2-yl)benzenesulfonamide;
(S)-5-chloro-2-fluoro-N-(thiazol-2-yl)-4-((1-(3-(trifluoromethyl)phenyl)ethyl)amino)benzenesulfonamide;
(R)-3-chloro-N-(thiazol-2-yl)-4-((2,2,2-trifluoro-1-phenylethyl)amino)benzenesulfonamide formic acid salt;
(S)-5-chloro-4-((1-(5-chloro-2-fluorophenyl)ethyl)amino)-2-fluoro-N-(thiazol-4-yl)benzenesulfonamide;
(S)-5-chloro-4-((1-(3-chloro-2-fluorophenyl)ethyl)amino)-2-fluoro-N-(thiazol-4-yl)benzenesulfonamide;
(S)-4-((1-(3-bromophenyl)ethyl)amino)-5-chloro-2-fluoro-N-(thiazol-2-yl)benzenesulfonamide;
(S)-5-chloro-4-((1-(5-chloro-2-fluorophenyl)ethyl)amino)-2-fluoro-N-(thiazol-2-yl)benzenesulfonamide;
(S)-3-chloro-2-fluoro-4-((1-(2-fluorophenyl)ethyl)amino)-N-(thiazol-2-yl)benzenesulfonamide;
(S)-5-chloro-4-((1-(4-chlorophenyl)ethyl)amino)-2-fluoro-N-(thiazol-2-yl)benzenesulfonamide;
(S)-5-chloro-2-fluoro-4-((1-(naphthalen-2-yl)ethyl)amino)-N-(thiazol-2-yl)benzenesulfonamide;
5-chloro-4-((2-cyanobenzyl)amino)-2-fluoro-N-(thiazol-2-yl)benzenesulfonamide;
5-chloro-2-fluoro-4-((1-phenylcyclobutyl)amino)-N-(thiazol-4-yl)benzenesulfonamide;
5-chloro-2-fluoro-4-((1-phenylcyclopropyl)amino)-N-(thiazol-4-yl)benzenesulfonamide;
(S)-3,5-dichloro-4-((1-(2-fluorophenyl)ethyl)amino)-N-(thiazol-2-yl)benzenesulfonamide;
(S)-3-chloro-4-((1-phenylethyl)amino)-N-(thiazol-4-yl)benzenesulfonamide;
(S)-2,5-difluoro-4-((1-(2-fluorophenyl)ethyl)amino)-N-(thiazol-2-yl)benzenesulfonamide;
(S)-2,6-difluoro-4-((1-(2-fluorophenyl)ethyl)amino)-N-(thiazol-2-yl)benzenesulfonamide;
(S)-5-chloro-2-fluoro-4-((1-(2-fluorophenyl)ethyl)amino)-N-(thiazol-4-yl)benzenesulfonamide;
5-chloro-2-fluoro-4-((1-(4-fluorophenyl)cyclopropyl)amino)-N-(thiazol-2-yl)benzenesulfonamide;
(S)-5-chloro-2-fluoro-4-((1-(3-fluorophenyl)ethyl)amino)-N-(thiazol-2-yl)benzenesulfonamide;
(S)-5-chloro-4-((1-(3-chlorophenyl)ethyl)amino)-2-fluoro-N-(thiazol-2-yl)benzenesulfonamide;
(S)-5-chloro-4-((1-(3,5-dichlorophenyl)ethyl)amino)-2-fluoro-N-(thiazol-2-yl)benzenesulfonamide;
(S)-5-chloro-4-((1-(2,4-difluorophenyl)ethyl)amino)-2-fluoro-N-(thiazol-2-yl)benzenesulfonamide;
(S)-5-chloro-4-((1-(3,4-difluorophenyl)ethyl)amino)-2-fluoro-N-(thiazol-2-yl)benzenesulfonamide;
(S)-5-chloro-4-((2-(dimethylamino)-1-phenylethyl)amino)-2-fluoro-N-(thiazol-2-yl)benzenesulfonamide 2,2,2-trifluoroacetate;
(R)-5-chloro-4-((2-(dimethylamino)-1-phenylethyl)amino)-2-fluoro-N-(thiazol-2-yl)benzenesulfonamide 2,2,2-trifluoroacetate;
(S)-4-((2-(azetidin-1-yl)-1-phenylethyl)amino)-5-chloro-2-fluoro-N-(thiazol-2-yl)benzenesulfonamide 2,2,2-trifluoroacetate;
(S)-5-chloro-4-((2-(3-fluoroazetidin-1-yl)-1-phenylethyl)amino)-2-fluoro-N-(thiazol-2-yl)benzenesulfonamide 2,2,2-trifluoroacetate;
(S)-5-chloro-4-((2-(3,3-difluoroazetidin-1-yl)-1-phenylethyl)amino)-2-fluoro-N-(thiazol-2-yl)benzenesulfonamide;
(S)-5-chloro-2-fluoro-4-((1-phenyl-2-(pyrrolidin-1-yl)ethyl)amino)-N-(thiazol-2-yl)benzenesulfonamide;
(R)-5-chloro-2-fluoro-4-((1-phenyl-2-(pyrrolidin-1-yl)ethyl)amino)-N-(thiazol-2-yl)benzenesulfonamide;
(S)-5-chloro-2-fluoro-4-((1-phenyl-2-(pyrrolidin-1-yl)ethyl)amino)-N-(thiazol-4-yl)benzenesulfonamide;
(S)-5-chloro-2-fluoro-4-((2-morpholino-1-phenylethyl)amino)-N-(thiazol-2-yl)benzenesulfonamide 2,2,2-trifluoroacetate;
(S)-3-chloro-4-((1-(2-fluorophenyl)ethyl)amino)-N-(thiazol-2-yl)benzenesulfonamide;
(S)-5-chloro-4-((1-(2-chlorophenyl)ethyl)amino)-2-fluoro-N-(thiazol-4-yl)benzenesulfonamide;
5-chloro-4-((cyclopropyl(phenyl)methyl)amino)-2-fluoro-N-(thiazol-2-yl)benzenesulfonamide;
5-chloro-2-fluoro-4-((1-(3-fluorophenyl)cyclobutyl)amino)-N-(thiazol-2-yl)benzenesulfonamide;

5-chloro-2-fluoro-4-((1-(2-fluorophenyl)cyclobutyl)
    amino)-N-(thiazol-2-yl)benzenesulfonamide;
(S)-5-chloro-2-fluoro-4-((3-methyl-1-phenylbutyl)amino)-
    N-(thiazol-2-yl)benzenesulfonamide;
(R)-5-chloro-2-fluoro-4-((3-methyl-1-phenylbutyl)amino)-
    N-(thiazol-2-yl)benzenesulfonamide;
(S)-5-chloro-2-fluoro-4-((1-phenylbutyl)amino)-N-(thiazol-
    2-yl)benzenesulfonamide;
(S)-5-chloro-4-((1-(2-((dimethylamino)methyl)phenyl)
    ethyl)amino)-2-fluoro-N-(thiazol-2-yl)benzenesulfona-
    mide;
(R)-5-chloro-4-((1-(2-((dimethylamino)methyl)phenyl)
    ethyl)amino)-2-fluoro-N-(thiazol-2-yl)benzenesulfona-
    mide;
4-((2-((tert-butyl(methyl)amino)methyl)benzyl)amino)-2,6-
    difluoro-N-(thiazol-4-yl)benzenesulfonamide;
(R)-2,6-difluoro-4-((2-fluoro-6-(1-hydroxyethyl)benzyl)
    amino)-N-(thiazol-4-yl)benzenesulfonamide;
4-((2-((tert-butyl(methyl)amino)methyl)-6-fluorobenzyl)
    amino)-2,3-difluoro-N-(thiazol-4-yl)benzenesulfona-
    mide;
2,6-difluoro-4-((2-fluoro-6-((methyl(tert-pentyl)amino)
    methyl)benzyl)amino)-N-(thiazol-4-yl)benzenesulfona-
    mide;
4-((2-(((cyclopropylmethyl)(methyl)amino)methyl)-6-fluo-
    robenzyl)amino)-2,6-difluoro-N-(thiazol-4-yl)benzene-
    sulfonamide;
4-((2-((tert-butylamino)methyl)-6-fluorobenzyl)amino)-2,
    6-difluoro-N-(thiazol-4-yl)benzenesulfonamide;
4-((2-((cyclobutylamino)methyl)-6-fluorobenzyl)amino)-2,
    6-difluoro-N-(thiazol-4-yl)benzenesulfonamide;
2,6-difluoro-4-((2-fluoro-6-((isobutyl(methyl)amino)
    methyl)benzyl)amino)-N-(thiazol-4-yl)benzenesulfona-
    mide;
2,6-difluoro-4-((2-fluoro-6-(2-methylpyridin-4-yl)benzyl)
    amino)-N-(thiazol-4-yl)benzenesulfonamide;
4-((2-((cyclobutyl(methyl)amino)methyl)-6-fluorobenzyl)
    amino)-2,6-difluoro-N-(thiazol-4-yl)benzenesulfona-
    mide;
4-((2-((tert-butyl(methyl)amino)methyl)-6-fluorobenzyl)
    amino)-2,6-difluoro-N-(thiazol-4-yl)benzenesulfona-
    mide;
2,6-difluoro-4-((2-fluoro-6-((methyl(oxetan-3-yl)amino)
    methyl)benzyl)amino)-N-(thiazol-4-yl)benzenesulfona-
    mide;
2,6-difluoro-4-((2-fluoro-6-((isopropyl(methyl)amino)
    methyl)benzyl)amino)-N-(thiazol-4-yl)benzenesulfona-
    mide;
2,6-difluoro-4-((2-fluoro-6-((1-methylazetidin-3-yl)oxy)
    benzyl)amino)-N-(thiazol-4-yl)benzenesulfonamide;
4-((2-((diethylamino)methyl)-6-fluorobenzyl)amino)-2,6-
    difluoro-N-(thiazol-4-yl)benzenesulfonamide;
2,6-difluoro-4-((2-fluoro-6-((methyl((3-methyloxetan-3-yl)
    methyl)amino)methyl)benzyl)amino)-N-(thiazol-4-yl)
    benzenesulfonamide;
2,6-difluoro-4-((2-fluoro-6-(((2-methoxyethyl)(methyl)
    amino)methyl)benzyl)amino)-N-(thiazol-4-yl)benzene-
    sulfonamide;
4-((2-((dimethylamino)methyl)-6-fluorobenzyl)amino)-2,6-
    difluoro-N-(thiazol-4-yl)benzenesulfonamide;
5-chloro-2-fluoro-4-((2-fluoro-6-(methoxymethyl)benzyl)
    amino)-N-(thiazol-4-yl)benzenesulfonamide;
(S)-5-chloro-2-fluoro-4-((1-(2-fluoro-5-(oxetan-3-yl-
    methoxy)phenyl)ethyl)amino)-N-(thiazol-4-yl)benzene-
    sulfonamide;
5-chloro-4-((1-(2-((dimethylamino)methyl)phenyl)cyclo-
    propyl)amino)-2-fluoro-N-(thiazol-4-yl)benzenesulfona-
    mide;
(S)-5-chloro-4-((1-(5-(2,2-difluoroethyl)-2-fluorophenyl)
    ethyl)amino)-2-fluoro-N-(thiazol-4-yl)benzenesulfona-
    mide;
(S)-5-chloro-2-fluoro-4-((1-(2-fluoro-5-((3-methyloxetan-
    3-yl)methoxy)phenyl)ethyl)amino)-N-(thiazol-4-yl)ben-
    zenesulfonamide;
(S)-3-cyano-4-((1-(2-fluorophenyl)ethyl)amino)-N-(thi-
    azol-4-yl)benzenesulfonamide;
(S)-2,6-difluoro-4-((1-(2-fluoro-5-methoxyphenyl)ethyl)
    amino)-N-(thiazol-4-yl)benzenesulfonamide;
(S)-4-((1-(5-cyano-2-fluorophenyl)ethyl)amino)-2,6-dif-
    luoro-N-(thiazol-4-yl)benzenesulfonamide;
4-((2-((dimethylamino)methyl)benzyl)amino)-2,6-difluoro-
    N-(thiazol-4-yl)benzenesulfonamide;
(S)-4-((1-(2,5-difluorophenyl)ethyl)amino)-2,6-difluoro-N-
    (isoxazol-3-yl)benzenesulfonamide;
(S)-4-((1-(5-(difluoromethyl)-2-fluorophenyl)ethyl)amino)-
    2,6-difluoro-N-(thiazol-4-yl)benzenesulfonamide;
2,6-difluoro-4-((1-phenylcyclopropyl)amino)-N-(thiazol-4-
    yl)benzenesulfonamide;
(R)-5-chloro-4-((1-(3-((dimethylamino)methyl)phenyl)
    ethyl)amino)-2-fluoro-N-(thiazol-4-yl)benzenesulfona-
    mide;
(S)-5-chloro-2-fluoro-4-((1-(2-fluoro-5-hydroxyphenyl)
    ethyl)amino)-N-(thiazol-4-yl)benzenesulfonamide;
(S)-5-chloro-2-fluoro-4-((1-(2-fluoro-5-(oxetan-3-yloxy)
    phenyl)ethyl)amino)-N-(thiazol-4-yl)benzenesulfona-
    mide;
(S)-2,6-difluoro-4-((1-(2-fluoro-5-(methoxymethyl)phenyl)
    ethyl)amino)-N-(thiazol-4-yl)benzenesulfonamide;
5-chloro-4-((2,5-difluorobenzyl)amino)-2-fluoro-N-(thi-
    azol-4-yl)benzenesulfonamide;
(S)-5-chloro-2-fluoro-4-((1-(2-fluoro-5-(methoxymethyl)
    phenyl)ethyl)amino)-N-(thiazol-4-yl)benzenesulfona-
    mide;
(R)-5-chloro-4-((1-(2,5-difluorophenyl)-2,2-difluoroethyl)
    amino)-2-fluoro-N-(thiazol-4-yl)benzenesulfonamide;
5-chloro-4-((3,6-difluoro-2-(hydroxymethyl)benzyl)
    amino)-2-fluoro-N-(thiazol-4-yl)benzenesulfonamide;
5-chloro-4-((2-chloro-6-methylbenzyl)amino)-2-fluoro-N-
    (thiazol-4-yl)benzenesulfonamide;
5-chloro-4-((2-((dimethylamino)methyl)-6-fluorobenzyl)
    amino)-2-fluoro-N-(thiazol-4-yl)benzenesulfonamide;
(S)-5-chloro-4-((1-(5-cyano-2-fluorophenyl)ethyl)amino)-
    2-fluoro-N-(thiazol-4-yl)benzenesulfonamide;
(S)-5-chloro-4-((1-(3-((dimethylamino)methyl)phenyl)
    ethyl)amino)-2-fluoro-N-(thiazol-4-yl)benzenesulfona-
    mide;
(S)-5-chloro-4-((1-(5-(difluoromethoxy)-2-fluorophenyl)
    ethyl)amino)-2-fluoro-N-(thiazol-4-yl)benzenesulfona-
    mide;
(S)-3-chloro-4-((1-(2,6-difluorophenyl)ethyl)amino)-2-
    fluoro-N-(thiazol-4-yl)benzenesulfonamide;
5-chloro-2-fluoro-4-((5-fluoro-2-methylbenzyl)amino)-N-
    (thiazol-4-yl)benzenesulfonamide;
(S)-4-((1-(5-chloro-2-fluorophenyl)ethyl)amino)-2,6-dif-
    luoro-N-(thiazol-4-yl)benzenesulfonamide;
(S)-5-chloro-2-fluoro-4-((1-(2-fluoro-5-methoxyphenyl)
    ethyl)amino)-N-(thiazol-4-yl)benzenesulfonamide;
(S)-4-((1-(2,5-difluorophenyl)ethyl)amino)-5-ethyl-2-
    fluoro-N-(thiazol-4-yl)benzenesulfonamide;
5-chloro-4-((1-(2,5-difluorophenyl)cyclopropyl)amino)-2-
    fluoro-N-(thiazol-4-yl)benzenesulfonamide;

(S)-4-((1-(2,5-difluorophenyl)ethyl)amino)-N-(thiazol-4-yl)-3-(trifluoromethyl)benzenesulfonamide;
(S)-3-chloro-4-((1-(5-chloro-2-fluorophenyl)ethyl)amino)-2-fluoro-N-(thiazol-4-yl)benzenesulfonamide;
(S)-5-chloro-4-((1-(2-fluorophenyl)ethyl)amino)-2-methyl-N-(thiazol-2-yl)benzenesulfonamide;
(S)-5-chloro-2-fluoro-N-(thiazol-4-yl)-4-((1-(2,4,5-trifluorophenyl)ethyl)amino)benzenesulfonamide;
(S)-2,6-difluoro-4-((1-(2-fluorophenyl)ethyl)amino)-N-(thiazol-4-yl)benzenesulfonamide;
5-chloro-4-((1-(2,4-difluorophenyl)cyclopropyl)amino)-2-fluoro-N-(thiazol-4-yl)benzenesulfonamide;
(S)-5-chloro-4-((1-(5-cyclopropyl-2-fluorophenyl)ethyl)amino)-2-fluoro-N-(thiazol-4-yl)benzenesulfonamide;
(R)-5-chloro-2-fluoro-N-(thiazol-2-yl)-4-((2,2,2-trifluoro-1-(2-fluorophenyl)ethyl)amino)benzenesulfonamide;
(S)-5-chloro-4-((1-(3,5-difluorophenyl)ethyl)amino)-2-fluoro-N-(thiazol-4-yl)benzenesulfonamide;
(S)-5-chloro-4-((1-(2-chlorophenyl)propyl)amino)-2-fluoro-N-(thiazol-4-yl)benzenesulfonamide;
5-chloro-2-fluoro-4-((1-(2-fluorophenyl)cyclopropyl)amino)-N-(thiazol-2-yl)benzenesulfonamide;
(S)-5-chloro-4-((1-(2,5-difluorophenyl)ethyl)amino)-2-fluoro-N-(thiazol-4-yl)benzenesulfonamide;
(S)-5-chloro-4-((1-(2,5-difluorophenyl)ethyl)amino)-2-fluoro-N-(thiazol-2-yl)benzenesulfonamide;
(S)-5-chloro-N-(5-chlorothiazol-2-yl)-2-fluoro-4-((1-(2-fluorophenyl)ethyl)amino)benzenesulfonamide;
(S)-5-chloro-2-fluoro-4-((1-(2-fluorophenyl)ethyl)amino)-N-(5-fluorothiazol-2-yl)benzenesulfonamide;
(S)-5-chloro-2-fluoro-N-(5-fluorothiazol-2-yl)-4-((1-phenylpropyl)amino)benzenesulfonamide;
(S)-3-chloro-4-((1-(2-chloro-6-fluorophenyl)ethyl)amino)-2-fluoro-N-(thiazol-4-yl)benzenesulfonamide; and
(S)-5-chloro-4-((1-(2,5-difluorophenyl)ethyl)amino)-2-fluoro-N-(thiazol-4-yl)benzenesulfonamide.

Of the embodiment of compounds of formula (Ib2) wherein $R^2$ is selected from optionally substituted thiazolyl, optionally substituted thiadiazolyl, optionally substituted isoxazolyl, optionally substituted isothiazolyl or optionally substituted oxazolyl, as described above, another preferred embodiment are those compounds of formula (Ib2) wherein:

$R^1$ is aryl substituted with optionally substituted heterocyclylalkyl and optionally substituted by one or more substituents selected from halo, alkyl, haloalkyl, optionally substituted cycloalkyl, cyano, —$R^9$—$OR^{12}$, —$R^9$—N($R^8$)$R^{11}$, —$R^9$—N($R^{10}$)—$R^{13}$—$OR^{12}$, optionally substituted heterocyclyl and optionally substituted heteroaryl;
$R^2$ is optionally substituted thiazolyl; and
$R^{13}$ is a branched or straight alkylene chain.

Of this embodiment, preferred embodiments for optionally substituted heterocyclylalkyl are selected from pyrrolidinylalkyl, piperazinylalkyl, piperidinylalkyl, morpholinylalkyl, azetidinylalkyl, 3-azabicyclo[3.1.0]hexan-3-ylalkyl, 1-azaspiro[3.3]heptan-1-ylalkyl, 5-azaspiro[2.3]hexan-5-ylalkyl, 2-oxa-6-azaspiro[3.3]heptan-6-ylalkyl, 1-oxa-6-azaspiro[3.4]octan-6-ylalkyl, 1-oxa-6-azaspiro[3.3]heptan-6-ylalkyl, 6-oxa-1-azaspiro[3.3]heptan-1-ylalkyl, 6-azaspiro[3.4]octan-6-ylalkyl, 7-oxa-2-azaspiro[3.5]nonan-2-ylalkyl, 2,6-diazaspiro[3.3]heptan-2-ylalkyl, all of which can be optionally substituted with one or more substituents selected from alkyl, halo, haloalkyl, —$R^9$—$OR^{12}$, where $R^9$ and $R^{12}$ as defined in the Summary of the Invention.

Of these embodiments, preferred compounds of formula (Ib2) are selected from:
4-((2-(azetidin-1-ylmethyl)benzyl)amino)-5-chloro-2-fluoro-N-(thiazol-2-yl)benzenesulfonamide 2,2,2-trifluoroacetate;
4-((2-(azetidin-1-ylmethyl)benzyl)amino)-5-chloro-2-fluoro-N-(thiazol-4-yl)benzenesulfonamide 2,2,2-trifluoroacetate;
5-chloro-4-((2-((2,2-dimethylazetidin-1-yl)methyl)-6-fluorobenzyl)amino)-2-fluoro-N-(thiazol-4-yl)benzenesulfonamide;
4-((2-(2-azaspiro[3.3]heptan-2-yl)methyl)-6-fluorobenzyl)amino)-5-chloro-2-fluoro-N-(thiazol-4-yl)benzenesulfonamide;
4-((2-chloro-6-((3-fluoroazetidin-1-yl)methyl)benzyl)amino)-2,6-difluoro-N-(thiazol-4-yl)benzenesulfonamide;
2-fluoro-4-((2-fluoro-6-((3-fluoroazetidin-1-yl)methyl)benzyl)amino)-3-methyl-N-(thiazol-4-yl)benzenesulfonamide;
4-((2-(azetidin-1-ylmethyl)-4-fluorobenzyl)amino)-5-chloro-2-fluoro-N-(thiazol-4-yl)benzenesulfonamide;
3-chloro-2-fluoro-4-((2-fluoro-6-((3-fluoroazetidin-1-yl)methyl)benzyl)amino)-N-(thiazol-4-yl)benzenesulfonamide;
4-((2-(azetidin-1-ylmethyl)-3,6-difluorobenzyl)amino)-2,6-difluoro-N-(thiazol-4-yl)benzenesulfonamide;
4-((2-(azetidin-1-ylmethyl)-6-fluorobenzyl)amino)-5-chloro-2-fluoro-N-(thiazol-4-yl)benzenesulfonamide;
2-fluoro-4-((2-fluoro-6-((3-fluoroazetidin-1-yl)methyl)benzyl)amino)-5-methyl-N-(thiazol-4-yl)benzenesulfonamide; and
4-((2-((3-ethoxy-3-methylazetidin-1-yl)methyl)-6-fluorobenzyl)amino)-2,6-difluoro-N-(thiazol-4-yl)benzenesulfonamide;
(S)-4-((2-(1-(azetidin-1-yl)ethyl)-6-fluorobenzyl)amino)-2,6-difluoro-N-(thiazol-4-yl)benzenesulfonamide;
(R)-4-((2-(1-(azetidin-1-yl)ethyl)-6-fluorobenzyl)amino)-2,6-difluoro-N-(thiazol-4-yl)benzenesulfonamide;
4-((2-(azetidin-1-ylmethyl)benzyl)amino)-2,3-difluoro-6-methyl-N-(thiazol-4-yl)benzenesulfonamide;
4-((2-(azetidin-1-ylmethyl)-3,6-difluorobenzyl)amino)-2,3,6-trifluoro-N-(thiazol-4-yl)benzenesulfonamide;
2,6-difluoro-4-((2-fluoro-6-((3-hydroxy-3-(trifluoromethyl)azetidin-1-yl)methyl)benzyl)amino)-N-(thiazol-4-yl)benzenesulfonamide;
4-((2-chloro-6-((2,2-dimethylazetidin-1-yl)methyl)benzyl)amino)-2,6-difluoro-N-(thiazol-4-yl)benzenesulfonamide;
4-((2-((2,2-dimethylazetidin-1-yl)methyl)-3-fluorobenzyl)amino)-2,6-difluoro-N-(thiazol-4-yl)benzenesulfonamide;
4-((2-((3-azabicyclo[3.1.0]hexan-3-yl)methyl)-6-fluorobenzyl)amino)-2,6-difluoro-N-(thiazol-4-yl)benzenesulfonamide;
2,6-difluoro-4-((2-((3-(2-methoxypropan-2-yl)azetidin-1-yl)methyl)benzyl)amino)-N-(thiazol-4-yl)benzenesulfonamide;
4-((2-((1-azaspiro[3.3]heptan-1-yl)methyl)-6-fluorobenzyl)amino)-2,6-difluoro-N-(thiazol-4-yl)benzenesulfonamide;
4-((2-(azetidin-1-ylmethyl)-3,6-difluorobenzyl)amino)-2,3-difluoro-N-(thiazol-4-yl)benzenesulfonamide;
4-((2-(2-(3,3-difluoroazetidin-1-yl)ethyl)benzyl)amino)-2,6-difluoro-N-(thiazol-4-yl)benzenesulfonamide;
2,6-difluoro-4-((2-fluoro-6-((3-methoxy-3-methylazetidin-1-yl)methyl)benzyl)amino)-N-(thiazol-4-yl)benzenesulfonamide;

4-((2-((5-azaspiro[2.3]hexan-5-yl)methyl)-6-fluorobenzyl) amino)-2,6-difluoro-N-(thiazol-4-yl)benzenesulfonamide;

2,6-difluoro-4-((2-(2-(3-fluoroazetidin-1-yl)ethyl)benzyl) amino)-N-(thiazol-4-yl)benzenesulfonamide;

4-((2-((2,2-dimethylazetidin-1-yl)methyl)-6-fluorobenzyl) amino)-2-fluoro-3-methyl-N-(thiazol-4-yl)benzenesulfonamide;

4-((2-((3-(difluoromethyl)azetidin-1-yl)methyl)-6-fluorobenzyl)amino)-2,6-difluoro-N-(thiazol-4-yl)benzenesulfonamide;

2,6-difluoro-4-((2-fluoro-6-((3-fluoro-3-methylazetidin-1-yl)methyl)benzyl)amino)-N-(thiazol-4-yl)benzenesulfonamide;

4-((2-((2,2-dimethylazetidin-1-yl)methyl)benzyl)amino)-2,6-difluoro-3-methyl-N-(thiazol-4-yl)benzenesulfonamide;

4-((2-(azetidin-1-ylmethyl)-6-chloro-3-fluorobenzyl) amino)-2,6-difluoro-N-(thiazol-4-yl)benzenesulfonamide;

4-((2-(azetidin-1-ylmethyl)-6-cyclopropylbenzyl)amino)-2,6-difluoro-N-(thiazol-4-yl)benzenesulfonamide;

2,6-difluoro-4-((2-fluoro-6-((3-hydroxy-3-methylazetidin-1-yl)methyl)benzyl)amino)-N-(thiazol-4-yl)benzenesulfonamide;

4-((2-(azetidin-1-ylmethyl)-6-ethylbenzyl)amino)-2,6-difluoro-N-(thiazol-4-yl)benzenesulfonamide;

4-((2-(azetidin-1-ylmethyl)-6-methylbenzyl)amino)-2,6-difluoro-N-(thiazol-4-yl)benzenesulfonamide;

4-((2-(azetidin-1-ylmethyl)benzyl)amino)-2-fluoro-N-(thiazol-4-yl)-5-vinylbenzenesulfonamide;

2,6-difluoro-4-((2-fluoro-6-(pyrrolidin-1-ylmethyl)benzyl) amino)-N-(thiazol-4-yl)benzenesulfonamide;

4-((2-((2-oxa-6-azaspiro[3.3]heptan-6-yl)methyl)-6-fluorobenzyl)amino)-2,6-difluoro-N-(thiazol-4-yl)benzenesulfonamide;

(R)-2,6-difluoro-4-((2-fluoro-6-((2-(methoxymethyl)pyrrolidin-1-yl)methyl)benzyl)amino)-N-(thiazol-4-yl)benzenesulfonamide;

4-((2-((1-oxa-6-azaspiro[3.4]octan-6-yl)methyl)-6-fluorobenzyl)amino)-2,6-difluoro-N-(thiazol-4-yl)benzenesulfonamide;

4-((2-((1-oxa-6-azaspiro[3.3]heptan-6-yl)methyl)-6-fluorobenzyl)amino)-2,6-difluoro-N-(thiazol-4-yl)benzenesulfonamide;

4-((2-((6-oxa-1-azaspiro[3.3]heptan-1-yl)methyl)-6-fluorobenzyl)amino)-2,6-difluoro-N-(thiazol-4-yl)benzenesulfonamide;

(S)-2,6-difluoro-4-((2-fluoro-6-((2-methylpyrrolidin-1-yl) methyl)benzyl)amino)-N-(thiazol-4-yl)benzenesulfonamide;

4-((2-((6-azaspiro[3.4]octan-6-yl)methyl)-6-fluorobenzyl) amino)-2,6-difluoro-N-(thiazol-4-yl)benzenesulfonamide;

4-((2-((6,6-difluoro-2-azaspiro[3.3]heptan-2-yl)methyl)-6-fluorobenzyl)amino)-2,6-difluoro-N-(thiazol-4-yl)benzenesulfonamide;

4-((2-((1,1-difluoro-5-azaspiro[2.3]hexan-5-yl)methyl)-6-fluorobenzyl)amino)-2,6-difluoro-N-(thiazol-4-yl)benzenesulfonamide;

(R)-2,6-difluoro-4-((2-fluoro-6-((3-fluoropyrrolidin-1-yl) methyl)benzyl)amino)-N-(thiazol-4-yl)benzenesulfonamide;

(S)-2,6-difluoro-4-((2-fluoro-6-((3-fluoropyrrolidin-1-yl) methyl)benzyl)amino)-N-(thiazol-4-yl)benzenesulfonamide;

2,6-difluoro-4-((2-fluoro-6-((3-methoxyazetidin-1-yl) methyl)benzyl)amino)-N-(thiazol-4-yl)benzenesulfonamide;

2,6-difluoro-4-((2-fluoro-6-((3-methylazetidin-1-yl)methyl) benzyl)amino)-N-(thiazol-4-yl)benzenesulfonamide;

4-((2-((3,3-dimethylazetidin-1-yl)methyl)-6-fluorobenzyl) amino)-2,6-difluoro-N-(thiazol-4-yl)benzenesulfonamide;

2,6-difluoro-4-((2-fluoro-6-((4-methylpiperazin-1-yl) methyl)benzyl)amino)-N-(thiazol-4-yl)benzenesulfonamide;

5-chloro-2-fluoro-4-((2-fluoro-5-(2-(3-fluoroazetidin-1-yl) ethyl)benzyl)amino)-N-(thiazol-4-yl)benzenesulfonamide;

4-((2-(azetidin-1-ylmethyl)-3-fluorobenzyl)amino)-3-chloro-2,6-difluoro-N-(thiazol-4-yl)benzenesulfonamide;

4-((2-(azetidin-1-ylmethyl)-3-fluorobenzyl)amino)-2,6-difluoro-N-(thiazol-4-yl)benzenesulfonamide;

4-((5-(2-(azetidin-1-yl)ethyl)-2-fluorobenzyl)amino)-5-chloro-2-fluoro-N-(thiazol-4-yl)benzenesulfonamide;

4-((2-(azetidin-1-ylmethyl)-6-methoxybenzyl)amino)-2,6-difluoro-N-(thiazol-4-yl)benzenesulfonamide;

4-((5-(azetidin-1-ylmethyl)-2-fluorobenzyl)amino)-2,6-difluoro-N-(thiazol-4-yl)benzenesulfonamide;

4-((2-(2-(azetidin-1-yl)ethyl)benzyl)amino)-5-chloro-2-fluoro-N-(thiazol-4-yl)benzenesulfonamide;

(S)-4-((1-(5-(azetidin-1-ylmethyl)-2-fluorophenyl)ethyl) amino)-5-chloro-2-fluoro-N-(thiazol-4-yl)benzenesulfonamide;

(S)-5-chloro-2-fluoro-4-((1-(2-fluoro-5-(piperidin-1-ylmethyl)phenyl)ethyl)amino)-N-(thiazol-4-yl)benzenesulfonamide;

(S)-4-((1-(5-(2-(azetidin-1-yl)ethyl)-2-fluorophenyl)ethyl) amino)-5-chloro-2-fluoro-N-(thiazol-4-yl)benzenesulfonamide;

4-((2-((2-azaspiro[3.3]heptan-2-yl)methyl)-6-fluorobenzyl) amino)-2,6-difluoro-N-(thiazol-4-yl)benzenesulfonamide;

4-((2-(azetidin-1-ylmethyl)-6-fluorobenzyl)amino)-2,5-difluoro-N-(thiazol-4-yl)benzenesulfonamide;

4-((2-(azetidin-1-ylmethyl)-6-fluorobenzyl)amino)-3-chloro-2,6-difluoro-N-(thiazol-4-yl)benzenesulfonamide;

4-((2-(azetidin-1-ylmethyl)-6-fluorobenzyl)amino)-2,6-difluoro-3-methyl-N-(thiazol-4-yl)benzenesulfonamide;

4-((2-(azetidin-1-ylmethyl)-6-fluorobenzyl)amino)-2,6-difluoro-N-(thiazol-4-yl)benzenesulfonamide;

4-((2-((2,2-dimethylazetidin-1-yl)methyl)-6-fluorobenzyl) amino)-2,6-difluoro-N-(thiazol-4-yl)benzenesulfonamide;

4-((2-(azetidin-1-ylmethyl)benzyl)amino)-2,6-difluoro-N-(thiazol-4-yl)benzenesulfonamide;

5-chloro-4-((2-((4,4-difluoropiperidin-1-yl)methyl)-6-fluorobenzyl)amino)-2-fluoro-N-(thiazol-4-yl)benzenesulfonamide;

4-((2-((7-oxa-2-azaspiro[3.5]nonan-2-yl)methyl)-3,6-difluorobenzyl)amino)-5-chloro-2-fluoro-N-(thiazol-4-yl) benzenesulfonamide;

4-((2-(azetidin-1-ylmethyl)-3,6-difluorobenzyl)(methyl) amino)-2,6-difluoro-N-(thiazol-4-yl)benzenesulfonamide;

5-chloro-4-((2-chloro-6-((6-methyl-2,6-diazaspiro[3.3]heptan-2-yl)methyl)benzyl)amino)-2-fluoro-N-(thiazol-4-yl) benzenesulfonamide;

4-((2-((2,6-diazaspiro[3.3]heptan-2-yl)methyl)-6-chlorobenzyl)amino)-5-chloro-2-fluoro-N-(thiazol-4-yl)benzenesulfonamide;

5-chloro-2-fluoro-4-((2-fluoro-6-(morpholinomethyl)benzyl)amino)-N-(thiazol-4-yl)benzenesulfonamide;
4-((2-(azetidin-1-ylmethyl)-6-chlorobenzyl)amino)-2,6-difluoro-N-(thiazol-4-yl)benzenesulfonamide;
2,6-difluoro-4-((2-fluoro-6-((3-fluoroazetidin-1-yl)methyl)benzyl)amino)-N-(thiazol-4-yl)benzenesulfonamide;
5-chloro-2-fluoro-4-((2-fluoro-6-((3-methoxyazetidin-1-yl)methyl)benzyl)amino)-N-(thiazol-4-yl)benzenesulfonamide;
4-((2-((2-oxa-6-azaspiro[3.3]heptan-6-yl)methyl)-6-chlorobenzyl)amino)-2,6-difluoro-N-(thiazol-4-yl)benzenesulfonamide;
4-((2-(azetidin-1-ylmethyl)-4,5-difluorobenzyl)amino)-5-chloro-2-fluoro-N-(thiazol-4-yl)benzenesulfonamide;
4-((2-(azetidin-1-ylmethyl)-6-fluorobenzyl)amino)-3-chloro-2-fluoro-N-(thiazol-4-yl)benzenesulfonamide;
5-chloro-2-fluoro-4-((2-fluoro-6-((3-fluoroazetidin-1-yl)methyl)benzyl)amino)-N-(thiazol-4-yl)benzenesulfonamide;
4-((2-(azetidin-1-ylmethyl)-3,6-difluorobenzyl)amino)-5-chloro-2-fluoro-N-(thiazol-4-yl)benzenesulfonamide;
4-((2-(azetidin-1-ylmethyl)-6-chloro-3-fluorobenzyl)amino)-2,6-difluoro-3-methyl-N-(thiazol-4-yl)benzenesulfonamide 2,2,2-trifluoroacetate; and
4-((2-((3,3-dimethylazetidin-1-yl)methyl)-6-fluorobenzyl)amino)-2,3-difluoro-6-methyl-N-(thiazol-4-yl)benzenesulfonamide 2,2,2-trifluoroacetate.

Of the embodiment of compounds of formula (Ib2) wherein $R^2$ is selected from optionally substituted thiazolyl, optionally substituted thiadiazolyl, optionally substituted isoxazolyl, optionally substituted isothiazolyl or optionally substituted oxazolyl, a preferred embodiment is a compound of formula (Ib2) wherein:

$R^1$ is aryl optionally substituted by one or more substituents selected from halo, alkyl, haloalkyl, optionally substituted cycloalkyl, cyano, —$R^9$—$OR^{12}$, —$R^9$—$N(R^{10})R^{11}$, —$R^9$—$N(R^{10})$—$R^{13}$—$OR^{12}$, optionally substituted heterocyclyl, optionally substituted heterocyclylalkyl and optionally substituted heteroaryl;

$R^2$ is optionally substituted thiadiazolyl, optionally substituted isothiazolyl, optionally substituted oxazolyl, optionally substituted isoxazolyl; and $R^{13}$ is a branched or straight alkylene chain.

Of this embodiment, preferred embodiments for optionally substituted heterocyclylalkyl are selected from pyrrolidinylalkyl, piperazinylalkyl, piperidinylalkyl, morpholinylalkyl, azetidinylalkyl, 3-azabicyclo[3.1.0]hexan-3-ylalkyl, 1-azaspiro[3.3]heptan-1-ylalkyl, 5-azaspiro[2.3]hexan-5-ylalkyl, 2-oxa-6-azaspiro[3.3]heptan-6-ylalkyl, 1-oxa-6-azaspiro[3.4]octan-6-ylalkyl, 1-oxa-6-azaspiro[3.3]heptan-6-ylalkyl, 6-oxa-1-azaspiro[3.3]heptan-1-ylalkyl, 6-azaspiro[3.4]octan-6-ylalkyl, 7-oxa-2-azaspiro[3.5]nonan-2-ylalkyl, 2,6-diazaspiro[3.3]heptan-2-ylalkyl, all of which can be optionally substituted with one or more substituents selected from alkyl, halo, haloalkyl, —$R^9$—$OR^{12}$, where $R^9$ and $R^{12}$ as defined in the Summary of the Invention.

Of these embodiments, preferred compounds of formula (Ib2) are selected from:
3-chloro-4-(1-phenylpropylamino)-N-(1,2,4-thiadiazol-5-yl)benzenesulfonamide;
(R)-3-chloro-4-(1-phenylpropylamino)-N-(1,2,4-thiadiazol-5-yl)benzenesulfonamide;
(S)-3-chloro-4-(1-phenylpropylamino)-N-(1,2,4-thiadiazol-5-yl)benzenesulfonamide;
3-chloro-4-(1-phenylethylamino)-N-(1,2,4-thiadiazol-5-yl)benzenesulfonamide;
2,5-difluoro-4-(1-phenylpropylamino)-N-(1,2,4-thiadiazol-5-yl)benzenesulfonamide;
4-(benzylamino)-3-chloro-N-(1,2,4-thiadiazol-5-yl)benzenesulfonamide;
3-chloro-4-(2-phenylpropylamino)-N-(1,2,4-thiadiazol-5-yl)benzenesulfonamide;
2,6-difluoro-4-((2-fluoro-6-((3-fluoro-3-methylazetidin-1-yl)methyl)benzyl)amino)-N-(isoxazol-3-yl)benzenesulfonamide;
4-((2-(azetidin-1-ylmethyl)-6-fluorobenzyl)amino)-2-fluoro-N-(isoxazol-3-yl)-5-methylbenzenesulfonamide;
2,6-difluoro-4-((2-fluoro-6-((isopropyl(methyl)amino)methyl)benzyl)amino)-N-(isoxazol-3-yl)benzenesulfonamide;
2,3-difluoro-4-((2-fluoro-6-(pyrrolidin-1-ylmethyl)benzyl)amino)-N-(isoxazol-3-yl)benzenesulfonamide;
4-((2-(azetidin-1-ylmethyl)-6-fluorobenzyl)amino)-2,6-difluoro-N-(isothiazol-4-yl)benzenesulfonamide;
4-((2-(azetidin-1-ylmethyl)-3,6-difluorobenzyl)amino)-2,6-difluoro-N-(5-methylisoxazol-3-yl)benzenesulfonamide;
4-((2-((tert-butyl(methyl)amino)methyl)-6-fluorobenzyl)amino)-2,6-difluoro-N-(isothiazol-3-yl)benzenesulfonamide;
4-((2-(azetidin-1-ylmethyl)-6-fluorobenzyl)amino)-2,6-difluoro-N-(isothiazol-3-yl)benzenesulfonamide;
4-((2-(azetidin-1-ylmethyl)benzyl)amino)-2,6-difluoro-3-methyl-N-(1,2,4-thiadiazol-5-yl)benzenesulfonamide;
4-((2-(azetidin-1-ylmethyl)benzyl)amino)-3-chloro-2,6-difluoro-N-(1,2,4-thiadiazol-5-yl)benzenesulfonamide;
4-((2-(azetidin-1-ylmethyl)-6-fluorobenzyl)amino)-2,6-difluoro-N-(isoxazol-3-yl)benzenesulfonamide;
4-((2-(azetidin-1-ylmethyl)benzyl)amino)-2,6-difluoro-N-(isoxazol-3-yl)benzenesulfonamide;
4-((2-(azetidin-1-ylmethyl)benzyl)amino)-5-chloro-2-fluoro-N-(isoxazol-3-yl)benzenesulfonamide;
4-((2-(azetidin-1-ylmethyl)-6-fluorobenzyl)amino)-5-chloro-2-fluoro-N-(isoxazol-3-yl)benzenesulfonamide;
(S)-5-chloro-4-((1-(2,5-difluorophenyl)ethyl)amino)-2-fluoro-N-(oxazol-2-yl)benzenesulfonamide; and
4-((2-(azetidin-1-ylmethyl)-6-fluorobenzyl)amino)-2-fluoro-N-(isoxazol-3-yl)-3-methylbenzenesulfonamide 2,2,2-trifluoroacetate.

In another embodiment, a compound of formula (Ib2), as defined above, is a compound of formula (Ib2) wherein:
$R^1$ is an optionally substituted aryl; and
$R^2$ is an optionally substituted 6-membered N-heteroaryl.

Of this embodiment, a preferred embodiment are compounds of formula (Ib2) wherein $R^2$ is selected from optionally substituted pyridinyl, optionally substituted pyrimidinyl, optionally substituted pyridazinyl and optionally substituted pyrazinyl.

Of this embodiment, preferred compounds of formula (Ib2) are selected from:
5-chloro-2-fluoro-N-(6-fluoropyridin-2-yl)-4-(1-phenylpropylamino)benzenesulfonamide;
(S)-5-chloro-2-fluoro-4-((1-(2-fluorophenyl)ethyl)amino)-N-(6-fluoropyridin-2-yl)benzenesulfonamide;
(S)-5-chloro-4-((1-(2-chlorophenyl)ethyl)amino)-2-fluoro-N-(6-fluoropyridin-2-yl)benzenesulfonamide;
(S)-5-chloro-2-fluoro-N-(6-fluoropyridin-2-yl)-4-((1-phenyl-2-(pyrrolidin-1-yl)ethyl)amino)benzenesulfonamide 2,2,2-trifluoroacetate;
4-((2-(azetidin-1-ylmethyl)-3,6-difluorobenzyl)amino)-5-chloro-2-fluoro-N-(6-fluoropyridin-2-yl)benzenesulfonamide;

4-((2-(azetidin-1-ylmethyl)-6-fluorobenzyl)amino)-5-chloro-2-fluoro-N-(6-fluoropyridin-2-yl)benzenesulfonamide;
4-((2-(azetidin-1-ylmethyl)-6-fluorobenzyl)amino)-2,6-difluoro-N-(pyrimidin-2-yl)benzenesulfonamide;
4-((2-(azetidin-1-ylmethyl)-6-fluorobenzyl)amino)-2,6-difluoro-N-(5-fluoropyridin-2-yl)benzenesulfonamide;
4-((2-(azetidin-1-ylmethyl)-6-fluorobenzyl)amino)-2,6-difluoro-N-(pyridazin-3-yl)benzenesulfonamide;
4-((2-(azetidin-1-ylmethyl)benzyl)amino)-2,6-difluoro-N-(pyrimidin-4-yl)benzenesulfonamide;
4-((2-(azetidin-1-ylmethyl)benzyl)amino)-2,6-difluoro-3-methyl-N-(pyrimidin-4-yl)benzenesulfonamide;
4-((2-(azetidin-1-ylmethyl)benzyl)amino)-2-fluoro-N-(6-fluoropyridin-2-yl)-5-methylbenzenesulfonamide;
4-((2-(azetidin-1-ylmethyl)-6-fluorobenzyl)amino)-2,6-difluoro-N-(pyridin-2-yl)benzenesulfonamide;
4-((2-(azetidin-1-ylmethyl)-6-fluorobenzyl)amino)-2,6-difluoro-N-(6-fluoropyridin-2-yl)benzenesulfonamide;
4-((2-(azetidin-1-ylmethyl)-6-fluorobenzyl)amino)-2,6-difluoro-N-(6-fluoropyridin-2-yl)benzenesulfonamide;
4-((2-(azetidin-1-ylmethyl)-6-fluorobenzyl)amino)-5-chloro-2-fluoro-N-(pyridazin-3-yl)benzenesulfonamide;
(S)-5-chloro-4-((1-(2-chlorophenyl)ethyl)amino)-2-fluoro-N-(2-(trifluoromethyl)pyrimidin-4-yl)benzenesulfonamide;
(S)-5-chloro-4-((1-(2-chlorophenyl)ethyl)amino)-2-fluoro-N-(6-methylpyrimidin-4-yl)benzenesulfonamide;
(S)-5-chloro-4-((1-(5-chloro-2-fluorophenyl)ethyl)amino)-2-fluoro-N-(pyrazin-2-yl)benzenesulfonamide;
(R)-5-chloro-4-((1-(5-chloro-2-fluorophenyl)-2,2,2-trifluoroethyl)amino)-2-fluoro-N-(pyrimidin-4-yl)benzenesulfonamide;
(S)-4-((1-(2,5-difluorophenyl)ethyl)amino)-2,6-difluoro-N-(pyrimidin-4-yl)benzenesulfonamide;
(S)-4-((1-(2-chloro-5-fluorophenyl)propyl)amino)-2,6-difluoro-N-(pyrimidin-4-yl)benzenesulfonamide;
(S)-4-((1-(5-chloro-2-fluorophenyl)ethyl)amino)-2,6-difluoro-N-(pyrimidin-4-yl)benzenesulfonamide;
5-chloro-2-fluoro-4-((1-(2-fluorophenyl)cyclopropyl)amino)-N-(pyrimidin-4-yl)benzenesulfonamide;
5-chloro-4-((1-(2,5-difluorophenyl)cyclopropyl)amino)-2-fluoro-N-(pyrimidin-4-yl)benzenesulfonamide;
(S)-3-chloro-4-((1-(2-chlorophenyl)ethyl)amino)-2-fluoro-N-(pyrimidin-4-yl)benzenesulfonamide;
(S)-4-((1-(5-chloro-2-fluorophenyl)ethyl)amino)-2-fluoro-5-methyl-N-(pyrimidin-4-yl)benzenesulfonamide;
(S)-4-((1-(2,5-difluorophenyl)ethyl)amino)-N-(pyrimidin-4-yl)-3-(trifluoromethyl)benzenesulfonamide;
4-((2-(azetidin-1-ylmethyl)benzyl)amino)-5-chloro-2-fluoro-N-(6-fluoropyridin-2-yl)benzenesulfonamide;
(S)-5-chloro-4-((1-(2-chlorophenyl)propyl)amino)-2-fluoro-N-(pyrimidin-4-yl)benzenesulfonamide; and
(S)-5-chloro-2-fluoro-4-((1-(2-fluorophenyl)propyl)amino)-N-(6-fluoropyridin-2-yl)benzenesulfonamide.

In another embodiment, a compound of formula (Ib2), as defined above, is a compound of formula (Ib2) wherein R¹ is an optionally substituted monocyclic heteroaryl or an optionally substituted bicyclic heteroaryl.

Of this embodiment, preferred compounds of formula (Ib2) are selected from:
5-chloro-2-fluoro-N-(6-fluoropyridin-2-yl)-4-((isoquinolin-8-ylmethyl)amino)benzenesulfonamide;
(S)-5-chloro-2-fluoro-4-((1-(isoquinolin-8-yl)ethyl)amino)-N-(thiazol-2-yl)benzenesulfonamide;
(R)-5-chloro-2-fluoro-4-((1-(isoquinolin-8-yl)ethyl)amino)-N-(thiazol-2-yl)benzenesulfonamide;
5-chloro-2-fluoro-4-(isoquinolin-8-ylmethylamino)-N-(thiazol-2-yl)benzenesulfonamide;
5-chloro-2-fluoro-4-((1-(pyridin-3-yl)propan-2-yl)amino)-N-(thiazol-2-yl)benzenesulfonamide;
5-chloro-2-fluoro-4-((1-(pyridin-3-yl)propyl)amino)-N-(thiazol-2-yl)benzenesulfonamide;
5-chloro-2-fluoro-4-((1-(pyridin-4-yl)propyl)amino)-N-(thiazol-2-yl)benzenesulfonamide;
3-chloro-4-((1-(pyridin-2-yl)propyl)amino)-N-(thiazol-2-yl)benzenesulfonamide;
(S)-3-chloro-4-((1-(pyridin-2-yl)ethyl)amino)-N-(thiazol-2-yl)benzenesulfonamide;
3-chloro-4-((1-(1-methyl-1H-pyrazol-4-yl)ethyl)amino)-N-(thiazol-2-yl)benzenesulfonamide;
5-chloro-2-fluoro-4-((isoquinolin-8-ylmethyl)amino)-N-(thiazol-4-yl)benzenesulfonamide 2,2,2-trifluoroacetate;
(R)-5-chloro-2-fluoro-4-((1-(pyridin-3-yl)ethyl)amino)-N-(thiazol-2-yl)benzenesulfonamide formic acid salt;
5-chloro-2-fluoro-4-(((6-fluoro-1H-indol-7-yl)methyl)amino)-N-(thiazol-4-yl)benzenesulfonamide; and
5-chloro-2-fluoro-4-(((6-fluoro-1H-indazol-7-yl)methyl)amino)-N-(thiazol-4-yl)benzenesulfonamide.

In another embodiment, a compound of formula (I) is a compound of formula (I) wherein R³ is —S(O)$_t$— (where t is 0, 1 or 2), wherein the compound has the following formula (Ic):

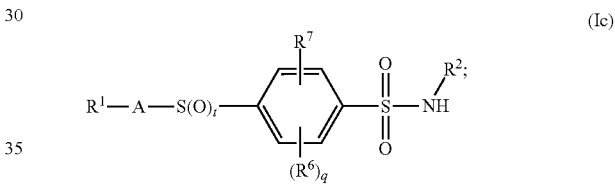

(Ic)

wherein q, t, A, R¹, R², R⁶ and R⁷ are each as defined above in claim 1;
as an individual stereoisomer, enantiomer or tautomer thereof or mixtures thereof;
or a pharmaceutically acceptable salt, solvate or prodrug thereof.

In another embodiment, a compound of formula (I) is a compound of formula (Ic), as defined above, wherein A is a direct bond, i.e., a compound of formula (Ic1):

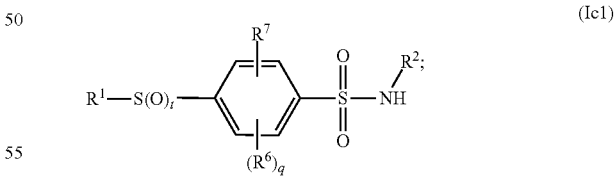

(Ic1)

wherein q, t, R¹, R², R⁶ and R⁷ are each as defined above in claim 1;
as an individual stereoisomer, enantiomer or tautomer thereof or mixtures thereof;
or a pharmaceutically acceptable salt, solvate or prodrug thereof.

In another embodiment, a compound of formula (I) is a compound of formula (Ic), as defined above, wherein A is —(CH$_2$)$_m$—C(R⁴)(R⁵)—(CH$_2$)$_n$—, i.e., a compound of formula (Ic2):

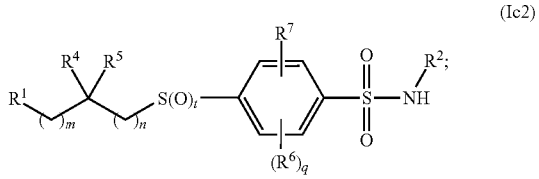

wherein m, n, t, $R^1$, $R^2$, $R^4$, $R^5$, $R^6$ and $R^7$ are each as defined above in claim 1; as an individual stereoisomer, enantiomer or tautomer thereof or mixtures thereof; or a pharmaceutically acceptable salt, solvate or prodrug thereof.

Of this embodiment, a preferred compound of formula (Ic2) is (S)-5-chloro-2-fluoro-4-((1-phenylethyl)thio)-N-(thiazol-2-yl)benzenesulfonamide.

Another embodiment of the invention are compounds of formula (I) wherein $R^7$ is in the ortho position relative to $R^3$.

Another embodiment of the invention are compounds of formula (I) wherein $R^7$ is in the ortho position relative to $R^3$ and is halo.

Another embodiment of the invention are compounds of formula (I) wherein $R^7$ is chloro or fluoro.

Another embodiment of the invention is a method of using the compounds of formula (I) as standards or controls in in vitro or in vivo assays in determining the efficacy of test compounds in modulating voltage-dependent sodium channels.

It is understood that any embodiment of the compounds of the invention, as set forth above, and any specific substituent set forth herein for a particular A, q, t, $R^1$, $R^2$, $R^3$, $R^4$, $R^5$, $R^6$, $R^7$, $R^8$, $R^9$, $R^{10}$, $R^{11}$ and $R^{12}$ group in the compounds of the invention, as set forth above, may be independently combined with other embodiments and/or substituents of compounds of the invention to form embodiments of the inventions not specifically set forth above. In addition, in the event that a list of substituents is disclosed for any particular A, q, t, $R^1$, $R^2$, $R^3$, $R^4$, $R^5$, $R^6$, $R^7$, $R^8$, $R^9$, $R^{10}$, $R^{11}$ and $R^{12}$ group in a particular embodiment and/or claim, it is understood that one or more substituents may be deleted from the list and that the remaining list of substituents will be considered to be an embodiment of the invention.

It is also understood that the proviso set forth above in the Summary of the Invention for the compounds of formula (I) applies to all of the relevant embodiments of the compounds of formula (I) as described above.

Another aspect of the invention is a pharmaceutical composition comprising a pharmaceutically acceptable excipient and a compound of the invention, as described above, as a stereoisomer, enantiomer or tautomer thereof or a mixture thereof; or a pharmaceutically acceptable salt, solvate or prodrug thereof.

Another aspect of the invention is a method of treating a disease or a condition associated with $Na_V1.6$ activity in a mammal wherein the disease or condition is epilepsy and/or epileptic seizure disorder and wherein the method comprises administering to the mammal in need thereof a therapeutically effective amount of a compound of the invention, as described above, as a stereoisomer, enantiomer or tautomer thereof or a mixture thereof; or a pharmaceutically acceptable salt, solvate or prodrug thereof.

In one embodiment of this aspect, the epilepsy or epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

In one embodiment of this embodiment, the epilepsy or epileptic seizure disorder is selected from Dravet syndrome, infantile spasms/West's syndrome, temporal lobe epilepsy, Lennox-Gastaut syndrome (LGS), generalized epilepsy with febrile seizures+ and early infantile epileptic encephalopathy.

Another aspect of the invention is a method of decreasing ion flux through $Na_V1.6$ in a mammalian cell, wherein the method comprises contacting the cell with a compound of the invention, as described above, as a stereoisomer, enantiomer or tautomer thereof or a mixture thereof; or a pharmaceutically acceptable salt, solvate or prodrug thereof.

Another aspect of the invention is a method of selectively inhibiting a first voltage-gated sodium channel over a second voltage-gated sodium channel in a mammal, wherein the method comprises administering to the mammal a modulating amount of a compound of the invention, as described above, as a stereoisomer, enantiomer or tautomer thereof or a mixture thereof; or a pharmaceutically acceptable salt, solvate or prodrug thereof.

In one embodiment of this aspect, the first voltage-gated sodium channel is $Na_V1.6$.

In another embodiment of this aspect, the first voltage-gated sodium channel is $Na_V1.6$ and the second voltage-gated sodium channel is $Na_V1.5$.

In another embodiment of this aspect, the first voltage-gated sodium channel is $Na_V1.6$ and the second voltage-gated sodium channel is $Na_V1.1$.

Specific embodiments of the compounds of the invention are described in more detail below in the Preparation of the Compounds of the Invention and in the Examples.

Utility and Testing of the Compounds of the Invention

The compounds of the invention modulate, preferably inhibit, ion flux through a voltage-dependent sodium channel, preferably $Na_V1.6$, in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a voltage-gated sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel, preferably $Na_V1.6$. The compounds of the invention are state or frequency dependent modifiers of the sodium channel, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestéle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are voltage-gated sodium channel inhibitors, preferably $Na_V1.6$ inhibitors, and are therefore useful for treating diseases and conditions, preferably epilepsy and/or epileptic seizure disorder, in mammals, preferably humans, and other organisms, including all those human diseases and conditions which are the result of aberrant voltage-dependent sodium channel biological activity, preferably aberrant $Na_V1.6$ activity, or which may be ameliorated by modulation of voltage-dependent sodium channel biological activity. In particular, the compounds of the invention, i.e., the compounds of formula (I), as set forth above in the Summary of the Invention, as individual stereoisomers, enantiomers or tautomers thereof or mixtures thereof; or as pharmaceutically acceptable salts, solvates or prodrugs thereof, are useful for treating diseases and conditions in mammals, preferably humans, which are the result of aberrant voltage-dependent $Na_V1.6$ biological activity or which may be ameliorated by the modulation, preferably the inhibition, of $Na_V1.6$ biological activity. Preferably the compounds of the invention selectively inhibit $Na_V1.6$ over $Na_V1.5$ and/or $Na_V1.1$.

As defined herein, a disease, disorder or condition associated with $Na_V1.6$ activity includes, but is not limited to, epilepsy and/or epileptic seizure disorder. Such epilepsy and/or epileptic seizure disorders include, but are not limited to, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

The present invention therefore relates to compounds, pharmaceutical compositions and methods of using the compounds and pharmaceutical compositions for the treatment of diseases or conditions associated by the activity of $Na_V1.6$ in a mammal, preferably a human, by administering to the mammal, preferably the human, in need of such treatment an effective amount of a compound of the invention or an pharmaceutical composition comprising a compound of the invention.

The general value of the compounds of the invention in inhibiting the $Na_V1.6$ ion flux can be determined using the assays described below in the Biological Assays section. Alternatively, the general value of the compounds in treating conditions and diseases in humans may be established in industry standard animal models for demonstrating the efficacy of compounds in treating epilepsy and/or epileptic seizure disorder. Animal models of human epileptic conditions have been developed that result in reproducible sensory deficits over a sustained period of time that can be evaluated by sensory testing.

For example, many rodent models have been developed to assess the propensity for seizures or epileptiform activity (Klein, B. R. et al., (2016), "Models Currently in Active Use. In: Epilepsy Therapy Screening Program", Vol. 2016, National Institute of Neurological Disorders and Stroke). These include acute chemical or electrical insults that induce seizures, as well as chronic chemical or genetic insults that create seizure prone animals. These models can be used to determine the relative ability of a compound to promote or prevent seizure activity. The maximal electroshock seizure (MES) assay and the 6 hertz psychomotor seizure test (6 Hz) are two examples of acute insult seizure assays used to evaluate anticonvulsive interventions (Suzuki, F. et al., *Neuroscience* (1995), Vo. 64, pp. 665-674; Barton, M. E. et al., *Epilepsy Research* (2001), Vol. 47, pp. 217-227). Both assays involve an electrical insult applied with electrodes placed on the corneas or ears in order to provoke an acute seizure. Acute seizures may also be induced chemically, for instance by administration of the proconvulsant ether compound flurothyl (Makinson, C. D. et al., *Exp. Neurol.* (2016), Vol. 275, Pt 1, pp. 46-58).

Genetic epilepsies have been linked to many distinct genes, including multiple voltage gated sodium channel genes. Genetically modified mice can be created that harbor mutations identified in human patients. In some cases these genetic modifications result in animals that behave much like the human patients in whom the genetic variations were initially identified. Mutant mice can be used to test anticonvulsant interventions. Such experiments can involve prevention of spontaneous seizures, or may make use of similar seizure provoking stimuli as those employed in wild type mice. Animal models of early infantile epileptic encephalopathy 6 (EIEE6), also known as severe myoclonic epilepsy of infancy or Dravet syndrome, have been created by mutating the SCN1A gene that encodes the $Na_V1.1$ voltage gated sodium channel (Yu, F. H. et al., *Nat. Neurosci.* (2006), Vol. 9, pp. 1142-1149). Models of EIEE13 have likewise been created by mutating the SCN6A gene that encodes the $Na_V1.6$ voltage gated sodium channel (Wagnon, J. L. et al., Human Molecular Genetics(2014)). Both of these mouse strains provide the opportunity to evaluate potential therapeutic interventions that might prove useful in clinical patient populations (Martin, M. S. et al., *J. Biol. Chem.* (2010), Vol. 285, pp. 9823-9834; and Martin, M. S. et al., *Human Molecular Genetics* (2007), Vol. 16, pp. 2892-2899).

The present invention readily affords many different means for identification of $Na_V1.6$ inhibitory agents that are useful as therapeutic agents. Identification of $Na_V1.6$ inhibitors can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc., Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they are useful in treating the disease or condition associated with the activity of the sodium channel of interest, preferably $Na_V1.6$, with minimal adverse events. The assays described below in the Biological Assays Section are useful in assessing the biological activity of the instant compounds.

Typically, the efficacy of a compound of the invention is expressed by its $IC_{50}$ value ("Inhibitory Concentration—50%"), which is the measure of the amount of compound required to achieve 50% inhibition of the activity of the target sodium channel over a specific time period. For example, representative compounds of the present invention have demonstrated $IC_{50}$'s ranging from less than 100 nanomolar to less than 10 micromolar in the patch voltage clamp $Na_V1.6$ electrophysiology assay described herein.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_V1.6$ activity in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.6$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of diseases or conditions associated with voltage-gated sodium channel activity, preferably $Na_V1.6$ activity, in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as epilepsy and/or epileptic seizure disorder, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., *The Merck Manual*, 19$^{th}$ edition, Merck and Co., Rahway, N.J., 2011; Brunton et al. eds., *Goodman and Cilman's The Pharmacological Basis of Therapeutics*, 12$^{th}$ edition, McGraw-Hill 2011; Avery's Drug Treatment: Principles and Practice of Clinical Pharmacology and Therapeutics, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, current edition, Mack Publishing Co., Easton, Pa.; Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats and hamsters), Lagamorpha (including rabbits) and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intraocular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of diseases and conditions associated with voltage-gated sodium channel activity. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetaminophen, salicylates (e.g., aspirin);

nonsteroidal anti-inflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, Ianepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuprorion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;
5-HT$_3$ antagonists such as ondansetron;
metabotropic glutamate receptor (mGluR) antagonists;
local anaesthetic such as mexiletine and lidocaine;
corticosteroid such as dexamethasone;
antiarrhythimics, e.g., mexiletine and phenytoin;
muscarinic antagonists, e.g., tolterodine, propiverine, tropsium chloride, darifenacin, solifenacin, temiverine and ipratropium;
cannabinoids;
vanilloid receptor agonists (e.g., resinferatoxin) or antagonists (e.g., capsazepine);
sedatives, e.g., glutethimide, meprobamate, methaqualone, and dichloralphenazone;
anxiolytics such as benzodiazepines,
antidepressants such as mirtazapine,
topical agents (e.g., lidocaine, capsacin and resiniferotoxin);
muscle relaxants such as benzodiazepines, baclofen, carisoprodol, chlorzoxazone, cyclobenzaprine, methocarbamol and orphrenadine;
anti-histamines or H1 antagonists;
NMDA receptor antagonists;
5-HT receptor agonists/antagonists;
PDEV inhibitors;
Tramadol®;
cholinergic (nicotinic) analgesics;
alpha-2-delta ligands;
prostaglandin E2 subtype antagonists;
leukotriene B4 antagonists;
5-lipoxygenase inhibitors; and
5-HT$_3$ antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for inhibiting the activity of voltage-gated sodium channels, preferably Na$_V$1.6, for the treatment of epilepsy, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I), as individual stereoisomers, enantiomers or tautomers thereof or mixtures thereof; or as pharmaceutically acceptable salts, solvates or prodrugs thereof It is also understood that one skilled in the art would be able to make the compounds of the invention by similar methods or by methods known to one skilled in the art. It is also understood that one skilled in the art would be able to make in a similar manner as described below other compounds of the invention not specifically illustrated below by using the appropriate starting components and modifying the parameters of the synthesis as needed. It is also understood that simple functional group transformations (see, e.g., Larock, R. C. *Comprehensive Organic Transformations*, 2$^{nd}$ edition (Wiley, 1999) can be effected by methods known to one skilled in the art. In general, starting components may be obtained from sources such as Sigma Aldrich, Combi-Blocks, Oakwood Chemicals, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The compounds of formula (I) may contain at least one asymmetric carbon atom and thus can exist as racemates, enantiomers and/or diastereoisomers. Specific enantiomers or diastereoisomers may be prepared by utilizing the appropriate chiral starting material. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

Preparation of Compounds of Formula (I)

In general, compounds of formula (I), as described above in the Summary of the Invention, can be synthesized following the general procedure described below in Reaction Scheme 1 where q, A, $R^1$, $R^2$, $R^3$, $R^6$ and $R^7$ are as described above in the Summary of the Invention for compounds of formula (I), X is bromo, chloro, or fluoro and $Z^1$ is hydrogen or a nitrogen protecting group, for example, but not limited to, tert-butyloxycarbonyl, 2,4-dimethoxybenzyl, or 4-methoxybenzyl:

REACTION SCHEME 1

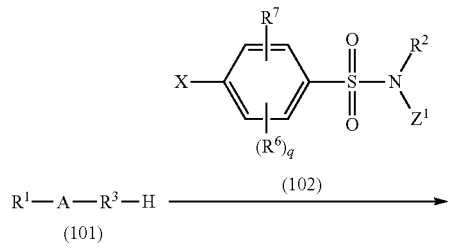

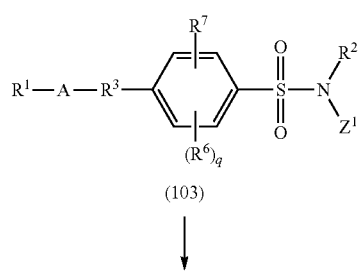

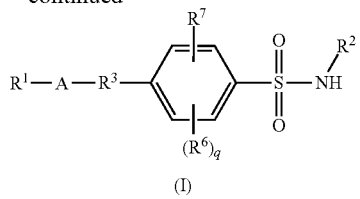

Compounds of formulae (101), (102) and (103) are commercially available or can be prepared according to methods known to one skilled in the art or by methods disclosed herein. In general, the compounds of formula (I) are prepared as described above in Reaction Scheme 1 as follows:

The compound of formula (101) is reacted with sulfonamide (102) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate, sodium hydride or N,N-diisopropylethylamine, at a temperature of between about 0° C. and 80° C., for about 1 to 48 hours to afford a compound of formula (103). The compound of formula (103) is then treated with an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Alternatively, compounds of formula (I), as described above in the Summary of the Invention, can be synthesized following the general procedure described below in Reaction Scheme 2 where q, A, $R^1$, $R^2$, $R^3$, $R^6$ and $R^7$ are as described above in the Summary of the Invention for compounds of formula (I), X is bromo, chloro, or iodo, and $Z^1$ is hydrogen or a nitrogen protecting group, for example, but not limited to, tert-butyloxycarbonyl, 2,4-dimethoxybenzyl, or 4-methoxybenzyl:

REACTION SCHEME 2

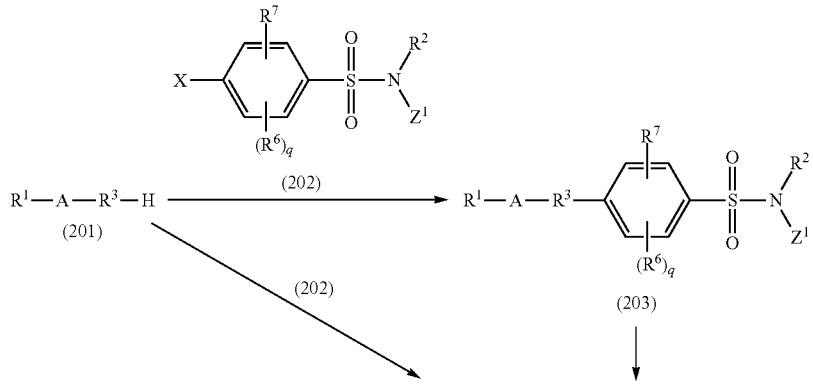

-continued

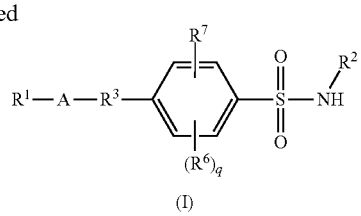
(I)

Compounds of formulae (201), (202) and (203) are commercially available or can be prepared according to methods known to one skilled in the art or by methods disclosed herein. In general, the compounds of formula (I) are prepared as described above in Reaction Scheme 2 as follows:

The compound of formula (201) is reacted with sulfonamide (202) under standard Buchwald-Hartwig cross coupling conditions, such as, but not limited to, the use of a solvent, such as, but not limited to, toluene, in the presence of a base, such as, but not limited to, sodium tert-butoxide, and in the presence of a palladium catalyst composed of, for example, but not limited to, 2-di-tert-butylphosphino-2',4',6'-triisopropylbiphenyl and bis(dibenzylideneacetone)palladium(0), at a temperature of between about ambient temperature and 150° C., for about 30 minutes to 72 hours to generate a compound of formula (203). The compound of formula (203) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Under certain conditions, the above transformation of the compound of formula (201) will afford a compound of formula (I) instead of a compound of formula (303). In this instance, the compound of formula (I) can be isolated from the reaction mixture by standard techniques.

Alternatively, compounds of formula (I), as described above in the Summary of the Invention, can be synthesized following the general procedure described below in Reaction Scheme 3 where q, A, $R^1$, $R^2$, $R^3$, $R^6$ are as described above in the Summary of the Invention for compounds of formula (I), X is bromo, chloro, or iodo, $R^{7b}$ is alkyl, alkenyl, haloalkyl, or cyano, and $Z^1$ is hydrogen or a nitrogen protecting group, for example, but not limited to, tert-butyloxycarbonyl, 2,4-dimethoxybenzyl, or 4-methoxybenzyl:

REACTION SCHEME 3

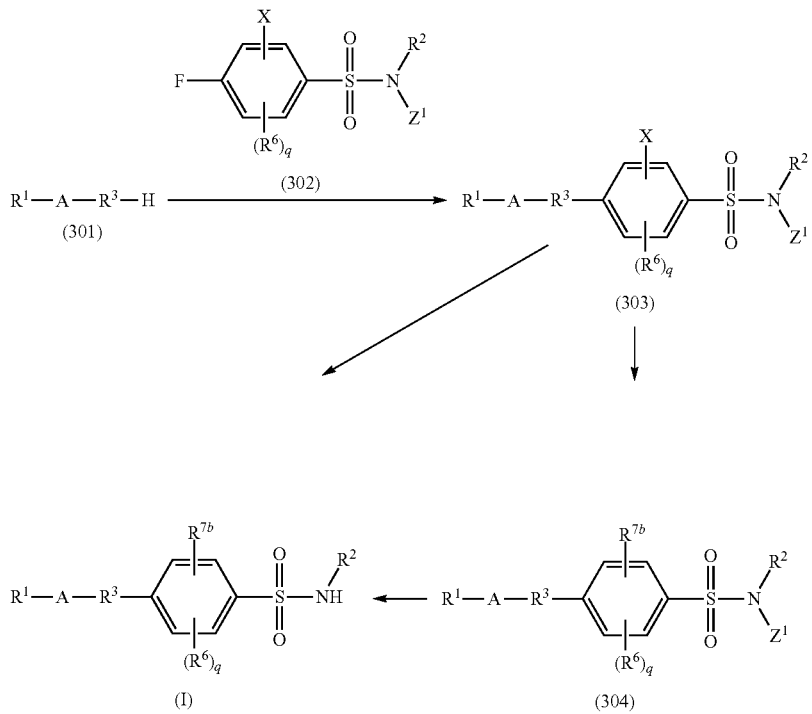

Compound of formulae (301) can be prepared according to methods known to one skilled in the art or by methods disclosed herein. In general, the compounds of formula (I) are prepared as described above in Reaction Scheme 3 as follows:

The compound of formula (301) is reacted with sulfonamide (302) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate, sodium hydride or N,N-diisopropylethylamine, at a temperature of between about 0° C. and 80° C., for about 1 to 48 hours to afford a compound of formula (303). The compound of formula (303) is reacted with a boronic acid derivative such as, but not limited to, $R^{7b}$—B(OH)$_2$ or $R^{7b}$—BF$_3$K, under standard Suzuki-Miyaura cross coupling conditions, such as, but not limited to, the use of a solvent, such as, but not limited to, 1,4-dioxane, in the presence of a base, such as, but not limited to, aqueous sodium carbonate, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to generate a compound of formula (304).

Alternatively, a compound of formula (303) can be treated with a reducing agent, such as, but not limited to, sodium formate, in the presence of a palladium catalyst composed of for example, but not limited to, tris(dibenzylideneacetone)dipalladium(0) and tri-tert-butylphosphine, in a polar solvent such as, but not limited to, dimethyl sulfoxide, at a temperature of between about ambient temperature and 120° C., for about 1 to 20 hours to afford a compound of formula (304).

Alternatively, a compound of formula (303) can be treated with a reducing agent, such as, but not limited to, hydrogen, in the presence of a palladium catalyst for example, but not limited to, palladium on carbon, in a polar solvent such as, but not limited to, methanol, in the presence of a base, such as, but not limited to, trimethylamine, at a temperature of between about ambient temperature and 120° C., for about 1 to 20 hours to afford a compound of formula (304).

The compound of formula (304) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Under certain conditions, the above transformations of the compound of formula (303) will afford a compound of formula (I) instead of a compound of formula (304). In these instances, the compound of formula (I) can be isolated from the reaction mixture by standard techniques.

Alternatively, compounds of formula (I), as described above in the Summary of the Invention, can be synthesized following the general procedure described below in Reaction Scheme 4 where q, A, $A^1$, $R^2$, $R^3$, $R^6$ and $R^7$ are as described above in the Summary of the Invention for compounds of formula (I) and X is fluoro, Y is oxygen or sulfur and $Z^1$ is hydrogen or a nitrogen protecting group, for example, but not limited to, tert-butyloxycarbonyl or 2,4-dimethoxybenzyl:

REACTION SCHEME 4

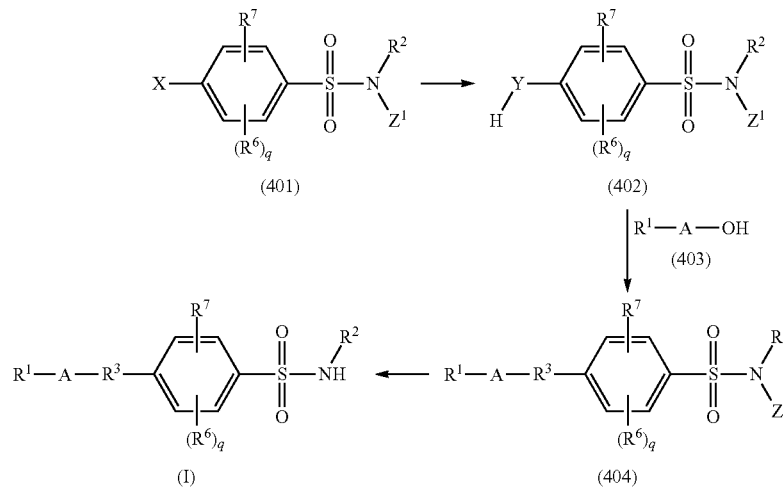

Compounds of formulae (401), (402) and (203) are commercially available or can be prepared according to methods known to one skilled in the art or by methods disclosed herein. In general, the compounds of formula (I) are prepared as described above in Reaction Scheme 4 as follows:

The sulfonamide of formula (401) is reacted under standard reaction conditions, such as, but not limited to, the use of a polar aprotic solvent, such as, but not limited to, dimethyl sulfoxide or N,N-dimethylformamide, in the presence of a nucleophile, such as, but not limited to, sodium sulfide, sodium hydroxide or sodium benzoate at a temperature of between about 0° C. and 80° C., for about 1 to 48 hours to afford a compound of formula (402). The compound of formula (402) is then reacted with the alcohol of formula (403) under Mitsunobu reaction conditions, such as, but not limited to, the use of a solvent, such as, but not limited to, diethyl ether, in the presence of a phosphine reagent, such as, but not limited to, triphenylphosphine, and in the presence of an azodicarboxylate reagent, such as, but not limited to, diisopropylazodicarboxylate, at a temperature of between about 0° C. and 80° C., for about 1 to 48 hours to afford a compound of formula (403). The compound of formula (404) is then treated with an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Alternatively, compounds of formula (Ib), as described above in the Summary of the Invention, can be synthesized following the general procedure described below in Reaction Scheme 5 where q, A, $R^1$, $R^2$, $R^6$, $R^7$ and $R^8$ are as described above in the Summary of the Invention for compounds of formula (Ib), $Z^1$ is hydrogen or a nitrogen protecting group, for example, but not limited to, tert-butyloxycarbonyl, 2,4-dimethoxybenzyl, or 4-methoxybenzyl, and $Z^2$ is hydrogen or a nitrogen protecting group, for example, but not limited to, tert-butyloxycarbonyl:

REACTION SCHEME 5

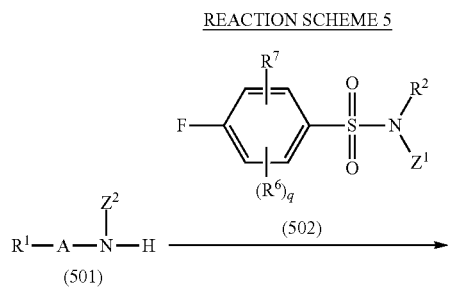

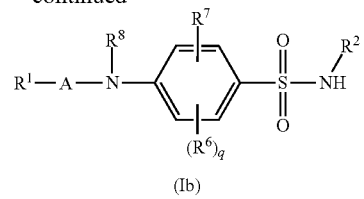

Compounds of formulae (501), (502) and (503) are commercially available or can be prepared according to methods known to one skilled in the art or by methods disclosed herein. In general, the compounds of formula (Ib) are prepared as described above in Reaction Scheme 5 as follows:

The compound of formula (501) is reacted with sulfonamide (502) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate, sodium hydride or N,N-diisopropylethylamine, at a temperature of between about 0° C. and 80° C., for about 1 to 48 hours to afford a compound of formula (503). The compound of formula (103) is then treated with an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Alternatively, compounds of formula (Ib), as described above in the Summary of the Invention, can be synthesized following the general procedure described below in Reaction Scheme 6 where q, A, $R^1$, $R^2$ and $R^6$ are as described above in the Summary of the Invention for compounds of formula (I), X is bromo, chloro, or iodo, $R^{7b}$ is alkyl, alkenyl, haloalkyl, or cyano, $Z^1$ is hydrogen or a nitrogen protecting group, for example, but not limited to, tert-butyloxycarbonyl, 2,4-dimethoxybenzyl, or 4-methoxybenzyl, and $Z^2$ is hydrogen or a nitrogen protecting group, for example, but not limited to, tert-butyloxycarbonyl:

REACTION SCHEME 6

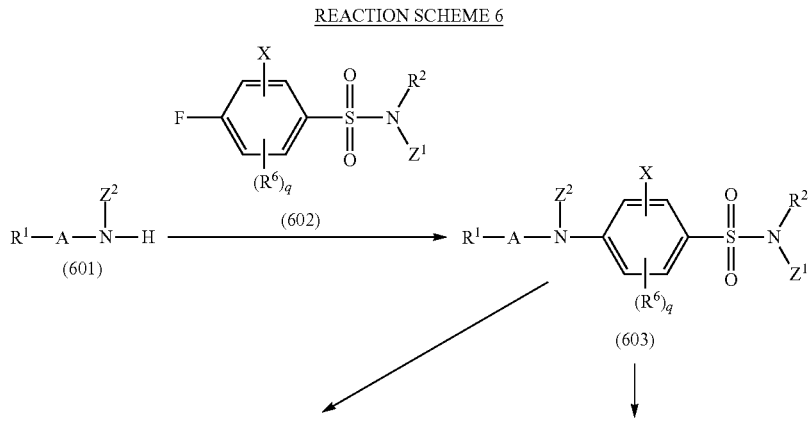

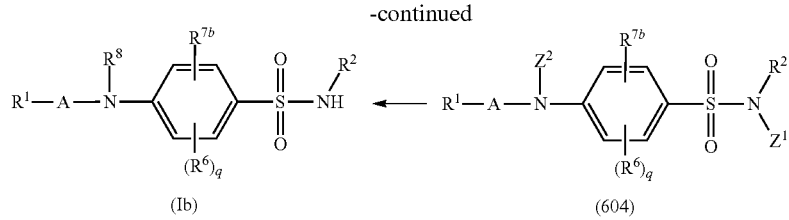

Compounds of formulae (601), (602), (603), and (604) are commercially available or can be prepared according to methods known to one skilled in the art or by methods disclosed herein. In general, the compounds of formula (Ib) are prepared as described above in Reaction Scheme 6 as follows:

The compound of formula (601) is reacted with sulfonamide (602) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate, sodium hydride or N,N-diisopropylethylamine, at a temperature of between about 0° C. and 80° C., for about 1 to 48 hours to afford a compound of formula (603).

The compound of formula (603) is reacted with a boronic acid derivative such as, but not limited to, $R^{7b}$—B(OH)$_2$ or $R^{7b}$—BF$_3$K, under standard Suzuki-Miyaura cross coupling conditions, such as, but not limited to, the use of a solvent, such as, but not limited to, 1,4-dioxane, in the presence of a base, such as, but not limited to, aqueous sodium carbonate, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to generate a compound of formula (604).

Alternatively, a compound of formula (603) can be treated with a reducing agent, such as, but not limited to, sodium formate, in the presence of a palladium catalyst composed of for example, but not limited to, tris(dibenzylideneacetone)dipalladium(0) and tri-tert-butylphosphine, in a polar solvent such as, but not limited to, dimethyl sulfoxide, at a temperature of between about ambient temperature and 120° C., for about 1 to 20 hours to afford a compound of formula (604).

Alternatively, a compound of formula (603) can be treated with a reducing agent, such as, but not limited to, hydrogen, in the presence of a palladium catalyst for example, but not limited to, palladium on carbon, in a polar solvent such as, but not limited to, methanol, in the presence of a base, such as, but not limited to, trimethylamine, at a temperature of between about ambient temperature and 120° C., for about 1 to 20 hours to afford a compound of formula (604).

The compound of formula (604) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Under certain conditions, the above transformations of the compound of formula (603) will afford a compound of formula (I) instead of a compound of formula (604). In these instances, the compound of formula (I) can be isolated from the reaction mixture by standard techniques.

Alternatively, compounds of formula (Ib), as described above in the Summary of the Invention, can be synthesized by one skilled in the art by simple functional group transformations. As such, but not limited to, a compound of formula (I), wherein $R^{7b}$ is alkenyl, can be converted into a compound of formula (Ib), wherein $R^{7b}$ is alkyl, by treatment with hydrogen in the presence of, but not limited to, palladium on carbon, in solvents such as, but not limited to, methanol and ethyl acetate.

Alternatively, compounds of formula (I), as described above in the Summary of the Invention, can be synthesized following the general procedure described below in Reaction Scheme 7 where q, A, $R^2$ and $R^6$ are as described above in the Summary of the Invention for compounds of formula (I), $R^{1b}$ is an optionally substituted aryl or an optionally substituted heteroaryl, X is bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, $R^{13}$ and $R^{14}$ are independently hydrogen, optionally substituted alkyl, or optionally substituted cycloalkyl, or $R^{13}$ and $R^{14}$, together with the nitrogen to which they are attached, form an optionally substituted heterocyclyl, and $Z^2$ is boronic acid derivative, such as, but not limited to, B(OH)$_2$ or BF$_3$K:

REACTION SCHEME 7

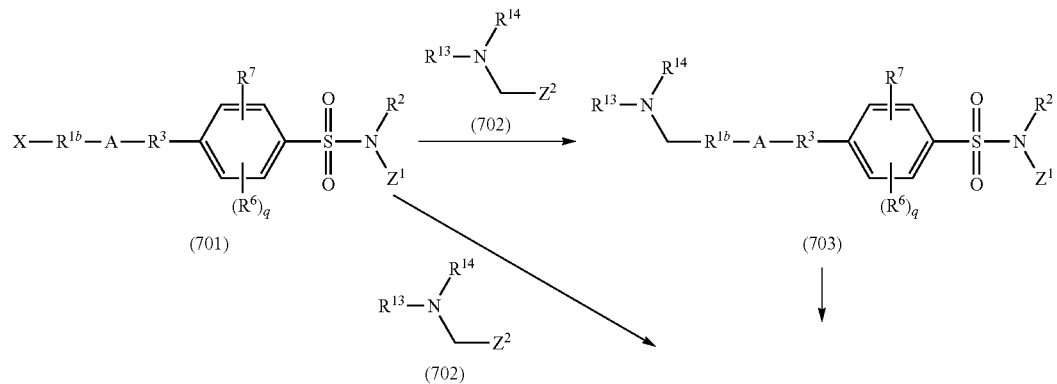

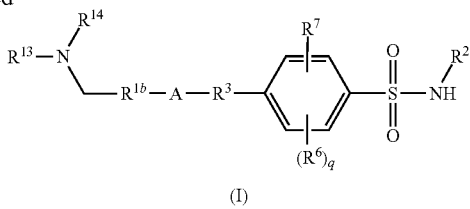

(I)

Compounds of formulae (701), (702), and (703) are commercially available or can be prepared according to methods known to one skilled in the art or by methods disclosed herein. In general, the compounds of formula (I) are prepared as described above in Reaction Scheme 7 as follows:

The compound of formula (701) is reacted with a boronic acid derivative (702), under standard Suzuki-Miyaura cross coupling conditions, such as, but not limited to, the use of a solvent mixture, such as, but not limited to, 1,4-dioxane and water, in the presence of a base, such as, but not limited to, cesium carbonate, and in the presence of a palladium catalyst composed of, for example, but not limited to, palladium (II) acetate and di(1-adamantyl)-n-butylphosphine, at a temperature of between about ambient temperature and 150° C., for about 30 minutes to 20 hours to generate a compound of formula (703).

The compound of formula (703) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Under certain conditions, the above transformation of the compound of formula (703) will afford a compound of formula (I) instead of a compound of formula (703). In these instances, the compound of formula (I) can be isolated from the reaction mixture by standard techniques.

Alternatively, compounds of formula (I), as described above in the Summary of the Invention, can be synthesized following the general procedure described below in Reaction Scheme 8 where q, A, $R^2$ and $R^6$ are as described above in the Summary of the Invention for compounds of formula (I), $R^{1b}$ is an optionally substituted aryl or an optionally substituted heteroaryl, X is bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, $R^{13}$ and $R^{14}$ are independently hydrogen, optionally substituted alkyl, or optionally substituted cycloalkyl, or $R^{13}$ and $R^{14}$, together with the nitrogen to which they are attached, form an optionally substituted heterocyclyl, and $Z^2$ is boronic acid derivative, such as, but not limited to, $B(OH)_2$ or $BF_3K$:

REACTION SCHEME 8

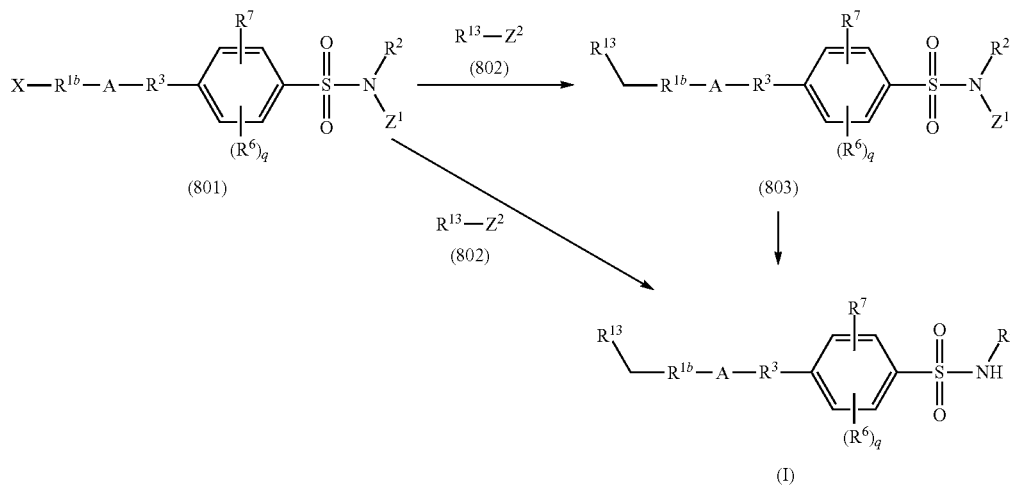

Compounds of formulae (801), (802), and (803) are commercially available or can be prepared according to methods known to one skilled in the art or by methods disclosed herein. In general, the compounds of formula (I) are prepared as described above in Reaction Scheme 8 as follows:

The compound of formula (801) is reacted with a boronic acid derivative (802), under standard Suzuki-Miyaura cross coupling conditions, such as, but not limited to, the use of a solvent mixture, such as, but not limited to, 1,4-dioxane and water, in the presence of a base, such as, but not limited to, cesium carbonate, and in the presence of a palladium catalyst composed of, for example, but not limited to, (2-dicyclohexylphosphino-2',6'-dimethoxybiphenyl) [2-(2'-amino-1,1'-biphenyl)]palladium(II) methanesulfonate and 2-dicyclohexylphosphino-2',6'-dimethoxybiphenyl, at a temperature of between about ambient temperature and 150° C., for about 30 minutes to 20 hours to generate a compound of formula (I), which can be isolated from the reaction mixture by standard techniques.

Under certain conditions, the above transformation of the compound of formula (801) will afford a compound of formula (803) instead of a compound of formula (I). In these instances, the compound of formula (803) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques.

Alternatively, a compound of formula (801) can be reacted with bis(pinacolato)diboron under Suzuki-Miyaura cross coupling conditions, such as, but not limited to, the use of a solvent mixture, such as, but not limited to, 1,4-dioxane and water, in the presence of a base, such as, but not limited to, potassium acetate, and in the presence of a palladium catalyst composed of, for example, but not limited to, [1,1'-bis(diphenylphosphino)ferrocene]dichloropalladium (II), at a temperature of between about ambient temperature and 150° C., for about 30 minutes to 20 hours to generate a compound. The compound that can be isolated from the reaction mixture by standard techniques can then be treated with for example, but not limited to, an oxidizing agent, such as, but not limited to, hydrogen peroxide, in the presence of a base, such as, but not limited to, sodium hydroxide, in a polar aprotic solvent, such as, but not limited to, tetrahydrofuran, at a temperature of between about 0° C. and ambient temperature for about 1 to 20 hours to generate a compound of (801), wherein X is hydroxyl and $Z^1$ is hydrogen.

Alternatively, compounds of formula (Ib), as described above in the Summary of the Invention, can be synthesized following the general procedure described below in Reaction Scheme 9 where m, n, q, A, $R^2$ and $R^6$ are as described above in the Summary of the Invention for compounds of formula (Ib), $R^8$ is hydrogen, A is —$(CH_2)_m$—$C(R^4)(R^5)$—$(CH_2)_n$—, $R^{1b}$ is an optionally substituted aryl or an optionally substituted heteroaryl, X is bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, $R^{13}$ and $R^{14}$ are independently hydrogen, optionally substituted alkyl, or optionally substituted cycloalkyl, or $R^{13}$ and $R^{14}$, together with the nitrogen to which they are attached, form an optionally substituted heterocyclyl, LG is a leaving group, such as, but not limited to, bromo, chloro, or iodo, and $Z^2$ is hydrogen or a nitrogen protecting group, such as, but not limited to, tert-butyloxycarbonyl:

REACTION SCHEME 9

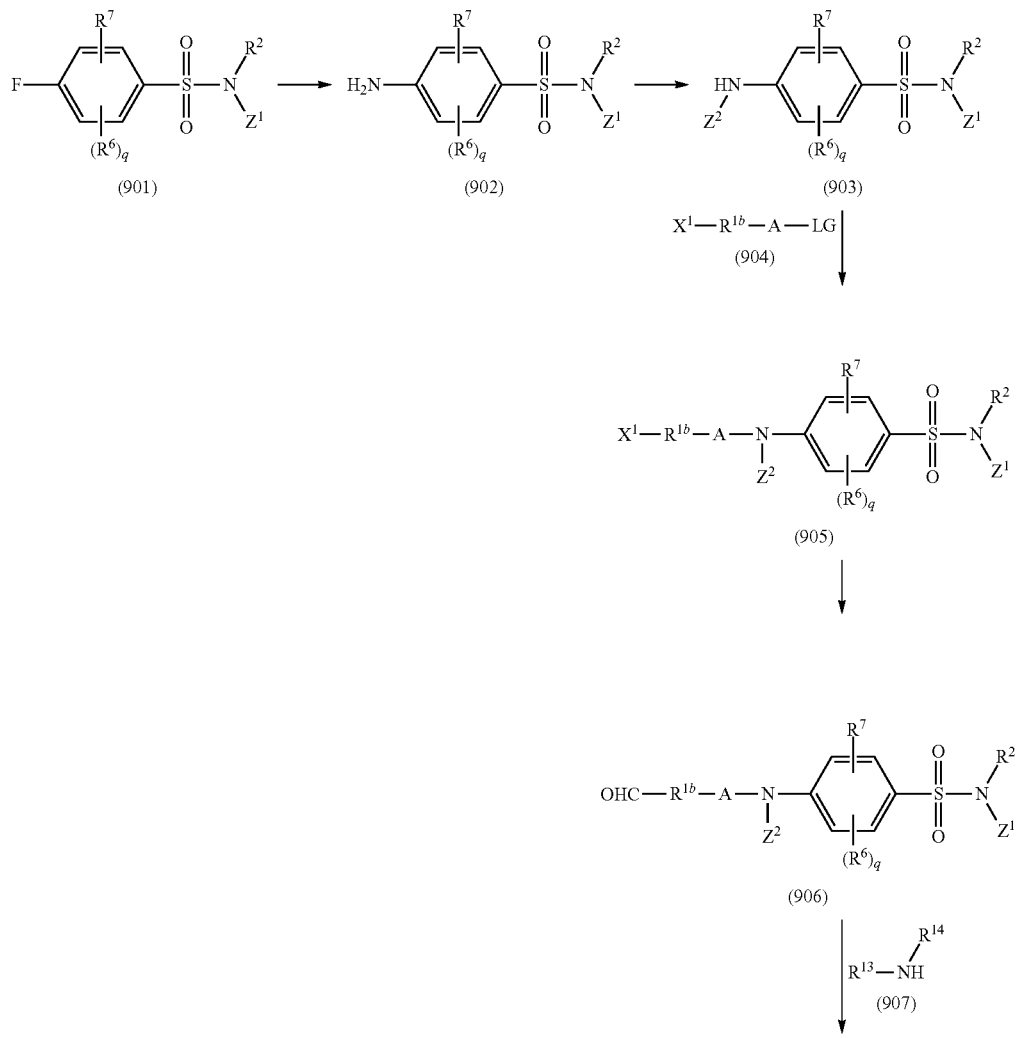

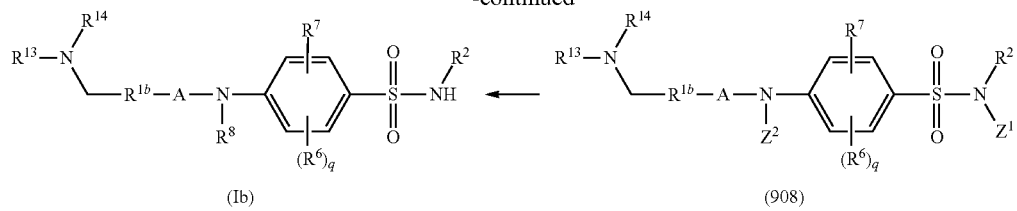

Compounds of formulae (901), (902), (903), (904), (905), (906), (907) and (908) are commercially available or can be prepared according to methods known to one skilled in the art or by methods disclosed herein. In general, the compounds of formula (Ib) are prepared as described above in Reaction Scheme 9 as follows:

The compound of formula (901) is reacted with a nitrogen nucleophile, such as, but not limited to, sodium azide, under standard reaction conditions, such as, but not limited to, the use of a polar aprotic solvent, such as, but not limited to, dimethyl sulfoxide or N,N-dimethylformamide, at a temperature of between about 0° C. and 80° C., for about 1 to 48 hours. The compound which can isolated from the reaction mixture by standard techniques is then treated with a reducing agent, such as, but not limited to, zinc dust, in a polar aprotic solvent, such as, but not limited to, tetrahydrofuran, in the presence of a weak acid, such as, but not limited to, aqueous ammonium chloride, to afford a compound of formula (902). The compound of formula (902) can then be reacted with, for example, but not limited to, di-tert-butyl dicarbonate, in a polar aprotic solvent such as, but not limited to, dichloromethane, in the presence of a base, such as, but not limited to, 4-(dimethylamino)pyridine, at a about ambient temperature, for about 1 to 20 hours to generate a compound of formula (903). The compound of formula (903) is then reacted with a compound of formula (904) under standard nucleophlic substitution conditions in a polar aprotic solvent, such as, but not limited to, N,N-dimethylformamide, in the presence of a base, such as, but not limited to, potassium carbonate, at ambient temperature for 1-20 h to afford a compound of formula (905). The compound of formula (905) is then reacted with tert-butyl isocyanide in the presence of a palladium catalyst composed of for example, but not limited to, palladium acetate and 2-(di-tert-butylphosphino)biphenyl, and the use of a solvent, such as, but not limited to, N,N-dimethylformamide, in the presence of a base, such as, but not limited to, sodium carbonate, and in the presence of a reducing agent, such as, but not limited to, triethylsilane, at a temperature of between about ambient temperature and 120° C., for about 1 to 20 hours to generate a compound of formula (906).

Alternatively, the compound of formula (905) can be reacted with a boronic acid derivative such as, but not limited to, vinylboronic acid pinacol ester, under standard Suzuki coupling conditions in the presence of palladium catalyst composed of for example, but not limited to, tetrakis (triphenylphosphine)palladium(0), in a solvent mixture for example, but not limited to, N,N-dimethylformamide and water, and in the presence of a base, for example, but not limited to, sodium carbonate, at a temperature of between about ambient temperature and 120° C., for about 1 to 20 hours. The compound that can be isolated from the reaction mixture by standard techniques can then be treated with an oxidizing reagent, such as, but not limited to, ozone, in a polar aprotic solvent, such as, but not limited to, dichloromethane, at a temperature of about −78° C. for 1-4 hours, to generate a compound of formula (906).

The compound of formula (906) is then reacted with, for example, but not limited to, an amine of formula (907) in the presence of a reducing agent, such as, but not limited to, sodium cyanoborohydride, in protic solvent such as, but not limited to, methanol, in the presence of an acid, such as, but not limited to, acetic acid, at a temperature of between about 0° C. and ambient temperature, for about 1 to 20 hours to generate a compound of formula (908).

Alternatively, the compound of formula (906) can be reacted with an amine of formula (907) in the presence of titanium(IV) isopropoxide in an aprotic polar solvent, such as, but not limited to, dichloromethane, and in the presence of a reduction agent, such as, but not limited to, sodium triacetoxy borohydride, at a temperature of between about 0° C. and ambient temperature, for about 1 to 20 hours to generate a compound of formula (908).

The compound of formula (908) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Alternatively, a compound of formula ((b), wherein $R^8$ is hydrogen, and $R^{13}$ and $R^{14}$ are not hydrogen, can be treated with an aldehyde, such as, but not limited paraformalhyde, in an acid as solvent, such as, but not limited to, trifluoroacetic acid, in the presence of a reducing agent, such as, but not limited to, sodium triacetoxyborohydride, at a temperature of about 0° C. for 10 minutes to 2 hours, to generate a compound of formula (Ib), wherein $R^8$ is alkyl, which can be isolated from the reaction mixture by standard techniques.

Alternatively, compounds of formula (Ib), as described above in the Summary of the Invention, can be synthesized following the general procedure described below in Reaction Scheme 10 where m, n, q, A, $R^2$ and $R^6$ are as described above in the Summary of the Invention for compounds of formula (Ib), $R^8$ is hydrogen, $R^{1b}$ is an optionally substituted aryl or an optionally substituted heteroaryl, LG is a leaving group, such as, but not limited to, bromo, chloro, or iodo, $Z^1$ is hydrogen or a nitrogen protecting group, for example, but not limited to, tert-butyloxycarbonyl, 2,4-dimethoxybenzyl, or 4-methoxybenzyl, $R^{13}$ and $R^{14}$ are independently hydrogen, optionally substituted alkyl, or optionally substituted cycloalkyl, or $R^{13}$ and $R^{14}$, together with the nitrogen to which they are attached, form an optionally substituted heterocyclyl, LG is a leaving group, such as, but not limited to, bromo, chloro, or iodo, and $Z^2$ is hydrogen or a nitrogen protecting group, such as, but not limited to, tert-butyloxycarbonyl:

REACTION SCHEME 10

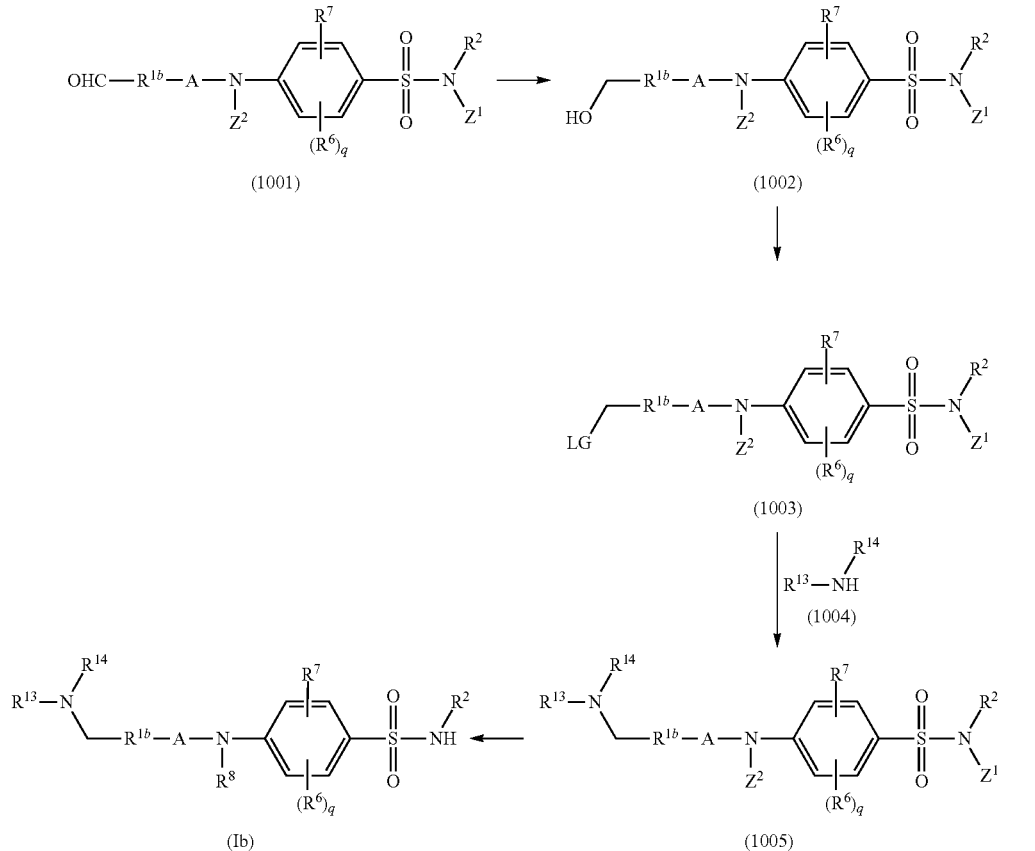

Compounds of formulae (1001), (1002), (1003), (1004), and (1005) are commercially available or can be prepared according to methods known to one skilled in the art or by methods disclosed herein. In general, the compounds of formula (Ib) are prepared as described above in Reaction Scheme 10 as follows:

The compound of formula (1001) is reacted with a reducing agent, for example, but not limited to, sodium cyanoborohydride, in a polar solvent, such as, but not limited to, methanol, at a temperature of between about 0° C. ambient temperature, for about 1 to 20 hours, to generate a compound of formula (1002). The compound of formula (1002) can then be treated with a reagent formed from, for example, but not limited to, carbon tetrabromide and triphenylphosphine, in a polar aprotic solvent such as dichloromethane, at a temperature of between about 0° C. ambient temperature, for about 1 to 20 hours, to generate a compound of formula (1003).

The compound of formula (1006) is then reacted with, for example, but not limited to, an amine of formula (1004) in the presence of a base, such as, but not limited to, potassium carbonate, in polar aprotic solvent such as, but not limited to, N,N-dimethylformamide, at a temperature of between about 0° C. and ambient temperature, for about 1 to 20 hours to generate a compound of formula (1005).

The compound of formula (1005) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Alternatively, compounds of formula (Ib), as described above in the Summary of the Invention, can be synthesized following the general procedure described below in Reaction Scheme 11 where m, n, q, A, $R^2$ and $R^6$ are as described above in the Summary of the Invention for compounds of formula (Ib), $R^8$ is hydrogen, $R^{1b}$ and $R^{13}$ are optionally substituted aryls or an optionally substituted heteroaryls, $X^1$ is bromo, chloro, or iodo, $X^2$ is boronic acid derivative, such as, but not limited to, $B(OH)_2$ or $BF_3K$, $Z^1$ is hydrogen or a nitrogen protecting group, for example, but not limited to, tert-butyloxycarbonyl, 2,4-dimethoxybenzyl, or 4-methoxybenzyl, and $Z^2$ is hydrogen or a nitrogen protecting group, such as, but not limited to, tert-butyloxycarbonyl:

REACTION SCHEME 11

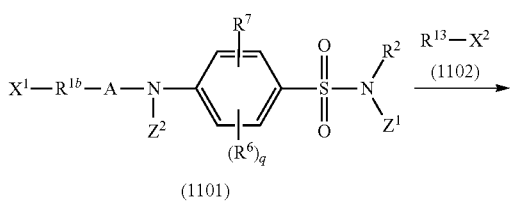

-continued

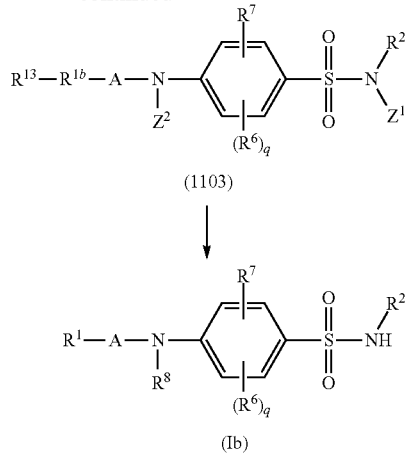

Compounds of formulae (1101), (112), and (1103) are commercially available or can be prepared according to methods known to one skilled in the art or by methods disclosed herein. In general, the compounds of formula (Ib) are prepared as described above in Reaction Scheme 11 as follows:

The compound of formula (1101) is reacted with boronic acid derivatives (1102) under standard Suzuki coupling conditions in the presence of palladium catalyst composed of for example, but not limited to, [1,1'-bis(diphenylphosphino)ferrocene]-dichloropalladium(II), in a solvent mixture for example, but not limited to, 1,4-dioxane and water, and in the presence of a base, for example, but not limited to, sodium carbonate, at a temperature of between about ambient temperature and 120° C., for about 1 to 20 hours to generate a compound of formula (1103). The compound of formula (1103) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Alternatively, a compound of formula (Ib), as described above in the Summary of the Invention, can be synthesized following the general procedure described below in Reaction Scheme 12 where q, $R^2$ and $R^6$ are as described above in the Summary of the Invention for compounds of formula (Ib), $R^8$ is hydrogen, A is methylene, $R^{1b}$ is an optionally substituted aryl or an optionally substituted heteroaryl, $Z^1$ is hydrogen or a nitrogen protecting group, for example, but not limited to, tert-butyloxycarbonyl, 2,4-dimethoxybenzyl, or 4-methoxybenzyl, $R^{13}$ and $R^{14}$ are independently hydrogen, optionally substituted alkyl, or optionally substituted cycloalkyl, or $R^{13}$ and $R^{14}$, together with the nitrogen to which they are attached, form an optionally substituted heterocyclyl, PG is a protecting group, such as, but not limited to, tert-butyldimethylsilyl, and $Z^2$ is hydrogen or a nitrogen protecting group, such as, but not limited to, tert-butyloxycarbonyl:

REACTION SCHEME 12

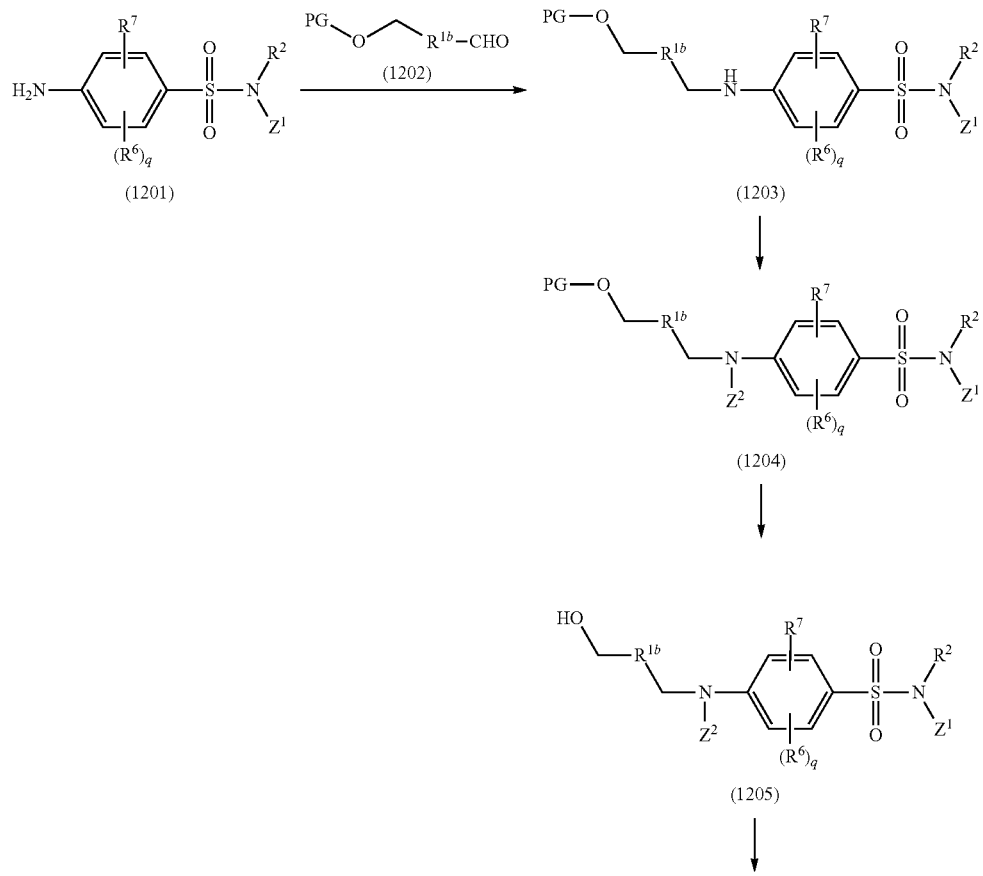

-continued

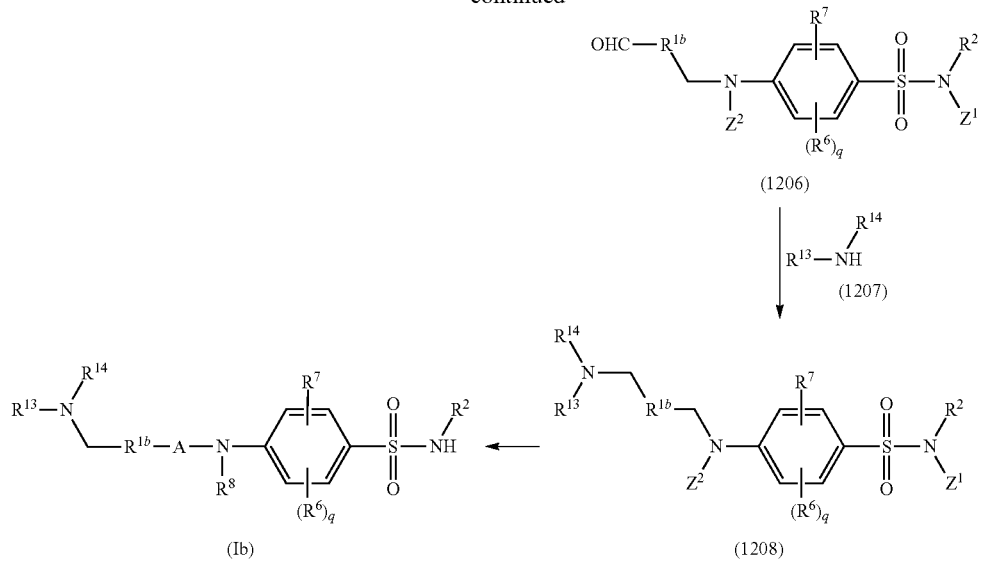

Compounds of formulae (1201), (1202), (1203), (1204), (1205), (1206), (1207) and (1208) are commercially available or can be prepared according to methods known to one skilled in the art or by methods disclosed herein. In general, the compounds of formula (Ib) are prepared as described above in Reaction Scheme 12 as follows:

The compound of formula (1201) is reacted with an aldehyde of formula (1202) in the presence of a reducing agent, such as, but not limited to, sodium triacetoxyborohydride, in a solvent mixture such as, but not limited to, trifluoroacetic acid and dichloromethane, at a temperature of between about 0° C. and ambient temperature, for about 1 to 20 hours to generate a compound of formula (1203). The compound of formula (1203) can then be reacted with, for example, but not limited to, di-tert-butyl dicarbonate, in a polar aprotic solvent such as, but not limited to, dichloromethane, in the presence of a base, such as, but not limited to, 4-(dimethylamino)pyridine, at a about ambient temperature, for about 1 to 20 hours to generate a compound of formula (1204). The compound of formula (1204) can then be treated with a reagent such as, but not limited to, tetra-n-butylammonium fluoride, in a polar aprotic solvent, such as, but not limited to, tetrahydrofuran, at ambient temperature for 30 minutes to 20 h to afford a compound of formula (1205). The compound of formula (1205) is then oxidized by a reagent such as, but not limited to, Dess-Martin periodinane reagent, in a polar aprotic solvent, such as, but not limited to, dichloromethane, at ambient temperature for 30 minutes to 20 h to afford a compound of formula (1206). The compound of formula (1206) is then reacted with, for example, but not limited to, an amine of formula (1207) in the presence of a reducing agent, such as, but not limited to, sodium triacetoxyborohydride, in a polar aprotic solvent such as, but not limited to, dichloromethane, at a temperature of between about 0° C. and ambient temperature, for about 1 to 20 hours to generate a compound of formula (1208). The compound of formula (1208) can then be treated with for example, but not limited to, an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

The following Examples, which are directed to the synthesis of the compounds of the invention; and the following Biological Examples are provided as a guide to assist in the practice of the invention, and are not intended as a limitation on the scope of the invention.

In the Examples below, unless otherwise indicated all temperatures are set forth in degrees Celsius. Commercially available reagents were purchased from suppliers such as Aldrich Chemical Company, Combi-Blocks, TCI or Oakwood Chemicals and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Yields were not optimized. Melting points were determined on a Büchi hot-stage apparatus and are uncorrected. $^1$H NMR, $^{19}$F and $^{13}$C NMR data were obtained in deuterated CDCl$_3$, DMSO-d$_6$, CD$_3$OD, CD$_3$CN, or acetone-d$_6$ solvent solutions with chemical shifts (δ) reported in parts-per-million (ppm) relative to trimethylsilane (TMS) or the residual non-deuterated solvent peaks as the reference standard. Data are reported as follows, if applicable: chemical shift, multiplicity, coupling constant in Hz, and number of protons, fluorine or carbon atoms. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

Example 1

Synthesis of (S)-5-bromo-2-fluoro-4-((1-phenylpropyl)amino)-N-(thiazol-2-yl)benzenesulfonamide

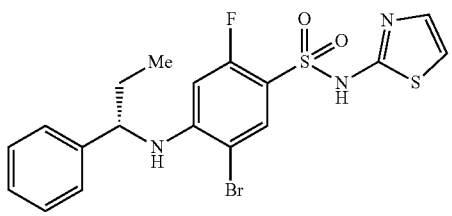 [SMILES: CC[C@H](Nc1cc(F)c(S(=O)(=O)Nc2nccs2)cc1Br)c1ccccc1]

Step 1. Preparation of 5-bromo-N-(2,4-dimethoxybenzyl)-2,4-difluoro-N-(thiazol-2-yl)benzenesulfonamide

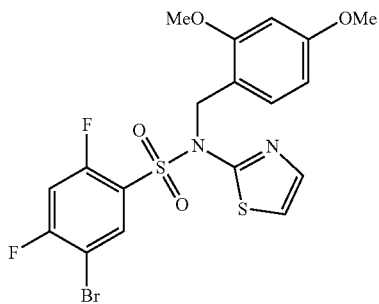 [SMILES: COc1ccc(CN(c2nccs2)S(=O)(=O)c2cc(Br)c(F)cc2F)c(OC)c1]

To a mixture of N-(2,4-dimethoxybenzyl)thiazol-2-amine (8.60 g, 34.4 mmol, prepared according to WO 2013063459) in anhydrous tetrahydrofuran (80 mL) was added a 1 M solution of lithium bis(trimethylsilyl)amide in tetrahydrofuran (39.6 mL, 39.6 mmol) at −78° C. The reaction mixture was allowed to warm to ambient temperature and stirred for 1 h. The reaction mixture was cooled to −78° C. and a solution of 5-bromo-2,4-difluorobenzenesulfonyl chloride (9.12 g, 31.3 mmol) in anhydrous tetrahydrofuran (20 mL) was added to it. The reaction mixture was allowed to warm to ambient temperature, and stirred for 16 h. The reaction mixture was quenched by addition of saturated ammonium chloride solution (100 mL) and ethyl acetate (400 mL) was added to it. The aqueous phase was extracted with ethyl acetate (2×50 mL) and the combined organic phase was washed with brine (50 mL), dried over anhydrous sodium sulfate, and filtered. Concentration of the filtrate in vacuo and purification of the residue by column chromatography, eluting with a gradient of 0 to 40% of ethyl acetate in hexanes, provided the title compound as a colorless solid (6.3 g, 40% yield): $^1$H NMR (300 MHz, CDCl$_3$) δ 8.06 (t, J=7.3 Hz, 1H), 7.42 (d, J=3.6 Hz, 1H), 7.19 (d, J=8.2 Hz, 1H), 7.03 (d, J 3.9 Hz, 1H), 6.97 (dd, J=9.1, 8.2 Hz, 1H), 6.38-6.34 (m, 2H), 5.19 (s, 2H), 3.37 (s, 3H), 3.73 (s, 3H); MS (ES+) m/z 504.9 (M+1), 506.9 (M+1).

Step 2. Preparation of (S)-5-bromo-N-(2,4-dimethoxybenzyl)-2-fluoro-4-((1-phenylpropyl)amino)-N-(thiazol-2-yl)benzenesulfonamide

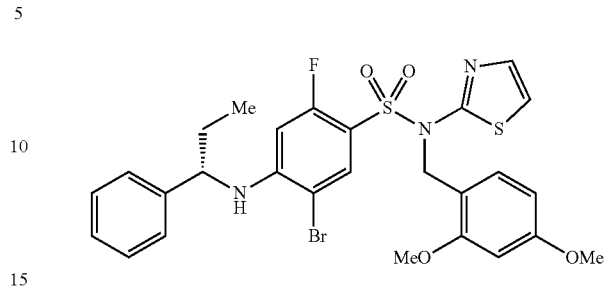

To a mixture of 5-bromo-N-(2,4-dimethoxybenzyl)-2,4-difluoro-N-(thiazol-2-yl)benzenesulfonamide (1.50 g, 2.97 mmol) and cesium carbonate (1.94 g, 5.94 mmol) in anhydrous dimethyl sulfoxide (20 mL) was added (S)-2-ethylbenzylamine (0.40 g, 2.97 mmol) and the reaction mixture was stirred at ambient temperature for 16 h. The mixture was diluted with ethyl acetate (200 mL) and washed with water (2×20 mL) and brine (20 mL). The organic phase was dried over anhydrous sodium sulfate and filtered. Concentration of the filtrate under reduced pressure gave a residue which was purified by column chromatography eluting with a gradient of 0 to 40% of ethyl acetate in hexanes to provide the title compound as a colorless amorphous solid (1.51 g, 82% yield): MS (ES+) m/z 620.0 (M+1), 622.0 (M+1).

Step 3. Preparation of (S)-5-bromo-2-fluoro-4-((1-phenylpropyl)amino)-N-(thiazol-2-yl)benzenesulfonamide To a mixture of (S)-5-bromo-N-(2,4-dimethoxybenzyl)-2-fluoro-4-((1-phenylpropyl)amino)-N-(thiazol-2-yl)benzenesulfonamide (1.51 g, 2.43 mmol) in dichloromethane (20 mL) was added trifluoroacetic acid (5 mL) and the reaction mixture was stirred at ambient temperature for 1 h. Concentration under reduced pressure provided a residue which was triturated in methanol (20 mL) and filtered. The filtrate was concentrated under reduced pressure and the residue triturated in diethyl ether (10 mL) to give the title compound as colorless solid (1.0 g, 88% yield): $^1$H NMR (300 MHz, DMSO-d$_6$) δ 12.73 (s, 1H), 7.73 (d, J=7.3 Hz, 1H), 7.43-7.17 (m, 5H), 6.83-6.78 (m, 1H), 6.41 (d, J=13.1 Hz, 1H), 6.09 (d, J=6.8 Hz, 1H), 4.49-4.39 (m, 1H), 3.33 (s, 1H), 2.07-1.91 (m, 1H), 1.86-1.72 (m, 1H), 0.89 (t, J=6.4 Hz, 3H); MS (ES+) m/z 469.9 (M+1), 471.9 (M+1).

Example 2

Synthesis of (S)-5-chloro-2-fluoro-4-((1-(naphthalen-1-yl)ethyl)amino)-N-(thiazol-2-yl)benzenesulfonamide

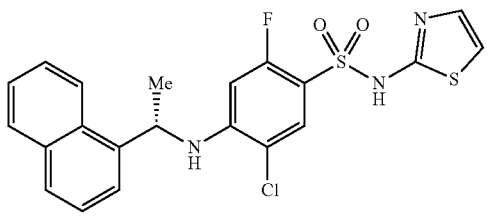 [SMILES: C[C@H](Nc1cc(F)c(S(=O)(=O)Nc2nccs2)cc1Cl)c1cccc2ccccc12]

Step 1. Preparation of 5-chloro-N-(2,4-dimethoxybenzyl)-2,4-difluoro-N-(thiazol-2-yl)benzenesulfonamide

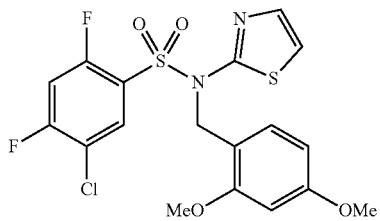 [SMILES: COc1ccc(CN(c2nccs2)S(=O)(=O)c2cc(Cl)c(F)cc2F)c(OC)c1]

A solution of N-(2,4-dimethoxybenzyl)thiazol-2-amine (20.86 g, 83.3 mmol, prepared according to WO2013063459) in anhydrous tetrahydrofuran (350 mL) was treated with a 1 M solution of bis(trimethylsilyl)amide in tetrahydrofuran (100.0 mL, 100.0 mmol) at −78° C. The resulting mixture was warmed to ambient temperature and stirred for 1 h. The reaction mixture was cooled to −78° C., and a solution of 5-chloro-2,4-difluorobenzenesulfonyl chloride (20.58 g, 83.3 mmol) in anhydrous tetrahydrofuran (75 mL) was added to it. The reaction mixture was allowed to warm to ambient temperature, stirred for 2 h, and diluted with ethyl acetate (700 mL). The organic phase was washed with saturated sodium bicarbonate (200 mL), saturated ammonium chloride (2×150 mL), brine (2×150 mL), dried over anhydrous sodium sulfate, and filtered. Concentration of the filtrate under reduced pressure gave a residue which was triturated with methanol (80 mL) to provide the title compound as a colorless solid (12.7 g, 33% yield): $^1$H NMR (300 MHz, CDCl$_3$) δ 7.94 (t, J=7.4 Hz, 1H), 7.44 (d, J=3.6 Hz, 1H) 7.21 (d, J=8.1 Hz, 1H), 7.06-6.99 (m, 2H), 6.41-6.36 (m, 2H), 5.20 (s, 2H), 3.78 (s, 3H), 3.74 (s, 3H); MS (ES+) m/z 461.0 (M+1), 463.0 (M+1).

Step 2. Preparation of (S)-5-chloro-N-(2,4-dimethoxybenzyl)-2-fluoro-4-((1-(naphthalen-1-yl)ethyl)amino)-N-(thiazol-2-yl)benzenesulfonamide

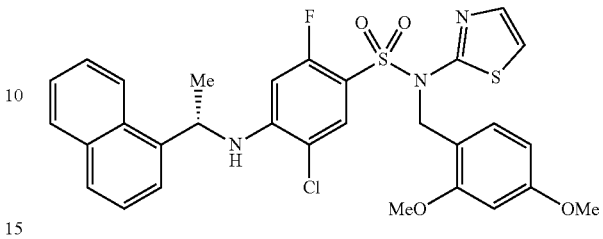

To a mixture of 5-chloro-N-(2,4-dimethoxybenzyl)-2,4-difluoro-N-(thiazol-2-yl)benzenesulfonamide (0.46 g, 1.0 mmol) and cesium carbonate (0.65 g, 2.0 mmol) in anhydrous dimethyl sulfoxide (5 mL) was added (S)-1-(1-naphthyl)ethylamine (0.17 g, 1.0 mmol) and the reaction mixture was stirred at ambient temperature for 16 h. Water (20 mL) was then added to the mixture and the precipitate filtered off. The precipitate was dissolved in dissolved in dichloromethane (100 mL), dried over anhydrous sodium sulfate, and filtered. Concentration of the filtrate under reduced pressure and purification of the residue by column chromatography eluting with a gradient of 0 to 40% of ethyl acetate in hexanes provided the title compound as a yellowish oil (0.55 g, 90% yield): MS (ES+) m/z 612.1 (M+1), 614.0 (M+1).

Step 3. Preparation of (S)-5-chloro-2-fluoro-4-((1-(naphthalen-1-yl)ethyl)amino)-N-(thiazol-2-yl)benzenesulfonamide

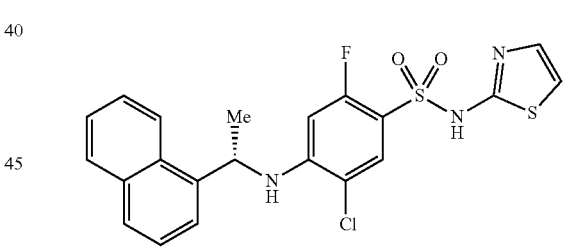

To a mixture of (S)-5-chloro-N-(2,4-dimethoxybenzyl)-2-fluoro-4-((1-(naphthalen-1-yl)ethyl)amino)-N-(thiazol-2-yl)benzenesulfonamide (0.55 g, 0.89 mmol) in dichloromethane (20 mL) was added trifluoroacetic acid (0.5 mL) at 0° C. and the reaction mixture was stirred for 30 minutes. Concentration under reduced pressure provided a residue which was purified by column chromatography eluting with a gradient of 0 to 50% of ethyl acetate in hexanes to give the title compound as an off-white solid (0.31 g, 74% yield): $^1$H NMR (300 MHz, DMSO-d$_6$) δ 12.73 (br s, 1H), 8.29 (d, J=8.3 Hz, 1H), 7.97 (dd, J=8.1, 1.3 Hz, 1H), 7.82 (d, J=7.5 Hz, 1H), 7.65-7.41 (m, 5H), 7.23 (d, J=4.6 Hz, 1H), 6.80 (d, J=4.6 Hz, 1H), 6.70 (dd, J=6.7, 1.2 Hz, 1H), 6.13 (d, J=13.0 Hz, 1H), 5.54-5.44 (m, 1H), 1.65 (d, J=6.6 Hz, 3H); MS (ES+) m/z 462.1 (M+1), 464.0 (M+1).

Example 3

Synthesis of (S)-5-chloro-2-fluoro-N-(thiazol-2-yl)-4-((1-(3-(trifluoromethyl)phenyl)ethyl)amino)benzenesulfonamide

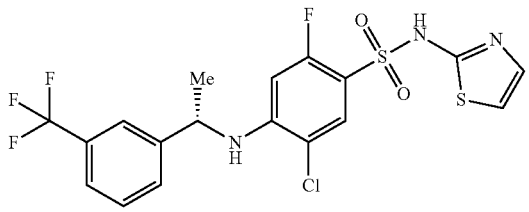 [SMILES: C[C@H](Nc1cc(F)c(S(=O)(=O)Nc2nccs2)cc1Cl)c1cccc(C(F)(F)F)c1]

Step 1. Preparation of (S)-5-chloro-N-(2,4-dimethoxybenzyl)-2-fluoro-N-(thiazol-2-yl)-4-((1-(3-(trifluoromethyl)phenyl)ethyl)amino)benzenesulfonamide

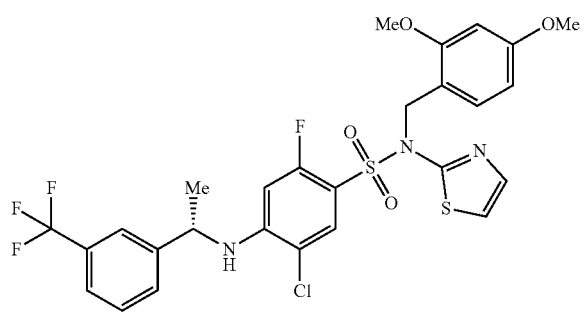 [SMILES: COc1ccc(CN(c2nccs2)S(=O)(=O)c2cc(Cl)c(N[C@@H](C)c3cccc(C(F)(F)F)c3)cc2F)c(OC)c1]

Following the procedure as described for EXAMPLE 2, Step 2 and making non-critical variations as required to replace (S)-1-(1-naphthyl)ethylamine with (S)-1-(3-(trifluoromethyl)phenyl)ethan-1-amine, the title compound was obtained as a yellowish oil (0.67 g, 80% yield): MS (ES+) m/z 630.1 (M+1), 632.1 (M+1).

Step 2. Preparation of (S)-5-chloro-2-fluoro-N-(thiazol-2-yl)-4-((1-(3-(trifluoromethyl)phenyl)ethyl)amino)benzenesulfonamide

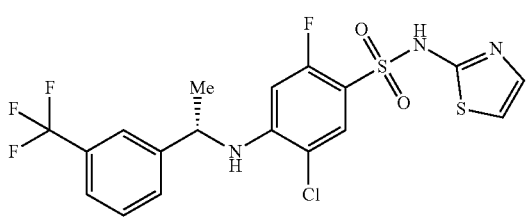 [SMILES: C[C@H](Nc1cc(F)c(S(=O)(=O)Nc2nccs2)cc1Cl)c1cccc(C(F)(F)F)c1]

Following the procedure as described for EXAMPLE 2, Step 3 and making non-critical variations as required to replace (S)-5-bromo-N-(2,4-dimethoxybenzyl)-2-fluoro-4-((1-phenylpropyl)amino)-N-(thiazol-2-yl)benzenesulfonamide with (S)-5-chloro-N-(2,4-dimethoxybenzyl)-2-fluoro-N-(thiazol-2-yl)-4-((1-(3-(trifluoromethyl)phenyl)ethyl)amino)benzenesulfonamide, the title compound was obtained as a colorless solid (0.37 g, 72% yield): $^1$H NMR (300 MHz, DMSO-$d_6$) δ 12.76 (br s, 1H), 7.84 (s, 1H), 7.77-7.71 (m, 1H), 7.62-7.52 (m, 3H), 7.25 (d, J=4.6 Hz, 1H), 6.81 (d, J=4.6 Hz, 1H), 6.68 (dd, J=7.8, 1.3 Hz, 1H), 6.50 (d, J=13.1 Hz, 1H), 4.91-4.80 (m, 1H), 1.54 (d, J=6.8 Hz, 3H); $^{19}$F NMR (282 MHz, DMSO-$d_6$) δ −60.9 (s, 3F), −109.3 (s, 1F); MS (ES+) m/z 480.0 (M+1), 482.0 (M+1).

Example 4

Synthesis of (R)-3-chloro-N-(thiazol-2-yl)-4-((2,2,2-trifluoro-1-phenylethyl)amino)benzenesulfonamide formate

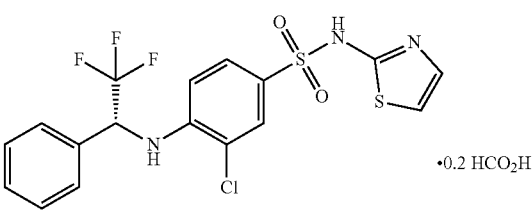 [SMILES: O=S(=O)(Nc1nccs1)c1ccc(N[C@H](c2ccccc2)C(F)(F)F)c(Cl)c1]

Step 1. Preparation of 4-bromo-3-chloro-N-(thiazol-2-yl)benzenesulfonamide

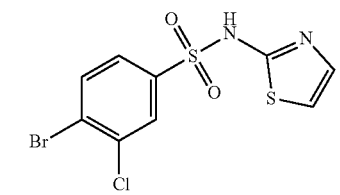 [SMILES: O=S(=O)(Nc1nccs1)c1ccc(Br)c(Cl)c1]

To a mixture of 2-aminothiazole (7.1 g, 70.7 mmol) in dichloromethane (190 mL) and pyridine (62 mL) was added 4-bromo-3-chlorobenzenesulfonyl chloride (20.5 g, 70.7 mmol) at 0° C. The reaction mixture was allowed to warm to ambient temperature and stirred for 16 h. The mixture was concentrated under reduced pressure and the residue co-evaporated with toluene (2×100 mL). Trituration in methanol (50-100 mL) provided a solid which was filtered off. The solid was washed with methanol (50 mL) to provide the title compound as a beige powder (14.6 g, 58% yield): $^1$H NMR (300 MHz, DMSO-$d_6$) δ 12.07 (br s, 1H), 7.96 (d, J=8.4 Hz, 1H), 7.90 (d, J=2.1 Hz, 1H), 7.65 (dd, J=8.4, 2.1 Hz, 1H), 7.32 (d, J=4.6 Hz, 1H), 6.90 (d, J 4.6 Hz, 1H); MS (ES+) m/z 352.9 (M+1), 354.9 (M+1).

Step 2. Preparation of (R)-3-chloro-N-(thiazol-2-yl)-4-((2,2,2-trifluoro-1-phenylethyl)amino)benzenesulfonamide formate

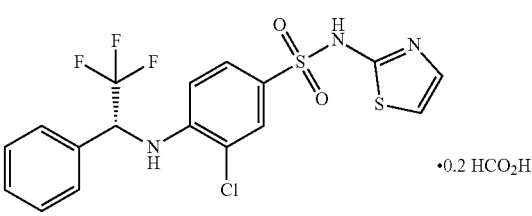 [SMILES: O=S(=O)(Nc1nccs1)c1ccc(N[C@H](c2ccccc2)C(F)(F)F)c(Cl)c1]

A mixture of 4-bromo-3-chloro-N-(thiazol-2-yl)benzenesulfonamide (0.35 g, 1.0 mmol), (R)-2,2,2-trifluoro-1-phenylethylamine (0.35 g, 2.0 mmol), 2-dicyclohexylphosphino-2',4',6'-triisopropylbiphenyl (0.058 g, 0.12 mmol), tris(dibenzylideneacetone)dipalladium(0) (0.036 g, 0.04 mmol), and sodium tert-butoxide (0.24 g, 2.5 mmol) in dioxane (5 mL) was degassed by passing a stream of argon through it and then heated in a sealed vial at 150° C. for 30 minutes using a microwave. The reaction mixture was allowed to cool ambient temperature and diluted with dichloromethane (200 mL) and saturated ammonium chloride solution (100 mL). The organic phase was washed with brine (20 mL), dried over anhydrous sodium sulfate, and filtered. The filtrate was concentrated in vacuo and purified by preparative reverse phase HPLC using acetonitrile in water containing 0.1% formic acid as eluent. The title compound was obtained as a beige solid (0.032 g, 7% yield): $^1$H NMR (300 MHz, DMSO-$d_6$) δ 8.14 (s, 0.2H), 7.70-7.63 (m, 3H), 7.52 (dd, J=8.7, 2.1 Hz, 1H), 7.47-7.36 (m, 3H), 7.18 (d, J=4.5 Hz, 1H), 7.07 (d, J=8.8 Hz, 1H), 6.74 (d, J=4.5 Hz, 1H), 6.11 (d, J=9.8 Hz, 1H), 5.90-5.77 (m, 1H), exchangeable protons not observed; $^{19}$F NMR (282 MHz, DMSO-$d_6$) δ−72.3 (s); MS (ES−) m/z 446.0 (M−1), 448.0 (M−1).

Example 5

Synthesis of (S)-5-chloro-4-((1-(5-chloro-2-fluorophenyl)ethyl)amino)-2-fluoro-N-(thiazol-4-yl)benzenesulfonamide

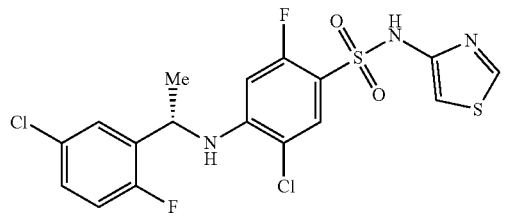 [SMILES: C[C@H](Nc1cc(F)c(S(=O)(=O)Nc2cscn2)cc1Cl)c1cc(Cl)ccc1F]

Step 1. Preparation of tert-butyl (S)-((5-chloro-4-((1-(5-chloro-2-fluorophenyl)ethyl)amino)-2-fluorophenyl)sulfonyl)(thiazol-4-yl)carbamate

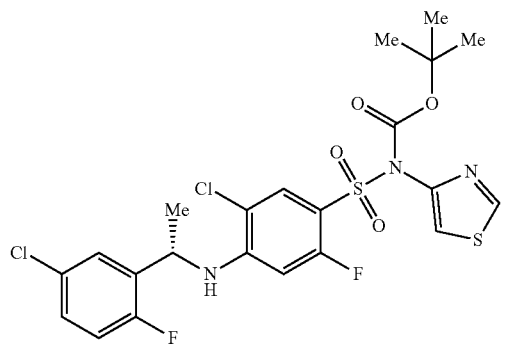 [SMILES: C[C@H](Nc1cc(F)c(S(=O)(=O)N(C(=O)OC(C)(C)C)c2cscn2)cc1Cl)c1cc(Cl)ccc1F]

To a mixture of (S)-1-(5-chloro-2-fluorophenyl)ethan-1-amine hydrochloride (0.092 g, 0.44 mmol) and tert-butyl ((5-chloro-2,4-difluorophenyl)sulfonyl)(thiazol-4-yl)carbamate (0.18 g, 0.44 mmol, prepared according to WO2010079443) in anhydrous dimethyl sulfoxide (1.0 mL) was added potassium carbonate (0.18 g, 1.3 mmol) and the reaction mixture was stirred at ambient temperature for 12 h. The mixture was poured onto a 1:1 ice/water mixture (50 mL) and extracted with ethyl acetate (3×60 mL). The combined organic phase was washed with brine (50 mL), dried over anhydrous Na$_2$SO$_4$, filtered and concentrated in vacuo. The residue was purified by preparative thin layer chromatography eluting with 25% ethyl acetate in petroleum ether to afford the title compound as a colorless oil (0.18 g, 73% yield): MS (ES+) m/z 563.9 (M+1), 565.9 (M+1).

Step 2. Preparation of (S)-5-chloro-4-((1-(5-chloro-2-fluorophenyl)ethyl)amino)-2-fluoro-N-(thiazol-4-yl)benzenesulfonamide

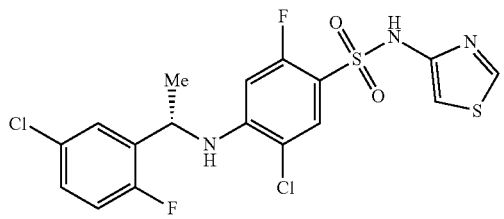 [SMILES: C[C@H](Nc1cc(F)c(S(=O)(=O)Nc2cscn2)cc1Cl)c1cc(Cl)ccc1F]

To tert-butyl(S)-((5-chloro-4-((1-(5-chloro-2-fluorophenyl)ethyl)amino)-2-fluorophenyl)sulfonyl)(thiazol-4-yl)carbamate (0.18 g, 0.32 mmol) was added a 4 M solution of hydrogen chloride in dioxane (10.0 mL, 40.0 mmol) and the reaction mixture was at ambient temperature for 12 h. The mixture was concentrated in vacuo and the residue was purified. The residue was purified by preparative reverse phase HPLC, using acetonitrile in water containing 0.2% formic acid as eluent, to afford the title compound as a colorless solid (0.082 g, 54% yield): $^1$H NMR (400 MHz, CDCl$_3$) δ 10.32 (s, 1H), 8.68 (d, J=2.0 Hz, 1H), 7.78 (d, J=6.8 Hz, 1H), 7.20-7.25 (m, 1H), 7.18-7.16 (m, 1H), 7.03 (t, J=9.2 Hz, 1H), 6.90 (d, J=2.0 Hz, 1H), 6.06 (d, J=12.4 Hz, 1H), 5.15 (d, J=5.2 Hz, 1H), 4.73 (quin, J=6.4 Hz, 1H), 1.61 (d, J=6.8 Hz, 3H); MS (ES+) m/z 464.0 (M+1), 466.0 (M+1).

Example 6

Synthesis of (S)-5-chloro-4-((1-(3-chloro-2-fluorophenyl)ethyl)amino)-2-fluoro-N-(thiazol-4-yl)benzenesulfonamide

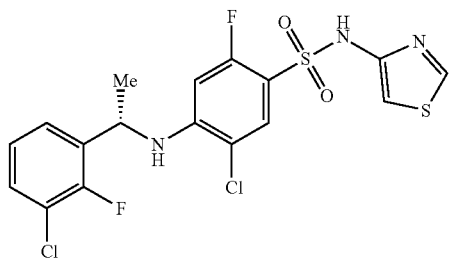 [SMILES: C[C@H](Nc1cc(F)c(S(=O)(=O)Nc2cscn2)cc1Cl)c1cccc(Cl)c1F]

Step 1. Preparation of tert-butyl (S)-((5-chloro-4-((1-(3-chloro-2-fluorophenyl)ethyl)amino)-2-fluorophenyl)sulfonyl)(thiazol-4-yl)carbamate

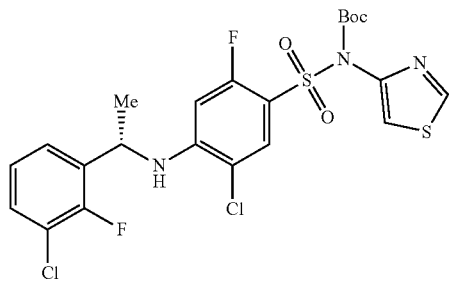 [SMILES: C[C@H](Nc1cc(F)c(S(=O)(=O)N(C(=O)OC(C)(C)C)c2cscn2)cc1Cl)c1cccc(Cl)c1F]

Following the procedure as described for EXAMPLE 5, Step 2 and making non-critical variations as required to replace (S)-1-(5-chloro-2-fluorophenyl)ethan-1-amine hydrochloride with (S)-1-(3-chloro-2-fluorophenyl)ethan-1-amine, the title compound was isolated as a colorless solid (0.15 g, 44% yield): MS (ES+) m/z 563.9 (M+1), 565.9 (M+1).

Step 2. Preparation of (S)-5-chloro-4-((1-(3-chloro-2-fluorophenyl)ethyl)amino)-2-fluoro-N-(thiazol-4-yl)benzenesulfonamide

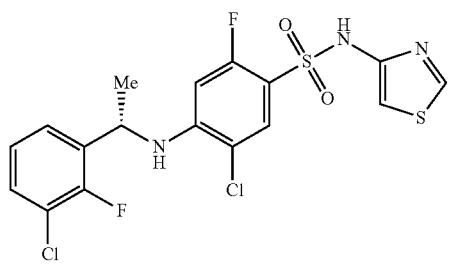 [SMILES: C[C@H](Nc1cc(F)c(S(=O)(=O)Nc2cscn2)cc1Cl)c1cccc(Cl)c1F]

Following the procedure as described for EXAMPLE 5, Step 2 and making non-critical variations as required to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl (S)-((5-chloro-4-((1-(3-chloro-2-fluorophenyl)ethyl)amino)-2-fluorophenyl)sulfonyl)(thiazol-4-yl)carbamate, the title compound was obtained as a colorless solid (0.058 g, 54% yield): $^1$H NMR (400 MHz, CDCl$_3$) δ 9.19 (s, 1H), 8.62 (d, J=2.4 Hz, 1H), 7.75 (d, J=7.2 Hz, 1H), 7.34 (td, J=7.2, 2.0 Hz, 1H), 7.02-7.16 (m, 2H), 6.94 (d, J=2.4 Hz, 1H), 6.07 (d, J=12.0 Hz, 1H), 5.19 (d, J=6.0 Hz, 1H), 4.78 (quin, J=6.4 Hz, 1H), 1.63 (d, J=6.8 Hz, 3H); MS (ES+) m/z 464.0 (M+1), 466.0 (M+1).

Example 7

Synthesis of (S)-4-((1-(3-bromophenyl)ethyl)amino)-5-chloro-2-fluoro-N-(thiazol-2-yl)benzenesulfonamide

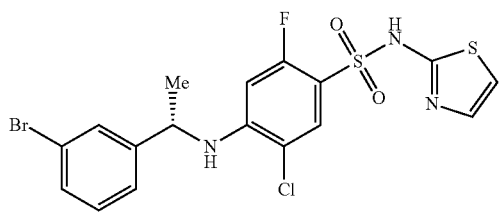 [SMILES: C[C@H](Nc1cc(F)c(S(=O)(=O)Nc2nccs2)cc1Cl)c1cccc(Br)c1]

Step 1. Preparation of (S)-4-((1-(3-bromophenyl)ethyl)amino)-5-chloro-N-(2,4-dimethoxybenzyl)-2-fluoro-N-(thiazol-2-yl)benzenesulfonamide

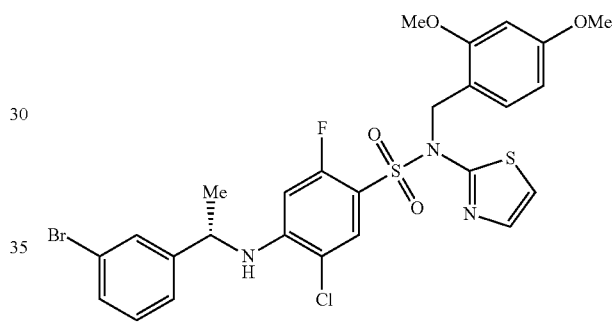

To a mixture of 5-chloro-N-(2,4-dimethoxybenzyl)-2,4-difluoro-N-(thiazol-2-yl)benzenesulfonamide (0.50 g, 1.1 mmol) and (S)-1-(3-bromophenyl)ethan-1-amine (0.26 g, 1.3 mmol) in anhydrous dimethyl sulfoxide (4 mL) was added potassium carbonate (0.30 g, 2.2 mmol) and the reaction mixture was stirred at ambient temperature for 12 h. After addition of water (20 mL), the mixture was extracted with ethyl acetate (3×20 mL). The combined organic phase was washed with brine (10 mL), dried over anhydrous sodium sulfate, and filtered. Concentration of the filtrate under reduced pressure and purification of the residue by preparative thin layer chromatography eluting with 30% ethyl acetate in petroleum ether provided the title compound as a yellowish solid (0.40 g, 58% yield): $^1$H NMR (400 MHz, CDCl$_3$) δ 7.74-7.68 (d, J=8.0 Hz, 1H), 7.46-7.41 (m, 2H), 7.40-7.36 (d, J=4.0 Hz, 1H), 7.26-7.16 (m, 3H), 6.98-6.94 (d, J=4.0 Hz, 1H), 6.39-6.34 (dd, J=8.0 Hz, 4.0 Hz, 1H), 6.33-6.30 (m, 1H), 6.08-6.02 (d, J=12.0 Hz, 1H), 5.19-5.12 (m, 3H), 4.49-4.39 (m, 1H), 3.77 (s, 3H), 3.67 (s, 3H), 1.63-1.59 (d, J=6.8 Hz, 3H).

Step 2. Preparation of (S)-4-((1-(3-bromophenyl)ethyl)amino)-5-chloro-2-fluoro-N-(thiazol-2-yl)benzenesulfonamide

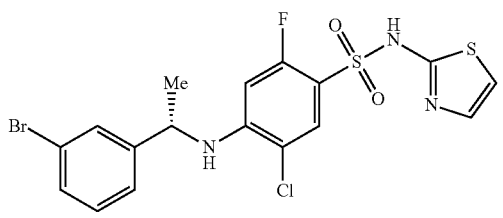 [SMILES: C[C@H](Nc1cc(F)c(S(=O)(=O)Nc2nccs2)cc1Cl)c1cccc(Br)c1]

To a mixture of (S)-4-((1-(3-bromophenyl)ethyl)amino)-5-chloro-N-(2,4-dimethoxybenzyl)-2-fluoro-N-(thiazol-2-yl)benzenesulfonamide (0.14 g, 0.22 mmol) in dichloromethane (5.0 mL) was added trifluoroacetic acid (0.5 mL) and the mixture was stirred at ambient temperature for 30 minutes. The mixture was concentrated in vacuo and the residue was purified was purified by preparative reverse phase HPLC using acetonitrile in water containing 0.2% formic acid as eluent to afford the title compound as a colorless solid (0.067 g, 62% yield): $^1$H NMR (400 MHz, CDCl$_3$) δ 12.80 (br s, 1H), 7.89 (d, J=8.0 Hz, 1H), 7.48-7.39 (m, 2H), 7.26-7.20 (m, 2H), 7.13 (d, J=4.0 Hz, 1H), 6.49 (d, J=4.0 Hz, 1H), 6.06 (d, J=12.0 Hz, 1H), 5.16-5.08 (m, 1H), 4.50-4.38 (m, 1H), 1.61 (d, J=8.0 Hz, 3H); MS (ES+) m/z 490.1 (M+1), 492.1 (M+1).

Example 8

Synthesis of (S)-5-chloro-4-((1-(5-chloro-2-fluorophenyl)ethyl)amino)-2-fluoro-N-(thiazol-2-yl)benzenesulfonamide

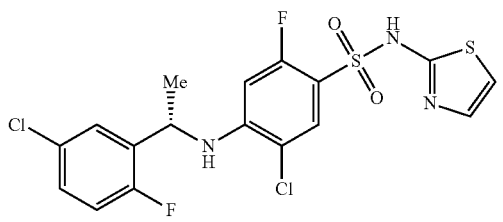 [SMILES: C[C@H](Nc1cc(F)c(S(=O)(=O)Nc2nccs2)cc1Cl)c1cc(Cl)ccc1F]

Step 1. Preparation of (R,E)-N-(5-chloro-2-fluorobenzylidene)-2-methylpropane-2-sulfinamide

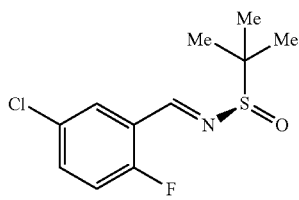 [SMILES: CC(C)(C)[S@@](=O)/N=C/c1cc(Cl)ccc1F]

To a solution of 5-chloro-2-fluorobenzaldehyde (5.00 g, 31.5 mmol) in dichloromethane (10.0 mL) were added pyridinium p-toluenesulfonate (0.40 g, 1.59 mmol), (R)-(+)-2-methyl-2-propanesulfinamide (3.82 g, 31.5 mmol) and anhydrous magnesium sulfate (19.0 g, 158 mmol). The reaction mixture was stirred at ambient temperature for 12 h. Filtration of the reaction mixture and concentration of the filtrate under reduced pressure provided a residue which was purified by column chromatography eluting with 10% of ethyl acetate in petroleum ether to provide the title compound as a yellow oil (2.45 g, 30% yield): $^1$H NMR (400 MHz, CDCl$_3$) δ 8.85-8.84 (m, 1H), 7.96-7.94 (dd, J=6.0, 2.8 Hz, 1H), 7.47-7.43 (m, 1H), 7.14-7.10 (t, J=8.0 Hz, 1H), 1.28 (s, 9H).

Step 2. Preparation of (R)—N—((S)-1-(5-chloro-2-fluorophenyl)ethyl)-2-methylpropane-2-sulfinamide

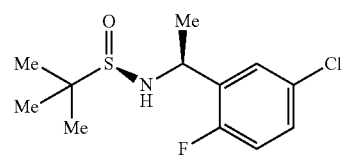 [SMILES: C[C@H](N[S@](=O)C(C)(C)C)c1cc(Cl)ccc1F]

To a mixture of (R,E)-N-(5-chloro-2-fluorobenzylidene)-2-methylpropane-2-sulfinamide (2.10 g, 8.02 mmol) in dichloromethane (5 mL) was added a 3M solution of methylmagnesium bromide in diethyl ether (5.35 mL, 16.05 mmol) in portions at −48° C. The reaction mixture was allowed to warm to ambient temperature and stirred for 12 h. The reaction mixture was poured into water (30 mL) and extracted with ethyl acetate (2×30 mL). The combined organic phase was washed with brine (2×30 mL), dried over anhydrous sodium sulfate, and filtered. Concentration of the filtrate under reduced pressure provided a residue which was purified by column chromatography eluting with 25% of ethyl acetate in petroleum ether to afford the title compound as a colorless oil (1.20 g, 54% yield): $^1$H NMR (400 MHz, CDCl$_3$) δ 7.35-7.33 (dd, J=8.0, 2.0 Hz, 1H), 7.22 (m, 1H), 7.02-6.98 (t, J=8.0 Hz, 1H), 4.79-4.72 (m, 1H), 1.54-1.52 (d, J=8.0 Hz, 3H), 1.70 (s, 1H), 1.24 (s, 9H).

Step 3. Preparation of (S)-1-(5-chloro-2-fluorophenyl)ethan-1-amine

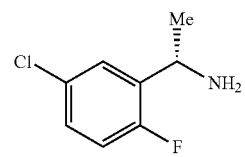 [SMILES: C[C@H](N)c1cc(Cl)ccc1F]

To a mixture of (R)—N—((S)-1-(5-chloro-2-fluorophenyl)ethyl)-2-methylpropane-2-sulfinamide (0.5 g, 1.80 mmol) in methanol (5 mL) was added a 4 M solution of hydrogen chloride in dioxane (0.9 mL, 3.6 mmol). The reaction mixture was stirred at ambient temperature for 2 h and then concentrated under reduced pressure. The residue was triturated in petroleum ether to afford the title compound as a colorless solid (0.25 g, 80% yield): $^1$H NMR (400 MHz, CD$_3$OD) δ 7.60-7.59 (m, 1H), 7.50-7.48 (m, 1H), 7.30-7.25 (dd, J=12.0, 8.0 Hz, 1H), 4.77-4.72 (m, 1H), 1.68-1.64 (m, 3H), exchangeable protons not observed.

Step 4. Preparation of (S)-5-chloro-4-((1-(5-chloro-2-fluorophenyl)ethyl)amino)-N-(2,4-dimethoxybenzyl)-2-fluoro-N-(thiazol-2-yl)benzenesulfonamide

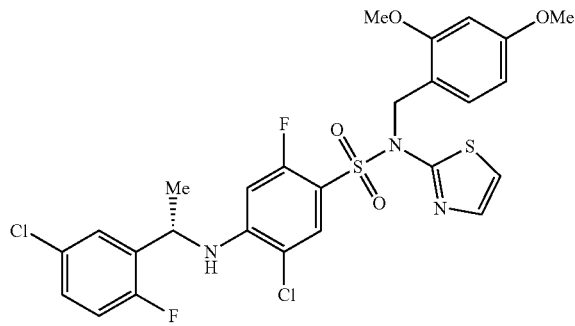 [SMILES: COc1ccc(CN(c2nccs2)S(=O)(=O)c2cc(Cl)c(N[C@@H](C)c3cc(Cl)ccc3F)cc2F)c(OC)c1]

Following the procedure as described for EXAMPLE 7, Step 1 and making non-critical variations as required to replace (S)-1-(3-bromophenyl)ethan-1-amine with (S)-1-(5-chloro-2-fluorophenyl)ethan-1-amine, the title compound was obtained as a colorless solid (0.12 g, 53% yield): $^1$H NMR (400 MHz, CDCl$_3$) δ 7.72 (d, J=8.0 Hz, 1H), 7.39 (d, J=4.0 Hz, 1H), 7.22-7.18 (m, 3H), 7.08-7.05 (m, 1H), 6.96 (d, J=4.0 Hz, 1H), 6.36 (dd, J=8.0, 4.0 Hz, 1H), 6.32 (d, J=4.0 Hz, 1H), 6.08 (d, J=12.0 Hz, 1H), 5.16-5.20 (m, 3H), 4.78-4.71 (m, 1H), 3.77-3.68 (m, 3H), 3.68 (s, 3H), 1.62 (d, J=8.0 Hz, 3H).

Step 5. Preparation of (S)-5-chloro-4-((1-(5-chloro-2-fluorophenyl)ethyl)amino)-2-fluoro-N-(thiazol-2-yl)benzenesulfonamide

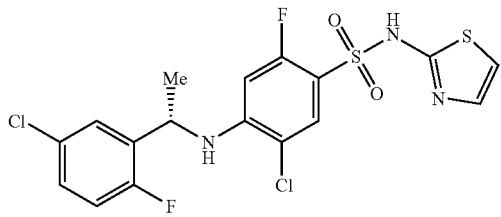 [SMILES: C[C@H](Nc1cc(F)c(S(=O)(=O)Nc2nccs2)cc1Cl)c1cc(Cl)ccc1F]

Following the procedure as described for EXAMPLE 7, Step 2 and making non-critical variations as required to replace (S)-4-((1-(3-bromophenyl)ethyl)amino)-5-chloro-N-(2,4-dimethoxybenzyl)-2-fluoro-N-(thiazol-2-yl)benzenesulfonamide with (S)-5-chloro-4-((1-(5-chloro-2-fluorophenyl)ethyl)amino)-N-(2,4-dimethoxybenzyl)-2-fluoro-N-(thiazol-2-yl)benzenesulfonamide, the title compound was obtained as a colorless solid (0.057 g, 63% yield): $^1$H NMR (400 MHz, CD$_3$OD) δ 7.76 (d, J=4.0 Hz, 1H), 7.36 (dd, J=4.0, 2.0 Hz, 1H), 7.28-7.32 (m, 1H), 7.18-7.10 (m, 2H), 6.73 (d, J=4.0 Hz, 1H), 6.25 (d, J=12.0 Hz, 1H), 4.80-4.95 (m, 1H), 1.64-1.62 (d, J=8.0 Hz, 3H), exchangeable protons not observed; MS (ES+) m/z 464.1 (M+1), 466.1 (M+1).

Example 9

Synthesis of (S)-3-chloro-2-fluoro-4-((1-(2-fluorophenyl)ethyl)amino)-N-(thiazol-2-yl)benzenesulfonamide

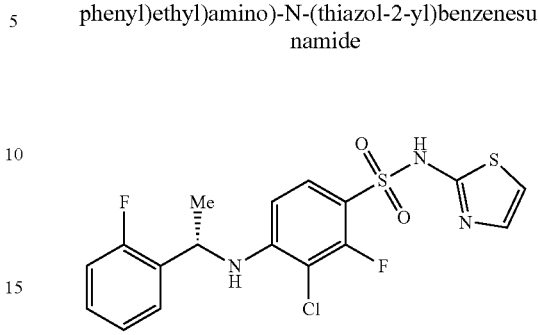

Step 1. Preparation of 3-chloro-N-(2,4-dimethoxybenzyl)-2,4-difluoro-N-(thiazol-2-yl)benzenesulfonamide

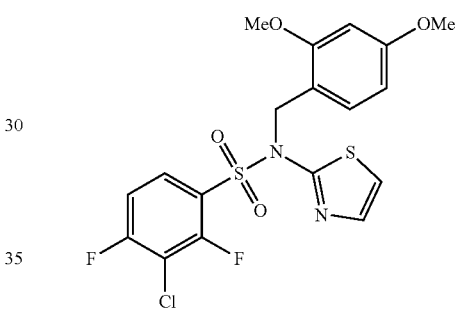

To a solution of N-(2,4-dimethoxybenzyl)thiazol-2-amine (1.24 g, 4.94 mmol) in anhydrous tetrahydrofuran (11 mL) was added a 1 M solution of lithium bis(trimethylsilyl)amide in tetrahydrofuran (4.9 mL, 4.9 mmol) at −78° C. The reaction mixture was stirred at −78° C. for 30 min, then allowed to warm to ambient temperature and stirred for 1 h. The reaction mixture was cooled to −78° C. and a solution of 3-chloro-2,4-difluorobenzenesulfonyl chloride (1.11 g, 4.49 mmol) in anhydrous tetrahydrofuran (5 mL) was added to it. The reaction mixture was allowed to warm to ambient temperature and stirred for 16 h. The reaction mixture was diluted with ethyl acetate (50 mL) and saturated aqueous ammonium chloride solution (20 mL), and the aqueous phase was extracted with ethyl acetate (3×50 mL). The combined organic phases were washed with brine (3×20 mL), dried over anhydrous sodium sulfate, and filtered. Concentration of the filtrate in vacuo and purification of the residue by column chromatography eluting with a gradient of 0 to 20% of ethyl acetate in hexanes provided the title compound as a yellow oil (0.992 g, 48% yield): $^1$H NMR (300 MHz, CDCl$_3$) δ 7.81 (ddd, J=9.0, 7.4, 5.8, 1H), 7.40 (d, J=3.6 Hz, 1H), 7.18 (dd, J=7.8, 0.7 Hz, 1H), 7.04 (ddd, J=9.0, 7.7, 1.8 Hz, 1H), 7.00 (d, J=3.6 Hz, 1H), 6.39-6.34 (m, 2H), 5.20 (s, 2H), 3.78 (s, 3H), 3.75 (s, 3H); MS (ES+) m/z 461.0 (M+1), 463.0 (M+1).

Step 2. Preparation of (S)-3-chloro-N-(2,4-dimethoxybenzyl)-2-fluoro-4-((1-(2-fluorophenyl)ethyl)amino)-N-(thiazol-2-yl)benzenesulfonamide

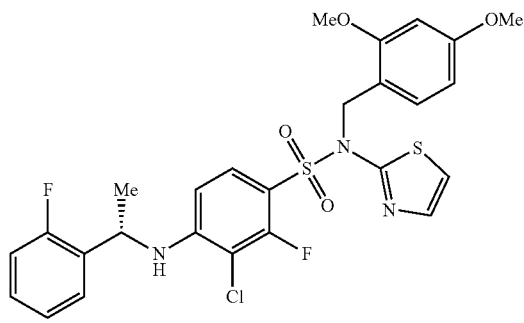 [SMILES: COc1ccc(CN(c2nccs2)S(=O)(=O)c2ccc(N[C@@H](C)c3ccccc3F)c(Cl)c2F)c(OC)c1]

To a suspension of 3-chloro-N-(2,4-dimethoxybenzyl)-2,4-difluoro-N-(thiazol-2-yl)benzenesulfonamide (0.375 g, 0.814 mmol) and (S)-1-(2-fluorophenyl)ethan-1-amine (0.136 g, 0.976 mmol) in anhydrous dimethyl sulfoxide (4 mL) was added cesium carbonate (0.665 g, 2.04 mmol) and the reaction mixture was stirred at ambient temperature for 18 h. The reaction mixture was diluted with ethyl acetate (50 mL) and water (20 mL), and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by column chromatography eluting with 0 to 40% of ethyl acetate in hexanes yielded to title compound as a yellow foam (0.352 g, 75% yield): MS (ES+) m/z 580.1 (M+1), 582.1 (M+1).

Step 3. Preparation of (S)-3-chloro-2-fluoro-4-((1-(2-fluorophenyl)ethyl)amino)-N-(thiazol-2-yl)benzenesulfonamide

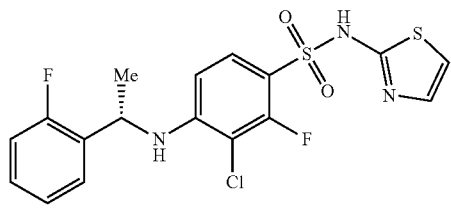 [SMILES: C[C@H](Nc1ccc(S(=O)(=O)Nc2nccs2)c(F)c1Cl)c1ccccc1F]

To a solution of (S)-3-chloro-N-(2,4-dimethoxybenzyl)-2-fluoro-4-((1-(2-fluorophenyl)ethyl) amino)-N-(thiazol-2-yl)benzenesulfonamide (0.352 g, 0.607 mmol) in dichloromethane (4 mL) was added trifluoroacetic acid (0.140 mL, 1.82 mmol) and the reaction mixture was stirred at ambient temperature for 30 minutes. After concentration in vacuo, the reaction mixture was diluted with methanol (20 mL) and stirred at ambient temperature for 1 h. The precipitate was removed by filtration and washed with methanol (2×15 mL). The combined filtrate was concentrated in vacuo and the residue was triturated in diethyl ether (10 mL) to provide the title compound as a pale yellow solid (0.123 g, 47% yield): $^1$H NMR (300 MHz, DMSO-$d_6$) δ 12.76 (br s, 1H), 7.46 (t, J=8.5 Hz, 1H), 7.38 (dt, J=7.8, 1.7 Hz, 1H), 7.32-7.11 (m, 4H), 6.81 (d, J=4.6 Hz, 1H), 6.52 (d, J=7.6 Hz, 1H), 6.32 (d, J=9.2 Hz, 1H), 4.99-4.89 (m, 1H), 1.56 (d, J=6.7 Hz, 3H); MS (ES+) m/z 430.0 (M+1), 432.0 (M+1).

Example 10

Synthesis of (S)-3-chloro-2-fluoro-4-(1-(2-fluorophenyl)ethoxy)-N-(thiazol-2-yl)benzenesulfonamide

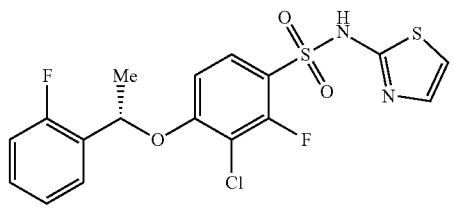 [SMILES: C[C@H](Oc1ccc(S(=O)(=O)Nc2nccs2)c(F)c1Cl)c1ccccc1F]

Step 1. Preparation of (S)-3-chloro-N-(2,4-dimethoxybenzyl)-2-fluoro-4-(1-(2-fluorophenyl)ethoxy)-N-(thiazol-2-yl)benzenesulfonamide

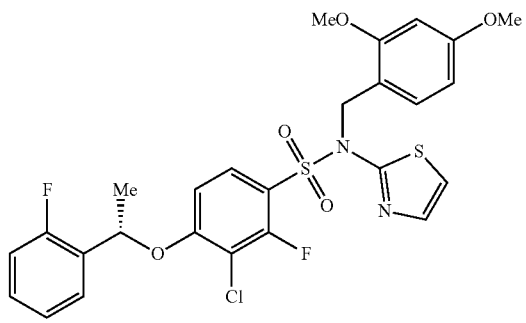 [SMILES: COc1ccc(CN(c2nccs2)S(=O)(=O)c2ccc(O[C@@H](C)c3ccccc3F)c(Cl)c2F)c(OC)c1]

To a solution of 3-chloro-N-(2,4-dimethoxybenzyl)-2,4-difluoro-N-(thiazol-2-yl)benzenesulfonamide (0.250 g, 0.56 mmol) and (S)-1-(2-fluorophenyl)ethan-1-ol (0.075 g, 0.540 mmol) in anhydrous N,N-dimethylformamide (5 mL) was added sodium hydride (60% dispersion in mineral oil, 0.043 g, 1.08 mmol) at 0° C. The reaction was allowed to warm to ambient temperature and stirred for 2 h. The reaction was diluted with ethyl acetate (50 mL) and saturated aqueous ammonium chloride solution (30 mL), and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by column chromatography eluting with a gradient of 0 to 40% of ethyl acetate in hexanes provided the title compound as a yellow oil (0.250 g, 80% yield): $^1$H NMR (300 MHz, CDCl$_3$) δ 7.65-7.59 (m, 1H), 7.41-7.36 (m, 2H), 7.33-7.25 (m, 2H), 7.18-7.04 (m, 2H), 6.95 (dd, J=3.6, 1.4, 1H), 6.60-6.57 (m, 1H), 6.37-6.31 (m, 2H), 5.79-5.72 (m, 1H), 5.18 (s, 2H), 3.75 (d, J=1.3 Hz, 3H), 3.69 (d, J=1.2 Hz, 3H), 1.72 (d, J=6.4 Hz, 3H); MS (ES+) m/z 581.1 (M+1), 583.1 (M+1).

Step 2. Preparation of (S)-3-chloro-2-fluoro-4-(1-(2-fluorophenyl)ethoxy)-N-(thiazol-2-yl)benzenesulfonamide

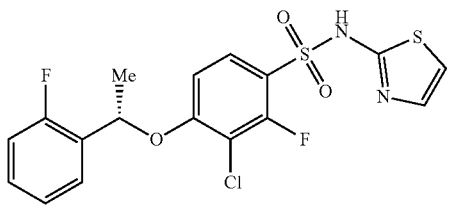 [SMILES: C[C@H](Oc1ccc(S(=O)(=O)Nc2nccs2)c(F)c1Cl)c1ccccc1F]

Following the procedure as described for EXAMPLE 9, Step 3 and making non critical variations as a required to replace (S)-3-chloro-N-(2,4-dimethoxybenzyl)-2-fluoro-4-((1-(2-fluorophenyl)ethyl) amino)-N-(thiazol-2-yl)benzenesulfonamide with (S)-3-chloro-N-(2,4-dimethoxybenzyl)-2-fluoro-4-(1-(2-fluorophenyl) ethoxy)-N-(thiazol-2-yl) benzenesulfonamide, the title compound was obtained as a ??? (0.029 g, 16% yield); $^1$H NMR (300 MHz, DMSO-$d_6$) δ 12.93 (br s, 1H), 7.71-7.65 (m, 1H), 7.46-7.18 (m, 5H), 7.02 (d, J=9.0 Hz, 1H), 6.87 (d, J=4.6 Hz, 1H), 5.98-5.92 (m, 1H), 1.64 (d, J=6.3 Hz, 3H); $^{19}$F NMR (282 MHz, DMSO-$d_6$) δ −108.9 (s, 1F), −118.5 (s, 1F); MS (ES+) m/z 431.0 (M+1), 433.0 (M+1).

Example 11

Synthesis of 5-chloro-2-fluoro-4-(isoquinolin-8-ylmethoxy)-N-(thiazol-2-yl)benzenesulfonamide

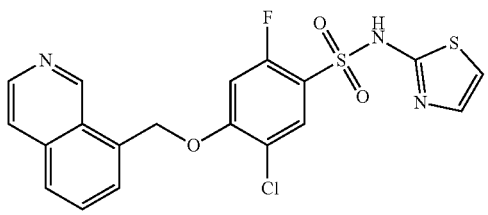 [SMILES: O=S(=O)(Nc1nccs1)c1cc(Cl)c(OCc2cccc3ccncc23)cc1F]

Step 1. Preparation of 5-chloro-N-(2,4-dimethoxybenzyl)-2-fluoro-4-(isoquinolin-8-ylmethoxy)-N-(thiazol-2-yl)benzenesulfonamide

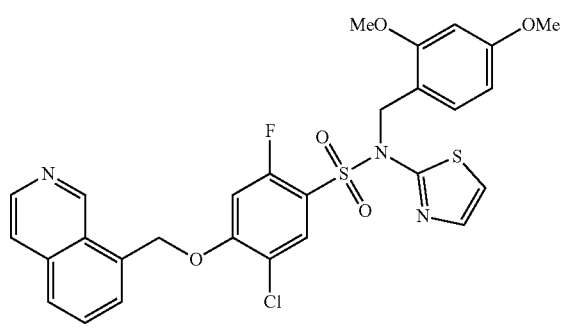 [SMILES: COc1ccc(CN(c2nccs2)S(=O)(=O)c2cc(Cl)c(OCc3cccc4ccncc34)cc2F)c(OC)c1]

To a suspension of 5-chloro-N-(2,4-dimethoxybenzyl)-2,4-difluoro-N-(thiazol-2-yl)benzenesulfonamide (0.475 g, 1.03 mmol) and isoquinolin-8-ylmethanol (0.164 g, 1.03 mmol) in anhydrous dimethyl sulfoxide (5 mL) was added cesium carbonate (0.671 g, 2.06 mmol). The reaction mixture was stirred at ambient temperature for 16 h and then heated at 75° C. for 4 h. The reaction mixture was allowed to cool to ambient temperature, diluted with ethyl acetate (50 mL) and water (20 mL), and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by column chromatography eluting with a gradient of 0 to 40% of ethyl acetate in hexanes provided the title compound as beige solid (0.106 g, 17% yield): MS (ES+) m/z 600.1 (M+1), 602.1 (M+1).

Step 2. Preparation of 5-chloro-2-fluoro-4-(isoquinolin-8-ylmethoxy)-N-(thiazol-2-yl)benzenesulfonamide

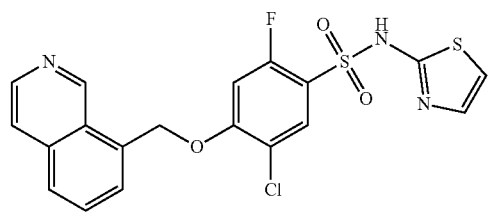 [SMILES: O=S(=O)(Nc1nccs1)c1cc(Cl)c(OCc2cccc3ccncc23)cc1F]

Following the procedure as described for EXAMPLE 9, Step 3 and making non critical variations as a required to replace (S)-3-chloro-N-(2,4-dimethoxybenzyl)-2-fluoro-4-((1-(2-fluorophenyl)ethyl) amino)-N-(thiazol-2-yl)benzenesulfonamide with 5-chloro-N-(2,4-dimethoxybenzyl)-2-fluoro-4-(isoquinolin-8-ylmethoxy)-N-(thiazol-2-yl)benzenesulfonamide, the title compound was obtained as ??? (0.074 g, 90% yield): $^1$H NMR (300 MHz, DMSO-$d_6$) δ 13.01 (br s, 1H), 9.78 (s, 1H), 8.69 (d, J=6.0 Hz, 1H), 8.25 (d, J=6.0 Hz, 1H), 8.19 (dd, J=7.4, 1.6 Hz, 1H), 8.07-7.98 (m, 2H), 7.82 (d, J=7.4 Hz, 1H), 7.67 (d, J=11.8 Hz, 1H), 7.33 (d, J=4.6 Hz, 1H), 6.90 (d, J=4.6 Hz, 1H), 5.90 (s, 2H); $^{19}$F NMR (282 MHz, DMSO-$d_6$) δ −74.46 (s); MS (ES+) m/z 450.0 (M+1), 452.0 (M+1).

Example 12

Synthesis of (S)-5-chloro-2-fluoro-4-((1-(isoquinolin-8-yl)ethyl)amino)-N-(thiazol-2-yl)benzenesulfonamide

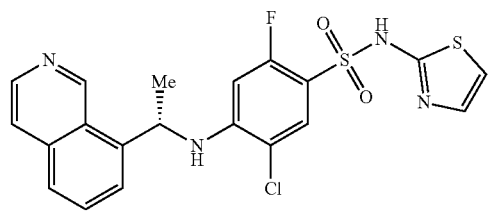 [SMILES: C[C@H](Nc1cc(F)c(S(=O)(=O)Nc2nccs2)cc1Cl)c1cccc2ccncc12]

Step 1. Preparation of (R)—N-(isoquinolin-8-ylmethylene)-2-methylpropane-2-sulfinamide

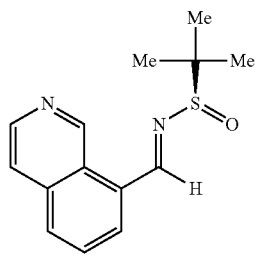 [SMILES: CC(C)(C)[S@@](=O)/N=C/c1cccc2ccncc12]

To a solution of isoquinoline-8-carbaldehyde (1.00 g, 6.36 mmol) and (R)-2-methylpropane-2-sulfinamide (0.700 g, 5.78 mmol) in anhydrous tetrahydrofuran (11 mL) was added titanium(IV)ethoxide (2.42 mL, 11.56 mmol) and the reaction mixture was stirred at ambient temperature for 4 h. The reaction mixture was diluted with brine (20 mL) and the resulting suspension was stirred for how long 15 minute. The suspension was filtered through a bed of Celite and the filter bed was washed with ethyl acetate (2×20 mL). The filtrate was washed with brine (2×20 mL) and the combined aqueous layers were extracted with ethyl acetate (2×50 mL). The combined organic layers were dried over magnesium sulfate, and filtered. The filtrate was concentrated in vacuo and the residue was triturated with diethyl ether (20 mL) to provide the title compound as a yellowish solid (1.52 g, quantitative yield): MS (ES+) m/z 261.3 (M+1).

Step 2. Preparation of (R)—N—((S)-1-(isoquinolin-8-yl)ethyl)-2-methylpropane-2-sulfinamide

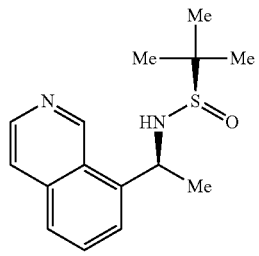 [SMILES: C[C@H](N[S@](=O)C(C)(C)C)c1cccc2ccncc12]

To a solution of (R)—N-(isoquinolin-8-ylmethylene)-2-methylpropane-2-sulfinamide (0.414 g, 1.59 mmol) in anhydrous dichloromethane (10 mL) was added a 3 M solution of methylmagnesium bromide in diethyl ether (1.23 mL, 3.69 mmol) at −45° C. The reaction mixture was allowed to warm to ambient temperature and stirred for 16 h. The reaction was quenched by addition of with saturated aqueous ammonium chloride solution (15 mL) and diluted with water (50 mL). The aqueous layer was extracted with dichloromethane (3×50 mL) and the combined organic layers were dried over anhydrous sodium sulfate and filtered. Concentration of the filtrate in vacuo and purification of the residue by column chromatography eluting with a gradient of 0 to 5% of methanol in dichloromethane provided the title compound in 67% diastereomeric excess (as determined by $^1$H NMR) as a yellow solid (0.361 g, 82% yield). Data for major diastereomer: $^1$H NMR (300 MHz, CDCl$_3$) δ 9.69 (s, 1H), 8.55 (d, J=5.7 Hz, 1H), 7.79-7.74 (m, 1H), 7.70-7.66 (m, 3H), 5.41 (dd, J=6.8, 4.7 Hz, 1H), 3.47 (d, J=4.5 Hz, 1H), 1.80 (d, J=6.8 Hz, 3H), 1.20 (s, 9H); MS (ES+) m/z 277.2 (M+1).

Step 3. Preparation of (S)-1-(isoquinolin-8-yl)ethan-1-amine hydrochloride

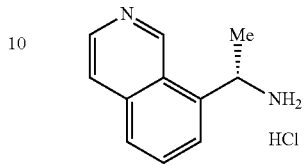

To a solution of (R)—N—((S)-1-(isoquinolin-8-yl)ethyl)-2-methylpropane-2-sulfinamide (0.361 g, 1.31 mmol) in methanol (15 mL) was added a 4 M solution of hydrogen chloride in dioxane (5 mL, 20.0 mmol) and the reaction mixture was stirred at ambient temperature for 2 h. The reaction was concentrated in vacuo and the residue was triturated with diethyl ether (amount) to provide the title compound as a pale yellow solid (0.247 g, 90% yield): $^1$H NMR (300 MHz, DMSO-d$_6$) δ 10.13 (s, 1H), 8.73 (d, J=6.3 Hz, 1H), 8.49 (d, J=6.3 Hz, 1H), 8.33-8.20 (m, 3H), 5.61-5.53 (m, 1H), 1.71 (d, J=6.7 Hz, 3H), exchangeable protons not observed; MS (ES+) m/z 173.2.

Step 4. Preparation of (S)-5-chloro-2-fluoro-4-((1-(isoquinolin-8-yl)ethyl)amino)-N-(thiazol-4-yl)benzenesulfonamide

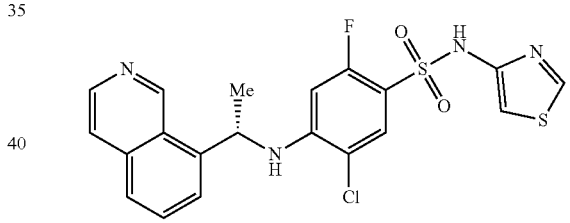

To a suspension of tert-butyl ((5-chloro-2,4-difluorophenyl)sulfonyl)(thiazol-4-yl)carbamate (0.225 g, 0.548 mmol) and (S)-1-(isoquinolin-8-yl)ethan-1-amine hydrochloride (0.106 g, 0.508 mmol) in anhydrous dimethyl sulfoxide was added potassium carbonate (0.210 g, 1.52 mmol) and the reaction mixture was headed at 80° C. for 48 h. The reaction mixture was allowed to cool to ambient temperature and diluted with ethyl acetate (50 mL) and saturated aqueous ammonium chloride solution (20 mL). The aqueous phase was extracted with ethyl acetate (3×50 mL). The combined organic phase was washed with brine (3×20 mL), dried over anhydrous sodium sulfate, and filtered. Concentration of the filtrate in vacuo and purification of the residue by reverse-phase HPLC, eluting with acetonitrile in water containing 0.1% trifluoroacetic acid, provided the title compound as a colorless solid (0.050 g, 21% yield): $^1$H NMR (300 MHz, DMSO-d$_6$) δ 11.11 (br s, 1H), 9.99 (s, 1H), 8.85 (d, J=2.2 Hz, 1H), 8.70 (d, J=6.2 Hz, 1H), 8.36 (d, J=6.2 Hz, 1H), 8.12 (d, J=8.1 Hz, 1H), 8.04-7.97 (m, 1H), 7.82 (d, J=7.0 Hz, 1H), 7.64 (d, J=7.4 Hz, 1H), 7.01-6.95 (m, 2H), 6.42 (d, J=13.1 Hz, 1H), 5.75-5.66 (m, 1H), 1.70 (d, J=6.7 Hz, 3H); $^{19}$F NMR (282 MHz, DMSO-d$_6$) δ−74.4 (s); MS (ES+) m/z 463.0 (M+1), 465.0 (M+1).

Example 13

Synthesis of (R)-5-chloro-2-fluoro-4-((1-(isoquinolin-8-yl)ethyl)amino)-N-(thiazol-2-yl)benzenesulfonamide

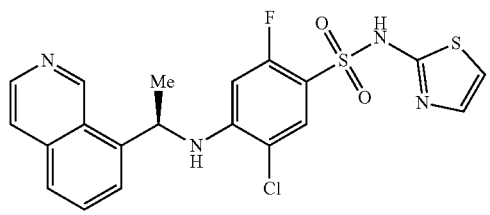 [SMILES: C[C@@H](Nc1cc(F)c(S(=O)(=O)Nc2nccs2)cc1Cl)c1cccc2ccncc12]

Step 1. Preparation of (S)—N-(isoquinolin-8-ylmethylene)-2-methylpropane-2-sulfinamide

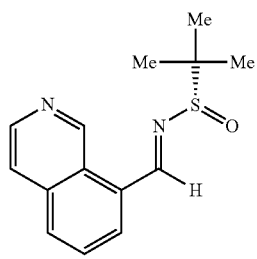 [SMILES: CC(C)(C)[S@](=O)/N=C/c1cccc2ccncc12]

Following the procedure as described for EXAMPLE 12, Step 1 and making non-critical variations as required to replace (R)-2-methylpropane-2-sulfinamide with (S)-2-methylpropane-2-sulfinamide (0.700 g, 5.78 mmol), the title compound was obtained as a yellow solid (1.36 g, 90% yield): MS (ES+) m/z 261.3.

Step 1. Preparation of (S)—N—((R)-1-(isoquinolin-8-yl)ethyl)-2-methylpropane-2-sulfinamide

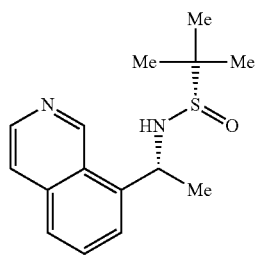 [SMILES: C[C@@H](N[S@@](=O)C(C)(C)C)c1cccc2ccncc12]

Following the procedure as described for EXAMPLE 12, Step 2 and making non-critical variations as required to replace (R)—N-(isoquinolin-8-ylmethylene)-2-methylpropane-2-sulfinamide with (S)—N-(isoquinolin-8-ylmethylene)-2-methylpropane-2-sulfinamide, the title compound was obtained in 67% diastereomeric excess (as determined by $^1$H NMR) as a yellow solid (0.498 g, 89% yield): $^1$H NMR (300 MHz, CDCl$_3$) δ 9.69 (s, 1H), 8.55 (d, J=5.6 Hz, 1H), 7.77 (dd, J=4.0, 5.4 Hz, 1H), 7.69-7.66 (m, 3H), 5.41 (dd, J=4.6, 6.8 Hz, 1H), 3.47 (d, J=4.5 Hz, 1H), 1.80 (d, J=6.8 Hz, 3H), 1.20 (s, 9H); MS (ES+) m/z 277.2 (M+1).

Step 3. Preparation of (R)-1-(isoquinolin-8-yl)ethan-1-amine hydrochloride

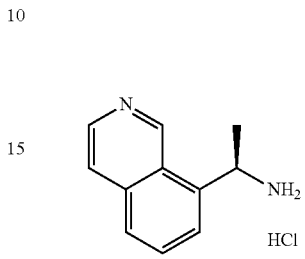

Following the procedure as described for EXAMPLE 12, Step 3 and making non-critical variations as required to replace (R)—N—((S)-1-(isoquinolin-8-yl)ethyl)-2-methylpropane-2-sulfinamide with (S)—N—((R)-1-(isoquinolin-8-yl)ethyl)-2-methylpropane-2-sulfinamide, the title compound was obtained as ??? (0.360 g, 96% yield): $^1$H NMR (300 MHz, DMSO-d$_6$) δ 10.10 (s, 1H), 8.73 (d, J=6.3 Hz, 1H), 8.46 (d, J=6.3 Hz, 1H), 8.31-8.18 (m, 3H), 5.60-5.52 (m, 1H), 1.70 (d, J=6.7 Hz, 3H), exchangeable protons not observed; MS (ES+) m/z 173.2.

Step 4. Preparation of (R)-5-chloro-2-fluoro-4-((1-(isoquinolin-8-yl)ethyl)amino)-N-(thiazol-4-yl)benzenesulfonamide

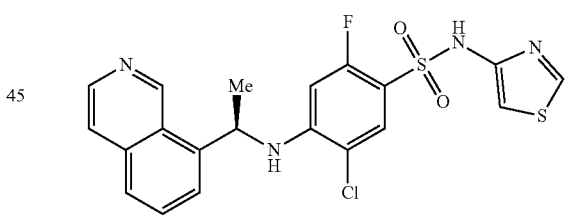

Following the procedure as described for EXAMPLE 12, Step 2 and making non-critical variations as required to replace (S)-1-(isoquinolin-8-yl)ethan-1-amine hydrochloride with (R)-1-(isoquinolin-8-yl)ethan-1-amine hydrochloride, the title compound was obtained as a colorless solid (0.096 g, 20% yield): $^1$H NMR (300 MHz, DMSO-d$_6$) δ 11.10 (br s, 1H), 9.95 (s, 1H), 8.85 (d, J=2.2 Hz, 1H), 8.68 (d, J=6.1 Hz, 1H), 8.30 (d, J=6.2 Hz, 1H), 8.09 (d, J=8.1 Hz, 1H), 8.01-7.93 (m, 1H), 7.79 (d, J=7.2 Hz, 1H), 7.64 (d, J=7.4 Hz, 1H), 6.98-6.96 (m, 2H), 6.41 (d, J=13.2 Hz, 1H), 5.75-5.66 (m, 1H), 1.70 (d, J=6.7 Hz, 3H); $^{19}$F NMR (282 MHz, DMSO-d$_6$) δ −74.3 (s); MS (ES+) m/z 463.0 (M+1), 465.0 (M+1).

Example 14

Synthesis of (S)-5-chloro-4-((1-(4-chlorophenyl)ethyl)amino)-2-fluoro-N-(thiazol-2-yl)benzenesulfonamide

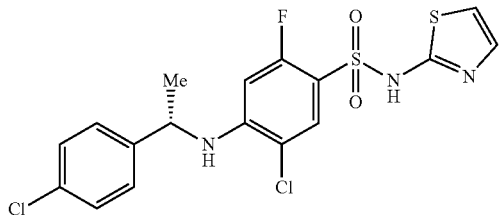 [SMILES: C[C@H](Nc1cc(F)c(S(=O)(=O)Nc2nccs2)cc1Cl)c1ccc(Cl)cc1]

Step 1. Preparation of (S)-5-chloro-4-((1-(4-chlorophenyl)ethyl)amino)-N-(2,4-dimethoxybenzyl)-2-fluoro-N-(thiazol-2-yl)benzenesulfonamide

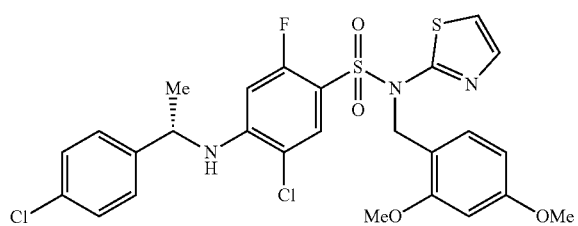 [SMILES: COc1ccc(CN(c2nccs2)S(=O)(=O)c2cc(Cl)c(N[C@@H](C)c3ccc(Cl)cc3)cc2F)c(OC)c1]

To a mixture of 5-chloro-N-(2,4-dimethoxybenzyl)-2,4-difluoro-N-(thiazol-2-yl)benzenesulfonamide (0.35 g, 0.76 mmol) and (S)-1-(4-chlorophenyl)ethylamine (0.107 mL, 0.76 mmol) in anhydrous dimethyl sulfoxide (4 mL) was added potassium carbonate (0.210 g, 1.52 mmol) and the reaction mixture was heated at 75° C. for 16 h. The reaction mixture was allowed cooled to ambient temperature, diluted with saturated aqueous ammonium chloride solution (20 mL), and extracted with ethyl acetate (3×30 mL). The combined organic layers were washed with water (40 mL), brine (40 mL), dried over anhydrous magnesium sulfate, and filtered. Concentration in vacuo and purification of the residue by column chromatography, eluting with 0% to 50% of ethyl acetate in hexanes, afforded the title compound as a colorless solid (0.16 g, 35% yield): MS (ES+) m/z 596.1 (M+1), 598.1 (M+1).

Step 2. Preparation of (S)-5-chloro-4-((1-(4-chlorophenyl)ethyl)amino)-2-fluoro-N-(thiazol-2-yl)benzenesulfonamide

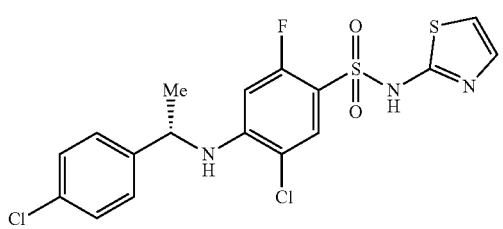 [SMILES: C[C@H](Nc1cc(F)c(S(=O)(=O)Nc2nccs2)cc1Cl)c1ccc(Cl)cc1]

To a solution of (S)-5-chloro-4-((1-(4-chlorophenyl)ethyl)amino)-N-(2,4-dimethoxybenzyl)-2-fluoro-N-(thiazol-2-yl)benzenesulfonamide (0.16 g, 0.27 mmol) in anhydrous dichloromethane (5 mL) was added trifluoroacetic acid (62 µL, 0.81 mmol) at 0° C. The reaction mixture was stirred at 0° C. for 30 minutes and concentrated in vacuo. The residue was purified by column chromatography, eluting with 0% to 35% of acetone in hexanes, to afford the title compound as colorless solid (0.089 g, 74% yield): $^1$H NMR (300 MHz, DMSO-$d_6$) δ 12.75 (s, 1H), 7.58 (d, J=7.3 Hz, 1H), 7.44-7.35 (m, 4H), 7.25 (d, J=4.6 Hz, 1H), 6.81 (d, J=4.6 Hz, 1H), 6.58-6.53 (m, 1H), 6.40 (d, J=13.2 Hz, 1H), 4.77-4.67 (m, 1H), 1.51 (d, J=6.7 Hz, 3H); MS (ES+) m/z 446.0 (M+1), 448.0 (M+1).

Example 15

Synthesis of (S)-5-chloro-2-fluoro-4-((1-(naphthalen-2-yl)ethyl)amino)-N-(thiazol-2-yl)benzenesulfonamide

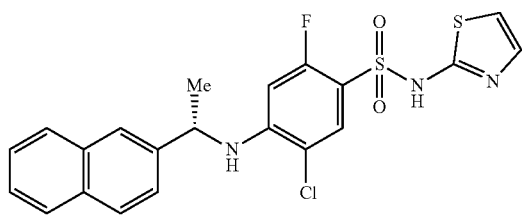 [SMILES: C[C@H](Nc1cc(F)c(S(=O)(=O)Nc2nccs2)cc1Cl)c1ccc2ccccc2c1]

Step 1. Preparation of (S)-5-chloro-N-(2,4-dimethoxybenzyl)-2-fluoro-4-((1-(naphthalen-2-yl)ethyl)amino)-N-(thiazol-2-yl)benzenesulfonamide

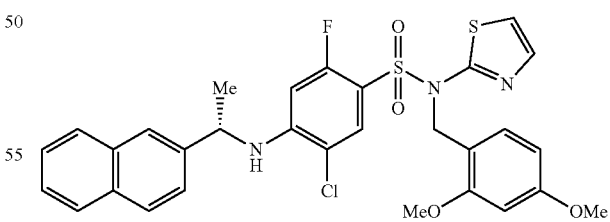

Following the procedure as described in EXAMPLE 14, Step 1 and making non-critical variations as required to replace (S)-1-(4-chlorophenyl)ethylamine with (S)-1-(naphthalen-2-yl)ethan-1-amine, the title compound was obtained as a colorless solid (0.16 g, 34% yield): MS (ES+) m/z 612.2 (M+1), 614.1 (M+1).

Step 2. Preparation of (S)-5-chloro-2-fluoro-4-((1-(naphthalen-2-yl)ethyl)amino)-N-(thiazol-2-yl)benzenesulfonamide

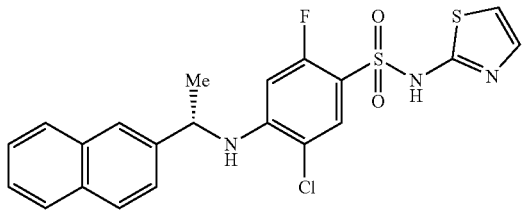 [SMILES: C[C@H](Nc1cc(F)c(S(=O)(=O)Nc2nccs2)cc1Cl)c1ccc2ccccc2c1]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)-5-chloro-N-(2,4-dimethoxybenzyl)-2-fluoro-4-((1-(naphthalen-2-yl)ethyl)amino)-N-(thiazol-2-yl)benzenesulfonamide, the title compound was obtained as a colorless solid (0.087 g, 73% yield): $^1$HNMR (300 MHz; DMSO-$d_6$) δ 12.70 (s, 1H), 7.91-7.83 (m, 4H), 7.61-7.56 (m, 2H), 7.52-7.44 (m, 2H), 7.22-7.20 (m, 1H), 6.80-6.78 (m, 1H), 6.64-6.60 (m, 1H), 6.46 (d, J=13.2 Hz, 1H), 4.91-4.83 (m, 1H), 1.61 (d, J=6.8 Hz, 3H); MS (ES+) m/z 462.1 (M+1), 464.1 (M+1).

Example 16

Synthesis of 4-((2-(azetidin-1-ylmethyl)benzyl)amino)-5-chloro-2-fluoro-N-(thiazol-2-yl)benzenesulfonamide 2,2,2-trifluoroacetate

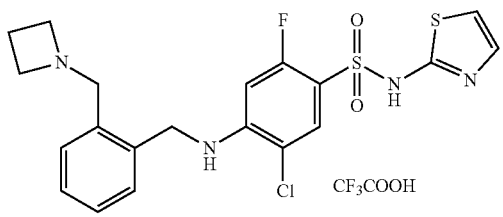

Step 1. Preparation of 2-(azetidin-1-ylmethyl)benzonitrile

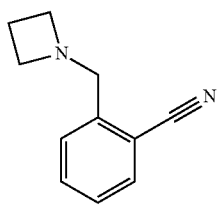 [SMILES: N#Cc1ccccc1CN1CCC1]

To a solution of 2-(bromomethyl)benzonitrile (1.8 g, 8.16 mmol) and azetidine (0.466 g, 8.16 mmol) in anhydrous dichloromethane (60 mL) was added N,N-diisopropylethylamine (1.78 mL, 10.2 mmol) at 0° C. The reaction mixture was allowed to warm to ambient temperature and stirred for 16 h. The reaction mixture was diluted with saturated aqueous ammonium chloride solution (20 mL) and extracted with dichloromethane (3×40 mL). The combined organic layers were washed with brine (80 mL), dried over anhydrous magnesium sulfate, and filtered. Concentration of the filtrate in vacuo and purification of the residue by column chromatography, eluting with 0% to 20% of methanol in dichloromethane, afforded the title compound as a pale yellow oil (0.61 g, 43% yield): MS (ES+) m/z 173.2 (M+1).

Step 2. Preparation of (2-(azetidin-1-ylmethyl)phenyl)methanamine

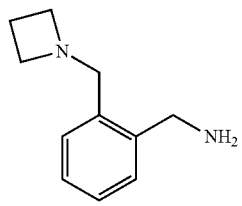 [SMILES: NCc1ccccc1CN1CCC1]

To a solution of 2-(azetidin-1-ylmethyl)benzonitrile (0.6 g, 3.46 mmol) in anhydrous tetrahydrofuran (35 mL) was added a 1 M of solution of lithium aluminum hydride in tetrahydrofuran (5.2 mL, 5.2 mmol) at 0° C. The reaction mixture was stirred at 0° C. for 3 h and sodium sulfate decahydrate (5 g) was added in small portions. The mixture was stirred at 0° C. for 30 minutes and then at ambient temperature for 1 h. The mixture was filtered and the filtrate was dried over anhydrous magnesium sulfate. Filtration and concentration of the filtrate in vacuo afforded the title compound as a pale brown oil (0.55 g, 90% yield): MS (ES+) m/z 177.2 (M+1).

Step 3. Preparation of 4-((2-(azetidin-1-ylmethyl)benzyl)amino)-5-chloro-N-(2,4-dimethoxybenzyl)-2-fluoro-N-(thiazol-2-yl)benzenesulfonamide

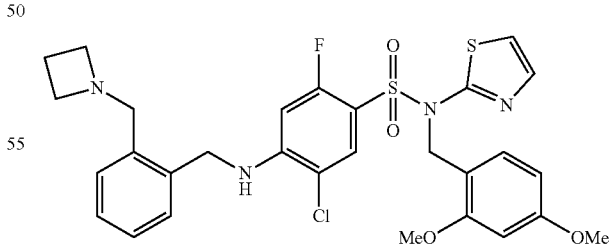

Following the procedure as described in EXAMPLE 14, Step 1 and making non-critical variations as required to replace (S)-1-(4-chlorophenyl)ethylamine with (2-(azetidin-1-ylmethyl)phenyl)methanamine, the title compound was obtained as a colorless solid (0.07 g, 15% yield): MS (ES+) m/z 617.1 (M+1), 619.1 (M+1).

Step 4. Preparation of 4-((2-(azetidin-1-ylmethyl)
benzyl)amino)-5-chloro-2-fluoro-N-(thiazol-2-yl)
benzenesulfonamide 2,2,2-trifluoroacetate

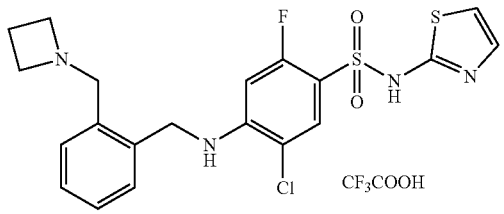

Following the procedure as described in EXAMPLE 1, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with 4-((2-(azetidin-1-ylmethyl)benzyl)amino)-5-chloro-N-(2,4-dimethoxybenzyl)-2-fluoro-N-(thiazol-2-yl)benzenesulfonamide, the title compound was obtained as a colorless solid (0.014 g, 27% yield): $^1$H NMR (300 MHz, DMSO-$d_6$) δ 12.78 (s, 1H), 9.97 (s, 1H), 7.63 (d, J=7.3 Hz, 1H), 7.44-7.31 (m, 3H), 7.27-7.25 (m, 2H), 7.11-7.03 (m, 1H), 6.83 (d, J=4.6 Hz, 1H), 6.48 (d, J=12.9 Hz, 1H), 4.58-4.49 (m, 4H), 4.22-4.01 (m, 4H), 2.45-2.25 (m, 2H); MS (ES+) m/z 467.0 (M+1), 469.0 (M+1).

Example 17

Synthesis of 5-chloro-4-((2-cyanobenzyl)amino)-2-fluoro-N-(thiazol-2-yl)benzenesulfonamide

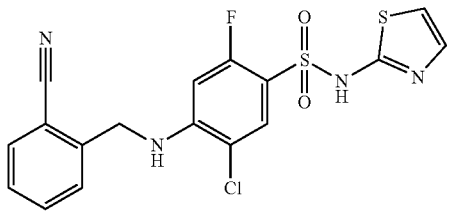 [SMILES: N#Cc1ccccc1CNc1cc(F)c(S(=O)(=O)Nc2nccs2)cc1Cl]

Step 1. Preparation of 5-chloro-4-((2-cyanobenzyl)amino)-N-(2,4-dimethoxybenzyl)-2-fluoro-N-(thiazol-2-yl)benzenesulfonamide

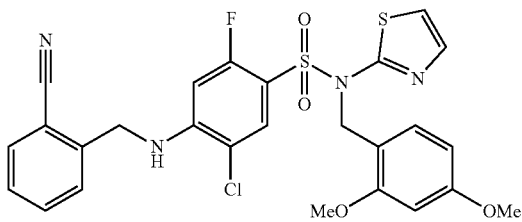 [SMILES: COc1ccc(CN(c2nccs2)S(=O)(=O)c2cc(Cl)c(NCc3ccccc3C#N)cc2F)c(OC)c1]

Following the procedure as described for EXAMPLE 14, Step 3 and making non-critical variations as required to replace (S)-1-(4-chlorophenyl)ethylamine with 2-(aminomethyl)benzonitrile hydrochloride, the title compound was obtained as a colorless solid (0.33 g, 66% yield): MS (ES+) m/z 573.0 (M+1), 575.0 (M+1).

Step 2. Preparation of 5-chloro-4-((2-cyanobenzyl)amino)-2-fluoro-N-(thiazol-2-yl)benzenesulfonamide

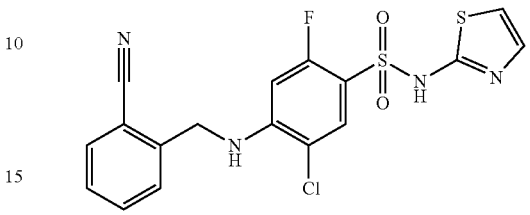

Following the procedure as described in EXAMPLE 1, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with 5-chloro-4-((2-cyanobenzyl)amino)-N-(2,4-dimethoxybenzyl)-2-fluoro-N-(thiazol-2-yl)benzenesulfonamide, the title compound was obtained as a colorless solid (0.065 g, 29% yield): $^1$H NMR (300 MHz, DMSO-$d_6$) δ 12.78 (s, 1H), 7.86 (dd, J=7.7, 1.2 Hz, 1H), 7.69-7.62 (m, 2H), 7.50-7.42 (m, 1H), 7.38-7.33 (m, 1H), 7.26 (d, J=4.6 Hz, 1H), 7.19-7.13 (m, 1H), 6.83 (d, J=4.6 Hz, 1H), 6.52 (d, J=12.8 Hz, 1H), 4.69-4.63 (m, 2H); MS (ES+) m/z 423.0 (M+1), 425.0 (M+1).

Example 18

Synthesis of 5-chloro-2-fluoro-4-((1-phenylcyclobutyl)amino)-N-(thiazol-4-yl)benzenesulfonamide

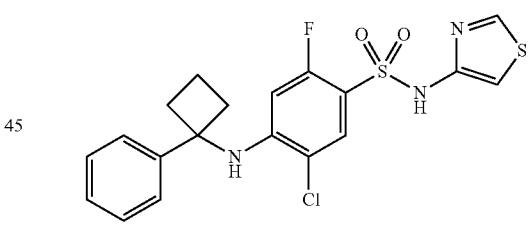

To a mixture of 1-phenylcyclobutan-1-amine hydrochloride (0.16 g 0.87 mmol) and tert-butyl ((5-chloro-2,4-difluorophenyl)sulfonyl)(thiazol-4-yl)carbamate (0.358 g, 0.87 mmol) in anhydrous dimethyl sulfoxide (4 mL) was added potassium carbonate (0.240 g, 1.74 mmol) and the reaction mixture was heated at 75° C. for 24 h. The reaction mixture was allowed to cool to ambient temperature, diluted with saturated aqueous ammonium chloride solution (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with 0% to 35% of acetone in hexanes, afforded the title compound as a colorless solid (0.067 g, 19% yield): $^1$H NMR (300 MHz, CDCl$_3$) δ 9.56 (s, 1H), 8.62 (s, 1H), 7.75-7.71 (m, 1H), 7.42-7.30 (m, 4H), 7.28-7.22 (m, 1H), 6.92-6.87 (m, 1H), 5.77-5.72 (m, 1H), 5.59 (s, 1H), 2.74-2.60 (m, 2H), 2.44-2.31 (m, 2H), 2.23-2.03 (m, 2H); MS (ES+) m/z 438.0 (M+1), 440.0 (M+1).

Example 19

Synthesis of 4-((2-(azetidin-1-ylmethyl)benzyl)amino)-5-chloro-2-fluoro-N-(thiazol-4-yl)benzenesulfonamide 2,2,2-trifluoroacetate

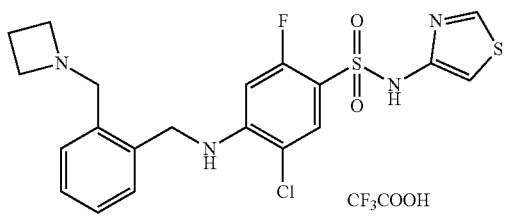 [SMILES: O=S(=O)(Nc1cscn1)c1cc(Cl)c(NCc2ccccc2CN2CCC2)cc1F ; "CF3COOH"]

Following the procedure as described for EXAMPLE 18 and making non-critical variations as required to replace 1-phenylcyclobutan-1-amine hydrochloride with (2-(azetidin-1-ylmethyl)phenyl)methanamine, the title compound was obtained as a colorless solid (0.02 g, 3% yield): $^1$H NMR (300 MHz; DMSO-d$_6$) δ 11.12 (s, 1H), 10.05 (s, 1H), 8.88 (d, J=2.2 Hz, 1H), 7.64 (d, J=7.4 Hz, 1H), 7.48-7.17 (m, 5H), 6.99 (d, J=2.1 Hz, 1H), 6.51 (d, J=13.0 Hz, 1H), 4.59-4.46 (m, 4H), 4.22-4.01 (m, 4H), 2.46-2.26 (m, 2H); MS (ES+) m/z 467.0 (M+1), 469.0 (M+1).

Example 20

Synthesis of 5-chloro-2-fluoro-4-((1-phenylcyclopropyl)amino)-N-(thiazol-4-yl)benzenesulfonamide

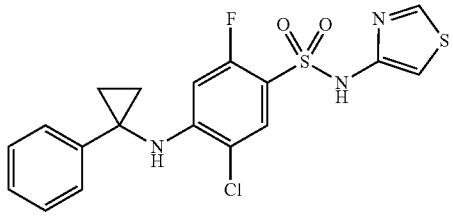 [SMILES: O=S(=O)(Nc1cscn1)c1cc(Cl)c(NC2(c3ccccc3)CC2)cc1F]

Following the procedure as described for EXAMPLE AZ5 and making non-critical variations as required to replace 1-phenylcyclobutan-1-amine hydrochloride with 1-phenylcyclopropan-1-amine, the title compound was obtained as a colorless solid (0.021 g, 2% yield): $^1$H NMR (300 MHz, CDCl$_3$) δ 9.78 (s, 1H), 8.70-8.63 (m, 1H), 7.76 (d, J=7.1 Hz, 1H), 7.33-7.24 (m, 2H), 7.23-7.16 (m, 1H), 7.05-7.00 (m, 2H), 6.92 (dd, J=4.2, 1.7 Hz, 1H), 6.43 (d, J=12.3 Hz, 1H), 5.69-5.64 (m, 1H), 1.45-1.27 (m, 4H); MS (ES+) m/z 424.1 (M+1), 426.0 (M+1).

Example 21

Synthesis of (S)-3,5-dichloro-4-((1-(2-fluorophenyl)ethyl)amino)-N-(thiazol-2-yl)benzenesulfonamide

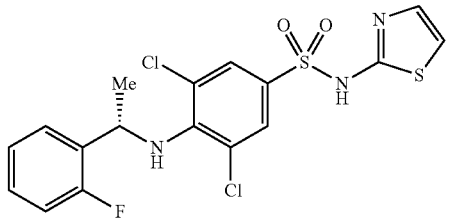 [SMILES: C[C@H](Nc1c(Cl)cc(S(=O)(=O)Nc2nccs2)cc1Cl)c1ccccc1F]

Step 1. Preparation of 3,5-dichloro-N-(2,4-dimethoxybenzyl)-4-fluoro-N-(thiazol-2-yl)benzenesulfonamide

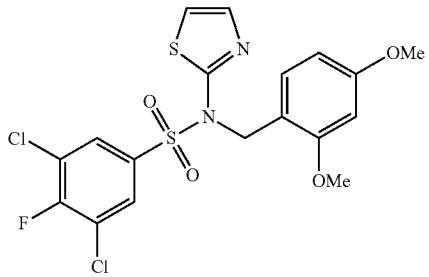 [SMILES: COc1ccc(CN(c2nccs2)S(=O)(=O)c2cc(Cl)c(F)c(Cl)c2)c(OC)c1]

To a mixture of N-(2,4-dimethoxybenzyl)thiazol-2-amine (8.60 g, 34.4 mmol, prepared according to WO 2013063459) in anhydrous tetrahydrofuran (100 mL) was added a 1 M solution of lithium bis(trimethylsilyl)amide in tetrahydrofuran (18.2 mL, 18.2 mmol) at −78° C. The reaction mixture was allowed to warm to ambient temperature and stirred for 1 h. The reaction mixture was cooled to −78° C., and 3,5-dichloro-4-fluorobenzenesulfonyl chloride (4.0 g, 15.2 mmol) was added to it. The reaction mixture was allowed to warm to ambient temperature and stirred for 16 h. The reaction mixture was quenched by addition of saturated ammonium chloride solution (50 mL) and diluted with ethyl acetate (300 mL). The organic phase was washed with brine (50 mL), dried over anhydrous sodium sulfate, and filtered. Concentration of the filtrate in vacuo and purification of the residue by column chromatography, eluting with a gradient of 0 to 50% of ethyl acetate in hexanes, and trituration with methanol (10 mL), provided the title compound as an off-white solid (5.5 g, 76% yield): $^1$H NMR (300 MHz, CDCl$_3$) δ 7.75 (dd, J=6.0 Hz, 2H), 7.50 (dd, J=3.6 Hz, 1H), 7.15 (d, J=8.0 Hz, 1H), 7.12 (dd, J=3.6 Hz, 1H), 6.40-6.34 (m, 2H), 5.07 (s, 2H), 3.79 (s, 3H), 3.68 (s, 3H).

Step 2. Preparation of (S)-3,5-dichloro-N-(2,4-dimethoxybenzyl)-4-((1-(2-fluorophenyl)ethyl)amino)-N-(thiazol-2-yl)benzenesulfonamide

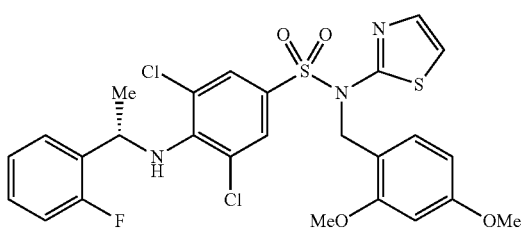 [SMILES: COc1ccc(CN(c2nccs2)S(=O)(=O)c2cc(Cl)c(N[C@@H](C)c3ccccc3F)c(Cl)c2)c(OC)c1]

Following the procedure as described in EXAMPLE 14, Step 1 and making non-critical variations as required to replace (S)-1-(4-chlorophenyl)ethylamine with (S)-1-(2-fluorophenyl)ethan-1-amine and 5-chloro-N-(2,4-dimethoxybenzyl)-2,4-difluoro-N-(thiazol-2-yl)benzenesulfonamide with 3,5-dichloro-N-(2,4-dimethoxybenzyl)-4-fluoro-N-(thiazol-2-yl)benzenesulfonamide, the title compound was obtained as a colorless solid (0.2 g, 41% yield): MS (ES+) m/z 596.1 (M+1), 598.1 (M+1).

Step 3. Preparation of (S)-3,5-dichloro-4-((1-(2-fluorophenyl)ethyl)amino)-N-(thiazol-2-yl)benzenesulfonamide

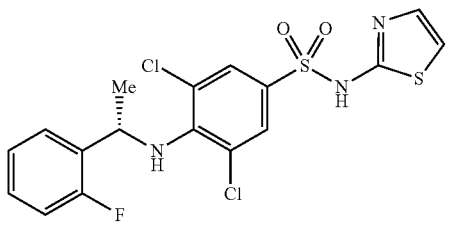 [SMILES: C[C@H](Nc1c(Cl)cc(S(=O)(=O)Nc2nccs2)cc1Cl)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)-3,5-dichloro-N-(2,4-dimethoxybenzyl)-4-((1-(2-fluorophenyl)ethyl)amino)-N-(thiazol-2-yl)benzenesulfonamide, the title compound was obtained as a colorless solid (0.085 g, 42% yield): $^1$H NMR (300 MHz; DMSO-d$_6$) δ 12.84 (s, 1H), 7.58 (s, 2H), 7.53-7.47 (m, 1H), 7.30-7.21 (m, 2H), 7.18-7.06 (m, 2H), 6.86 (d, J=4.5 Hz, 1H), 5.46-5.31 (m, 2H), 1.54 (d, J=6.4 Hz, 3H); MS (ES+) m/z 446.0 (M+1), 448.0 (M+1).

Example 22

Synthesis of (S)-5-chloro-2-fluoro-4-((1-(2-fluorophenyl)ethyl)amino)-N-(6-fluoropyridin-2-yl)benzenesulfonamide

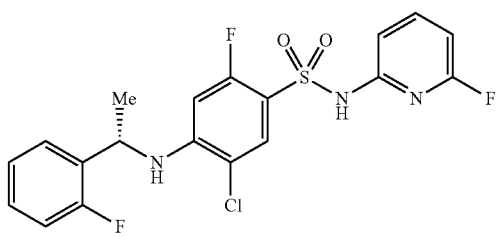 [SMILES: C[C@H](Nc1cc(F)c(S(=O)(=O)Nc2cccc(F)n2)cc1Cl)c1ccccc1F]

Step 1. Preparation of 5-chloro-N-(2,4-dimethoxybenzyl)-2,4-difluoro-N-(6-fluoropyridin-2-yl)benzenesulfonamide

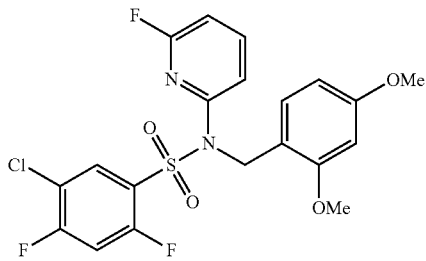 [SMILES: COc1ccc(CN(c2cccc(F)n2)S(=O)(=O)c2cc(Cl)c(F)cc2F)c(OC)c1]

To a solution of N-(2,4-dimethoxybenzyl)-6-fluoropyridin-2-amine (prepared according to WO2014066490, 20.00 g, 76.25 mmol) in anhydrous tetrahydrofuran (200 mL) was added a 1.6 M solution of methyl lithium in diethyl ether (66.7 mL, 106.7 mmol) dropwise at −78° C. The reaction mixture was allowed to warm to 0° C. and stirred for 30 minutes. The reaction mixture was cooled to −78° C. and a solution of 5-chloro-2,4-difluorobenzenesulfonyl chloride (33.9 g, 137.3 mmol) in anhydrous tetrahydrofuran (100 mL) was added dropwise to it. The reaction mixture was allowed to warm to ambient temperature and stirred for 12 h. The mixture was diluted with water (200 mL) and extracted with ethyl acetate (3×200 mL). The combined organic phase was washed with brine (50 mL), dried over anhydrous sodium sulfate, and filtered. Concentration of the filtrate in vacuo and trituration of the residue in a mixture of methanol and dichloromethane (20:1, 2×150 mL) provided the title compound as a colorless solid (12.1 g, 32% yield): $^1$H NMR (300 MHz, CDCl$_3$) δ 8.02 (t, J=8.0 Hz, 1H), 7.77-7.66 (m, 1H), 7.27-7.15 (m, 2H), 7.01 (t, J=8.0 Hz, 1H), 6.72 (dd, J=8.0, 2.8 Hz, 1H), 6.43-6.35 (m, 2H), 5.07 (s, 2H), 3.78 (s, 3H), 3.73 (s, 3H).

Step 2. Preparation of (S)-5-chloro-N-(2,4-dimethoxybenzyl)-2-fluoro-4-((1-(2-fluorophenyl)ethyl)amino)-N-(6-fluoropyridin-2-yl)benzenesulfonamide

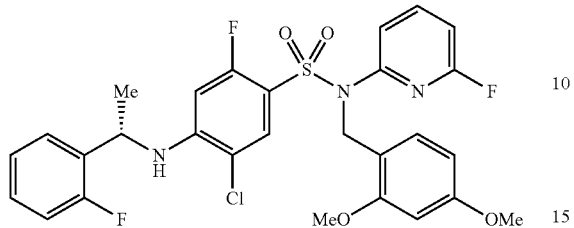

Following the procedure as described in EXAMPLE 14, Step 1 and making non-critical variations as required to replace (S)-1-(4-chlorophenyl)ethylamine with (S)-1-(2-fluorophenyl)ethan-1-amine and 5-chloro-N-(2,4-dimethoxybenzyl)-2,4-difluoro-N-(thiazol-2-yl)benzenesulfonamide with 5-chloro-N-(2,4-dimethoxybenzyl)-2,4-difluoro-N-(6-fluoropyridin-2-yl)benzenesulfonamide, the title compound was obtained as a colorless solid (0.34 g, 70% yield): MS (ES+) m/z 592.2 (M+1), 594.2 (M+1).

Step 3. Preparation of (S)-5-chloro-2-fluoro-4-((1-(2-fluorophenyl)ethyl)amino)-N-(6-fluoropyridin-2-yl)benzenesulfonamide

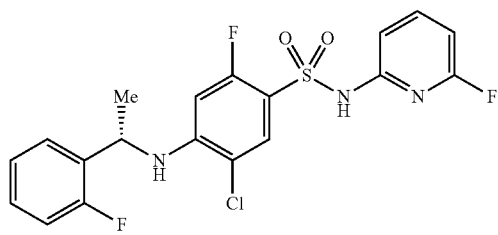

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)-5-chloro-N-(2,4-dimethoxybenzyl)-2-fluoro-4-((1-(2-fluorophenyl)ethyl)amino)-N-(6-fluoropyridin-2-yl)benzenesulfonamide, the title compound was obtained as a colorless solid (0.095 g, 38% yield): $^1$H NMR (300 MHz, DMSO-$d_6$) δ 11.50 (s, 1H), 7.86-7.74 (m, 2H), 7.43-7.37 (m, 1H), 7.33-7.25 (m, 1H), 7.22-7.12 (m, 2H), 6.83 (dd, J=7.9, 2.1 Hz, 1H), 6.74-6.68 (m, 2H), 6.34 (d, J=13.4 Hz, 1H), 4.99-4.87 (m, 1H), 1.55 (d, J=6.7 Hz, 3H); MS (ES+) m/z 442.1 (M+1), 444.1 (M+1).

Example 23

Synthesis of (S)-5-chloro-4-((1-(2-chlorophenyl)ethyl)amino)-2-fluoro-N-(6-fluoropyridin-2-yl)benzenesulfonamide

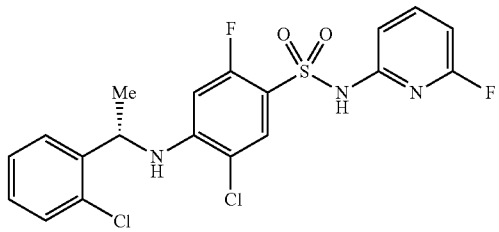

Step 1. Preparation of (S)-5-chloro-4-((1-(2-chlorophenyl)ethyl)amino)-N-(2,4-dimethoxybenzyl)-2-fluoro-N-(6-fluoropyridin-2-yl)benzenesulfonamide

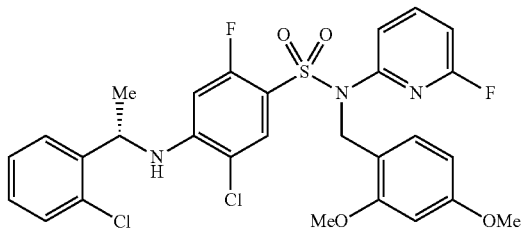 [SMILES: COc1ccc(CN(c2cccc(F)n2)S(=O)(=O)c2cc(Cl)c(N[C@@H](C)c3ccccc3F)cc2F)c(OC)c1]

Following the procedure as described in EXAMPLE 14, Step 1 and making non-critical variations as required to replace (S)-1-(4-chlorophenyl)ethylamine with (S)-1-(2-chlorophenyl)ethan-1-amine hydrochloride and 5-chloro-N-(2,4-dimethoxybenzyl)-2,4-difluoro-N-(thiazol-2-yl)benzenesulfonamide with 5-chloro-N-(2,4-dimethoxybenzyl)-2,4-difluoro-N-(6-fluoropyridin-2-yl)benzenesulfonamide, the title compound was obtained as a colorless solid (0.26 g, 51% yield): MS (ES+) m/z 608.1 (M+1), 610.0 (M+1).

Step 2. Preparation of (S)-5-chloro-4-((1-(2-chlorophenyl)ethyl)amino)-2-fluoro-N-(6-fluoropyridin-2-yl)benzenesulfonamide

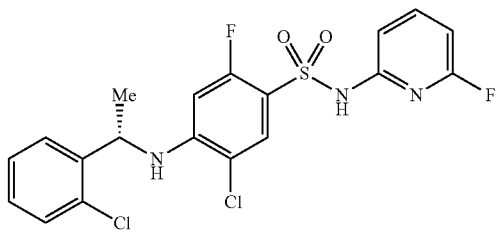 [SMILES: C[C@H](Nc1cc(F)c(S(=O)(=O)Nc2cccc(F)n2)cc1Cl)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)-5-chloro-4-((1-(2-chlorophenyl)ethyl)amino)-N-(2,4-dimethoxybenzyl)-2-fluoro-N-(6- fluoropyridin-2-yl)benzenesulfonamide, the title compound was obtained as a colorless solid (0.041 g, 21% yield): $^1$H NMR (300 MHz, DMSO-d$_6$) δ 11.52 (s, 1H), 7.87-7.74 (m, 2H), 7.50-7.44 (m, 2H), 7.34-7.24 (m, 2H), 6.99-6.93 (m, 1H), 6.82 (dd, J=7.9, 2.1 Hz, 1H), 6.70 (dd, J=8.0, 2.4 Hz, 1H), 6.05 (d, J=13.3 Hz, 1H), 4.96-4.83 (m, 1H), 1.53 (d, J=6.7 Hz, 3H); MS (ES+) m/z 458.1 (M+1), 460.1 (M+1).

Example 24

Synthesis of (S)-3-chloro-4-((1-phenylethyl)amino)-N-(thiazol-4-yl)benzenesulfonamide

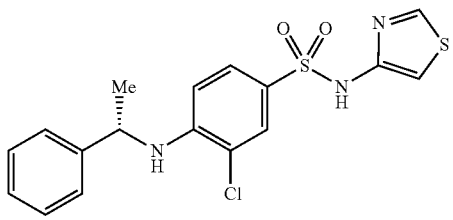 [SMILES: C[C@H](Nc1ccc(S(=O)(=O)Nc2cscn2)cc1Cl)c1ccccc1]

To a mixture of 4-bromo-3-chloro-N-(thiazol-4-yl)benzenesulfonamide (0.25 g, 0.71 mmol), 4,5-bis(diphenylphosphino)-9,9-dimethylxanthene (0.025 g, 0.042 mmol), and tris(dibenzylideneacetone)dipalladium (0.013 mg, 0.014 mmol) in anhydrous 1,4-dioxane (6 mL) was added sodium tert-butoxide (0.163 g, 1.70 mmol) and the mixture was purged with argon for 15 minutes. To the mixture was then added (S)-1-phenylethan-1-amine (0.11 mL, 0.85) and the reaction mixture was heated to 100° C. for 16 h. The reaction mixture was allowed to cool to ambient temperature and filtered through a pad of Celite. The filtrate was diluted with ethyl acetate (30 mL) and saturated aqueous sodium bicarbonate solution (15 mL), and the aqueous layer was extracted with ethyl acetate (3×30 mL). The combined organic layers were washed with brine (40 mL), dried over anhydrous magnesium sulfate, and filtered. Concentration of the filtrate in vacuo and purification of the residue by column chromatography, eluting with 0% to 50% of ethyl acetate in hexanes, afforded the title compound as a colorless solid (0.116 g, 42% yield): $^1$H NMR (300 MHz, CDCl$_3$) δ 9.47 (s, 1H), 8.65 (d, J=2.1 Hz, 1H), 7.68 (d, J=2.2 Hz, 1H), 7.39-7.25 (m, 6H), 6.95 (d, J=2.2 Hz, 1H), 6.33 (d, J=8.9 Hz, 1H), 5.12 (s, 1H), 4.56-4.49 (m, 1H), 1.58 (d, J=6.8 Hz, 3H); MS (ES+) m/z 394.1 (M+1), 396.1 (M+1).

Example 25

Synthesis of (S)-2,5-difluoro-4-((1-(2-fluorophenyl)ethyl)amino)-N-(thiazol-2-yl)benzenesulfonamide

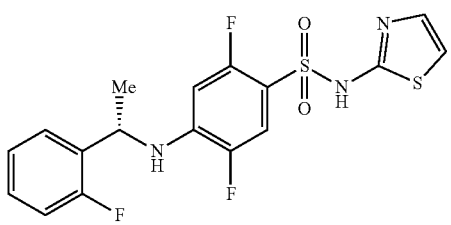 [SMILES: C[C@H](Nc1cc(F)c(S(=O)(=O)Nc2nccs2)cc1F)c1ccccc1F]

Step 1. Preparation of (S)—N-(2,4-dimethoxybenzyl)-2,5-difluoro-4-((1-(2-fluorophenyl)ethyl)amino)-N-(thiazol-2-yl)benzenesulfonamide

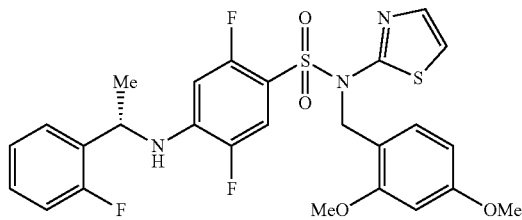 [SMILES: COc1ccc(CN(c2nccs2)S(=O)(=O)c2cc(F)c(N[C@@H](C)c3ccccc3F)cc2F)c(OC)c1]

Following the procedure as described in EXAMPLE 14, Step 1 and making non-critical variations as required to replace (S)-1-(4-chlorophenyl)ethylamine with (S)-1-(2-fluorophenyl)ethan-1-amine, and 5-chloro-N-(2,4-dimethoxybenzyl)-2,4-difluoro-N-(thiazol-2-yl)benzenesulfonamide with N-(2,4-dimethoxybenzyl)-2,4,5-trifluoro-N-(thiazol-2-yl)benzenesulfonamide (prepared according to WO 2013118854), the title compound was obtained as a colorless solid (0.26 g, 41% yield): MS (ES+) m/z 564.2 (M+1).

Step 2. Preparation of (S)-2,5-difluoro-4-((1-(2-fluorophenyl)ethyl)amino)-N-(thiazol-2-yl)benzenesulfonamide

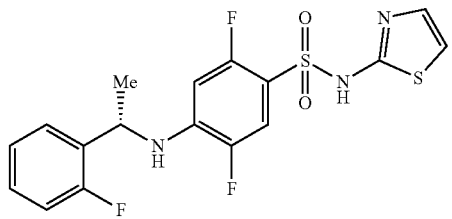 [SMILES: C[C@H](Nc1cc(F)c(S(=O)(=O)Nc2nccs2)cc1F)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)—N-(2,4-dimethoxybenzyl)-2,5-difluoro-4-((1-(2-fluorophenyl)ethyl)amino)-N-(thiazol-2-yl)benzenesulfonamide, the title compound was obtained as a colorless solid (0.15 g, 79% yield): $^1$H NMR (300 MHz, CDCl$_3$) δ 13.04 (s, 1H), 7.56 (dd, J=10.8, 6.3 Hz, 1H), 7.31-7.20 (m, 2H), 7.15-7.02 (m, 3H), 6.46 (d, J=4.5 Hz, 1H), 6.09 (dd, J=11.7, 6.6 Hz, 1H), 4.83-4.69 (m, 2H), 1.59 (d, J=6.0 Hz, 3H); MS (ES+) m/z 414.1 (M+1).

Example 26

Synthesis of (S)-2,5-difluoro-4-(1-(2-fluorophenyl)ethoxy)-N-(thiazol-2-yl)benzenesulfonamide

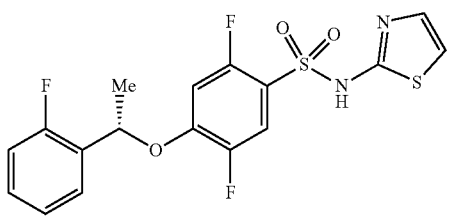 [SMILES: C[C@H](Oc1cc(F)c(S(=O)(=O)Nc2nccs2)cc1F)c1ccccc1F]

Step 1. Preparation of (S)—N-(2,4-dimethoxybenzyl)-2,5-difluoro-4-(1-(2-fluorophenyl)ethoxy)-N-(thiazol-2-yl)benzenesulfonamide

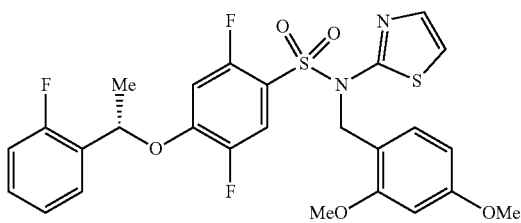 [SMILES: COc1ccc(CN(c2nccs2)S(=O)(=O)c2cc(F)c(O[C@@H](C)c3ccccc3F)cc2F)c(OC)c1]

To a mixture of (S)-1-(2-fluorophenyl)ethan-1-ol (0.14 g, 1.0 mmol) and N-(2,4-dimethoxybenzyl)-2,4,5-trifluoro-N-(thiazol-2-yl)benzenesulfonamide (0.49 g, 1.1 mmol) in anhydrous N,N-dimethylformamide (10 mL) was added sodium hydride (60% dispersion in mineral oil, 0.08 g, 2.0 mmol) at 0° C. The mixture was stirred at ambient temperature for 2 h, cooled to 0° C., and quenched by addition of saturated ammonium chloride solution (20 mL). The mixture was ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with 0% to 50% of ethyl acetate in hexanes, afforded the title compound as a colorless solid (0.56 g, 99% yield): MS (ES+) m/z 565.1 (M+1).

Step 2. Preparation of (S)-2,5-difluoro-4-(1-(2-fluorophenyl)ethoxy)-N-(thiazol-2-yl)benzenesulfonamide

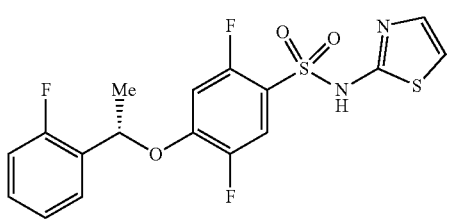 [SMILES: C[C@H](Oc1cc(F)c(S(=O)(=O)Nc2nccs2)cc1F)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)—N-(2,4-dimethoxybenzyl)-2,5-difluoro-4-(1-(2-fluorophenyl)ethoxy)-N-(thiazol-2-yl)benzenesulfonamide, the title compound was obtained as a colorless solid (0.165 g, 40% yield): $^1$H NMR (300 MHz, DMSO-$d_6$) δ 12.91 (s, 1H), 7.59 (dd, J=10.4, 6.7 Hz, 1H), 7.47 (td, J=7.7, 1.8 Hz, 1H), 7.42-7.34 (m, 1H), 7.32-7.16 (m, 4H), 6.87 (d, J=4.6 Hz, 1H), 5.95-5.87 (m, 1H), 1.63 (d, J=6.3 Hz, 3H); MS (ES+) m/z 415.0 (M+1).

Example 27

Synthesis of (S)-2,6-difluoro-4-((1-(2-fluorophenyl)ethyl)amino)-N-(thiazol-2-yl)benzenesulfonamide

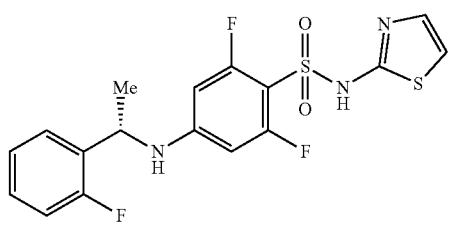 [SMILES: C[C@H](Nc1cc(F)c(S(=O)(=O)Nc2nccs2)c(F)c1)c1ccccc1F]

Step 1. Preparation of N-(2,4-dimethoxybenzyl)-2,4,6-trifluoro-N-(thiazol-2-yl)benzenesulfonamide

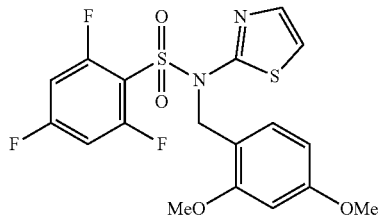 [SMILES: COc1ccc(CN(c2nccs2)S(=O)(=O)c2c(F)cc(F)cc2F)c(OC)c1]

To a solution of N-(2,4-dimethoxybenzyl)thiazol-2-amine (3.0 g, 11.98 mmol) in anhydrous tetrahydrofuran (23 mL) was added a 1 M solution of lithium bis(trimethylsilyl)amide in tetrahydrofuran (14.4 mL, 14.4 mmol) at −78° C. The reaction mixture was allowed to warm to ambient temperature and stirred for 1 h. The reaction mixture was cooled to −78° C., and a solution of 2,4,6-trifluorobenzenesulfonyl chloride (2.76 g, 11.98 mmol) in anhydrous tetrahydrofuran (10 mL) was added dropwise to it. The reaction mixture was allowed to warm to ambient temperature, stirred for 16 h, and diluted with saturated ammonium chloride solution (50 mL). The mixture was extracted with ethyl acetate (3×60 mL). The combined organic layers were washed with brine (100 mL), dried over anhydrous magnesium sulfate, and filtered. Concentration of the filtrate in vacuo and purification of the residue by column chromatography, eluting with 0% to 25% of ethyl acetate in hexanes, afforded the title compound as a colorless solid (1.28 g, 24% yield): MS (ES+) m/z 445.1 (M+1).

Step 2. Preparation of (S)—N-(2,4-dimethoxyben-
zyl)-2,6-difluoro-4-((1-(2-fluorophenyl)ethyl)
amino)-N-(thiazol-2-yl)benzenesulfonamide

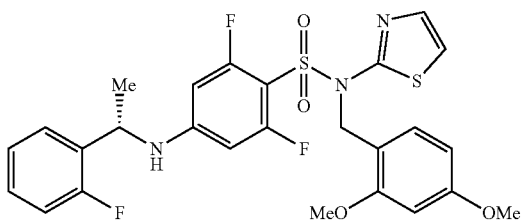 [SMILES: COc1ccc(CN(c2nccs2)S(=O)(=O)c2c(F)cc(N[C@@H](C)c3ccccc3F)cc2F)c(OC)c1]

Following the procedure as described in EXAMPLE 14, Step 1 and making non-critical variations as required to replace (S)-1-(4-chlorophenyl)ethylamine with (S)-1-(2-fluorophenyl)ethan-1-amine and 5-chloro-N-(2,4-dimethoxybenzyl)-2,4-difluoro-N-(thiazol-2-yl)benzenesulfonamide with N-(2,4-dimethoxybenzyl)-2,4,6-trifluoro-N-(thiazol-2-yl)benzenesulfonamide, the title compound was obtained as a colorless solid (0.21 g, 33% yield): MS (ES+) m/z 564.1 (M+1).

Step 3. Preparation of (S)-2,6-difluoro-4-((1-(2-fluorophenyl)ethyl)amino)-N-(thiazol-2-yl)benzenesulfonamide

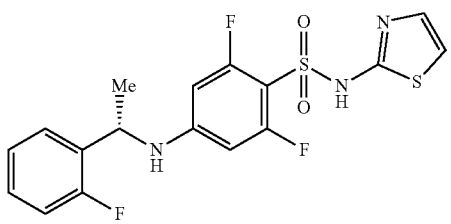 [SMILES: C[C@H](Nc1cc(F)c(S(=O)(=O)Nc2nccs2)c(F)c1)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with (S)—N-(2,4-dimethoxybenzyl)-2,6-difluoro-4-((1-(2-fluorophenyl)ethyl)amino)-N-(thiazol-2-yl)benzenesulfonamide, the title compound was obtained as a colorless solid (0.105 g, 68% yield): $^1$H NMR (300 MHz, DMSO-$d_6$) δ 12.73 (s, 1H), 7.48 (d, J=7.0 Hz, 1H), 7.36-7.25 (m, 3H), 7.22-7.13 (m, 2H), 6.81 (d, J=4.6 Hz, 1H), 6.12 (d, J=12.4 Hz, 2H), 4.83-4.72 (m, 1H), 1.44 (d, J=6.7 Hz, 3H); MS (ES+) m/z 414.0 (M+1).

Example 28

Synthesis of (S)-5-chloro-2-fluoro-4-((1-(2-fluorophenyl)ethyl)amino)-N-(thiazol-4-yl)benzenesulfonamide

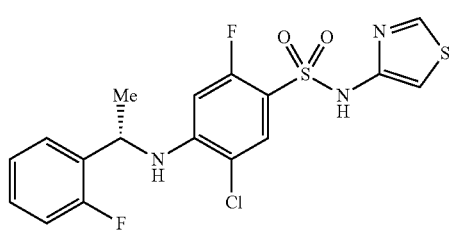 [SMILES: C[C@H](Nc1cc(F)c(S(=O)(=O)Nc2cscn2)cc1Cl)c1ccccc1F]

Step 1. Preparation of tert-butyl (S)-((5-chloro-2-fluoro-4-((1-(2-fluorophenyl)ethyl)amino)phenyl)sulfonyl)(thiazol-4-yl)carbamate

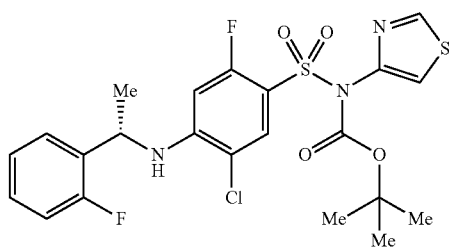 [SMILES: C[C@H](Nc1cc(F)c(S(=O)(=O)N(C(=O)OC(C)(C)C)c2cscn2)cc1Cl)c1ccccc1F]

To a mixture of tert-butyl ((5-chloro-2,4-difluorophenyl)sulfonyl)(thiazol-4-yl)carbamate, (0.54 g, 1.31 mmol) and (S)-1-(2-fluorophenyl)ethan-1-amine (0.15 g, 1.09 mmol) in anhydrous dimethyl sulfoxide (10 mL) was added cesium carbonate (0.82 g, 2.51 mmol) and the reaction mixture was stirred at 50° C. for 16 h. The reaction mixture was allowed to cool to ambient temperature, diluted with saturated ammonium chloride solution (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with 0% to 25% of ethyl acetate in hexanes, afforded the title compound as a colorless solid (0.18 g, 31% yield): MS (ES+) m/z 530.1 (M+1), 532.1 (M+1).

Step 2. Preparation of (S)-5-chloro-2-fluoro-4-((1-(2-fluorophenyl)ethyl)amino)-N-(thiazol-4-yl)benzenesulfonamide

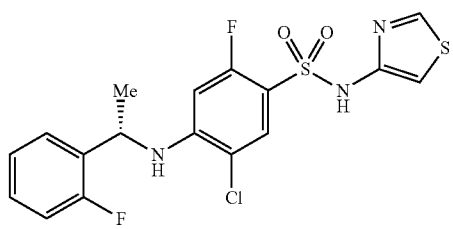 [SMILES: C[C@H](Nc1cc(F)c(S(=O)(=O)Nc2cscn2)cc1Cl)c1ccccc1F]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with tert-butyl (S)-((5-chloro-2-fluoro-4-((1-(2-fluorophenyl)ethyl)amino)phenyl)sulfonyl)(thiazol-4-yl)carbamate, the title compound was obtained as a colorless solid (0.093 g, 64% yield): $^1$H NMR (300 MHz, CDCl$_3$) δ 9.67 (s, 1H), 8.63 (d, J=2.3 Hz, 1H), 7.73 (d, J=7.2 Hz, 1H), 7.29-7.16 (m, 2H), 7.12-7.03 (m, 2H), 6.91 (d, J=2.3 Hz, 1H), 6.09 (d, J=12.3 Hz, 1H), 5.21-5.17 (m, 1H), 4.82-4.72 (m, 1H), 1.61 (d, J=6.7 Hz, 3H); MS (ES+) m/z 430.0 (M+1), 432.0 (M+1).

Example 29

Synthesis of 5-chloro-2-fluoro-N-(thiazol-4-yl)-4-((4-(trifluoromethyl)-2,3-dihydro-1H-inden-1-yl)oxy)benzenesulfonamide

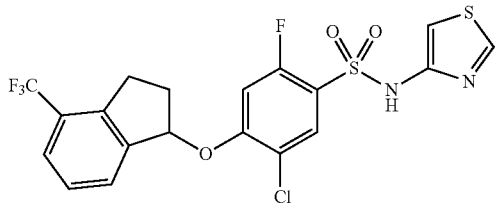 [SMILES: O=S(=O)(Nc1cscn1)c1cc(Cl)c(OC2CCc3c2cccc3C(F)(F)F)cc1F]

To a solution of 4-(trifluoromethyl)-2,3-dihydro-1H-inden-1-ol (0.24 g, 1.19 mmol, prepared according to WO 2009157418) in anhydrous N,N-dimethylformamide (8 mL) was added sodium hydride (60% dispersion in mineral oil, 0.057 g, 1.43 mmol) at 0° C. The reaction mixture was stirred at 0° C. for 30 min and at ambient temperature for 15 min. The reaction mixture was then cooled to 0° C. and tert-butyl ((5-chloro-2,4-difluorophenyl)sulfonyl)(thiazol-4-yl)carbamate (0.49 g, 1.19 mmol) was added to it. The reaction mixture was allowed to warm to ambient temperature and stirred for 2 h. The reaction mixture was then diluted with water (20 mL) and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with 0% to 70% of ethyl acetate in hexanes, afforded the title compound as a colorless solid (0.02 g, 3% yield): $^1$H NMR (300 MHz, CDCl$_3$) δ 9.90 (s, 1H), 8.72 (d, J=2.0 Hz, 1H), 7.90 (d, J=7.5 Hz, 1H), 7.61 (dd, J=10.5, 7.9 Hz, 2H), 7.42-7.37 (m, 1H), 7.03 (d, J=2.0 Hz, 1H), 6.88 (d, J=11.3 Hz, 1H), 5.77-5.73 (m, 1H), 3.40-3.27 (m, 1H), 3.18-3.07 (m, 1H), 2.73-2.61 (m, 1H), 2.29-2.18 (m, 1H); MS (ES−) m/z 491.0 (M−1), 493.0 (M−1).

Example 30

Synthesis of (S)-5-chloro-2-fluoro-4-((1-phenylethyl)amino)-N-(thiazol-4-yl)benzenesulfonamide

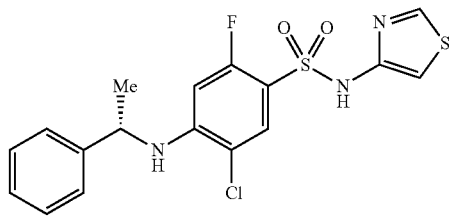 [SMILES: C[C@H](Nc1cc(F)c(S(=O)(=O)Nc2cscn2)cc1Cl)c1ccccc1]

Step 1. Preparation of tert-butyl (S)-((5-chloro-2-fluoro-4-((1-phenylethyl)amino)phenyl)sulfonyl)(thiazol-4-yl)carbamate

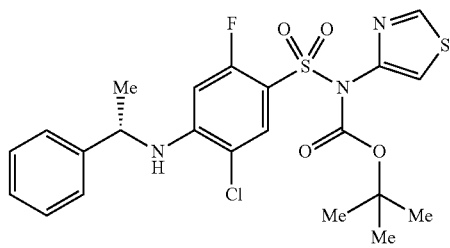 [SMILES: C[C@H](Nc1cc(F)c(S(=O)(=O)N(C(=O)OC(C)(C)C)c2cscn2)cc1Cl)c1ccccc1]

To a mixture of tert-butyl ((5-chloro-2,4-difluorophenyl)sulfonyl)(thiazol-4-yl)carbamate (0.4 g, 0.97 mmol) and (S)-1-phenylethan-1-amine (0.12 mL, 0.97 mmol) in anhydrous dimethyl sulfoxide (10 mL) was added potassium carbonate (0.32 g, 2.33 mmol). The reaction mixture was stirred at ambient temperature for 2 h and then heated at 50° C. for 16 h. The reaction mixture was allowed to cool to ambient temperature, diluted with water (30 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with 0% to 100% of ethyl acetate in hexanes, afforded the title compound as a colorless solid (0.11 g, 22% yield): MS (ES+) m/z 512.0 (M+1), 514.1 (M+1).

Step 2. Preparation of (S)-5-chloro-2-fluoro-4-((1-phenylethyl)amino)-N-(thiazol-4-yl)benzenesulfonamide

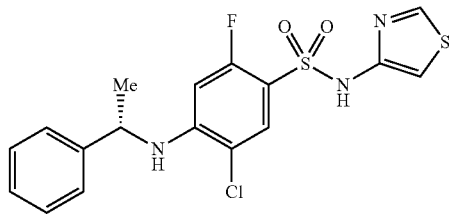 [SMILES: C[C@H](Nc1cc(F)c(S(=O)(=O)Nc2cscn2)cc1Cl)c1ccccc1]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with tert-butyl (S)-((5-chloro-2-fluoro-4-((1-phenylethyl)amino)phenyl)sulfonyl)(thiazol-4-yl)carbamate, the title compound was obtained as a colorless solid (0.047 g, 53% yield): $^1$H NMR (300 MHz, CDCl$_3$) δ 9.59 (s, 1H), 8.61 (s, 1H), 7.73 (d, J=7.2 Hz, 1H), 7.36-7.24 (m, 5H), 6.89 (s, 1H), 6.08 (d, J=12.4 Hz, 1H), 5.21-5.18 (m, 1H), 4.50-4.41 (m, 1H), 1.59 (d, J=6.8 Hz, 3H); MS (ES+) m/z 412.0 (M+1), 414.0 (M+1).

Example 31

Synthesis of (R)-3-chloro-4-((1-phenylpropyl)amino)-N-(1,2,4-thiadiazol-5-yl)benzenesulfonamide

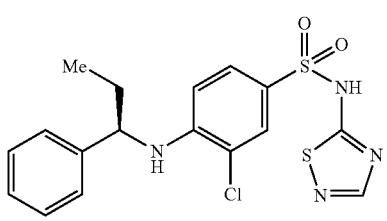 [SMILES: CC[C@@H](Nc1ccc(S(=O)(=O)Nc2ncns2)cc1Cl)c1ccccc1]

To a mixture of 3-chloro-N-(2,4-dimethoxybenzyl)-4-fluoro-N-(1,2,4-thiadiazol-5-yl)benzenesulfonamide (0.250 g, 0.563 mmol) and (R)-1-phenylpropan-1-amine (0.115 g, 0.563 mmol) in anhydrous dimethyl sulfoxide (5 mL) was added cesium carbonate (0.440 g, 1.35 mmol) and the reaction mixture was stirred at ambient temperature in 17 h. The reaction mixture was diluted with ethyl acetate (5 mL) and water (5 mL) and the aqueous phase was extracted with ethyl acetate (3×3 mL). The combined organic phases were washed with brine (1×5 mL), dried over anhydrous sodium sulfate, and filtered. The filtrate was concentrated in vacuo, dissolved in dichloromethane (5 mL), and trifluoroacetic acid (1 mL) was added to it. The reaction mixture was stirred at ambient temperature for 1 h and then methanol (10 mL) was added to it. The suspension was filtered and the filtrate concentrated in vacuo. Purification of the residue by column chromatography, eluting with a gradient of 12 to 80% of ethyl acetate in hexanes, provided the title compound as a colorless solid (0.026 g, 9% yield): $^1$H NMR (300 MHz, DMSO-d$_6$) δ 8.38 (s, 1H), 7.54 (d, J=2.1 Hz, 1H), 7.38-7.34 (m, 3H), 7.31-7.24 (m, 2H), 7.20-7.13 (m, 1H), 6.60 (d, J=9.0 Hz, 1H), 6.26 (d, J=7.5 Hz, 1H), 4.39 (q, J=7.5 Hz, 1H), 2.01-1.90 (m, 1H), 1.83-1.66 (m, 1H), 0.86 (t, J=7.2 Hz, 3H), sulfonamide NH not observed; MS (ES-) m/z 407.0 (M-1), 409.0 (M-1).

Example 32

Synthesis of (S)-3-chloro-4-((1-phenylpropyl)amino)-N-(1,2,4-thiadiazol-5-yl)benzenesulfonamide

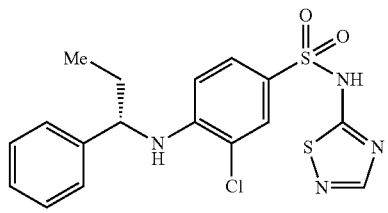 [SMILES: CC[C@H](Nc1ccc(S(=O)(=O)Nc2ncns2)cc1Cl)c1ccccc1]

Following the procedure as described for EXAMPLE 31 and making non-critical variations as required to replace (R)-1-phenylpropan-1-amine with (S)-1-phenylpropan-1-amine, the title compound was obtained as a colorless solid (0.118 g, 43% yield): $^1$H NMR (300 MHz, DMSO-d$_6$) δ 8.38 (s, 1H), 7.54 (d, J=2.1 Hz, 1H), 7.38-7.34 (m, 3H), 7.30-7.25 (m, 2H), 7.20-7.13 (m, 1H), 6.60 (d, J=9.0 Hz, 1H), 6.26 (d, J=7.5 Hz, 1H), 4.39 (q, J=7.2 Hz, 1H), 2.01-1.89 (m, 1H), 1.82-1.68 (m, 1H), 0.86 (t, J=7.2 Hz, 3H); sulfonamide NH not observed; MS (ES-) m/z 407.0 (M-1), 409.0 (M-1).

Example 33

Synthesis of 4-(Benzylamino)-3-chloro-N-(1,2,4-thiadiazol-5-yl)benzenesulfonamide

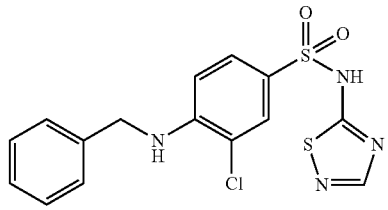 [SMILES: O=S(=O)(Nc1ncns1)c1ccc(NCc2ccccc2)c(Cl)c1]

Following the procedure as described for EXAMPLE 31 and making non-critical variations as required to replace (R)-1-phenylpropan-1-amine with benzyl amine, the title compound was obtained as a colorless solid (0.086 g, 40% yield): $^1$H NMR (300 MHz, DMSO-d$_6$) δ 8.40 (s, 1H), 7.55 (d, J=2.1 Hz, 1H), 7.39 (dd, J=8.7, 2.1 Hz, 1H), 7.31-7.25 (m, 4H), 7.22-7.15 (m, 1H), 7.02 (t, J=6.0 Hz, 1H), 6.58 (d, J=9.9 Hz, 1H), 4.43 (d, J=6.0 Hz, 2H), sulfonamide NH not observed; MS (ES+) m/z 381.0 (M+1), 383.0 (M+1).

Example 34

Synthesis of 3-chloro-4-((2-phenylpropyl)amino)-N-(1,2,4-thiadiazol-5-yl)benzenesulfonamide

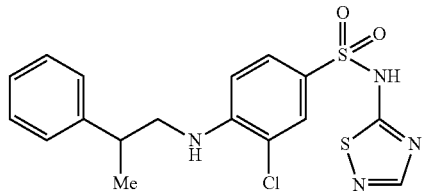 [SMILES: CC(CNc1ccc(S(=O)(=O)Nc2ncns2)cc1Cl)c1ccccc1]

Following the procedure as described for EXAMPLE 31 and making non-critical variations as required to replace (R)-1-phenylpropan-1-amine with 2-phenylpropan-1-amine, the title compound was obtained as a colorless solid (0.088 g, 38% yield): $^1$H NMR (300 MHz, DMSO-$d_6$) δ 8.42 (s, 1H), 7.52-7.47 (m, 2H), 7.31-7.27 (m, 4H), 7.19-7.13 (m, 1H), 6.82 (d, J=8.7 Hz, 1H), 6.04 (t, J=5.7 Hz, 1H), 3.32 (m, 2H), 3.12-2.98 (m, 1H), 1.19 (d, J=6.9 Hz, 3H), sulfonamide NH not observed; MS (ES+) m/z 409.0 (M+1), 411.0 (M+1).

Example 35

Synthesis of (R)-3-chloro-4-((2,3-dihydro-1H-inden-1-yl)amino)-N-(1,2,4-thiadiazol-5-yl)benzenesulfonamide

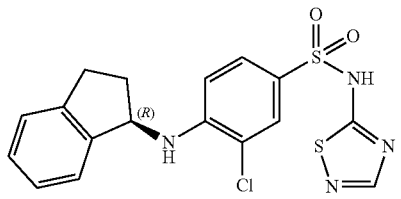

Following the procedure as described for EXAMPLE 31 and making non-critical variations as required to replace (R)-1-phenylpropan-1-amine with (R)-2,3-dihydro-1H-inden-1-amine, the title compound was obtained as a colorless solid (0.046 g, 20% yield): $^1$H NMR (300 MHz, DMSO-$d_6$) δ 8.46 (s, 1H), 7.62 (d, J=2.1 Hz, 1H), 7.57 (dd, J=8.7, 2.1 Hz, 1H), 7.30-7.15 (m, 4H), 7.07 (d, J=9.0 Hz, 1H), 6.18 (d, J=8.1 Hz, 1H), 5.20 (q, J=7.8 Hz, 1H), 3.03-2.94 (m, 1H), 2.90-2.79 (m, 1H), 2.56-2.45 (m, 1H), 2.08-1.96 (m, 1H), sulfonamide NH not observed; MS (ES−) m/z 405.0 (M−1), 407.0 (M−1).

Example 36

Synthesis of (S)-3-chloro-4-((2,3-dihydro-1H-inden-1-yl)amino)-N-(1,2,4-thiadiazol-5-yl)benzenesulfonamide

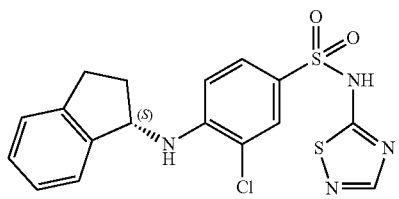

Following the procedure as described for EXAMPLE 31 and making non-critical variations as required to replace (R)-1-phenylpropan-1-amine with (S)-2,3-dihydro-1H-inden-1-amine, the title compound was obtained as a colorless solid (0.061 g, 27% yield): $^1$H NMR (300 MHz, DMSO-$d_6$) δ 8.46 (s, 1H), 7.62 (d, J=2.1 Hz, 1H), 7.57 (dd, J=8.7, 2.1 Hz, 1H), 7.31-7.17 (m, 4H), 7.06 (d, J=9.0 Hz, 1H), 6.17 (d, J=8.1 Hz, 1H), 5.20 (q, J=7.8 Hz, 1H), 3.03-2.93 (m, 1H), 2.90-2.78 (m, 1H), 2.56-2.45 (m, 1H), 2.08-1.95 (m, 1H), sulfonamide NH not observed; MS (ES−) m/z 405.0 (M−1), 407.0 (M−1).

Example 37

Synthesis of (R)-5-chloro-2-fluoro-4-((1-phenylethyl)amino)-N-(thiazol-2-yl)benzenesulfonamide

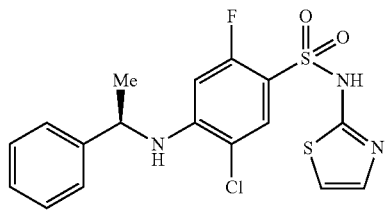 [SMILES: C[C@@H](Nc1cc(F)c(S(=O)(=O)Nc2nccs2)cc1Cl)c1ccccc1]

To a mixture of 5-chloro-N-(2,4-dimethoxybenzyl)-2,4-difluoro-N-(thiazol-2-yl)benzenesulfonamide (0.250 g, 0.543 mmol) and (R)-1-phenylethan-1-amine (0.065 mg, 0.54 mmol) in anhydrous dimethyl sulfoxide (5 mL) was added cesium carbonate (0.424 g, 1.30 mmol) and the reaction mixture was stirred at ambient temperature for 17 h. The reaction mixture was diluted with ethyl acetate (5 mL) and water (5 mL) and the aqueous phase was extracted with ethyl acetate (3×3 mL). The combined organic phases were washed with brine (5 mL), dried over anhydrous sodium sulfate, and filtered. The filtrate was concentrated in vacuo, the residue dissolved in dichloromethane (5 mL), and trifluoroacetic acid (1 mL) was added to it. The reaction mixture was stirred at ambient temperature for 1 h and then methanol (10 mL) was added to it. The suspension was filtered and the filtrate was concentrated in vacuo. Purification of the residue by column chromatography, eluting with a gradient of 12 to 80% of ethyl acetate in hexanes, provided the title compound as a colorless solid (0.111 g, 50% yield): $^1$H NMR (300 MHz, DMSO-$d_6$) δ 12.73 (s, 1H), 7.58 (d, J=7.2 Hz, 1H), 7.42-7.35 (m, 2H), 7.34-7.29 (m, 2H), 7.25-7.17 (m, 2H), 6.81 (d, J=4.5 Hz, 1H), 6.49 (dd, J=7.2, 1.5 Hz, 1H), 6.39 (d, J=13.2 Hz, 1H), 4.69 (dq, J=7.2, 6.9 Hz, 1H), 1.52 (d, J=6.9 Hz, 3H); MS (ES−) m/z 410.0 (M−1), 412.0 (M−1).

Example 38

Synthesis of (S)-5-chloro-2-fluoro-4-((1-phenylethyl)amino)-N-(thiazol-2-yl)benzenesulfonamide

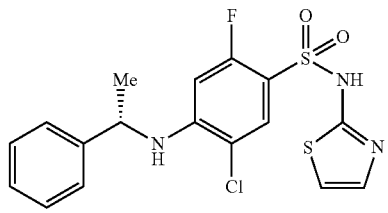 [SMILES: C[C@H](Nc1cc(F)c(S(=O)(=O)Nc2nccs2)cc1Cl)c1ccccc1]

Following the procedure as described for EXAMPLE 37 and making non-critical variations as required to replace (R)-1-phenylethan-1-amine with (S)-1-phenylethan-1-amine, and purification by preparative reverse-phase HPLC using acetonitrile in water containing 0.1% trifluoroacetic acid as eluent, afforded the title compound as a colorless solid (0.062 g, 28% yield): $^1$H NMR (300 MHz, DMSO-$d_6$) δ 12.74 (s, 1H), 7.58 (d, J=7.5 Hz, 1H), 7.43-7.36 (m, 2H), 7.36-7.29 (m, 2H), 7.27-7.16 (m, 2H), 6.81 (d, J=4.5 Hz, 1H), 6.49 (dd, J=7.2, 1.2 Hz, 1H), 6.39 (d, J=13.2 Hz, 1H), 4.69 (dq, J=7.2, 6.9 Hz, 1H), 1.52 (d, J=6.9 Hz, 3H); MS (ES-) m/z 410.0 (M-1), 412.0 (M-1).

Example 39

Synthesis of (R)-5-chloro-2-fluoro-4-((1-phenylpropyl)amino)-N-(thiazol-2-yl)benzenesulfonamide

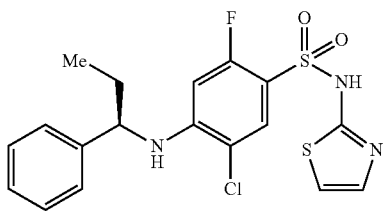 [SMILES: CC[C@@H](Nc1cc(F)c(S(=O)(=O)Nc2nccs2)cc1Cl)c1ccccc1]

Following the procedure as described for EXAMPLE 37 and making non-critical variations as required to replace (R)-1-phenylethan-1-amine with (R)-1-phenylpropan-1-amine, the title compound was obtained as a colorless solid (0.116 g, 50% yield): $^1$H NMR (300 MHz, DMSO-$d_6$) δ 12.74 (s, 1H), 7.56 (d, J=7.5 Hz, 1H), 7.44-7.38 (m, 2H), 7.35-7.26 (m, 2H), 7.26-7.17 (m, 2H), 6.81 (d, J=4.5 Hz, 1H), 6.49-6.45 (m, 1H), 6.44 (d, J=13.2 Hz, 1H), 4.42 (q, J=7.2 Hz, 1H), 2.07-1.90 (m, 1H), 1.84-1.60 (m, 1H), 0.88 (t, J=7.2 Hz, 3H); MS (ES-) m/z 424.1 (M-1), 426.1 (M-1).

Example 40

Synthesis of (S)-5-chloro-2-fluoro-4-((1-phenylpropyl)amino)-N-(thiazol-2-yl)benzenesulfonamide

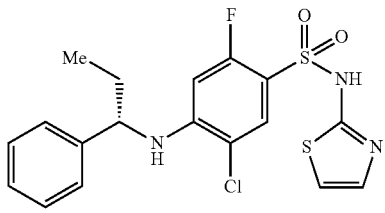 [SMILES: CC[C@H](Nc1cc(F)c(S(=O)(=O)Nc2nccs2)cc1Cl)c1ccccc1]

Following the procedure as described for EXAMPLE 37 and making non-critical variations as required to replace (R)-1-phenylethan-1-amine with (S)-1-phenylpropan-1-amine, the title compound was obtained as a colorless solid (0.134 g, 58% yield): $^1$H NMR (300 MHz, DMSO-$d_6$) δ 12.73 (s, 1H), 7.56 (d, J=7.5 Hz, 1H), 7.44-7.38 (m, 2H), 7.35-7.26 (m, 2H), 7.25-7.17 (m, 2H), 6.81 (d, J=4.5 Hz, 1H), 6.46-6.43 (m, 1H), 6.44 (d, J=13.2 Hz, 1H), 4.42 (q, J=7.2 Hz, 1H), 2.07-1.90 (m, 1H), 1.84-1.60 (m, 1H), 0.88 (t, J=7.2 Hz, 3H); MS (ES-) m/z 424.1 (M-1), 426.1 (M-1).

Example 41

Synthesis of 5-chloro-2-fluoro-N-(thiazol-2-yl)-4-((3,3,3-trifluoro-1-phenylpropyl)amino)benzenesulfonamide

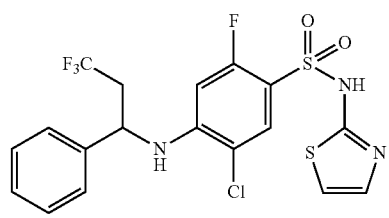 [SMILES: O=S(=O)(Nc1nccs1)c1cc(Cl)c(NC(CC(F)(F)F)c2ccccc2)cc1F]

Following the procedure as described for EXAMPLE 37 and making non-critical variations as required to replace (R)-1-phenylethan-1-amine with 3,3,3-trifluoro-1-phenylpropan-1-amine, the title compound was obtained as a colorless solid (0.062 g, 24% yield) $^1$H NMR (300 MHz, DMSO-$d_6$) δ 12.76 (s, 1H), 7.58 (d, J=7.5 Hz, 1H), 7.52 (d, J=7.2 Hz, 2H), 7.38-7.30 (m, 2H), 7.29-7.21 (m, 2H), 6.85 (d, J=7.5 Hz, 1H), 6.81 (d, J=4.5 Hz, 1H), 6.68 (d, J=12.9 Hz, 1H), 5.06-4.94 (m, 1H), 3.39-3.18 (m, 1H), 2.85-2.62 (m, 1H); $^{19}$F NMR (282 MHz, DMSO-$d_6$) δ-62.1 (s, 3F), -109.2 (s, 1F); MS (ES-) m/z 478.1 (M-1), 480.1 (M-1).

Example 42

Synthesis of (S)-5-chloro-4-((1-cyclohexylethyl)amino)-2-fluoro-N-(thiazol-2-yl)benzenesulfonamide

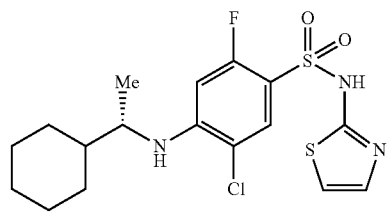 [SMILES: C[C@H](Nc1cc(F)c(S(=O)(=O)Nc2nccs2)cc1Cl)C1CCCCC1]

Following the procedure as described for EXAMPLE 37 and making non-critical variations as required to replace (R)-1-phenylethan-1-amine with (S)-1-cyclohexylethan-1-amine, and purification by preparative reverse-phase HPLC using acetonitrile in water containing 0.1% trifluoroacetic acid as eluent, afforded the title compound as a colorless solid (0.007 g, 3% yield); $^1$H NMR (300 MHz, DMSO-$d_6$) δ 12.76 (s, 1H), 7.55 (d, J=7.5 Hz, 1H), 7.26 (d, J=4.8 Hz, 1H), 6.82 (d, J=4.5 Hz, 1H), 6.68 (d, J=13.5 Hz, 1H), 5.67 (d, J=9.0 Hz, 1H), 3.51-3.34 (m, 1H), 1.80-1.41 (m, 5H), 1.26-1.03 (m, 3H), 1.10 (d, J=6.3 Hz, 3H), 1.01-0.82 (m, 2H); sulfonamide NH not observed; $^{19}$F NMR (282 MHz, DMSO-$d_6$) δ-109.1 (s); MS (ES-) m/z 416.1 (M-1), 418.1 (M-1).

Example 43

Synthesis of 5-chloro-2-fluoro-4-((1-phenylcyclopropyl)amino)-N-(thiazol-2-yl)benzenesulfonamide

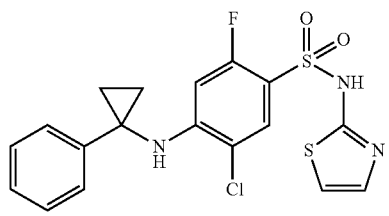 [SMILES: O=S(=O)(Nc1nccs1)c1cc(Cl)c(NC2(c3ccccc3)CC2)cc1F]

Step 1. Preparation of 5-chloro-N-(2,4-dimethoxybenzyl)-2-fluoro-4-((1-phenylcyclopropyl)amino)-N-(thiazol-2-yl)benzenesulfonamide

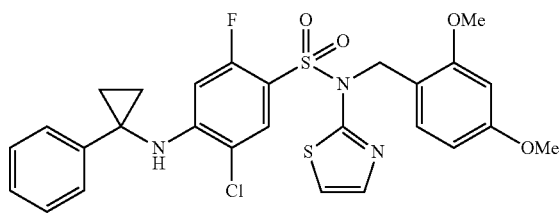 [SMILES: COc1ccc(CN(c2nccs2)S(=O)(=O)c2cc(Cl)c(NC3(c4ccccc4)CC3)cc2F)c(OC)c1]

To a solution of 5-chloro-N-(2,4-dimethoxybenzyl)-2,4-difluoro-N-(thiazol-2-yl)benzenesulfonamide (0.250 g, 0.543 mmol) and 1-phenylcyclopropan-1-amine (0.072 mg, 0.543 mmol) in anhydrous dimethyl sulfoxide (5 mL) was added cesium carbonate (0.424 g, 1.30 mmol) and the reaction mixture was at ambient temperature for 17 h. The reaction mixture was diluted with ethyl acetate (5 mL) and water (5 mL) and the aqueous phase was extracted with ethyl acetate (3×3 mL). The combined organic phases were washed with brine (5 mL), dried over anhydrous sodium sulfate, and filtered. Concentration of the filtrate in vacuo and purification of the residue by column chromatography, eluting with a gradient of 12 to 80% of ethyl acetate, provided the title compound as a colorless solid (0.253 g, 81% yield): $^1$H NMR (300 MHz, CDCl$_3$) δ 7.71 (d, J=6.6 Hz, 1H), 7.40-7.23 (m, 3H), 7.22-7.13 (m, 2H), 7.05 (d, J=7.5 Hz, 2H), 6.97-6.89 (m, 1H), 6.41 (d, J=12.3 Hz, 1H), 6.34 (d, J=8.4 Hz, 1H), 6.31 (s, 1H), 5.67 (s, 1H), 5.16 (s, 2H), 3.74 (s, 3H), 3.67 (s, 3H), 1.42 (s, 2H), 1.37 (s, 2H).

Step 2. Preparation of 5-chloro-2-fluoro-4-((1-phenylcyclopropyl)amino)-N-(thiazol-2-yl)benzenesulfonamide

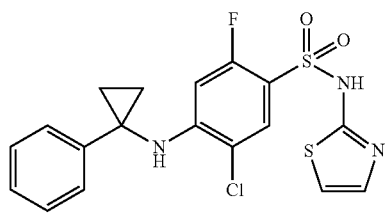 [SMILES: O=S(=O)(Nc1nccs1)c1cc(Cl)c(NC2(c3ccccc3)CC2)cc1F]

To a mixture of 5-chloro-N-(2,4-dimethoxybenzyl)-2-fluoro-4-((1-phenylcyclopropyl)amino)-N-(thiazol-2-yl)benzenesulfonamide in dichloromethane (5 mL) was added trifluoroacetic acid (1 mL) and the reaction mixture was stirred at ambient temperature for 1 h. Methanol (10 mL) was added to the mixture and the resulting suspension was filtered. The filtrate was concentrated in vacuo and the residue was purified by trituration with methanol (3×5 mL) to provide a colorless solid (0.075 g, 40% yield): $^1$H NMR (300 MHz, DMSO-d$_6$) δ 12.76 (s, 1H), 7.61 (d, J=7.2 Hz, 1H), 7.56-7.50 (m, 1H), 7.33-7.23 (m, 3H), 7.20-7.09 (m, 3H), 6.82 (d, J=4.5 Hz, 1H), 6.37 (d, J=12.0 Hz, 1H), 1.44-1.33 (m, 2H), 1.33-1.22 (m, 2H); $^{19}$F NMR (282 MHz, DMSO-d$_6$) δ −109.7 (s); MS (ES−) m/z 422.0 (M−1), 424.0 (M−1).

Example 44

Synthesis of 5-chloro-2-fluoro-4-((1-(4-fluorophenyl)cyclopropyl)amino)-N-(thiazol-2-yl)benzenesulfonamide

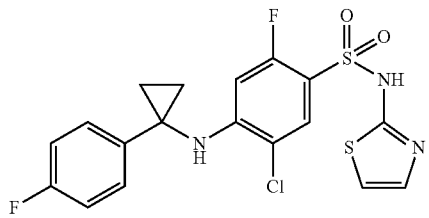 [SMILES: O=S(=O)(Nc1nccs1)c1cc(Cl)c(NC2(c3ccc(F)cc3)CC2)cc1F]

Step 1. Preparation of 5-chloro-N-(2,4-dimethoxybenzyl)-2-fluoro-4-((1-(4-fluorophenyl)cyclopropyl)amino)-N-(thiazol-2-yl)benzenesulfonamide

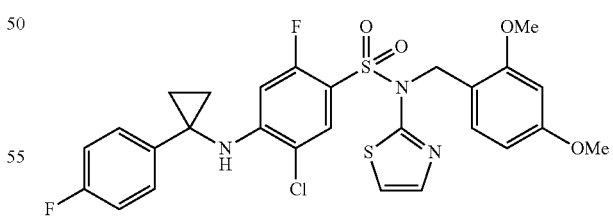

Following the procedure as described for EXAMPLE 43, Step 1 and making non-critical variations as required to replace 1-phenylcyclopropan-1-amine with 1-(4-fluorophenyl)cyclopropan-1-amine, the title compound was obtained as a colorless solid (0.246 g, 77% yield): MS (ES+) m/z 592.4 (M+1), 594.4 (M+1).

Step 2. Preparation 5-chloro-2-fluoro-4-((1-(4-fluorophenyl)cyclopropyl)amino)-N-(thiazol-2-yl)benzenesulfonamide

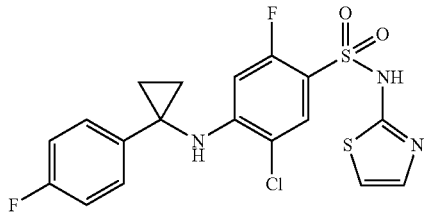 [SMILES: O=S(=O)(Nc1nccs1)c1cc(Cl)c(NC2(c3ccc(F)cc3)CC2)cc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((1-(4-fluorophenyl)cyclopropyl)amino)-N-(thiazol-2-yl) benzenesulfonamide, the title compound was obtained as a colorless solid (0.095 g, 40% yield): $^1$H NMR (300 MHz, DMSO-$d_6$) δ 12.77 (s, 1H), 7.60 (d, J=7.2 Hz, 1H), 7.55 (d, J=1.2 Hz, 1H), 7.26 (d, J=4.2 Hz, 1H), 7.23-7.15 (m, 2H), 7.14-7.05 (m, 2H), 6.82 (d, J=4.5 Hz, 1H), 6.40 (d, J=12.9 Hz, 1H), 1.41-1.33 (m, 2H), 1.30-1.22 (m, 2H); $^{19}$F NMR (282 MHz, DMSO-$d_6$) δ −109.5 (s, 1F), −117.3 (s, 1F); MS (ES+) m/z 441.9 (M+1), 443.9 (M+1).

Example 45

Synthesis of (S)-5-chloro-2-fluoro-4-((1-(2-fluorophenyl)ethyl)amino)-N-(thiazol-2-yl)benzenesulfonamide

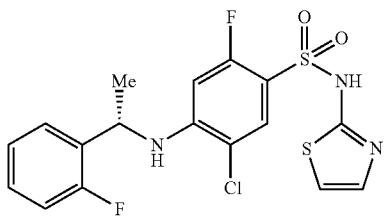

Step 1: (S)-5-chloro-N-(2,4-dimethoxybenzyl)-2-fluoro-4-((1-(2-fluorophenyl)ethyl)amino)-N-(thiazol-2-yl)benzenesulfonamide

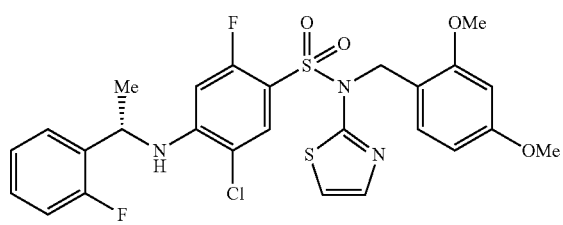 [SMILES: COc1ccc(CN(c2nccs2)S(=O)(=O)c2cc(Cl)c(N[C@@H](C)c3ccccc3F)cc2F)c(OC)c1]

Following the procedure as described for EXAMPLE 43, Step 1 and making non-critical variations as required to replace 1-phenylcyclopropan-1-amine with (S)-1-(2-fluorophenyl)ethan-1-amine, the title compound was obtained as a colorless solid (0.257 g, 82% yield): MS (ES+) m/z 580.1 (M+1), 582.1 (M+1).

Step 2: (S)-5-chloro-2-fluoro-4-((1-(2-fluorophenyl)ethyl)amino)-N-(thiazol-2-yl)benzenesulfonamide

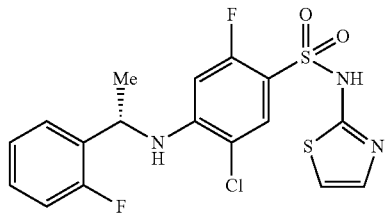 [SMILES: C[C@H](Nc1cc(F)c(S(=O)(=O)Nc2nccs2)cc1Cl)c1ccccc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-4-((1-(2-fluorophenyl)ethyl)amino)-N-(thiazol-2-yl) benzenesulfonamide, and trituration with acetonitrile (2×1 mL), the title compound was obtained as a colorless solid (0.037 g, 20% yield): $^1$H NMR (300 MHz, DMSO-$d_6$) δ 12.76 (s, 1H), 7.60 (d, J=7.2 Hz, 1H), 7.45-7.36 (m, 1H), 7.34-7.16 (m, 4H), 6.81 (d, J=4.8 Hz, 1H), 6.49 (d, J=6.6 Hz, 1H), 6.32 (d, J=12.9 Hz, 1H), 4.98-4.84 (m, 1H), 1.56 (d, J=6.9 Hz, 3H); $^{19}$F NMR (282 MHz, DMSO-$d_6$) δ −109.2 (s, 1F), −119.7 (s, 1F); MS (ES−) m/z 428.1 (M−1), 430.1 (M−1).

Example 46

Synthesis of (S)-5-chloro-2-fluoro-4-((1,2,3,4-tetrahydronaphthalen-1-yl)amino)-N-(thiazol-2-yl)benzenesulfonamide

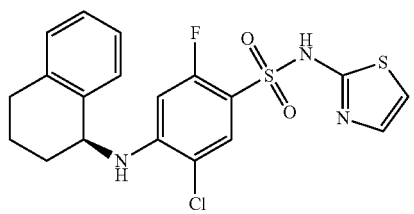 [SMILES: O=S(=O)(Nc1nccs1)c1cc(Cl)c(N[C@H]2CCCc3ccccc32)cc1F]

To a mixture of (S)-1,2,3,4-tetrahydronaphthalen-1-amine (0.096 g, 0.65 mmol) and 5-chloro-N-(2,4-dimethoxybenzyl)-2,4-difluoro-N-(thiazol-2-yl)benzenesulfonamide (0.300 g, 0.652 mmol) in anhydrous dimethyl sulfoxide (2.6 mL) was added cesium carbonate (0.509 g, 1.56 mmol) and the reaction mixture was stirred at ambient temperature for 17 h. The reaction mixture was diluted with ethyl acetate (5 mL) and water (5 mL) and the aqueous phase was extracted with ethyl acetate (3×3 mL). The combined organic phases were washed with brine (5 mL), dried over anhydrous sodium sulfate, and filtered. The filtrate was concentrated in vacuo and the residue purified by column chromatography, eluting with a gradient of 0 to 30% of ethyl acetate in hexanes. The obtained material was then dissolved in dichloromethane (5 mL) and trifluoroacetic acid (0.5 mL) was added to it. The reaction mixture was stirred at ambient temperature for 10 minutes, concentrated in vacuo, and methanol was added to it. The suspension was filtered and the filtrate concentrated in vacuo. Purification of the residue by column chromatography, eluting with a gradient of 0 to 10% of methanol in dichloromethane, followed by purification by preparative reverse phase HPLC using acetonitrile in water containing 0.1% trifluoroacetic acid as eluent, afforded the title compound as a colorless solid (0.011 g, 4% yield): $^1$H NMR (300 MHz, DMSO-$d_6$) δ 12.79 (s, 1H), 7.60 (d, J=7.0 Hz, 1H), 7.28 (s, 1H), 7.15 (s, 4H), 6.91-6.79 (m, 2H), 6.27 (d, J=8.2 Hz, 1H), 4.91-4.79 (m, 1H), 2.89-2.65 (m, 2H), 2.04-1.67 (m, 4H); MS (ES+) m/z 438.0, 440.0 (M+1).

Example 47

Synthesis of (S)-5-chloro-2-fluoro-4-((1-(2-fluorophenyl)propyl)amino)-N-(thiazol-2-yl)benzenesulfonamide

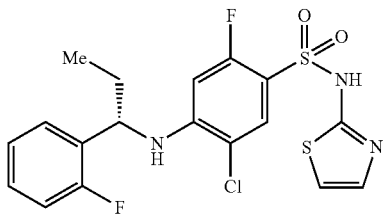 [SMILES: CC[C@H](Nc1cc(F)c(S(=O)(=O)Nc2nccs2)cc1Cl)c1ccccc1F]

Step 1. Preparation of (S)-5-chloro-N-(2,4-dimethoxybenzyl)-2-fluoro-4-((1-(2-fluorophenyl)propyl)amino)-N-(thiazol-2-yl)benzenesulfonamide

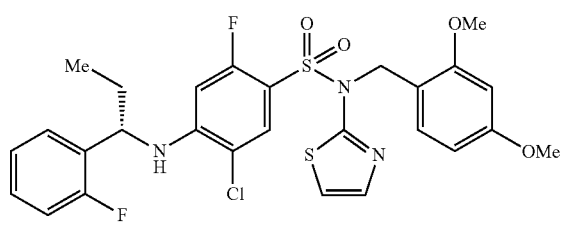 [SMILES: CC[C@H](Nc1cc(F)c(S(=O)(=O)N(Cc2ccc(OC)cc2OC)c2nccs2)cc1Cl)c1ccccc1F]

Following the procedure as described for EXAMPLE 43, Step 1 and making non-critical variations as required to replace 1-phenylcyclopropan-1-amine with (S)-1-(2-fluorophenyl)propan-1-amine hydrochloride, the title compound was obtained as a colorless solid (0.265 g, 82% yield): MS (ES+) m/z 594.2 (M+1), 596.2 (M+1).

Step 2. Preparation of (S)-5-chloro-2-fluoro-4-((1-(2-fluorophenyl)propyl)amino)-N-(thiazol-2-yl)benzenesulfonamide

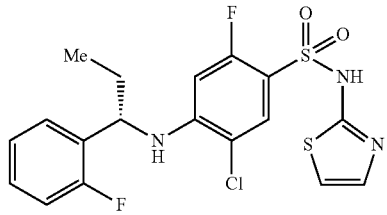 [SMILES: CC[C@H](Nc1cc(F)c(S(=O)(=O)Nc2nccs2)cc1Cl)c1ccccc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-4-((1-(2-fluorophenyl)propyl)amino)-N-(thiazol-2-yl) benzenesulfonamide, and purification by recrystallization from acetonitrile (5 mL), afforded the title compound a colorless solid (0.045 g, 23% yield): $^1$H NMR (300 MHz, DMSO-$d_6$) δ 12.76 (s, 1H), 7.59 (d, J=6.9 Hz, 1H), 7.50-7.41 (m, 1H), 7.35-7.12 (m, 4H), 6.82 (d, J=3.6 Hz, 1H), 6.78 (d, J=7.8 Hz, 1H), 6.36 (d, J=12.9 Hz, 1H), 4.66 (q, J=7.2 Hz, 1H), 2.13-1.95 (m, 1H), 1.90-1.75 (m, 1H), 1.56 (d, J=7.2 Hz, 3H); $^{19}$F NMR (282 MHz, DMSO-$d_6$) δ−109.16 (s, 1F), −119.67 (s, 1F); MS (ES−) m/z 442.1 (M−1), 444.1 (M−1).

Example 48

Synthesis of (S)-5-chloro-2-fluoro-4-((1-(4-fluorophenyl)ethyl)amino)-N-(thiazol-2-yl)benzenesulfonamide

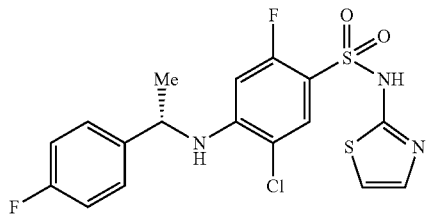 [SMILES: C[C@H](Nc1cc(F)c(S(=O)(=O)Nc2nccs2)cc1Cl)c1ccc(F)cc1]

Step 1. Preparation of (S)-5-chloro-N-(2,4-dimethoxybenzyl)-2-fluoro-4-((1-(4-fluorophenyl)ethyl)amino)-N-(thiazol-2-yl)benzenesulfonamide

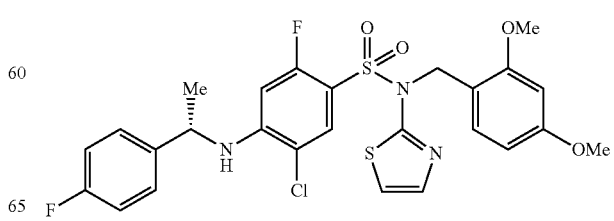

Following the procedure as described for EXAMPLE 43, Step 1 and making non-critical variations as required to replace 1-phenylcyclopropan-1-amine with (S)-1-(4-fluorophenyl)ethan-1-amine, the title compound was obtained as a colorless solid (0.235 g, 75% yield): MS (ES+) m/z 580.1 (M+1), 582.1 (M+1).

Step 2. Preparation of (S)-5-chloro-2-fluoro-4-((1-(4-fluorophenyl)ethyl)amino)-N-(thiazol-2-yl)benzenesulfonamide

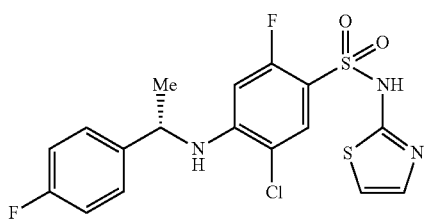 [SMILES: C[C@H](Nc1cc(F)c(S(=O)(=O)Nc2nccs2)cc1Cl)c1ccc(F)cc1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-4-((1-(4-fluorophenyl)ethyl)amino)-N-(thiazol-2-yl) benzenesulfonamide, and purification by column chromatography eluting with a gradient of 6 to 80% of ethyl acetate in hexanes, the title compound was obtained as a colorless solid (0.037 g, 20% yield): $^1$H NMR (300 MHz, DMSO-$d_6$) δ 12.75 (s, 1H), 7.57 (d, J=7.2 Hz, 1H), 7.45 (dd, J=8.7, 5.7 Hz, 2H), 7.24 (d, J=4.5 Hz, 1H), 7.14 (dd, J=9.0, 8.7 Hz, 2H), 6.81 (d, J=4.5 Hz, 1H), 6.52 (d, J=6.9 Hz, 1H), 6.42 (d, J=13.2 Hz, 1H), 4.72 (dq, J=7.2, 6.9 Hz, 1H), 1.51 (d, J=6.9 Hz, 3H); MS (ES−) m/z 428.0 (M−1), 430.0 (M−1).

Example 49

Synthesis of (S)-5-chloro-2-fluoro-4-((1-(3-fluorophenyl)ethyl)amino)-N-(thiazol-2-yl)benzenesulfonamide

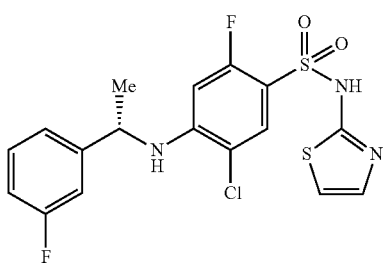 [SMILES: C[C@H](Nc1cc(F)c(S(=O)(=O)Nc2nccs2)cc1Cl)c1cccc(F)c1]

Step 1. Preparation of (S)-5-chloro-N-(2,4-dimethoxybenzyl)-2-fluoro-4-((1-(3-fluorophenyl)ethyl)amino)-N-(thiazol-2-yl)benzenesulfonamide

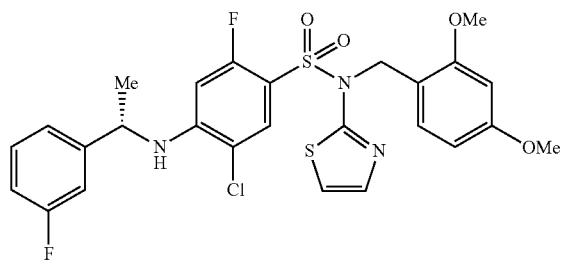 [SMILES: COc1ccc(CN(c2nccs2)S(=O)(=O)c2cc(Cl)c(N[C@@H](C)c3cccc(F)c3)cc2F)c(OC)c1]

Following the procedure as described for EXAMPLE 43, Step 1 and making non-critical variations as required to replace 1-phenylcyclopropan-1-amine with (S)-1-(3-fluorophenyl)ethan-1-amine, the title compound was obtained as a colorless solid (0.220 g, 70% yield): MS (ES+) m/z 580.1 (M+1), 582.0 (M+1).

Step 2. Preparation of (S)-5-chloro-2-fluoro-4-((1-(3-fluorophenyl)ethyl)amino)-N-(thiazol-2-yl)benzenesulfonamide

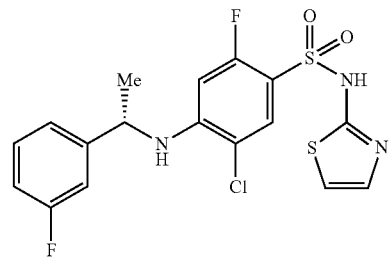 [SMILES: C[C@H](Nc1cc(F)c(S(=O)(=O)Nc2nccs2)cc1Cl)c1cccc(F)c1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-4-((1-(3-fluorophenyl)ethyl)amino)-N-(thiazol-2-yl) benzenesulfonamide, and recrystallization from acetonitrile (10 mL), the title compound was obtained as a colorless solid (0.119 g, 51% yield): $^1$H NMR (300 MHz, DMSO-$d_6$) δ 12.76 (s, 1H), 7.58 (d, J=6.0 Hz, 1H), 7.43-7.31 (m, 1H), 7.31-7.20 (m, 3H), 7.10-6.97 (m, 1H), 6.85-6.77 (m, 1H), 6.56 (d, J=6.6 Hz, 1H), 6.44 (d, J=12.6 Hz, 1H), 4.81-4.67 (m, 1H), 1.52 (d, J=5.4 Hz, 3H); MS (ES−) m/z 428.0 (M−1), 430.0 (M−1).

Example 50

Synthesis of (S)-5-chloro-4-((1-(3-chlorophenyl)ethyl)amino)-2-fluoro-N-(thiazol-2-yl)benzenesulfonamide

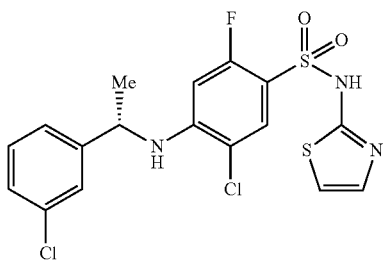

Step 1. Preparation of (S)-5-chloro-4-((1-(3-chlorophenyl)ethyl)amino)-N-(2,4-dimethoxybenzyl)-2-fluoro-N-(thiazol-2-yl)benzenesulfonamide

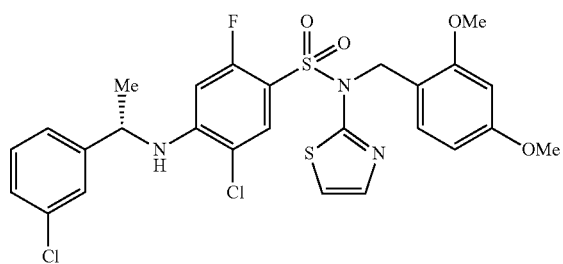 [SMILES: COc1ccc(CN(c2nccs2)S(=O)(=O)c2cc(Cl)c(N[C@@H](C)c3cccc(Cl)c3)cc2F)c(OC)c1]

Following the procedure as described for EXAMPLE 43, Step 1 and making non-critical variations as required to replace 1-phenylcyclopropan-1-amine with (S)-1-(3-chlorophenyl)ethan-1-amine, the title compound was obtained as a colorless solid (0.280 g, 87% yield): MS (ES+) m/z 595.1 (M+1), 597.9 (M+1).

Step 2. Preparation of (S)-5-chloro-4-((1-(3-chlorophenyl)ethyl)amino)-2-fluoro-N-(thiazol-2-yl)benzenesulfonamide

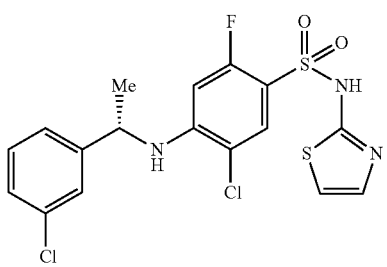

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-4-((1-(3-chlorophenyl)ethyl)amino)-N-(2,4-dimethoxybenzyl)-2-fluoro-N-(thiazol-2-yl) benzenesulfonamide, the title compound was obtained as a colorless solid (0.152 g, 63% yield): $^1$H NMR (300 MHz, DMSO-$d_6$) δ 12.76 (s, 1H), 7.59 (d, J=7.2 Hz, 1H), 7.53-7.50 (m, 1H), 7.41-7.31 (m, 2H), 7.31-7.26 (m, 1H), 7.25 (d, J=4.8 Hz, 1H), 6.81 (d, J=4.8 Hz, 1H), 6.59 (dd, J=7.5, 1.2 Hz, 1H), 6.46 (d, J=13.2 Hz, 1H) 4.78-4.69 (m, 1H), 1.51 (d, J=6.9 Hz, 3H); MS (ES−) m/z 443.9 (M−1), 446.0 (M−1).

Example 51

Synthesis of (S)-5-chloro-4-((1-(3,5-dichlorophenyl)ethyl)amino)-2-fluoro-N-(thiazol-2-yl)benzenesulfonamide

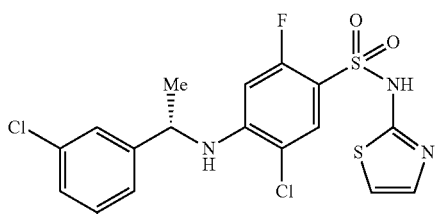

Step 1. Preparation of (S)-5-chloro-4-((1-(3,5-dichlorophenyl)ethyl)amino)-N-(2,4-dimethoxybenzyl)-2-fluoro-N-(thiazol-2-yl)benzenesulfonamide

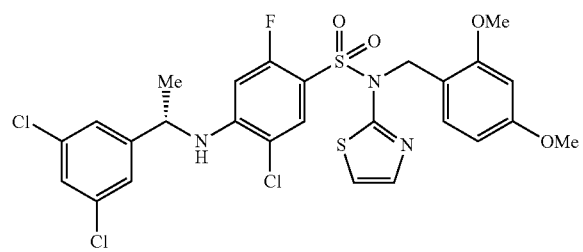 [SMILES: COc1ccc(CN(c2nccs2)S(=O)(=O)c2cc(Cl)c(N[C@@H](C)c3cc(Cl)cc(Cl)c3)cc2F)c(OC)c1]

Following the procedure as described for EXAMPLE 43, Step 1 and making non-critical variations as required to replace 1-phenylcyclopropan-1-amine with (S)-1-(3,5-dichlorophenyl)ethan-1-amine, the title compound was obtained as a colorless solid (0.234 g, 71% yield): MS (ES+) m/z 630.0 (M+1), 632.0 (M+1).

Step 2: (S)-5-chloro-4-((1-(3,5-dichlorophenyl)ethyl)amino)-2-fluoro-N-(thiazol-2-yl)benzenesulfonamide

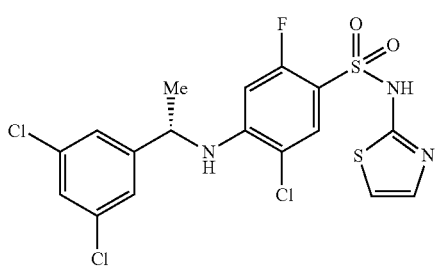 [SMILES: C[C@H](Nc1cc(F)c(S(=O)(=O)Nc2nccs2)cc1Cl)c1cc(Cl)cc(Cl)c1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-4-((1-(3,5-dichlorophenyl)ethyl)amino)-N-(2,4-dimethoxybenzyl)-2-fluoro-N-(thiazol-2-yl)benzenesulfonamide, the title compound was obtained as a colorless solid (0.152 g, 63% yield): $^1$H NMR (300 MHz, DMSO-$d_6$) δ 12.77 (s, 1H), 7.59 (d, J=7.5 Hz, 1H), 7.54 (d, J=1.8 Hz, 2H), 7.46 (t, J=1.8 Hz, 1H), 7.25 (d, J=4.5 Hz, 1H), 6.82 (d, J=4.5 Hz, 1H), 6.66 (d, J=13.3 Hz, 1H), 6.53 (d, J=12.9 Hz, 1H), 4.83-4.68 (m, 1H), 1.51 (d, J=6.9 Hz, 3H); MS (ES+) m/z 479.7 (M+1); 481.7 (M+1).

Example 52

Synthesis of (S)-5-chloro-4-((1-(2,4-difluorophenyl)ethyl)amino)-2-fluoro-N-(thiazol-2-yl)benzenesulfonamide

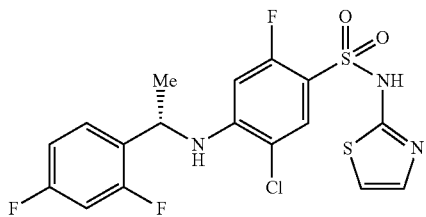 [SMILES: C[C@H](Nc1cc(F)c(S(=O)(=O)Nc2nccs2)cc1Cl)c1ccc(F)cc1F]

Step 1. Preparation of (S)-5-chloro-4-((1-(2,4-difluorophenyl)ethyl)amino)-N-(2,4-dimethoxybenzyl)-2-fluoro-N-(thiazol-2-yl)benzenesulfonamide

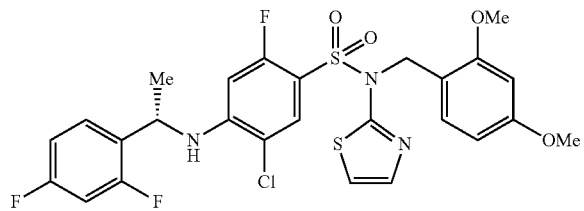 [SMILES: COc1ccc(CN(c2nccs2)S(=O)(=O)c2cc(Cl)c(N[C@@H](C)c3ccc(F)cc3F)cc2F)c(OC)c1]

Following the procedure as described for EXAMPLE 43, Step 1 and making non-critical variations as required to replace 1-phenylcyclopropan-1-amine with (S)-1-(2,4-difluorophenyl)ethan-1-amine, the title compound was obtained as a colorless solid (0.220 g, 70% yield): MS (ES+) m/z 598.0 (M+1), 600.0 (M+1).

Step 2. Preparation of (S)-5-chloro-4-((1-(2,4-difluorophenyl)ethyl)amino)-2-fluoro-N-(thiazol-2-yl)benzenesulfonamide

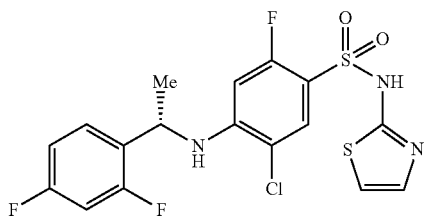 [SMILES: C[C@H](Nc1cc(F)c(S(=O)(=O)Nc2nccs2)cc1Cl)c1ccc(F)cc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-4-((1-(2,4-difluorophenyl)ethyl)amino)-N-(2,4-dimethoxybenzyl)-2-fluoro-N-(thiazol-2-yl)benzenesulfonamide, the title compound was obtained as a colorless solid (0.088 g, 36% yield): $^1$H NMR (300 MHz, DMSO-$d_6$) δ 12.78 (s, 1H), 7.60 (d, J=7.2 Hz, 1H), 7.44 (dt, J=6.9, 8.7 Hz, 1H), 7.29-7.18 (m, 2H), 7.05 (dt, J=2.1, 8.4 Hz, 1H), 6.82 (d, J=3.2 Hz, 1H), 6.52 (d, J=8.7 Hz, 1H), 6.36 (d, J=12.9 Hz, 1H), 4.94-4.85 (m, 1H), 1.54 (d, J=6.9 Hz, 3H); $^{19}$F NMR (282 MHz, DMSO-$d_6$) δ −109.1 (s, 1F), −111.7 (d, J=7.3 Hz, 1F), −115.3 (d, J=7.3 Hz, 1F); MS (ES−) m/z 446.0 (M−1), 447.9 (M−1).

Example 53

Synthesis of (S)-5-chloro-4-((1-(3,4-difluorophenyl)ethyl)amino)-2-fluoro-N-(thiazol-2-yl)benzenesulfonamide

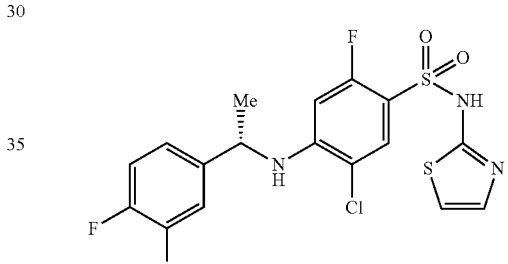

Step 1. Preparation of (S)-5-chloro-4-((1-(3,4-difluorophenyl)ethyl)amino)-N-(2,4-dimethoxybenzyl)-2-fluoro-N-(thiazol-2-yl)benzenesulfonamide

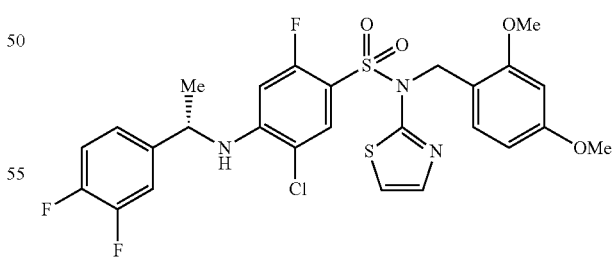

Following the procedure as described for EXAMPLE 43, Step 1 and making non-critical variations as required to replace 1-phenylcyclopropan-1-amine with (S)-1-(3,4-difluorophenyl)ethan-1-amine hydrochloride, the title compound was obtained as a colorless solid (257 g, 79% yield): MS (ES+) m/z 598.4 (M+1), 600.4 (M+1).

Step 2. Preparation of (S)-5-chloro-4-((1-(3,4-difluorophenyl)ethyl)amino)-2-fluoro-N-(thiazol-2-yl)benzenesulfonamide

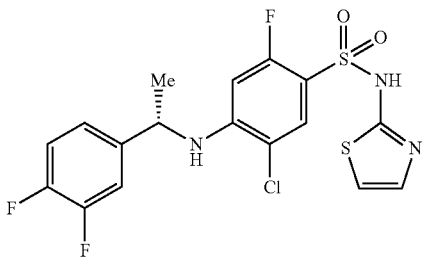 [SMILES: C[C@H](Nc1cc(F)c(S(=O)(=O)Nc2nccs2)cc1Cl)c1ccc(F)c(F)c1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-4-((1-(3,4-difluorophenyl)ethyl)amino)-N-(2,4-dimethoxybenzyl)-2-fluoro-N-(thiazol-2-yl)benzenesulfonamide, the title compound was obtained as a colorless solid (0.088 g, 36% yield): $^1$H NMR (300 MHz, DMSO-$d_6$) δ 12.77 (s, 1H), 7.58 (d, J=7.2 Hz, 1H), 7.52 (ddd, J=12.0, 8.1, 2.1 Hz, 1H), 7.42-7.31 (m, 1H), 7.31-7.27 (m, 1H), 7.25 (d, J=4.5 Hz, 1H), 6.81 (d, J=4.8 Hz, 1H), 6.57 (dd, J=7.8, 1.2 Hz, 1H), 6.48 (d, J=13.2 Hz, 1H) 4.80-4.65 (m, 1H), 1.51 (d, J=6.9 Hz, 3H); $^{19}$F NMR (282 MHz, DMSO-$d_6$) δ−109.22 (s, 1F), −138.21 (d, J=22 Hz, 1F), −140.82 (d, J=23.7 Hz, 1F); MS (ES+) m/z 447.9 (M+1), 449.9 (M+1).

Example 54

Synthesis of (S)-5-chloro-2-fluoro-N-(thiazol-2-yl)-4-((1-(o-tolyl)propyl)amino)benzenesulfonamide

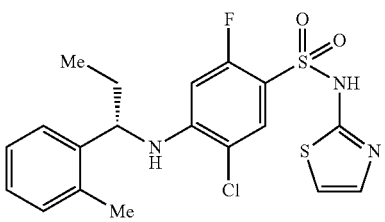

Step 1. Preparation of (S)-5-chloro-N-(2,4-dimethoxybenzyl)-2-fluoro-N-(thiazol-2-yl)-4-((1-(o-tolyl)propyl)amino)benzenesulfonamide

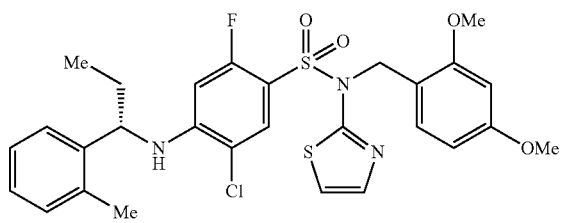 [SMILES: CC[C@H](Nc1cc(F)c(S(=O)(=O)N(Cc2ccc(OC)cc2OC)c2nccs2)cc1Cl)c1ccccc1C]

Following the procedure as described for EXAMPLE 43, Step 1 and making non-critical variations as required to replace 1-phenylcyclopropan-1-amine with (S)-1-(o-tolyl)propan-1-amine hydrochloride, the title compound was obtained as a colorless solid (0.096 g, 30% yield): MS (ES+) m/z 590.0 (M+1), 592.0 (M+1).

Step 2. Preparation of (S)-5-chloro-2-fluoro-N-(thiazol-2-yl)-4-((1-(o-tolyl)propyl)amino)benzenesulfonamide

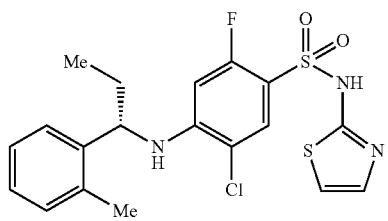

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-N-(thiazol-2-yl)-4-((1-(o-tolyl)propyl)amino)benzenesulfonamide, and purification by preparative reverse phase HPLC using acetonitrile in water containing 0.1% trifluoroacetic acid, the title compound was obtained as a colorless solid (0.010 g, 4% yield): $^1$H NMR (300 MHz, DMSO-$d_6$) δ 12.74 (s, 1H), 7.58 (d, J=7.2 Hz, 1H), 7.31-7.22 (m, 2H), 7.20-7.08 (m, 3H), 6.81 (d, J=4.5 Hz, 1H), 6.40 (d, J=7.5 Hz, 1H), 6.11 (d, J=13.2 Hz, 1H), 4.58-4.47 (m, 1H), 2.40 (s, 3H), 2.02-1.86 (m, 1H), 1.80-1.64 (m, 1H), 0.97 (d, J=7.2 Hz, 3H); MS (ES−) m/z 438.0 (M−1), 440.0 (M−1).

Example 55

Synthesis of 5-chloro-2-fluoro-4-((1-(5,6,7,8-tetrahydronaphthalen-2-yl)propyl)amino)-N-(thiazol-2-yl)benzenesulfonamide

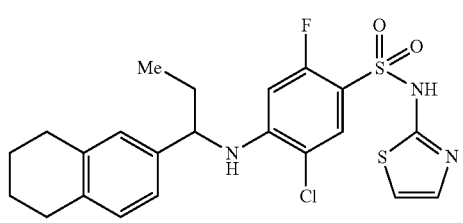 [SMILES: CCC(Nc1cc(F)c(S(=O)(=O)Nc2nccs2)cc1Cl)c1ccc2c(c1)CCCC2]

Step 1. Preparation of 5-chloro-N-(2,4-dimethoxy-benzyl)-2-fluoro-4-((1-(5,6,7,8-tetrahydronaphthalen-2-yl)propyl)amino)-N-(thiazol-2-yl)benzenesulfonamide

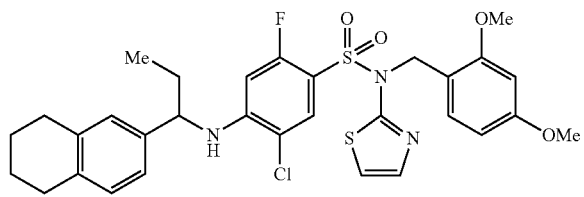 [SMILES: CCC(Nc1cc(F)c(S(=O)(=O)N(Cc2ccc(OC)cc2OC)c2nccs2)cc1Cl)c1ccc2c(c1)CCCC2]

Following the procedure as described for EXAMPLE 43, Step 1 and making non-critical variations as required to replace 1-phenylcyclopropan-1-amine with 1-(5,6,7,8-tetrahydronaphthalen-2-yl)propan-1-amine, the title compound was obtained as a colorless oil (0.272 g, 80% yield): MS (ES+) m/z 630.2 (M+1), 632.2 (M+1).

Step 2. Preparation of 5-chloro-2-fluoro-4-((1-(5,6,7,8-tetrahydronaphthalen-2-yl)propyl)amino)-N-(thiazol-2-yl)benzenesulfonamide

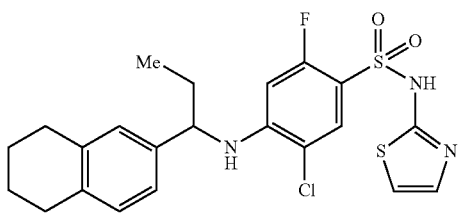 [SMILES: CCC(Nc1cc(F)c(S(=O)(=O)Nc2nccs2)cc1Cl)c1ccc2c(c1)CCCC2]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with of 5-chloro-N-(2,4-dimethoxybenzyl)-2-fluoro-4-((1-(5,6,7,8-tetrahydronaphthalen-2-yl)propyl)amino)-N-(thiazol-2-yl)benzenesulfonamide, and purification by column chromatography eluting with a gradient of 12 to 80% of ethyl acetate in hexanes, the title compound was obtained as a colorless solid (0.036 g, 14% yield): $^1$H NMR (300 MHz, DMSO-$d_6$) δ 12.74 (s, 1H), 7.56 (d, J=7.5 Hz, 1H), 7.24 (d, J=4.8 Hz, 1H), 7.13-7.05 (m, 2H), 6.97 (d, J=8.4 Hz, 1H), 6.80 (d, J=4.8 Hz, 1H), 6.44 (d, J=13.2 Hz, 1H), 6.37 (dd, J=7.8, 1.2 Hz, 1H), 4.30 (q, J=6.9 Hz, 1H), 2.73-2.56 (m, 4H), 2.03-1.86 (m, 1H), 1.78-1.60 (m, 5H), 0.87 (t, J=7.2 Hz, 3H); $^{19}$F NMR (282 MHz, DMSO-$d_6$) δ−109.3 (s); MS (ES−) m/z 478.1 (M−1), 480.1 (M−1).

Example 56

Synthesis of 5-chloro-2-fluoro-4-((1-(pyridin-3-yl)propan-2-yl)amino)-N-(thiazol-2-yl)benzenesulfonamide

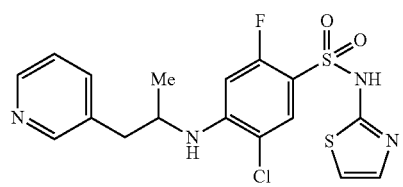 [SMILES: CC(Cc1cccnc1)Nc1cc(F)c(S(=O)(=O)Nc2nccs2)cc1Cl]

Step 1. Preparation of 5-chloro-N-(2,4-dimethoxy-benzyl)-2-fluoro-4-((1-(pyridin-3-yl)propan-2-yl)amino)-N-(thiazol-2-yl)benzenesulfonamide

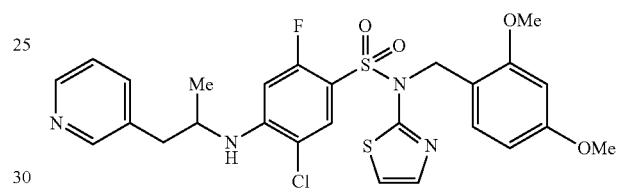

Following the procedure as described for EXAMPLE 43, Step 1 and making non-critical variations as required to replace 1-phenylcyclopropan-1-amine with 1-(pyridin-3-yl)propan-2-amine, the title compound was obtained as a colorless oil (0.248 g, 79% yield): MS (ES+) m/z 577.1 (M+1), 579.0 (M+1).

Step 2. Preparation 5-chloro-2-fluoro-4-((1-(pyridin-3-yl)propan-2-yl)amino)-N-(thiazol-2-yl)benzenesulfonamide

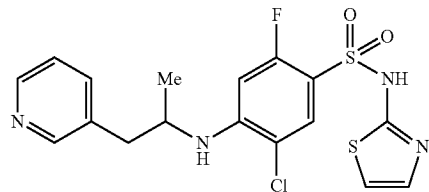 [SMILES: CC(Cc1cccnc1)Nc1cc(F)c(S(=O)(=O)Nc2nccs2)cc1Cl]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((1-(pyridin-3-yl)propan-2-yl)amino)-N-(thiazol-2-yl)benzenesulfonamide, and purification by column chromatography eluting with a gradient of 12 to 80% of ethyl acetate in hexanes, the title compound was obtained as a colorless solid (0.127 g, 53% yield): $^1$H NMR (300 MHz, DMSO-$d_6$) δ 12.78 (s, 1H), 8.65 (d, J=1.8 Hz, 1H), 8.60 (dd, J=5.4, 1.4 Hz, 1H), 8.15-8.12 (m, 1H), 7.69 (dd, J=7.8, 5.4 Hz, 1H), 7.53 (d, J=7.4 Hz, 1H), 7.27 (d, J=4.6 Hz, 1H), 6.83 (d, J=4.6 Hz, 1H), 6.69 (d, J=13.5 Hz, 1H), 6.04 (ddd, J=9.3, 1.4, 0.5 Hz, 1H), 4.03-3.93 (m, 1H), 3.07 (dd, J=13.8, 1.8 Hz, 1H), 2.94 (dd, J=13.5, 1.8 Hz, 1H), 1.18 (d, J=6.3 Hz, 3H); MS (ES+) m/z 426.9 (M+1), 428.9 (M+1).

Example 57

Synthesis of 5-chloro-2-fluoro-4-((1-(pyridin-3-yl)propan-2-yl)amino)-N-(thiazol-2-yl)benzenesulfonamide

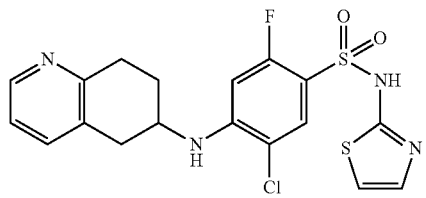 [SMILES: O=S(=O)(Nc1nccs1)c1cc(Cl)c(NC2CCc3ncccc3C2)cc1F]

Step 1. Preparation of 5-chloro-N-(2,4-dimethoxybenzyl)-2-fluoro-4-((5,6,7,8-tetrahydroquinolin-6-yl)amino)-N-(thiazol-2-yl)benzenesulfonamide

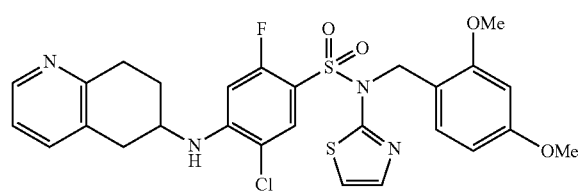 [SMILES: COc1ccc(CN(c2nccs2)S(=O)(=O)c2cc(Cl)c(NC3CCc4ncccc4C3)cc2F)c(OC)c1]

Following the procedure as described for EXAMPLE 43, Step 1 and making non-critical variations as required to replace 1-phenylcyclopropan-1-amine with 5,6,7,8-tetrahydroquinolin-6-amine, the title compound was obtained as a colorless oil (0.180 g, 56% yield): MS (ES+) m/z 589.0 (M+1), 591.0 (M+1).

Step 2. Preparation of 5-chloro-2-fluoro-4-((1-(pyridin-3-yl)propan-2-yl)amino)-N-(thiazol-2-yl)benzenesulfonamide

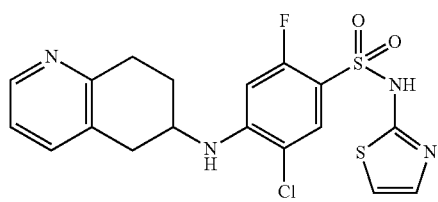 [SMILES: O=S(=O)(Nc1nccs1)c1cc(Cl)c(NC2CCc3ncccc3C2)cc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((5,6,7,8-tetrahydroquinolin-6-yl)amino)-N-(thiazol-2-yl)benzenesulfonamide, and purification by column chromatography eluting with a gradient of 12 to 80% of ethyl acetate in hexanes, the title compound was obtained as a colorless solid (0.043 g, 19% yield): $^1$H NMR (300 MHz, DMSO-$d_6$) δ 12.82 (s, 1H), 8.62 (d, J=5.1 Hz, 1H), 8.13 (d, J=7.8 Hz, 1H), 7.69 (dd, J=7.8, 5.7 Hz, 1H), 7.62 (d, J=7.5 Hz, 1H), 7.27 (d, J=4.5 Hz, 1H), 6.90 (d, J=13.2 Hz, 1H), 6.84 (d, J=4.5 Hz, 1H), 6.22 (d, J=7.8 Hz, 1H), 3.98-3.90 (m, 1H), 3.26-3.14 (m, 3H), 3.08-2.98 (m, 1H), 2.18-2.11 (m, 1H), 1.99-1.85 (m, 1H); MS (ES+) m/z 438.9 (M+1), 440.9 (M+1).

Example 58

Synthesis of 5-chloro-2-fluoro-4-((1-(pyridin-3-yl)propyl)amino)-N-(thiazol-2-yl)benzenesulfonamide

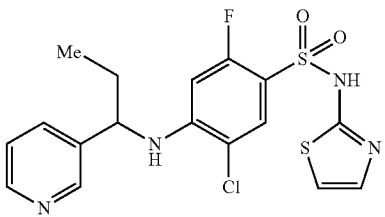 [SMILES: CCC(Nc1cc(F)c(S(=O)(=O)Nc2nccs2)cc1Cl)c1cccnc1]

Step 1. Preparation of 5-chloro-N-(2,4-dimethoxybenzyl)-2-fluoro-4-((1-(pyridin-3-yl)propyl)amino)-N-(thiazol-2-yl)benzenesulfonamide

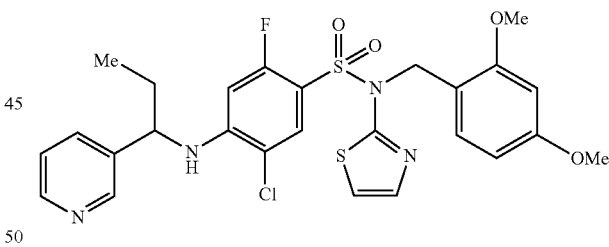

Following the procedure as described for EXAMPLE 43, Step 1 and making non-critical variations as required to replace 1-phenylcyclopropan-1-amine with 1-(pyridin-3-yl)propan-1-amine, the title compound was obtained as a colorless solid (0.215 g, 69% yield): $^1$H NMR (300 MHz, CDCl$_3$) δ 8.64-8.53 (m, 2H), 7.72 (d, J=7.2 Hz, 1H), 7.70-7.61 (m, 1H), 7.46-7.38 (m, 1H), 7.36 (d, J=4.5 Hz, 1H), 7.17 (d, J=8.4 Hz, 1H), 6.95 (dd, J=3.6, 0.6 Hz, 1H), 6.35 (dd, J=8.1, 2.1 Hz, 1H), 6.32-6.29 (m, 1H), 6.02 (d, J=12.0 Hz, 1H), 5.26 (d, J=5.1 Hz, 1H), 5.13 (s, 2H), 4.30 (q, J=7.2 Hz, 1H), 3.76 (s, 3H), 3.67 (s, 3H), 1.99-1.85 (m, 2H), 1.04 (t, J=7.5 Hz, 3H); MS (ES+) m/z 577.0 (M+1), 579.0 (M+1).

Step 2. Preparation of 5-chloro-2-fluoro-4-((1-(pyridin-3-yl)propyl)amino)-N-(thiazol-2-yl)benzenesulfonamide

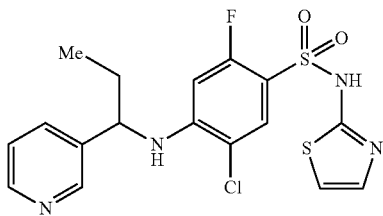 [SMILES: CCC(Nc1cc(F)c(S(=O)(=O)Nc2nccs2)cc1Cl)c1cccnc1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with of 5-chloro-N-(2,4-dimethoxybenzyl)-2-fluoro-4-((1-(pyridin-3-yl)propyl)amino)-N-(thiazol-2-yl) benzenesulfonamide, and trituration with acetonitrile (3×volume), the title compound was obtained as a colorless solid (0.159 g, 69% yield): $^1$H NMR (300 MHz, DMSO-$d_6$) δ 12.76 (s, 1H), 8.85 (s, 1H), 8.68-8.59 (m, 1H), 8.26 (d, J=7.8 Hz, 1H), 7.76-7.66 (m, 1H), 7.61 (d, J=6.9 Hz, 1H), 7.29-7.21 (m, 1H), 6.86-6.77 (m, 1H), 6.67 (d, J=8.4 Hz, 1H), 6.62 (d, J=13.5 Hz, 1H), 4.66 (q, J=6.9 Hz, 1H), 2.13-1.96 (m, 1H), 1.93-1.75 (m, 1H), 0.91 (t, J=6.9 Hz, 3H); MS (ES+) m/z 427.0 (M+1), 427.9 (M+1).

Example 59

Synthesis of 5-chloro-2-fluoro-4-((1-(pyridin-3-yl)propyl)amino)-N-(thiazol-2-yl)benzenesulfonamide

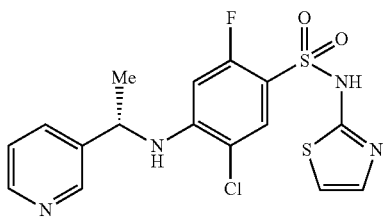 [SMILES: C[C@H](Nc1cc(F)c(S(=O)(=O)Nc2nccs2)cc1Cl)c1cccnc1]

Step 1. Preparation of (S)-5-chloro-N-(2,4-dimethoxybenzyl)-2-fluoro-4-((1-(pyridin-3-yl)ethyl)amino)-N-(thiazol-2-yl)benzenesulfonamide

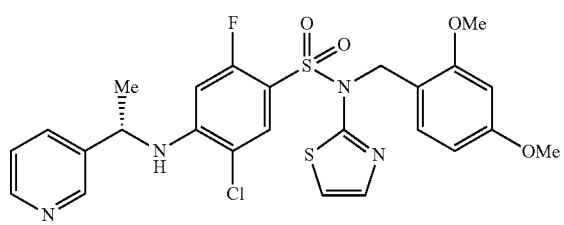 [SMILES: COc1ccc(CN(c2nccs2)S(=O)(=O)c2cc(Cl)c(N[C@@H](C)c3cccnc3)cc2F)c(OC)c1]

Following the procedure as described for EXAMPLE 43, Step 1 and making non-critical variations as required to replace 1-phenylcyclopropan-1-amine with (S)-1-(pyridin-3-yl)ethan-1-amine, and purification by column chromatography eluting with a gradient of 12 to 80% of ethyl acetate in hexanes, the title compound was obtained as a colorless oil (0.145 g, 47% yield): MS (ES+) m/z 563.0 (M+1), 565.0 (M+1).

Step 2. Preparation of 5-chloro-2-fluoro-4-((1-(pyridin-3-yl)propyl)amino)-N-(thiazol-2-yl)benzenesulfonamide

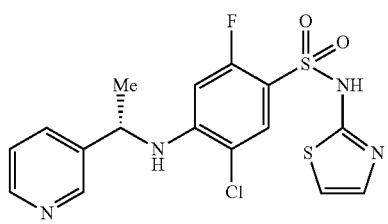 [SMILES: C[C@H](Nc1cc(F)c(S(=O)(=O)Nc2nccs2)cc1Cl)c1cccnc1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-4-((1-(pyridin-3-yl)ethyl)amino)-N-(thiazol-2-yl)benzenesulfonamide, and trituration with acetonitrile (3×5 mL), the title compound was obtained as a colorless solid (0.080 g, 28% yield): $^1$H NMR (300 MHz, DMSO-$d_6$) δ 12.78 (s, 1H), 8.82 (d, J=1.5 Hz, 1H), 8.64 (d, J=4.5 Hz, 1H), 8.23 (d, J=8.1 Hz, 1H), 7.71 (dd, J=7.8, 2.4 Hz, 1H), 7.60 (d, J=7.2 Hz, 1H), 7.26 (d, J=4.5 Hz, 1H), 6.82 (d, J=4.8 Hz, 1H), 6.70 (d, J=7.5 Hz, 1H), 6.57 (d, J=12.9 Hz, 1H), 4.92 (dq, J=6.9, 7.2 Hz, 1H), 1.58 (d, J=6.6 Hz, 3H); MS (ES+) m/z 412.9 (M+1), 414.9 (M+1).

Example 60

Synthesis of 5-chloro-2-fluoro-4-((1-(pyridin-4-yl)propyl)amino)-N-(thiazol-2-yl)benzenesulfonamide

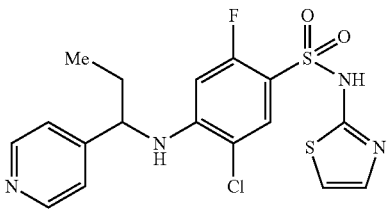 [SMILES: CCC(Nc1cc(F)c(S(=O)(=O)Nc2nccs2)cc1Cl)c1ccncc1]

Step 1. Preparation of 5-chloro-N-(2,4-dimethoxybenzyl)-2-fluoro-4-((1-(pyridin-4-yl)propyl)amino)-N-(thiazol-2-yl)benzenesulfonamide

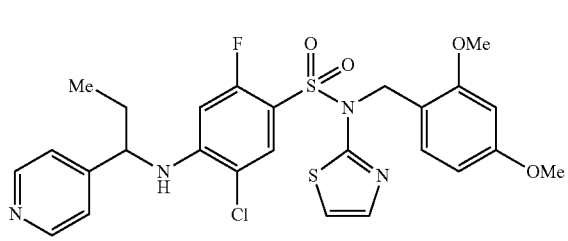 [SMILES: CCC(Nc1cc(F)c(S(=O)(=O)N(Cc2ccc(OC)cc2OC)c2nccs2)cc1Cl)c1ccncc1]

Following the procedure as described for EXAMPLE 43, Step 1 and making non-critical variations as required to replace 1-phenylcyclopropan-1-amine with 1-(pyridin-4-yl)propan-1-amine, and purification by column chromatography eluting with a gradient of 5-25% of methanol in dichloromethane, the title compound was obtained as a colorless oil (0.235 g, 75% yield): $^1$H NMR (300 MHz, CDCl$_3$) δ 8.59 (d, J=6.0 Hz, 2H), 7.70 (d, J=6.9 Hz, 1H), 7.35 (d, J=3.6 Hz, 1H), 7.19 (d, J=6.0 Hz, 2H), 7.15 (d, J=8.1 Hz, 1H), 6.93 (d, J=3.6 Hz, 1H), 6.33 (dd, J=8.4, 2.1 Hz, 1H), 6.30-6.26 (m, 1H), 5.96 (d, J=12.0 Hz, 1H), 5.26 (d, J=5.4 Hz, 1H), 5.11 (s, 2H), 4.21 (q, J=6.3 Hz, 1H), 3.73 (s, 3H), 3.65 (s, 3H), 1.97-1.82 (m, 2H), 1.01 (t, J=7.5 Hz, 3H); MS (ES+) m/z 577.0 (M+1), 579.0 (M+1).

Step 2. Preparation of 5-chloro-2-fluoro-4-((1-(pyridin-4-yl)propyl)amino)-N-(thiazol-2-yl)benzenesulfonamide

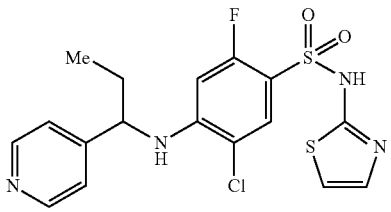 [SMILES: CCC(Nc1cc(F)c(S(=O)(=O)Nc2nccs2)cc1Cl)c1ccncc1]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((1-(pyridin-4-yl)propyl)amino)-N-(thiazol-2-yl)benzenesulfonamide, and trituration with acetonitrile (3×volume), the title compound was obtained as a colorless solid (0.077 g, 33% yield): $^1$H NMR (300 MHz, DMSO-d$_6$) δ 12.79 (s, 1H), 8.76 (d, J=5.7 Hz, 2H), 7.90 (d, J=6.3 Hz, 2H), 7.61 (d, J=7.2 Hz, 1H), 7.25 (d, J=4.5 Hz, 1H), 6.82 (d, J=4.5 Hz, 1H), 6.76 (d, J=7.8 Hz, 1H), 6.52 (d, J=13.2 Hz, 1H), 4.80-4.69 (m, 1H), 2.12-1.96 (m, 1H), 1.93-1.75 (m, 1H), 0.94 (t, J=7.2 Hz, 3H); MS (ES+) m/z 427.0 (M+1), 429.0 (M+1).

Example 61

Synthesis of 5-chloro-2-fluoro-4-((isoquinolin-8-ylmethyl)amino)-N-(thiazol-2-yl)benzenesulfonamide

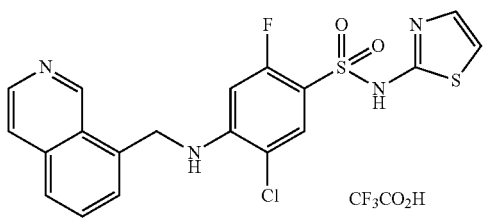 [SMILES: O=S(=O)(Nc1nccs1)c1cc(Cl)c(NCc2cccc3ccncc23)cc1F ; "CF3CO2H"]

Step 1. Preparation of 5-chloro-N-(2,4-dimethoxybenzyl)-2-fluoro-4-((isoquinolin-8-ylmethyl)amino)-N-(thiazol-2-yl)benzenesulfonamide

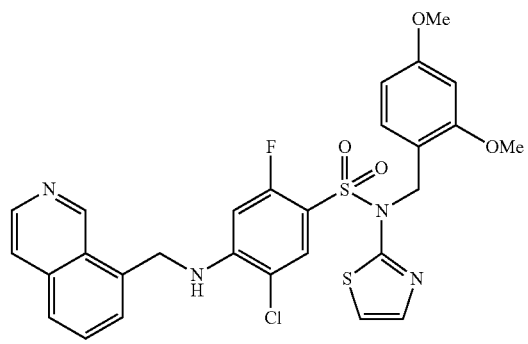 [SMILES: COc1ccc(CN(c2nccs2)S(=O)(=O)c2cc(Cl)c(NCc3cccc4ccncc34)cc2F)c(OC)c1]

To a mixture of 5-chloro-N-(2,4-dimethoxybenzyl)-2,4-difluoro-N-(thiazol-2-yl)benzenesulfonamide (0.250 g, 0.543 mmol) and isoquinolin-8-ylmethanamine (0.086 mg, 0.54 mmol) in anhydrous dimethyl sulfoxide (5 mL) was added cesium carbonate (0.424 g, 1.30 mmol) and the reaction mixture was heated at 90° C. for 17 h. The reaction mixture was allowed to cool to ambient temperature, diluted with ethyl acetate (5 mL) and water (5 mL), and the aqueous phase was extracted with ethyl acetate (3×3 mL). The combined organic phases were washed with brine (1×5 mL), dried over anhydrous sodium sulfate, and filtered. Concentration in vacuo and purification of the residue by column chromatography, eluting with a gradient of 6 to 80% of ethyl acetate in hexanes, provided the title compound as a colorless oil (0.062 g, 19% yield): MS (ES+) m/z 599.0 (M+1), 601.0 (M+1).

Step 2. Preparation of 5-chloro-2-fluoro-4-((isoquinolin-8-ylmethyl)amino)-N-(thiazol-2-yl)benzenesulfonamide

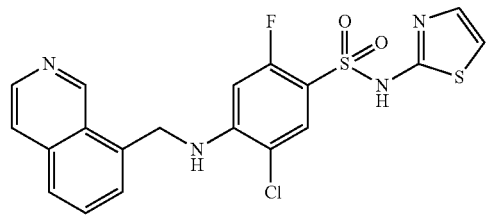 [SMILES: O=S(=O)(Nc1nccs1)c1cc(Cl)c(NCc2cccc3ccncc23)cc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((isoquinolin-8-ylmethyl)amino)-N-(thiazol-2-yl)benzenesulfonamide, the title compound was obtained as a colorless solid (0.033 g, 13% yield): $^1$H NMR (300 MHz, DMSO-d$_6$) δ 12.77 (s, 1H), 9.87 (s, 1H), 8.66 (d, J=6.3 Hz, 1H), 8.24 (d, J=6.0 Hz, 1H), 8.06 (d, J=8.1 Hz, 1H), 7.94 (dd, J=7.2, 7.2 Hz, 1H), 7.63 (d, J=7.2 Hz, 2H), 7.33 (t, J=4.8 Hz, 1H), 7.26 (d, J=4.8 Hz, 1H), 6.82 (d, J=4.5 Hz, 1H), 6.59 (d, J=12.9 Hz, 1H), 5.13 (d, J=5.7 Hz, 2H); MS (ES+) m/z 449.0 (M+1), 451.0 (M+1).

Example 62

Synthesis of 5-chloro-2-fluoro-N-(6-fluoropyridin-2-yl)-4-((isoquinolin-8-ylmethyl)amino)benzenesulfonamide

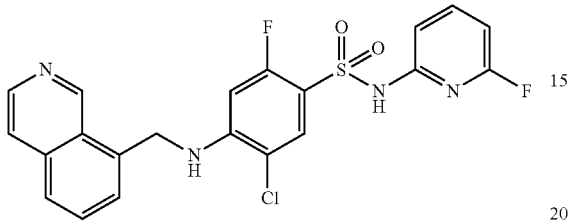

Step 1. Preparation of 5-chloro-N-(2,4-dimethoxybenzyl)-2-fluoro-N-(6-fluoropyridin-2-yl)-4-((isoquinolin-8-ylmethyl)amino)benzenesulfonamide

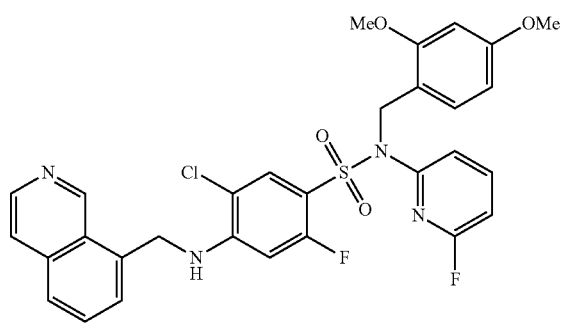 [SMILES: COc1ccc(CN(c2cccc(F)n2)S(=O)(=O)c2cc(Cl)c(NCc3cccc4ccncc34)cc2F)c(OC)c1]

To a mixture of 5-chloro-N-(2,4-dimethoxybenzyl)-2,4-difluoro-N-(6-fluoropyridin-2-yl)benzenesulfonamide (0.256 g, 0.543 mmol) and isoquinolin-8-ylmethanamine (0.086 mg, 0.54 mmol) in anhydrous dimethyl sulfoxide (5 mL) was added potassium carbonate (0.233 g, 1.69 mmol) and the reaction mixture was heated to 110° C. for 18 h. The reaction mixture was allowed to cool to ambient temperature, diluted with ethyl acetate (5 mL) and water (5 mL), and the aqueous phase was extracted with ethyl acetate (3×3 mL). The combined organic phases were washed with brine (1×5 mL), dried over anhydrous sodium sulfate, and filtered. Concentration of the filtrate in vacuo purification of the residue by column chromatography, eluting with a gradient of 6 to 80% of ethyl acetate in hexanes, provided the title compound as a brown oil (0.062 g, 19% yield): MS (ES+) m/z 611.1 (M+1), 613.0 (M+1).

Step 2. Preparation of 5-chloro-2-fluoro-N-(6-fluoropyridin-2-yl)-4-((isoquinolin-8-ylmethyl)amino)benzenesulfonamide

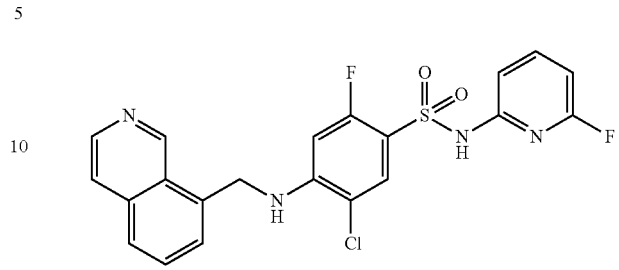

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-N-(6-fluoropyridin-2-yl)-4-((isoquinolin-8-ylmethyl)amino)benzenesulfonamide, and purification by column chromatography, eluting with a gradient of 0 to 25% of methanol in dichloromethane, the title compound was obtained as a colorless solid (0.044 g, 17% yield): $^1$H NMR (300 MHz, DMSO-$d_6$) δ 11.48 (s, 1H), 9.65 (s, 1H), 8.56 (d, J=5.7 Hz, 1H), 7.90-7.80 (m, 3H), 7.77 (d, J=7.5 Hz, 1H), 7.69 (dd, J=7.2, 7.2 Hz, 1H), 7.51-7.40 (m, 1H), 7.47 (d, J=6.9 Hz, 1H), 6.85 (dd, J=7.8, 2.1 Hz, 1H), 6.71 (dd, J=8.1, 2.4 Hz, 1H), 6.61 (d, J=13.2 Hz, 1H), 5.09 (d, J=5.7 Hz, 2H); MS (ES+) m/z 460.9 (M+1), 462.9 (M+1).

Example 63

Synthesis of 5-Chloro-4-((2-(dimethylamino)-1-phenylethyl)amino)-2-fluoro-N-(thiazol-2-yl)benzenesulfonamide 2,2,2-trifluoroacetate

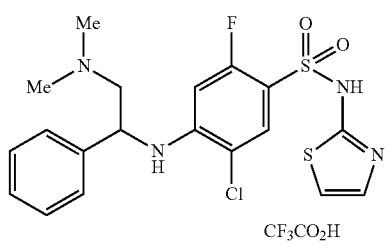 [SMILES: CN(C)CC(Nc1cc(F)c(S(=O)(=O)Nc2nccs2)cc1Cl)c1ccccc1 ; "CF3CO2H"]

CF$_3$CO$_2$H

Step 1. Preparation of 5-chloro-N-(2,4-dimethoxybenzyl)-4-((2-(dimethylamino)-1-phenylethyl)amino-2-fluoro-N-(thiazol-2-yl)benzenesulfonamide

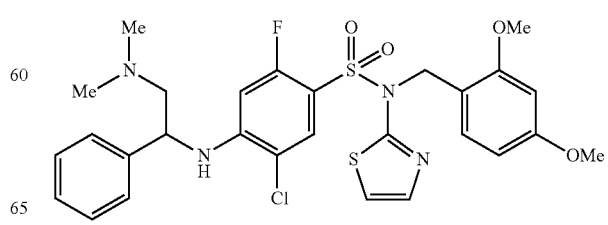

Following the procedure as described for EXAMPLE 43, Step 1 and making non-critical variations as required to replace 1-phenylcyclopropan-1-amine with $N^1,N^1$-dimethyl-2-phenylethane-1,2-diamine, the title compound was obtained as a colorless oil (0.158 g, 48% yield): MS (ES+) m/z 605.2 (M+1), 607.2 (M+1).

Step 2. Preparation of 5-chloro-4-((2-(dimethylamino)-1-phenylethyl)amino)-2-fluoro-N-(thiazol-2-yl)benzenesulfonamide 2,2,2-trifluoroacetate

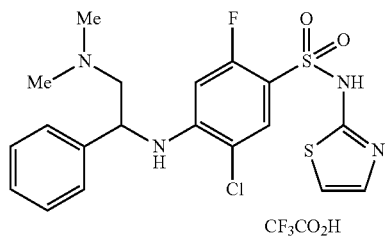 [SMILES: CN(C)CC(Nc1cc(F)c(S(=O)(=O)Nc2nccs2)cc1Cl)c1ccccc1 ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with of 5-chloro-N-(2,4-dimethoxybenzyl)-4-((2-(dimethylamino)-1-phenylethyl)amino-2-fluoro-N-(thiazol-2-yl)benzenesulfonamide, and trituration with acetonitrile (3×5 mL), the title compound was obtained as a colorless solid (0.072 g, 29% yield): $^1$H NMR (300 MHz, DMSO-$d_6$) δ 7.63 (d, J=7.2 Hz, 1H), 7.48-7.34 (m, 4H), 7.33-7.28 (m, 1H), 7.26 (d, J=4.8 Hz, 1H), 6.99 (d, J=9.0 Hz, 1H), 6.89-6.77 (m, 2H), 5.32-5.19 (m, 1H), 3.84 (t, J=11.7 Hz, 1H), 3.33 (dd, J=13.5, 3.0 Hz, 1H), 2.87 (s, 6H); sulfonamide NH and COOH not observed; MS (ES+) m/z 455.0 (M+1), 457.0 (M+1).

Example 64

Synthesis of (S)-5-chloro-4-((2-(dimethylamino)-1-phenylethyl)amino)-2-fluoro-N-(thiazol-2-yl)benzenesulfonamide 2,2,2-trifluoroacetate

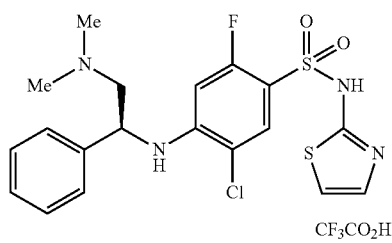 [SMILES: CN(C)C[C@@H](Nc1cc(F)c(S(=O)(=O)Nc2nccs2)cc1Cl)c1ccccc1 ; "CF3CO2H"]

Step 1. Preparation of (S)—$N^1,N^1$-dimethyl-2-phenylethane-1,2-diamine hydrochloride

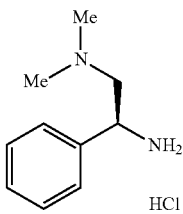 [SMILES: CN(C)C[C@@H](N)c1ccccc1 ; Cl]

To tert-butyl (S)-4-phenyl-1,2,3-oxathiazolidine-3-carboxylate 2,2-dioxide (0.200 g, 0.67 mmol, prepared as described in James et al., Org. Lett. 2013; 15 (23):6094-6097) was added a 2 M solution of in methanol (1.7 mL, 3.33 mmol) and the reaction mixture was stirred at ambient temperature for 3 h. The reaction mixture was concentrated in vacuo, the residue dissolved in dioxane (3 mL), and a 4 M solution of hydrogen chloride dioxane (0.50 mL, 2.0 mmol) was added to it. The reaction mixture was stirred at ambient temperature for 17 h. Concentration in vacuo provided the title compound as a brownish, hygroscopic solid (0.080 g, 77% yield): MS (ES+) m/z 165.1 (M+1).

Step 2. Preparation of (S)-5-chloro-N-(2,4-dimethoxybenzyl)-4-((2-(dimethylamino)-1-phenylethyl)amino-2-fluoro-N-(thiazol-2-yl)benzenesulfonamide

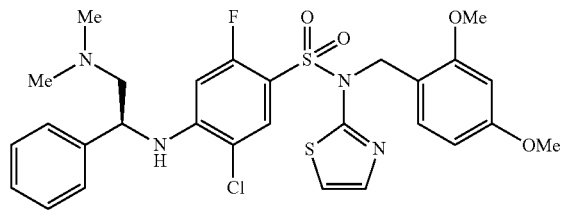 [SMILES: COc1ccc(CN(c2nccs2)S(=O)(=O)c2cc(Cl)c(N[C@H](CN(C)C)c3ccccc3)cc2F)c(OC)c1]

Following the procedure as described for EXAMPLE 43, Step 1 and making non-critical variations as required to replace 1-phenylcyclopropan-1-amine with (S)—$N^1,N^1$-dimethyl-2-phenylethane-1,2-diamine hydrochloride, the title compound was obtained as a colorless oil (0.085 g, 21% yield): MS (ES+) m/z 605.0 (M+1), 607.0 (M+1).

Step 3: (S)-5-Chloro-4-((2-(dimethylamino)-1-phenylethyl)amino)-2-fluoro-N-(thiazol-2-yl)benzenesulfonamide 2,2,2-trifluoroacetate

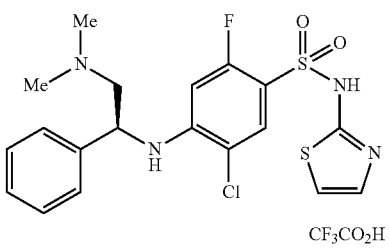 [SMILES: CN(C)C[C@@H](Nc1cc(F)c(S(=O)(=O)Nc2nccs2)cc1Cl)c1ccccc1 ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-4-((2-(dimethylamino)-1-phenylethyl)amino-2-fluoro-N-(thiazol-2-yl)benzenesulfonamide, and purification by preparative reverse phase HPLC using acetonitrile in water containing 0.1% trifluoroacetic acid as eluent, the title compound was obtained as a colorless solid (0.017 g, 6% yield): $^1$H NMR (300 MHz, DMSO-$d_6$) δ 12.80 (s, 1H), 9.25 (s, 1H), 7.62 (d, J=7.2 Hz, 1H), 7.48-7.34 (m, 4H), 7.33-7.29 (m, 1H), 7.25 (d, J=4.5 Hz, 1H), 7.00 (d, J=8.7 Hz, 1H), 6.83 (d, J=4.5 Hz, 1H), 6.83 (d, J=12.9 Hz, 1H), 5.32-5.19 (m, 1H), 3.85 (t, J=11.7 Hz, 1H), 3.40-3.28 (m, 1H), 2.86 (s, 6H); $^{19}$F NMR (282 MHz, DMSO-$d_6$) δ−73.7 (s, 3F), −109.4 (s, 1F); MS (ES+) m/z 454.9 (M+1), 456.9 (M+1).

Example 65

Synthesis of (R)-5-chloro-4-((2-(dimethylamino)-1-phenylethyl)amino)-2-fluoro-N-(thiazol-2-yl)benzenesulfonamide 2,2,2-trifluoroacetate

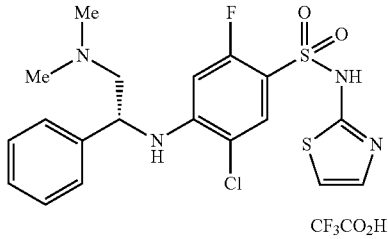 [SMILES: CN(C)C[C@H](Nc1cc(F)c(S(=O)(=O)Nc2nccs2)cc1Cl)c1ccccc1 ; "CF3CO2H"]

CF$_3$CO$_2$H

Step 1. Preparation of (R)—N$^1$,N$^1$-dimethyl-2-phenylethane-1,2-diamine hydrochloride

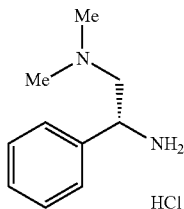 [SMILES: CN(C)C[C@H](N)c1ccccc1 ; Cl]

HCl

Following the procedure as described for EXAMPLE 64, Step 1 and making non-critical variations as required to replace tert-butyl (S)-4-phenyl-1,2,3-oxathiazolidine-3-carboxylate 2,2-dioxide with tert-butyl (R)-4-phenyl-1,2,3-oxathiazolidine-3-carboxylate 2,2-dioxide, the title compound was obtained as a brown oil (0.133 g, quantitative yield): MS (ES+) m/z 165.1 (M+1).

Step 2. Preparation of (S)-5-chloro-N-(2,4-dimethoxybenzyl)-4-((2-(dimethylamino)-1-phenylethyl)amino-2-fluoro-N-(thiazol-2-yl)benzenesulfonamide

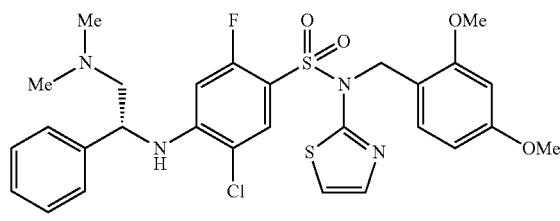 [SMILES: COc1ccc(CN(c2nccs2)S(=O)(=O)c2cc(Cl)c(N[C@@H](CN(C)C)c3ccccc3)cc2F)c(OC)c1]

Following the procedure as described for EXAMPLE 43, Step 1 and making non-critical variations as required to replace 1-phenylcyclopropan-1-amine with (R)—N$^1$,N$^1$-dimethyl-2-phenylethane-1,2-diamine hydrochloride, the title compound was obtained as a colorless oil (0.075 g, 18% yield): MS (ES+) m/z 605.0 (M+1), 607.0 (M+1).

Step 3: (S)-5-Chloro-4-((2-(dimethylamino)-1-phenylethyl)amino)-2-fluoro-N-(thiazol-2-yl)benzenesulfonamide 2,2,2-trifluoroacetate

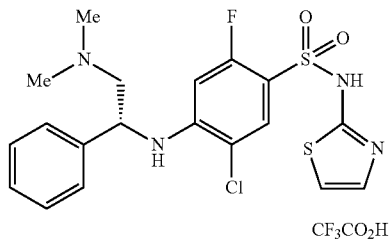 [SMILES: CN(C)C[C@H](Nc1cc(F)c(S(=O)(=O)Nc2nccs2)cc1Cl)c1ccccc1 ; "CF3CO2H"]

CF$_3$CO$_2$H

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-4-((2-(dimethylamino)-1-phenylethyl)amino-2-fluoro-N-(thiazol-2-yl)benzenesulfonamide, and purification by preparative reverse phase HPLC using acetonitrile in water containing 0.1% trifluoroacetic acid as eluent, the title compound was obtained as a colorless solid (0.027 g, 8% yield): $^1$H NMR (300 MHz, DMSO-$d_6$) δ 12.79 (s, 1H), 9.20 (s, 1H), 7.62 (d, J=7.2 Hz, 1H), 7.47-7.35 (m, 4H), 7.29-7.27 (m, 1H), 7.26 (d, J=4.5 Hz, 1H), 6.99 (d, J=8.7 Hz, 1H), 6.83 (d, J=4.5 Hz, 1H), 6.83 (d, J=12.9 Hz, 1H), 5.33-5.19 (m, 1H), 3.85 (t, J=11.7 Hz, 1H), 3.40-3.29 (m, 1H), 2.88 (s, 3H), 2.86 (s, 3H); $^{19}$F NMR (282 MHz, DMSO-$d_6$) δ−73.7 (s, 3F), −109.4 (s, 1F); MS (ES+) m/z 455.0 (M+1), 457.0 (M+1).

Example 66

Synthesis of (R)-4-((2-(azetidin-1-yl)-1-phenylethyl)amino)-5-chloro-2-fluoro-N-(thiazol-2-yl)benzenesulfonamide 2,2,2-trifluoroacetate

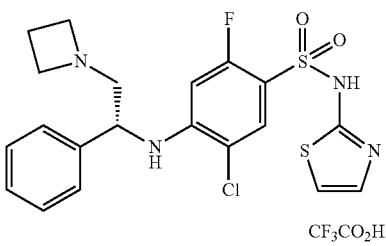 [SMILES: O=S(=O)(Nc1nccs1)c1cc(Cl)c(N[C@@H](CN2CCC2)c2ccccc2)cc1F ; "CF3CO2H"]

CF₃CO₂H

Step 1. Preparation of tert-butyl (R)-(2-(azetidin-1-yl)-1-phenylethyl)carbamate

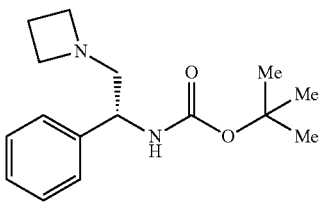 [SMILES: CC(C)(C)OC(=O)N[C@@H](CN1CCC1)c1ccccc1]

To a mixture of (R)-2-((tert-butoxycarbonyl)amino)-2-phenylethyl methanesulfonate (0.50 g, 1.58 mmol, prepared according to WO2009013171) and azetidine (0.45 mL, 7.9 mmol) in anhydrous tetrahydrofuran (4.5 mL) was added N,N-diisopropylethylamine (0.83 mL, 4.8 mmol) and the reaction mixture was stirred at 60° C. for 17 h. The suspension was diluted with water (10 mL) and ethyl acetate (10 mL), and the aqueous phase was extracted with ethyl acetate (3×10 mL). The combined organic phases were washed with brine (5 mL), dried over anhydrous sodium sulfate, and filtered. Concentration of the filtrate in vacuo and trituration the residue with hexanes (20 mL) provided the title compound as a colorless solid (0.136 g, 31% yield): MS (ES+) m/z 277.3 (M+1).

Step 2. Preparation of (R)-2-(azetidin-1-yl)-1-phenylethan-1-amine hydrochloride

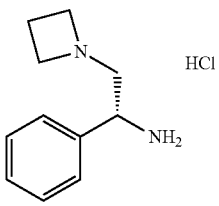 [SMILES: N[C@@H](CN1CCC1)c1ccccc1 ; Cl]

To a mixture of tert-butyl (R)-(2-(azetidin-1-yl)-1-phenylethyl)carbamate (0.136 g, 0.492 mmol) in anhydrous dioxane (3 mL) was added a 4.0 M solution of hydrogen chloride in dioxane (0.37 mL, 1.5 mmol) and the reaction mixture was stirred at ambient temperature for 2 h. The reaction mixture was diluted with diethyl ether (10 mL) and the formed precipitate was collected by filtration to provide the title compound as a colorless solid (0.279 g, 77% yield): MS (ES+) m/z 177.2 (M+1).

Step 3. Preparation of (R)-4-((2-(azetidin-1-yl)-1-phenylethyl)amino)-5-chloro-N-(2,4-dimethoxybenzyl)-2-fluoro-N-(thiazol-2-yl)benzenesulfonamide

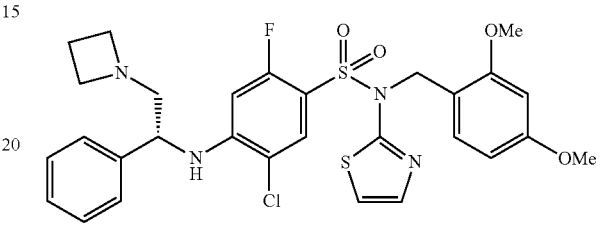

Following the procedure as described for EXAMPLE 43, Step 1 and making non-critical variations as required to replace 1-phenylcyclopropan-1-amine with (R)-2-(azetidin-1-yl)-1-phenylethan-1-amine hydrochloride, the title compound was obtained as a colorless oil (0.163 g, 75% yield): MS (ES+) m/z 617.1 (M+1), 619.1 (M+1).

Step 4. (R)-4-((2-(azetidin-1-yl)-1-phenylethyl)amino)-5-chloro-2-fluoro-N-(thiazol-2-yl)benzenesulfonamide 2,2,2-trifluoroacetate

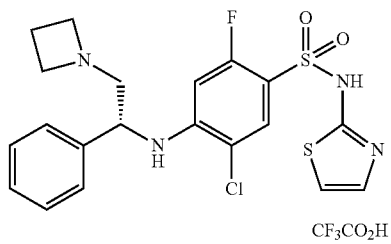

CF₃CO₂H

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (R)-4-((2-(azetidin-1-yl)-1-phenylethyl)amino)-5-chloro-N-(2,4-dimethoxybenzyl)-2-fluoro-N-(thiazol-2-yl)benzenesulfonamide, and trituration with acetonitrile (5 mL), the title compound was obtained as a colorless solid (0.084 g, 39% yield): $^1$H NMR (300 MHz, DMSO-$d_6$) δ 12.76 (s, 1H), 9.70 (s, 1H), 7.58 (d, J=7.2 Hz, 1H), 7.45-7.39 (m, 2H), 7.38-7.31 (m, 2H), 7.30-7.26 (m, 1H), 7.22 (d, J=4.5 Hz, 1H), 6.86 (d, J=8.1 Hz, 1H), 6.79 (d, J=4.8 Hz, 1H), 6.63 (d, J=12.9 Hz, 1H), 5.00-5.89 (m, 1H), 4.27-3.99 (m, 2H), 3.85-3.67 (m, 2H), 3.64-3.46 (m, 2H), 2.41-2.18 (m, 2H); MS (ES+) m/z 467.0 (M+1), 469.0 (M+1).

Example 67

Synthesis of (S)-4-((2-(azetidin-1-yl)-1-phenylethyl)amino)-5-chloro-2-fluoro-N-(thiazol-2-yl)benzenesulfonamide 2,2,2-trifluoroacetate

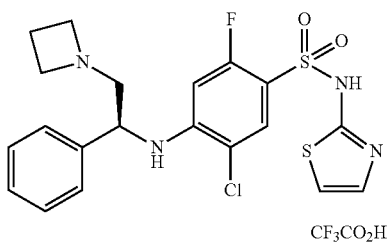 [SMILES: O=S(=O)(Nc1nccs1)c1cc(Cl)c(N[C@H](CN2CCC2)c2ccccc2)cc1F ; "CF3CO2H"]

CF₃CO₂H

Step 1. Preparation of (S)-2-(azetidin-1-yl)-1-phenylethan-1-amine hydrochloride

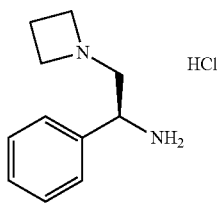 [SMILES: N[C@H](CN1CCC1)c1ccccc1 ; Cl]

Following the procedure as described for EXAMPLE 43, Step 1 and Step 2, the title compound as a brownish solid (0.279 g, 83% yield): MS (ES+) m/z 177.2 (M+1).

Step 2. Preparation of (S)-4-((2-(azetidin-1-yl)-1-phenylethyl)amino)-5-chloro-N-(2,4-dimethoxybenzyl)-2-fluoro-N-(thiazol-2-yl)benzenesulfonamide

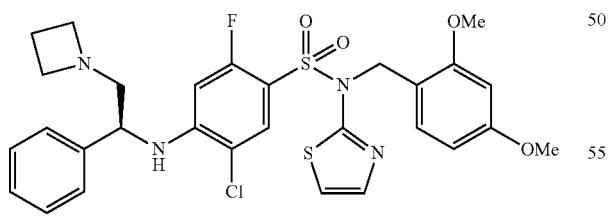

Following the procedure as described for EXAMPLE 43, Step 1 and making non-critical variations as required to replace 1-phenylcyclopropan-1-amine with (S)-2-(azetidin-1-yl)-1-phenylethan-1-amine hydrochloride, the title compound was obtained as a colorless oil (0.106 g, 32% yield): MS (ES+) m/z 617.1 (M+1), 619.1 (M+1).

Step 3: (S)-4-((2-(azetidin-1-yl)-1-phenylethyl)amino)-5-chloro-2-fluoro-N-(thiazol-2-yl)benzenesulfonamide 2,2,2-trifluoroacetate

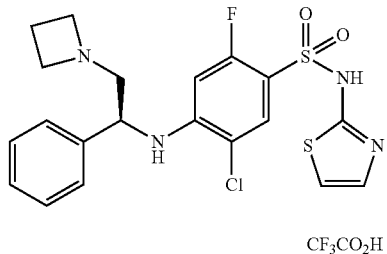 [SMILES: O=S(=O)(Nc1nccs1)c1cc(Cl)c(N[C@H](CN2CCC2)c2ccccc2)cc1F ; "CF3CO2H"]

CF₃CO₂H

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-4-((2-(azetidin-1-yl)-1-phenylethyl)amino)-5-chloro-N-(2,4-dimethoxybenzyl)-2-fluoro-N-(thiazol-2-yl)benzenesulfonamide, the title compound was obtained as a colorless solid (0.095 g, 29% yield): ¹H NMR (300 MHz, DMSO-d₆) δ 12.80 (s, 1H), 9.72 (s, 1H), 7.62 (d, J=7.2 Hz, 1H), 7.48-7.43 (m, 2H), 7.42-7.35 (m, 2H), 7.33-7.29 (m, 1H), 7.26 (d, J=4.5 Hz, 1H), 6.89 (d, J=8.4 Hz, 1H), 6.83 (d, J=4.5 Hz, 1H), 6.67 (d, J=12.9 Hz, 1H), 5.04-4.91 (m, 1H), 4.27-4.04 (m, 4H), 3.89-3.75 (m, 1H), 3.64-3.49 (m, 1H), 2.46-2.20 (m, 2H); MS (ES+) m/z 467.0 (M+1), 469.0 (M+1).

Example 68

Synthesis of (S)-5-chloro-4-((2-(3-fluoroazetidin-1-yl)-1-phenylethyl)amino)-2-fluoro-N-(thiazol-2-yl)benzenesulfonamide 2,2,2-trifluoroacetate

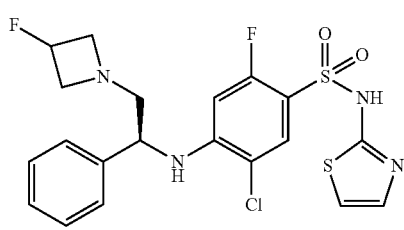

CF₃CO₂H

Step 1. Preparation of (S)-2-(3-fluoroazetidin-1-yl)-1-phenylethan-1-amine hydrochloride

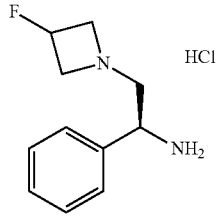 [SMILES: N[C@H](CN1CC(F)C1)c1ccccc1 ; Cl]

To a solution of tert-butyl (S)-4-phenyl-1,2,3-oxathiazolidine-3-carboxylate 2,2-dioxide (0.200 g, 0.67 mmol) in anhydrous acetonitrile (3 mL) was added 3-fluoroazetidine (0.750 g, 6.70 mmol) and the reaction mixture was stirred at ambient temperature for 3 h. The reaction mixture was concentrated in vacuo, the residue dissolved in dioxane (3 mL), and a 4 M solution of hydrogen chloride dioxane (0.84 mL, 3.4 mmol) was added to it. The reaction mixture was stirred at ambient temperature for 2 h. Concentration in vacuo provided the title compound as a brownish solid (0.137 g, 89% yield): MS (ES+) m/z 195.1 (M+1).

Step 2. Preparation of (S)-4-((2-(3-fluoroazetidin-1-yl)-1-phenylethyl)amino)-5-chloro-N-(2,4-dimethoxybenzyl)-2-fluoro-N-(thiazol-2-yl)benzenesulfonamide

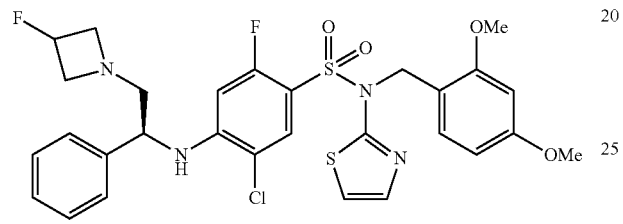

Following the procedure as described for EXAMPLE 43, Step 1 and making non-critical variations as required to replace 1-phenylcyclopropan-1-amine with (S)-2-(3-fluoroazetidin-1-yl)-1-phenylethan-1-amine hydrochloride, the title compound was obtained as a colorless oil (0.045 g, 11% yield): MS (ES+) m/z 635.4 (M+1), 637.4 (M+1).

Step 3: (S)-5-chloro-4-((2-(3-fluoroazetidin-1-yl)-1-phenylethyl)amino)-2-fluoro-N-(thiazol-2-yl)benzenesulfonamide 2,2,2-trifluoroacetate

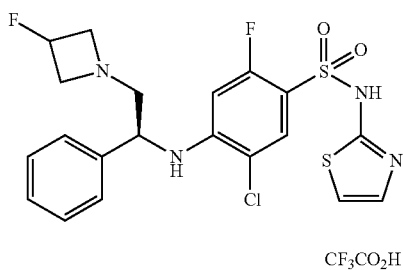 [SMILES: O=S(=O)(Nc1nccs1)c1cc(Cl)c(N[C@H](CN2CC(F)C2)c2ccccc2)cc1F ; "CF3CO2H"]

Following the procedure as described for EXAMPLE 43, Step 2 and making non-critical variations as required to The procedure as described for EXAMPLE 43, Step 2 to replace 5-chloro-N-(2,4-dimethoxybenzyl)-2-fluoro-4-((1-phenylcyclopropyl)amino)-N-(thiazol-2-yl)benzenesulfonamide with (S)-4-((2-(3-fluoroazetidin-1-yl)-1-phenylethyl)amino)-5-chloro-N-(2,4-dimethoxybenzyl)-2-fluoro-N-(thiazol-2-yl)benzenesulfonamide, and purification by preparative reverse phase HPLC using acetonitrile in water containing 0.1% trifluoroacetic acid as eluent, the title compound was obtained as a colorless solid (0.013 g, 4% yield): $^1$H NMR (300 MHz, DMSO-$d_6$) δ 12.79 (s, 1H), 10.54 (broad s, 0.5H), 9.71 (broad s, 0.5H), 7.62 (d, J=7.5 Hz, 1H), 7.49-7.42 (m, 2H), 7.40-7.35 (m, 2H), 7.34-7.30 (m, 1H), 7.26 (d, J=4.8 Hz, 1H), 6.90 (d, J=7.5 Hz, 1H), 6.83 (d, J=4.5 Hz, 1H), 6.61 (d, J=12.9 Hz, 1H), 5.59-5.19 (m, 1H), 5.08-4.92 (m, 1H), 4.69-4.24 (m, 4H), 4.02-3.80 (m, 1H), 3.70-3.55 (m, 1H); MS (ES+) m/z 485.0 (M+1), 487.0 (M+1).

Example 69

Synthesis of (S)-5-chloro-4-((2-(3,3-difluoroazetidin-1-yl)-1-phenylethyl)amino)-2-fluoro-N-(thiazol-2-yl)benzenesulfonamide

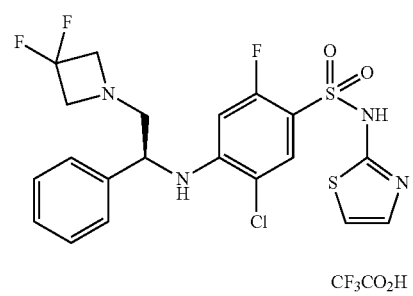

Step 1. Preparation of (S)-2-(3-fluoroazetidin-1-yl)-1-phenylethan-1-amine hydrochloride

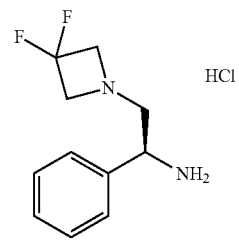 [SMILES: N[C@H](CN1CC(F)(F)C1)c1ccccc1 ; Cl]

Following the procedure as described for EXAMPLE 68, Step 1 and making non-critical variations as required to replace 3-fluoroazetidine with 3,3-difluoroazetidine, the title compound was obtained as a colorless oil (0.164 g, 99% yield): MS (ES+) m/z 213.1 (M+1).

Step 2. Preparation of (S)-4-((2-(3,3-difluoroazetidin-1-yl)-1-phenylethyl)amino)-5-chloro-N-(2,4-dimethoxybenzyl)-2-fluoro-N-(thiazol-2-yl)benzenesulfonamide

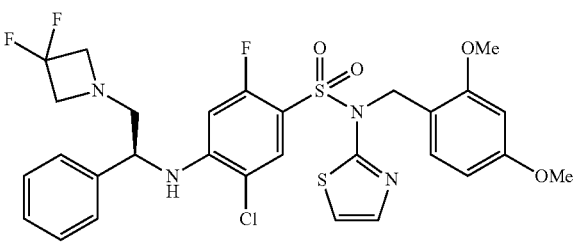 [SMILES: COc1ccc(CN(c2nccs2)S(=O)(=O)c2cc(Cl)c(N[C@H](CN3CC(F)(F)C3)c3ccccc3)cc2F)c(OC)c1]

Following the procedure as described for EXAMPLE 43, Step 1 and making non-critical variations as required to replace 1-phenylcyclopropan-1-amine with (S)-2-(3,3-difluoroazetidin-1-yl)-1-phenylethan-1-amine hydrochloride, the title compound was obtained as a colorless oil (0.032 g, 9% yield): MS (ES+) m/z 653.4 (M+1), 655.4 (M+1).

Step 3: (S)-5-chloro-4-((2-(3-fluoroazetidin-1-yl)-1-phenylethyl)amino)-2-fluoro-N-(thiazol-2-yl)benzenesulfonamide

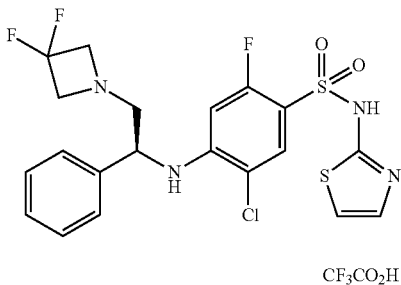 [SMILES: O=S(=O)(Nc1nccs1)c1cc(Cl)c(N[C@H](CN2CC(F)(F)C2)c2ccccc2)cc1F ; "CF3CO2H"]

CF$_3$CO$_2$H

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-4-((2-(3,3-difluoroazetidin-1-yl)-1-phenylethyl)amino)-5-chloro-N-(2,4-dimethoxybenzyl)-2-fluoro-N-(thiazol-2-yl)benzenesulfonamide, and purification by preparative reverse phase HPLC using acetonitrile in water containing 0.1% trifluoroacetic acid as eluent, the title compound was obtained as a colorless solid (0.010 g, 4% yield): $^1$H NMR (300 MHz, DMSO-d$_6$) δ 12.78 (s, 1H), 7.60 (d, J=6.9 Hz, 1H), 7.47-7.40 (m, 2H), 7.39-7.30 (m, 2H), 7.30-7.22 (m, 2H), 6.86-6.79 (m, 1H), 6.66-6.56 (m, 1H), 6.44 (d, J=12.9 Hz, 1H), 4.79-4.63 (m, 1H), 4.20-3.79 (m, 4H), 3.53-3.30 (m, 1H), 3.25-3.03 (m, 1H); MS (ES+) m/z 503.0 (M+1), 505.0 (M+1).

Example 70

Synthesis of (S)-5-chloro-2-fluoro-4-((1-phenyl-2-(pyrrolidin-1-yl)ethyl)amino)-N-(thiazol-2-yl)benzenesulfonamide

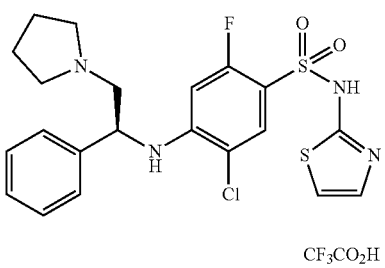 [SMILES: O=S(=O)(Nc1nccs1)c1cc(Cl)c(N[C@H](CN2CCCC2)c2ccccc2)cc1F ; "CF3CO2H"]

CF$_3$CO$_2$H

Step 1. Preparation of (S)-1-phenyl-2-(pyrrolidin-1-yl)ethan-1-amine hydrochloride

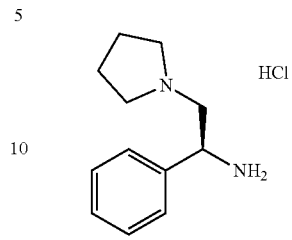

Following the procedure as described for EXAMPLE 66, Step 1 and making non-critical variations as required to replace (R)-2-((tert-butoxycarbonyl)amino)-2-phenylethyl methanesulfonate with (S)-2-((tert-butoxycarbonyl)amino)-2-phenylethyl methanesulfonate, and azetidine with pyrrolidine, the title compound was obtained as a brownish solid (0.198 g, 55% yield): MS (ES+) m/z 191.2 (M+1).

Step 2. Preparation of (S)-5-chloro-N-(2,4-dimethoxybenzyl)-2-fluoro-4-((1-phenyl-2-(pyrrolidin-1-yl)ethyl)amino)-N-(thiazol-2-yl)benzenesulfonamide

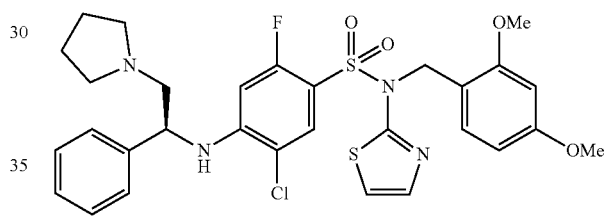

Following the procedure as described for EXAMPLE 43, Step 1 and making non-critical variations as required to replace 1-phenylcyclopropan-1-amine with (S)-1-phenyl-2-(pyrrolidin-1-yl)ethan-1-amine hydrochloride, the title compound was obtained as a colorless oil (147 g, 43% yield): MS (ES+) m/z 631.1 (M+1), 633.1 (M+1).

Step 3. Preparation of (S)-5-chloro-2-fluoro-4-((1-phenyl-2-(pyrrolidin-1-yl)ethyl)amino)-N-(thiazol-2-yl)benzenesulfonamide

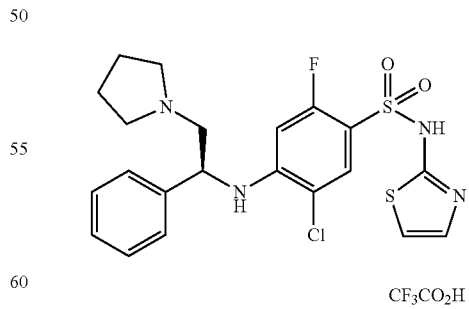

CF$_3$CO$_2$H

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro- 4-((1-phenyl-2-(pyrrolidin-1-yl)ethyl)amino)-N-(thiazol-2-yl)benzenesulfonamide, and purification by preparative reverse phase HPLC using acetonitrile in water containing 0.1% trifluoroacetic acid as eluent, the title compound was obtained as a colorless solid (0.023 g, 9% yield): $^1$H NMR (300 MHz, DMSO-$d_6$) δ 12.80 (s, 1H), 9.45 (s, 1H), 7.62 (d, J=7.2 Hz, 1H), 7.52-7.43 (m, 2H), 7.43-7.34 (m, 2H), 7.33-7.29 (m, 1H), 7.26 (d, J=4.8 Hz, 1H), 6.99 (d, J=8.1 Hz, 1H), 6.87-6.75 (m, 2H), 5.26-5.13 (m, 1H), 3.97 (t, J=12.3 Hz, 1H), 3.64-3.46 (m, 2H), 3.45-3.34 (m, 1H), 3.33-3.22 (m, 1H), 3.21-3.06 (m, 1H), 2.12-1.82 (m, 4H); $^{19}$F NMR (282 MHz, DMSO-$d_6$) δ −73.7 (s, 3F), −109.3 (s, 1F); MS (ES+) m/z 480.9 (M+1), 482.9 (M+1).

Example 71

Synthesis of (R)-5-chloro-2-fluoro-4-((1-phenyl-2-(pyrrolidin-1-yl)ethyl)amino)-N-(thiazol-2-yl)benzenesulfonamide

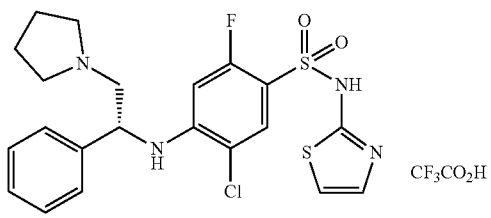 [SMILES: O=S(=O)(Nc1nccs1)c1cc(Cl)c(N[C@@H](CN2CCCC2)c2ccccc2)cc1F ; "CF3CO2H"]

Step 1. Preparation of (R)-1-phenyl-2-(pyrrolidin-1-yl)ethan-1-amine hydrochloride

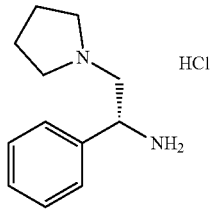 [SMILES: N[C@@H](CN1CCCC1)c1ccccc1 ; Cl]

Following the procedure as described for EXAMPLE 66, Step 1 and making non-critical variations as required to replace azetidine with pyrrolidine, the title compound was obtained as a brownish solid (0.313 g, quantitative yield): MS (ES+) m/z 191.2 (M+1).

Step 2. Preparation of (R)-5-chloro-N-(2,4-dimethoxybenzyl)-2-fluoro-4-((1-phenyl-2-(pyrrolidin-1-yl)ethyl)amino)-N-(thiazol-2-yl)benzenesulfonamide

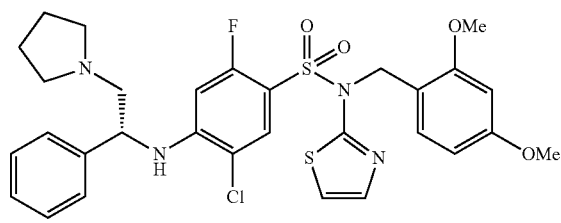 [SMILES: COc1ccc(CN(c2nccs2)S(=O)(=O)c2cc(Cl)c(N[C@@H](CN3CCCC3)c3ccccc3)cc2F)c(OC)c1]

Following the procedure as described for EXAMPLE 43, Step 1 and making non-critical variations as required to replace 1-phenylcyclopropan-1-amine with (R)-1-phenyl-2-(pyrrolidin-1-yl)ethan-1-amine hydrochloride, the title compound was obtained as a colorless oil (0.169 g, 49% yield): MS (ES+) m/z 631.1 (M+1), 633.1 (M+1).

Step 3. Preparation of (R)-5-chloro-2-fluoro-4-((1-phenyl-2-(pyrrolidin-1-yl)ethyl)amino)-N-(thiazol-2-yl)benzenesulfonamide

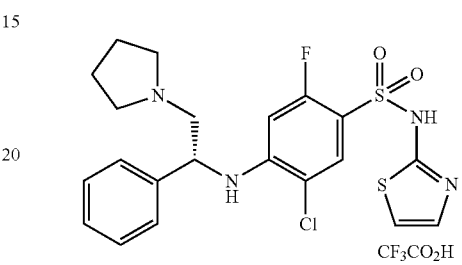

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (R)-5-chloro-N-(2,4-dimethoxybenzyl)-2-fluoro-4-((1-phenyl-2-(pyrrolidin-1-yl)ethyl)amino)-N-(thiazol-2-yl)benzenesulfonamide, and purification by preparative reverse phase HPLC using acetonitrile in water containing 0.1% trifluoroacetic acid as eluent, the title compound was obtained as a colorless solid (0.045 g, 17% yield): $^1$H NMR (300 MHz, DMSO-$d_6$) δ 12.80 (s, 1H), 9.48 (s, 1H), 7.62 (d, J=6.3 Hz, 1H), 7.51-7.43 (m, 2H), 7.42-7.34 (m, 2H), 7.31 (d, J=6.3 Hz, 1H), 7.28-7.22 (m, 1H), 6.99 (d, J=8.1 Hz, 1H), 6.86-6.73 (m, 2H), 5.25-5.12 (m, 1H), 3.97 (t, J=12.3 Hz, 1H), 3.63-3.47 (m, 2H), 3.56-3.34 (m, 1H), 3.33-3.24 (m, 1H), 3.21-3.06 (m, 1H), 2.12-1.81 (m, 4H); MS (ES+) m/z 480.9 (M+1), 482.9 (M+1).

Example 72

Synthesis of (S)-5-chloro-2-fluoro-N-(6-fluoropyridin-2-yl)-4-((1-phenyl-2-(pyrrolidin-1-yl)ethyl)amino)benzenesulfonamide 2,2,2-trifluoroacetate

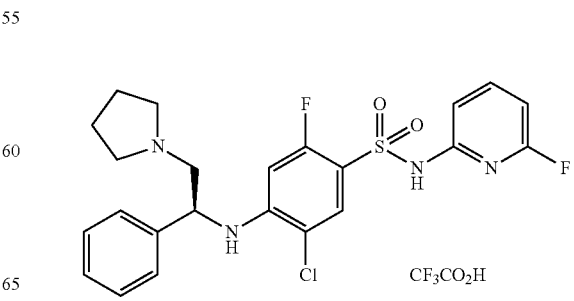

Step 1. Preparation of (S)-5-chloro-N-(2,4-dimethoxybenzyl)-2-fluoro-N-(6-fluoropyridin-2-yl)-4-((1-phenyl-2-(pyrrolidin-1-yl)ethyl)amino)benzenesulfonamide

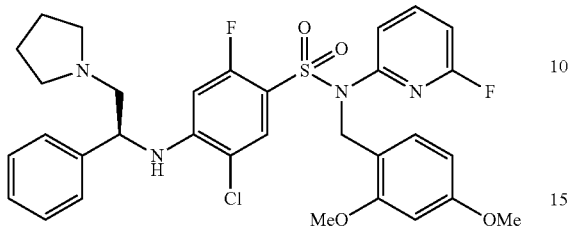

To a solution of 5-chloro-N-(2,4-dimethoxybenzyl)-2,4-difluoro-N-(6-fluoropyridin-2-yl)benzenesulfonamide (0.457 g, 0.969 mmol) in anhydrous dimethyl sulfoxide (10 mL) was added (S)-1-phenyl-2-(pyrrolidin-1-yl)ethan-1-amine hydrochloride (0.220 g, 0.969 mmol) and potassium carbonate (0.669 g, 4.85 mmol) and the reaction mixture was stirred at 75° C. for 18 h. The reaction mixture was allowed to cool to ambient temperature, an diluted with ethyl acetate (5 mL) and water (5 mL). The aqueous phase was extracted with ethyl acetate (3×3 mL). The combined organic phases were washed with brine (1×5 mL), dried over anhydrous sodium sulfate, and filtered. Concentration of the filtrate in vacuo and purification of the residue by column chromatography, eluting with a gradient of 12-80% of ethyl acetate in hexanes, afforded the title compound as a colorless oil (0.312 g, 49% yield): MS (ES+) m/z 643.1 (M+1), 645.1 (M+1).

Step 2. Preparation of (S)-5-chloro-2-fluoro-N-(6-fluoropyridin-2-yl)-4-((1-phenyl-2-(pyrrolidin-1-yl)ethyl)amino)benzenesulfonamide 2,2,2-trifluoroacetate

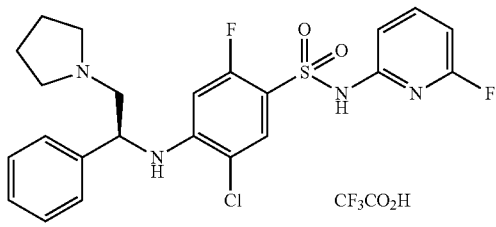 [SMILES: O=S(=O)(Nc1cccc(F)n1)c1cc(Cl)c(N[C@H](CN2CCCC2)c2ccccc2)cc1F ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-N-(2,4-dimethoxybenzyl)-2-fluoro-N-(6-fluoropyridin-2-yl)-4-((1-phenyl-2-(pyrrolidin-1-yl)ethyl)amino)benzenesulfonamide, and purification by preparative reverse phase HPLC using acetonitrile in water containing 0.1% trifluoroacetic acid as eluent, the title compound was obtained as a colorless solid (0.074 g, 15% yield): $^1$H NMR (300 MHz, DMSO-$d_6$) δ 11.55 (s, 1H), 9.45 (broad s, 1H), 7.83 (dd, J=16.5, 8.1 Hz, 1H), 7.79 (d, J=7.5 Hz, 1H), 7.48-7.45 (m, 2H), 7.41-7.34 (m, 2H), 7.32-7.27 (m, 1H), 7.19 (d, J=9.3 Hz, 1H), 6.84 (dd, J=7.8, 1.8 Hz, 1H), 6.82 (d, J=13.5 Hz, 1H), 6.71 (dd, J=8.0, 2.5 Hz, 1H), 5.23-5.15 (m, 1H), 4.03-3.94 (m, 1H), 3.95-3.51 (m, 2H), 3.44-3.35 (m, 1H), 3.29-3.22 (m, 1H), 3.17-3.10 (m, 1H), 2.05-1.97 (m, 2H), 1.92-1.86 (m, 2H); $^{19}$F NMR (282 MHz, DMSO-$d_6$) δ −69.0 (s, 1F), −73.8 (s, 3F), −110.1 (s, 1F); MS (ES+) m/z 493.0 (M+1), 495.0 (M+1).

Example 73

Synthesis of (S)-5-chloro-2-fluoro-4-((1-phenyl-2-(pyrrolidin-1-yl)ethyl)amino)-N-(thiazol-4-yl)benzenesulfonamide

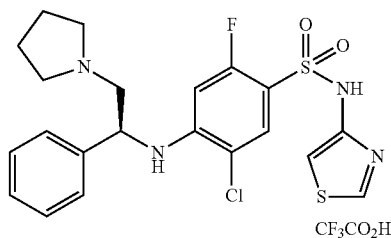 [SMILES: O=S(=O)(Nc1cscn1)c1cc(Cl)c(N[C@H](CN2CCCC2)c2ccccc2)cc1F ; "CF3CO2H"]

Step 1. Preparation tert-butyl (S)-((5-chloro-2-fluoro-4-((1-phenyl-2-(pyrrolidin-1-yl)ethyl)amino)phenyl)sulfonyl)(thiazol-4-yl)carbamate

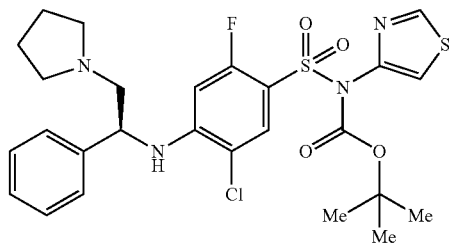 [SMILES: CC(C)(C)OC(=O)N(c1cscn1)S(=O)(=O)c1cc(Cl)c(N[C@H](CN2CCCC2)c2ccccc2)cc1F]

Following the procedure as described for EXAMPLE 72, Step 1 and making non-critical variations as required to replace 5-chloro-N-(2,4-dimethoxybenzyl)-2,4-difluoro-N-(6-fluoropyridin-2-yl)benzenesulfonamide with tert-butyl ((5-chloro-2,4-difluorophenyl)sulfonyl)(thiazol-4-yl)carbamate, the title compound was obtained as an orange oil (0.062 g, 11% yield); MS (ES+) m/z 581.1 (M+1), 583.1 (M+1).

Step 2. Preparation of (S)-5-chloro-2-fluoro-4-((1-phenyl-2-(pyrrolidin-1-yl)ethyl)amino)-N-(thiazol-4-yl)benzenesulfonamide

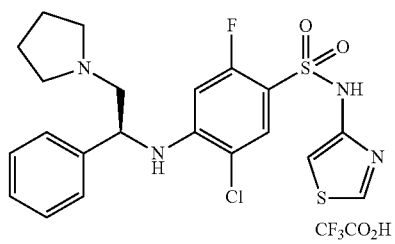 [SMILES: O=S(=O)(Nc1cscn1)c1cc(Cl)c(N[C@H](CN2CCCC2)c2ccccc2)cc1F ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with tert-butyl (S)-((5-chloro-2-fluoro-4-((1-phenyl-2-(pyrrolidin-1-yl)ethyl)amino)phenyl)sulfonyl)(thiazol-4-yl)carbamate, and purification by preparative reverse phase HPLC using acetonitrile in water containing 0.1% trifluoroacetic acid as eluent, the title compound was obtained as a colorless solid (0.025 g, 5% yield): $^1$H NMR (300 MHz, DMSO-$d_6$) δ 11.18 (s, 1H), 9.47 (broad s, 1H), 8.85 (d, J=2.2 Hz, 1H), 7.64 (d, J=7.4 Hz, 1H), 7.48-7.46 (m, 2H), 7.41-7.36 (m, 2H), 7.33-7.28 (m, 1H), 7.14-7.11 (m, 1H), 6.98 (d, J=2.2 Hz, 1H), 6.82 (d, J=13.3 Hz, 1H), 5.23-5.15 (m, 1H), 4.02-3.93 (m, 1H), 3.60-3.50 (m, 2H), 3.44-3.36 (m, 1H), 3.32-3.21 (m, 1H), 3.17-3.10 (m, 1H), 2.06-1.97 (m, 2H), 1.95-1.87 (m, 2H); MS (ES+) m/z 481.0 (M+1), 483.0 (M+1).

Example 74

Synthesis of 5-chloro-2-fluoro-4-((2-morpholino-1-phenylethyl)amino)-N-(thiazol-2-yl)benzenesulfonamide 2,2,2-trifluoroacetate

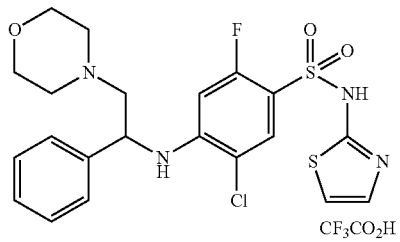 [SMILES: O=S(=O)(Nc1nccs1)c1cc(Cl)c(NC(CN2CCOCC2)c2ccccc2)cc1F ; "CF3CO2H"]

Step 1. Preparation of 5-chloro-N-(2,4-dimethoxybenzyl)-2-fluoro-4-((2-morpholino-1-phenylethyl)amino)-N-(thiazol-2-yl)benzenesulfonamide

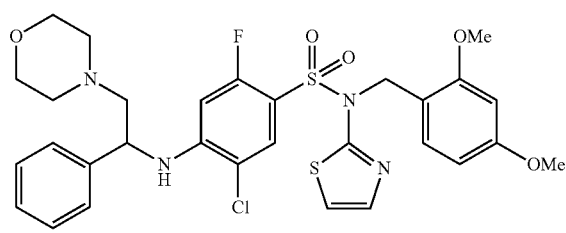 [SMILES: COc1ccc(CN(c2nccs2)S(=O)(=O)c2cc(Cl)c(NC(CN3CCOCC3)c3ccccc3)cc2F)c(OC)c1]

Following the procedure as described for EXAMPLE 43, Step 1 and making non-critical variations as required to replace 1-phenylcyclopropan-1-amine with 2-morpholino-1-phenylethan-1-amine, the title compound was obtained as a colorless oil (0.310 g, 88% yield): MS (ES+) m/z 647.1 (M+1), 649.1 (M+1).

Step 2. Preparation of 5-chloro-2-fluoro-4-((2-morpholino-1-phenylethyl)amino)-N-(thiazol-2-yl)benzenesulfonamide 2,2,2-trifluoroacetate

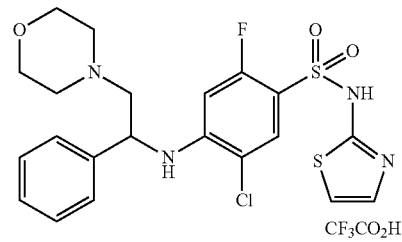 [SMILES: O=S(=O)(Nc1nccs1)c1cc(Cl)c(NC(CN2CCOCC2)c2ccccc2)cc1F ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with 5-chloro-N-(2,4-dimethoxybenzyl)-2-fluoro-4-((2-morpholino-1-phenylethyl)amino)-N-(thiazol-2-yl)benzenesulfonamide, and trituration with acetonitrile (2×5 mL), the title compound was obtained as a colorless solid (0.075 g, 28% yield): $^1$H NMR (300 MHz, DMSO-$d_6$) δ 12.78 (s, 1H), 9.81 (s, 1H), 7.62 (d, J=7.5 Hz, 1H), 7.48-7.34 (m, 4H), 7.31 (d, J=7.2 Hz, 1H), 7.25 (d, J=4.5 Hz, 1H), 6.97-6.86 (m, 1H), 6.82 (d, J=4.5 Hz, 1H), 6.78-6.65 (m, 1H), 5.37-5.13 (m, 1H), 4.10-3.86 (m, 3H), 3.86-3.62 (m, 3H), 3.52-3.31 (m, 2H), 3.29-3.05 (m, 2H); MS (ES+) m/z 497.1 (M+1), 499.1 (M+1).

Example 75

Synthesis of (S)-5-chloro-2-fluoro-4-((2-morpholino-1-phenylethyl)amino)-N-(thiazol-2-yl)benzenesulfonamide 2,2,2-trifluoroacetate

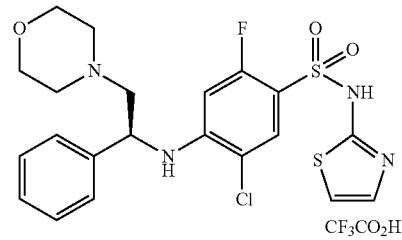 [SMILES: O=S(=O)(Nc1nccs1)c1cc(Cl)c(N[C@H](CN2CCOCC2)c2ccccc2)cc1F ; "CF3CO2H"]

Step 1. Preparation of (S)-2-morpholino-1-phenylethan-1-amine hydrochloride

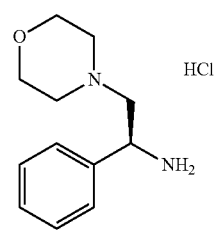 [SMILES: N[C@H](CN1CCOCC1)c1ccccc1 ; Cl]

Following the procedure as described for EXAMPLE 66, Step 1 and making non-critical variations as required to replace (R)-2-((tert-butoxycarbonyl)amino)-2-phenylethyl methanesulfonate with (S)-2-((tert-butoxycarbonyl)amino)-2-phenylethyl methanesulfonate, and azetidine with morpholine, the title compound was obtained as a brownish solid (0.186 g, 48% yield): MS (ES+) m/z 207.2 (M+1).

Step 2. Preparation of (S)-5-chloro-N-(2,4-dimethoxybenzyl)-2-fluoro-4-((2-morpholino-1-phenylethyl)amino)-N-(thiazol-2-yl)benzenesulfonamide

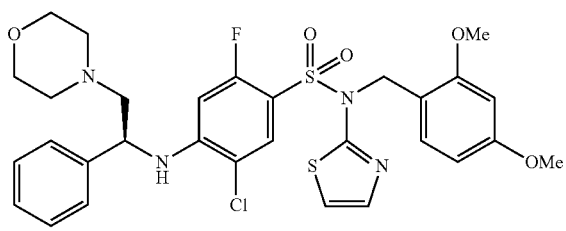 [SMILES: COc1ccc(CN(c2nccs2)S(=O)(=O)c2cc(Cl)c(N[C@H](CN3CCOCC3)c3ccccc3)cc2F)c(OC)c1]

Following the procedure as described for EXAMPLE 43, Step 1 and making non-critical variations as required to replace 1-phenylcyclopropan-1-amine with (S)-2-morpholino-1-phenylethan-1-amine hydrochloride, the title compound was obtained as a colorless oil (0.138 g, 39% yield): MS (ES+) m/z 647.1 (M+1), 649.1 (M+1).

Step 3. Preparation of (S)-5-chloro-2-fluoro-4-((2-morpholino-1-phenylethyl)amino)-N-(thiazol-2-yl) benzenesulfonamide 2,2,2-trifluoroacetate

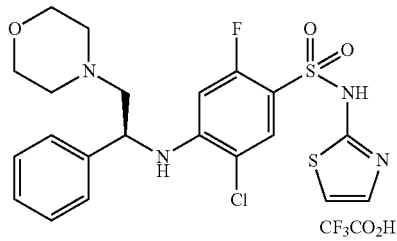 [SMILES: O=S(=O)(Nc1nccs1)c1cc(Cl)c(N[C@H](CN2CCOCC2)c2ccccc2)cc1F ; "CF3CO2H"]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with S)-5-chloro-N-(2,4-dimethoxybenzyl)-2-fluoro-4-((2-morpholino-1-phenylethyl)amino)-N-(thiazol-2-yl) benzenesulfonamide, and purification by preparative reverse phase HPLC using acetonitrile in water containing 0.1% trifluoroacetic acid as eluent, the title compound was obtained as a colorless solid (0.042 g, 16% yield): $^1$H NMR (300 MHz, DMSO-$d_6$) δ 12.79 (s, 1H), 9.86 (s, 1H), 7.61 (d, J=7.2 Hz, 1H), 7.48-7.34 (m, 4H), 7.31 (d, J=6.9 Hz, 1H), 7.25 (d, J=4.5 Hz, 1H), 6.97-6.86 (m, 1H), 6.82 (d, J=4.5 Hz, 1H), 6.80-6.66 (m, 1H), 5.37-5.13 (m, 1H), 4.10-3.86 (m, 3H), 3.86-3.62 (m, 3H), 3.52-3.31 (m, 2H), 3.29-3.05 (m, 2H); $^{19}$F NMR (282 MHz, DMSO-$d_6$) δ −73.8 (s, 3F), −109.5 (s, 1F); MS (ES+) m/z 496.9 (M+1), 498.9 (M+1).

Example 76

Synthesis of (S)-3-chloro-4-((1-phenylethyl)amino)-N-(thiazol-2-yl)benzenesulfonamide

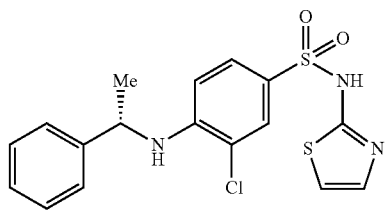 [SMILES: C[C@H](Nc1ccc(S(=O)(=O)Nc2nccs2)cc1Cl)c1ccccc1]

To a solution of 5-chloro-N-(2,4-dimethoxybenzyl)-4-difluoro-N-(thiazol-2-yl)benzenesulfonamide (0.250 g, 0.543 mmol) and (S)-1-phenylethan-1-amine (0.065 mg, 0.54 mmol) in anhydrous dimethyl sulfoxide (5 mL) was added cesium carbonate (0.424 g, 1.30 mmol) and the reaction mixture was stirred at ambient temperature for 17 h. The reaction mixture was diluted with ethyl acetate (5 mL) and water (5 mL), and the aqueous phase was extracted with ethyl acetate (3×3 mL). The combined organic phases were washed with brine (5 mL), dried over anhydrous sodium sulfate, and filtered. The filtrate was concentrated in vacuo, the residue dissolved in dichloromethane (5 mL), and trifluoroacetic acid (1 mL) was added to it. The reaction mixture was stirred at ambient temperature for 1 h and then diluted with methanol (10 mL). The suspension was filtered and the filtrate concentrated in vacuo. Purification of the residue by column chromatography, eluting with a gradient of 12-80% of ethyl acetate in hexanes, provided the title compound was a colorless solid (0.106 g, 49% yield): $^1$H NMR (300 MHz, DMSO-$d_6$) δ 12.60 (s, 1H), 7.56 (d, J=2.1 Hz, 1H), 7.42-7.34 (m, 3H), 7.30 (t, J=7.8 Hz, 2H), 7.21 (d, J=4.8 Hz, 1H), 7.20-7.16 (m, 1H), 6.77 (d, J=4.5 Hz, 1H), 6.56 (d, J=8.7 Hz, 1H), 6.19 (d, J=7.2 Hz, 1H), 4.68 (dq, J=7.2, 6.6 Hz, 1H), 1.53 (d, J=6.6 Hz, 3H); MS (ES−) m/z 392.1 (M−1), 394.1 (M−1).

Example 77

Synthesis of (S)-3-chloro-4-((5,6,7,8-tetrahydroquinolin-8-yl)amino)-N-(thiazol-2-yl)benzenesulfonamide

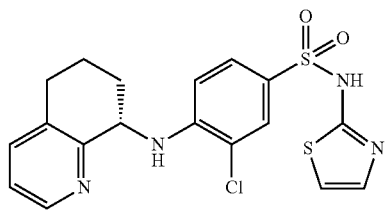 [SMILES: O=S(=O)(Nc1nccs1)c1ccc(N[C@H]2CCCc3cccnc32)c(Cl)c1]

Step 1. Preparation of (S)-3-chloro-N-(2,4-dimethoxybenzyl)-4-((5,6,7,8-tetrahydroquinolin-8-yl)amino)-N-(thiazol-2-yl)benzenesulfonamide

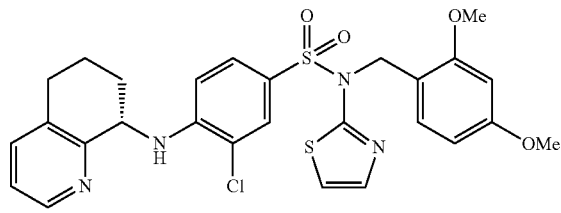 [SMILES: COc1ccc(CN(c2nccs2)S(=O)(=O)c2ccc(N[C@H]3CCCc4cccnc43)c(Cl)c2)c(OC)c1]

To a mixture of 5-chloro-N-(2,4-dimethoxybenzyl)-4-difluoro-N-(thiazol-2-yl)benzenesulfonamide (0.250 g, 0.566 mmol) and (S)-5,6,7,8-tetrahydroquinolin-8-amine dihydrochloride (0.124 mg, 0.566 mmol) in anhydrous dimethyl sulfoxide (5 mL) was added potassium carbonate (0.390 g, 2.83 mmol) and the reaction mixture was stirred at 60° C. for 17 h. The reaction mixture was allowed to cool to ambient temperature, and diluted with ethyl acetate (5 mL) and water (5 mL). The aqueous phase was extracted with ethyl acetate (3×3 mL). The combined organic phases were washed with brine (1×5 mL), dried over anhydrous sodium sulfate, and filtered. Concentration of the filtrate in vacuo and purification of the residue by column chromatography, eluting with a gradient of 6-80% of ethyl acetate in hexanes, afforded the title compound as a colorless solid (0.226 g, 95% yield): MS (ES+) m/z 571.1 (M+1), 573.1 (M+1).

Step 2. Preparation of (S)-3-chloro-4-((5,6,7,8-tetrahydroquinolin-8-yl)amino)-N-(thiazol-2-yl)benzenesulfonamide

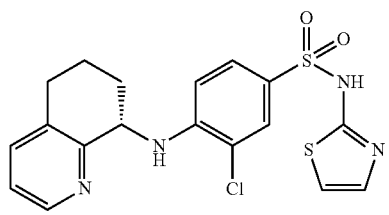 [SMILES: O=S(=O)(Nc1nccs1)c1ccc(N[C@H]2CCCc3cccnc32)c(Cl)c1]

To a solution of (S)-3-chloro-N-(2,4-dimethoxybenzyl)-4-((5,6,7,8-tetrahydroquinolin-8-yl)amino)-N-(thiazol-2-yl)benzenesulfonamide (226 mg, 0.396 mmol) in dichloromethane (5 mL) was added trifluoroacetic acid (0.092 mL, 1.2 mmol) at 0° C. The reaction mixture was stirred at 0° C. for 10 minutes and then diluted with methanol (10 mL). The obtained suspension was filtered and the filtrate concentrated in vacuo. Purification of the residue by preparative reverse phase HPLC, using acetonitrile in water containing 0.1% trifluoroacetic acid as eluent, afforded the title compound as a colorless solid (0.016 mg, 7% yield): $^1$H NMR (300 MHz, DMSO-$d_6$) δ 12.68 (s, 1H), 8.53 (d, J=4.5 Hz, 1H), 8.00 (d, J=7.5 Hz, 1H), 7.64 (d, J=2.1 Hz, 1H), 7.57 (dd, J=8.4, 1.8 Hz, 2H), 7.26 (d, J=4.5 Hz, 1H), 7.06 (d, J=9.0 Hz, 1H), 6.81 (d, J=4.5 Hz, 1H), 6.54 (d, J=7.5 Hz, 1H), 5.05-4.93 (m, 1H), 2.96-2.85 (m, 2H), 2.25-2.09 (m, 1H), 1.98-1.75 (m, 3H); MS (ES+) m/z 421.0 (M+1), 423.0 (M+1).

Example 78

Synthesis of (S)-5-chloro-4-((1-(2-chlorophenyl)ethyl)amino)-2-fluoro-N-(thiazol-2-yl)benzenesulfonamide

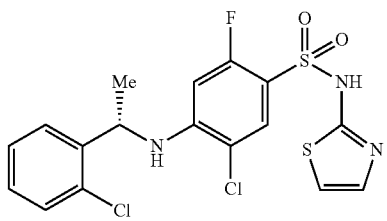 [SMILES: C[C@H](Nc1cc(F)c(S(=O)(=O)Nc2nccs2)cc1Cl)c1ccccc1Cl]

Step 1. Preparation of (S)-5-chloro-4-((1-(2-chlorophenyl)ethyl)amino)-N-(2,4-dimethoxybenzyl)-2-fluoro-N-(thiazol-2-yl)benzenesulfonamide

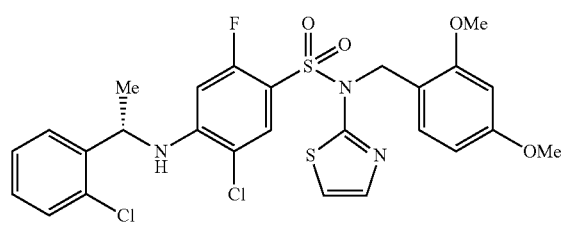

Following the procedure as described for EXAMPLE 77, Step 1 and making non-critical variations as required to replace (S)-5,6,7,8-tetrahydroquinolin-8-amine dihydrochloride with (S)-1-(2-chlorophenyl)ethan-1-amine hydrochloride, the title compound was obtained as a colorless oil (0.137 g, 83% yield): MS (ES+) m/z 596.0 (M+1), 598.0 (M+1).

Step 2. Preparation of (S)-5-chloro-4-((1-(2-chlorophenyl)ethyl)amino)-2-fluoro-N-(thiazol-2-yl)benzenesulfonamide

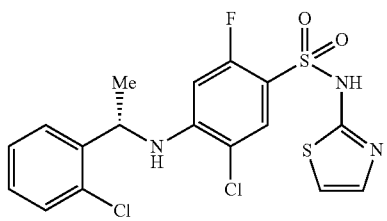

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-5-chloro-4-((1-(2-chlorophenyl)ethyl)amino)-N-(2,4-dimethoxybenzyl)-2-fluoro-N-(thiazol-2-yl)benzenesulfonamide, the title compound was obtained as a colorless solid (0.042 g, 17% yield): $^1$H NMR (300 MHz, DMSO-$d_6$) δ 12.76 (s, 1H), 7.60 (d, J=7.5 Hz, 1H), 7.45 (dd, J=6.0, 1.5 Hz, 2H), 7.36-7.26 (m, 2H), 7.25 (d, J=4.5 Hz, 1H), 6.81 (d, J=4.8 Hz, 1H), 6.73 (d, J=6.0 Hz, 1H), 6.05 (d, J=12.9 Hz, 1H), 4.97-4.81 (m, 1H), 1.54 (d, J=6.6 Hz, 3H); $^{19}$F NMR (282 MHz, DMSO-d$_6$), δ−109.2 (s); MS (ES−) m/z 444.0 (M−1), 446.0 (M−1).

Example 79

Synthesis of (S)-3-chloro-4-((1-(2-fluorophenyl) ethyl)amino)-N-(thiazol-2-yl)benzenesulfonamide

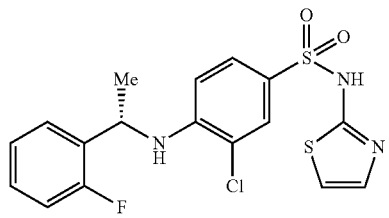 [SMILES: C[C@H](Nc1ccc(S(=O)(=O)Nc2nccs2)cc1Cl)c1ccccc1F]

Step 1. Preparation of (S)-3-chloro-N-(2,4-dimethoxybenzyl)-4-((1-(2-fluorophenyl)ethyl)amino)-N-(thiazol-2-yl)benzenesulfonamide

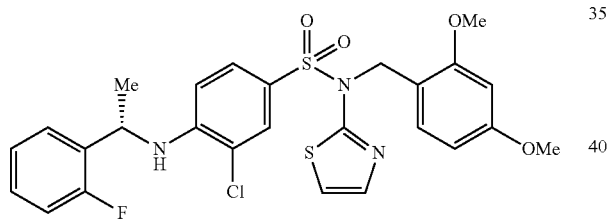

To a mixture of 5-chloro-N-(2,4-dimethoxybenzyl)-4-difluoro-N-(thiazol-2-yl)benzenesulfonamide (0.300 g, 0.679 mmol) and (S)-(2-fluorophenyl)ethylamine (0.94 mg, 0.679 mmol) in anhydrous dimethyl sulfoxide (6 mL) was added potassium carbonate (0.224 g, 1.63 mmol) and the reaction mixture was stirred at 75° C. for 17 h. The reaction mixture was allowed to cool to ambient temperature, and diluted with ethyl acetate (5 mL) and water (5 mL). The aqueous phase was extracted with ethyl acetate (3×3 mL). The combined organic phases were washed with brine (1×5 mL), dried over anhydrous sodium sulfate, and filtered. Concentration of the filtrate in vacuo and purification of the residue by column chromatography, eluting with a gradient of 5-60% of ethyl acetate in hexanes, afforded the title compound as a colorless oil (0.305 g, 80% yield): MS (ES+) m/z 561.9 (M+1), 563.9 (M+1).

Step 2. Preparation of (S)-3-chloro-4-((1-(2-fluorophenyl)ethyl)amino)-N-(thiazol-2-yl)benzenesulfonamide

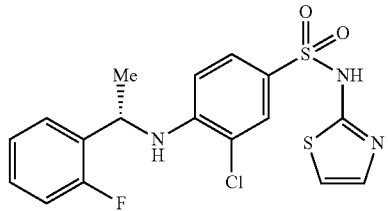 [SMILES: C[C@H](Nc1ccc(S(=O)(=O)Nc2nccs2)cc1Cl)c1ccccc1F]

Following the procedure as described for EXAMPLE 43, Step 2 and making non-critical variations as required to replace 5-chloro-N-(2,4-dimethoxybenzyl)-2-fluoro-4-((1-phenylcyclopropyl)amino)-N-(thiazol-2-yl)benzenesulfonamide with (S)-3-chloro-N-(2,4-dimethoxybenzyl)-4-((1-(2-fluorophenyl)ethyl)amino)-N-(thiazol-2-yl) benzenesulfonamide, and purification by preparative reverse phase HPLC using acetonitrile in water containing 0.1% trifluoroacetic acid as eluent, the title compound was obtained as a colorless solid (0.084 mg, 30% yield): $^1$H NMR (300 MHz, DMSO-d$_6$) δ 12.61 (s, 1H), 7.59 (d, J=2.1 Hz, 1H), 7.42 (dd, J=8.7, 1.8 Hz, 1H), 7.36 (dd, J=7.5, 1.5 Hz, 1H), 7.31-7.10 (m, 4H), 6.78 (d, J=4.5 Hz, 1H), 6.49 (d, J=8.8 Hz, 1H), 6.23 (d, J=7.5 Hz, 1H), 4.96-4.87 (m, 1H), 1.56 (d, J=6.7 Hz, 3H); $^{19}$F NMR (282 MHz, DMSO-d$_6$) δ−120.1 (s); MS (ES+) m/z 411.9 (M+1), 413.9 (M+1).

Example 80

Synthesis of (R)-5-chloro-2-fluoro-N-(thiazol-2-yl)-4-(2,2,2-trifluoro-1-phenylethoxy)benzenesulfonamide

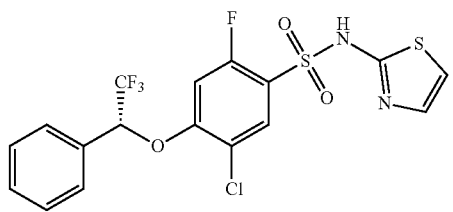 [SMILES: O=S(=O)(Nc1nccs1)c1cc(Cl)c(O[C@H](c2ccccc2)C(F)(F)F)cc1F]

To a solution of (R)-2,2,2-trifluoro-1-phenylethan-1-ol (0.114 g, 0.648 mmol) and 5-chloro-N-(2,4-dimethoxybenzyl)-2,4-difluoro-N-(thiazol-2-yl)benzenesulfonamide (0.300 g, 0.652 mmol) in anhydrous dimethyl sulfoxide (2.5 mL) was added cesium carbonate (0.509 g, 1.56 mmol) and the reaction mixture was stirred at ambient temperature for 65 h. The reaction mixture was diluted with ethyl acetate (5 mL) and water (5 mL), and the aqueous phase was extracted with ethyl acetate (5 mL). The combined organic extracts were washed with brine (2×5 mL), dried over anhydrous magnesium sulfate, and filtered. The filtrate was concentrated in vacuo and the residue purified by column chromatography, eluting with 0-60% of ethyl acetate in hexanes. The obtained residue was dissolved in dichloromethane (4 mL) and trifluoroacetic acid (0.7 mL) was added to it. The reaction mixture was stirred at ambient temperature for 10 minutes and then concentrated in vacuo. The residue was triturated in methanol (5 mL) using charcoal (0.3 g) and the resulting suspension was filtered. Concentration of the filtrate in vacuo afforded the title compound as a colorless solid (0.074 g, 24% yield): $^1$H NMR (300 MHz, DMSO-$d_6$) δ 12.96 (br s, 1H), 7.83 (d, J=7.3 Hz, 1H), 7.60-7.52 (m, 2H), 7.52-7.44 (m, 3H), 7.38-7.27 (m, 2H), 6.88 (d, J=4.6 Hz, 1H), 6.59 (q, J=6.5 Hz, 1H); MS (ES+) m/z 467.0, 469.0 (M+1).

Example 81

Synthesis of 3-chloro-4-((1-(pyridin-2-yl)propyl)amino)-N-(thiazol-2-yl)benzenesulfonamide

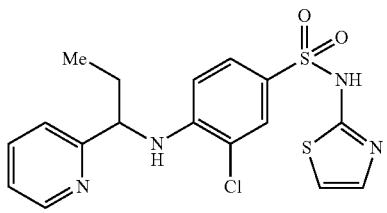 [SMILES: CCC(Nc1ccc(S(=O)(=O)Nc2nccs2)cc1Cl)c1ccccn1]

To a mixture of 1-(pyridin-2-yl)propan-1-amine dihydrochloride (0.129 g, 0.625 mmol), 4-bromo-3-chloro-N-(thiazol-2-yl)benzenesulfonamide (0.200 g, 0.568 mmol), 2-di-tert-butylphosphino-2',4',6'-triisopropylbiphenyl (0.012 g, 0.028 mmol), tris(dibenzylideneacetone)dipalladium(0) (0.013 g, 0.014 mmol), and sodium tert-butoxide (0.273 g, 2.84 mmol) was added anhydrous toluene (3 mL) and the reaction mixture was degassed for 10 minutes by passing a stream of nitrogen through it. The reaction mixture was stirred at 100° C. for 72 h. The reaction mixture was allowed to cool to ambient temperature, diluted with ethyl acetate (5 mL), and filtered through a pad of Celite. The filter pad was washed with ethyl acetate (20 mL), and the combined filtrate was concentrated in vacuo. Purification of residue by column chromatography, eluting with a gradient of 0-25% of methanol in dichloromethane, and trituration in methanol (2×5 mL), provided the title compound as a colorless solid (0.074 g, 3% yield): $^1$H NMR (300 MHz, DMSO-$d_6$) δ 12.60 (s, 1H), 8.55 (d, J=4.2 Hz, 1H), 7.77 (dt, J=1.5, 7.5 Hz, 1H), 7.59 (d, J=2.1 Hz, 1H), 7.49-7.39 (m, 2H), 7.31-7.25 (m, 1H), 7.22 (d, J=4.8 Hz, 1H), 6.78 (d, J=4.5 Hz, 1H), 6.73 (d, J=9.0 Hz, 1H), 6.29 (d, J=7.8 Hz, 1H), 4.61 (q, J=7.2 Hz, 1H), 2.00-1.80 (m, 2H), 0.91 (t, J=7.2 Hz, 3H); MS (ES+) m/z 409.1 (M+1), 411.1 (M+1).

Example 82

Synthesis of (S)-3-chloro-4-((1-(pyridin-2-yl)ethyl)amino)-N-(thiazol-2-yl)benzenesulfonamide

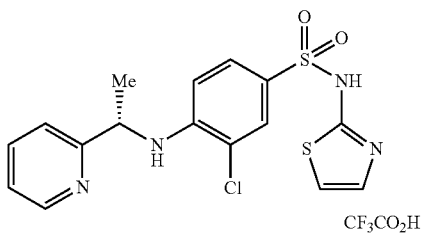 [SMILES: C[C@H](Nc1ccc(S(=O)(=O)Nc2nccs2)cc1Cl)c1ccccn1 ; "CF3CO2H"]

Following the procedure as described for EXAMPLE 81 and making non-critical variations as required to replace 1-(pyridin-2-yl)propan-1-amine dihydrochloride with (S)-1-(pyridin-2-yl)ethan-1-amine dihydrochloride, the title compound was obtained as a colorless solid (0.018 g, 8.1% yield): $^1$H NMR (300 MHz, DMSO-$d_6$) δ 12.97 (s, 1H), 7.78 (dt, J=7.5, 1.5 Hz, 1H), 7.60 (d, J=2.1 Hz, 1H), 7.49-7.40 (m, 2H), 7.28 (ddd, J=7.2, 3.6, 1.2 Hz, 1H), 7.22 (d, J=4.5 Hz, 1H), 6.79 (d, J=4.5 Hz, 1H), 6.68 (d, J=9.0 Hz, 1H), 6.70 (d, J=7.5 Hz, 1H), 6.39 (d, J=7.2 Hz, 1H), 4.80 (dq, J=6.9, 7.2 Hz, 1H), 1.51 (d, J=6.9 Hz, 3H); MS (ES+) m/z 395.0 (M+1), 397.0 (M+1).

Example 83

Synthesis of 3-chloro-4-((1-(1-methyl-1H-pyrazol-4-yl)ethyl)amino)-N-(thiazol-2-yl)benzenesulfonamide

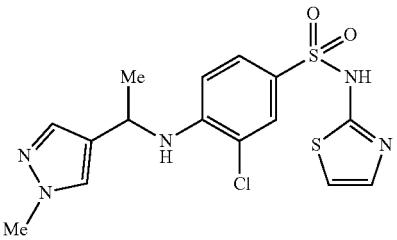 [SMILES: CC(Nc1ccc(S(=O)(=O)Nc2nccs2)cc1Cl)c1cnn(C)c1]

Following the procedure as described for EXAMPLE 81 and making non-critical variations as required to replace 1-(pyridin-2-yl)propan-1-amine dihydrochloride with 1-(1-methyl-1H-pyrazol-4-yl)ethan-1-amine, and purification by preparative reverse phase HPLC using acetonitrile in water containing 0.1% ammonium hydroxide as eluent, the title compound was obtained as a colorless solid (0.012 g, 5% yield): $^1$H NMR (300 MHz, DMSO-$d_6$) δ 7.57 (s, 1H), 7.56 (d, J=2.1 Hz, 1H), 7.46 (dd, J=8.7, 2.1 Hz, 1H), 7.37 (s, 1H), 7.13 (d, J=4.2 Hz, 1H), 6.77 (d, J=8.7 Hz, 1H), 6.68 (d, J=4.2 Hz, 1H), 5.69 (d, J=7.8 Hz, 1H), 4.67 (dq, J=7.2, 6.6 Hz, 1H), 3.75 (s, 3H), 1.52 (d, J=6.6 Hz, 3H), sulfonamide NH not observed; MS (ES+) m/z 398.0 (M+1), 400.0 (M+1).

Example 84

Synthesis of (S)-4-((1-phenylpropyl)amino)-N-(thiazol-2-yl)benzenesulfonamide

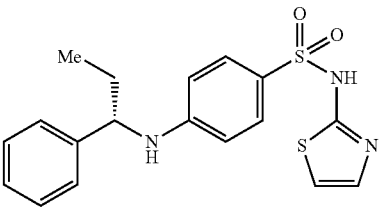 [SMILES: CC[C@H](Nc1ccc(S(=O)(=O)Nc2nccs2)cc1)c1ccccc1]

Step 1. Preparation of N-(2,4-dimethoxybenzyl)-4-fluoro-N-(thiazol-2-yl)benzenesulfonamide

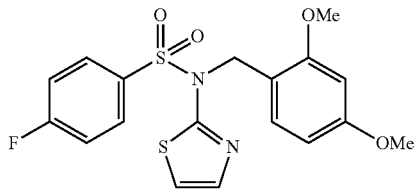 [SMILES: COc1ccc(CN(c2nccs2)S(=O)(=O)c2ccc(F)cc2)c(OC)c1]

To a mixture of (N-(2,4-dimethoxybenzyl)thiazol-2-amine (1.251 g, 5.03 mmol) in anhydrous tetrahydrofuran (20 mL) was added a 1 M solution of lithium bis(trimethylsilyl)amide in tetrahydrofuran (5.0 mL, 5.03 mmol) at −78° C. The reaction mixture was allowed to warm to ambient temperature and stirred for 1 h. After cooling the reaction mixture to −78° C., a solution of 4-fluorobenzenesulfonyl chloride (0.750 g, 3.86 mmol) in anhydrous tetrahydrofuran (20 mL) was added to it. The reaction mixture was allowed to warm to ambient temperature, and stirred for 16 h. The reaction mixture was quenched by addition of saturated ammonium chloride solution (50 mL) and diluted with ethyl acetate (100 mL). The aqueous phase was extracted with ethyl acetate (2×50 mL) and the combined organic phase was washed with brine (50 mL), dried over anhydrous sodium sulfate, and filtered. Concentration of the filtrate in vacuo and purification of the residue by column chromatography, eluting with a gradient of 12 to 80% of ethyl acetate in hexanes, provided the title compound as a colorless solid (0.841 g, 53% yield): $^1$H-NMR (300 MHz, CDCl$_3$): δ 7.88-7.83 (m, 2H), 7.44-7.42 (m, 1H), 7.29-7.27 (m, 1H), 7.20-7.14 (m, 2H), 7.05-7.04 (m, 1H), 6.39-6.36 (m, 2H), 5.06 (s, 2H), 3.78 (s, 3H), 3.74 (s, 3H).

Step 2. Preparation of (S)—N-(2,4-dimethoxybenzyl)-4-((1-phenylpropyl)amino)-N-(thiazol-2-yl)benzenesulfonamide

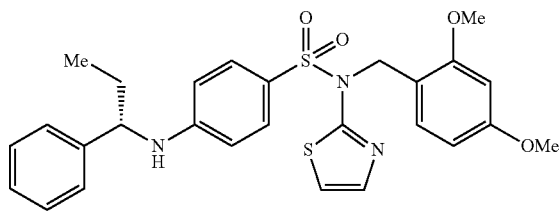 [SMILES: CC[C@H](Nc1ccc(S(=O)(=O)N(Cc2ccc(OC)cc2OC)c2nccs2)cc1)c1ccccc1]

To a mixture of N-(2,4-dimethoxybenzyl)-4-fluoro-N-(thiazol-2-yl)benzenesulfonamide (0.200 g, 0.490 mmol) and (S)-1-phenylpropan-1-amine (0.066 g, 0.490 mmol) in anhydrous dimethyl sulfoxide (5 mL) was added potassium carbonate (0.162 g, 1.18 mmol) and the reaction mixture was stirred at 90° C. for 17 h. The reaction mixture was allowed to cool to ambient temperature and diluted with ethyl acetate (5 mL) and water (5 mL). The aqueous phase was extracted with ethyl acetate (3×5 mL). The combined organic phases were washed with brine (5 mL), dried over anhydrous sodium sulfate, and filtered. Concentration of the filtrate in vacuo and purification of the residue by column chromatography, eluting with a gradient of 5-60% of ethyl acetate in hexanes, afforded the title compound as a colorless oil (0.084 g, 33% yield): MS (ES+) m/z 524.1 (M+1).

Step 3. Preparation of (S)-4-((1-phenylpropyl)amino)-N-(thiazol-2-yl)benzenesulfonamide

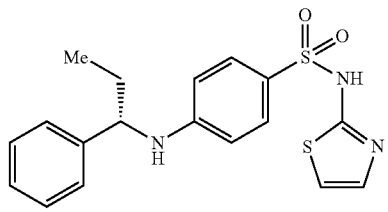 [SMILES: CC[C@H](Nc1ccc(S(=O)(=O)Nc2nccs2)cc1)c1ccccc1]

To a solution of (S)—N-(2,4-dimethoxybenzyl)-4-((1-phenylpropyl)amino)-N-(thiazol-2-yl)benzenesulfonamide (0.084 g, 0.16 mmol) in dichloromethane (5 mL) was added trifluoroacetic acid (0.5 mL) and the reaction mixture was stirred at ambient temperature for 2 h. Concentration of the reaction mixture in vacuo and purification the residue by column chromatography, eluting with a gradient of 10-100% of ethyl acetate in hexanes, provided the title compound as a colorless solid (0.029 g, 16% yield): $^1$H NMR (300 MHz, DMSO-d$_6$) δ 12.40 (s, 1H), 7.39-7.26 (m, 6H), 7.20-7.15 (m, 2H), 6.93 (d, J=7.4 Hz, 1H), 6.46-6.43 (m, 1H), 6.71 (d, J=4.7 Hz, 1H), 6.53 (d, J=8.8 Hz, 1H), 4.26 (q, J=6.5 Hz, 1H), 1.843-1.62 (m, 2H), 0.88 (t, J=7.3 Hz, 3H); MS (ES+) m/z 374.1 (M+1).

Example 85

Synthesis of 2,5-difluoro-4-((1-phenylpropyl)amino)-N-(1,2,4-thiadiazol-5-yl)benzenesulfonamide

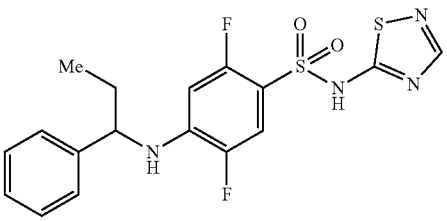 [SMILES: CCC(Nc1cc(F)c(S(=O)(=O)Nc2ncns2)cc1F)c1ccccc1]

To a mixture of 2,4,5-trifluoro-N-(1,2,4-thiadiazol-5-yl)benzenesulfonamide (0.40 g, 0.90 mmol) and 1-phenylpropan-1-amine (0.13 mL, 0.90 mmol) in anhydrous dimethyl sulfoxide (5 mL) was added cesium carbonate (0.703 g, 2.16 mmol) and the reaction mixture was at ambient temperature for 17 h. The reaction mixture was diluted with ethyl acetate (5 mL) and water (5 mL) and the aqueous phase was extracted with ethyl acetate (3×5 mL). The combined organic phases were washed with brine (1×5 mL), dried over anhydrous sodium sulfate, and filtered. The filtrate was concentrated in vacuo, dissolved in dichloromethane (5 mL), and trifluoroacetic acid (1 mL) was added to it. The reaction mixture was stirred at ambient temperature for 2 h and then methanol (10 mL) was added to it. The suspension was filtered and the filtrate concentrated in vacuo. Purification of the residue by column chromatography, eluting with a gradient of 12 to 100% of ethyl acetate in hexanes, provided the title compound as a colorless solid (195 g, 53% yield):

¹H NMR (300 MHz, DMSO-d₆) δ 8.42 (s, 1H), 7.46-7.22 (m, 5H), 7.21-7.06 (m, 2H), 6.51-6.36 (m, 1H), 4.40-4.23 (m, 1H), 2.00-1.81 (m, 1H), 1.78-1.58 (m, 1H), 0.84 (t, J=6.9 Hz, 3H), sulfonamide NH not observed; ¹⁹F NMR (282 MHz, DMSO-d₆) δ−112.6 (d, J=15 Hz, 1F), −134.7 (d, J=15 Hz, 1F); MS (ES+) m/z 411.0 (M+1), 412.0 (M+1).

Example 86

Synthesis of 5-chloro-2-fluoro-N-(6-fluoropyridin-2-yl)-4-((1-phenylpropyl)amino)benzenesulfonamide

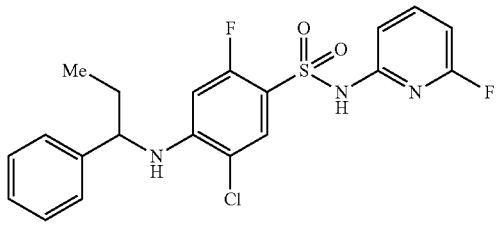 [SMILES: CCC(Nc1cc(F)c(S(=O)(=O)Nc2cccc(F)n2)cc1Cl)c1ccccc1]

Following the procedure as described for EXAMPLE 85 and making non-critical variations as required to replace 2,4,5-trifluoro-N-(1,2,4-thiadiazol-5-yl)benzenesulfonamide with 5-chloro-N-(2,4-dimethoxybenzyl)-2,4-difluoro-N-(6-fluoropyridin-2-yl)benzenesulfonamide, the title compound was obtained as a colorless solid (0.251 g, 68% yield): ¹H NMR (300 MHz, DMSO-d₆) δ 11.43 (s, 1H), 7.83-7.74 (m, 1H), 7.69 (d, J=7.5 Hz, 1H), 7.39 (d, J=7.5 Hz, 2H), 7.30-7.25 (m, 2H), 7.20-7.15 (m, 1H), 6.81 (d, J=7.8 Hz, 1H), 6.68-6.61 (m, 2H), 6.44 (d, J=13.5 Hz, 1H), 4.43-4.32 (m, 1H), 2.00-1.87 (m, 1H), 1.81-1.65 (m, 1H), 0.84 (t, J=6.9 Hz, 3H); ¹⁹F NMR (282 MHz, DMSO-d₆) δ−69.0 (s, 1F), −110.1 (s, 1F); MS (ES+) m/z 436.0 (M+1), 438.0 (M+1).

Example 87

Synthesis of (R) and (S)-3-chloro-4-(1-phenylethoxy)-N-(1,2,4-thiadiazol-5-yl)benzenesulfonamide

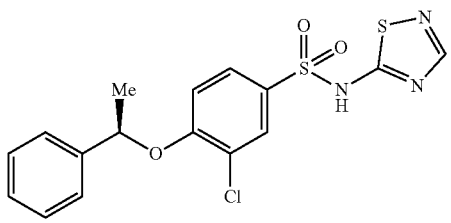 [SMILES: C[C@@H](Oc1ccc(S(=O)(=O)Nc2ncns2)cc1Cl)c1ccccc1]

To a mixture of 3-chloro-N-(2,4-dimethoxybenzyl)-4-fluoro-N-(1,2,4-thiadiazol-5-yl)benzenesulfonamide (0.20 g, 0.45 mmol) and (R)-1-phenylethan-1-ol (0.055 mL, 0.45 mmol) in anhydrous dimethyl sulfoxide (2 mL) was added cesium carbonate (0.352 g, 1.08 mmol) and the reaction mixture was stirred at ambient temperature for 24 h. The mixture was diluted with ethyl acetate (5 mL) and water (5 mL), and the aqueous phase was with ethyl acetate (3×5 mL). The combined organic phases were washed with brine (5 mL), dried over anhydrous sodium sulfate, and filtered. The filtrate was concentrated in vacuo, dissolved in dichloromethane (5 mL), and trifluoroacetic acid (0.025 mL) was added to it. The reaction mixture was stirred at ambient temperature for 15 minutes h and then methanol (10 mL) was added to it. The suspension was filtered and the filtrate concentrated in vacuo. Purification of the residue by column chromatography, eluting with a gradient of 0 to 20% of methanol in dichloromethane, afforded the title compound as a colorless solid (0.036 g, 20% yield): ¹H NMR (300 MHz, DMSO-d₆) δ 8.46 (s, 1H), 7.75 (d, J=2.1 Hz, 1H), 7.61 (dd, J=8.7, 2.4 Hz, 1H), 7.43-7.24 (m, 5H), 7.20 (d, J=8.7 Hz, 1H), 5.75 (q, J=6.3 Hz, 1H), 1.60 (d, J=6.3 Hz, 3H), sulfonamide NH not observed; MS (ES−) m/z 394.0 (M−1), 396.0 (M−1).

Example 88

Synthesis of (S)-3-chloro-4-(1-phenylethoxy)-N-(1,2,4-thiadiazol-5-yl)benzenesulfonamide

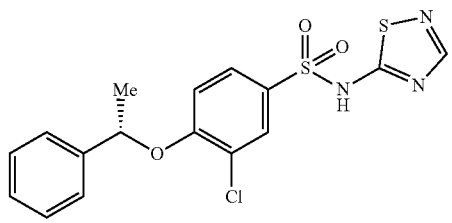 [SMILES: C[C@H](Oc1ccc(S(=O)(=O)Nc2ncns2)cc1Cl)c1ccccc1]

Following the procedure as described for EXAMPLE 87 and making non-critical variations as required to replace (R)-1-phenylethan-1-ol with (S)-1-phenylethan-1-ol, the title compound was obtained as a colorless solid (0.014 g, 8% yield): ¹H NMR (300 MHz, DMSO-d₆) δ 8.42 (s, 1H), 7.75 (d, J=2.1 Hz, 1H), 7.60 (dd, J=8.7, 2.4 Hz, 1H), 7.41-7.23 (m, 5H), 7.19 (d, J=8.7 Hz, 1H), 5.73 (q, J=6.3 Hz, 1H), 1.59 (d, J=6.3 Hz, 3H), sulfonamide NH not observed; MS (ES−) m/z 394.0 (M−1), 396.0 (M−1).

Example 89

Synthesis of (S)-5-chloro-2-fluoro-4-((1-phenylpropyl)amino)-N-(thiazol-4-yl)benzenesulfonamide

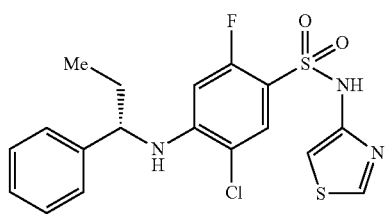 [SMILES: CC[C@H](Nc1cc(F)c(S(=O)(=O)Nc2cscn2)cc1Cl)c1ccccc1]

Step 1. Preparation of tert-butyl (S)-5-chloro-2-fluoro-4-((1-phenylpropyl)amino)phenyl)sulfonyl)(thiazol-4-yl)carbamate

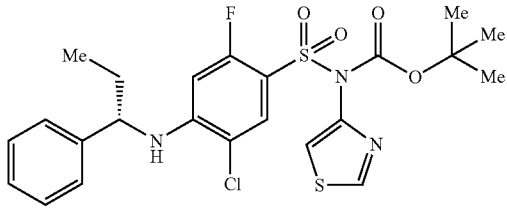 [SMILES: CC[C@H](Nc1cc(F)c(S(=O)(=O)N(C(=O)OC(C)(C)C)c2cscn2)cc1Cl)c1ccccc1]

To a mixture of tert-butyl ((5-chloro-2,4-difluorophenyl)sulfonyl)(thiazol-4-yl)carbamate (0.317 g, 0.732 mmol) and (S)-1-phenylpropan-1-amine (0.098 g, 0.73 mmol) in anhydrous dimethyl sulfoxide (5 mL) was added cesium carbonate (0.573 g, 1.76 mmol) and the reaction mixture was stirred at ambient temperature for 17 h. The reaction mixture was diluted with ethyl acetate (5 mL) and water (5 mL), and the aqueous phase was extracted with ethyl acetate (3×5 mL). The combined organic phases were washed with brine (5 mL), dried over anhydrous sodium sulfate, and filtered. Concentration of the filtrate in vacuo afforded the title compound as a colorless oil (0.143 g, 37% yield): MS (ES−) m/z 524.1 (M−1), 526.1 (M−1).

Step 2. Preparation of (S)-5-chloro-2-fluoro-4-((1-phenylpropyl)amino)-N-(thiazol-4-yl)benzenesulfonamide

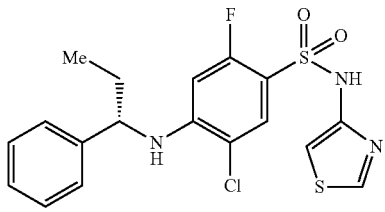 [SMILES: CC[C@H](Nc1cc(F)c(S(=O)(=O)Nc2cscn2)cc1Cl)c1ccccc1]

To a mixture of tert-butyl (S)-5-chloro-2-fluoro-4-((1-phenylpropyl)amino)phenyl)-sulfonyl)(thiazol-4-yl)carbamate (0.143 g, 0.273 mmol) in dichloromethane (5 mL) was added trifluoroacetic acid (1 mL) and the reaction mixture was stirred at ambient temperature for 1 h. The reaction mixture was diluted with methanol (10 mL), and the obtained suspension was filtered. Concentration of the filtrate in vacuo and purification of the residue by column chromatography, eluting with a gradient of 12 to 70% of ethyl acetate in hexanes, afforded the title compound as a colorless solid (0.060 g, 19% yield): $^1$H NMR (300 MHz, DMSO-$d_6$) δ 11.04 (s, 1H), 8.82 (d, J=2.1 Hz, 1H), 7.54 (d, J=7.2 Hz, 1H), 7.38 (d, J=7.2 Hz, 1H), 7.28 (t, J=6.9 Hz, 1H), 7.20-7.16 (m, 1H), 6.92 (d, J=2.1 Hz, 1H), 6.58 (d, J=7.8 Hz, 1H), 6.44 (d, J=13.5 Hz, 1H), 4.40 (q, J=6.9 Hz, 1H), 2.04-1.89 (m, 1H), 1.80-1.66 (m, 1H), 0.84 (t, J=7.2 Hz, 3H); MS (ES−) m/z 424.1 (M−1), 426.1 (M−1).

Example 90

Synthesis of 3-chloro-4-(methyl(1-phenylpropyl)amino)-N-(thiazol-2-yl)benzenesulfonamide

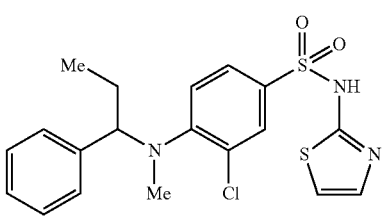 [SMILES: CCC(c1ccccc1)N(C)c1ccc(S(=O)(=O)Nc2nccs2)cc1Cl]

To a mixture of 4-bromo-3-chloro-N-(thiazol-2-yl)benzenesulfonamide (0.200 g, 0.568 mmol), 2-di-tert-butylphosphino-2',4',6'-triisopropylbiphenyl (0.012 g, 0.028 mmol), tris(dibenzylideneacetone)dipalladium (0.013 g, 0.014 mmol), and sodium tert-butoxide (0.164 g, 1.70 mmol) in anhydrous toluene (3 mL) was added N-methyl-1-phenylpropan-1-amine (0.093 g, 0.625 mmol). The reaction mixture degassed by passing a stream of nitrogen through it and then heated to 100° C. for 18 h. The reaction mixture was allowed to cool to ambient temperature, diluted with ethyl acetate (10 mL) and filtered through a pad of Celite. The filtrate was concentrated in vacuo and the residue was purified twice by column chromatography, eluting with a gradient of 20 to 100% of ethyl acetate in hexanes, to provide the title compound a colorless solid (0.011 g, 4% yield): $^1$H NMR (300 MHz, DMSO-$d_6$) δ 12.80 (s, 1H), 7.75-7.69 (m, 1H), 7.55 (d, J=8.4 Hz, 1H), 7.35-7.19 (m, 4H), 7.17-7.09 (m, 2H), 6.93 (d, J=8.7 Hz, 1H), 6.86-6.80 (m, 1H), 4.57-4.47 (m, 1H), 2.52 (s, 3H), 2.14-1.89 (m, 2H), 0.81 (t, J=6.6 Hz, 3H); MS (ES−) m/z 420.1 (M−1), 422.1 (M−1).

Example 91

Synthesis of (R)-3-chloro-4-((2-hydroxy-1-phenylethyl)amino)-N-(thiazol-2-yl)benzenesulfonamide

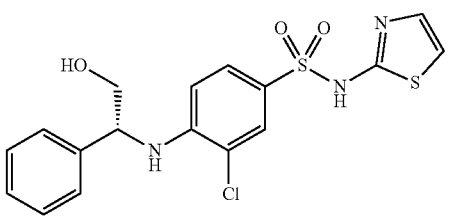 [SMILES: O=S(=O)(Nc1nccs1)c1ccc(N[C@@H](CO)c2ccccc2)c(Cl)c1]

Step 1. Preparation of (R)-3-chloro-N-(2,4-dimethoxybenzyl)-4-((2-hydroxy-1-phenylethyl)amino)-N-(thiazol-2-yl)benzenesulfonamide

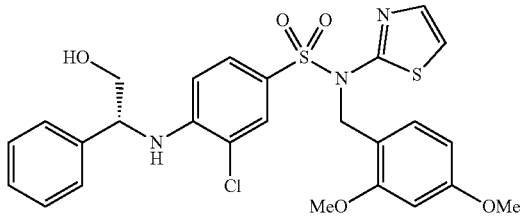 [SMILES: COc1ccc(CN(c2nccs2)S(=O)(=O)c2ccc(N[C@@H](CO)c3ccccc3)c(Cl)c2)c(OC)c1]

Following the procedure as described for EXAMPLE 2, Step 2 and making non-critical variations as required to replace (S)-1-(1-naphthyl)ethylamine with (R)-2-amino-2-phenylethan-1-ol, the title compound was obtained as a colorless solid (0.23 g, 7% yield): $^1$H NMR (300 MHz, CDCl$_3$) δ 7.67 (dd, J=2.2, 0.8 Hz, 1H), 7.43-7.32 (m, 8H), 7.14 (d, J=9.0 Hz, 1H), 6.96 (dd, J=3.6, 0.9 Hz, 1H), 6.39-6.34 (m, 2H), 5.78 (d, J=5.5 Hz, 1H), 5.03 (s, 2H), 4.60-4.54 (m, 1H), 4.07-4.02 (m, 1H), 3.91-3.84 (m, 2H), 3.77 (s, 3H), 3.69 (s, 3H); MS (ES+) m/z 560.1 (M+1), 562.1 (M+1).

Step 2. Preparation of (R)-3-chloro-4-((2-hydroxy-1-phenylethyl)amino)-N-(thiazol-2-yl)benzenesulfonamide

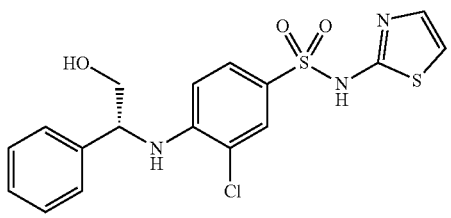 [SMILES: O=S(=O)(Nc1nccs1)c1ccc(N[C@@H](CO)c2ccccc2)c(Cl)c1]

Following the procedure as described for EXAMPLE 2, Step 3 and making non-critical variations as required to replace (S)-5-bromo-N-(2,4-dimethoxybenzyl)-2-fluoro-4-((1-phenylpropyl)amino)-N-(thiazol-2-yl)benzenesulfonamide with (R)-3-chloro-N-(2,4-dimethoxybenzyl)-4-((2-hydroxy-1-phenylethyl)amino)-N-(thiazol-2-yl) benzenesulfonamide and purification by preparative reverse-phase HPLC using acetonitrile in water containing 0.1% trifluoroacetic acid as eluent, the title compound was obtained as a colorless solid (0.10 g, 59% yield): 1H NMR (300 MHz, DMSO-d$_6$) δ 12.57 (br s, 1H), 7.57 (d, J=2.2 Hz, 1H), 7.38-7.24 (m, 5H), 7.22-7.15 (m, 2H), 7.73 (d, J=4.5 Hz, 1H), 6.46 (d, J=8.7 Hz, 1H), 6.07 (d, J=5.8 Hz, 1H), 4.57-4.49 (m, 1H), 3.75-3.58 (m, 2H), OH not observed; MS (ES+) m/z 410.1 (M+1), 412.1 (M+1).

Example 92

Synthesis of (S)-5-chloro-4-((1-(2-chlorophenyl)ethyl)amino)-2-fluoro-N-(thiazol-4-yl)benzenesulfonamide

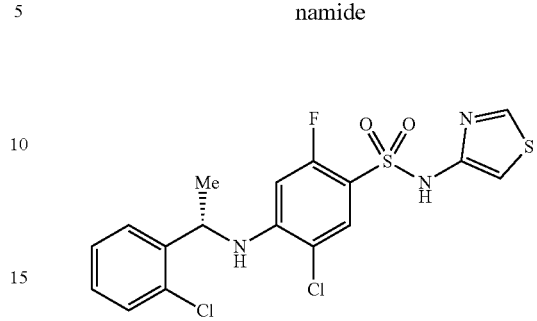

Following the procedure as described for EXAMPLE 5, Step 1 and making non-critical variations as required to replace (S)-1-(5-chloro-2-fluorophenyl)ethan-1-amine hydrochloride with (S)-1-(2-chlorophenyl)ethan-1-amine, and purification by preparative reverse-phase HPLC using acetonitrile in water containing 0.1% trifluoroacetic acid as eluent, the title compound was obtained as a colorless solid (0.085 g, 28% yield): $^1$H NMR (300 MHz, DMSO-d$_6$) δ 11.10 (s, 1H), 8.82 (d, J=2.2 Hz, 1H), 7.58 (d, J=7.6 Hz, 1H), 7.45-7.39 (m, 2H), 7.31-7.20 (m, 2H), 6.93 (d, J=2.2 Hz, 1H), 6.87-6.81 (m, 1H), 6.02 (d, J=13.1 Hz, 1H), 4.92-4.80 (m, 1H), 1.50 (d, J=6.7 Hz, 3H); MS (ES+) m/z 446.0 (M+1), 448.0 (M+1).

Example 93

Synthesis of 5-chloro-2-fluoro-4-((5,6,7,8-tetrahydroisoquinolin-8-yl)amino)-N-(thiazol-2-yl)benzenesulfonamide 2,2,2-trifluoroacetate

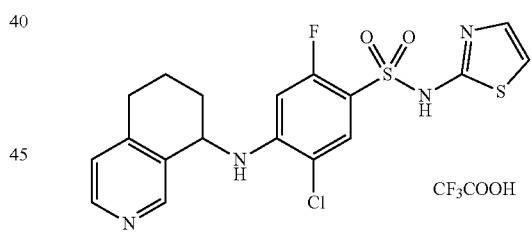

To a mixture of 5-chloro-N-(2,4-dimethoxybenzyl)-2,4-difluoro-N-(thiazol-2-yl)benzenesulfonamide (0.46 g, 1.0 mmol) and 5,6,7,8-tetrahydroisoquinolin-8-amine (0.15, 1.0 mmol) in anhydrous dimethylsulfoxide (8 mL) was added potassium carbonate (0.41 g, 3.0 mmol) and the mixture was heated to 60° C. for 3 h. The reaction mixture was allowed to cool to ambient temperature, diluted with ethyl acetate (60 mL), and washed with saturated ammonium chloride (50 mL) and brine (30 mL). The organic layer was dried over anhydrous sodium sulfate and filtered. The filtrate was concentrated in vacuo and the residue dissolved in dichloromethane (20 mL). To this solution was then added trifluoroacetic acid (5 mL) and the reaction mixture was stirred at ambient temperature for 40 minutes. The reaction mixture was concentrated in vacuo and methanol (20 mL) added to the residue. The suspension was filtered and the filtrate concentrated in vacuo. The residue was purified by preparative reverse phase HPLC using acetonitrile in water containing 0.1% of trifluoroacetic acid as eluent to afford the title compound as colorless solid (0.075 g, 14% yield): $^1$H NMR (300 MHz, DMSO-$d_6$) δ 12.84 (br s, 1H), 8.62 (s, 1H), 8.57 (d, J=5.8 Hz, 1H), 7.68 (d, J=5.8 Hz, 1H), 7.64 (d, J=7.4 Hz, 1H), 7.29 (d, J=4.6 Hz, 1H), 7.01 (d, J=13.4 Hz, 1H), 6.85 (d, J=4.6 Hz, 1H), 6.72-6.69 m, 1H), 5.07-4.99 (m, 2H), 2.03-1.79 (m, 4H), NH and COOH not observed; $^{19}$F NMR (282 MHz, DMSO-$d_6$) δ 73.9 (s, 3F), 109.2 (s, 1F); MS (ES+) m/z 439.0 (M+1), 441.0 (M+1).

Example 94

Synthesis of 5-chloro-2-fluoro-4-((5,6,7,8-tetrahydroisoquinolin-5-yl)amino)-N-(thiazol-2-yl)benzenesulfonamide 2,2,2-trifluoroacetate

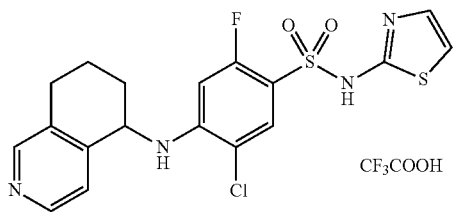 [SMILES: O=S(=O)(Nc1nccs1)c1cc(Cl)c(NC2CCCc3cnccc32)cc1F ; "CF3COOH"]

Following the procedure as described for EXAMPLE 93 and making non-critical variations as required to replace 5,6,7,8-tetrahydroisoquinolin-8-amine with 5,6,7,8-tetrahydroisoquinolin-5-amine, the title compound was obtained as a colorless solid (0.070 g, 13% yield): $^1$H NMR (300 MHz, DMSO-$d_6$) δ 12.86 (br s, 1H), 8.68 (s, 1H), 8.55 (d, J=5.8 Hz, 1H), 7.67-7.61 (m, 2H), 7.29 (d, J=4.6 Hz, 1H), 6.97 (d, J=13.3 Hz, 1H), 6.85 (d, J=4.6 Hz, 1H), 6.97 (dd, J=9.0, 1.4 Hz, 1H), 5.08-5.00 (m, 2H), 2.96-2.83 (m, 2H), 2.13-1.83 (m, 4H), NH and COOH not observed; $^{19}$F NMR (282 MHz, DMSO-$d_6$) δ−73.9 (s, 3F), −109.1 (s, 1F); MS (ES+) m/z 439.0 (M+1), 441.0 (M+1).

Example 95

Synthesis of (S)-5-chloro-4-(1-(5-chloro-2-fluorophenyl)ethoxy)-2-fluoro-N-(thiazol-2-yl)benzenesulfonamide

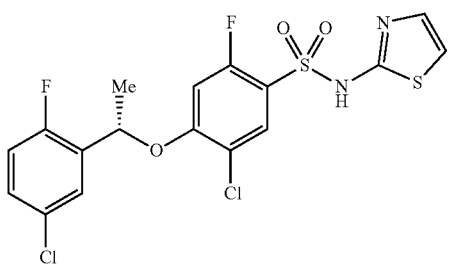 [SMILES: C[C@H](Oc1cc(F)c(S(=O)(=O)Nc2nccs2)cc1Cl)c1cc(Cl)ccc1F]

Following the procedure as described for EXAMPLE 93 and making non-critical variations as required to replace 5,6,7,8-tetrahydroisoquinolin-8-amine with (S)-1-(5-chloro-2-fluorophenyl)ethan-1-ol, the title compound was obtained as a colorless solid (0.10 g, 43% yield): $^1$H NMR (300 MHz, DMSO-$d_6$) δ 12.95 (br s, 1H), 7.79 (d, J=7.4 Hz, 1H), 7.53 (dd, J=6.2, 2.7 Hz, 1H), 7.45 (ddd, J=8.8, 4.5, 2.7 Hz, 1H), 7.35-7.29 (m, 3H), 6.88 (d, J=4.6 Hz, 1H), 5.94 (q, J=6.3 Hz, 1H), 1.63 (d, J=6.3 Hz, 3H); MS (ES+) m/z 465.0 (M+1), 467.0 (M+1).

Example 96

Synthesis of 5-chloro-2-fluoro-4-((isoquinolin-8-ylmethyl)amino)-N-(thiazol-4-yl)benzenesulfonamide 2,2,2-trifluoroacetate

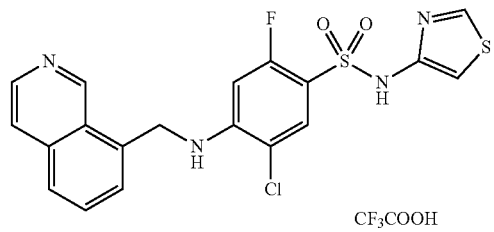 [SMILES: O=S(=O)(Nc1cscn1)c1cc(Cl)c(NCc2cccc3ccncc23)cc1F ; "CF3COOH"]

To a mixture of tert-butyl ((5-chloro-2,4-difluorophenyl)sulfonyl)(thiazol-4-yl)carbamate (0.82 g, 2.00 mmol) and isoquinolin-8-ylmethanamine (0.32 g, 2.00 mmol) in anhydrous DMSO (12 mL) was added potassium carbonate (0.28 g, 2.00 mmol) and the reaction mixture was heated to 80° C. for 2 h. The reaction mixture was allowed to cool to ambient temperature and diluted with ethyl acetate (100 mL). The mixture was washed with saturated ammonium chloride (2×100 mL), brine (50 mL), dried over anhydrous sodium sulfate, and filtered. The filtrate was concentrated in vacuo, the residue dissolved in dichloromethane (30 mL), and trifluoroacetic acid (10 mL) was added to it. The reaction mixture was stirred at ambient temperature for 40 minutes and then concentrated in vacuo. The obtained residue was purified by preparative reverse phase HPLC using acetonitrile in water containing 0.1% of trifluoroacetic acid as eluent followed by trituration with methanol (35 mL) to provide the title compound as a colorless solid (0.30 g, 33% yield): $^1$H NMR (300 MHz, DMSO-$d_6$) δ 11.08 (br s, 1H), 9.85 (s, 1H), 8.84 (d, J=2.2 Hz, 1H), 8.64 (d, J=6.1 Hz, 1H), 8.23 (d, J=6.1 Hz, 1H), 8.04 (d, J=8.3 Hz, 1H), 7.94-7.87 (m, 1H), 7.64-7.57 (m, 2H), 7.46-7.38 (m, 1H), 6.95 (d, J=2.0 Hz, 1H), 6.59 (d, J=13.3 Hz, 1H), 5.10 (d, J=6.0 Hz, 2H), COOH not observed; $^{19}$F NMR (282 MHz, DMSO-$d_6$) δ−74.1 (s, 3F), −109.6 (s, 1F); MS (ES+) m/z 449.0 (M+1), 451.0 (M+1).

Example 97

Synthesis of (R)-5-chloro-2-fluoro-4-((1-(pyridin-3-yl)ethyl)amino)-N-(thiazol-2-yl)benzenesulfonamide formate

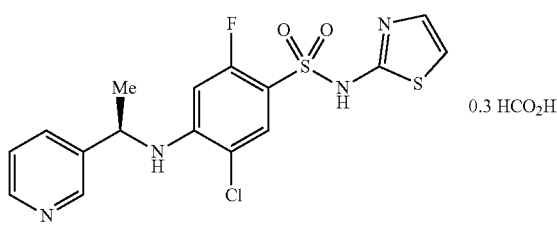

Following the procedure as described for EXAMPLE 93 and making non-critical variations as required to replace 5,6,7,8-tetrahydroisoquinolin-8-amine with (R)-1-(pyridin-3-yl)ethan-1-amine, the title compound was obtained as a colorless solid (0.125 g, 30% yield): ¹H NMR (300 MHz, DMSO-d₆) δ 12.78 (br s, 1H), 8.65 (d, J=1.9 Hz, 1H), 8.43 (dd, J=4.7, 1.5 Hz, 1H), 8.14 (s, 0.3H), 7.81 (dt, J=8.0, 1.9 Hz, 1H), 7.59 (d, J=7.3 Hz, 1H), 7.34 (dd, J=7.8, 4.8 Hz, 1H), 7.25 (d, J=4.6 Hz, 1H), 6.81 (d, J=4.5 Hz, 1H), 6.60 (dd, J=7.7, 1.4 Hz, 1H), 6.51 (d, J=13.1 Hz, 1H), 4.86-4.76 (m, 1H), 1.56 (d, J=6.8 Hz, 3H), COOH not observed; MS (ES+) m/z 413.0 (M+1), 415.0 (M+1).

Example 98

Synthesis of 5-chloro-2-fluoro-4-((5,6,7,8-tetrahydroquinolin-5-yl)amino)-N-(thiazol-2-yl)benzenesulfonamide formate

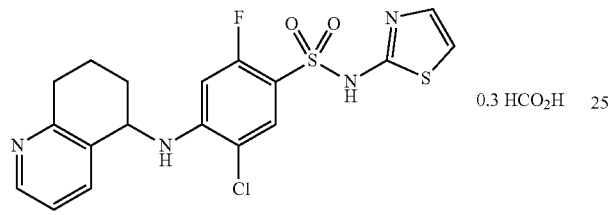

Following the procedure as described for EXAMPLE 93 and making non-critical variations as required to replace 5,6,7,8-tetrahydroisoquinolin-8-amine with 5,6,7,8-tetrahydroquinolin-5-amine, the title compound was obtained as a colorless solid (0.195 g, 44% yield): ¹H NMR (300 MHz, DMSO-d₆) δ 12.84 (br s, 1H), 8.44 (dd, 4.9, 1.5 Hz, 1H), 8.14 (s, 0.3H), 7.67 (dd, J=7.8, 0.9 Hz, 1H), 7.32-7.27 (m, 2H), 6.93 (d, 13.4 Hz, 1H), 6.84 (d, J=4.6 Hz, 1H), 6.57-6.53 (m, 1H), 4.98-4.92 (m, 1H), 2.98-2.82 (m, 2H), 2.04-1.78 (m, 4H), NH and COOH not observed; MS (ES+) m/z 439.0 (M+1), 441.0 (M+1).

Example 99

Synthesis of 3-chloro-4-((cyclopropyl(phenyl)methyl)amino)-N-(thiazol-2-yl)benzenesulfonamide

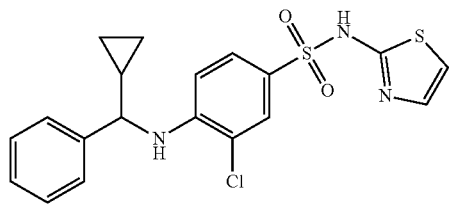 [SMILES: O=S(=O)(Nc1nccs1)c1ccc(NC(c2ccccc2)C2CC2)c(Cl)c1]

To a solution of 4-bromo-3-chloro-N-(thiazol-2-yl)benzenesulfonamide (0.200 g, 0.568 mmol), 2-di-tert-butylphosphino-2',4',6'-triisopropylbiphenyl (0.012 g, 0.028 mmol), tris(dibenzylideneacetone)dipalladium(0) (0.013 g, 0.014), and sodium tert-butoxide (0.273 g, 2.85 mmol) in anhydrous toluene (3 mL) was added cyclopropyl(phenyl)methanamine (0.096 g, 0.62 mmol) mmol). The reaction mixture was purged with argon and then heated to 100° C. for 17 h. The reaction mixture was allowed to cool to ambient temperature, diluted with ethyl acetate (5 mL), and filtered through a pad of Celite. The filtrate was concentrated in vacuo and the residue was purified by column chromatography, eluting with a gradient of 0 to 80% of ethyl acetate in hexanes. Further purification by preparative reverse phase HPLC using acetonitrile in water containing 0.1% of trifluoroacetic acid as eluent afforded the title compound as a colorless solid (0.010 g, 4% yield): ¹H NMR (300 MHz, DMSO-d₆) δ 12.58 (br s, 1H), 7.57 (s, 1H), 7.42 (d, J=7.5 Hz, 2H), 7.32 (dd, J=6.5, 8.2 Hz, 3H), 7.26-7.16 (m, 2H), 6.80-6.73 (m, 1H), 6.47 (d, J=8.9 Hz, 1H), 6.31 (d, J=6.4 Hz, 1H), 3.80 (t, J=7.7 Hz, 1H), 1.51-1.35 (m, 1H), 0.66-0.53 (m, 1H), 0.53-0.31 (m, 3H); MS (ES+) m/z 420.0 (M+1), 422.0 (M+1).

Example 100

Synthesis of 5-chloro-4-((cyclopropyl(phenyl)methyl)amino)-2-fluoro-N-(thiazol-2-yl)benzenesulfonamide

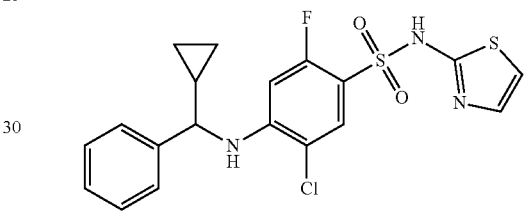

To a solution of cyclopropyl(phenyl)methanamine (0.096 g, 0.65 mmol) and 5-chloro-N-(2,4-dimethoxybenzyl)-2,4-difluoro-N-(thiazol-2-yl)benzenesulfonamide (0.300 g, 0.652 mmol) in anhydrous dimethylsulfoxide (2.6 mL) was added cesium carbonate (0.509 g, 1.56 mmol) and the reaction mixture was stirred at ambient temperature for 17 h. The reaction mixture was diluted with ethyl acetate (5 mL) and water (5 mL), and the aqueous phase was extracted with ethyl acetate (2×5 mL). The combined organic layers were washed with brine (2×5 mL), dried over anhydrous magnesium sulfate, and filtered. The filtrate was concentrated in vacuo and the residue dissolved in dichloromethane (9 mL). To this solution was added trifluoroacetic acid (0.14 mL, 1.8 mmol) at 0° C. and the reaction mixture was stirred at 0° C. for 30 min. The reaction mixture was quenched by addition of saturated sodium bicarbonate solution (6 mL), and the aqueous phase was extracted with dichloromethane (2×5 mL). The combined organic layers were washed with water (5 mL), dried over anhydrous magnesium sulfate, and filtered. The filtrate was concentrated in vacuo and the residue was triturated in methanol (7 mL). The resulting suspension was filtered and the filtrate was concentrated in vacuo. Purification of the residue by preparative reverse phase HPLC using acetonitrile in water containing 0.1% of ammonium hydroxide as eluent afforded the title compound as a colorless solid (0.025 g, 9% yield): ¹H NMR (300 MHz, DMSO-d₆) δ 12.71 (br s, 1H), 7.57 (d, J=7.1 Hz, 1H), 7.48-7.40 (m, 2H), 7.32 (t, J=7.3 Hz, 2H), 7.26-7.18 (m, 2H), 6.78 (d, J=4.5 Hz, 1H), 6.62 (d, J=7.1 Hz, 1H), 6.30 (d, J=13.3 Hz, 1H), 3.87-3.75 (m, 1H), 1.53-1.36 (m, 1H), 0.65-0.53 (m, 1H), 0.53-0.31 (m, 3H); MS (ES+) m/z 438.0 (M+1), 440.0 (M+1).

Example 101

Synthesis of (S)-5-chloro-2-fluoro-4-(1-(2-fluorophenyl)ethoxy)-N-(thiazol-4-yl)benzenesulfonamide

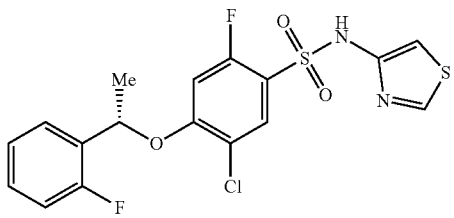 [SMILES: C[C@H](Oc1cc(F)c(S(=O)(=O)Nc2cscn2)cc1Cl)c1ccccc1F]

To a solution of (S)-1-(2-fluorophenyl)ethan-1-ol (0.102 g, 0.730 mmol) and tert-butyl ((5-chloro-2,4-difluorophenyl)sulfonyl)(thiazol-4-yl)carbamate (0.30 g, 0.730 mmol) in anhydrous dimethyl sulfoxide (3 mL) was added cesium carbonate (0.571 g, 1.75 mmol) and the reaction mixture was heated at 75° C. for 17 h. The reaction mixture was diluted with ethyl acetate (5 mL) and water (5 mL), and the aqueous phase was extracted with ethyl acetate (2×5 mL). The combined organic layers were washed with brine (5 mL), dried over anhydrous magnesium sulfate, and filtered. Concentration of the filtrate in vacuo and purification of the residue by preparative reverse phase HPLC using acetonitrile in water containing 0.1% of trifluoroacetic acid as eluent afforded the title compound as a colorless solid (0.062 g, 20% yield): $^1$H NMR (300 MHz, DMSO-$d_6$) δ 11.34 (s, 1H), 8.88 (d, J=2.2 Hz, 1H), 7.80 (d, J=7.5 Hz, 1H), 7.51-7.33 (m, 2H), 7.30-7.18 (m, 3H), 7.06 (d, J=2.2 Hz, 1H), 5.97 (q, J=6.4 Hz, 1H), 1.63 (d, J=6.4 Hz, 3H); MS (ES+) m/z 431.0 (M+1), 432.9 (M+1).

Example 102

Synthesis of (R)-5-chloro-2-fluoro-4-((1,2,3,4-tetrahydronaphthalen-1-yl)amino)-N-(thiazol-2-yl)benzenesulfonamide

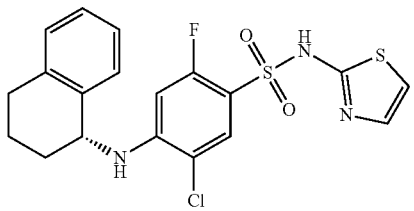 [SMILES: O=S(=O)(Nc1nccs1)c1cc(Cl)c(N[C@@H]2CCCc3ccccc32)cc1F]

To a solution of (R)-1,2,3,4-tetrahydronaphthalen-1-amine (0.096 g, 0.65 mmol) and 5-chloro-N-(2,4-dimethoxybenzyl)-2,4-difluoro-N-(thiazol-2-yl)benzenesulfonamide (0.300 g, 0.652 mmol) in anhydrous dimethyl sulfoxide (2.6 mL) was added cesium carbonate (0.509 g, 1.56 mmol) and the resulting suspension was stirred at ambient temperature for 17 h. The reaction mixture was diluted with ethyl acetate (5 mL) and water (5 mL), and the aqueous phase was extracted with ethyl acetate (2×5 mL). The combined organic layers were washed with brine (2×5 mL), dried over anhydrous magnesium sulfate, and filtered. The filtrate was concentrated in vacuo and the residue purified by column chromatography, eluting with a gradient of 0 to 30% of ethyl acetate in hexanes. The obtained residue was then dissolved in dichloromethane (7 mL) and trifluoroacetic acid (0.12 mL, 1.6 mmol) was added to it at 0° C. The reaction mixture was stirred at 0° C. for 10 minutes and then concentrated in vacuo. The residue was triturated in methanol (5 mL), and the resulting suspension filtered. Concentration of the filtrate in vacuo and purification of the residue by column chromatography, eluting with a gradient of 0 to 15% of methanol in dichloromethane, afforded the title compound as a colorless solid (0.041 g, 14% yield): $^1$H NMR (300 MHz, DMSO-$d_6$) δ 12.78 (s, 1H), 7.61 (d, J=7.7 Hz, 1H), 7.27 (d, J=5.1 Hz, 1H), 7.22-7.08 (m, 4H), 6.91-6.78 (m, 2H), 6.33-6.22 (m, 1H), 4.92-4.78 (m, 1H), 2.88-2.65 (m, 2H), 2.03-1.68 (m, 4H); MS (ES+) m/z 438.0 (M+1), 440.0 (M+1).

Example 103

Synthesis of 3-chloro-4-((3-phenyloxetan-3-yl)amino)-N-(thiazol-2-yl)benzenesulfonamide

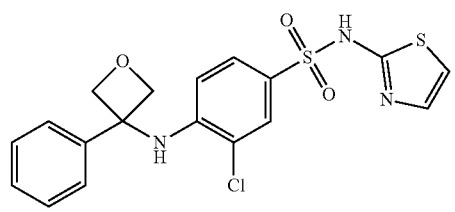 [SMILES: O=S(=O)(Nc1nccs1)c1ccc(NC2(c3ccccc3)COC2)c(Cl)c1]

Following the procedure as described in EXAMPLE 99, and making non-critical variations as required to replace cyclopropyl(phenyl)methanamine with 3-phenyloxetan-3-amine, the title compound was obtained as a colorless solid (0.015 g, 6% yield): $^1$H NMR (300 MHz, DMSO-$d_6$) δ 12.59 (br s, 1H), 7.63 (d, J=2.2 Hz, 1H), 7.58-7.50 (m, 2H), 7.44-7.35 (m, 2H), 7.33-7.25 (m, 3H), 7.19 (d, J=4.5 Hz, 1H), 6.74 (d, J=4.5 Hz, 1H), 5.74 (d, J=8.6 Hz, 1H), 4.94 (d, J=6.4 Hz, 2H), 4.82 (d, J=6.4 Hz, 2H); MS (ES+) m/z 422.1 (M+1), 424.1 (M+1).

Example 104

Synthesis of 3-chloro-4-((1-phenylcyclobutyl)amino)-N-(thiazol-2-yl)benzenesulfonamide

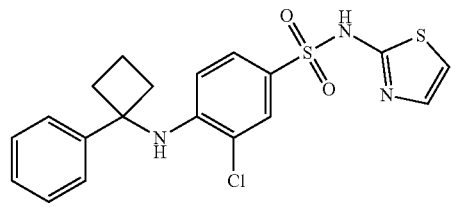 [SMILES: O=S(=O)(Nc1nccs1)c1ccc(NC2(c3ccccc3)CCC2)c(Cl)c1]

Following the procedure as described in EXAMPLE 99, and making non-critical variations as required to replace cyclopropyl(phenyl)methanamine with 1-phenylcyclobutan-1-amine, the title compound was obtained as a colorless solid (0.015 g, 5% yield): $^1$H NMR (300 MHz, DMSO-$d_6$) δ 7.57 (d, J=2.1 Hz, 1H), 7.53-7.46 (m, 2H), 7.37-7.28 (m, 2H), 7.28-7.12 (m, 3H), 6.70 (d, J=4.5 Hz, 1H), 6.59 (s, 1H), 6.03 (d, J=8.7 Hz, 1H), 2.65-2.40 (m, 4H), 2.12-1.85 (m, 2H), sulfonamide NH not observed; MS (ES+) m/z 420.1 (M+1), 422.1 (M+1).

Example 105

Synthesis of 5-chloro-2-fluoro-4-((1-phenylcyclobutyl)amino)-N-(thiazol-2-yl)benzenesulfonamide

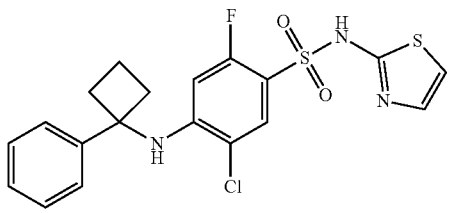 [SMILES: O=S(=O)(Nc1nccs1)c1cc(Cl)c(NC2(c3ccccc3)CCC2)cc1F]

To a solution of 1-phenylcyclobutan-1-amine (0.120 g, 0.65 mmol) and 5-chloro-N-(2,4-dimethoxybenzyl)-2,4-difluoro-N-(thiazol-2-yl)benzenesulfonamide (0.300 g, 0.652 mmol) in anhydrous dimethyl sulfoxide (2.5 mL) was added cesium carbonate (0.509 g, 1.56 mmol) and the resulting suspension was stirred at ambient temperature for 17 h. The reaction mixture was diluted with ethyl acetate (5 mL) and water (5 mL), and the aqueous phase was extracted with ethyl acetate (2×5 mL). The combined organic layers were washed with brine (2×5 mL), dried over anhydrous magnesium sulfate, and filtered. The filtrate was concentrated in vacuo and the obtained residue was dissolved in dichloromethane (6 mL). To it was added trifluoroacetic acid (0.16 mL, 2.1 mmol) at 0° C. The reaction mixture was stirred at 0° C. for 20 minutes and then concentrated in vacuo. The residue was triturated in methanol (5 mL), and the resulting suspension filtered. Concentration of the filtrate in vacuo and purification of the residue by preparative reverse phase HPLC using acetonitrile in water containing 0.1% formic acid as eluent afforded the title compound as a colorless solid (0.016 g, 6% yield): $^1$H NMR (300 MHz, DMSO-$d_6$) δ 7.57 (d, J=7.3 Hz, 1H), 7.51 (d, J=7.5 Hz, 2H), 7.35 (t, J=7.8 Hz, 2H), 7.26-7.17 (m, 2H), 6.96 (s, 1H), 6.75 (d, J=4.6 Hz, 1H), 5.71 (d, J=12.7 Hz, 1H), 2.63-2.43 (m, 4H), 2.09-1.84 (m, 2H), sulfonamide NH not observed; MS (ES+) m/z 438.1 (M+1), 440.1 (M+1).

Example 106

Synthesis of 5-chloro-2-fluoro-4-((1-(3-fluorophenyl)cyclobutyl)amino)-N-(thiazol-2-yl)benzenesulfonamide

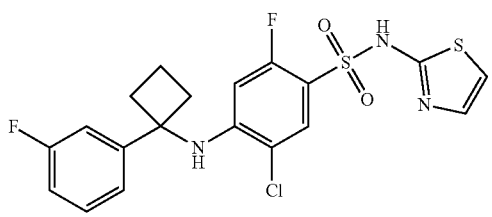 [SMILES: O=S(=O)(Nc1nccs1)c1cc(Cl)c(NC2(c3cccc(F)c3)CCC2)cc1F]

Following the procedure as described in EXAMPLE 105, and making non-critical variations as required to replace 1-phenylcyclobutan-1-amine with 1-(3-fluorophenyl)cyclobutan-1-amine, the title compound was obtained as a colorless solid (0.011 g, 4% yield): $^1$H NMR (300 MHz, DMSO-$d_6$) δ 12.75 (s, 1H), 7.59 (d, J=7.4 Hz, 1H), 7.45-7.30 (m, 3H), 7.25 (d, J=4.6 Hz, 1H), 7.08-7.02 (m, 1H), 6.82 (d, J=4.6 Hz, 1H), 6.56 (s, 1H), 5.74 (d, J=12.7 Hz, 1H), 2.66-2.44 (m, 4H), 2.07-1.86 (m, 2H); MS (ES+) m/z 456.0 (M+1), 458.0 (M+1).

Example 107

Synthesis of 5-chloro-2-fluoro-4-((1-(2-fluorophenyl)cyclobutyl)amino)-N-(thiazol-2-yl)benzenesulfonamide

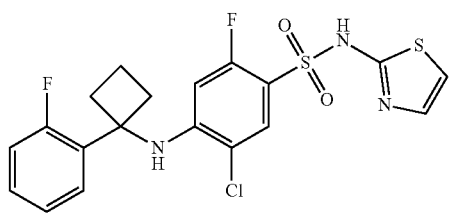 [SMILES: O=S(=O)(Nc1nccs1)c1cc(Cl)c(NC2(c3ccccc3F)CCC2)cc1F]

Following the procedure as described in EXAMPLE 105, and making non-critical variations as required to replace 1-phenylcyclobutan-1-amine with 1-(2-fluorophenyl)cyclobutan-1-amine, the title compound was obtained as a colorless solid (0.008 g, 3% yield): $^1$H NMR (300 MHz, DMSO-$d_6$) δ 12.75 (s, 1H), 7.64 (t, J=8.0 Hz, 1H), 7.57 (d, J=7.3 Hz, 1H), 7.36-7.10 (m, 4H), 6.82 (d, J=4.8 Hz, 1H), 6.59-6.52 (m, 1H), 6.08 (d, J=12.9 Hz, 1H), 2.81-2.66 (m, 2H), 2.66-2.54 (m, 2H), 2.13-1.96 (m, 1H), 1.96-1.78 (m, 1H); MS (ES+) m/z 456.0 (M+1), 458.0 (M+1).

Example 108

Synthesis of (S)-5-chloro-4-(1-(3,4-dichlorophenyl)ethoxy)-2-fluoro-N-(thiazol-2-yl)benzenesulfonamide

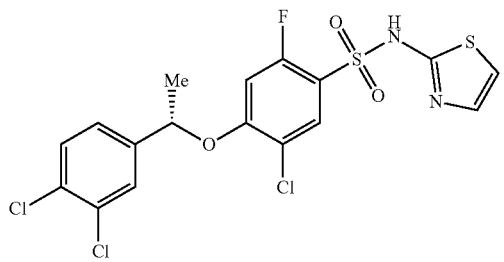 [SMILES: C[C@H](Oc1cc(F)c(S(=O)(=O)Nc2nccs2)cc1Cl)c1ccc(Cl)c(Cl)c1]

Following the procedure as described in EXAMPLE 105, and making non-critical variations as required to replace 1-phenylcyclobutan-1-amine with (S)-1-(3,4-dichlorophenyl)ethan-1-ol, the title compound was obtained as a colorless solid (0.106 g, 34% yield): $^1$H NMR (300 MHz, DMSO-$d_6$) δ 12.93 (s, 1H), 7.77 (d, J=7.4 Hz, 1H), 7.70 (d, J=2.1 Hz, 1H), 7.65 (d, J=8.4 Hz, 1H), 7.38 (dd, J=2.1, 8.4 Hz, 1H), 7.30 (d, J=4.6 Hz, 1H), 7.26 (d, J=11.9 Hz, 1H), 6.88 (d, J=4.6 Hz, 1H), 5.79 (q, J=6.4 Hz, 1H), 1.59 (d, J=6.4 Hz, 3H); MS (ES+) m/z 480.9 (M+1), 482.9 (M+1), 484.9 (M+1).

Example 109

Synthesis of (S)-5-chloro-2-fluoro-4-((3-methyl-1-phenylbutyl)amino)-N-(thiazol-2-yl)benzenesulfonamide

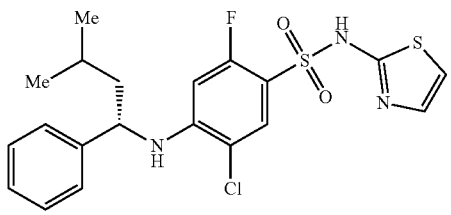 [SMILES: CC(C)C[C@H](Nc1cc(F)c(S(=O)(=O)Nc2nccs2)cc1Cl)c1ccccc1]

Following the procedure as described in EXAMPLE 105, and making non-critical variations as required to replace 1-phenylcyclobutan-1-amine with (S)-3-methyl-1-phenylbutan-1-amine, the title compound was obtained as a colorless solid (0.038 g, 10% yield): $^1$H NMR (300 MHz, DMSO-$d_6$) δ 12.74 (s, 1H), 7.55 (d, J=7.4 Hz, 1H), 7.48-7.39 (m, 2H), 7.35-7.26 (m, 2H), 7.26-7.16 (m, 2H), 6.81 (d, J=4.5 Hz, 1H), 6.54 (d, J=13.3 Hz, 1H), 6.51-6.44 (m, 1H), 4.63-4.50 (m, 1H), 2.04-1.89 (m, 1H), 1.68-1.43 (m, 2H), 0.93 (d, J=6.3 Hz, 3H), 0.87 (d, J=6.3 Hz, 3H); MS (ES+) m/z 454.1 (M+1), 456.1 (M+1).

Example 110

Synthesis of (R)-5-chloro-2-fluoro-4-((3-methyl-1-phenylbutyl)amino)-N-(thiazol-2-yl)benzenesulfonamide

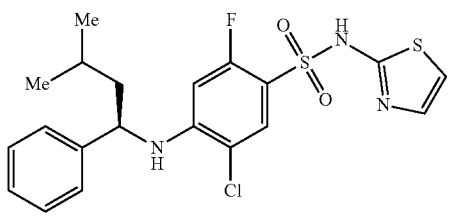 [SMILES: CC(C)C[C@@H](Nc1cc(F)c(S(=O)(=O)Nc2nccs2)cc1Cl)c1ccccc1]

Following the procedure as described in EXAMPLE 105, and making non-critical variations as required to replace 1-phenylcyclobutan-1-amine with (R)-3-methyl-1-phenylbutan-1-amine, the title compound was obtained as a colorless solid (0.056 g, 14% yield): $^1$H NMR (300 MHz, DMSO-$d_6$) δ 12.73 (s, 1H), 7.55 (d, J=7.4 Hz, 1H), 7.47-7.40 (m, 2H), 7.34-7.27 (m, 2H), 7.26-7.16 (m, 2H), 6.81 (d, J=4.5 Hz, 1H), 6.54 (d, J=13.3 Hz, 1H), 6.51-6.44 (m, 1H), 4.63-4.49 (m, 1H), 2.05-1.89 (m, 1H), 1.68-1.43 (m, 2H), 0.93 (d, J=6.3 Hz, 3H), 0.87 (d, J=6.3 Hz, 3H); MS (ES+) m/z 454.1 (M+1), 456.1 (M+1).

Example 111

Synthesis of (S)-5-chloro-2-fluoro-4-((1-phenylbutyl)amino)-N-(thiazol-2-yl)benzenesulfonamide

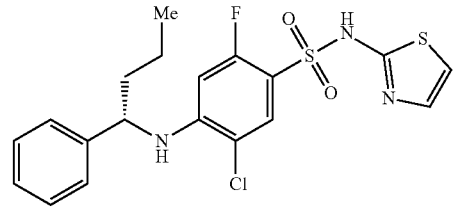 [SMILES: CCC[C@H](Nc1cc(F)c(S(=O)(=O)Nc2nccs2)cc1Cl)c1ccccc1]

To a solution of (S)-1-phenylbutan-1-amine (0.130 g, 0.872 mmol) and 5-chloro-N-(2,4-dimethoxybenzyl)-2,4-difluoro-N-(thiazol-2-yl)benzenesulfonamide (0.400 g, 0.870 mmol) in anhydrous dimethyl sulfoxide (3.5 mL) was added cesium carbonate (0.685 g, 2.10 mmol) and the resulting suspension was stirred at ambient temperature for 17 h. The reaction mixture was diluted with ethyl acetate (5 mL) and water (5 mL), and the aqueous phase was extracted with ethyl acetate (2×5 mL). The combined organic layers were washed with brine (5 mL), dried over anhydrous magnesium sulfate, and filtered. The filtrate was concentrated in vacuo and purified by column chromatography, eluting with a gradient of 0 to 50% of ethyl acetate in hexanes. The obtained residue was then dissolved in dichloromethane (7.5 mL) and trifluoroacetic acid (0.12 mL, 1.6 mmol) was added to it at 0° C. The reaction mixture was stirred at 0° C. for 30 minutes and then concentrated in vacuo. The residue was triturated in methanol (5 mL), and the resulting suspension filtered. Concentration of the filtrate in vacuo and purification of the residue by preparative reverse phase HPLC using acetonitrile in water containing 0.1% formic acid as eluent afforded the title compound as a colorless solid (0.004 g, 1% yield): $^1$H NMR (300 MHz, DMSO-$d_6$) δ 12.66 (br s, 1H), 7.55 (d, J=7.3 Hz, 1H), 7.45-7.38 (m, 2H), 7.35-7.26 (m, 2H), 7.25-7.15 (m, 2H), 6.75 (d, J=4.4 Hz, 1H), 6.58-6.40 (m, 2H), 4.50 (dt, J=7.7, 6.6 Hz, 1H), 2.07-1.90 (m, 1H), 1.80-1.60 (m, 1H), 1.48-1.31 (m, 1H), 1.31-1.16 (m, 1H), 0.88 (t, J=7.3 Hz, 3H); MS (ES+) m/z 440.0 (M+1), 442.0 (M+1).

Example 112

Synthesis of (S)-5-chloro-2-fluoro-4-((2-methoxy-1-phenylethyl)amino)-N-(thiazol-2-yl)benzenesulfonamide

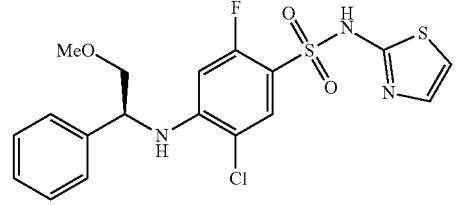 [SMILES: COC[C@@H](Nc1cc(F)c(S(=O)(=O)Nc2nccs2)cc1Cl)c1ccccc1]

Following the procedure as described in EXAMPLE 105, and making non-critical variations as required to replace 1-phenylcyclobutan-1-amine with (S)-2-methoxy-1-phenylethan-1-amine, the title compound was obtained as a colorless solid (0.014 g, 5% yield): $^1$H NMR (300 MHz, DMSO-$d_6$) δ 12.71 (br s, 1H), 7.59 (d, J=7.4 Hz, 1H), 7.45-7.39 (m, 2H), 7.37-7.29 (m, 2H), 7.28-7.21 (m, 1H), 7.19 (d, J=4.5 Hz, 1H), 6.75 (d, J=4.5 Hz, 1H), 6.40 (d, J=13.0 Hz, 1H), 6.37-6.32 (m, 1H), 4.87-4.76 (m, 1H), 3.77 (dd, J=10.0, 8.0 Hz, 1H), 3.56 (dd, J=10.0, 4.6 Hz, 1H), 3.29 (s, 3H); MS (ES+) m/z 442.1 (M+1), 444.1 (M+1).

Example 113

Synthesis of (R)-5-chloro-2-fluoro-4-((2-methoxy-1-phenylethyl)amino)-N-(thiazol-2-yl)benzenesulfonamide

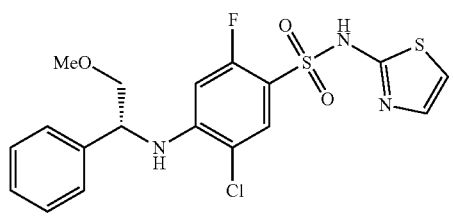 [SMILES: COC[C@H](Nc1cc(F)c(S(=O)(=O)Nc2nccs2)cc1Cl)c1ccccc1]

Following the procedure as described in EXAMPLE 111, and making non-critical variations as required to replace (S)-1-phenylbutan-1-amine with (R)-2-methoxy-1-phenylethan-1-amine, the title compound was obtained as a colorless solid (0.037 g, 13% yield): $^1$H NMR (300 MHz, DMSO-$d_6$) δ 12.74 (br s, 1H), 7.59 (d, J=7.3 Hz, 1H), 7.45-7.38 (m, 2H), 7.37-7.29 (m, 2H), 7.29-7.20 (m, 2H), 6.79 (d, J=4.6 Hz, 1H), 6.47-6.35 (m, 2H), 4.88-4.77 (m, 1H), 3.78 (dd, J=10.1, 8.0 Hz, 1H), 3.56 (dd, J=10.1, 4.6 Hz, 1H), 3.29 (s, 3H); MS (ES+) m/z 442.0 (M+1), 444.0 (M+1).

Example 114

Synthesis of (S)-5-chloro-2-fluoro-4-(1-(3-fluorophenyl)ethoxy)-N-(thiazol-2-yl)benzenesulfonamide

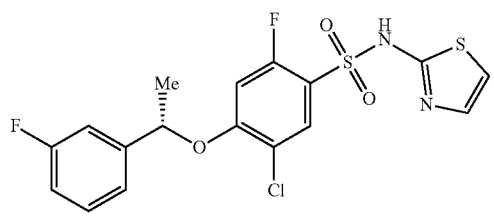 [SMILES: C[C@H](Oc1cc(F)c(S(=O)(=O)Nc2nccs2)cc1Cl)c1cccc(F)c1]

Following the procedure as described in EXAMPLE 105, and making non-critical variations as required to replace 1-phenylcyclobutan-1-amine with (S)-1-(3-fluorophenyl)ethan-1-ol, the title compound was obtained as a colorless solid (0.105 g, 38% yield): $^1$H NMR (300 MHz, DMSO-$d_6$) δ 12.92 (s, 1H), 7.77 (d, J=7.4 Hz, 1H), 7.30 (d, J=4.6 Hz, 1H), 7.28-7.20 (m, 3H), 7.18-7.08 (m, 1H), 6.87 (d, J=4.6 Hz, 1H), 6.88 (d, J=4.6 Hz, 1H), 5.79 (q, J=6.4 Hz, 1H), 1.59 (d, J=6.4 Hz, 3H); MS (ES+) m/z 431.0 (M+1), 433.0 (M+1).

Example 115

Synthesis of (S)-5-chloro-2-fluoro-4-(1-phenylethoxy)-N-(thiazol-2-yl)benzenesulfonamide

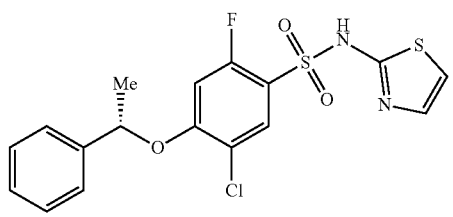

Following the procedure as described in EXAMPLE 102, and making non-critical variations as required to replace (R)-1,2,3,4-tetrahydronaphthalen-1-amine with (S)-1-phenylethan-1-ol, the title compound was obtained as a colorless solid (0.041 g, 15% yield): $^1$H NMR (300 MHz, DMSO-$d_6$) δ 12.90 (br s, 1H), 7.75 (d, J=7.5 Hz, 1H), 7.45-7.22 (m, 6H), 7.17 (d, J=11.9 Hz, 1H), 6.83 (br s, 1H), 5.77 (q, J=6.4 Hz, 1H), 1.59 (d, J=6.3 Hz, 3H); MS (ES+) m/z 413.0 (M+1), 415.0 (M+1).

Example 116

Synthesis of (S)-5-chloro-2-fluoro-4-(1-(2-fluorophenyl)ethoxy)-N-(thiazol-2-yl)benzenesulfonamide

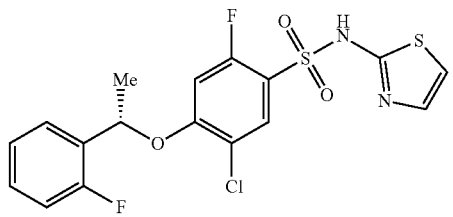 [SMILES: C[C@H](Oc1cc(F)c(S(=O)(=O)Nc2nccs2)cc1Cl)c1ccccc1F]

Following the procedure as described in EXAMPLE 111, and making non-critical variations as required to replace (S)-1-phenylbutan-1-amine with (S)-1-(2-fluorophenyl)ethan-1-ol, the title compound was obtained as a colorless solid (0.027 g, 10% yield): $^1$H NMR (300 MHz, DMSO-$d_6$) δ 12.92 (br s, 1H), 7.77 (d, J=7.4 Hz, 1H), 7.51-7.42 (m, 1H), 7.42-7.32 (m, 1H), 7.30-7.15 (m, 4H), 6.86 (d, J=4.5 Hz, 1H), 5.95 (q, J=6.3 Hz, 1H), 1.63 (d, J=6.3 Hz, 3H); MS (ES+) m/z 431.0 (M+1), 433.0 (M+1).

Example 117

Synthesis of (S)-5-chloro-4-(1-(2-chlorophenyl)ethoxy)-2-fluoro-N-(thiazol-2-yl)benzenesulfonamide

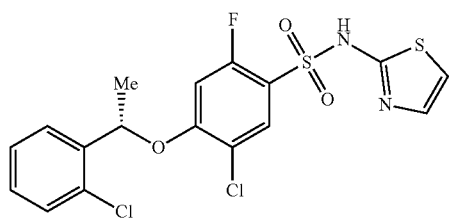 [SMILES: C[C@H](Oc1cc(F)c(S(=O)(=O)Nc2nccs2)cc1Cl)c1ccccc1Cl]

Following the procedure as described in EXAMPLE 105, and making non-critical variations as required to replace 1-phenylcyclobutan-1-amine with (S)-1-(2-chlorophenyl)ethan-1-ol, the title compound was obtained as a colorless solid (0.015 g, 5% yield): $^1$H NMR (300 MHz, DMSO-$d_6$) δ 12.94 (s, 1H), 7.79 (d, J=7.4 Hz, 1H), 7.53-7.45 (m, 2H), 7.42-7.31 (m, 2H), 7.30 (d, J=4.6 Hz, 1H), 6.96 (d, J=11.8 Hz, 1H), 6.88 (d, J=4.6 Hz, 1H), 5.94 (q, J=6.3 Hz, 1H), 1.62 (d, J=6.3 Hz, 3H); MS (ES+) m/z 447.0 (M+1), 449.0 (M+1).

Example 118

Synthesis of (S)-5-chloro-2-fluoro-4-(1-(3-fluorophenyl)ethoxy)-N-(thiazol-4-yl)benzenesulfonamide

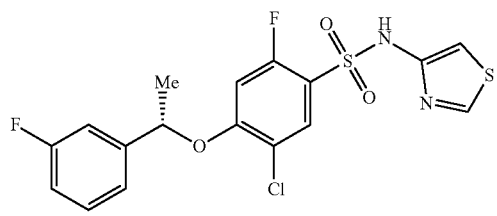 [SMILES: C[C@H](Oc1cc(F)c(S(=O)(=O)Nc2cscn2)cc1Cl)c1cccc(F)c1]

Following the procedure as described in EXAMPLE 101, and making non-critical variations as required to replace (S)-1-(2-fluorophenyl)ethan-1-ol with (S)-1-(3-fluorophenyl)ethan-1-ol, the title compound was obtained as a colorless solid (0.039 g, 12% yield): $^1$H NMR (300 MHz, DMSO-$d_6$) δ 11.33 (s, 1H), 8.88 (s, 1H), 7.80 (d, J=7.5 Hz, 1H), 7.48-7.37 (m, 1H), 7.32-7.20 (3H), 7.18-7.09 (m, 1H), 7.06 (d, J=2.2 Hz, 1H), 5.81 (q, J=6.4 Hz, 1H), 1.59 (q, J=6.4 Hz, 3H); MS (ES+) m/z 431.0 (M+1), 432.9 (M+1).

Example 119

Synthesis of (S)-5-chloro-4-(1-(2,6-difluorophenyl)ethoxy)-2-fluoro-N-(thiazol-2-yl)benzenesulfonamide

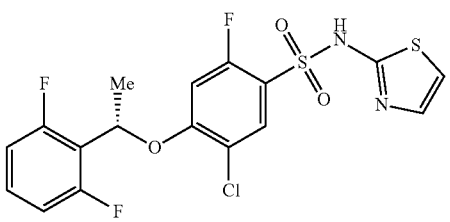 [SMILES: C[C@H](Oc1cc(F)c(S(=O)(=O)Nc2nccs2)cc1Cl)c1c(F)cccc1F]

Following the procedure as described in EXAMPLE 105, and making non-critical variations as required to replace 1-phenylcyclobutan-1-amine with (S)-1-(2,6-difluorophenyl)ethan-1-ol, the title compound was obtained as a colorless solid (0.046 g, 16% yield): $^1$H NMR (300 MHz, DMSO-$d_6$) δ 12.94 (s, 1H), 7.76 (d, J=7.4 Hz, 1H), 7.51-7.38 (m, 1H), 7.30 (d, J=4.6 Hz, 1H), 7.19-7.07 (m, 3H), 6.88 (d, J=4.6 Hz, 1H), 6.02 (q, J=6.5 Hz, 1H), 1.74 (d, J=6.5 Hz, 3H); MS (ES+) m/z 449.0 (M+1), 451.0 (M+1).

Example 120

Synthesis of (S)-5-chloro-4-(1-(2,6-difluorophenyl)ethoxy)-2-fluoro-N-(thiazol-4-yl)benzenesulfonamide

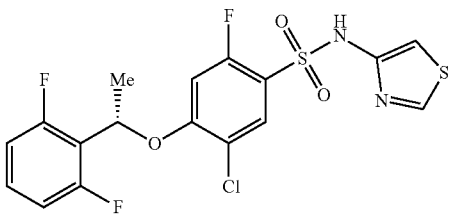 [SMILES: C[C@H](Oc1cc(F)c(S(=O)(=O)Nc2cscn2)cc1Cl)c1c(F)cccc1F]

Following the procedure as described in EXAMPLE 101, and making non-critical variations as required to replace (S)-1-(2-fluorophenyl)ethan-1-ol with (S)-1-(2,6-difluorophenyl)ethan-1-ol, the title compound was obtained as a colorless solid (0.028 g, 9% yield): $^1$H NMR (300 MHz, DMSO-$d_6$) δ 11.35 (s, 1H), 8.88 (s, 1H), 7.78 (d, J=7.5 Hz, 1H), 7.52-7.39 (m, 1H), 7.24-7.08 (m, 3H), 7.06 (d, J=2.2 Hz, 1H), 6.04 (q, J=6.5 Hz, 1H), 1.74 (d, J=6.5 Hz, 3H); MS (ES+) m/z 448.9 (M+1), 450.8 (M+1).

Example 121

Synthesis of (R)-5-chloro-2-fluoro-4-(1-(2-fluorophenyl)ethoxy)-N-(thiazol-2-yl)benzenesulfonamide

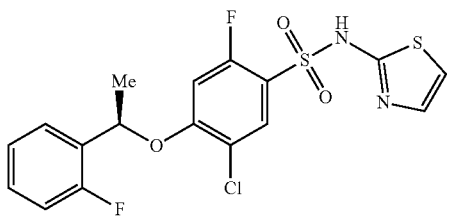 [SMILES: C[C@@H](Oc1cc(F)c(S(=O)(=O)Nc2nccs2)cc1Cl)c1ccccc1F]

Following the procedure as described in EXAMPLE 105, and making non-critical variations as required to replace 1-phenylcyclobutan-1-amine with (R)-1-(2-fluorophenyl)ethan-1-ol, the title compound was obtained as a colorless solid (0.056 g, 20% yield): $^1$H NMR (300 MHz, DMSO-d$_6$) δ 12.93 (s, 1H), 7.77 (d, J=7.4 Hz, 1H), 7.51-7.43 (m, 1H), 7.42-7.33 (m, 1H), 7.30 (d, J=4.6 Hz, 1H), 7.28-7.16 (m, 3H), 6.87 (d, J=4.6 Hz, 1H), 5.96 (q, J=6.4 Hz, 1H), 1.63 (d, J=6.4 Hz, 3H); MS (ES+) m/z 431.0 (M+1), 433.0 (M+1).

Example 122

Synthesis of 5-chloro-2-fluoro-4-((2-fluorobenzyl)oxy)-N-(thiazol-2-yl)benzenesulfonamide

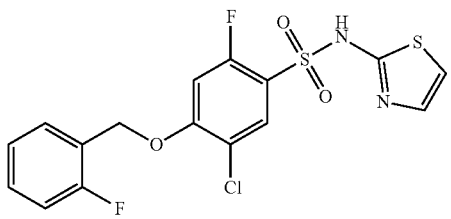 [SMILES: O=S(=O)(Nc1nccs1)c1cc(Cl)c(OCc2ccccc2F)cc1F]

Following the procedure as described in EXAMPLE 105, and making non-critical variations as required to replace 1-phenylcyclobutan-1-amine with (2-fluorophenyl)methanol, the title compound was obtained as a colorless solid (0.003 g, 1% yield): $^1$H NMR (300 MHz, DMSO-d$_6$) δ 12.98 (s, 1H), 7.80 (d, J=7.3 Hz, 1H), 7.59 (dt, J=1.8, 7.6 Hz, 1H), 7.53-7.41 (m, 2H), 7.34-7.23 (m, 3H), 6.89 (d, J=4.6 Hz, 1H), 5.32 (s, 2H); MS (ES+) m/z 417.1 (M+1), 419.0 (M+1).

Example 123

Synthesis of (S)-5-chloro-4-(1-(2-chlorophenyl)ethoxy)-2-fluoro-N-(thiazol-4-yl)benzenesulfonamide

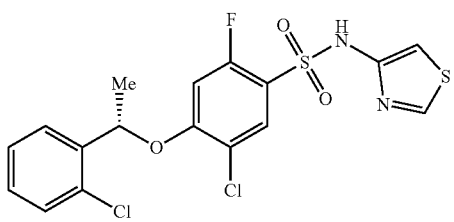 [SMILES: C[C@H](Oc1cc(F)c(S(=O)(=O)Nc2cscn2)cc1Cl)c1ccccc1Cl]

Following the procedure as described in EXAMPLE 101, and making non-critical variations as required to replace (S)-1-(2-fluorophenyl)ethan-1-ol with (S)-1-(2-chlorophenyl)ethan-1-ol, the title compound was obtained as a colorless solid (0.041 g, 13% yield): $^1$H NMR (300 MHz, DMSO-d$_6$) δ 11.36 (s, 1H), 8.88 (d, J=2.2 Hz, 1H), 7.82 (d, J=7.5 Hz, 1H), 7.53-7.45 (m, 2H), 7.43-7.32 (m, 2H), 7.06 (d, J=2.2 Hz, 1H), 7.02 (d, J=12.0 Hz, 1H), 5.96 (q, J=6.4 Hz, 1H), 1.62 (d, J=6.4 Hz, 3H); MS (ES+) m/z 447.0 (M+1), 449.0 (M+1).

Example 124

Synthesis of (S)-5-chloro-4-(1-(5-chloro-2-fluorophenyl)ethoxy)-2-fluoro-N-(thiazol-4-yl)benzenesulfonamide

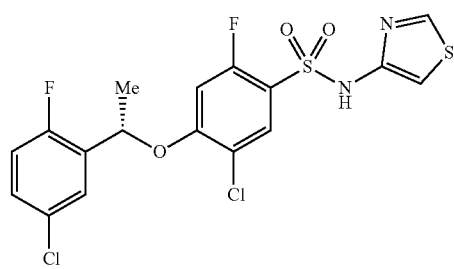 [SMILES: C[C@H](Oc1cc(F)c(S(=O)(=O)Nc2cscn2)cc1Cl)c1cc(Cl)ccc1F]

Following the procedure as described for EXAMPLE 96 and making non-critical variations as required to replace isoquinolin-8-ylmethanamine with (S)-1-(5-chloro-2-fluorophenyl)ethan-1-ol, the title compound was obtained as a colorless solid (0.135 g, 58% yield): $^1$H NMR (300 MHz, DMSO-d$_6$) δ 11.36 (br s, 1H), 8.88 (d, J=2.2 Hz, 1H), 7.82 (d, J=7.5 Hz, 1H), 7.52 (dd, J=6.2, 2.7 Hz, 1H), 7.46 (ddd, J=8.8, 4.5, 2.7 Hz, 1H), 7.39-7.29 (m, 2H), 7.06 (d, J=2.2 Hz, 1H), 5.96 (q, J=6.3 Hz, 1H), 1.63 (d, J=6.3 Hz, 3H); MS (ES+) m/z 465.0 (M+1), 467.0 (M+1).

Example 125

Synthesis of (S)-5-chloro-2-fluoro-4-((1-phenylethyl)thio)-N-(thiazol-2-yl)benzenesulfonamide

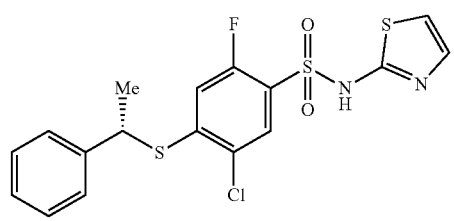 [SMILES: C[C@H](Sc1cc(F)c(S(=O)(=O)Nc2nccs2)cc1Cl)c1ccccc1]

Step 1. Preparation of (S)-5-chloro-N-(2,4-dimethoxybenzyl)-2-fluoro-4-((1-phenylethyl)thio)-N-(thiazol-2-yl)benzenesulfonamide

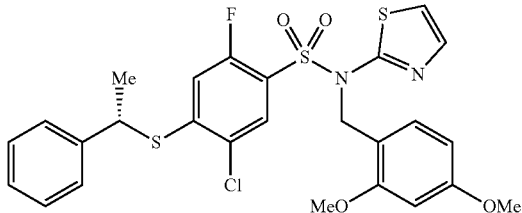 [SMILES: COc1ccc(CN(c2nccs2)S(=O)(=O)c2cc(Cl)c(S[C@@H](C)c3ccccc3)cc2F)c(OC)c1]

To a solution of 5-chloro-N-(2,4-dimethoxybenzyl)-2,4-difluoro-N-(thiazol-2-yl)benzenesulfonamide (0.23 g, 0.50 mmol) in anhydrous DMF (4 mL) was added sodium sulfide (0.04 g, 0.55 mmol) and the reaction mixture was stirred for 3 h. The reaction mixture was quenched by addition of a saturated aqueous solution of ammonium chloride (10 mL) and extracted with diethyl ether (2×10 mL). The organic layers were dried over anhydrous sodium sulfate, and filtered. After concentration of the filtrate in vacuo, the residue was dissolved in anhydrous diethyl ether (2 mL) and triphenyl phosphine (0.24 g, 0.90 mmol) and (R)-1-phenylethan-1-ol (0.07 g, 0.60 mmol) were added to it. The reaction mixture was cooled to 0° C. and diisopropyl azodicarboxylate (0.18 mL, 0.9 mmol) was added dropwise over 10 minutes. The reaction mixture was stirred at 0° C. for 2 h and then concentrated in vacuo. The obtained residue was purified by column chromatography, eluting with a gradient of 0-30% of ethyl acetate in hexanes to afford the title compound as a colorless oil (0.14 g, 48% yield): MS (ES+) m/z 579.0 (M+1), 581.0 (M+1).

Step 2. Preparation of (S)-5-chloro-2-fluoro-4-((1-phenylethyl)thio)-N-(thiazol-2-yl)benzenesulfonamide

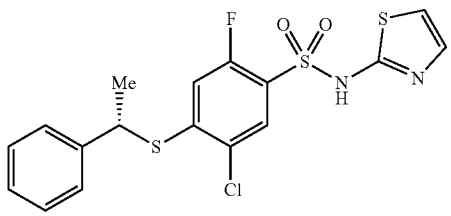 [SMILES: C[C@H](Sc1cc(F)c(S(=O)(=O)Nc2nccs2)cc1Cl)c1ccccc1]

Following the procedure as described for EXAMPLE 9, Step 3 and making non-critical variations as required to replace (S)-3-chloro-N-(2,4-dimethoxybenzyl)-2-fluoro-4-((1-(2-fluorophenyl)ethyl) amino)-N-(thiazol-2-yl)benzenesulfonamide with (S)-5-chloro-N-(2,4-dimethoxybenzyl)-2-fluoro-4-((1-phenylethyl)thio)-N-(thiazol-2-yl)benzenesulfonamide, the title compound was obtained as a colorless solid (0.07 g, 33% yield): $^1$H NMR (300 MHz, DMSO d$_6$) δ 12.87 (br s, 1H), 7.92 (d, J=6.6 Hz, 1H), 7.45-7.42 (m, 2H), 7.38-7.30 (m, 3H), 7.18 (d, J=4.6 Hz, 1H), 6.90 (d, J=10.6 Hz, 1H), 6.57 (d, J=4.5 Hz, 1H), 4.51-4.43 (m, 1H), 1.72 (d, J=7.0 Hz, 3H); MS (ES+) m/z 431.0 (M+1), 429.0 (M+1).

Example 126

Synthesis of (S)-2-fluoro-5-methyl-4-((1-phenylpropyl)amino)-N-(thiazol-2-yl)benzenesulfonamide

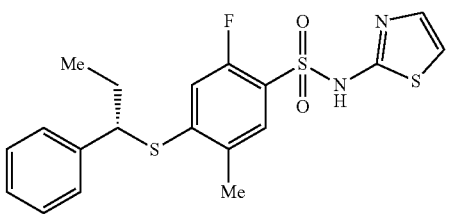 [SMILES: CC[C@H](Sc1cc(F)c(S(=O)(=O)Nc2nccs2)cc1C)c1ccccc1]

To a mixture of (S)-5-bromo-2-fluoro-4-((1-phenylpropyl)amino)-N-(thiazol-2-yl)benzenesulfonamide (0.410 g, 0.87 mmol), tetrakis(triphenylphosphine)palladium(0) (0.10 g, 0.087 mmol), and methylboronic acid (0.208 g, 3.48 mmol) in 1,4-dioxane (10.4 mL) was added a 2 M solution of sodium carbonate (2.6 mL, 5.2 mmol). The reaction mixture was degassed for 10 minutes by passing a stream of nitrogen through it and then heated at 100° C. for 16 h. The reaction mixture was allowed to cool to ambient temperature, adjusted to pH 5-6 by addition of a 1 N solution of hydrochloric acid, and extracted with ethyl acetate (3×40 mL). The combined organic layers were washed with brine (10 mL), dried over anhydrous sodium sulfate, and filtered. Concentration of the filtrate in vacuo and purification of the residue by column chromatography, eluting with a gradient of 0 to 100% of ethyl acetate in hexanes, provided the title compound as a colorless solid (0.065 g, 18% yield): $^1$H NMR (300 MHz, DMSO-d$_6$) δ 12.54 (s, 1H), 7.42-7.36 (m, 2H), 7.36-7.26 (m, 3H), 7.22-7.15 (m, 2H), 6.75 (d, J=4.6 Hz, 1H), 6.13 (d, J=13.8 Hz, 1H), 6.01 (d, J=6.6 Hz, 1H), 4.36-4.27 (m, 1H), 2.19 (s, 3H), 2.01-1.88 (m, 1H), 1.81-1.66 (m, 1H), 0.91 (t, J=7.3 Hz, 3H). MS (ES+) m/z 406.2 (M+1).

Examples 127-144

In a similar manner as described in the Examples above, utilizing the appropriately substituted starting materials and intermediates, the following compounds were prepared:

| Example No | Compound Name | MS (ES+) m/z |
|---|---|---|
| 127 | 5-chloro-4-((2-((2,2-dimethylazetidin-1-yl)methyl)-6-fluorobenzyl)amino)-2-fluoro-N-(thiazol-4-yl)benzenesulfonamide | 513.1 (M + 1), 515.1 (M + 1) |
| 128 | 4-((2-((2-azaspiro[3.3]heptan-2-yl)methyl)-6-fluorobenzyl)amino)-5-chloro-2-fluoro-N-(thiazol-4-yl)benzenesulfonamide | 525.2 (M + 1), 527.2 (M + 1) |
| 129 | 4-((2-chloro-6-((3-fluoroazetidin-1-yl)methyl)benzyl)amino)-2,6-difluoro-N-(thiazol-4-yl)benzenesulfonamide | 503.2 (M + 1), 505.2 (M + 1) |
| 130 | 2-fluoro-4-((2-fluoro-6-((3-fluoroazetidin-1-yl)methyl)benzyl)amino)-3-methyl-N-(thiazol-4-yl)benzenesulfonamide | 483.0 (M + 1) |
| 131 | 4-((2-(azetidin-1-ylmethyl)-3,6-difluorobenzyl)amino)-5-chloro-2-fluoro-N-(6-fluoropyridin-2-yl)benzenesulfonamide | 517.3 (M + 1), 515.3 (M + 1) |

-continued

| Example No | Compound Name | MS (ES+) m/z |
|---|---|---|
| 132 | 4-((2-(azetidin-1-ylmethyl)-4-fluorobenzyl)amino)-5-chloro-2-fluoro-N-(thiazol-4-yl)benzenesulfonamide | 485.1 (M + 1), 487.1 (M + 1) |
| 133 | 3-chloro-2-fluoro-4-((2-fluoro-6-((3-fluoroazetidin-1-yl)methyl)benzyl)amino)-N-(thiazol-4-yl)benzenesulfonamide | 503.0 (M + 1), 505.0 (M + 1) |
| 134 | (S)-5-chloro-4-((1-(2-((dimethylamino)methyl)phenyl)ethyl)amino)-2-fluoro-N-(thiazol-2-yl)benzenesulfonamide | 469.2 (M + 1), 471.2 (M + 1) |
| 135 | (R)-5-chloro-4-((1-(2-((dimethylamino)methyl)phenyl)ethyl)amino)-2-fluoro-N-(thiazol-2-yl)benzenesulfonamide | 469.2 (M + 1), 471.2 (M + 1) |
| 136 | 4-((2-(azetidin-1-ylmethyl)benzyl)oxy)-5-chloro-2-fluoro-N-(thiazol-2-yl)benzenesulfonamide | 468.0 (M + 1), 470.1 (M + 1) |
| 137 | 2-fluoro-4-((2-fluoro-6-((3-fluoroazetidin-1-yl)methyl)benzyl)amino)-5-methyl-N-(thiazol-4-yl)benzenesulfonamide | 483.0 (M + 1) |
| 138 | 4-((2-(azetidin-1-ylmethyl)-6-fluorobenzyl)amino)-5-chloro-2-fluoro-N-(6-fluoropyridin-2-yl)benzenesulfonamide | 497.2 (M + 1), 499.2 (M + 1) |
| 139 | 3-chloro-4-(1-phenylpropylamino)-N-(1,2,4-thiadiazol-5-yl)benzenesulfonamide | 407.1 (M + 1), 409.1 (M + 1) |
| 140 | 3-chloro-4-(1-phenylpropylamino)-N-(thiazol-2-yl)benzenesulfonamide | 407.9 (M + 1), 409.9 (M + 1) |
| 141 | 5-chloro-2-fluoro-4-(1-phenylpropylamino)-N-(thiazol-2-yl)benzenesulfonamide | 424.0 (M − 1), 426.0 (M − 1) |
| 142 | 3-chloro-4-(1-phenylethylamino)-N-(1,2,4-thiadiazol-5-yl)benzenesulfonamide | 393.0 (M + 1), 395.0 (M + 1) |
| 143 | 5-chloro-2-fluoro-4-(3-methyl-1-phenylbutylamino)-N-(thiazol-2-yl)benzenesulfonamide | 454.1 (M + 1), 456.1 (M + 1) |
| 144 | 5-chloro-2-fluoro-4-((1-(2-fluorophenyl)ethyl)amino)-N-(thiazol-2-yl)benzenesulfonamide | 428.1 (M + 1), 430.1 (M + 1) |

Example 145

Synthesis of 4-((2-(azetidin-1-ylmethyl)-6-fluorobenzyl)amino)-2,6-difluoro-N-(pyrimidin-2-yl)benzenesulfonamide 2,2,2-trifluoroacetate

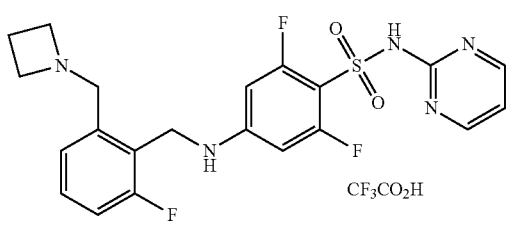

Step 1. Preparation of N-(2,4-dimethoxybenzyl)pyrimidin-2-amine

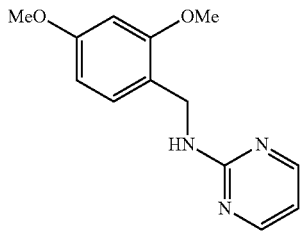 [SMILES: COc1ccc(CNc2ncccn2)c(OC)c1]

A mixture of 2-chloropyrimidine (2.00 g, 17.50 mmol), (2,4-dimethoxyphenyl)methanamine (2.92 g, 17.50 mmol) and potassium carbonate (2.90 g, 21.00 mmol) in anhydrous acetonitrile (20 mL) was degassed with by sparging with nitrogen, and then stirred to 80° C. for 10 h. After cooling to ambient temperature, the reaction mixture was concentrated in vacuo. The residue was purified by column chromatography, eluting with 50% of petroleum ether in ethyl acetate, to afford the title compound as a yellow solid (2.10 g, 49% yield): $^1$H NMR (400 MHz, CDCl$_3$) δ 8.27 (d, J=4.5 Hz, 2H), 7.24 (d, J=8.3 Hz, 1H), 6.50 (t, J=4.8 Hz, 1H), 6.47 (d, J=2.5 Hz, 1H), 6.43 (dd, J=8.3, 2.5 Hz, 1H), 5.58 (br s, 1H), 4.55 (d, J=6.0 Hz, 2H), 3.83 (s, 3H), 3.80 (s, 3H).

Step 2. Preparation of N-(2,4-dimethoxybenzyl)-2,4,6-trifluoro-N-(pyrimidin-2-yl)benzenesulfonamide

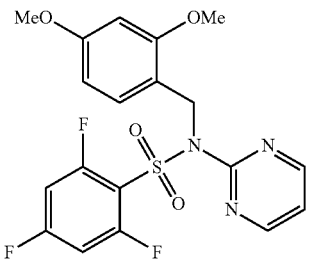 [SMILES: COc1ccc(CN(c2ncccn2)S(=O)(=O)c2c(F)cc(F)cc2F)c(OC)c1]

To a solution of N-(2,4-dimethoxybenzyl)pyrimidin-2-amine (1.00 g, 4.10 mmol) in anhydrous tetrahydrofuran (10 mL) was added a 1.6 M solution of methyl lithium in tetrahydrofuran (3.57 mL, 5.80 mmol) at −78° C. The reaction mixture was stirred at 0° C. for 30 minutes, after which 2,4,6-trifluorobenzenesulfonyl chloride (1.00 g, 4.48 mmol) in anhydrous tetrahydrofuran (2 mL) was added to it. The reaction mixture was stirred at 0° C. for 4 h, warmed to ambient temperature and quenched with water (10 mL). The mixture was extracted with ethyl acetate (3×30 mL). The combined organic extracts were washed with brine (2×40 mL), dried over anhydrous sodium sulfate, and filtered. Concentration of the filtrate in vacuo and purification of the residue by column chromatography, eluting with 50% of petroleum ether in ethyl acetate, afforded the title compound as a yellow solid (0.30 g, 17% yield): $^1$H NMR (400 MHz, CDCl$_3$) δ 8.42 (d, J=4.8 Hz, 2H), 7.24 (d, J=8.3 Hz, 1H), 6.89 (t, J=4.8 Hz, 1H), 6.81-6.72 (m, 2H), 6.48 (d, J=2.3 Hz, 1H), 6.43 (dd, J=8.4, 2.4 Hz, 1H), 5.42 (s, 2H), 3.87 (s, 3H), 3.79 (s, 3H).

Step 3. Preparation of tert-butyl (2-(azetidin-1-ylmethyl)-6-fluorobenzyl)carbamate

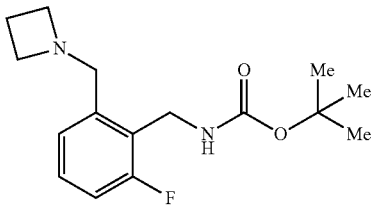 [SMILES: CC(C)(C)OC(=O)NCc1c(F)cccc1CN1CCC1]

To a solution of (2-(azetidin-1-ylmethyl)-6-fluorophenyl)methanamine (0.30 g, 1.50 mmol) in dichloromethane (4 mL) was added di-tert-butyl dicarbonate (0.37 g, 1.70 mmol) and triethylamine (0.43 mL, 3.10 mmol). The mixture was stirred at ambient temperature for 2 h, and then concentrated in vacuo. Purification of the residue by column chromatography, eluting with 50% of petroleum ether in ethyl acetate, provided the title compound as a colorless solid (0.38 g, 84% yield): $^1$H NMR (400 MHz, CDCl$_3$) δ 7.22-7.14 (m, 1H), 7.06-6.96 (m, 2H), 4.39 (br s, 2H), 3.62 (br s, 2H), 3.21 (t, J=6.8 Hz, 4H), 2.14-2.00 (m, 2H), 1.46 (s, 9H), NH not observed.

Step 4. Preparation of tert-butyl (2-(azetidin-1-ylmethyl)-6-fluorobenzyl)(4-(N-(2,4-dimethoxybenzyl)-N-(pyrimidin-2-yl)sulfamoyl)-3,5-difluorophenyl)carbamate

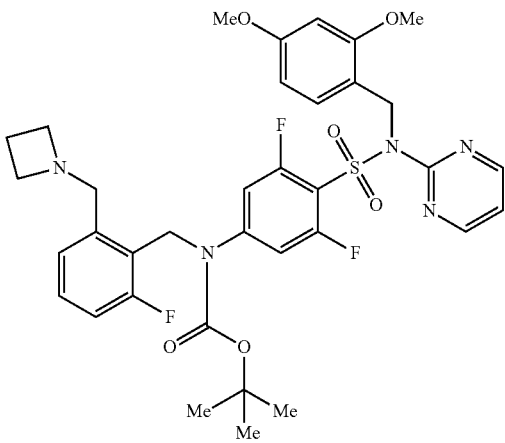 [SMILES: COc1ccc(CN(c2ncccn2)S(=O)(=O)c2c(F)cc(N(Cc3c(F)cccc3CN3CCC3)C(=O)OC(C)(C)C)cc2F)c(OC)c1]

To a solution of tert-butyl 2-(azetidin-1-ylmethyl)-6-fluorobenzylcarbamate (0.10 g, 0.34 mmol) in anhydrous N,N-dimethylformamide (3 mL) was added a 60% dispersion of sodium hydride in mineral (0.016 g, 0.41 mmol) at 0° C. The mixture was stirred for 5 min at 0° C., and then a solution of N-(2,4-dimethoxybenzyl)-2,4,6-trifluoro-N-(pyrimidin-2-yl)benzenesulfonamide (0.15 g, 0.34 mmol) in anhydrous N,N-dimethylformamide (1 mL) was added dropwise to it. The resulting mixture was stirred at ambient temperature for 1 h and then quenched by addition of water (2 mL). The mixture was extracted with ethyl acetate (2×30 mL). The combined organic extracts were washed with brine (2×30 mL), dried over anhydrous sodium sulfate, and filtered. Concentration of the filtrate in vacuo and purification of the residue by preparative reverse-phase HPLC, eluting with a gradient of acetonitrile in water (containing 0.05% of ammonium hydroxide) afford the title compound as a colorless solid (0.10 g, 41% yield): $^1$H NMR (400 MHz, CDCl$_3$) δ 8.58 (d, J=4.9 Hz, 1H), 8.50-8.37 (m, 1H), 8.04-7.93 (m, 2H), 7.35 (d, J=4.9 Hz, 1H), 7.23-7.07 (m, 1H), 7.06-6.99 (m, 1H), 6.92-6.71 (m, 2H), 6.68-6.27 (m, 2H), 4.90 (s, 2H), 4.74-4.51 (m, 2H), 4.38 (br s, 2H), 4.11-3.96 (m, 3H), 3.88-3.77 (m, 5H), 3.74-3.60 (m, 2H), 2.71 (d, J=7.8 Hz, 1H), 2.52 (s, 1H), 1.47-1.33 (m, 9H).

Step 5. Preparation of 4-((2-(azetidin-1-ylmethyl)-6-fluorobenzyl)amino)-2,6-difluoro-N-(pyrimidin-2-yl)benzenesulfonamide 2,2,2-trifluoroacetate

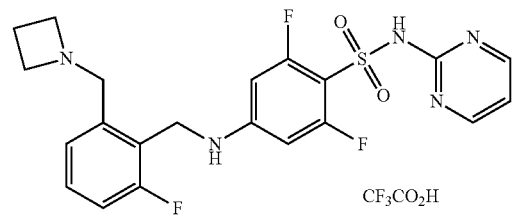 [SMILES: O=S(=O)(Nc1ncccn1)c1c(F)cc(NCc2c(F)cccc2CN2CCC2)cc1F ; "CF3CO2H"]

To tert-butyl(2-(azetidin-1-ylmethyl)-6-fluorobenzyl)(4-(N-(2,4-dimethoxybenzyl)-N-(pyrimidin-2-yl)sulfamoyl)-3,5-difluorophenyl)carbamate (0.090 g, 0.13 mmol) was added a 4 M solution of hydrogen chloride in 1,4-dioxane (1.50 mL) and the reaction mixture was stirred at ambient temperature for 1 h. The reaction mixture was concentrated in vacuo and the residue purified by preparative reverse phase HPLC, eluting with a gradient of acetonitrile in water (containing 0.1% of trifluoroacetic acid), to afford 4-((2-(azetidin-1-ylmethyl)-6-fluorobenzyl)amino)-2,6-difluoro-N-(pyrimidin-2-yl)benzenesulfonamide as a colorless solid (0.061 g, 97% yield): $^1$H NMR (400 MHz, DMSO-d$_6$) δ 11.92 (br s, 1H), 10.90 (br s, 1H), 8.51 (d, J=4.9 Hz, 2H), 7.54-7.47 (m, 1H), 7.46-7.41 (m, 1H), 7.41-7.32 (m, 2H), 7.06 (t, J=4.8 Hz, 1H), 6.39 (d, J=12.5 Hz, 2H), 4.46 (d, J=6.1 Hz, 2H), 4.38 (d, J=3.9 Hz, 2H), 4.15-4.06 (m, 2H), 4.04-3.96 (m, 2H), 2.43-2.35 (m, 1H), 2.27 (td, J=9.5, 4.4 Hz, 1H); MS (ES+) m/z 464.2 (M+1).

Example 146

Synthesis of (S)-5-chloro-4-((1-(5-cyclopropyl-2-fluorophenyl)ethyl)amino)-2-fluoro-N-(thiazol-4-yl)benzenesulfonamide

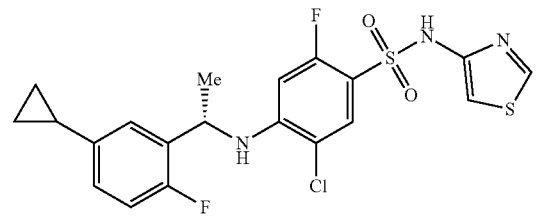 [SMILES: C[C@H](Nc1cc(F)c(S(=O)(=O)Nc2cscn2)cc1Cl)c1cc(C2CC2)ccc1F]

Step 1. Preparation of 5-cyclopropyl-2-fluorobenzaldehyde

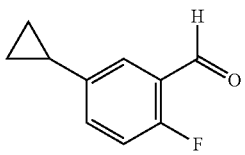 [SMILES: O=Cc1cc(C2CC2)ccc1F]

A mixture of 5-bromo-2-fluoro-benzaldehyde (10.00 g, 49.20 mmol), cyclopropylboronic acid (21.10 g, 246.30 mmol), potassium phosphate (41.80 g, 197.00 mmol), palladium acetate (2.2 g, 9.80 mmol) and tricyclohexylphosphonium tetrafluoroborate (3.60 g, 9.80 mmol) in anhydrous toluene (120 mL) was degassed by sparging with nitrogen, and then heated to 90° C. for 12 h. After cooling to ambient temperature, the reaction mixture was diluted with water (100 mL) and extracted with ethyl acetate (3×200 mL). The combined organic extracts were concentrated in vacuo, and the resulting residue was purified by column chromatography, eluting with a gradient of 2 to 10% of ethyl acetate in petroleum ether, to afford the title compound as a yellow oil (6.50 g, 80% yield): $^1$H NMR (400 MHz, CDCl$_3$) δ 10.26 (s, 1H), 7.46 (dd, J=6.4, 2.4 Hz, 1H), 7.30-7.22 (m, 1H), 6.99 (dd, J=10.0, 8.4 Hz, 1H), 1.91-1.80 (m, 1H), 0.98-0.88 (m, 2H), 0.67-0.58 (m, 2H).

Step 2. Preparation of (R)—N-(5-cyclopropyl-2-fluorobenzylidene)-2-methylpropane-2-sulfinamide

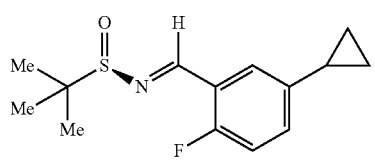

To a solution of 5-cyclopropyl-2-fluorobenzaldehyde (4.00 g, 24.30 mmol) and (R)-2-methylpropane-2-sulfinamide (5.90 g, 48.70 mmol) in anhydrous dichloromethane (40 mL) was added pyridinium para-toluenesulfonate (0.31 g, 1.20 mmol) and anhydrous magnesium sulfate (14.60 g, 121.80 mmol). The mixture was stirred at ambient temperature for 12 h and then filtered. Concentration of the filtrate in vacuo and purification of the residue by column chromatography, eluting with a gradient of 1 to 2% of ethyl acetate in petroleum ether, afforded the title compound as a colorless oil (1.80 g, 28% yield): $^1$H NMR (400 MHz, CDCl$_3$) δ 8.88 (s, 1H), 7.71 (dd, J=6.4, 2.0 Hz, 1H), 7.24-7.15 (m, 1H), 7.11-7.01 (m, 1H), 2.02-1.88 (m, 1H), 1.30 (s, 9H), 1.08-0.94 (m, 2H), 0.77-0.64 (m, 2H).

Step 3. Preparation of (R)—N—((S)-1-(5-cyclopropyl-2-fluorophenyl)ethyl)-2-methylpropane-2-sulfinamide

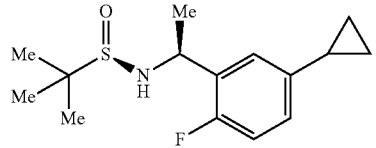 [SMILES: C[C@H](N[S@](=O)C(C)(C)C)c1cc(C2CC2)ccc1F]

To a solution of (R)—N-(5-cyclopropyl-2-fluorobenzylidene)-2-methylpropane-2-sulfinamide (1.50 g, 5.60 mmol) in anhydrous dichloromethane (20 mL) was added a 3.0 M solution of methylmagnesium bromide in diethyl ether (3.70 mL) dropwise at −48° C. The reaction mixture was warmed to ambient temperature and stirred for 12 h, and then quenched by addition of saturated ammonium chloride (10 mL). The mixture was extracted with dichloromethane (3×20 mL) and the combined organic extracts were concentrated in vacuo. Purification of the residue by column chromatography, eluting with a gradient of 5 to 20% of ethyl acetate in petroleum ether, afforded the title compound as a colorless oil (0.80 g, 50% yield): $^1$H NMR (400 MHz, CDCl$_3$) δ 7.06 (d, J=7.6 Hz, 1H), 6.98-6.89 (m, 2H), 4.87-4.75 (m, 1H), 1.96-1.82 (m, 1H), 1.59 (d, J=6.8 Hz, 3H), 1.22 (s, 9H), 0.96 (d, J=8.0 Hz, 2H), 0.73-0.59 (m, 2H), NH not observed.

Step 4. Preparation of (S)-1-(5-cyclopropyl-2-fluorophenyl)ethan-1-amine hydrochloride

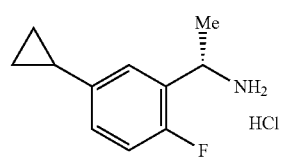 [SMILES: C[C@H](N)c1cc(C2CC2)ccc1F ; Cl]

To (R)—N—((S)-1-(5-cyclopropyl-2-fluorophenyl)ethyl)-2-methylpropane-2-sulfinamide (0.70 g, 2.40 mmol) was added a 4 M solution of hydrogen chloride in 1,4-dioxane (2.6 mL) and the reaction mixture was stirred at ambient temperature for 2 h. The reaction mixture was concentrated under reduced pressure. The resulting residue was diluted with methanol (1 mL) and crystallized from methyl tert-butyl ether (30 mL) to afford the title compound as a colorless solid: (0.35 g, 68% yield).

Step 5. Preparation of tert-butyl (S)-((5-chloro-4-((1-(5-cyclopropyl-2-fluorophenyl)ethyl)amino)-2-fluorophenyl)sulfonyl)(thiazol-4-yl)carbamate

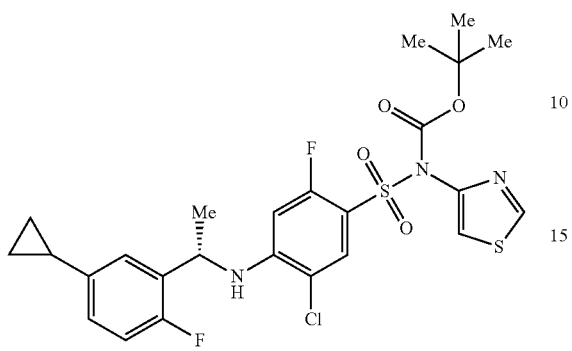

To a solution of tert-butyl (5-chloro-2,4-difluorophenyl)sulfonyl(thiazol-4-yl)carbamate (0.25 g, 0.61 mmol) and (S)-1-(5-cyclopropyl-2-fluorophenyl)ethan-1-amine hydrochloride (0.11 g, 0.51 mmol) in N,N-dimethylformamide (5 mL) was added potassium carbonate (0.25 g, 1.80 mmol). The mixture was stirred at ambient temperature for 12 h. The reaction mixture was quenched by addition of water (50 mL) and then extracted with ethyl acetate (3×80 mL). The combined organic layers were concentrated under reduced pressure. The residue was purified by preparative thin layer chromatography, eluting with 33% of petroleum ether in ethyl acetate, to afford the title compound as a colorless oil (0.12 g, 41% yield): MS (ES+) m/z 470.1 (M−100+1)

Step 6. Preparation of (S)-5-chloro-4-((1-(5-cyclopropyl-2-fluorophenyl)ethyl)amino)-2-fluoro-N-(thiazol-4-yl)benzenesulfonamide

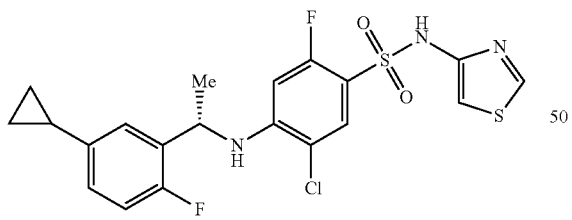

To (S)-tert-butyl(5-chloro-4-((1-(5-cyclopropyl-2-fluorophenyl)ethyl)amino)-2-fluorophenyl)sulfonyl(thiazol-4-yl)carbamate (0.11 g, 0.19 mmol) was added a 4 M solution of hydrogen chloride in 1,4-dioxane (6.6 mL) and the mixture was stirred at ambient temperature for 12 h. The reaction mixture was concentrated under reduced pressure. The obtained residue was purified by preparative reverse phase HPLC, eluting with a gradient of acetonitrile in water (containing 0.05% of ammonium hydroxide), to afford the title compound as a colorless solid (0.043 g, 47% yield): $^1$H NMR (400 MHz, CDCl$_3$) δ 8.59 (s, 1H), 7.73 (d, J=7.2 Hz, 1H), 7.03-6.81 (m, 4H), 6.15 (d, J=12.4 Hz, 1H), 5.20 (d, J=6.0 Hz, 1H), 4.73 (quin, J=6.4 Hz, 1H), 1.89-1.76 (m, 1H), 1.60 (d, J=6.8 Hz, 3H), 0.93 (dd, J=8.4, 1.6 Hz, 2H), 0.65-0.48 (m, 2H), NH not observed; MS (ES+) m/z 470.1 (M+1).

Example 147

Synthesis of 5-chloro-2-fluoro-4-((5-fluoro-2-methylbenzyl)amino)-N-(thiazol-4-yl)benzenesulfonamide

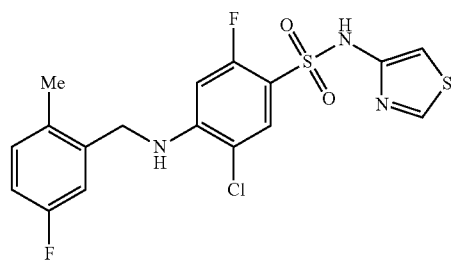 [SMILES: Cc1ccc(F)cc1CNc1cc(F)c(S(=O)(=O)Nc2cscn2)cc1Cl]

Step 1. Preparation of tert-butyl ((5-chloro-2-fluoro-4-((5-fluoro-2-methylbenzyl)amino)phenyl)sulfonyl)(thiazol-4-yl)carbamate

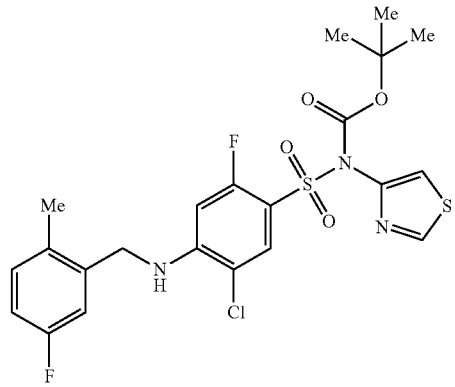 [SMILES: Cc1ccc(F)cc1CNc1cc(F)c(S(=O)(=O)N(C(=O)OC(C)(C)C)c2cscn2)cc1Cl]

Following the procedure as described in Example 146, Step 5 and making non-critical variations to replace (S)-1-(5-cyclopropyl-2-fluorophenyl)ethan-1-amine hydrochloride with (5-fluoro-2-methylphenyl)methanamine, and the title compound was afforded as a colorless solid (0.25 g, 65% yield): $^1$H NMR (400 MHz, CDCl$_3$) δ 8.79 (d, J=2.2 Hz, 1H), 8.04-8.00 (m, 1H), 7.50 (d, J=2.2 Hz, 1H), 7.23-7.18 (m, 1H), 6.97-6.91 (m, 2H), 6.31 (d, J=12.0 Hz, 1H), 5.30 (br s, 1H), 4.39 (d, J=5.6 Hz, 2H), 2.33 (s, 3H), 1.39 (s, 9H); MS (ES+) m/z 530.1 (M+1).

Step 2. Preparation of 5-chloro-2-fluoro-4-((5-fluoro-2-methylbenzyl)amino)-N-(thiazol-4-yl)benzenesulfonamide

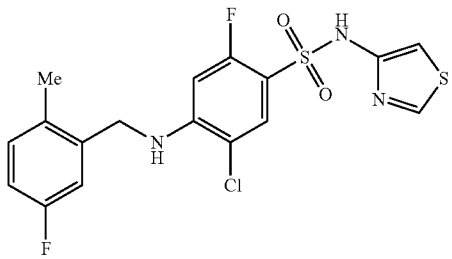 [SMILES: Cc1ccc(F)cc1CNc1cc(F)c(S(=O)(=O)Nc2cscn2)cc1Cl]

Following the procedure as described in Example 5, step 2 and making non-critical variations to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl ((5-chloro-2-fluoro-4-((5-fluoro-2-methylbenzyl)amino)phenyl)sulfonyl)(thiazol-4-yl)carbamate, the title compound was afforded as a colorless solid (0.15 g, 73% yield): $^1$H NMR (400 MHz, CDCl$_3$) δ 9.03 (br s, 1H), 8.64 (d, J=2.2 Hz, 1H), 7.77 (d, J=7.2 Hz, 1H), 7.18 (dd, J=8.0, 5.8 Hz, 1H), 6.99 (d, J=2.2 Hz, 1H), 6.97-6.88 (m, 2H), 6.25 (d, J=12.0 Hz, 1H), 5.14 (br s, 1H), 4.31 (d, J=5.6 Hz, 2H), 2.30 (s, 3H); MS (ES+) m/z 430.0 (M+1).

Example 148

Synthesis of (S)-3-chloro-4-((1-(2-chloro-6-fluorophenyl)ethyl)amino)-2-fluoro-N-(thiazol-4-yl)benzenesulfonamide

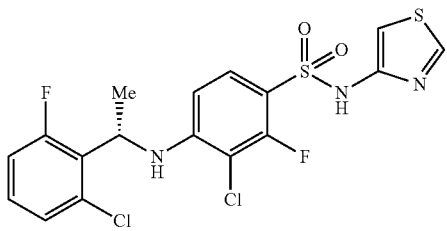 [SMILES: C[C@H](Nc1ccc(S(=O)(=O)Nc2cscn2)c(F)c1Cl)c1c(F)cccc1Cl]

Step 1. Preparation of (R,E)-N-(2-chloro-6-fluorobenzylidene)-2-methylpropane-2-sulfinamide

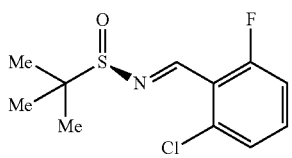 [SMILES: CC(C)(C)[S@@](=O)/N=C/c1c(F)cccc1Cl]

To a solution of 2-chloro-6-fluorobenzaldehyde (10.43 g, 65.8 mmol) and (R)-2-methylpropane-2-sulfinamide (7.97 g, 65.8 mmol) in anhydrous dichloromethane (100 mL) was added cesium carbonate (22.1 g, 67.8 mmol). The mixture was stirred at ambient temperature for 17 h then filtered through a pad of diatomaceous earth. The filter pad was washed with dichloromethane (150 mL). The combined filtrate was concentrated in vacuo to afford the title compound as a light brown oil (17.4 g, quantitative yield): $^1$H NMR (300 MHz, CDCl$_3$) δ 8.89 (s, 1H), 7.42-7.35 (m, 1H), 7.29-7.26 (m, 1H), 7.12-7.06 (m, 1H), 1.28 (s, 9H); MS (ES+) m/z 262.1 (M+1), 264.1 (M+1).

Step 2. Preparation of (R)—N—((S)-1-(2-chloro-6-fluorophenyl)ethyl)-2-methylpropane-2-sulfinamide

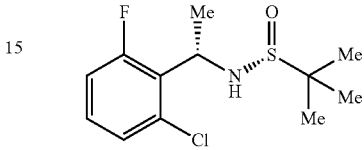

To a cold (−78° C.) solution of (R,E)-N-(2-chloro-6-fluorobenzylidene)-2-methylpropane-2-sulfinamide (5.34 g, 20.4 mmol) in anhydrous dichloromethane (75 mL) was added methylmagnesium bromide (3 M in diethyl ether, 10.0 mL, 30.0 mmol) dropwise over 30 minutes. The reaction mixture was allowed to warm to ambient temperature and stirred for 5 days. The reaction mixture was then quenched with saturated ammonium chloride (5 mL). The reaction mixture was diluted with saturated ammonium chloride (75 mL), brine (75 mL) and extracted with dichloromethane (2×150 mL). The combined organic layers were dried over anhydrous magnesium sulfate, filtered and the filtrate was concentrated in vacuo. The residue was purified by column chromatography, eluting with a 0-70% gradient of ethyl acetate in hexanes, to afford the title compound as a colorless syrup (0.38 g, 7% yield): $^1$H NMR (300 MHz, CDCl$_3$) δ 7.19-7.15 (m, 2H), 7.01-6.94 (m, 1H), 5.21-5.11 (m, 1H), 3.91 (d, J=8.3 Hz, 1H), 1.67 (dd, J=1.0, 7.0 Hz, 3H), 1.14 (s, 9H); MS (ES+) m/z 278.1 (M+1), 280.1 (M+1).

Step 3. Preparation of (S)-1-(2-chloro-6-fluorophenyl)ethan-1-amine hydrochloride

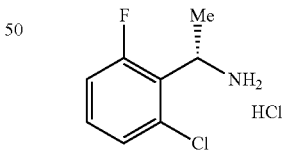

To a solution of (R)—N—((S)-1-(2-chloro-6-fluorophenyl)ethyl)-2-methylpropane-2-sulfinamide (0.90 g, 3.24 mmol) in anhydrous methanol (10 mL) was added a 4 M solution of hydrogen chloride (2.0 mL, 8.0 mmol). The reaction mixture was stirred at ambient temperature for 2 h, and then concentrated in vacuo to afford to title compound as a colorless syrup (1.03 g, quantitative yield): $^1$H NMR (300 MHz, CDCl$_3$) δ 8.88 (br s, 3H), 7.27-7.19 (m, 2H), 7.08-7.02 (m, 1H), 5.10-5.00 (m, 1H), 1.76 (d, J=6.9 Hz, 3H); MS (ES+) m/z 174.1 (M+1), 176.1 (M+1).

Step 4. Preparation of tert-butyl ((3-chloro-2,4-difluorophenyl)sulfonyl)(thiazol-4-yl)carbamate

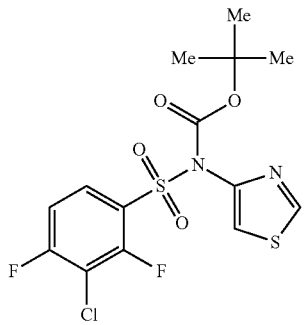 [SMILES: CC(C)(C)OC(=O)N(c1cscn1)S(=O)(=O)c1ccc(F)c(Cl)c1F]

To a solution of tert-butyl N-thiazol-4-ylcarbamate (110 g, 549 mmol) in anhydrous tetrahydrofuran (1000 mL) was added lithium bis(trimethylsilyl)amide (1 M in tetrahydrofuran, 659 mL, 659 mmol) at −78° C. The mixture was warmed to 5° C. before a cooled (−78° C.) solution of 3-chloro-2,4-difluoro-benzenesulfonyl chloride (163 g, 659 mmol) in tetrahydrofuran (300 mL) was added dropwise to it. The reaction mixture was allowed to warm to ambient temperature and stirred for 12 h. After dilution with saturated aqueous ammonium chloride (200 mL), the mixture was extracted with ethyl acetate (3×1000 mL). The combined organic layers were washed with brine (3×1000 mL), dried over anhydrous sodium sulfate, and filtered. Concentration of the filtrate in vacuo and trituration of the residue with methanol (300 mL) afforded the title compound as a colorless solid (75 g, 33% yield) $^1$H NMR (400 MHz, CDCl$_3$) δ 9.14 (s, 1H), 8.26-8.09 (m, 1H), 8.03 (s, 1H), 7.66 (t, J=8.6 Hz, 1H), 1.27 (s, 9H); MS (ES+) m/z 432.8 (M+23), 434.8 (M+23).

Step 5. Preparation of tert-butyl (S)-((3-chloro-4-((1-(2-chloro-6-fluorophenyl)ethyl)amino)-2-fluorophenyl)sulfonyl)(thiazol-4-yl)carbamate

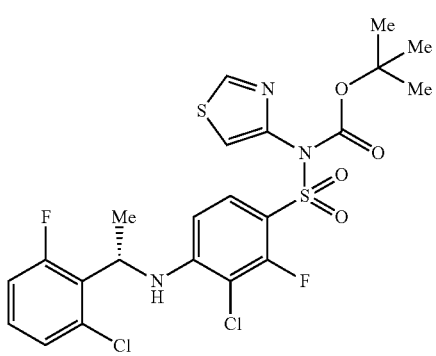 [SMILES: C[C@H](Nc1ccc(S(=O)(=O)N(C(=O)OC(C)(C)C)c2cscn2)c(F)c1Cl)c1c(F)cccc1Cl]

To a solution of (S)-1-(2-chloro-6-fluorophenyl)ethan-1-amine hydrochloride (0.19 g, 0.91 mmol) and tert-butyl ((3-chloro-2,4-difluorophenyl)sulfonyl)(thiazol-4-yl)carbamate (0.26 g, 0.64 mmol) in anhydrous dimethylsulfoxide (5 mL) was added N,N-diisopropylethylamine (0.56 mL, 3.2 mmol). The solution was stirred at ambient temperature for 18 h, and then quenched with saturated ammonium chloride (15 mL). The reaction mixture was diluted with brine (100 mL) and extracted with ethyl acetate (2×100 mL). The combined organic layers were dried over anhydrous magnesium sulfate, filtered and the filtrate concentrated in vacuo. The residue was purified by column chromatography, eluting with a 0-30% gradient of ethyl acetate in hexanes, to afford the title compound as a colorless solid (0.11 g, 32% yield): $^1$H NMR (300 MHz, CDCl$_3$) δ 8.80 (d, J=2.3 Hz, 1H), 7.77 (dd, J=9.0, 7.7 Hz, 1H), 7.52 (dd, J=2.2, 0.3 Hz, 1H), 7.22-7.18 (m, 2H), 7.02-6.96 (m, 1H), 6.49 (dd, J=9.2, 1.1 Hz, 1H), 5.67 (d, J=8.9 Hz, 1H), 5.36-5.26 (m, 1H), 1.76 (d, J=6.9 Hz, 3H), 1.29 (s, 9H); MS (ES+) m/z 564.1 (M+1), 566.1 (M+1).

Step 6. Preparation of (S)-3-chloro-4-((1-(2-chloro-6-fluorophenyl)ethyl)amino)-2-fluoro-N-(thiazol-4-yl)benzenesulfonamide

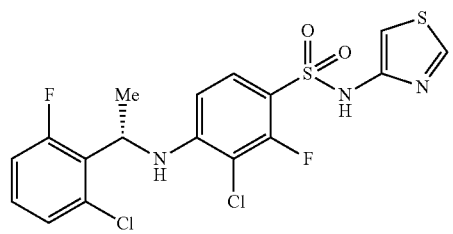 [SMILES: C[C@H](Nc1ccc(S(=O)(=O)Nc2cscn2)c(F)c1Cl)c1c(F)cccc1Cl]

To a solution of tert-butyl (S)-((3-chloro-4-((1-(2-chloro-6-fluorophenyl)ethyl)amino)-2-fluorophenyl)sulfonyl)(thiazol-4-yl)carbamate (0.11 g, 0.20 mmol) in dichloromethane (5 mL) was added trifluoroacetic acid (2 mL). The reaction mixture was stirred at ambient temperature for 1 h, and then concentrated in vacuo. The residue was purified by column chromatography, eluting with a 0-30% gradient of ethyl acetate (containing 0.1% formic acid) in hexanes, to afford the title compound as a colorless solid (0.047 g, 50% yield): $^1$H NMR (300 MHz, DMSO-d$_6$) δ 11.16 (s, 1H), 8.85 (d, J=2.2 Hz, 1H), 7.51 (t, J=8.5 Hz, 1H), 7.36-7.31 (m, 2H), 7.23-7.16 (m, 1H), 6.95 (d, J=2.2 Hz, 1H), 6.37-6.31 (m, 2H), 5.23-5.13 (m, 1H), 1.65 (d, J=6.9 Hz, 3H); MS (ES+) m/z 464.1 (M+1), 466.1 (M+1).

Example 149

Synthesis of (S)-3-chloro-4-((1-(2,6-difluorophenyl)ethyl)amino)-2-fluoro-N-(thiazol-4-yl)benzenesulfonamide

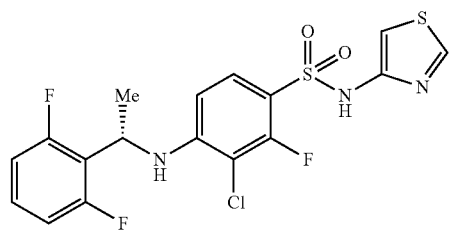

Step 1. Preparation of (R,E)-N-(2,6-difluorobenzylidene)-2-methylpropane-2-sulfinamide

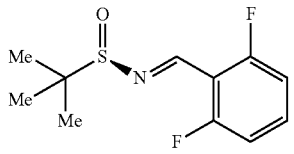 [SMILES: CC(C)(C)[S@@](=O)/N=C/c1c(F)cccc1F]

Following the procedure as described in Example 148, Step 1 and making non-critical variations as required to replace 2-chloro-6-fluorobenzaldehyde with 2,6-difluorobenzaldehyde, the title compound was obtained as alight yellow oil (19.2 g, quantitative yield): ¹H NMR (300 MHz, CDCl₃) δ 8.81 (s, 1H), 7.50-7.41 (m, 1H), 7.03-6.95 (m, 2H), 1.27 (s, 9H); MS (ES+) m/z 246.1 (M+1).

Step 2. Preparation of (R)—N—((S)-1-(2,6-difluorophenyl)ethyl)-2-methylpropane-2-sulfinamide

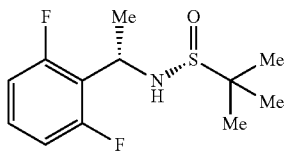 [SMILES: C[C@H](N[S@](=O)C(C)(C)C)c1c(F)cccc1F]

Following the procedure as described in Example 148, Step 2 and making non-critical variations as required to replace (R,E)-N-(2-chloro-6-fluorobenzylidene)-2-methylpropane-2-sulfinamide with (R,E)-N-(2,6-difluorobenzylidene)-2-methylpropane-2-sulfinamide, the title compound was obtained as a colorless syrup (0.68 g, 13% yield): ¹H NMR (300 MHz, CDCl₃) δ 7.24-7.16 (m, 1H), 6.90-6.84 (m, 2H), 5.03-4.93 (m, 1H), 3.75 (d, J=8.0 Hz, 1H), 1.67 (d, J=6.9 Hz, 3H), 1.15 (s, 9H); MS (ES+) m/z 262.2 (M+1).

Step 3. Preparation of (S)-1-(2,6-difluorophenyl)ethan-1-amine hydrochloride

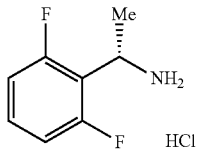

Following the procedure as described in Example 148, Step 3 and making non-critical variations as required to replace (R)—N—((S)-1-(2-chloro-6-fluorophenyl)ethyl)-2-methylpropane-2-sulfinamide with (R)—N—((S)-1-(2,6-difluorophenyl)ethyl)-2-methylpropane-2-sulfinamide, the title compound was obtained as a colorless solid (0.73 g, quantitative yield): ¹H NMR (300 MHz, CDCl₃) δ 8.83 (br s, 3H), 7.34-7.24 (m, 1H), 6.97-6.86 (m, 2H), 4.88-4.84 (m, 1H), 1.74 (d, J=6.9 Hz, 3H); MS (ES+) m/z 158.1 (M+1).

Step 4. Preparation of tert-butyl (S)-((3-chloro-4-((1-(2,6-difluorophenyl)ethyl)amino)-2-fluorophenyl)sulfonyl)(thiazol-4-yl)carbamate

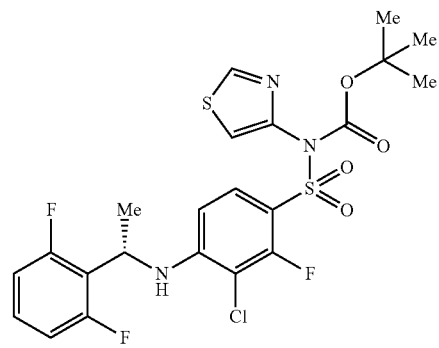

Following the procedure as described in EXAMPLE 148, Step 5 and making non-critical variations as required to replace (S)-1-(2-chloro-6-fluorophenyl)ethan-1-amine hydrochloride with (S)-1-(2,6-difluorophenyl)ethan-1-amine hydrochloride, the title compound was obtained as a light yellow syrup (0.10 g, 37% yield): ¹H NMR (300 MHz, CDCl₃) δ 8.80 (d, J=2.3 Hz, 1H), 7.79 (dd, J=9.0, 7.7 Hz, 1H), 7.51 (dd, J=2.3, 0.7 Hz, 1H), 7.26-7.20 (m, 1H), 6.93-6.87 (m, 2H), 6.53 (dd, J=9.2, 1.2 Hz, 1H), 5.54 (d, J=8.8 Hz, 1H), 5.20-5.10 (m, 1H), 1.76 (d, J=6.9 Hz, 3H), 1.30 (s, 9H); MS (ES+) m/z 548.2 (M+1), 550.2 (M+1).

Step 5. Preparation of (S)-3-chloro-4-((1-(2,6-difluorophenyl)ethyl)amino)-2-fluoro-N-(thiazol-4-yl)benzenesulfonamide

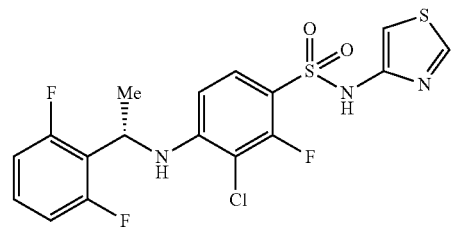

Following the procedure as described in EXAMPLE 148, Step 6 and making non-critical variations as required to replace tert-butyl (S)-((3-chloro-4-((1-(2-chloro-6-fluorophenyl)ethyl)amino)-2-fluorophenyl)sulfonyl)(thiazol-4-yl)carbamate with tert-butyl (S)-((3-chloro-4-((1-(2,6-difluorophenyl)ethyl)amino)-2-fluorophenyl)sulfonyl)(thiazol-4-yl)carbamate, the title compound was obtained as a colorless solid (0.045 g, 56% yield): ¹H NMR (300 MHz, DMSO-d₆) δ 11.15 (s, 1H), 8.85 (d, J=2.2 Hz, 1H), 7.52 (t, J=8.5 Hz, 1H), 7.41-7.31 (m, 1H), 7.11-7.05 (m, 2H), 6.95 (d, J=2.2 Hz, 1H), 6.46 (d, J=8.3 Hz, 1H), 6.28 (d, J=7.8 Hz, 1H), 5.14-5.04 (m, 1H), 1.65 (d, J=6.9 Hz, 3H); MS (ES+) m/z 448.0 (M+1), 450.0 (M+1).

Example 150

Synthesis of 4-((2-(azetidin-1-ylmethyl)-3,6-difluorobenzyl)oxy)-5-chloro-2-fluoro-N-(thiazol-4-yl)benzenesulfonamide

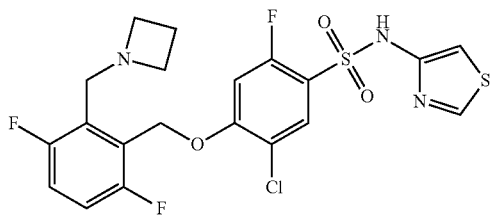 [SMILES: O=S(=O)(Nc1cscn1)c1cc(Cl)c(OCc2c(F)ccc(F)c2CN2CCC2)cc1F]

Step 1. Preparation of tert-butyl ((4-((2-(azetidin-1-ylmethyl)-3,6-difluorobenzyl)oxy)-5-chloro-2-fluorophenyl)sulfonyl)(thiazol-4-yl)carbamate

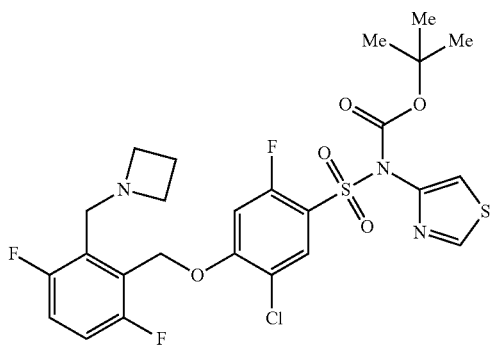 [SMILES: CC(C)(C)OC(=O)N(c1cscn1)S(=O)(=O)c1cc(Cl)c(OCc2c(F)ccc(F)c2CN2CCC2)cc1F]

To a solution of (2-(azetidin-1-ylmethyl)-3,6-difluorophenyl)methanol (0.39 g, 0.94 mmol) in anhydrous N,N-dimethylformamide (3 mL) was added tert-butyl ((5-chloro-2,4-difluorophenyl)sulfonyl)(thiazol-4-yl)carbamate (0.30 g, 1.41 mmol) and sodium hydride (60% dispersion in mineral oil, 0.075 g, 1.88 mmol). The solution was stirred at ambient temperature for 16 h, and then purified by column chromatography, eluting with a gradient from 10 to 60% of ethyl acetate in hexanes, to provide the title compound as yellow syrup (yield not determined): MS (ES+) m/z 604.3 (M+1), 606.3 (M+1).

Step 2. Preparation of 4-((2-(azetidin-1-ylmethyl)-3,6-difluorobenzyl)oxy)-5-chloro-2-fluoro-N-(thiazol-4-yl)benzenesulfonamide

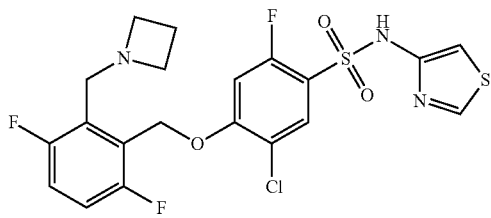 [SMILES: O=S(=O)(Nc1cscn1)c1cc(Cl)c(OCc2c(F)ccc(F)c2CN2CCC2)cc1F]

To a solution of tert-butyl ((4-((2-(azetidin-1-ylmethyl)-3,6-difluorobenzyl)oxy)-5-chloro-2-fluorophenyl)sulfonyl)(thiazol-4-yl)carbamate in dichloromethane (2 mL) was added trifluoroacetic acid (0.70 mL) and the resulting solution was stirred for 16 h. The reaction mixture was concentrated in vacuo, triturated with methano (3 mL), and filtered. Concentration of the filtrate in vacuo and purification of the residue by reverse-phase HPLC, using a gradient of acetonitrile in water containing 0.5% formic acid, afforded the title compound as a colorless solid (0.004 g, 1% yield over two steps): $^1$H-NMR (300 MHz, DMSO-d$_6$) δ 11.46-11.44 (m, 1H), 8.92 (d, J=2.2 Hz, 1H), 7.85 (d, J=7.4 Hz, 1H), 7.61-7.54 (m, 3H), 7.11 (d, J=2.2 Hz, 1H), 5.40 (s, 2H), 4.57-4.56 (m, 2H), 4.14-4.01 (m, 4H), 2.38-2.21 (m, 2H); MS (ES+) m/z 504.2, 506.2 (M+1).

Example 151

Synthesis of 2,6-difluoro-4-((2-fluoro-6-((4-methylpiperazin-1-yl)methyl)-benzyl)amino)-N-(thiazol-4-yl)benzenesulfonamide formate

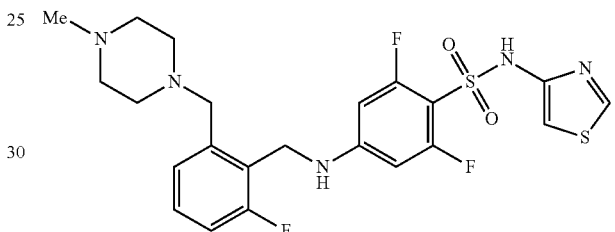

Step 1. Preparation of tert-butyl thiazol-4-yl((2,4,6-trifluorophenyl)-sulfonyl)carbamate

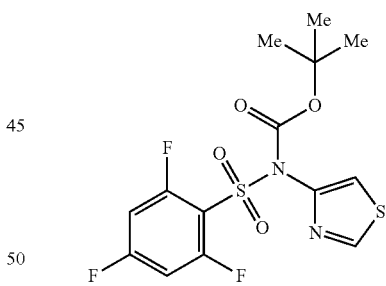

To a solution of tert-butyl thiazol-4-ylcarbamate (140.0 g, 699.1 mmol) in anhydrous tetrahydrofuran (700 mL) was added a 1 M solution of lithium bis(trimethylsilyl)amide in tetrahydrofuran (758.9 mL, 758.0 mmol) at −78° C. The reaction mixture was allowed to warm to 0° C. and stirred for 20 minutes. After cooling the reaction mixture to −78° C., a solution of 2,4,6-trifluorobenzenesulfonyl chloride (175.0 g, 758.9 mmol) in anhydrous tetrahydrofuran (200 mL) was added slowly to it. The reaction mixture was allowed to warm to ambient temperature, stirred for 12 h, and then quenched by addition of saturated ammonium chloride (200 mL). The mixture was extracted with ethyl acetate (3×1000 mL). The organic phase was washed with brine (3×1000 mL), dried over anhydrous sodium sulfate, and filtered. Concentration in vacuo and trituration of the residue in methanol (100 mL) provided the title compound as a colorless solid (140.0 g, 58% yield): $^1$H NMR (400 MHz, CDCl$_3$) δ 8.81 (d, J=2.1 Hz, 1H), 7.53 (d, J=2.1 Hz, 1H), 6.85 (br t, J=8.4 Hz, 2H), 1.39 (s, 9H); MS (ES+) m/z 417.0 (M+23).

Step 2. Preparation of tert-butyl ((4-azido-2,6-difluorophenyl)sulfonyl)(thiazol-4-yl)carbamate

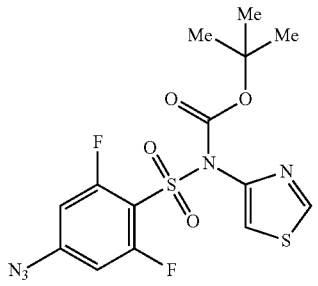 [SMILES: CC(C)(C)OC(=O)N(c1cscn1)S(=O)(=O)c1c(F)cc(N=[N+]=[N-])cc1F]

To a solution of tert-butyl thiazol-4-yl((2,4,6-trifluorophenyl)sulfonyl)carbamate (10.0 g, 25.3 mmol) in anhydrous N,N-dimethylformamide (200 mL) was added sodium azide (1.81 g, 27.9 mmol) in small portions at 0° C. The reaction mixture was allowed to warm to ambient temperature, stirred for 3 h, and then poured into water (300 mL). The precipitate was collected by filtration to afford the title compound as a colorless solid (15.0 g, quantitative yield): $^1$H NMR (400 MHz, CDCl$_3$) δ 8.72 (d, J=2.2 Hz, 1H), 7.44 (d, J=2.2 Hz, 1H), 6.68-6.62 (m, 2H), 1.31 (s, 9H).

Step 3. Preparation of tert-butyl ((4-amino-2,6-difluorophenyl)sulfonyl)-(thiazol-4-yl)carbamate

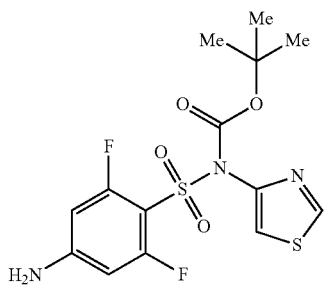 [SMILES: CC(C)(C)OC(=O)N(c1cscn1)S(=O)(=O)c1c(F)cc(N)cc1F]

To a mixture of tert-butyl (4-azido-2,6-difluorophenyl)sulfonyl(thiazol-4-yl)carbamate (10.0 g, 23.9 mmol) in tetrahydrofuran (180 mL) and saturated ammonium chloride (50 mL) was added zinc powder (4.7 g, 71.8 mmol) at 0° C. The reaction mixture was allowed to warm to ambient temperature and stirred for 12 h. The mixture was filtered through a pad of celite and the filtrate diluted with ethyl acetate (200 mL). The organic layer was washed with brine (3×100 mL), dried over anhydrous sodium sulfate, and filtered. Concentration of the filtrate in vacuo afforded the title compound as a colorless solid (9.0 g, 96% yield): $^1$H NMR (400 MHz, DMSO-d$_6$) δ 9.12 (d, J=2.2 Hz, 1H), 7.81 (d, J=2.2 Hz, 1H), 6.93 (s, 2H), 6.36 (d, J=12.4 Hz, 2H), 1.35 (s, 9H); MS (ES+) m/z 291.5 (M−100).

Step 4. Preparation of tert-butyl ((4-((tert-butoxycarbonyl)amino)-2,6-difluorophenyl)sulfonyl)(thiazol-4-yl)carbamate

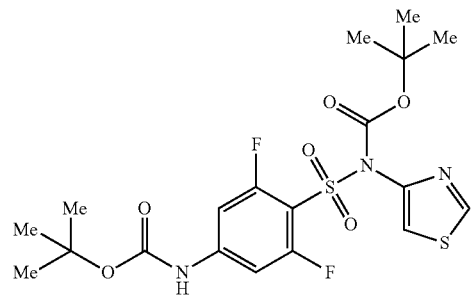 [SMILES: CC(C)(C)OC(=O)Nc1cc(F)c(S(=O)(=O)N(C(=O)OC(C)(C)C)c2cscn2)c(F)c1]

To a mixture of tert-butyl N-(4-amino-2,6-difluoro-phenyl)sulfonyl-N-thiazol-4-yl-carbamate (11.5 g, 29.3 mmol) and di-tert-butyl dicarbonate (7.7 g, 35.3 mmol) in dichloromethane (100 mL) was added 4-(dimethylamino)pyridine (0.717 mg, 5.88 mmol) and triethylamine (5.95 g, 58.7 mmol) and the mixture was stirred at ambient temperature for 12 h. Concentration in vacuo and purification of the residue by column chromatography, eluting with 30% of ethyl acetate in petroleum ether, provided the title compound as a colorless solid (7.30 g, 50% yield): $^1$H NMR (400 MHz, CDCl$_3$) δ 8.79 (d, J=2.2 Hz, 1H), 7.50 (d, J=2.2 Hz, 1H), 7.28 (s, 1H), 7.19-7.14 (m, 2H), 1.51 (s, 9H), 1.38 (s, 9H); MS (ES+) m/z 392.0 (M−99).

Step 5. Preparation of tert-butyl ((4-((2-bromo-6-fluorobenzyl)(tert-butoxycarbonyl)amino)-2,6-difluorophenyl)sulfonyl)(thiazol-4-yl)carbamate

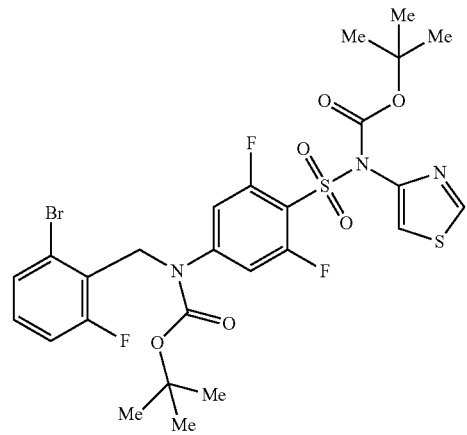 [SMILES: CC(C)(C)OC(=O)N(Cc1c(F)cccc1Br)c1cc(F)c(S(=O)(=O)N(C(=O)OC(C)(C)C)c2cscn2)c(F)c1]

To a mixture of tert-butyl(4-((tert-butoxycarbonyl) amino)-2,6-difluorophenyl)-sulfonyl(thiazol-4-yl) carbamate (7.30 g, 14.8 mmol) and 1-bromo-2-(chloromethyl)-3-fluorobenzene (6.64 g, 29.7 mmol) in anhydrous N,N-dimethylformamide (100 mL) was added potassium carbonate (8.21 g, 59.4 mmol), and the mixture was stirred at ambient temperature for 12 h. Water (100 mL) was added, and the mixture was extracted with ethyl acetate (3×100 mL). The combined organic phase was washed with brine (3×50 mL), dried over anhydrous sodium sulfate, and filtered. Concentration in vacuo and purification of the residue by column chromatography, eluting with 6% of ethyl acetate in hexanes, provided the title compound as a colorless solid (7.0 g, 69% yield): $^1$H NMR (400 MHz, CDCl$_3$) δ 8.80 (d, J=2.2 Hz, 1H), 7.50 (d, J=2.2 Hz, 1H), 7.32 (d, J=8.0 Hz, 1H), 7.11 (dt, J=6.0, 8.2 Hz, 1H), 7.03-6.94 (m, 3H), 5.18 (s, 2H), 1.50 (s, 9H), 1.32 (s, 9H); MS (ES+) m/z 521.9 (M−155), 523.9 (M−155).

Step 6. Preparation of tert-butyl ((4-((tert-butoxycarbonyl)(2-fluoro-6-formylbenzyl)amino)-2,6-difluorophenyl)sulfonyl)(thiazol-4-yl)carbamate

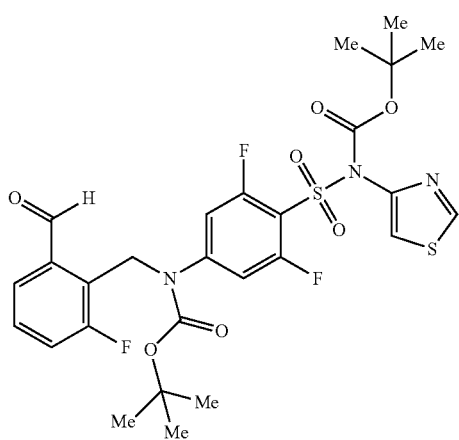 [SMILES: CC(C)(C)OC(=O)N(Cc1c(F)cccc1C=O)c1cc(F)c(S(=O)(=O)N(C(=O)OC(C)(C)C)c2cscn2)c(F)c1]

To a mixture of tert-butyl ((4-((2-bromo-6-fluorobenzyl)(tert-butoxycarbonyl)amino)-2,6-difluorophenyl)sulfonyl)(thiazol-4-yl)carbamate (3.50 g, 5.16 mmol), tert-butyl isocyanide (0.643 g, 7.74 mmol), palladium(II) acetate (0.115 g, 0.516 mmol), sodium carbonate (0.546 g, 5.16 mmol), and 2-(di-tert-butylphosphino)biphenyl (0.307 g, 1.03 mmol) in anhydrous N,N-dimethylformamide (30 mL) was added triethylsilane (1.80 g, 15.48 mmol). The reaction mixture was degassed with nitrogen and then heated to 65° C. for 12 h. Water (30 mL) was added and the mixture was extracted with ethyl acetate (3×30 mL). The combined organic phase was washed with brine (3×30 mL), dried over anhydrous sodium sulfate, and filtered. Concentration in vacuo and purification of the residue by column chromatography, eluting with 30% of ethyl acetate in petroleum ether, afforded the title compound as a yellow solid (1.00 g, 30% yield): $^1$H NMR (400 MHz, CDCl$_3$) δ 10.13 (s, 1H), 8.72 (d, J=1.0 Hz, 1H), 7.55 (d, J=7.4 Hz, 1H), 7.43 (s, 1H), 7.41-7.35 (m, 1H), 7.22-7.15 (m, 1H), 6.88 (d, J=10.8 Hz, 2H), 5.43 (s, 2H), 1.40 (s, 9H), 1.25 (s, 9H); $^{19}$F NMR (376.5 MHz, CDCl$_3$) δ−105.0 (s, 2F), −115.6 (s, 1F); MS (ES+) m/z 471.9 (M−155).

Step 7. Preparation of tert-butyl (4-(N-(tert-butoxycarbonyl)-N-(thiazol-4-yl)sulfamoyl)-3,5-difluorophenyl)(2-fluoro-6-((4-methylpiperazin-1-yl)methyl)benzyl)carbamate

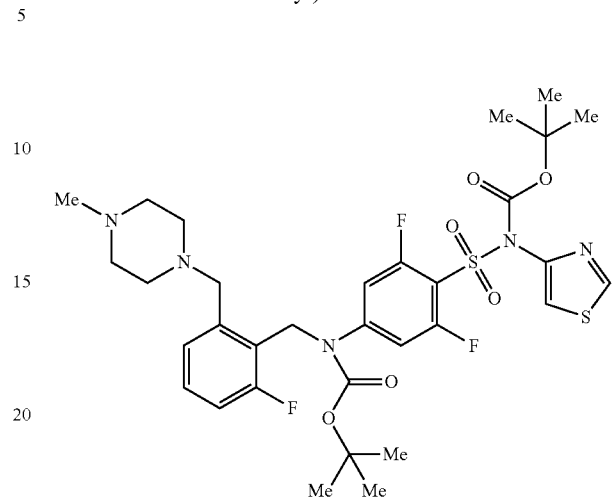

To a mixture of tert-butyl ((4-((tert-butoxycarbonyl)(2-fluoro-6-formylbenzyl)amino)-2,6-difluorophenyl)sulfonyl)(thiazol-4-yl)carbamate (0.10 g, 0.159 mmol), 1-methylpiperazine (0.015 g, 0.159 mmol) and acetic acid (0.009 g, 0.159 mmol) in methanol (1 mL) was added sodium cyanoborohydride (0.020 g, 0.318 mmol). The reaction mixture was stirred at ambient temperature for 1 h, and the concentrated in vacuo. Water (5 mL) was added to the residue, and the mixture was extracted with ethyl acetate (3×10 mL). The combined organic phase was washed with brine (20 mL), dried over sodium sulfate, and filtered. Concentration in vacuo and purification of the residue by preparative thin layer chromatography, eluting with 50% of ethyl acetate in petroleum ether, provided the title compound as a yellow oil (0.050 g, 44% yield): MS (ES+) m/z 712.2 (M+1).

Step 8. Preparation of 2,6-difluoro-4-((2-fluoro-6-((4-methylpiperazin-1-yl)methyl)benzyl)amino)-N-(thiazol-4-yl)benzenesulfonamide formate

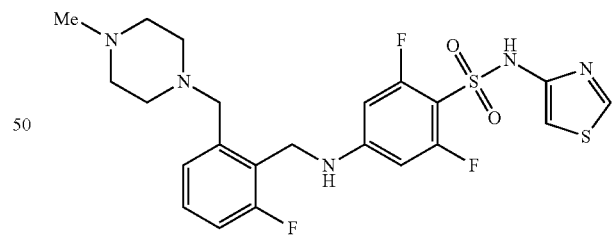

To a mixture of tert-butyl (4-(N-(tert-butoxycarbonyl)-N-(thiazol-4-yl)sulfamoyl)-3,5-difluorophenyl)(2-fluoro-6-((4-methylpiperazin-1-yl)methyl)benzyl)carbamate (0.040 g, 0.056 mmol) in dichloromethane (2 mL) was added trifluoroacetic acid (0.83 mL) and the reaction mixture was stirred at ambient temperature for 12 h. Concentration in vacuo and purification of the residue by preparative reverse phase HPLC, using acetonitrile in water containing 0.225% formic acid as eluent, afforded the title compound as a colorless solid (0.011 g, 36% yield): $^1$H NMR (400 MHz, CD$_3$OD) δ 8.76 (d, J=2.2 Hz, 1H), 8.49 (s, 1H), 7.34 (dt, J=5.8, 7.8 Hz, 1H), 7.21-7.09 (m, 2H), 6.98 (d, J=2.2 Hz, 1H), 6.34-6.28 (m, 2H), 4.45 (s, 2H), 3.64 (s, 2H), 2.86 (s, 4H), 2.59 (s, 7H), NH and COOH not observed; $^{19}$F NMR (376.5 MHz, CD$_3$OD) δ −109.6 (br s, 2F), 119.3 (s, 1F); MS (ES+) m/z 512.0 (M+1).

Example 152

Synthesis of 4-((2-((3-ethoxy-3-methylazetidin-1-yl)methyl)-6-fluorobenzyl)amino)-2,6-difluoro-N-(thiazol-4-yl)benzenesulfonamide formate

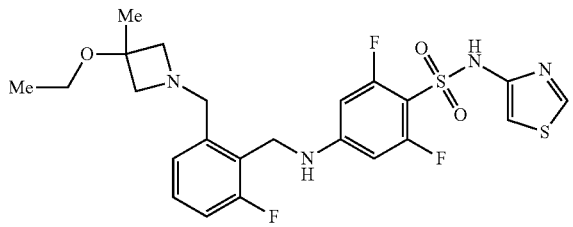 [SMILES: CCOC1(C)CN(Cc2cccc(F)c2CNc2cc(F)c(S(=O)(=O)Nc3cscn3)c(F)c2)C1]

Step 1. Preparation of 2-fluoro-6-((3-hydroxy-3-methylazetidin-1-yl)methyl)benzonitrile

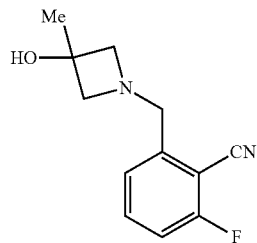 [SMILES: CC1(O)CN(Cc2cccc(F)c2C#N)C1]

To a mixture of 3-methylazetidin-3-ol hydrochloride (1.40 g, 11.33 mmol) and 2-(bromomethyl)-6-fluoro-benzonitrile (1.21 g, 5.67 mmol) in dichloromethane (20 mL) was added triethylamine (2.29 g, 22.6 mmol) and the reaction mixture was stirred at ambient temperature for 12 h. Concentration in vacuo and purification of the residue by column chromatography, eluting with 50% of ethyl acetate in petroleum ether, provided the title compound as a colorless solid (0.90 g, 72% yield): $^1$H NMR (400 MHz, CDCl$_3$) δ 7.55 (dt, J=5.6, 8.2 Hz, 1H), 7.32 (d, J=7.6 Hz, 1H), 7.10 (t, J=8.6 Hz, 1H), 3.85 (s, 2H), 3.43-3.31 (m, 2H), 3.15 (d, J=8.2 Hz, 2H), 2.28 (br s, 1H), 1.52 (s, 3H).

Step 2. Preparation of 2-((3-ethoxy-3-methylazetidin-1-yl)methyl)-6-fluorobenzonitrile

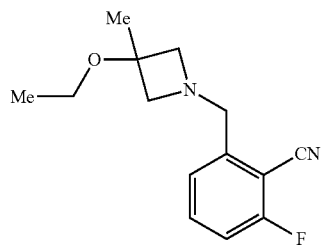 [SMILES: CCOC1(C)CN(Cc2cccc(F)c2C#N)C1]

To a solution of 2-fluoro-6-((3-hydroxy-3-methylazetidin-1-yl)methyl)benzonitrile (0.200 g, 0.908 mmol) in anhydrous N,N-dimethylformamide (5 mL) was added a 60% dispersion of sodium hydride in mineral oil (0.072 g, 1.82 mmol) at 0° C. The reaction mixture was stirred at 0° C. for 1 h, and then iodoethane (0.283 g, 1.82 mmol) was added to it. The reaction mixture was allowed to warm to ambient temperature and stirred 11 h. Water (10 mL) was added, and the mixture was extracted with ethyl acetate (3×10 mL). The combined organic phase was washed with brine (3×10 mL), dried over anhydrous sodium sulfate, and filtered. Concentration of the filtrate in vacuo and purification of the residue by preparative thin layer chromatography, eluting with 50% of ethyl acetate in petroleum ether, provided the title compound as a yellow oil (0.100 g, 44% yield): $^1$H NMR (400 MHz, CDCl$_3$) δ 7.55 (dt, J=5.6, 8.2 Hz, 1H), 7.34 (d, J=7.8 Hz, 1H), 7.10 (t, J=8.4 Hz, 1H), 3.88 (s, 2H), 3.40 (q, J=7.0 Hz, 2H), 3.35-3.28 (m, 2H), 3.17 (d, J=7.6 Hz, 2H), 1.53 (s, 3H), 1.22 (t, J=7.0 Hz, 3H).

Step 3. Preparation of (2-((3-ethoxy-3-methylazetidin-1-yl)methyl)-6-fluorophenyl)methanamine

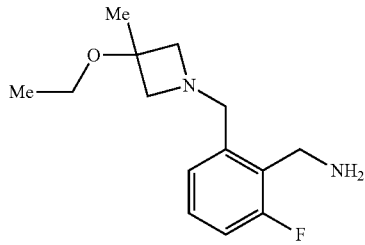 [SMILES: CCOC1(C)CN(Cc2cccc(F)c2CN)C1]

To a solution of 2-((3-ethoxy-3-methylazetidin-1-yl)methyl)-6-fluorobenzonitrile (0.100 g, 0.402 mmol) in methanol (20 mL) and ammonium hydroxide (5 mL) was added Raney-Ni (0.100 g). The suspension was degassed under vacuum and purged with hydrogen several times. The reaction mixture was stirred under an atmosphere of hydrogen (50 psi) at ambient temperature for 12 h. Filtration and concentration of the filtrate in vacuo afforded the title compound as yellow oil (0.100 g, 98% yield): $^1$H NMR (400 MHz, CDCl$_3$) δ 7.38-7.30 (m, 1H), 7.21-7.10 (m, 2H), 6.2 (br s, 2H), 4.39 (s, 2H), 4.15 (s, 2H), 3.61 (d, J=8.4 Hz, 2H), 3.45 (d, J=7.8 Hz, 2H), 3.38 (q, J=6.8 Hz, 2H), 1.50 (s, 3H), 1.21 (br t, J=6.8 Hz, 3H); MS (ES+) m/z 253.3 (M+1).

Step 4. Preparation of tert-butyl ((4-((2-((3-ethoxy-3-methylazetidin-1-yl)methyl)-6-fluorobenzyl)amino)-2,6-difluorophenyl)sulfonyl)(thiazol-4-yl)carbamate

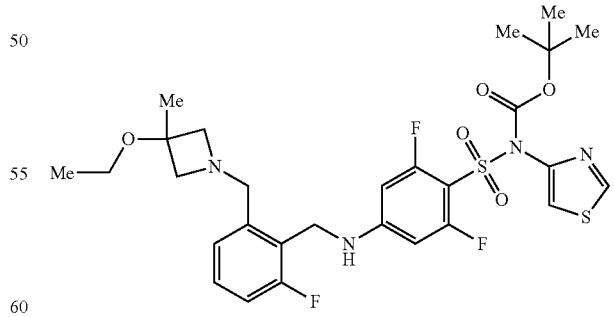

To a mixture of tert-butyl thiazol-4-yl((2,4,6-trifluorophenyl)-sulfonyl)carbamate (0.156 g, 0.396 mmol) and (2-((3-ethoxy-3-methylazetidin-1-yl)methyl)-6-fluorophenyl)methanamine (0.100 g, 0.396 mmol) in anhydrous N,N-dimethylformamide (5 mL) was added potassium carbonate (0.109 g, 0.792 mmol). The reaction mixture was heated to 30° C. for 12 h. Water (10 mL) was added, and the mixture was extracted with ethyl acetate (3×10 mL). The combined organic phase was washed with brine (3×10 mL), dried over anhydrous sodium sulfate, and filtered. Concentration of the filtrate in vacuo and purification of the residue by preparative reverse phase HPLC, using acetonitrile in water containing 0.05% of ammonium hydroxide, afforded the title compound as a colorless solid (0.050 g, 20% yield): $^1$H NMR (400 MHz, CDCl$_3$) δ 8.81 (d, J=2.2 Hz, 1H), 7.89 (br s, 1H), 7.52 (d, J=2.2 Hz, 1H), 7.25 (dd, J=5.8, 8.0 Hz, 1H), 7.11-7.05 (m, 2H), 6.33 (d, J=12.0 Hz, 2H), 4.40 (br d, J=4.2 Hz, 2H), 3.72 (s, 2H), 3.49-3.37 (m, 2H), 3.25-3.21 (m, 2H), 3.16-3.11 (m, 2H), 1.51 (s, 3H), 1.41 (s, 9H), 1.26 (t, J=7.0 Hz, 3H); MS (ES+) m/z 627.3 (M+1).

Step 5. Preparation of 4-((2-((3-ethoxy-3-methyl-azetidin-1-yl)methyl)-6-fluorobenzyl)amino)-2,6-difluoro-N-(thiazol-4-yl)benzenesulfonamide

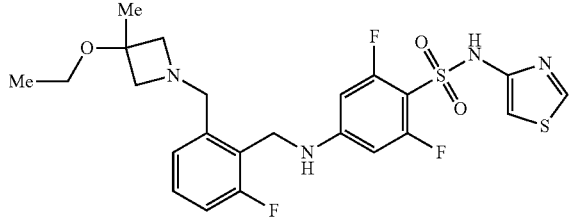 [SMILES: CCOC1(C)CN(Cc2cccc(F)c2CNc2cc(F)c(S(=O)(=O)Nc3cscn3)c(F)c2)C1]

To a solution of tert-butyl ((4-((2-((3-ethoxy-3-methyl-azetidin-1-yl)methyl)-6-fluorobenzyl)amino)-2,6-difluoro-phenyl)sulfonyl)(thiazol-4-yl)carbamate (0.050 g, 0.079 mmol) in dichloromethane (5 mL) was added trifluoroacetic acid (0.770 g, 6.75 mmol) and the reaction mixture was stirred at ambient temperature for 1 h. Concentration in vacuo and purification of the residue by preparative reverse phase HPLC, using acetonitrile in water containing 0.255% of formic acid, provided the title compound as a colorless solid (0.034 g, 71% yield): $^1$H NMR (400 MHz, CD$_3$OD) δ 8.75 (d, J=2.2 Hz, 1H), 8.38 (br s, 0.6H), 7.41-7.32 (m, 1H), 7.21 (d, J=7.6 Hz, 1H), 7.14 (t, J=9.0 Hz, 1H), 6.98 (d, J=2.2 Hz, 1H), 6.37-6.29 (m, 2H), 4.40 (d, J=1.0 Hz, 2H), 3.94 (br s, 2H), 3.47-3.37 (m, 6H), 1.46 (s, 3H), 1.18 (t, J=7.0 Hz, 3H), NH and COOH not observed; $^{19}$F NMR (376 MHz, CD$_3$OD) δ−109.6 (s, 2F), −118.6 (s, 1F); MS (ES+) m/z 527.2 (M+1).

Examples 153-182

In a similar manner as described in EXAMPLE 151, utilizing the appropriately substituted starting materials and intermediates, the following compounds were prepared:

| Example No | Name | MS (ES+) m/z |
|---|---|---|
| 153 | 4-((2-((2-oxa-6-azaspiro[3.3]heptan-6-yl)methyl)-6-fluorobenzyl)amino)-2,6-difluoro-N-(thiazol-4-yl)benzenesulfonamide formate | 510.1 (M + 1) |
| 154 | (R)-2,6-difluoro-4-((2-fluoro-6-((2-(methoxymethyl)pyrrolidin-1-yl)methyl)benzyl)amino)-N-(thiazol-4-yl)benzenesulfonamide formate | 527.1 (M + 1) |
| 155 | 4-((2-((1-oxa-6-azaspiro[3.4]octan-6-yl)methyl)-6-fluorobenzyl)amino)-2,6-difluoro-N-(thiazol-4-yl)benzenesulfonamide formate | 525.1 (M + 1) |
| 156 | 4-((2-((1-oxa-6-azaspiro[3.3]heptan-6-yl)methyl)-6-fluorobenzyl)amino)-2,6-difluoro-N-(thiazol-4-yl)benzenesulfonamide formate | 511.1 (M + 1) |
| 157 | 4-((2-((6-oxa-1-azaspiro[3.3]heptan-1-yl)methyl)-6-fluorobenzyl)amino)-2,6-difluoro-N-(thiazol-4-yl)benzenesulfonamide formate | 511.2 (M + 1) |
| 158 | (S)-2,6-difluoro-4-((2-fluoro-6-((2-methylpyrrolidin-1-yl)methyl)benzyl)amino)-N-(thiazol-4-yl)benzenesulfonamide formate | 497.1 (M + 1) |
| 159 | 4-((2-((6-azaspiro[3.4]octan-6-yl)methyl)-6-fluorobenzyl)amino)-2,6-difluoro-N-(thiazol-4-yl)benzenesulfonamide formate | 523.1 (M + 1) |
| 160 | 4-((2-((6,6-difluoro-2-azaspiro[3.3]heptan-2-yl)methyl)-6-fluorobenzyl)amino)-2,6-difluoro-N-(thiazol-4-yl)benzenesulfonamide formate | 545.1 (M + 1) |
| 161 | (R)-2,6-difluoro-4-((2-fluoro-6-((3-fluoropyrrolidin-1-yl)methyl)benzyl)amino)-N-(thiazol-4-yl)benzenesulfonamide formate | 500.9 (M + 1) |
| 162 | 2,6-difluoro-4-((2-fluoro-6-(((2-methoxyethyl)(methyl)amino)methyl)benzyl)amino)-N-(thiazol-4-yl)benzenesulfonamide formate | 501.1 (M + 1) |
| 163 | 4-((2-((1,1-difluoro-5-azaspiro[2.3]hexan-5-yl)methyl)-6-fluorobenzyl)amino)-2,6-difluoro-N-(thiazol-4-yl)benzenesulfonamide | 531.0 (M + 1) |
| 164 | 2,6-difluoro-4-((2-fluoro-6-((3-methylazetidin-1-yl)methyl)benzyl)amino)-N-(thiazol-4-yl)benzenesulfonamide formate | 482.9 (M + 1) |
| 165 | 4-((2-((dimethylamino)methyl)-6-fluorobenzyl)amino)-2,6-difluoro-N-(thiazol-4-yl)benzenesulfonamide formate | 457.0 (M + 1) |
| 166 | 2,6-difluoro-4-((2-fluoro-6-(pyrrolidin-1-ylmethyl)benzyl)amino)-N-(thiazol-4-yl)benzenesulfonamide formate | 482.1 (M + 1) |
| 167 | 2,6-difluoro-4-((2-fluoro-6-((methyl((3-methyloxetan-3-yl)methyl)amino)methyl)benzyl)amino)-N-(thiazol-4-yl)benzenesulfonamide formate | 527.2 (M + 1) |
| 168 | 4-((2-((3-(difluoromethyl)azetidin-1-yl)methyl)-6-fluorobenzyl)amino)-2,6-difluoro-N-(thiazol-4-yl)benzenesulfonamide formate | 518.1 (M + 1) |
| 169 | 2,6-difluoro-4-((2-fluoro-6-((3-hydroxy-3-methylazetidin-1-yl)methyl)benzyl)amino)-N-(thiazol-4-yl)benzenesulfonamide formate | 498.1 (M + 1) |
| 170 | 4-((2-((3,3-dimethylazetidin-1-yl)methyl)-6-fluorobenzyl)amino)-2,6-difluoro-N-(thiazol-4-yl)benzenesulfonamide formate | 497.0 (M + 1) |
| 171 | 2,6-difluoro-4-((2-fluoro-6-((3-methoxyazetidin-1-yl)methyl)benzyl)amino)-N-(thiazol-4-yl)benzenesulfonamide formate | 498.1 (M + 1) |
| 172 | 2,6-difluoro-4-((2-fluoro-6-((3-methoxy-3-methylazetidin-1-yl)methyl)benzyl)amino)-N-(thiazol-4-yl)benzenesulfonamide formate | 513.1 (M + 1) |
| 173 | 4-((2-((1-azaspiro[3.3]heptan-1-yl)methyl)-6-fluorobenzyl)amino)-2,6-difluoro-N-(thiazol-4-yl)benzenesulfonamide formate | 509.2 (M + 1) |
| 174 | 4-((2-((3-azabicyclo[3.1.0]hexan-3-yl)methyl)-6-fluorobenzyl)amino)-2,6-difluoro-N-(thiazol-4-yl)benzenesulfonamide | 495.1 (M + 1) |
| 175 | 2,6-difluoro-4-((2-fluoro-6-((isobutyl(methyl)amino)methyl)benzyl)amino)-N-(thiazol-4-yl)benzenesulfonamide | 499.1 (M + 1) |
| 176 | 2,6-difluoro-4-((2-fluoro-6-((3-hydroxy-3-(trifluoromethyl)azetidin-1-yl)methyl)benzyl)amino)-N-(thiazol-4-yl)benzenesulfonamide formate | 553.0 (M + 1) |
| 177 | 4-((2-((cyclobutylamino)methyl)-6-fluorobenzyl)amino)-2,6-difluoro-N-(thiazol-4-yl)benzenesulfonamide formate | 483.1 (M + 1) |
| 178 | 4-((2-((tert-butylamino)methyl)-6-fluorobenzyl)amino)-2,6-difluoro-N-(thiazol-4-yl)benzenesulfonamide formate | 485.1 (M + 1) |
| 179 | 4-((2-((cyclobutyl(methyl)amino)methyl)-6-fluorobenzyl)amino)-2,6-difluoro-N-(thiazol-4-yl)benzenesulfonamide formate | 497.1 (M + 1) |
| 180 | 2,6-difluoro-4-((2-fluoro-6-((3-fluoro-3-methylazetidin-1-yl)methyl)benzyl)amino)-N-(thiazol-4-yl)benzenesulfonamide formate | 501.1 (M + 1) |
| 181 | 2,6-difluoro-4-((2-fluoro-6-((methyl(oxetan-3-yl)amino)methyl)benzyl)amino)-N-(thiazol-4-yl)benzenesulfonamide formate | 499.2 (M + 1) |
| 182 | (S)-2,6-difluoro-4-((2-fluoro-6-((3-fluoropyrrolidin-1-yl)methyl)benzyl)amino)-N-(thiazol-4-yl)benzenesulfonamide formate | 500.9 (M + 1) |

Examples 183-184

In a similar manner as described in EXAMPLE 152, utilizing the appropriately substituted starting materials and intermediates, the following compounds were prepared:

| Example No | Name | MS (ES+) m/z | $^1$H NMR |
|---|---|---|---|
| 183 | 4-((2-((diethylamino)methyl)-6-fluorobenzyl)amino)-2,6-difluoro-N-(thiazol-4-yl)benzenesulfonamide formate | 485.1 (M +1) | (400 MHz, CD$_3$OD) δ 8.75 (d, J = 2.4 Hz, 1H), 8.40 (br s, 1H), 7.48-7.39 (m, 1H), 7.31 (d, J = 7.8 Hz, 1H), 7.21 (t, J = 8.8 Hz, 1H), 6.98 (d, J = 2.2 Hz, 1H), 6.31 (d, J = 12.2 Hz, 2H), 4.42 (d, J = 1.4 Hz, 2H), 4.02 (br s, 2H), 2.88 (br d, J = 7.2 Hz, 4H), 1.16 (t, J = 7.2 Hz, 6H), NH and COOH not observed. |
| 184 | 2,6-difluoro-4-((2-fluoro-6-((methyl(tert-pentyl)amino)methyl)benzyl)amino)-N-(thiazol-4-yl)benzenesulfonamide formate | 513.1 (M + 1). | (400 MHz, CD$_3$OD) δ 8.75 (d, J = 2.2 Hz, 1H), 8.40 (br s, 1H), 7.50-7.41 (m, 1H), 7.37 (br d, J = 7.6 Hz, 1H), 7.22 (br t, J = 8.8 Hz, 1H), 6.98 (d, J = 2.0 Hz, 1H), 6.33 (br d, J = 12.2 Hz, 2H), 4.42 (s, 2H), 4.10 (br s, 2H), 2.40 (br s, 3H), 1.71 (br d, J = 7.2 Hz, 2H), 1.27 (br s, 6H), 0.94 (t, J = 7.4 Hz, 3H), NH and COOH not observed. |

Example 185

Synthesis of 2,6-difluoro-4-((2-fluoro-6-((isopropyl (methyl)amino)methyl)benzyl)amino)-N-(thiazol-4-yl)benzenesulfonamide formate

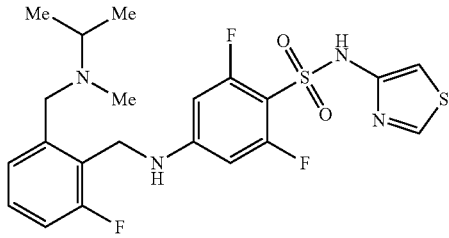 [SMILES: CC(C)N(C)Cc1cccc(F)c1CNc1cc(F)c(S(=O)(=O)Nc2cscn2)c(F)c1]

Step 1. Preparation of tert-butyl (4-(N-(tert-butoxycarbonyl)-N-(thiazol-4-yl)sulfamoyl)-3,5-difluorophenyl)(2-fluoro-6-(hydroxymethyl)benzyl) carbamate

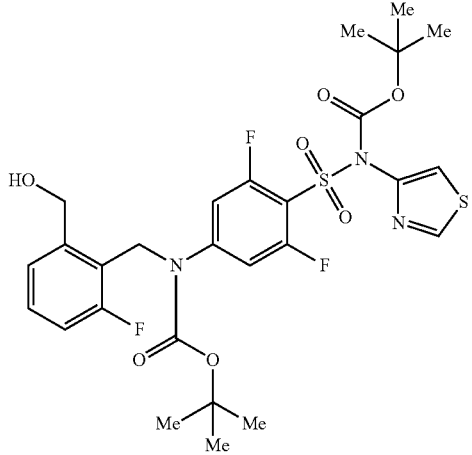 [SMILES: CC(C)(C)OC(=O)N(Cc1c(F)cccc1CO)c1cc(F)c(S(=O)(=O)N(C(=O)OC(C)(C)C)c2cscn2)c(F)c1]

To a mixture of tert-butyl ((4-((tert-butoxycarbonyl)(2-fluoro-6-formylbenzyl)amino)-2,6-difluorophenyl)sulfonyl) (thiazol-4-yl)carbamate (0.100 g, 0.159 mmol) and N,2-dimethylpropan-2-amine (0.020 g, 0.238 mmol) in methanol (1 mL) was added sodium cyanoborohydride (0.010 g, 0.159 mmol) and the reaction mixture was stirred at ambient temperature 1 h. Concentration in vacuo and purification of the residue by preparative thin layer chromatography, eluting with 50% of ethyl acetate in petroleum ether, afforded the title compound as a colorless solid (0.160 g, quantitative yield): $^1$H NMR (400 MHz, CDCl$_3$) δ 8.83 (d, J=2.2 Hz, 1H), 7.55 (d, J=2.2 Hz, 1H), 7.28-7.14 (m, 3H), 6.97 (d, J=10.2 Hz, 2H), 5.14 (s, 2H), 4.77 (s, 2H), 1.46 (s, 9H), 1.37 (s, 9H), OH not observed; MS (ES+) m/z 474.1 (M−155).

Step 2. Preparation of tert-butyl (2-(bromomethyl)-6-fluorobenzyl)(4-(N-(tert-butoxycarbonyl)-N-(thiazol-4-yl)sulfamoyl)-3,5-difluorophenyl)carbamate

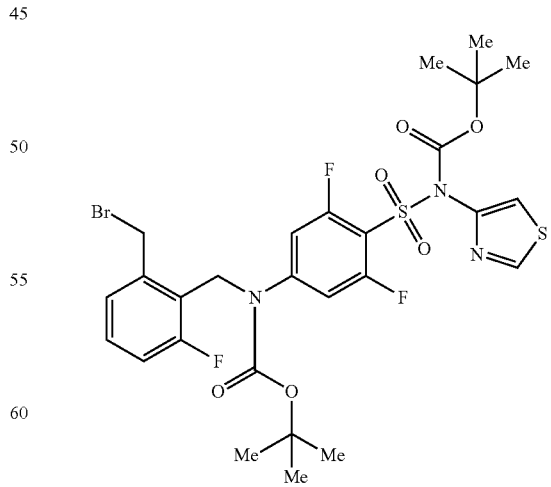

To a solution of tert-butyl (4-(N-(tert-butoxycarbonyl)-N-(thiazol-4-yl)sulfamoyl)-3,5-difluorophenyl)(2-fluoro-6-(hydroxymethyl)benzyl)carbamate (0.160 g, 0.254 mmol) and carbon tetrabromide (0.168 g, 0.508 mmol) in dichloromethane (2.00 mL) was added triphenylphosphine (0.133 g, 0.508 mmol) at 0° C. The reaction mixture was allowed to warm to ambient temperature and stirred for 2 h. Concentration in vacuo and purification by preparative thin layer chromatography, eluting with 30% of ethyl acetate in petroleum ether, provided the title compound as a colorless solid (0.100 g, 0.090 mmol, 35% yield): $^1$H NMR (400 MHz, CDCl$_3$) δ 8.83 (d, J=2.2 Hz, 1H), 7.54 (d, J=2.2 Hz, 1H), 7.26-7.20 (m, 2H), 7.04 (d, J=10.4 Hz, 2H), 6.93-6.89 (m, 1H), 5.18 (s, 2H), 4.70 (s, 2H), 1.51 (s, 9H), 1.34 (s, 9H); MS (ES+) m/z 536.0 (M-155), 538.0 (M-155).

Step 3. Preparation of tert-butyl (4-(N-(tert-butoxycarbonyl)-N-(thiazol-4-yl)sulfamoyl)-3,5-difluorophenyl)(2-fluoro-6-((isopropyl(methyl)amino)methyl)-benzyl)carbamate

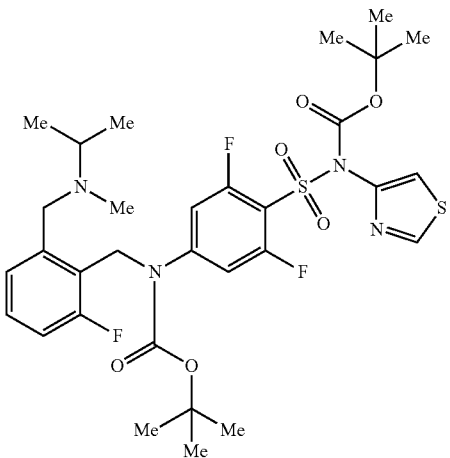 [SMILES: CC(C)N(C)Cc1cccc(F)c1CN(C(=O)OC(C)(C)C)c1cc(F)c(S(=O)(=O)N(C(=O)OC(C)(C)C)c2cscn2)c(F)c1]

To a mixture of N-methylpropan-2-amine (0.010 g, 0.144 mmol) and tert-butyl (2-(bromomethyl)-6-fluorobenzyl)(4-(N-(tert-butoxycarbonyl)-N-(thiazol-4-yl)sulfamoyl)-3,5-difluorophenyl)carbamate (0.050 g, 0.072 mmol) in anhydrous N,N-dimethylformamide (2 mL) was added potassium carbonate (0.019 g, 0.144 mmol) at 0° C. The Reaction mixture was stirred at ambient temperature for 12 h, and then water (10 mL) was added to it. The mixture was extracted with ethyl acetate (3×10 mL). The combined organic phase was washed with brine (3×10 mL), dried over anhydrous sodium sulfate, and filtered. Concentration of the filtrate in vacuo and purification provided the title compound as a yellow solid (0.050 mg, quantitive yield): MS (ES+) m/z 685.3 (M+1).

Step 4. Preparation of 2,6-difluoro-4-((2-fluoro-6-((isopropyl(methyl)amino)-methyl)benzyl)amino)-N-(thiazol-4-yl)benzenesulfonamide formate

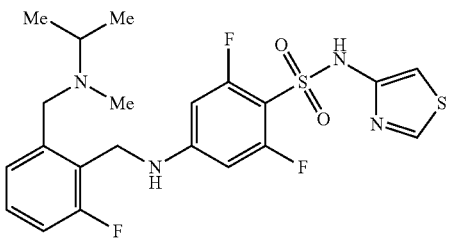 [SMILES: CC(C)N(C)Cc1cccc(F)c1CNc1cc(F)c(S(=O)(=O)Nc2cscn2)c(F)c1]

To a solution of tert-butyl (4-(N-(tert-butoxycarbonyl)-N-(thiazol-4-yl)sulfamoyl)-3,5-difluorophenyl)(2-fluoro-6-((isopropyl(methyl)amino)methyl)benzyl)carbamate (0.050 g, 0.073 mmol) in dichloromethane (2 mL) was added trifluoroacetic acid (6.16 g, 54.03 mmol) and the reaction mixture was stirred at ambient temperature for 3 h. Concentration in vacuo and purification of the residue by preparative reverse phase HPLC, using acetonitrile in water containing 0.255% of formic acid, provided the title compound as a colorless solid (0.012 g, 29% yield): $^1$H NMR (400 MHz, CD$_3$OD) δ 8.75 (d, J=2.2 Hz, 1H), 8.50-8.41 (m, 1H), 7.46-7.37 (m, 1H), 7.33-7.25 (m, 1H), 7.25-7.16 (m, 1H), 6.98 (d, J=2.2 Hz, 1H), 6.32 (d, J=12.3 Hz, 2H), 4.42 (d, J=1.3 Hz, 2H), 4.00-3.89 (m, 2H), 3.30-3.16 (m, 1H), 2.42-2.30 (m, 3H), 1.27-1.13 (m, 6H), NH and COOH not observed; MS (ES+) 485.2 (M+1).

Example 186

Synthesis of 4-((2-((5-azaspiro[2.3]hexan-5-yl)methyl)-6-fluorobenzyl)amino)-2,6-difluoro-N-(thiazol-4-yl)benzenesulfonamide formate

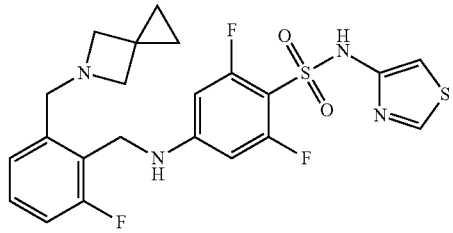 [SMILES: O=S(=O)(Nc1cscn1)c1c(F)cc(NCc2c(F)cccc2CN2CC3(CC3)C2)cc1F]

Following the procedure as described for EXAMPLE 201, Step 3 to 4, and making non-critical variations as required to replace N-methylpropan-2-amine with 5-azaspiro[2.3]hexane, the title compound was obtained as a colorless solid (3.5 mg, 22% yield): $^1$H NMR (400 MHz, CD$_3$OD) δ 8.75 (d, J=2.2 Hz, 1H), 8.51-8.47 (m, 1H), 7.44-7.39 (m, 1H), 7.27-7.26 (m, 1H), 7.21-7.16 (m, 1H), 6.98 (d, J=2.2 Hz, 1H), 6.32 (d, J=12.3 Hz, 2H), 4.40 (d, J=0.8 Hz, 2H), 4.17 (s, 2H), 3.77 (s, 4H), 0.67 (s, 4H), NH and COOH not observed; MS (ES+) m/z 495.3 (M+1).

Example 187

Synthesis of 4-((2-(((cyclopropylmethyl)(methyl)amino)methyl)-6-fluorobenzyl)amino)-2,6-difluoro-N-(thiazol-4-yl)benzenesulfonamide formate

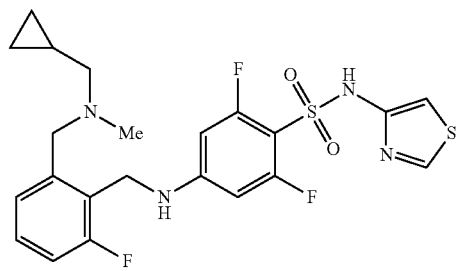 [SMILES: CN(Cc1cccc(F)c1CNc1cc(F)c(S(=O)(=O)Nc2cscn2)c(F)c1)CC1CC1]

Step 1. Preparation of tert-butyl (4-(N-(tert-butoxy-carbonyl)-N-(thiazol-4-yl)sulfamoyl)-3,5-difluoro-phenyl)(2-(((cyclopropylmethyl)(methyl)amino)methyl)-6-fluorobenzyl)carbamate

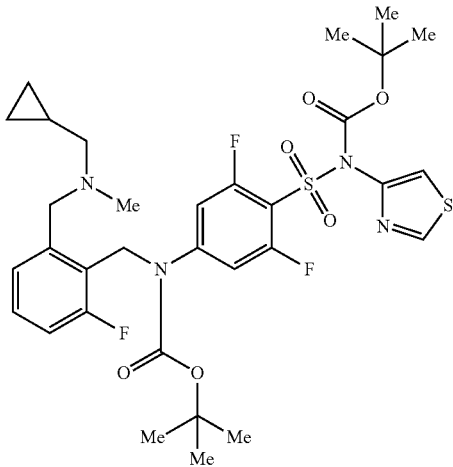 [SMILES: CN(Cc1cccc(F)c1CN(C(=O)OC(C)(C)C)c1cc(F)c(S(=O)(=O)N(C(=O)OC(C)(C)C)c2cscn2)c(F)c1)CC1CC1]

To a mixture of 1-cyclopropyl-N-methylmethanamine hydrochloride (0.038 g, 0.318 mmol) and tert-butyl ((4-((tert-butoxycarbonyl)(2-fluoro-6-formylbenzyl)amino)-2,6-difluorophenyl)sulfonyl)(thiazol-4-yl)carbamate (0.100 g, 0.159 mmol) in dichloromethane (2 mL) was added titanium (IV) isopropoxide (0.090 g, 0.318 mmol) and the reaction mixture was stirred at ambient temperature for 1 h. To it was then added sodium triacetoxy borohydride (0.135 g, 0.637 mmol) and the reaction mixture was stirred at ambient temperature for 11 h. Saturated sodium bicarbonate (1 mL) was added and the mixture was stirred for 30 minutes. After dilution with water (10 mL), the mixture was extracted with dichloromethane (3×10 mL). The combined organic phase was washed with brine (3×10 mL), dried over anhydrous sodium sulfate, and filtered. Concentration in vacuo provided the title compound as oily residue (0.072 g, 65% yield) which was used without further purification: MS (ES+) m/z 697.2 (M+1).

Step 2. Preparation of 4-((2-(((cyclopropylmethyl)(methyl)amino)methyl)-6-fluorobenzyl)amino)-2,6-difluoro-N-(thiazol-4-yl)benzenesulfonamide formate

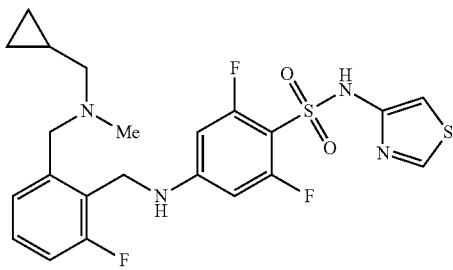 [SMILES: CN(Cc1cccc(F)c1CNc1cc(F)c(S(=O)(=O)Nc2cscn2)c(F)c1)CC1CC1]

To a solution of tert-butyl (4-(N-(tert-butoxycarbonyl)-N-(thiazol-4-yl)sulfamoyl)-3,5-difluorophenyl)(2-(((cyclopropylmethyl)(methyl)amino)methyl)-6-fluorobenzyl)carbamate (0.070 g, 0.100 mmol) in dichloromethane (2 mL) was added trifluoroacetic acid (3.08 g, 27.0 mmol), and the reaction mixture was stirred at ambient temperature for 12 h. Concentration in vacuo and purification of the residue in vacuo and purification of the residue by preparative reverse phase HPLC, using acetonitrile in water containing 0.05% of ammonium hydroxide, provided the title compound as a colorless solid (0.032 g, 62% yield): $^1$H NMR (400 MHz, DMSO-$d_6$) δ 8.78 (br s, 1H), 7.37-7.24 (m, 1H), 7.20-7.07 (m, 3H), 6.64 (br s, 1H), 6.30 (d, J=12.4 Hz, 2H), 4.34 (d, J=3.8 Hz, 2H), 3.51 (s, 2H), 2.18 (d, J=6.6 Hz, 2H), 2.09 (s, 3H), 0.75-0.80 (m, 1H), 0.35 (q, J=5.0, 2H), −0.01 (q, J=5.0 Hz, 2H), NH and COOH not observed; MS (ES+) m/z 497.3 (M+1).

Example 188

Synthesis of 4-((2-(azetidin-1-ylmethyl)-6-fluorobenzyl)amino)-2,6-difluoro-N-(isothiazol-3-yl)benzenesulfonamide 2,2,2-trifluoroacetate

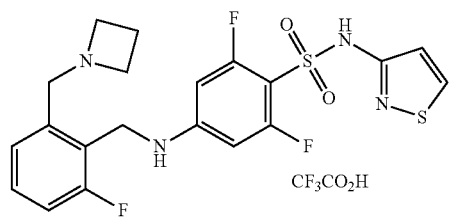

Step 1. Preparation of tert-butyl isothiazol-3-ylcarbamate

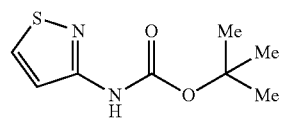 [SMILES: CC(C)(C)OC(=O)Nc1ccsn1]

To a slurry of isothiazole-3-carboxylic acid (5.0 g, 38.7 mmol) in tert-butanol (194 mL) was added triethylamine (4.3 g, 42.6 mmol) followed by diphenyl phosphoryl azide (11.9 g, 43.3 mmol). The reaction mixture was heated to reflux for 9 h. After cooling the ambient temperature, the reaction mixture was concentrated in vacuo and the residue dissolved in ethyl acetate (300 mL). The organic layer was washed with water (100 mL), 1 N sodium hydroxide solution (50 mL), water (100 mL), brine (50 mL), and dried over anhydrous magnesium sulfate. Filtration and concentration of the filtrate in vacuo afforded a residue. Purification of the residue by column chromatography, eluting with a gradient of 0 to 10% of ethyl acetate in heptane, provided the title compound as a colorless solid (6.16 g, 79% yield): $^1$H NMR (300 MHz, CDCl$_3$) δ 9.03-8.98 (m, 1H), 8.58 (d, J=4.9 Hz, 1H), 7.70 (d, J=4.9 Hz, 1H), 1.53 (d, J=0.7 Hz, 9H).

Step 2. Preparation of 3-bromo-2,4,6-trifluorobenzenesulfonyl chloride

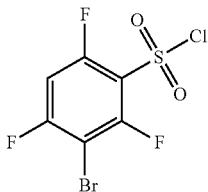 [SMILES: O=S(=O)(Cl)c1c(F)cc(F)c(Br)c1F]

To 4-bromo-1,3,5-trifluorobenzene (25 g, 0.118 mmol) was added chlorosulfonic acid (24 mL) and the reaction mixture was heated to 80° C. for 72 h. The reaction mixture was allowed to cool to ambient temperature and slowly added onto ice. The resulting solid was filtered off and dissolved in dichloromethane (200 mL). The organic phase was washed with water (2×50 mL), brine (50 mL), dried over anhydrous magnesium sulfate. Filtration over through a pad of celite and concentration of the filtrate in vacuo provided the title compound as a colorless solid (28.6 g, 78% yield): $^1$H NMR (300 MHz, CDCl$_3$) δ 7.06 (ddd, J=9.9, 7.8, 2.2 Hz, 1H).

Step 3. Preparation of tert-butyl ((3-bromo-2,4,6-trifluorophenyl)sulfonyl)-(isothiazol-3-yl)carbamate

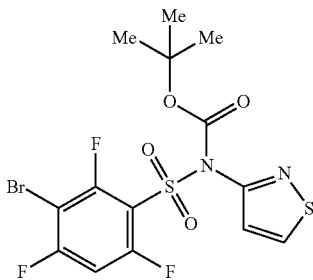 [SMILES: CC(C)(C)OC(=O)N(c1ccsn1)S(=O)(=O)c1c(F)cc(F)c(Br)c1F]

To a solution of tert-butyl isothiazol-3-ylcarbamate (0.9 g, 4.49 mmol) in anhydrous tetrahydrofuran (12 mL) was added a 1 M solution of lithium bis(trimethylsilyl)amide in tetrahydrofuran (4.94 mL, 4.94 mmol) at −78° C. The reaction mixture was stirred for 10 minutes at −78° C., and then allowed to warm to ambient temperature and stirred for 1 h. After cooling the reaction mixture to −78° C., a solution of 5-bromo-2,4,6-trifluorobenzenesulfonyl chloride (1.39 g, 4.49 mmol) in anhydrous tetrahydrofuran (2.6 mL) was added to it. The reaction mixture was allowed to warm to ambient temperature and stirred for 12 h. The reaction mixture was quenched by the addition of saturated ammonium chloride solution (50 mL), and the aqueous layer was extracted with ethyl acetate (3×50 mL). The combined organic layers were washed with water (50 mL), brine (50 mL), dried over magnesium sulfate, and filtered. Concentration of the filtrate in vacuo and purification of the residue by column chromatography, eluting with a gradient of 0 to 5% of ethyl acetate in heptane, provided the title compound as a beige solid (1.08 g, 97% yield): $^1$H NMR (300 MHz, CDCl$_3$) δ 8.76 (d, J=4.7 Hz, 1H), 7.33 (d, J=4.7 Hz, 1H), 6.99 (ddd, J=9.9, 7.9, 2.1 Hz, 1H), 1.44-1.35 (m, 9H).

Step 4: Preparation of tert-butyl ((4-((2-(azetidin-1-ylmethyl)-6-fluorobenzyl)amino)-3-bromo-2,6-difluorophenyl)sulfonyl)(isothiazol-3-yl)carbamate

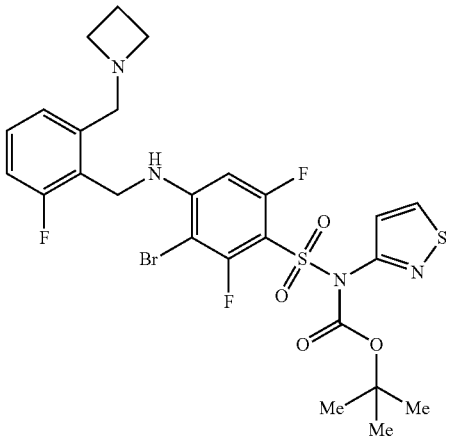 [SMILES: CC(C)(C)OC(=O)N(c1ccsn1)S(=O)(=O)c1c(F)cc(NCc2c(F)cccc2CN2CCC2)c(Br)c1F]

To a solution of tert-butyl ((3-bromo-2,4,6-trifluorophenyl)sulfonyl)(isothiazol-3-yl)carbamate (0.50 g, 1.1 mmol) in anhydrous N,N-dimethylformamide (5.3 mL) was added (2-(azetidin-1-ylmethyl)-6-fluorophenyl)methanamine (0.25 g, 1.3 mmol) followed by N,N-diisopropylethylamine (0.27 g, 2.12 mmol). The reaction mixture was stirred at ambient temperature for 16 h. The reaction mixture was diluted with ethyl acetate (150 mL). The organic layer was washed with water (2×50 mL), brine (50 mL), dried over anhydrous magnesium sulfate, and filtered. Concentration of the filtrate in vacuo and purification of the residue by column chromatography, eluting with a gradient of 10 to 50% of ethyl acetate in heptane, provided the title product as a colorless solid (0.37 g, 54% yield): LCMS (ES+) m/z 647.4 (M+1), 649.4 (M+1).

Step 5: Preparation of 4-((2-(azetidin-1-ylmethyl)-6-fluorobenzyl)amino)-2,6-difluoro-N-(isothiazol-3-yl)benzenesulfonamide 2,2,2-trifluoroacetate

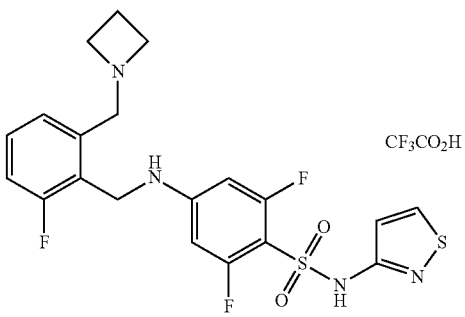 [SMILES: O=S(=O)(Nc1ccsn1)c1c(F)cc(NCc2c(F)cccc2CN2CCC2)cc1F ; "CF3CO2H"]

To a solution of tert-butyl ((4-((2-(azetidin-1-ylmethyl)-6-fluorobenzyl)amino)-3-bromo-2,6-difluorophenyl)sulfonyl)(isothiazol-3-yl)carbamate (0.33 g, 0.50 mmol) in anhydrous dimethyl sulfoxide (2 mL) was added sodium formate (0.068 g, 1.0 mmol) and the mixture was degassed with argon for 10 minutes. To it was then added tris(dibenzylideneacetone)dipalladium(0) (0.014 g, 0.015 mmol) and tri-tert-butylphosphine (0.006 g, 0.03 mmol) and the reaction mixture was heated to 80° C. for 16 h. After cooling to ambient temperature, the reaction mixture was diluted with ethyl acetate (100 mL). The organic phase was washed with water (4×30 mL), brine (30 mL), dried over magnesium sulfate, and filtered through a pad of celite. Concentration in vacuo and purification of the residue by preparative reverse-phase HPLC, using acetonitrile in water containing 0.1% trifluoroacetic acid as eluent, afforded the title compound as a colorless solid (0.037 g, 13% yield): $^1$H NMR (300 MHz, DMSO-$d_6$) δ 11.76 (s, 1H), 10.06 (s, 1H), 8.93 (d, J=4.8 Hz, 1H), 7.56-7.49 (m, 1H), 7.41-7.32 (m, 2H), 7.29-7.25 (m, 1H), 6.93 (d, J=4.8 Hz, 1H), 6.42-6.35 (m, 2H), 4.50-4.41 (m, 2H), 4.37-4.30 (m, 2H), 4.17-3.94 (m, 4H), 2.46-2.22 (m, 2H); $^{19}$F NMR (282 MHz, DMSO-$d_6$) δ−73.6 (s, 3F), −108.3 (s, 2F), −115.3 (s, 1F); MS (ES+) m/z 469.1 (M+1).

Example 189

Synthesis of 4-((2-((tert-butyl(methyl)amino)methyl)-6-fluorobenzyl)amino)-2,6-difluoro-N-(isothiazol-3-yl)benzenesulfonamide formate

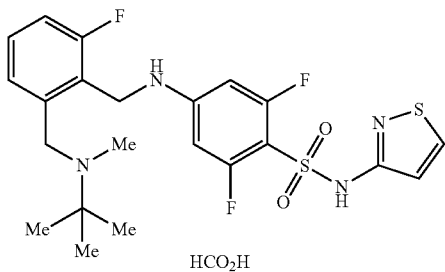 [SMILES: CN(Cc1cccc(F)c1CNc1cc(F)c(S(=O)(=O)Nc2ccsn2)c(F)c1)C(C)(C)C ; "HCO2H"]

Step 1. Preparation of tert-butyl ((3-bromo-4-((2-((tert-butyl(methyl)amino)methyl)-6-fluorobenzyl)amino)-2,6-difluorophenyl)sulfonyl)(isothiazol-3-yl)carbamate

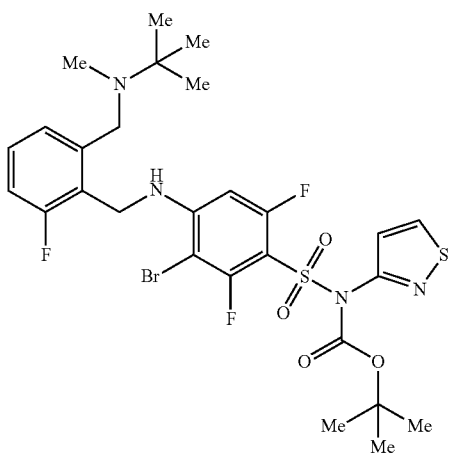 [SMILES: CN(Cc1cccc(F)c1CNc1cc(F)c(S(=O)(=O)N(C(=O)OC(C)(C)C)c2ccsn2)c(F)c1Br)C(C)(C)C]

To a solution of tert-butyl ((3-bromo-2,4,6-trifluorophenyl)sulfonyl)(isothiazol-3-yl)carbamate (0.88 g, 1.85 mmol) in anhydrous N,N-dimethylformamide (10 mL) was added N-(2-(aminomethyl)-3-fluorobenzyl)-N,2-dimethylpropan-2-amine (0.83 g, 3.7 mmol) followed by N,N-diisopropylethylamine (0.72 g, 5.5 mmol). The reaction mixture was stirred at ambient temperature for 12 h, and then diluted with ethyl acetate (150 mL). The organic layer was washed with water (3×50 mL), brine (50 mL), dried over anhydrous magnesium sulfate, and filtered. Concentration of the filtrate in vacuo and purification of the residue by column chromatography, eluting with a gradient of 10 to 50% of ethyl acetate in heptane, afforded the title compound as an orange oil (0.42 g, 34% yield): LCMS (ES+) m/z 577.4 (M−99), 579.4 (M−99).

Step 2: Preparation of 4-((2-((tert-butyl(methyl)amino)methyl)-6-fluorobenzyl)amino)-2,6-difluoro-N-(isothiazol-3-yl)benzenesulfonamide formate

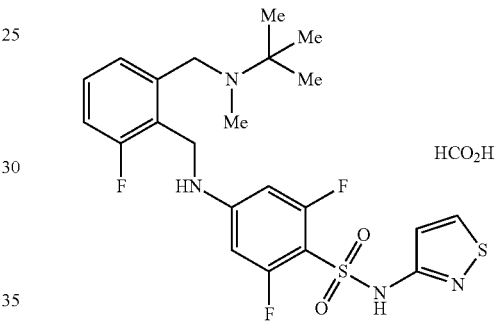

To a solution tert-butyl ((3-bromo-4-((2-((tert-butyl(methyl)amino)methyl)-6-fluorobenzyl)amino)-2,6-difluorophenyl)sulfonyl)(isothiazol-3-yl)carbamate (0.42 g, 0.62 mmol) in anhydrous dimethyl sulfoxide (1 mL) was added sodium formate (0.13 g, 1.86 mmol) and the mixture was degassed with argon for 10 minutes. To it was then added tris(dibenzylideneacetone)dipalladium(0) (0.057 g, 0.062 mmol) and tri-tert-butylphosphine (0.025 g, 0.124 mmol) was added and the reaction mixture was heated to 80° C. for 16 h. After cooling to ambient temperature, the reaction mixture was diluted with ethyl acetate (100 mL). The organic phase was washed with water (4×30 mL), brine (30 mL), and dried over anhydrous magnesium sulfate. Filtration and concentration of the filtrate in vacuo provided a residue. Purification of the residue by column chromatography, eluting with a gradient of 10 to 80% of ethyl acetate in heptane, followed by purification by preparative reverse-phase HPLC, using acetonitrile in water containing 0.5% formic acid, provided the title compound as a colorless solid (0.013 g, 4% yield): $^1$H-NMR (300 MHz, DMSO-$d_6$) δ 8.79 (t, J=3.3 Hz, 1H), 8.19 (s, 1H), 7.38-7.25 (m, 2H), 7.16-7.10 (m, 2H), 6.87 (d, J=4.8 Hz, 1H), 6.35 (d, J=12.6 Hz, 2H), 4.34 (s, 2H), 3.57 (s, 2H), 1.96 (s, 3H), 1.03 (s, 9H), NH not observed; MS (ES+) m/z 499.1 (M+1).

Example 190

Synthesis of (S)-3-chloro-4-((1-(5-chloro-2-fluorophenyl)ethyl)amino)-2-fluoro-N-(thiazol-4-yl)benzenesulfonamide

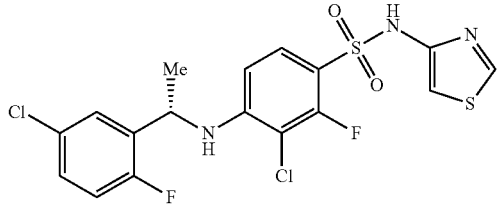 [SMILES: C[C@H](Nc1ccc(S(=O)(=O)Nc2cscn2)c(F)c1Cl)c1cc(Cl)ccc1F]

To a mixture of (S)-1-(5-chloro-2-fluorophenyl)ethan-1-amine hydrochloride (0.24 g, 1.15 mmol) and tert-butyl ((3-chloro-2,4-difluorophenyl)sulfonyl)(thiazol-4-yl)carbamate (0.47 g, 1.15 mmol) in anhydrous dimethyl sulfoxide (6 mL) was added potassium carbonate (0.48 g, 3.45 mmol) and the reaction mixture was stirred at 75° C. for 1 h. The reaction mixture was allowed to cool to ambient temperature, and then diluted with water (20 mL) and ethyl acetate (30 mL). The aqueous layer was extracted with ethyl acetate (2×30 mL). The combined organic phase was washed with brine (50 mL), dried over anhydrous sodium sulfate, and filtered. Concentration of the filtrate in vacuo afforded a residue, which was dissolved in anhydrous dichloromethane (6 mL). To it was added trifluoroacetic acid (0.26 mL, 3.46 mmol) and the reaction mixture was stirred at ambient temperature for 5 h. The reaction mixture was concentrated in vacuo and the residue purified by preparative reverse-phase HPLC, eluting with a gradient of acetonitrile in water containing 0.1% of formic acid, to afford the title compound as a colorless solid (0.059 g, 11% yield over 2 steps): $^1$H-NMR (300 MHz, CDCl$_3$) δ 10.09 (s, 1H), 8.71 (d, J=2.2 Hz, 1H), 7.59-7.53 (m, 1H), 7.26-7.18 (m, 2H), 7.05 (t, J=9.2 Hz, 1H), 6.87 (d, J=2.2 Hz, 1H), 6.18-6.15 (m, 1H), 5.13 (d, J=5.9 Hz, 1H), 4.88-4.79 (m, 1H), 1.63 (d, J=6.7 Hz, 3H); MS (ES+) m/z 463.9 (M+1), 465.9 (M+1), 467.9 (M+1)

Example 191

Synthesis of (S)-3-chloro-4-((1-(2-chlorophenyl)ethyl)amino)-2-fluoro-N-(pyrimidin-4-yl)benzenesulfonamide

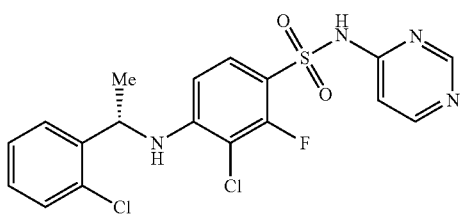 [SMILES: C[C@H](Nc1ccc(S(=O)(=O)Nc2ccncn2)c(F)c1Cl)c1ccccc1Cl]

Step 1. Preparation of N-(2,4-dimethoxybenzyl)pyrimidin-4-amine

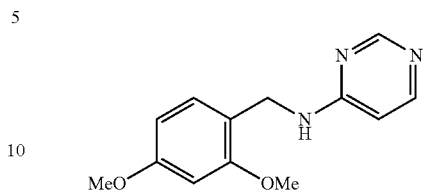

To a solution of 4-aminopyrimidine (1.50 g, 15.8 mmol) and 2,4-dimethoxybenzaldehyde (2.62 g, 15.8 mmol) in toluene (80 mL) was added acetic acid (0.090 mL, 1.6 mmol) and the mixture was heated to reflux for 23 h using a Dean-Stark trap for azeotropic removal of water. After cooling to ambient temperature, the mixture was then concentrated in vacuo and anhydrous methanol (50 mL) was added to the residue. To the mixture was then added sodium borohydride (1.2 g, 32 mmol) at ambient temperature over a period of 40 minutes. The mixture was stirred at ambient temperature for 16 h and then concentrated in vacuo. The residue was partitioned between ethyl acetate (50 mL) and 1 M sodium hydroxide (30 mL). The aqueous phase was extracted with ethyl acetate (40 mL), and the combined organic layers were dried over anhydrous magnesium sulfate and filtered. Concentration of the filtrate in vacuo and purification of the residue by column chromatography, eluting with a gradient of 25 to 50% of ethyl acetate (containing 10% of isopropanol and 10% of triethylamine) in heptane, afforded the title compound as a yellow oil (2.69 g, 70% yield): $^1$H NMR (300 MHz, CDCl$_3$) δ 8.52 (s, 1H), 8.12 (d, J=6.0 Hz, 1H), 7.17 (d, J=8.2 Hz, 1H), 6.46 (d, J=2.3 Hz, 1H), 6.42 (dd, J=8.2, 2.4 Hz, 1H), 6.32 (d, J=6.0 Hz, 1H), 5.54 (br s, 1H), 4.43-4.41 (m, 2H), 3.82 (s, 3H), 3.79 (s, 3H); MS (ES+) m/z 246.3 (M+1).

Step 2. Preparation of 3-chloro-N-(2,4-dimethoxybenzyl)-2,4-difluoro-N-(pyrimidin-4-yl)benzenesulfonamide

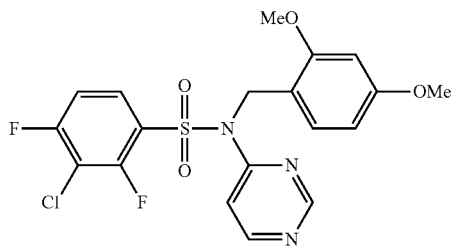 [SMILES: COc1ccc(CN(c2ccncn2)S(=O)(=O)c2ccc(F)c(Cl)c2F)c(OC)c1]

To a mixture of N-(2,4-dimethoxybenzyl)pyrimidin-4-amine (prepared according to WO2012004743, 3.28 g, 13.4 mmol) in anhydrous tetrahydrofuran (60 mL) was added a 1 M solution of lithium bis(trimethylsilyl)amide in tetrahydrofuran (13.4 mL, 13.4 mmol) at −50° C. The reaction mixture was allowed to warm to ambient temperature and stirred for 1 h. The reaction mixture was then added to a cold (−78° C.) solution of 3-chloro-2,4-difluorobenzenesulfonyl chloride (3.00 g, 12.1 mmol) in anhydrous tetrahydrofuran (60 mL). The reaction mixture was allowed to warm to ambient temperature, and stirred for 16 h. The reaction mixture was then quenched by addition of saturated ammonium chloride solution (80 mL) and ethyl acetate (100 mL) was added to it. The aqueous phase was extracted with ethyl acetate (2×100 mL). The combined organic phase was washed with brine (50 mL), dried over anhydrous sodium sulfate, and filtered. Concentration of the filtrate in vacuo and purification of the residue by column chromatography, eluting with a gradient of 0 to 50% of ethyl acetate in hexanes, provided the title compound as a yellow oil (0.86 g, 15% yield): $^1$H NMR (300 MHz, CDCl$_3$) δ 8.75 (t, J=0.6 Hz, 1H), 8.46 (dd, J=5.9, 0.4 Hz, 1H), 8.03 (ddd, J=9.0, 7.6, 5.7 Hz, 1H), 7.23-7.20 (m, 1H), 7.17-7.13 (m, 1H), 7.11-7.09 (m, 1H), 6.42 (dd, J=6.9, 2.3 Hz, 2H), 5.25 (s, 2H), 3.81 (s, 3H), 3.78 (s, 3H); MS (ES+) m/z 456.1 (M+1), 458.1 (M+1).

Step 3. Preparation of (S)-3-chloro-4-((1-(2-chlorophenyl)ethyl)amino)-2-fluoro-N-(pyrimidin-4-yl)benzenesulfonamide

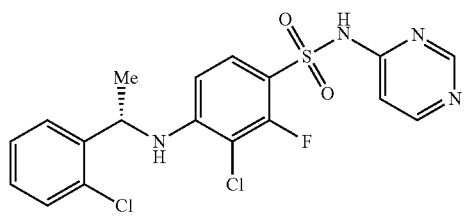 [SMILES: C[C@H](Nc1ccc(S(=O)(=O)Nc2ccncn2)c(F)c1Cl)c1ccccc1Cl]

To a mixture of (S)-1-(2-chlorophenyl)ethan-1-amine (0.18 g, 0.93 mmol) and 3-chloro-N-(2,4-dimethoxybenzyl)-2,4-difluoro-N-(pyrimidin-4-yl)benzenesulfonamide (0.42 g, 0.93 mmol) in anhydrous dimethyl sulfoxide (5 mL) was added potassium carbonate (0.39 g, 2.80 mmol) and the reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. The filtrate was concentrated in vacuo to provide a residue which was dissolved in anhydrous dichloromethane (5 mL). To it was added trifluoroacetic acid (0.80 mL, 11.6 mmol) and the reaction mixture was stirred at ambient temperature for 5 h. The reaction mixture was diluted with methanol (20 mL) and filtered. Concentration of the filtrate in vacuo and purification of the residue by preparative reverse-phase HPLC, eluting with a gradient of acetonitrile in water containing 0.1% of formic acid, afforded the title compound as a colorless solid (0.10 g, 24% yield over 2 steps): $^1$H-NMR (300 MHz, DMSO-d$_6$) δ 8.54 (s, 1H), 8.26 (d, J=7.2 Hz, 1H), 7.56 (t, J=8.5 Hz, 1H), 7.48-7.43 (m, 2H), 7.33-7.25 (m, 2H), 6.94 (d, J=6.6 Hz, 1H), 6.79 (d, J=7.2 Hz, 1H), 6.15 (d, J=9.3 Hz, 1H), 5.00-4.92 (m, 1H), 1.55 (d, J=6.7 Hz, 3H), NH not observed; MS (ES+) m/z 441.0 (M+1), 443.0 (M+1), 445.0 (M+1).

Example 192

Synthesis of 4-((2-(azetidin-1-ylmethyl)-6-fluorobenzyl)amino)-3-chloro-2-fluoro-N-(thiazol-4-yl)benzenesulfonamide formate

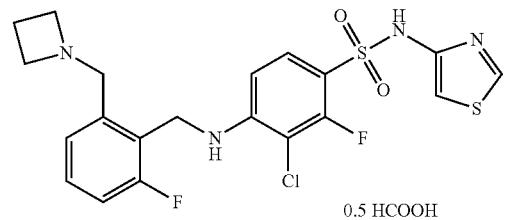 [SMILES: O=S(=O)(Nc1cscn1)c1ccc(NCc2c(F)cccc2CN2CCC2)c(Cl)c1F]

To a mixture of (2-(azetidin-1-ylmethyl)-6-fluorophenyl)methanamine (0.10 g, 0.51 mmol) and tert-butyl ((3-chloro-2,4-difluorophenyl)sulfonyl)(thiazol-4-yl)carbamate (0.21 g, 0.51 mmol) in anhydrous dimethyl sulfoxide (3 mL) was added potassium carbonate (0.14 g, 1.03 mmol) and the reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. Concentration of the filtrate in vacuo provided a residue which was dissolved in anhydrous dichloromethane (3 mL). To it was added trifluoroacetic acid (0.47 mL, 6.18 mmol) and the reaction mixture was stirred at ambient temperature for 2.5 h. The reaction mixture was concentrated in vacuo and the residue purified by preparative reverse-phase HPLC, eluting with a gradient of acetonitrile in water containing 0.5% of formic acid, to afford the title compound as a colorless solid (0.074 g, 30% yield over 2 steps): $^1$H-NMR (300 MHz, DMSO-d$_6$) δ 11.17-11.01 (m, 1H), 8.88 (d, J=2.2 Hz, 1H), 8.14 (s, 0.5H), 7.59 (t, J=8.6 Hz, 1H), 7.37-7.34 (m, 1H), 7.24 (d, J=7.8 Hz, 2H), 6.97 (d, J=2.2 Hz, 1H), 6.82 (d, J=9.6 Hz, 1H), 4.50-4.49 (m, 2H), 4.06-3.99 (m, 2H), 3.58-3.44 (m, 4H), 2.19-2.10 (m, 2H), two exchangeable protons not observed; MS (ES+) m/z 485.0 (M+1), 487.0 (M+1).

Example 193

Synthesis of 4-((2-(azetidin-1-ylmethyl)-4,5-difluorobenzyl)amino)-5-chloro-2-fluoro-N-(thiazol-4-yl)benzenesulfonamide formate

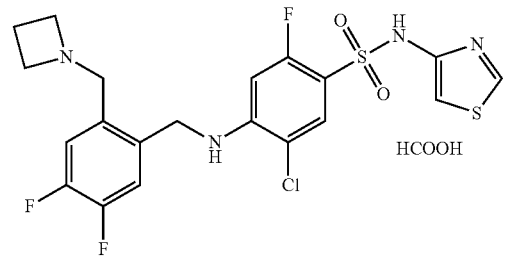 [SMILES: O=S(=O)(Nc1cscn1)c1cc(Cl)c(NCc2cc(F)c(F)cc2CN2CCC2)cc1F ; "HCOOH"]

Step 1. Preparation of 2-(azetidin-1-ylmethyl)-4,5-difluorobenzonitrile

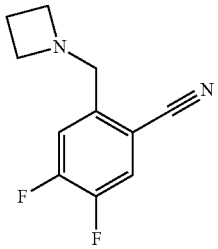 [SMILES: N#Cc1cc(F)c(F)cc1CN1CCC1]

Following the procedure as described in EXAMPLE 16, Step 1 and making variations as required to replace 2-(bromomethyl)benzonitrile with (2-(bromomethyl)-4,5-difluorobenzonitrile, the title compound was obtained as a yellow oil (6.99 g, 79% yield): $^1$H NMR (300 MHz, CDCl$_3$) δ 7.61 (dd, J=8.6, 5.4 Hz, 1H), 7.02 (ddd, J=8.5, 7.9, 2.6 Hz, 1H), 3.33-3.28 (m, 4H), 2.18-2.09 (m, 2H); MS (ES+) m/z 191.2 (M+1).

Step 2. Preparation of 4-((2-(azetidin-1-ylmethyl)-4,5-difluorobenzyl)amino)-5-chloro-2-fluoro-N-(thiazol-4-yl)benzenesulfonamide formate

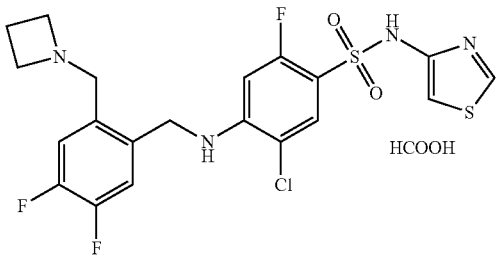 [SMILES: O=S(=O)(Nc1cscn1)c1cc(Cl)c(NCc2cc(F)c(F)cc2CN2CCC2)cc1F ; "HCOOH"]

Following the procedure as described in EXAMPLE 16, Step 2 and making variations as required to replace 2-(azetidin-1-ylmethyl)benzonitrile with 2-(azetidin-1-ylmethyl)-4,5-difluorobenzonitrile provided a red oil as residue. To a mixture of this residue in anhydrous dimethyl sulfoxide (5 mL) was added tert-butyl ((5-chloro-2,4-difluorophenyl)sulfonyl)(thiazol-4-yl)carbamate (0.39 g, 0.94 mmol) and potassium carbonate (0.26 g, 1.88 mmol). The reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. Concentration of the filtrate in vacuo afforded a residue which was dissolved in anhydrous dichloromethane (5 mL). To it was added trifluoroacetic acid (1.1 mL, 14.1 mmol) and the reaction mixture was stirred at ambient temperature for 1 h. The reaction mixture was concentrated in vacuo and the residue purified by preparative reverse-phase HPLC, eluting with a gradient of acetonitrile in water containing 0.5% of formic acid, to afford the title compound as a colorless solid (0.057 g, 11% yield over 3 steps): $^1$H-NMR (300 MHz, DMSO-d$_6$) δ 11.09 (s, 1H), 8.88 (d, J=2.2 Hz, 1H), 8.14 (s, 1H), 7.63 (d, J=7.4 Hz, 1H), 7.52-7.45 (m, 2H), 7.30 (dd, J=11.7, 8.3 Hz, 1H), 6.99 (d, J=2.2 Hz, 1H), 6.79 (d, J=13.7 Hz, 1H), 4.49-4.47 (m, 2H), 3.97 (s, 2H), 3.56 (s, 4H), 2.20-2.13 (m, 2H), one exchangeable proton not observed; MS (ES+) m/z 501.0 (M+1), 503.1 (M+1).

Example 194

Synthesis of 2,6-difluoro-4-((2-fluoro-6-((3-fluoroazetidin-1-yl)methyl)benzyl)amino)-N-(thiazol-4-yl)benzenesulfonamide formate

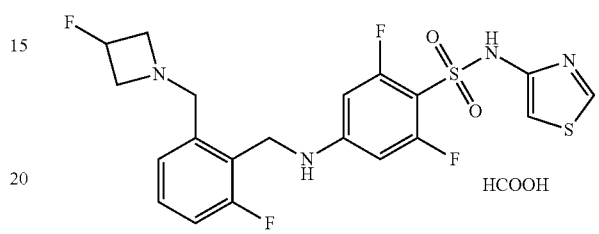

To a mixture of (2-fluoro-6-((3-fluoroazetidin-1-yl)methyl)phenyl)methanamine (0.50 g, 2.36 mmol) and tert-butyl thiazol-4-yl((2,4,6-trifluorophenyl)sulfonyl)carbamate (0.93 g, 2.36 mmol) in anhydrous dimethyl sulfoxide (12 mL) was added N,N-diisopropylethylamine (2.1 mL, 11.8 mmol) and the reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. Concentration of the filtrate in vacuo provided a residue which dissolved in anhydrous dichloromethane (12 mL). To it was added trifluoroacetic acid (5.4 mL, 70.7 mmol) and the reaction mixture was stirred at ambient temperature for 2 h. The reaction mixture was concentrated in vacuo and the residue purified by preparative reverse-phase HPLC, eluting with a gradient of acetonitrile in water containing 0.5% of formic acid, to afford the title compound as a pale yellow solid (0.062 g, 5% yield over 2 steps): $^1$H-NMR (300 MHz, DMSO-d$_6$) δ 11.24-11.17 (m, 1H), 8.90 (d, J=2.1 Hz, 1H), 8.14 (s, 1H), 7.41-7.15 (m, 4H), 6.91-6.90 (m, 1H), 6.40-6.36 (m, 2H), 5.29-5.07 (m, 1H), 4.32-4.30 (m, 2H), 3.11-3.03 (m, 2H), 1.29-1.21 (m, 4H), one exchangeable proton not observed; MS (ES+) m/z 487.0 (M+1).

Example 195

Synthesis of 4-((5-(azetidin-1-ylmethyl)-2-fluorobenzyl)amino)-2,6-difluoro-N-(thiazol-4-yl)benzenesulfonamide formate

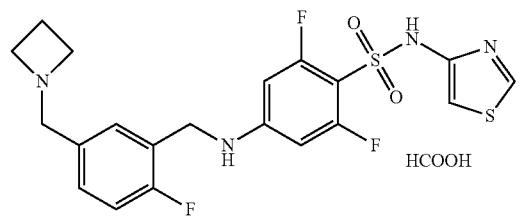 [SMILES: O=S(=O)(Nc1cscn1)c1c(F)cc(NCc2cc(CN3CCC3)ccc2F)cc1F ; "HCOOH"]

Step 1. Preparation of 5-(azetidin-1-ylmethyl)-2-fluorobenzonitrile

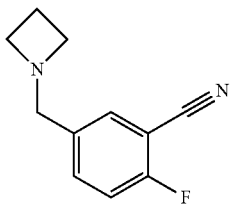 [SMILES: N#Cc1cc(CN2CCC2)ccc1F]

Following the procedure as described in EXAMPLE 16, Step 1 and making variations as required to replace 2-(bromomethyl)benzonitrile with 5-(bromomethyl)-2-fluorobenzonitrile, the title compound was obtained as a colorless oil (1.73 g, 89% yield): $^1$H NMR (300 MHz, CDCl$_3$) δ 7.57-7.50 (m, 2H), 7.16 (t, J=8.6 Hz, 1H), 5.27-5.01 (m, 2H), 3.71-3.61 (m, 4H), 3.26-3.13 (m, 2H); MS (ES+) m/z 209.2 (M+1).

Step 2. Preparation of (5-(azetidin-1-ylmethyl)-2-fluorophenyl)methanamine

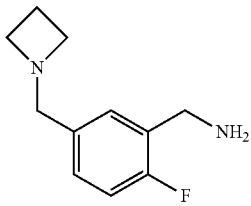 [SMILES: NCc1cc(CN2CCC2)ccc1F]

Following the procedure as described in EXAMPLE 16, Step 2 and making variations as required to replace (2-fluoro-6-((3-fluoroazetidin-1-yl)methyl)phenyl)-methanamine with(5-(azetidin-1-ylmethyl)-2-fluorophenyl)methanamine, the title compound was obtained as a yellow oil (1.37 g, quantitative yield): $^1$H NMR (300 MHz, CDCl$_3$) δ 7.36-7.25 (m, 1H), 7.24-7.12 (m, 1H), 7.02-6.94 (m, 1H), 3.89-3.86 (m, 2H), 3.60-3.56 (m, 2H), 3.30-3.24 (m, 4H), 2.17-2.10 (m, 2H), NH not observed; MS (ES+) m/z 195.2 (M+1).

Step 3. Preparation of 4-((5-(azetidin-1-ylmethyl)-2-fluorobenzyl)amino)-2,6-difluoro-N-(thiazol-4-yl)benzenesulfonamide formate

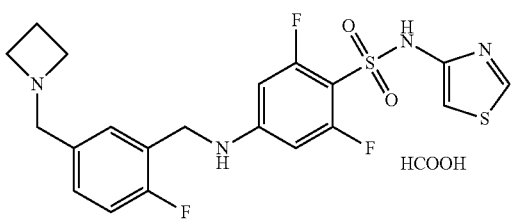 [SMILES: O=S(=O)(Nc1cscn1)c1c(F)cc(NCc2cc(CN3CCC3)ccc2F)cc1F ; "HCOOH"]

Following the procedure as described in EXAMPLE 194 and making variations as required to replace (2-fluoro-6-((3-fluoroazetidin-1-yl)methyl)phenyl)methanamine with (5-(azetidin-1-ylmethyl)-2-fluorophenyl)methanamine, the title compound was obtained as a colorless solid (0.13 g, 27% yield): $^1$H-NMR (300 MHz, DMSO-d$_6$): δ 10.80 (s, 1H), 8.89 (d, J=2.2 Hz, 1H), 8.15 (s, 1H), 7.62-7.58 (m, 1H), 7.40-7.25 (m, 3H), 6.89 (d, J=2.2 Hz, 1H), 6.34-6.30 (m, 2H), 4.36 (d, J=5.6 Hz, 2H), 4.12 (s, 2H), 3.80-3.74 (m, 4H), 2.28-2.17 (m, 2H), one exchangeable proton not observed; MS (ES+) m/z 469.2 (M+1).

Example 196

Synthesis of 4-((2-(azetidin-1-ylmethyl)-3-fluorobenzyl)amino)-2,6-difluoro-N-(thiazol-4-yl)benzenesulfonamide 2,2,2-trifluoroacetate

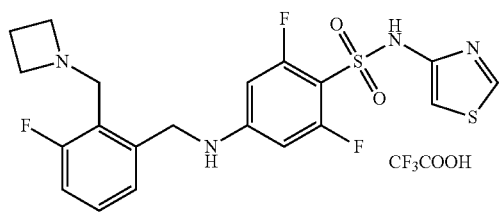 [SMILES: O=S(=O)(Nc1cscn1)c1c(F)cc(NCc2cccc(F)c2CN2CCC2)cc1F ; "CF3COOH"]

Step 1. Preparation of 2-(azetidin-1-ylmethyl)-3-fluorobenzonitrile

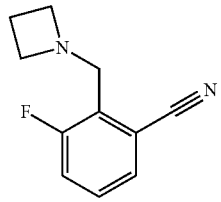 [SMILES: N#Cc1cccc(F)c1CN1CCC1]

Following the procedure as described in EXAMPLE 16, Step 1 and making variations as required to replace 2-(bromomethyl)benzonitrile with 2-(bromomethyl)-3-fluorobenzonitrile, the title compound was obtained as a yellow oil (0.72 g, 81% yield): $^1$H NMR (300 MHz, CDCl$_3$) δ 7.47-7.44 (m, 1H), 7.39-7.28 (m, 2H), 3.78 (d, J=1.8 Hz, 2H), 3.36-3.31 (m, 4H), 2.11-2.01 (m, 2H); MS (ES+) m/z 191.2 (M+1).

Step 2. Preparation of (2-(azetidin-1-ylmethyl)-3-fluorophenyl)methanamine

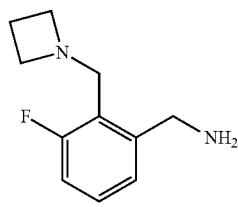 [SMILES: NCc1cccc(F)c1CN1CCC1]

Following the procedure as described in EXAMPLE 16, Step 2 and making variations as required to replace (2-fluoro-6-((3-fluoroazetidin-1-yl)methyl)phenyl)-methanamine with 2-(azetidin-1-ylmethyl)-3-fluorobenzonitrile, the title compound was obtained as a orange oil (0.84 g, quantitative yield): ¹H NMR (300 MHz, CDCl₃) δ 7.23-7.12 (m, 2H), 6.97 (dddd, J=9.6, 8.1, 4.5, 1.6 Hz, 1H), 4.40-4.39 (m, 1H), 3.91-3.89 (m, 1H), 3.67 (dd, J=4.3, 1.6 Hz, 1H), 3.65-3.62 (m, 1H), 3.29-3.21 (m, 4H), 2.10-1.97 (m, 2H), NH not observed; MS (ES+) m/z 195.2 (M+1).

Step 3. Preparation of 4-((2-(azetidin-1-ylmethyl)-3-fluorobenzyl)amino)-2,6-difluoro-N-(thiazol-4-yl)benzenesulfonamide 2,2,2-trifluoroacetate

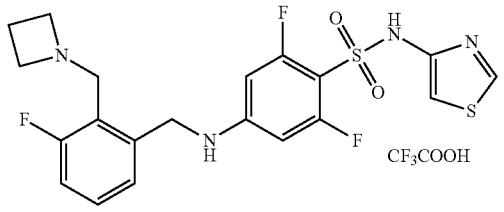 [SMILES: O=S(=O)(Nc1cscn1)c1c(F)cc(NCc2cccc(F)c2CN2CCC2)cc1F ; "CF3COOH"]

To a mixture of (2-(azetidin-1-ylmethyl)-3-fluorophenyl)methanamine (0.25 g, 1.29 mmol) and tert-butyl thiazol-4-yl((2,4,6-trifluorophenyl)sulfonyl)carbamate (0.51 g, 1.29 mmol) in anhydrous dimethyl sulfoxide (6 mL) was added N,N-diisopropylethylamine (1.1 mL, 6.44 mmol) and the reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. Concentration of the filtrate and purification of the residue by column chromatography, eluting with a gradient of 0 to 50% of ethyl acetate (containing 10% triethylamine and 10% 2-propanol) in hexanes, provided tert-butyl ((4-((2-(azetidin-1-ylmethyl)-3-fluorobenzyl)amino)-2,6-difluorophenyl)sulfonyl)(thiazol-4-yl)carbamate (yield not determined): MS (ES+) m/z 569.0 (M+1). To it was then added anhydrous dichloromethane (5 mL) and trifluoroacetic acid (2.2 mL, 28.3 mmol). The reaction mixture was stirred at ambient temperature for 1 h and then concentrated in vacuo to afford the title compound as a colorless solid (0.15 g, 25% yield over 2 steps): ¹H-NMR (300 MHz, DMSO-d₆) δ 11.21 (s, 1H), 10.03-9.89 (m, 1H) 8.90 (d, J=2.2 Hz, 1H), 7.55-7.46 (m, 2H), 7.32-7.26 (m, 1H), 7.20-7.17 (m, 1H), 6.91 (d, J=2.2 Hz, 1H), 6.33 (d, J=12.4 Hz, 2H), 4.49-4.46 (m, 4H), 4.23-4.02 (m, 4H), 2.41-2.23 (m, 2H); MS (ES+) m/z 469.1 (M+1).

Example 197

Synthesis of 4-((2-(azetidin-1-ylmethyl)-3-fluorobenzyl)amino)-3-chloro-2,6-difluoro-N-(thiazol-4-yl)benzenesulfonamide 2,2,2-trifluoroacetate

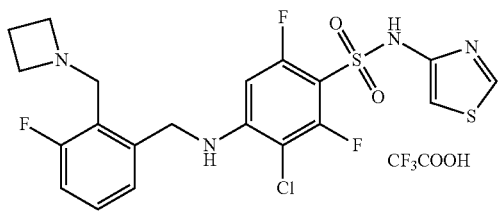 [SMILES: O=S(=O)(Nc1cscn1)c1c(F)cc(NCc2cccc(F)c2CN2CCC2)c(Cl)c1F ; "CF3COOH"]

Step 1. Preparation of 3-chloro-2,4,6-trifluorobenzenesulfonyl chloride

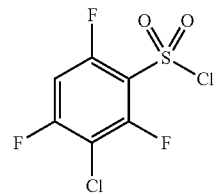 [SMILES: O=S(=O)(Cl)c1c(F)cc(F)c(Cl)c1F]

To chlorosulfonic acid (18.0 mL, 270.3 mmol) was added 2-chloro-1,3,5-trifluorobenzene (7.20 g, 43.3 mmol) at 0° C. The resulting mixture was stirred for 18 h at ambient temperature and then heated to 65° C. The reaction mixture was allowed to cool to ambient temperature and then added dropwise to a mixture of ice (400 g) and concentrated hydrochloric acid (125 mL), maintaining a temperature below 5° C. After the addition was complete, the mixture was vigorously stirred at 0° C. for 1 h. The precipitate was filtered off and rinsed with water (250 mL) to provide the title compound as a colorless amorphous solid (8.02 g, 70% yield): ¹H NMR (300 MHz, CDCl₃) δ 7.07 (ddd, J=9.8, 8.3, 2.3 Hz, 1H).

Step 2. Preparation of tert-butyl ((3-chloro-2,4,6-trifluorophenyl)sulfonyl)(thiazol-4-yl)carbamate

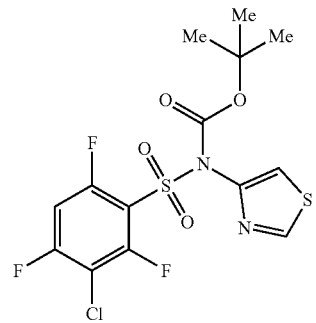 [SMILES: CC(C)(C)OC(=O)N(c1cscn1)S(=O)(=O)c1c(F)cc(F)c(Cl)c1F]

To a solution of tert-butyl thiazol-4-ylcarbamate (3.32 g, 16.6 mmol) in anhydrous tetrahydrofuran (210 mL) was added a 1 M solution of lithium bis(trimethylsilyl)amide in tetrahydrofuran (16.6 mL, 16.6 mmol) at 0° C. The reaction mixture was stirred at 0° C. for 1 h, cooled to −78° C., and a solution of 3-chloro-2,4,6-trifluorobenzenesulfonyl chloride (4.00 g, 15.09 mmol) in anhydrous tetrahydrofuran (15 mL) was then added dropwise to it. The reaction mixture was allowed to warm to ambient temperature and stirred for 16 h. The reaction mixture was concentrated in vacuo to a volume of approximately 50 mL. After dilution with ethyl acetate (160 mL), the organic layer was washed with saturated ammonium chloride (150 mL), saturated sodium bicarbonate (150 mL), brine (50 mL), and dried over anhydrous sodium sulfate. Filtration and concentration of the filtrate in vacuo provided a residue which was purified by column chromatography, eluting with a gradient of 10 to 50% of ethyl acetate in hexanes, to provide the title compound as a colorless solid (3.35 g, 52% yield): ¹H NMR (300 MHz, CDCl₃) δ 8.83 (d, J=2.2 Hz, 1H), 7.55 (d, J=2.2 Hz, 1H), 6.99 (ddd, J=10.0, 8.2, 2.0 Hz, 1H), 1.40 (s, 9H); MS (ES+) m/z 329.0 (M−99), 331.0 (M−99).

Step 3. Preparation of 4-((2-(azetidin-1-ylmethyl)-3-fluorobenzyl)amino)-3-chloro-2,6-difluoro-N-(thiazol-4-yl)benzenesulfonamide 2,2,2-trifluoroacetate

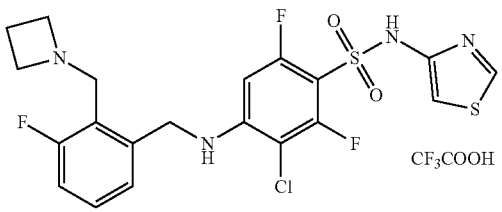 [SMILES: O=S(=O)(Nc1cscn1)c1c(F)cc(NCc2cccc(F)c2CN2CCC2)c(Cl)c1F ; "CF3COOH"]

Following the procedure as described in EXAMPLE 196, Step 3 and making variations as required to replace tert-butyl thiazol-4-yl((2,4,6-trifluorophenyl)sulfonyl)carbamate with tert-butyl ((3-chloro-2,4,6-trifluorophenyl)sulfonyl)(thiazol-4-yl)carbamate, the title compound was obtained as a colorless solid (0.24 g, 47% yield): $^1$H-NMR (300 MHz, DMSO-$d_6$) δ 11.39-11.37 (m, 1H), 10.08-9.90 (m, 1H), 8.92-8.89 (m, 1H), 7.55-7.43 (m, 2H), 7.29-7.23 (m, 1H), 7.12-7.09 (m, 1H), 7.02-6.98 (m, 1H), 6.47-6.42 (m, 1H), 4.62-4.53 (m, 4H), 4.22-4.07 (m, 4H), 2.41-2.26 (m, 2H); MS (ES+) m/z 503.1 (M+1), 505.1 (M+1).

Example 198

Synthesis of 4-((2-((2,2-dimethylazetidin-1-yl)methyl)-3-fluorobenzyl)amino)-2,6-difluoro-N-(thiazol-4-yl)benzenesulfonamide formate

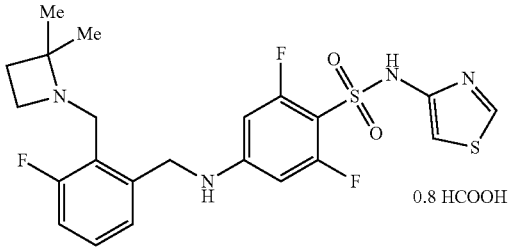 [SMILES: CC1(C)CCN1Cc1c(F)cccc1CNc1cc(F)c(S(=O)(=O)Nc2cscn2)c(F)c1 ; "0.8 HCOOH"]

Step 1. Preparation of 2-((2,2-dimethylazetidin-1-yl)methyl)-3-fluorobenzonitrile

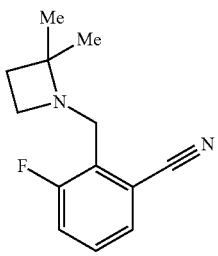 [SMILES: CC1(C)CCN1Cc1c(F)cccc1C#N]

To a solution of 2-(bromomethyl)-3-fluorobenzonitrile (0.35 g, 1.6 mmol) and 2,2-dimethylazetidine (0.15 g, 1.7 mmol) in anhydrous dichloromethane (12 mL) was added N,N-diisopropylethylamine (0.37 mL, 2.1 mmol) and the reaction mixture was stirred at ambient temperature for 16 h. The reaction mixture was diluted with saturated ammonium chloride solution (20 mL) and extracted with dichloromethane (3×40 mL). The combined organic layers were washed with brine (80 mL), dried over anhydrous sodium sulfate, and filtered. Concentration of the filtrate in vacuo afforded the title compound as yellow oil (0.34 g, 96% yield): $^1$H NMR (300 MHz, CDCl$_3$) δ 7.44 (dt, J=7.5, 2.0 Hz, 1H), 7.36-7.27 (m, 1H), 7.26-7.23 (m, 1H), 3.77-3.67 (m, 2H), 3.33-3.22 (m, 2H), 1.98-1.87 (m, 2H), 1.35-1.25 (m, 6H); MS (ES+) m/z 219.2 (M+1).

Step 2. Preparation of (2-((2,2-dimethylazetidin-1-yl)methyl)-3-fluorophenyl)-methanamine

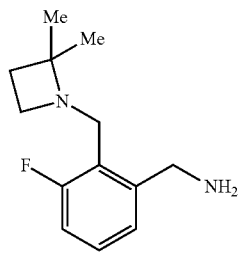 [SMILES: CC1(C)CCN1Cc1c(F)cccc1CN]

To a mixture of Raney-Nickel (0.7 mL) and 2-((2,2-dimethylazetidin-1-yl)methyl)-3-fluorobenzonitrile (0.34 g, 1.6 mmol) in ethanol (22 mL) was added concentrated ammonium hydroxide (5.4 mL). The reaction mixture was stirred under an atmosphere of hydrogen (1 atm) at ambient temperature for 16 h. The reaction mixture was filtered through celite, and the filtrate was dried over anhydrous magnesium sulfate. Filtration and concentration of the filtrate in vacuo afforded the title compound as an orange oil (0.38 g, quantitative yield): $^1$H NMR (300 MHz, CDCl$_3$) δ 7.20 (d, J=1.5 Hz, 2H), 7.03-6.99 (m, 1H), 4.02 (s, 2H), 3.69 (d, J=1.2 Hz, 2H), 3.10 (s, 2H), 1.85 (d, J=7.4 Hz, 2H), 1.30 (s, 6H), NH not observed; MS (ES+) m/z 223.2 (M+1).

Step 3. Preparation of tert-butyl ((3-bromo-2,4,6-trifluorophenyl)sulfonyl)(thiazol-4-yl)carbamate

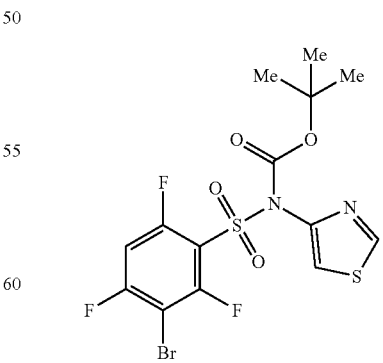

To a solution of tert-butyl thiazol-4-ylcarbamate (26.90 g, 134.00 mmol) in anhydrous tetrahydrofuran (500 mL) was added lithium bis(trimethylsilyl)amide (1 M in tetrahydrofuran, 168 mL, 168.0 mmol) at −78° C. The reaction mixture was stirred at −78° C. for 20 minutes, after which a solution of 3-bromo-2,4,6-trifluorobenzene-1-sulfonyl chloride (50.00 g, 161.00 mmol) in anhydrous tetrahydrofuran (100 mL) was added dropwise at −78° C. The reaction mixture was allowed to warm to ambient temperature and stirred for 12 h. The reaction mixture was concentrated in vacuo and the residue was diluted with ethyl acetate (3×400 mL). The organic phase was washed with water (3×400 mL), dried over anhydrous sodium sulfate, and filtered. Concentration of the filtrate in vacuo and trituration of the residue in methanol (100 mL) afforded the title compound as a colorless solid (40.00 g, 62% yield): $^1$H NMR (400 MHz, CDCl$_3$) δ 8.81 (d, J=2.3 Hz, 1H), 7.54 (d, J=2.2 Hz, 1H), 6.97 (ddd, J=9.8, 8.0, 2.2 Hz, 1H), 1.47-1.34 (m, 9H); MS (ES+) m/z 496.9 (M+23).

Step 4. Preparation of tert-butyl ((3-bromo-4-((2-((2,2-dimethylazetidin-1-yl)methyl)-3-fluorobenzyl)amino)-2,6-difluorophenyl)sulfonyl)(thiazol-4-yl)carbamate

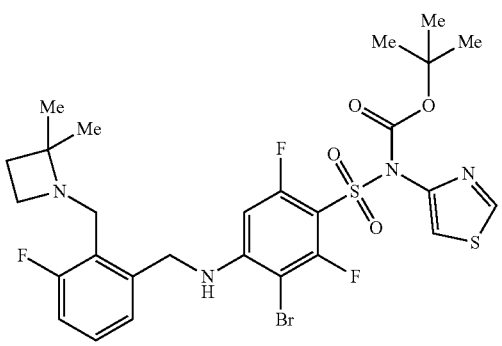 [SMILES: CC(C)(C)OC(=O)N(c1cscn1)S(=O)(=O)c1c(F)cc(NCc2cccc(F)c2CN2CCC2(C)C)c(Br)c1F]

To a mixture of tert-butyl ((3-bromo-2,4,6-trifluorophenyl)sulfonyl)(thiazol-4-yl)carbamate (0.34 g, 0.71 mmol) and potassium carbonate (0.20 g, 1.42 mmol) in anhydrous dimethyl sulfoxide (4 mL) was slowly added a solution of (2-((2,2-dimethylazetidin-1-yl)methyl)-3-fluorophenyl)methanamine (0.19 g, 0.85 mmol) in anhydrous dimethyl sulfoxide (3 mL) and the reaction mixture was stirred at ambient temperature for 16 h. The reaction mixture was diluted with water (20 mL) and ethyl acetate (20 mL). The aqueous layer was extracted with ethyl acetate (2×30 mL). The combined organic phase was washed with brine (50 mL), dried over anhydrous sodium sulfate, and filtered. Concentration of the filtrate in vacuo and purification of the residue by column chromatography, eluting with a gradient of 0 to 40% of ethyl acetate (containing 0.2% of ammonium hydroxide) in heptane, afforded the title compound as a yellow solid (0.19 g, 40% yield): $^1$H NMR (300 MHz, CDCl$_3$) δ 8.80 (d, J=2.3 Hz, 1H), 7.51 (d, J=2.2 Hz, 1H), 7.22-7.17 (m, 1H), 7.08-6.88 (m, 3H), 6.62-6.57 (m, 1H), 4.52-4.50 (m, 2H), 3.67-3.66 (m, 2H), 3.14-3.10 (m, 2H), 1.95-1.90 (m, 2H), 1.38 (s, 9H), 1.27 (s, 6H); MS (ES+) m/z 675.2 (M+1), 677.2 (M+1).

Step 5. Preparation of 4-((2-((2,2-dimethylazetidin-1-yl)methyl)-3-fluorobenzyl)amino)-2,6-difluoro-N-(thiazol-4-yl)benzenesulfonamide formate

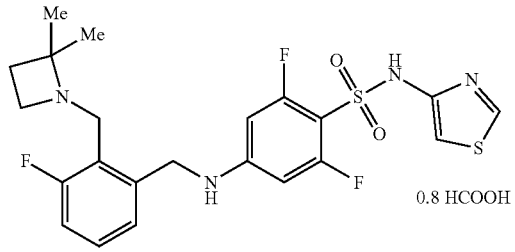 [SMILES: CC1(C)CCN1Cc1c(F)cccc1CNc1cc(F)c(S(=O)(=O)Nc2cscn2)c(F)c1 ; "0.8 HCOOH"]

To a mixture of tert-butyl ((3-bromo-4-((2-((2,2-dimethylazetidin-1-yl)methyl)-3-fluorobenzyl)amino)-2,6-difluorophenyl)sulfonyl)(thiazol-4-yl)carbamate (0.19 g, 0.29 mmol) and palladium on carbon (4.5% palladium, wet, 0.034 g) in methanol (6 mL) was added triethylamine (0.16 mL, 1.15 mmol). The reaction mixture was stirred under an atmosphere of hydrogen (1 atm) at 60° C. for 7 h. The reaction mixture was allowed to cool to ambient temperature, filtered through a pad celite, and the filtrate was concentrated in vacuo. To the residue was added methanol (6 mL), alladium on carbon (4.5% palladium, wet, 0.034 g), and triethylamine (0.16 mL, 1.15 mmol). The reaction mixture was stirred under an atmosphere of hydrogen (1 atm) at 60° C. for 2 h. After cooling to ambient temperature, the mixture was filtered through a pad of celite. Concentration of the filtrate in vacuo provided a residue which was dissolved in anhydrous dichloromethane (7 mL). To it was added trifluoroacetic acid (0.52 mL, 6.73 mmol) and the reaction mixture was stirred at ambient temperature for 3.5 h. The reaction mixture was concentrated in vacuo and the residue purified by preparative reverse-phase HPLC, eluting with a gradient of acetonitrile in water containing 0.5% of formic acid, to afford the title compound as a colorless solid (0.097 g, 58% yield over 2 steps): $^1$H-NMR (300 MHz, DMSO-d$_6$) δ 8.88 (d, J=2.1 Hz, 1H), 8.14 (s, 0.8H), 7.74 (s, 1H), 7.29-7.22 (m, 1H), 7.10-7.04 (m, 2H), 6.89 (d, J=2.2 Hz, 1H), 6.42 (d, J=12.6 Hz, 2H), 4.50 (d, J=3.3 Hz, 2H), 3.66 (s, 2H), 3.14-3.08 (m, 2H), 1.85 (t, J=6.9 Hz, 2H), 1.23 (s, 6H), NH and COOH not observed; MS (ES+) m/z 497.2 (M+1).

Example 199

Synthesis of 4-((2-chloro-6-((2,2-dimethylazetidin-1-yl)methyl)benzyl)amino)-2,6-difluoro-N-(thiazol-4-yl)benzenesulfonamide formate

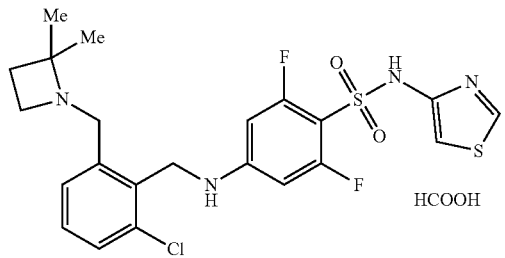 [SMILES: CC1(C)CCN1Cc1cccc(Cl)c1CNc1cc(F)c(S(=O)(=O)Nc2cscn2)c(F)c1 ; "HCOOH"]

Step 1. Preparation of 2-chloro-6-((2,2-dimethylazetidin-1-yl)methyl)benzonitrile

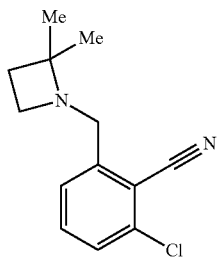 [SMILES: CC1(C)CCN1Cc1cccc(Cl)c1C#N]

Following the procedure as described in EXAMPLE 198, Step 1 and making variations as required to replace 2-(bromomethyl)-3-fluorobenzonitrile with 2-(bromomethyl)-6-chlorobenzonitrile, the title compound was obtained as a yellow oil (1.06 g, quantitative yield): $^1$H NMR (300 MHz, CDCl$_3$) δ 7.48-7.34 (m, 3H), 3.73 (s, 2H), 3.19-3.14 (m, 2H), 1.95-1.90 (m, 2H), 1.61-1.43 (m, 2H), 1.33-1.23 (m, 6H); MS (ES+) m/z 235.1 (M+1), 237.1 (M+1).

Step 2. Preparation of (2-chloro-6-((2,2-dimethylazetidin-1-yl)methyl)phenyl)-methanamine

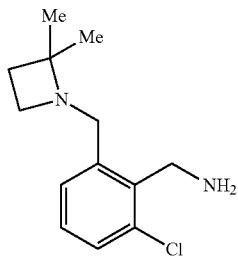 [SMILES: CC1(C)CCN1Cc1cccc(Cl)c1CN]

Following the procedure as described in EXAMPLE 198, Step 2 and making variations as required to replace 2-((2,2-dimethylazetidin-1-yl)methyl)-3-fluorobenzonitrile with 2-chloro-6-((2,2-dimethylazetidin-1-yl)methyl)benzonitrile, the title compound was obtained as an orange oil (0.99 g, quantitative yield): MS (ES+) m/z 239.2 (M+1), 241.2 (M+1).

Step 3. Preparation of tert-butyl ((3-bromo-4-((2-chloro-6-((2,2-dimethylazetidin-1-yl)methyl)benzyl)amino)-2,6-difluorophenyl)sulfonyl)(thiazol-4-yl)carbamate

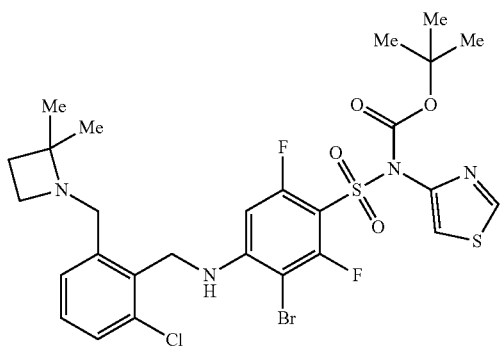 [SMILES: CC(C)(C)OC(=O)N(c1cscn1)S(=O)(=O)c1c(F)cc(NCc2c(Cl)cccc2CN2CCC2(C)C)c(Br)c1F]

Following the procedure as described in EXAMPLE 198, Step 3 and making variations as required to replace (2-((2,2-dimethylazetidin-1-yl)methyl)-3-fluorophenyl)methanamine with (2-chloro-6-((2,2-dimethylazetidin-1-yl)methyl)phenyl)methanamine, the title compound was obtained as beige solid (0.41 g, 71% yield): $^1$H NMR (300 MHz, CDCl$_3$) δ 8.81 (d, J=2.2 Hz, 1H), 7.52 (d, J=2.3 Hz, 1H), 7.37 (dd, J=7.6, 1.7 Hz, 1H), 7.23-7.14 (m, 2H), 6.93-6.87 (m, 1H), 6.66-6.61 (m, 1H), 4.58 (d, J=5.6 Hz, 2H), 3.63 (s, 2H), 3.07 (t, J=7.0 Hz, 2H), 1.95-1.91 (m, 2H), 1.40 (s, 9H), 1.24 (s, 6H); MS (ES+) m/z 691.1 (M+1), 693.1 (M+1), 695.1 (M+1).

Step 4. Preparation of 4-((2-chloro-6-((2,2-dimethylazetidin-1-yl)methyl)benzyl)amino)-2,6-difluoro-N-(thiazol-4-yl)benzenesulfonamide formate

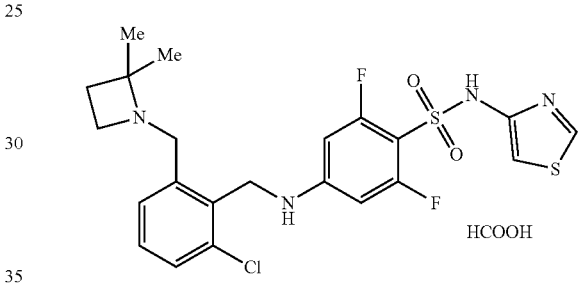

To a mixture of tert-butyl ((3-bromo-4-((2-chloro-6-((2,2-dimethylazetidin-1-yl)methyl)benzyl)amino)-2,6-difluorophenyl)sulfonyl)(thiazol-4-yl)carbamate (0.40 g, 0.59 mmol) and palladium on carbon (4.5% palladium, wet, 0.070 g) in methanol (6 mL) was added triethylamine (0.33 mL, 2.37 mmol). The reaction mixture was stirred under an atmosphere of hydrogen (1 atm) at 60° C. for 7 h. After cooling to ambient temperature, the mixture was filtered through a pad of celite. Concentration of the filtrate in vacuo provided a residue which was dissolved in anhydrous dichloromethane (14 mL). To it was added trifluoroacetic acid (1.08 mL, 14.1 mmol) and the reaction mixture was stirred at ambient temperature for 3.5 h. The reaction mixture was concentrated in vacuo and the residue purified by preparative reverse-phase HPLC, eluting with a gradient of acetonitrile in water containing 0.5% of formic acid, to afford the title compound as a colorless solid (0.14 g, 39% yield): $^1$H-NMR (300 MHz, DMSO-d$_6$) δ 8.89 (d, J=2.2 Hz, 1H), 8.19 (s, 1H), 7.42-7.27 (m, 3H), 7.18-7.15 (m, 1H), 6.87 (d, J=2.2 Hz, 1H), 6.40 (d, J=12.6 Hz, 2H), 4.44 (s, 2H), 3.51 (s, 2H), 2.96 (t, J=6.8 Hz, 2H), 1.76 (t, J=6.9 Hz, 2H), 1.09 (s, 6H), NH and COOH not observed; MS (ES+) m/z 513.2 (M+1), 515.2 (M+1).

Example 200

Synthesis of 4-((2-(azetidin-1-ylmethyl)benzyl)amino)-5-chloro-2-fluoro-N-(6-fluoropyridin-2-yl)benzenesulfonamide

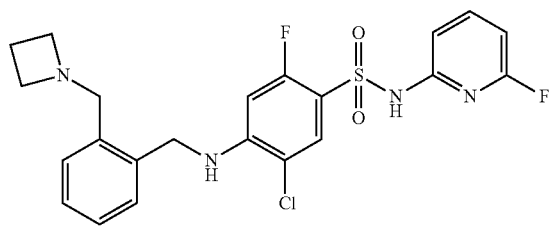 [SMILES: O=S(=O)(Nc1cccc(F)n1)c1cc(Cl)c(NCc2ccccc2CN2CCC2)cc1F]

Step 1. Preparation of 4-((2-(azetidin-1-ylmethyl)benzyl)amino)-5-chloro-N-(2,4-dimethoxybenzyl)-2-fluoro-N-(6-fluoropyridin-2-yl)benzenesulfonamide

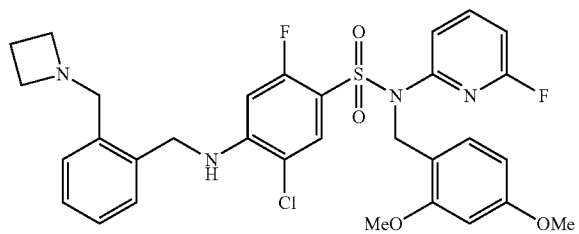 [SMILES: COc1ccc(CN(c2cccc(F)n2)S(=O)(=O)c2cc(Cl)c(NCc3ccccc3CN3CCC3)cc2F)c(OC)c1]

Following the procedure as described in EXAMPLE 72, Step 1 and making non-critical variations as required to replace (S)-1-phenyl-2-(pyrrolidin-1-yl)ethan-1-amine hydrochloride with (2-(azetidin-1-ylmethyl)phenyl)methanamine, the title compound was obtained as a colorless solid (0.21 g, 30% yield): MS (ES+) m/z 629.2, 631.2 (M+1).

Step 2. Preparation of 4-((2-(azetidin-1-ylmethyl)benzyl)amino)-5-chloro-2-fluoro-N-(6-fluoropyridin-2-yl)benzenesulfonamide

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with 4-((2-(azetidin-1-ylmethyl)benzyl)amino)-5-chloro-N-(2,4-dimethoxybenzyl)-2-fluoro-N-(6-fluoropyridin-2-yl)benzenesulfonamide, the title compound was obtained as a colorless solid (0.012 g, 13% yield): ¹H NMR (300 MHz, DMSO-d₆) δ 11.33 (s, 1H), 7.83-7.70 (m, 3H), 7.32-7.19 (m, 4H), 6.90-6.80 (m, 2H), 6.68-6.61 (m, 1H), 4.49-4.47 (m, 2H), 3.69 (s, 2H), 3.29-3.19 (m, 4H), 2.09-1.97 (m, 2H); MS (ES+) m/z 479.1 (M+1), 481.1 (M+1).

Example 201

Synthesis of 2,6-difluoro-4-((2-fluoro-6-((isopropyl(methyl)amino)methyl) benzyl)amino)-N-(isoxazol-3-yl)benzenesulfonamide 2,2,2-trifluoroacetate

Step 1. Preparation of tert-butyl isoxazol-3-yl((2,4,6-trifluorophenyl)sulfonyl)carbamate

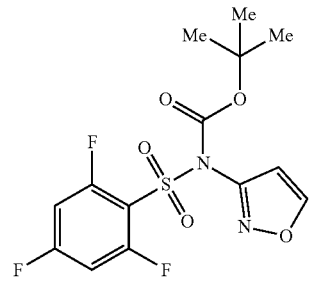 [SMILES: CC(C)(C)OC(=O)N(c1ccon1)S(=O)(=O)c1c(F)cc(F)cc1F]

Following the procedure as described in EXAMPLE 27, Step 1 and making non-critical variations as required to replace N-(2,4-dimethoxybenzyl)thiazol-2-amine with tert-butyl isoxazol-3-ylcarbamate (prepared according to WO2001040222), the title compound was obtained as a colorless solid (2.56 g, 38% yield): MS (ES+) m/z 379.1 (M+1).

Step 2. Preparation of tert-butyl ((2,6-difluoro-4-((2-fluoro-6-((isopropyl(methyl)amino)methyl)benzyl)amino)phenyl)sulfonyl)(isoxazol-3-yl)carbamate

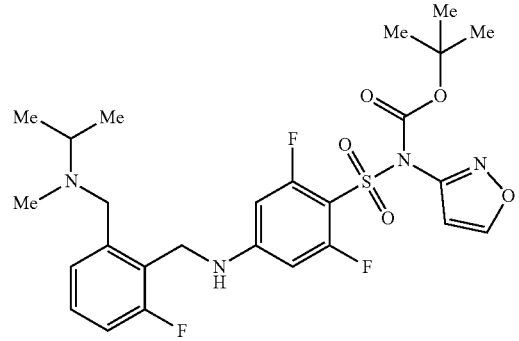 [SMILES: CC(C)N(C)Cc1cccc(F)c1CNc1cc(F)c(S(=O)(=O)N(C(=O)OC(C)(C)C)c2ccon2)c(F)c1]

To a mixture of tert-butyl isoxazol-3-yl((2,4,6-trifluorophenyl)sulfonyl)carbamate (1.0 g, 2.64 mmol), N-(2-(aminomethyl)-3-fluorobenzyl)-N-methylpropan-2-amine (0.56 g, 2.64 mmol), and in anhydrous dimethyl sulfoxide (25 mL) was added potassium carbonate (0.73 g, 5.28 mmol) and the reaction mixture was stirred at ambient temperature for 2 h. The reaction mixture was then diluted with saturated ammonium chloride (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in heptane, afforded the title compound as a colorless solid (0.21 g, 11% yield): MS (ES+) m/z 469.2 (M−99).

Step 3. Preparation of 2,6-difluoro-4-((2-fluoro-6-((isopropyl(methyl)amino)methyl)-benzyl)amino)-N-(isoxazol-3-yl)benzenesulfonamide 2,2,2-trifluoroacetate

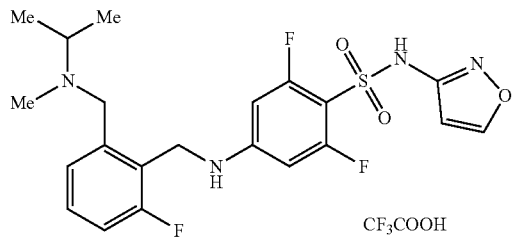 [SMILES: CC(C)N(C)Cc1cccc(F)c1CNc1cc(F)c(S(=O)(=O)Nc2ccon2)c(F)c1 ; "CF3COOH"]

To a solution of tert-butyl ((2,6-difluoro-4-((2-fluoro-6-((isopropyl(methyl)amino)methyl)-benzyl)amino)phenyl)sulfonyl)(isoxazol-3-yl)carbamate (0.2 g, 0.35 mmol) in anhydrous dichloromethane (3 mL) was added trifluoroacetic acid (0.4 mL, 5.28 mmol) at 0° C. The reaction mixture was stirred at ambient temperature for 16 h and then concentrated in vacuo. The residue was purified by column chromatography, eluting with a gradient of 0 to 20% of methanol in dichloromethane, to afford the title compound as colorless solid (0.089 g, 54% yield): $^1$H NMR (300 MHz, DMSO-$d_6$) δ 11.77 (s, 1H), 9.33 (s, 1H), 8.75-8.72 (m, 1H), 7.65-7.28 (m, 4H), 6.46-6.36 (m, 2H), 6.33-6.30 (m, 1H), 4.45-4.10 (m, 4H), 3.62-3.49 (m, 1H), 2.54 (s, 3H), 1.27-1.17 (m, 6H); MS (ES+) m/z 469.0 (M+1).

Example 202

Synthesis of 4-((2-((tert-butyl(methyl)amino) methyl)benzyl)amino)-2,6-difluoro-N-(thiazol-4-yl) benzenesulfonamide 2,2,2-trifluoroacetate

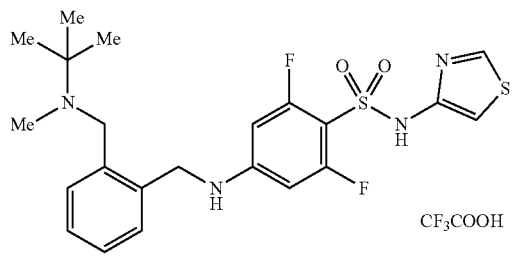 [SMILES: CN(Cc1ccccc1CNc1cc(F)c(S(=O)(=O)Nc2cscn2)c(F)c1)C(C)(C)C ; "CF3COOH"]

Step 1. Preparation of 2-((tert-butyl(methyl)amino)methyl)benzonitrile

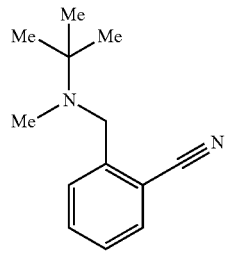 [SMILES: CN(Cc1ccccc1C#N)C(C)(C)C]

To a mixture of 2-(bromomethyl)benzonitrile (3.37 g, 17.21 mmol) and N-tert-butylmethylamine (1.5 g, 17.21 mmol) in anhydrous dimethyl sulfoxide (28 mL) was added potassium carbonate (4.76 g, 34.42 mmol) and the reaction mixture was stirred at ambient temperature for 16 h. The mixture was then diluted with water (40 mL) and extracted with diethyl ether (3×40 mL). The combined organic layers were washed water (30 mL), brine (40 mL), dried over anhydrous magnesium sulfate, filtered and the filtrate concentrated in vacuo. The residue was purified by column chromatography, eluting with a gradient of 0 to 10% of methanol in dichloromethane, to afford the title compound as a colorless oil (2.38 g, 51% yield): MS (ES+) m/z 203.3 (M+1).

Step 2. Preparation of N-(2-(aminomethyl)benzyl)-N,2-dimethylpropan-2-amine

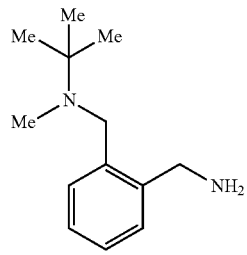 [SMILES: CN(Cc1ccccc1CN)C(C)(C)C]

Following the procedure as described in EXAMPLE 16, Step 2 and making non-critical variations as required to replace 2-(azetidin-1-ylmethyl)benzonitrile with 2-((tert-butyl(methyl)amino)methyl)benzonitrile, the title compound was obtained as a pale yellow solid (2.1 g, 86% yield): MS (ES+) m/z 207.3 (M+1).

Step 3. Preparation of 2,4,6-trifluoro-N-(thiazol-4-yl)benzenesulfonamide

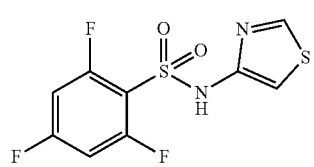 [SMILES: O=S(=O)(Nc1cscn1)c1c(F)cc(F)cc1F]

To a solution of tert-butyl thiazol-4-yl((2,4,6-trifluorophenyl)sulfonyl)carbamate (21.0 g, 53.1 mmol) in dichloromethane (25 mL) was added trifluoroacetic acid (12 mL). The mixture was stirred at ambient temperature for 16 h and then concentrated in vacuo to afforded the title compound as a colorless solid (15.5 g, 99% yield): MS (ES+) m/z 295.2 (M+1).

Step 4. Preparation of 2,4,6-trifluoro-N-(4-methoxybenzyl)-N-(thiazol-4-yl)benzenesulfonamide

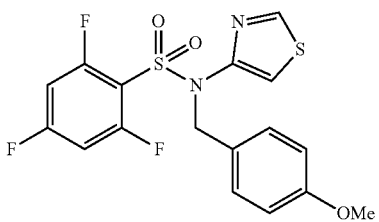 [SMILES: COc1ccc(CN(c2cscn2)S(=O)(=O)c2c(F)cc(F)cc2F)cc1]

To a solution of 2,4,6-trifluoro-N-(thiazol-4-yl)benzenesulfonamide (15.5 g, 52.5 mmol) in anhydrous dimethyl sulfoxide (75 mL) was added 4-methoxybenzyl chloride (12.3 g, 78.8 mmol) and sodium bicarbonate (22.1 g, 262.5 mmol) and the reaction mixture was stirred at ambient temperature for 16 h. The reaction mixture was diluted with ethyl acetate (200 mL), washed with saturated ammonium chloride (2×150 mL), brine (100 mL), and dried over anhydrous sodium sulfate. Concentration of the filtrate in vacuo and purification of the residue by column chromatography, eluting with a gradient of 0 to 40% of ethyl acetate in hexanes, provided the title compound as a colorless solid (18.6 g, 85% yield): $^1$H NMR (300 MHz, CDCl$_3$) δ 8.57 (d, J=2.3 Hz, 1H), 7.25-7.21 (m, 3H), 6.81-6.72 (m, 4H), 5.07 (s, 2H), 3.77 (s, 3H); MS (ES+) m/z 415.0 (M+1).

Step 3. Preparation of 4-((2-((tert-butyl(methyl)amino)methyl)benzyl)amino)-2,6-difluoro-N-(4-methoxybenzyl)-N-(thiazol-4-yl)benzenesulfonamide

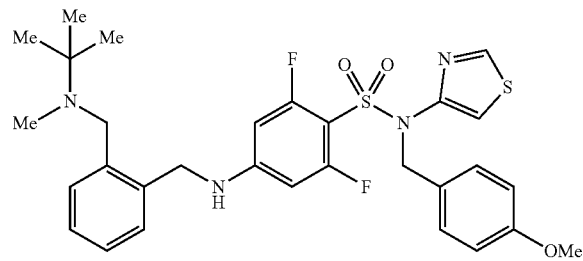 [SMILES: COc1ccc(CN(c2cscn2)S(=O)(=O)c2c(F)cc(NCc3ccccc3CN(C)C(C)(C)C)cc2F)cc1]

To a mixture of 2,4,6-trifluoro-N-(4-methoxybenzyl)-N-(thiazol-4-yl)benzenesulfonamide (1.05 g, 2.54 mmol), and N-(2-(aminomethyl)benzyl)-N,2-dimethylpropan-2-amine (0.52 g, 2.54 mmol) in anhydrous dimethyl sulfoxide (20 mL) was added potassium carbonate (0.70 g, 5.08 mmol) and the reaction mixture was stirred at ambient temperature for 16 h. The reaction mixture was diluted with saturated ammonium chloride (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in heptane, afforded the title compound as a colorless solid (0.52 g, 34% yield): MS (ES+) m/z 601.6 (M+1).

Step 4. Preparation of 4-((2-((tert-butyl(methyl)amino)methyl)benzyl)amino)-2,6-difluoro-N-(thiazol-4-yl)benzenesulfonamide 2,2,2-trifluoroacetate

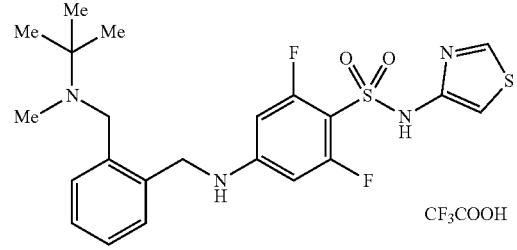 [SMILES: CN(Cc1ccccc1CNc1cc(F)c(S(=O)(=O)Nc2cscn2)c(F)c1)C(C)(C)C ; "CF3COOH"]

To a solution of 4-((2-((tert-butyl(methyl)amino)methyl)benzyl)amino)-2,6-difluoro-N-(4-methoxybenzyl)-N-(thiazol-4-yl)benzenesulfonamide (0.52 g, 0.87 mmol) in anhydrous dichloromethane (7 mL) was added trifluoroacetic acid (7 mL) and the mixture was heated to reflux for 16 h. After cooling to ambient temperature, the mixture was concentrated in vacuo. Purification of the residue by column chromatography, eluting with a gradient of 0 to 20% of methanol in dichloromethane, afforded the title compound as colorless solid (0.495 g, 96% yield): $^1$H NMR (300 MHz, DMSO-d$_6$) δ 11.20 (s, 1H), 9.01-8.89 (m, 2H), 7.64-7.34 (m, 5H), 6.90 (d, J=2.2 Hz, 1H), 6.33 (d, J=12.6 Hz, 2H), 4.75-4.65 (m, 1H), 4.52-4.45 (m, 2H), 4.04-3.92 (m, 1H), 2.65-2.55 (m, 3H), 1.43 (s, 9H); MS (ES+) m/z 481.1 (M+1).

Example 203

Synthesis of 4-((2-((tert-butyl(methyl)amino)methyl)-6-fluorobenzyl)amino)-2,3-difluoro-N-(thiazol-4-yl)benzenesulfonamide 2,2,2-trifluoroacetate

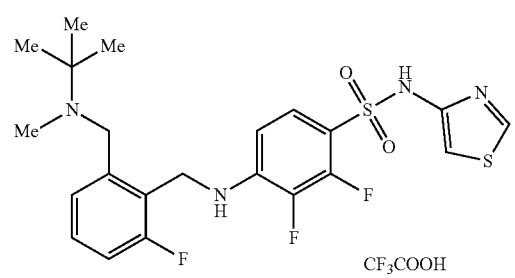 [SMILES: CN(Cc1cccc(F)c1CNc1ccc(S(=O)(=O)Nc2cscn2)c(F)c1F)C(C)(C)C ; "CF3COOH"]

Step 1. Preparation of tert-butyl ((4-((tert-butoxy-carbonyl)(2-((tert-butyl(methyl)amino)methyl)-6-fluorobenzyl)amino)-2,3-difluorophenyl)sulfonyl)(thiazol-4-yl)carbamate

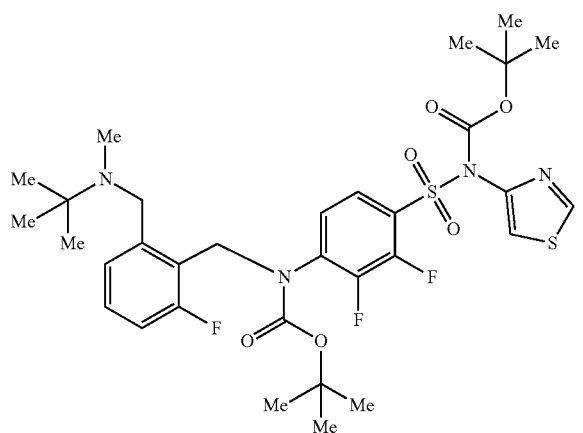 [SMILES: CN(Cc1cccc(F)c1CN(C(=O)OC(C)(C)C)c1ccc(S(=O)(=O)N(C(=O)OC(C)(C)C)c2cscn2)c(F)c1F)C(C)(C)C]

To a solution of tert-butyl (2-((tert-butyl(methyl)amino)methyl)-6-fluorobenzyl)carbamate (0.82 g, 2.54 mmol) in anhydrous N,N-dimethylformamide (25 mL) was added sodium hydride (60% dispersion in mineral oil, 0.122 g, 3.05 mmol) at 0° C. The mixture was stirred at 0° C. for 30 minutes and then added dropwise to a stirred solution of tert-butyl thiazol-4-yl((2,3,4-trifluorophenyl)sulfonyl)carbamate (1.0 g, 2.54 mmol) in anhydrous N,N-dimethylformamide (10 mL) at 0° C. The reaction mixture was allowed to warm to ambient temperature and stirred for 6 h. The mixture was then cooled to 0° C., quenched by addition of saturated ammonium chloride (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in heptane, afforded the title compound as a colorless solid (0.13 g, 7% yield): MS (ES+) m/z 699.3 (M+1).

Step 2. Preparation of 4-((2-((tert-butyl(methyl)amino)methyl)-6-fluorobenzyl)amino)-2,3-difluoro-N-(thiazol-4-yl)benzenesulfonamide 2,2,2-trifluoroacetate

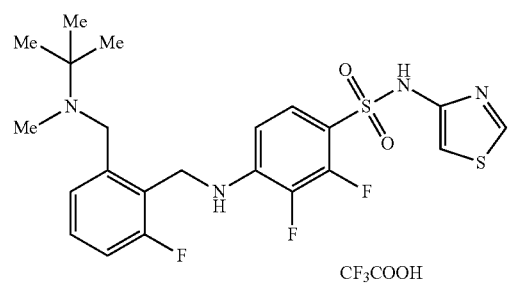 [SMILES: CN(Cc1cccc(F)c1CNc1ccc(S(=O)(=O)Nc2cscn2)c(F)c1F)C(C)(C)C ; "CF3COOH"]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with tert-butyl ((4-((tert-butoxycarbonyl)(2-((tert-butyl(methyl)amino)methyl)-6-fluorobenzyl)amino)-2,3-difluorophenyl)sulfonyl)(thiazol-4-yl)carbamate, the title compound was obtained as a colorless solid (0.099 g, 87% yield): $^1$HNMR (300 MHz, DMSO-$d_6$) δ 11.19 (s, 1H), 8.98 (s, 1H), 8.89 (d, J=2.2 Hz, 1H), 7.59-7.35 (m, 4H), 7.06-6.99 (m, 2H), 6.77-6.69 (m, 1H), 4.73-4.62 (m, 1H), 4.48-4.38 (m, 2H), 4.13-4.01 (m, 1H), 2.58 (d, J=4.7 Hz, 3H), 1.39 (s, 9H); MS (ES+) m/z 499.4 (M+1).

Example 204

Synthesis of 4-((2-(azetidin-1-ylmethyl)-6-fluorobenzyl)amino)-2,6-difluoro-N-(isoxazol-3-yl)benzenesulfonamide 2,2,2-trifluoroacetate

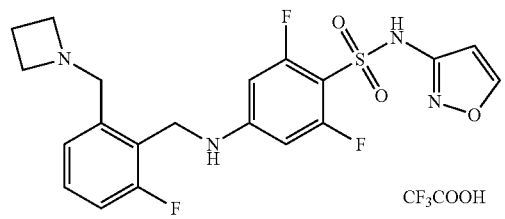 [SMILES: O=S(=O)(Nc1ccon1)c1c(F)cc(NCc2c(F)cccc2CN2CCC2)cc1F ; "CF3COOH"]

Step 1. Preparation of tert-butyl ((4-((2-(azetidin-1-ylmethyl)-6-fluorobenzyl)(tert-butoxycarbonyl)amino)-2,6-difluorophenyl)sulfonyl)(isoxazol-3-yl)carbamate

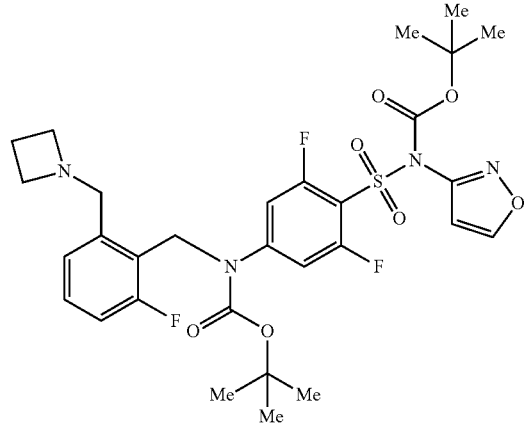 [SMILES: CC(C)(C)OC(=O)N(Cc1c(F)cccc1CN1CCC1)c1cc(F)c(S(=O)(=O)N(C(=O)OC(C)(C)C)c2ccon2)c(F)c1]

To a solution of tert-butyl (2-(azetidin-1-ylmethyl)-6-fluorobenzyl)carbamate (0.78 g, 2.65 mmol) in anhydrous N,N-dimethylformamide (27 mL) was added sodium hydride (60% dispersion in mineral oil, 0.127 g, 3.18 mmol) at 0° C. The mixture was stirred at 0° C. for 30 minutes and then added dropwise to a stirred solution of tert-butyl isoxazol-3-yl((2,4,6-trifluorophenyl)sulfonyl)carbamate (1.0 g, 2.65 mmol) in anhydrous N,N-dimethylformamide (15 mL) at 0° C. The reaction mixture was allowed to warm to ambient temperature and stirred for 18 h. The mixture was then cooled to 0° C., quenched by addition of saturated ammonium chloride (20 mL), and extracted with ethyl acetate (3×30 mL). The combined organic layers were washed with water (40 mL), brine (40 mL), dried over anhydrous magnesium sulfate, and filtered. Concentration of the filtrate in vacuo and purification of the residue by column chromatography, eluting with a gradient of 0 to 60% of ethyl acetate (containing 10% of isopropanol and 10% of triethylamine) in heptane, afforded the title compound as a colorless solid (0.37 g, 21% yield): MS (ES+) m/z 653.3 (M+1).

Step 2. Synthesis of 4-((2-(azetidin-1-ylmethyl)-6-fluorobenzyl)amino)-2,6-difluoro-N-(isoxazol-3-yl) benzenesulfonamide 2,2,2-trifluoroacetate

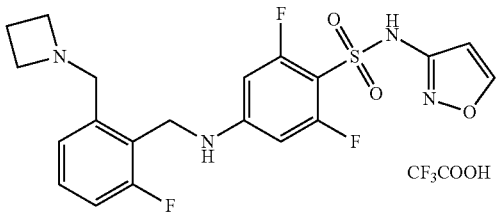 [SMILES: O=S(=O)(Nc1ccon1)c1c(F)cc(NCc2c(F)cccc2CN2CCC2)cc1F ; "CF3COOH"]

Following the procedure as described in EXAMPLE 14, Step 2 and making non-critical variations as required to replace (S)-5-chloro-4-((1-(4-chlorophenyl)ethyl)amino)-N-(2,4-dimethoxybenzyl)-2-fluoro-N-(thiazol-2-yl)benzenesulfonamide with tert-butyl ((4-((2-(azetidin-1-ylmethyl)-6-fluorobenzyl)(tert-butoxycarbonyl)amino)-2,6-difluorophenyl)sulfonyl)(isoxazol-3-yl)carbamate, the title compound was obtained as a colorless solid (0.22 g, 52% yield): $^1$H NMR (300 MHz, DMSO-$d_6$) δ 11.76 (s, 1H), 10.19 (s, 1H), 8.73 (d, J=1.8 Hz, 1H), 7.57-7.47 (m, 1H), 7.39-7.33 (m, 3H), 6.44-6.36 (m, 2H), 6.32 (d, J=1.8 Hz, 1H), 4.49-4.42 (m, 2H), 4.38-4.31 (m, 2H), 4.15-3.98 (m, 4H), 2.45-2.21 (m, 2H); MS (ES+) m/z 453.4 (M+1).

Example 205

Synthesis of (S)-2,6-difluoro-4-((1-(2-fluorophenyl) ethyl)amino)-N-(thiazol-4-yl)benzenesulfonamide 2,2,2-trifluoroacetate

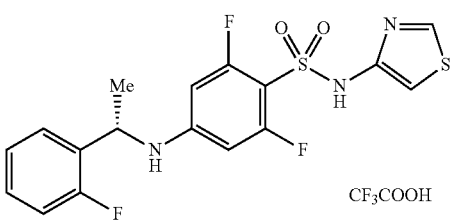 [SMILES: C[C@H](Nc1cc(F)c(S(=O)(=O)Nc2cscn2)c(F)c1)c1ccccc1F ; "CF3COOH"]

Step 1. Preparation of tert-butyl (S)-((2,6-difluoro-4-((1-(2-fluorophenyl)ethyl)amino)-phenyl)sulfonyl) (thiazol-4-yl)carbamate

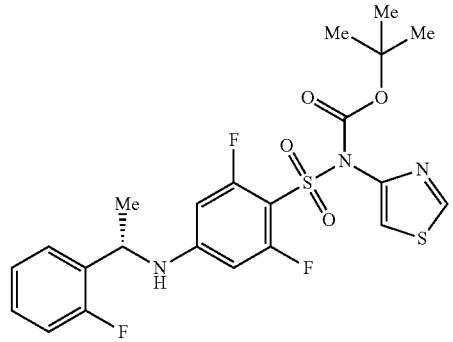 [SMILES: C[C@H](Nc1cc(F)c(S(=O)(=O)N(C(=O)OC(C)(C)C)c2cscn2)c(F)c1)c1ccccc1F]

To a solution of tert-butyl thiazol-4-yl((2,4,6-trifluorophenyl)sulfonyl)carbamate (1.20 g, 3.03 mmol) and (S)-1-(2-fluorophenyl)ethan-1-amine hydrochloride (0.464 g, 3.34 mmol) in anhydrous dimethyl sulfoxide (20 mL) was added and potassium carbonate (1.03 mL, 7.50 mmol) and the mixture was stirred at ambient temperature for 12 h. Saturated ammonium chloride (20 mL) was then added to it and the mixture extracted with ethyl acetate (3×30 mL). The combined organic phases were washed with brine (20 mL), dried over anhydrous sodium sulfate, and filtered. Concentration of the filtrate in vacuo and purification of the residue by column chromatography, eluting with a gradient of 0-50% ethyl acetate in hexanes, afforded the title compound as a yellow oil (0.750 g, 48% yield): MS (ES+) m/z 514.1 (M+1).

Step 2: Preparation of (S)-2,6-difluoro-4-((1-(2-fluorophenyl)ethyl)amino)-N-(thiazol-4-yl)benzenesulfonamide 2,2,2-trifluoroacetate

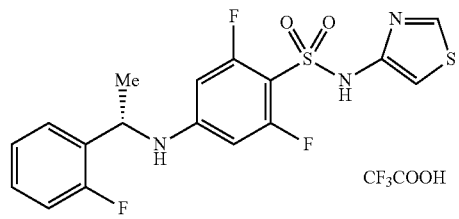 [SMILES: C[C@H](Nc1cc(F)c(S(=O)(=O)Nc2cscn2)c(F)c1)c1ccccc1F ; "CF3COOH"]

To tert-butyl (S)-((2,6-difluoro-4-((1-(2-fluorophenyl) ethyl)amino)phenyl)-sulfonyl)(thiazol-4-yl)carbamate (0.75 g, 1.46 mmol) in dichloromethane (6 mL) was added trifluoroacetic acid (3 mL). The reaction mixture was stirred for 1 h and then concentrated in vacuo Purification of the residue by column chromatography, eluting with a gradient of 0 to 60% of ethyl acetate (containing 0.1% of trifluroracetic acid) in hexane, provided the title compound as a colorless foam (0.42 g, 69% yield): $^1$H-NMR (300 MHz, DMSO-$d_6$) δ 11.17 (s, 1H), 8.87 (d, J=2.1 Hz, 1H), 7.64 (d, J=6.7 Hz, 1H), 7.36-7.26 (m, 2H), 7.22-7.13 (m, 2H), 6.87 (d, J=2.1 Hz, 1H), 6.16 (d, J=13.5 Hz, 2H), 4.79 (quintet, J=7.0 Hz, 1H), 1.44 (d, J=6.8 Hz, 3H), one exchangeable proton not observed; MS (ES+) m/z 414.1 (M+1).

Example 206

Synthesis of (S)-4-((1-(5-chloro-2-fluorophenyl)ethyl)amino)-2,6-difluoro-N-(pyrimidin-4-yl)benzenesulfonamide 2,2,2-trifluoroacetate

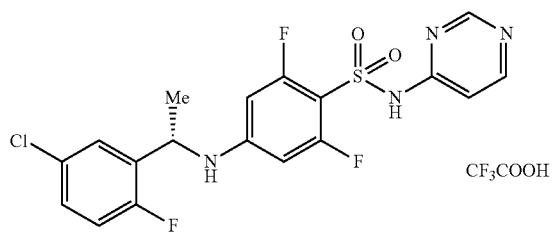 [SMILES: C[C@H](Nc1cc(F)c(S(=O)(=O)Nc2ccncn2)c(F)c1)c1cc(Cl)ccc1F ; "CF3COOH"]

Step 1. Preparation of N-(2,4-dimethoxybenzyl)-2,4,6-trifluoro-N-(pyrimidin-4-yl)benzenesulfonamide

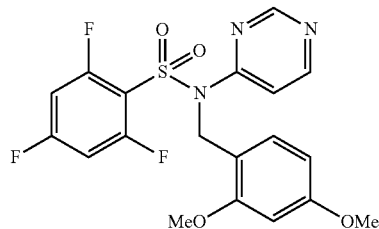 [SMILES: COc1ccc(CN(c2ccncn2)S(=O)(=O)c2c(F)cc(F)cc2F)c(OC)c1]

To a solution of N-(2,4-dimethoxybenzyl)pyrimidin-4-amine (2.35 g, 9.59 mmol) in anhydrous tetrahydrofuran (50 mL) was added a 1 M solution of lithium bis(trimethylsilyl)amide in tetrahydrofuran (11.5 mL, 11.5 mmol) at −78° C. The reaction mixture was allowed to warm to ambient temperature and stirred for 1 h. The reaction mixture was cooled to −78° C., and a solution of 2,4,6-trifluorobenzenesulfonyl chloride (2.20 g, 9.59 mmol) in anhydrous tetrahydrofuran (10 mL) was added to it. The reaction mixture was allowed to warm to ambient temperature and stirred for 3 h. The mixture was diluted with ethyl acetate (100 mL), washed with saturated ammonium chloride (2×100 mL), brine (2×50 mL), dried over anhydrous sodium sulfate, and filtered. Concentration of the filtrate in vacuo and purification of the residue by column chromatography, eluting with a gradient of 0 to 50% of ethyl acetate in heptane, provided the title compound as a colorless solid (3.70 g, 87% yield): MS (ES+) m/z 440.1 (M+1).

Step 2. Preparation of (S)-4-((1-(5-chloro-2-fluorophenyl)ethyl)amino)-N-(2,4-dimethoxybenzyl)-2,6-difluoro-N-(pyrimidin-4-yl)benzenesulfonamide

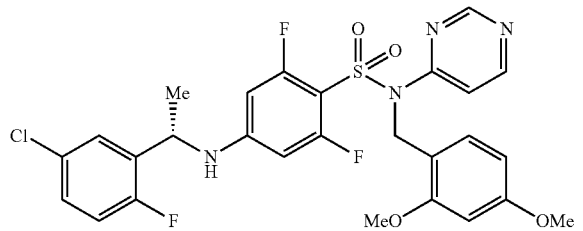 [SMILES: COc1ccc(CN(c2ccncn2)S(=O)(=O)c2c(F)cc(N[C@@H](C)c3cc(Cl)ccc3F)cc2F)c(OC)c1]

To a solution of N-(2,4-dimethoxybenzyl)-2,4,6-trifluoro-N-(pyrimidin-4-yl)benzenesulfonamide (0.20 g, 0.45 mmol) and (S)-1-(5-chloro-2-fluorophenyl)ethan-1-amine (0.085 g, 0.49 mmol) in anhydrous dimethyl sulfoxide (5 mL) was added potassium carbonate (0.155 g, 1.125 mmol). The mixture was stirred at ambient temperature for 16 h and was then diluted with water (20 mL) and extracted with ethyl acetate (3×30 mL). The combined organic layers were washed with brine (20 mL), dried over sodium sulfate, and filtered. Concentration of the filtrate in vacuo and purification of the residue by column chromatography, eluting with a gradient of 0 to 60% of ethyl acetate in hexanes, provided the title compound as a colorless solid (0.120 g, 45% yield): MS (ES+) m/z 593.1 (M+1), 595.1 (M+1).

Step 3. Preparation of (S)-4-((1-(5-chloro-2-fluorophenyl)ethyl)amino)-2,6-difluoro-N-(pyrimidin-4-yl)benzenesulfonamide 2,2,2-trifluoroacetate

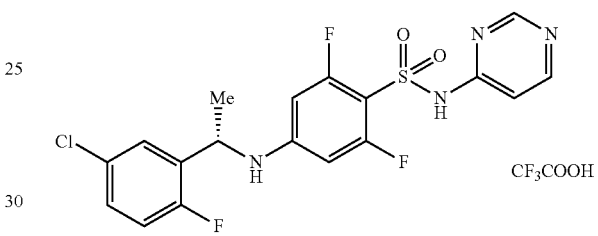

To a solution of (S)-4-((1-(5-chloro-2-fluorophenyl)ethyl)amino)-N-(2,4-dimethoxybenzyl)-2,6-difluoro-N-(pyrimidin-4-yl)benzenesulfonamide (0.12 g, 0.20 mmol) in dichloromethane (6 mL) was added trifluoroacetic acid (3 mL). The mixture was stirred at ambient temperature for 1 h and then concentrated in vacuo. The residue was purified by preparative reverse-phase HPLC, eluting with a gradient of 10 to 60% of acetonitrile in water containing 0.1% of trifluoroacetic acid, to afford the title compound as a colorless solid (0.024 g, 27% yield): $^1$H NMR (300 MHz, DMSO-$d_6$) δ 8.63 (s, 1H), 8.54-8.33 (m, 1H), 7.62 (s, 1H), 7.47-7.24 (m, 3H), 6.96 (s, 1H), 6.23 (t, J=9.9 Hz, 2H), 4.79 (s, 1H), 1.44-1.42 (m, 3H), COOH and NH not observed; MS (ES+) m/z 443.1 (M+1), 445.1 (M+1).

Example 207

Synthesis of (S)-4-((1-(5-chloro-2-fluorophenyl)ethyl)amino)-2,6-difluoro-N-(thiazol-4-yl)benzenesulfonamide 2,2,2-trifluoroacetate

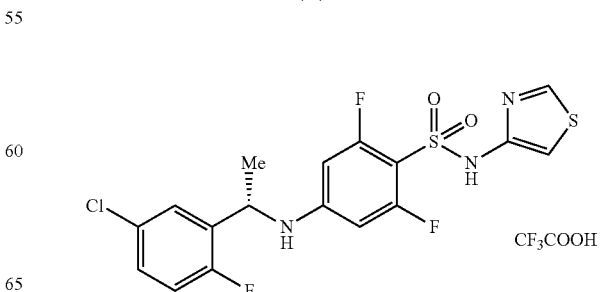

Step 1. Preparation of tert-butyl (S)-((4-((1-(5-chloro-2-fluorophenyl)ethyl)amino)-2,6-difluorophenyl)sulfonyl)(thiazol-4-yl)carbamate

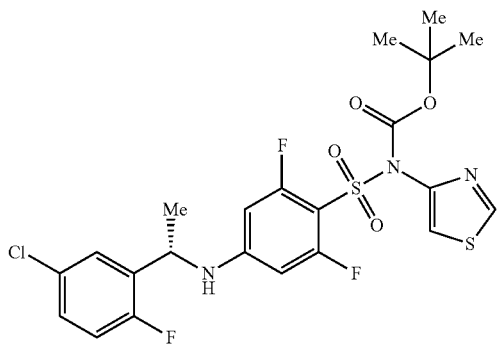 [SMILES: C[C@H](Nc1cc(F)c(S(=O)(=O)N(C(=O)OC(C)(C)C)c2cscn2)c(F)c1)c1cc(Cl)ccc1F]

To a solution of tert-butyl thiazol-4-yl((2,4,6-trifluorophenyl)sulfonyl)carbamate (0.20 g, 0.50 mmol) and (S)-1-(5-chloro-2-fluorophenyl)ethan-1-amine (0.065 g, 0.55 mmol) in anhydrous dimethyl sulfoxide (5 mL) was added potassium carbonate (0.172 g, 1.25 mmol). The mixture was stirred at ambient temperature for 16 h and was then diluted with water (20 mL) and extracted with ethyl acetate (3×30 mL). The combined organic layers were washed with brine (20 mL), dried over anhydrous sodium sulfate, and filtered. The residue was purified by column chromatography eluting with a gradient of 0 to 60% of ethyl acetate in hexanes provided the title compound as a colorless solid (0.142 g, 50% yield): MS (ES+) m/z 548.2 (M+1), 550.2 (M+1).

Step 2. Preparation of (S)-4-((1-(5-chloro-2-fluorophenyl)ethyl)amino)-2,6-difluoro-N-(thiazol-4-yl)benzenesulfonamide 2,2,2-trifluoroacetate

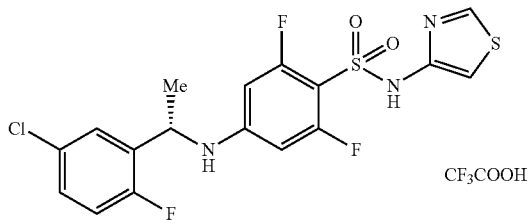 [SMILES: C[C@H](Nc1cc(F)c(S(=O)(=O)Nc2cscn2)c(F)c1)c1cc(Cl)ccc1F ; "CF3COOH"]

To a solution of tert-butyl (S)-((4-((1-(5-chloro-2-fluorophenyl)ethyl)amino)-2,6-difluorophenyl)sulfonyl)(thiazol-4-yl)carbamate (0.142 g, 0.26 mmol) in dichloromethane (6.0 mL) was added trifluoroacetic acid (3.0 mL). The mixture was stirred at ambient temperature for 1 h and then concentrated in vacuo. The residue was purified by column chromatography eluting with a gradient of 0 to 60% of ethyl acetate in hexanes provided the title compound as a colorless solid (0.081 g, 69% yield): $^1$H NMR (300 MHz, DMSO-$d_6$): δ 11.18 (s, 1H), 8.87 (d, J=2.2 Hz, 1H), 7.60 (d, J=7.4 Hz, 1H), 7.39-7.34 (m, 2H), 7.30-7.24 (m, 1H), 6.88 (d, J=2.2 Hz, 1H), 6.19 (d, J=13.0 Hz, 2H), 4.79 (quintet, J=6.9 Hz, 1H), 1.43 (d, J=6.7 Hz, 3H). Note: NH not observed; MS (ES+) m/z 448.1 (M+1), 450.1 (M+1).

Example 208

Synthesis of (S)-4-((1-(2,5-difluorophenyl)ethyl)amino)-2,6-difluoro-N-(pyrimidin-4-yl)benzenesulfonamide 2,2,2-trifluoroacetate

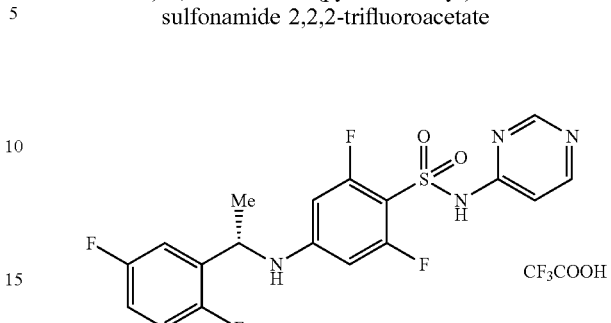

Step 1. Preparation of (S)-4-((1-(2,5-difluorophenyl)ethyl)amino)-N-(2,4-dimethoxybenzyl)-2,6-difluoro-N-(pyrimidin-4-yl)benzenesulfonamide

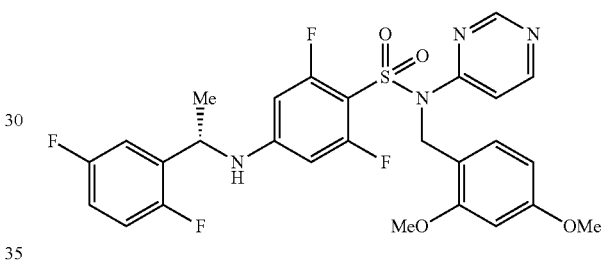

To a solution of N-(2,4-dimethoxybenzyl)-2,4,6-trifluoro-N-(pyrimidin-4-yl)benzenesulfonamide (0.16 g, 0.36 mmol) and (S)-1-(2,5-difluorophenyl)ethan-1-amine (0.057 g, 0.36 mmol) in anhydrous dimethyl sulfoxide (3.0 mL) was added potassium carbonate (0.248 g, 1.80 mmol). The mixture was stirred at ambient temperature for 16 h and was then diluted with water (10 mL) and extracted with ethyl acetate (3×20 mL). The combined organic layers were washed with brine (20 mL), dried over anhydrous sodium sulfate, and filtered. Concentration of the filtrate in vacuo and purification of the residue by column chromatography, eluting with a gradient of 0 to 60% of ethyl acetate in hexanes, provided the title compound as a colorless solid (0.080 g, 38% yield): MS (ES+) m/z 577.2 (M+1).

Step 2. Preparation of (S)-4-((1-(2,5-difluorophenyl)ethyl)amino)-2,6-difluoro-N-(pyrimidin-4-yl)benzenesulfonamide 2,2,2-trifluoroacetate

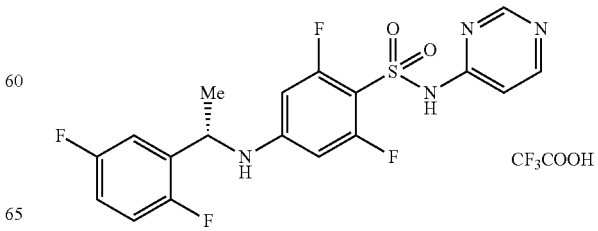

To a solution of (S)-4-((1-(2,5-difluorophenyl)ethyl)amino)-N-(2,4-dimethoxybenzyl)-2,6-difluoro-N-(pyrimidin-4-yl)benzenesulfonamide (0.080 g, 0.14 mmol) in dichloromethane (5.0 mL) was added trifluoroacetic acid (2.0 mL). The mixture was stirred at ambient temperature for 1 h and then concentrated in vacuo. The residue was purified by preparative reverse-phase HPLC, eluting with a gradient of 10 to 50% of acetonitrile in water containing 0.1% of trifluoroacetic acid, to afford the title compound as a colorless solid (0.022 g, 36% yield): $^1$H NMR (300 MHz, DMSO-$d_6$) δ 8.60 (s, 1H), 8.37 (s, 1H), 7.62 (d, J=5.9 Hz, 1H), 7.28-7.14 (m, 3H), 6.95 (s, 1H), 6.20 (d, J=12.7 Hz, 2H), 4.81-4.76 (m, 1H), 1.45-1.43 (m, 3H), COOH and NH not observed; MS (ES+) m/z 427.2 (M+1).

Example 209

Synthesis of 4-((2-(azetidin-1-ylmethyl)-6-methoxybenzyl)amino)-2,6-difluoro-N-(thiazol-4-yl)benzenesulfonamide 2,2,2-trifluoroacetate

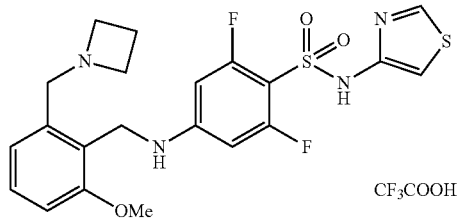 [SMILES: COc1cccc(CN2CCC2)c1CNc1cc(F)c(S(=O)(=O)Nc2cscn2)c(F)c1 ; "CF3COOH"]

Step 1. Preparation of 2-bromo-3-methoxybenzaldehyde

To a mixture of 2-bromo-3-hydroxybenzaldehyde (1.30 g, 6.50 mmol) and potassium carbonate (2.70 g, 19.5 mmol) in N,N-dimethylformamide (60 mL) was added iodomethane (0.80 g, 12.9 mmol). The reaction mixture was stirred at ambient temperature for 16 h and then diluted with ethyl acetate (60 mL). The mixture was washed with saturated ammonium chloride (2×50 mL), dried over anhydrous sodium sulfate, and filtered. The filtrate was concentrated in vacuo and the residue purified by column chromatography, eluting with a gradient of 0 to 30% of ethyl acetate in hexanes, to afford the title compound as a yellow oil (1.50 g, quantitative yield): MS (ES+) m/z 215.1 (M+1).

Step 2. Preparation of 1-(2-bromo-3-methoxybenzyl)azetidine

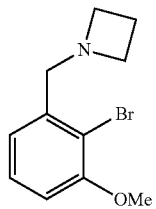 [SMILES: COc1cccc(CN2CCC2)c1Br]

To a mixture of 2-bromo-3-methoxybenzaldehyde (1.50 g, 6.50 mmol) and azetidine (0.44 g, 7.80 mmol) in anhydrous 1,2-dichloroethane (10 mL) was added sodium triacetoxyborohydride (2.70 g, 13.0 mmol) and the resulting mixture was stirred for 18 h. The mixture was diluted with ethyl acetate (30 mL), washed with saturated ammonium chloride (2×30 mL), and the organic phase was concentrated in vacuo. The residue was purified by column chromatography, eluting with a gradient of 0 to 10% of methanol in dichloromethane, to provide the title compound as a colorless solid (1.35 g, 81% yield): MS (ES+) m/z 256.2 (M+1).

Step 3. Preparation of 2-(azetidin-1-ylmethyl)-6-methoxybenzaldehyde

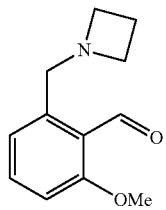 [SMILES: COc1cccc(CN2CCC2)c1C=O]

To a solution of 1-(2-bromo-3-methoxybenzyl)azetidine (0.27 g, 1.64 mmol) in anhydrous tetrahydrofuran (10 mL) was added a 1.6 M solution of N-butyllithium in tetrahydrofuran (1.30 mL, 1.97 mmol) dropwise at −78° C. The reaction mixture was stirred −78° C. for 20 minutes, and N,N-dimethylformamide (0.663 mL, 8.20 mmol) was added to it. The reaction mixture was allowed to warm to ambient temperature. After stirring for 30 minutes at ambient temperature, the reaction mixture was diluted with dichloromethane (50 mL). The mixture was washed with brine (20 mL), dried over anhydrous sodium sulfate, and filtered. Concentration of the filtrate in vacuo provided a colorless oil (0.22 g, 65% yield): MS (ES+) m/z 206.2 (M+1).

Step 4. Preparation of 4-((2-(azetidin-1-ylmethyl)-6-methoxybenzyl)amino)-2,6-difluoro-N-(thiazol-4-yl)benzenesulfonamide 2,2,2-trifluoroacetate

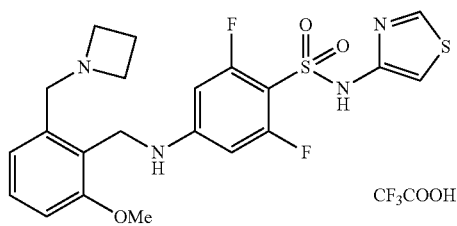 [SMILES: COc1cccc(CN2CCC2)c1CNc1cc(F)c(S(=O)(=O)Nc2cscn2)c(F)c1 ; "CF3COOH"]

To a mixture of tert-butyl ((4-amino-2,6-difluorophenyl)sulfonyl)(thiazol-4-yl)carbamate (0.38 g, 0.975 mmol) and 2-(azetidin-1-ylmethyl)-6-methoxybenzaldehyde (0.20 g, 0.975 mmol) in trifluoroacetic acid (2.0 mL) was added sodium triacetoxyborohydride (0.41 g, 1.95 mmol) at 0° C. The resulting mixture was stirred at ambient temperature for 15 minutes. The reaction mixture was diluted with ethyl acetate (30 mL), washed with saturated ammonium chloride (2×30 mL), and the organic phase was concentrated in vacuo. The residue was purified by preparative reverse-phase HPLC, eluting with a gradient of 10 to 50% of acetonitrile in water containing 0.1% of trifluoroacetic acid, to afford the title compound as a colorless solid (0.014 g, 3% yield): $^1$H NMR (300 MHz, DMSO-$d_6$) δ 8.74 (d, J=2.2 Hz, 1H), 8.43 (s, 1H), 7.42 (t, J=8.0 Hz, 1H), 7.14 (d, J=8.4 Hz, 1H), 7.03 (d, J=7.5 Hz, 1H), 6.95 (d, J=2.2 Hz, 1H), 6.29 (d, J=12.3 Hz, 2H), 4.39 (s, 2H), 4.35 (s, 2H), 4.09 (t, J=8.1 Hz, 4H), 3.86 (s, 3H), 2.45 (quintet, J=8.1 Hz, 2H), COOH and NH not observed; MS (ES+) m/z 481.2 (M+1).

Example 210

Synthesis of 4-((2-(azetidin-1-ylmethyl)-6-ethylbenzyl)amino)-2,6-difluoro-N-(thiazol-4-yl)benzenesulfonamide 2,2,2-trifluoroacetate

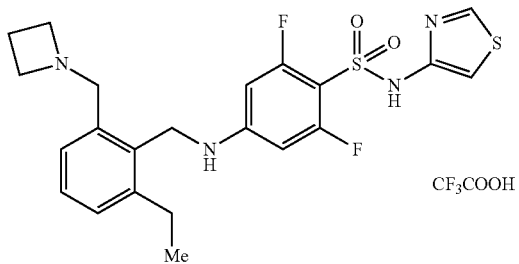 [SMILES: CCc1cccc(CN2CCC2)c1CNc1cc(F)c(S(=O)(=O)Nc2cscn2)c(F)c1 ; "CF3COOH"]

Step 1. Preparation of (S)-4-((1-(2,5-difluorophenyl)ethyl)amino)-N-(2,4-dimethoxybenzyl)-2,6-difluoro-N-(pyrimidin-4-yl)benzenesulfonamide

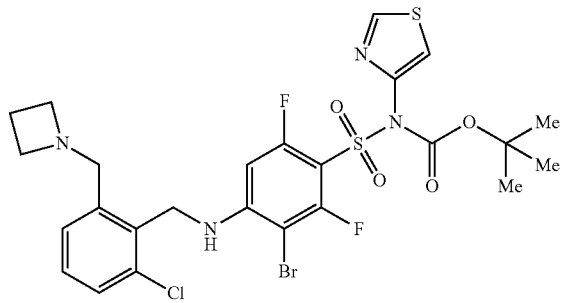 [SMILES: CC(C)(C)OC(=O)N(c1cscn1)S(=O)(=O)c1c(F)cc(NCc2c(Cl)cccc2CN2CCC2)c(Br)c1F]

To a solution of tert-butyl ((3-bromo-2,4,6-trifluorophenyl)sulfonyl)(thiazol-4-yl)carbamate (11.6 g, 24.7 mmol) and (2-(azetidin-1-ylmethyl)-6-chlorophenyl)methanamine (5.20 g, 24.7 mmol) in anhydrous dimethyl sulfoxide (250 mL) was added potassium carbonate (6.80 g, 49.4 mmol). The mixture was stirred at ambient temperature for 16 h and was then diluted with water (200 mL) and extracted with ethyl acetate (3×300 mL). The combined organic layers were washed with brine (200 mL), dried over anhydrous sodium sulfate, and filtered. Concentration of the filtrate in vacuo and trituration of the residue in diethyl ether (50 mL) provided the title compound as a colorless solid (5.0 g, 36% yield): MS (ES+) m/z 563.0 (M+1), 565.0 (M+1).

Step 2. Preparation of tert-butyl ((4-((2-(azetidin-1-ylmethyl)-6-chlorobenzyl)amino)-2,6-difluorophenyl)sulfonyl)(thiazol-4-yl)carbamate

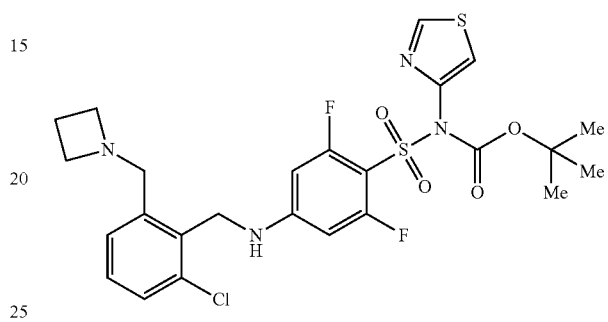

To a mixture of (S)-4-((1-(2,5-difluorophenyl)ethyl)amino)-N-(2,4-dimethoxybenzyl)-2,6-difluoro-N-(pyrimidin-4-yl)benzenesulfonamide (3.0 g, 5.33 mmol) in ethanol (30 mL) was added triethylamine (2.90 mL, 21.3 mmol) and 15% palladium on carbon (500 mg). The suspension was degassed under vacuum and purged with hydrogen several times. The mixture was stirred under an atmosphere of hydrogen pressure (50 psi) at 80° C. for 16 h. After cooling to ambient temperature, the reaction mixture was filtered. Concentration of the filtrate in vacuo provided the title compound as a colorless foam (3.1 g, quantitative yield): MS (ES+) m/z 585.2 (M+1).

Step 3. Preparation of 4-((2-(azetidin-1-ylmethyl)-6-chlorobenzyl)amino)-2,6-difluoro-N-(thiazol-4-yl)benzenesulfonamide 2,2,2-trifluoroacetate

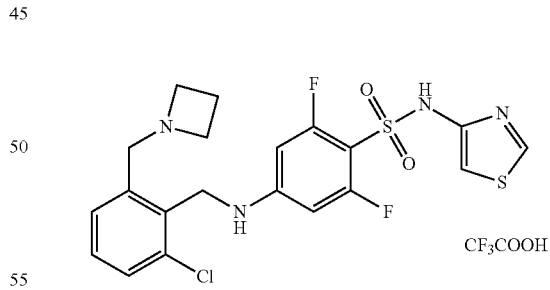

To a solution of tert-butyl ((4-((2-(azetidin-1-ylmethyl)-6-chlorobenzyl)amino)-2,6-difluorophenyl)sulfonyl)(thiazol-4-yl)carbamate (3.10 g, 5.29 mmol) in dichloromethane (10 mL) was added trifluoroacetic acid (5 mL). The mixture was stirred at ambient temperature for 1 h and then concentrated in vacuo. The residue was purified by column chromatography, eluting with a gradient of 0 to 15% of methanol in dichloromethane, to afforded the title compound as a colorless foam (1.0 g, 39% yield): MS (ES+) m/z 485.2 (M+1), 487.2 (M+1).

Step 4. Preparation of 4-((2-(azetidin-1-ylmethyl)-6-ethylbenzyl)amino)-2,6-difluoro-N-(thiazol-4-yl)benzenesulfonamide 2,2,2-trifluoroacetate

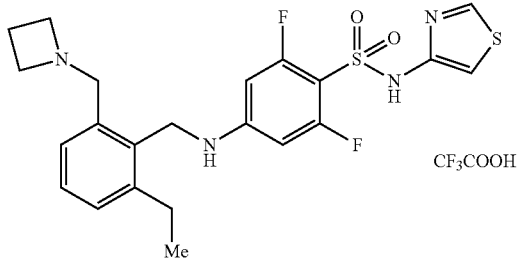 [SMILES: CCc1cccc(CN2CCC2)c1CNc1cc(F)c(S(=O)(=O)Nc2cscn2)c(F)c1 ; "CF3COOH"]

To a mixture of 4-((2-(azetidin-1-ylmethyl)-6-chlorobenzyl)amino)-2,6-difluoro-N-(thiazol-4-yl)benzenesulfonamide (0.053 g, 0.11 mmol) in 1,4-dioxane (1.5 mL) was added ethylboronic acid (0.049 g, 0.66 mmol), (2-dicyclohexylphosphino-2',6'-dimethoxybiphenyl) [2-(2'-amino-1,1'-biphenyl)]palladium(II) methanesulfonate (3.7 mg, 0.003 mmol), 2-dicyclohexylphosphino-2',6'-dimethoxybiphenyl (2.2 mg, 0.003 mmol), and potassium phosphate (0.088 g, 0.24 mmol). The resulting mixture was degassed by passing a stream of argon through it for 15 minutes and then heated to 160° C. for 45 minutes in a microwave. The reaction mixture was allowed to cool to ambient temperature and filtered through a pad of Celite. The filter pad was washed with ethyl acetate (30 mL) and the combined filtrate concentrated in vacuo. Purification of the residue by preparative reverse-phase HPLC, eluting with a gradient of 10 to 50% of acetonitrile in water containing 0.1% of trifluoroacetic acid, afforded the title compound as a colorless solid (0.021 g, 40% yield): $^1$H NMR (300 MHz, DMSO-$d_6$) δ 11.24 (s, 1H), 10.19 (s, 1H), 8.92 (d, J=2.2 Hz, 1H), 7.42-7.31 (m, 3H), 7.04 (s, 1H), 6.92 (d, J=2.2 Hz, 1H), 6.39 (d, J=12.6 Hz, 2H), 4.38 (d, J=5.5 Hz, 2H), 4.24 (d, J=3.4 Hz, 2H), 4.14-3.97 (m, 4H), 2.68-2.60 (m, 2H), 2.46-2.21 (m, 2H), 1.13 (t, J=7.5 Hz, 3H); MS (ES+) m/z 479.1 (M+1).

Example 211

Synthesis of 4-((2-(azetidin-1-ylmethyl)-6-cyclopropylbenzyl)amino)-2,6-difluoro-N-(thiazol-4-yl)benzenesulfonamide 2,2,2-trifluoroacetate

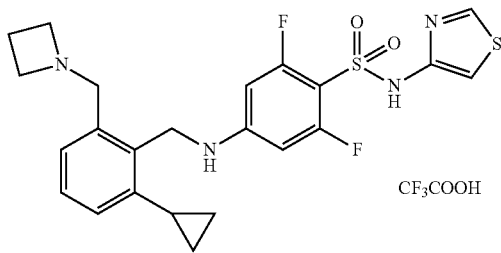 [SMILES: O=S(=O)(Nc1cscn1)c1c(F)cc(NCc2c(CN3CCC3)cccc2C2CC2)cc1F ; "CF3COOH"]

Following the procedure as described in Example 210, Step 4 and making variations as required to replace ethylboronic acid with cyclopropylboronic acid, the title compound was obtained as a colorless solid (0.015 g, 5% yield): $^1$H NMR (300 MHz, DMSO-$d_6$) δ 11.23 (s, 1H), 10.34 (s, 1H), 8.94-8.92 (m, 1H), 7.38-7.31 (m, 2H), 7.11 (td, J=5.8, 2.3 Hz, 2H), 6.92 (d, J=7.7 Hz, 1H), 6.39 (d, J=12.6 Hz, 2H), 4.43-4.40 (m, 4H), 4.14-3.98 (m, 4H), 2.42-2.18 (m, 2H), 2.00-1.91 (m, 1H), 0.91-0.85 (m, 2H), 0.67-0.62 (m, 2H); MS (ES+) m/z 491.2 (M+1).

Example 212

Synthesis of 4-((2-((tert-butyl(methyl)amino)methyl)-6-fluorobenzyl)amino)-2,6-difluoro-N-(thiazol-4-yl)benzenesulfonamide 2,2,2-trifluoroacetate

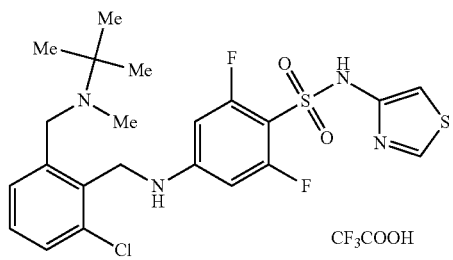 [SMILES: CN(Cc1cccc(Cl)c1CNc1cc(F)c(S(=O)(=O)Nc2cscn2)c(F)c1)C(C)(C)C ; "CF3COOH"]

Step 1. Preparation of 2-((tert-butyl(methyl)amino)methyl)-6-fluorobenzonitrile

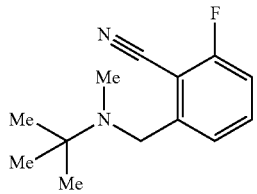 [SMILES: CN(Cc1cccc(F)c1C#N)C(C)(C)C]

To a solution of 2-(bromomethyl)-6-fluorobenzonitrile (0.737 g, 3.40 mmol) in N,N-dimethylformamide (5 mL) was added N,2-dimethylpropan-2-amine (0.30 g, 3.40 mmol) and N,N-diisopropylethylamine (1.10 mL, 6.80 mmol). The reaction mixture was stirred at ambient temperature for 16 h and then diluted with ethyl acetate (20 mL). The mixture was washed with saturated ammonium chloride (2×20 mL), dried over anhydrous sodium sulfate, and filtered. The filtrate was concentrated in vacuo and the residue purified by column chromatography, eluting with a gradient of 0 to 10% of methanol in dichloromethane, to afford the title compound as a yellow oil (0.45 g, 60% yield): MS (ES+) m/z 221.3 (M+1).

Step 2. Preparation of N-(2-(aminomethyl)-3-fluorobenzyl)-N,2-dimethylpropan-2-amine

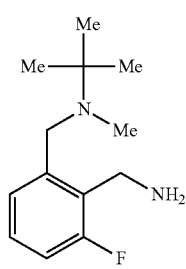 [SMILES: CN(Cc1cccc(F)c1CN)C(C)(C)C]

To a solution of 2-((tert-butyl(methyl)amino)methyl)-6-fluorobenzonitrile (0.450 g, 2.04 mmol) in methanol (20.0 ml) and ammonium hydroxide (5.00 mL) was added Raney nickel (0.175 g, 2.04 mmol). The suspension was degassed and purged with hydrogen three times. The mixture was stirred under a hydrogen atmosphere (50 psi) at ambient temperature for 12 h. The reaction mixture was filtered and the filtrate concentrated under reduced pressure to afford the title compound as a yellow oil (0.300 g, 65% yield): MS (ES+) m/z 225.3 (M+1).

Step 3. Preparation of tert-butyl ((3-bromo-4-((2-((tert-butyl(methyl)amino)methyl)-6-fluorobenzyl)amino)-2,6-difluorophenyl)sulfonyl)(thiazol-4-yl)carbamate

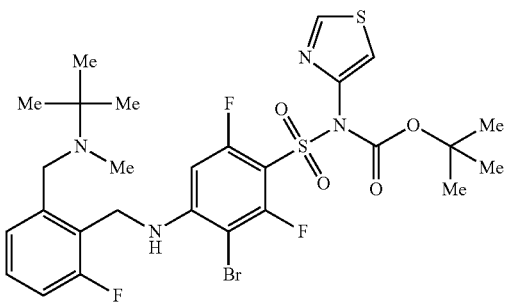 [SMILES: CN(Cc1cccc(F)c1CNc1cc(F)c(S(=O)(=O)N(C(=O)OC(C)(C)C)c2cscn2)c(F)c1Br)C(C)(C)C]

To a solution of tert-butyl ((3-bromo-2,4,6-trifluorophenyl)sulfonyl)(thiazol-4-yl)carbamate (0.30 g, 1.33 mmol) and N-(2-(aminomethyl)-3-fluorobenzyl)-N,2-dimethylpropan-2-amine (0.632 g, 1.33 mmol) in anhydrous dimethyl sulfoxide (6 mL) was added potassium carbonate (0.369 g, 2.68 mmol). The mixture was stirred at ambient temperature for 16 h and then diluted with water (20 mL) and extracted with ethyl acetate (2×30 mL). The combined organic layers were washed with brine (20 mL), dried over anhydrous sodium sulfate, and filtered. Concentration of the filtrate in vacuo and purification of the residue by column chromatography, eluting with a gradient of 0 to 10% of methanol in dichloromethane, provided the title compound as a colorless foam (0.35 g, 38% yield): MS (ES+) m/z 677.4 (M+1), 679.4 (M+1).

Step 4. Preparation of tert-butyl ((4-((2-((tert-butyl(methyl)amino)methyl)-6-fluorobenzyl)amino)-2,6-difluorophenyl)sulfonyl)(thiazol-4-yl)carbamate

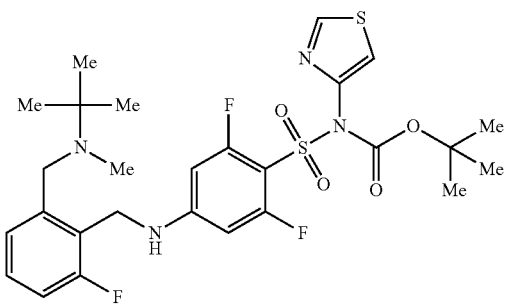 [SMILES: CN(Cc1cccc(F)c1CNc1cc(F)c(S(=O)(=O)N(C(=O)OC(C)(C)C)c2cscn2)c(F)c1)C(C)(C)C]

To a mixture of tert-butyl ((3-bromo-4-((2-((tert-butyl(methyl)amino)methyl)-6-fluorobenzyl)amino)-2,6-difluorophenyl)sulfonyl)(thiazol-4-yl)carbamate (0.35 g, 0.51 mmol) in ethanol (5 mL) was added triethylamine (0.288 mL, 2.07 mmol) and 15% palladium on carbon (51 mg). The suspension was degassed under vacuum and purged with hydrogen several times. The reaction mixture was stirred under a hydrogen atmosphere (50 psi) at 70° C. for 16 h. The reaction mixture was filtered and the filtrate concentrated in vacuo to provide the title compound as a colorless foam (0.21 g, 68% yield): MS (ES+) m/z 599.2 (M+1).

Step 5. Preparation of 4-((2-((tert-butyl(methyl)amino)methyl)-6-fluorobenzyl)amino)-2,6-difluoro-N-(thiazol-4-yl)benzenesulfonamide 2,2,2-trifluoroacetate

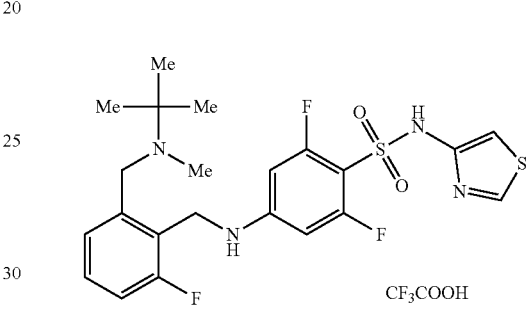

To a solution of tert-butyl ((4-((2-((tert-butyl(methyl)amino)methyl)-6-fluorobenzyl)amino)-2,6-difluorophenyl)sulfonyl)(thiazol-4-yl)carbamate (0.21 g, 0.35 mmol) in dichloromethane (5 mL) was added trifluoroacetic acid (2 mL). The mixture was stirred at ambient temperature for 1 h and then concentrated in vacuo. The residue was purified by column chromatography, eluting with a gradient of 0 to 12% of methanol in dichloromethane, to afford the title compound as a colorless foam (0.090 g, 51% yield): $^1$H NMR (300 MHz, DMSO-$d_6$) δ 11.24 (s, 1H), 9.52 (s, 1H), 8.91 (s, 1H), 7.57-7.34 (m, 4H), 6.92 (s, 1H), 6.39 (d, J=12.7 Hz, 2H), 4.65-4.57 (m, 1H), 4.35 (s, 2H), 4.08-3.97 (m, 1H), 2.54 (s, 3H), 1.39 (s, 9H); MS (ES+) m/z 499.2 (M+1).

Example 213

Synthesis of 4-((2-(azetidin-1-ylmethyl)-3,6-difluorobenzyl)amino)-2,3-difluoro-N-(thiazol-4-yl)benzenesulfonamide 2,2,2-trifluoroacetate

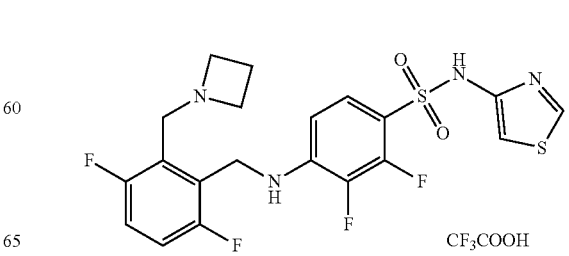

Step 1. Preparation of tert-butyl thiazol-4-yl((2,3,4-trifluorophenyl)sulfonyl)carbamate

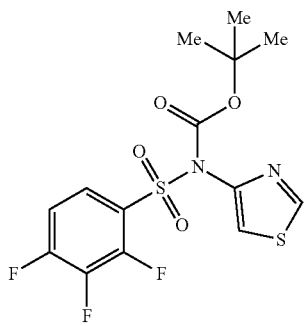 [SMILES: CC(C)(C)OC(=O)N(c1cscn1)S(=O)(=O)c1ccc(F)c(F)c1F]

To a solution of tert-butyl thiazol-4-ylcarbamate (4.90 g, 34.7 mmol) in anhydrous tetrahydrofuran (150 mL) was added a 1 M solution of lithium bis(trimethylsilyl)amide in tetrahydrofuran (41.6 mL, 41.6 mmol) at −78° C. The reaction mixture was allowed to warm to ambient temperature and stirred for 1 h. The reaction mixture was cooled to −78° C., and a solution of 2,3,4-trifluorobenzenesulfonyl chloride (8.0 g, 34.7 mmol) in anhydrous tetrahydrofuran (20 mL) was added to it. The reaction mixture was allowed to warm to ambient temperature and stirred for 3 h. The mixture was diluted with ethyl acetate (200 mL), washed with saturated ammonium chloride (2×200 mL), brine (2×100 mL), dried over anhydrous sodium sulfate, and filtered. Concentration of the filtrate in vacuo and purification of the residue by column chromatography, eluting with a gradient of 10 to 50% of ethyl acetate in heptane, provided the title compound as a colorless solid (6.70 g, 50% yield): MS (ES+) m/z 395.1 (M+1).

Step 2. Preparation of tert-butyl ((4-((2-(azetidin-1-ylmethyl)-3,6-difluorobenzyl)amino)-2,3-difluorophenyl)sulfonyl)(thiazol-4-yl)carbamate

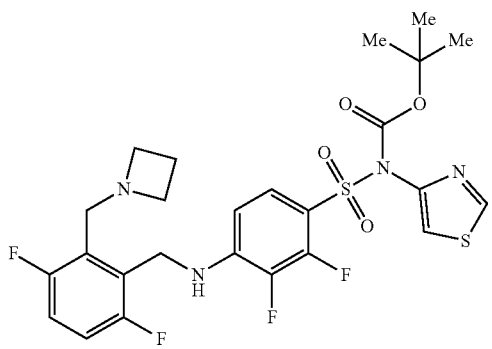 [SMILES: CC(C)(C)OC(=O)N(c1cscn1)S(=O)(=O)c1ccc(NCc2c(F)ccc(F)c2CN2CCC2)c(F)c1F]

To a solution of tert-butyl thiazol-4-yl((2,3,4-trifluorophenyl)sulfonyl)carbamate (0.256 g, 0.64 mmol) and (2-(azetidin-1-ylmethyl)-3,6-difluorophenyl)methanamine (0.165 g, 0.77 mmol) in anhydrous dimethyl sulfoxide (5 mL) was added potassium carbonate (0.76 g, 1.28 mmol). The mixture was stirred at ambient temperature for 16 h and was then diluted with water (20 mL) and extracted with ethyl acetate (3×30 mL). The combined organic layers were washed with brine (20 mL), dried over anhydrous sodium sulfate, and filtered. Concentration of the filtrate in vacuo and purification of the residue by column chromatography, eluting with a gradient of 0 to 8% of methanol in dichloromethane, provided the title compound as a colorless solid (0.095 g, 25% yield): MS (ES+) m/z 587.2 (M+1).

Step 3. Preparation of 4-((2-(azetidin-1-ylmethyl)-3,6-difluorobenzyl)amino)-2,3-difluoro-N-(thiazol-4-yl)benzenesulfonamide 2,2,2-trifluoroacetate

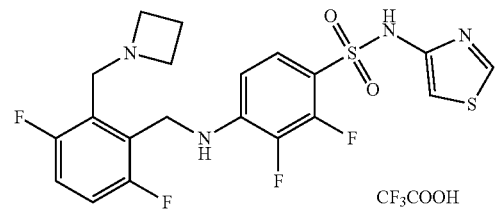 [SMILES: O=S(=O)(Nc1cscn1)c1ccc(NCc2c(F)ccc(F)c2CN2CCC2)c(F)c1F ; "CF3COOH"]

To a solution of tert-butyl ((4-((2-(azetidin-1-ylmethyl)-3,6-difluorobenzyl)amino)-2,3-difluorophenyl)sulfonyl)(thiazol-4-yl)carbamate (0.095 g, 0.16 mmol) in dichloromethane (5 mL) was added trifluoroacetic acid (2 mL). The mixture was stirred at ambient temperature for 1 h and then concentrated in vacuo. The residue was purified by preparative reverse-phase HPLC, eluting with a gradient of 10 to 50% of acetonitrile in water containing 0.1% of trifluoroacetic acid, to afford the title compound as a colorless solid (0.060 g, 77% yield): $^1$H NMR (300 MHz, DMSO-$d_6$) δ 11.20 (s, 1H), 10.33 (s, 1H), 8.89 (d, J=2.2 Hz, 1H), 7.48-7.40 (m, 3H), 7.05 (s, 1H), 6.99 (d, J=2.1 Hz, 1H), 6.73-6.68 (m, 1H), 4.53 (s, 2H), 4.47-4.46 (m, 2H), 4.21-4.12 (m, 2H), 4.09-3.99 (m, 2H), 2.37 (dd, J=18.6, 10.3 Hz, 1H), 2.30-2.17 (m, 1H); MS (ES+) m/z 487.2 (M+1).

Example 214

Synthesis of 2,6-difluoro-4-((2-((3-(2-methoxypropan-2-yl)azetidin-1-yl)methyl)benzyl)amino)-N-(thiazol-4-yl)benzenesulfonamide 2,2,2-trifluoroacetate

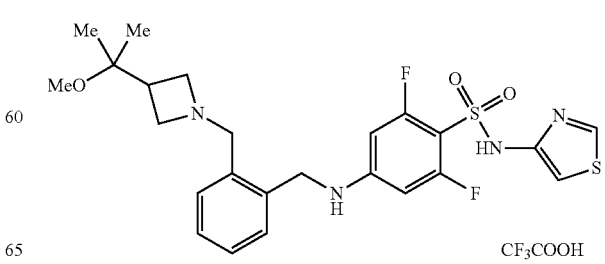

Step 1. Preparation of tert-butyl 3-(2-hydroxypropan-2-yl)azetidine-1-carboxylate

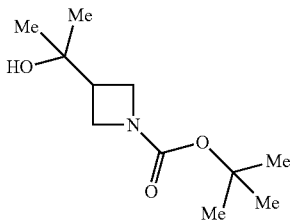 [SMILES: CC(C)(C)OC(=O)N1CC(C(C)(C)O)C1]

To a solution of 1-(tert-butyl) 3-methyl azetidine-1,3-dicarboxylate (3.00 g, 13.9 mmol) in anhydrous tetrahydrofuran (30 mL) at 0° C. was added a 3 M solution of methylmagnesium bromide in diethyl ether (11.1 mL, 33.4 mmol). The reaction mixture was allowed to warm to ambient temperature and stirred for 16 h. The reaction mixture and was then diluted with saturated ammonium chloride (20 mL) and extracted with ethyl acetate (2×30 mL). The combined organic layers were washed with brine (20 mL), dried over anhydrous sodium sulfate, and filtered. Concentration of the filtrate in vacuo provided the title compound as a yellow foam (2.85 g, 95% yield): $^1$H NMR (300 MHz, CDCl$_3$) δ 3.89 (dt, J=14.4, 7.3 Hz, 4H), 2.57 (dd, J=10.4, 4.3 Hz, 1H), 1.44-1.43 (m, 9H), 1.19 (s, 6H), OH not observed.

Step 2. Preparation of tert-butyl 3-(2-methoxypropan-2-yl)azetidine-1-carboxylate

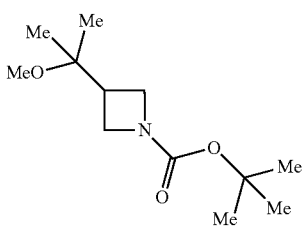 [SMILES: COC(C)(C)C1CN(C(=O)OC(C)(C)C)C1]

To a solution of tert-butyl 3-(2-hydroxypropan-2-yl)azetidine-1-carboxylate (0.67 g, 3.11 mmol) in anhydrous tetrahydrofuran (6 mL) at −78° C. was added a 1.6 M solution of n-butyl lithium in hexane (2.5 mL, 4.0 mmol). The mixture was stirred at −78° C. for 30 minutes and then methyl iodide (0.50 mL, 8.10 mmol) was added to it. The mixture was allowed to warm to ambient temperature and stirred for 16 h. The reaction mixture was then diluted with saturated ammonium chloride (10 mL) and extracted with diethyl ether (2×20 mL). The combined organic layers were washed with brine (20 mL), dried over anhydrous sodium sulfate, and filtered. Concentration of the filtrate in vacuo provided the title compound as a yellow foam (1.06 g, 99% yield): $^1$H-NMR (300 MHz, CDCl$_3$) δ 3.91-3.83 (m, 4H), 3.21 (s, 3H), 2.63-2.56 (m, 1H), 1.45 (s, 9H), 1.19 (s, 3H), 1.12 (s, 3H).

Step 3. Preparation of 2-((3-(2-methoxypropan-2-yl)azetidin-1-yl)methyl)benzonitrile

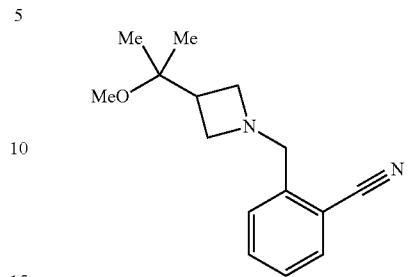

To a solution of tert-butyl 3-(2-methoxypropan-2-yl)azetidine-1-carboxylate (1.06 g, 4.65 mmol) in dichloromethane (5 mL) was added trifluoroacetic acid (5 mL) and the reaction mixture was stirred at ambient temperature for 1 h. The mixture was concentrated in vacuo and the residue was diluted in dichloromethane (5 mL). To this solution was added 2-formylbenzonitrile (0.61 g, 4.65 mmol) and sodium triacetoxyborohydride (2.76 g, 13.6 mmol) in one portion. The mixture was stirred at ambient temperature for 1 h. The mixture was diluted with a saturated sodium bicarbonate (30 mL) and extracted with dichloromethane (3×20 mL). The combined organic layers were washed with brine (20 mL), dried over anhydrous sodium sulfate, and filtered. Concentration of the filtrate in vacuo provided the title compound as a yellow foam (1.00 g, 88% yield): MS (ES+) m/z 245.2 (M+1).

Step 4. Preparation of (2-((3-(2-methoxypropan-2-yl)azetidin-1-yl)methyl)phenyl)methanamine

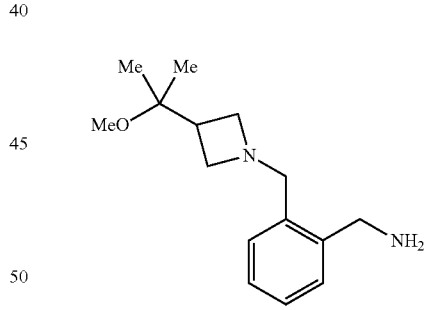

To a solution of 2-((3-(2-methoxypropan-2-yl)azetidin-1-yl)methyl)benzonitrile (0.72 g, 3.00 mmol) in anhydrous tetrahydrofuran (10 mL) was added a 1.0 M solution of lithium aluminum hydride in tetrahydrofuran (3.00 mL, 3.00 mmol) at 0° C. The mixture was stirred at 0° C. for 15 minutes and then at ambient temperature for 1 h. The mixture was then quenched by addition of sodium sulfate decahydrate (3.00 g) and then the mixture was stirred for 16 h. The mixture was filtered through a pad of diatomaceous earth and the filter cake was rinsed with dichloromethane (30 mL). Concentration of the combined filtrate under reduced pressure afforded the title compound as a colorless oil (0.59 g, 79%): MS (ES+) m/z 249.1 (M+1).

Step 5. Preparation of tert-butyl ((3-bromo-2,6-difluoro-4-((2-((3-(2-methoxypropan-2-yl)azetidin-1-yl)methyl)benzyl)amino)phenyl)sulfonyl)(thiazol-4-yl)carbamate

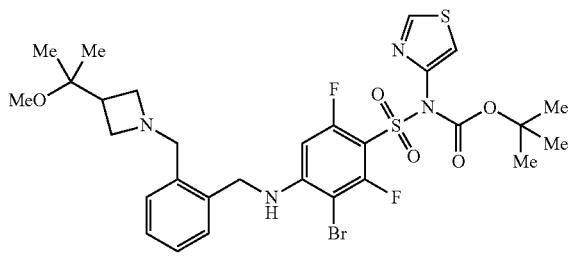 [SMILES: COC(C)(C)C1CN(Cc2ccccc2CNc2cc(F)c(S(=O)(=O)N(C(=O)OC(C)(C)C)c3cscn3)c(F)c2Br)C1]

To a solution of tert-butyl ((3-bromo-2,4,6-trifluorophenyl)sulfonyl)(thiazol-4-yl)carbamate (0.247 g, 0.52 mmol) and (2-((3-(2-methoxypropan-2-yl)azetidin-1-yl)methyl)phenyl)methanamine (0.13 g, 0.52 mmol) in anhydrous dimethyl sulfoxide (6 mL) was added potassium carbonate (0.072 g, 1.08 mmol). The mixture was stirred at ambient temperature for 16 h and was then diluted with water (20 mL) and extracted with ethyl acetate (2×30 mL). The combined organic layers were washed with brine (20 mL), dried over sodium sulfate, filtered. Concentration of the filtrate in vacuo and purification of the residue by column chromatography, eluting with a gradient of 0 to 10% of methanol in dichloromethane, provided the title compound as a colorless foam (0.040 g, 10% yield): MS (ES+) m/z 701.4 (M+1), 703.4 (M+1).

Step 6. Preparation of tert-butyl ((2,6-difluoro-4-((2-((3-(2-methoxypropan-2-yl)azetidin-1-yl)methyl)benzyl)amino)phenyl)sulfonyl)(thiazol-4-yl)carbamate

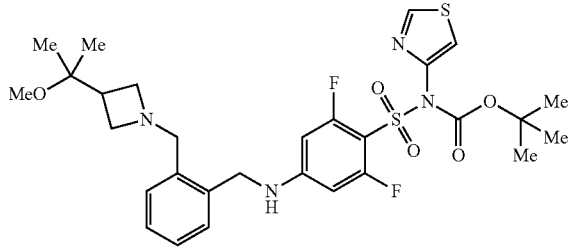 [SMILES: COC(C)(C)C1CN(Cc2ccccc2CNc2cc(F)c(S(=O)(=O)N(C(=O)OC(C)(C)C)c3cscn3)c(F)c2)C1]

To a mixture of tert-butyl ((3-bromo-2,6-difluoro-4-((2-((3-(2-methoxypropan-2-yl)azetidin-1-yl)methyl)benzyl)amino)phenyl)sulfonyl)(thiazol-4-yl)carbamate (0.040 g, 0.05 mmol) in ethanol (5 mL) was added triethylamine (0.028 mL, 0.20 mmol) and 15% palladium on carbon (5 mg). The suspension was degassed under vacuum and purged with hydrogen several times. The mixture was stirred under an atmosphere of hydrogen (50 psi) at 70° C. for 16 h. The reaction mixture was filtered and the filtrate concentrated in vacuo to provide the title compound as a colorless foam (0.036 g, quantitative yield): MS (ES+) m/z 623.3 (M+1).

Step 7. Preparation of 2,6-difluoro-4-((2-((3-(2-methoxypropan-2-yl)azetidin-1-yl)methyl)benzyl)amino)-N-(thiazol-4-yl)benzenesulfonamide 2,2,2-trifluoroacetate

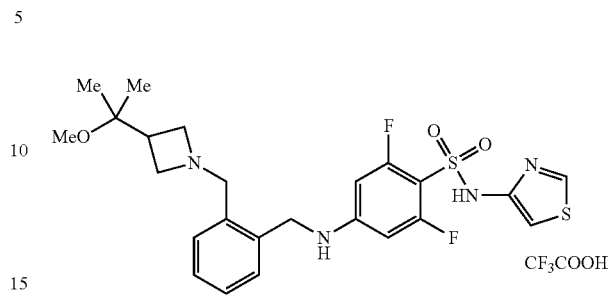

To a solution of tert-butyl ((2,6-difluoro-4-((2-((3-(2-methoxypropan-2-yl)azetidin-1-yl)methyl)benzyl)amino)phenyl)sulfonyl)(thiazol-4-yl)carbamate (0.036 g, 0.057 mmol) in dichloromethane (4 mL) was added trifluoroacetic acid (2 mL). The mixture was stirred at ambient temperature for 1 h and then concentrated in vacuo. The residue was purified by column chromatography, eluting with a gradient of 0 to 10% of methanol in dichloromethane, to afford the title compound as a colorless foam (0.023 g, 77% yield): $^1$H NMR (300 MHz, DMSO-$d_6$) δ 11.22 (s, 1H), 10.37 (s, 1H), 8.90 (d, J=2.2 Hz, 1H), 7.52-7.36 (m, 5H), 6.91 (d, J=2.2 Hz, 1H), 6.35 (d, J=12.6 Hz, 2H), 4.50-4.32 (m, 4H), 4.20-4.04 (m, 2H), 3.96-3.84 (m, 2H), 3.18-3.10 (m, 3H), 2.89-2.77 (m, 1H), 1.04-0.98 (m, 6H); MS (ES+) m/z 523.3 (M+1).

Example 215

Synthesis of 4-((2-(azetidin-1-ylmethyl)-3,6-difluorobenzyl)amino)-2,3,6-trifluoro-N-(thiazol-4-yl)benzenesulfonamide 2,2,2-trifluoroacetate

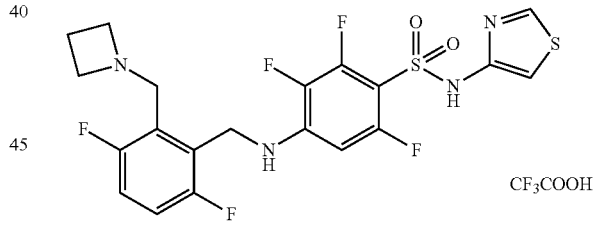

Step 1. Preparation of tert-butyl ((2,3,4,6-tetrafluorophenyl)sulfonyl)(thiazol-4-yl)carbamate

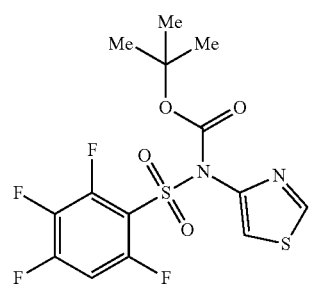 [SMILES: CC(C)(C)OC(=O)N(c1cscn1)S(=O)(=O)c1c(F)cc(F)c(F)c1F]

To a solution of tert-butyl thiazol-4-ylcarbamate (0.80 g, 4.03 mmol) in anhydrous tetrahydrofuran (20 mL) was added a 1 M solution of lithium bis(trimethylsilyl)amide in tetrahydrofuran (4.83 mL, 4.83 mmol) at −78° C. The reaction mixture was allowed to warm to ambient temperature and stirred for 1 h. The reaction mixture was cooled to −78° C., and a solution of 2,3,4,6-tetrafluorobenzenesulfonyl chloride (1.0 g, 4.03 mmol) in anhydrous tetrahydrofuran (10 mL) was added to it. The reaction mixture was allowed to warm to ambient temperature and stirred for 3 h. The mixture was diluted with ethyl acetate (50 mL), washed with saturated ammonium chloride (2×50 mL), brine (20 mL), dried over anhydrous sodium sulfate, and filtered. Concentration of the filtrate in vacuo and trituration of the residue in methanol (20 mL) provided the title compound as a colorless solid (0.80 g, 63% yield): MS (ES+) m/z 313.2 (M−99).

Step 2. Preparation of tert-butyl ((4-((2-(azetidin-1-ylmethyl)-3,6-difluorobenzyl)amino)-2,3,6-trifluorophenyl)sulfonyl)(thiazol-4-yl)carbamate

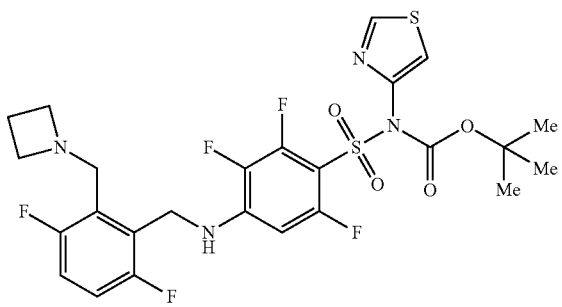 [SMILES: CC(C)(C)OC(=O)N(c1cscn1)S(=O)(=O)c1c(F)cc(NCc2c(F)ccc(F)c2CN2CCC2)c(F)c1F]

To a solution of tert-butyl ((2,3,4,6-tetrafluorophenyl)sulfonyl)(thiazol-4-yl)carbamate (0.20 g, 0.48 mmol) and (2-(azetidin-1-ylmethyl)-3,6-difluorophenyl)methanamine (0.103 g, 0.48 mmol) in anhydrous dimethyl sulfoxide (3 mL) was added potassium carbonate (0.132 g, 0.96 mmol). The mixture was stirred at ambient temperature for 16 h and was then diluted with water (20 mL) and extracted with ethyl acetate (2×15 mL). The combined organic layers were washed with brine (15 mL), dried over anhydrous sodium sulfate, and filtered. Concentration of the filtrate in vacuo and purification of the residue by column chromatography, eluting with a gradient of 0 to 10% of methanol in dichloromethane, provided the title compound as a colorless solid (0.075 g, 26% yield): MS (ES+) m/z 605.0 (M+1).

Step 3. Preparation of 4-((2-(azetidin-1-ylmethyl)-3,6-difluorobenzyl)amino)-2,3,6-trifluoro-N-(thiazol-4-yl)benzenesulfonamide 2,2,2-trifluoroacetate

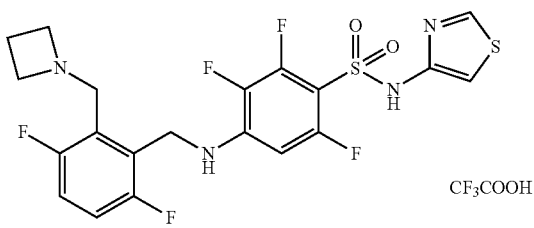 [SMILES: O=S(=O)(Nc1cscn1)c1c(F)cc(NCc2c(F)ccc(F)c2CN2CCC2)c(F)c1F ; "CF3COOH"]

To a solution of tert-butyl ((4-((2-(azetidin-1-ylmethyl)-3,6-difluorobenzyl)amino)-2,3,6-trifluorophenyl)sulfonyl)(thiazol-4-yl)carbamate (0.075 g, 0.12 mmol) in dichloromethane (4 mL) was added trifluoroacetic acid (2 mL). The mixture was stirred at ambient temperature for 1 h and then concentrated in vacuo. The residue was purified by column chromatography, eluting with a gradient of 0 to 10% of methanol in dichloromethane, to afford the title compound as a colorless solid (0.052 g, 85% yield): $^1$H NMR (300 MHz, DMSO-$d_6$) δ 11.40 (s, 1H), 8.92 (d, J=2.1 Hz, 1H), 7.45-7.39 (m, 3H), 7.00 (d, J=2.1 Hz, 1H), 6.67 (dd, J=13.5, 6.5 Hz, 1H), 4.54-4.44 (m, 4H), 4.13-4.00 (m, 4H), 2.36-2.21 (m, 2H), one exchangeable proton not observed; MS (ES+) m/z 505.0.

Example 216

Synthesis of 4-((2-(azetidin-1-ylmethyl)-3,6-difluorobenzyl)amino)-2,6-difluoro-N-(5-methylisoxazol-3-yl)benzenesulfonamide 2,2,2-trifluoroacetate

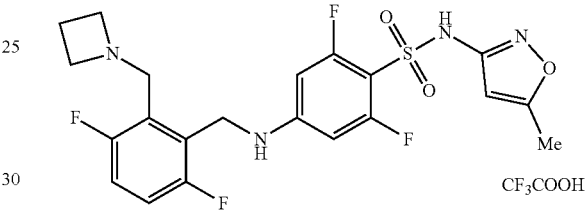

Step 1. Preparation of tert-butyl (5-methylisoxazol-3-yl)((2,4,6-trifluorophenyl)sulfonyl)-carbamate

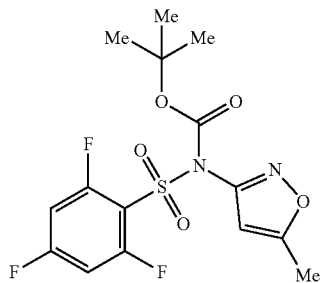 [SMILES: Cc1cc(N(C(=O)OC(C)(C)C)S(=O)(=O)c2c(F)cc(F)cc2F)no1]

To a solution of tert-butyl (5-methylisoxazol-3-yl)carbamate (1.98 g, 10.0 mmol) in anhydrous tetrahydrofuran (20 mL) at −78° C. was added lithium bis(trimethylsilyl)amide 1M solution in tetrahydrofuran (11.0 mL, 11.0 mmol). The reaction mixture was stirred at −78° C. for 15 minutes, then warmed up to ambient temperature and stirred for 10 minutes. The reaction mixture was cooled to −78° C. and a solution of 2,4,6-trifluorobenzenesulfonyl chloride (2.30 g, 10.0 mmol) in anhydrous tetrahydrofuran (20 mL) was added to it. The reaction mixture stirred at −78° C. for 2 h and then allowed to warm to ambient temperature. After stirring at ambient temperature for 16 h, the reaction mixture was diluted with saturated ammonium chloride (50 mL) and extracted with ethyl acetate (2×40 mL). The combined organic phases were washed with brine (30 mL), dried over anhydrous sodium sulfate, and filtered. Concentration of the filtrate in vacuo and trituration of the residue in methanol (10 mL) provided the title compound as a colorless solid (1.51 g, 38% yield): MS (ES+) m/z 393.1 (M+1).

Step 2. Preparation of tert-butyl (2-(azetidin-1-ylmethyl)-3,6-difluorobenzyl)(4-(N-(tert-butoxycarbonyl)-N-(5-methylisoxazol-3-yl)sulfamoyl)-3,5-difluorophenyl)carbamate

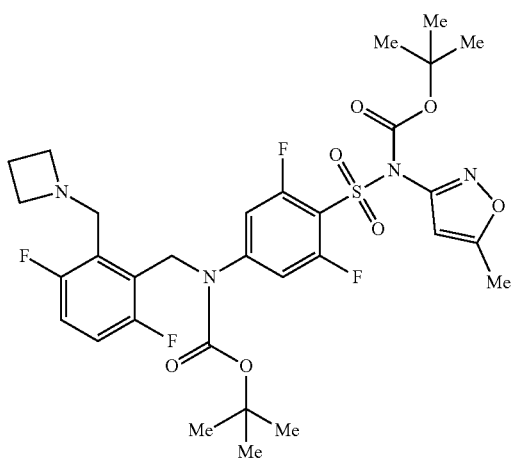 [SMILES: Cc1cc(N(C(=O)OC(C)(C)C)S(=O)(=O)c2c(F)cc(N(Cc3c(F)ccc(F)c3CN3CCC3)C(=O)OC(C)(C)C)cc2F)no1]

To a solution of tert-butyl (2-(azetidin-1-ylmethyl)-3,6-difluorobenzyl)carbamate (0.30 g, 0.95 mmol) in anhydrous N,N-dimethylformamide (20 mL) was added a dispersion of 60% sodium hydride in mineral oil (0.115 g, 2.87 mmol) at 0° C. The reaction mixture was allowed to warm to ambient temperature and stirred for 25 minutes. To it was then added tert-butyl (5-methylisoxazol-3-yl)((2,4,6-trifluorophenyl)sulfonyl)carbamate (0.372 g, 0.95 mmol) and the reaction mixture was stirred at ambient temperature for 1 h. The reaction mixture was quenched by addition of water (50 mL), and extracted with ethyl acetate (70 mL). The organic layer was washed with saturated ammonium chloride (2×50 mL), brine (20 mL), dried over anhydrous sodium sulfate, and filtered. Concentration of the filtrate in vacuo gave a residue which was purified by column chromatography, eluting with a gradient of 0 to 5% of methanol in dichloromethane, to provide the title compound as a colorless foam (0.12 g, 18% yield): MS (ES+) m/z 685.2 (M+1).

Step 3. Preparation of 4-((2-(azetidin-1-ylmethyl)-3,6-difluorobenzyl)amino)-2,6-difluoro-N-(5-methylisoxazol-3-yl)benzenesulfonamide 2,2,2-trifluoroacetate

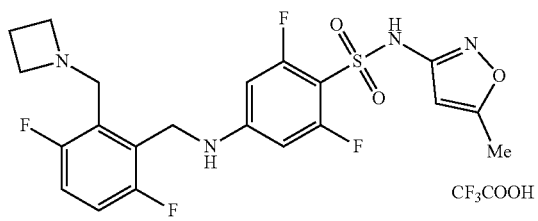 [SMILES: Cc1cc(NS(=O)(=O)c2c(F)cc(NCc3c(F)ccc(F)c3CN3CCC3)cc2F)no1 ; "CF3COOH"]

To a solution of tert-butyl (2-(azetidin-1-ylmethyl)-3,6-difluorobenzyl)(4-(N-(tert-butoxycarbonyl)-N-(5-methylisoxazol-3-yl)sulfamoyl)-3,5-difluorophenyl)carbamate (0.12 g, 0.17 mmol) in dichloromethane (4 mL) was added trifluoroacetic acid (2 mL). The reaction mixture was stirred at ambient temperature for 1 h and then concentrated in vacuo. The residue was purified by preparative reverse-phase HPLC, eluting with a gradient of 10 to 50% of acetonitrile in water containing 0.1% of formic acid, to afford the title compound as a colorless solid (0.072 g, 87% yield): $^1$H NMR (300 MHz, DMSO-$d_6$) δ 11.62 (s, 1H), 10.35 (s, 1H), 7.53-7.43 (m, 2H), 7.38-7.36 (m, 1H), 6.39 (d, J=12.6 Hz, 2H), 6.03 (d, J=0.9 Hz, 1H), 4.49 (d, J=0.4 Hz, 2H), 4.38-4.37 (m, 2H), 4.19-4.01 (m, 4H), 2.46-2.13 (m, 5H); MS (ES+) m/z 485.1 (M+1).

Example 217

Synthesis of 5-chloro-4-((1-(2-((dimethylamino)methyl)phenyl)cyclopropyl)-amino)-2-fluoro-N-(thiazol-4-yl)benzenesulfonamide 2,2,2-trifluoroacetate

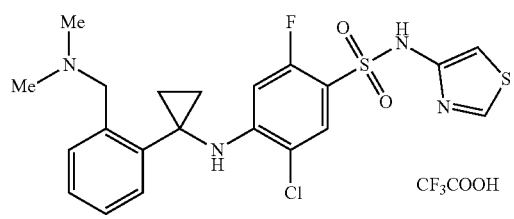 [SMILES: CN(C)Cc1ccccc1C1(Nc2cc(F)c(S(=O)(=O)Nc3cscn3)cc2Cl)CC1 ; "CF3COOH"]

Step 1. Preparation of tert-butyl ((4-((1-(2-bromophenyl)cyclopropyl)amino)-5-chloro-2-fluorophenyl)sulfonyl)(thiazol-4-yl)carbamate

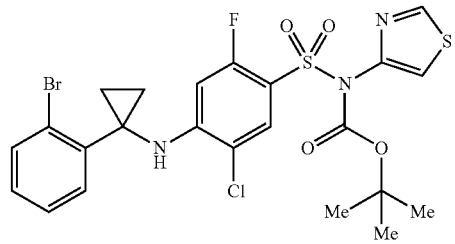 [SMILES: CC(C)(C)OC(=O)N(c1cscn1)S(=O)(=O)c1cc(Cl)c(NC2(c3ccccc3Br)CC2)cc1F]

To a solution of tert-butyl ((5-chloro-2,4-difluorophenyl)sulfonyl)(thiazol-4-yl)carbamate (1.23 g, 3.00 mmol) and diisopropylethylamine (1.00 mL, 6.00 mmol) in anhydrous N,N-dimethylformamide (10 mL) was added 1-(2-bromophenyl)cyclopropan-1-amine (0.64 g, 3.00 mmol). The resulting mixture was stirred at ambient temperature for 18 h and then diluted with ethyl acetate (200 mL). The mixture was washed with 1 M hydrochloric acid (2×20 mL), brine (20 mL), dried over anhydrous sodium sulfate, and filtered. The filtrate was concentrated in vacuo and the residue purified by column chromatography, eluting with a gradient of 0 to 40% of ethyl acetate in hexanes, to afford the title compound as an off-white solid (0.60 g, 33% yield): MS (ES+) m/z 602.1 (M+1), 604.1 (M+1), 606.1 (M+1).

Step 2. Preparation 5-chloro-4-((1-(2-((dimethyl-amino)methyl)phenyl)cyclopropyl)-amino)-2-fluoro-N-(thiazol-4-yl)benzenesulfonamide 2,2,2-trifluoro-acetate

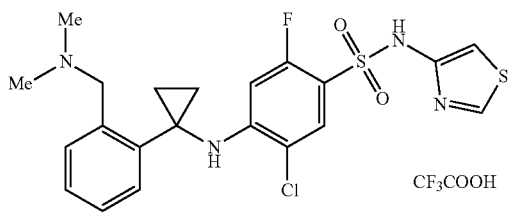

To mixture of tert-butyl ((4-((1-(2-bromophenyl)cyclopropyl)amino)-5-chloro-2-fluorophenyl)sulfonyl)(thiazol-4-yl)carbamate (0.60 g, 1.00 mmol), potassium dimethylaminomethyltrifluoroboronate (0.20 g, 1.20 mmol), and 2 M sodium carbonate (1.50 mL, 3.00 mmol) in dioxane (6 mL) was added palladium acetate (0.023 g, 0.10 mmol) and di(1-adamantyl)-n-butylphosphine (0.070 g, 0.02 mmol). The mixture was degassed and heated to 100° C. for 16 h. After cooling to ambient temperature, the mixture was diluted with ethyl acetate (50 mL), and filtered through a pad of Celite. The filtrate was concentrated in vacuo and the residue purified by column chromatography, eluting with a gradient of 0 to 100% of ethyl acetate (containing 10% isopropanol and 10% triethylamine) in hexanes. Additional purification by preparative reverse-phase HPLC, eluting with a gradient of 20 to 80% of acetonitrile in water containing 0.1% of trifluoroacetic acid, afforded the title compound as a colorless solid (0.015 g, 3% yield): $^1$H NMR (300 MHz, DMSO-$d_6$) δ 11.20-11.17 (m, 1H), 9.61-9.57 (m, 1H), 8.86 (d, J=2.2 Hz, 1H), 7.83-7.79 (m, 1H), 7.56 (d, J=7.3 Hz, 2H), 7.42-7.39 (m, 3H), 6.97-6.94 (m, 2H), 4.74-4.69 (m, 2H), 2.79-2.76 (m, 6H), 1.34-1.30 (m, 4H); MS (ES+) m/z 481.3 (M+1) 483.3 (M+1).

Example 218

Synthesis of 5-chloro-2-fluoro-4-((2-fluoro-6-(methoxymethyl)benzyl)amino)-N-(thiazol-4-yl)benzenesulfonamide

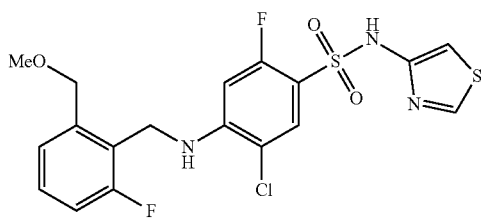 [SMILES: COCc1cccc(F)c1CNc1cc(F)c(S(=O)(=O)Nc2cscn2)cc1Cl]

Step 1. Preparation of 2-fluoro-6-(methoxymethyl)benzonitrile

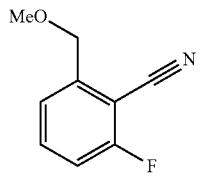 [SMILES: COCc1cccc(F)c1C#N]

To anhydrous methanol (20 mL) was added a dispersion of 60% sodium hydride in mineral oil (0.21 g, 5.13 mmol) at 0° C. The mixture was stirred for 1 h and then 2-(bromomethyl)-6-fluorobenzonitrile (1.10 g, 5.13 mmol) was added to it. The mixture was stirred at 0° C. for 5 h and at ambient temperature for 16 h. The mixture was then quenched by addition of saturated ammonium chloride (5 mL) and concentrated in vacuo. The residue was diluted with water (5 mL) and extracted with ethyl acetate (3×5 mL). The combined organic layer was washed with brine (5 mL), dried over anhydrous magnesium sulfate, and filtered. The filtrate was concentrated in vacuo and the residue purified by column chromatography, eluting with a gradient of 0 to 20% of ethyl acetate in hexanes, to afford the title compound as a colorless oil (0.40 g, 47% yield): $^1$H NMR (300 MHz, CDCl$_3$) δ 7.64-7.57 (m, 1H), 7.39 (dd, J=7.8, 0.6 Hz, 1H), 7.19-7.13 (m, 1H), 4.65 (s, 2H), 3.50 (s, 3H).

Step 2. Preparation of (2-fluoro-6-(methoxymethyl)phenyl)methanamine

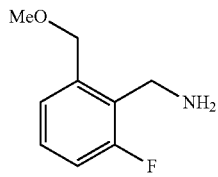 [SMILES: COCc1cccc(F)c1CN]

To a solution of 2-fluoro-6-(methoxymethyl)benzonitrile (0.40 g, 2.40 mmol) in anhydrous tetrahydrofuran (16 mL) was added a 1.0 M solution of lithium aluminum hydride in tetrahydrofuran (3.60 mL, 3.60 mmol) at 0° C. The mixture was stirred at 0° C. for 15 minutes and then at ambient temperature for 18 h. The mixture was then quenched by addition of sodium sulfate decahydrate (8.30 g) and then the mixture was stirred for 18 h. The mixture was filtered through a pad of Celite and the filtered cake was rinsed with ethyl acetate (100 mL). Concentration of the combined filtrate afforded the title compound as a colorless oil (0.31 g, 75%): $^1$H NMR (300 MHz, CDCl$_3$) δ 7.20 (td, J=7.8, 5.6 Hz, 1H), 7.11-7.00 (m, 2H), 4.51 (s, 2H), 3.88 (d, J=1.4 Hz, 2H), 3.41 (s, 3H), 1.76 (s, 2H); MS (ES+) m/z 170.2 (M+1).

Step 3. Preparation of 5-chloro-N-(2,4-dimethoxybenzyl)-2-fluoro-4-((2-fluoro-6-(methoxymethyl)benzyl)amino)-N-(thiazol-4-yl)benzenesulfonamide

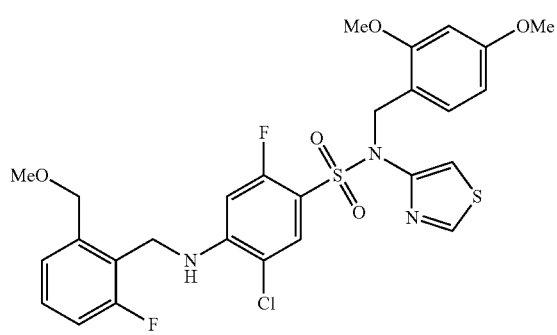 [SMILES: COCc1cccc(F)c1CNc1cc(F)c(S(=O)(=O)N(Cc2ccc(OC)cc2OC)c2cscn2)cc1Cl]

To a mixture of 5-chloro-N-(2,4-dimethoxybenzyl)-2,4-difluoro-N-(thiazol-4-yl)benzenesulfonamide (0.41 g, 0.89 mmol) and (2-fluoro-6-(methoxymethyl)phenyl)methanamine (0.15 g, 0.89 mmol) in anhydrous dimethyl sulfoxide (3.5 mL) was added diisopropylethylamine (0.40 mL, 2.13 mmol). The mixture was stirred for 18 h, then diluted with water (2 mL), and extracted with ethyl acetate (3×5 mL). The combined organic fractions were washed with brine (5 mL), dried over anhydrous magnesium sulfate, and filtered. The filtrate was concentrated in vacuo and the residue purified by column chromatography, eluting with a gradient of 0 to 50% of ethyl acetate in hexanes, to afford the title compound as a colorless oil (0.36 g, 66%): MS (ES+) m/z 610.3 (M+1), 612.3 (M+1).

Step 3. Preparation of 5-chloro-2-fluoro-4-((2-fluoro-6-(methoxymethyl)benzyl)amino)-N-(thiazol-4-yl)benzenesulfonamide

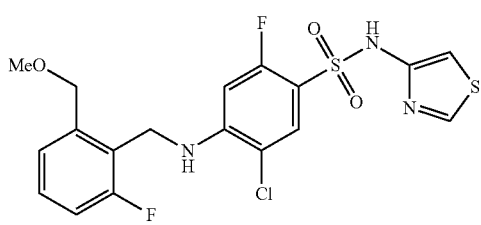 [SMILES: COCc1cccc(F)c1CNc1cc(F)c(S(=O)(=O)Nc2cscn2)cc1Cl]

To a solution of 5-chloro-N-(2,4-dimethoxybenzyl)-2-fluoro-4-((2-fluoro-6-(methoxymethyl)benzyl)amino)-N-(thiazol-4-yl)benzenesulfonamide (0.36 g, 0.59 mmol) in dichloromethane (6 mL) was added trifluoroacetic acid (1.5 mL). The mixture was stirred for 1 h and then concentrated in vacuo. To the residue was added methanol (20 mL) and the mixture was filtered. The filtrate was concentrated in vacuo and the residue was purified by preparative reverse-phase HPLC, eluting with a gradient of 20 to 80% of acetonitrile in water containing 0.1% of trifluoroacetic acid, to afford the title compound as a colorless solid (0.055 g, 20% yield): $^1$H NMR (300 MHz, DMSO-$d_6$) δ 11.14-11.12 (m, 1H), 8.88 (d, J=2.2 Hz, 1H), 7.59 (d, J=7.3 Hz, 1H), 7.36 (td, J=7.9, 5.8 Hz, 1H), 7.25-7.16 (m, 2H), 6.99 (d, J=2.1 Hz, 1H), 6.86 (d, J=13.3 Hz, 1H), 6.49-6.46 (m, 1H), 4.54 (s, 2H), 4.48-4.47 (m, 2H), 3.30 (s, 3H); MS (ES+) m/z 460.1 (M+1), 462.1 (M+1).

Example 219

Synthesis of 4-((2-(azetidin-1-ylmethyl)-6-fluorobenzyl)amino)-2-fluoro-N-(isoxazol-3-yl)-5-methylbenzenesulfonamide

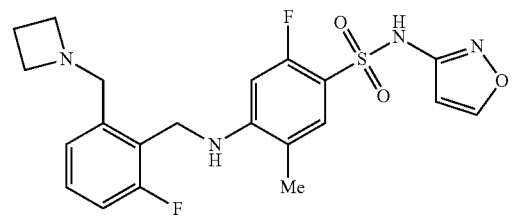 [SMILES: Cc1cc(S(=O)(=O)Nc2ccon2)c(F)cc1NCc1c(F)cccc1CN1CCC1]

Step 1. Preparation of 4-((2-(azetidin-1-ylmethyl)-6-fluorobenzyl)amino)-5-chloro-2-fluoro-N-(isoxazol-3-yl)-N-(4-methoxybenzyl)benzenesulfonamide

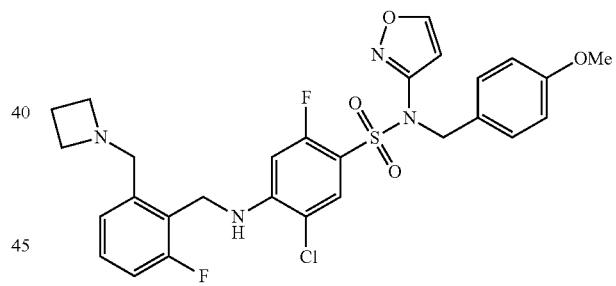

To a mixture of (2-(azetidin-1-ylmethyl)-6-fluorophenyl)methanamine (0.95 g, 4.89 mmol) and N,N-diisopropylethylamine (6.32 g, 48.9 mmol) in N,N-dimethylformamide (20 mL) was added 5-chloro-2,4-difluoro-N-(isoxazol-3-yl)-N-(4-methoxybenzyl)benzenesulfonamide (2.03 g, 4.89 mmol). The reaction mixture was stirred at ambient temperature for 72 h. The reaction mixture was adjusted to pH 6 with 1 M hydrochloride solution and the mixture was extracted with ethyl acetate (2×80 mL). The combined organic fractions were washed with saturated ammonium chloride (30 mL), brine (30 mL), dried over anhydrous sodium sulfate, and filtered. The filtrate was concentrated in vacuo. Crystallization of the residue from ethyl acetate (60 mL) afforded the title compound as colorless solid (2.30 g, 80%): MS (ES+) m/z 589.2 (M+1), 591.2 (M+1).

Step 2. Preparation of 4-((2-(azetidin-1-ylmethyl)-6-fluorobenzyl)amino)-2-fluoro-N-(isoxazol-3-yl)-N-(4-methoxybenzyl)-5-methylbenzenesulfonamide

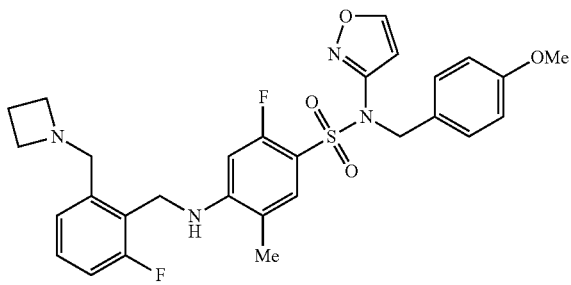 [SMILES: COc1ccc(CN(c2ccon2)S(=O)(=O)c2cc(C)c(NCc3c(F)cccc3CN3CCC3)cc2F)cc1]

To a microwave vial was added 4-((2-(azetidin-1-ylmethyl)-6-fluorobenzyl)amino)-5-chloro-2-fluoro-N-(isoxazol-3-yl)-N-(4-methoxybenzyl)-benzenesulfonamide (0.20 g, 0.34 mmol), methylboronic acid (0.08 g, 1.36 mmol) potassium phosphate tribasic (0.22 g, 1.02 mmol), tricyclohexylphosphine tetrafluoroborate (0.03 g, 0.07 mmol), palladium acetate (0.01 g, 0.03 mmol) and anhydrous 1,4-dioxane (2 mL). The mixture was degassed and then heated to 130° C. for 30 minutes in a microwave reactor. The reaction mixture was allowed to cool to ambient temperature, diluted with ethyl acetate (100 mL) and saturated ammonium chloride (30 mL), and filtered. The filtrate was collected and the layers were separated. The organic layer was washed with saturated ammonium chloride (20 mL), brine (20 mL), dried over anhydrous sodium sulfate, and filtered. The filtrate was concentrated in vacuo and the residue purified by column chromatography eluting with a gradient of 20 to 100% of ethyl acetate (containing 20% ethanol and 0.2% of ammonium hydroxide) in heptane to afford the title compound as a viscous oil (0.14 g, 70% yield): $^1$H NMR (300 MHz, CDCl$_3$) δ 8.14 (d, J=1.8 Hz, 1H), 7.45-7.39 (m, 3H), 7.29-7.22 (m, 1H), 7.12-7.02 (m, 3H), 6.83 (d, J=8.7 Hz, 2H), 6.67 (d, J=1.8 Hz, 2H), 5.04 (s, 2H), 4.40 (s, 2H), 3.77 (s, 3H), 3.64 (s, 2H), 3.25 (t, J=7.1 Hz, 4H), 2.16 (s, 3H), 2.14 (s, 2H); MS (ES+) m/z 568.9 (M+1).

Step 2. Preparation of 4-((2-(azetidin-1-ylmethyl)-6-fluorobenzyl)amino)-2-fluoro-N-(isoxazol-3-yl)-5-methylbenzenesulfonamide

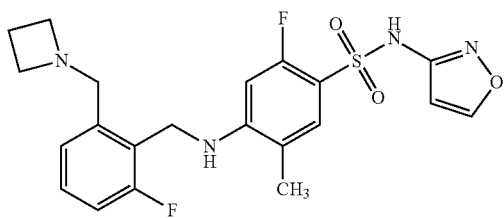 [SMILES: Cc1cc(S(=O)(=O)Nc2ccon2)c(F)cc1NCc1c(F)cccc1CN1CCC1]

To a mixture of 4-((2-(azetidin-1-ylmethyl)-6-fluorobenzyl)amino)-2-fluoro-N-(isoxazol-3-yl)-N-(4-methoxybenzyl)-5-methylbenzenesulfonamide (0.12 g, 0.21 mmol) in anhydrous 1,2-dichloroethane (2 mL) was added trifluoroacetic acid (1 mL). The reaction mixture was stirred at 65° C. for 1 h and then concentrated in vacuo. Purification of the residue by preparative reverse-phase HPLC, eluting with a gradient of 15 to 60% of acetonitrile in water containing 0.5% of formic acid, afforded the title compound as colorless solid (0.05 g, 30% yield): $^1$H NMR (300 MHz, DMSO-d$_6$) δ 11.52-11.31 (m, 1H), 8.64 (d, J=1.7 Hz, 1H), 7.46-7.39 (m, 1H), 7.37-7.27 (m, 1H), 7.24-7.11 (m, 2H), 7.04-6.88 (m, 1H), 6.73 (d, J=14.0 Hz, 1H), 6.31 (d, J=1.7 Hz, 1H), 4.41 (s, 2H), 3.73 (s, 2H), 3.32-3.17 (m, 4H), 2.16-2.09 (m, 3H), 2.06-1.94 (m, 2H); MS (ES+) m/z 449.2 (M+1).

Example 220

Synthesis of 5-chloro-2-fluoro-4-((1-(2-fluorophenyl)cyclopropyl)amino)-N-(thiazol-2-yl)benzenesulfonamide

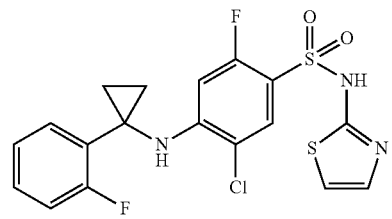 [SMILES: O=S(=O)(Nc1nccs1)c1cc(Cl)c(NC2(c3ccccc3F)CC2)cc1F]

Step 1. Preparation of 5-chloro-N-(2,4-dimethoxybenzyl)-2-fluoro-4-((1-(2-fluorophenyl)cyclopropyl)amino)-N-(thiazol-2-yl)benzenesulfonamide

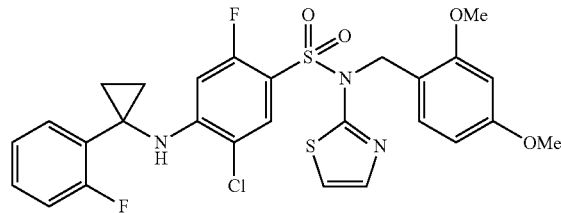 [SMILES: COc1ccc(CN(c2nccs2)S(=O)(=O)c2cc(Cl)c(NC3(c4ccccc4F)CC3)cc2F)c(OC)c1]

To a solution of 5-chloro-N-(2,4-dimethoxybenzyl)-2,4-difluoro-N-(thiazol-2-yl)benzenesulfonamide (0.250 g, 0.543 mmol) in anhydrous dimethyl sulfoxide (5 mL) was added 1-(2-fluorophenyl)cyclopropan-1-amine (0.082 g, 0.54 mmol) and potassium carbonate (0.180 g, 1.30 mmol). The resulting suspension was stirred at 60° C. for 16 h. The mixture was diluted with ethyl acetate (5 mL) and water (5 mL). The layers were separated and the aqueous phase was extracted with ethyl acetate (3×3 mL). The combined organic phase was washed with brine (1×5 mL), dried over anhydrous sodium sulfate, and filtered. Concentration of the filtrate in vacuo and purification of the residue The residue was purified by column chromatography, eluting with a gradient of 5 to 60% of ethyl acetate in hexanes, to afford the title compound as a colorless oil (0.153 g, 48% yield): MS (ES+) m/z 592.0 (M+1), 594.0 (M+1).

Step 2. Preparation of 5-chloro-2-fluoro-4-((1-(2-fluorophenyl)cyclopropyl)amino)-N-(thiazol-2-yl)benzenesulfonamide

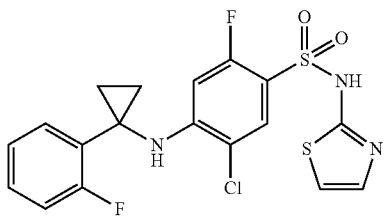 [SMILES: O=S(=O)(Nc1nccs1)c1cc(Cl)c(NC2(c3ccccc3F)CC2)cc1F]

To a solution of 5-chloro-N-(2,4-dimethoxybenzyl)-2-fluoro-4-((1-(2-fluorophenyl)cyclopropyl)amino)-N-(thiazol-2-yl)benzenesulfonamide (0.153 g, 0.258 mmol) in dichloromethane (5 mL) was added trifluoroacetic acid (1 mL) and the mixture was stirred at ambient temperature for 1 h. To it was then added Methanol (10 mL) and the resulting white precipitate was removed by filtration. The filtrate was concentrated in vacuo and the residue triturated with methanol (2×5 mL) to afford the title compound as a colorless solid (0.040 g, 32% yield): $^1$H-NMR (300 MHz, DMSO-$d_6$) δ 12.77 (d, J=0.4 Hz, 1H), 7.60-7.54 (m, 2H), 7.31-7.23 (m, 2H), 7.20-7.10 (m, 3H), 6.82 (d, J=4.6 Hz, 1H), 6.77 (d, J=12.7 Hz, 1H), 1.39-1.37 (m, 2H), 1.28-1.23 (m, 2H); MS (ES+) m/z 441.9 (M+1), 443.9 (M+1).

Example 221

Synthesis of 5-chloro-2-fluoro-4-(1-phenylcyclopropoxy)-N-(thiazol-4-yl)benzenesulfonamide

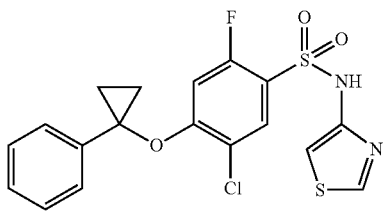 [SMILES: O=S(=O)(Nc1cscn1)c1cc(Cl)c(OC2(c3ccccc3)CC2)cc1F]

To a mixture of tert-butyl ((5-chloro-2,4-difluorophenyl)sulfonyl)(thiazol-4-yl)carbamate (0.223 g, 0.543 mmol) and 1-phenylcyclopropan-1-ol (0.087 g, 0.65 mmol), in anhydrous N,N-dimethylformamide (5 mL) was added sodium hydride (60% dispersion in mineral oil, 0.073 g, 1.19 mmol) at ambient temperature and the mixture reaction was stirred for 17 h. The reaction mixture was then diluted with ethyl acetate (5 mL), and saturated ammonium chloride (5 mL) was added to it. The layers were separated and the aqueous phase was extracted with ethyl acetate (3×5 mL). The combined organic phase was washed with brine (5 mL), dried over anhydrous sodium sulfate, and filtered. Concentration of the filtrate in vacuo and purification of the residue by column chromatography, eluting with a gradient of 5-100% of ethyl acetate in hexanes, followed by preparative reverse phase HPLC, using acetonitrile in water (containing 0.1% of trifluoroacetic acid) as eluent, afforded the title compound as a colorless solid (0.014 g, 6% yield): $^1$H-NMR (300 MHz, DMSO-$d_6$) δ 11.38 (s, 1H), 8.89-8.88 (m, 1H), 7.84 (d, J=7.4 Hz, 1H), 7.34 (t, J=7.4 Hz, 2H), 7.25 (d, J=7.3 Hz, 1H), 7.22-7.16 (m, 2H), 7.04 (d, J=2.1 Hz, 1H), 6.98 (d, J=11.5 Hz, 1H), 1.48 (s, 4H); MS (ES+) m/z 424.9 (M+1), 426.9 (M+1).

Example 222

Synthesis of (S)-5-chloro-4-((1-(2-chlorophenyl)propyl)amino)-2-fluoro-N-(thiazol-4-yl)benzenesulfonamide

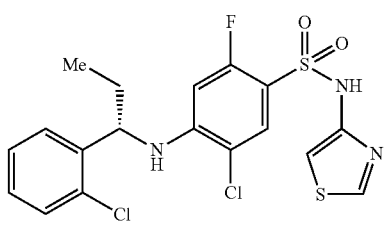 [SMILES: CC[C@H](Nc1cc(F)c(S(=O)(=O)Nc2cscn2)cc1Cl)c1ccccc1Cl]

Step 1. Preparation of tert-butyl (S)-((5-chloro-4-((1-(2-chlorophenyl)propyl)amino)-2-fluorophenyl)sulfonyl)(thiazol-4-yl)carbamate

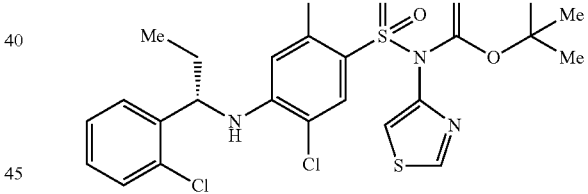

To a solution of tert-butyl ((5-chloro-2,4-difluorophenyl)sulfonyl)(thiazol-4-yl)carbamate (0.250 g, 0.543 mmol) in anhydrous dimethyl sulfoxide (5 mL) was added (S)-1-(2-chlorophenyl)propan-1-amine hydrochloride (0.223 g, 0.543 mmol) and potassium carbonate (0.254 g, 1.85 mmol). The resulting suspension was stirred at 75° C. for 18 h. The mixture was diluted with ethyl acetate (5 mL) and water (5 mL). The layers were separated and the aqueous phase was extracted with ethyl acetate (3×3 mL). The combined organic phase was washed with brine (1×5 mL), dried over anhydrous sodium sulfate, and filtered. Concentration of the filtrate in vacuo and purification of the residue by column chromatography, eluting with a gradient of 5 to 70% of ethyl acetate in hexanes, afforded the title compound as a colorless oil (0.112 g, 37% yield): MS (ES+) m/z 459.9 (M−99), 461.9 (M−99).

Step 2. Preparation of (S)-5-chloro-4-((1-(2-chlorophenyl)propyl)amino)-2-fluoro-N-(thiazol-4-yl)benzenesulfonamide

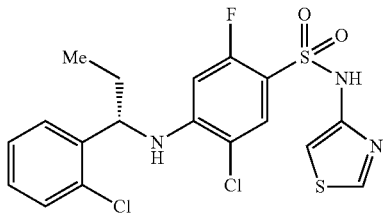 [SMILES: CC[C@H](Nc1cc(F)c(S(=O)(=O)Nc2cscn2)cc1Cl)c1ccccc1Cl]

To a solution of tert-butyl (S)-((5-chloro-4-((1-(2-chlorophenyl)propyl)amino)-2-fluorophenyl)sulfonyl)(thiazol-4-yl)carbamate (0.112 g, 0.200 mmol) in dichloromethane (5 mL) was added trifluoroacetic acid (1 mL) and the mixture was stirred at ambient temperature for 1 h. To it was added methanol (10 mL) was added and the resulting precipitate was removed by filtration. The filtrate was concentrated in vacuo. The obtained residue was purified by preparative reverse phase HPLC, using acetonitrile in water (containing 0.1% trifluoroacetic acid) as eluent, to afford the title compound as a colorless solid (0.051 g, 55% yield): $^1$H-NMR (300 MHz, DMSO-$d_6$) δ 11.14 (s, 1H), 8.86 (d, J=2.2 Hz, 1H), 7.61 (d, J=7.4 Hz, 1H), 7.52-7.44 (m, 2H), 7.35-7.24 (m, 2H), 6.96 (d, J=2.2 Hz, 1H), 6.86-6.83 (m, 1H), 6.12 (d, J=13.2 Hz, 1H), 4.71-4.63 (m, 1H), 2.09-1.94 (m, 1H), 1.87-1.73 (m, 1H), 0.94 (t, J=7.3 Hz, 3H); MS (ES+) m/z 459.9 (M+1), 462.0 (M+1).

Example 223

Synthesis of (S)-5-chloro-4-((1-(3,5-difluorophenyl)ethyl)amino)-2-fluoro-N-(thiazol-4-yl)benzenesulfonamide

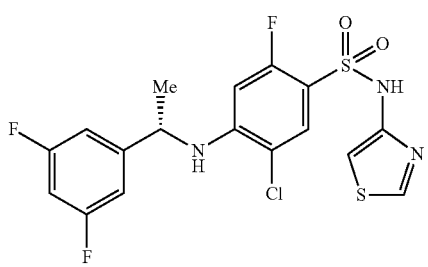

Step 1. Synthesis of tert-butyl (S)-((5-chloro-4-((1-(3,5-difluorophenyl)propyl)amino)-2-fluorophenyl)sulfonyl)(thiazol-4-yl)carbamate

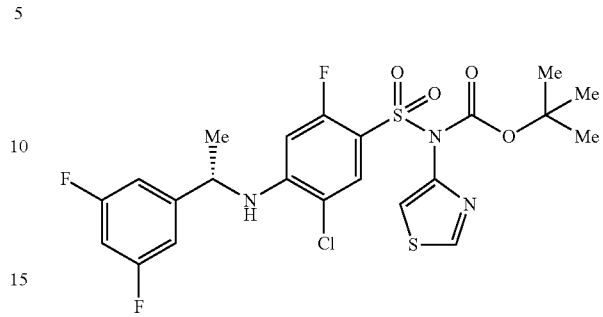

Following the procedure as described for EXAMPLE 222, Step 1 and making non-critical variations as required to replace (S)-1-(2-chlorophenyl)propan-1-amine hydrochloride with (S)-1-(3,5-difluorophenyl)ethan-1-amine hydrochloride, the title compound was obtained as a colorless solid (0.087 g, 29% yield): MS (ES) m/z 448.2 (M−99), 450.2 (M−99).

Step 2. Preparation of (S)-5-chloro-4-((1-(3,5-difluorophenyl)ethyl)amino)-2-fluoro-N-(thiazol-4-yl)benzenesulfonamide

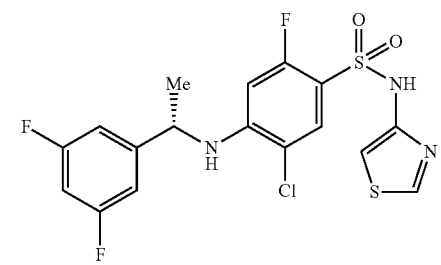 [SMILES: C[C@H](Nc1cc(F)c(S(=O)(=O)Nc2cscn2)cc1Cl)c1cc(F)cc(F)c1]

Following the procedure as described for EXAMPLE 222, Step 2 and making non-critical variations as required to replace tert-butyl (S)-((5-chloro-4-((1-(2-chlorophenyl)propyl)amino)-2-fluorophenyl)sulfonyl)(thiazol-4-yl)carbamate with tert-butyl (S)-((5-chloro-4-((1-(3,5-difluorophenyl)propyl)amino)-2-fluorophenyl)sulfonyl)(thiazol-4-yl)carbamate, the title compound was obtained as a colorless solid (0.010 g, 4% yield): $^1$H-NMR (300 MHz, DMSO-$d_6$) δ 11.12 (s, 1H), 8.87 (d, J=2.1 Hz, 1H), 7.61 (d, J=7.4 Hz, 1H), 7.24-7.19 (m, 1H), 7.13-6.98 (m, 1H), 6.97-6.96 (m, 1H), 6.77-6.74 (m, 1H), 6.54 (d, J=13.3 Hz, 1H), 6.49-6.46 (d, J=7.8 Hz, 1H), 4.79-4.67 (m, 1H), 1.52 (d, J=6.7 Hz, 3H); MS (ES+) m/z 447.9 (M+1), 449.9 (M+1).

Example 224

Synthesis of 5-chloro-4-((1-(2,4-difluorophenyl)cyclopropyl)amino)-2-fluoro-N-(thiazol-4-yl)benzenesulfonamide

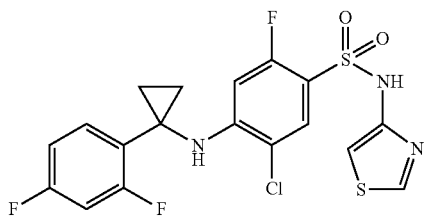 [SMILES: O=S(=O)(Nc1cscn1)c1cc(Cl)c(NC2(c3ccc(F)cc3F)CC2)cc1F]

To a solution of tert-butyl ((5-chloro-2,4-difluorophenyl)sulfonyl)(thiazol-4-yl)carbamate (0.250 g, 0.543 mmol) in anhydrous dimethyl sulfoxide (5 mL) was added 1-(2,4-difluorophenyl)cyclopropan-1-amine hydrochloride (0.223 g, 0.543 mmol) and cesium carbonate (0.792 g, 2.49 mmol). The resulting suspension was stirred at 75° C. for 18 h. After cooling toe ambient temperature, the mixture was diluted with ethyl acetate (5 mL) and water (5 mL). The layers were separated and the aqueous phase was extracted with ethyl acetate (3×3 mL). The combined organic phase was washed with brine (1×5 mL), dried over anhydrous sodium sulfate, and filtered. Concentration of the filtrate in vacuo provided a residue which was dissolved in dichloromethane (10 mL). To it was added trifluoroacetic acid (1 mL) and the mixture was stirred at ambient temperature for 18 h. The solution was concentrated in vacuo and the obtained residue purified by column chromatography, eluting with a gradient of 5 to 80% of ethyl acetate in hexanes. Further purification by preparative reverse phase HPLC, using acetonitrile in water containing 0.1% trifluoroacetic acid as eluent, afforded the title compound as a colorless solid (0.014 g, 4% yield): $^1$H-NMR (300 MHz, DMSO-$d_6$) δ 11.16 (s, 1H), 8.87 (d, J=2.2 Hz, 1H), 7.68 (td, J=8.9, 6.7 Hz, 1H), 7.59 (d, J=7.3 Hz, 1H), 7.34 (d, J=1.4 Hz, 1H), 7.19 (ddd, J=11.6, 9.2, 2.5 Hz, 1H), 7.07-7.01 (m, 1H), 6.98 (d, J=2.1 Hz, 1H), 6.80 (d, J=12.9 Hz, 1H), 1.39-1.34 (m, 2H), 1.27-1.24 (m, 2H); MS (ES+) m/z 460.0 (M+1), 462.0 (M+1).

Example 225

Synthesis of 5-chloro-4-((1-(2,5-difluorophenyl)cyclopropyl)amino)-2-fluoro-N-(thiazol-4-yl)benzenesulfonamide

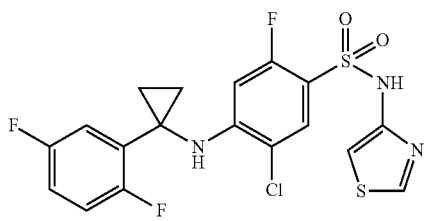 [SMILES: O=S(=O)(Nc1cscn1)c1cc(Cl)c(NC2(c3cc(F)ccc3F)CC2)cc1F]

Following the procedure as described for EXAMPLE 224, and making non-critical variations as required to replace 1-(2,4-difluorophenyl)cyclopropan-1-amine hydrochloride with 1-(2,5-difluorophenyl)cyclopropan-1-amine hydrochloride, and purification by column chromatography, eluting with a gradient of 5 to 80% of ethyl acetate in hexanes, followed by trituration with methanol (2×5 mL), afforded the title compound as a colorless solid (0.037 g, 15% yield): $^1$H-NMR (300 MHz, DMSO-$d_6$) δ 11.16 (s, 1H), 8.86 (d, J=2.2 Hz, 1H), 7.72-7.64 (m, 1H), 7.58 (d, J=7.3 Hz, 1H), 7.34-7.34 (m, 1H), 7.18 (ddd, J=11.7, 9.1, 2.6 Hz, 1H), 7.07-7.00 (m, 1H), 6.97 (d, J=2.2 Hz, 1H), 6.80 (d, J=13.0 Hz, 1H), 1.36-1.34 (m, 2H), 1.25-1.22 (m, 2H); MS (ES+) m/z 460.0 (M+1), 462.0 (M+1).

Example 226

Synthesis of 5-chloro-4-((2-chloro-6-methylbenzyl)amino)-2-fluoro-N-(thiazol-4-yl)benzenesulfonamide

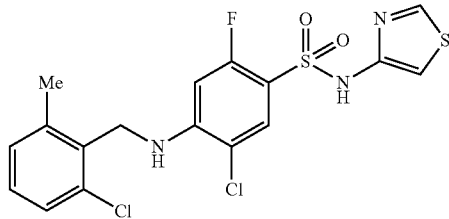 [SMILES: Cc1cccc(Cl)c1CNc1cc(F)c(S(=O)(=O)Nc2cscn2)cc1Cl]

Step 1. Preparation of tert-butyl ((5-chloro-4-((2-chloro-6-methylbenzyl)amino)-2-fluorophenyl)sulfonyl)(thiazol-4-yl)carbamate

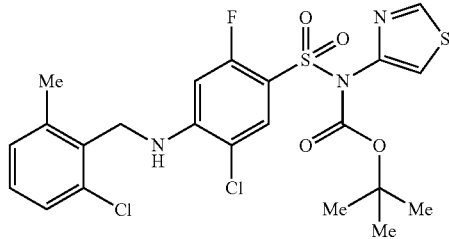 [SMILES: Cc1cccc(Cl)c1CNc1cc(F)c(S(=O)(=O)N(C(=O)OC(C)(C)C)c2cscn2)cc1Cl]

To a solution of tert-butyl ((5-chloro-2,4-difluorophenyl)sulfonyl)(thiazol-4-yl)carbamate (0.250 g, 0.610 mmol) in anhydrous dimethyl sulfoxide (5 mL) was added (2-chloro-6-methylphenyl)methanamine (0.095 g, 0.610 mmol) and triethylamine (0.34 mL, 2.43 mmol). The resulting solution was stirred at ambient temperature for 18 h. The mixture was diluted with ethyl acetate (5 mL) and water (5 mL). The layers were separated and the aqueous phase was extracted with ethyl acetate (3×5 mL). The combined organic phase was washed with brine (1×5 mL), dried over anhydrous sodium sulfate, and filtered. Concentration of the filtrate in vacuo and purification of the residue by column chromatography, eluting with a gradient of 5 to 60% of ethyl acetate in hexanes, afforded the title compound as a colorless oil (0.261 g, 78% yield): MS (ES+) m/z 546.1 (M+1), 548.1 (M+1).

Step 2. Preparation of 5-chloro-4-((2-chloro-6-methylbenzyl)amino)-2-fluoro-N-(thiazol-4-yl)benzenesulfonamide

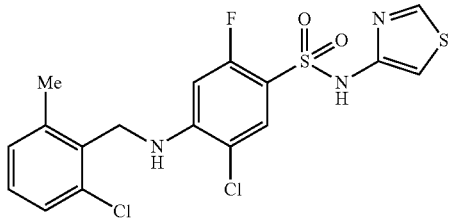 [SMILES: Cc1cccc(Cl)c1CNc1cc(F)c(S(=O)(=O)Nc2cscn2)cc1Cl]

To a solution of tert-butyl ((5-chloro-4-((2-chloro-6-methylbenzyl)amino)-2-fluorophenyl)sulfonyl)(thiazol-4-yl)carbamate (0.261 g, 0.478 mmol) in dichloromethane (5 mL) was added trifluoroacetic acid (1 mL) and the reaction mixture was stirred at ambient temperature for 2 h. The mixture was concentrated in vacuo to afford the title compound as a colorless solid (0.145 g, 68% yield): $^1$H-NMR (300 MHz, DMSO-$d_6$) δ 11.14 (s, 1H), 8.89 (d, J=2.2 Hz, 1H), 7.60 (d, J=7.4 Hz, 1H), 7.33 (dd, J=7.8, 1.3 Hz, 1H), 7.28-7.15 (m, 2H), 7.00-6.99 (m, 1H), 6.80 (d, J=13.2 Hz, 1H), 6.39-6.36 (m, 1H), 4.47 (d, J=4.6 Hz, 2H), 2.36 (s, 3H); MS (ES+) m/z 446.0 (M+1), 448.0 (M+1).

Example 227

Synthesis of (S)-5-chloro-4-((1-(5-(2,2-difluoroethyl)-2-fluorophenyl)ethyl)amino)-2-fluoro-N-(thiazol-4-yl)benzenesulfonamide

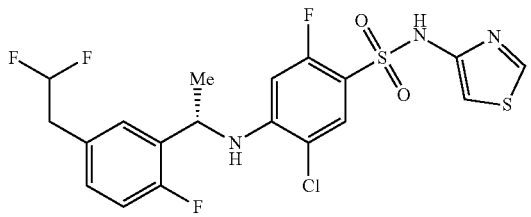 [SMILES: C[C@H](Nc1cc(F)c(S(=O)(=O)Nc2cscn2)cc1Cl)c1cc(CC(F)F)ccc1F]

Step 1. Preparation of tert-butyl (S,E)-((5-chloro-4-((1-(5-(2-ethoxyvinyl)-2-fluorophenyl)ethyl)amino)-2-fluorophenyl)sulfonyl)(thiazol-4-yl)carbamate

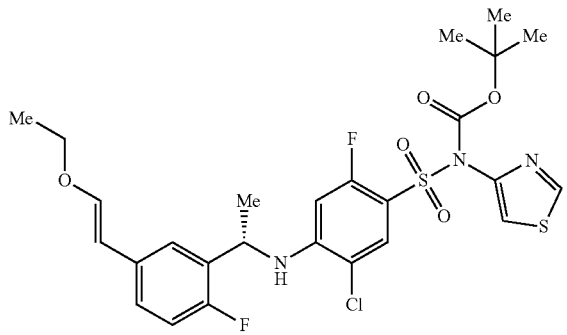 [SMILES: CCO/C=C/c1ccc(F)c([C@H](C)Nc2cc(F)c(S(=O)(=O)N(C(=O)OC(C)(C)C)c3cscn3)cc2Cl)c1]

To a solution of (S)-tert-butyl (4-((1-(5-bromo-2-fluorophenyl)ethyl)amino)-5-chloro-2-fluorophenyl)sulfonyl(thiazol-4-yl)carbamate (1.00 g, 1.64 mmol), (E)-2-(2-ethoxyvinyl)-4,4,5,5-tetramethyl-1,3,2-dioxaborolane (0.65 g, 3.3 mmol) and sodium carbonate (0.35 g, 3.3 mmol) in toluene (5 mL), ethanol (5 mL) and water (5 mL) was added tetrakis(triphenylphosphine)-palladium(0) (0.38 g, 0.33 mmol). The reaction mixture was heated 90° C. for 12 h. After cooling to ambient temperature, the reaction mixture was diluted with water (50 mL) and extracted with ethyl acetate (3×50 mL). The combined organic layer was washed with brine (20 mL), dried over anhydrous sodium sulfate, and filtered. Concentration of the filtrate in vacuo and purification of the residue by silica gel chromatography, eluting with a gradient of 10 to 33% of ethyl acetate in petroleum ether, afforded the title compound as a colorless oil (0.90 g, 91% yield): $^1$H NMR (400 MHz, CDCl$_3$) δ 8.77 (d, J=2.0 Hz, 1H), 7.96 (d, J=7.2 Hz, 1H), 7.47 (d, J=2.0 Hz, 1H), 7.14-7.09 (m, 1H), 7.04-6.97 (m, 2H), 6.86 (d, J=12.8 Hz, 1H), 6.21 (d, J=12.0 Hz, 1H), 5.74 (d, J=12.8 Hz, 1H), 4.81 (t, J=6.4 Hz, 1H), 3.87 (q, J=7.2 Hz, 3H), 1.65 (d, J=6.4 Hz, 3H), 1.34 (s, 9H), 1.33-1.30 (m, 3H); MS (ES+) m/z 499.9 (M−99).

Step 2. Preparation of (S)-5-chloro-2-fluoro-4-((1-(2-fluoro-5-(2-oxoethyl)phenyl)ethyl)amino)-N-(thiazol-4-yl)benzenesulfonamide

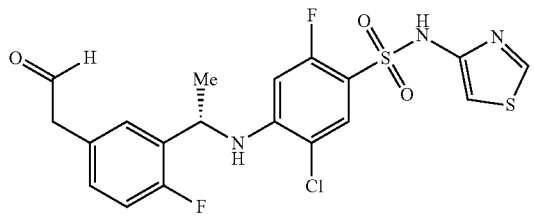 [SMILES: C[C@H](Nc1cc(F)c(S(=O)(=O)Nc2cscn2)cc1Cl)c1cc(CC=O)ccc1F]

A solution of (S)-tert-butyl(5-chloro-4-((1-(5-(2-ethoxyvinyl)-2-fluorophenyl)ethyl)amino)-2-fluorophenyl)sulfonyl(thiazol-4-yl)carbamate (0.90 g, 1.5 mmol) in formic acid (10 mL) was stirred at ambient temperature for 30 minutes. The mixture was then concentrated in vacuo. To the residue was added aqueous sodium hydrogencarbonate (30 mL) and the mixture extracted with ethyl acetate (3×30 mL). The combined organic layer was washed with brine (20 mL), dried over anhydrous sodium sulfate, and filtered. Concentration of the filtrate in vacuo and purification of the residue by column chromatography, eluting with a gradient of 5-50% of ethyl acetate in petroleum ether, afforded the title compound as a yellow solid (0.23 g, 32% yield): $^1$H NMR (400 MHz, CDCl$_3$) δ 9.71 (t, J=2.0 Hz, 1H), 9.06 (s, 1H), 8.63 (d, J=2.0 Hz, 1H), 7.75 (d, J=7.2 Hz, 1H), 7.14-7.10 (m, 2H), 7.04 (d, J=5.6 Hz, 1H), 6.96 (d, J=2.0 Hz, 1H), 6.11 (d, J=12.4 Hz, 1H), 5.25-5.18 (m, 1H), 4.78 (t, J=6.4 Hz, 1H), 3.66 (s, 2H), 1.63 (d, J=6.8 Hz, 3H); MS (ES+) m/z 472.0 (M+1), 474.0 (M+1).

Step 3. Preparation of (S)-5-chloro-4-((1-(5-(2,2-difluoroethyl)-2-fluorophenyl)ethyl)amino)-2-fluoro-N-(thiazol-4-yl)benzenesulfonamide

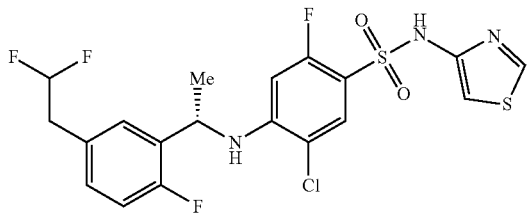 [SMILES: C[C@H](Nc1cc(F)c(S(=O)(=O)Nc2cscn2)cc1Cl)c1cc(CC(F)F)ccc1F]

To a solution of (S)-5-chloro-2-fluoro-4-((1-(2-fluoro-5-(2-oxoethyl)phenyl)ethyl)amino)-N-(thiazol-4-yl)benzenesulfonamide (0.100 g, 0.212 mmol) in anhydrous dichloromethane (4 mL) was added (diethylamino)sulfur trifluoride (0.068 g, 0.424 mmol) dropwise at −78° C. The mixture was stirred at 0° C. for 30 minutes. The mixture was quenched with aqueous sodium hydrogencarbonate (30 mL) and extracted with dichloromethane (3×30 mL). The combined organic phase was washed with brine (20 mL), dried over anhydrous sodium sulfate, and filtered. Concentration of the filtrate in vacuo and purification of the residue preparative reverse phase HPLC, using acetonitrile in water containing 0.225% formic acid as eluent, afforded the title compound as a colorless solid (0.016 g, 15% yield): $^1$H NMR (400 MHz, CDCl$_3$) δ 8.60 (d, J=2.4 Hz, 1H), 7.75 (d, J=7.2 Hz, 1H), 7.21-7.14 (m, 1H), 7.11-7.04 (m, 2H), 6.97 (d, J=2.0 Hz, 1H), 6.12 (d, J=12.0 Hz, 1H), 6.03-5.68 (m, 1H), 5.21 (d, J=5.6 Hz, 1H), 4.77 (q, J=6.4 Hz, 1H), 3.08 (td, J=17.2, 4.4 Hz, 2H), 1.63 (d, J=6.4 Hz, 3H), NH not observed; MS (ES+) m/z 494.0 (M+1), 496.0 (M+1).

Example 228

Synthesis of (S)-2,6-difluoro-4-((1-(2-fluoro-5-(methoxymethyl)phenyl)ethyl)amino)-N-(thiazol-4-yl)benzenesulfonamide

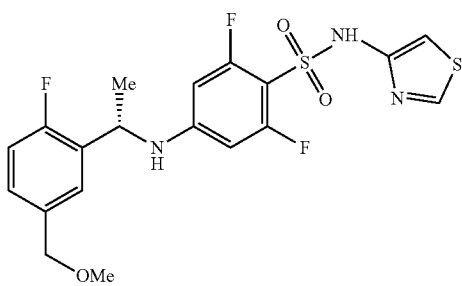 [SMILES: COCc1ccc(F)c([C@H](C)Nc2cc(F)c(S(=O)(=O)Nc3cscn3)c(F)c2)c1]

Step 1. Preparation of 2-bromo-1-fluoro-4-(methoxymethyl)benzene

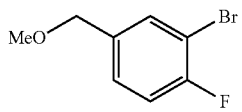

To a solution of (3-bromo-4-fluorophenyl)methanol (5.00 g, 24.4 mmol) in N,N-anhydrous N,N-dimethylformamide (50 mL) was added a 60% suspension of sodium hydride in mineral oil (1.37 g, 34.2 mmol) in portions at 0° C., and the mixture was stirred at 0° C. for 30 minutes. To it was then added iodomethane (4.15 g, 29.3 mmol) at 0° C. The mixture was allowed to warm to ambient temperature and stirred for 1 h. The reaction was quenched by addition of water (200 mL) and extracted with ethyl acetate (3×200 mL). The combined organic layers were washed with brine (50 mL), dried over anhydrous sodium sulfate, and filtered. Concentration of the filtrate in vacuo and purification of the residue by column chromatography, eluting with 2 to 5% of ethyl acetate in petroleum ether, afforded the title compound as a colorless oil (4.50 g, 84% yield): $^1$H NMR (400 MHz, CDCl$_3$) δ 7.57 (dd, J=6.4, 2.0 Hz, 1H), 7.28-7.23 (m, 1H), 7.11 (t, J=8.0 Hz, 1H), 4.42 (s, 2H), 3.41 (s, 3H).

Step 2. Preparation of 2-fluoro-5-(methoxymethyl)benzaldehyde

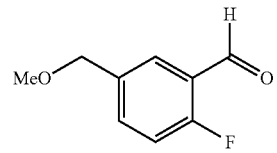

To a solution of 2-bromo-1-fluoro-4-(methoxymethyl)benzene (4.50 g, 20.54 mmol) in anhydrous tetrahydrofuran (50 mL) was added a 2.5 M solution of n-butyllithium in diethyl ether (9.86 mL, 3.94 mmol) −78° C. The reaction mixture was stirred for 30 minutes −78° C., and then anhydrous N,N-dimethylformamide (3.00 g, 41.09 mmol) was added to it. The reaction mixture was allowed to warm to ambient temperature and stirred for 1 h, and then quenched with water (50 mL) and extracted with ethyl acetate (3×50 mL). The combined organic layers were washed with brine (20 mL), dried over anhydrous sodium sulfate, and filtered. Concentration of the filtrate in vacuo and purification of the residue by column chromatography, eluting with 2 to 10% of ethyl acetate in petroleum ether, afforded the title compound as a colorless oil (2.30 g, 66% yield): $^1$H NMR (400 MHz, CDCl$_3$) δ 10.30 (s, 1H), 7.76 (dd, J=6.4, 2.0 Hz, 1H), 7.59-7.50 (m, 1H), 7.10 (dd, J=10.0, 8.4 Hz, 1H), 4.39 (s, 2H), 3.33 (s, 3H); MS (ES+) m/z 169.1 (M+1)

Step 3. Preparation of (R)—N-(2-fluoro-5-(methoxymethyl)benzylidene)-2-methylpropane-2-sulfinamide

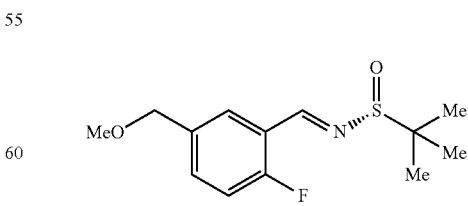

To a solution of 2-fluoro-5-(methoxymethyl)benzaldehyde (2.30 g, 13.7 mmol) and (R)-2-methylpropane-2-sulfinamide (1.82 g, 15.1 mmol) in anhydrous dichloromethane (40 mL) was added cesium carbonate (8.91 g, 27.4 mmol).

The mixture was stirred at ambient temperature for 12 h. The mixture was filtered and the filtrate concentrated in vacuo. The residue was purified by column chromatography, eluting with 3 to 17% of ethyl acetate in petroleum ether, to afford the title compound as a colorless oil (3.50 g, 94% yield): ¹H NMR (400 MHz, CDCl₃) δ 8.92 (s, 1H), 7.96 (dd, J=6.4, 2.0 Hz, 1H), 7.54-7.47 (m, 1H), 7.17 (dd, J=9.6, 8.4 Hz, 1H), 4.48 (s, 2H), 3.44 (s, 3H), 1.30 (s, 9H).

Step 4. (R)—N—((S)-1-(2-fluoro-5-(methoxymethyl)phenyl)ethyl)-2-methylpropane-2-sulfinamide

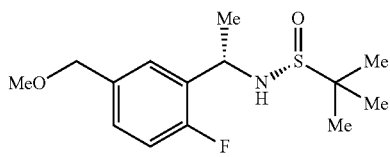 [SMILES: COCc1ccc(F)c([C@H](C)N[S@](=O)C(C)(C)C)c1]

To a solution of (R)—N-(2-fluoro-5-(methoxymethyl)benzylidene)-2-methylpropane-2-sulfinamide (3.50 g, 12.9 mmol) in dichloromethane (40 mL) was added a 3 M solution of methylmagnesium bromide in diethyl ether (8.60 mL, 25.80 mmol) at −50° C. The reaction mixture was stirred at ambient temperature for 1 h, and then quenched with saturated ammonium chloride (100 mL) and extracted with dichloromethane (3×100 mL). The combined organic layers were washed with brine (50 mL) and dried over anhydrous sodium sulfate, and filtered. Concentration of the filtrate and purification of the residue by column chromatography, eluting with 10 to 50% of ethyl acetate in petroleum ether, provided the title compound as a colorless oil (2.20 g, 59% yield): ¹H NMR (400 MHz, CDCl₃) δ 7.34 (dd, J=7.2, 2.0 Hz, 1H), 7.26-7.20 (m, 1H), 7.03 (dd, J=10.0, 8.4 Hz, 1H), 4.90-4.81 (m, 1H), 4.42 (s, 2H), 3.40 (s, 3H), 1.61 (d, J=6.4 Hz, 3H), 1.21 (s, 9H), NH not observed.

Step 5. Preparation of (S)-1-(2-fluoro-5-(methoxymethyl)phenyl)ethanamine hydrochloride

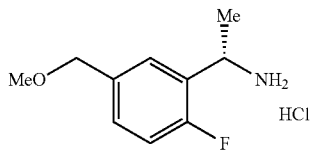 [SMILES: COCc1ccc(F)c([C@H](C)N)c1 ; Cl]

To (R)—N—((S)-1-(2-fluoro-5-(methoxymethyl)phenyl)ethyl)-2-methylpropane-2-sulfinamide (2.20 g, 7.66 mmol) was added a 4 M solution of hydrogen chloride in methanol (20 mL) and the reaction mixture was stirred at ambient temperature for 2 h. The mixture was concentrated in vacuo, diluted with water (50 mL) and extracted with ethyl acetate (3×30 mL). To the aqueous phase was added saturated sodium bicarbonate (5 mL) and the mixture was then extracted with ethyl acetate (3×30 mL). The combined organic extracts were washed with brine (20 mL), dried over anhydrous sodium sulfate, and filtered. Concentration of the filtrate in vacuo provided the title compound as a colorless oil (1.30 g, 93% yield): ¹H NMR (400 MHz, CDCl₃) δ 7.40 (dd, J=7.2, 1.6 Hz, 1H), 7.22-7.16 (m, 1H), 7.00 (dd, J=10.4, 8.4 Hz, 1H), 4.43 (s, 2H), 4.41-4.35 (m, 1H), 3.41 (s, 3H), 1.43 (d, J=6.8 Hz, 3H), exchangeable protons not observed; MS (ES+) m/z 184.0 (M+1).

Step 6. Preparation of (S)-tert-butyl(2,6-difluoro-4-((1-(2-fluoro-5-(methoxymethyl)phenyl)ethyl)amino)phenyl) sulfonyl(thiazol-4-yl)carbamate

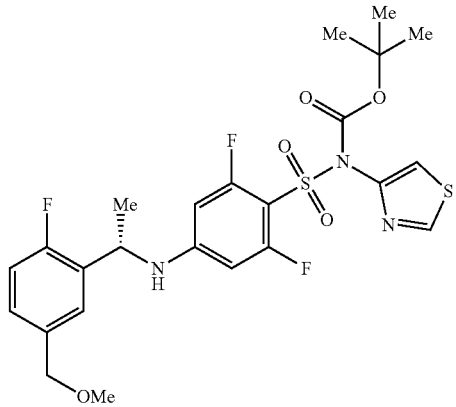 [SMILES: COCc1ccc(F)c([C@H](C)Nc2cc(F)c(S(=O)(=O)N(C(=O)OC(C)(C)C)c3cscn3)c(F)c2)c1]

To a solution of tert-butyl thiazol-4-yl((2,4,6-trifluorophenyl)sulfonyl)carbamate (0.30 g, 0.76 mmol) and (S)-1-(2-fluoro-5-(methoxymethyl)phenyl)ethanamine hydrochloride (0.15 g, 0.68 mmol) in anhydrous dimethyl sulfoxide (8 mL) was added cesium carbonate (0.49 g, 1.5 mmol) in one portion. The mixture was stirred at ambient temperature for 12 h and was then diluted with water (30 mL) and extracted with ethyl acetate (3×30 mL). The combined organic layers were washed with brine (20 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless oil (0.10 g, 26% yield): ¹H NMR (400 MHz, CDCl₃) δ 8.77 (d, J=2.0 Hz, 1H), 7.47 (d, J=2.0 Hz, 1H), 7.25-7.19 (m, 2H), 7.06 (t, J=9.6 Hz, 1H), 6.09 (d, J=12.0 Hz, 2H), 4.94 (d, J=6.4 Hz, 1H), 4.87-4.75 (m, 1H), 4.38 (s, 2H), 3.37 (s, 3H), 1.59 (d, J=6.4 Hz, 3H), 1.34 (s, 9H); MS (ES+) m/z 558.1 (M+1).

Step 7. Preparation of (S)-2,6-difluoro-4-((1-(2-fluoro-5-(methoxymethyl)phenyl)ethyl)amino)-N-(thiazol-4-yl)benzenesulfonamide

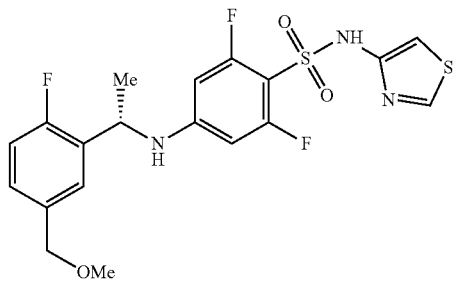 [SMILES: COCc1ccc(F)c([C@H](C)Nc2cc(F)c(S(=O)(=O)Nc3cscn3)c(F)c2)c1]

To (S)-tert-butyl(2,6-difluoro-4-((1-(2-fluoro-5-(methoxymethyl)phenyl)ethyl)-amino)phenyl)sulfonyl(thiazol-4-yl)carbamate (0.10 g, 0.18 mmol) was added a 4 M solution of hydrogen chloride in ethyl acetate (5 mL), and the mixture was stirred at ambient temperature for 1 h. The mixture was concentrated in vacuo and the residue was purified by preparative reverse phase HPLC, using acetonitrile in water containing 0.225% formic acid as eluent, to afford the title compound as a colorless solid (0.021 g, 26% yield): $^1$H NMR (400 MHz, CDCl$_3$) δ 9.47-8.92 (m, 1H), 8.64 (s, 1H), 7.26-7.20 (m, 2H), 7.12-7.04 (m, 1H), 7.03-7.00 (m, 1H), 6.01 (d, J=11.6 Hz, 2H), 4.82-4.70 (m, 2H), 4.39 (s, 2H), 3.36 (s, 3H), 1.56 (d, J=6.4 Hz, 3H); MS (ES+) m/z 458.1 (M+1), 459.1 (M+1).

Example 229

Synthesis of (S)-5-chloro-4-((1-(5-cyano-2-fluorophenyl)ethyl)amino)-2-fluoro-N-(thiazol-4-yl)benzenesulfonamide

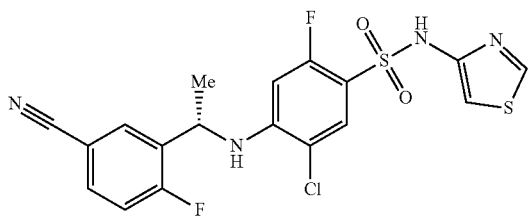 [SMILES: C[C@H](Nc1cc(F)c(S(=O)(=O)Nc2cscn2)cc1Cl)c1cc(C#N)ccc1F]

Step 1. Preparation of (R)—N-(5-bromo-2-fluorobenzylidene)-2-methylpropane-2-sulfinamide

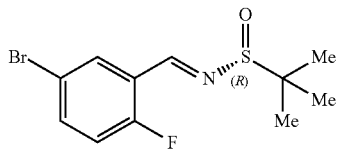

A mixture of 5-bromo-2-fluoro-benzaldehyde (3.00 g, 14.8 mmol), (R)-2-methylpropane-2-sulfinamide (2.15 g, 17.7 mmol) and cesium carbonate (7.22 g, 22.1 mmol) in anhydrous dichloromethane (30 mL) was stirred at ambient temperature for 10 h. The reaction mixture was filtered and the filtrate concentrated in vacuo. The residue was purified by column chromatography, eluting with 25% of ethyl acetate in hexanes, to afford the title compound as a colorless solid (3.70 g, 82% yield): $^1$H NMR (400 MHz, CDCl$_3$) δ 8.84 (s, 1H), 8.11 (dd, J=6.0, 2.8 Hz, 1H), 7.63-7.58 (m, 1H), 7.12-7.04 (m, 1H), 1.29 (s, 9H); MS (ES+) m/z 305.9 (M+1), 307.9 (M+1).

Step 2. Preparation of (R)—N—((S)-1-(5-bromo-2-fluorophenyl)ethyl)-2-methylpropane-2-sulfinamide

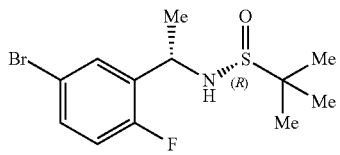

To a solution of (R)—N-(5-bromo-2-fluorobenzylidene)-2-methylpropane-2-sulfinamide (2.00 g, 6.53 mmol) in anhydrous dichloromethane (20 mL) was added a 3.0 M solution of methylmagnesium bromide in tetrahydrofuran (3.3 mL, 9.9 mmol) dropwise at −50° C. The mixture was allowed to warm to ambient temperature and stirred for 1 h, and then quenched by addition aqueous ammonium chloride (50 mL). The mixture was extracted with ethyl acetate (2×50 mL). The combined organic layers were washed with brine (2×30 mL), dried over anhydrous sodium sulfate, and filtered. Concentration of the filtrate in vacuo and purification of the residue by column chromatography, eluting with ethyl acetate in petroleum ether, afforded the title compound as a colorless oil (1.40 g, 67% yield): $^1$H NMR (400 MHz, CDCl$_3$) δ 7.50 (dd, J=6.8, 2.8 Hz, 1H), 7.41-7.34 (m, 1H), 7.00-6.91 (m, 1H), 4.85 (m, 1H), 3.35 (br d, J=4.4 Hz, 1H), 1.58 (d, J=6.8 Hz, 3H), 1.23 (s, 9H); MS (ES+) m/z 322.0 (M+1), 324.0 (M+1).

Step 3. Preparation of (R)—N—((S)-1-(5-cyano-2-fluorophenyl)ethyl)-2-methylpropane-2-sulfinamide

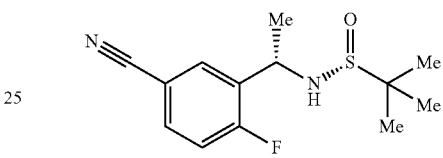

A mixture of (R)—N—((S)-1-(5-bromo-2-fluorophenyl)ethyl)-2-methylpropane-2-sulfinamide (1.50 g, 4.65 mmol), zinc powder (0.030 g, 0.465 mmol), zinc cyanide (0.546 g, 4.65 mmol), 1,1′-bis(diphenylphosphino)ferrocene (0.516 g, 0.93 mmol) and tris(dibenzylideneacetone)dipalladium(0) (0.426 g, 0.465 mmol) in anhydrous N,N-dimethylacetamide (10 mL) was stirred at 120° C. for 12 h. After cooling to ambient temperature, the mixture was diluted with ethyl acetate (50 mL) and washed with brine (2×20 mL). The organic layer was dried over anhydrous sodium sulfate, and filtered. Concentration of the filtrate in vacuo and purification of the residue by column chromatography, eluting with a gradient of 9 to 50% of ethyl acetate in petroleum ether, afforded the title compound as a brown oil (1.50 g, 96% yield): $^1$H NMR (400 MHz, CDCl$_3$) δ 7.74 (dd, J=6.7, 2.2 Hz, 1H), 7.65-7.56 (m, 1H), 7.24-7.14 (m, 1H), 4.99-4.87 (m, 1H), 3.39 (br d, J=3.8 Hz, 1H), 1.59 (d, J=6.8 Hz, 3H), 1.24 (s, 9H); MS (ES+) m/z 269.1 (M+1).

Step 4. Preparation of (S)-3-(1-aminoethyl)-4-fluorobenzonitrile

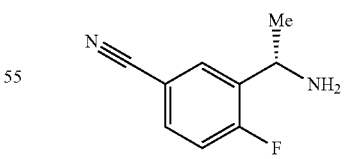

To a mixture of (R)—N—((S)-1-(5-cyano-2-fluorophenyl)ethyl)-2-methylpropane-2-sulfinamide (1.50 g, 4.47 mmol) in diethyl ether (10 mL) was added a 1 M solution of hydrogen chloride in dioxane (10 mL) and the mixture was stirred at ambient temperature for 12 h. The obtained solid was filtered off. To it was added saturated sodium bicarbonate (10 mL), and the mixture was extracted with dichloromethane (3×20 mL). The organic phase was dried over anhydrous sodium sulfate, filtered and the filtrate concentrated in vacuo to yield the title compound as a brown oil (1.00 g, 90% yield): ¹H NMR (400 MHz, CDCl₃) δ 7.88 (dd, J=6.8, 1.8 Hz 1H), 7.56 (ddd, J=8.6, 4.8, 2.2 Hz, 1H), 7.14 (dd, J=10.0, 8.6 Hz, 1H), 4.46 (q, J=6.8 Hz, 1H), 1.43 (d, J=6.6 Hz, 3H), NH not observed; MS (ES+) m/z 165.0 (M+1).

Step 5. Preparation of (S)-tert-butyl (5-chloro-4-((1-(5-cyano-2-fluorophenyl)ethyl)amino)-2-fluorophenyl)sulfonyl(thiazol-4-yl)carbamate

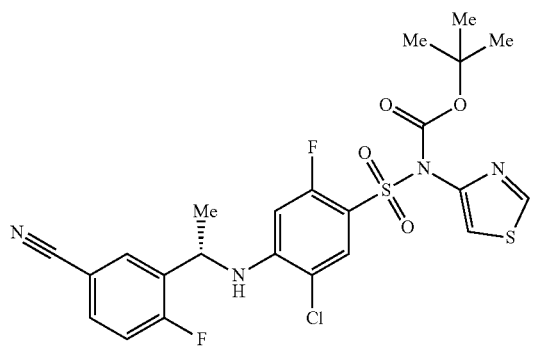 [SMILES: C[C@H](Nc1cc(F)c(S(=O)(=O)N(C(=O)OC(C)(C)C)c2cscn2)cc1Cl)c1cc(C#N)ccc1F]

To a mixture of (S)-3-(1-aminoethyl)-4-fluorobenzonitrile (0.100 g, 0.609 mmol) and tert-butyl N-(5-chloro-2,4-difluoro-phenyl)sulfonyl-N-thiazol-4-yl-carbamate (0.300 g, 0.730 mmol) in anhydrous N,N-dimethylformamide (2 mL) was added cesium carbonate (0.396 g, 1.22 mmol) and the reaction mixture was stirred at ambient temperature for 10 h. The mixture was diluted with ethyl acetate (80 mL) and filtered. The filtrate was washed with brine (2×30 mL), dried over anhydrous sodium sulfate, and filtered. Concentration of the filtrate in vacuo and purification of the residue by preparative thin layer chromatography, eluting with 25% of ethyl acetate in petroleum ether, afforded the title compound as a colorless solid (0.130 g, 38% yield): ¹H NMR (400 MHz, CDCl₃) δ 8.77 (d, J=2.0 Hz, 1H), 8.01 (d, J=6.8 Hz, 1H), 7.68-7.60 (m, 1H), 7.58 (br d, J=6.4 Hz, 1H), 7.48 (s, 1H), 7.29-7.23 (m, 1H), 6.08 (d, J=12.0 Hz, 1H), 5.34-5.26 (m, 1H), 4.91-4.85 (m, 1H), 1.68 (d, J=6.8 Hz, 3H), 1.36 (s, 9H).

Step 6. Preparation of (S)-5-chloro-4-((1-(5-cyano-2-fluorophenyl)ethyl)amino)-2-fluoro-N-(thiazol-4-yl)benzenesulfonamide

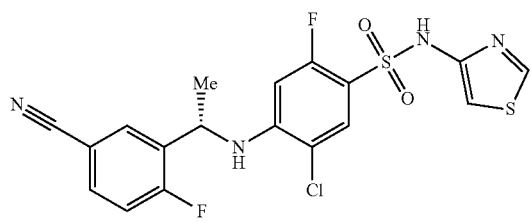 [SMILES: C[C@H](Nc1cc(F)c(S(=O)(=O)Nc2cscn2)cc1Cl)c1cc(C#N)ccc1F]

To a mixture of (S)-tert-butyl (5-chloro-4-((1-(5-cyano-2-fluorophenyl)ethyl)amino)-2-fluorophenyl)sulfonyl (thiazol-4-yl)carbamate (0.100 mg, 0.180 mmol) in dichloromethane (5 mL) was added trifluoroacetic acid (1 mL) and the reaction mixture was stirred at ambient temperature for 10 h. The mixture was concentrated in vacuo and the residue was purified by preparative reverse phase HPLC, using acetonitrile in water containing 0.225% formic acid as eluent, to afford the title compound as a colorless solid (0.0616 mg, 75% yield): ¹H NMR (400 MHz, CD₃OD) δ 8.68 (d, J=2.0 Hz, 1H), 7.76-7.65 (m, 3H), 7.33 (dd, J=10.0, 8.0 Hz, 1H), 6.95 (d, J=2.0 Hz, 1H), 6.23 (d, J=12.4 Hz, 1H), 4.98-4.92 (m, 1H), 1.61 (d, J=6.8 Hz, 3H), exchangeable protons not observed; MS (ES+) m/z 454.8 (M+1), 456.8 (M+1).

Example 230

Synthesis of (S)-4-((1-(5-cyano-2-fluorophenyl)ethyl)amino)-2,6-difluoro-N-(thiazol-4-yl)benzenesulfonamide

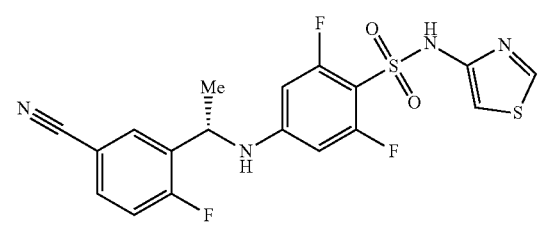 [SMILES: C[C@H](Nc1cc(F)c(S(=O)(=O)Nc2cscn2)c(F)c1)c1cc(C#N)ccc1F]

Step 1. Preparation of (S)-tert-butyl (4-((1-(5-cyano-2-fluorophenyl)ethyl)amino)-2,6-difluorophenyl)sulfonyl(thiazol-4-yl)carbamate

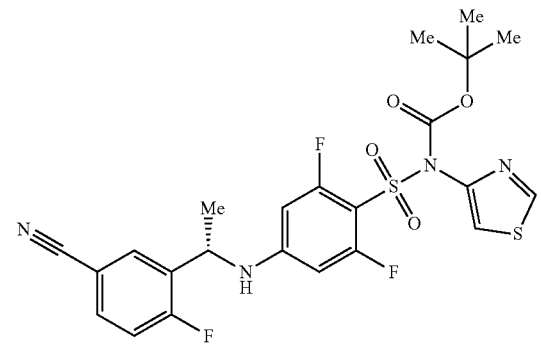 [SMILES: C[C@H](Nc1cc(F)c(S(=O)(=O)N(C(=O)OC(C)(C)C)c2cscn2)c(F)c1)c1cc(C#N)ccc1F]

To a mixture of (S)-3-(1-aminoethyl)-4-fluorobenzonitrile (0.150 g, 0.914 mmol) and tert-butyl thiazol-4-yl((2,4,6-trifluorophenyl)sulfonyl)carbamate (0.342 g, 0.868 mmol) in anhydrous dimethyl sulfoxide (6 mL) was added N,N-diisopropylethylamine (0.191 mL, 1.10 mmol). The reaction mixture was stirred at 36° C. for 12 h. The residue was poured into ice-water ((30 mL) and the aqueous phase was extracted with ethyl acetate (3×30 mL). The combined organic phase was washed with brine (50 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless oil (0.180 g, 37% yield): ¹H NMR (400 MHz, CDCl₃) δ 8.79 (d, J=2.4 Hz, 1H), 7.70-7.61 (m, 2H), 7.50 (d, J=2.4 Hz, 1H), 7.25 (br d, J=8.6 Hz, 1H), 6.09 (d, J=11.2 Hz, 2H), 4.93 (br d, J=5.6 Hz, 1H), 4.88-4.80 (m, 1H), 1.62 (m, 3H), 1.37 (s, 9H); MS (ES+) m/z 438.9 (M−99).

Step 2. Preparation of (S)-4-((1-(5-cyano-2-fluorophenyl)ethyl)amino)-2,6-difluoro-N-(thiazol-4-yl)benzenesulfonamide

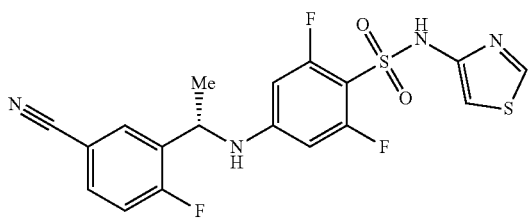 [SMILES: C[C@H](Nc1cc(F)c(S(=O)(=O)Nc2cscn2)c(F)c1)c1cc(C#N)ccc1F]

To a mixture of (S)-tert-butyl (4-((1-(5-cyano-2-fluorophenyl)ethyl)amino)-2,6-difluorophenyl) sulfonyl(thiazol-4-yl)carbamate (0.180 g, 0.334 mmol) in dichloromethane (10 mL) was added trifluoroacetic acid (2 mL). Concentration in vacuo and purification of the residue by preparative reverse phase HPLC, using acetonitrile in water containing 0.225% formic acid as eluent, afforded the title compound as a colorless solid (0.127 g, 87% yield): $^1$H NMR (400 MHz, CD$_3$OD) δ 8.72 (d, J=2.4 Hz, 1H), 7.77-7.65 (m, 2H), 7.35 (dd, J=10.0, 8.4 Hz, 1H), 6.95 (d, J=2.4 Hz, 1H), 6.10 (br d, J=12.4 Hz, 2H), 4.86-4.81 (m, 1H), 1.54 (d, J=6.8 Hz, 3H), exchangeable protons not observed; MS (ES+) m/z 439.0 (M+1), 441.0 (M+1).

Example 231

Synthesis of 2,6-difluoro-4-[(1-phenylcyclopropyl)amino]-N-thiazol-4-yl-benzenesulfonamide

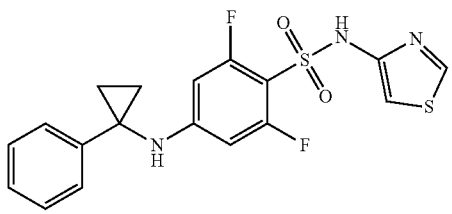 [SMILES: O=S(=O)(Nc1cscn1)c1c(F)cc(NC2(c3ccccc3)CC2)cc1F]

Step 1. Preparation of tert-butyl (2,6-difluoro-4-((1-phenylcyclopropyl)amino)phenyl)sulfonyl(thiazol-4-yl)carbamate

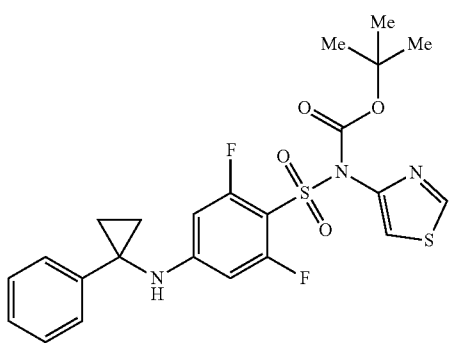 [SMILES: CC(C)(C)OC(=O)N(c1cscn1)S(=O)(=O)c1c(F)cc(NC2(c3ccccc3)CC2)cc1F]

To a solution of tert-butyl N-thiazol-4-yl-N-(2,4,6-trifluorophenyl)sulfonyl-carbamate (0.236 g, 0.590 mmol) in anhydrous N,N-dimethylformamide (5 mL) was added potassium carbonate (0.332 g, 2.36 mmol) and 1-phenylcyclopropanamine (0.080 g, 0.60 mmol). The mixture was stirred at 60° C. for 12 h. After cooling to ambient temperature, the mixture was diluted with saturated ammonium chloride (5 mL) and extracted with ethyl acetate (3×20 mL). The combined organic phase was washed with brine (3×20 mL), dried over anhydrous sodium sulfate, and filtered. Concentration of the filtrate in vacuo and purification of the residue by preparative thin layer chromatography, eluting with 40% of ethyl acetate in petroleum ether, afforded the title compound as a yellow oil (0.100 g, 43% yield): $^1$H NMR (400 MHz, CDCl$_3$) δ 8.78 (d, J=2.4 Hz, 1H), 7.48 (d, J=2.4 Hz, 1H), 7.33-7.28 (m, 2H), 7.25-7.19 (m, 1H), 7.12-7.06 (m, 2H), 6.26 (d, J=11.4 Hz, 2H), 5.32 (br s, 1H), 1.46-1.42 (m, 2H), 1.37 (s, 9H), 1.35-1.31 (m, 2H).

Step 2. Preparation of 2,6-difluoro-4-[(1-phenylcyclopropyl)amino]-N-thiazol-4-yl-benzenesulfonamide

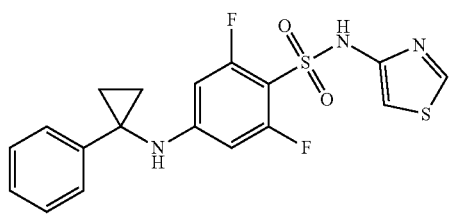 [SMILES: O=S(=O)(Nc1cscn1)c1c(F)cc(NC2(c3ccccc3)CC2)cc1F]

To a solution of tert-butyl (2,6-difluoro-4-((1-phenylcyclopropyl)amino)phenyl)-sulfonyl(thiazol-4-yl)carbamate (0.080 g, 0.16 mmol) in dichloromethane (5 mL) was added trifluoroacetic acid (1 mL) and the reaction mixture was stirred at ambient temperature for 12 h. The reaction mixture was concentrated in vacuo and the obtained residue was purified by preparative reverse phase HPLC, using acetonitrile in water containing 0.225% formic acid as eluent, to afford the title compound as a colorless solid (0.428 g, 67% yield): $^1$H NMR (400 MHz, CDCl$_3$) δ 8.83 (d, J=1.8 Hz, 1H), 8.02 (br s, 1H), 7.33-7.22 (m, 2H), 7.17 (d, J=7.3 Hz, 1H), 7.15-7.10 (m, 2H), 6.76 (br s, 1H), 6.16 (br s, 2H), 1.37-1.30 (m, 2H), 1.16 (br d, J=1.9 Hz, 2H), NH not observed; MS (ES+) m/z 408.0 (M+1).

Example 232

Synthesis of (S)-2,6-difluoro-4-(1-(2-fluorophenyl)ethoxy)-N-(thiazol-4-yl)benzenesulfonamide

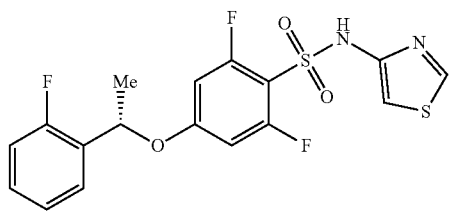 [SMILES: C[C@H](Oc1cc(F)c(S(=O)(=O)Nc2cscn2)c(F)c1)c1ccccc1F]

Step 1. Preparation of (S)-1-(2-fluorophenyl)ethanol

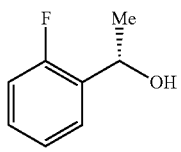

To anhydrous tetrahydrofuran (20 mL) was added (R)-2-methyl-CBS-oxazaborolidine (1.0 M, 2.9 mL) and borane dimethyl sulfide complex (10.0 M, 1.88 mL) and the mixture was stirred at ambient temperature for 1 h. To this mixture was then added dropwise a solution of 1-(2-fluorophenyl)ethanone (2.00 g, 14.5 mmol, 1.75 mL) in anhydrous tetrahydrofuran (5 mL). The reaction mixture was stirred at ambient temperature for 2 h. The mixture was quenched by addition of methanol (20 mL) and concentrated in vacuo to afford the title compound as a colorless oil (2.00 g, 98% yield) that was used without further purification: $^1$H NMR (400 MHz, CDCl$_3$) δ 7.53-7.49 (m, 1H), 7.28-7.24 (m, 1H), 7.20-7.16 (m, 1H), 7.04 (ddd, J=10.8, 8.2, 1.2 Hz, 1H), 5.23 (q, J=6.4 Hz, 1H), 1.54 (d, J=6.4 Hz, 3H), OH not observed.

Step 2. Preparation of (S)-tert-butyl (2,6-difluoro-4-(1-(2-fluorophenyl)ethoxy)phenyl)sulfonyl(thiazol-4-yl)carbamate

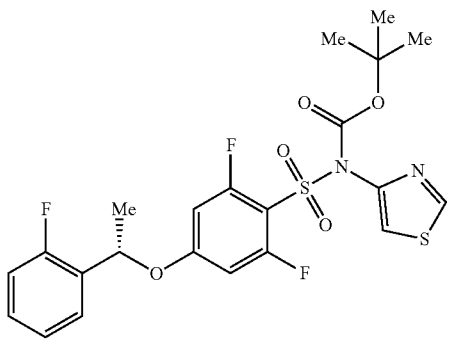 [SMILES: C[C@H](Oc1cc(F)c(S(=O)(=O)N(C(=O)OC(C)(C)C)c2cscn2)c(F)c1)c1ccccc1F]

To a solution of tert-butyl thiazol-4-yl((2,4,6-trifluorophenyl)sulfonyl)carbamate (0.150 g, 0.380 mmol) in anhydrous dimethyl sulfoxide (2 mL) was added (S)-1-(2-fluorophenyl)ethanol (0.106 g, 0.760 mmol) and cesium carbonate (0.248 g, 0.760 mmol). The reaction mixture was stirred at ambient temperature for 12 h. The reaction mixture was diluted with water (10 mL) and extracted with ethyl acetate (2×10 mL). The combined organic layers were washed with brine (10 mL), dried over anhydrous sodium sulfate, and filtered. Concentration of the filtrate in vacuo and purification of the residue by preparative thin layer chromatography, eluting with 20% of ethyl acetate in petroleum ether, afforded the title compound as a yellow oil (0.100 g, 51% yield): MS (ES+) m/z 414.9 (M−99).

Step 3. Preparation of (S)-2,6-difluoro-4-(1-(2-fluorophenyl)ethoxy)-N-(thiazol-4-yl)benzenesulfonamide

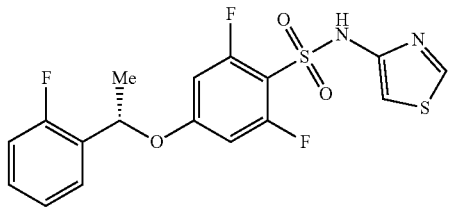 [SMILES: C[C@H](Oc1cc(F)c(S(=O)(=O)Nc2cscn2)c(F)c1)c1ccccc1F]

To (S)-tert-butyl(2,6-difluoro-4-(1-(2-fluorophenyl)ethoxy)phenyl)sulfonyl(thiazol-4-yl) carbamate (0.100 g, 0.194 mmol) was added a 3 M of hydrogen chloride in methanol (5 mL) and the reaction mixture was stirred at ambient temperature for 30 minutes. The reaction mixture was concentrated under reduced pressure. The residue was purified by preparative reverse phase HPLC, using acetonitrile in water containing 0.225% formic acid as eluent, to afford the title compound as a colorless solid (0.020 g, 25% yield): $^1$H NMR (400 MHz, CD$_3$OD) δ 8.72 (d, J=2.4 Hz, 1H), 7.46-7.29 (m, 2H), 7.24-7.10 (m, 2H), 6.94 (br s, 1H), 6.65-6.54 (m, 2H), 5.77 (q, J=6.4 Hz, 1H), 1.66 (d, J=6.4 Hz, 3H), NH not observed; MS (ES+) m/z 415.0 (M+1).

Example 233

Synthesis of (S)-4-((1-(5-(difluoromethyl)-2-fluorophenyl)ethyl)amino)-2,6-difluoro-N-(thiazol-4-yl)benzenesulfonamide

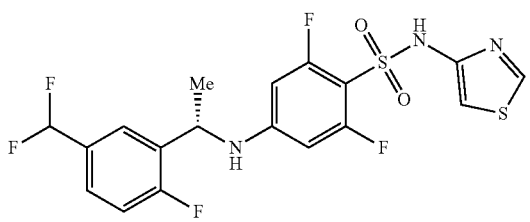 [SMILES: C[C@H](Nc1cc(F)c(S(=O)(=O)Nc2cscn2)c(F)c1)c1cc(C(F)F)ccc1F]

Step 1. Preparation of (R)—N-(5-(difluoromethyl)-2-fluorobenzylidene)-2-methylpropane-2-sulfinamide

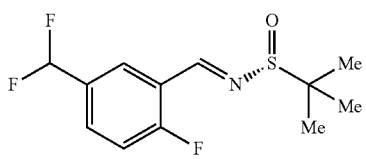 [SMILES: CC(C)(C)[S@@](=O)/N=C/c1cc(C(F)F)ccc1F]

To a solution of 5-(difluoromethyl)-2-fluorobenzaldehyde (preparated according to WO2008051494, 2.50 g, 14.4 mmol) and (R)-2-methylpropane-2-sulfinamide (1.91 g, 15.8 mmol) in anhydrous dichloromethane (40 mL) was added cesium carbonate (7.02 g, 21.5 mmol). The resulting mixture was stirred at ambient temperature for 12 h. The reaction mixture was diluted with water (20 mL) and extracted with dichloromethane (3×20 mL). The combined organic phase was washed with brine (3×20 mL), dried over anhydrous sodium sulfate, and filtered. Concentration of the filtrate in vacuo and purification of the residue by column chromatography, eluting with a gradient of 1 to 15% of ethyl acetate in petroleum ether, afforded the title compound as a yellow oil (3.45 g, 87% yield): $^1$H NMR (300 MHz, CDCl$_3$) δ 8.92 (s, 1H), 8.15 (br d, J=5.2 Hz, 1H), 7.68 (dt, J=5.4, 2.4 Hz, 1H), 7.31-7.24 (m, 1H), 6.69 (t, J=56.0 Hz, 1H), 1.29 (s, 9H).

Step 2. Preparation of (R)—N—((S)-1-(5-(difluoromethyl)-2-fluorophenyl) ethyl)-2-methylpropane-2-sulfinamide

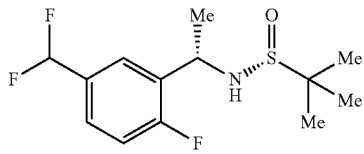 [SMILES: C[C@H](N[S@](=O)C(C)(C)C)c1cc(C(F)F)ccc1F]

To a solution of (R)—N-(5-(difluoromethyl)-2-fluorobenzylidene)-2-methylpropane-2-sulfinamide (3.45 g, 12.4 mmol) in anhydrous dichloromethane (30 mL) was added dropwise a 3.0 M solution of methylmagnesium bromide in diethyl ether (8.29 mL) at −50° C. The reaction mixture was allowed to warm to ambient temperature, stirred for 1 h, and was then carefully quenched by addition of saturated ammonium chloride (30 mL). The layers were separated and the aqueous layer was extracted with dichloromethane (2×30 mL). The combined organic layers were dried over anhydrous sodium sulfate, and filtered. Concentration of the filtrate in vacuo and purification of the residue by column chromatography, eluting with a gradient of 10 to 25% of ethyl acetate in petroleum ether, afforded the title compound as a yellow oil (1.71 g, 47% yield): $^1$H NMR (400 MHz, CDCl$_3$) δ 7.57 (br d, J=7.0 Hz, 1H), 7.43 (br s, 1H), 7.15 (t, J=9.2 Hz, 1H), 6.64 (t, J=56.4 Hz, 1H), 5.01-4.87 (m, 1H), 3.39 (br d, J=3.4 Hz, 1H), 1.62 (s, 3H), 1.23 (s, 9H).

Step 3. Preparation of (S)-1-(5-(difluoromethyl)-2-fluorophenyl)ethanamine hydrochloride

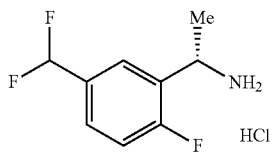 [SMILES: C[C@H](N)c1cc(C(F)F)ccc1F ; Cl]

To (R)—N—((S)-1-(5-(difluoromethyl)-2-fluorophenyl) ethyl)-2-methylpropane-2-sulfinamide (1.71 g, 5.83 mmol) was added a 4 M solution of hydrogen chloride in methanol (20 mL) and the reaction mixture was stirred at ambient temperature for 1 h. The reaction mixture was concentrated in vacuo to afford the title compound as a colorless solid that was used without purification (1.00 g, 76% yield).

Step 4. Preparation of (S)-tert-butyl (4-((1-(5-(difluoromethyl)-2-fluorophenyl)ethyl)amino)-2,6-difluorophenyl)sulfonyl(thiazol-4-yl)carbamate

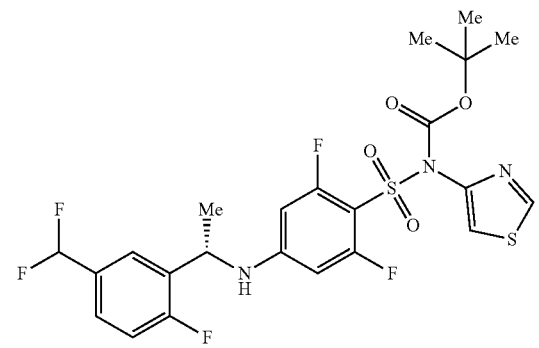 [SMILES: C[C@H](Nc1cc(F)c(S(=O)(=O)N(C(=O)OC(C)(C)C)c2cscn2)c(F)c1)c1cc(C(F)F)ccc1F]

To a solution of tert-butyl thiazol-4-yl ((2,4,6-trifluorophenyl)sulfonyl)carbamate (0.200 g, 0.507 mmol) in anhydrous N,N-dimethylformamide (8 mL) was added cesium carbonate (0.330 g, 1.01 mmol) and (S)-1-(5-(difluoromethyl)-2-fluorophenyl)ethanamine hydrochloride (0.200 g, 0.89 mmol). The reaction mixture was stirred at ambient temperature for 12 h, and then diluted with brine (30 mL) and extracted with ethyl acetate (2×30 mL). The combined organic layers were washed with brine (2×20 mL), dried over anhydrous sodium sulfate, and filtered. Concentration of the filtrate in vacuo afford the title compound as a colorless oil that was used without further purification (0.150 g, 30% yield): MS (ES+) m/z 564.1 (M+1).

Step 5. Preparation of (S)-4-((1-(5-(difluoromethyl)-2-fluorophenyl)ethyl)amino)-2,6-difluoro-N-(thiazol-4-yl)benzenesulfonamide

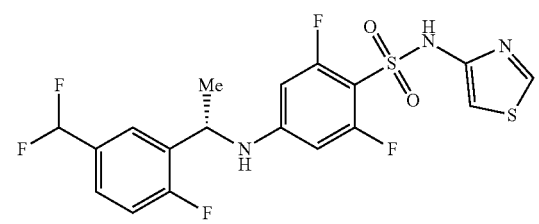 [SMILES: C[C@H](Nc1cc(F)c(S(=O)(=O)Nc2cscn2)c(F)c1)c1cc(C(F)F)ccc1F]

To (S)-tert-butyl (4-((1-(5-(difluoromethyl)-2-fluorophenyl)ethyl)amino)-2,6-difluorophenyl)sulfonyl(thiazol-4-yl) carbamate (0.130 g, 0.231 mmol) was added a 5 M solution of hydrogen chloride in ethyl acetate (5 mL) and the reaction mixture was stirred at ambient temperature for 30 minutes. The solvent was removed in vacuo and the residue purified by preparative reverse phase HPLC, using acetonitrile in water containing 0.225% formic acid as eluent, to afford the title compound as a colorless solid (0.410 g, 38% yield): $^1$H NMR (400 MHz, CDCl$_3$) δ 10.38-9.77 (br s, 1H), 8.68 (d, J=2.2 Hz, 1H), 7.51-7.35 (m, 2H), 7.19 (t, J=9.2 Hz, 1H), 6.99 (d, J=2.2 Hz, 1H), 6.60 (t, J=56.4 Hz, 1H), 6.00 (d, J=11.6 Hz, 2H), 4.89-4.69 (m, 2H), 1.58 (d, J=6.2 Hz, 3H); MS (ES+) m/z 463.9 (M+1).

Example 234

Synthesis of (S)-5-chloro-2-fluoro-4-((1-(2-fluoro-5-hydroxyphenyl)ethyl)amino)-N-(thiazol-4-yl)benzenesulfonamide

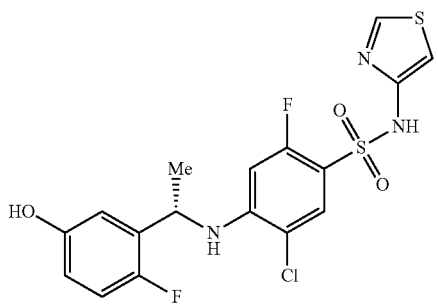 [SMILES: C[C@H](Nc1cc(F)c(S(=O)(=O)Nc2cscn2)cc1Cl)c1cc(O)ccc1F]

Step 1. Preparation of (R)—N-(5-bromo-2-fluorobenzylidene)-2-methylpropane-2-sulfinamide

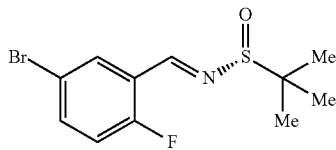 [SMILES: CC(C)(C)[S@@](=O)/N=C/c1cc(Br)ccc1F]

To a solution of 5-bromo-2-fluorobenzaldehyde (10.5 g, 51.7 mmol) and (R)-2-methylpropane-2-sulfinamide (7.52 g, 62.1 mmol) in dichloromethane (50 mL) was added cesium carbonate (33.7 g, 103 mmol) in one portion and the reaction mixture was stirred at ambient temperature for 3 h. The mixture was filtered and the filtrate concentrated in vacuo. The obtained residue was purified by column chromatography, eluting with a gradient of 2 to 10% of ethyl acetate in petroleum ether, to afford the title compound as a colorless oil (15.0 g, 95% yield): $^1$H NMR (400 MHz, CDCl$_3$) δ 8.85 (s, 1H), 8.12 (dd, J=6.0, 2.4 Hz, 1H), 7.61 (ddd, J=8.8, 4.4, 2.4 Hz, 1H), 7.08 (t, J=8.0 Hz, 1H), 1.30 (s, 9H).

Step 2. Preparation of (R)—N-((S)-1-(5-bromo-2-fluorophenyl)ethyl)-2-methylpropane-2-sulfinamide

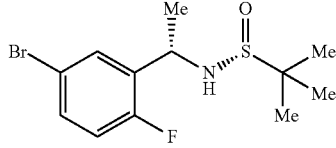 [SMILES: C[C@H](N[S@](=O)C(C)(C)C)c1cc(Br)ccc1F]

To a solution of (R)—N-(5-bromo-2-fluorobenzylidene)-2-methylpropane-2-sulfinamide (15.0 g, 49.0 mmol) in anhydrous dichloromethane (200 mL) was added dropwise a 3.0 M solution of methylmagnesium bromide in diethyl ether (32.7 mL, 98.1 mmol) at −45° C. The reaction mixture was allowed to warm to ambient temperature, and stirred for 1 h, and then quenched by addition of aqueous ammonium chloride (200 mL). The mixture was extracted with dichloromethane (2×200 mL). The combined organic layers were washed with brine (50 mL) and dried over anhydrous sodium sulfate, and filtered. Concentration of the filtrate in vacuo and purification of the residue by column gel chromatography, eluting with a gradient of 10 to 33% of ethyl acetate in petroleum ether, afforded the title compound as a colorless oil (11.0 g, 70% yield): $^1$H NMR (400 MHz, CDCl$_3$) δ 7.41 (dd, J=6.4, 2.4 Hz, 1H), 7.28 (ddd, J=8.4, 4.4, 2.4 Hz, 1H), 6.86 (dd, J=9.6, 8.8 Hz, 1H), 4.82-4.69 (m, 1H), 3.27 (d, J=4.0 Hz, 1H), 1.49 (d, J=6.8 Hz, 3H), 1.14 (s, 9H).

Step 3. Preparation of (S)-1-(5-bromo-2-fluorophenyl)ethanamine hydrochloride

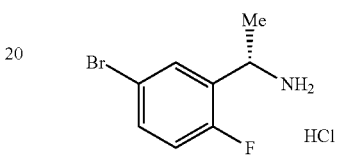

To (R)—N—((S)-1-(5-bromo-2-fluorophenyl)ethyl)-2-methylpropane-2-sulfinamide (10.0 g, 31.0 mmol) was added a 4 M solution of hydrogen chloride in methanol (100 mL) and the reaction mixture was stirred at ambient temperature for 1 h. The mixture was concentrated in vacuo. The residue was diluted with methanol (5 mL) and purified by crystallization from methyl tert-butyl ether (300 mL) to afford the title compound as a colorless solid (5.00 g, 63% yield): $^1$H NMR (400 MHz, CDCl$_3$) δ 7.59 (dd, J=6.4, 2.4 Hz, 1H), 7.33 (ddd, J=8.4, 4.4, 2.4 Hz, 1H), 6.92 (dd, J=10.0, 8.8 Hz, 1H), 4.38 (q, J=6.4 Hz, 1H), 1.42 (d, J=6.4 Hz, 3H), exchangeable protons not observed; MS (ES+) m/z 217.9 (M+1), 219.9 (M+1).

Step 4. Preparation of (S)-tert-butyl (4-((1-(5-bromo-2-fluorophenyl)ethyl)amino)-5-chloro-2-fluorophenyl)sulfonyl(thiazol-4-yl)carbamate

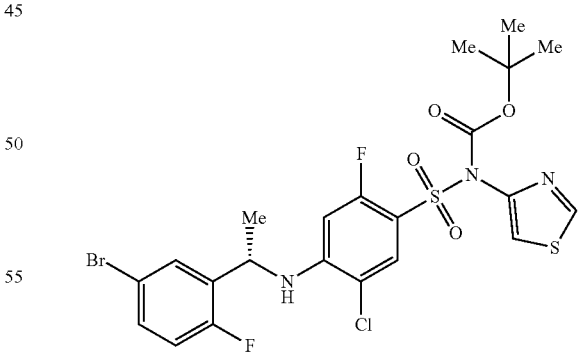

To a solution of tert-butyl (5-chloro-2,4-difluorophenyl)sulfonyl(thiazol-4-yl)carbamate (5.00 g, 12.2 mmol) and (S)-1-(5-bromo-2-fluorophenyl)ethanamine (3.18 g, 14.6 mmol) in anhydrous dimethyl sulfoxide (50 mL) was added cesium carbonate (7.93 g, 24.3 mmol). The reaction mixture was stirred at ambient temperature for 12 h and was then diluted with water (200 mL) and extracted with ethyl acetate (3×30 mL). The combined organic layers were washed with brine (50 mL), dried over anhydrous sodium sulfate, and filtered. Concentration of the filtrate in vacuo and purification of the residue by preparative reverse phase HPLC, using acetonitrile in water containing 0.225% formic acid as eluent, afforded the title compound as a yellow solid (1.80 g, 24% yield): ¹H NMR (400 MHz, CDCl₃) δ 8.79 (d, J=2.0 Hz, 1H), 8.00 (d, J=7.2 Hz, 1H), 7.50 (d, J=2.0 Hz, 1H), 7.41 (ddd, J=8.4, 4.4, 2.4 Hz, 1H), 7.35 (dd, J=6.4, 2.4 Hz, 1H), 7.03 (dd, J=10.0, 8.8 Hz, 1H), 6.16 (d, J=12.0 Hz, 1H), 5.29 (d, J=5.6 Hz, 1H), 4.84 (q, J=6.4 Hz, 1H), 1.67 (d, J=6.8 Hz, 3H), 1.37 (s, 9H); MS (ES+) m/z 507.9 (M−99), 509.9 (M−99).

Step 5. Preparation of tert-butyl (S)-((5-chloro-2-fluoro-4-((1-(2-fluoro-5-(4,4,5,5-tetramethyl-1,3,2-dioxaborolan-2-yl)phenyl)ethyl)amino)phenyl)sulfonyl)(thiazol-4-yl)carbamate

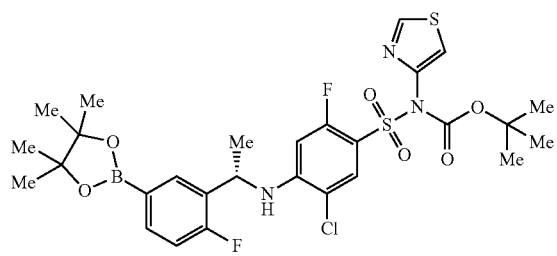 [SMILES: C[C@H](Nc1cc(F)c(S(=O)(=O)N(C(=O)OC(C)(C)C)c2cscn2)cc1Cl)c1cc(B2OC(C)(C)C(C)(C)O2)ccc1F]

To a solution of (S)-tert-butyl (4-((1-(5-bromo-2-fluorophenyl)ethyl)amino)-5-chloro-2-fluorophenyl)sulfonyl(thiazol-4-yl)carbamate (0.30 g, 0.49 mmol) in anhydrous dioxane (10 mL) was added bis(pinacolato)diboron (0.25 g, 0.99 mmol), potassium acetate (0.097 g, 0.99 mmol) and [1,1'-bis(diphenylphosphino)ferrocene]dichloropalladium (II) (0.036 g, 0.049 mmol). The reaction mixture was stirred at 100° C. for 12 h. After cooling to ambient temperature, the reaction mixture was diluted with water (30 mL) and extracted with ethyl acetate (3×30 mL). The combined organic layers were washed with brine (20 mL), dried over anhydrous sodium sulfate, and filtered. Concentration of the filtrate in vacuo and purification of the residue by column chromatography, eluting with a gradient of 10 to 33% of ethyl acetate in petroleum ether, afforded the title compound as a colorless oil (0.32 g, quantitative yield): MS (ES+) m/z 556.0 (M−99).

Step 6. Preparation of tert-butyl (S)-((5-chloro-2-fluoro-4-((1-(2-fluoro-5-hydroxyphenyl)ethyl)amino)phenyl)sulfonyl)(thiazol-4-yl)carbamate

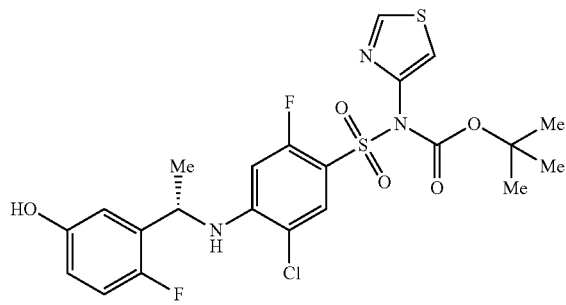 [SMILES: C[C@H](Nc1cc(F)c(S(=O)(=O)N(C(=O)OC(C)(C)C)c2cscn2)cc1Cl)c1cc(O)ccc1F]

To a mixture of tert-butyl (S)-((5-chloro-2-fluoro-4-((1-(2-fluoro-5-(4,4,5,5-tetramethyl-1,3,2-dioxaborolan-2-yl)phenyl)ethyl)amino)phenyl)sulfonyl)(thiazol-4-yl)carbamate (0.32 g, 0.49 mmol) and sodium hydroxide (1.0 M, 0.73 mL) in tetrahydrofuran (5 mL) was added dropwise hydrogen peroxide (0.050 g, 1.46 mmol) at 0° C. The mixture was allowed to warm to ambient temperature and stirred for 2 h. To it was then added 2 M hydrochloric acid to adjust to the mixture to pH 7. The mixture was diluted with water (30 mL) and extracted with ethyl acetate (3×30 mL). The combined organic layers were washed with brine (20 mL), dried over anhydrous sodium sulfate, and filtered. Concentration of the filtrate in vacuo and purification of the residue by preparative thin layer chromatography, eluting with 50% of ethyl acetate in petroleum ether, afforded the title compound as a colorless solid (0.10 g, 38% yield): ¹H NMR (400 MHz, CDCl₃) δ 8.75 (d, J=2.0 Hz, 1H), 7.92 (d, J=7.2 Hz, 1H), 7.48 (d, J=2.0 Hz, 1H), 6.92 (t, J=9.2 Hz, 1H), 6.73-6.63 (m, 2H), 6.55-6.30 (m, 1H), 6.20 (d, J=12.4 Hz, 1H), 5.35 (d, J=6.0 Hz, 1H), 4.78 (q, J=6.4 Hz, 1H), 1.62 (d, J=6.4 Hz, 3H), 1.33 (s, 9H); MS (ES+) m/z 446.0 (M−99), 447.9 (M−99).

Step 7. Preparation of (S)-5-chloro-2-fluoro-4-((1-(2-fluoro-5-hydroxyphenyl)ethyl)amino)-N-(thiazol-4-yl)benzenesulfonamide

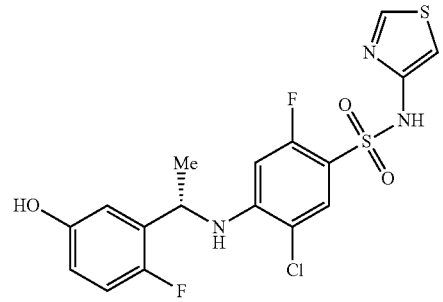 [SMILES: C[C@H](Nc1cc(F)c(S(=O)(=O)Nc2cscn2)cc1Cl)c1cc(O)ccc1F]

To (S)-tert-butyl (5-chloro-2-fluoro-4-((1-(2-fluoro-5-hydroxyphenyl)ethyl)amino)phenyl)-sulfonyl(thiazol-4-yl) carbamate (0.10 g, 0.19 mmol) was added a 4 M solution of hydrogen chloride in 1,4-dioxane (5 mL) and the reaction mixture was stirred at ambient temperature for 1 h. The mixture was concentrated in vacuo and the residue was purified by preparative reverse phase HPLC, using acetonitrile in water containing 0.225% formic acid as eluent, to afford the title compound as a colorless solid (0.05 g, 59% yield): ¹H NMR (400 MHz, CDCl₃) δ 9.85-9.45 (m, 1H), 8.65 (d, J=2.0 Hz, 1H), 7.70 (d, J=7.2 Hz, 1H), 7.00-6.92 (m, 2H), 6.73-6.67 (m, 1H), 6.65 (dd, J=5.6, 3.2 Hz, 1H), 6.07 (d, J=12.4 Hz, 1H), 5.16 (d, J=6.0 Hz, 1H), 4.72 (q, J=6.4 Hz, 1H), 1.61 (d, J=6.4 Hz, 3H), one exchangeable proton not observed; MS (ES+) m/z 446.0 (M+1), 448.0 (M+1).

Example 235

Synthesis of (S)-5-chloro-2-fluoro-4-((1-(2-fluoro-5-(oxetan-3-yloxy)phenyl)ethyl)amino)-N-(thiazol-4-yl)benzenesulfonamide

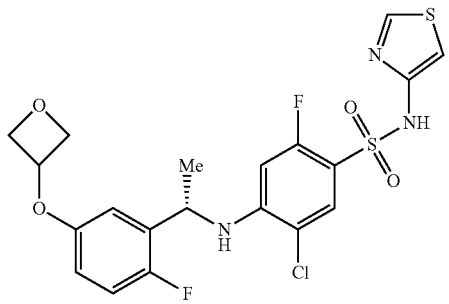 [SMILES: C[C@H](Nc1cc(F)c(S(=O)(=O)Nc2cscn2)cc1Cl)c1cc(OC2COC2)ccc1F]

To a solution of (S)-5-chloro-2-fluoro-4-((1-(2-fluoro-5-hydroxyphenyl)ethyl)amino)-N-(thiazol-4-yl)benzenesulfonamide (0.09 g, 0.2 mmol) in anhydrous N,N-dimethylformamide (3 mL) was added 3-iodooxetane (0.074 g, 0.40 mmol) and potassium carbonate (0.07 g, 0.5 mmol). The mixture was stirred at 60° C. for 3 h. After cooling to ambient temperature, the reaction mixture was filtered and the filtrate concentrated in vacuo. The residue was purified by preparative reverse phase HPLC, using acetonitrile in water containing 0.225% formic acid as eluent, to afford the title compound as a colorless solid (0.065 g, 64% yield): $^1$H NMR (400 MHz, CDCl$_3$) δ 8.64 (d, J=2.0 Hz, 1H), 7.76 (d, J=7.2 Hz, 1H), 7.01 (t, J=9.2 Hz, 1H), 6.96 (d, J=2.4 Hz, 1H), 6.57 (dd, J=6.0, 3.2 Hz, 1H), 6.48 (td, J=8.8, 3.6 Hz, 1H), 6.08 (d, J=12.2 Hz, 1H), 5.16 (br d, J=5.2 Hz, 1H), 5.10 (quin, J=5.6 Hz, 1H), 4.92 (t, J=6.8 Hz, 1H), 4.86 (t, J=6.8 Hz, 1H), 4.74 (q, J=6.2 Hz, 2H), 4.67-4.61 (m, 1H), 1.62 (d, J=6.8 Hz, 3H), NH not observed; MS (ES+) m/z 502.0 (M+1), 504.0 (M+1).

Example 236

Synthesis of (S)-5-chloro-2-fluoro-4-((1-(2-fluoro-5-(oxetan-3-ylmethoxy)phenyl)ethyl)amino)-N-(thiazol-4-yl)benzenesulfonamide

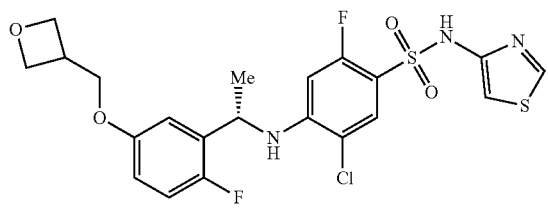 [SMILES: C[C@H](Nc1cc(F)c(S(=O)(=O)Nc2cscn2)cc1Cl)c1cc(OCC2COC2)ccc1F]

Step 1. Preparation of oxetan-3-ylmethyl methanesulfonate

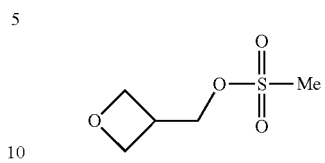

To a solution of oxetan-3-ylmethanol (0.300 g, 3.41 mmol) in anhydrous dichloromethane (10 mL) was added triethylamine (0.516 g, 5.11 mmol) followed by methanesulfonyl chloride (0.468 g, 4.09 mmol) at 0° C. The mixture was stirred at ambient temperature for 1 h. The reaction mixture was then quenched by addition of water (10 mL) and extracted with dichloromethane (10 mL). The organic layer was washed with brine (10 mL), dried over anhydrous sodium sulfate, and filtered. Concentration of the filtrate under reduced pressure provided the title compound as a colorless oil (0.500 g, 88% yield): $^1$H NMR (400 MHz, CDCl$_3$) δ 4.86 (dd, J=6.6, 7.6 Hz, 2H), 4.55-4.44 (m, 4H), 3.48-3.35 (m, 1H), 3.08 (s, 3H).

Step 2. Preparation of (S)-5-chloro-2-fluoro-4-((1-(2-fluoro-5-(oxetan-3-ylmethoxy)phenyl)ethyl)amino)-N-(thiazol-4-yl)benzenesulfonamide

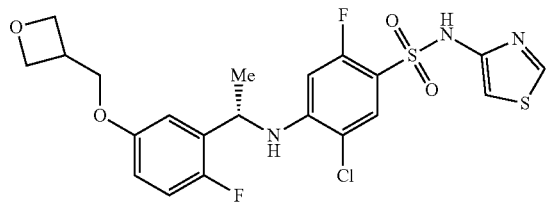 [SMILES: C[C@H](Nc1cc(F)c(S(=O)(=O)Nc2cscn2)cc1Cl)c1cc(OCC2COC2)ccc1F]

To a solution of (S)-5-chloro-2-fluoro-4-((1-(2-fluoro-5-hydroxyphenyl)ethyl)amino)-N-(thiazol-4-yl)benzenesulfonamide (0.080 g, 0.18 mmol) in anhydrous N,N-dimethylformamide (5 mL) was added oxetan-3-ylmethyl methanesulfonate (0.030 g, 0.18 mmol) and potassium carbonate (0.049 g, 0.36 mmol). The mixture was stirred at 60° C. for 12 h. After cooling to ambient temperature, the reaction mixture was filtered and the filtrate concentrated under reduced pressure. The obtained residue was purified by preparative reverse phase HPLC, using acetonitrile in water containing 0.225% formic acid as eluent, to afford the title compound as a colorless solid (0.012 g, 13% yield): $^1$H NMR (400 MHz, CDCl$_3$) δ 8.53 (d, J=2.2 Hz, 1H), 7.66 (d, J=7.2 Hz, 1H), 6.94 (t, J=9.2 Hz, 1H), 6.87 (d, J=2.2 Hz, 1H), 6.69 (td, J=3.6, 8.8 Hz, 1H), 6.65 (dd, J=3.0, 6.0 Hz, 1H), 6.04 (d, J=12.2 Hz, 1H), 5.10 (br d, J=5.2 Hz, 1H), 4.79 (t, J=7.0 Hz, 2H), 4.65 (quin, J=6.6 Hz, 1H), 4.47 (t, J=6.0 Hz, 2H), 4.08-3.98 (m, 2H), 3.38-3.24 (m, 1H), 1.52 (br s, 3H), NH not observed; MS (ES+) m/z 516.0 (M+1), 518.0 (M+1).

Example 237

Synthesis of (S)-5-chloro-2-fluoro-4-((1-(2-fluoro-5-((3-methyloxetan-3-yl)methoxy)phenyl)ethyl)amino)-N-(thiazol-4-yl)benzenesulfonamide

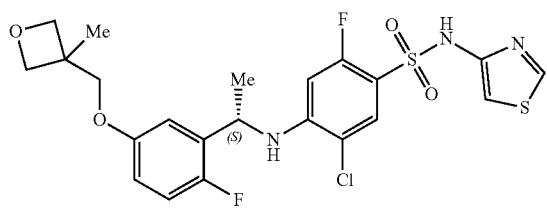

Step 1. Preparation of (3-methyloxetan-3-yl)methyl methanesulfonate

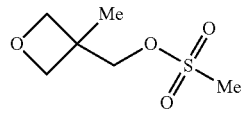 [SMILES: CC1(COS(C)(=O)=O)COC1]

To a solution of (3-methyloxetan-3-yl)methanol (0.400 g, 3.92 mmol) in anhydrous dichloromethane (10 mL) was added triethylamine (0.594 g, 5.87 mmol, 0.814 mL), followed by methanesulfonyl chloride (0.538 g, 4.70 mmol, 0.363 mL) at 0° C. The mixture was stirred at ambient temperature for 1 h and then quenched by addition of water (10 mL). The mixture was extracted with dichloromethane (10 mL). The organic layer was washed with brine (10 mL), dried over anhydrous sodium sulfate, filtered and the filtrate concentrated in vacuo to afford the title compound as a yellow oil (0.500 g, 71% yield): $^1$H NMR (400 MHz, CDCl$_3$) δ 4.54 (d, J=6.4 Hz, 2H), 4.45 (d, J=6.4 Hz, 2H), 4.34 (s, 2H), 3.09 (s, 3H), 1.41 (s, 3H).

Step 2. Preparation of (S)-5-chloro-2-fluoro-4-((1-(2-fluoro-5-((3-methyloxetan-3-yl)methoxy)phenyl)ethyl)amino)-N-(thiazol-4-yl)benzenesulfonamide TF057E

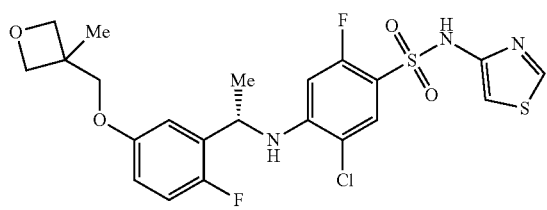 [SMILES: C[C@H](Nc1cc(F)c(S(=O)(=O)Nc2cscn2)cc1Cl)c1cc(OCC2(C)COC2)ccc1F]

To a solution of (S)-5-chloro-2-fluoro-4-((1-(2-fluoro-5-hydroxyphenyl)ethyl)amino)-N-(thiazol-4-yl)benzenesulfonamide (0.080 g, 0.179 mmol) in anhydrous N,N-dimethylformamide (5 mL) was added (3-methyloxetan-3-yl)methyl methanesulfonate (0.032 g, 0.179 mmol) and potassium carbonate (0.049 g, 0.36 mmol). The mixture was stirred at 60° C. for 12 h. After cooling to ambient temperature, the reaction mixture was filtered and the filtrate concentrated under reduced pressure. The residue was purified by preparative reverse phase HPLC, using acetonitrile in water containing 0.225% formic acid as eluent, to afford the title compound as a colorless solid (0.015 g, 16% yield): $^1$H NMR (400 MHz, CDCl$_3$) δ 9.43 (br s, 1H), 8.64 (d, J=2.4 Hz, 1H), 7.76 (d, J=7.2 Hz, 1H), 7.03 (t, J=9.2 Hz, 1H), 6.95 (d, J=2.0 Hz, 1H), 6.85-6.70 (m, 2H), 6.14 (d, J=12.4 Hz, 1H), 5.19 (br d, J=5.4 Hz, 1H), 4.75 (quin, J=6.6 Hz, 1H), 4.61 (d, J=6.0 Hz, 2H), 4.46 (d, J=6.0 Hz, 2H), 4.00-3.88 (m, 2H), 1.62 (d, J=6.8 Hz, 3H), 1.42 (s, 3H), NH not observed; MS (ES+) m/z 530.0 (M+1), 532.0 (M+1).

Example 238

Synthesis of (S)-2,6-difluoro-4-((1-(2-fluoro-5-methoxyphenyl)ethyl)amino)-N-(thiazol-4-yl)benzenesulfonamide

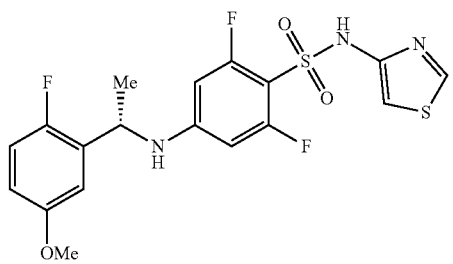 [SMILES: COc1ccc(F)c([C@H](C)Nc2cc(F)c(S(=O)(=O)Nc3cscn3)c(F)c2)c1]

Step 1. Preparation of (R)—N-(2-fluoro-5-methoxybenzylidene)-2-methylpropane-2-sulfinamide

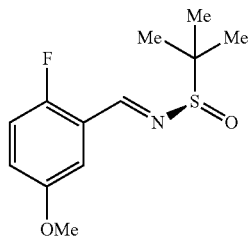 [SMILES: COc1ccc(F)c(/C=N/[S@](=O)C(C)(C)C)c1]

To a solution of 2-fluoro-5-methoxybenzaldehyde (2.00 g, 13.0 mmol) in anhydrous dichloromethane (20 mL) was added cesium carbonate (8.46 g, 26.0 mmol) and (R)-2-methylpropane-2-sulfinamide (2.36 g, 19.5 mmol). The mixture was stirred at ambient temperature for 12 h and then filtered. Concentration of the filtrate in vacuo and purification of the residue by column chromatography, eluting with a gradient of 5 to 50% of ethyl acetate in petroleum ether, afforded the title compound as a colorless solid (2.50 g, 75% yield): $^1$H NMR (400 MHz, CDCl$_3$) δ 8.88 (s, 1H), 7.46 (dd, J=3.0, 5.2 Hz, 1H), 7.12-7.06 (m, 1H), 7.06-7.01 (m, 1H), 3.85 (s, 3H), 1.28 (s, 9H).

Step 2. Preparation of (R)—N—((S)-1-(2-fluoro-5-methoxyphenyl)ethyl)-2-methylpropane-2-sulfinamide

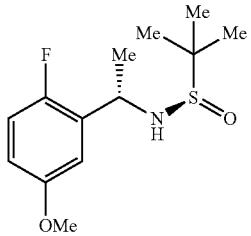 [SMILES: COc1ccc(F)c([C@H](C)N[S@](=O)C(C)(C)C)c1]

To a solution of (R)—N-(2-fluoro-5-methoxybenzylidene)-2-methylpropane-2-sulfinamide (1.50 g, 5.83 mmol) in anhydrous dichloromethane (20 mL) was added dropwise methylmagnesium bromide (3.0 M, 3.9 mL, 11.7 mmol) at −50° C. The reaction mixture was warmed to ambient temperature and stirred for 12 h. The mixture was diluted with saturated ammonium chloride (20 mL) and extracted with dichloromethane (3×20 mL). The combined organic phase was washed with brine (3×20 mL), dried over anhydrous sodium sulfate, and filtered. Concentration of the filtrate in vacuo and purification of the residue by column chromatography, eluting with a gradient of 5 to 25% of ethyl acetate in petroleum ether, afforded the title compound as a yellow oil (1.00 g, 63% yield): $^1$H NMR (400 MHz, CDCl$_3$) δ 6.95 (t, J=9.3 Hz, 1H), 6.87 (dd, J=5.8, 3.2 Hz, 1H), 6.74 (td, J=8.9, 3.5 Hz, 1H), 4.85-4.74 (m, 1H), 3.77 (s, 3H), 3.38 (br d, J=4.3 Hz, 1H), 1.56 (d, J=6.7 Hz, 3H), 1.20 (s, 9H).

Step 3. Preparation of (S)-1-(2-fluoro-5-methoxyphenyl)ethanamine hydrochloride

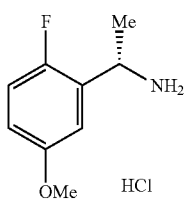 [SMILES: COc1ccc(F)c([C@H](C)N)c1 ; Cl]

To (R)—N—((S)-1-(2-fluoro-5-methoxyphenyl)ethyl)-2-methylpropane-2-sulfinamide (0.90 g, 3.3 mmol) was added a 4 M solution of hydrogen chloride in 1,4-dioxane (10 mL) and the reaction mixture was stirred at ambient temperature for 30 minutes. The reaction mixture was concentrated in vacuo. To the residue were added two drops of methanol and tert-butyl methyl ether (10 mL), and the mixture was stirred for 6 h. The solid was then filtered off and dried in vacuo to afford the title compound as a colorless solid (0.40 g, 59% yield): $^1$H NMR (400 MHz, CDCl$_3$) δ 8.87 (br s, 3H), 7.23 (dd, J=5.7, 2.8 Hz, 1H), 6.99 (t, J=9.4 Hz, 1H), 6.82 (td, J=8.8, 3.6 Hz, 1H), 4.76 (br s, 1H), 3.68 (s, 3H), 1.69 (d, J=6.8 Hz, 3H).

Step 4. Preparation of (S)-tert-butyl (2,6-difluoro-4-((1-(2-fluoro-5-methoxyphenyl)ethyl)amino)phenyl)sulfonyl(thiazol-4-yl)carbamate

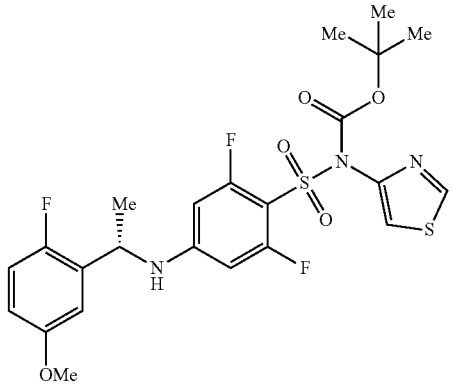 [SMILES: COc1ccc(F)c([C@H](C)Nc2cc(F)c(S(=O)(=O)N(C(=O)OC(C)(C)C)c3cscn3)c(F)c2)c1]

To a solution of (S)-1-(2-fluoro-5-methoxyphenyl)ethanamine hydrochloride (0.15 g, 0.73 mmol) in anhydrous N,N-dimethylformamide (5 mL) was added tert-butyl thiazol-4-yl((2,4,6-trifluorophenyl)sulfonyl)carbamate (0.29 g, 0.73 mmol) and potassium carbonate (0.40 g, 2.9 mmol). The mixture was stirred at 60° C. for 12 h. After cooling to ambient temperature, the reaction mixture was then diluted with saturated ammonium chloride (5 mL) and extracted with ethyl acetate (3×20 mL). The combined organic phase was washed with brine (3×20 mL), dried over anhydrous sodium sulfate, and filtered. Concentration of the filtrate in vacuo and purification of the residue by preparative thin layer chromatography, eluting with 40% of ethyl acetate in petroleum ether, afforded the title compound as a colorless solid (0.08 g, 20% yield): $^1$H NMR (400 MHz, CDCl$_3$) δ 8.77 (d, J=2.4 Hz, 1H), 7.47 (d, J=221 Hz, 1H), 7.05-6.97 (m, 1H), 6.78-6.69 (m, 2H), 6.09 (d, J=11.6 Hz, 2H), 5.10 (br d, J=6.2 Hz, 1H), 4.79-4.69 (m, 1H), 3.73 (s, 3H), 1.56 (d, J=6.8 Hz, 3H), 1.33 (s, 9H).

Step 5. Preparation of (S)-2,6-difluoro-4-((1-(2-fluoro-5-methoxyphenyl)ethyl)amino)-N-(thiazol-4-yl)benzenesulfonamide

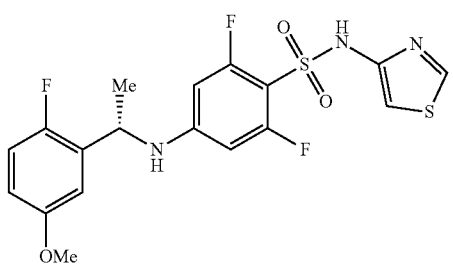 [SMILES: COc1ccc(F)c([C@H](C)Nc2cc(F)c(S(=O)(=O)Nc3cscn3)c(F)c2)c1]

To a solution of (S)-2,6-difluoro-4-((1-(2-fluoro-5-methoxyphenyl)ethyl)amino)-N-(thiazol-4-yl)benzenesulfonamide (0.10 g, 0.18 mmol) in dichloromethane (10 mL) was added trifluoroacetic acid (3.08 g, 27.0 mmol, 2 mL). The mixture was stirred at ambient temperature for 12 h and then concentrated in vacuo. The residue was purified by preparative reverse phase HPLC, using acetonitrile in water containing 0.225% formic acid as eluent, to afford the title compound as a colorless solid (0.063 g, 69% yield): ¹H NMR (400 MHz, CDCl₃) δ 10.92 (br s, 1H), 8.73 (d, J=2.1 Hz, 1H), 7.03-6.97 (m, 1H), 6.96 (d, J=2.3 Hz, 1H), 6.78-6.72 (m, 2H), 6.00 (d, J=11.7 Hz, 2H), 4.86 (br d, J=6.1 Hz, 1H), 4.69 (quin, J=6.6 Hz, 1H), 3.74 (s, 3H), 1.54 (d, J=6.7 Hz, 3H); MS (ES+) m/z 444.0 (M+1).

Example 239

Synthesis of (S)-3-cyano-4-((1-(2-fluorophenyl)ethyl)amino)-N-(thiazol-4-yl)benzenesulfonamide

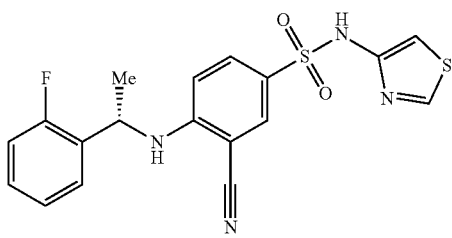 [SMILES: C[C@H](Nc1ccc(S(=O)(=O)Nc2cscn2)cc1C#N)c1ccccc1F]

Step 1. Preparation of tert-butyl ((3-cyano-4-fluorophenyl)sulfonyl)(thiazol-4-yl)carbamate

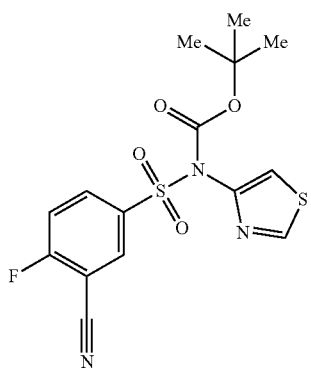 [SMILES: CC(C)(C)OC(=O)N(c1cscn1)S(=O)(=O)c1ccc(F)c(C#N)c1]

To a solution of tert-butyl thiazol-4-ylcarbamate (0.500 g, 2.50 mmol) in anhydrous N,N-dimethylformamide (20 mL) was added sodium hydride (60% dispersion in mineral oil, 0.120 g, 3.00 mmol) at 0° C. The mixture was warmed to 10° C., and stirred for 1 h, and cooled to 0° C. 3-cyano-4-fluorobenzenesulfonyl chloride (0.713 g, 3.25 mmol) was added to it at 0° C. The reaction mixture was allowed to warm to ambient temperature and stirred for 4 h. The mixture was diluted with saturated ammonium chloride (20 mL) and extracted with ethyl acetate (3×20 mL). The combined organic phase was washed with brine (3×20 mL), dried over anhydrous sodium sulfate, and filtered. Concentration of the filtrate in vacuo and purification of the residue by column chromatography, eluting with a gradient of 5 to 50% of ethyl acetate in petroleum ether, afforded the title compound as a colorless solid (0.500 g, 52% yield): ¹H NMR (400 MHz, CDCl₃) δ 8.80 (d, J=2.2 Hz, 1H), 8.49 (dd, J=2.2, 5.8 Hz, 1H), 8.46-8.42 (m, 1H), 7.56 (d, J=2.2 Hz, 1H), 7.43 (t, J=8.6 Hz, 1H), 1.36 (s, 9H).

Step 2. Preparation of tert-butyl (S)-((3-cyano-4-((1-(2-fluorophenyl)ethyl)amino)phenyl)sulfonyl)(thiazol-4-yl)carbamate

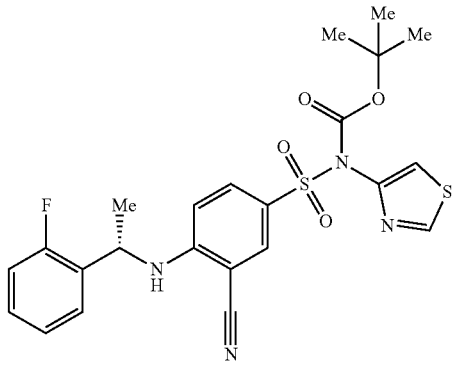 [SMILES: C[C@H](Nc1ccc(S(=O)(=O)N(C(=O)OC(C)(C)C)c2cscn2)cc1C#N)c1ccccc1F]

To a solution of tert-butyl ((3-cyano-4-fluorophenyl)sulfonyl)(thiazol-4-yl)carbamate (0.200 g, 0.521 mmol) in anhydrous N,N-dimethylformamide (3 mL) was added potassium carbonate (0.288 g, 2.09 mmol) and (S)-1-(2-fluorophenyl)ethanamine hydrochloride (0.916 g, 0.521 mmol). The mixture was stirred at ambient temperature for 12 h. It was then diluted with saturated ammonium chloride (20 mL) and extracted with ethyl acetate (3×20 mL). The combined organic layers were washed with brine (3×20 mL), dried over anhydrous sodium sulfate, and filtered. Concentration of the filtrate in vacuo and purification of the residue by preparative thin layer chromatography, eluting with 40% of ethyl acetate in petroleum ether, afforded the title compound as a colorless solid (0.120 g, 46% yield): ¹H NMR (400 MHz, CDCl₃) δ 8.78 (d, J=2.4 Hz, 1H), 8.19 (d, J=2.4 Hz, 1H), 7.98 (dd, J=9.0, 2.0 Hz, 1H), 7.50 (d, J=2.4 Hz, 1H), 7.31-7.27 (m, 2H), 7.17-7.08 (m, 2H), 6.58 (d, J=9.2 Hz, 1H), 5.47 (br d, J=6.2 Hz, 1H), 5.01 (t, J=6.6 Hz, 1H), 1.69 (d, J=6.8 Hz, 3H), 1.34 (s, 9H).

Step 3. Preparation of (S)-3-cyano-4-((1-(2-fluorophenyl)ethyl)amino)-N-(thiazol-4-yl)benzenesulfonamide

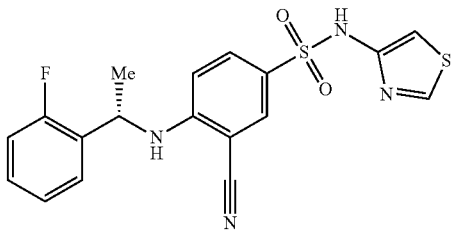 [SMILES: C[C@H](Nc1ccc(S(=O)(=O)Nc2cscn2)cc1C#N)c1ccccc1F]

To a solution of tert-butyl (S)-((3-cyano-4-((1-(2-fluorophenyl)ethyl)amino)phenyl)sulfonyl)(thiazol-4-yl)carbamate (0.120 g, 0.239 mmol) in dichloromethane (10 mL) was added trifluoroacetic acid (3.08 g, 27.0 mmol, 2 mL). The mixture was stirred at ambient temperature for 12 h and then concentrated in vacuo. The residue was purified by preparative reverse phase HPLC, using acetonitrile in water containing 0.225% formic acid as eluent, to afford the title compound as a colorless solid (0.074 g, 69% yield): ¹H NMR (400 MHz, CDCl₃) δ 10.28 (s, 1H), 8.72 (d, J=2.4 Hz, 1H), 7.82 (d, J=2.0 Hz, 1H), 7.59 (dd, J=9.0, 1.8 Hz, 1H), 7.28-7.21 (m, 2H), 7.16-7.04 (m, 2H), 6.97 (d, J=2.2 Hz, 1H), 6.44 (d, J=9.0 Hz, 1H), 5.34 (br d, J=6.2 Hz, 1H), 4.91 (quin, J=6.6 Hz, 1H), 1.63 (d, J=6.8 Hz, 3H); MS (ES+) m/z 403.0 (M+1), 425.0 (M+23).

Example 240

Synthesis of (S)-4-((1-(2,5-difluorophenyl)ethyl)amino)-2,6-difluoro-N-(isoxazol-3-yl)benzenesulfonamide

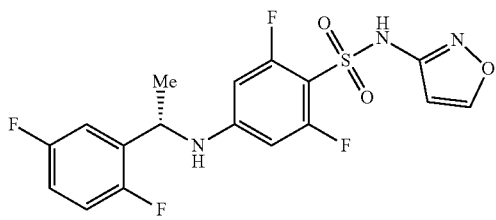

Step 1. Preparation of 2,4,6-trifluoro-N-(isoxazol-3-yl)benzenesulfonamide

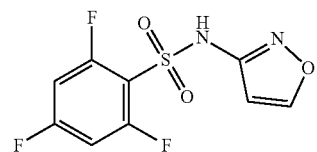

To a mixture of isoxazol-3-amine (1.00 g, 11.9 mmol, 0.877 mL), 4-(dimethylamino)pyridine (0.291 g, 2.38 mmol) and pyridine (1.88 g, 23.8 mmol, 1.92 mL) in anhydrous dichloromethane (20 mL) was added a solution of 2,4,6-trifluorobenzenesulfonyl chloride (3.02 g, 13.1 mmol) in dichloromethane (4 mL) at 0° C. The mixture was stirred at 0° C. for 30 minutes and ambient temperature for 12 h. The mixture was concentrated in vacuo and the residue was purified by preparative reverse phase HPLC, using acetonitrile in water containing 0.225% formic acid as eluent, to afford the title compound as a yellow solid (1.18 g, 36% yield): $^1$H NMR (400 MHz, CDCl$_3$) δ 8.28 (d, J=1.8 Hz, 1H), 6.81 (t, J=8.4 Hz, 2H), 6.61 (d, J=1.8 Hz, 1H), NH not observed.

Step 2. Preparation of 2,4,6-trifluoro-N-(isoxazol-3-yl)-N-((2-(trimethylsilyl)ethoxy)methyl)-benzenesulfonamide

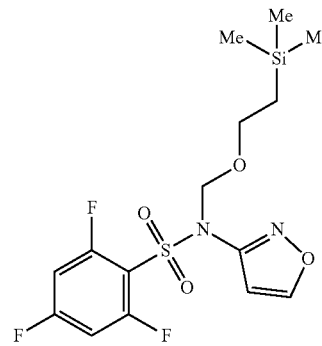

To a mixture of 2,4,6-trifluoro-N-(isoxazol-3-yl)benzenesulfonamide (1.18 g, 4.24 mmol) and potassium carbonate (1.17 g, 8.48 mmol) in anhydrous N,N-dimethylformamide (10 mL) was added (2-(chloromethoxy)ethyl)trimethylsilane (0.849 g, 5.09 mmol, 0.902 mL) at 0° C. The reaction mixture was allowed to warm to ambient temperature and was stirred for 1 h. The residue was poured into ice-water (50 mL) and the aqueous phase was extracted with ethyl acetate (3×30 mL). The combined organic phase was washed with brine (3×30 mL), dried over anhydrous sodium sulfate, and filtered. Concentration of the filtrate in vacuo and purification of the residue by column chromatography, eluting with 10% of ethyl acetate in petroleum ether, afforded the title compound as a colorless oil (1.60 g, 92% yield): $^1$H NMR (400 MHz, CDCl$_3$) δ 8.30 (d, J=1.8 Hz, 1H), 6.78 (t, J=8.6 Hz, 2H), 6.65 (d, J=1.8 Hz, 1H), 5.44 (s, 2H), 3.77-3.69 (m, 2H), 0.98-0.86 (m, 2H), 0.05 (s, 9H); MS (ES+) m/z 430.9 (M+23).

Step 3. Preparation of (S)-4-((1-(2,5-difluorophenyl)ethyl)amino)-2,6-difluoro-N-(isoxazol-3-yl)-N-((2-(trimethylsilyl)ethoxy)methyl)benzenesulfonamide

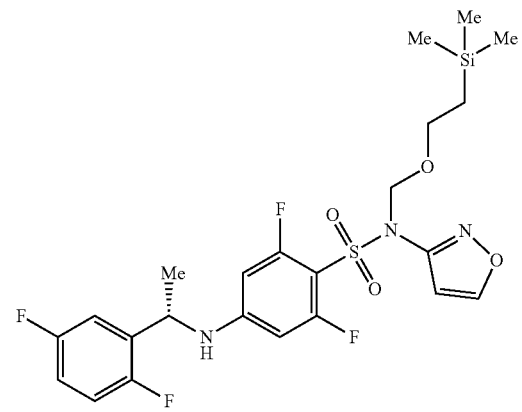 [SMILES: C[C@H](Nc1cc(F)c(S(=O)(=O)N(COCC[Si](C)(C)C)c2ccon2)c(F)c1)c1cc(F)ccc1F]

A mixture of 2,4,6-trifluoro-N-(isoxazol-3-yl)-N-((2-(trimethylsilyl)ethoxy)methyl)benzenesulfonamide (0.250 g, 0.612 mmol), (S)-1-(2,5-difluorophenyl)ethanamine hydrochloride (0.142 g, 0.734 mmol), and potassium carbonate (0.338 g, 2.45 mmol) in anhydrous N,N-dimethylformamide (6 mL) was stirred at 60° C. for 12 h. The mixture was poured into ice-water (30 mL) and the aqueous phase was extracted with ethyl acetate (3×30 mL). The combined organic phase was washed with brine (50 mL), dried over anhydrous sodium sulfate, and filtered. Concentration of the filtrate in vacuo and purification of the residue by preparative thin layer chromatography, eluting with 20% of ethyl acetate in petroleum ether, afforded the title compound as a colorless oil (0.150 g, 45% yield): $^1$H NMR (400 MHz, CDCl$_3$) δ 8.24 (d, J=2.0 Hz, 1H), 7.07 (td, J=9.2, 4.6 Hz, 1H), 7.02-6.93 (m, 2H), 6.65 (d, J=1.8 Hz, 1H), 6.02 (d, J=11.6 Hz, 2H), 5.44 (s, 2H), 4.75 (br s, 1H), 3.75-3.72 (m, 2H), 3.04-2.90 (m, 1H), 1.57 (br s, 3H), 0.97-0.91 (m, 2H), 0.00 (s, 9H); MS (ES+) m/z 546.1 (M+1).

Step 4. Preparation of (S)-4-((1-(2,5-difluorophenyl)ethyl)amino)-2,6-difluoro-N-(isoxazol-3-yl)benzenesulfonamide

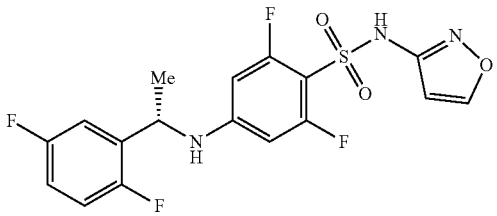 [SMILES: C[C@H](Nc1cc(F)c(S(=O)(=O)Nc2ccon2)c(F)c1)c1cc(F)ccc1F]

To a solution of (S)-4-((1-(2,5-difluorophenyl)ethyl)amino)-2,6-difluoro-N-(isoxazol-3-yl)-N-((2-(trimethylsilyl)ethoxy)methyl)benzenesulfonamide (0.150 g, 0.275 mmol) in dioxane (5 mL) was added a 4 M solution of HCl in dioxane (15 mL) and the reaction mixture stirred at ambient temperature for 12 h. The mixture was concentrated in vacuo and the residue was purified by preparative reverse phase HPLC, using acetonitrile in water containing 0.225% formic acid as eluent, to afford the title compound as a colorless solid (0.049 g, 43% yield): $^1$H NMR (400 MHz, CDCl$_3$) δ 8.21 (d, J=1.6 Hz, 1H), 7.07 (dt, J=4.4, 9.2 Hz, 1H), 6.98-6.87 (m, 2H), 6.58 (d, J=1.6 Hz, 1H), 6.02 (d, J=11.6 Hz, 2H), 4.82 (br d, J=5.6 Hz, 1H), 4.72 (quin, J=6.6 Hz, 1H), 1.56 (d, J=6.8 Hz, 3H), NH not observed; MS (ES+) m/z 416.0 (M+1).

Example 241

Synthesis of 5-chloro-4-((1-(2,5-difluorophenyl)cyclopropyl)amino)-2-fluoro-N-(pyrimidin-4-yl)benzenesulfonamide

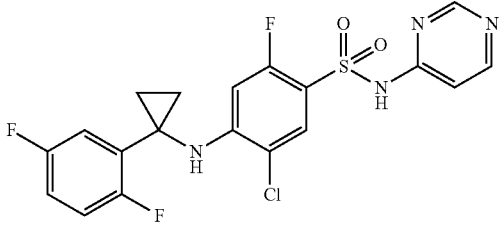 [SMILES: O=S(=O)(Nc1ccncn1)c1cc(Cl)c(NC2(c3cc(F)ccc3F)CC2)cc1F]

Step 1. Preparation of 5-chloro-4-((1-(2,5-difluorophenyl)cyclopropyl)amino)-N-(2,4-dimethoxybenzyl)-2-fluoro-N-(pyrimidin-4-yl)benzenesulfonamide

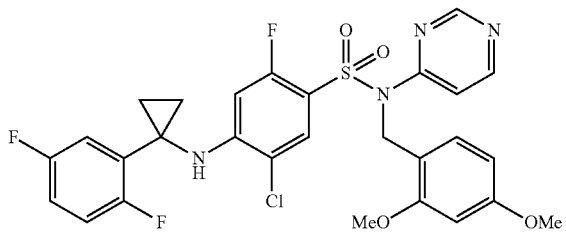 [SMILES: COc1ccc(CN(c2ccncn2)S(=O)(=O)c2cc(Cl)c(NC3(c4cc(F)ccc4F)CC3)cc2F)c(OC)c1]

To a mixture of 5-chloro-N-(2,4-dimethoxybenzyl)-2,4-difluoro-N-(pyrimidin-4-yl)benzenesulfonamide (0.200 g, 0.441 mmol) and 1-(2,5-difluorophenyl)cyclopropan-1-amine hydrochloride (0.091 g, 0.44 mmol) in anhydrous dimethyl sulfoxide (5 mL) was added potassium carbonate (0.207 g, 1.50 mmol) and the reaction mixture was stirred at 70° C. for 18 h. The mixture was cooled to ambient temperature and diluted with ethyl acetate (5 mL) and water (5 mL). The layers were separated and the aqueous phase was extracted with ethyl acetate (3×5 mL). The combined organic phase was washed with brine (1×5 mL), dried over anhydrous sodium sulfate, and filtered. Concentration of the filtrate in vacuo and purification of the residue by column chromatography, eluting with a gradient of 0 to 60% of ethyl acetate in hexanes, afforded the title compound as a colorless oil (0.107 g, 40% yield): MS (ES+) m/z 605.4 (M+1), 607.4 (M+1).

Step 2. Preparation of 5-chloro-4-((1-(2,5-difluorophenyl)cyclopropyl)amino)-2-fluoro-N-(pyrimidin-4-yl)benzenesulfonamide

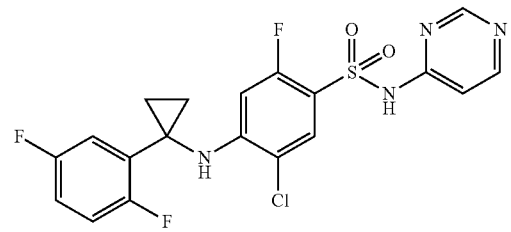 [SMILES: O=S(=O)(Nc1ccncn1)c1cc(Cl)c(NC2(c3cc(F)ccc3F)CC2)cc1F]

Following the procedure as described for EXAMPLE 222, Step 2 making non-critical variations as required to replace tert-butyl (S)-((5-chloro-4-((1-(2-chlorophenyl)propyl)amino)-2-fluorophenyl)sulfonyl)(thiazol-4-yl)carbamate with 5-chloro-4-((1-(2,5-difluorophenyl)cyclopropyl)amino)-N-(2,4-dimethoxybenzyl)-2-fluoro-N-(pyrimidin-4-yl)benzenesulfonamide and purification by preparative reverse phase HPLC, using acetonitrile in water containing 0.1% trifluoroacetic acid as eluent, afforded the title compound as a colorless solid (0.029 g, 35% yield): $^1$H-NMR (300 MHz, DMSO-d$_6$) δ 8.58 (s, 1H), 8.30 (br s, 1H), 7.72-7.69 (m, 1H), 7.53-7.47 (m, 1H), 7.33-7.29 (m, 1H), 7.25-7.10 (m, 2H), 7.00-6.94 (m, 1H), 6.83-6.79 (m, 1H), 1.43-1.40 (m, 2H), 1.28-1.25 (m, 2H), NH not observed; MS (ES+) m/z 455.2 (M+1), 457.2 (M+1).

Example 242

Synthesis of 5-chloro-2-fluoro-4-((1-(2-fluorophenyl)cyclopropyl)amino)-N-(pyrimidin-4-yl)benzenesulfonamide

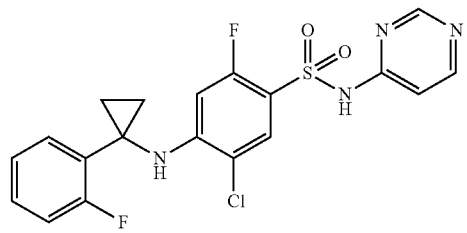 [SMILES: O=S(=O)(Nc1ccncn1)c1cc(Cl)c(NC2(c3ccccc3F)CC2)cc1F]

Step 1. Preparation of 5-chloro-N-(2,4-dimethoxybenzyl)-2-fluoro-4-((1-(2-fluorophenyl)cyclopropyl)amino)-N-(pyrimidin-4-yl)benzenesulfonamide

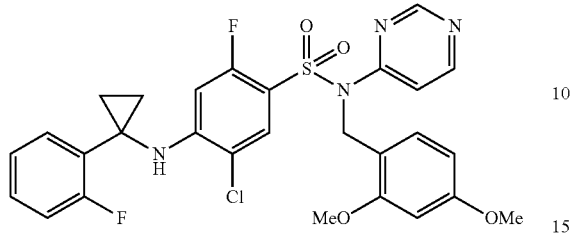

Following the procedure as described for EXAMPLE 241, Step 1 and making non-critical variations as required to replace 1-(2,5-difluorophenyl)cyclopropan-1-amine hydrochloride with 1-(2-fluorophenyl)cyclopropan-1-amine hydrochloride, the title compound was obtained as a colorless oil (0.101 g, 39% yield): MS (ES+) m/z 587.4 (M+1), 589.4 (M+1).

Step 2. Preparation of 5-chloro-2-fluoro-4-((1-(2-fluorophenyl)cyclopropyl)amino)-N-(pyrimidin-4-yl)benzenesulfonamide

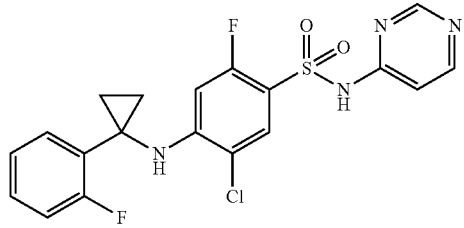 [SMILES: O=S(=O)(Nc1ccncn1)c1cc(Cl)c(NC2(c3ccccc3F)CC2)cc1F]

Following the procedure as described for EXAMPLE 241, Step 2 and making non-critical variations as required to replace 5-chloro-4-((1-(2,5-difluorophenyl)cyclopropyl)amino)-N-(2,4-dimethoxybenzyl)-2-fluoro-N-(pyrimidin-4-yl)benzenesulfonamide with 5-chloro-N-(2,4-dimethoxybenzyl)-2-fluoro-4-((1-(2-fluorophenyl)cyclopropyl)amino)-N-(pyrimidin-4-yl)benzenesulfonamide and purification by trituration with methanol (3×5 mL), the title compound was obtained as a colorless solid (0.047 g, 63% yield): $^1$H-NMR (300 MHz, DMSO-$d_6$) δ 8.57 (s, 1H), 8.30 (br s, 1H), 7.69 (d, J=7.3 Hz, 1H), 7.61-7.55 (m, 1H), 7.31-7.23 (m, 2H), 7.16-7.10 (m, 2H), 6.98-6.95 (m, 1H), 6.77 (d, J=12.9 Hz, 1H), 1.38-1.37 (m, 2H), 1.27-1.23 (m, 2H), NH not observed; MS (ES+) m/z 437.2 (M+1), 439.2 (M+1).

Example 243

Synthesis of (S)-5-chloro-4-((1-(2-chloro-5-fluorophenyl)ethyl)amino)-2-fluoro-N-(pyrazin-2-yl)benzenesulfonamide

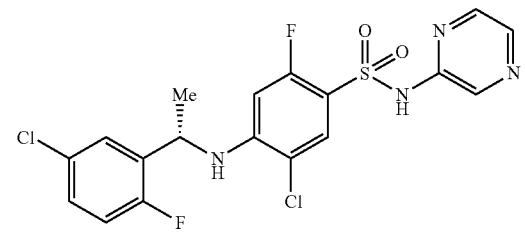

Step 1. Preparation of N-(2,4-dimethoxybenzyl)pyrazin-2-amine

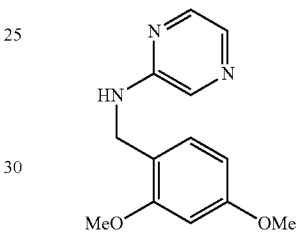

A mixture of pyrazin-2-amine (2.000 g, 21.03 mmol), 2,4-dimethoxybenzaldehyde (3.851 g, 23.19 mmol) and sodium triacetoxyborohydride (6.233 g, 29.54 mmol) in dichloromethane (90 mL) was stirred at ambient temperature for 18 h. To it was then added water (50 mL) and the layers were separated. The aqueous phase was extracted with dichloromethane (3×40 mL). The combined organic phase was washed with brine (50 mL), dried with sodium sulfate, and filtered. Concentration of the filtrate in vacuo and purification of the residue by column chromatography, eluting with a gradient of 10 to 80% of ethyl acetate in hexanes, yielded the title compound as a colorless oil (2.914 g, 56% yield): $^1$H-NMR (300 MHz, CDCl$_3$) δ 7.97 (dd, J=2.8, 1.5 Hz, 1H), 7.88 (d, J=1.5 Hz, 1H), 7.76 (d, J=2.8 Hz, 1H), 7.21 (d, J=8.2 Hz, 1H), 6.47 (d, J=2.4 Hz, 1H), 6.42 (dd, J=8.2, 2.4 Hz, 1H), 5.07-5.06 (m, 1H), 4.46 (d, J=5.8 Hz, 2H), 3.83 (s, 3H), 3.79 (s, 3H).

Step 2. Preparation of 5-chloro-N-(2,4-dimethoxybenzyl)-2,4-difluoro-N-(pyrazin-2-yl)benzenesulfonamide

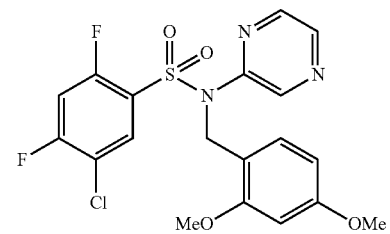 [SMILES: COc1ccc(CN(c2cnccn2)S(=O)(=O)c2cc(Cl)c(F)cc2F)c(OC)c1]

To a solution of N-(2,4-dimethoxybenzyl)pyrazin-2-amine (2.411 g, 9.840 mmol) in anhydrous tetrahydrofuran (30 mL) was added a 1.0 M solution of lithium bis(trimethylsilyl)amide in tetrahydrofuran (10.3 mL, 10.3 mmol) at −78° C. The reaction mixture was warmed to ambient temperature for 30 minutes, cooled to −78° C., and a solution of 5-chloro-2,4-difluorobenzenesulfonyl chloride (2.430 g, 9.841 mmol) in anhydrous tetrahydrofuran (10 mL) was then added to it. The mixture was allowed to warm to ambient temperature and stirred for 18 h. To it was then added saturated ammonium chloride (20 mL) and the mixture was extracted with ethyl acetate (3×20 mL). The combined organic phase was washed with brine (20 mL), dried over anhydrous sodium sulfate, and filtered. Concentration of the filtrate in vacuo and purification of the residue by column chromatography, eluting with a gradient of 5 to 80% of ethyl acetate in hexanes, yielded the title compound as a colorless oil (1.408 g, 31% yield): $^1$H-NMR (300 MHz, CDCl$_3$) δ 8.63 (d, J=1.3 Hz, 1H), 8.37 (d, J=2.5 Hz, 1H), 8.29 (dd, J=2.5, 1.5 Hz, 1H), 7.94 (dd, J=7.8, 7.0 Hz, 1H), 7.18 (d, J=8.3 Hz, 1H), 6.99 (dd, J=9.2, 8.4 Hz, 1H), 6.38-6.33 (m, 2H), 5.03 (s, 2H), 3.75 (s, 3H), 3.65 (s, 3H).

Step 3. Preparation of (S)-5-chloro-4-((1-(5-chloro-2-fluorophenyl)ethyl)amino)-N-(2,4-dimethoxybenzyl)-2-fluoro-N-(pyrazin-2-yl)benzenesulfonamide

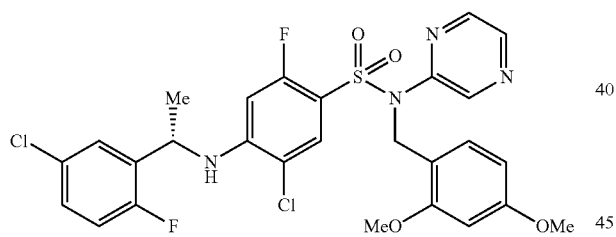

To a mixture of 5-chloro-N-(2,4-dimethoxybenzyl)-2,4-difluoro-N-(pyrazin-2-yl)benzenesulfonamide (0.250 g, 0.548 mmol) and (S)-1-(5-chloro-2-fluorophenyl)ethan-1-amine (0.115 g, 0.548 mmol) in anhydrous dimethyl sulfoxide (5 mL) was added cesium carbonate (0.178 g, 1.86 mmol). The reaction mixture was stirred at 70° C. for 18 h. The mixture was cooled to ambient temperature and diluted with ethyl acetate (5 mL) and water (5 mL). The layers were separated and the aqueous phase was extracted with ethyl acetate (3×5 mL). The combined organic phase was washed with brine (1×5 mL), dried over anhydrous sodium sulfate, and filtered. Concentration of the filtrate in vacuo and purification of the residue by column chromatography, eluting with a gradient of 5 to 60% of ethyl acetate in hexanes, afforded the title compound as a colorless oil (0.084 g, 25% yield): MS (ES+) m/z 609.4 (M+1), 611.4 (M+1).

Step 4. Preparation of (S)-5-chloro-4-((1-(2-chloro-5-fluorophenyl)ethyl)amino)-2-fluoro-N-(pyrazin-2-yl)benzenesulfonamide

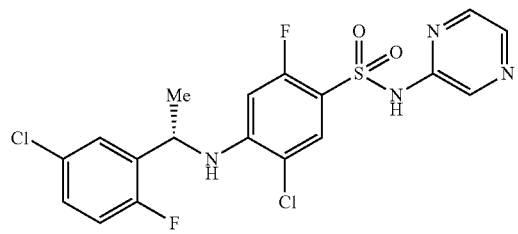 [SMILES: C[C@H](Nc1cc(F)c(S(=O)(=O)Nc2cnccn2)cc1Cl)c1cc(Cl)ccc1F]

Following the procedure as described for EXAMPLE 222 step 2 and making non-critical variations as required to replace tert-butyl (S)-((5-chloro-4-((1-(2-chlorophenyl)propyl)amino)-2-fluorophenyl)sulfonyl)(thiazol-4-yl)carbamate with (S)-5-chloro-4-((1-(5-chloro-2-fluorophenyl)ethyl)amino)-N-(2,4-dimethoxybenzyl)-2-fluoro-N-(pyrazin-2-yl)benzenesulfonamide and purification by column chromatography, eluting with a gradient of 5 to 60% of ethyl acetate in hexanes, afforded the title compound as a colorless solid (0.050 g, 20% yield): $^1$H-NMR (300 MHz, DMSO-d$_6$) δ 11.70 (s, 1H), 8.29 (d, J=1.4 Hz, 1H), 8.20 (d, J=2.7 Hz, 1H), 8.19-8.17 (m, 1H), 7.76 (d, J=7.5 Hz, 1H), 7.50 (dd, J=6.5, 2.7 Hz, 1H), 7.36 (ddd, J=8.7, 4.6, 2.7 Hz, 1H), 7.26 (dd, J=9.8, 8.8 Hz, 1H), 6.79-6.76 (m, 1H), 6.41 (d, J=13.4 Hz, 1H), 4.98-4.88 (m, 1H), 1.54 (d, J=6.7 Hz, 3H); MS (ES+) m/z: 459.0 (M+1), 461.0 (M+1).

Example 244

Synthesis of (S)-5-chloro-4-((1-(2-chlorophenyl)ethyl)amino)-2-fluoro-N-(6-methylpyrimidin-4-yl)benzenesulfonamide

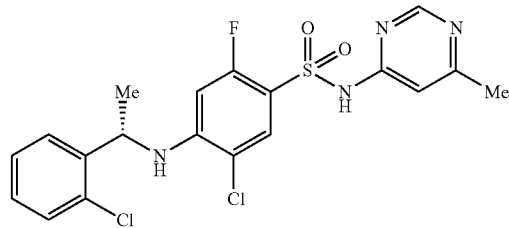 [SMILES: Cc1cc(NS(=O)(=O)c2cc(Cl)c(N[C@@H](C)c3ccccc3Cl)cc2F)ncn1]

Step 1. Preparation of 2-chloro-N-(2,4-dimethoxybenzyl)-6-methylpyrimidin-4-amine

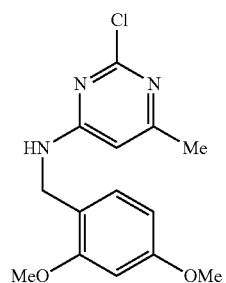 [SMILES: COc1ccc(CNc2cc(C)nc(Cl)n2)c(OC)c1]

A solution of 2,4-dichloro-6-methylpyrimidine (3.931 g, 24.12 mmol), (2,4-dimethoxyphenyl)methanamine (4.430 g, 26.53 mmol), and triethylamine (17 mL, 121 mmol) in acetonitrile (92 mL) was stirred at ambient temperature for 18 h. The resulting suspension was filtered, and the filtrate was concentrated in vacuo. The residue was dissolved in dichloromethane (50 mL), washed with water (3×30 mL), dried over anhydrous sodium sulfate, and filtered. Concentration of the filtrate in vacuo and purification of the residue by column chromatography, eluting with a gradient of 10 to 80% of ethyl acetate in hexanes, yielded the title compound as a colorless solid (4.020 g, 57% yield): $^1$H-NMR (300 MHz, CDCl$_3$) δ 7.17-7.14 (m, 1H), 6.47-6.44 (m, 1H), 6.42 (d, J=2.3 Hz, 1H), 6.10 (br s, 1H), 4.39 (br s, 2H), 3.82 (s, 3H), 3.80 (s, 3H), 2.30 (s, 3H), NH not observed.

Step 2. Preparation of N-(2,4-dimethoxybenzyl)-6-methylpyrimidin-4-amine

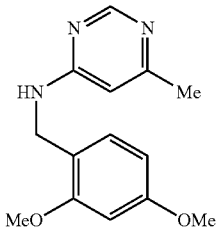 [SMILES: COc1ccc(CNc2cc(C)ncn2)c(OC)c1]

To a mixture of 2-chloro-N-(2,4-dimethoxybenzyl)-6-methylpyrimidin-4-amine (4.020 g, 13.41 mmol) in ethanol (30 mL) was added Pd/C (10% wet, 0.402 g) and ammonium formate (1.246 g, 19.78 mmol). The mixture was then heated to 80° C. and stirred for 18 h. After cooling to ambient temperature, the mixture was filtered through a pad of Celite. The filtrate was concentrated in vacuo to provide a residue, which was partitioned between water (30 mL) and ethyl acetate (30 mL). The organic phase was washed with water (2×20 mL), brine (1×20 mL), dried with sodium sulfate, and filtered. Concentration in vacuo provided the title compound as a colorless powder (2.787 g, 78% yield): $^1$H-NMR (300 MHz, CDCl$_3$) δ 8.30 (s, 1H), 7.71-7.67 (m, 1H), 7.08 (d, J=8.3 Hz, 1H), 6.55 (d, J=2.4 Hz, 1H), 6.46 (dd, J=8.3, 2.4 Hz, 1H), 6.38-6.37 (m, 1H), 4.38-4.35 (m, 2H), 3.79 (s, 3H), 3.79-3.72 (s, 3H), 2.19 (s, 3H).

Step 3. Preparation of 5-chloro-N-(2,4-dimethoxybenzyl)-2,4-difluoro-N-(6-methylpyrimidin-4-yl)benzenesulfonamide

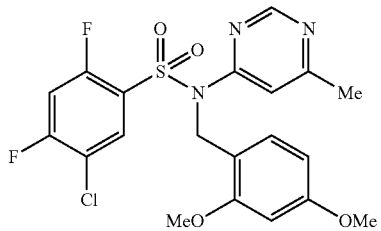 [SMILES: COc1ccc(CN(c2cc(C)ncn2)S(=O)(=O)c2cc(Cl)c(F)cc2F)c(OC)c1]

To a solution of N-(2,4-dimethoxybenzyl)-6-methylpyrimidin-4-amine (1.002 g, 3.85 mmol) in tetrahydrofuran (15 mL) was added a 1.0 M solution of lithium bis(trimethylsilyl)amide in tetrahydrofuran (4 mL, 4.0 mmol) at −78° C. The mixture was stirred for ten minutes −78° C. and then warmed to ambient temperature for 30 minutes. The suspension was cooled to −78° C. and a solution of 5-chloro-2,4-difluorobenzenesulfonyl chloride (0.951 g, 3.85 mmol) in tetrahydrofuran (5 mL) was added to it. The mixture was allowed to warm to ambient temperature and stirred for 18 h. Saturated ammonium chloride (20 mL) was added to it and the mixture was extracted with ethyl acetate (3×20 mL). The combined organic phase was washed with brine (20 mL), dried over anhydrous sodium sulfate, and filtered. Concentration of the filtrate in vacuo and purification of the residue by column chromatography, eluting with a gradient of 10 to 70% of ethyl acetate in hexanes, yielded the title compound as a colorless oil (1.275 g, 70% yield): $^1$H-NMR (300 MHz, CDCl$_3$) δ 8.66 (s, 1H), 8.12 (t, J=7.5 Hz, 1H), 7.22 (d, J=9.0 Hz, 1H), 7.00-6.96 (m, 2H), 6.44-6.40 (m, 2H), 5.19 (s, 2H), 3.79 (d, J=5.3 Hz, 6H), 2.42 (s, 3H).

Step 4. Preparation of (S)-5-chloro-4-((1-(2-chlorophenyl)ethyl)amino)-2-fluoro-N-(6-methylpyrimidin-4-yl)benzenesulfonamide

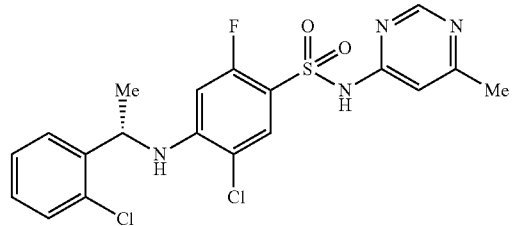 [SMILES: Cc1cc(NS(=O)(=O)c2cc(Cl)c(N[C@@H](C)c3ccccc3Cl)cc2F)ncn1]

To a solution of 5-chloro-N-(2,4-dimethoxybenzyl)-2,4-difluoro-N-(6-methylpyrimidin-4-yl)benzenesulfonamide (0.250 g, 0.531 mmol) and (S)-1-(2-chlorophenyl)ethan-1-amine hydrochloride (0.101 g, 0.526 mmol) in dimethyl sulfoxide (5 mL) was added triethylamine (0.30 mL, 2.1 mmol) and the reaction mixture was stirred at ambient temperature for 20 h. The mixture was diluted with ethyl acetate (5 mL) and water (5 mL). The layers were separated and the aqueous phase was extracted with ethyl acetate (3×3 mL). The combined organic phase was washed with brine (1×5 mL), dried over anhydrous sodium sulfate, and filtered. Concentration of the filtrate in vacuo and purification of the residue by column chromatography, eluting with a gradient of 5 to 60% of ethyl acetate in hexanes, provided a colorless oil. To it was then added dichloromethane (5 mL) and trifluoroacetic acid (1 mL), and the mixture was stirred at ambient temperature for 1 h. The mixture was concentrated in vacuo and purified by column chromatography, eluting with a gradient of 20 to 80% of ethyl acetate in hexanes, to afford the title compound as a colorless solid (0.177 g, 73% yield): $^1$H-NMR (300 MHz, DMSO-d$_6$) δ 8.45 (s, 1H), 7.73 (d, J=7.4 Hz, 1H), 7.48-7.44 (m, 2H), 7.34-7.24 (m, 2H), 6.87-6.80 (m, 2H), 6.03 (d, J=13.0 Hz, 1H), 4.93-4.85 (m, 1H), 2.29 (s, 3H), 1.54 (d, J=6.7 Hz, 3H), NH not observed; MS (ES+) m/z 455.1 (M+1), 457.1 (M+1).

Example 245

Synthesis of (S)-5-chloro-4-((1-(2-chlorophenyl)ethyl)amino)-2-fluoro-N-(2-(trifluoromethyl)pyrimidin-4-yl)benzenesulfonamide

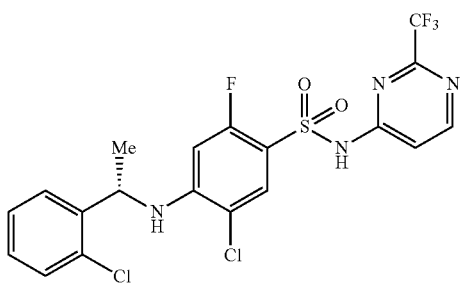 [SMILES: C[C@H](Nc1cc(F)c(S(=O)(=O)Nc2ccnc(C(F)(F)F)n2)cc1Cl)c1ccccc1Cl]

Step 1. Preparation of 5-chloro-N-(2,4-dimethoxybenzyl)-2,4-difluorobenzenesulfonamide

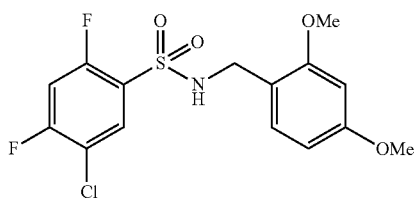 [SMILES: COc1ccc(CNS(=O)(=O)c2cc(Cl)c(F)cc2F)c(OC)c1]

A mixture of 5-chloro-2,4-difluorobenzenesulfonyl chloride (5.000 g, 20.2 mmol), (2,4-dimethoxyphenyl)methanamine (3.38 g, 20.2 mmol), and N,N-diisopropylethylamine (4.2 mL, 24 mmol) in anhydrous dichloromethane (100 mL) was stirred at ambient temperature for 18 h. The mixture was then washed with 1 N hydrochloric acid (50 mL), saturated ammonium chloride(50 mL), and brine (50 mL). The organic phase was dried over anhydrous sodium sulfate, and filtered. Concentration of the filtrate in vacuo and crystallization of the residue from dichloromethane and hexanes afforded the title compound as pale yellow crystals (5.26 g, 69% yield): MS (ES−) m/z 376.2 (M−1), 378.2 (M−1).

Step 2. Preparation of 5-chloro-N-(2,4-dimethoxybenzyl)-2,4-difluoro-N-(2-(trifluoromethyl)pyrimidin-4-yl)benzenesulfonamide

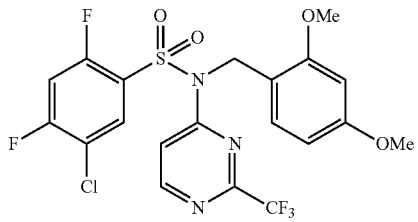 [SMILES: COc1ccc(CN(c2ccnc(C(F)(F)F)n2)S(=O)(=O)c2cc(Cl)c(F)cc2F)c(OC)c1]

A mixture of 5-chloro-N-(2,4-dimethoxybenzyl)-2,4-difluorobenzenesulfonamide (1.000 g, 2.65 mmol), 4-chloro-2-(trifluoromethyl)pyrimidine (0.482 g, 2.65 mmol), and potassium carbonate (0.549 g, 3.98 mmol) in anhydrous dimethyl sulfoxide (20 mL) was stirred at 50° C. for 18 h. To it was added saturated ammonium chloride (10 mL) and the mixture was extracted with ethyl acetate (3×10 mL). The combined organic phase was washed with brine (10 mL), dried over anhydrous sodium sulfate, and filtered. Concentration of the filtrate in vacuo and purification of the residue by column chromatography, eluting with a gradient of 5 to 60% of ethyl acetate in hexanes, afforded the title compound as a colorless solid (0.919 g, 66% yield): $^1$H-NMR (300 MHz, DMSO-$d_6$) δ 8.94 (d, J=5.1 Hz, 1H), 8.13 (t, J=7.6 Hz, 1H), 7.86 (t, J=9.8 Hz, 1H), 7.65 (d, J=4.9 Hz, 1H), 7.04 (d, J=8.2 Hz, 1H), 6.59 (d, J=2.2 Hz, 1H), 6.49 (dd, J=8.4, 2.2 Hz, 1H), 5.30 (s, 2H), 3.77 (s, 3H), 3.74 (s, 3H).

Step 3. Preparation of (S)-5-chloro-4-((1-(2-chlorophenyl)ethyl)amino)-N-(2,4-dimethoxybenzyl)-2-fluoro-N-(2-(trifluoromethyl)pyrimidin-4-yl)benzenesulfonamide

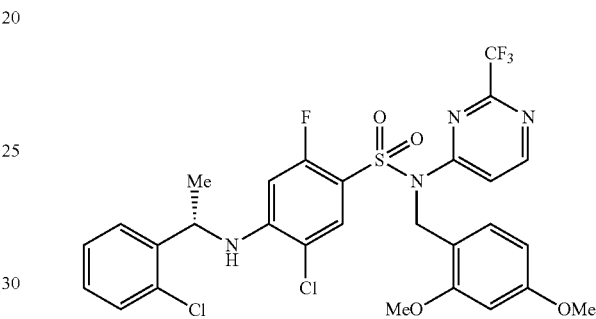

To a mixture of 5-chloro-N-(2,4-dimethoxybenzyl)-2,4-difluoro-N-(2-(trifluoromethyl)pyrimidin-4-yl)benzenesulfonamide (0.250 g, 0.478 mmol) and (S)-1-(2-chlorophenyl)ethan-1-amine hydrochloride (0.092 g, 0.48 mmol) in anhydrous dimethyl sulfoxide (5 mL) was added triethylamine (0.27 mL, 1.9 mmol) and the reaction mixture was stirred at ambient temperature for 22 h. The mixture was diluted with ethyl acetate (5 mL) and water (5 mL). The layers were separated and the aqueous phase was extracted with ethyl acetate (3×3 mL). The combined organic phase was washed with brine (1×5 mL), dried over anhydrous sodium sulfate, and filtered. Concentration of the filtrate in vacuo and purification of the residue by column chromatography, eluting with a gradient of 0 to 60% of ethyl acetate in hexanes, afforded the title compound as a colorless oil (0.198 g, 62% yield): MS (ES) m/z 659.3 (M+1), 661.2 (M+1).

Step 4. Preparation of (S)-5-chloro-4-((1-(2-chlorophenyl)ethyl)amino)-2-fluoro-N-(2-(trifluoromethyl)pyrimidin-4-yl)benzenesulfonamide

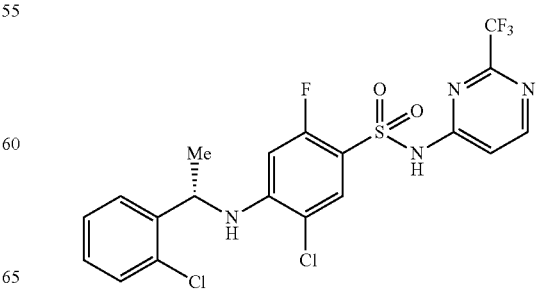

To a mixture of (S)-5-chloro-4-((1-(2-chlorophenyl)ethyl)amino)-N-(2,4-dimethoxybenzyl)-2-fluoro-N-(2-(trifluoromethyl)pyrimidin-4-yl)benzenesulfonamide (0.198 g, 0.301 mmol) in dichloromethane (5 mL) was added trifluoroacetic acid (1 mL) and the reaction mixture was stirred at ambient temperature for 1 h. To it was added methanol (10 mL) and the resulting precipitate was removed by filtration. The filtrate was concentrated in vacuo and the residue was purified by column chromatography, eluting with a gradient of 10 to 80% of ethyl acetate in hexanes, to afford the title compound as a colorless solid (0.104 g, 68% yield): $^1$H-NMR (300 MHz, DMSO-$d_6$) δ 12.57 (s, 1H), 8.84 (d, J=4.8 Hz, 1H), 7.79 (d, J=7.4 Hz, 1H), 7.49 (d, J=4.8 Hz, 1H), 7.47-7.43 (m, 2H), 7.32-7.23 (m, 2H), 6.96-6.93 (m, 1H), 6.05 (d, J=13.4 Hz, 1H), 4.95-4.85 (m, 1H), 1.53 (d, J=6.7 Hz, 3H); MS (ES+) m/z 509.0 (M+1), 511.0 (M+1).

Example 246

Synthesis of 4-((2-(azetidin-1-ylmethyl)-6-fluorobenzyl)amino)-5-chloro-2-fluoro-N-(thiazol-4-yl)benzenesulfonamide 2,2,2-trifluoroacetate

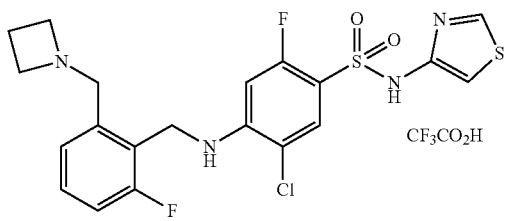 [SMILES: O=S(=O)(Nc1cscn1)c1cc(Cl)c(NCc2c(F)cccc2CN2CCC2)cc1F ; "CF3CO2H"]

Step 1. Synthesis of 2-(azetidin-1-ylmethyl)-6-fluorobenzonitrile

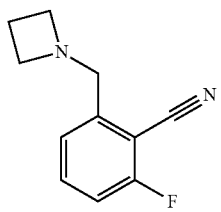 [SMILES: N#Cc1c(F)cccc1CN1CCC1]

To a mixture of azetidine (0.266 g, 7.01 mmol) and 2-(bromomethyl)-6-fluorobenzonitrile (1.00 g, 4.67 mmol) in dichloromethane (30 mL) was added N,N-diisopropylethylamine (1.2 mL, 7.0 mmol) and the reaction mixture was stirred at ambient temperature for 18 h. To it was then added saturated ammonium chloride (20 mL) and the mixture was extracted with dichloromethane (3×20 mL). The combined organic phase was washed with brine (20 mL), dried over anhydrous sodium sulfate, and filtered. Concentration of the filtrate in vacuo and purification of the residue by column chromatography, eluting with a gradient of 0 to 20% methanol in dichloromethane, yielded the title compound as a colorless oil (0.819 g, 92% yield); $^1$H-NMR (300 MHz, CDCl$_3$) δ 7.56-7.50 (m, 1H), 7.33-7.31 (m, 1H), 7.11-7.05 (m, 1H), 3.78 (s, 2H), 3.33-3.29 (m, 4H), 2.17-2.10 (m, 2H).

Step 2. Synthesis of (2-(azetidin-1-ylmethyl)-6-fluorophenyl)methanamine

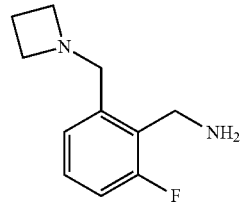 [SMILES: NCc1c(F)cccc1CN1CCC1]

To a solution of 2-(azetidin-1-ylmethyl)-6-fluorobenzonitrile (0.819 g, 4.51 mmol) in anhydrous tetrahydrofuran (40 mL) was added lithium aluminum hydride (1.0 M in tetrahydrofuran, 6.8 mL, 6.8 mmol) at 0° C. The reaction mixture was allowed to warm to ambient temperature and stirred for 4 h. To it was then added sodium sulfate decahydrate (5.0 g) in portions at 0° C. The mixture was stirred for 30 minutes and then filtered. The filter cake was washed ethyl acetate (20 mL). The combined filtrate was concentrated in vacuo to afford the title compound as a red oil (0.811 mg, 99% yield): $^1$H-NMR (300 MHz, CDCl$_3$) δ 7.13 (td, J=7.8, 5.6 Hz, 1H), 7.01-6.93 (m, 2H), 3.85 (d, J=1.9 Hz, 2H), 3.60 (s, 2H), 3.16 (t, J=7.0 Hz, 4H), 2.03 (quintet, J=7.0 Hz, 2H).

Step 3. Synthesis of tert-butyl ((4-((2-(azetidin-1-ylmethyl)-6-fluorobenzyl)amino)-5-chloro-2-fluorophenyl)sulfonyl)(thiazol-4-yl)carbamate

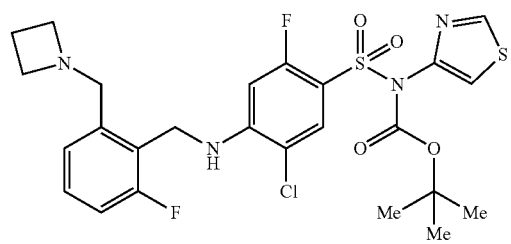 [SMILES: CC(C)(C)OC(=O)N(c1cscn1)S(=O)(=O)c1cc(Cl)c(NCc2c(F)cccc2CN2CCC2)cc1F]

A mixture of (2-(azetidin-1-ylmethyl)-6-fluorophenyl)methanamine (0.152 g, 0.780 mmol), tert-butyl ((5-chloro-2,4-difluorophenyl)sulfonyl)(thiazol-4-yl)carbamate (0.321 g, 0.0.780 mmol), and potassium carbonate (0.258 g, 1.46 mmol) in anhydrous dimethyl sulfoxide (5 mL) was stirred at ambient temperature for 3 h. To it was then added water (5 mL) and ethyl acetate (5 mL). The aqueous phase was extracted with ethyl acetate (3×5 mL). The combined organic phase was washed with brine (5 mL), dried with anhydrous sodium sulfate, and filtered. Concentration of the filtrate in vacuo and purification of the residue by column chromatography, eluting with a gradient of 20 to 80% of ethyl acetate in hexanes, yielded the title compound as a colorless oil (0.223 g, 49% yield): MS (ES+) m/z 585.4 (M+1), 587.4 (M+1).

Step 4: Synthesis of 4-((2-(azetidin-1-ylmethyl)-6-fluorobenzyl)amino)-5-chloro-2-fluoro-N-(thiazol-4-yl)benzenesulfonamide 2,2,2-trifluoroacetate

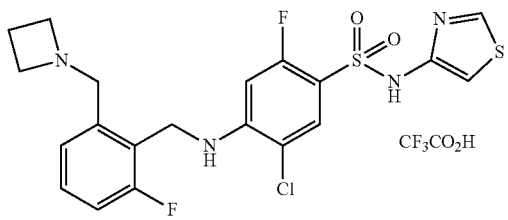 [SMILES: O=S(=O)(Nc1cscn1)c1cc(Cl)c(NCc2c(F)cccc2CN2CCC2)cc1F ; "CF3CO2H"]

To a solution of tert-butyl ((4-((2-(azetidin-1-ylmethyl)-6-fluorobenzyl)amino)-5-chloro-2-fluorophenyl)sulfonyl)(thiazol-4-yl)carbamate (0.223 g, 0.382 mmol) in dichloromethane (5 mL) was added trifluoroacetic acid (1 mL) and the reaction mixture was stirred at ambient temperature for 1 h. The mixture was concentrated in vacuo to afford the title compound as a colorless solid (0.197 g, 86% yield): $^1$H-NMR (300 MHz, DMSO-$d_6$) δ 11.18 (br s, 1H), 10.10 (br s, 1H), 8.89 (d, J=2.1 Hz, 1H), 7.62 (d, J=7.4 Hz, 1H), 7.52-7.45 (m, 1H), 7.37-7.30 (m, 2H), 7.00 (d, J=2.4 Hz, 1H), 6.84-6.82 (m, 1H), 6.77-6.72 (d, J=12.9 Hz, 1H), 4.53-4.48 (m, 4H), 4.12-4.01 (m, 4H), 2.39-2.27 (m, 2H); MS (ES+) m/z 485.1 (M+1), 487.1 (M+1).

Example 247

Synthesis of 5-chloro-2-fluoro-4-((2-fluoro-6-((3-fluoroazetidin-1-yl)methyl)benzyl)amino)-N-(thiazol-4-yl)benzenesulfonamide

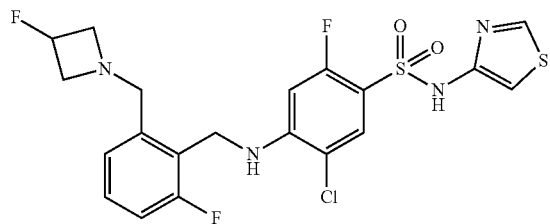 [SMILES: O=S(=O)(Nc1cscn1)c1cc(Cl)c(NCc2c(F)cccc2CN2CC(F)C2)cc1F]

Step 1. Synthesis of 2-fluoro-6-((3-fluoroazetidin-1-yl)methyl)benzonitrile

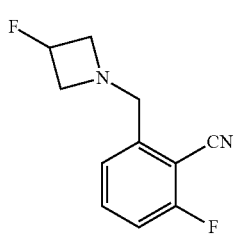 [SMILES: N#Cc1c(F)cccc1CN1CC(F)C1]

Following the procedure as described for EXAMPLE 246, Step 1 and making non-critical variations to replace azetidine with 3-fluoroazetidine hydrochloride, the title compound was isolated as a colorless oil (0.815 g, 93% yield); $^1$H-NMR (300 MHz, CDCl$_3$) δ 7.56 (td, J=8.1, 5.7 Hz, 1H), 7.31 (d, J=7.8 Hz, 1H), 7.11 (t, J=8.5 Hz, 1H), 5.16 (dquintet, J=57.2, 5.3 Hz, 1H), 3.87 (s, 2H), 3.77-3.68 (m, 2H), 3.38-3.25 (m, 2H).

Step 2. Synthesis of (2-fluoro-6-((3-fluoroazetidin-1-yl)methyl)phenyl)methanamine

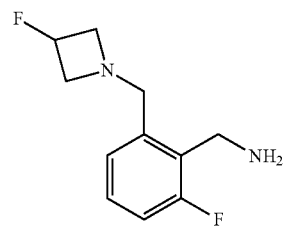 [SMILES: NCc1c(F)cccc1CN1CC(F)C1]

Following the procedure as described for EXAMPLE 246, Step 2 and making non-critical variations to replace 2-(azetidin-1-ylmethyl)-6-fluorobenzonitrile with 2-fluoro-6-((3-fluoroazetidin-1-yl)methyl)benzonitrile, title compound was isolated as an orange oil (0.776 g, 89% yield): $^1$H-NMR (300 MHz, CDCl$_3$) δ 7.31-7.24 (m, 1H), 7.19-7.14 (m, 1H), 7.05-6.99 (m, 1H), 5.22-4.97 (m, 1H), 3.88-3.85 (m, 2H), 3.74-3.71 (m, 2H), 3.66-3.57 (m, 2H), 3.26-3.13 (m, 2H), NH not observed.

Step 3. Synthesis of tert-butyl ((5-chloro-2-fluoro-4-((2-fluoro-6-((3-fluoroazetidin-1-yl)methyl)benzyl)amino)phenyl)sulfonyl)(thiazol-4-yl)carbamate

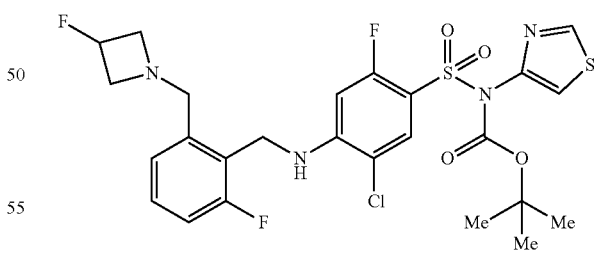

Following the procedure as described for EXAMPLE 246, Step 3 and making non-critical variations as required to replace (2-(azetidin-1-ylmethyl)-6-fluorophenyl)methanamine with (2-fluoro-6-((3-fluoroazetidin-1-yl)methyl)phenyl)methanamine, title compound was isolated as a colorless oil (0.187 g, 44% yield): MS (ES−) m/z 603.4 (M−1), 605.4 (M−1).

Step 4. Synthesis of 5-chloro-2-fluoro-4-((2-fluoro-6-((3-fluoroazetidin-1-yl)methyl)benzyl)amino)-N-(thiazol-4-yl)benzenesulfonamide

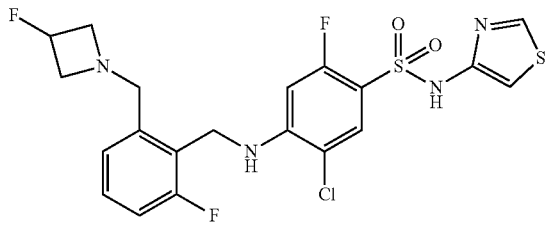 [SMILES: O=S(=O)(Nc1cscn1)c1cc(Cl)c(NCc2c(F)cccc2CN2CC(F)C2)cc1F]

Following the procedure as described for EXAMPLE 246, Step 4 and making non-critical variations as required to replace tert-butyl ((4-((2-(azetidin-1-ylmethyl)-6-fluorobenzyl)amino)-5-chloro-2-fluorophenyl)sulfonyl)(thiazol-4-yl)carbamate with tert-butyl ((5-chloro-2-fluoro-4-((2-fluoro-6-((3-fluoroazetidin-1-yl)methyl)benzyl)amino)phenyl)sulfonyl)(thiazol-4-yl)carbamate, and purification by preparative reverse phase HPLC, using acetonitrile in water containing 0.1% trifluoroacetic acid as eluent, the title compound was obtained as a colorless solid (0.506 g, 14% yield): $^1$H-NMR (300 MHz, DMSO-$d_6$) δ 11.16 (s, 1H), 8.89 (d, J=2.2 Hz, 1H), 7.61 (d, J=7.4 Hz, 1H), 7.51-7.35 (m, 1H), 7.33-7.30 (m, 2H), 7.00 (d, J=2.2 Hz, 1H), 6.87-6.71 (m, 2H), 5.50-5.22 (m, 2H) 4.76-4.19 (m, 7H); MS (ES+) m/z 503.2 (M+1), 505.2 (M+1).

Example 248

Synthesis of 5-chloro-2-fluoro-4-((2-fluoro-6-((3-methoxyazetidin-1-yl)methyl)benzyl)amino)-N-(thiazol-4-yl)benzenesulfonamide 2,2,2-trifluoroacetate

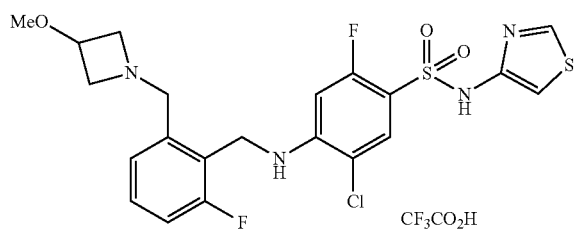 [SMILES: COC1CN(Cc2cccc(F)c2CNc2cc(F)c(S(=O)(=O)Nc3cscn3)cc2Cl)C1 ; "CF3CO2H"]

Step 1. Preparation of 2-fluoro-6-((3-methoxyazetidin-1-yl)methyl)benzonitrile

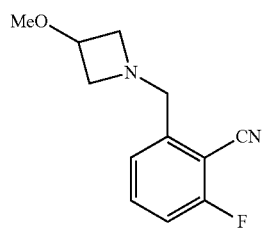 [SMILES: COC1CN(Cc2cccc(F)c2C#N)C1]

Following the procedure as described for EXAMPLE 246, Step 1 and making non-critical variations as required to replace azetidine with 3-methoxyazetidine hydrochloride, the title compound was isolated as a colorless oil (0.287 g, 55% yield): $^1$H-NMR (300 MHz, CDCl$_3$) δ 7.56 (td, J=8.1, 5.7 Hz, 1H), 7.33 (d, J=7.4, Hz, 1H), 7.14-7.08 (m, 1H), 4.15-4.06 (m, 1H), 3.86 (s, 2H), 3.71-3.66 (m, 2H), 3.27 (s, 3H), 3.12-3.08 (m, 2H).

Step 2. Preparation of (2-fluoro-6-((3-methoxyazetidin-1-yl)methyl)phenyl)methanamine

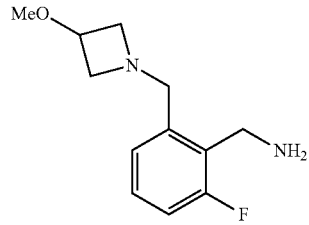 [SMILES: COC1CN(Cc2cccc(F)c2CN)C1]

Following the procedure as described for EXAMPLE 246, Step 2 and making non-critical variations as required to replace 2-(azetidin-1-ylmethyl)-6-fluorobenzonitrile with azetidine with 2-fluoro-6-((3-methoxyazetidin-1-yl)methyl)benzonitrile, title compound was isolated as a colorless oil, which was used without further purification.

Step 3. Preparation of tert-butyl ((5-chloro-2-fluoro-4-((2-fluoro-6-((3-methoxyazetidin-1-yl)methyl)benzyl)amino)phenyl)sulfonyl)(thiazol-4-yl)carbamate

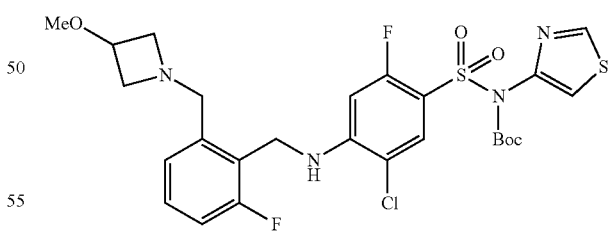

Following the procedure as described for EXAMPLE 246, Step 3 and making non-critical variations as required to replace (2-(azetidin-1-ylmethyl)-6-fluorophenyl)methanamine methanamine with (2-fluoro-6-((3-methoxyazetidin-1-yl)methyl)phenyl)methanamine, the title compound was isolated as a colorless oil (0.159 g, 42% yield): MS (ES+) m/z 615.2 (M+1), 617.2 (M+1).

335

Step 4. Preparation of 5-chloro-2-fluoro-4-((2-fluoro-6-((3-methoxyazetidin-1-yl)methyl)benzyl)amino)-N-(thiazol-4-yl)benzenesulfonamide 2,2,2-trifluoroacetate

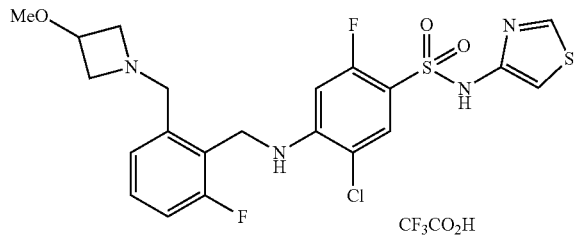 [SMILES: COC1CN(Cc2cccc(F)c2CNc2cc(F)c(S(=O)(=O)Nc3cscn3)cc2Cl)C1 ; "CF3CO2H"]

Following the procedure as described for EXAMPLE 246, Step 4 and making non-critical variations as required to replace tert-butyl ((4-((2-(azetidin-1-ylmethyl)-6-fluorobenzyl)amino)-5-chloro-2-fluorophenyl)sulfonyl)(thiazol-4-yl)carbamate with tert-butyl ((5-chloro-2-fluoro-4-((2-fluoro-6-((3-methoxyazetidin-1-yl)methyl)benzyl)amino)phenyl)sulfonyl)(thiazol-4-yl)carbamate, the title compound was obtained as a colorless solid (0.068 g, 42% yield): $^1$H-NMR (300 MHz, DMSO-$d_6$) δ 11.19 (s, 1H), 10.61-10.45 (m, 0.5H), 10.14-9.98 (m, 0.5H), 8.89 (d, J=2.2 Hz, 1H), 7.61 (d, J=7.2 Hz, 1H), 7.51-7.44 (m, 1H), 7.37-7.30 (m, 2H), 7.00 (m, J=2.1 Hz, 1H), 6.84-6.77 (m, 1H), 6.74 (d, J=12.6 Hz, 1H), 4.59-4.53 (m, 2H), 4.49-4.45 (m, 2H), 4.33-4.21 (m, 3H), 4.04-3.97 (m, 2H), 3.24-3.21 (m, 3H); MS (ES+) m/z 515.2, 517.2 (M+1).

Example 249

Synthesis of 5-chloro-4-((2-((dimethylamino)methyl)-6-fluorobenzyl)amino)-2-fluoro-N-(thiazol-4-yl)benzenesulfonamide 2,2,2-trifluoroacetate

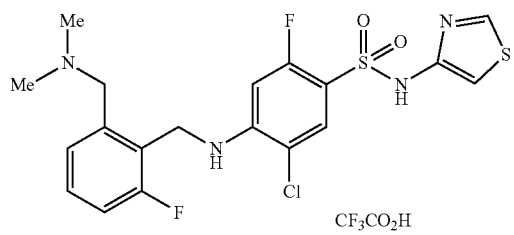 [SMILES: CN(C)Cc1cccc(F)c1CNc1cc(F)c(S(=O)(=O)Nc2cscn2)cc1Cl ; "CF3CO2H"]

Step 1. Preparation of tert-butyl ((4-((2-bromo-6-fluorobenzyl)amino)-5-chloro-2-fluorophenyl)sulfonyl)(thiazol-4-yl)carbamate

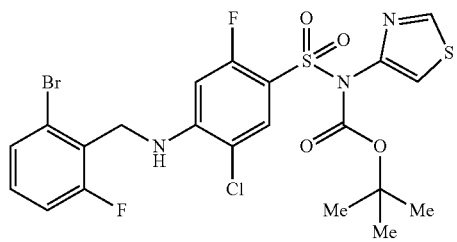 [SMILES: CC(C)(C)OC(=O)N(c1cscn1)S(=O)(=O)c1cc(Cl)c(NCc2c(F)cccc2Br)cc1F]

336

To a mixture of (2-bromo-6-fluorophenyl)methanamine (0.995 g, 4.88 mmol) and tert-butyl ((5-chloro-2,4-difluorophenyl)sulfonyl)(thiazol-4-yl)carbamate (2.000 g, 4.88 mmol) in anhydrous dimethyl sulfoxide (40 mL) was added potassium carbonate (1.643 g, 11.91 mmol) and the reaction mixture was stirred at ambient temperature for 4 h. To it was then added saturated ammonium chloride (20 mL) and the mixture was extracted with ethyl acetate (3×30 mL). The combined organic phase was washed with brine (30 mL), dried over anhydrous sodium sulfate, and filtered. Concentration of the filtrate in vacuo and purification of the residue by column chromatography, eluting with a gradient of 10 to 80% of ethyl acetate in hexanes, afforded the title compound as a colorless solid (1.078 g, 37% yield): $^1$H-NMR (300 MHz, CDCl$_3$) δ 8.79 (d, J=2.3 Hz, 1H), 7.93 (d, J=7.1 Hz, 1H), 7.50 (d, J=2.3 Hz, 1H), 7.43 (dd, J=7.9, 0.8 Hz, 1H), 7.24-7.19 (m, 1H), 7.14-7.08 (m, 1H), 6.69-6.65 (m, 1H), 5.60-5.55 (m, 1H), 4.61-4.59 (m, 2H), 1.36 (s, 9H); MS (ES+) m/z 494.2 (M+1), 496.2 (M+1).

Step 2. Preparation of 5-chloro-4-((2-((dimethylamino)methyl)-6-fluorobenzyl)amino)-2-fluoro-N-(thiazol-4-yl)benzenesulfonamide 2,2,2-trifluoroacetate

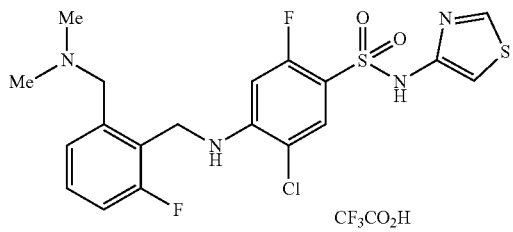 [SMILES: CN(C)Cc1cccc(F)c1CNc1cc(F)c(S(=O)(=O)Nc2cscn2)cc1Cl ; "CF3CO2H"]

To a mixture of tert-butyl ((4-((2-bromo-6-fluorobenzyl)amino)-5-chloro-2-fluorophenyl)sulfonyl)(thiazol-4-yl)carbamate (0.200 g, 0.338 mmol), potassium dimethylaminomethyltrifluoroboronate (0.067 g, 0.41 mmol), cesium carbonate (0.330 g, 1.01 mmol), palladium(II) acetate (0.008 g, 0.03 mmol), and di(1-adamantyl)-n-butylphosphine (0.024 g, 0.068 mmol) was added a degassed mixture of water (0.53 mL) and dioxane (2.6 mL). The reaction mixture to 85° C. and stirred for 18 h. After cooling to ambient temperature, the mixture was filtered through a pad of Celite. The filter cake was washed with ethyl acetate (10 mL) and the combined filtrate was concentrated in vacuo. To the residue was added dichloromethane (5 mL) and trifluoroacetic acid (1 mL) and the reaction mixture was stirred for 5 h. Concentration in vacuo provided a residue which was purified by column chromatography, eluting with a gradient of 20 to 100% of ethyl acetate (containing 10% of isopropanol and 10% of triethylamine) in hexanes. Further purification by preparative reverse phase HPLC, using acetonitrile in water containing 0.1% trifluoroacetic acid as eluent, afforded the title compound as a colorless solid (0.008 g, 4% yield): $^1$H-NMR (300 MHz, DMSO-$d_6$) δ 11.17 (s, 1H), 9.67 (br s, 1H), 8.89 (d, J=2.2 Hz, 1H), 7.61 (d, J=7.5 Hz, 1H), 7.56-7.48 (m, 1H), 7.45-7.29 (m, 2H), 7.00 (d, J=2.2 Hz, 1H), 6.80-6.75 (m, 2H), 4.50-4.43 (m, 4H), 2.78-2.76 (m, 6H); MS (ES+) m/z 473.1 (M+1), 475.1 (M+1).

Example 250

Synthesis of 5-chloro-2-fluoro-4-((2-fluoro-6-(morpholinomethyl)benzyl)amino)-N-(thiazol-4-yl)benzenesulfonamide

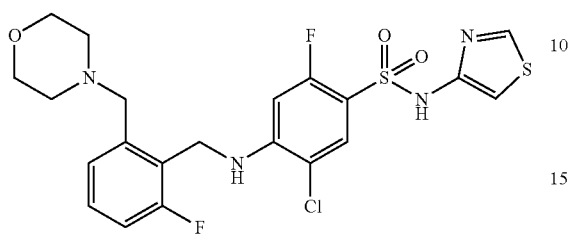

Following the procedure as described for EXAMPLE 249, Step 2 and making non-critical variations as required to replace potassium dimethylaminomethyltrifluoroboronate with potassium (morpholin-4-yl)methyltrifluoroborate, the title compound was obtained as a colorless solid (0.046 g, 26% yield): $^1$H-NMR (300 MHz, DMSO-$d_6$) δ 11.21 (s, 1H), 8.86 (d, J=2.2 Hz, 1H), 7.60 (d, J=7.4 Hz, 1H), 7.34-7.28 (m, 1H), 7.19-7.12 (m, 2H), 6.97-6.90 (m, 2H), 6.41-6.35 (m, 1H), 4.54-4.52 (m, 2H), 3.56-3.53 (m, 6H), 2.37-2.34 (m, 4H); MS (ES+) m/z 515.1 (M+1), 517.1 (M+1).

Example 251

Synthesis of 5-chloro-4-((2-((4,4-difluoropiperidin-1-yl)methyl)-6-fluorobenzyl)amino)-2-fluoro-N-(thiazol-4-yl)benzenesulfonamide

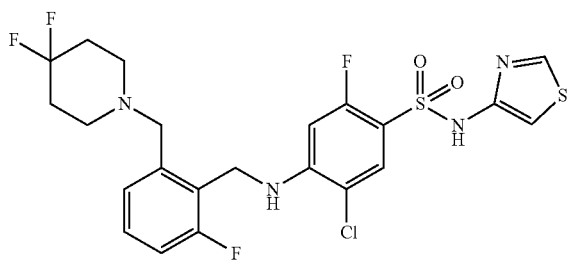 [SMILES: O=S(=O)(Nc1cscn1)c1cc(Cl)c(NCc2c(F)cccc2CN2CCC(F)(F)CC2)cc1F]

Following the procedure as described for EXAMPLE 249, Step 2 and making non-critical variations as required to replace potassium dimethylaminomethyltrifluoroboronate with potassium (4,4-difluoropiperidenyl)methyltrifluoroborate, the title compound was obtained as a colorless solid (0.043 g, 23% yield): $^1$H-NMR (300 MHz, DMSO-$d_6$) δ 11.1 (s, 1H), 8.88 (d, J=2.2 Hz, 1H), 7.61 (d, J=7.4 Hz, 1H), 7.36-7.31 (m, 1H), 7.20-7.15 (m, 2H), 6.99-6.94 (m, 2H), 6.51-6.47 (m, 1H), 4.55-4.52 (m, 2H), 3.65-3.63 (m, 2H), 3.40-3.38 (m, 2H), 2.58-2.43 (m, 2H), 1.99-1.87 (m, 4H); MS (ES+) m/z 549.0 (M+1), 551.0 (M+1).

Example 252

4-((2-((2-azaspiro[3.3]heptan-2-yl)methyl)-6-fluorobenzyl)amino)-2,6-difluoro-N-(thiazol-4-yl)benzenesulfonamide formate

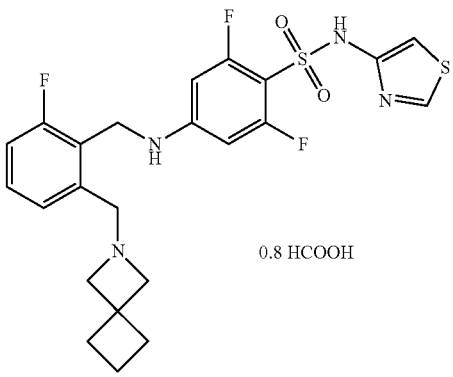 [SMILES: O=S(=O)(Nc1cscn1)c1c(F)cc(NCc2c(F)cccc2CN2CC3(CCC3)C2)cc1F]

0.8 HCOOH

Step 1. Synthesis of 2-((2-azaspiro[3.3]heptan-2-yl)methyl)-6-fluorobenzonitrile

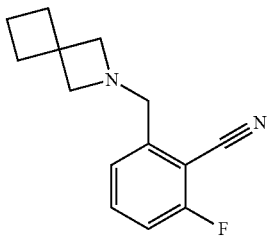 [SMILES: N#Cc1c(F)cccc1CN1CC2(CCC2)C1]

A solution of 2-azaspiro[3.3]heptane (0.250 g, 2.34 mmol), 2-(bromomethyl)-6-fluorobenzonitrile (0.500 g, 2.34 mmol), and N,N-diisopropylethylamine (610 μL, 3.50 mmol) in dichloromethane (10 mL) was stirred at ambient temperature for 18 h. To it was then added saturated ammonium chloride (10 mL) and the mixture was extracted with dichloromethane (3×10 mL). The combined organic phase was washed with brine (10 mL), dried over anhydrous sodium sulfate, and filtered. Concentration of the filtrate in vacuo and purification of the residue by column chromatography, eluting with a gradient of 10 to 80% of ethyl acetate in hexanes, yielded the title compound as a colorless oil (0.413 g, 75% yield); $^1$H-NMR (300 MHz, CDCl$_3$) δ 7.53 (td, J=8.1, 5.8 Hz, 1H), 7.33 (d, J=7.8 Hz, 1H), 7.07 (t, J=8.5 Hz, 1H), 3.77 (s, 2H), 3.28 (s, 4H), 2.12 (t, J=7.5 Hz, 4H), 1.85-1.75 (m, 2H).

Step 2. Synthesis of (2-((2-azaspiro[3.3]heptan-2-yl)methyl)-6-fluorophenyl)methanamine

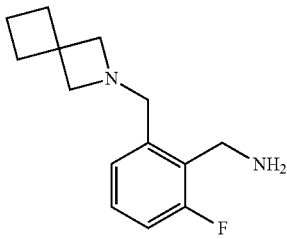 [SMILES: NCc1c(F)cccc1CN1CC2(CCC2)C1]

To a solution of 2-((2-azaspiro[3.3]heptan-2-yl)methyl)-6-fluorobenzonitrile (0.413 g, 1.75 mmol) in anhydrous tetrahydrofuran (20 mL) at 0° C. was added a 1.0 M solution of lithium aluminum hydride in tetrahydrofuran (5.3 mL, 5.3 mmol). The reaction mixture was stirred for 4 h. To it was then added sodium sulfate decahydrate (2.5 g) in portions at 0° C. The mixture was allowed to warm to ambient temperature, stirred for 30 minutes, and then filtered. The filter cake was washed with ethyl acetate (50 mL). The combined filtrate was concentrated in vacuo to afford the title compound as a yellow oil; $^1$H-NMR (300 MHz, CDCl$_3$): δ 7.16-7.09 (m, 1H), 6.99-6.93 (m, 2H), 3.84-3.81 (m, 2H), 3.69-3.66 (m, 1H), 3.58 (d, J=1.2 Hz, 2H), 3.11 (d, J=1.8 Hz, 3H), 2.29-2.17 (m, 2H), 2.05 (t, J=7.5 Hz, 4H), 1.82-1.74 (m, 2H).

Step 3. Synthesis of 4-((2-((2-azaspiro[3.3]heptan-2-yl)methyl)-6-fluorobenzyl)amino)-2,6-difluoro-N-(thiazol-4-yl)benzenesulfonamide formate

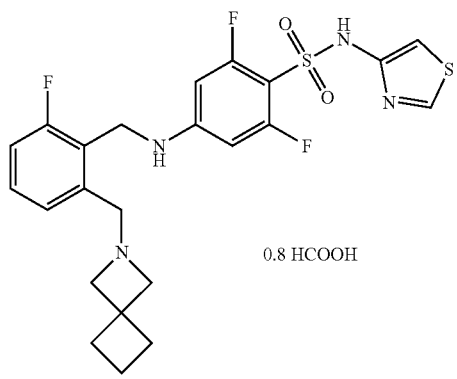 [SMILES: O=S(=O)(Nc1cscn1)c1c(F)cc(NCc2c(F)cccc2CN2CC3(CCC3)C2)cc1F]

To a solution of (2-((2-azaspiro[3.3]heptan-2-yl)methyl)-6-fluorophenyl)methanamine (0.269 g, 1.14 mmol) and tert-butyl thiazol-4-yl((2,4,6-trifluorophenyl)sulfonyl)carbamate (0.449 g, 1.14 mmol) in anhydrous dimethyl sulfoxide (5 mL) was added N,N-diisopropylethylamine (0.5 mL, 3 mmol) and the mixture was stirred at ambient temperature for 12 h. To it was then added water (10 mL) and the mixture extracted with ethyl acetate (3×10 mL). The combined organic phase was washed with brine (20 mL), dried over anhydrous sodium sulfate, and filtered. Concentration of the filtrate in vacuo provided a residue, which was dissolved in dichloromethane (10 mL). To it was added trifluoroacetic acid (2 mL) and the reaction mixture was stirred at ambient temperature for 4 h. The mixture was concentrated in vacuo and the residue was purified by reverse phase preparative HPLC, eluting with acetonitrile in water containing 0.5% formic acid eluent, to provide the title compound as a colorless solid (0.099 g, 17% yield): $^1$H-NMR (300 MHz, DMSO-d$_6$) δ 8.89 (d, J=2.2 Hz, 1H), 8.15 (s, 0.8H), 7.36-7.28 (m, 2H), 7.18-7.10 (m, 2H), 6.88 (d, J=2.2 Hz, 1H), 6.34 (d, J=12.8 Hz, 2H), 4.30 (s, 2H), 3.56 (s, 2H), 3.10 (s, 4H), 2.00 (t, J=7.4 Hz, 4H), 1.77-1.67 (m, 2H), NH not observed; MS (ES+) n/z 509.2 (M+1).

Example 253

Synthesis of (S)-5-chloro-4-((1-(3-((dimethylamino)methyl)phenyl)ethyl)amino)-2-fluoro-N-(thiazol-4-yl)benzenesulfonamide formate

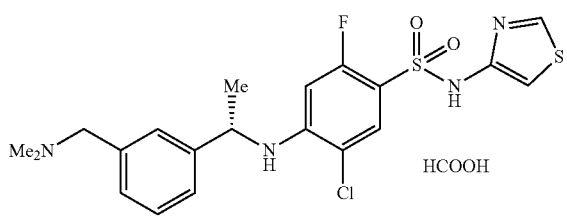 [SMILES: C[C@H](Nc1cc(F)c(S(=O)(=O)Nc2cscn2)cc1Cl)c1cccc(CN(C)C)c1 ; "HCOOH"]

Step 1. Preparation of tert-butyl (S)-((4-((1-(3-bromophenyl)ethyl)amino)-5-chloro-2-fluorophenyl)sulfonyl)(thiazol-4-yl)carbamate

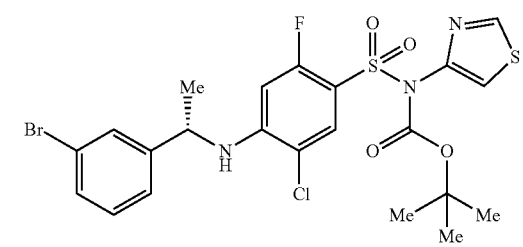 [SMILES: C[C@H](Nc1cc(F)c(S(=O)(=O)N(C(=O)OC(C)(C)C)c2cscn2)cc1Cl)c1cccc(Br)c1]

A solution of tert-butyl ((5-chloro-2,4-difluorophenyl)sulfonyl)(thiazol-4-yl)carbamate (0.500 g, 2.44 mmol), (S)-1-(3-bromophenyl)ethan-1-amine (0.244 g, 2.44 mmol), and triethylamine (0.65 mL, 9.8 mmol) in anhydrous dimethyl sulfoxide (10 mL) was stirred at ambient temperature for 3 h. Saturated ammonium chloride (10 mL) was added and the mixture was extracted with ethyl acetate (3×10 mL). The combined organic phases were washed with brine (10 mL), dried over anhydrous sodium sulfate, and filtered. Concentration of the filtrate in vacuo and purification of the residue by column chromatography, eluting with a gradient of 5 to 60% of ethyl acetate in hexanes, afforded the title compound as a colorless solid (0.504 g, 70% yield): MS (ES+) m/z 592.0 (M+1), 594.0 (M+1).

Step 2. Preparation of (S)-5-chloro-4-((1-(3-((dimethylamino)methyl)phenyl)-ethyl)amino)-2-fluoro-N-(thiazol-4-yl)benzenesulfonamide formate

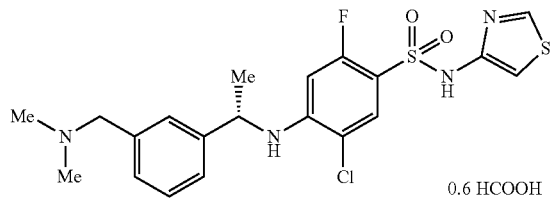 [SMILES: C[C@H](Nc1cc(F)c(S(=O)(=O)Nc2cscn2)cc1Cl)c1cccc(CN(C)C)c1 ; "0.6 HCOOH"]

0.6 HCOOH

To a mixture of tert-butyl (S)-((4-((1-(3-bromophenyl)ethyl)amino)-5-chloro-2-fluorophenyl)sulfonyl)(thiazol-4-yl)carbamate (0.200 g, 0.338 mmol), potassium dimethylaminomethyltrifluoroboronate (0.067 g, 0.41 mmol), cesium carbonate (0.330 g, 1.01 mmol), palladium acetate (0.008 g, 0.03 mmol), and di(1-adamantyl)-n-butylphosphine (0.024 g, 0.068 mmol) was added a solution of water (0.53 mL) and 1,4-dioxane (2.6 mL), which was degassed by purging with nitrogen. The reaction mixture was heated to 85° C. for 18 h. Upon cooling to ambient temperature, the mixture was filtered through a pad of Celite. The filter cake was washed with ethyl acetate (10 mL), and the combined filtrate concentrated in vacuo. To the residue was added dichloromethane (5 mL) and trifluoroacetic acid (1 mL), and the mixture was stirred at ambient temperature for 5 h. The mixture was then concentrated in vacuo and the residue purified by column chromatography, eluting with a gradient of 0 to 20% methanol in dichloromethane. Further purification by preparative reverse phase HPLC, using acetonitrile in water containing 0.1% formic acid as eluent, afforded the title compound as a colorless solid (0.035 g, 22% yield): $^1$H-NMR (300 MHz, DMSO-$d_6$) δ 8.82 (d, J=2.1 Hz, 1H), 8.20 (s, 0.6H), 7.57 (d, J=7.4 Hz, 1H), 7.33-7.25 (m, 3H), 7.13-7.10 (m, 1H), 6.82 (d, J=2.1 Hz, 1H), 6.59-6.56 (m, 1H), 6.37 (d, J=12.9 Hz, 1H), 4.75-4.59 (m, 1H), 3.37 (s, 2H), 2.08 (s, 6H), 1.51 (d, J=6.9 Hz, 3H), NH and COOH not observed; MS (ES+) m/z 469.1 (M+1), 471.1 (M+1).

Example 254

Synthesis of (R)-5-chloro-4-((1-(3-((dimethylamino)methyl)phenyl)ethyl)amino)-2-fluoro-N-(thiazol-4-yl)benzenesulfonamide formate

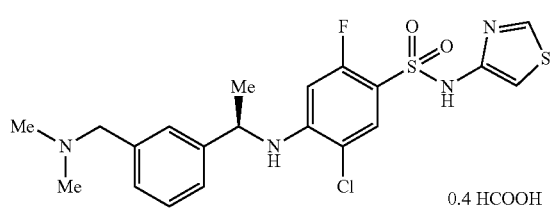 [SMILES: C[C@@H](Nc1cc(F)c(S(=O)(=O)Nc2cscn2)cc1Cl)c1cccc(CN(C)C)c1 ; "0.4 HCOOH"]

0.4 HCOOH

Step 1. Preparation of tert-butyl (R)-((4-((1-(3-bromophenyl)ethyl)amino)-5-chloro-2-fluorophenyl)sulfonyl)(thiazol-4-yl)carbamate

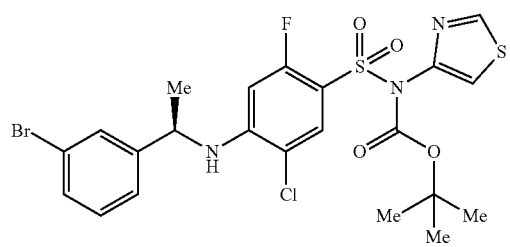 [SMILES: C[C@@H](Nc1cc(F)c(S(=O)(=O)N(C(=O)OC(C)(C)C)c2cscn2)cc1Cl)c1cccc(Br)c1]

Following the procedure as described for EXAMPLE 253, Step 1 and making non-critical variations as required to replace (S)-1-(3-bromophenyl)ethan-1-amine with (R)-1-(3-bromophenyl)ethan-1-amine, the title compound was obtained as a colorless solid (0.978 g, 68% yield): MS (ES+) m/z 592.0 (M+1), 594.0 (M+1).

Step 2. Preparation of (R)-5-chloro-4-((1-(3-((dimethylamino)methyl)phenyl)ethyl)amino)-2-fluoro-N-(thiazol-4-yl)benzenesulfonamide formate

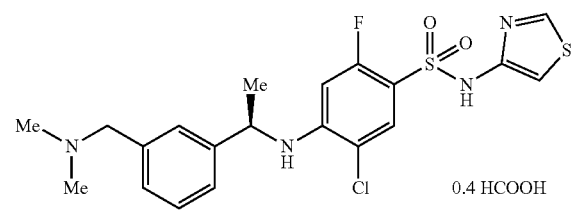 [SMILES: C[C@@H](Nc1cc(F)c(S(=O)(=O)Nc2cscn2)cc1Cl)c1cccc(CN(C)C)c1]

0.4 HCOOH

Following the procedure as described for EXAMPLE 253, Step 2 and making non-critical variations as required to replace tert-butyl (S)-((4-((1-(3-bromophenyl)ethyl)amino)-5-chloro-2-fluorophenyl)sulfonyl)(thiazol-4-yl)carbamate with tert-butyl (R)-((4-((1-(3-bromophenyl)ethyl)amino)-5-chloro-2-fluorophenyl)sulfonyl)(thiazol-4-yl)carbamate, the title compound was obtained as a colorless solid (0.023 g, 15% yield): $^1$H-NMR (300 MHz, DMSO-$d_6$) δ 8.83 (d, J=2.2 Hz, 1H), 8.17 (s, 0.4H), 7.57 (d, J=7.4 Hz, 1H), 7.33-7.26 (m, 3H), 7.13-7.10 (m, 1H), 6.87 (d, J=2.2 Hz, 1H), 6.61-6.59 (m, 1H), 6.38 (d, J=13.5 Hz, 1H), 4.73-4.66 (m, 1H), 3.38 (s, 2H), 2.09 (s, 6H), 1.52-1.50 (d, J=6.3 Hz, 3H), NH and COOH not observed; MS (ES+) m/z 469.1 (M+1), 471.1 (M+1).

Example 255

Synthesis of (S)-4-((1-(5-(azetidin-1-ylmethyl)-2-fluorophenyl)ethyl)amino)-5-chloro-2-fluoro-N-(thiazol-4-yl)benzenesulfonamide

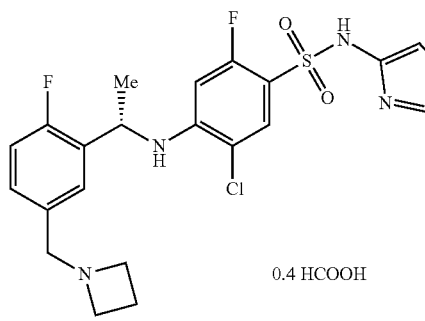

0.4 HCOOH

Step 1. Preparation of (S)-tert-butyl (5-chloro-2-fluoro-4-((1-(2-fluoro-5-vinylphenyl)ethyl)amino)phenyl)sulfonyl(thiazol-4-yl)carbamate

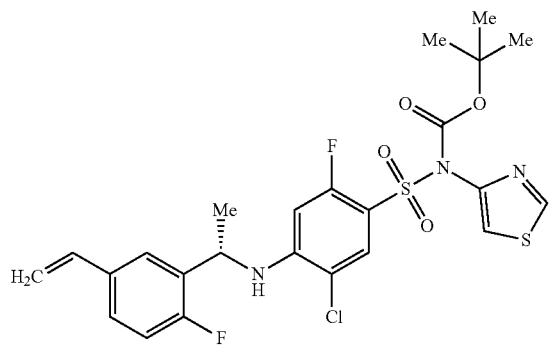 [SMILES: C=Cc1ccc(F)c([C@H](C)Nc2cc(F)c(S(=O)(=O)N(C(=O)OC(C)(C)C)c3cscn3)cc2Cl)c1]

To a solution of (S)-tert-butyl (4-((1-(5-bromo-2-fluorophenyl)ethyl)amino)-5-chloro-2-fluorophenyl)sulfonyl(thiazol-4-yl)carbamate (0.80 g, 1.3 mmol), vinylboronic acid pinacol ester (0.40 g, 2.6 mmol) and sodium carbonate (0.56 g, 5.2 mmol) in N,N-dimethylformamide (10 mL) and water (2 mL) was added tetrakis(triphenylphosphine)palladium(0) (0.30 g, 0.26 mmol). The reaction mixture was stirred at 80° C. for 12 h. After cooling to ambient temperature, the mixture was diluted with water (30 mL) and extracted with ethyl acetate (3×30 mL). The combined organic layer was washed with brine (20 mL), dried over anhydrous sodium sulfate, and filtered. Concentration of the filtrate in vacuo and purification of the residue by column chromatography, eluting with a gradient of 10 to 33% of ethyl acetate in petroleum ether, afforded the title compound as a colorless oil (0.65 g, 89% yield): $^1$H NMR (400 MHz, CDCl$_3$) δ 8.79-8.76 (m, 1H), 7.98 (d, J=7.2 Hz, 1H), 7.48 (d, J=2.4 Hz, 1H), 7.38-7.32 (m, 1H), 7.23 (dd, J=7.2, 2.4 Hz, 1H), 7.11-7.05 (m, 1H), 6.63 (dd, J=17.6, 10.8 Hz, 1H), 6.22 (d, J=12.4 Hz, 1H), 5.64 (d, J=17.6 Hz, 1H), 5.35 (d, J=5.6 Hz, 1H), 5.24 (d, J=10.8 Hz, 1H), 4.90-4.82 (m, 1H), 1.68 (d, J=6.8 Hz, 3H), 1.35 (s, 9H); MS (ES+) m/z 456.0 (M−99), 458.0 (M−99).

Step 2. Preparation of (S)-tert-butyl (5-chloro-2-fluoro-4-((1-(2-fluoro-5-formylphenyl)ethyl)amino)phenyl)sulfonyl(thiazol-4-yl)carbamate

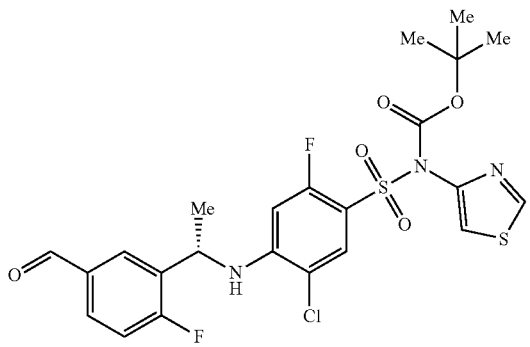 [SMILES: C[C@H](Nc1cc(F)c(S(=O)(=O)N(C(=O)OC(C)(C)C)c2cscn2)cc1Cl)c1cc(C=O)ccc1F]

A solution of (S)-tert-butyl(5-chloro-2-fluoro-4-((1-(2-fluoro-5-vinylphenyl)ethyl)amino)phenyl) sulfonyl (thiazol-4-yl)carbamate (0.65 g, 1.2 mmol) in dichloromethane (10 mL) was sparged with ozone at −78° C. until the color of the reaction mixture turned blue. The stream of ozone was stopped, and triphenylphosphine (0.61 g, 2.3 mmol) was then added to the reaction mixture in portions at −78° C. The mixture was then allowed to warm to ambient temperature and stirred for 2 h. Concentration in vacuo and purification of the residue by preparative thin layer chromatography, eluting with a gradient of 33% of ethyl acetate in petroleum ether, afforded the title compound as a colorless solid (0.15 g, 23% yield): $^1$H NMR (400 MHz, CDCl$_3$) δ 9.93 (s, 1H), 8.76 (d, J=2.0 Hz, 1H), 7.98 (d, J=6.8 Hz, 1H), 7.89-7.80 (m, 2H), 7.47 (d, J=2.0 Hz, 1H), 7.31 (d, J=9.6 Hz, 1H), 6.13 (d, J=12.0 Hz, 1H), 5.35 (d, J=5.6 Hz, 1H), 4.99-4.86 (m, 1H), 1.70 (d, J=6.8 Hz, 3H), 1.34 (s, 9H); MS (ES+) m/z 458.0 (M−99), 460.0 (M−99).

Step 3. Preparation of (S)-tert-butyl (4-((1-(5-(azetidin-1-ylmethyl)-2-fluorophenyl)ethyl)amino)-5-chloro-2-fluorophenyl)sulfonyl(thiazol-4-yl)carbamate

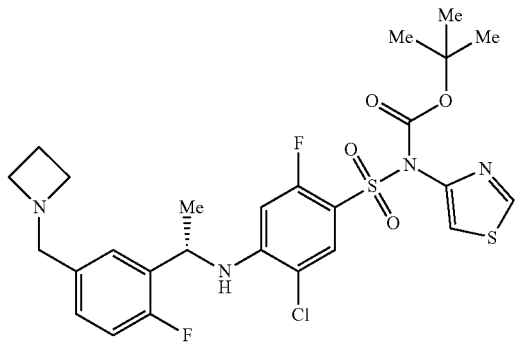 [SMILES: C[C@H](Nc1cc(F)c(S(=O)(=O)N(C(=O)OC(C)(C)C)c2cscn2)cc1Cl)c1cc(CN2CCC2)ccc1F]

To a solution of (S)-tert-butyl(5-chloro-2-fluoro-4-((1-(2-fluoro-5-formylphenyl)ethyl)amino)phenyl) sulfonyl(thiazol-4-yl)carbamate (0.070 g, 0.13 mmol), azetidine hydrochloride (0.023 g, 0.25 mmol) and acetic acid (0.0015 g, 0.025 mmol) in dichloromethane (3 mL) was added sodium triacetoxyborohydride (0.053 g, 0.25 mmol) in one portion.

The mixture was stirred at ambient temperature for 2 h. The mixture was diluted with water (30 mL) and extracted with dichloromethane (3×20 mL). The combined organic layer was washed with brine (10 mL), dried over anhydrous sodium sulfate, and filtered. Concentration of the filtrate in vacuo afforded the title compound as a colorless oil (0.07 g, 90% yield): MS (ES+) m/z 599.0 (M+1), 601.1 (M+1).

Step 4. Synthesis of (S)-4-((1-(5-(azetidin-1-ylmethyl)-2-fluorophenyl) ethyl)amino)-5-chloro-2-fluoro-N-(thiazol-4-yl)benzenesulfonamide formate

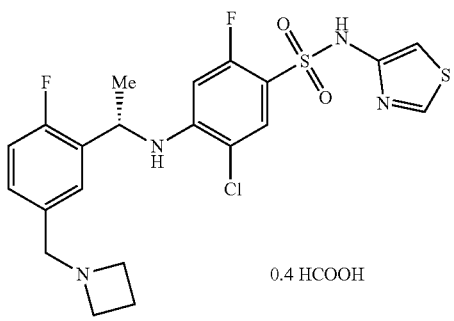 [SMILES: C[C@H](Nc1cc(F)c(S(=O)(=O)Nc2cscn2)cc1Cl)c1cc(CN2CCC2)ccc1F]

0.4 HCOOH

To (S)-tert-butyl(4-((1-(5-(azetidin-1-ylmethyl)-2-fluorophenyl)ethyl)amino)-5-chloro-2-fluorophenyl)sulfonyl(thiazol-4-yl)carbamate (0.070 g, 0.12 mmol) was added a 4.0 M solution of hydrogen chloride in 1,4-dioxane (5 mL) and the reaction mixture was stirred at ambient temperature for 30 minutes. The mixture was concentrated in vacuo and the residue was purified by preparative reverse phase HPLC, using acetonitrile in water containing 0.225% formic acid as the eluent, to afford the title compound as a colorless solid (0.0317 g, 54% yield): $^1$H NMR (400 MHz, CDCl$_3$) δ 8.58 (d, J=2.0 Hz, 1H), 8.51 (s, 0.4H), 7.75 (d, J=7.2 Hz, 1H), 7.31-7.29 (m, 1H), 7.26-7.19 (m, 1H), 7.09-7.03 (m, 1H), 6.92 (d, J=2.0 Hz, 1H), 6.10 (d, J=12.4 Hz, 1H), 5.30 (d, J=6.0 Hz, 1H), 4.76 (quin, J=6.4 Hz, 1H), 3.78 (q, J=12.8 Hz, 2H), 3.49 (t, J=7.6 Hz, 4H), 2.25 (quin, J=7.6 Hz, 2H), 1.63 (d, J=6.8 Hz, 3H), NH and COOH not observed; MS (ES+) m/z 499.1 (M+1).

Example 256

Synthesis of (S)-5-chloro-2-fluoro-4-((1-(2-fluoro-5-(piperidin-1-ylmethyl)phenyl)ethyl)amino)-N-(thiazol-4-yl)benzenesulfonamide formate

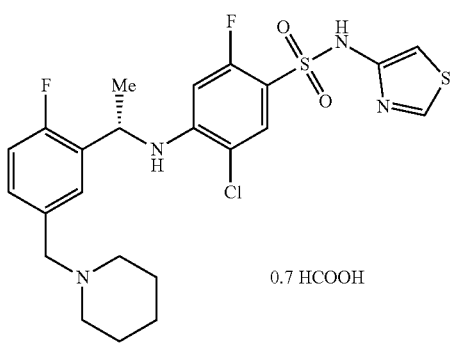 [SMILES: C[C@H](Nc1cc(F)c(S(=O)(=O)Nc2cscn2)cc1Cl)c1cc(CN2CCCCC2)ccc1F]

0.7 HCOOH

Step 1. Preparation of (S)-tert-butyl(5-chloro-2-fluoro-4-((1-(2-fluoro-5-(piperidin-1-ylmethyl) phenyl)ethyl)amino)phenyl)sulfonyl(thiazol-4-yl)carbamate

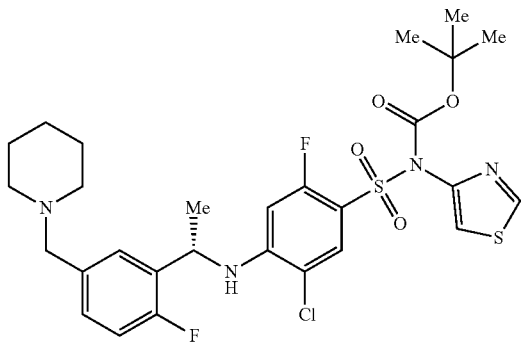 [SMILES: C[C@H](Nc1cc(F)c(S(=O)(=O)N(C(=O)OC(C)(C)C)c2cscn2)cc1Cl)c1cc(CN2CCCCC2)ccc1F]

To a solution of (S)-tert-butyl(5-chloro-2-fluoro-4-((1-(2-fluoro-5-formylphenyl)ethyl)amino)phenyl) sulfonyl(thiazol-4-yl)carbamate (0.070 g, 0.13 mmol), piperidine (0.0214 g, 0.251 mmol) and trifluoroacetic acid (0.0043 g, 0.038 mmol) in tetrahydrofuran (2 mL) was added sodium triacetoxyborohydride (0.0532 g, 0.251 mmol) in one portion. The mixture was stirred at ambient temperature for 12 h. The mixture was diluted with water (30 mL) and extracted with ethyl acetate (3×30 mL). The combined organic layers were washed with brine (20 mL), dried over anhydrous sodium sulfate, and filtered. Concentration in vacuo provided the title compound as a colorless oil (0.08 g, 98% yield): MS (ES+) m/z 527.1 (M−99), 529.0 (M−99).

Step 2. Preparation of (S)-5-chloro-2-fluoro-4-((1-(2-fluoro-5-(piperidin-1-ylmethyl)phenyl)ethyl) amino)-N-(thiazol-4-yl)benzenesulfonamide formate

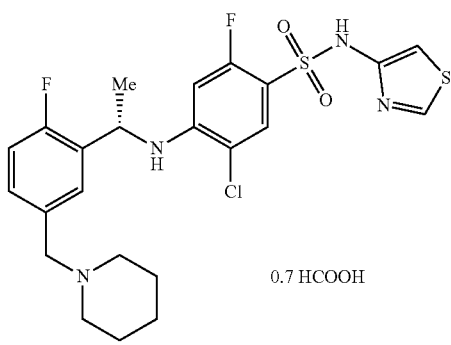 [SMILES: C[C@H](Nc1cc(F)c(S(=O)(=O)Nc2cscn2)cc1Cl)c1cc(CN2CCCCC2)ccc1F]

0.7 HCOOH

To a solution of (S)-tert-butyl(5-chloro-2-fluoro-4-((1-(2-fluoro-5-(piperidin-1-ylmethyl)phenyl)ethyl)amino)phenyl) sulfonyl(thiazol-4-yl)carbamate (0.070 g, 0.112 mmol) in dichloromethane (3 mL) was added trifluoroacetic acid (0.77 g, 6.8 mmol). The reaction mixture was stirred at ambient temperature for 30 minutes and then concentrated in vacuo. The residue was purified by preparative reverse phase HPLC, using acetonitrile in water containing 0.225% formic acid as the eluent, to afford the title compound as a colorless solid (0.018 g, 30% yield): $^1$H NMR (400 MHz, CDCl$_3$) δ 8.64 (d, J=2.0 Hz, 1H), 8.49 (s, 0.7H), 7.76 (d, J=7.2 Hz, 1H), 7.41 (d, J=5.6 Hz, 1H), 7.34-7.29 (m, 1H), 7.08 (dd, J=9.6, 8.4 Hz, 1H), 6.91 (d, J=2.0 Hz, 1H), 6.08 (d, J=12.4 Hz, 1H), 5.34 (d, J=6.0 Hz, 1H), 4.83-4.74 (m, 1H), 3.96-3.77 (m, 2H), 2.71 (s, 4H), 1.80-1.71 (m, 4H), 1.65 (d, J=6.4 Hz, 3H), 1.51 (s, 2H), NH and COOH not observed; MS (ES+) m/z 527.1 (M+1).

Example 257

Synthesis of (S)-4-((1-(5-(2-(azetidin-1-yl)ethyl)-2-fluorophenyl)ethyl)amino)-5-chloro-2-fluoro-N-(thiazol-4-yl)benzenesulfonamide formate

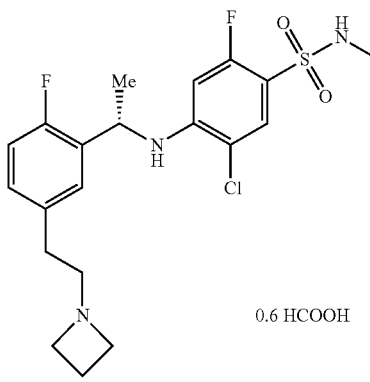

To a solution of (S)-5-chloro-2-fluoro-4-((1-(2-fluoro-5-(2-oxoethyl)phenyl)ethyl)amino)-N-(thiazol-4-yl) benzenesulfonamide (0.080 g, 0.17 mmol), azetidine hydrochloride (0.032 g, 0.34 mmol) and acetic acid (0.015 g, 0.25 mmol) in methanol (3 mL) was added sodium cyanoborohydride (0.021 g, 0.34 mmol). The reaction mixture was stirred at ambient temperature for 12 h and then concentrated in vacuo. The residue was purified by preparative reverse phase HPLC, using acetonitrile in water containing 0.225% formic acid as eluent, to afford the title compound as a colorless solid (0.022 g, 25% yield): $^1$H NMR (400 MHz, CDCl$_3$) δ 8.61 (d, J=2.0 Hz, 1H), 8.58 (s, 0.6H), 7.77 (d, J=7.2 Hz, 1H), 7.16-7.10 (m, 2H), 7.07-6.99 (m, 1H), 6.90 (d, J=2.0 Hz, 1H), 6.10 (d, J=12.4 Hz, 1H), 5.31 (d, J=5.6 Hz, 1H), 4.75 (q, J=6.40 Hz, 1H), 3.82-3.72 (m, 4H), 3.10 (t, J=7.6 Hz, 2H), 2.85 (t, J=7.6 Hz, 2H), 2.38 (q, J=8.0 Hz, 2H), 1.63 (d, J=6.8 Hz, 3H), NH and COOH not observed.

Example 258

Synthesis of 4-((2-(azetidin-1-ylmethyl)benzyl)amino)-5-chloro-2-fluoro-N-(isoxazol-3-yl)benzenesulfonamide

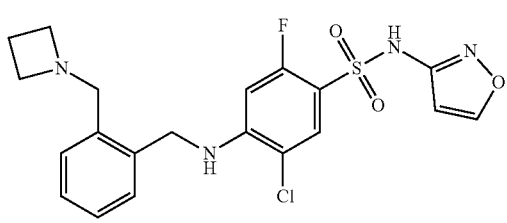 [SMILES: O=S(=O)(Nc1ccon1)c1cc(Cl)c(NCc2ccccc2CN2CCC2)cc1F]

Step 1. Preparation of 5-chloro-2,4-difluoro-N-isoxazol-3-yl-N-(2-trimethylsilylethoxymethyl)-benzenesulfonamide

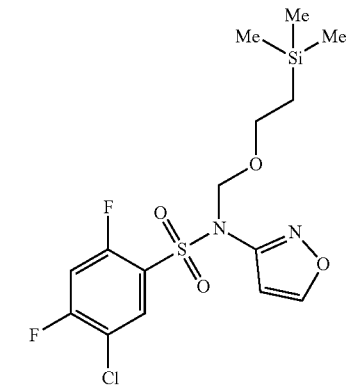 [SMILES: C[Si](C)(C)CCOCN(c1ccon1)S(=O)(=O)c1cc(Cl)c(F)cc1F]

To a solution of 5-chloro-2,4-difluoro-N-(isoxazol-3-yl) benzenesulfonamide (1.00 g, 3.39 mmol) and potassium carbonate (0.937 g, 6.78 mmol) in anhydrous N,N-dimethylformamide (10 mL) was added 2-(trimethylsilyl)ethoxymethyl chloride (0.678 g, 4.07 mmol) at 0° C. The reaction mixture was allowed to warm to ambient temperature and was stirred for 1 h. The mixture was poured into ice-water (50 mL) and the aqueous phase was extracted with ethyl acetate (3×30 mL). The combined organic phase was washed with brine (3×30 mL), dried over anhydrous sodium sulfate, and filtered. Concentration of the filtrate in vacuo and purification of the residue by column chromatography, eluting with 10% of ethyl acetate in petroleum ether, afforded the title compound as a colorless oil (1.40 g, 97% yield): $^1$H NMR (400 MHz, CDCl$_3$) δ 8.30 (d, J=1.8 Hz, 1H), 8.06 (t, J=7.4 Hz, 1H), 7.03 (dd, J=9.2, 8.2 Hz, 1H), 6.61 (d, J=1.8 Hz, 1H), 5.40 (s, 2H), 3.75-3.66 (m, 2H), 0.94-0.85 (m, 2H), 0.00 (s, 9H).

Step 2. Preparation of 4-((2-(azetidin-1-ylmethyl) benzyl)amino)-5-chloro-2-fluoro-N-(isoxazol-3-yl)-N-((2-(trimethylsilyl)ethoxy)methyl)benzenesulfonamide

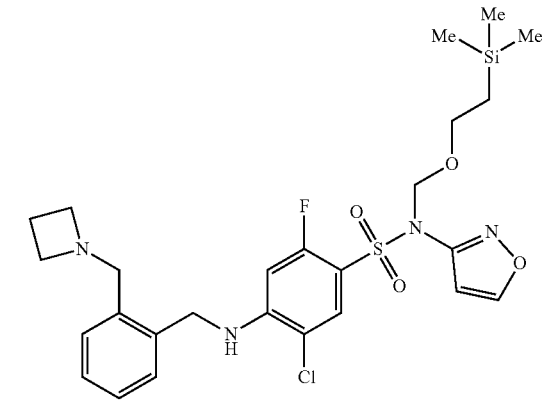 [SMILES: C[Si](C)(C)CCOCN(c1ccon1)S(=O)(=O)c1cc(Cl)c(NCc2ccccc2CN2CCC2)cc1F]

A mixture of (2-(azetidin-1-ylmethyl)phenyl)methanamine (0.103 g, 0.588 mmol), 5-chloro-2,4-difluoro-N- isoxazol-3-yl-N-(2-trimethylsilylethoxymethyl)benzenesulfonamide (0.250 g, 0.588 mmol) and potassium carbonate (0.243 g, 1.77 mmol) in anhydrous N,N-dimethylformamide (5 mL) was stirred at ambient temperature for 12 h. To it was then added water (10 mL) and the mixture was extracted with ethyl acetate (3×10 mL). The combined organic layers were washed with brine (3×10 mL), dried over anhydrous sodium sulfate, and filtered. Concentration of the filtrate under reduced pressure afforded the title compound as a yellow oil (0.300 g, 71% yield): MS (ES+) m/z 581.4 (M+1), 583.4 (M+1).

Step 2. Preparation of 4-((2-(azetidin-1-ylmethyl)benzyl)amino)-5-chloro-2-fluoro-N-(isoxazol-3-yl)benzenesulfonamide

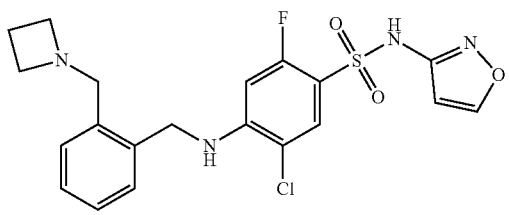 [SMILES: O=S(=O)(Nc1ccon1)c1cc(Cl)c(NCc2ccccc2CN2CCC2)cc1F]

To a solution of 4-((2-(azetidin-1-ylmethyl)benzyl)amino)-5-chloro-2-fluoro-N-(isoxazol-3-yl)-N-((2-(trimethylsilyl)ethoxy)methyl)benzenesulfonamide (0.300 g, 0.516 mmol) in 1,4-dioxane (2 mL) was added a 4.0 M solution of hydrogen chloride in 1,4-dioxane (6 mL) and the mixture was stirred at ambient temperature for 12 h. The reaction mixture was concentrated in vacuo. The residue was purified by preparative reverse phase HPLC, using acetonitrile in water containing 0.225% formic acid as eluent, to afford the title compound as a colorless solid (0.066 g, 28% yield): $^1$H NMR (400 MHz, CDCl$_3$) δ 8.21 (d, J=1.8 Hz, 1H), 7.72 (d, J=7.2 Hz, 1H), 7.39-7.32 (m, 4H), 6.54-6.48 (m, 2H), 4.52 (s, 2H), 3.93 (s, 2H), 3.63 (t, J=7.4 Hz, 4H), 2.35-2.28 (m, 2H), exchangeable protons not observed; MS (ES+) m/z 451.0 (M+1), 453.0 (M+1).

Example 259

Synthesis of 4-((2-(azetidin-1-ylmethyl)benzyl)amino)-2,6-difluoro-N-(isoxazol-3-yl)benzenesulfonamide

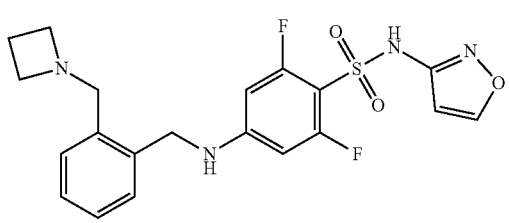 [SMILES: O=S(=O)(Nc1ccon1)c1c(F)cc(NCc2ccccc2CN2CCC2)cc1F]

Step 1. Preparation of 4-((2-(azetidin-1-ylmethyl)benzyl) amino)-2,6-difluoro-N-(isoxazol-3-yl)-N-((2-(trimethylsilyl)ethoxy)methyl)benzenesulfonamide

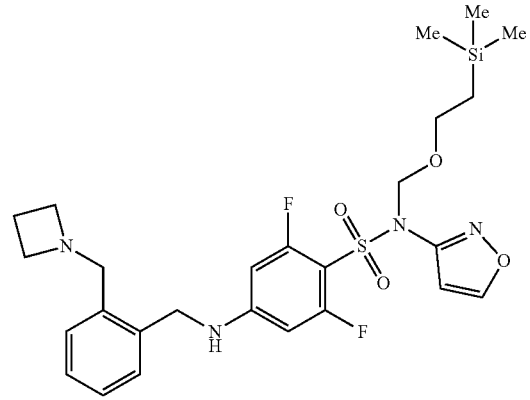 [SMILES: C[Si](C)(C)CCOCN(c1ccon1)S(=O)(=O)c1c(F)cc(NCc2ccccc2CN2CCC2)cc1F]

A mixture of (2-(azetidin-1-ylmethyl)phenyl)methanamine (0.200 g, 1.13 mmol), 2,4,6-trifluoro-N-(isoxazol-3-yl)-N-((2-(trimethylsilyl)ethoxy)methyl)benzenesulfonamide (0.461 g, 1.13 mmol) and potassium carbonate (0.468 g, 3.39 mmol) in N,N-dimethylformamide (5 mL) was stirred at ambient temperature for 12 h. The mixture was diluted with water (30 mL) and extracted with ethyl acetate (3×10 mL). The combined organic fractions were washed with brine (3×10 mL), dried over anhydrous sodium sulfate, and filtered. Concentration of the filtrate in vacuo and purification of the residue by preparative thin layer chromatography, eluting with 25% of ethyl acetate in petroleum ether, afforded the title compound as a yellow oil (0.130 g, 20% yield): $^1$H NMR (400 MHz, CDCl$_3$) δ 8.24 (d, J=1.6 Hz, 1H), 7.36-7.27 (m, 4H), 6.69-6.65 (m, 1H), 6.32-6.20 (m, 2H), 5.46 (s, 2H), 4.33 (s, 2H), 3.88 (s, 2H), 3.77-3.70 (m, 2H), 3.61 (s, 4H), 2.37-2.24 (m, 2H), 0.98-0.91 (m, 2H), 0.00 (s, 9H), NH not observed; MS (ES+) m/z 565.1 (M+1).

Step 2. Synthesis of 4-((2-(azetidin-1-ylmethyl)benzyl)amino)-2,6-difluoro-N-(isoxazol-3-yl)benzenesulfonamide

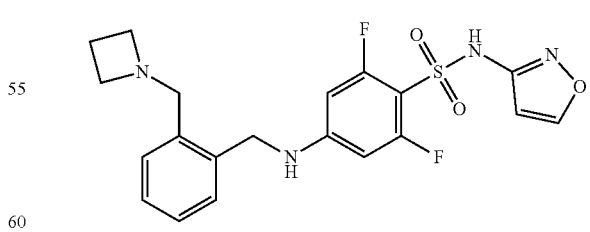

To a solution of 4-((2-(azetidin-1-ylmethyl)benzyl)amino)-2,6-difluoro-N-(isoxazol-3-yl)-N-((2-(trimethylsilyl)ethoxy)methyl)benzenesulfonamide (0.130 g, 0.230 mmol) in 1,4-dioxane (2 mL) was added a 4.0 M solution of hydrogen chloride in 1,4-dioxane (2 mL) and the mixture was stirred at ambient temperature for 4 h. The reaction mixture was concentrated under reduced pressure. The obtained residue was purified by preparative reverse-phase HPLC, using acetonitrile in water containing 0.225% formic acid as eluent, to afford the title compound as a colorless solid (0.021 g, 21% yield): ¹H NMR (400 MHz, DMSO-d₆) δ 8.39 (s, 1H), 7.33-7.19 (m, 4H), 6.27 (d, J=12.4 Hz, 2H), 6.21 (s, 1H), 4.37 (s, 2H), 3.69 (s, 2H), 3.28-3.25 (m, 4H), 2.10-1.99 (m, 2H), exchangeable protons not observed; MS (ES+) m/z 435.0 (M+1).

Example 260

Synthesis of 4-((2-(azetidin-1-ylmethyl)-6-fluorobenzyl)amino)-5-chloro-2-fluoro-N-(pyridazin-3-yl)benzenesulfonamide

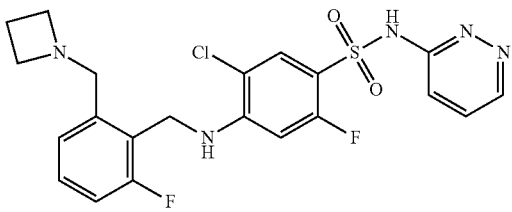 [SMILES: O=S(=O)(Nc1cccnn1)c1cc(Cl)c(NCc2c(F)cccc2CN2CCC2)cc1F]

Step 1. Preparation of 5-chloro-2,4-difluoro-N-(pyridazin-3-yl)benzenesulfonamide

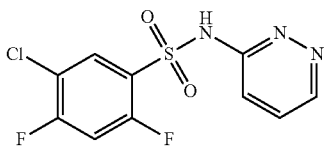 [SMILES: O=S(=O)(Nc1cccnn1)c1cc(Cl)c(F)cc1F]

To a solution of pyridazin-3-amine (1.00 g, 10.5 mmol) in acetonitrile (15 mL) was added 1,4-diazabicyclo[2.2.2]octane (2.36 g, 21.0 mmol) and 5-chloro-2,4-difluorobenzenesulfonyl chloride (3.12 g, 12.6 mmol,). The mixture was stirred at ambient temperature for 12 h and was then concentrated in vacuo. The residue was purified by preparative reverse phase HPLC, using acetonitrile in water containing 0.225% formic acid as eluent, to afford the title compound as a yellow solid (0.400 g, 12% yield): ¹H NMR (400 MHz, CDCl₃) δ 8.19 (dd, J=4.0, 1.6 Hz, 1H), 8.14 (t, J=7.6 Hz, 1H), 7.45 (dd, J=9.4, 4.0 Hz, 1H), 7.33 (dd, J=9.4, 1.4 Hz, 1H), 7.06-6.99 (m, 1H), NH not observed.

Step 2. Preparation of 5-chloro-2,4-difluoro-N-(pyridazin-3-yl)-N-((2-(trimethylsilyl)ethoxy)methyl)benzenesulfonamide

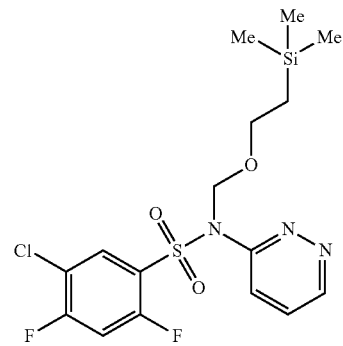 [SMILES: C[Si](C)(C)CCOCN(c1cccnn1)S(=O)(=O)c1cc(Cl)c(F)cc1F]

To a solution of 5-chloro-2,4-difluoro-N-pyridazin-3-yl-benzenesulfonamide (0.200 g, 0.654 mmol) in anhydrous N,N-dimethylformamide (1 mL) was added 2-(trimethylsilyl)ethoxy-methyl chloride (0.131 g, 0.785 mmol, 0.139 mL) and potassium carbonate (0.181 g, 1.31 mmol) at 0° C. The mixture was stirred at ambient temperature for 30 minutes. To the mixture was then added water (10 mL) and ethyl acetate (10 mL). The aqueous phase was extracted with ethyl acetate (3×10 mL). The combined organic phase was washed with brine (2×10 mL), dried over anhydrous sodium sulfate, and filtered. Concentration of the filtrate in vacuo and purification of the residue by preparative reverse-phase HPLC, using acetonitrile in water containing 0.225% formic acid as eluent, afforded the title compound as a colorless solid (0.080 g, 82% yield): ¹H NMR (400 MHz, CDCl₃) δ 8.39 (dd, J=9.6, 1.4 Hz, 1H), 8.16-8.11 (m, 1H), 8.10 (dd, J=4.0, 1.6 Hz, 1H), 7.40 (dd, J=9.6, 4.0 Hz, 1H), 7.00 (t, J=8.8 Hz, 1H), 5.62 (s, 2H), 3.72-3.62 (m, 2H), 0.98-0.80 (m, 2H), 0.11-0.01 (m, 9H).

Step 3. Preparation of 4-((2-(azetidin-1-ylmethyl)-6-fluorobenzyl)amino)-5-chloro-2-fluoro-N-(pyridazin-3-yl)-N-((2-(trimethylsilyl)ethoxy)methyl)benzenesulfonamide

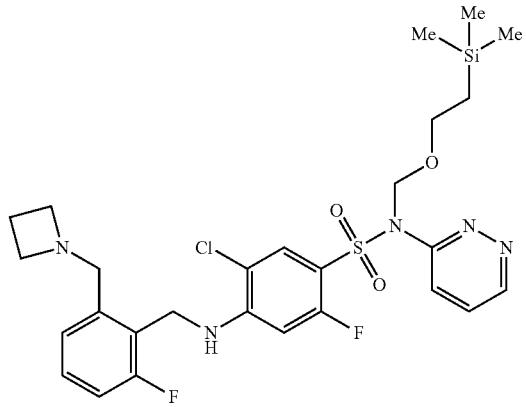 [SMILES: C[Si](C)(C)CCOCN(c1cccnn1)S(=O)(=O)c1cc(Cl)c(NCc2c(F)cccc2CN2CCC2)cc1F]

To a solution of (2-(azetidin-1-ylmethyl)-6-fluorophenyl)methanamine (0.047 g, 0.24 mmol) and 5-chloro-2,4-difluoro-N-(pyridazin-3-yl)-N-((2-(trimethylsilyl)ethoxy)

methyl)benzenesulfonamide (0.070 g, 0.16 mmol) in anhydrous N,N-dimethylformamide (1 mL) was added potassium carbonate (0.044 g, 0.32 mmol). The mixture was stirred at 60° C. for 12 h. To the mixture was then added water (10 mL) and ethyl acetate (10 mL) and layers were separated. The aqueous phase was extracted with ethyl acetate (3×10 mL). The combined organic phase was washed with brine (2×10 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless solid (0.080 g, 82% yield): $^1$H NMR (400 MHz, CD$_3$OD) δ 8.39 (dd, J=9.6, 1.5 Hz, 1H), 8.03 (dd, J=4.0, 1.6 Hz, 1H), 7.87 (d, J=7.4 Hz, 1H), 7.59-7.41 (m, 1H), 7.31 (dd, J=9.6, 4.0 Hz, 1H), 7.24 (td, J=8.0, 5.8 Hz, 1H), 7.11-6.94 (m, 2H), 6.70 (d, J=12.6 Hz, 1H), 5.65 (s, 2H), 4.42 (s, 2H), 3.77-3.68 (m, 2H), 3.65 (s, 2H), 3.25 (t, J=7.0 Hz, 4H), 2.14-2.09 (m, 2H), 0.86-1.00 (m, 2H), 0.08-0.00 (m, 9H); MS (ES+) m/z 610.1 (M+1), 612.1 (M+1).

Step 4. Synthesis of 4-((2-(azetidin-1-ylmethyl)-6-fluorobenzyl)amino)-5-chloro-2-fluoro-N-(pyridazin-3-yl)benzenesulfonamide

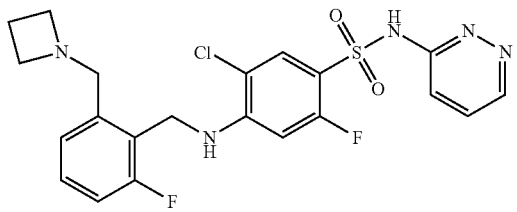 [SMILES: O=S(=O)(Nc1cccnn1)c1cc(Cl)c(NCc2c(F)cccc2CN2CCC2)cc1F]

To 4-((2-(azetidin-1-ylmethyl)-6-fluorobenzyl)amino)-5-chloro-2-fluoro-N-(pyridazin-3-yl)-N-((2-(trimethylsilyl)ethoxy)methyl)benzenesulfonamide (0.0800 g, 0.131 mmol) was added a 4.0 M solution of hydrogen chloride in 1,4-dioxane (2 mL) and the reaction mixture was stirred at ambient temperature for 1 h. The mixture was concentrated in vacuo and the obtained residue was purified by preparative reverse phase HPLC, using acetonitrile in water containing 0.225% formic acid as eluent, to afford the title compound as a colorless solid (0.019 g, 30% yield): $^1$H NMR (400 MHz, CDCl$_3$) δ 8.15 (dd, J=4.0, 1.6 Hz, 2H), 7.86 (d, J=7.2 Hz, 1H), 7.38-7.32 (m, 1H), 7.27-7.23 (m, 1H), 7.10-7.04 (m, 2H), 6.69 (d, J=13.0 Hz, 1H), 4.44 (s, 2H), 3.73 (s, 2H), 3.37-3.32 (m, 4H), 2.17 (dd, J=14.4, 7.8 Hz, 2H), exchangeable protons not observed; MS (ES+) m/z 480.0 (M+1), 482.1 (M+1).

Example 261

Synthesis of 4-((2-(2-(azetidin-1-yl)ethyl)benzyl)amino)-5-chloro-2-fluoro-N-(thiazol-4-yl)benzenesulfonamide formate

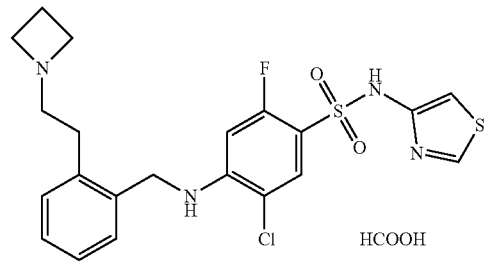 [SMILES: O=S(=O)(Nc1cscn1)c1cc(Cl)c(NCc2ccccc2CCN2CCC2)cc1F ; "HCOOH"]

Step 1. Preparation of (E)-2-(2-ethoxyvinyl)benzonitrile

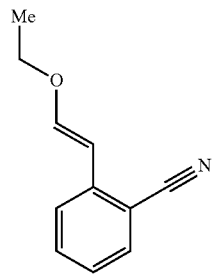 [SMILES: CCO/C=C/c1ccccc1C#N]

To a mixture of 2-bromobenzonitrile (1.00 g, 5.49 mmol), trans-2-ethoxyvinylboronic acid pinacol ester (1.20 g, 6.04 mmol) and sodium carbonate (1.16 g, 11.0 mmol) in toluene (5 mL), ethanol (5 mL) and water (5 mL), was added tetrakis(triphenylphosphine)palladium(0) (0.63 g, 0.55 mmol) and the mixture was heated to 80° C. for 3 h. After cooling to ambient temperature, the reaction mixture was diluted with water (30 mL) and extracted with ethyl acetate (3×30 mL). The combined organic layers were washed with brine (10 mL), dried over anhydrous sodium sulfate, and filtered. Concentration of the filtrate in vacuo and purification of the residue by column chromatography, eluting with a gradient of 0 to 2% of ethyl acetate in petroleum ether, afforded the title compound as a yellow oil (0.80 g, 84% yield); $^1$H NMR (400 MHz, CDCl$_3$) δ 7.58 (d, J=7.6 Hz, 1H), 7.47-7.43 (m, 2H), 7.25-7.17 (m, 2H), 6.14 (d, J=12.8 Hz, 1H), 4.00 (q, J=7.2 Hz, 2H), 1.40 (t, J=7.2 Hz, 3H).

Step 2. Preparation of 2-(2-oxoethyl)benzonitrile

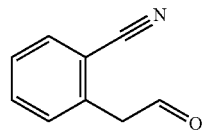 [SMILES: N#Cc1ccccc1CC=O]

A solution of (E)-2-(2-ethoxyvinyl)benzonitrile (0.40 g, 2.3 mmol) in formic acid (0.11 g, 2.3 mmol, 5 mL) was stirred at ambient temperature for 30 minutes. The mixture was concentrated in vacuo and the residue diluted with aqueous sodium hydrogencarbonate (30 mL). The mixture was extracted with ethyl acetate (3×30 mL). The combined organic extracts were washed with brine (20 mL), dried over anhydrous sodium sulfate, and filtered. Concentration of the filtrate in vacuo afforded the title compound as a yellow oil (0.3 g, 90% yield): MS (ES+) m/z 146.1 (M+1).

Step 3. Preparation of 2-(2-(azetidin-1-yl)ethyl)benzonitrile

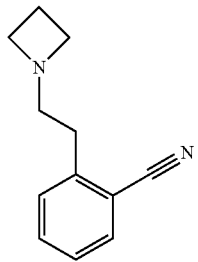 [SMILES: N#Cc1ccccc1CCN1CCC1]

To a solution of 2-(2-oxoethyl)benzonitrile (0.30 g, 2.1 mmol), acetic acid (0.025 mg, 0.41 mmol) and azetidine hydrochloride (0.387 g, 4.14 mmol) in methanol (5 mL) was added sodium cyanoborohydride (0.26 g, 4.1 mmol) in portions. The mixture was stirred at ambient temperature for 3 h, and then concentrated in vacuo. To the residue was added water (30 mL), and the mixture was extracted with dichloromethane (3×30 mL). The combined organic phase was washed with brine (10 mL), dried over anhydrous sodium sulfate, and filtered. Concentration of the filtrate in vacuo and purification of the residue by preparative reverse-phase HPLC, using acetonitrile in water containing 0.225% formic acid as eluent, afforded the title compound as a colorless oil (0.15 g, 39% yield): $^1$H NMR (400 MHz, CDCl$_3$) δ 7.63 (d, J=7.6 Hz, 1H), 7.57-7.49 (m, 1H), 7.39-7.29 (m, 2H), 3.27 (t, J=7.2 Hz, 4H), 2.93-2.85 (m, 2H), 2.79-2.68 (m, 2H), 2.18-2.02 (m, 2H); MS (ES+) m/z 187.1 (M+1).

Step 4. Preparation of (2-(2-(azetidin-1-yl)ethyl)phenyl)methanamine

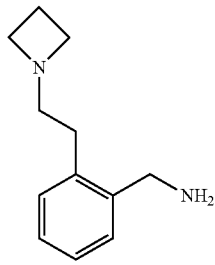 [SMILES: NCc1ccccc1CCN1CCC1]

To a mixture of 2-(2-(azetidin-1-yl)ethyl)benzonitrile (0.15 g, 0.81 mmol) in methanol (20 mL) and concentrated ammonium hydroxide (5 mL) was added Raney-Ni (0.014 g, 0.161 mmol) in one portion. The mixture was stirred at ambient temperature under a hydrogen atmosphere (50 psi) for 12 h. The mixture was then filtered and the filtrate concentrated in vacuo to afford the title compound as a yellow oil (0.120 g, 78% yield): $^1$H NMR (400 MHz, CDCl$_3$) δ 7.34-7.29 (m, 1H), 7.18-7.08 (m, 3H), 3.92 (s, 2H), 3.18 (t, J=7.2 Hz, 4H), 2.66 (s, 4H), 2.05 (q, J=7.2 Hz, 2H), NH not observed; MS (ES+) m/z 191.1 (M+1).

Step 5. Preparation of tert-butyl (4-((2-(2-(azetidin-1-yl)ethyl)benzyl)amino)-5-chloro-2-fluorophenyl) sulfonyl(thiazol-4-yl)carbamate

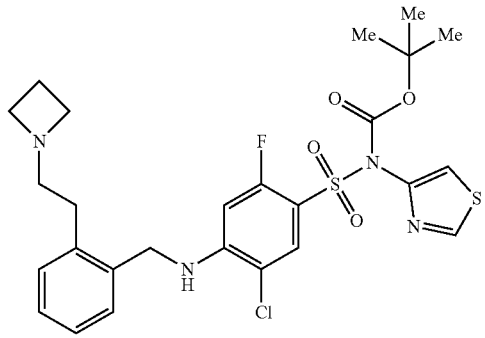 [SMILES: CC(C)(C)OC(=O)N(c1cscn1)S(=O)(=O)c1cc(Cl)c(NCc2ccccc2CCN2CCC2)cc1F]

To a solution of (2-(2-(azetidin-1-yl)ethyl)phenyl)methanamine (0.11 g, 0.58 mmol) and tert-butyl(5-chloro-2,4-difluorophenyl)sulfonyl(thiazol-4-yl)carbamate (0.238 g, 0.578 mmol) in anhydrous N,N-dimethylformamide (4 mL) was added potassium carbonate (0.16 g, 1.2 mmol). The reaction mixture was stirred at ambient temperature for 12 h. The mixture was diluted with water (30 mL) and extracted with ethyl acetate (3×30 mL). The combined organic phase was washed with brine (20 mL), dried over anhydrous sodium sulfate, and filtered. Concentration of the filtrate in vacuo afforded the title compound as a yellow oil (0.20 g, 59% yield); MS (ES+) m/z 581.1 (M+1).

Step 6. Preparation of 4-((2-(2-(azetidin-1-yl)ethyl) benzyl)amino)-5-chloro-2-fluoro-N-(thiazol-4-yl) benzenesulfonamide formate

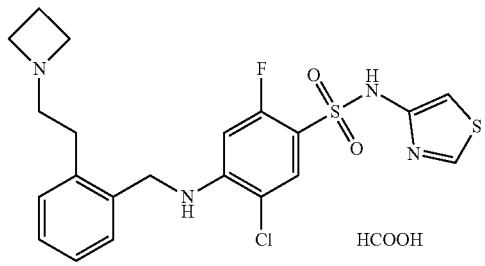 [SMILES: O=S(=O)(Nc1cscn1)c1cc(Cl)c(NCc2ccccc2CCN2CCC2)cc1F ; "HCOOH"]

To tert-butyl(4-((2-(2-(azetidin-1-yl)ethyl)benzyl) amino)-5-chloro-2-fluorophenyl)sulfonyl(thiazol-4-yl)carbamate (0.19 g, 0.33 mmol) was added a 4.0 M solution of hydrogen chloride in 1,4-dioxane (20 mL) and the reaction mixture was stirred at ambient temperature for 30 minutes. The mixture was concentrated in vacuo and the residue was purified by preparative reverse phase HPLC, using acetonitrile in water containing 0.225% formic acid as eluent, to afford the title compound as a colorless solid (0.068 g, 42% yield): $^1$H NMR (400 MHz, CDCl$_3$) δ 8.63 (d, J=2.0 Hz, 1H), 8.54 (s, 1H), 7.74 (d, J=7.2 Hz, 1H), 7.34-7.29 (m, 2H), 7.28-7.24 (m, 1H), 7.24-7.20 (m, 1H), 6.95-6.91 (m, 1H), 6.40 (d, J=12.4 Hz, 1H), 5.88 (s, 1H), 4.43 (d, J=2.8 Hz, 2H), 3.87 (t, J=8.0 Hz, 4H), 3.18-3.10 (m, 2H), 3.06-2.96 (m, 2H), 2.46 (quin, J=8.0 Hz, 2H), NH and COOH not observed; MS (ES+) m/z 481.1 (M+1), 483.1 (M+1).

Example 262

Synthesis of 4-((5-(2-(azetidin-1-yl)ethyl)-2-fluorobenzyl)amino)-5-chloro-2-fluoro-N-(thiazol-4-yl)benzenesulfonamide formate

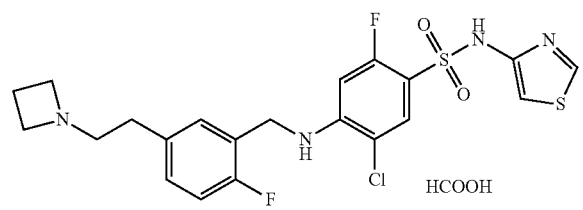 [SMILES: O=S(=O)(Nc1cscn1)c1cc(Cl)c(NCc2cc(CCN3CCC3)ccc2F)cc1F ; "HCOOH"]

Step 1. Preparation of (E)-5-(2-ethoxyvinyl)-2-fluorobenzonitrile

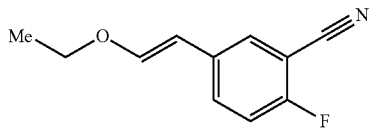 [SMILES: CCO/C=C/c1ccc(F)c(C#N)c1]

Following the procedure as described for EXAMPLE 261, Step 1 and making non-critical as required to replace 2-bromobenzonitrile with 5-bromo-2-fluorobenzonitrile, the title compound was obtained as a colorless solid (0.74 g, 88% yield): $^1$H NMR (400 MHz, CDCl$_3$) δ 7.43-7.39 (m, 2H), 7.15-7.07 (m, 1H), 6.96 (d, J=12.8 Hz, 1H), 5.78 (d, J=12.8 Hz, 1H), 3.93 (q, J=7.2 Hz, 2H), 1.37 (t, J=7.2 Hz, 3H).

Step 2. Preparation of 2-fluoro-5-(2-oxoethyl)benzonitrile

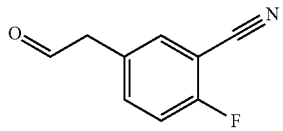 [SMILES: N#Cc1cc(CC=O)ccc1F]

Following the procedure as described for EXAMPLE 261, Step 2 and making non-critical as required to replace (E)-2-(2-ethoxyvinyl)benzonitrile with (E)-5-(2-ethoxyvinyl)-2-fluorobenzonitrile, the title compound was obtained as a yellow oil (0.54 g, 97% yield): MS (ES+) m/z 164.1 (M+1).

Step 3. Preparation of 5-(2-(azetidin-1-yl)ethyl)-2-fluorobenzonitrile

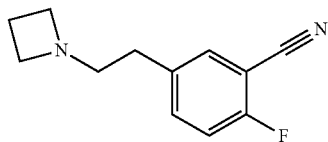 [SMILES: N#Cc1cc(CCN2CCC2)ccc1F]

Following the procedure as described for EXAMPLE 261, Step 3 and making non-critical as required to replace of 2-(2-oxoethyl)benzonitrile with 2-fluoro-5-(2-oxoethyl)benzonitrile, the title compound was obtained as a colorless oil (0.15 g, 22% yield): $^1$H NMR (400 MHz, CDCl$_3$) δ 7.50-7.41 (m, 2H), 7.14 (t, J=8.4 Hz, 1H), 3.22 (t, J=7.2 Hz, 4H), 2.66 (s, 4H), 2.16-2.06 (m, 2H).

Step 4. Preparation of (5-(2-(azetidin-1-yl)ethyl)-2-fluorophenyl)methanamine

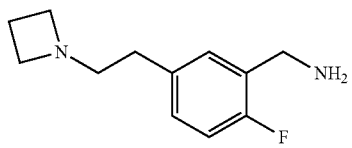 [SMILES: NCc1cc(CCN2CCC2)ccc1F]

Following the procedure as described for EXAMPLE 261, Step 4 and making non-critical as required to replace 2-(2-(azetidin-1-yl)ethyl)benzonitrile with 5-(2-(azetidin-1-yl)ethyl)-2-fluorobenzonitrile, the title compound was obtained as a yellow oil (0.1 g, 65% yield): MS (ES+) m/z 209.1 (M+1).

Step 5. Preparation of tert-butyl (4-((5-(2-(azetidin-1-yl)ethyl)-2-fluorobenzyl)amino)-5-chloro-2-fluorophenyl)sulfonyl(thiazol-4-yl)carbamate

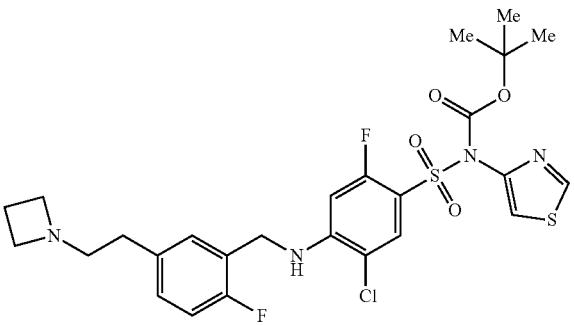 [SMILES: CC(C)(C)OC(=O)N(c1cscn1)S(=O)(=O)c1cc(Cl)c(NCc2cc(CCN3CCC3)ccc2F)cc1F]

Following the procedure as described for EXAMPLE 261, Step 5 and making non-critical as required to replace (2-(2-(azetidin-1-yl)ethyl)phenyl)methanamine with (5-(2-(azetidin-1-yl)ethyl)-2-fluorophenyl)methanamine, the title compound was obtained as a yellow oil (0.080 g, 70% yield): MS (ES+) m/z 599.1 (M+1), 601.1 (M+1).

Step 6. Preparation of 4-((5-(2-(azetidin-1-yl)ethyl)-2-fluorobenzyl)amino)-5-chloro-2-fluoro-N-(thiazol-4-yl)benzenesulfonamide formate

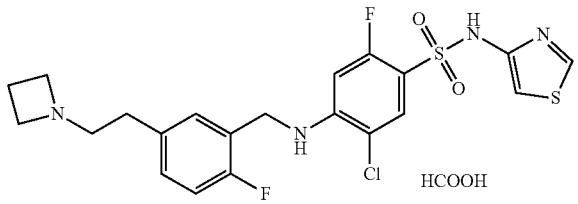 [SMILES: O=S(=O)(Nc1cscn1)c1cc(Cl)c(NCc2cc(CCN3CCC3)ccc2F)cc1F ; "HCOOH"]

Following the procedure as described for EXAMPLE 261, Step 6 and making non-critical as required to replace tert-butyl(4-((2-(2-(azetidin-1-yl)ethyl)benzyl)amino)-5-chloro-2-fluorophenyl)sulfonyl(thiazol-4-yl)carbamate with tert-butyl(4-((5-(2-(azetidin-1-yl)ethyl)-2-fluorobenzyl)amino)-5-chloro-2-fluorophenyl)sulfonyl(thiazol-4-yl)carbamate, the title compound was obtained as a colorless solid (0.024 g, 35% yield): $^1$H NMR (400 MHz, CDCl$_3$) δ 8.55 (d, J=2.4 Hz, 1H), 8.46 (s, 1H), 7.69 (d, J=7.2 Hz, 1H), 7.12-7.05 (m, 2H), 6.95 (t, J=9.2 Hz, 1H), 6.84 (d, J=2.4 Hz, 1H), 6.23 (d, J=12.0 Hz, 1H), 5.43 (t, J=5.2 Hz, 1H), 4.34 (d, J=5.6 Hz, 2H), 3.70 (t, J=8.0 Hz, 4H), 3.03 (t, J=7.2 Hz, 2H), 2.77 (t, J=7.6 Hz, 2H), 2.30 (q, J=8.0 Hz, 2H), NH and COOH not observed; MS (ES+) m/z 499.0 (M+1), 501.0 (M+1).

Example 263

Synthesis of 5-chloro-2-fluoro-4-((2-fluoro-5-(2-(3-fluoroazetidin-1-yl)ethyl)benzyl)amino)-N-(thiazol-4-yl)benzenesulfonamide formate

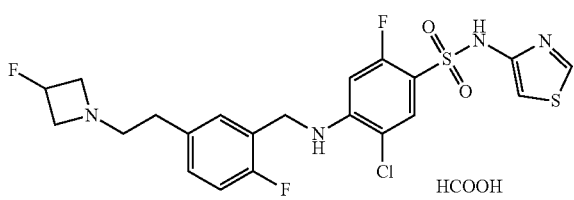 [SMILES: O=S(=O)(Nc1cscn1)c1cc(Cl)c(NCc2cc(CCN3CC(F)C3)ccc2F)cc1F ; "HCOOH"]

Step 1. Preparation of 2-fluoro-5-(2-(3-fluoroazetidin-1-yl)ethyl)benzonitrile

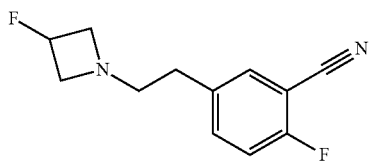 [SMILES: N#Cc1cc(CCN2CC(F)C2)ccc1F]

To a solution of 2-fluoro-5-(2-oxoethyl)benzonitrile (0.55 g, 3.4 mmol), 3-fluoroazetidine (0.564 g, 5.06 mmol), and acetic acid (0.04 g, 0.7 mmol) in methanol (4 mL) was added sodium cyanoborohydride (0.424 g, 6.74 mmol) in one portion. The mixture was stirred at ambient temperature for 12 h. The mixture was diluted with water (50 mL) and extracted with ethyl acetate (3×50 mL). The combined organic phase was washed with brine (10 mL), dried over anhydrous sodium sulfate, and filtered. Concentration of the filtrate in vacuo and purification of the residue by reverse-phase column chromatography, eluting with acetonitrile in water, afforded the title compound as a yellow oil (0.30 g, 40% yield): $^1$H NMR (400 MHz, CDCl$_3$) δ 7.41-7.31 (m, 2H), 7.06 (t, J=8.4 Hz, 1H), 5.15-4.93 (m, 1H), 3.65-3.51 (m, 2H), 3.14-2.98 (m, 2H), 2.73-2.53 (m, 4H); MS (ES+) m/z 222.9 (M+1).

Step 2. Preparation of (2-fluoro-5-(2-(3-fluoroazetidin-1-yl)ethyl)phenyl)methanamine

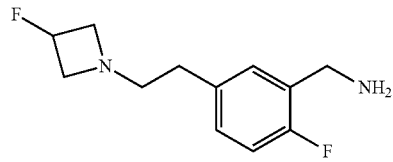 [SMILES: NCc1cc(CCN2CC(F)C2)ccc1F]

To a solution of 2-fluoro-5-(2-(3-fluoroazetidin-1-yl)ethyl)benzonitrile (0.30 g, 1.4 mmol) and concentrated ammonium hydroxide (2 mL) in methanol (8 mL) was added Raney-Ni (0.023 g, 0.27 mmol). The mixture was stirred at ambient temperature under a hydrogen atmosphere (50 Psi) for 12 h. The mixture was filtered and the filtrate concentrated in vacuo to afford the title compound as a yellow oil (0.3 g, 95% yield): MS (ES+) m/z 227.1 (M+1).

Step 3. Preparation of tert-butyl (5-chloro-2-fluoro-4-((2-fluoro-5-(2-(3-fluoroazetidin-1-yl)ethyl)benzyl)amino)phenyl)sulfonyl(thiazol-4-yl)carbamate

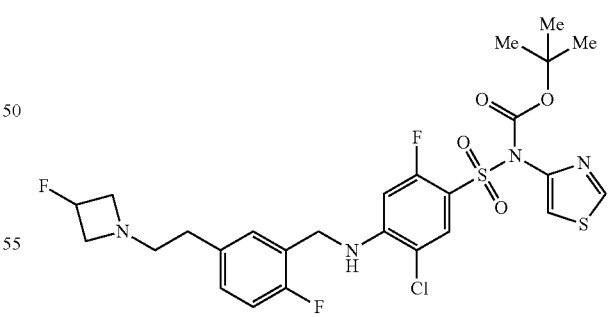

Following the procedure as described for EXAMPLE 261, Step 5 and making non-critical as required to replace (2-(2-(azetidin-1-yl)ethyl)phenyl)methanamine with (2-fluoro-5-(2-(3-fluoroazetidin-1-yl)ethyl)phenyl)methanamine, the title compound was obtained as a yellow oil (0.06 g, 22% yield): MS (ES+) m/z 617.1 (M+1), 619.0 (M+1).

Step 4. Synthesis of 5-chloro-2-fluoro-4-((2-fluoro-5-(2-(3-fluoroazetidin-1-yl)ethyl)benzyl)amino)-N-(thiazol-4-yl)benzenesulfonamide formate

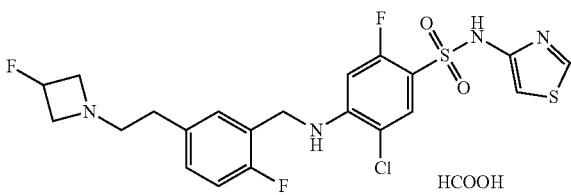 [SMILES: O=S(=O)(Nc1cscn1)c1cc(Cl)c(NCc2cc(CCN3CC(F)C3)ccc2F)cc1F ; "HCOOH"]

Following the procedure as described for EXAMPLE 261, Step 6 and making non-critical as required to replace tert-butyl(4-((2-(2-(azetidin-1-yl)ethyl)benzyl)amino)-5-chloro-2-fluorophenyl)sulfonyl(thiazol-4-yl)carbamate with tert-butyl(5-chloro-2-fluoro-4-((2-fluoro-5-(2-(3-fluoroazetidin-1-yl)ethyl)benzyl) amino)phenyl)sulfonyl(thiazol-4-yl)carbamate, the title compound was obtained as a colorless solid (0.034 g, 50% yield): $^1$H NMR (400 MHz, CDCl$_3$) δ 8.66 (d, J=2.2 Hz, 1H), 8.26 (s, 1H), 7.77 (d, J=7.2 Hz, 1H), 7.19-7.10 (m, 2H), 7.08-7.01 (m, 1H), 6.97 (d, J=2.2 Hz, 1H), 6.34 (d, J=12.0 Hz, 1H), 5.38 (t, J=5.2 Hz, 1H), 5.33-5.10 (m, 1H), 4.42 (d, J=5.6 Hz, 2H), 4.07-3.97 (m, 2H), 3.42-3.39 (m, 1H), 3.37-3.34 (m, 1H), 3.04-2.96 (m, 2H), 2.79-2.73 (m, 2H), NH and COOH not observed; MS (ES+) m/z 517.0 (M+1), 519.0 (M+1).

Example 264

Synthesis of 4-(((1S,3S)-3-(azetidin-1-yl)-2,3-dihydro-1H-inden-1-yl)amino)-5-chloro-2-fluoro-N-(thiazol-4-yl)benzenesulfonamide formate

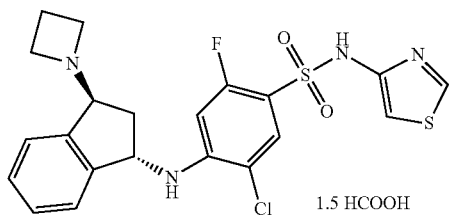 [SMILES: O=S(=O)(Nc1cscn1)c1cc(Cl)c(N[C@H]2C[C@H](N3CCC3)c3ccccc32)cc1F]

Step 1. Preparation of (S)-3-phenyl-3-(2,2,2-trifluoroacetamido)propanoic acid

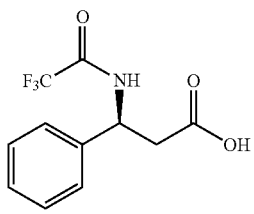 [SMILES: O=C(O)C[C@H](NC(=O)C(F)(F)F)c1ccccc1]

A mixture of (S)-3-amino-3-phenylpropanoic acid (1.00 g, 6.05 mmol) in trifluoroacetic anhydride (3.75 mL) was stirred at ambient temperature for 12 h. The mixture was concentrated in vacuo and the residue was triturated in ether (15 mL) to give the title compound as a colorless solid (1.40 g, 59% yield): $^1$H NMR (400 MHz, DMSO-d$_6$) δ 12.44 (br s, 1H), 9.96 (d, J=8.4 Hz, 1H), 7.40-7.35 (m, 5H), 5.25 (dt, J=8.8, 5.8 Hz, 1H), 2.93-2.74 (m, 2H); MS (ES+) m/z 284.1 (M+23).

Step 2. Preparation of (S)-3-phenyl-3-(2,2,2-trifluoroacetamido)propanoyl chloride

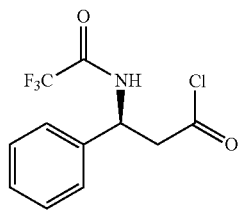 [SMILES: O=C(Cl)C[C@H](NC(=O)C(F)(F)F)c1ccccc1]

A solution of (S)-3-phenyl-3-(2,2,2-trifluoroacetamido) propanoic acid (3.00 g, 11.5 mmol) in thionyl chloride (30 mL) was heated to 80° C. for 12 h. Concentration in vacuo and trituration of the residue in petroleum ether provided the title compound a yellow solid (3.00 g, 93% yield): $^1$H NMR (300 MHz, DMSO-d$_6$) δ 9.97 (br d, J=8.1 Hz, 1H), 7.40-7.36 (m, 3H), 7.34-7.23 (m, 2H), 5.27-5.20 (m, 1H), 2.97-2.84 (m, 1H), 2.84-2.71 (m, 1H).

Step 3. Preparation of (S)-2,2,2-trifluoro-N-(3-oxo-2,3-dihydro-1H-inden-1-yl)acetamide

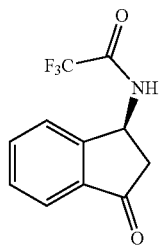 [SMILES: O=C1C[C@H](NC(=O)C(F)(F)F)c2ccccc21]

To a solution of (S)-3-phenyl-3-(2,2,2-trifluoroacetamido)propanoyl chloride (3.00 g, 10.7 mmol) in anhydrous dichloromethane (20 mL) was added a solution of aluminium trichloride (2.86 g, 21.5 mmol) in anhydrous dichloromethane (20 mL) at 0° C. The mixture was then heated to 40° C. for 12 h. Concentration in vacuo provided a brown solid that was triturated in water (30 mL). The solid was filtered off, washed with water (3×30 mL), and dried under reduced pressure to give the title compound as a colorless solid (2.50 g, 96% yield): $^1$H NMR (400 MHz, DMSO-d$_6$) δ 10.01 (br d, J=8.0 Hz, 1H), 7.81-7.74 (m, 1H), 7.71 (d, J=7.8 Hz, 1H), 7.63-7.54 (m, 2H), 5.63 (dt, J=8.0, 3.4 Hz, 1H), 3.17-3.10 (m, 1H), 2.65-2.60 (m, 1H).

Step 4. Preparation of N-((1S,3S)-3-(azetidin-1-yl)-2,3-dihydro-1H-inden-1-yl)-2,2,2-trifluoroacetamide

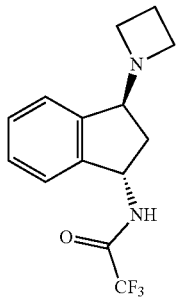 [SMILES: O=C(N[C@H]1C[C@H](N2CCC2)c2ccccc21)C(F)(F)F]

To a mixture of (S)-2,2,2-trifluoro-N-(3-oxo-2,3-dihydro-1H-inden-1-yl)acetamide (1.00 g, 4.11 mmol), azetidine hydrochloride (0.480 g, 5.14 mmol) and triethylamine (2.28 mL, 16.4 mmol) in anhydrous dichloromethane (30 mL) was added titanium(IV) isopropoxide (2.34 g, 8.22 mmol, 2.43 mL) and the mixture was stirred at ambient temperature for 1 h. Sodium triacetoxyborohydride (2.18 g, 10.3 mmol) was then added in portions and the reaction mixture was stirred at ambient temperature for 47 h. The mixture was diluted with dichloromethane (20 mL) and saturated ammonium chloride (30 mL) was added to it. The organic layer was washed with brine (20 mL), dried over anhydrous magnesium sulfate, and filtered. Concentration of the filtrate in vacuo and purification of the residue by preparative reverse phase HPLC, using acetonitrile in water containing 0.225% formic acid as eluent, afforded the title compound as a yellow solid (0.200 g, 17% yield): $^1$H NMR (400 MHz, CDCl$_3$) δ 7.38-7.29 (m, 4H), 6.41 (br s, 1H), 5.71 (q, J=7.6 Hz, 1H), 3.94 (dd, J=6.8, 2.0 Hz, 1H), 3.36 (q, J=6.8 Hz, 2H), 3.24 (q, J=6.8 Hz, 2H), 2.54 (ddd, J=13.4, 7.4, 2.0 Hz, 1H), 2.09 (quin, J=7.0 Hz, 2H), 1.92 (td, J=13.6, 7.0 Hz, 1H); MS (ES+) m/z 285.0 (M+1).

Step 5. Preparation of (1S,3S)-3-(azetidin-1-yl)-2,3-dihydro-1H-inden-1-amine

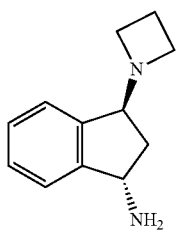 [SMILES: N[C@H]1C[C@H](N2CCC2)c2ccccc21]

To a solution of N-((1S,3S)-3-(azetidin-1-yl)-2,3-dihydro-1H-inden-1-yl)-2,2,2-trifluoroacetamide (0.150 g, 0.527 mmol) in methanol (10 mL) was added 1.0 M sodium hydroxide (2.6 mL) and the reaction mixture was heated to 80° C. for 24 h. After cooling to ambient temperature, the reaction mixture was diluted with water (30 mL) and extracted with ethyl acetate (3×30 mL). The combined organic phase was washed with brine (30 mL), dried over anhydrous sodium sulfate, and filtered. Concentration of the filtrate under reduced pressure afforded the title compound as a yellow solid (0.100 g, quantitative yield): MS (ES+) m/z 189.2 (M+1).

Step 6. Preparation of tert-butyl (4-(((1S,3S)-3-(azetidin-1-yl)-2,3-dihydro-1H-inden-1-yl)amino)-5-chloro-2-fluorophenyl)sulfonyl(thiazol-4-yl)carbamate

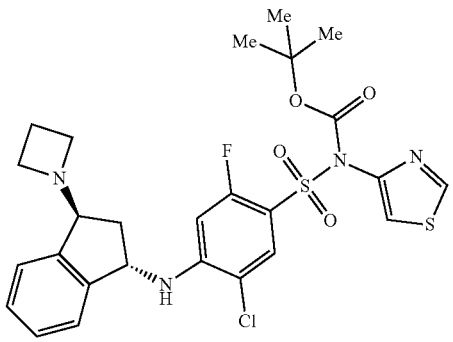 [SMILES: CC(C)(C)OC(=O)N(c1cscn1)S(=O)(=O)c1cc(Cl)c(N[C@H]2C[C@H](N3CCC3)c3ccccc32)cc1F]

To a solution of tert-butyl (5-chloro-2,4-difluorophenyl)sulfonyl(thiazol-4-yl)carbamate (0.100 g, 0.243 mmol) in anhydrous N,N-dimethylformamide (5 mL) was added (1S,3S)-3-(azetidin-1-yl)-2,3-dihydro-1H-inden-1-amine (0.080 g, 0.43 mmol) and potassium carbonate (0.067 g, 0.49 mmol) and the reaction mixture was stirred at ambient temperature for 12 h. The reaction mixture was diluted with water (10 mL) and extracted with ethyl acetate (2×10 mL). The combined organic layers were washed with brine (10 mL), dried over anhydrous sodium sulfate, and filtered. Concentration of the filtrate under pressure and purification of the residue by preparative thin layer chromatography, eluting with a gradient of 33% of ethyl acetate in petroleum ether, afforded the title compound as a yellow oil (0.100 g, 71% yield): MS (ES+) m/z 579.0 (M+1), 581.0 (M+1).

Step 7. Synthesis of 4-(((1S,3S)-3-(azetidin-1-yl)-2,3-dihydro-1H-inden-1-yl)amino)-5-chloro-2-fluoro-N-(thiazol-4-yl)benzenesulfonamide formate

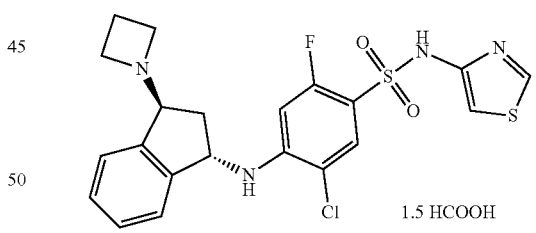

To tert-butyl (4-(((1S,3S)-3-(azetidin-1-yl)-2,3-dihydro-1H-inden-1-yl)amino)-5-chloro-2-fluorophenyl)sulfonyl(thiazol-4-yl)carbamate (0.100 g, 0.208 mmol) was added a 4 M solution of hydrogen chloride in 1,4-dioxane (5 mL) and the reaction mixture was stirred at ambient temperature for 1 h. The reaction mixture was concentrated under reduced pressure and the residue was purified by preparative reverse phase HPLC, using acetonitrile in water containing 0.225% formic acid as eluent, to afford the title compound as a colorless solid (0.035 g, 35% yield): $^1$H NMR (400 MHz, DMSO-d$_6$) δ 8.86 (d, J=2.0 Hz, 1H), 8.24 (s, 1.5H), 7.61 (d, J=7.2 Hz, 1H), 7.36-7.32 (m, 1H), 7.29-7.25 (m, 2H), 7.19-7.11 (m, 1H), 6.91-6.81 (m, 2H), 6.39 (d, J=9.2 Hz, 1H), 5.27 (q, J=8.0 Hz, 1H), 3.86 (d, J=6.0 Hz, 1H), 3.35-3.21 (m, 2H), 3.14-3.07 (m, 2H), 2.32-2.27 (m, 1H), 2.12-2.06 (m, 1H), 1.93 (quin, J=6.8 Hz, 2H), NH and COOH not observed; MS (ES+) m/z 478.9 (M+1), 479.9 (M+1).

Example 265

Synthesis of (S)-5-chloro-2-fluoro-N-(5-fluorothiazol-2-yl)-4-((1-phenylpropyl)amino)benzenesulfonamide

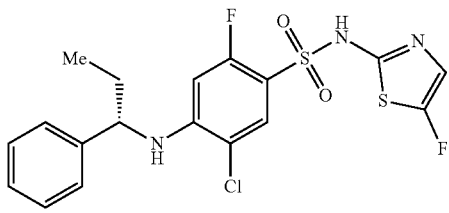 [SMILES: CC[C@H](Nc1cc(F)c(S(=O)(=O)Nc2ncc(F)s2)cc1Cl)c1ccccc1]

Step 1. Preparation of 5-chloro-N-(2,4-dimethoxybenzyl)-2,4-difluoro-N-(5-fluorothiazol-2-yl)benzenesulfonamide

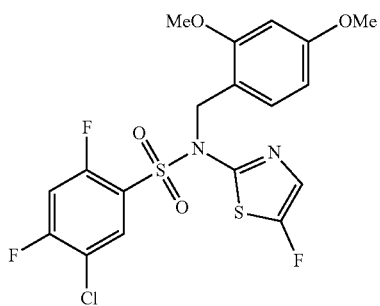 [SMILES: COc1ccc(CN(c2ncc(F)s2)S(=O)(=O)c2cc(Cl)c(F)cc2F)c(OC)c1]

To a solution of N-(2,4-dimethoxybenzyl)-5-fluorothiazol-2-amine (0.30 g, 1.12 mmol) in anhydrous tetrahydrofuran (15 mL) was added a 1 M solution of lithium bis(trimethylsilyl)amide in tetrahydrofuran (1.68 mL, 1.68 mmol) at −78° C. The reaction mixture was stirred for 50 minutes at −78° C. To it was then added a solution of 5-chloro-2,4-difluorobenzene-1-sulfonyl chloride (0.33 g, 1.34 mmol) in anhydrous tetrahydrofuran (3 mL) at −78° C. The reaction mixture was allowed to warm to ambient temperature and stirred for 2 hours. The reaction mixture was diluted with water (30 mL) and extracted with ethyl acetate (2×20 mL). The combined organic layers were washed with brine (30 mL), dried over anhydrous sodium sulfate, and filtered. Concentration of the filtrate in vacuo and purification of the residue by preparative thin layer chromatography, eluting with 20% ethyl acetate in petroleum ether, provided the title compound as a colorless solid (0.30 g, 81% yield): $^1$H NMR (400 MHz, CDCl$_3$) δ 7.89 (t, J=7.2 Hz, 1H), 7.18 (d, J=8.4 Hz, 1H), 7.01-7.08 (m, 2H), 6.38-6.42 (m, 1H), 6.36 (d, J=2.4 Hz, 1H), 5.06 (s, 2H), 3.80 (s, 3H), 3.75 (s, 3H).

Step 2. Preparation of (S)-5-chloro-N-(2,4-dimethoxybenzyl)-2-fluoro-N-(5-fluorothiazol-2-yl)-4-((1-phenylpropyl)amino)benzenesulfonamide

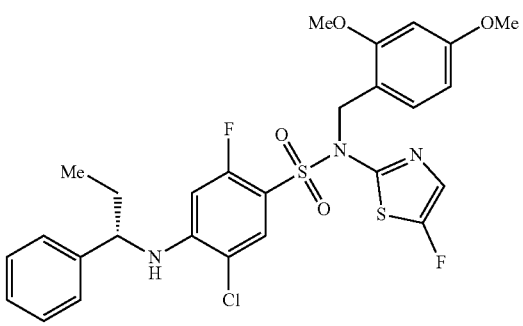 [SMILES: CC[C@H](Nc1cc(F)c(S(=O)(=O)N(Cc2ccc(OC)cc2OC)c2ncc(F)s2)cc1Cl)c1ccccc1]

To a solution of 5-chloro-N-(2,4-dimethoxybenzyl)-2,4-difluoro-N-(5-fluorothiazol-2-yl) benzenesulfonamide (0.12 g, 0.25 mmol) in anhydrous dimethyl sulfoxide (5 mL) was added potassium carbonate (0.069 g, 0.50 mmol) and (S)-1-phenylpropan-1-amine (0.067 g, 0.50 mmol). The mixture was stirred at ambient temperature for 12 hours. The reaction mixture was diluted with water (10 mL) and extracted with ethyl acetate (2×10 mL). The combined organic layers were washed with brine (10 mL), dried over anhydrous sodium sulfate, and filtered. Concentration of the filtrate under reduced pressure provided the title compound as a crude yellow oil (0.15 g, quantitative yield) which was used without further purification: MS (ES+) m/z 594.1 (M+1), 596.1 (M+1).

Step 3. Preparation of (S)-5-chloro-2-fluoro-N-(5-fluorothiazol-2-yl)-4-((1-phenylpropyl)amino)benzenesulfonamide

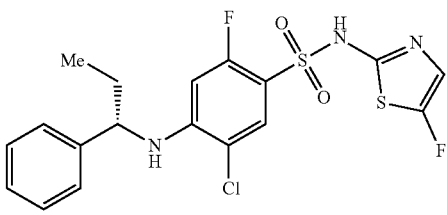 [SMILES: CC[C@H](Nc1cc(F)c(S(=O)(=O)Nc2ncc(F)s2)cc1Cl)c1ccccc1]

To a mixture of (S)-5-chloro-N-(2,4-dimethoxybenzyl)-2-fluoro-N-(5-fluorothiazol-2-yl)-4-((1-phenylpropyl)amino)benzenesulfonamide (0.13 g, 0.22 mmol) in dichloromethane (5 mL) was added trifluoroacetic acid (1 mL) and the reaction mixture was stirred at ambient temperature for 15 minutes. The reaction mixture was concentrated in vacuo and the residue was triturated with methanol (5 mL). Filtration and concentration of the filtrate afforded a residue, which was purified by preparative reverse phase HPLC, using acetonitrile in water containing 0.225% formic acid as eluent, to give the title compound as a colorless solid (0.080 g, 82% yield): $^1$H NMR (400 MHz, CDCl$_3$) δ 7.80 (d, J=7.2 Hz, 1H), 7.33-7.41 (m, 2H), 7.29-7.33 (m, 1H), 7.26 (s, 2H), 6.77 (s, 1H), 6.12 (d, J=12.4 Hz, 1H), 5.27 (d, J=4.8 Hz, 1H), 4.23 (q, J=6.4 Hz, 1H), 1.93 (dq, J=11.6, 7.2 Hz, 2H), 1.01 (t, J=7.2 Hz, 3H), NH not observed; MS (ES+) m/z 444.0 (M+1), 446.0 (M+1).

Example 266

Synthesis of (S)-5-chloro-2-fluoro-4-((1-(2-fluorophenyl)ethyl)amino)-N-(5-fluorothiazol-2-yl)benzenesulfonamide

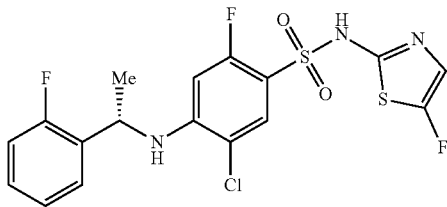 [SMILES: C[C@H](Nc1cc(F)c(S(=O)(=O)Nc2ncc(F)s2)cc1Cl)c1ccccc1F]

Step 1. Preparation of (S)-5-chloro-N-(2,4-dimethoxybenzyl)-2-fluoro-4-((1-(2-fluorophenyl)ethyl)amino)-N-(5-fluorothiazol-2-yl)benzenesulfonamide

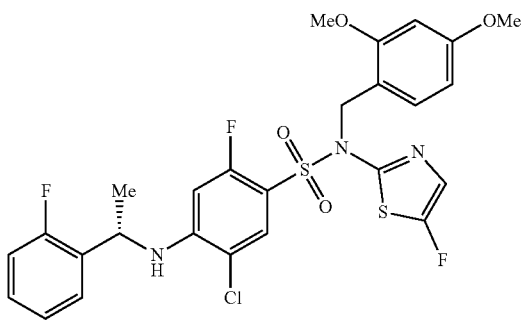 [SMILES: COc1ccc(CN(c2ncc(F)s2)S(=O)(=O)c2cc(Cl)c(N[C@@H](C)c3ccccc3F)cc2F)c(OC)c1]

To a solution of 5-chloro-N-(2,4-dimethoxybenzyl)-2,4-difluoro-N-(5-fluorothiazol-2-yl) benzenesulfonamide (0.10 g, 0.21 mmol) in anhydrous dimethyl sulfoxide (5 mL) was added potassium carbonate (0.058 g, 0.42 mmol) and (S)-1-(2-fluorophenyl)ethanamine (0.058 g, 0.42 mmol). The mixture was stirred at ambient temperature for 12 hours. The reaction mixture was diluted with water (10 mL) and extracted with ethyl acetate (2×10 mL). The combined organic layers were washed with brine (10 mL), dried over anhydrous sodium sulfate, and filtered. Concentration of the filtrate in vacuo and purification of the residue by preparative thin layer chromatography, eluting with 20% of ethyl acetate in petroleum ether, provided the title compound as a colorless solid (0.060, 48% yield): MS (ES+) m/z 598.1 (M+1), 600.1 (M+1).

Step 2. Preparation of (S)-5-chloro-2-fluoro-4-((1-(2-fluorophenyl)ethyl)amino)-N-(5-fluorothiazol-2-yl)benzenesulfonamide

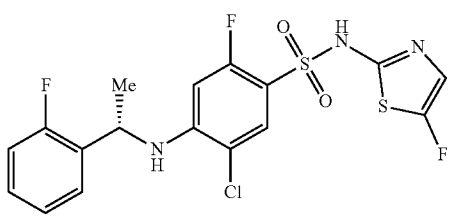 [SMILES: C[C@H](Nc1cc(F)c(S(=O)(=O)Nc2ncc(F)s2)cc1Cl)c1ccccc1F]

To a mixture of (S)-5-chloro-N-(2,4-dimethoxybenzyl)-2-fluoro-4-((1-(2-fluorophenyl)ethyl)amino)-N-(5-fluorothiazol-2-yl)benzenesulfonamide (0.060 g, 0.10 mmol) in dichloromethane (5 mL) was added trifluoroacetic acid (1 mL) and the mixture was stirred at ambient temperature for 15 minutes. Concentration in vacuo afforded a residue which was triturated with methanol (5 mL). The mixture was filtered and the filtrate was concentrated under reduced pressure. Purification of the residue by preparative reverse phase HPLC, using acetonitrile in water containing 0.225% formic acid as eluent, afforded the title compound as a colorless solid (0.025 g, 55% yield): $^1$H NMR (400 MHz, CDCl$_3$) δ 7.82 (d, J=7.2 Hz, 1H), 7.31 (s, 1H), 7.22-7.27 (m, 1H), 7.05-7.17 (m, 2H), 6.77 (s, 1H), 6.13 (d, J=12.4 Hz, 1H), 5.21 (d, J=5.6 Hz, 1H), 4.82 (t, J=6.4 Hz, 1H), 1.65 (d, J=6.8 Hz, 3H), NH not observed; MS (ES+) m/z 448.0 (M+1), 450.0 (M+1).

Example 267

Synthesis of (S)-5-chloro-2-fluoro-4-((1-(2-fluorophenyl)ethyl)amino)-N-(5-chlorothiazol-2-yl)benzenesulfonamide

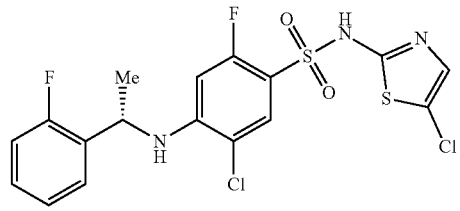 [SMILES: C[C@H](Nc1cc(F)c(S(=O)(=O)Nc2ncc(Cl)s2)cc1Cl)c1ccccc1F]

Step 1. Preparation of (S)-5-chloro-N-(2,4-dimethoxybenzyl)-2-fluoro-4-((1-(2-fluorophenyl)ethyl)amino)-N-(5-chlorothiazol-2-yl)benzenesulfonamide

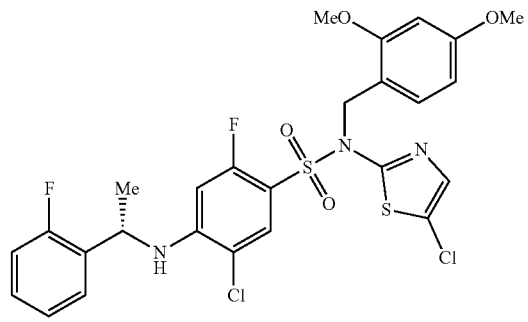 [SMILES: COc1ccc(CN(c2ncc(Cl)s2)S(=O)(=O)c2cc(Cl)c(N[C@@H](C)c3ccccc3F)cc2F)c(OC)c1]

To a solution of 5-chloro-N-(2,4-dimethoxybenzyl)-2,4-difluoro-N-(5-chlorothiazol-2-yl)benzenesulfonamide (prepared according to WO 2015077905, 0.10 g, 0.20 mmol) in anhydrous dimethyl sulfoxide (3 mL) was added potassium carbonate (0.084 g, 0.61 mmol) and (S)-1-(2-fluorophenyl)ethanamine (0.039 g, 0.22 mmol). The mixture was stirred at ambient temperature for 12 hours. The residue was poured onto ice-water (30 mL) and the aqueous phase was extracted with ethyl acetate (3×50 mL). The combined organic extracts were washed with brine (30 mL), dried over anhydrous sodium sulfate, and filtered. Concentration of the filtrate in vacuo afforded the title compound as a yellow oil (0.15, quantitative yield): MS (ES+) m/z 614.0 (M+1), 616.0 (M+1).

Step 2. Preparation of (S)-5-chloro-2-fluoro-4-((1-(2-fluorophenyl)ethyl)amino)-N-(5-chlorothiazol-2-yl)benzenesulfonamide

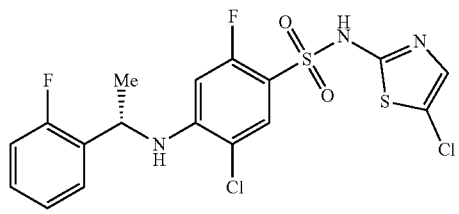 [SMILES: C[C@H](Nc1cc(F)c(S(=O)(=O)Nc2ncc(Cl)s2)cc1Cl)c1ccccc1F]

To a mixture of (S)-5-chloro-N-(2,4-dimethoxybenzyl)-2-fluoro-4-((1-(2-fluorophenyl)ethyl)amino)-N-(5-chlorothiazol-2-yl)benzenesulfonamide (0.15 g, 0.17 mmol) in dichloromethane (5 mL) was added trifluoroacetic acid (0.50 mL). The mixture was stirred at ambient temperature for 12 hours. Concentration in vacuo and purification of the residue by preparative reverse-phase HPLC, using acetonitrile in water containing 0.225% formic acid as eluent, afforded the title compound as a colorless solid (0.043 g, 54% yield): $^1$H NMR (400 MHz, CDCl$_3$) δ 7.81 (d, J=6.8 Hz, 1H), 7.29 (m, 1H), 7.25-7.21 (m, 1H), 7.13-7.06 (m, 2H), 6.99 (s, 1H), 6.12 (d, J=8.4 Hz, 1H), 5.20 (d, J=5.6 Hz, 1H), 4.83-4.77 (m, 1H), 1.64 (d, J=6.8 Hz, 3H), NH not observed; MS (ES+) m/z 464.0 (M+1), 486.0 (M+1+23).

Example 268

Synthesis of (S)-5-chloro-4-((1-(2,5-difluorophenyl)ethyl)amino)-2-fluoro-N-(thiazol-2-yl)benzenesulfonamide

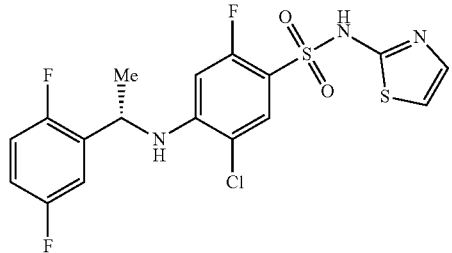 [SMILES: C[C@H](Nc1cc(F)c(S(=O)(=O)Nc2nccs2)cc1Cl)c1cc(F)ccc1F]

Step 1. Preparation of (R)—N-(2,5-difluorobenzylidene)-2-methylpropane-2-sulfinamide

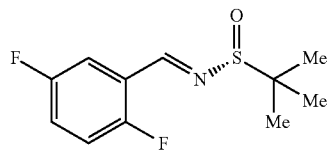 [SMILES: CC(C)(C)[S@@](=O)/N=C/c1cc(F)ccc1F]

To a solution of 2,5-difluorobenzaldehyde (3.00 g, 21.1 mmol) in anhydrous dichloromethane (20 mL) was added pyridinium p-toluenesulfonate (0.26 g, 1.06 mmol), (R)-2-methylpropane-2-sulfinamide (2.81 g, 23.2 mmol) and anhydrous magnesium sulfate (12.7 g, 105 mmol). The reaction mixture was stirred at ambient temperature for 12 hours. The reaction mixture was filtered and the filtrate was concentrated in vacuo. Purification of the residue by column chromatography, eluting with a gradient of 1-2% of ethyl acetate in petroleum ether, afforded the title compound as a colorless oil (3.20 g, 61% yield): $^1$H NMR (400 MHz, CDCl$_3$) δ 8.85 (d, J=2.0 Hz, 1H), 7.66 (ddd, J=8.4, 5.2, 3.2 Hz, 1H), 7.23-7.10 (m, 2H), 1.27 (s, 9H).

Step 2. Preparation of (R)—N—((S)-1-(2,5-difluorophenyl)ethyl)-2-methylpropane-2-sulfinamide

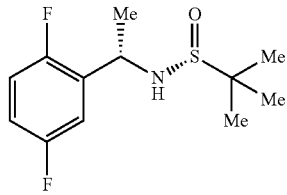 [SMILES: C[C@H](N[S@](=O)C(C)(C)C)c1cc(F)ccc1F]

To a solution of (R)—N-(2,5-difluorobenzylidene)-2-methylpropane-2-sulfinamide (3.20 g, 13.0 mmol) in anhydrous dichloromethane (20 mL) was added dropwise a 3 M solution of methylmagnesium bromide in diethyl ether (8.7 mL, 26 mmol) at −50° C. The reaction mixture was warmed to ambient temperature and stirred for 12 hours. The reaction mixture was diluted with ammonium chloride (50 mL), water (100 mL), and extracted with dichloromethane (3×80 mL). The combined organic layers were washed with brine (3×60 mL), dried over anhydrous sodium sulfate, and filtered. Concentration of the filtrate in vacuo and purification of the residue by column chromatography, eluting with 20% of ethyl acetate in petroleum ether, afforded the title compound as a colorless solid (1.50 g, 43% yield): $^1$H NMR (400 MHz, CDCl$_3$) δ 7.09-6.88 (m, 3H), 4.90-4.79 (m, 1H), 3.41 (d, J=4.0 Hz, 1H), 1.55 (d, J=6.8 Hz, 3H), 1.21 (s, 9H).

Step 3. Preparation of (S)-1-(2,5-difluorophenyl)ethan-1-amine

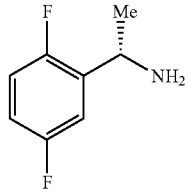 [SMILES: C[C@H](N)c1cc(F)ccc1F]

To (R)—N—((S)-1-(2,5-difluorophenyl)ethyl)-2-methylpropane-2-sulfinamide (1.00 g, 3.83 mmol) was added a 0.4 M solution hydrogen chloride in methanol (10 mL) and the reaction mixture was stirred at ambient temperature for 1 hour. To it was added saturated sodium bicarbonate (100 mL) and the mixture was stirred at ambient temperature for 30 minutes. The mixture was then extracted with ethyl acetate (3×30 mL). The combined organic layers were washed with brine (30 mL), dried over anhydrous sodium sulfate, and filtered. Concentration of the filtrate under reduced pressure provided the title compound as a colorless oil (0.40 g, 66% yield): $^1$H NMR (400 MHz, CDCl$_3$) δ 7.36 (ddd, J=8.8, 5.6, 3.2 Hz, 1H), 7.30-7.17 (m, 2H), 4.74 (q, J=6.8 Hz, 1H), 1.66 (d, J=6.8 Hz, 3H), NH not observed.

Step 4. Preparation of (S)-5-chloro-4-((1-(2,5-difluorophenyl)ethyl)amino)-N-(2,4-dimethoxybenzyl)-2-fluoro-N-(thiazol-2-yl)benzenesulfonamide

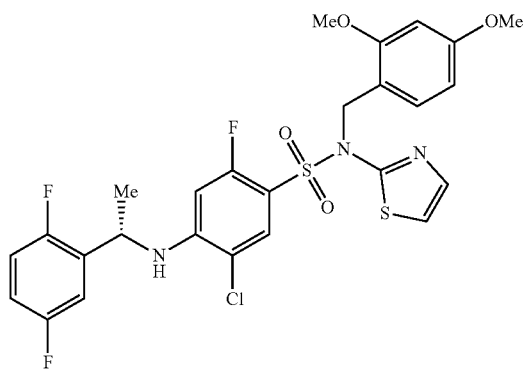 [SMILES: COc1ccc(CN(c2nccs2)S(=O)(=O)c2cc(Cl)c(N[C@@H](C)c3cc(F)ccc3F)cc2F)c(OC)c1]

To a mixture of 5-chloro-N-[(2,4-dimethoxyphenyl)methyl]-2,4-difluoro-N-thiazol-2-yl-benzenesulfonamide (0.30 g, 0.65 mmol) and (S)-1-(2,5-difluorophenyl)ethanamine (0.10 g, 0.65 mmol) in anhydrous dimethyl sulfoxide (5 mL) was added potassium carbonate (0.18 g, 1.3 mmol) and the reaction mixture was stirred at ambient temperature for 12 hours. To it was then added water (80 mL) and the mixture was extracted with ethyl acetate (3×50 mL). The combined organic layers were washed with brine (3×50 mL), dried over anhydrous sodium sulfate, and filtered. Concentration of the filtrate under reduced pressure and purification by preparative thin layer chromatography, eluting with 25% of ethyl acetate in petroleum ether, afforded the title compound as a colorless solid (0.16 g, 41% yield): MS (ES+) m/z 598.2 (M+1), 600.2 (M+1).

Step 5. Preparation of (S)-5-chloro-4-((1-(2,5-difluorophenyl)ethyl)amino)-2-fluoro-N-(thiazol-2-yl)benzenesulfonamide

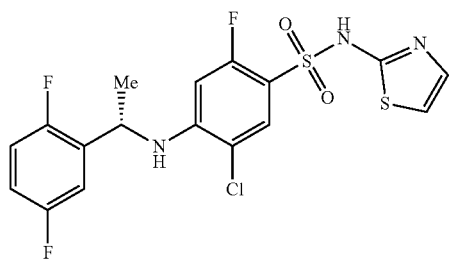 [SMILES: C[C@H](Nc1cc(F)c(S(=O)(=O)Nc2nccs2)cc1Cl)c1cc(F)ccc1F]

To a solution of (S)-5-chloro-4-((1-(2,5-difluorophenyl)ethyl)amino)-N-(2,4-dimethoxybenzyl)-2-fluoro-N-(thiazol-2-yl)benzenesulfonamide (0.16 g, 0.27 mmol) in dichloromethane (2 mL) was added trifluoroacetic acid (0.31 g, 2.70 mmol) and the mixture was stirred at ambient temperature for 1 hour. Water (20 mL) was added and the mixture was extracted with dichloromethane (3×10 mL). The combined organic extracts were washed with brine (3×10 mL), dried over anhydrous sodium sulfate, filtered and concentrated under reduced pressure. Purification of the residue by preparative reverse phase HPLC, using acetonitrile in water containing 0.225% formic acid as eluent, afforded the title compound as a colorless solid (0.068 g, 56% yield): $^1$H NMR (400 MHz, CDCl$_3$) δ 7.88 (d, J=7.2 Hz, 1H), 7.12 (d, J=4.4 Hz, 1H), 7.09-7.01 (m, 1H), 6.98-6.89 (m, 2H), 6.49 (d, J=4.4 Hz, 1H), 6.06 (d, J=12.0 Hz, 1H), 5.09 (d, J=5.6 Hz, 1H), 4.75 (quin, J=6.4 Hz, 1H), 1.62 (d, J=6.8 Hz, 3H), missing sulfonamide N—H signal; MS (ES+) m/z 448.1 (M+1), 450.1 (M+1).

Example 269

Synthesis of (S)-5-chloro-4-((1-(2-fluorophenyl)ethyl)amino)-2-methyl-N-(thiazol-2-yl)benzenesulfonamide

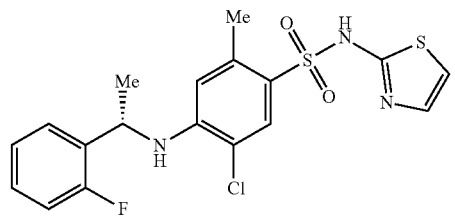 [SMILES: Cc1cc(N[C@@H](C)c2ccccc2F)c(Cl)cc1S(=O)(=O)Nc1nccs1]

Step 1. Preparation of 4-bromo-5-chloro-2-methylbenzenesulfonyl chloride

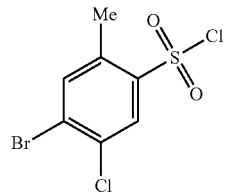

A saturated sulfur dioxide solution was formed by bubbling sulfur dioxide gas into acetic acid (20 mL) at 0° C. for 15 minutes, and copper (II) chloride (0.67 g, 6.8 mmol) was added to it. To a suspension of 4-bromo-5-chloro-2-methylaniline (5.0 g, 23 mmol) in concentrated hydrochloric acid (20.0 mL) was added a solution of sodium nitrite (2.3 g, 34 mmol) in water (10 mL) at 0° C. After stirring for 30 minutes, the reaction mixture was added to the sulfur dioxide solution at 0° C. over a period of 15 minutes. The reaction mixture was then allowed to warm to ambient temperature and stirred for 30 minutes. The residue was poured onto ice-water (30 mL) and the aqueous phase was extracted with ethyl acetate (3×100 mL). The combined organic phase was washed with brine (50 mL), dried over anhydrous sodium sulfate, and filtered. Concentration of the filtrate in vacuo and purification of the residue by column chromatography, eluting with 10% of ethyl acetate in petroleum ether, afforded the title compound as a yellow solid (4.0 g, 58% yield): $^1$H NMR (400 MHz, CDCl$_3$) δ 8.13 (s, 1H), 7.73 (s, 1H), 2.74 (s, 3H).

Step 3. Preparation of 4-bromo-5-chloro-N-(2,4-dimethoxybenzyl)-2-methyl-N-(thiazol-2-yl)benzenesulfonamide

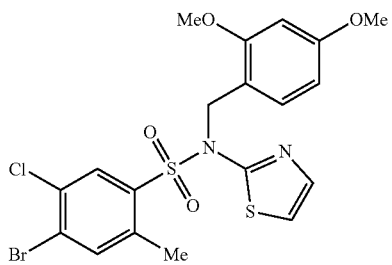 [SMILES: COc1ccc(CN(c2nccs2)S(=O)(=O)c2cc(Cl)c(Br)cc2C)c(OC)c1]

To a mixture of N-(2,4-dimethoxybenzyl)thiazol-2-amine (0.30 g, 1.2 mmol) in anhydrous tetrahydrofuran (10 mL) was added a 1 M solution of lithium bis(trimethylsilyl)amide in tetrahydrofuran (1.7 mL, 1.7 mmol) at −78° C. The mixture was warmed to 0° C. and stirred for 30 minutes. The mixture was then cooled to −78° C. and a solution of 4-bromo-5-chloro-2-methylbenzenesulfonyl chloride (0.40 g, 1.3 mmol) in anhydrous tetrahydrofuran (2 mL) was added to it. The mixture was stirred at −78° C. for 30 minutes, warmed to ambient temperature, and stirred for 11 hours. The mixture was poured into saturated ammonium chloride solution (10 mL) and the aqueous phase was extracted with ethyl acetate (3×30 mL). The combined organic phase was washed with brine (30 mL), dried over anhydrous sodium sulfate, and filtered. Concentration of the filtrate in vacuo and purification of the residue by preparative thin layer chromatography, using 20% of ethyl acetate in petroleum ether as eluent, afforded the title compound as a yellow solid (0.26 g, 26% yield): $^1$H NMR (400 MHz, CDCl$_3$) δ 8.01 (s, 1H), 7.52 (s, 1H), 7.46 (d, J=3.6 Hz, 1H), 7.18 (d, J=8.4 Hz, 1H), 7.04 (d, J=3.6 Hz, 1H), 6.39-6.31 (m, 2H), 5.13 (s, 2H), 3.80-3.67 (m, 6H), 2.46 (s, 3H); MS (ES+) m/z 519.0 (M+1), 521.0 (M+1).

Step 4. Preparation of (S)-5-chloro-N-(2,4-dimethoxybenzyl)-4-((1-(2-fluorophenyl)ethyl)amino)-2-methyl-N-(thiazol-2-yl)benzenesulfonamide

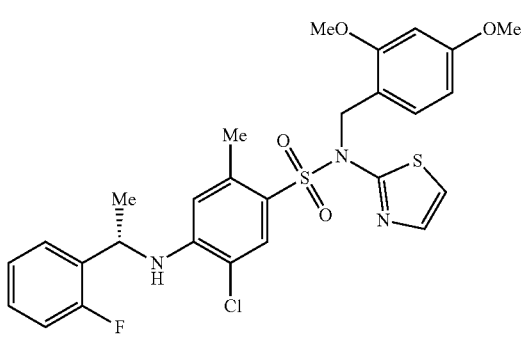 [SMILES: COc1ccc(CN(c2nccs2)S(=O)(=O)c2cc(Cl)c(N[C@@H](C)c3ccccc3F)cc2C)c(OC)c1]

A solution of 4-bromo-5-chloro-N-(2,4-dimethoxybenzyl)-2-methyl-N-(thiazol-2-yl)benzenesulfonamide (0.14 g, 0.27 mmol), (S)-1-(2-fluorophenyl)ethanamine (0.071 g, 0.40 mmol), bis(dibenzylideneacetone)palladium(0) (0.031 g, 0.054 mmol), 4,5-bis(diphenylphosphino)-9,9-dimethylxanthene (0.031 g, 0.054 mmol) and cesium carbonate (0.35 g, 1.1 mmol) in anhydrous toluene (2.0 mL) was degassed by sparging with nitrogen and then heated to 100° C. for 12 hours. The mixture was poured into water (10 mL) and the aqueous phase was extracted with ethyl acetate (3×30 mL). The combined organic phase was washed with brine (30 mL), dried over anhydrous sodium sulfate, and filtered. Concentration of the filtrate in vacuo and purification by preparative thin layer chromatography, eluting with 25% of ethyl acetate in petroleum ether, afforded the title compound as a yellow oil (0.12 g, 77% yield): MS (ES+) m/z 576.1 (M+1), 578.1 (M+1).

Step 5. Preparation of (S)-5-chloro-4-((1-(2-fluorophenyl)ethyl)amino)-2-methyl-N-(thiazol-2-yl)benzenesulfonamide

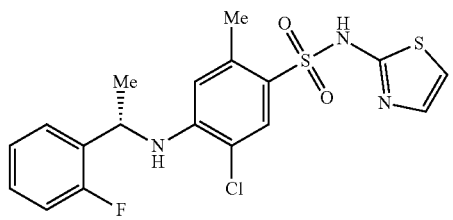 [SMILES: Cc1cc(N[C@@H](C)c2ccccc2F)c(Cl)cc1S(=O)(=O)Nc1nccs1]

To (S)-5-chloro-N-(2,4-dimethoxybenzyl)-4-((1-(2-fluorophenyl)ethyl)amino)-2-methyl-N-(thiazol-2-yl)benzenesulfonamide (0.11 g, 0.19 mmol) was added a 4 M solution of hydrogen chloride in 1,4-dioxane (110 mL, 440 mmol) and the reaction mixture was stirred at ambient temperature for 1 h. Concentration in vacuo and purification of the residue by preparative reverse phase HPLC, using acetonitrile in water containing 0.225% formic acid as eluent, afforded the title compound as a colorless solid (0.038 g, 46% yield): $^1$H NMR (400 MHz, CDCl$_3$) δ 12.41 (s, 1H), 8.01 (s, 1H), 7.27-7.20 (m, 2H), 7.14-7.04 (m, 2H), 7.01 (d, J=4.4 Hz, 1H), 6.43 (d, J=4.4 Hz, 1H), 6.24 (s, 1H), 5.01 (d, J=6.4 Hz, 1H), 4.90 (quin, J=6.4 Hz, 1H), 2.32 (s, 3H), 1.62 (d, J=6.4 Hz, 3H); MS (ES+) m/z 426.1 (M+1), 428.1 (M+1).

Example 270

Synthesis of (R)-5-chloro-4-((1-(5-chloro-2-fluorophenyl)-2,2,2-trifluoroethyl)amino)-2-fluoro-N-(pyrimidin-4-yl)benzenesulfonamide

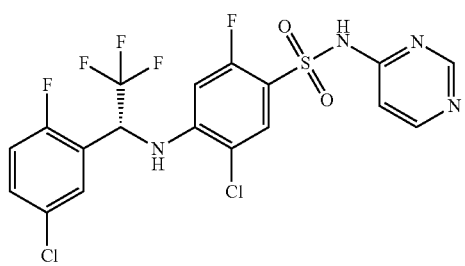 [SMILES: O=S(=O)(Nc1ccncn1)c1cc(Cl)c(N[C@H](c2cc(Cl)ccc2F)C(F)(F)F)cc1F]

Step 1. Preparation of 4-bromo-5-chloro-N-(2,4-dimethoxybenzyl)-2-fluoro-N-(pyrimidin-4-yl)benzenesulfonamide

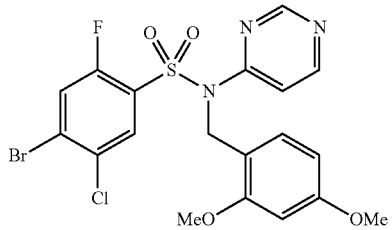 [SMILES: COc1ccc(CN(c2ccncn2)S(=O)(=O)c2cc(Cl)c(Br)cc2F)c(OC)c1]

To a solution of N-(2,4-dimethoxybenzyl)pyrimidin-4-amine (1.65 g, 6.71 mmol) and 1,4-diazabicyclo[2.2.2]octane (1.51 g, 13.43 mmol) in acetonitrile (20 mL) was added a solution of 4-bromo-5-chloro-2-fluorobenzene-1-sulfonyl chloride (3.10 g, 10.07 mmol) in acetonitrile (10 mL) at 0° C. The mixture was stirred at 15° C. for 12 h and then diluted with water (30 mL). The mixture was extracted with ethyl acetate (3×30 mL) and the organic layers were combined. The organic layer was washed with brine (3×10 mL), dried over sodium sulfate, and filtered. The filtrate was concentrated under reduced pressure and the residue was purified by column chromatography eluting with 50% ethyl acetate in petroleum ether to afford the title compound as a yellow solid (2.00 g, 58% yield): $^1$H NMR (400 MHz, CDCl$_3$) δ 8.80 (d, J=0.8 Hz, 1H), 8.49 (d, J=6.0 Hz, 1H), 8.10 (d, J=6.6 Hz, 1H), 7.44 (d, J=9.0 Hz, 1H), 7.21 (d, J=9.0 Hz, 1H), 7.16 (dd, J=5.8, 1.2 Hz, 1H), 6.44-6.39 (m, 2H), 5.23 (s, 2H), 3.78 (d, 6H); MS (ES+) m/z 538 (M+23), 540 (M+23).

Step 1. Preparation of 1-(5-chloro-2-fluorophenyl)-2,2,2-trifluoroethan-1-ol

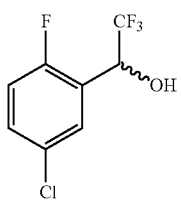

To a mixture of 5-chloro-2-fluorobenzaldehyde (3.00 g, 18.9 mmol) in anhydrous tetrahydrofuran (30 mL) was added trimethyl(trifluoromethyl)silane (3.50 g, 24.6 mmol) and the mixture was stirred at 0° C. for 10 minutes. To it was then added a 1 M solution of tetrabutylammonium fluoride in tetrahydrofuran (0.95 mL, 0.95 mmol) at 0° C. The reaction mixture was allowed to warm to ambient temperature and stirred for 12 hours. The mixture was diluted with water (50 mL) and extracted with ethyl acetate (3×50 mL). The combined organic layers were washed with brine (30 mL), dried over anhydrous sodium sulfate, and filtered. Concentration of the filtrate in vacuo and purification of the residue by column chromatography, eluting with a gradient of 1-2% of ethyl acetate in petroleum ether, provided the title compound as a colorless solid (4.20 g, 97% yield): $^1$H NMR (400 MHz, CDCl$_3$) δ 7.54 (dd, J=6.0, 2.4 Hz, 1H), 7.28 (ddd, J=8.8, 4.4, 2.8 Hz, 1H), 6.98 (t, J=9.2 Hz, 1H), 5.32 (quin, J=6.0 Hz, 1H), 2.76 (d, J=5.2 Hz, 1H).

Step 2. Preparation of 1-(5-chloro-2-fluorophenyl)-2,2,2-trifluoroethan-1-one

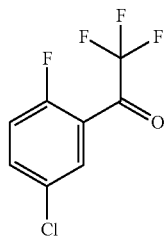 [SMILES: O=C(c1cc(Cl)ccc1F)C(F)(F)F]

To a solution of 1-(5-chloro-2-fluorophenyl)-2,2,2-trifluoroethanol (4.20 g, 18.4 mmol) in ethyl acetate (50 mL) was added 2-iodoxybenzoic acid (15.4 g, 55.1 mmol) in portions. The mixture was heated to reflux for 36 h. After cooling to ambient temperature, the mixture was filtered and the filtrate concentrated in vacuo to provide the title compound as a colorless oil (4.00 g, 96% yield): $^1$H NMR (400 MHz, CDCl$_3$) δ 7.86 (dd, J=5.6, 2.4 Hz, 1H), 7.66 (ddd, J=8.8, 4.0, 2.8 Hz, 1H), 7.23 (dd, J=10.0, 8.8 Hz, 1H).

Step 3. Preparation of (R)—N-(1-(5-chloro-2-fluorophenyl)-2,2,2-trifluoroethylidene)-2-methylpropane-2-sulfinamide

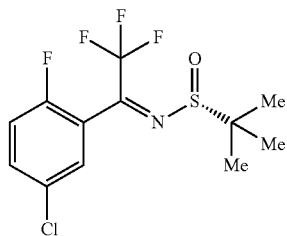 [SMILES: CC(C)(C)[S@@](=O)/N=C(/c1cc(Cl)ccc1F)C(F)(F)F]

To a solution of 1-(5-chloro-2-fluorophenyl)-2,2,2-trifluoroethanone (2.00 g, 8.83 mmol) and (R)-2-methylpropane-2-sulfinamide (1.28 g, 10.6 mmol) in anhydrous diethyl ether (20 mL) was added titanium(IV) isopropoxide (6.27 g, 22.1 mmol) dropwise. The reaction mixture was then heated to 50° C. for 12 hours. After cooling to ambient temperature, the reaction mixture was diluted with water (30 mL) and filtered. The filtrate was extracted with ethyl acetate (3×30 mL). The combined organic layers were washed with brine (10 mL), dried over anhydrous sodium sulfate, and filtered. Concentration of the filtrate in vacuo and purification of the residue by column chromatography, eluting with a gradient of 5 to 20% of ethyl acetate in petroleum ether, afforded the title compound as a colorless solid (1.50 g, 52% yield): $^1$H NMR (400 MHz, CDCl$_3$) δ 7.46 (ddd, J=8.8, 4.4, 2.4 Hz, 1H), 7.34-7.30 (m, 1H), 7.11 (t, J=8.8 Hz, 1H), 1.35 (s, 9H).

Step 4. Preparation of (R)—N—((R)-1-(5-chloro-2-fluorophenyl)-2,2,2-trifluoroethyl)-2-methylpropane-2-sulfinamide

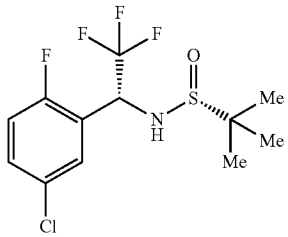 [SMILES: CC(C)(C)[S@@](=O)N[C@H](c1cc(Cl)ccc1F)C(F)(F)F]

To a solution of (R,Z)—N-(1-(5-chloro-2-fluorophenyl)-2,2,2-trifluoroethylidene)-2-methylpropane-2-sulfinamide (1.50 g, 4.55 mmol) and titanium(IV) isopropoxide (1.29 g, 4.55 mmol) in diethyl ether (15 mL) was added sodium borohydride (0.52 mg, 13 mmol) in portions at −78° C. The reaction mixture was stirred at −78° C. for 5 hours. The mixture was then quenched with water (30 mL) and filtered. The filtrate was extracted with ethyl acetate (3×30 mL). The combined organic layers were washed with brine (20 mL), dried over anhydrous sodium sulfate, and filtered. Concentration in vacuo and purification of the residue by column chromatography, eluting with a gradient of 10-25% of ethyl acetate in petroleum ether, provided the title compound as a colorless oil (1.00 g, 66% yield): $^1$H NMR (400 MHz, CDCl$_3$) δ 7.45-7.36 (m, 2H), 7.12 (t, J=9.2 Hz, 1H), 5.29-5.20 (m, 1H), 3.94 (d, J=4.4 Hz, 1H), 1.26 (s, 9H).

Step 5. Preparation of (R)-1-(5-chloro-2-fluorophenyl)-2,2,2-trifluoroethan-1-amine hydrochloride

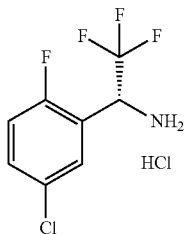 [SMILES: N[C@H](c1cc(Cl)ccc1F)C(F)(F)F ; Cl]

To (R)—N—((R)-1-(5-chloro-2-fluorophenyl)-2,2,2-trifluoroethyl)-2-methylpropane-2-sulfinamide (1.00 g, 3.01 mmol) was added a 4 M solution of hydrogen chloride in methanol (10 mL, 40 mmol) and the mixture was stirred at ambient temperature for 2 hours. The mixture was concentrated in vacuo. The residue was diluted with methanol (1 mL) and purified by recrystallization from methyl tert-butyl ether (30 mL) to give the title compound as a colorless solid (0.63 g, 79% yield): $^1$H NMR (400 MHz, CD$_3$OD) δ 7.75-7.63 (m, 2H), 7.41 (t, J=9.4 Hz, 1H), 5.69 (q, J=7.2 Hz, 1H), exchangeable protons not observed.

Step 6. Preparation of (R)-5-chloro-4-((1-(5-chloro-2-fluorophenyl)-2,2,2-trifluoroethyl)amino)-N-(2,4-dimethoxybenzyl)-2-fluoro-N-(pyrimidin-4-yl)benzenesulfonamide

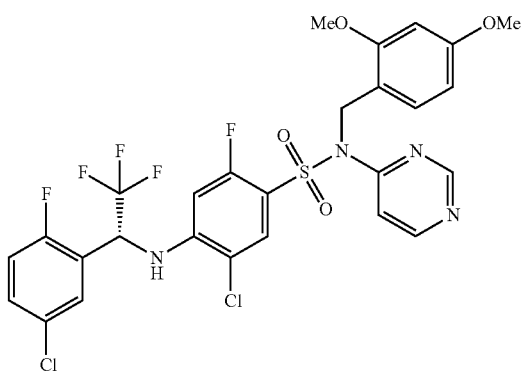 [SMILES: COc1ccc(CN(c2ccncn2)S(=O)(=O)c2cc(Cl)c(N[C@H](c3cc(Cl)ccc3F)C(F)(F)F)cc2F)c(OC)c1]

To a solution of (R)-1-(5-chloro-2-fluorophenyl)-2,2,2-trifluoroethanamine (0.10 g, 0.38 mmol) and 4-bromo-5-chloro-N-(2,4-dimethoxybenzyl)-2-fluoro-N-(pyrimidin-4-yl)benzenesulfonamide (0.16 g, 0.32 mmol) in anhydrous toluene (2.0 mL) was added potassium tert-butoxide (0.14 g, 1.26 mmol) and chloro(2-dicyclohexylphosphino-2',6'-dimethoxy-1,1'-biphenyl)[2-(2'-amino-1,1'-biphenyl)]palladium(II) (0.048 g, 0.063 mmol). The mixture was then heated to 60° C. for 12 h. After cooling to ambient temperature, the reaction mixture was concentrated in vacuo and diluted with water (30 mL). The mixture was extracted with ethyl acetate (3×20 mL). The combined organic extracts were washed with brine (10 mL), dried over anhydrous sodium sulfate, and filtered. Concentration of the filtrate in vacuo and purification of the residue by preparative thin layer chromatography, eluting with 50% of ethyl acetate in petroleum ether, provided the title compound as a yellow oil (0.016 g, 8% yield): $^1$H NMR (400 MHz, CDCl$_3$) δ 8.81 (s, 1H), 8.47 (d, J=6.0 Hz, 1H), 7.97 (d, J=6.8 Hz, 1H), 7.46-7.39 (m, 2H), 7.25 (dd, J=6.0, 1.2 Hz, 1H), 7.23-7.14 (m, 2H), 6.44-6.38 (m, 2H), 6.31 (d, J=11.6 Hz, 1H), 5.62 (d, J=7.6 Hz, 1H), 5.30-5.25 (m, 1H), 5.24 (s, 2H), 3.78 (d, J=4.0 Hz, 6H); MS (ES+) m/z 663.1 (M+1), 665.1 (M+1).

Step 7. Preparation of (R)-5-chloro-4-((1-(5-chloro-2-fluorophenyl)-2,2,2-trifluoroethyl)amino)-2-fluoro-N-(pyrimidin-4-yl)benzenesulfonamide

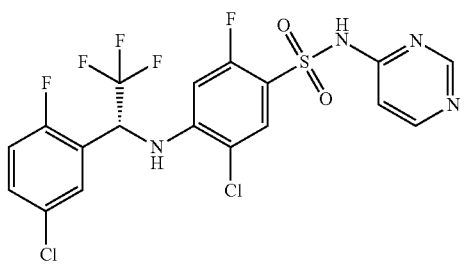 [SMILES: O=S(=O)(Nc1ccncn1)c1cc(Cl)c(N[C@H](c2cc(Cl)ccc2F)C(F)(F)F)cc1F]

To a solution of (R)-5-chloro-4-((1-(5-chloro-2-fluorophenyl)-2,2,2-trifluoroethyl)amino)-N-(2,4-dimethoxybenzyl)-2-fluoro-N-(pyrimidin-4-yl)benzenesulfonamide (0.020 g, 0.030 mmol) in dichloromethane (5 mL) was added trifluoroacetic acid (1.54 g, 13.5 mmol) at ambient temperature and the resulting mixture was stirred for 30 minutes. Concentration in vacuo and purification of the residue by preparative reverse phase HPLC, using acetonitrile in water containing 0.225% formic acid as eluent, afforded the title compound as a colorless solid (0.011 g, 71% yield): $^1$H NMR (400 MHz, CDCl$_3$) δ 8.72 (s, 1H), 8.32 (d, J=6.0 Hz, 1H), 7.89 (d, J=7.2 Hz, 1H), 7.37-7.28 (m, 2H), 7.16 (d, J=5.6 Hz, 1H), 7.07 (t, J=9.2 Hz, 1H), 6.26 (d, J=11.6 Hz, 1H), 5.51 (d, J=7.6 Hz, 1H), 5.23-5.12 (m, 1H), NH not observed; MS (ES+) m/z 513.0 (M+1), 515.0 (M+1).

Example 271

Synthesis of 4-((2-((dimethylamino)methyl)benzyl)amino)-2,6-difluoro-N-(thiazol-4-yl)benzenesulfonamide

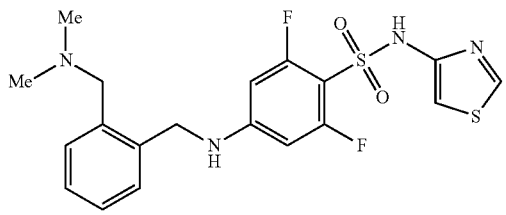 [SMILES: CN(C)Cc1ccccc1CNc1cc(F)c(S(=O)(=O)Nc2cscn2)c(F)c1]

Step 1. Preparation of 2-((dimethylamino)methyl)benzonitrile

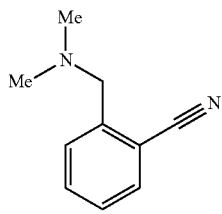 [SMILES: CN(C)Cc1ccccc1C#N]

Following the procedure as described for EXAMPLE 16, Step 1 and making non critical variations as required to replace azetidine with dimethylamine hydrochloride, the title compound was obtained as a yellow oil (0.600 g, 73% yield): $^1$H NMR (400 MHz, CDCl$_3$) δ 7.64 (d, J=7.4 Hz, 1H), 7.60-7.54 (m, 2H), 7.39-7.33 (m, 1H), 3.63 (s, 2H), 2.30 (s, 6H); MS (ES+) m/z 161.0 (M+1).

Step 2. Preparation of 1-(2-(aminomethyl)phenyl)-N,N-dimethylmethanamine

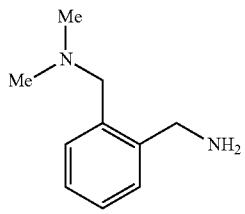 [SMILES: CN(C)Cc1ccccc1CN]

To a mixture of 2-((dimethylamino)methyl)benzonitrile (0.600 g, 3.74 mmol) in concentrated ammonium hydroxide (4 mL) and methanol (20 mL) was added Raney-Ni (0.320 g, 3.74 mmol). The suspension was degassed under vacuum and purged with hydrogen several times. The mixture was stirred under a hydrogen atmosphere (50 psi) at ambient temperature for 12 h. The reaction mixture was filtered and the filtrate concentrated under in vacuo to afford the title compound as a colorless oil (0.300 g, 49% yield): $^1$H NMR (400 MHz, CDCl$_3$) δ 7.19-7.12 (m, 2H), 7.11-7.05 (m, 2H), 3.71 (s, 2H), 3.31 (s, 2H), 2.09 (s, 6H), NH not observed; MS (ES+) m/z 147.9 (M+1-14).

Step 3. Preparation of tert-butyl (4-((2-((dimethylamino)methyl)benzyl)amino)-2,6-difluorophenyl)sulfonyl(thiazol-4-yl)carbamate

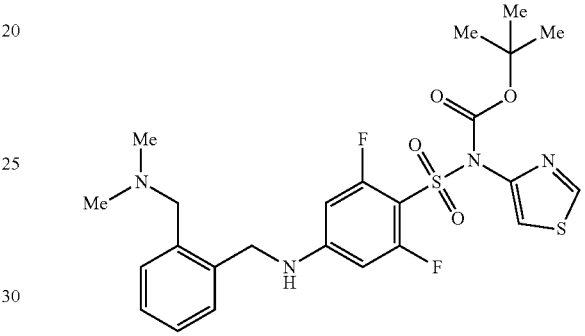

To a solution of tert-butyl thiazol-4-yl((2,4,6-trifluorophenyl)sulfonyl)carbamate (0.721 g, 1.83 mmol) and 1-(2-(aminomethyl)phenyl)-N,N-dimethylmethanamine (0.300 g, 1.83 mmol) in anhydrous N,N-dimethylformamide (10 mL) was added potassium carbonate (0.505 g, 3.66 mmol). The reaction mixture was stirred at ambient temperature for 3 h. To it was then added water (10 mL) and the mixture was extracted with ethyl acetate (3×10 mL). The combined organic layers were washed with brine (3×10 mL), dried over anhydrous sodium sulfate, and filtered. Concentration of the filtrate in vacuo and purification of the residue by preparative thin layer chromatography, eluting with 25% of ethyl acetate in petroleum ether, afforded the title compound as a colorless solid (0.080 g, 8% yield): $^1$H NMR (400 MHz, CDCl$_3$) δ 8.81 (d, J=2.2 Hz, 1H), 7.51 (d, J=2.2 Hz, 1H), 7.37-7.30 (m, 3H), 7.27-7.25 (m, 1H), 6.18 (d, J=11.8 Hz, 2H), 4.34 (s, 2H), 3.47 (s, 2H), 2.30 (s, 6H), 1.40 (s, 9H), NH not observed; MS (ES+) m/z 438.9 (M−99).

Step 4. Preparation of 4-((2-((dimethylamino)methyl)benzyl)amino)-2,6-difluoro-N-(thiazol-4-yl)benzenesulfonamide

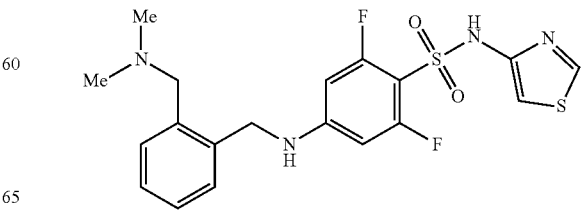

381

To (4-((2-((dimethylamino)methyl)benzyl)amino)-2,6-difluorophenyl)sulfonyl(thiazol-4-yl) carbamate (0.080 g, 0.148 mmol) was added a 4 M solution of hydrogen chloride in dioxane (2 mL) and the reaction mixture was stirred at ambient temperature for 8 h. The reaction mixture was then concentrated in vacuo and the residue was purified by preparative reverse-phase HPLC, using acetonitrile in water containing 0.225% of formic acid as eluent, to afford the title compound as a colorless solid (0.012 g, 19% yield): $^1$H NMR (400 MHz, CD$_3$OD) δ 8.74 (d, J=2.2 Hz, 1H), 7.49-7.35 (m, 4H), 6.97 (d, J=2.2 Hz, 1H), 6.30-6.23 (m, 2H), 4.45 (s, 2H), 4.04 (s, 2H), 2.64 (s, 6H), NH not observed; MS (ES+) m/z 439.0 (M+1).

Example 272

Synthesis of 4-((2-(azetidin-1-ylmethyl)benzyl)amino)-2,6-difluoro-N-(thiazol-4-yl)benzenesulfonamide formate

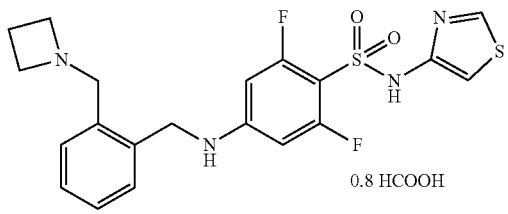 [SMILES: O=S(=O)(Nc1cscn1)c1c(F)cc(NCc2ccccc2CN2CCC2)cc1F]

A solution of 2,4,6-trifluoro-N-(thiazol-4-yl)benzenesulfonamide (1.00 g, 2.54 mmol), (2-(azetidin-1-ylmethyl)phenyl)methanamine (0.446 g, 2.53 mmol), and N,N-diisopropylethylamine (1.0 mL, 6.1 mmol) in anhydrous dimethylsulfoxide (10 mL) was stirred at ambient temperature for 2 h. To the mixture was then added saturated ammonium chloride (10 mL) and the mixture was extracted with ethyl acetate (3×10 mL). The combined organic phase was washed with brine (10 mL), dried over anhydrous sodium sulfate, and filtered. Concentration of the filtrate in vacuo provided a residue which was dissolved in dichloromethane (5 mL). To it was then added trifluoroacetic acid (2 mL) and the reaction mixture was stirred at ambient temperature for 18 h. The reaction mixture was concentrated in vacuo and the residue purified by preparative reverse-phase HPLC, using acetonitrile in water containing 0.05% formic acid as eluent, to afford the title compound as a colorless solid (0.128 g, 11% yield): $^1$H-NMR (300 MHz, DMSO-d$_6$) δ 8.89 (d, J=2.2 Hz, 1H), 8.16 (s, 0.8H), 7.65-7.63 (m, 1H), 7.30-7.29 (m, 1H), 7.27-7.21 (m, 3H), 6.88 (d, J=2.1 Hz, 1H), 6.37 (d, J=12.6 Hz, 2H), 4.39 (s, 2H), 3.65 (s, 2H), 3.22 (t, J=7.1 Hz, 4H), 2.07-2.00 (m, 2H), NH and COOH not observed; MS (ES+) m/z 451.1 (M+1).

Example 273

Synthesis of (S)-4-((1-(2,5-difluorophenyl)ethyl)amino)-N-(pyrimidin-4-yl)-3-(trifluoromethyl)benzenesulfonamide

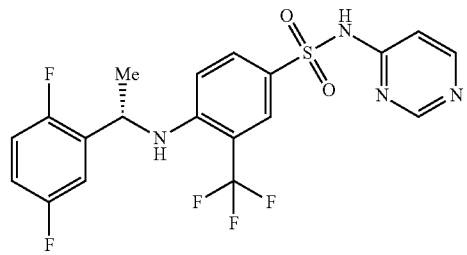 [SMILES: C[C@H](Nc1ccc(S(=O)(=O)Nc2ccncn2)cc1C(F)(F)F)c1cc(F)ccc1F]

Step 1. Preparation of N-(2,4-dimethoxybenzyl)-4-fluoro-N-(pyrimidin-4-yl)-3-(trifluoromethyl)benzenesulfonamide

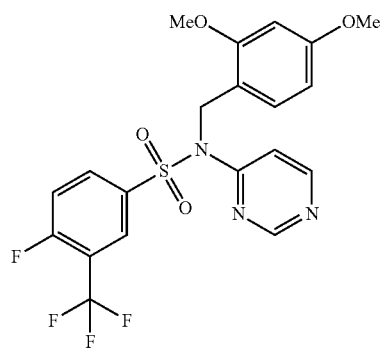 [SMILES: COc1ccc(CN(c2ccncn2)S(=O)(=O)c2ccc(F)c(C(F)(F)F)c2)c(OC)c1]

To a solution of N-(2,4-dimethoxybenzyl)pyrimidin-4-amine (0.70 g, 2.80 mmol) and 1,4-diazabicyclo[2.2.2]octane (0.64 g, 5.70 mmol) in anhydrous acetonitrile (30 mL) was added 4-fluoro-3-(trifluoromethyl)benzenesulfonyl chloride (1.50 g, 5.70 mmol) dropwise at 0° C. The reaction mixture was allowed to warm to ambient temperature and stirred for 12 h. The reaction mixture was then filtered and the filtrate concentrated in vacuo. Concentration of the filtrate in vacuo and purification of the residue by column chromatography, eluting with 10% of ethyl acetate in petroleum ether, provided the title compound as a colorless solid (0.90 g, 67% yield): $^1$H NMR (400 MHz, CDCl$_3$) δ 8.86 (d, J=0.8 Hz, 1H), 8.53 (d, J=6.0 Hz, 1H), 8.08-8.22 (m, 2H), 7.27-7.34 (m, 1H), 7.10-7.17 (m, 2H), 6.41 (dd, J=8.4, 2.4 Hz, 1H), 6.37 (d, J=2.4 Hz, 1H), 5.17 (s, 2H), 3.78 (s, 3H), 3.65 (s, 3H).

Step 2. Preparation of (S)-4-((1-(2,5-difluorophenyl)ethyl)amino)-N-(2,4-dimethoxybenzyl)-N-(pyrimidin-4-yl)-3-(trifluoromethyl)benzenesulfonamide

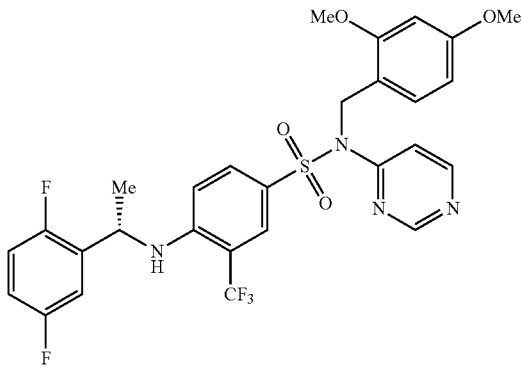 [SMILES: COc1ccc(CN(c2ccncn2)S(=O)(=O)c2ccc(N[C@@H](C)c3cc(F)ccc3F)c(C(F)(F)F)c2)c(OC)c1]

To a solution of N-(2,4-dimethoxybenzyl)-4-fluoro-N-(pyrimidin-4-yl)-3-(trifluoromethyl)benzenesulfonamide (0.40 g, 0.85 mmol) and (S)-1-(2,5-difluorophenyl)ethanamine hydrochloride (0.20 g, 1.00 mmol) in anhydrous N,N-dimethylformamide (5 mL) was added potassium carbonate (0.47 g, 3.3 mmol). The mixture was stirred at ambient temperature for 12 h. The reaction was quenched by addition of water (50 mL) and extracted with ethyl acetate (3×40 mL). The combined organic layers were concentrated under reduced pressure to give a residue, which was purified by preparatory thin layer chromatography, eluting with 33% ethyl acetate in petroleum ether, to obtain the title compound as a colorless solid (0.090 g, 17% yield): MS (ES+) m/z 609.1 (M+1).

Step 2. Preparation of (S)-4-((1-(2,5-difluorophenyl)ethyl)amino)-N-(pyrimidin-4-yl)-3-(trifluoromethyl)benzenesulfonamide

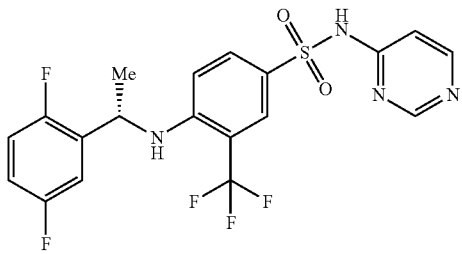 [SMILES: C[C@H](Nc1ccc(S(=O)(=O)Nc2ccncn2)cc1C(F)(F)F)c1cc(F)ccc1F]

To a mixture of (S)-4-((1-(2,5-difluorophenyl)ethyl)amino)-N-(2,4-dimethoxybenzyl)-N-(pyrimidin-4-yl)-3-(trifluoromethyl)benzenesulfonamide (0.080 g, 0.13 mmol) in dichloromethane (5 mL) was added trifluoroacetic acid (1 mL) and the reaction mixture was stirred at ambient temperature for 2 h. The reaction mixture was concentrated under reduced pressure, diluted with methanol (1 mL) and filtered. The filtrate was concentrated in vacuo to afford a residue which was purified by reverse phase HPLC, eluting with a gradient of acetonitrile in water (containing 0.225% of formic acid), to afford the title compound as a colorless solid (0.018 g, 29% yield): $^1$H NMR (400 MHz, CDCl$_3$) δ 8.87 (s, 1H), 8.50 (d, J=6.0 Hz, 1H), 8.06 (d, J=2.0 Hz, 1H), 7.80 (dd, J=8.8, 2.0 Hz, 1H), 7.23 (d, J=5.6 Hz, 1H), 7.08 (td, J=9.2, 4.4 Hz, 1H), 6.90-7.00 (m, 2H), 6.53 (d, J=8.8 Hz, 1H), 5.17 (br s, 1H), 4.83-4.96 (m, 1H), 1.63 (d, J=6.8 Hz, 3H), NH not observed; MS (ES+) m/z 459.0 (M+1).

Example 274

Synthesis of (S)-4-((1-(2,5-difluorophenyl)ethyl)amino)-N-(thiazol-4-yl)-3-(trifluoromethyl)benzenesulfonamide

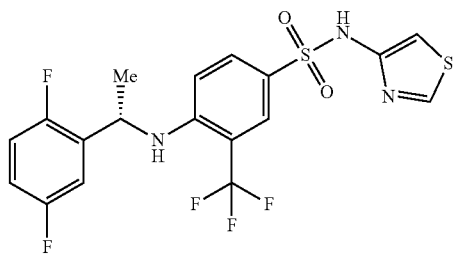 [SMILES: C[C@H](Nc1ccc(S(=O)(=O)Nc2cscn2)cc1C(F)(F)F)c1cc(F)ccc1F]

Step 1. Preparation tert-butyl ((4-bromo-3-(trifluoromethyl)phenyl)sulfonyl)(thiazol-4-yl)carbamate

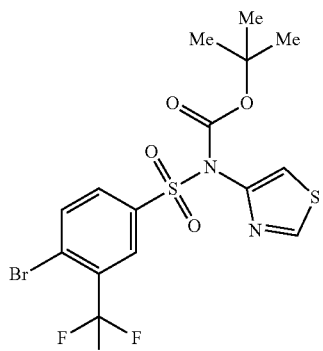

To a solution of tert-butyl thiazol-4-ylcarbamate (1.00 g, 4.99 mmol) in anhydrous tetrahydrofuran (15 mL) was added a 1 M solution of lithium bis(trimethylsilyl)amide in tetrahydrofuran (6.99 mL, 6.99 mmol) dropwise at −78° C. The reaction mixture was warmed to 0° C., stirred for 30 minutes, and cooled to −78° C. To it was then added a solution of 4-bromo-3-(trifluoromethyl)benzenesulfonyl chloride (2.26 g, 6.99 mmol) in tetrahydrofuran (8 mL) at −78° C. The reaction mixture was stirred at ambient temperature for 2 h, and then diluted with water (50 mL) and extracted with ethyl acetate (3×50 mL). The combined organic layers were washed with brine (20 mL), dried over anhydrous sodium sulfate, and filtered. Concentration of the filtrate in vacuo and purification of the residue by reverse phase HPLC, eluting with acetonitrile in water (containing 0.225% formic acid), provided the title compound as a yellow solid (1.10 g, 45% yield): $^1$H NMR (400 MHz, CDCl$_3$) δ 8.81 (d, J=2.0 Hz, 1H), 8.48 (d, J=2.0 Hz, 1H), 8.20 (dd, J=8.4, 2.0 Hz, 1H), 7.96 (d, J=8.4 Hz, 1H), 7.58 (d, J=2.0 Hz, 1H), 1.37 (s, 9H); MS (ES+) m/z 387.0 (M−99), 389.0 (M−99).

Step 2. Preparation of tert-butyl (S)-((4-((1-(2,5-difluorophenyl)ethyl)amino)-3-(trifluoromethyl)phenyl)sulfonyl)(thiazol-4-yl)carbamate

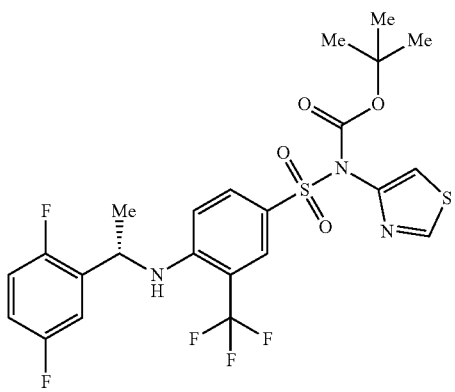 [SMILES: C[C@H](Nc1ccc(S(=O)(=O)N(C(=O)OC(C)(C)C)c2cscn2)cc1C(F)(F)F)c1cc(F)ccc1F]

To a solution of tert-butyl (4-bromo-3-(trifluoromethyl)phenyl)sulfonyl(thiazol-4-yl)carbamate (0.20 g, 0.41 mmol), (S)-1-(2,5-difluorophenyl)ethanamine hydrochloride (0.095 g, 0.49 mmol) and potassium tert-butoxide (0.18 g, 1.64 mmol) in anhydrous tetrahydrofuran (3 mL) was added chloro(2-dicyclohexylphosphino-2',6'-di-i-propoxy-1,1'-biphenyl)[2-(2-aminoethylphenyl)]palladium(II) methyl-t-butylether adduct (0.062 g, 0.082 mmol). The mixture was heated to 80° C. for 12 h, and then concentrated in vacuo. The residue was purified by preparative thin layer chromatography, eluting with 25% of ethyl acetate in petroleum ether, to afford the title compound as a yellow oil (0.10 g, 43% yield): $^1$H NMR (400 MHz, CDCl$_3$) δ 8.78 (d, J=2.0 Hz, 1H), 8.24 (d, J=2.0 Hz, 1H), 8.00 (dd, J=9.2, 2.0 Hz, 1H), 7.51 (d, J=2.0 Hz, 1H), 7.13-7.04 (m, 1H), 7.00-6.90 (m, 2H), 6.57 (d, J=8.6 Hz, 1H), 5.20 (d, J=4.4 Hz, 1H), 4.97 (q, J=6.4 Hz, 1H), 1.65 (d, J=6.4 Hz, 3H), 1.33 (s, 9H).

Step 2. Preparation of (S)-4-((1-(2,5-difluorophenyl)ethyl)amino)-N-(thiazol-4-yl)-3-(trifluoromethyl)benzenesulfonamide

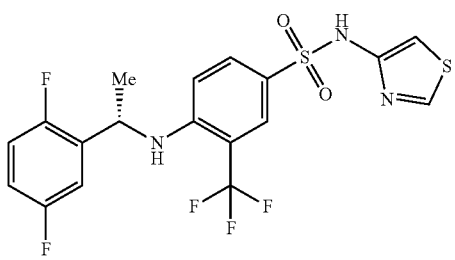 [SMILES: C[C@H](Nc1ccc(S(=O)(=O)Nc2cscn2)cc1C(F)(F)F)c1cc(F)ccc1F]

To (S)-tert-butyl(4-((1-(2,5-difluorophenyl)ethyl)amino)-3-(trifluoromethyl) phenyl)sulfonyl-(thiazol-4-yl)carbamate (0.10 g, 0.18 mmol) was added a 4 M solution of hydrogen chloride in 1,4-dioxane (8 mL) and the reaction mixture was stirred at ambient temperature for 12 h. Concentration in vacuo and purification of the residue by preparative reverse-phase HPLC, eluting with a gradient of acetonitrile in water (containing 0.225% of formic acid), afforded the title compound as a colorless solid (0.047 g, 54% yield): $^1$H NMR (400 MHz, CDCl$_3$) δ 9.06 (s, 1H), 8.66 (d, J=2.0 Hz, 1H), 7.90 (d, J=2.0 Hz, 1H), 7.64 (dd, J=8.4, 2.0 Hz, 1H), 7.10-7.04 (m, 1H), 7.03 (d, J=2.0 Hz, 1H), 6.99-6.88 (m, 2H), 6.43 (d, J=8.8 Hz, 1H), 5.07 (d, J=4.0 Hz, 1H), 4.93-4.81 (m, 1H), 1.61 (d, J=6.4 Hz, 3H).

Example 275

Synthesis of (S)-4-((1-(5-chloro-2-fluorophenyl)ethyl)amino)-2-fluoro-5-methyl-N-(pyrimidin-4-yl)benzenesulfonamide

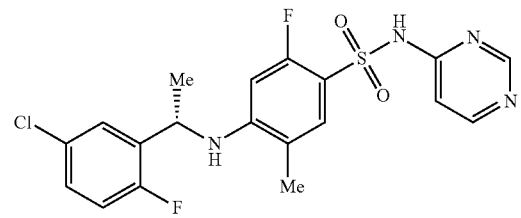 [SMILES: Cc1cc(S(=O)(=O)Nc2ccncn2)c(F)cc1N[C@@H](C)c1cc(Cl)ccc1F]

Step 1. Preparation of 4-bromo-N-(2,4-dimethoxybenzyl)-2-fluoro-5-methyl-N-(pyrimidin-4-yl)benzenesulfonamide

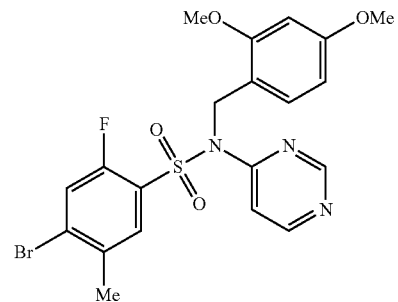 [SMILES: COc1ccc(CN(c2ccncn2)S(=O)(=O)c2cc(C)c(Br)cc2F)c(OC)c1]

To a mixture of N-(2,4-dimethoxybenzyl)pyrimidin-4-amine (3.00 g, 12.20 mmol) and 1,4-diazabicyclo[2.2.2]octane (2.74 g, 24.5 mmol) in acetonitrile (30 mL) was added a solution of 4-bromo-2-fluoro-5-methylbenzenesulfonyl chloride (5.28 g, 18.40 mmol) in acetonitrile (2 mL) at 0° C. The reaction mixture was stirred at 0° C. for 30 minutes and then at ambient temperature for 12 h. The reaction mixture was concentrated in vacuo and the residue was purified by column chromatography, eluting with a gradient of 10 to 30% of ethyl acetate in petroleum ether, to afford the title compound as a yellow oil (4.82 g, 79% yield): $^1$H NMR (400 MHz, CDCl$_3$) δ 8.78 (s, 1H), 8.46 (d, J=5.8 Hz, 1H), 7.87 (d, J=7.2 Hz, 1H), 7.36 (d, J=9.4 Hz, 1H), 7.22 (dd, J=5.6, 4.8 Hz, 2H), 6.43-6.40 (m, 2H), 5.25 (s, 2H), 3.79 (s, 3H), 3.78 (s, 3H), 2.44 (s, 3H); MS (ES+) m/z 496.0 (M+1).

Step 2. Preparation of (S)-4-((1-(5-chloro-2-fluoro-phenyl)ethyl)amino)-N-(2,4-dimethoxybenzyl)-2-fluoro-5-methyl-N-(pyrimidin-4-yl)benzenesulfonamide

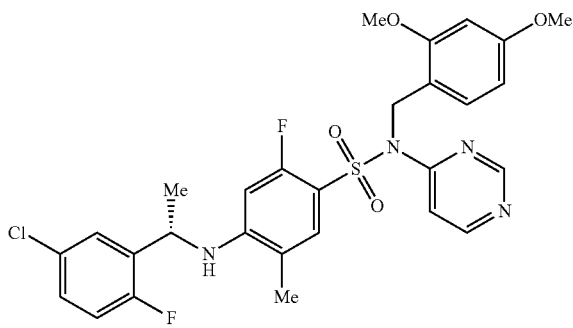 [SMILES: COc1ccc(CN(c2ccncn2)S(=O)(=O)c2cc(C)c(N[C@@H](C)c3cc(Cl)ccc3F)cc2F)c(OC)c1]

A mixture of 4-bromo-N-(2,4-dimethoxybenzyl)-2-fluoro-5-methyl-N-(pyrimidin-4-yl)benzenesulfonamide (2.00 g, 4.03 mmol), (S)-1-(5-chloro-2-fluorophenyl)ethanamine hydrochloride (1.27 g, 6.05 mmol), bis(dibenzylideneacetone)palladium(0) (0.46 g, 0.81 mmol), 4,5-bis(diphenylphosphino)-9,9-dimethylxanthene (0.47 g, 0.81 mmol) and cesium carbonate (5.25 g, 16.10 mmol) in anhydrous toluene (20 mL) was degassed and then heated to 100° C. for 12 hours. The mixture was poured into ice-water (20 mL) and extracted with ethyl acetate (3×30 mL). The combined organic extracts were washed with brine (20 mL), dried over anhydrous sodium sulfate, and filtered. Concentration of the filtrate in vacuo and purification of the residue by preparative thin layer chromatography, eluting with 25% of ethyl acetate in petroleum ether, afforded the title compound as a yellow oil (2.37 g, quantitative yield): $^1$H NMR (400 MHz, CDCl$_3$) δ 8.76 (s, 1H), 8.40 (d, J=5.8 Hz, 1H), 7.62 (d, J=7.8 Hz, 1H), 7.33 (d, J=6.2 Hz, 1H), 7.25-7.16 (m, 3H), 7.04 (t, J=9.2 Hz, 1H), 6.40-6.38 (m, 2H), 5.98 (d, J=13.0 Hz, 1H), 5.25 (d, J=2.8 Hz, 2H), 4.73 (q, J=6.4 Hz, 1H), 4.40 (d, J=5.2 Hz, 1H), 3.77 (s, 3H), 3.76 (s, 3H), 2.22 (s, 3H), 1.60 (d, J=6.6 Hz, 3H); MS (ES+) m/z 589.1 (M+1).

Step 3. Preparation of (S)-4-((1-(5-chloro-2-fluorophenyl)ethyl)amino)-2-fluoro-5-methyl-N-(pyrimidin-4-yl)benzenesulfonamide

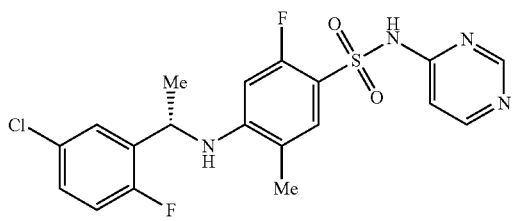 [SMILES: Cc1cc(S(=O)(=O)Nc2ccncn2)c(F)cc1N[C@@H](C)c1cc(Cl)ccc1F]

Following the procedure as described in Example 7, step 2 and making non-critical variations to replace (S)-4-((1-(3-bromophenyl)ethyl)amino)-5-chloro-N-(2,4-dimethoxybenzyl)-2-fluoro-N-(thiazol-2-yl)benzenesulfonamide with (S)-4-((1-(5-chloro-2-fluorophenyl)ethyl)amino)-N-(2,4-dimethoxybenzyl)-2-fluoro-5-methyl-N-(pyrimidin-4-yl)benzenesulfonamide, the title compound was afforded as a colorless solid (0.83 g, 79% yield): $^1$H NMR (400 MHz, CDCl$_3$) δ 11.80 (br s, 1H), 8.90 (s, 1H), 8.41 (d, J=6.0 Hz, 1H), 7.64 (d, J=8.0 Hz, 1H), 7.27-7.17 (m, 3H), 7.02 (t, J=9.2 Hz, 1H), 6.01 (d, J=12.4 Hz, 1H), 4.73 (q, J=6.4 Hz, 1H), 4.41 (d, J=5.4 Hz, 1H), 2.23 (s, 3H), 1.60 (d, J=6.8 Hz, 3H).

Example 276

Synthesis of (S)-4-((1-(2-chloro-5-fluorophenyl)propyl)amino)-2,6-difluoro-N-(pyrimidin-4-yl)benzenesulfonamide

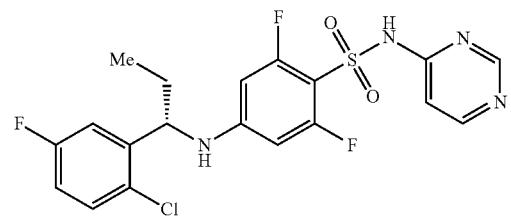 [SMILES: CC[C@H](Nc1cc(F)c(S(=O)(=O)Nc2ccncn2)c(F)c1)c1cc(F)ccc1Cl]

Step 1. Preparation of N-(2,4-dimethoxybenzyl)-2,4,6-trifluoro-N-(pyrimidin-4-yl)benzenesulfonamide

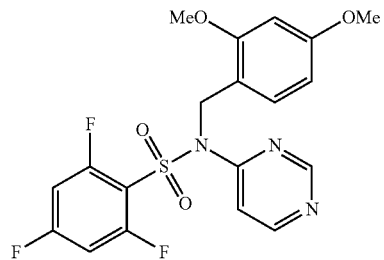 [SMILES: COc1ccc(CN(c2ccncn2)S(=O)(=O)c2c(F)cc(F)cc2F)c(OC)c1]

To a mixture of N-(2,4-dimethoxybenzyl)pyrimidin-4-amine (1.12 g, 4.56 mmol) and 1,4-diazabicyclo[2.2.2]octane (1.02 g, 9.11 mmol) in anhydrous acetonitrile (2 mL) was added a solution of 2,4,6-trifluorobenzenesulfonyl chloride (2.10 g, 9.11 mmol) in anhydrous acetonitrile (1 mL) at 0° C. The reaction mixture was allowed to warm to ambient temperature and stirred for 10 h. To it was then added water (15 mL) and ethyl acetate (100 mL). The organic layer was washed with brine (2×30 mL), dried over anhydrous sodium sulfate, and filtered. Concentration of the filtrate in vacuo and purification of the residue by column chromatography, eluting with 33% of ethyl acetate in petroleum ether, provided the title compound as a yellow solid (0.35 g, 17% yield): $^1$H NMR (400 MHz, CDCl$_3$) δ 8.79 (s, 1H), 8.48-8.46 (d, J=5.6 Hz, 1H), 7.26-7.24 (d, J=8.0 Hz, 1H), 7.07-7.06 (d, J=5.6 Hz, 1H), 6.81-6.76 (t, J=8.4 Hz, 2H), 6.47-6.43 (m, 2H), 5.26 (s, 2H), 3.84 (s, 3H), 3.79 (s, 3H).

389

Step 2. Preparation of (S)-4-((1-(2-chloro-5-fluoro-phenyl)propyl)amino)-N-(2,4-dimethoxybenzyl)-2,6-difluoro-N-(pyrimidin-4-yl)benzenesulfonamide

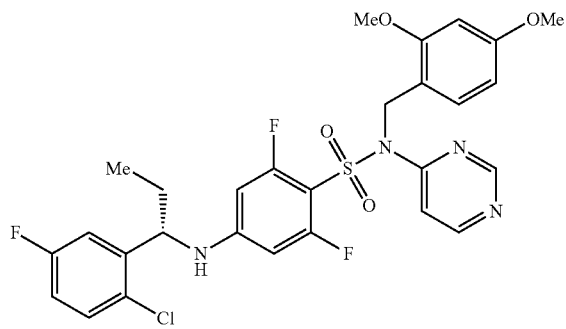 [SMILES: CC[C@H](Nc1cc(F)c(S(=O)(=O)N(Cc2ccc(OC)cc2OC)c2ccncn2)c(F)c1)c1cc(F)ccc1Cl]

A solution of N-(2,4-dimethoxybenzyl)-2,4,6-trifluoro-N-(pyrimidin-4-yl)benzenesulfonamide (0.17 g, 0.39 mmol), (S)-1-(2-chloro-5-fluorophenyl)propan-1-amine (0.073 g, 0.39 mmol) and cesium carbonate (0.19 g, 0.58 mmol) in anhydrous N,N-dimethylformamide (2 mL) was heated to 80° C. for 3 h. After cooling to ambient temperature, the reaction mixture was quenched by addition of water (10 mL), and extracted with ethyl acetate (50 mL). The organic extract was washed with brine (10 mL), dried over anhydrous sodium sulfate, and filtered. Concentration of the filtrate in vacuo and purification of the residue by preparative thin layer chromatography, eluting with 33% of petroleum ether in ethyl acetate, afforded the title compound as a colorless solid (0.070 g, 30% yield): MS (ES+) m/z 607.0 (M+1).

Step 2. Preparation of (S)-4-((1-(2-chloro-5-fluoro-phenyl)propyl)amino)-2,6-difluoro-N-(pyrimidin-4-yl)benzenesulfonamide

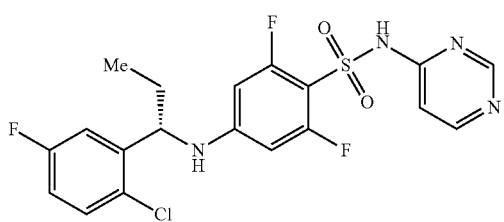 [SMILES: CC[C@H](Nc1cc(F)c(S(=O)(=O)Nc2ccncn2)c(F)c1)c1cc(F)ccc1Cl]

Following the procedure as described in Example 2, Step 3 and making non-critical variations to replace (S)-5-chloro-N-(2,4-dimethoxybenzyl)-2-fluoro-4-((1-(naphthalen-1-yl)ethyl)amino)-N-(thiazol-2-yl)benzenesulfonamide with (S)-4-((1-(2-chloro-5-fluorophenyl)propyl)amino)-N-(2,4-dimethoxybenzyl)-2,6-difluoro-N-(pyrimidin-4-yl)benzenesulfonamide, the title compound was afforded as a colorless solid (0.028 g, 52% yield): $^1$H NMR (400 MHz, CD$_3$OD) δ 8.57 (s, 1H), 8.31 (d, J=6.0 Hz, 1H), 7.44 (dd, J=4.8, 8.8 Hz, 1H), 7.07-7.00 (m, 3H), 6.07-6.04 (d, J=12.4 Hz, 2H), 4.65-4.62 (t, J=6.4 Hz, 1H), 1.87-1.75 (m, 2H), 1.04-1.00 (t, J=7.6 Hz, 3H), exchangeable protons not observed; MS (ES+) m/z 457.1 (M+1).

Example 277

Synthesis of (S)-5-chloro-4-((1-(2-chlorophenyl)propyl)amino)-2-fluoro-N-(pyrimidin-4-yl)benzenesulfonamide 2,2,2-trifluoroacetate

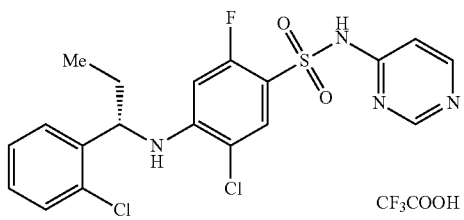 [SMILES: CC[C@H](Nc1cc(F)c(S(=O)(=O)Nc2ccncn2)cc1Cl)c1ccccc1Cl ; "CF3COOH"]

CF$_3$COOH

Step 1. Preparation of 5-chloro-N-(2,4-dimethoxy-benzyl)-2,4-difluoro-N-(pyrimidin-4-yl)benzene-sulfonamide

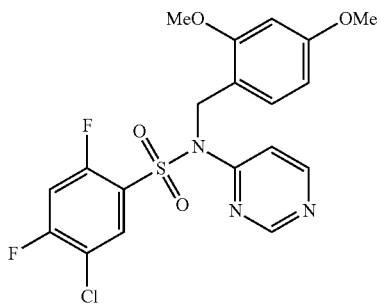 [SMILES: COc1ccc(CN(c2ccncn2)S(=O)(=O)c2cc(Cl)c(F)cc2F)c(OC)c1]

Following the procedure as described in EXAMPLE 191, Step 2, and making non-critical variations as required to replace 3-chloro-2,4-difluorobenzenesulfonyl chloride with 5-chloro-2,4-difluorobenzenesulfonyl chloride, the title compound was obtained as a colorless solid (0.9 g, 35% yield): MS (ES+) m/z 456.1 (M+1), 458.1 (M+1).

Step 2. Preparation of (S)-5-chloro-4-((1-(2-chloro-phenyl)propyl)amino)-N-(2,4-dimethoxybenzyl)-2-fluoro-N-(pyrimidin-4-yl)benzenesulfonamide

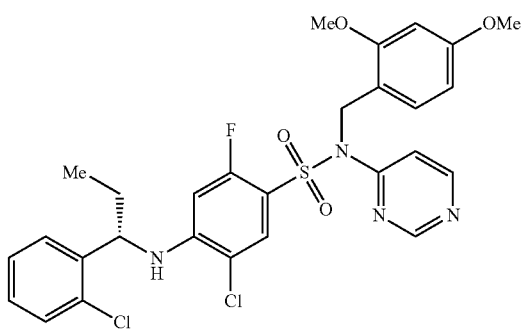 [SMILES: CC[C@H](Nc1cc(F)c(S(=O)(=O)N(Cc2ccc(OC)cc2OC)c2ccncn2)cc1Cl)c1ccccc1Cl]

A mixture of 5-chloro-N-(2,4-dimethoxybenzyl)-2,4-difluoro-N-(pyrimidin-4-yl)benzenesulfonamide (0.225 g, 0.492 mmol), (S)-1-(2-chlorophenyl)propan-1-amine (0.111 g, 0.54 mmol), and potassium carbonate (0.169 g, 1.23 mmol) in anhydrous dimethyl sulfoxide (4 mL) was heated to 65° C. for 3 h. After cooling to ambient temperature, saturated ammonium chloride (20 mL) was added to it and the mixture was extracted with ethyl acetate (2×20 mL). The combined organic phase was washed with brine (10 mL), dried over anhydrous sodium sulfate, and filtered. Concentration of the filtrate in vacuo and purification of the residue by column chromatography, eluting with a gradient of 0-60% ethyl acetate in hexanes, afforded the title compound as a yellow oil (0.140 g, 47% yield): MS (ES+) m/z 605.0 (M+1), 607.0 (M+1).

Step 3. Preparation of (S)-5-chloro-4-((1-(2-chlorophenyl)propyl)amino)-2-fluoro-N-(pyrimidin-4-yl)benzenesulfonamide 2,2,2-trifluoroacetate

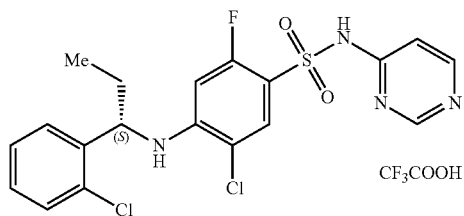

To a mixture of (S)-5-chloro-4-((1-(2-chlorophenyl)propyl)amino)-N-(2,4-dimethoxybenzyl)-2-fluoro-N-(pyrimidin-4-yl)benzenesulfonamide (0.140 g, 0.231 mmol) in dichloromethane (4 mL) was added trifluoroacetic acid (2 mL) and the mixture was stirred at ambient temperature for 1 h and then concentrated in vacuo. The residue was purified by column chromatography, eluting with a gradient of 0 to 60% of ethyl acetate (containing 0.1% of trifluroracetic acid) in hexanes, to provide the title compound as a colorless foam (0.089 g, 85% yield): $^1$H-NMR (300 MHz, DMSO-$d_6$) δ 8.59 (s, 1H), 8.29 (d, J=6.1 Hz, 1H), 7.73 (d, J=7.4 Hz, 1H), 7.51 (dd, J=7.5, 1.9 Hz, 1H), 7.45 (dd, J=7.6, 1.6 Hz, 1H), 7.34-7.23 (m, 2H), 6.95 (d, J=6.3 Hz, 1H), 6.81 (d, J=7.0 Hz, 1H), 6.12 (d, J=13.1 Hz, 1H), 4.67 (q, J=6.9 Hz, 1H), 2.10-1.95 (m, 1H), 1.87-1.73 (m, 1H), 0.94 (t, J=7.3 Hz, 3H), NH and COOH not observed; $^{19}$F NMR (282 MHz, DMSO-$d_6$) δ −74.8 (s, 3F), −109.6 (s, 1F); MS (ES+) m/z 455.0 (M+1), 457.0 (M+1).

Example 278

Synthesis of (S)-4-((2-(1-(azetidin-1-yl)ethyl)-6-fluorobenzyl)amino)-2,6-difluoro-N-(thiazol-4-yl)benzenesulfonamide formate

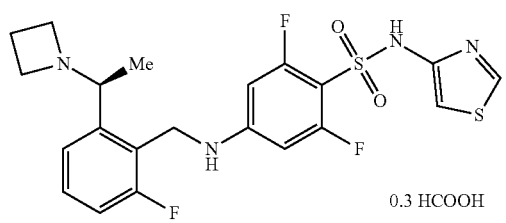 [SMILES: C[C@@H](c1cccc(F)c1CNc1cc(F)c(S(=O)(=O)Nc2cscn2)c(F)c1)N1CCC1]

Step 1. Preparation of (2-bromo-6-fluorophenyl)methanol

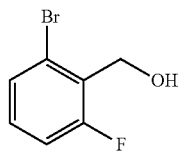

To a solution of 2-bromo-6-fluorobenzaldehyde (35.0 g, 172 mmol) in methanol (200 mL) was added sodium borohydride (3.26 g, 86.2 mmol) at 0° C. The mixture was stirred at 0° C. for 1 h, diluted with water (100 ml), and then concentrated under reduced pressure. The remaining aqueous phase was extracted with ethyl acetate (3×200 mL). The combined organic layers were washed with brine (3×100 mL), dried over anhydrous sodium sulfate, and filtered. Concentration of the filtrate in vacuo and purification of the residue by column chromatography, eluting with gradient of 10-20% of ethyl acetate in petroleum ether, afforded the title compound as a colorless solid (33.4 g, 94% yield): $^1$H NMR (400 MHz, CDCl$_3$) δ 7.45-7.33 (m, 1H), 7.23-6.98 (m, 2H), 4.86 (br s, 2H), OH not observed.

Step 2. Preparation of ((2-bromo-6-fluorobenzyl)oxy)triisopropylsilane

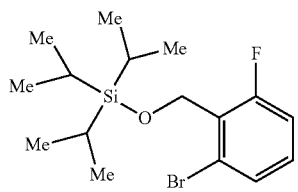 [SMILES: CC(C)[Si](OCc1c(F)cccc1Br)(C(C)C)C(C)C]

To a solution of (2-bromo-6-fluorophenyl)methanol (57.0 g, 278 mmol) and imidazole (37.9 g, 556 mmol) in dichloromethane (300 mL) was added chlorotriisopropylsilane (107 g, 556 mmol) and the mixture was stirred at ambient temperature for 12 h. The reaction mixture was concentrated under reduced pressure and the residue was diluted with water (400 mL) and extracted with ethyl acetate (3×400 mL). The combined organic layers were washed with brine (3×100 mL), dried over anhydrous sodium sulfate, and filtered. Concentration of the filtrate in vacuo and purification of the residue by column chromatography, eluting with a gradient of 0-5% gradient of ethyl acetate in petroleum ether, provided the title compound as a yellow oil (95.0 g, 94% yield): $^1$H NMR (400 MHz, CDCl$_3$) δ 7.39 (d, J=7.8 Hz, 1H), 7.15 (dt, J=6.0, 8.0 Hz, 1H), 7.07-6.99 (m, 1H), 4.94 (d, J=1.8 Hz, 2H), 1.24-1.15 (m, 3H), 1.14-1.10 (m, 18H).

Step 3. Preparation of 3-fluoro-2-(((triisopropylsilyl)oxy)methyl)benzaldehyde

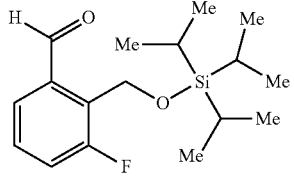 [SMILES: CC(C)[Si](OCc1c(F)cccc1C=O)(C(C)C)C(C)C]

To a mixture of ((2-bromo-6-fluorobenzyl)oxy)triisopropylsilane (65.0 g, 180 mmol), 2-isocyano-2-methylpropane (22.4 g, 270 mmol), palladium(II) acetate (4.04 g, 18.0 mmol), sodium carbonate (19.1 g, 180 mmol), and (2-biphenyl)di-tert-butylphosphine (10.7 g, 36.0 mmol) in N,N-dimethylformamide (500 mL) was added triethylsilane (62.8 g, 540 mmol). The reaction mixture was degassed and then heated to 65° C. for 12 h. After cooling to ambient temperature, the reaction mixture was diluted with water (100 mL) and extracted with ethyl acetate (3×100 mL). The combined organic layers were washed with brine (3×50 mL), dried over anhydrous sodium sulfate, and filtered. Concentration of the filtrate in vacuo and purification of the residue by column chromatography, eluting with a gradient of 0-5% of ethyl acetate in petroleum ether, afforded the title compound as a yellow oil (28.0 g, 50% yield): $^1$H NMR (400 MHz, CDCl$_3$) δ 10.45 (s, 1H), 7.70-7.64 (m, 1H), 7.35-7.27 (m, 2H), 5.10 (d, J=1.4 Hz, 2H), 1.03 (s, 3H), 0.99-0.95 (m, 18H).

Step 4. Preparation of (R)—N-(3-fluoro-2-(((triisopropylsilyl)oxy)methyl)benzylidene)-2-methylpropane-2-sulfinamide

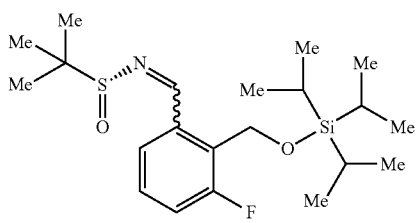 [SMILES: CC(C)[Si](OCc1c(F)cccc1C=N[S@](=O)C(C)(C)C)(C(C)C)C(C)C]

To a solution of 3-fluoro-2-(((triisopropylsilyl)oxy)methyl)benzaldehyde (14.0 g, 45.1 mmol) and (R)-2-methyl-2-propanesulfinamide (6.01 g, 49.6 mmol) in dichloromethane (150 mL) was added cesium carbonate (29.4 g, 90.2 mmol) and the mixture was stirred at ambient temperature for 12 h. The reaction mixture was then filtered and the filtrate concentrated in vacuo. Purification of the residue by column chromatography, eluting with petroleum ether, afforded the title compound as a colorless oil (9.00 g, 48% yield): $^1$H NMR (400 MHz, CDCl$_3$) δ 9.11 (s, 1H), 7.90 (d, J=7.6 Hz, 1H), 7.42-7.33 (m, 1H), 7.25-7.15 (m, 1H), 5.11 (qd, J=12.0, 1.6 Hz, 2H), 1.30 (s, 9H), 1.22-1.13 (m, 3H), 1.09-1.05 (m, 18H); MS (ES+) m/z 414.4 (M+1).

Step 5. Preparation of (R)—N—((S)-1-(3-fluoro-2-(((triisopropylsilyl)oxy)methyl)phenyl)ethyl)-2-methylpropane-2-sulfinamide

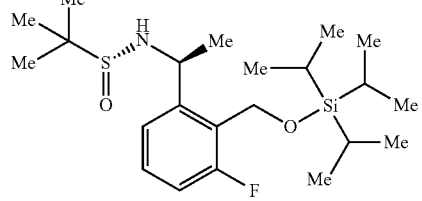

To a solution of (R)—N-(3-fluoro-2-(((triisopropylsilyl)oxy)methyl)benzylidene)-2-methylpropane-2-sulfinamide (9.00 g, 21.8 mmol) in dichloromethane (100 mL) was added dropwise a 3.0 M solution of methylmagnesium bromide in diethyl ether (14.5 mL, 43.5 mmol) at −45° C. The mixture was allowed to warm to ambient temperature and stirred for 2 h. To it was then added saturated ammonium chloride (500 mL), and the mixture was extracted with dichloromethane (3×500 mL). The combined organic layers were washed with brine (200 mL) and dried over anhydrous sodium sulfate, and filtered. Concentration of the filtrate in vacuo and purification of the residue by column chromatography, eluting with a gradient of 5-30% of ethyl acetate in petroleum ether, afforded the title compound as a colorless oil (7.60 g, 63% yield): $^1$H NMR (400 MHz, CDCl$_3$) δ 7.32-7.28 (m, 1H), 7.27-7.22 (m, 1H), 6.97 (ddd, J=9.6, 8.0, 1.6 Hz, 1H), 5.13 (q, J=6.4 Hz, 1H), 5.06-4.80 (m, 2H), 3.38 (br s, 1H), 1.59-1.56 (m, 3H), 1.19 (s, 9H), 1.18-1.13 (m, 3H), 1.10-1.05 (m, 18H).

Step 6. Preparation of (S)-(2-(1-aminoethyl)-6-fluorophenyl)methanol hydrochloride

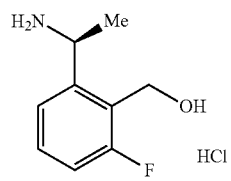 [SMILES: C[C@H](N)c1cccc(F)c1CO ; Cl]

To (R)—N—((S)-1-(3-fluoro-2-(((triisopropylsilyl)oxy)methyl)phenyl)ethyl)-2-methylpropane-2-sulfinamide (7.60 g, 17.7 mmol) was added a 4.0 M solution of hydrogen chloride in methanol (100 mL, 400.0 mmol) and the mixture was stirred at ambient temperature for 12 h. The mixture was concentrated in vacuo to give the title compound as a colorless oil (3.60 g, 100% yield): $^1$H NMR (400 MHz, DMSO-d$_6$) δ 7.31-7.26 (m, 2H), 7.02 (ddd, J=9.6, 8.0, 1.6 Hz, 1H), 4.57 (d, J=2.0 Hz, 2H), 4.36 (q, J=6.4 Hz, 1H), 1.32 (d, J=6.4 Hz, 3H), exchangeable proton not observed.

Step 7. Preparation of tert-butyl (S)-(1-(3-fluoro-2-(hydroxymethyl)phenyl)ethyl)carbamate

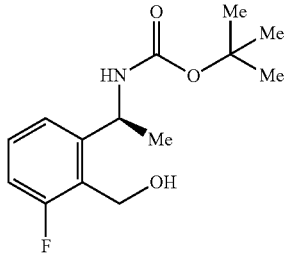 [SMILES: C[C@H](NC(=O)OC(C)(C)C)c1cccc(F)c1CO]

To a solution of (S)-(2-(1-aminoethyl)-6-fluorophenyl)methanol (3.60 g, 17.5 mmol) in dichloromethane (50.0 mL) was added triethylamine (7.08 g, 70.0 mmol) and di-tert-butyldicarbonate (4.20 g, 19.2 mmol). The mixture was stirred at ambient temperature for 1 h and then diluted with water (200 mL) and extracted with dichloromethane (3×100 mL). The combined organic layers were washed with brine (50 mL), dried over anhydrous sodium sulfate, and filtered. Concentration of the filtrate in vacuo provided the title compound as a colorless solid (5.00 g, quantitative yield): MS (ES+) m/z 292.3 (M+23).

Step 8. Preparation of (S)-2-(1-((tert-butoxycarbonyl)amino)ethyl)-6-fluorobenzyl methanesulfonate

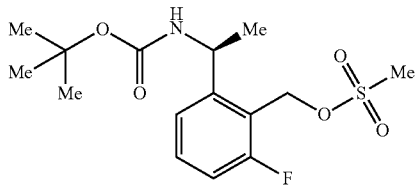 [SMILES: C[C@H](NC(=O)OC(C)(C)C)c1cccc(F)c1COS(C)(=O)=O]

To a solution of (S)-tert-butyl (1-(3-fluoro-2-(hydroxymethyl)phenyl)ethyl)carbamate (5.00 g, 18.6 mmol) in anhydrous dichloromethane (50.0 mL) was added triethylamine (3.76 g, 37.1 mmol) at 0° C. followed by dropwise addition of methanesulfonyl chloride (3.40 g, 29.7 mmol). The mixture was allowed to warm to ambient temperature and stirred for 1 h. After addition of water (100 mL), the mixture was extracted with dichloromethane (3×100 mL). The combined organic layers were washed with brine (50 mL), dried over anhydrous sodium sulfate, and filtered. Concentration of the filtrate in vacuo afforded the title compound as a yellow solid (6.50 g, quantitative yield): MS (ES+) m/z 370.3 (M+23).

Step 9. Preparation of tert-butyl (S)-(1-(2-((1,3-dioxoisoindolin-2-yl)methyl)-3-fluorophenyl)ethyl)carbamate

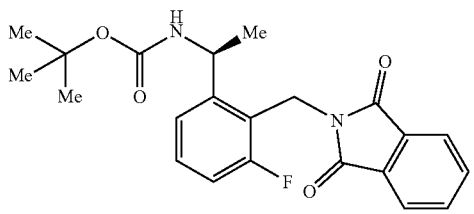 [SMILES: C[C@H](NC(=O)OC(C)(C)C)c1cccc(F)c1CN1C(=O)c2ccccc2C1=O]

To a solution of (S)-2-(1-((tert-butoxycarbonyl)amino)ethyl)-6-fluorobenzyl methanesulfonate (6.50 g, 18.7 mmol) in N,N-dimethylformamide (70 mL) was added potassium carbonate (5.17 g, 37.4 mmol) and phthalimide (4.13 g, 28.1 mmol). The mixture was stirred at ambient temperature for 12 h and then diluted with water (200 mL) and extracted with ethyl acetate (3×200 mL). The combined organic layers were washed with brine (30 mL), dried over anhydrous sodium sulfate, and filtered. Concentration of the filtrate in vacuo and purification of the residue by reverse phase column chromatography, eluting with a gradient of acetonitrile in water containing 0.1% of ammonium hydroxide, afforded the title compound as a yellow solid (4.00 g, 54% yield): $^1$H NMR (400 MHz, CDCl$_3$) δ 7.91-7.75 (m, 2H), 7.70-7.63 (m, 2H), 7.33-7.25 (m, 1H), 7.16 (br d, J=7.6 Hz, 1H), 6.96 (br t, J=9.2 Hz, 1H), 5.42-5.27 (m, 1H), 5.12-5.02 (m, 2H), 4.93-4.85 (m, 1H), 1.53-1.44 (m, 3H), 1.35 (s, 9H); MS (ES+) m/z 421.4 (M+23).

Step 10. Preparation of (S)-2-(2-(1-aminoethyl)-6-fluorobenzyl)isoindoline-1,3-dione hydrochloride

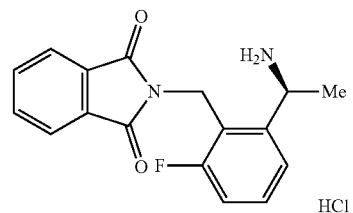 [SMILES: C[C@H](N)c1cccc(F)c1CN1C(=O)c2ccccc2C1=O ; Cl]

To (S)-tert-butyl(1-(2-((1,3-dioxoisoindolin-2-yl)methyl)-3-fluorophenyl) ethyl)carbamate (4.00 g, 10.0 mmol) was added a 4.0 M solution of hydrogen chloride in methanol (40 mL, 160 mmol), and the mixture was stirred at ambient temperature for 1 h. Concentration in vacuo provided the title compound as a colorless solid (3.40 g, 100% yield): MS (ES+) m/z 299.3 (M+1).

Step 11. Preparation of (S)-2-(2-(1-(azetidin-1-yl)ethyl)-6-fluorobenzyl)isoindoline-1,3-dione

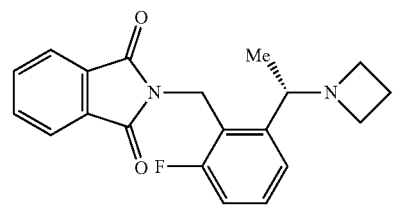 [SMILES: C[C@@H](c1cccc(F)c1CN1C(=O)c2ccccc2C1=O)N1CCC1]

To a solution of (S)-2-(2-(1-aminoethyl)-6-fluorobenzyl)isoindoline-1,3-dione hydrochloride (3.40 g, 10.2 mmol) and 1,3-dibromopropane (2.26 g, 11.2 mmol) in N,N-dimethylformamide (40 mL) was added potassium carbonate (5.62 g, 40.6 mmol) and the mixture was stirred at 80° C. for 12 h. The reaction mixture was then diluted with water (200 mL) and extracted with ethyl acetate (3×200 mL). The combined organic layers were washed with brine (50 mL), dried over anhydrous sodium sulfate, and filtered. Concentration of the filtrate in vacuo and purification of the residue by reverse phase column chromatography, eluting with a gradient of acetonitrile in water containing 0.1% of ammonium hydroxide, provided the title compound as a yellow oil (0.46 g, 13% yield): ¹H NMR (400 MHz, CDCl₃) δ 7.80-7.72 (m, 2H), 7.62-7.58 (m, 2H), 7.30 (br d, J=8.0 Hz, 1H), 7.13-7.10 (m, 1H), 6.83 (t, J=9.2 Hz, 1H), 5.04 (d, J=14.8 Hz, 1H), 4.82 (br d, J=14.8 Hz, 1H), 3.82 (br s, 1H), 3.20-2.98 (m, 4H), 1.90-1.89 (m, 2H), 1.07 (br d, J=6.4 Hz, 3H); MS (ES+) m/z 339.3 (M+1).

Step 12. Preparation of (S)-(2-(1-(azetidin-1-yl) ethyl)-6-fluorophenyl)methanamine

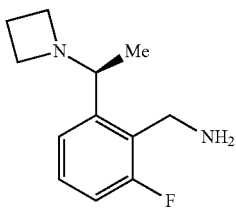 [SMILES: C[C@@H](c1cccc(F)c1CN)N1CCC1]

To a solution of (S)-2-(2-(1-(azetidin-1-yl)ethyl)-6-fluorobenzyl)isoindoline-1,3-dione (0.20 g, 0.59 mmol) in ethanol (5 mL) was added hydrazine monohydrate (0.15 g, 2.96 mmol) and the mixture was stirred at 80° C. for 12 h. The mixture was allowed to cool to ambient temperature and then filtered. Concentration of the filtrate in vacuo gave a residue, which was diluted with 1 M sodium hydroxide (20 mL) and extracted with dichloromethane (3×200 mL). The combined organic layer was washed with brine (10 mL), dried over anhydrous sodium sulfate, and filtered. Concentration of the filtrate in vacuo afforded the title compound as a colorless oil (0.10 g, 81% yield): MS (ES+) m/z 209.3 (M+1).

Step 13. Preparation of tert-butyl (S)-((4-((2-(1-(azetidin-1-yl)ethyl)-6-fluorobenzyl)amino)-2,6-difluorophenyl)sulfonyl)(thiazol-4-yl)carbamate

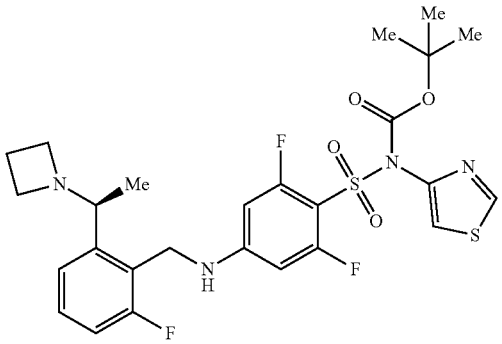 [SMILES: C[C@@H](c1cccc(F)c1CNc1cc(F)c(S(=O)(=O)N(C(=O)OC(C)(C)C)c2cscn2)c(F)c1)N1CCC1]

To a solution of (S)-(2-(1-(azetidin-1-yl)ethyl)-6-fluorophenyl) methanamine (0.18 g, 0.86 mmol) and tert-butyl thiazol-4-yl((2,4,6-trifluorophenyl)sulfonyl)carbamate (0.34 g, 0.86 mmol) in N,N-dimethylformamide (3 mL) was added potassium carbonate (0.24 g, 1.73 mmol) and the mixture was stirred at ambient temperature for 12 h. The mixture was diluted with water (100 mL) and extracted with ethyl acetate (3×100 mL). The combined organic layers were washed with brine (50 mL), dried over anhydrous sodium sulfate, and filtered. Concentration of the filtrate in vacuo and purification of the residue by preparative thin layer chromatography, eluting with 10% methanol in dichloromethane, afforded the title compound as a colorless oil (0.10 g, 20% yield): ¹H NMR (400 MHz, CDCl₃) δ 8.81 (d, J=2.2 Hz, 1H), 7.52 (d, J=2.2 Hz, 1H), 7.28-7.25 (m, 1H), 7.23-7.20 (m, 1H), 7.07-7.00 (m, 1H), 6.61-6.55 (br s, 1H), 6.30 (d, J=11.6 Hz, 2H), 4.63-4.48 (m, 2H), 3.60-3.53 (m, 1H), 3.21-3.17 (m, 2H), 3.12-3.07 (m, 2H), 2.08-2.05 (m, 2H), 1.41 (s, 9H), 1.29 (d, J=6.8 Hz, 3H); MS (ES+) m/z 583.4 (M+1).

Step 14. Preparation of (S)-4-((2-(1-(azetidin-1-yl) ethyl)-6-fluorobenzyl)amino)-2,6-difluoro-N-(thiazol-4-yl)benzenesulfonamide formate

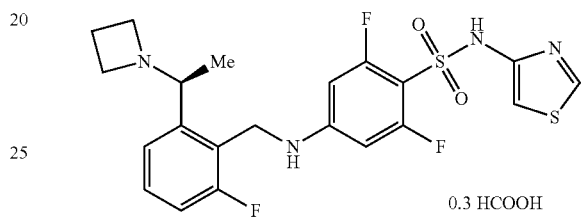

To a solution of (S)-tert-butyl(4-((2-(1-(azetidin-1-yl) ethyl)-6-fluorobenzyl)amino)-2,6-difluorophenyl) sulfonyl (thiazol-4-yl)carbamate (0.10 g, 0.17 mmol) in dichloromethane (2 mL) was added trifluoroacetic acid (1.0 mL) and the mixture was stirred at ambient temperature for 1 h. The mixture was then concentrated under reduced pressure to give a residue which was purified by preparative reverse phase column chromatography, eluting with a gradient of acetonitrile in water containing 0.1% of formic acid, to give the title compound as a colorless solid (0.05 g, 52% yield): ¹H NMR (400 MHz, CDCl₃) δ 8.68 (d, J=2.0 Hz, 1H), 8.43 (s, 0.3H), 7.38-7.32 (m, 1H), 7.32-7.30 (m, 1H), 7.11-7.06 (m, 1H), 7.05 (d, J=2.0 Hz, 1H), 6.23 (d, J=11.6 Hz, 2H), 4.48-4.37 (m, 2H), 4.06-3.95 (m, 1H), 3.48 (q, J=7.2 Hz, 2H), 3.39 (q, J=7.2 Hz, 2H), 2.17 (quin, J=7.2 Hz, 2H), 1.37 (d, J=6.8 Hz, 3H), NH and COOH not observed; MS (ES+) m/z 483.1 (M+1).

Example 279

Synthesis of (R)-4-((2-(1-(azetidin-1-yl)ethyl)-6-fluorobenzyl)amino)-2,6-difluoro-N-(thiazol-4-yl) benzenesulfonamide formate

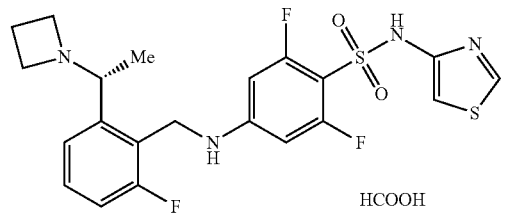 [SMILES: C[C@H](c1cccc(F)c1CNc1cc(F)c(S(=O)(=O)Nc2cscn2)c(F)c1)N1CCC1 ; "HCOOH"]

Step 1. Preparation of (S)—N-(3-fluoro-2-(((triiso-propylsilyl)oxy)methyl)benzylidene)-2-methylpropane-2-sulfinamide

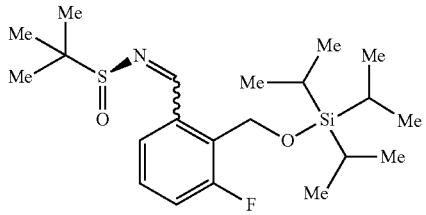 [SMILES: CC(C)[Si](OCc1c(F)cccc1C=N[S@@](=O)C(C)(C)C)(C(C)C)C(C)C]

Following the procedure as described in EXAMPLE 278, Step 4, and making non-critical variations as required to replace (S)-2-methylpropane-2-sulfinamide with ((R)-2-methylpropane-2-sulfinamide, the title compound was obtained as a yellow oil (7.80 g, 41% yield): $^1$H NMR (400 MHz, CDCl$_3$) δ 9.01 (s, 1H), 7.81 (d, J=7.8 Hz, 1H), 7.35-7.24 (m, 1H), 7.15-7.07 (m, 1H), 5.01 (dq, J=1.6, 11.8 Hz, 2H), 1.20 (s, 9H), 1.10-1.03 (m, 3H), 1.00-0.95 (m, 18H).

Step 2. Preparation of (S)—N—((R)-1-(3-fluoro-2-(((triisopropylsilyl)oxy)methyl)phenyl)ethyl)-2-methylpropane-2-sulfinamide

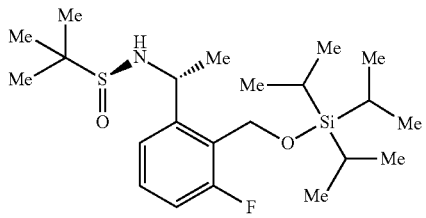 [SMILES: CC(C)[Si](OCc1c(F)cccc1[C@@H](C)N[S@@](=O)C(C)(C)C)(C(C)C)C(C)C]

Following the procedure as described in EXAMPLE 278, Step 5, and making non-critical variations as required to replace (R)—N-(3-fluoro-2-(((triisopropylsilyl)oxy)methyl)benzylidene)-2-methylpropane-2-sulfinamide with (S)—N-(3-fluoro-2-(((triisopropylsilyl)oxy)methyl)benzylidene)-2-methylpropane-2-sulfinamide, the title compound was obtained as a colorless solid (6.00 g, 73% yield): $^1$H NMR (400 MHz, CDCl$_3$) δ 7.19-7.11 (m, 2H), 6.91-6.84 (m, 1H), 5.04 (q, J=6.6 Hz, 1H), 4.96-4.72 (m, 2H), 3.29 (br s, 1H), 1.49 (d, J=6.8 Hz, 3H), 1.10 (s, 9H), 1.09-1.04 (m, 3H), 1.02-0.97 (m, 18H).

Step 3. Preparation of (R)-(2-(1-aminoethyl)-6-fluorophenyl)methanol hydrochloride

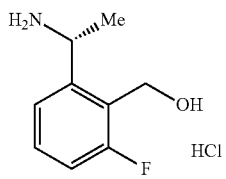 [SMILES: C[C@@H](N)c1cccc(F)c1CO ; Cl]

Following the procedure as described in EXAMPLE 278, Step 6, and making non-critical variations as required to replace ((R)—N—((S)-1-(3-fluoro-2-(((triisopropylsilyl)oxy)methyl)phenyl)ethyl)-2-methylpropane-2-sulfinamide with (S)—N—((R)-1-(3-fluoro-2-(((triisopropylsilyl)oxy)methyl)phenyl)ethyl)-2-methylpropane-2-sulfinamide, the title compound was obtained as a colorless solid (3.00 g, quantitative yield) which was used without purification Step 4. Preparation of tert-butyl (R)-(1-(3-fluoro-2-(hydroxymethyl)phenyl)-ethyl)carbamate

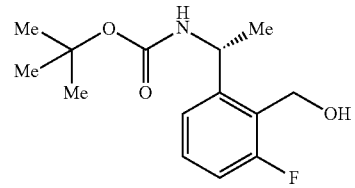 [SMILES: C[C@@H](NC(=O)OC(C)(C)C)c1cccc(F)c1CO]

Following the procedure as described in EXAMPLE 278, Step 7, and making non-critical variations as required to replace (S)-(2-(1-aminoethyl)-6-fluorophenyl) methanol with (R)-(2-(1-aminoethyl)-6-fluorophenyl) methanol, the title compound was obtained as a colorless solid (2.42 g, 66% yield): $^1$H NMR (400 MHz, CDCl$_3$) δ 7.34-7.29 (m, 1H), 7.12 (br d, J=7.8 Hz, 1H), 7.00 (t, J=8.8 Hz, 1H), 5.16-5.03 (m, 2H), 4.86 (br s, 2H), 1.48 (br d, J=6.3 Hz, 3H), 1.39 (s, 9H), OH not observed.

Step 5. Preparation of (R)-2-(1-((tert-butoxycarbonyl)amino)ethyl)-6-fluorobenzyl methanesulfonate

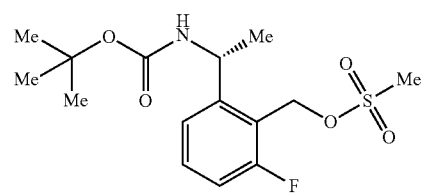 [SMILES: C[C@@H](NC(=O)OC(C)(C)C)c1cccc(F)c1COS(C)(=O)=O]

Following the procedure as described in EXAMPLE 278, Step 8, and making non-critical variations as required to replace (S)-tert-butyl (1-(3-fluoro-2-(hydroxymethyl)phenyl)ethyl)carbamate with (R)-tert-butyl (1-(3-fluoro-2-(hydroxymethyl)phenyl)ethyl)carbamate, the title compound was obtained as an oil (3.40 g, quantitative yield) which was used without purification.

Step 6. Preparation of tert-butyl (R)-(1-(2-((1,3-dioxoisoindolin-2-yl)methyl)-3-fluorophenyl)ethyl)carbamate

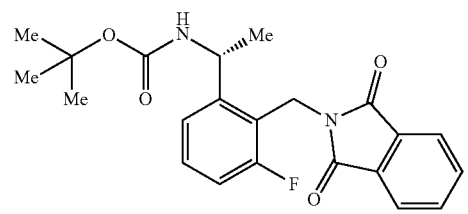 [SMILES: C[C@@H](NC(=O)OC(C)(C)C)c1cccc(F)c1CN1C(=O)c2ccccc2C1=O]

Following the procedure as described in EXAMPLE 278, Step 9, and making non-critical variations as required to replace (S)-2-(1-((tert-butoxycarbonyl)amino)ethyl)-6-fluorobenzyl methanesulfonate with (R)-2-(1-((tert-butoxycarbonyl)amino)ethyl)-6-fluorobenzyl methanesulfonate, the title compound was obtained as a yellow solid (2.40 g, 65% yield): ¹H NMR (400 MHz, CDCl₃) δ 7.89-7.79 (m, 2H), 7.70 (dd, J=3.0, 5.4 Hz, 2H), 7.38-7.29 (m, 1H), 7.16 (d, J=7.8 Hz, 1H), 7.02-6.95 (m, 1H), 5.43-5.27 (m, 1H), 5.15-5.02 (m, 2H), 4.92 (br s, 1H), 1.51 (br d, J=6.4 Hz, 3H), 1.36 (s, 9H); MS (ES+) m/z 299.3 (M−100+1).

Step 7. Preparation of (R)-2-(2-(1-aminoethyl)-6-fluorobenzyl)isoindoline-1,3-dione hydrochloride

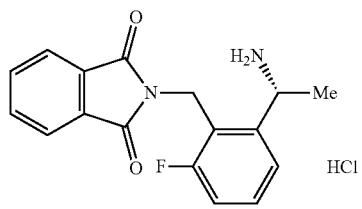 [SMILES: C[C@@H](N)c1cccc(F)c1CN1C(=O)c2ccccc2C1=O ; Cl]

Following the procedure as described in EXAMPLE 278, Step 10, and making non-critical variations as required to replace (S)-tert-butyl(1-(2-((1,3-dioxoisoindolin-2-yl)methyl)-3-fluorophenyl) ethyl)carbamate with (R)-tert-butyl (1-(2-((1,3-dioxoisoindolin-2-yl)methyl)-3-fluorophenyl) ethyl)carbamate, the title compound was obtained as a yellow solid (2.00 g, quantitative yield): MS (ES+) m/z 299.3 (M+1).

Step 8. Preparation of (R)-2-(2-(1-(azetidin-1-yl)ethyl)-6-fluorobenzyl)isoindoline-1,3-dione

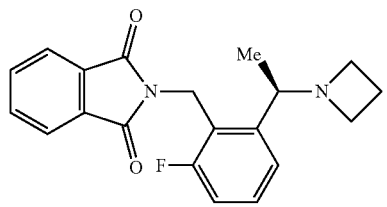 [SMILES: C[C@H](c1cccc(F)c1CN1C(=O)c2ccccc2C1=O)N1CCC1]

Following the procedure as described in EXAMPLE 278, Step 11, and making non-critical variations as required to replace (S)-2-(2-(1-aminoethyl)-6-fluorobenzyl)isoindoline-1,3-dione hydrochloride with (R)-2-(2-(1-aminoethyl)-6-fluorobenzyl)isoindoline-1,3-dione hydrochloride, the title compound was obtained (0.40 g, 20% yield): ¹H NMR (400 MHz, CDCl₃) δ 7.86 (dd, J=5.6, 2.8 Hz, 2H), 7.73 (dd, J=5.6, 3.2 Hz, 2H), 7.49-7.40 (m, 2H), 6.95-6.91 (m, 1H), 5.14 (dd, J=14.8, 1.4 Hz, 1H), 4.92-4.80 (m, 2H), 3.43-3.22 (m, 4H), 2.15-2.04 (m, 2H), 1.21 (d, J=6.4 Hz, 3H); MS (ES+) m/z 339.3 (M+1)

Step 9. Preparation of (R)-(2-(1-(azetidin-1-yl)ethyl)-6-fluorophenyl)methanamine

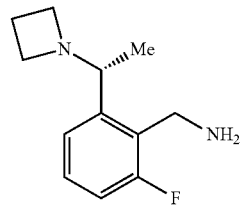 [SMILES: C[C@H](c1cccc(F)c1CN)N1CCC1]

Following the procedure as described in EXAMPLE 278, Step 12, and making non-critical variations as required to replace (S)-2-(2-(1-(azetidin-1-yl)ethyl)-6-fluorobenzyl)isoindoline-1,3-dione with (R)-2-(2-(1-(azetidin-1-yl)ethyl)-6-fluorobenzyl)isoindoline-1,3-dione, the title compound was obtained as a yellow solid (0.21 g, 85%): MS (ES+) m/z 192.0 (M−16).

Step 10. Preparation of tert-butyl (R)-((4-((2-(1-(azetidin-1-yl)ethyl)-6-fluorobenzyl)amino)-2,6-difluorophenyl)sulfonyl)(thiazol-4-yl)carbamate

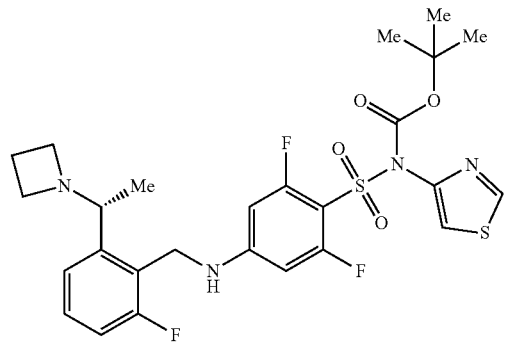 [SMILES: C[C@H](c1cccc(F)c1CNc1cc(F)c(S(=O)(=O)N(C(=O)OC(C)(C)C)c2cscn2)c(F)c1)N1CCC1]

Following the procedure as described in EXAMPLE 278, Step 13, and making non-critical variations as required to replace (S)-(2-(1-(azetidin-1-yl)ethyl)-6-fluorophenyl)methanamine with (R)-(2-(1-(azetidin-1-yl)ethyl)-6-fluorophenyl) methanamine, the title compound was obtained as a yellow solid (0.05 g, 11% yield): ¹H NMR (400 MHz, CDCl₃) δ 8.81 (d, J=2.4 Hz, 1H), 7.52 (d, J=2.4 Hz, 1H), 7.28-7.21 (m, 2H), 7.08-7.01 (m, 1H), 6.33-6.24 (m, 2H), 4.60-4.47 (m, 2H), 4.46-4.36 (m, 1H), 3.25-3.06 (m, 4H), 2.08 (quin, J=7.0 Hz, 2H), 1.42-1.40 (m, 9H), 1.29 (d, J=6.8 Hz, 3H), NH proton not observed; MS (ES+) m/z 583.4 (M+1).

Step 11. Preparation of (R)-4-((2-(1-(azetidin-1-yl)ethyl)-6-fluorobenzyl)amino)-2,6-difluoro-N-(thiazol-4-yl)benzenesulfonamide formate

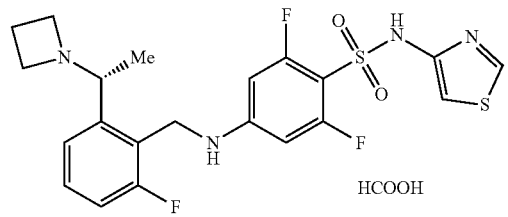 [SMILES: C[C@H](c1cccc(F)c1CNc1cc(F)c(S(=O)(=O)Nc2cscn2)c(F)c1)N1CCC1 ; "HCOOH"]

Following the procedure as described in EXAMPLE 278, Step 14, and making non-critical variations as required to replace (S)-tert-butyl(4-((2-(1-(azetidin-1-yl)ethyl)-6-fluorobenzyl)amino)-2,6-difluorophenyl) sulfonyl(thiazol-4-yl)carbamate with (R)-tert-butyl(4-((2-(1-(azetidin-1-yl)ethyl)-6-fluorobenzyl)amino)-2,6-difluorophenyl) sulfonyl (thiazol-4-yl)carbamate, the title compound was obtained as a colorless solid (0.02 g, 45% yield): $^1$H NMR (400 MHz, CDCl$_3$) δ 8.68 (d, J=2.4 Hz, 1H), 8.39 (s, 1H), 7.41-7.30 (m, 2H), 7.14-7.03 (m, 2H), 6.24 (d, J=11.8 Hz, 2H), 4.49-4.32 (m, 2H), 4.21-4.12 (m, 1H), 3.58 (q, J=7.8 Hz, 2H), 3.47 (q, J=7.6 Hz, 2H), 2.20 (quin, J=7.6 Hz, 2H), 1.41 (d, J=6.8 Hz, 3H), NH and COOH not observed; MS (ES+) m/z 483.1 (M+1).

Example 280

Synthesis of (S)-5-chloro-2-fluoro-4-((1-(2-fluoro-5-(methoxymethyl)phenyl)ethyl)amino)-N-(thiazol-4-yl)benzenesulfonamide

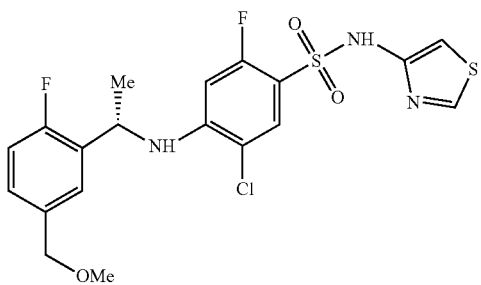 [SMILES: COCc1ccc(F)c([C@H](C)Nc2cc(F)c(S(=O)(=O)Nc3cscn3)cc2Cl)c1]

Step 1. Preparation of tert-butyl (S)-((5-chloro-2-fluoro-4-((1-(2-fluoro-5-(methoxymethyl)phenyl)ethyl)amino)phenyl)sulfonyl)(thiazol-4-yl)carbamate

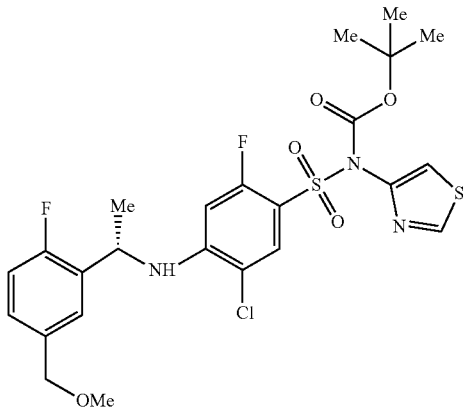 [SMILES: COCc1ccc(F)c([C@H](C)Nc2cc(F)c(S(=O)(=O)N(C(=O)OC(C)(C)C)c3cscn3)cc2Cl)c1]

To a solution of tert-butyl (5-chloro-2,4-difluorophenyl)sulfonyl(thiazol-4-yl)carbamate (0.30 g, 0.73 mmol) and (S)-1-(2-fluoro-5-(methoxymethyl)phenyl)ethanamine hydrochloride (0.16 g, 0.73 mmol) in anhydrous N,N-dimethylformamide (5 mL) was added cesium carbonate (0.48 g, 1.46 mmol). The mixture was stirred at ambient temperature for 12 h, diluted with water (30 mL) and extracted with ethyl acetate (3×30 mL). The combined organic extracts were washed with brine (10 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless oil (0.15 g, 36% yield): $^1$H NMR (400 MHz, CDCl$_3$) δ 8.77 (d, J=2.0 Hz, 1H), 7.96 (d, J=7.2 Hz, 1H), 7.48 (d, J=2.0 Hz, 1H), 7.26-7.20 (m, 2H), 7.08 (dd, J=10.0, 8.4 Hz, 1H), 6.20 (d, J=12.4 Hz, 1H), 5.36 (d, J=5.6 Hz, 1H), 4.85 (q, J=6.4 Hz, 1H), 4.38 (s, 2H), 3.37 (s, 3H), 1.67 (d, J=6.4 Hz, 3H), 1.36 (s, 9H); MS (ES+) m/z 574.0 (M+1), 576.0 (M+1).

Step 2. Preparation of (S)-5-chloro-2-fluoro-4-((1-(2-fluoro-5-(methoxymethyl)phenyl)ethyl)amino)-N-(thiazol-4-yl)benzenesulfonamide

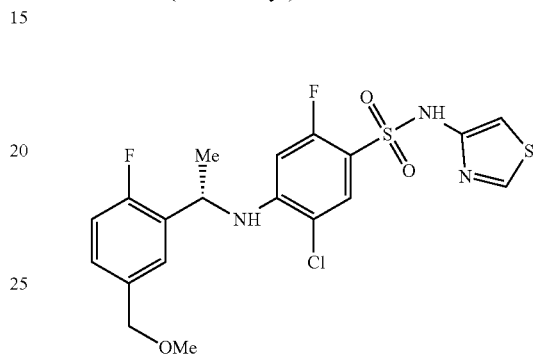

Following the procedure as described in Example 5, step 2 and making non-critical variations to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl (S)-((5-chloro-2-fluoro-4-((1-(2-fluoro-5-(methoxymethyl)phenyl)ethyl)amino)phenyl)sulfonyl)(thiazol-4-yl)carbamate, the title compound was afforded as a colorless solid (0.032 g, 26% yield): $^1$H NMR (400 MHz, CDCl$_3$) δ 10.22 (s, 1H), 8.68 (d, J=2.0 Hz, 1H), 7.77 (d, J=7.2 Hz, 1H), 7.26-7.20 (m, 1H), 7.19 (d, J=6.0 Hz, 1H), 7.06 (t, J=9.2 Hz, 1H), 6.91 (d, J=2.0 Hz, 1H), 6.12 (d, J=12.4 Hz, 1H), 5.22 (d, J=5.6 Hz, 1H), 4.78 (q, J=6.4 Hz, 1H), 4.37 (s, 2H), 3.35 (s, 3H), 1.63 (d, J=6.4 Hz, 3H); MS (ES+) m/z 474.0 (M+1), 476.0 (M+1).

Example 281

Synthesis of (S)-5-chloro-4-((1-(5-(difluoromethoxy)-2-fluorophenyl)ethyl)amino)-2-fluoro-N-(thiazol-4-yl)benzenesulfonamide

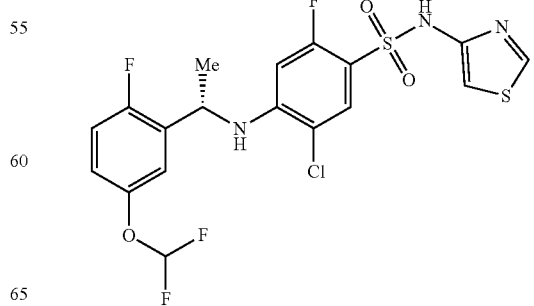

Step 1. Preparation of 5-(difluoromethoxy)-2-fluorobenzaldehyde

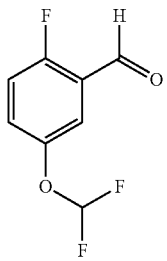

To a solution of 2-fluoro-5-hydroxybenzaldehyde (0.30 g, 2.14 mmol) in 1,4-dioxane (10 mL) and water (2 mL) was added sodium hydroxide (0.25 g, 6.42 mmol) and the chloro(difluoro)methane was bubbled through the mixture. The mixture was was stirred at ambient temperature for 30 minutes. The mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with 2 to 20% of ethyl acetate in petroleum ether, afforded the title compound as a yellow oil (0.18 g, 44% yield): $^1$H NMR (400 MHz, CDCl$_3$) δ 10.34 (s, 1H), 7.62 (dd, J=5.4, 3.2 Hz, 1H), 7.45-7.36 (m, 1H), 7.21 (t, J=9.2 Hz, 1H), 6.52 (t, J=72.4 Hz, 1H).

Step 2. Preparation of (R)—N-(5-(difluoromethoxy)-2-fluorobenzylidene)-2-methylpropane-2-sulfinamide

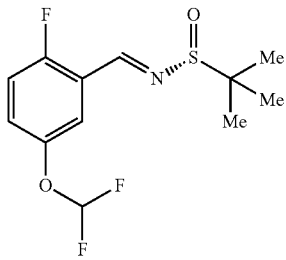 [SMILES: CC(C)(C)[S@@](=O)/N=C/c1cc(OC(F)F)ccc1F]

To a solution of 5-(difluoromethoxy)-2-fluorobenzaldehyde (0.90 g, 4.73 mmol) and (R)-2-methylpropane-2-sulfinamide (0.68 g, 5.68 mmol) in dichloromethane (20 mL) was added cesium carbonate (3.08 g, 9.46 mmol) and the mixture was stirred at ambient temperature for 12 h. The reaction mixture was filtered and the filtrate concentrated in vacuo. The residue was purified by column chromatography, eluting with a gradient of 5 to 50% of petroleum ether in ethyl acetate, to afford the title compound as a colorless solid (0.90 g, 64% yield): $^1$H NMR (400 MHz, CDCl$_3$) δ 8.86 (s, 1H), 7.75 (dd, J=5.6, 3.0 Hz, 1H), 7.31-7.27 (m, 1H), 7.20-7.15 (m, 1H), 6.52 (t, J=73.2 Hz, 1H), 1.28 (s, 9H); MS (ES+) m/z 294.1 (M+1).

Step 3. Preparation of (R)—N—((S)-1-(5-(difluoromethoxy)-2-fluorophenyl)ethyl)-2-methylpropane-2-sulfinamide

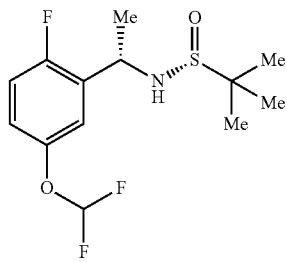 [SMILES: C[C@H](N[S@](=O)C(C)(C)C)c1cc(OC(F)F)ccc1F]

Following the procedure as described in EXAMPLE 146, Step 3 and making non-critical variations to replace (R)—N-(5-cyclopropyl-2-fluorobenzylidene)-2-methylpropane-2-sulfinamide with (R)—N-(5-(difluoromethoxy)-2-fluorobenzylidene)-2-methylpropane-2-sulfinamide), the title compound was afforded as colorless solid (0.20 g, 63% yield): $^1$H NMR (400 MHz, CDCl$_3$) δ 7.20-7.12 (m, 1H), 7.05-6.97 (m, 2H), 6.45 (t, J=73.2 Hz, 1H), 4.87 (dd, J=6.8, 4.2 Hz, 1H), 1.55 (d, J=6.8 Hz, 3H), 1.24-1.19 (m, 9H), NH not observed; MS (ES+) m/z 332.1 (M+23).

Step 4. Preparation of (S)-1-(5-(difluoromethoxy)-2-fluorophenyl)ethan-1-amine hydrochloride

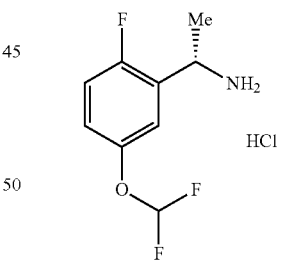

Following the procedure as described in EXAMPLE 146, Step 4 and making non-critical variations to replace ((R)—N—((S)-1-(5-cyclopropyl-2-fluorophenyl)ethyl)-2-methylpropane-2-sulfinamide with (R)—N—((S)-1-(5-(difluoromethoxy)-2-fluorophenyl)ethyl)-2-methylpropane-2-sulfinamide, the title compound was afforded as a colorless solid (0.12 g, 90% yield): $^1$H NMR (400 MHz, CDCl$_3$) δ 8.91 (s, 3H), 7.47 (d, J=5.0 Hz, 1H), 7.19-7.02 (m, 2H), 6.55 (t, J=73.2 Hz, 1H), 4.74 (d, J=6.8 Hz, 1H), 1.70 (d, J=6.8 Hz, 3H); MS (ES+) m/z 206.0 (M+1).

Step 5. Preparation of tert-butyl (S)-((5-chloro-4-((1-(5-(difluoromethoxy)-2-fluorophenyl)ethyl)amino)-2-fluorophenyl)sulfonyl)(thiazol-4-yl)carbamate

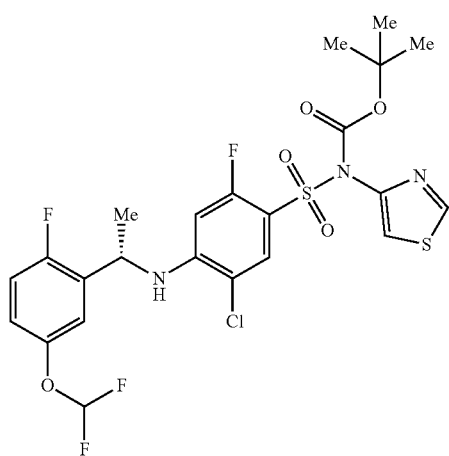 [SMILES: C[C@H](Nc1cc(F)c(S(=O)(=O)N(C(=O)OC(C)(C)C)c2cscn2)cc1Cl)c1cc(OC(F)F)ccc1F]

Following the procedure as described in Example 146, Step 5 and making non-critical variations to replace (S)-1-(5-cyclopropyl-2-fluorophenyl)ethan-1-amine hydrochloride with (S)-1-(5-(difluoromethoxy)-2-fluorophenyl)ethan-1-amine hydrochloride, the title compound was afforded as a colorless solid (0.15 g, 100% yield): $^1$H NMR (400 MHz, CDCl$_3$) δ 8.76 (d, J=2.0 Hz, 1H), 7.97 (d, J=7.0 Hz, 1H), 7.47 (d, J=2.0 Hz, 1H), 7.10 (d, J=9.4 Hz, 1H), 7.07-7.03 (m, 1H), 7.00-6.97 (m, 1H), 6.42 (t, J=73.2 Hz, 1H), 6.15 (d, J=12.0 Hz, 1H), 5.28 (d, J=5.6 Hz, 1H), 4.83 (t, J=6.6 Hz, 1H), 1.66 (d, J=6.8 Hz, 3H), 1.34 (s, 9H); MS (ES+) m/z 595.9 (M+1).

Step 6. Preparation of (S)-5-chloro-4-((1-(5-(difluoromethoxy)-2-fluorophenyl)ethyl)amino)-2-fluoro-N-(thiazol-4-yl)benzenesulfonamide

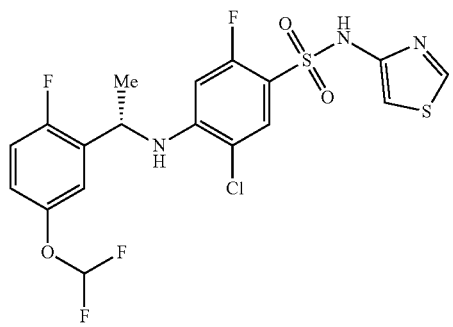 [SMILES: C[C@H](Nc1cc(F)c(S(=O)(=O)Nc2cscn2)cc1Cl)c1cc(OC(F)F)ccc1F]

Following the procedure as described in Example 5, Step 2 and making non-critical variations to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl (S)-((5-chloro-4-((1-(5-(difluoromethoxy)-2-fluorophenyl)ethyl)amino)-2-fluorophenyl)sulfonyl)(thiazol-4-yl)carbamate, the title compound was afforded as a colorless solid (0.056 g, 45% yield): $^1$H NMR (400 MHz, CDCl$_3$) δ 9.90 (s, 1H), 8.64 (d, J=2.0 Hz, 1H), 7.75 (d, J=7.2 Hz, 1H), 7.11-7.05 (m, 1H), 7.04-6.99 (m, 1H), 6.95 (dd, J=2.8, 6.0 Hz, 1H), 6.91 (d, J=2.4 Hz, 1H), 6.40 (t, J=73.2 Hz, 1H), 6.05 (d, J=12.0 Hz, 1H), 5.15 (d, J=5.6 Hz, 1H), 4.74 (q, J=6.6 Hz, 1H), 1.61 (d, J=6.8 Hz, 3H); MS (ES+) m/z 517.9 (M+23).

Example 282

Synthesis of 4-((2-((7-oxa-2-azaspiro[3.5]nonan-2-yl)methyl)-3,6-difluorobenzyl)amino)-5-chloro-2-fluoro-N-(thiazol-4-yl)benzenesulfonamide 2,2,2-trifluoroacetate

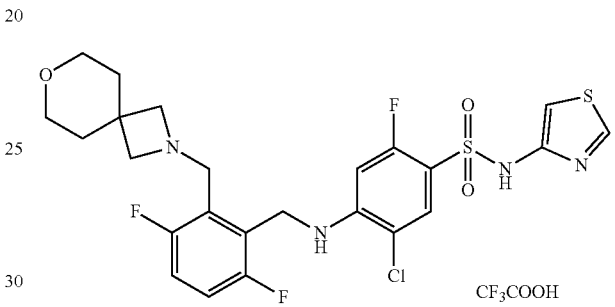

Step 1. Preparation of 4-amino-5-chloro-2-fluoro-N-(thiazol-4-yl)benzenesulfonamide

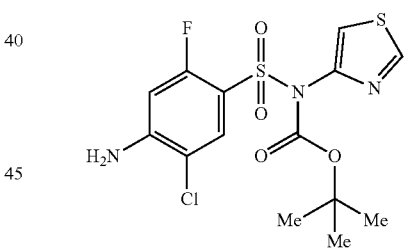

To a solution of tert-butyl ((5-chloro-2,4-difluorophenyl)sulfonyl)(thiazol-4-yl)carbamate (1.23 g, 3.00 mmol) in N,N-dimethylformamide (10 mL) was added sodium azide (0.19 g, 3.00 mmol) and the reaction mixture was stirred at ambient temperature for 20 minutes. To the reaction mixture was then added zinc dust (1.00 g, 16.0 mmol) and saturated ammonium chloride (10 mL) and the reaction mixture was stirred for 16 h. The reaction was diluted with water (20 mL) and ethyl acetate (30 mL), and filtered over diatomaceous earth. The filtrate was extracted with ethyl acetate (2×30 mL). The combined organic layers were washed with brine (2×40 mL), dried over anhydrous sodium sulfate and filtered. Concentration of the filtrate in vacuo afforded the title compound as a colorless solid (1.22 g, 99% yield): MS (ES+) m/z 308.2 (M−Boc+1), 310.2 (M− Boc+1).

Step 2. Preparation of 4-((2-(((tert-butyldimethylsilyl)oxy)methyl)-3,6-difluorobenzyl)amino)-5-chloro-2-fluoro-N-(thiazol-4-yl)benzenesulfonamide

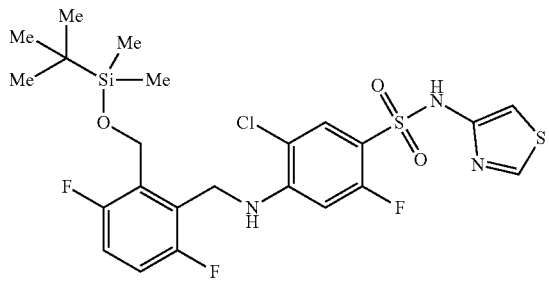 [SMILES: CC(C)(C)[Si](C)(C)OCc1c(F)ccc(F)c1CNc1cc(F)c(S(=O)(=O)Nc2cscn2)cc1Cl]

To trifluoroacetic acid (5 mL) was added tert-butyl ((4-amino-5-chloro-2-fluorophenyl)sulfonyl)(thiazol-4-yl)carbamate (1.22 g, 3.00 mmol) at 0° C. followed by sodium triacetoxyborohydride (1.02 g, 4.80 mmol) and the mixture was stirred for 5 minutes. To it was then added at 0° C. a solution of 2-(((tert-butyldimethylsilyl)oxy)methyl)-3,6-difluorobenzaldehyde (0.86 g, 3.00 mmol) in dichloromethane (10 mL) and the reaction mixture was stirred at 0° C. for 10 minutes. The reaction mixture was poured into cold saturated sodium bicarbonate (50 mL) and extracted with ethyl acetate (3×30 mL). The combined organic phase was dried over anhydrous sodium sulfate and filtered. Concentration of the filtrate in vacuo and purification of the residue by column chromatography, eluting with a gradient of 0-50% of ethyl acetate in hexanes, afforded the title compound as a colorless oil (0.98 g, 57% yield): MS (ES+) m/z 580.2 (M+1), 578.2 (M+1).

Step 3. Preparation of tert-butyl (2-(((tert-butyldimethylsilyl)oxy)methyl)-3,6-difluorobenzyl)(2-chloro-5-fluoro-4-(N-(thiazol-4-yl)sulfamoyl)phenyl)carbamate

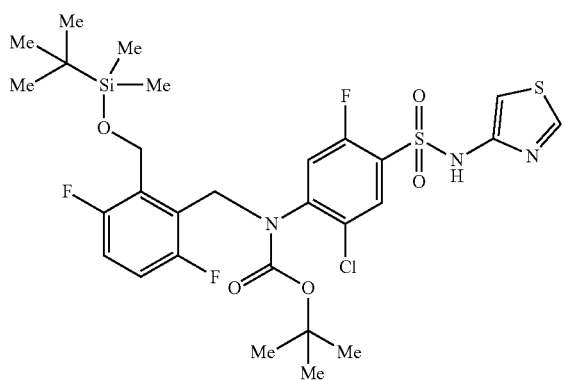 [SMILES: CC(C)(C)OC(=O)N(Cc1c(F)ccc(F)c1CO[Si](C)(C)C(C)(C)C)c1cc(F)c(S(=O)(=O)Nc2cscn2)cc1Cl]

To a solution of 4-((2-(((tert-butyldimethylsilyl)oxy)methyl)-3,6-difluorobenzyl)amino)-5-chloro-2-fluoro-N-(thiazol-4-yl)benzenesulfonamide (0.98 g, 1.72 mmol) in dichloromethane (10 mL) was added di-tert-butyl dicarbonate (0.75 g, 3.45 mmol) and 4-(dimethylamino)pyridine (0.42 g, 3.45 mmol) and the reaction mixture was stirred at ambient temperature for 16 h. Concentration of the reaction mixture in vacuo and purification of the residue by column chromatography, eluting with a gradient of 0-50% of ethyl acetate in hexanes, afforded the title compound as a colorless oil (0.28 g, 24% yield): MS (ES+) m/z 680.2 (M+1), 678.2 (M+1).

Step 4. Preparation of tert-butyl (2-chloro-5-fluoro-4-(N-(thiazol-4-yl)sulfamoyl)phenyl)(3,6-difluoro-2-(hydroxymethyl)benzyl)carbamate

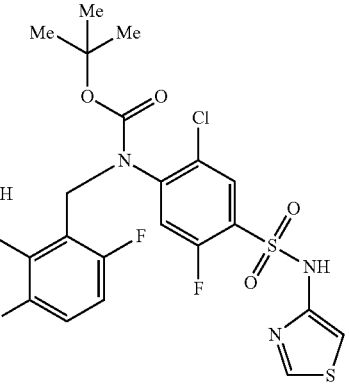

To a solution of tert-butyl (2-(((tert-butyldimethylsilyl)oxy)methyl)-3,6-difluorobenzyl)(2-chloro-5-fluoro-4-(N-(thiazol-4-yl)sulfamoyl)phenyl)carbamate (0.28 g, 0.41 mmol) in anhydrous tetrahydrofuran (4 mL) was added a 1.0 M solution of tetra-n-butylammonium fluoride in tetrahydrofuran (0.63 mL, 0.63 mmol) and the reaction mixture was stirred at ambient temperature for 45 minutes. Concentration of the reaction mixture in vacuo and purification of the residue by column chromatography, eluting with a gradient of 0-80% of ethyl acetate in hexanes, afforded the title compound as a colorless oil (0.23 g, 100% yield): MS (ES+) m/z 566.2 (M+1), 564.2 (M+1).

Step 5. Preparation of tert-butyl (2-chloro-5-fluoro-4-(N-(thiazol-4-yl)sulfamoyl)phenyl)(3,6-difluoro-2-formylbenzyl)carbamate

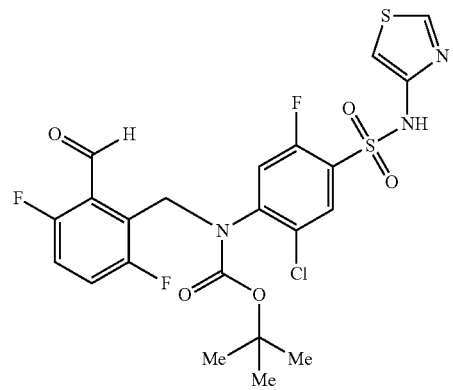 [SMILES: CC(C)(C)OC(=O)N(Cc1c(F)ccc(F)c1C=O)c1cc(F)c(S(=O)(=O)Nc2cscn2)cc1Cl]

To a solution of tert-butyl (2-chloro-5-fluoro-4-(N-(thiazol-4-yl)sulfamoyl)phenyl)(3,6-difluoro-2-(hydroxymethyl)benzyl)carbamate (0.23 g, 0.41 mmol) in dichloromethane (3 mL) was added Dess-Martin periodinane reagent (0.27 g, 0.63 mmol) and the reaction mixture was stirred at ambient temperature for 1 h. The reaction mixture was filtered through a pad of diatomaceous earth and filtrate concentrated in vacuo to give the title compound as an oil which was used without further purification: MS (ES+) m/z 564.2 (M+1), 562.2 (M+1).

Step 6. Preparation of tert-butyl (2-((7-oxa-2-azaspiro[3.5]nonan-2-yl)methyl)-3,6-difluorobenzyl)(2-chloro-5-fluoro-4-(N-(thiazol-4-yl)sulfamoyl)phenyl)carbamate

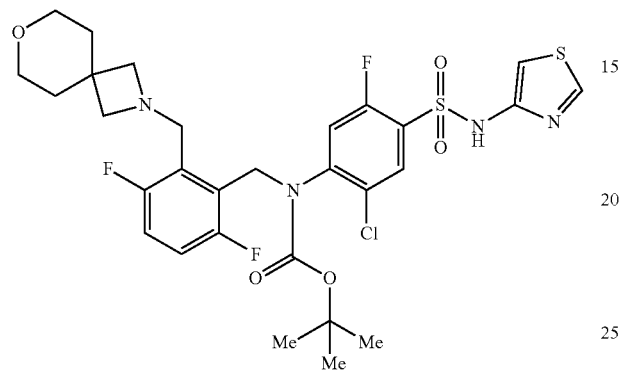

To a solution of tert-butyl (2-chloro-5-fluoro-4-(N-(thiazol-4-yl)sulfamoyl)phenyl)(3,6-difluoro-2-formylbenzyl)carbamate (0.08 g, 0.14 mmol) in dichloromethane (2 mL) was added 8-oxa-2-azaspiro[4.5]decane oxalic acid salt (0.02 g, 0.14 mmol) and sodium triacetoxyborohydride (0.07 g, 0.35 mmol) and the reaction mixture was stirred at ambient temperature for 2 h. To it was then added saturated sodium bicarbonate (5 mL) and the mixture was extracted with ethyl acetate (2×10 mL). The combined organic phase was washed with brine (5 mL), dried over anhydrous sodium sulfate and filtered. Concentration of the filtrate in vacuo and purification of the residue by column chromatography, eluting with a gradient of 0-10% of methanol in dichloromethane, afforded the title compound as an oil (0.01 g, 10% yield): MS (ES+) m/z 675.2 (M+1), 673.2 (M+1).

Step 7. Preparation of 4-((2-((7-oxa-2-azaspiro[3.5]nonan-2-yl)methyl)-3,6-difluorobenzyl)amino)-5-chloro-2-fluoro-N-(thiazol-4-yl)benzenesulfonamide 2,2,2-trifluoroacetate

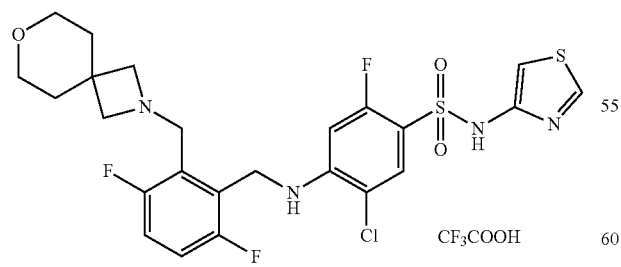

To a solution of tert-butyl (2-((7-oxa-2-azaspiro[3.5]nonan-2-yl)methyl)-3,6-difluorobenzyl)(2-chloro-5-fluoro-4-(N-(thiazol-4-yl)sulfamoyl)phenyl)carbamate (0.01 g, 0.01 mmol) in dichloromethane (3 mL) was added trifluoroacetic acid (3 mL) and the reaction mixture was stirred at ambient temperature for 1 h. The mixture was then concentrated in vacuo to afford the title compound as a colorless solid (0.01 g, 100% yield): $^1$H NMR (300 MHz, DMSO d$_6$) δ 11.18-11.17 (br s, 1H), 10.35-10.31 (br s, 1H), 8.90-8.88 (m, 1H), 7.65-7.60 (m, 1H), 7.48-7.41 (m, 2H), 7.02-6.99 (m, 1H), 6.86-6.73 (m, 2H), 4.64-4.60 (m, 2H), 4.55-4.51 (m, 2H), 4.01-3.97 (m, 4H), 3.52-3.46 (m, 4H), 1.83-1.72 (m, 4H); MS (ES+) m/z 575.2 (M+1), 573.2 (M+1).

Example 283

Synthesis of 4-((2-(azetidin-1-ylmethyl)-3,6-difluorobenzyl)amino)-2,6-difluoro-N-(thiazol-4-yl)benzenesulfonamide

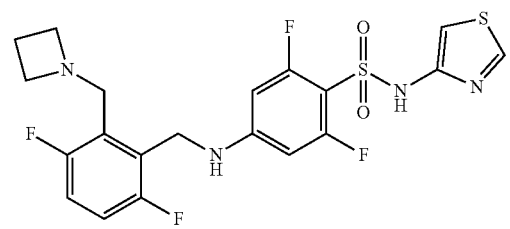 [SMILES: O=S(=O)(Nc1cscn1)c1c(F)cc(NCc2c(F)ccc(F)c2CN2CCC2)cc1F]

Step 1. Preparation of 1-(2-bromo-3,6-difluorobenzyl)azetidine

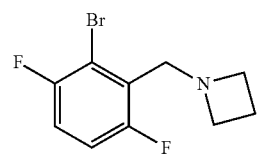 [SMILES: Fc1ccc(F)c(CN2CCC2)c1Br]

To a solution of 2-bromo-3,6-difluorobenzaldehyde (8.84 g, 40.0 mmol) in dichloromethane (160 mL) was added azetidine (2.28 g, 40 mmol) followed by sodium triacetoxyborohydride (15.3 g, 72.0 mmol) and the reaction mixture was stirred at ambient temperature for 16 h. The reaction was quenched by addition of 2 M sodium hydroxide (80 mL) and stirred for 30 minutes. The mixture was concentrated under reduced pressure and the remaining aqueous layer was extracted with ethyl acetate (2×60 mL). The combined organic phase was washed with brine (40 mL), dried over anhydrous sodium sulfate and filtered. Concentration of the filtrate in vacuo provided the title compound as ac colorless oil (8.82 g, 84% yield): MS (ES+) m/z 264.1 (M+1), 262.1 (M+1).

Step 2. Preparation of 2-(azetidin-1-ylmethyl)-3,6-difluorobenzaldehyde

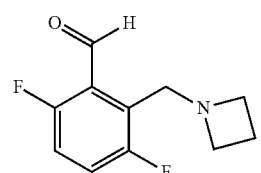

To a solution of 1-(2-bromo-3,6-difluorobenzyl)azetidine (8.82 g, 33.8 mmol) in anhydrous tetrahydrofuran (70 mL) was added a 1.6 M solution of n-Butyllithium in hexane (25.3 mL, 40.5 mmol) at −78° C. The reaction mixture was stirred at −78° C. for 10 minutes and then N,N-dimethylformamide (4.18 mL, 54.1 mmol) was added to it. The reaction mixture was stirred at −78° C. for 1 h, allowed to warm to ambient temperature, and stirred for 40 minutes. The reaction mixture was poured onto ice (50 mL), and extracted with dichloromethane (3×100 mL). The organic phase was washed with brine (50 mL), dried over anhydrous sodium sulfate and filtered. Concentration of the filtrate in vacuo and purification of the residue by column chromatography, eluting with a gradient of 0-10% of methanol in dichloromethane, afforded the title compound as a colorless oil (3.08 g, 42% yield): MS (ES+) m/z 212.2 (M+1).

Step 3. Preparation of 4-((2-(azetidin-1-ylmethyl)-3,6-difluorobenzyl)amino)-2,6-difluoro-N-(thiazol-4-yl)benzenesulfonamide

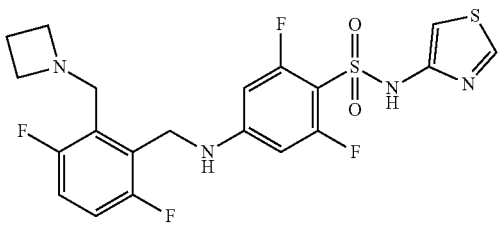 [SMILES: O=S(=O)(Nc1cscn1)c1c(F)cc(NCc2c(F)ccc(F)c2CN2CCC2)cc1F]

To a trifluoroacetic acid (3 mL) was added 4-amino-2,6-difluoro-N-(thiazol-4-yl)benzenesulfonamide (0.65 g, 1.66 mmol) at 0° C. followed by triacetoxyborohydride (0.56 g, 2.66 mmol) and the mixture was stirred for 5 minutes. To it was then added a solution of 2-(azetidin-1-ylmethyl)-3,6-difluorobenzaldehyde (0.35 g, 1.66 mmol) in dichloromethane (5 mL) at 0° C. The reaction mixture was stirred for 1 hour at 0° C., and then poured onto cold sodium bicarbonate (50 mL) and extracted with ethyl acetate (3×30 mL). The combined organic phase was dried over anhydrous sodium sulfate and filtered. Concentration of the filtrate in vacuo and purification of the residue by column chromatography, eluting with a gradient of 0-90% of ethyl acetate in hexanes followed by a gradient of 0-10% of methanol in dichloromethane, afforded the title compound as a colorless solid (0.18 g, 22% yield): $^1$H NMR (300 MHz, DMSO-$d_6$) δ 11.23-11.09 (br s, 1H), 8.90-8.88 (m, 1H), 7.46-7.33 (m, 3H), 6.92-6.90 (m, 1H), 6.40-6.33 (m, 2H), 4.39-4.31 (m, 4H), 3.96-3.87 (m, 4H), 2.24-2.18 (m, 2H); MS (ES+) m/z 487.2 (M+1).

Example 284

Synthesis of 4-((2-(azetidin-1-ylmethyl)-3,6-difluorobenzyl)(methyl)amino)-2,6-difluoro-N-(thiazol-4-yl)benzenesulfonamide 2,2,2-trifluoroacetate

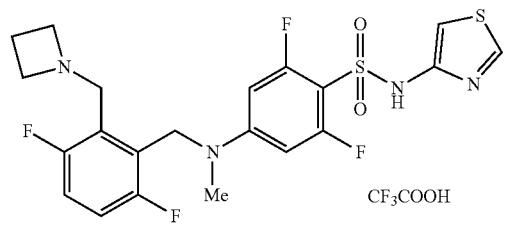 [SMILES: CN(Cc1c(F)ccc(F)c1CN1CCC1)c1cc(F)c(S(=O)(=O)Nc2cscn2)c(F)c1 ; "CF3COOH"]

To a solution of 4-((2-(azetidin-1-ylmethyl)-3,6-difluorobenzyl)amino)-2,6-difluoro-N-(thiazol-4-yl)benzenesulfonamide (0.10 g, 0.20 mmol) in trifluoroacetic acid (2 mL) was added sodium triacetoxyborohydride (0.12 g, 0.60 mmol) at 0° C. followed by formaldehyde (0.01 g, 0.30 mmol) and the reaction mixture was stirred for 10 minutes at 0° C. The reaction was quenched by addition of water (1 mL) and concentrated in vacuo. Purification of the residue by preparative reverse phase HPLC, using acetonitrile in water containing 0.1% trifluoroacetic acid as eluent, afforded the title compound as a colorless solid (0.02 g, 20% yield): $^1$H NMR (300 MHz, DMSO-$d_6$) δ 11.28 (br s, 1H), 10.36-10.34 (br s, 1H), 8.90 (d, J=2.1 Hz, 1H), 7.45-7.40 (m, 2H), 6.94 (d, J=2.2 Hz, 1H), 6.62 (dd, J=13.4, 0.3 Hz, 2H), 4.74-4.73 (m, 2H), 4.51-4.49 (m, 2H), 4.11-3.99 (m, 4H), 2.69 (s, 3H), 2.36-2.22 (m, 2H); MS (ES+) m/z 501.2 (M+1).

Example 285

Synthesis of 4-((2-(Azetidin-1-ylmethyl)-6-methylbenzyl)amino)-2,6-difluoro-N-(thiazol-4-yl)benzenesulfonamide formate

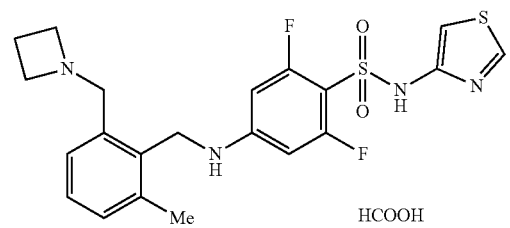 [SMILES: Cc1cccc(CN2CCC2)c1CNc1cc(F)c(S(=O)(=O)Nc2cscn2)c(F)c1 ; "HCOOH"]

Step 1. Preparation of 1-(3-chlorobenzyl)azetidine

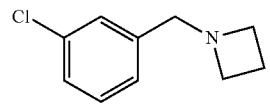 [SMILES: Clc1cccc(CN2CCC2)c1]

To a solution of 3-chlorobenzaldehyde (20.0 g, 142 mmol) in dichloromethane (460 mL) was added azetidine (8.10 g, 142.0 mmol) followed by sodium triacetoxyborohydride (45.1 g, 213 mmol) and the reaction mixture was stirred at ambient temperature for 16 h. The reaction was quenched by addition of 28% aqueous ammonium hydroxide solution (70 mL) and stirred for 30 minutes. The aqueous layer was extracted with dichloromethane (2×200 mL). The combined organic phase was washed with brine (40 mL), dried over anhydrous sodium sulfate and filtered. Concentration of the filtrate in vacuo and purification of the residue by column chromatography, eluting with a gradient of 0-10% methanol in dichloromethane, afforded the title compound as a colorless oil (11.5 g, 45% yield): $^1$H-NMR (300 MHz, CDCl$_3$) δ 7.30-7.28 (m, 1H), 7.25-7.16 (m, 3H), 3.55 (s, 2H), 3.23 (t, J=7.0 Hz, 4H), 2.11 (quintet, J=7.0 Hz, 2H).

Step 2. Preparation of 2-(azetidin-1-ylmethyl)-6-chlorobenzaldehyde oxime

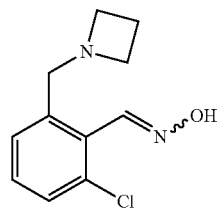 [SMILES: ON=Cc1c(Cl)cccc1CN1CCC1]

To a solution of 1-(3-chlorobenzyl)azetidine (10.5 g, 58.0 mmol) in anhydrous tetrahydrofuran (150 mL) was added dropwise a 1.4 M solution of sec-butyllithium in hexane (53.8 mL, 78.4 mmol) at −78° C. The reaction mixture was stirred at −78° C. for 1 h and then N,N-dimethylformamide (8.00 mL, 104 mmol) was added to it. The reaction mixture was stirred for at −78° C. for 1 h and then warmed to ambient temperature. To it was added a solution of hydroxylamine hydrochloric acid salt (5.64 g, 81.2 mmol) in methanol (20 mL) and water (20 mL) and the reaction mixture was stirred at ambient temperature for 1 h. The reaction mixture was concentrated under reduced pressure and water (50 mL) was added to it. The mixture was extracted with ethyl acetate (2×50 mL). The combined organic phase was washed with brine (30 mL), dried over anhydrous sodium sulfate and filtered. Concentration of the filtrate in vacuo afforded the title compound as a colorless solid (13.0 g, quantitative yield) as E/Z 1:3 mixture of isomers: $^1$H-NMR (300 MHz, CDCl$_3$) δ 8.57 (s, 0.75H), 7.74 (s, 0.25H), 7.39-7.27 (m, 3H), 3.92 (s, 1.5H), 3.61 (s, 0.5H), 3.29 (td, J=7.1, 3.8 Hz, 4H), 2.13 (quintet, J=7.1 Hz, 2H), OH not observed.

Step 3. Preparation of (2-(azetidin-1-ylmethyl)-6-chlorophenyl)methanamine

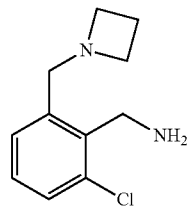 [SMILES: NCc1c(Cl)cccc1CN1CCC1]

To a solution of 2-(azetidin-1-ylmethyl)-6-chlorobenzaldehyde oxime (13.0 g, 58.0 mmol) in methanol (35 mL) was added zinc powder (7.59 g, 116.0 mmol) and the mixture was heated to reflux. To the mixture was then added dropwise 6 M hydrochloric acid (67 mL, 406.0 mmol) over a period of 10 minutes. After complete addition, more zinc powder (3.80 g, 58.0 mmol) was added to the reaction mixture. The reaction mixture was heated to reflux for another 15 minutes and was then allowed to cool to ambient temperature. The reaction mixture was cooled to 0° C. and 18 M sodium hydroxide (40 mL) was added to it. The mixture was extracted with ethyl acetate (3×80 mL) and the combined organic phase was concentrated in vacuo. The residue was dissolved in diethyl ether (50 mL) and extracted with 3.5 M ammonium chloride solution (2×30 mL). The combined aqueous layers were washed with diethyl ether (20 mL), and the pH was then adjusted with sodium hydroxide (10.0 g, 250.0 mmol). The aqueous phase was extracted with ethyl acetate (2×40 mL). The combined organic ethyl acetate phase was washed with brine (30 mL), dried over anhydrous sodium sulfate and filtered. Concentration of the filtrate in vacuo afforded the title compound as an oil (7.80 g, 58% yield): $^1$H-NMR (300 MHz, CDCl$_3$) δ 7.30 (dd, J=6.5, 2.8 Hz, 1H), 7.14-7.08 (m, 2H), 3.94 (s, 2H), 3.62 (s, 2H), 3.17 (t, J=7.0 Hz, 4H), 2.04 (dt, J=14.0, 7.0 Hz, 2H), NH not observed.

Step 4. Preparation of tert-butyl ((4-((2-(azetidin-1-ylmethyl)-6-chlorobenzyl)amino)-3-bromo-2,6-difluorophenyl)sulfonyl)(thiazol-4-yl)carbamate

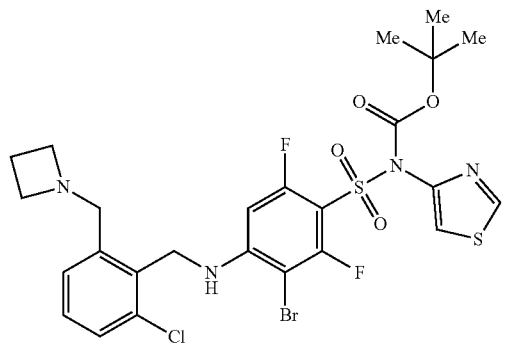 [SMILES: CC(C)(C)OC(=O)N(c1cscn1)S(=O)(=O)c1c(F)cc(NCc2c(Cl)cccc2CN2CCC2)c(Br)c1F]

To a mixture of (2-(azetidin-1-ylmethyl)-6-chlorophenyl)methanamine (2.10 g, 10.0 mmol) and tert-butyl ((3-bromo-2,4,6-trifluorophenyl)sulfonyl)(thiazol-4-yl)carbamate (4.73 g, 10.0 mmol), in anhydrous dimethyl sulfoxide (50 mL) was added potassium carbonate (2.76 g, 20.0 mmol) and the reaction mixture was stirred at ambient temperature for 2 h. Water (50 mL) was added and the mixture was extracted with ethyl acetate (3×50 mL). The combined organic phase was washed with brine (50 mL), dried over anhydrous sodium sulfate and filtered. Concentration of the filtrate in vacuo and trituration of the residue in diethyl ether (5 mL) afforded the title compound as a colorless solid (3.10 g, 47% yield): $^1$H-NMR (300 MHz, CDCl$_3$) δ 8.82 (d, J=2.3 Hz, 1H), 7.75-7.72 (m, 1H), 7.54 (d, J=2.2 Hz, 1H), 7.40 (dd, J=7.7, 1.7 Hz, 1H), 7.27-7.18 (m, 2H), 6.66 (dd, J=13.7, 1.6 Hz, 1H), 4.62 (d, J=5.6 Hz, 2H), 3.68 (s, 2H), 3.27 (dd, J=8.8, 5.5 Hz, 4H), 2.17-2.08 (m, 2H), 1.41-1.39 (m, 9H).

Step 5. Preparation of tert-butyl ((4-((2-(azetidin-1-ylmethyl)-6-chlorobenzyl)amino)-2,6-difluorophenyl)sulfonyl)(thiazol-4-yl)carbamate

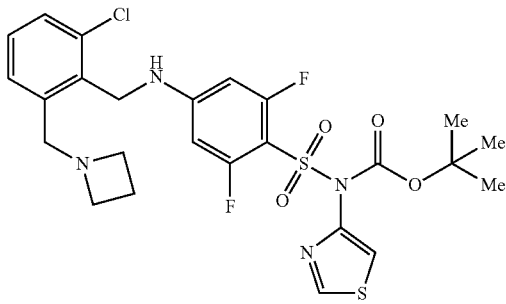 [SMILES: CC(C)(C)OC(=O)N(c1cscn1)S(=O)(=O)c1c(F)cc(NCc2c(Cl)cccc2CN2CCC2)cc1F]

To a mixture of tert-butyl ((4-((2-(azetidin-1-ylmethyl)-6-chlorobenzyl)amino)-3-bromo-2,6-difluorophenyl)sulfonyl)(thiazol-4-yl)carbamate (3.0 g, 4.53 mmol) in ethanol (20 mL) was added triethylamine (2.30 mL, 18.1 mmol) and 5% palladium on carbon (wet, 0.24 g). The reaction mixture was then heated to 60° C. for 1 h. After cooling to ambient temperature, the reaction mixture was filtered through a pad of diatomaceous earth and the filter pad was rinsed with ethanol (2×5 mL). To the combined filtrate were added triethylamine (2.30 mL, 18.1 mmol) and 5% palladium on carbon (wet, 0.24 g). The reaction mixture was then heated to 60° C. for 1 h. After cooling to ambient temperature, the reaction mixture was filtered through a pad of diatomaceous earth and the filter pad was rinsed with ethanol (2×5 mL). The combined filtrate was concentrated in vacuo and the residue purified by column chromatography, eluting with a gradient of 0-40% of ethyl acetate (containing 15% ethanol and 5% triethylamine) in hexanes to afford the title compound as a colorless oil (1.23 g, 46% yield): MS (ES+) m/z 587.2 (M+1), 585.2 (M+1).

Step 6. Preparation of 4-((2-(azetidin-1-ylmethyl)-6-chlorobenzyl)amino)-2,6-difluoro-N-(thiazol-4-yl)benzenesulfonamide 2,2,2-trifluoroacetate

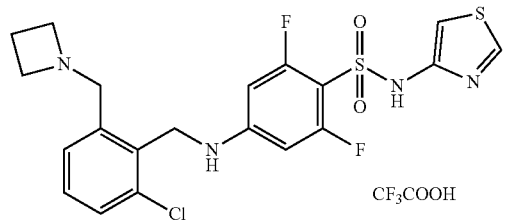 [SMILES: O=S(=O)(Nc1cscn1)c1c(F)cc(NCc2c(Cl)cccc2CN2CCC2)cc1F ; "CF3COOH"]

To a solution of tert-butyl ((4-((2-(azetidin-1-ylmethyl)-6-chlorobenzyl)amino)-2,6-difluorophenyl)sulfonyl)(thiazol-4-yl)carbamate (1.30 g, 2.22 mmol) in dichloromethane (5 mL) was added trifluoroacetic acid (5 mL) and the reaction mixture was stirred at ambient temperature for 1 h. The mixture was then concentrated in vacuo and triturated in ethanol (5 mL). Filtration provided the title compound as a colorless solid (0.91 g, 84% yield): $^1$H NMR (300 MHz, DMSO-d$_6$) δ 11.25 (s, 1H), 10.19-10.17 (br s, 1H), 8.92 (d, J=2.2 Hz, 1H), 7.62 (dd, J=5.8, 3.6 Hz, 1H), 7.53-7.48 (m, 2H), 7.17-7.15 (m, 1H), 6.93 (d, J=2.2 Hz, 1H), 6.40-6.35 (m, 2H), 4.47-4.38 (m, 4H), 4.15-4.01 (m, 4H), 2.41-2.25 (m, 2H); MS (ES+) m/z 487.3 (M+1), 485.2 (M+1).

Step 7. Preparation of 4-((2-(Azetidin-1-ylmethyl)-6-methylbenzyl)amino)-2,6-difluoro-N-(thiazol-4-yl)benzenesulfonamide formate

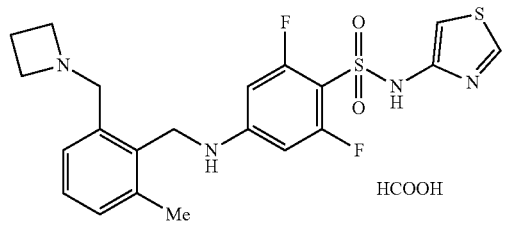 [SMILES: Cc1cccc(CN2CCC2)c1CNc1cc(F)c(S(=O)(=O)Nc2cscn2)c(F)c1 ; "HCOOH"]

To a mixture of (2-dicyclohexylphosphino-2',6'-dimethoxy-1,1'-biphenyl)[2-(2-aminoethylphenyl)]palladium(II) chloride (0.004 g, 0.006 mmol), 2-dicyclohexylphosphino-2',6'-dimethoxybiphenyl (0.003 g, 0.0006 mmol), potassium phosphate tribasic (0.33 g, 1.56 mmol) and methylboronic acid (0.05 g, 0.78 mmol) was added a solution of 4-((2-(azetidin-1-ylmethyl)-6-chlorobenzyl)amino)-2,6-difluoro-N-(thiazol-4-yl)benzenesulfonamide 2,2,2-trifluoroacetate (0.06 g, 0.12 mmol) in 1,4-dioxane (1.5 mL) and water (0.5 mL). The reaction mixture was then heated in a microwave reactor to 160° C. for 45 minutes. After cooling to ambient temperature, saturated ammonium chloride (5 mL) was added and the mixture was extracted with ethyl acetate (2×10 mL) and dichloromethane (10 mL). The combined organic layers were concentrated in vacuo. The residue was purified by column chromatography, eluting with a gradient of 0-15% of methanol (containing 0.5% of formic acid) in dichloromethane to afford the title compound as a colorless solid (0.03 g, 47% yield): $^1$H NMR (300 MHz, DMSO-d$_6$) δ 8.91-8.91 (m, 1H), 8.16 (s, 1H), 7.27-7.18 (m, 3H), 7.13-7.11 (m, 1H), 6.91 (dd, J=2.2, 0.6 Hz, 1H), 6.40 (d, J=12.7 Hz, 2H), 4.25 (s, 2H), 3.84 (d, J=0.3 Hz, 2H), 3.44 (t, J=7.4 Hz, 4H), 2.29 (s, 3H), 2.10-2.05 (m, 2H), NH and COOH not observed; MS (ES+) m/z 467.1 (M+1).

Example 286

Synthesis of (S)-5-chloro-2-fluoro-N-(thiazol-4-yl)-4-((1-(2,4,5-trifluorophenyl)ethyl)amino)benzenesulfonamide

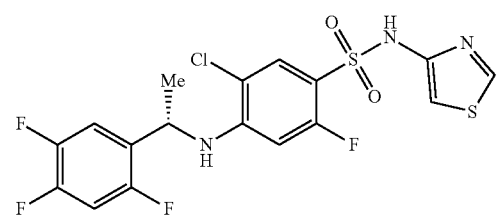 [SMILES: C[C@H](Nc1cc(F)c(S(=O)(=O)Nc2cscn2)cc1Cl)c1cc(F)c(F)cc1F]

Step 1. Preparation of (R,E)-2-methyl-N-(2,4,5-trifluorobenzylidene)propane-2-sulfinamide

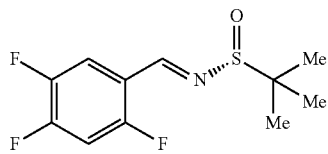 [SMILES: CC(C)(C)[S@@](=O)/N=C/c1cc(F)c(F)cc1F]

To a mixture of 2,4,5-trifluorobenzaldehyde (6.75 g, 42.2 mmol), (R)-2-methylpropane-2-sulfinamide (5.62 g, 46.4 mmol) and pyridinium p-toluenesulfonate (0.53 g, 2.12 mmol) in anhydrous dichloromethane (40 mL) was added anhydrous magnesium sulfate (25.4 g, 210 mmol) and the reaction was stirred at ambient temperature for 16 h. The reaction mixture was filtered and the filtrate concentrated in vacuo. The residue was purified by column chromatography, eluting with 20% of ethyl acetate in petroleum ether, to afford the title compound as a colorless solid (5.60 g, 50% yield): MS (ES+) m/z 264.1 (M+1).

Step 2. Preparation of (R)-2-methyl-N—((S)-1-(2,4,5-trifluorophenyl)ethyl)propane-2-sulfinamide

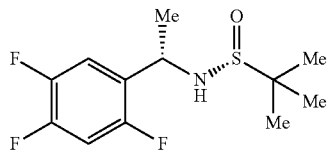 [SMILES: C[C@H](N[S@](=O)C(C)(C)C)c1cc(F)c(F)cc1F]

To a mixture of (R,E)-2-methyl-N-(2,4,5-trifluorobenzylidene)propane-2-sulfinamide (2.65 g, 10 mmol) in dichloromethane (40 mL) was added a 3 M solution of methylmagnesium bromide in diethyl ether (6.60 mL, 20 mmol) at −50° C. The reaction mixture was allowed to warm to ambient temperature and stirred for 16 h. Water (60 mL) was added and the mixture was extracted with dichloromethane (3×30 mL). The combined organic layers were washed with brine (3×30 mL), dried over anhydrous sodium sulfate, and filtered. Concentration of the filtrate in vacuo and purification of the residue by column chromatography, eluting with 40% of ethyl acetate in hexanes, afforded the title compound as colorless oil (2.73 g, 98% yield): MS (ES+) m/z 280.1 (M+1).

Step 3. Preparation of (S)-1-(2,4,5-trifluorophenyl)ethan-1-amine

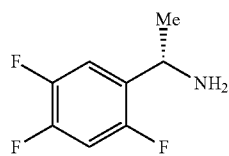 [SMILES: C[C@H](N)c1cc(F)c(F)cc1F]

To (R)-2-methyl-N—((S)-1-(2,4,5-trifluorophenyl)ethyl)propane-2-sulfinamide (2.70 g, 10 mmol) was added a 1.5 M solution of hydrogen chloride in methanol (10.5 mmol, 7.00 mL) and the reaction mixture was stirred at ambient temperature for 1 h. The reaction mixture was then concentrated in vacuo. Ethyl acetate (20 mL) and saturated sodium bicarbonate (10 mL) were added, and the mixture was stirred at ambient temperature for 30 minutes. The aqueous phase was extracted with ethyl acetate (30 mL). The combined organic layers were washed with brine (30 mL), dried over anhydrous sodium sulfate, and filtered. Concentration of the filtrate in vacuo afforded the title compound as a colorless oil (1.43 g, 82% yield): MS (ES+) m/z 176.1 (M+1).

Step 4. Preparation of tert-butyl (S)-((5-chloro-2-fluoro-4-((1-(2,4,5-trifluorophenyl)ethyl)amino)phenyl)sulfonyl)(thiazol-4-yl)carbamate

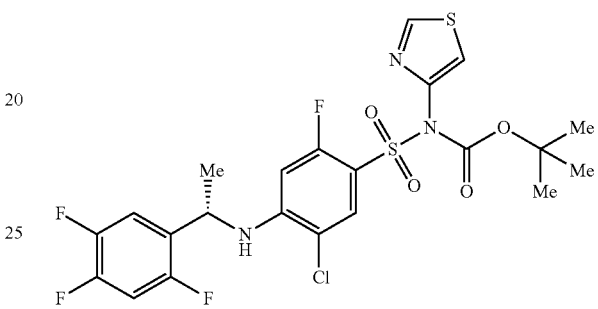

To a mixture of (S)-1-(2,4,5-trifluorophenyl)ethan-1-amine (0.17 g, 1.00 mmol) and tert-butyl ((5-chloro-2,4-difluorophenyl)sulfonyl)(thiazol-4-yl)carbamate (0.41 g, 1.00 mmol) in anhydrous dimethylsulfoxide (6 mL) was added potassium carbonate (0.28 g, 2.00 mmol) and the reaction mixture was stirred at ambient temperature for 16 h. Water (15 mL) was added and the mixture was extracted with diethyl ether (2×20 mL). The combined organic phase was washed with brine (30 mL), dried over anhydrous sodium sulfate, and filtered. Concentration of the filtrate in vacuo and purification of the residue by column chromatography, eluting with a gradient of 0-30% of ethyl acetate in hexanes, afforded the title compound as a colorless solid (0.05 g, 8% yield): MS (ES+) m/z 566.0 (M+1), 568.0 (M+1).

Step 5. Preparation of (S)-5-chloro-2-fluoro-N-(thiazol-4-yl)-4-((1-(2,4,5-trifluorophenyl)ethyl)amino)benzenesulfonamide

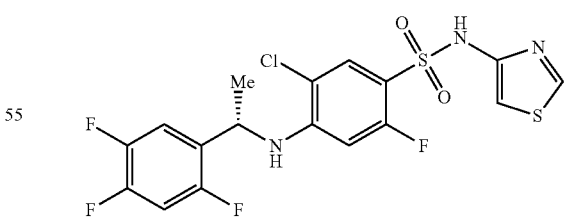

To a solution of tert-butyl (S)-((5-chloro-2-fluoro-4-((1-(2,4,5-trifluorophenyl)ethyl)amino)phenyl)sulfonyl)(thiazol-4-yl)carbamate (0.05 g, 0.09 mmol) in dichloromethane (1 mL) was added trifluoroacetic acid (1 mL) and the reaction mixture was stirred at ambient temperature for 1 h. Concentration of the reaction mixture in vacuo afforded the title compound as a colorless solid (0.04 g, 100% yield): $^1$H NMR (300 MHz, DMSO-d₆) δ 11.15 (s, 1H), 8.87 (dd, J=2.2, 0.7 Hz, 1H), 7.64-7.50 (m, 3H), 6.97 (d, J=2.1 Hz, 1H), 6.66-6.63 (m, 1H), 6.43 (d, J=13.2 Hz, 1H), 4.95-4.90 (m, 1H), 1.55-1.51 (m, 3H); MS (ES+) m/z 446.0 (M+1).

Example 287

Synthesis of (S)-5-Chloro-4-((1-(2,5-difluorophenyl)ethyl)amino)-2-fluoro-N-(oxazol-2-yl)benzenesulfonamide

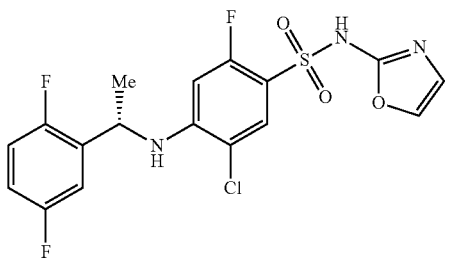 [SMILES: C[C@H](Nc1cc(F)c(S(=O)(=O)Nc2ncco2)cc1Cl)c1cc(F)ccc1F]

Step 1. Preparation of 5-chloro-2,4-difluoro-N-(oxazol-2-yl)benzenesulfonamide

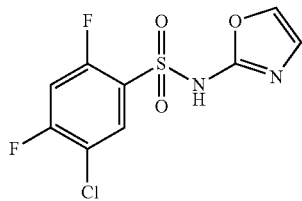 [SMILES: O=S(=O)(Nc1ncco1)c1cc(Cl)c(F)cc1F]

To a solution of tert-butyl oxazol-2-ylcarbamate (1.98 g, 10.7 mmol) in anhydrous tetrahydrofuran (20 mL) was added a 1 M solution of lithium bis(trimethylsilyl)amide in tetrahydrofuran (15.0 mL, 15.0 mmol) at −78° C. and the reaction mixture was stirred at −78° C. for 15 minutes. The reaction mixture was then warmed to ambient temperature, stirred for 10 minutes, and cooled to −78° C. To it was then added a solution of 5-chloro-2,4-difluorobenzenesulfonyl chloride (2.65 g, 10.7 mmol) in anhydrous tetrahydrofuran (20 mL) and the reaction mixture was stirred at −78° C. for 2 h. The reaction mixture was allowed to warm to ambient temperature and stirred for 16 h. The reaction mixture was diluted with an saturated ammonium chloride (50 mL) and extracted with ethyl acetate (2×40 mL). The combined organic phase was washed with brine (30 mL), dried over anhydrous sodium sulfate, and filtered. Concentration of the filtrate in vacuo and purification of the residue by column chromatography, eluting with a gradient of 0-65% of ethyl acetate in hexanes, afforded the title compound as a colorless solid (0.43 g, 13% yield); ¹H-NMR (300 MHz, CDCl₃) δ 8.14-8.08 (m, 1H), 7.16 (d, J=1.7 Hz, 1H), 7.05-6.99 (m, 1H), 6.98 (d, J=1.7 Hz, 1H); MS (ES+) m/z 297.1 (M+1), 295.1 (M+1).

Step 2. Preparation of 5-chloro-2,4-difluoro-N-(4-methoxybenzyl)-N-(oxazol-2-yl)benzenesulfonamide

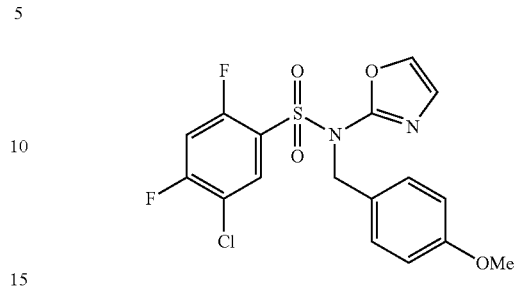

To a solution of 5-chloro-2,4-difluoro-N-(oxazol-2-yl)benzenesulfonamide (0.43 g, 1.47 mmol) in dimethylsulfoxide (5 mL) was added cesium carbonate (1.05 g, 3.23 mmol) and 4-methoxybenzyl chloride (0.28 mL, 2.06 mmol) and the reaction mixture was stirred at 40° C. for 16 h. The reaction mixture was diluted with water (10 mL) and extracted with ethyl acetate (2×15 mL). The combined organic phase was washed with brine (30 mL), dried over anhydrous sodium sulfate and filtered. Concentration of the filtrate in vacuo and purification of the residue by column chromatography, eluting with a gradient of 0-80% of ethyl acetate in hexanes, afforded the title compound as a colorless oil (0.21 g, 34% yield): MS (ES+) m/z 417.2 (M+1), 415.2 (M+1).

Step 3. Preparation of (S)-5-chloro-4-((1-(2,5-difluorophenyl)ethyl)amino)-2-fluoro-N-(4-methoxybenzyl)-N-(oxazol-2-yl)benzenesulfonamide

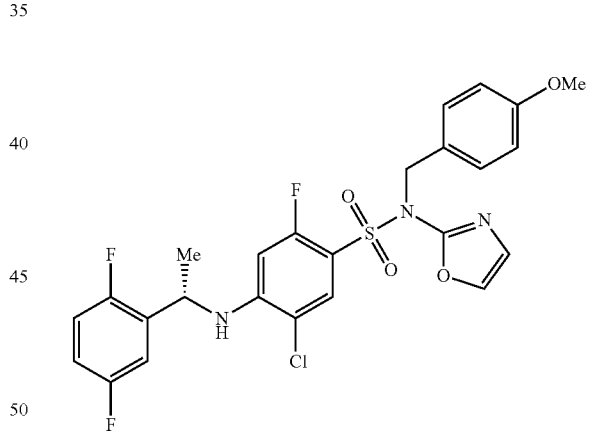

To a mixture of (S)-1-(2,5-difluorophenyl)ethan-1-amine (0.01 g, 0.50 mmol) and 5-chloro-2,4-difluoro-N-(4-methoxybenzyl)-N-(oxazol-2-yl)benzenesulfonamide (0.21 g, 0.50 mmol) in anhydrous dimethyl sulfoxide (4 mL) was added potassium carbonate (0.28 g, 2.00 mmol) and the reaction mixture was stirred at ambient temperature for 16 h. Water (10 mL) was added and the mixture was extracted with diethyl ether (2×20 mL). The combined organic phase was washed with brine (30 mL), dried over anhydrous sodium sulfate and filtered. Concentration of the filtrate in vacuo and purification of the residue by column chromatography, eluting with a gradient of 0-100% of ethyl acetate in hexanes, afforded the title compound as a colorless solid (0.05 g, 18% yield): MS (ES+) m/z 554.2 (M+1), 552.2 (M+1).

Step 4. Preparation of (S)-5-chloro-4-((1-(2,5-difluorophenyl)ethyl)amino)-2-fluoro-N-(oxazol-2-yl)benzenesulfonamide

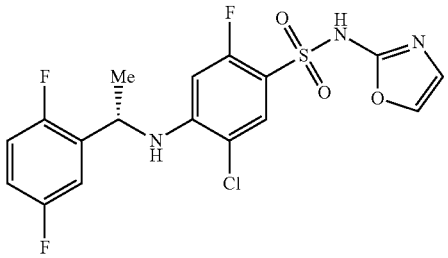 [SMILES: C[C@H](Nc1cc(F)c(S(=O)(=O)Nc2ncco2)cc1Cl)c1cc(F)ccc1F]

To (S)-5-chloro-4-((1-(2,5-difluorophenyl)ethyl)amino)-2-fluoro-N-(4-methoxybenzyl)-N-(oxazol-2-yl)benzenesulfonamide (0.05 g, 0.09 mmol) was added trifluoroacetic acid (3 mL) and the reaction mixture was stirred at ambient temperature for 96 h. The mixture was then concentrated in vacuo and the residue purified by preparative reverse phase HPLC, using acetonitrile in water containing 0.1% of trifluoroacetic acid as eluent, to afford the title compound as a colorless solid (0.004 g, 25% yield): $^1$H-NMR (300 MHz, DMSO-$d_6$) δ 11.64-11.48 (br s, 1H), 10.38-10.17 (br s, 1H), 7.85 (q, J=8.2 Hz, 1H), 7.77 (d, J=7.4 Hz, 1H), 7.45-7.41 (m, 2H), 6.89-6.86 (m, 1H), 6.78-6.70 (m, 2H), 4.52-4.50 (m, 1H), 2.44-2.13 (m, 3H); MS (ES+) m/z 434.2 (M+1), 432.2 (M+1).

Example 288

Synthesis of 4-((2-(Azetidin-1-ylmethyl)-3,6-difluorobenzyl)amino)-5-chloro-2-fluoro-N-(thiazol-4-yl)benzenesulfonamide hydrochloride

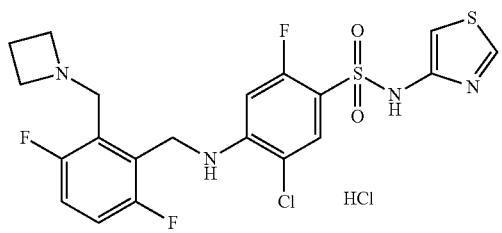 [SMILES: O=S(=O)(Nc1cscn1)c1cc(Cl)c(NCc2c(F)ccc(F)c2CN2CCC2)cc1F ; Cl]

Step 1. Preparation of (2-(azetidin-1-ylmethyl)-3,6-difluorophenyl)methanol

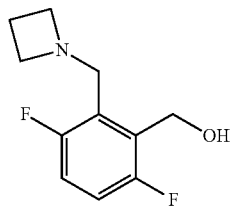 [SMILES: OCc1c(F)ccc(F)c1CN1CCC1]

To 3,6-difluorophthalic anhydride (1.84 g, 10.0 mmol) was added anhydrous tetrahydrofuran (20 mL) and azetidine (0.57 mL, 10 mmol) and the mixture was stirred at ambient temperature for 2 h. To it was then added a 1.0 M solution of borane in tetrahydrofuran (25 mL, 25 mmol) was then added and the mixture was stirred at ambient temperature for 16 h. The mixture was poured slowly into 2 M sodium hydroxide (30 mL) and stirred for 2 h. The solution was extracted with ethyl acetate (3×30 mL), washed with brine (20 mL), dried over anhydrous sodium sulfate, and filtered. Concentration of the filtrate in vacuo afforded the title compound as colorless oil (2.16 g, 99% yield): MS (ES+) m/z 214.1 (M+1).

Step 2. Preparation of 2-(2-(azetidin-1-ylmethyl)-3,6-difluorobenzyl)isoindoline-1,3-dione

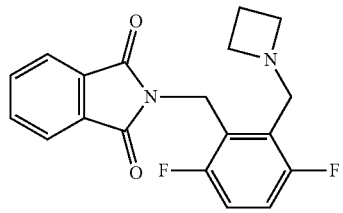 [SMILES: O=C1c2ccccc2C(=O)N1Cc1c(F)ccc(F)c1CN1CCC1]

To a solution of (2-(azetidin-1-ylmethyl)-3,6-difluorophenyl)methanol (1.93 g, 8.90 mmol), phthalimide (1.43 g, 9.8 mmol) and triphenylphosphine (3.96 g, 15.1 mmol) in anhydrous tetrahydrofuran (30 mL) was added dropwise diisopropyl azodicarboxylate (2.70 mL, 13.3 mmol) at 0° C. The reaction mixture was allowed to warm to ambient temperature, stirred for 1 h, and then concentrated in vacuo. The residue was purified by column chromatography, eluting with a gradient of 0-50% of ethyl acetate in hexanes, to afford the title compound as an oil (3.08 g, 99% yield): MS (ES+) m/z 343.2 (M+1).

Step 3. Preparation of (2-(azetidin-1-ylmethyl)-3,6-difluorophenyl)methanamine

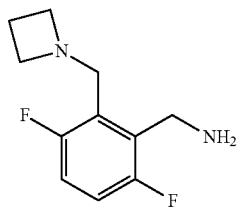 [SMILES: NCc1c(F)ccc(F)c1CN1CCC1]

To a solution of 2-(2-(azetidin-1-ylmethyl)-3,6-difluorobenzyl)isoindoline-1,3-dione (3.08 g, 8.9 mmol) in ethanol (30 mL) was added hydrazine monohydrate (5.00 mL, 100 mmol) and the mixture was heated to reflux for 1 h. After cooling to ambient temperature, the reaction mixture was concentrated in vacuo. To the residue was added water (20 mL), and the mixture was extracted with ethyl acetate (3×30 mL). The combined organic layers were washed with brine (20 mL), dried over anhydrous sodium sulfate, and filtered. Concentration of the filtrate in vacuo provided the title compound as a colorless oil (1.88 g, 99% yield): MS (ES+) m/z 213.1 (M+1).

Step 4. Preparation of tert-butyl ((4-((2-(azetidin-1-ylmethyl)-3,6-difluorobenzyl)amino)-5-chloro-2-fluorophenyl)sulfonyl)(thiazol-4-yl)carbamate

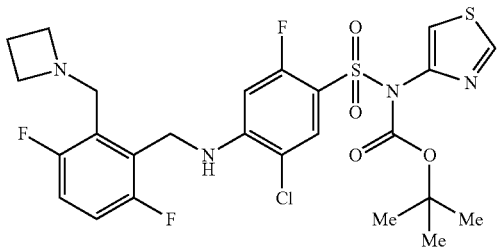 [SMILES: CC(C)(C)OC(=O)N(c1cscn1)S(=O)(=O)c1cc(Cl)c(NCc2c(F)ccc(F)c2CN2CCC2)cc1F]

To a mixture of (2-(azetidin-1-ylmethyl)-3,6-difluorophenyl)methanamine (2.40 g, 11.4 mmol) and tert-butyl ((5-chloro-2,4-difluorophenyl)sulfonyl)(thiazol-4-yl)carbamate (4.68 g, 11.4 mmol) in anhydrous dimethyl sulfoxide (30 mL) was added potassium carbonate (3.93 g, 28.5 mmol) and the reaction mixture was stirred at ambient temperature for 16 h. Water (70 mL) was added and the mixture was extracted with a 1:1 mixture of diethyl ether and ethyl acetate (2×50 mL). The combined organic phase was washed with brine (50 mL), dried over anhydrous sodium sulfate and filtered. Concentration of the filtrate in vacuo provided a residue which was purified by column chromatography, eluting with a gradient of 0-50% of ethyl acetate in hexanes. Further purification by column chromatography, eluting with a gradient of 0-10% of methanol in dichloromethane, afforded the title compound as a colorless solid (1.08 g, 16% yield): MS (ES+) m/z 603.2 (M+1), 605.2 (M+1).

Step 5. Preparation of 4-((2-(azetidin-1-ylmethyl)-3,6-difluorobenzyl)amino)-5-chloro-2-fluoro-N-(thiazol-4-yl)benzenesulfonamide hydrochloride

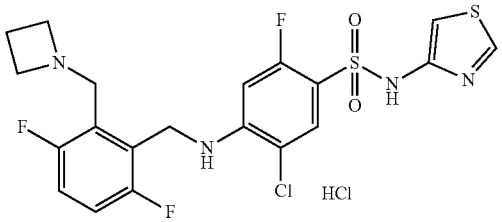 [SMILES: O=S(=O)(Nc1cscn1)c1cc(Cl)c(NCc2c(F)ccc(F)c2CN2CCC2)cc1F ; Cl]

To a solution of tert-butyl ((4-((2-(azetidin-1-ylmethyl)-3,6-difluorobenzyl)amino)-5-chloro-2-fluorophenyl)sulfonyl)(thiazol-4-yl)carbamate (1.08 g, 1.79 mmol) in dichloromethane (5 mL) was added trifluoroacetic acid (5 mL) and the reaction mixture was stirred at ambient temperature for 1 h. The mixture was concentrated in vacuo and the residue dissolved in methanol (5 mL). To it was then added a 7 M solution of ammonium hydroxide (5 mL) in methanol at −40° C. Concentration in vacuo provided a residue which was dissolved in dichloromethane (10 mL) and washed with 2 M hydrochloric acid (10 mL). The aqueous layer was extracted with dichloromethane (2×10 mL). The combined organic phase was concentrated in vacuo. The residue was purified by column chromatography, eluting with a gradient of 0-10% of methanol in dichloromethane, to afford the title compound as a colorless solid (0.610 g, 63% yield): $^1$H NMR (300 MHz, DMSO-$d_6$) δ 11.19 (s, 1H), 10.52-10.47 (m, 1H), 8.89 (d, J=2.2 Hz, 1H), 7.62 (d, J=7.3 Hz, 1H), 7.47-7.41 (m, 2H), 7.01-7.00 (m, 1H), 6.94-6.92 (m, 1H), 6.78-6.73 (m, 1H), 4.58-4.53 (m, 4H), 4.20-4.14 (m, 2H), 4.05-3.99 (m, 2H), 2.39-2.27 (m, 2H); MS (ES+) m/z 505.2 (M+1), 503.2 (M+1).

Example 289

Synthesis of 4-(((1R,3S)-3-(azetidin-1-yl)-2,3-dihydro-1H-inden-1-yl)amino)-2,6-difluoro-N-(thiazol-4-yl)benzenesulfonamide

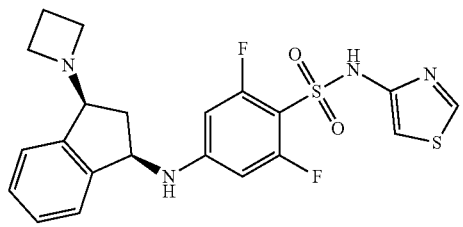 [SMILES: O=S(=O)(Nc1cscn1)c1c(F)cc(N[C@@H]2C[C@H](N3CCC3)c3ccccc32)cc1F]

Step 1. Preparation of tert-butyl ((4-(((1R,3S)-3-(azetidin-1-yl)-2,3-dihydro-1H-inden-1-yl)amino)-3-bromo-2,6-difluorophenyl)sulfonyl)(thiazol-4-yl)carbamate

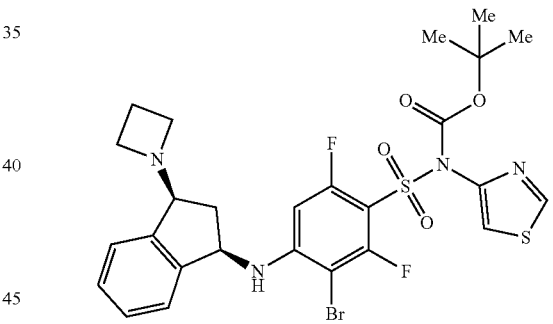

To a solution of tert-butyl (3-bromo-2,4,6-trifluorophenyl)sulfonyl(thiazol-4-yl)carbamate (0.30 g, 0.63 mmol) in anhydrous N,N-dimethylformamide (8 mL) was added (1R,3S)-3-(azetidin-1-yl)-2,3-dihydro-1H-inden-1-amine (0.12 g, 0.63 mmol) and potassium carbonate (0.18 g, 1.27 mmol). The mixture was stirred at ambient temperature for 12 h, and then diluted with water (10 mL) and extracted with ethyl acetate (2×10 mL). The combined organic extracts were washed with brine (10 mL), dried over anhydrous sodium sulfate, and filtered. Concentration of the filtrate in vacuo and purification of the residue by preparative thin layer chromatography, eluting with 100% of ethyl acetate, afforded the title compound as a yellow solid (0.25 g, 55% yield): $^1$H NMR (400 MHz, CDCl$_3$) δ 8.72 (d, J=2.4 Hz, 1H), 7.44 (d, J=2.2 Hz, 1H), 7.32-7.28 (m, 2H), 7.28-7.23 (m, 2H), 6.58 (d, J=8.4 Hz, 1H), 6.54-6.44 (m, 1H), 4.87 (dt, J=7.6, 3.4 Hz, 1H), 4.05-3.94 (m, 1H), 3.46 (q, J=7.2 Hz, 2H), 3.42-3.34 (m, 2H), 2.55 (td, J=13.4, 6.8 Hz, 1H), 2.09 (quin, J=7.2 Hz, 2H), 1.89 (t, J=3.4 Hz, 1H), 1.34 (s, 9H); MS (ES+) m/z 641.0 (M+1).

Step 2. Preparation of tert-butyl ((4-(((1R,3S)-3-(azetidin-1-yl)-2,3-dihydro-1H-inden-1-yl)amino)-2,6-difluorophenyl)sulfonyl)(thiazol-4-yl)carbamate

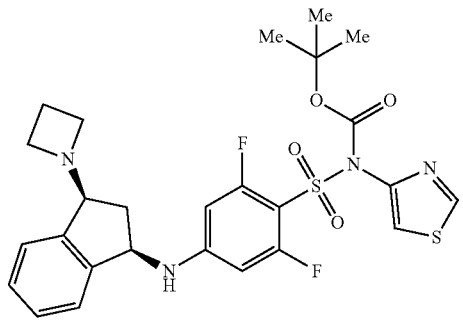 [SMILES: CC(C)(C)OC(=O)N(c1cscn1)S(=O)(=O)c1c(F)cc(N[C@@H]2C[C@H](N3CCC3)c3ccccc32)cc1F]

To a solution of tert-butyl ((4-(((1R,3S)-3-(azetidin-1-yl)-2,3-dihydro-1H-inden-1-yl)amino)-3-bromo-2,6-difluorophenyl)sulfonyl)(thiazol-4-yl)carbamate (0.16 g, 0.25 mmol) in methanol (10 mL) was added palladium on charcoal (0.020 g). The suspension was stirred under a hydrogen atmosphere (50 psi) at 50° C. for 12 h. After cooling to ambient temperature, the reaction mixture was filtered, and the filtrate was concentrated in vacuo. The residue was purified by preparative reverse-phase HPLC, eluting with a gradient of acetonitrile in water containing 0.225% formic acid, to afford the title compound as a yellow solid (0.13 g, 93% yield): $^1$H NMR (400 MHz, CDCl$_3$) δ 8.78 (d, J=2.2 Hz, 1H), 7.62 (d, J=8.8 Hz, 1H), 7.50 (dd, J=4.4, 2.0 Hz, 2H), 7.47-7.38 (m, 3H), 6.46 (d, J=12.0 Hz, 2H), 5.05 (t, J=8.4 Hz, 1H), 4.55 (d, J=7.6 Hz, 1H), 4.23-4.13 (m, 2H), 4.06 (d, J=7.6 Hz, 2H), 2.94-2.85 (m, 1H), 2.75-2.45 (m, 2H), 2.30-2.05 (m, 1H), 1.42 (s, 9H); MS (ES+) m/z 563.1 (M+1).

Step 3. Preparation of 4-(((1R,3S)-3-(azetidin-1-yl)-2,3-dihydro-1H-inden-1-yl)amino)-2,6-difluoro-N-(thiazol-4-yl)benzenesulfonamide

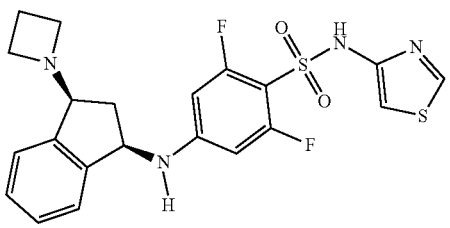 [SMILES: O=S(=O)(Nc1cscn1)c1c(F)cc(N[C@@H]2C[C@H](N3CCC3)c3ccccc32)cc1F]

Following the procedure as described in Example 5, Step 2 and making non-critical variations to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl ((4-(((1R,3S)-3-(azetidin-1-yl)-2,3-dihydro-1H-inden-1-yl)amino)-2,6-difluorophenyl)sulfonyl)(thiazol-4-yl)carbamate, the title compound was afforded as a colorless solid (0.080 g, 96% yield): $^1$H NMR (400 MHz, CD$_3$OD) δ 8.76 (d, J=2.4 Hz, 1H), 8.55 (s, 1H), 7.42-7.36 (m, 1H), 7.34-7.29 (m, 3H), 6.95 (d, J=2.0 Hz, 1H), 6.35 (d, J=12.4 Hz, 2H), 4.97-4.94 (m, 1H), 4.07 (t, J=6.8 Hz, 1H), 3.61-3.51 (m, 4H), 2.78 (td, J=13.0, 7.2 Hz, 1H), 2.20 (quin, J=7.2 Hz, 2H), 1.64 (td, J=13.2, 6.6 Hz, 1H), NH not observed; MS (ES+) m/z 463.1 (M+1).

Example 290

Synthesis of 4-((2-(azetidin-1-ylmethyl)-6-chlorobenzyl)amino)-2,6-difluoro-N-(thiazol-4-yl)benzenesulfonamide 2,2,2-trifluoroacetate

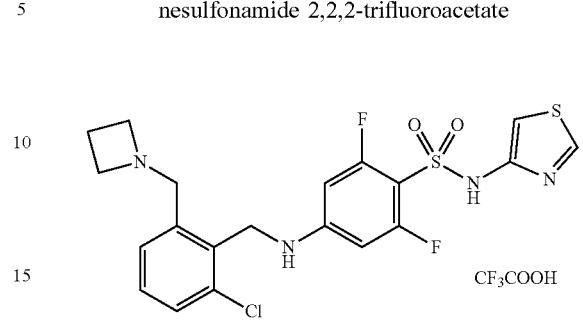

Step 1. Preparation of 4-chloro-1,3-dihydroisobenzofuran-1-ol

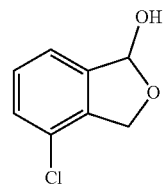 [SMILES: OC1OCc2c(Cl)cccc21]

To a mixture of 4-chloroisobenzofuran-1(3H)-one (3.37 g, 20.0 mmol) in anhydrous dichloromethane (50 mL) was added a 1 M solution of diisobutylaluminium hydride in toluene (44.0 mL, 44.0 mmol) at −78° C. The reaction mixture was stirred at −78° C. for 2 h, and then quenched by addition of 1 M hydrochloric acid (50 mL). The aqueous layer was extracted with dichloromethane (2×30 mL). The combined organic layers were washed with brine (50 mL), dried over anhydrous sodium sulfate, and filtered. Concentration of the filtrate in vacuo afforded the title compound as a colorless solid (2.85 g, 84% yield): $^1$H NMR (300 MHz, CDCl$_3$) δ 7.42-7.29 (m, 3H), 6.55-6.53 (m, 1H), 5.27-5.23 (m, 1H), 5.08-5.03 (m, 1H), 3.40-3.37 (m, 1H).

Step 2. Preparation of (2-(azetidin-1-ylmethyl)-6-chlorophenyl)methanol

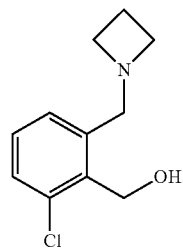 [SMILES: OCc1c(Cl)cccc1CN1CCC1]

To a solution of 4-chloro-1,3-dihydroisobenzofuran-1-ol (0.75 g, 4.41 mmol) and azetidine (0.30 mL, 5.3 mmol) in dichloromethane (10 mL) was added sodium triacetoxyborohydride (2.60 g, 12.3 mmol) and the reaction mixture was stirred at ambient temperature for 16 h. To it was then added saturated sodium bicarbonate (20 mL) and the mixture was extracted with dichloromethane (3×20 mL). The combined organic phase was washed with brine (50 mL), dried over anhydrous sodium sulfate and filtered. Concentration of the filtrate in vacuo and purification of the residue by column chromatography, eluting with a gradient of 0-70% of ethyl acetate in hexanes, afforded the title compound as an colorless oil (0.90 g, 96% yield): MS (ES+) m/z 212.1 (M+1), 214.1 (M+1).

Step 3. Preparation of 2-(2-(azetidin-1-ylmethyl)-6-chlorobenzyl)isoindoline-1,3-dione

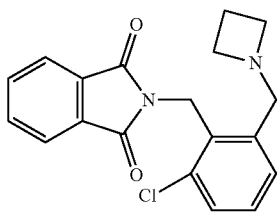 [SMILES: O=C1c2ccccc2C(=O)N1Cc1c(Cl)cccc1CN1CCC1]

Following the procedure as described in EXAMPLE 288, Step 2, and making non-critical variations as required to replace (2-(azetidin-1-ylmethyl)-3,6-difluorophenyl)methanol with (2-(azetidin-1-ylmethyl)-6-chlorophenyl)methanol, the title compound was obtained as an oil (1.38 g, 95% yield): MS (ES+) m/z 341.1 (M+1), 343.2 (M+1).

Step 4. Preparation of (2-(azetidin-1-ylmethyl)-6-chlorophenyl)methanamine

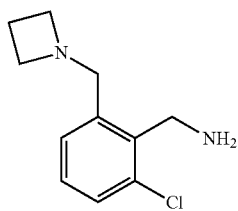 [SMILES: NCc1c(Cl)cccc1CN1CCC1]

Following the procedure as described in EXAMPLE 288, Step 3, and making non-critical variations as required to replace 2-(2-(azetidin-1-ylmethyl)-3,6-difluorobenzyl)isoindoline-1,3-dione with 2-(2-(azetidin-1-ylmethyl)-6-chlorobenzyl)isoindoline-1,3-dione, the title compound was obtained as a colorless oil (1.88 g, 99% yield): MS (ES+) m/z 211.1 (M+1), 213.1 (M+1).

Step 5. Preparation of tert-butyl ((4-((2-(azetidin-1-ylmethyl)-6-chlorobenzyl)amino)-2,6-difluorophenyl)sulfonyl)(thiazol-4-yl)carbamate

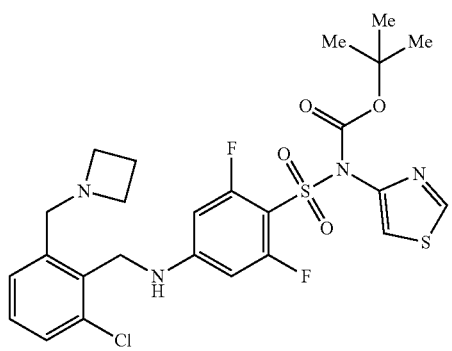 [SMILES: CC(C)(C)OC(=O)N(c1cscn1)S(=O)(=O)c1c(F)cc(NCc2c(Cl)cccc2CN2CCC2)cc1F]

To a mixture of (2-(azetidin-1-ylmethyl)-6-chlorophenyl)methanamine (0.89 g, 4.24 mmol) and tert-butyl thiazol-4-yl((2,4,6-trifluorophenyl)sulfonyl)carbamate (1.67 g, 4.24 mmol) in anhydrous N,N-dimethylformamide (10 mL) was added cesium carbonate (4.12 g, 12.7 mmol) and the reaction mixture was heated to 45° C. for 1 h. The reaction mixture was allowed to cool down to ambient temperature, and water (40 mL) was added to it. The mixture was extracted with ethyl acetate (2×50 mL). The combined organic phase was washed with brine (50 mL), dried over anhydrous sodium sulfate and filtered. Concentration of the filtrate in vacuo provided a residue which was purified by column chromatography, eluting with a gradient of 0-100% of ethyl acetate in hexanes. Further purification by column chromatography, eluting with a gradient of 0-10% of methanol in dichloromethane, afforded the title compound as a colorless solid (0.10 g, 4% yield): MS (ES+) m/z 587.2 (M+1), 585.2 (M+1).

Step 6. 4-(((2-(azetidin-1-ylmethyl-$d_2$)-3,6-difluorophenyl)methyl-$d_2$)amino)-2,6-difluoro-N-(thiazol-4-yl)benzenesulfonamide 2,2,2-trifluoroacetate

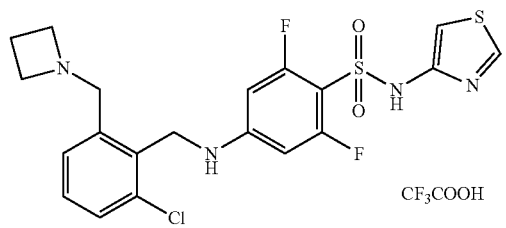 [SMILES: O=S(=O)(Nc1cscn1)c1c(F)cc(NCc2c(Cl)cccc2CN2CCC2)cc1F ; "CF3COOH"]

To a solution of tert-butyl ((4-((2-(azetidin-1-ylmethyl)-6-chlorobenzyl)amino)-2,6-difluorophenyl)sulfonyl)(thiazol-4-yl)carbamate (0.10 g, 0.17 mmol) in dichloromethane (3 mL) was added trifluoroacetic acid (3 mL) and the reaction mixture was stirred at ambient temperature for 1 h. The mixture was then concentrated in vacuo to afford the title compound as a colorless solid (0.10 g, quantitative yield): $^1$H NMR (300 MHz, DMSO-$d_6$) δ 11.25 (s, 1H), 10.19-10.17 (br s, 1H), 8.92 (d, J=2.2 Hz, 1H), 7.62 (dd, J=5.8, 3.6 Hz, 1H), 7.53-7.48 (m, 2H), 7.17-7.15 (m, 1H), 6.93 (d, J=2.2 Hz, 1H), 6.40-6.35 (m, 2H), 4.47-4.38 (m, 4H), 4.15-4.01 (m, 4H), 2.41-2.25 (m, 2H); MS (ES+) m/z 487.3, 485.2 (M+1).

Example 291

Synthesis of 4-((2-((2,6-diazaspiro[3.3]heptan-2-yl)methyl)-6-chlorobenzyl)amino)-5-chloro-2-fluoro-N-(thiazol-4-yl)benzenesulfonamide 2,2,2-trifluoroacetate

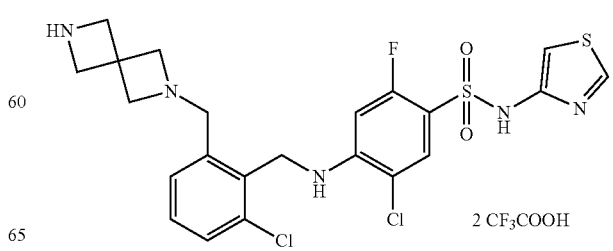

Step 1. Preparation of tert-butyl 6-(3-chloro-2-(hydroxymethyl)benzyl)-2,6-diazaspiro[3.3]heptane-2-carboxylate

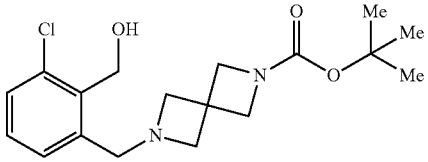 [SMILES: CC(C)(C)OC(=O)N1CC2(CN(Cc3cccc(Cl)c3CO)C2)C1]

Following the procedure as described in EXAMPLE 290, Step 2, and making non-critical variations as required to replace azetidine with tert-butyl 2,6-diazaspiro[3.3]heptane-2-carboxylate, the title compound was obtained (1.51 g, 92% yield): MS (ES+) m/z 355.2 (M+1), 353.2 (M+1).

Step 2. Preparation of tert-butyl 6-(3-chloro-2-((1,3-dioxoisoindolin-2-yl)methyl)benzyl)-2,6-diazaspiro[3.3]heptane-2-carboxylate

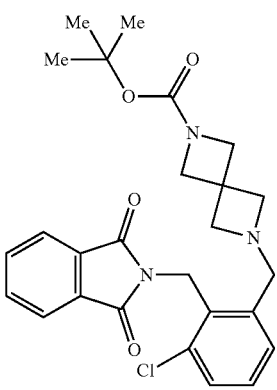 [SMILES: CC(C)(C)OC(=O)N1CC2(CN(Cc3cccc(Cl)c3CN3C(=O)c4ccccc4C3=O)C2)C1]

Following the procedure as described in EXAMPLE 288, Step 2, and making non-critical variations as required to replace (2-(azetidin-1-ylmethyl)-3,6-difluorophenyl)methanol with tert-butyl 6-(3-chloro-2-(hydroxymethyl)benzyl)-2,6-diazaspiro[3.3]heptane-2-carboxylate, the title compound was obtained as an oil (1.38 g, 95% yield): MS (ES+) m/z 484.2 (M+1), 482.2 (M+1).

Step 3. Preparation of tert-butyl 6-(2-(aminomethyl)-3-chlorobenzyl)-2,6-diazaspiro[3.3]heptane-2-carboxylate

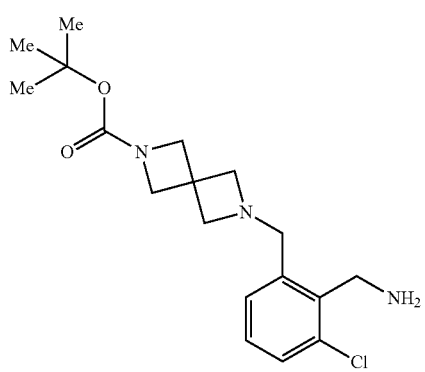 [SMILES: CC(C)(C)OC(=O)N1CC2(CN(Cc3cccc(Cl)c3CN)C2)C1]

Following the procedure as described in EXAMPLE 288, Step 3, and making non-critical variations as required to replace 2-(2-(azetidin-1-ylmethyl)-3,6-difluorobenzyl)isoindoline-1,3-dione with tert-butyl 6-(3-chloro-2-((1,3-dioxoisoindolin-2-yl)methyl)benzyl)-2,6-diazaspiro[3.3]heptane-2-carboxylate, the title compound was obtained as an oil (1.12 g, 79% yield): MS (ES+) m/z 354.2 (M+1), 352.2 (M+1).

Step 4. Preparation of tert-butyl 6-(2-(((4-(N-(tert-butoxycarbonyl)-N-(thiazol-4-yl)sulfamoyl)-2-chloro-5-fluorophenyl)amino)methyl)-3-chlorobenzyl)-2,6-diazaspiro[3.3]heptane-2-carboxylate

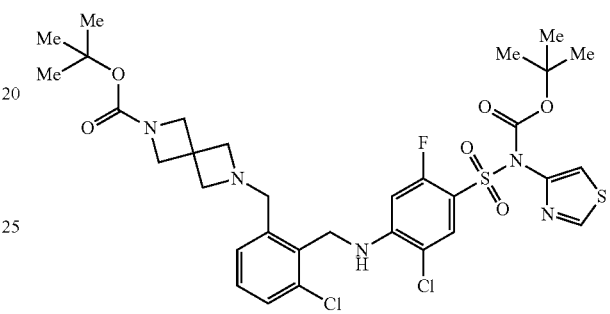

Following the procedure as described in EXAMPLE 288, Step 4, and making non-critical variations as required to replace (2-(azetidin-1-ylmethyl)-3,6-difluorophenyl)methanamine with tert-butyl 6-(2-(aminomethyl)-3-chlorobenzyl)-2,6-diazaspiro[3.3]heptane-2-carboxylate, the title compound was obtained as a colorless solid (0.18 g, 13% yield): MS (ES+) m/z 728.3 (M+1), 726.3 (M+1).

Step 5. 4-((2-((2,6-diazaspiro[3.3]heptan-2-yl)methyl)-6-chlorobenzyl)amino)-5-chloro-2-fluoro-N-(thiazol-4-yl)benzenesulfonamide 2,2,2-trifluoroacetate

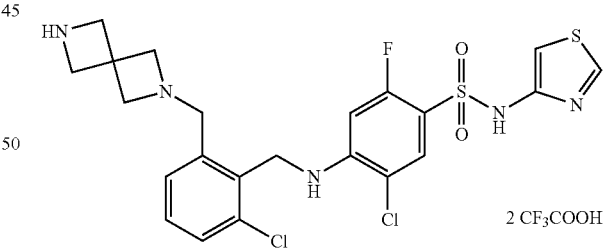

Following the procedure as described in EXAMPLE 290, Step 6, and making non-critical variations as required to replace tert-butyl ((4-((2-(azetidin-1-ylmethyl)-6-chlorobenzyl)amino)-2,6-difluorophenyl)sulfonyl)(thiazol-4-yl)carbamate with tert-butyl 6-(2-(((4-(N-(tert-butoxycarbonyl)-N-(thiazol-4-yl)sulfamoyl)-2-chloro-5-fluorophenyl)amino)methyl)-3-chlorobenzyl)-2,6-diazaspiro[3.3]heptane-2-carboxylate, the title compound was obtained as a colorless solid (0.18 g, 100% yield): $^{1}$H NMR (300 MHz, DMSO-$d_6$) δ 11.21-11.18 (br s, 1H), 10.60-10.58 (m, 1H), 8.90-8.83 (m, 3H), 7.64-7.58 (m, 2H), 7.50-7.41 (m, 2H), 7.01-7.00 (m, 1H), 6.78 (d, J=13.1 Hz, 1H), 6.55-6.54 (m, 1H), 4.49-4.46 (m, 4H), 4.33-4.28 (m, 4H), 4.16-4.10 (m, 4H); MS (ES+) m/z 544.1, 542.1 (M+1).

Example 292

Synthesis of 5-chloro-4-((2-chloro-6-((6-methyl-2,6-diazaspiro[3.3]heptan-2-yl)methyl)benzyl)amino)-2-fluoro-N-(thiazol-4-yl)benzenesulfonamide 2,2,2-trifluoroacetate

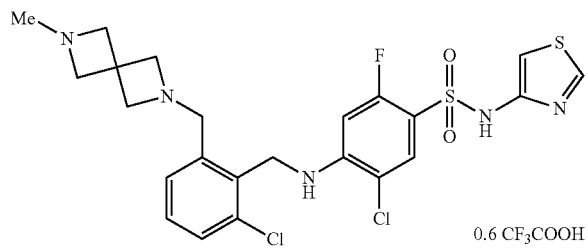 [SMILES: CN1CC2(C1)CN(Cc1cccc(Cl)c1CNc1cc(F)c(S(=O)(=O)Nc3cscn3)cc1Cl)C2]

To 4-((2-((2,6-diazaspiro[3.3]heptan-2-yl)methyl)-6-chlorobenzyl)amino)-2,6-difluoro-N-(thiazol-4-yl)benzenesulfonamide 2,2,2-trifluoroacetate (0.16 g, 0.24 mmol) was added tetrahydrofuran (2 mL), 37% aqueous formaldehyde (0.1 mL, 1.2 mmol), and sodium cyanoborohydride (0.03 g, 0.48 mmol). The reaction mixture was stirred for 2 hours at ambient temperature and then quenched by addition of a saturated sodium bicarbonate (10 mL). The mixture was extracted with dichloromethane (3×10 mL). The combined organic phase was washed with brine (10 mL), dried over anhydrous sodium sulfate, and filtered. Concentration of the filtrate in vacuo and purification of the residue by preparative reverse phase HPLC, using acetonitrile in water containing 0.1% trifluoroacetic acid as eluent, afforded the title compound as a colorless solid (0.04 g, 25% yield): $^1$H NMR (300 MHz, DMSO-$d_6$) δ 8.87 (d, J=2.1 Hz, 1H), 8.19 (m, 0.6H), 7.61 (d, J=7.3 Hz, 1H), 7.45-7.42 (m, 1H), 7.32 (dd, J=3.2, 2.7 Hz, 2H), 7.08-6.99 (m, 2H), 6.88-6.88 (m, 1H), 4.53-4.50 (m, 2H), 3.91-3.86 (m, 4H), 3.66 (d, J=4.9 Hz, 2H), 3.34-3.31 (m, 4H), 2.59-2.57 (s, 3H), NH not observed; MS (ES+) m/z 558.2 (M+1), 556.2 (M+1).

Example 293

Synthesis of 5-Chloro-4-((3,6-difluoro-2-(hydroxymethyl)benzyl)amino)-2-fluoro-N-(thiazol-4-yl)benzenesulfonamide

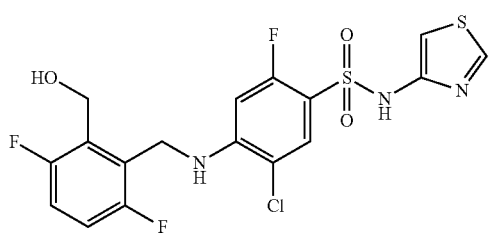 [SMILES: O=S(=O)(Nc1cscn1)c1cc(Cl)c(NCc2c(F)ccc(F)c2CO)cc1F]

Step 1. Preparation of (2-bromo-3,6-difluorophenyl)methanol

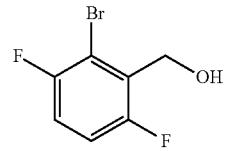

To a solution of 2-bromo-3,6-difluorobenzaldehyde (10.0 g, 45.2 mmol) in a 1:1 mixture of dichloromethane and methanol (150 mL) was added sodium borohydride (2.58 g, 67.8 mmol) at 0° C. in portions over 15 minutes. The reaction mixture was stirred at 0° C. for 2 hours, and then quenched by addition of saturated ammonium chloride (50 mL). The reaction mixture was concentrated under reduced pressure and the remaining aqueous layer was extracted with ethyl acetate (2×70 mL). The combined the organic layers were washed with brine (10 mL), dried over anhydrous sodium sulfate and filtered. Concentration of the filtrate in vacuo provided the title compound as a colorless solid (9.70 g, 96% yield) which was used in the next step without further purification.

Step 2. Preparation of ((2-bromo-3,6-difluorobenzyl)oxy)(tert-butyl)dimethylsilane

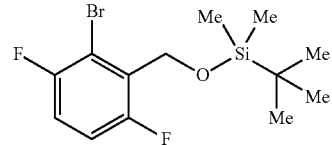 [SMILES: CC(C)(C)[Si](C)(C)OCc1c(F)ccc(F)c1Br]

To a solution of (2-bromo-3,6-difluorophenyl)methanol (9.70 g, 43.5 mmol) in N,N-dimethylformamide (85 mL) was added imidazole (3.84 g, 56.5 mmol) followed by tert-Butyldimethylsilyl chloride (6.85 g, 45.6 mmol) at 0° C. and the reaction mixture was stirred for 1 hour at 0° C. To it was then added saturated ammonium chloride (50 mL) and the mixture was extracted with diethyl ether (2×60 mL). The combined organic layers were washed with brine (2×30 mL), dried over anhydrous sodium sulfate, and filtered. Concentration of the filtrate in vacuo provided the title compound as a colorless oil (14.0 g, 96% yield): $^1$H-NMR (300 MHz, CDCl$_3$) δ 7.08-7.04 (m, 2H), 4.85 (dd, J=2.4, 0.7 Hz, 2H), 0.92 (s, 9H), 0.13 (s, 6H).

Step 3. Preparation of 2-(((tert-butyldimethylsilyl)oxy)methyl)-3,6-difluorobenzaldehyde

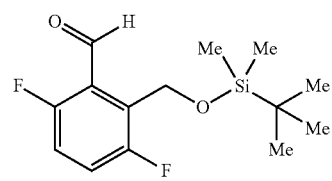 [SMILES: CC(C)(C)[Si](C)(C)OCc1c(F)ccc(F)c1C=O]

To a solution of ((2-bromo-3,6-difluorobenzyl)oxy)(tert-butyl)dimethylsilane (14.0 g, 41.5 mmol) in anhydrous tetrahydrofuran (120 mL) was added dropwise a 1.5 M solution of n-butyllithium in hexane (36.0 mL, 54.0 mmol) at −78° C. The reaction mixture was stirred for 10 minutes at −78° C. and then N,N-dimethylformamide (5.10 mL, 66.4 mmol) was added to it. The reaction mixture was stirred at −78° C. for 15 minutes, then allowed to warm to ambient temperature, and stirred for 40 minutes. To it was added saturated ammonium chloride (50 mL) and the mixture was extracted with diethyl ether (2×80 mL). The combined the organic layers were washed with brine (2×40 mL), dried over anhydrous sodium sulfate and filtered. Concentration of the filtrate in vacuo afforded the title compound as a colorless oil (11.7 g, 96% yield): $^1$H-NMR (300 MHz, CDCl$_3$) δ 10.46 (t, J=0.4 Hz, 1H), 7.29-7.22 (m, 1H), 7.12 (dd, J=9.5, 4.1 Hz, 1H), 5.04 (d, J=1.9 Hz, 2H), 0.89 (s, 9H), 0.11 (s, 6H).

Step 4. Preparation of (E)-2-(((tert-butyldimethylsilyl)oxy)methyl)-3,6-difluorobenzaldehyde oxime

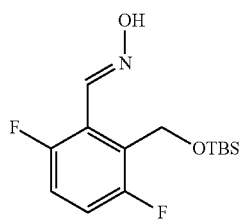

To a solution of 2-(((tert-butyldimethylsilyl)oxy)methyl)-3,6-difluorobenzaldehyde (4.25 g, 14.9 mmol) in acetonitrile (18 mL) and water (32 mL) was added sodium bicarbonate (3.70 g, 45.0 mmol) followed by hydroxylamine hydrochloride (2.10 g, 29.7 mmol) and tetrabutylammonium chloride (0.21 g, 0.75 mmol) and the reaction mixture was stirred at ambient temperature for 45 minutes. To it was added acetic acid (1.2 mL) to adjust the pH to 6.7 followed by water (30 mL) and the mixture was extracted with diethyl ether (3×60 mL). The combined organic layers were washed with brine (40 mL), dried over anhydrous sodium sulfate and filtered. Concentration of the filtrate in vacuo afforded the title compound as a yellow solid (4.53 g, 100% yield): MS (ES+) m/z 302.2 (M+1).

Step 5. Preparation of (2-(((tert-butyldimethylsilyl)oxy)methyl)-3,6-difluorophenyl)methanamine

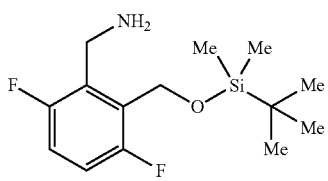 [SMILES: CC(C)(C)[Si](C)(C)OCc1c(F)ccc(F)c1CN]

To a solution of (E)-2-(((tert-butyldimethylsilyl)oxy)methyl)-3,6-difluorobenzaldehyde oxime (4.53 g, 14.9 mmol) in diethyl ether (150 mL) was added a 1.0 M solution of lithium aluminum hydride solution in diethyl ether (37.7 mL, 37.7 mmol) at 0° C. and the reaction mixture was stirred at 0° C. for 2 h. The reaction was then quenched by slow addition of water (1.4 mL) and stirred for 5 minutes. To it was then added 2 M sodium hydroxide (2.8 mL). The mixture was stirred for 15 minutes, and water (4.2 mL) was added to it, followed by anhydrous sodium sulfate (10 g). The mixture was filtered and the filter cake rinsed with diethyl ether (3×15 mL). Concentration of the filtrate in vacuo provided the title compound as a yellow solid (3.57 g, 83% yield): MS (ES+) m/z 288.2 (M+1).

Step 6. Preparation of tert-butyl ((5-chloro-4-((3,6-difluoro-2-(hydroxymethyl)benzyl)amino)-2-fluorophenyl)sulfonyl)(thiazol-4-yl)carbamate

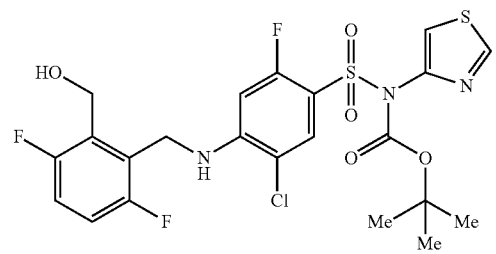 [SMILES: CC(C)(C)OC(=O)N(c1cscn1)S(=O)(=O)c1cc(Cl)c(NCc2c(F)ccc(F)c2CO)cc1F]

Following the procedure as described in EXAMPLE 288, Step 4, and making non-critical variations as required to replace (2-(azetidin-1-ylmethyl)-3,6-difluorophenyl)methanamine with (2-(((tert-butyldimethylsilyl)oxy)methyl)-3,6-difluorophenyl)methanamine, the title compound was obtained as a colorless oil (1.41 g, 42% yield): MS (ES+) m/z 566.2 (M+1), 564.2 (M+1).

Step 7. Preparation of 5-chloro-4-((3,6-difluoro-2-(hydroxymethyl)benzyl)amino)-2-fluoro-N-(thiazol-4-yl)benzenesulfonamide

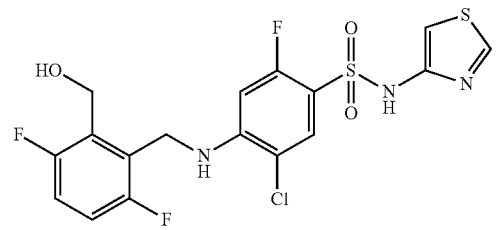 [SMILES: O=S(=O)(Nc1cscn1)c1cc(Cl)c(NCc2c(F)ccc(F)c2CO)cc1F]

To a solution of tert-butyl ((5-chloro-4-((3,6-difluoro-2-(hydroxymethyl)benzyl)amino)-2-fluorophenyl)sulfonyl)(thiazol-4-yl)carbamate (0.2 g, 0.35 mmol) in dichloromethane (5 mL) was added trifluoroacetic acid (5 mL) and the reaction mixture was stirred at ambient temperature for 1 h. The mixture was then concentrated in vacuo. The residue was purified by preparative reverse phase HPLC, using acetonitrile in water containing 0.1% trifluoroacetic acid as eluent, to give the title compound as a colorless solid (0.03 g, 18% yield): $^1$H NMR (300 MHz, DMSO-d$_6$) δ 11.14 (s, 1H), 8.89 (dd, J=2.2, 0.8 Hz, 1H), 7.59 (d, J=7.4 Hz, 1H), 7.24 (t, J=6.9 Hz, 2H), 7.00-6.93 (m, 2H), 6.64-6.60 (m, 1H), 5.65-5.63 (m, 1H), 4.63-4.61 (m, 2H), 4.55-4.53 (m, 2H); MS (ES+) m/z 466.1 (M+1), 464.1 (M+1).

Example 294

Synthesis of 2,3-difluoro-4-((2-fluoro-6-(pyrrolidin-1-ylmethyl)benzyl)amino)-N-(isoxazol-3-yl)benzenesulfonamide 2,2,2-trifluoroacetate

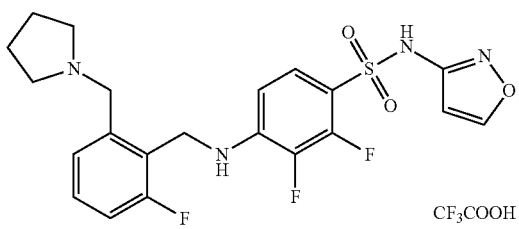 [SMILES: O=S(=O)(Nc1ccon1)c1ccc(NCc2c(F)cccc2CN2CCCC2)c(F)c1F ; "CF3COOH"]

Step 1. Preparation of 2-fluoro-6-(pyrrolidin-1-ylmethyl)phenyl)methanamine

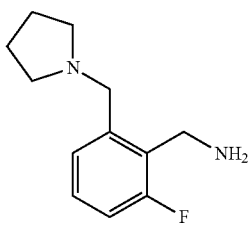 [SMILES: NCc1c(F)cccc1CN1CCCC1]

Following the procedure as described in EXAMPLE 246, Steps 1 and 2, and making non-critical variations as required to azetidine with pyrrolidine, the title compound was obtained as a colorless oil (0.37 g, 78% yield): $^1$H-NMR (300 MHz, DMSO-d$_6$) δ 7.20 (td, J=7.8, 5.9 Hz, 1H), 7.12-7.03 (m, 2H), 3.76-3.69 (m, 2H), 3.69-3.62 (m, 2H), 2.43-2.38 (m, 4H), 1.83-1.77 (m, 2H), 1.70-1.63 (m, 4H); MS (ES+) m/z 209.3 (M+1).

Step 2. Preparation of tert-butyl isoxazol-3-yl((2,3,4-trifluorophenyl)sulfonyl)carbamate

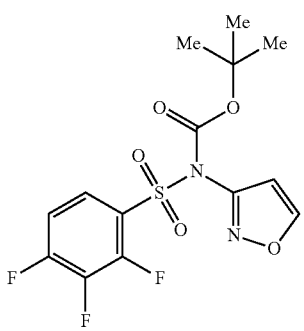 [SMILES: CC(C)(C)OC(=O)N(c1ccon1)S(=O)(=O)c1ccc(F)c(F)c1F]

To a solution of tert-butyl isoxazol-3-ylcarbamate (3.30 g, 17.9 mmol) in anhydrous tetrahydrofuran (100 mL) was added a 1 M solution of lithium bis(trimethylsilyl)amide in tetrahydrofuran (21.5 mL, 21.5 mmol) at −78° C. The reaction mixture was allowed to warm to ambient temperature and stirred for 1 h. The reaction mixture was cooled to −78° C., and a solution of 2,3,4-trifluorobenzenesulfonyl chloride (4.10 g, 17.9 mmol) in anhydrous tetrahydrofuran (20 mL) was added to it. The reaction mixture was allowed to warm to ambient temperature and stirred for 3 h. The mixture was diluted with ethyl acetate (200 mL), washed with saturated ammonium chloride (2×200 mL), brine (2×100 mL), dried over anhydrous sodium sulfate, and filtered. Concentration of the filtrate in vacuo and purification of the residue by column chromatography, eluting with a gradient of 0 to 60% of ethyl acetate in heptane, provided the title compound as a colorless solid (5.20 g, 77% yield): MS (ES+) m/z 379.1 (M+1).

Step 2. Preparation of tert-butyl ((2,3-difluoro-4-((2-fluoro-6-(pyrrolidin-1-ylmethyl)benzyl)amino)phenyl)sulfonyl)(isoxazol-3-yl)carbamate

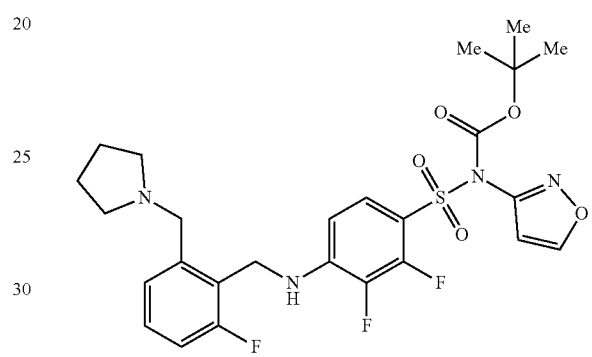

To a mixture of (2-fluoro-6-(pyrrolidin-1-ylmethyl)phenyl)methanamine (0.21 g, 1.00 mmol) and tert-butyl isoxazol-3-yl((2,3,4-trifluorophenyl)sulfonyl)carbamate (0.38 g, 1.00 mmol) in anhydrous N,N-dimethylformamide (4 mL) was added potassium carbonate (0.28 g, 2.00 mmol) and the reaction was stirred at ambient temperature for 16 h. The reaction mixture was and water (10 mL) was added to it. The mixture was extracted with ethyl acetate (2×15 mL). The combined organic phase was washed with brine (25 mL), dried over anhydrous sodium sulfate and filtered. Concentration of the filtrate in vacuo provided a residue which was purified by column chromatography, eluting with a gradient of 0-100% of ethyl acetate in hexanes to give the title compound as a colorless solid (0.03 g, 5% yield): MS (ES+) m/z 567.2 (M+1).

Step 3. Preparation of 2,3-difluoro-4-((2-fluoro-6-(pyrrolidin-1-ylmethyl)benzyl)amino)-N-(isoxazol-3-yl)benzenesulfonamide 2,2,2-trifluoroacetate

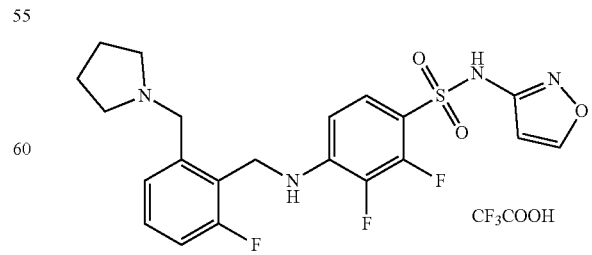

Following the procedure as described in EXAMPLE 290, Step 6, and making non-critical variations as required to tert-butyl ((4-((2-(azetidin-1-ylmethyl)-6-chlorobenzyl)amino)-2,6-difluorophenyl)sulfonyl)(thiazol-4-yl)carbamate with tert-butyl ((2,3-difluoro-4-((2-fluoro-6-(pyrrolidin-1-ylmethyl)benzyl)amino)phenyl)-sulfonyl)(isoxazol-3-yl)carbamate, the title compound was obtained as a colorless solid (0.03 g, quantitative yield): $^1$H-NMR (300 MHz, DMSO-$d_6$) δ 11.78-11.72 (br s, 1H), 10.17-9.91 (br s, 1H), 8.72 (d, J=1.8 Hz, 1H), 7.55-7.42 (m, 3H), 7.37-7.30 (m, 1H), 7.20-7.16 (m, 1H), 6.80-6.74 (m, 1H), 6.35 (d, J=1.8 Hz, 1H), 4.49 (m, 4H), 3.34-3.03 (m, 4H), 2.05-1.80 (m, 4H); MS (ES+) m/z 467.2 (M+1).

Example 295

Synthesis of 4-((2-((2-oxa-6-azaspiro[3.3]heptan-6-yl)methyl)-6-chlorobenzyl)amino)-2,6-difluoro-N-(thiazol-4-yl)benzenesulfonamide formate

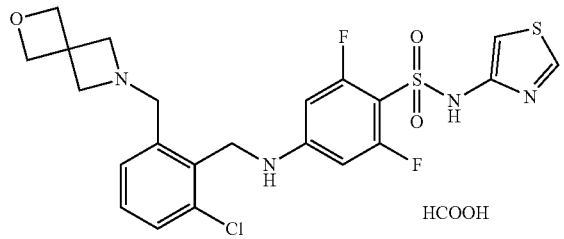 [SMILES: O=S(=O)(Nc1cscn1)c1c(F)cc(NCc2c(Cl)cccc2CN2CC3(COC3)C2)cc1F ; "HCOOH"]

Step 1. Preparation of (2-((2-oxa-6-azaspiro[3.3]heptan-6-yl)methyl)-6-chlorophenyl)methanol

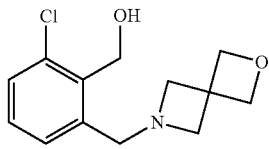 [SMILES: OCc1c(Cl)cccc1CN1CC2(COC2)C1]

Following the procedure as described in EXAMPLE 290, Step 2, and making non-critical variations as required to replace azetidine with 2-oxa-6-azaspiro[3.3]heptane oxalate, the title compound was obtained as a colorless solid (0.29 g, 34% yield): MS (ES+) m/z 256.2 (M+1), 254.2 (M+1).

Step 2. Preparation of 2-(2-((2-oxa-6-azaspiro[3.3]heptan-6-yl)methyl)-6-chlorobenzyl)isoindoline-1,3-dione

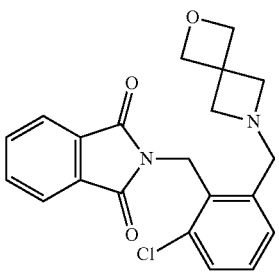 [SMILES: O=C1c2ccccc2C(=O)N1Cc1c(Cl)cccc1CN1CC2(COC2)C1]

Following the procedure as described in EXAMPLE 288, Step 2, and making non-critical variations as required to replace (2-(azetidin-1-ylmethyl)-3,6-difluorophenyl)methanol with (2-((2-oxa-6-azaspiro[3.3]heptan-6-yl)methyl)-6-chlorophenyl)methanol, the title compound was obtained as an oil (0.32 g, 95% yield): MS (ES+) m/z 385.2 (M+1), 383.2 (M+1).

Step 3. Preparation of (2-((2-oxa-6-azaspiro[3.3]heptan-6-yl)methyl)-6-chlorophenyl)methanamine

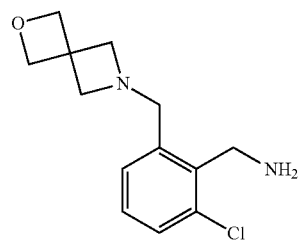 [SMILES: NCc1c(Cl)cccc1CN1CC2(COC2)C1]

Following the procedure as described in EXAMPLE 288, Step 3, and making non-critical variations as required to replace 2-(2-(azetidin-1-ylmethyl)-3,6-difluorobenzyl)isoindoline-1,3-dione with 2-(2-((2-oxa-6-azaspiro[3.3]heptan-6-yl)methyl)-6-chlorobenzyl)isoindoline-1,3-dione, the title compound was obtained as an oil (0.14 g, 67% yield): MS (ES+) m/z 255.3 (M+1), 253.3 (M+1).

Step 4. Preparation of tert-butyl ((4-((2-((2-oxa-6-azaspiro[3.3]heptan-6-yl)methyl)-6-chlorobenzyl)amino)-2,6-difluorophenyl)sulfonyl)(thiazol-4-yl)carbamate

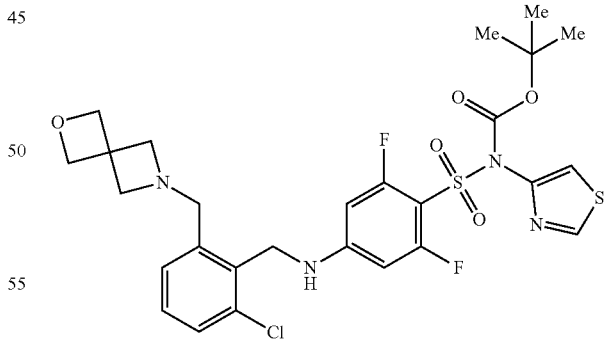

Following the procedure as described in EXAMPLE 290, Step 5, and making non-critical variations as required to replace (2-(azetidin-1-ylmethyl)-6-chlorophenyl)methanamine with (2-((2-oxa-6-azaspiro[3.3]heptan-6-yl)methyl)-6-chlorophenyl)methanamine, the title compound was obtained as a colorless solid (0.12 g, 37% yield): MS (ES+) m/z 645.3 (M+1), 643.3 (M+1).

Step 5. Preparation of 4-((2-((2-oxa-6-azaspiro[3.3]heptan-6-yl)methyl)-6-chlorobenzyl)amino)-2,6-difluoro-N-(thiazol-4-yl)benzenesulfonamide formate

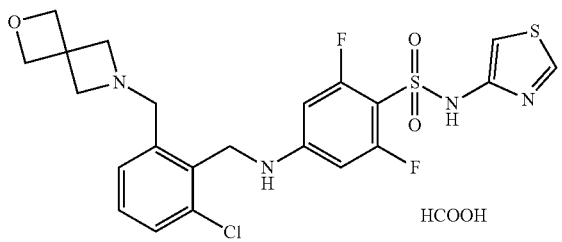 [SMILES: O=S(=O)(Nc1cscn1)c1c(F)cc(NCc2c(Cl)cccc2CN2CC3(COC3)C2)cc1F ; "HCOOH"]

Following the procedure as described in EXAMPLE 290, Step 6, and making non-critical variations as required to replace tert-butyl ((4-((2-(azetidin-1-ylmethyl)-6-chlorobenzyl)amino)-2,6-difluorophenyl)sulfonyl)(thiazol-4-yl) carbamate with tert-butyl ((4-((2-((2-oxa-6-azaspiro[3.3]heptan-6-yl)methyl)-6-chlorobenzyl)amino)-5-chloro-2-fluorophenyl)sulfonyl)(thiazol-4-yl)carbamate, and purification by preparative reverse phase HPLC, eluting with a gradient of acetonitrile in water containing 0.2% of formic acid, the title compound was obtained as a colorless solid (0.18 g, 100% yield): $^1$H NMR (300 MHz, DMSO-$d_6$) δ 8.91 (dd, J=1.3, 0.8 Hz, 1H), 8.14-8.13 (br s, 1H), 7.44-7.31 (m, 3H), 7.12-7.10 (m, 1H), 6.91 (d, J=2.2 Hz, 1H), 6.39-6.34 (m, 2H), 4.56-4.54 (m, 2H), 4.36-4.34 (m, 2H), 3.31-3.25 (m, 8H), NH and COOH not observed; MS (ES+) m/z 529.2 (M+1), 527.2 (M+1).

Example 296

Synthesis of 4-((2-(azetidin-1-ylmethyl)-6-fluorobenzyl)amino)-2,6-difluoro-N-(5-fluoropyridin-2-yl)benzenesulfonamide formate

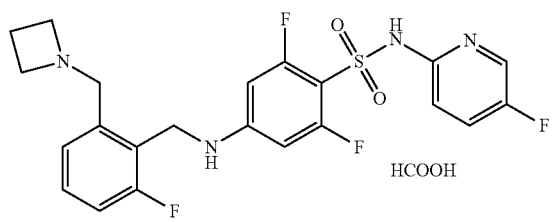 [SMILES: O=S(=O)(Nc1ccc(F)cn1)c1c(F)cc(NCc2c(F)cccc2CN2CCC2)cc1F ; "HCOOH"]

Step 1. Preparation of N-(2,4-dimethoxybenzyl)-5-fluoropyridin-2-amine

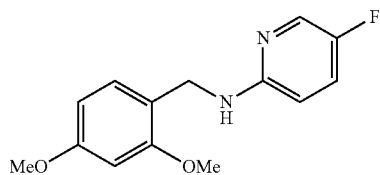 [SMILES: COc1ccc(CNc2ccc(F)cn2)c(OC)c1]

To a solution of 5-fluoropyridin-2-amine (3.00 g, 26.8 mmol) in anhydrous toluene (80 mL) was added 2,4-dimethoxybenzaldehyde (6.67 g, 40.2 mmol) in one portion. The mixture was heated to 140° C. for 12 h using a Dean-Stark trap for removal of water. The mixture was then concentrated under reduced pressure. The residue was dissolved in methanol (80 mL) and the mixture cooled to 0° C. To it was then added sodium borohydride (2.02 g, 53.5 mmol) at 0° C. The mixture was allowed to warm to ambient temperature and stirred for 12 h. The reaction mixture was diluted with water (100 ml) and extracted with dichloromethane (3×100 ml). The combined organic layers were washed with brine (3×50 ml), dried over anhydrous sodium sulfate, filtered, and the filtrate concentrated under reduced pressure. Purification of the residue by column chromatography, eluting with a gradient of 9 to 20% of ethyl acetate in petroleum ether, afforded the title compound as a colorless solid (4.40 g, 63% yield): $^1$H NMR (400 MHz, CDCl$_3$) δ 7.98 (d, J=2.8 Hz, 1H), 7.24-7.15 (m, 2H), 6.51-6.34 (m, 3H), 4.89 (br s, 1H), 4.39 (d, J=5.8 Hz, 2H), 3.83 (d, J=14.4 Hz, 6H); MS (ES+) m/z 263.1 (M+1).

Step 2. Preparation of N-(2,4-dimethoxybenzyl)-2,4,6-trifluoro-N-(5-fluoropyridin-2-yl)benzenesulfonamide

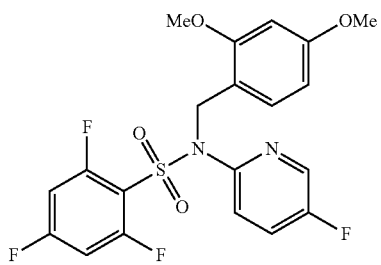 [SMILES: COc1ccc(CN(c2ccc(F)cn2)S(=O)(=O)c2c(F)cc(F)cc2F)c(OC)c1]

To a solution of N-(2,4-dimethoxybenzyl)-5-fluoropyridin-2-amine (2.00 g, 7.63 mmol) in anhydrous tetrahydrofuran (20 mL) was added a 1.6 M solution of methyllithium in diethyl ether (6.67 mL, 10.6 mmol) at −78° C. The reaction mixture was warmed to 0° C., stirred for 1 h at 0° C., and then cooled to −78° C. To it was then added a solution of 2,4,6-trifluorobenzene-1-sulfonyl chloride (2.64 g, 11.4 mmol) in anhydrous tetrahydrofuran (20 mL) at −78° C. The mixture was allowed to warm to ambient temperature and stirred for 3 h. The reaction mixture was diluted with saturated ammonium chloride (200 mL) and extracted with ethyl acetate (3×200 mL). The combined organic layers were washed with brine (3×50 mL), dried over anhydrous sodium sulfate, filtered, and the filtrate concentrated under reduced pressure. Purification of the residue by column chromatography, eluting with a gradient of 9 to 20% of ethyl acetate in petroleum ether, afforded the title compound as a colorless solid (3.00 g, 86% yield): $^1$H NMR (400 MHz, CDCl$_3$) δ 8.06 (d, J=2.8 Hz, 1H), 7.31-7.18 (m, 2H), 7.12-7.07 (m, 1H), 6.66 (t, J=8.6 Hz, 2H), 6.32-6.24 (m, 2H), 4.97 (s, 2H), 3.68 (s, 3H), 3.62 (s, 3H).

Step 3. Preparation of 4-((2-(azetidin-1-ylmethyl)-6-fluorobenzyl)amino)-N-(2,4-dimethoxybenzyl)-2,6-difluoro-N-(5-fluoropyridin-2-yl)benzenesulfonamide

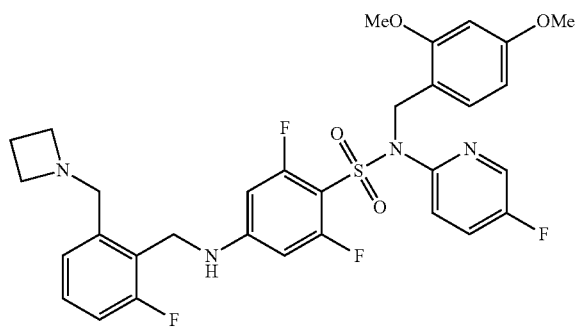 [SMILES: COc1ccc(CN(c2ccc(F)cn2)S(=O)(=O)c2c(F)cc(NCc3c(F)cccc3CN3CCC3)cc2F)c(OC)c1]

To a mixture of N-(2,4-dimethoxybenzyl)-2,4,6-trifluoro-N-(5-fluoropyridin-2-yl)benzenesulfonamide (0.500 g, 1.10 mmol) and (2-(azetidin-1-ylmethyl)-6-fluorophenyl)methanamine (0.320 g, 1.65 mmol) in anhydrous N,N-dimethylformamide (6 mL) was added potassium carbonate (0.456 g, 3.30 mmol) in one portion. The mixture was stirred at ambient temperature for 12 h. The reaction mixture was diluted with water (100 ml) and extracted with ethyl acetate (3×100 ml). The combined organic layers were washed with brine (3×50 ml), dried over anhydrous sodium sulfate, filtered, and the filtrate concentrated under reduced pressure. Purification of the residue by column chromatography, eluting with a gradient of 9 to 20% of ethyl acetate in petroleum ether, afforded the title compound as a yellow oil (0.200 g, 29% yield): $^1$H NMR (400 MHz, CDCl$_3$) δ 8.07 (d, J=3.0 Hz, 1H), 7.37 (dd, J=8.8, 4.2 Hz, 1H), 7.25 (dt, J=8.4, 3.0 Hz, 1H), 7.18-7.12 (m, 2H), 7.01-6.93 (m, 2H), 6.30-6.24 (m, 2H), 6.10 (d, J=11.8 Hz, 2H), 5.00 (s, 2H), 4.25 (s, 2H), 3.67 (s, 3H), 3.62 (s, 3H), 3.52 (s, 2H), 3.14 (t, J=7.0 Hz, 4H), 2.04 (quin, J=7.0 Hz, 2H), NH not observed; MS (ES+) m/z 631.2 (M+1).

Step 4. Preparation of 4-((2-(azetidin-1-ylmethyl)-6-fluorobenzyl)amino)-2,6-difluoro-N-(5-fluoropyridin-2-yl)benzenesulfonamide formate

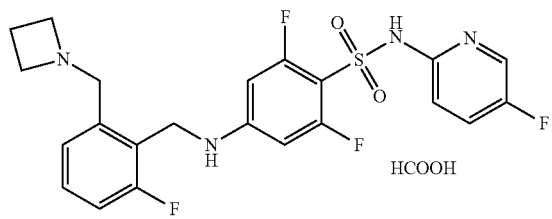 [SMILES: O=S(=O)(Nc1ccc(F)cn1)c1c(F)cc(NCc2c(F)cccc2CN2CCC2)cc1F ; "HCOOH"]

To a solution of 4-((2-(azetidin-1-ylmethyl)-6-fluorobenzyl)amino)-N-(2,4-dimethoxybenzyl)-2,6-difluoro-N-(5-fluoropyridin-2-yl)benzenesulfonamide (0.100 g, 0.159 mmol) in dichloromethane (4 mL) was added trifluoroacetic acid (3.08 g, 27.0 mmol). After concentration in vacuo, the residue was purified by preparative reverse phase HPLC, using acetonitrile in water containing 0.225% formic acid as eluent, to afford the title compound as a colorless solid (0.0623 g, 74% yield): $^1$H NMR (400 MHz, CD$_3$OD) δ 8.42 (br s, 1H), 8.08 (d, J=3.0 Hz, 1H), 7.57-7.44 (m, 2H), 7.30-7.15 (m, 3H), 6.37-6.29 (m, 2H), 4.39 (s, 2H), 4.29 (s, 2H), 3.95 (t, J=7.8 Hz, 4H), 2.40 (quin, J=7.8 Hz, 2H), NH and COOH not observed; MS (ES+) m/z 481.2 (M+1).

Example 297

Synthesis of (S)-4-((1-(2,5-difluorophenyl)ethyl)amino)-5-ethyl-2-fluoro-N-(thiazol-4-yl)benzenesulfonamide

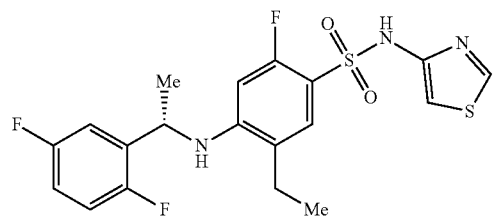 [SMILES: CCc1cc(S(=O)(=O)Nc2cscn2)c(F)cc1N[C@@H](C)c1cc(F)ccc1F]

Step 1. Preparation of (S)-4-((1-(2,5-difluorophenyl)ethyl)amino)-2-fluoro-N-(thiazol-4-yl)-5-vinylbenzenesulfonamide

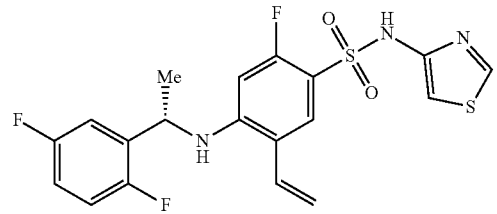 [SMILES: C=Cc1cc(S(=O)(=O)Nc2cscn2)c(F)cc1N[C@@H](C)c1cc(F)ccc1F]

To a mixture of (S)-tert-butyl (5-chloro-4-((1-(2,5-difluorophenyl)ethyl)amino)-2-fluorophenyl)sulfonyl(thiazol-4-yl)carbamate (0.800 g, 1.46 mmol), 4,4,5,5-tetramethyl-2-vinyl-1,3,2-dioxaborolane (2.25 g, 14.60 mmol, 2.47 mL) and potassium phosphate (0.115 g, 0.545 mmol) in water (2 mL) and toluene (8 mL) was added palladium(II) acetate (0.164 g, 0.730 mmol) and tricyclohexylphosphonium tetrafluoroborate (1.60 g, 4.36 mmol). The reaction mixture degassed and heated to 100° C. for 12 h. After cooling to ambient temperature, the mixture was diluted with water (20 mL) and extracted with ethyl acetate (3×20 mL). The combined organic layers were washed with brine (20 mL), dried over anhydrous sodium sulfate, filtered, and the filtrate concentrated in vacuo. Purification of the residue by preparative reverse phase HPLC, using acetonitrile in water containing 0.225% formic acid as eluent, afforded the title compound as a colorless solid (0.060 g, 9% yield): $^1$H NMR (400 MHz, CDCl$_3$) δ 8.63 (br s, 1H), 8.58 (d, J=2.0 Hz, 1H), 7.66 (d, J=8.0 Hz, 1H), 7.05 (td, J=9.2, 4.0 Hz, 1H), 6.94 (d, J=2.2 Hz, 2H), 6.84-6.92 (m, 1H), 6.62 (dd, J=17.2, 10.8 Hz, 1H), 6.02 (d, J=12.8 Hz, 1H), 5.66 (d, J=17.6 Hz, 1H), 5.50 (d, J=11.2 Hz, 1H), 4.70-4.77 (m, 1H), 4.66 (d, J=4.8 Hz, 1H), 1.57 (d, J=6.8 Hz, 3H); MS (ES+) m/z 440.0 (M+1).

Step 2. Preparation of (S)-4-((1-(2,5-difluorophenyl)ethyl)amino)-5-ethyl-2-fluoro-N-(thiazol-4-yl)benzenesulfonamide

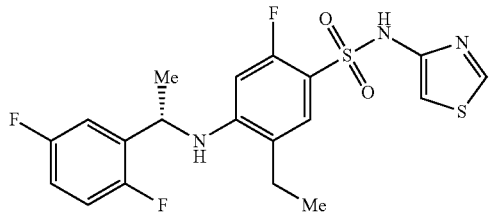 [SMILES: CCc1cc(S(=O)(=O)Nc2cscn2)c(F)cc1N[C@@H](C)c1cc(F)ccc1F]

To a solution of (S)-4-((1-(2,5-difluorophenyl)ethyl)amino)-2-fluoro-N-(thiazol-4-yl)-5-vinylbenzenesulfonamide (0.030 g, 0.068 mmol) in methanol (10 mL) was added Pd/C (0.010 g). The mixture was stirred under an atmosphere of hydrogen (45 psi) at ambient temperature for 12 h. The mixture was then filtered and concentrated in vacuo. Purification of the residue by preparative reverse phase HPLC, using acetonitrile in water containing 0.225% formic acid as eluent, afforded the title compound as a colorless solid (0.019 g, 63% yield): $^1$H NMR (400 MHz, CDCl$_3$) δ 8.69 (br s, 1H), 8.60 (d, J=2.4 Hz, 1H), 7.50 (d, J=8.0 Hz, 1H), 7.06 (td, J=9.2, 4.4 Hz, 1H), 6.92-6.99 (m, 2H), 6.89 (ddd, J=8.4, 5.6, 3.2 Hz, 1H), 6.02 (d, J=12.8 Hz, 1H), 4.72 (t, J=6.4 Hz, 1H), 4.46 (d, J=4.8 Hz, 1H), 2.51 (q, J=7.4 Hz, 2H), 1.60 (d, J=6.8 Hz, 3H), 1.30 (t, J=7.6 Hz, 3H).

Example 298

Synthesis of 5-chloro-2-fluoro-4-(((6-fluoro-1H-indol-7-yl)methyl)amino)-N-(thiazol-4-yl)benzenesulfonamide

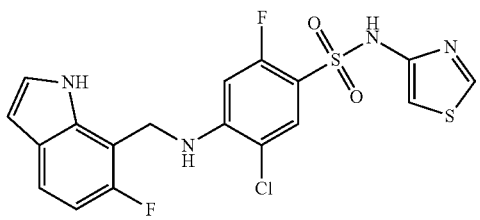 [SMILES: O=S(=O)(Nc1cscn1)c1cc(Cl)c(NCc2c(F)ccc3cc[nH]c23)cc1F]

Step 1. Preparation of 7-bromo-6-fluoro-1H-indole

To a mixture of 2-bromo-1-fluoro-3-nitrobenzene (2.30 g, 10.5 mmol) in anhydrous tetrahydrofuran (30 mL) was added vinylmagnesium bromide (1.0 M, 31.4 mL, 31.4 mmol) at −78° C. The mixture was stirred at −78° C. for 30 minutes, and then warmed to ambient temperature and stirred for 2 h. The mixture was diluted with saturated ammonium chloride (50 mL) and extracted with ethyl acetate (3×50 mL). The combined organic extracts were washed with brine (3×50 mL), dried over anhydrous sodium sulfate, and filtered. Concentration of the filtrate in vacuo afforded a residue, which was purified by column chromatography, eluting with a gradient of 0 to 9% of ethyl acetate in petroleum ether. Further purification by preparative thin layer chromatography, eluting with 9% of ethyl acetate in petroleum ether, afforded the title compound as a yellow oil (0.250 g, 11% yield): $^1$H NMR (400 MHz, DMSO-d$_6$) δ 11.46 (br s, 1H), 7.55 (dd, J=8.6, 5.0 Hz, 1H), 7.40 (t, J=2.8 Hz, 1H), 7.01 (dd, J=9.6, 8.6 Hz, 1H), 6.58 (dd, J=3.2, 1.8 Hz, 1H).

Step 2. Preparation of 6-fluoro-1H-indole-7-carbonitrile

To a mixture of 7-bromo-6-fluoro-1H-indole (0.400 g, 1.87 mmol) and zinc cyanide (0.658 g, 5.61 mmol) in anhydrous N,N-dimethylformamide (10 mL) was added tetrakis[triphenylphosphine]palladium(0) (0.432 g, 0.374 mmol). The mixture was degassed by purging with nitrogen and then heated to 120° C. for 2 h in a microwave reactor. After cooling to ambient temperature, the reaction mixture was diluted with water (5 mL), and extracted with ethyl acetate (3×10 mL). The combined organic layers were washed with brine (3×10 mL), dried over anhydrous sodium sulfate, and filtered. Concentration of the filtrate under reduced pressure and purification of the residue by preparative thin layer chromatography, eluting with 9% of ethyl acetate in petroleum ether, afforded the title compound as a yellow solid (0.190 g, 63% yield): $^1$H NMR (400 MHz, DMSO-d$_6$) δ 12.17 (br s, 1H), 7.94 (dd, J=8.5, 5.6 Hz, 1H), 7.51 (t, J=2.6 Hz, 1H), 7.12 (t, J=9.6 Hz, 1H), 6.74-6.58 (m, 1H).

Step 3. Preparation of (6-fluoro-1H-indol-7-yl)methanamine

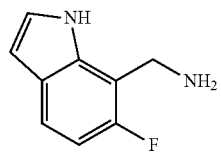 [SMILES: NCc1c(F)ccc2cc[nH]c12]

To a solution of 6-fluoro-1H-indole-7-carbonitrile (0.190 g, 1.19 mmol) in methanol (20 mL) and ammonium hydroxide (5 mL) was added Raney-Ni (0.102 g, 1.19 mmol). The reaction mixture was stirred under an atmosphere of hydrogen (50 psi) at ambient temperature for 12 h. Filtration and concentration of the filtrate under reduced pressure afforded the title compound as a yellow solid (0.190 g, 97% yield): $^1$H NMR (400 MHz, CDCl$_3$) δ 9.85 (br s, 1H), 7.36 (dd, J=5.0, 8.6 Hz, 1H), 7.15-7.10 (m, 1H), 6.76 (dd, J=8.6, 10.8 Hz, 1H), 6.44-6.38 (m, 1H), 4.27 (br s, 2H), 1.36 (br s, 2H).

Step 4. Preparation of tert-butyl ((5-chloro-2-fluoro-4-(((6-fluoro-1H-indol-7-yl)methyl)amino)phenyl)sulfonyl)(thiazol-4-yl)carbamate

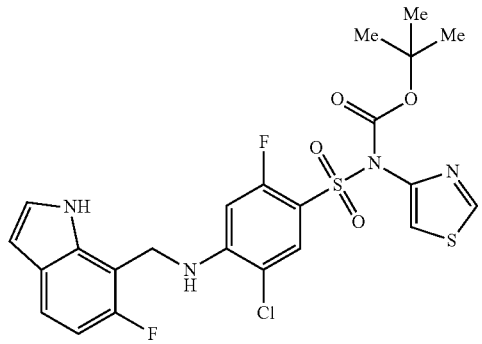 [SMILES: CC(C)(C)OC(=O)N(c1cscn1)S(=O)(=O)c1cc(Cl)c(NCc2c(F)ccc3cc[nH]c23)cc1F]

To a mixture of (6-fluoro-1H-indol-7-yl)methanamine (0.190 g, 1.16 mmol) and tert-butyl (5-chloro-2,4-difluorophenyl)sulfonyl(thiazol-4-yl)carbamate (0.477 g, 1.16 mmol) in anhydrous N,N-dimethylformamide (5 mL) was added potassium carbonate (0.481 g, 3.48 mmol) and the mixture was stirred at ambient temperature for 12 h. The reaction mixture was diluted with water (5 mL), and extracted with ethyl acetate (3×10 mL). The combined organic layers were washed with brine (3×10 mL), dried over anhydrous sodium sulfate, filtered, and the filtrate concentrated under reduced pressure. Purification of the residue by preparative thin layer chromatography, eluting with 25% of ethyl acetate in petroleum ether, afforded the title compound as a yellow solid (0.250 g, 39% yield): $^1$H NMR (400 MHz, CDCl$_3$) δ 8.69 (d, J=2.2 Hz, 1H), 8.49 (br d, J=2.2 Hz, 1H), 7.90 (d, J=7.2 Hz, 1H), 7.51 (dd, J=8.6, 5.2 Hz, 1H), 7.42 (d, J=2.2 Hz, 1H), 7.17 (dd, J=3.2, 2.4 Hz, 1H), 6.89 (dd, J=10.6, 8.8 Hz, 1H), 6.55 (d, J=12.2 Hz, 1H), 6.51 (dd, J=3.2, 2.2 Hz, 1H), 4.61 (d, J=4.6 Hz, 2H), 1.30 (s, 9H), NH not observed; MS (ES+) m/z 554.9 (M+1).

Step 5. Preparation of 5-chloro-2-fluoro-4-(((6-fluoro-1H-indol-7-yl)methyl)amino)-N-(thiazol-4-yl)benzenesulfonamide

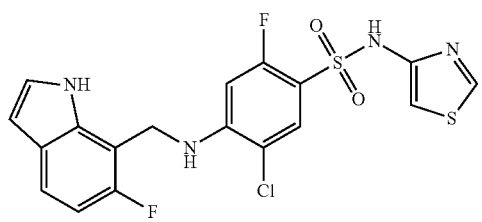 [SMILES: O=S(=O)(Nc1cscn1)c1cc(Cl)c(NCc2c(F)ccc3cc[nH]c23)cc1F]

To a mixture of tert-butyl(5-chloro-2-fluoro-4-(((6-fluoro-1H-indol-7-yl)methyl)amino)phenyl)sulfonyl (thiazol-4-yl)carbamate (0.240 g, 0.432 mmol) in tert-butyl alcohol (3 mL) was added potassium tert-butoxide (0.146 g, 1.30 mmol) and the reaction mixture was stirred at ambient temperature for 1 h. The mixture was filtered and the filtrate concentrated under reduced pressure. Purification of the residue by preparative reverse phase HPLC, using acetonitrile in water containing 0.05% ammonium hydroxide as eluent, afforded the title compound as a colorless solid (0.057 g, 28% yield): $^1$H NMR (400 MHz, CD$_3$OD) δ 8.62 (d, J=1.8 Hz, 1H), 7.65 (d, J=7.4 Hz, 1H), 7.48 (dd, J=8.6, 5.2 Hz, 1H), 7.27 (d, J=3.2 Hz, 1H), 6.85 (dd, J=10.8, 8.8 Hz, 1H), 6.65 (d, J=12.6 Hz, 1H), 6.47 (d, J=3.2 Hz, 1H), 6.40 (br s, 1H), 4.70 (s, 2H), exchangeable protons not observed; MS (ES+) m/z 455.0 (M+1).

Example 299

Synthesis of (R)-2,6-difluoro-4-((2-fluoro-6-(1-hydroxyethyl)benzyl)amino)-N-(thiazol-4-yl)benzenesulfonamide

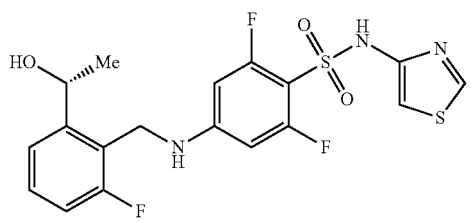 [SMILES: C[C@@H](O)c1cccc(F)c1CNc1cc(F)c(S(=O)(=O)Nc2cscn2)c(F)c1]

Step 1. Preparation of tert-butyl ((4-(((tert-butoxycarbonyl)(2-fluoro-6-(1-hydroxyethyl)benzyl)amino)-2,6-difluorophenyl)sulfonyl)(thiazol-4-yl)carbamate

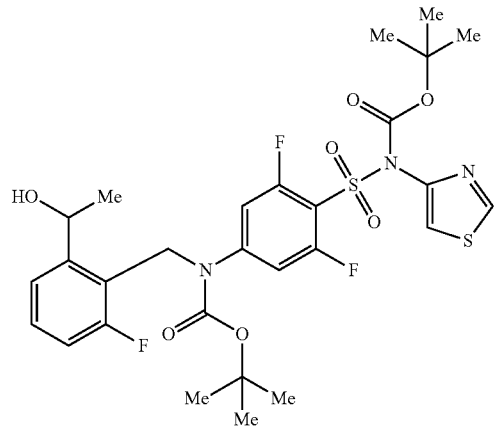 [SMILES: CC(O)c1cccc(F)c1CN(C(=O)OC(C)(C)C)c1cc(F)c(S(=O)(=O)N(C(=O)OC(C)(C)C)c2cscn2)c(F)c1]

To a solution of tert-butyl ((4-((tert-butoxycarbonyl)(2-fluoro-6-formylbenzyl)amino)-2,6-difluorophenyl)sulfonyl)(thiazol-4-yl)carbamate (0.500 g, 0.776 mmol) in anhydrous tetrahydrofuran (8 mL) was added a 3.0 M solution of methylmagnesium bromide in diethyl ether (0.52 mL, 1.56 mmol) at 0° C. and the mixture was stirred at 0° C. for 3 h. Saturated ammonium chloride (2 mL) was added and the resulting solution was concentrated in vacuo. Purification of the residue by column chromatography, eluting with a gradient of 9 to 50% of ethyl acetate in petroleum ether, afforded the title compound as a colorless solid (0.350 g, 70% yield): $^1$H NMR (400 MHz, CDCl$_3$) δ 8.73 (d, J=2.2 Hz, 1H), 7.45 (d, J=2.2 Hz, 1H), 7.31-7.26 (m, 1H), 7.24-7.20 (m, 1H), 6.89-6.77 (m, 3H), 5.21 (br dd, J=6.2, 3.4 Hz, 1H), 5.03 (s, 2H), 1.43 (d, J=6.4 Hz, 3H), 1.37 (s, 9H), 1.28 (s, 9H), OH not observed.

Step 2. Preparation of tert-butyl ((4-((2-acetyl-6-fluorobenzyl)(tert-butoxycarbonyl)amino)-2,6-difluorophenyl)sulfonyl)(thiazol-4-yl)carbamate

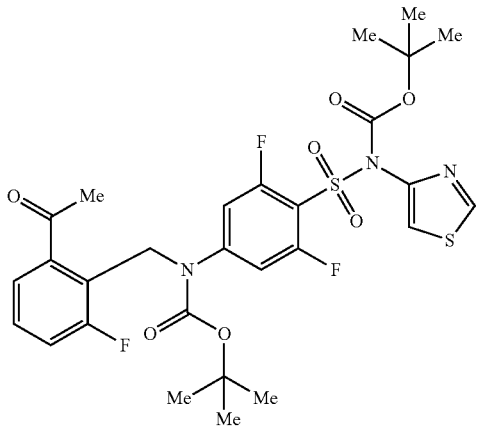 [SMILES: CC(=O)c1cccc(F)c1CN(C(=O)OC(C)(C)C)c1cc(F)c(S(=O)(=O)N(C(=O)OC(C)(C)C)c2cscn2)c(F)c1]

To a solution of tert-butyl ((4-((tert-butoxycarbonyl)(2-fluoro-6-(1-hydroxyethyl)benzyl)amino)-2,6-difluorophenyl)sulfonyl)(thiazol-4-yl)carbamate (0.340 g, 0.528 mmol) in anhydrous dichloromethane (6 mL) was added Dess-Martin periodinane (0.269 g, 0.634 mmol) and the mixture was stirred at ambient temperature for 1 h. The mixture was concentrated in vacuo. Purification of the residue by column chromatography, eluting with a gradient of 5 to 33% of ethyl acetate in petroleum ether, afforded the title compound as a colorless solid (0.260 g, 77% yield): $^1$H NMR (400 MHz, CDCl$_3$) δ 8.81 (d, J=2.2 Hz, 1H), 7.52 (d, J=2.2 Hz, 1H), 7.43-7.38 (m, 1H), 7.37-7.31 (m, 1H), 7.15 (ddd, J=10.0, 8.4, 1.2 Hz, 1H), 6.99 (d, J=10.6 Hz, 2H), 5.29 (s, 2H), 2.59 (s, 3H), 1.48 (s, 9H), 1.36 (s, 9H).

Step 3. Preparation of tert-butyl (R)-(4-(N-(tert-butoxycarbonyl)-N-(thiazol-4-yl)sulfamoyl)-3,5-difluorophenyl)(2-fluoro-6-(1-hydroxyethyl)benzyl)carbamate

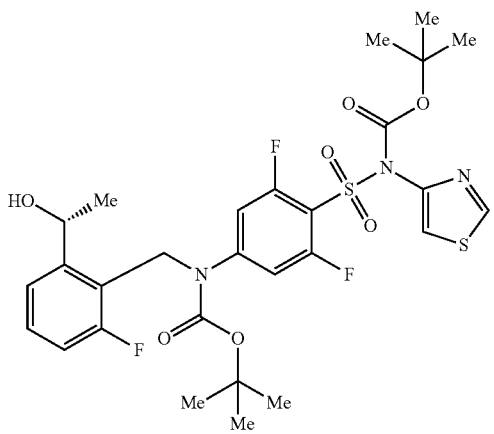 [SMILES: C[C@@H](O)c1cccc(F)c1CN(C(=O)OC(C)(C)C)c1cc(F)c(S(=O)(=O)N(C(=O)OC(C)(C)C)c2cscn2)c(F)c1]

To a 1.0 M solution of (S)-1-methyl-3,3-diphenyl-tetrahydro-pyrrolo[1,2-c][1,3,2]oxazaborole in tetrahydrofuran (0.0312 mL, 0.031 mmol) was added anhydrous tetrahydrofuran (2 mL) and a 10.0 M solution of borane dimethyl sulfide complex (0.020 mL, 0.20 mmol) at −20° C. The mixture was stirred at −20° C. for 1 h. To it was then added a solution of tert-butyl ((4-((2-acetyl-6-fluorobenzyl)(tert-butoxycarbonyl)amino)-2,6-difluorophenyl)sulfonyl)(thiazol-4-yl)carbamate (0.100 g, 0.156 mmol) in anhydrous tetrahydrofuran (1 mL) at −20° C., and the reaction mixture was stirred at −20° C. for 3 h. Saturated ammonium chloride (1 mL) was added and the mixture was concentrated in vacuo. Purification of the residue by column chromatography, eluting with a gradient of 9 to 20% of ethyl acetate in petroleum ether, afforded the title compound as a colorless solid (0.050 g, 47% yield): $^1$H NMR (400 MHz, CDCl$_3$) δ 8.82 (d, J=2.2 Hz, 1H), 7.54 (d, J=2.2 Hz, 1H), 7.39-7.34 (m, 1H), 7.31 (dd, J=8.0, 5.6 Hz, 1H), 6.99-6.88 (m, 3H), 5.34-5.27 (m, 1H), 5.11 (s, 2H), 1.52 (d, J=6.4 Hz, 3H), 1.46 (s, 9H), 1.37 (s, 9H), OH not observed.

Step 4. Preparation of (R)-2,6-difluoro-4-((2-fluoro-6-(1-hydroxyethyl)benzyl)amino)-N-(thiazol-4-yl)benzenesulfonamide

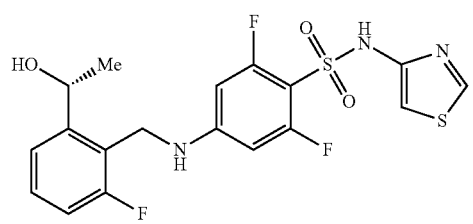 [SMILES: C[C@@H](O)c1cccc(F)c1CNc1cc(F)c(S(=O)(=O)Nc2cscn2)c(F)c1]

To a solution of tert-butyl (R)-(4-(N-(tert-butoxycarbonyl)-N-(thiazol-4-yl)sulfamoyl)-3,5-difluorophenyl)(2-fluoro-6-(1-hydroxyethyl)benzyl)carbamate (0.0400 g, 0.0621 mmol) in dichloromethane (2 mL) was added trifluoroacetic acid (1.54 g, 13.5 mmol). The reaction mixture was stirred at ambient temperature for 1 h and then concentrated in vacuo. Purification of the residue by preparative reverse phase HPLC, using acetonitrile in water containing 0.225% formic acid as eluent, afforded the title compound as a colorless solid (0.014 g, 46% yield): $^1$H NMR (400 MHz, CD$_3$OD) δ 8.75 (d, J=2.2 Hz, 1H), 7.47-7.34 (m, 2H), 7.16-7.02 (m, 1H), 6.97 (d, J=2.0 Hz, 1H), 6.28 (d, J=12.2 Hz, 2H), 5.08 (q, J=6.4 Hz, 1H), 4.36 (s, 2H), 1.44 (d, J=6.4 Hz, 3H), exchangeable protons not observed; MS (ES+) m/z 444.1 (M+1).

Example 300

Synthesis of 4-((2-((2,2-dimethylazetidin-1-yl)methyl)-6-fluorobenzyl)amino)-2,6-difluoro-N-(thiazol-4-yl)benzenesulfonamide

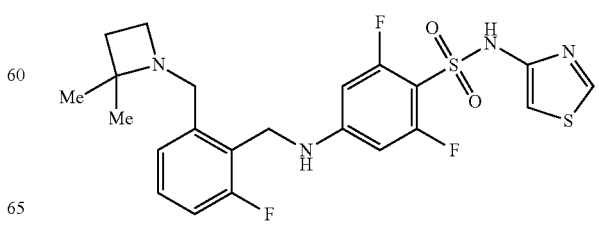

Step 1. Preparation of 2-((2,2-dimethylazetidin-1-yl)methyl)-6-fluorobenzonitrile

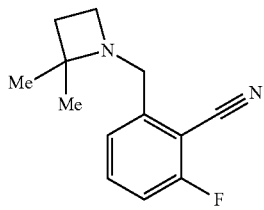 [SMILES: CC1(C)CCN1Cc1cccc(F)c1C#N]

To a solution of 2,2-dimethylazetidine (4.29 g, 50.38 mmol) and N,N-diisopropylethylamine (13.16 mL, 75.57 mmol) in anhydrous N,N-dimethylformamide (100 mL) was added 2-(bromomethyl)-6-fluorobenzonitrile (9.80 g, 45.80 mmol) at 0° C. The mixture was stirred at ambient temperature for 2 h and then diluted with ethyl acetate (170 mL). The mixture was washed with saturated ammonium chloride (2×100 mL), brine (100 mL), dried over anhydrous sodium sulfate, and filtered. The filtrate was concentrated in vacuo to afford the title compound as a pink oil (9.97 g, 99% yield): $^1$H NMR (300 MHz, CDCl$_3$) δ 7.52 (td, J=8.1, 5.7 Hz, 1H), 7.40-7.36 (m, 1H), 7.10-7.04 (m, 1H), 3.73 (s, 2H), 3.18 (t, J=7.0 Hz, 2H), 1.94 (t, J=7.0 Hz, 2H), 1.26 (s, 6H); MS (ES+) m/z 219.3 (M+1).

Step 2. Preparation of (2-((2,2-dimethylazetidin-1-yl)methyl)-6-fluorophenyl)-methanamine

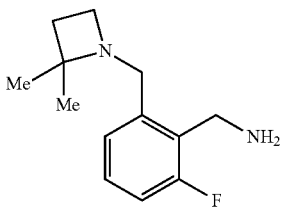 [SMILES: CC1(C)CCN1Cc1cccc(F)c1CN]

To Raney nickel (50% in water, 0.70 mL) was added ethanol (50 mL), concentrated aqueous ammonium hydroxide (3 mL), and 2-((2,2-dimethylazetidin-1-yl)methyl)-6-fluorobenzonitrile (1.02 g, 4.67 mmol). The mixture was stirred under an atmosphere of hydrogen (1 atm) for 18 h. The mixture was filtered through a pad of Celite and concentrated in vacuo to afford the title compound as a red oil (0.96 g, 92% yield): $^1$H NMR (300 MHz, CDCl$_3$) δ 7.10-6.95 (m, 3H), 3.97-3.83 (m, 2H), 3.60 (s, 2H), 3.03 (t, J=6.7 Hz, 2H), 1.83 (t, J=6.7 Hz, 2H), 1.25 (s, 6H), NH not observed; MS (ES+) m/z 223.3 (M+1).

Step 3. Preparation of 4-((2-((2,2-dimethylazetidin-1-yl)methyl)-6-fluorobenzyl)amino)-2,6-difluoro-N-(thiazol-4-yl)benzenesulfonamide

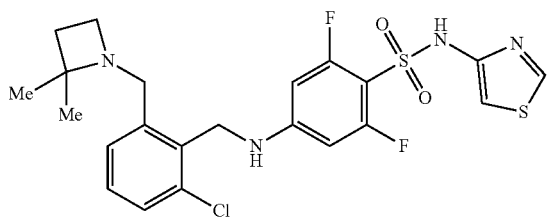 [SMILES: CC1(C)CCN1Cc1cccc(Cl)c1CNc1cc(F)c(S(=O)(=O)Nc2cscn2)c(F)c1]

To a mixture of (2-((2,2-dimethylazetidin-1-yl)methyl)-6-fluorophenyl)methanamine (0.22 g, 1.00 mmol) and cesium carbonate (0.33 g, 1.00 mmol) in anhydrous N,N-dimethylformamide (12 mL) was added a solution of tert-butyl thiazol-4-yl((2,4,6-trifluorophenyl)sulfonyl)carbamate (0.39 g, 1.00 mmol) in N,N-dimethylformamide (5 mL) at −42° C. The mixture was stirred at −42° C. for 3 h and then at ambient temperature for 15 h. The mixture was diluted with ethyl acetate (60 mL), saturated ammonium chloride (2×50 mL), brine (50 mL), dried over anhydrous sodium sulfate, and filtered. The residue was dissolved in dichloromethane (20 mL) and trifluoroacetic acid (6 mL) was added to it. The mixture was stirred at ambient temperature for 2 h and then concentrated in vacuo. The residue was diluted with 2 M sodium hydroxide (30 mL) and brine (30 mL) and the mixture was extracted with ethyl acetate (2×50 mL). The combined organic phase was washed with saturated ammonium chloride (50 mL), brine (30 mL), dried over anhydrous sodium sulfate, and filtered. The filtrate was concentrated in vacuo and the residue was purified by column chromatography, eluting with a gradient of 0 to 10% of methanol (+0.2% of formic acid) in dichloromethane to afford the title compound as a colorless solid (0.045 g, 10% yield): $^1$H NMR (300 MHz, DMSO-d$_6$) δ 11.16 (s, 1H), 8.89 (d, J=2.2 Hz, 1H), 7.37-7.27 (m, 2H), 7.22-7.10 (m, 2H), 6.89 (d, J=2.2 Hz, 1H), 6.47-6.39 (m, 2H), 4.41-4.35 (m, 2H), 3.56 (s, 2H), 3.02-2.97 (m, 2H), 1.84-1.74 (m, 2H), 1.13 (s, 6H); MS (ES+) m/z 497.3 (M+1).

Example 301

Synthesis of 4-((2-(azetidin-1-ylmethyl)-6-fluorobenzyl)amino)-5-chloro-2-fluoro-N-(isoxazol-3-yl)benzenesulfonamide formate

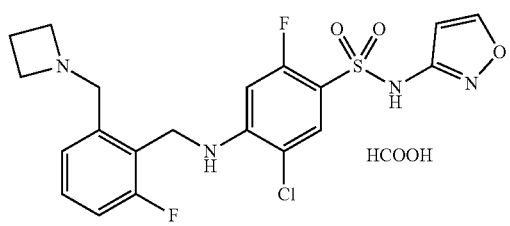 [SMILES: O=S(=O)(Nc1ccon1)c1cc(Cl)c(NCc2c(F)cccc2CN2CCC2)cc1F ; "HCOOH"]

Step 1. Preparation of 5-chloro-2,4-difluoro-N-(isoxazol-3-yl)benzenesulfonamide

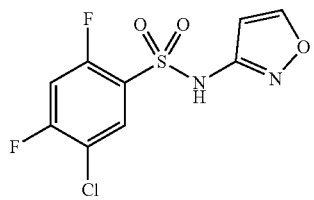

To a solution of isoxazol-3-amine (2.16 g, 25.69 mmol), pyridine (4.10 mL, 51.38 mmol), and 4-(dimethylamino)pyridine (0.69 g, 5.65 mmol) in anhydrous dichloromethane (50 mL) was added a solution of 5-chloro-2,4-difluorobenzenesulfonyl chloride in anhydrous dichloromethane (20 mL) at 0° C. The mixture was stirred at 0° C. for 2 h and then ambient temperature for 18 h. The mixture was diluted with ethyl acetate (120 mL), washed with 1 M hydrochloric acid (3×60 mL), brine (60 mL), dried over anhydrous sodium sulfate, and filtered. The filtrate was concentrated in vacuo to afford the title compound as a red solid (6.80 g, 82% yield): ¹H NMR (300 MHz, DMSO-d₆) δ 12.23 (s, 1H), 8.77-8.75 (m, 1H), 8.10 (t, J=7.6 Hz, 1H), 7.87 (t, J=9.6 Hz, 1H), 6.44-6.39 (m, 1H); MS (ES−) m/z 293.2 (M−1), 295.0 (M−1).

Step 2. Preparation of 5-chloro-2,4-difluoro-N-(isoxazol-3-yl)-N-(4-methoxybenzyl)-benzenesulfonamide

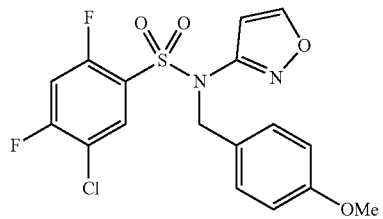 [SMILES: COc1ccc(CN(c2ccon2)S(=O)(=O)c2cc(Cl)c(F)cc2F)cc1]

To a mixture of 5-chloro-2,4-difluoro-N-(isoxazol-3-yl)benzenesulfonamide (6.80 g, 23.08 mmol) and sodium bicarbonate (9.69 g, 115.4 mmol) in anhydrous N,N-dimethylformamide (100 mL) was added 4-methoxybenzylchloride (6.26 mL, 46.15 mmol). The mixture was heated to 35° C. for 18 h and then diluted with ethyl acetate (120 mL). The mixture was washed with water (2×150 mL), saturated ammonium chloride (100 mL), brine (60 mL), dried over anhydrous sodium sulfate, and filtered. The filtrate was concentrated in vacuo and the residue was triturated with methanol (50 mL) to afford the title compound as a colorless solid (4.76 g, 50% yield): ¹H NMR (300 MHz, CDCl₃) δ 8.24 (d, J=1.8 Hz, 1H), 7.83 (t, J=7.3 Hz, 1H), 7.39-7.32 (m, 2H), 7.01 (t, J=8.8 Hz, 1H), 6.83-6.77 (m, 2H), 6.62 (d, J=1.8 Hz, 1H), 5.07 (s, 2H), 3.79 (s, 3H); MS (ES+) m/z 415.2 (M+1), 417.2 (M+1).

Step 2. Preparation of 4-((2-(azetidin-1-ylmethyl)-6-fluorobenzyl)amino)-5-chloro-2-fluoro-N-(isoxazol-3-yl)benzenesulfonamide formate

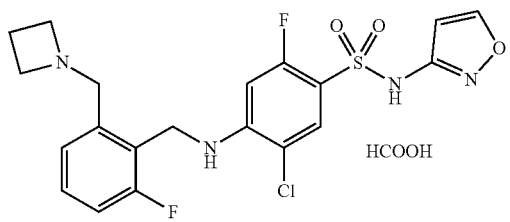 [SMILES: O=S(=O)(Nc1ccon1)c1cc(Cl)c(NCc2c(F)cccc2CN2CCC2)cc1F ; "HCOOH"]

To a mixture of (2-(azetidin-1-ylmethyl)-6-fluorophenyl)methanamine (0.31 g, 1.60 mmol) and cesium carbonate (0.65 g, 2.00 mmol) in anhydrous N,N-dimethylformamide (10 mL) was added 5-chloro-2,4-difluoro-N-(isoxazol-3-yl)-N-(4-methoxybenzyl)benzenesulfonamide (0.62 g, 1.50 mmol) at −42° C. The mixture was stirred at −42° C. for 3 h and then at ambient temperature for 18 h. The mixture was diluted with ethyl acetate (60 mL). The organic phase was washed with saturated ammonium chloride (2×40 mL), brine (30 mL), dried over anhydrous sodium sulfate, and filtered. The filtrate was concentrated in vacuo and the residue dissolved in dichloromethane (40 mL). To it was added trifluoroacetic acid (10 mL) and the mixture was heated to reflux for 2 h and then concentrated in vacuo. The residue was diluted with 2 M aqueous sodium hydroxide (30 mL) and brine (30 mL). The mixture was extracted with ethyl acetate (2×50 mL) and the organic fractions were combined. The organic layer was washed with saturated ammonium chloride (50 mL), brine (30 mL), dried over anhydrous sodium sulfate, and filtered. The filtrate was concentrated in vacuo and the residue was purified by column chromatography, eluting with a gradient of 0 to 10% of methanol (containing 0.2% of formic acid) in dichloromethane to afford the title compound as a colorless solid (0.26 g, 34% yield): ¹H NMR (300 MHz, DMSO-d₆) δ 8.61 (d, J=1.8 Hz, 1H), 8.15 (s, 1H), 7.64 (d, J=7.4 Hz, 1H), 7.34 (td, J=7.9, 5.8 Hz, 1H), 7.22-7.15 (m, 2H), 6.95 (d, J=13.4 Hz, 1H), 6.31 (d, J=1.8 Hz, 1H), 4.47 (s, 2H), 3.86 (s, 2H), 3.37 (t, J=7.2 Hz, 4H), 2.12-2.04 (m, 2H), NH and COOH not observed; MS (ES+) m/z 469.2 (M+1), 471.2 (M+1).

Example 302

Synthesis of 4-((2-(azetidin-1-ylmethyl)-6-fluorobenzyl)amino)-2,6-difluoro-N-(thiazol-4-yl)benzenesulfonamide 2,2,2-trifluoroacetate

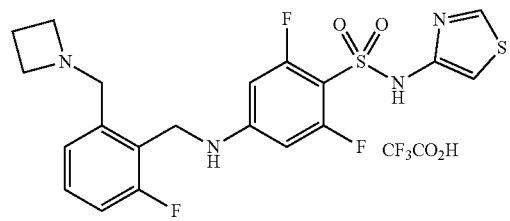 [SMILES: O=S(=O)(Nc1cscn1)c1c(F)cc(NCc2c(F)cccc2CN2CCC2)cc1F ; "CF3CO2H"]

Following the procedure as described for EXAMPLE 300, Step 3 and making non-critical variations as required to replace (2-((2,2-dimethylazetidin-1-yl)methyl)-6-fluorophenyl)methanamine with (2-(azetidin-1-ylmethyl)-6-fluorophenyl)methanamine, and additional purification by preparative reverse-phase HPLC, eluting with a gradient of 10 to 55% of acetonitrile in water containing 0.1% of trifluoroacetic acid, afforded the title compound as a colorless solid (0.040 g, 3% yield): ¹H NMR (300 MHz, DMSO-d₆) δ 11.24 (s, 1H), 10.29 (s, 1H), 8.91 (d, J=2.1 Hz, 1H), 7.55-7.46 (m, 1H), 7.39-7.31 (m, 2H), 7.29-7.24 (m, 1H), 6.92 (d, J=2.2 Hz, 1H), 6.40-6.32 (m, 2H), 4.49-4.43 (m, 2H), 4.37-4.30 (m, 2H), 4.13-4.00 (m, 4H), 2.41-2.24 (m, 2H); MS (ES+) m/z 469.2 (M+1).

Example 303

Synthesis of 4-((2-(azetidin-1-ylmethyl)-6-fluorobenzyl)amino)-3-chloro-2,6-difluoro-N-(thiazol-4-yl)benzenesulfonamide 2,2,2-trifluoroacetate

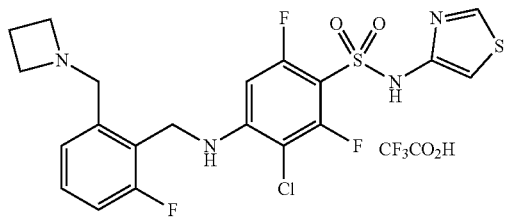 [SMILES: O=S(=O)(Nc1cscn1)c1c(F)cc(NCc2c(F)cccc2CN2CCC2)c(Cl)c1F ; "CF3CO2H"]

Step 1. Preparation of tert-butyl ((4-((2-(azetidin-1-ylmethyl)-6-fluorobenzyl)amino)-3-chloro-2,6-difluorophenyl)sulfonyl)(thiazol-4-yl)carbamate

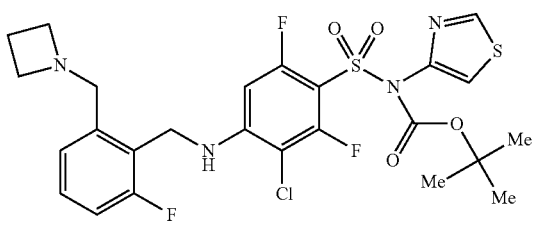 [SMILES: CC(C)(C)OC(=O)N(c1cscn1)S(=O)(=O)c1c(F)cc(NCc2c(F)cccc2CN2CCC2)c(Cl)c1F]

To a mixture of tert-butyl ((3-chloro-2,4,6-trifluorophenyl)sulfonyl)(thiazol-4-yl)carbamate (1.07 g, 2.50 mmol) and N,N-diisopropylethylamine (0.87 mL, 5.00 mmol) in anhydrous dimethyl sulfoxide (20 mL) was added (2-(azetidin-1-ylmethyl)-6-fluorophenyl)methanamine (0.49 g, 2.50 mmol). The mixture was stirred at ambient temperature for 3 h and then diluted with ethyl acetate (80 mL). The organic phase was washed with saturated ammonium chloride (2×50 mL), brine (40 mL), dried over anhydrous sodium sulfate, and filtered. The filtrate was concentrated in vacuo and the residue was purified by column chromatography, eluting with a gradient of 10 to 70% of ethyl acetate (containing 20% ethanol and 0.2% ammonium hydroxide) in hexanes, to afford the title compound as a colorless foam (0.88 g, 58% yield): MS (ES+) m/z 603.4 (M+1), 605.4 (M+1).

Step 2. Preparation of 4-((2-(azetidin-1-ylmethyl)-6-fluorobenzyl)amino)-3-chloro-2,6-difluoro-N-(thiazol-4-yl)benzenesulfonamide 2,2,2-trifluoroacetate

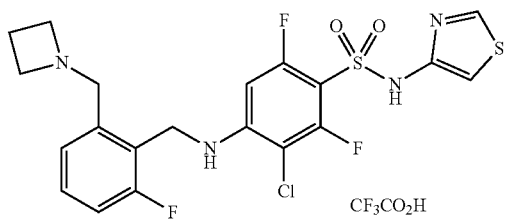 [SMILES: O=S(=O)(Nc1cscn1)c1c(F)cc(NCc2c(F)cccc2CN2CCC2)c(Cl)c1F ; "CF3CO2H"]

To a mixture of tert-butyl ((4-((2-(azetidin-1-ylmethyl)-6-fluorobenzyl)amino)-3-chloro-2,6-difluorophenyl)sulfonyl)(thiazol-4-yl)carbamate (0.28 g, 0.46 mmol) in dichloromethane (10 mL) was added trifluoroacetic acid (4 mL). The mixture was stirred at ambient temperature for 3 h and then concentrated in vacuo. Purification of the residue by preparative reverse-phase HPLC, eluting with a gradient of 10 to 55% of acetonitrile in water containing 0.1% of trifluoroacetic acid, afforded the title compound as a colorless solid (0.050 g, 18% yield): $^1$H NMR (300 MHz, DMSO-$d_6$) δ 11.42 (s, 1H), 10.33 (s, 1H), 8.91 (d, J=2.2 Hz, 1H), 7.49 (td, J=8.0, 5.9 Hz, 1H), 7.36-7.30 (m, 2H), 7.17-7.14 (m, 1H), 7.00 (d, J=2.2 Hz, 1H), 6.63 (dd, J=13.7, 1.3 Hz, 1H), 4.52 (s, 4H), 4.08-4.04 (m, 4H), 2.41-2.26 (m, 2H); MS (ES+) m/z 503.2 (M+1), 505.2 (M+1).

Example 304

Synthesis of 4-((2-(azetidin-1-ylmethyl)-6-fluorobenzyl)amino)-2,6-difluoro-3-methyl-N-(thiazol-4-yl)benzenesulfonamide 2,2,2-trifluoroacetate

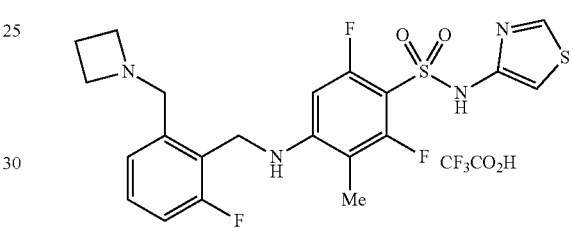

Step 1. Preparation of tert-butyl ((4-((2-(azetidin-1-ylmethyl)-6-fluorobenzyl)amino)-2,6-difluoro-3-methylphenyl)sulfonyl)(thiazol-4-yl)carbamate

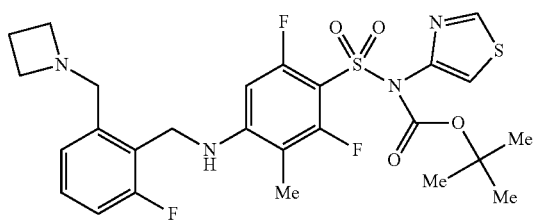 [SMILES: Cc1c(NCc2c(F)cccc2CN2CCC2)cc(F)c(S(=O)(=O)N(C(=O)OC(C)(C)C)c2cscn2)c1F]

To a mixture of tert-butyl ((4-((2-(azetidin-1-ylmethyl)-6-fluorobenzyl)amino)-3-chloro-2,6-difluorophenyl)sulfonyl)(thiazol-4-yl)carbamate (0.60 g, 1.00 mmol), methylboronic acid (0.60 g, 10.0 mmol), and potassium phosphate (1.06 g, 5.00 mmol) in anhydrous dioxane (12 mL) was added palladium(II) acetate (0.045 g, 0.20 mmol) and tricyclohexylphosphine tetrafluoroborate (0.15 g, 0.40 mmol). The mixture was degassed and heated to 90° C. in a sealed tube for 1.5 h. After cooling to ambient temperature, the mixture was diluted with ethyl acetate (30 mL) and filtered through a pad of celite. The filtrate was concentrated in vacuo and the residue was purified by column chromatography, eluting with a gradient of 10 to 70% of ethyl acetate (containing 20% of ethanol and 0.2% of ammonium of hydroxide) in hexanes, to afford the title compound as a colorless foam (0.32 g, 55% yield): MS (ES+) m/z 583.4 (M+1).

Step 2. Preparation of 4-((2-(azetidin-1-ylmethyl)-6-fluorobenzyl)amino)-2,6-difluoro-3-methyl-N-(thiazol-4-yl)benzenesulfonamide 2,2,2-trifluoroacetate

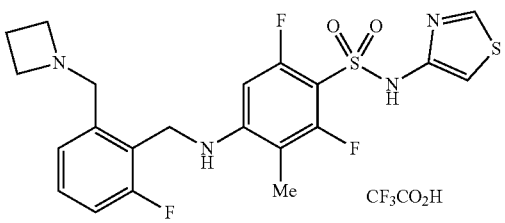 [SMILES: Cc1c(NCc2c(F)cccc2CN2CCC2)cc(F)c(S(=O)(=O)Nc2cscn2)c1F ; "CF3CO2H"]

Following the procedure as described for EXAMPLE 303, Step 2 and making non-critical variations as required to replace tert-butyl ((4-((2-(azetidin-1-ylmethyl)-6-fluorobenzyl)amino)-3-chloro-2,6-difluorophenyl)sulfonyl)(thiazol-4-yl)carbamate with tert-butyl ((4-((2-(azetidin-1-ylmethyl)-6-fluorobenzyl)amino)-2,6-difluoro-3-methylphenyl)sulfonyl)(thiazol-4-yl)carbamate, afforded the title compound as a colorless solid (0.165 g, 51% yield): $^1$H NMR (300 MHz, DMSO-$d_6$) δ 11.25 (s, 1H), 10.32 (s, 1H), 8.89 (d, J=2.2 Hz, 1H), 7.52-7.45 (m, 1H), 7.33 (t, J=9.0 Hz, 2H), 6.91 (d, J=2.2 Hz, 1H), 6.57-6.53 (m, 1H), 6.40 (d, J=13.8 Hz, 1H), 4.50 (d, J=0.3 Hz, 2H), 4.41 (d, J=3.7 Hz, 2H), 4.11-4.04 (m, 4H), 2.43-2.26 (m, 2H), 1.92 (d, J=1.8 Hz, 3H); MS (ES+) m/z 483.2 (M+1).

Example 305

Synthesis of 4-((2-((2,2-dimethylazetidin-1-yl)methyl)benzyl)amino)-2,6-difluoro-3-methyl-N-(thiazol-4-yl)benzenesulfonamide 2,2,2-trifluoroacetate

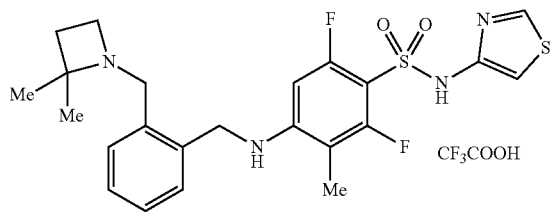 [SMILES: Cc1c(NCc2ccccc2CN2CCC2(C)C)cc(F)c(S(=O)(=O)Nc2cscn2)c1F ; "CF3COOH"]

Step 1. Preparation of 2-((2,2-dimethylazetidin-1-yl)methyl)benzonitrile

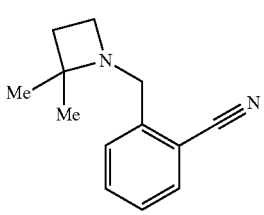 [SMILES: CC1(C)CCN1Cc1ccccc1C#N]

Following the procedure as described in EXAMPLE 300, Step 1 and making non-critical variations as required to replace 2-(bromomethyl)-6-fluorobenzonitrile with 2-(bromomethyl)benzonitrile, afforded the title compound as a pink oil (1.29 g, 93% yield): $^1$H NMR (300 MHz, CDCl$_3$) δ 7.62-7.49 (m, 3H), 7.33-7.28 (m, 1H), 3.73 (s, 2H), 3.17 (t, J=7.0 Hz, 2H), 1.92 (t, J=7.0 Hz, 2H), 1.25 (s, 6H); MS (ES+) m/z 201.2 (M+1).

Step 2. Preparation of (2-((2,2-dimethylazetidin-1-yl)methyl)phenyl)methanamine

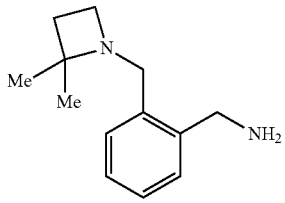 [SMILES: CC1(C)CCN1Cc1ccccc1CN]

To a solution of 2-((2,2-dimethylazetidin-1-yl)methyl)benzonitrile (1.29 g, 6.44 mmol) in anhydrous tetrahydrofuran (50 mL) was added a 1.0 M solution of lithium aluminum hydride in tetrahydrofuran (19.30 mL, 19.30 mmol) at 0° C. The mixture was stirred at 0° C. for 1 h and then at ambient temperature for 4 h. The mixture was cooled to 0° C. and quenched by slow addition of sodium sulfate decahydrate (19.30 g, 59.90 mmol). The mixture was stirred vigorously for 18 h, and then filtered through a pad of Celite. The filter cake was rinsed with ethyl acetate (200 mL). The combined filtrate was concentrated in vacuo to afford the title compound as a pink oil (1.30 g, 99% yield): $^1$H NMR (300 MHz, CDCl$_3$) δ 7.28-7.17 (m, 4H), 3.85 (s, 2H), 3.58 (s, 2H), 3.04 (t, J=6.9 Hz, 2H), 2.64 (s, 2H), 1.84 (t, J=6.9 Hz, 2H), 1.26 (s, 6H); MS (ES+) m/z 205.3 (M+1).

Step 3. Preparation of tert-butyl ((3-bromo-4-((2-((2,2-dimethylazetidin-1-yl)methyl)benzyl)amino)-2,6-difluorophenyl)sulfonyl)(thiazol-4-yl)carbamate

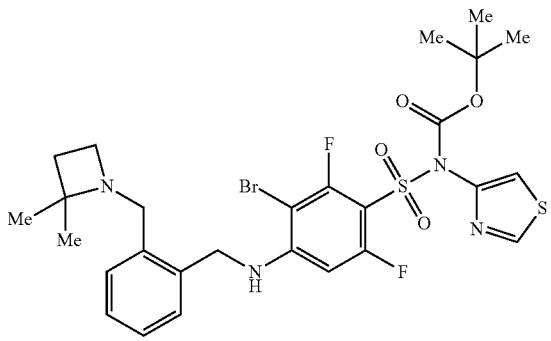 [SMILES: CC(C)(C)OC(=O)N(c1cscn1)S(=O)(=O)c1c(F)cc(NCc2ccccc2CN2CCC2(C)C)c(Br)c1F]

To a mixture of tert-butyl ((3-bromo-2,4,6-trifluorophenyl)sulfonyl)(thiazol-4-yl)carbamate (1.51 g, 3.18 mmol) and potassium carbonate (0.44 g, 3.18 mmol) in anhydrous dimethyl sulfoxide (10 mL) was added a solution of (2-((2,2-dimethylazetidin-1-yl)methyl)phenyl)methanamine (0.65 g, 3.18 mmol) in anhydrous dimethyl sulfoxide (15 mL). The mixture was stirred at ambient temperature for 18 h and then diluted with ethyl acetate (80 mL). The organic phase was washed with water (50 mL), saturated ammonium chloride (50 mL), brine (50 mL), dried over anhydrous sodium sulfate, and filtered. The filtrate was concentrated in vacuo and the residue was purified by column chromatography, eluting with a gradient of 10 to 70% of ethyl acetate (containing 20% of ethanol and 0.2% of ammonium of hydroxide) in heptane, to afford the title compound as a colorless foam (1.00 g, 48% yield): $^1$H NMR (300 MHz, CDCl$_3$) δ 8.81 (d, J=2.3 Hz, 1H), 7.52 (d, J=2.3 Hz, 1H), 7.29-7.25 (m, 4H), 6.91 (s, 1H), 6.59 (d, J=12.9 Hz, 1H), 4.53 (s, 2H), 3.64 (s, 2H), 3.10 (s, 2H), 1.95 (s, 2H), 1.39 (s, 9H), 1.29 (s, 6H); MS (ES+) m/z 657.4 (M+1), 659.4 (M+1).

Step 4. Preparation of 4-((2-((2,2-dimethylazetidin-1-yl)methyl)benzyl)amino)-2,6-difluoro-3-methyl-N-(thiazol-4-yl)benzenesulfonamide 2,2,2-trifluoroacetate

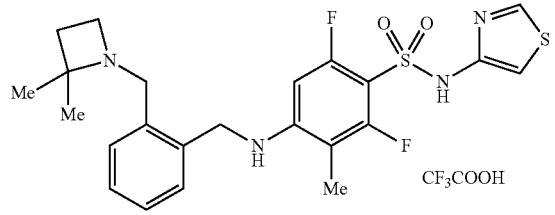 [SMILES: Cc1c(NCc2ccccc2CN2CCC2(C)C)cc(F)c(S(=O)(=O)Nc2cscn2)c1F ; "CF3COOH"]

To a mixture of tert-butyl ((3-bromo-4-((2-((2,2-dimethylazetidin-1-yl)methyl)benzyl)amino)-2,6-difluorophenyl)sulfonyl)(thiazol-4-yl)carbamate (1.00 g, 1.52 mmol), methylboronic acid (0.46 g, 7.60 mmol), and potassium phosphate (1.61 g, 7.60 mmol) in anhydrous dioxane (20 mL) was added palladium(II) acetate (0.068 g, 0.30 mmol) and tricyclohexylphosphine tetrafluoroborate (0.22 g, 0.61 mmol). The mixture was degassed and heated to reflux for 6 h. After cooling to ambient temperature, the mixture was diluted with ethyl acetate (80 mL). The organic phase was washed with saturated ammonium chloride (2×60 mL), brine (30 mL), dried over anhydrous sodium sulfate, and filtered. The filtrate was concentrated in vacuo and the residue was purified by column chromatography, eluting with a gradient of 10 to 70% of ethyl acetate (containing 20% of ethanol and 0.2% of ammonium of hydroxide) in heptane. Additional purification by preparative reverse-phase HPLC, eluting with a gradient of 10 to 55% of acetonitrile in water containing 0.1% of trifluoroacetic acid, afforded the title compound as a colorless solid (0.335 g, 36% yield): $^1$H NMR (300 MHz, DMSO-d$_6$) δ 11.22 (s, 1H), 9.81 (s, 1H), 8.89 (d, J=2.2 Hz, 1H), 7.50-7.45 (m, 1H), 7.40-7.26 (m, 3H), 7.02-6.98 (m, 1H), 6.88 (d, J=2.2 Hz, 1H), 6.13 (d, J=13.6 Hz, 1H), 4.54-4.49 (m, 3H), 4.31-4.17 (m, 2H), 3.93-3.87 (m, 1H), 2.42-2.31 (m, 1H), 2.20-2.11 (m, 1H), 2.04 (d, J=1.7 Hz, 3H), 1.68 (s, 3H), 1.55 (s, 3H); MS (ES+) m/z 493.3 (M+1).

Example 306

Synthesis of 4-((2-((2,2-dimethylazetidin-1-yl)methyl)-6-fluorobenzyl)amino)-2-fluoro-3-methyl-N-(thiazol-4-yl)benzenesulfonamide

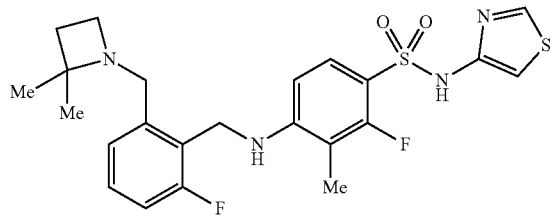 [SMILES: Cc1c(NCc2c(F)cccc2CN2CCC2(C)C)ccc(S(=O)(=O)Nc2cscn2)c1F]

To a mixture of (2-((2,2-dimethylazetidin-1-yl)methyl)-6-fluorophenyl)methanamine (0.96 g, 4.32 mmol) and potassium carbonate (0.60 g, 4.32 mmol) in anhydrous dimethyl sulfoxide (25 mL) was added tert-butyl ((3-chloro-2,4-difluorophenyl)sulfonyl)(thiazol-4-yl)carbamate (1.77 g, 4.32 mmol). The mixture was stirred at ambient temperature for 3 h and then diluted with ethyl acetate (80 mL). The organic phase was washed with water (50 mL), saturated ammonium chloride (50 mL), brine (50 mL), dried over anhydrous sodium sulfate, and filtered. The filtrate was concentrated in vacuo and the residue was dissolved in anhydrous dioxane (45 mL). The mixture was degassed by purging with argon. To this mixture was then added methylboronic acid (1.29 g, 21.60 mmol), potassium phosphate (4.59 g, 21.60 mmol), palladium acetate (0.19 g, 0.86 mmol) and tricyclohexylphosphine tetrafluoroborate (0.64 g, 1.73 mmol). The mixture was heated to reflux for 6 h. After cooling to ambient temperature, the mixture was diluted with ethyl acetate (80 mL). The organic phase was washed with saturated ammonium chloride (2×60 mL), brine (30 mL), dried over anhydrous sodium sulfate, and filtered. The filtrate was concentrated in vacuo and the residue was purified by column chromatography, eluting with a gradient of 10 to 70% of ethyl acetate (containing 20% of ethanol and 0.2% of ammonium of hydroxide) in heptane. Additional purification by preparative reverse-phase HPLC, eluting with a gradient of 10 to 55% of acetonitrile in water containing 0.1% of trifluoroacetic acid, afforded the title compound as a colorless solid (0.30 g, 14% yield): $^1$H NMR (300 MHz, DMSO-d$_6$) δ 8.85 (d, J=2.2 Hz, 1H), 7.52 (t, J=8.6 Hz, 1H), 7.27 (td, J=7.8, 5.8 Hz, 1H), 7.19-7.07 (m, 2H), 6.84 (d, J=2.2 Hz, 1H), 6.73 (d, J=9.0 Hz, 1H), 6.43 (s, 1H), 4.45 (s, 2H), 3.62 (s, 2H), 3.00 (t, J=6.8 Hz, 2H), 1.99 (d, J=1.9 Hz, 3H), 1.79 (t, J=6.9 Hz, 2H), 1.13 (s, 6H), NH not observed; MS (ES+) m/z 493.3 (M+1).

Example 307

Synthesis of 5-chloro-4-((2,5-difluorobenzyl)amino)-2-fluoro-N-(thiazol-4-yl)benzenesulfonamide

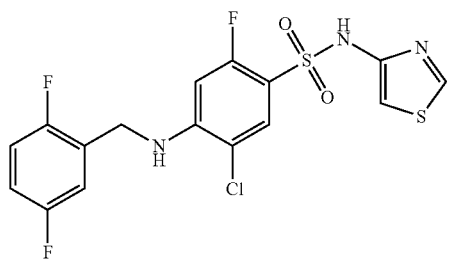 [SMILES: O=S(=O)(Nc1cscn1)c1cc(Cl)c(NCc2cc(F)ccc2F)cc1F]

To a mixture of tert-butyl ((5-chloro-2,4-difluorophenyl)sulfonyl)(thiazol-4-yl)carbamate (0.41 g, 1.00 mmol) and N,N-diisopropylethylamine (0.35 mL) in anhydrous N,N-dimethylformamide (5 mL) was added (2,5-difluorophenyl)methanamine (0.14 mL), 1.20 mmol). The mixture was stirred at ambient temperature for 18 h and then diluted with ethyl acetate (100 mL). The organic phase was washed with 1 M hydrochloric acid (2×10 mL), brine (10 mL), dried over anhydrous sodium sulfate, and filtered. The filtrate was concentrated in vacuo and the residue was purified by column chromatography, eluting with a gradient of 0 to 40% of ethyl acetate in hexane. The purified residue was then diluted with dichloromethane (10 mL) and trifluoroacetic acid (0.5 mL) was added to it. The mixture was stirred at ambient temperature for 2 h and then concentrated in vacuo. The residue was purified by trituration with diethyl ether (10 mL) to afford the title compound as a colorless solid (0.22 g, 51% yield): $^1$H NMR (300 MHz, DMSO-$d_6$) δ 11.13 (s, 1H), 8.88 (d, J=2.0 Hz, 1H), 7.62 (d, J=7.4 Hz, 1H), 7.33-6.94 (m, 5H), 6.57 (d, J=13.2 Hz, 1H), 4.49 (d, J=5.9 Hz, 2H); MS (ES+) m/z 434.1 (M+1), 436.1 (M+1).

Example 308

Synthesis of 4-((2-(azetidin-1-ylmethyl)-6-fluorobenzyl)amino)-2,5-difluoro-N-(thiazol-4-yl)benzenesulfonamide

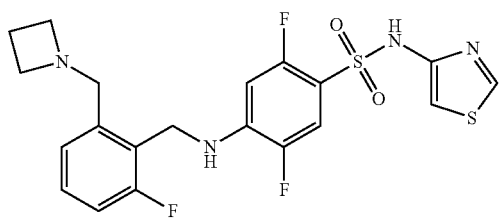 [SMILES: O=S(=O)(Nc1cscn1)c1cc(F)c(NCc2c(F)cccc2CN2CCC2)cc1F]

Step 1. Preparation of tert-butyl thiazol-4-yl((2,4,5-trifluorophenyl)sulfonyl)carbamate

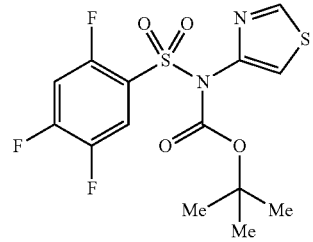 [SMILES: CC(C)(C)OC(=O)N(c1cscn1)S(=O)(=O)c1cc(F)c(F)cc1F]

To a solution of tert-butyl thiazol-4-ylcarbamate (3.46 g, 17.30 mmol) in anhydrous tetrahydrofuran (150 mL) was added a 1.0 M solution of lithium bis(trimethylsilyl)amide in tetrahydrofuran (20.80 mL, 20.80 mmol) at −78° C. The mixture was stirred at −78° C. for 2 h and then at ambient temperature for 1 h. The mixture was cooled to −78° C. and a solution of 2,4,5-trifluorobenzenesulfonyl chloride (3.99 g, 17.30 mmol) in anhydrous tetrahydrofuran (30 mL) was added to it. The mixture was stirred at −78° C. for 2 h and then at ambient temperature for 18 h. The mixture was diluted with ethyl acetate (250 mL), washed with saturated ammonium chloride (2×100 mL), brine (2×100 mL), dried over anhydrous sodium sulfate, and filtered. The filtrate was concentrated in vacuo and the residue was purified by column chromatography, eluting with a gradient of 10 to 70% of ethyl acetate in hexanes, to afford the title compound as a colorless solid (4.23 g, 62% yield): $^1$H NMR (300 MHz, CDCl$_3$) δ 8.81-8.80 (m, 1H), 8.09-8.01 (m, 1H), 7.54 (dd, J=1.6, 0.6 Hz, 1H), 7.17-7.09 (m, 1H), 1.38 (d, J=0.9 Hz, 9H); MS (ES+) m/z 394.7 (M+1).

Step 2. Preparation of 4-((2-(azetidin-1-ylmethyl)-6-fluorobenzyl)amino)-2,5-difluoro-N-(thiazol-4-yl)benzenesulfonamide

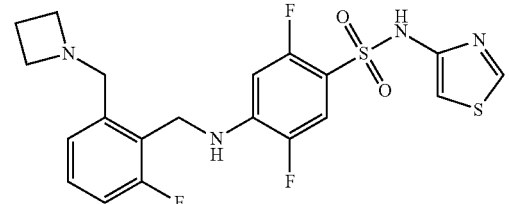

To a mixture of tert-butyl thiazol-4-yl((2,4,5-trifluorophenyl)sulfonyl)carbamate (0.43 g, 1.09 mmol) and N,N-diisopropylethylamine (0.38 mL, 2.20 mmol) in anhydrous N,N-dimethylformamide (5 mL) was added (2-(azetidin-1-ylmethyl)-6-fluorophenyl)methanamine (0.23 g, 1.20 mmol). The mixture was stirred at ambient temperature for 18 h and then diluted with ethyl acetate (100 mL). The organic phase was washed with water (2×10 mL), dried over anhydrous sodium sulfate, and filtered. The filtrate was concentrated in vacuo and the residue was purified by column chromatography, eluting with a gradient of 0 to 80% of ethyl acetate (containing 10% of isopropanol and 10% of triethylamine) in hexanes. Additional purification by trituration with diethyl ether (10 mL) afforded the title compound as a colorless solid (0.052 g, 10% yield): $^1$H NMR (300 MHz, DMSO-$d_6$) δ 11.14-10.93 (m, 1H), 8.88 (s, 1H), 8.02-7.93 (m, 1H), 7.38 (dd, J=11.1, 6.2 Hz, 1H), 7.34-7.25 (m, 1H), 7.21-7.10 (m, 2H), 7.01-6.92 (m, 2H), 4.42 (s, 2H), 3.67 (s, 2H), 3.15 (t, J=7.0 Hz, 4H), 2.06-1.91 (m, 2H); MS (ES+) m/z 469.1 (M+1).

Example 309

Synthesis of 4-((2-(azetidin-1-ylmethyl)-6-chloro-3-fluorobenzyl)amino)-2,6-difluoro-N-(thiazol-4-yl)benzenesulfonamide 2,2,2-trifluoroacetate

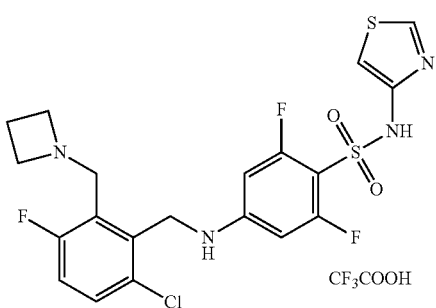

Step 1. Preparation of 1-(5-chloro-2-fluorobenzyl)azetidine

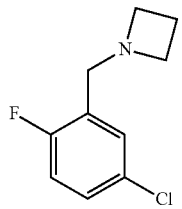 [SMILES: Fc1ccc(Cl)cc1CN1CCC1]

To a mixture of 5-chloro-2-fluorobenzaldehyde (3.95 g, 24.9 mmol) and azetidine (1.71 g, 29.9 mmol) in anhydrous 1,2-dichloroethane (50 mL) was added sodium triacetoxyborohydride (10.6 g, 50.0 mmol), and the reaction mixture was stirred at ambient temperature for 16 h. The reaction mixture was diluted with ethyl acetate (100 mL), washed with saturated ammonium chloride (80 mL) and brine (50 mL), and then concentrated in vacuo. Purification of the residue by column chromatography, eluting with a gradient of 0 to 10% of methanol in dichloromethane, afforded the title compound as a colorless oil (2.0 g, 40% yield): $^1$H NMR (300 MHz, CDCl$_3$) δ 7.38 (dd, J=6.3, 2.7 Hz, 1H), 7.28-7.20 (m, 1H), 6.99 (m, 1H), 3.82 (s, 2H), 3.55 (t, J=7.5 Hz, 4H), 2.27-2.17 (m, 2H); MS (ES+) m/z 200.2 (M+1), 202.0 (M+1).

Step 2. Preparation of (E)-2-(azetidin-1-ylmethyl)-6-chloro-3-fluorobenzaldehyde oxime

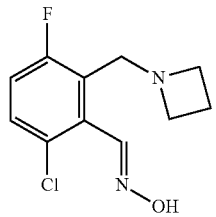 [SMILES: O/N=C/c1c(Cl)ccc(F)c1CN1CCC1]

To a solution of 1-(5-chloro-2-fluorobenzyl)azetidine (2.53 g, 12.7 mmol) in anhydrous tetrahydrofuran (36 mL) was added a 0.64 M solution of sec-butyllithium in cyclohexane (25.7 mL, 16.4 mmol) at −78° C. The mixture was stirred at −78° C. for 80 minutes, and then anhydrous N,N-dimethylformamide (1.77 mL, 22.9 mmol) was added to it at −78° C. The mixture was stirred at −78° C. for 50 minutes, and then a solution of hydroxylamine hydrochloride (1.32 g, 19.0 mmol) in a 1:1 mixture of methanol and water (6 mL) was added at −78° C. The mixture was stirred at ambient temperature for 2 h and then concentrated in vacuo. To the residue was added water (50 mL), and the mixture was extracted with a 10:1 mixture of dichloromethane and methanol (6×40 mL). The combined organic extracts were dried over anhydrous magnesium sulfate and filtered. Concentration of the filtrate in vacuo afforded the title compound as a yellow oil (2.64 g, 86% yield) which was used without further purification: MS (ES+) m/z 243.2 (M+1).

Step 3. Preparation of (2-(azetidin-1-ylmethyl)-6-chloro-3-fluorophenyl)methanamine

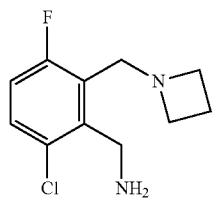 [SMILES: NCc1c(Cl)ccc(F)c1CN1CCC1]

To a solution of (E)-2-(azetidin-1-ylmethyl)-6-chloro-3-fluorobenzaldehyde oxime (2.64 g, 10.87 mmol) in methanol (3 mL) was added zinc dust (2.12 g, 32.4 mmol). The mixture was cooled to 0° C., 6 M hydrochloric acid (18 mL, 108 mmol) was slowly added to it, and the mixture was heated to reflux for 1 h. The mixture was cooled to 0° C. and 3.5 M sodium hydroxide (30 mL, 105 mmol) was slowly added to it followed by concentrated ammonium hydroxide (50 mL) and dichloromethane (10 mL). The mixture was stirred for 16 h. The layers were separated and the aqueous layer was extracted with dichloromethane (2×25 mL). The combined organic layers were dried over anhydrous magnesium sulfate and filtered. Concentration of the filtrate in vacuo afforded the title compound as a yellow oil (2.03 g, 82% yield) which was used without further purification: MS (ES+) m/z 229.2 (M+1).

Step 4. Preparation of tert-butyl ((4-((2-(azetidin-1-ylmethyl)-6-chloro-3-fluorobenzyl)amino)-3-bromo-2,6-difluorophenyl)sulfonyl)(thiazol-4-yl)carbamate

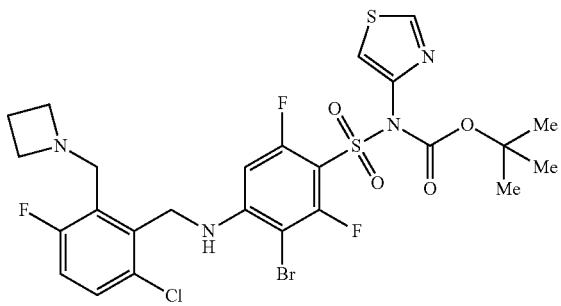

To a mixture of tert-butyl ((3-bromo-2,4,6-trifluorophenyl)sulfonyl)-(thiazol-4-yl)carbamate (1.62 g, 3.42 mmol) and potassium carbonate (0.944 g, 6.83 mmol) in anhydrous dimethyl sulfoxide (17 mL) was added a solution of (2-(azetidin-1-ylmethyl)-6-chloro-3-fluorophenyl)methanamine (2.03 g, 8.88 mmol) in anhydrous dimethyl sulfoxide (2 mL), and the reaction mixture was stirred at ambient temperature for 2.5 h. The mixture was cooled to 0° C., and water (40 mL) was added to it followed by ethyl acetate (60 mL). The organic layer was washed with brine (5×20 mL), dried over anhydrous magnesium sulfate and filtered. Concentration of the filtrate in vacuo and purification of the residue by column chromatography, eluting with a gradient of 20 to 35% of ethyl acetate (containing 10% of isopropanol and 10% of triethylamine) in heptane, afforded the title compound as a light yellow foam (0.503 g, 22% yield): $^1$H NMR (300 MHz, CDCl$_3$) δ 8.81 (d, J=2.3 Hz, 1H), 7.92-7.86 (m, 1H), 7.52 (d, J=2.3 Hz, 1H), 7.34 (dd, J=8.9, 5.1 Hz, 1H), 7.06-7.00 (m, 1H), 6.63 (dd, J=13.5, 1.7 Hz, 1H), 4.58 (d, J=5.3 Hz, 2H), 3.74 (d, J=2.6 Hz, 2H), 3.33 (t, J=7.1 Hz, 4H), 2.16-2.06 (m, 2H), 1.41 (s, 9H); MS (ES+) m/z 681.1 (M+1), 683.2 (M+1).

Step 5. Preparation of tert-butyl ((4-((2-(azetidin-1-ylmethyl)-6-chloro-3-fluorobenzyl)amino)-2,6-difluorophenyl)sulfonyl)(thiazol-4-yl)carbamate

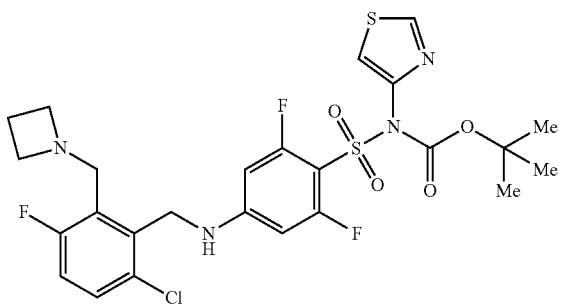 [SMILES: CC(C)(C)OC(=O)N(c1cscn1)S(=O)(=O)c1c(F)cc(NCc2c(Cl)ccc(F)c2CN2CCC2)cc1F]

To a mixture of tert-butyl ((4-((2-(azetidin-1-ylmethyl)-6-chloro-3-fluorobenzyl)amino)-3-bromo-2,6-difluorophenyl)sulfonyl)(thiazol-4-yl)carbamate (0.491 g, 0.720 mmol), tetrakis(triphenylphosphine)palladium(0) (0.083 g, 0.072 mmol), formic acid (0.14 mL, 3.7 mmol) in anhydrous 1,4-dioxane (7.2 mL) was added triethylamine (1.0 mL, 7.2 mmol) and the mixture was degassed by purging with nitrogen for 10 minutes. The reaction mixture was then heated to reflux for 4 h. The mixture was allowed to cool to ambient temperature and diluted with ethyl acetate (60 mL). The mixture was washed with saturated sodium bicarbonate (2×25 mL), brine (20 mL), dried over anhydrous magnesium sulfate, and filtered. Concentration of the filtrate and purification of the residue by column chromatography, eluting with a gradient of 40 to 80% of ethyl acetate (containing 10% of isopropanol and 10% of triethylamine) in heptane, afforded the title compound as a yellow foam (0.146 g, 34% yield): $^1$H NMR (300 MHz, CDCl$_3$) δ 8.79 (d, J=2.3 Hz, 1H), 8.18-8.12 (m, 1H), 7.50 (d, J=2.3 Hz, 1H), 7.34 (dd, J=8.9, 5.1 Hz, 1H), 7.05-6.99 (m, 1H), 6.30-6.25 (m, 2H), 4.52-4.51 (m, 2H), 3.68 (d, J=2.7 Hz, 2H), 3.30 (t, J=7.1 Hz, 4H), 2.17-2.07 (m, 2H), 1.40 (s, 9H); MS (ES+) m/z 603.3 (M+1), 605.3 (M+1).

Step 6. Preparation of 4-((2-(azetidin-1-ylmethyl)-6-chloro-3-fluorobenzyl)amino)-2,6-difluoro-N-(thiazol-4-yl)benzenesulfonamide 2,2,2-trifluoroacetate

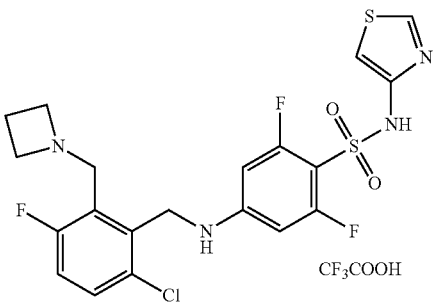

To a solution of tert-butyl ((4-((2-(azetidin-1-ylmethyl)-6-chloro-3-fluorobenzyl)amino)-2,6-difluorophenyl)sulfonyl)(thiazol-4-yl)carbamate (0.050 g, 0.083 mmol) in dichloromethane (3 mL) was added trifluoroacetic acid (1.5 mL). The reaction mixture was stirred at ambient temperature for 1 h and then concentrated in vacuo. Trituration of the residue in diethyl ether (8 mL) provided the title compound as a colourless solid (0.044 g, 86% yield): $^1$H NMR (300 MHz, DMSO-d$_6$) δ 11.25 (br s, 1H), 10.09 (br s, 1H), 8.91 (d, J=2.2 Hz, 1H), 7.73 (dd, J=9.0, 5.2 Hz, 1H), 7.47 (m, 1H), 7.14 (m, 1H), 6.93 (d, J=2.2 Hz, 1H), 6.37 (d, J=12.4 Hz, 2H), 4.48 (br s, 2H), 4.39 (d, J=3.9 Hz, 2H), 4.20-4.00 (m, 4H), 2.39-2.17 (m, 2H); MS (ES+) m/z 503.2 (M+1), 505.2 (M+1).

Example 310

Synthesis of 4-((2-(azetidin-1-ylmethyl)benzyl)amino)-2,6-difluoro-3-methyl-N-(pyrimidin-4-yl)benzenesulfonamide 2,2,2-trifluoroacetate

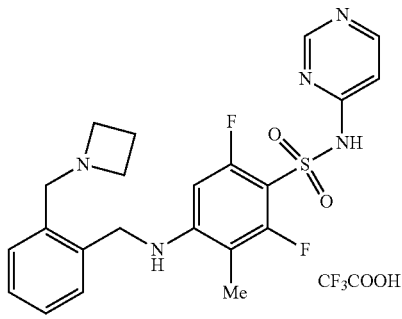 [SMILES: Cc1c(NCc2ccccc2CN2CCC2)cc(F)c(S(=O)(=O)Nc2ccncn2)c1F ; "CF3COOH"]

Step 1. Preparation of 3-chloro-N-(2,4-dimethoxybenzyl)-2,4,6-trifluoro-N-(pyrimidin-4-yl)benzenesulfonamide

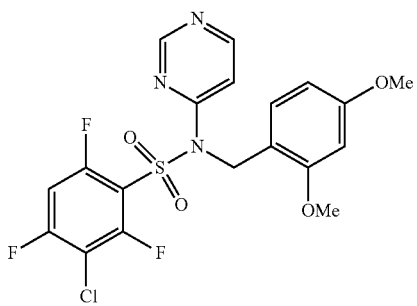 [SMILES: COc1ccc(CN(c2ccncn2)S(=O)(=O)c2c(F)cc(F)c(Cl)c2F)c(OC)c1]

To a solution of N-(2,4-dimethoxybenzyl)pyrimidin-4-amine (2.67 g, 10.9 mmol) in anhydrous tetrahydrofuran (40 mL) was added lithium bis(trimethylsilyl)amide (1.0 M in tetrahydrofuran, 13.1 mL, 13.1 mmol) at −78° C. The mixture was warmed to 0° C., stirred for 1 h, and then cooled to −78° C. To it was added a solution of 3-chloro-2,4,6-trifluorobenzenesulfonyl chloride (3.46 g, 13.1 mmol) in anhydrous tetrahydrofuran (14 mL) at −78° C. The mixture was allowed to warm to ambient temperature and stirred for 16 h. The mixture was concentrated in vacuo, and the residue was partitioned between ethyl acetate (150 mL) and water (30 mL). The organic layer was washed with brine (30 mL), dried over anhydrous magnesium sulfate, and filtered. Concentration of the filtrate in vacuo and purification of the residue by column chromatography, eluting with a gradient of 20 to 25% of ethyl acetate (containing 10% of isopropanol and 10% of triethylamine) in heptane, afforded the title compound as a light yellow foam (0.619 g, 12% yield): $^1$H NMR (300 MHz, CDCl$_3$) δ 8.78 (d, J=0.9 Hz, 1H), 8.48 (d, J=5.9 Hz, 1H), 7.25-7.22 (m, 1H), 7.02 (dd, J=5.9, 1.3 Hz, 1H), 6.94-6.87 (m, 1H), 6.46-6.42 (m, 2H), 5.25 (s, 2H), 3.83 (s, 3H), 3.78 (s, 3H); MS (ES+) m/z 474.2 (M+1), 476.2 (M+1).

Step 3. Preparation of 4-((2-(azetidin-1-ylmethyl)benzyl)amino)-3-chloro-N-(2,4-dimethoxybenzyl)-2,6-difluoro-N-(pyrimidin-4-yl)benzenesulfonamide

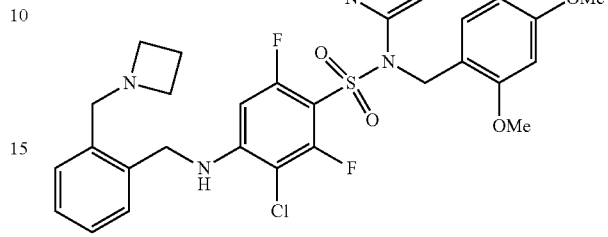

To a mixture of 3-chloro-N-(2,4-dimethoxybenzyl)-2,4,6-trifluoro-N-(pyrimidin-4-yl)benzenesulfonamide (0.593 g, 1.25 mmol) and potassium carbonate (0.346 g, 2.50 mmol) in anhydrous dimethyl sulfoxide (4 mL) was added a solution of (2-(azetidin-1-ylmethyl)phenyl)methanamine (0.221 g, 1.25 mmol) in anhydrous dimethyl sulfoxide (2 mL) and the reaction mixture was stirred at ambient temperature for 4 h. The mixture was partitioned between ethyl acetate (25 mL) and water (20 mL), and the aqueous phase was extracted with ethyl acetate (25 mL). The combined organic layers were washed with brine (5×15 mL), dried over anhydrous magnesium sulfate, and filtered. Concentration of the filtrate in vacuo and purification of the residue by column chromatography, eluting with a gradient of 25 to 30% of ethyl acetate (containing 10% of isopropanol and 10% of triethylamine) in heptane, afforded the title compound as a pale foam (0.532 g, 67% yield): $^1$H NMR (300 MHz, CDCl$_3$) δ 8.80 (d, J=1.0 Hz, 1H), 8.44 (d, J=6.0 Hz, 1H), 8.21 (br s, 1H), 7.29-7.21 (m, 6H), 6.44-6.36 (m, 3H), 5.31 (s, 2H), 4.33 (s, 2H), 3.82 (s, 3H), 3.76 (s, 3H), 3.59 (s, 2H), 3.24-3.19 (m, 4H), 2.11-2.02 (m, 2H); MS (ES+) m/z 630.3 (M+1), 632.3 (M+1).

Step 4. Preparation of 4-((2-(azetidin-1-ylmethyl)benzyl)amino)-N-(2,4-dimethoxybenzyl)-2,6-difluoro-3-methyl-N-(pyrimidin-4-yl)benzenesulfonamide

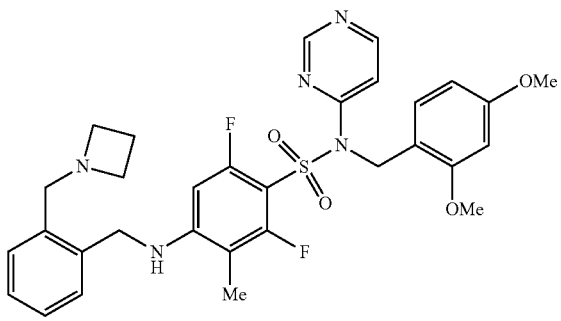 [SMILES: COc1ccc(CN(c2ccncn2)S(=O)(=O)c2c(F)cc(NCc3ccccc3CN3CCC3)c(Cl)c2F)c(OC)c1]

To a mixture of 4-((2-(azetidin-1-ylmethyl)benzyl)amino)-3-chloro-N-(2,4-dimethoxybenzyl)-2,6-difluoro-N-(pyrimidin-4-yl)benzenesulfonamide (0.250 g, 0.397 mmol), methylboronic acid (0.190 g, 3.17 mmol), tricyclohexylphosphine tetrafluoroborate (0.029 g, 0.079 mmol) and palladium(II) acetate (0.0089 g, 0.040 mmol) in anhydrous 1,4-dioxane (7.9 mL) was added potassium phosphate tribasic (0.253 g, 1.19 mmol). The mixture was degassed by sparging with nitrogen for 20 minutes and then heated to 100° C. for 2.5 h. The mixture was allowed to cool to ambient temperature and partitioned between ethyl acetate (50 mL) and water (10 mL). The mixture was filtered through a pad of Celite, and the organic phase of the filtrate was washed with brine (20 mL), dried over anhydrous magnesium sulfate, and filtered. Concentration of the filtrate in vacuo and purification of the residue by column chromatography, eluting with a gradient of 30 to 40% of ethyl acetate (containing 10% of isopropanol and 10% of triethylamine) in heptane, afforded the title compound as a pale foam (0.194 g, 80% yield): $^1$H NMR (300 MHz, CDCl$_3$) δ 8.78 (d, J=1.2 Hz, 1H), 8.42 (d, J=6.0 Hz, 1H), 7.46 (br s, 1H), 7.36 (dd, J=6.0, 1.2 Hz, 1H), 7.31-7.21 (m, 5H), 6.44 (d, J=2.3 Hz, 1H), 6.40 (dd, J=8.3, 2.4 Hz, 1H), 6.30-6.25 (m, 1H), 5.35 (s, 2H), 4.28 (s, 2H), 3.83 (s, 3H), 3.76 (s, 3H), 3.58 (s, 2H), 3.21 (t, J=7.1 Hz, 4H), 2.10-2.00 (m, 5H); MS (ES+) m/z 610.3 (M+1).

Step 5. Preparation of 4-((2-(azetidin-1-ylmethyl) benzyl)amino)-2,6-difluoro-3-methyl-N-(pyrimidin-4-yl)benzenesulfonamide 2,2,2-trifluoroacetate

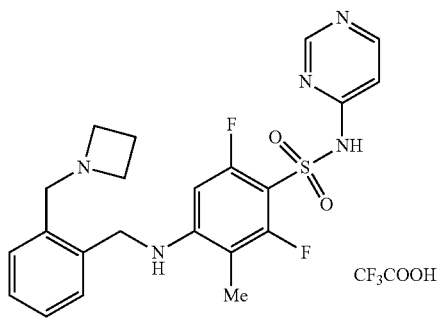 [SMILES: Cc1c(NCc2ccccc2CN2CCC2)cc(F)c(S(=O)(=O)Nc2ccncn2)c1F ; "CF3COOH"]

To a solution of 4-((2-(azetidin-1-ylmethyl)benzyl) amino)-N-(2,4-dimethoxybenzyl)-2,6-difluoro-3-methyl-N-(pyrimidin-4-yl)benzenesulfonamide (0.184 g, 0.302 mmol) in dichloromethane (2.8 mL) was added trifluoroacetic acid (2.8 mL). The reaction mixture was stirred at ambient temperature for 3 h and then concentrated in vacuo. Methanol (10 mL) was added to the residue, and the mixture was filtered through a pad of Celite. The filtrate was concentrated in vacuo, and the residue was purified by column chromatography, eluting with 15% of methanol in dichloromethane, to provide the title compound as a colourless solid (0.116 g, 67% yield): $^1$H NMR (300 MHz, DMSO-d$_6$) δ 12.47 (br s, 1H), 10.30 (br s, 1H), 8.61 (s, 1H), 8.42-8.33 (m, 1H), 7.44-7.25 (m, 4H), 6.98-6.97 (m, 2H), 6.16 (d, J=14.0 Hz, 1H), 4.51-4.50 (m, 4H), 4.12 (t, J=8.0 Hz, 4H), 2.44-2.33 (m, 2H), 2.03 (d, J=1.6 Hz, 3H); $^{19}$F NMR (282 MHz, DMSO-d$_6$) δ −73.5 (s, 3F), −111.4 (s, 1F), −112.4 (s, 1F); MS (ES+) m/z 460.3 (M+1).

Example 311

Synthesis of 4-((2-(azetidin-1-ylmethyl)benzyl) amino)-2,6-difluoro-N-(pyrimidin-4-yl)benzenesulfonamide formate

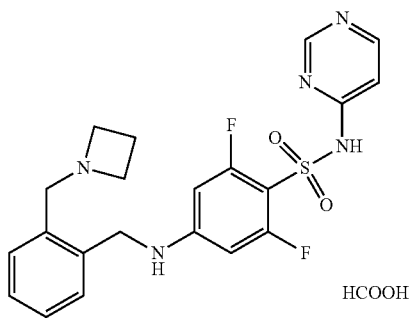 [SMILES: O=S(=O)(Nc1ccncn1)c1c(F)cc(NCc2ccccc2CN2CCC2)cc1F ; "HCOOH"]

To a solution of 4-((2-(azetidin-1-ylmethyl)benzyl) amino)-3-chloro-N-(2,4-dimethoxybenzyl)-2,6-difluoro-N-(pyrimidin-4-yl)benzenesulfonamide (0.261 g, 0.414 mmol) in ethanol (8 mL) was added 10% palladium on carbon (0.047 g) followed by triethylamine (0.23 mL, 1.6 mmol). The mixture was heated to 60° C. under a hydrogen atmosphere for 23 h. After cooling to ambient temperature, the mixture was filtered through a pad of Celite. The filtrate was concentrated in vacuo, and the residue was purified by column chromatography, eluting with a gradient of 20 to 50% of ethyl acetate (containing 10% of isopropanol and 10% of triethylamine) in heptane, to give a yellow film (0.029 g). To this residue was added dichloromethane (2.4 mL) and trifluoroacetic acid (2.4 mL), and the solution was stirred at ambient temperature for 2 h. Concentration in vacuo provided a residue. To this residue was added a 1:1 mixture of methanol and dichloromethane (10 mL), and the mixture was filtered through a pad of Celite. The filtrate was concentrated in vacuo, and the residue was purified by preparative reverse-phase HPLC, eluting with a gradient of 10 to 40% of acetonitrile in water containing 0.5% of formic acid, to provide the title compound as a colorless solid (0.010 g, 5% yield over 2 steps): $^1$H NMR (300 MHz, DMSO-d$_6$) δ 8.38 (s, 1H), 8.15 (s, 1H), 8.06 (d, J=5.7 Hz, 1H), 7.31-7.19 (m, 4H), 6.70 (d, J=5.9 Hz, 1H), 6.26 (d, J=12.3 Hz, 2H), 4.35 (s, 2H), 3.68 (s, 2H), 3.25 (t, J=7.1 Hz, 4H), 2.08-1.99 (m, 2H), NH and COOH not observed; $^{19}$F NMR (282 MHz, DMSO-d$_6$) δ−108.6 (s, 2F); MS (ES+) m/z 446.3 (M+1).

Example 312

Synthesis of 4-((2-(azetidin-1-ylmethyl)benzyl) amino)-2,3-difluoro-6-methyl-N-(thiazol-4-yl)benzenesulfonamide 2,2,2-trifluoroacetate

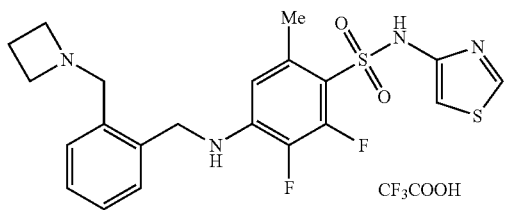 [SMILES: Cc1cc(NCc2ccccc2CN2CCC2)c(F)c(F)c1S(=O)(=O)Nc1cscn1 ; "CF3COOH"]

Step 1. Preparation of tert-butyl ((4-((2-(azetidin-1-ylmethyl)benzyl)amino)-6-bromo-2,3-difluorophenyl)sulfonyl)(thiazol-4-yl)carbamate

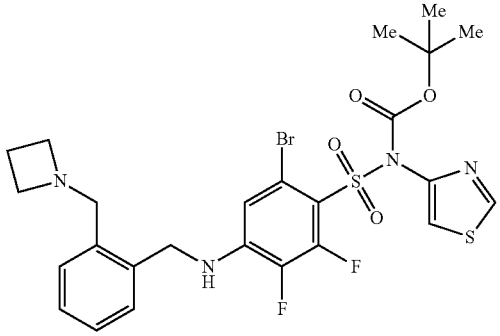

To a mixture of tert-butyl ((6-bromo-2,3,4-trifluorophenyl)sulfonyl)(thiazol-4-yl)carbamate (2.11 g, 4.46 mmol) and potassium carbonate (1.23 g, 8.90 mmol) in dimethyl sulfoxide (15 mL) was added a solution of (2-(azetidin-1-ylmethyl)phenyl)methanamine (0.786 g, 4.46 mmol) in dimethyl sulfoxide (7 mL) and the mixture was stirred at ambient temperature for 18 h. The mixture was partitioned between ethyl acetate (50 mL) and ice-water (70 mL). The organic layer was washed with brine (5×25 mL), dried over anhydrous magnesium sulfate, and filtered. Concentration of the filtrate in vacuo and purification of the residue by column chromatography, eluting with a gradient of 20 to 30% of ethyl acetate (containing 10% of isopropanol and 10% of triethylamine) in heptane, afforded the title compound as a pale foam (1.55 g, 55% yield): $^1$H NMR (300 MHz, CDCl$_3$) δ 8.93 (br s, 1H), 8.79 (d, J=2.3 Hz, 1H), 7.54 (m, 1H), 7.35-7.24 (m, 4H), 6.96 (dd, J=7.2, 1.8 Hz, 1H), 4.34 (s, 2H), 3.60 (s, 2H), 3.19 (t, J=7.0 Hz, 4H), 2.15-2.06 (m, 2H), 1.37 (s, 9H); MS (ES+) m/z 629.2 (M+1), 631.2 (M+1).

Step 2. Preparation of tert-butyl ((4-((2-(azetidin-1-ylmethyl)benzyl)amino)-2,3-difluoro-6-methylphenyl)sulfonyl)(thiazol-4-yl)carbamate

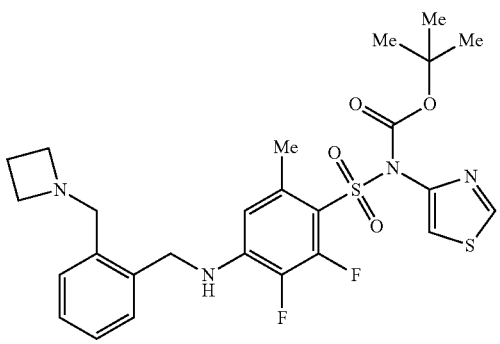 [SMILES: Cc1cc(NCc2ccccc2CN2CCC2)c(F)c(F)c1S(=O)(=O)N(C(=O)OC(C)(C)C)c1cscn1]

To a mixture of tert-butyl ((4-((2-(azetidin-1-ylmethyl)benzyl)amino)-6-bromo-2,3-difluorophenyl)sulfonyl)(thiazol-4-yl)carbamate (0.504 g, 0.801 mmol), methylboronic acid (0.384 g, 6.41 mmol) and tetrakis(triphenylphosphine)palladium(0) (0.093 g, 0.080 mmol) in anhydrous 1,4-dioxane (16 mL) was added potassium phosphate tribasic (0.510 g, 2.40 mmol). The mixture was degassed by sparging with nitrogen for 15 minutes and then heated to 90° C. for 3 h. The mixture was allowed to cool to ambient temperature and partitioned between ethyl acetate (60 mL) and water (20 mL). The mixture was filtered through a pad of Celite, and the organic layer of the filtrate was washed with brine (20 mL), dried over anhydrous magnesium sulfate, and filtered. Concentration of the filtrate in vacuo and purification of the residue by column chromatography, eluting with a gradient of 10 to 30% of ethyl acetate (containing 10% of isopropanol and 10% of triethylamine) in heptane, afforded the title compound as a pale oil (0.312 g, 69% yield): $^1$H NMR (300 MHz, CDCl$_3$) δ 8.78 (d, J=2.3 Hz, 1H), 7.50 (dd, J=2.2, 0.8 Hz, 1H), 7.38-7.26 (m, 4H), 6.46-6.43 (m, 1H), 4.38 (s, 2H), 3.62 (s, 2H), 3.27-3.18 (m, 4H), 2.66 (s, 3H), 2.16-2.07 (m, 2H), 1.33 (s, 9H), NH not observed; MS (ES+) m/z 565.4 (M+1).

Step 3. Preparation of 4-((2-(azetidin-1-ylmethyl)benzyl)amino)-2,3-difluoro-6-methyl-N-(thiazol-4-yl)benzenesulfonamide 2,2,2-trifluoroacetate

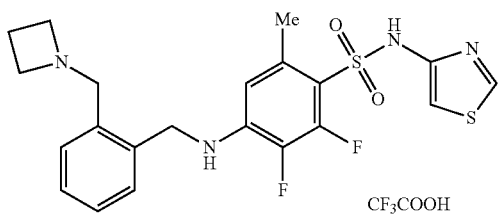 [SMILES: Cc1cc(NCc2ccccc2CN2CCC2)c(F)c(F)c1S(=O)(=O)Nc1cscn1 ; "CF3COOH"]

To a solution of tert-butyl ((4-((2-(azetidin-1-ylmethyl)benzyl)amino)-2,3-difluoro-6-methylphenyl)sulfonyl)(thiazol-4-yl)carbamate (0.295 g, 0.522 mmol) in dichloromethane (4 mL) was added trifluoroacetic acid (2 mL), and the solution was stirred at ambient temperature for 1 h. Concentration in vacuo provided a residue which was dissolved in methanol (1 mL) and triturated with diethyl ether (80 mL) to provide the title compound as a colourless solid (0.254 g, 84% yield): $^1$H NMR (300 MHz, DMSO-d$_6$) δ 11.08 (br s, 1H), 10.13 (br s, 1H), 8.88 (d, J=2.2 Hz, 1H), 7.43-7.32 (m, 4H), 7.24-7.19 (m, 1H), 6.92 (d, J=2.2 Hz, 1H), 6.35 (d, J=7.8 Hz, 1H), 4.50-4.48 (m, 4H), 4.14-4.04 (m, 4H), 2.44-2.27 (m, 5H); $^{19}$F NMR (282 MHz, DMSO-d$_6$) δ −73.4 (s, 3F), −135.1 (d, J=21.7 Hz, 1F), −161.9 (d, J=21.7 Hz, 1F); MS (ES+) m/z 465.4 (M+1).

Example 313

Synthesis of 4-((2-(azetidin-1-ylmethyl)-6-chloro-3-fluorobenzyl)amino)-2,6-difluoro-3-methyl-N-(thiazol-4-yl)benzenesulfonamide 2,2,2-trifluoroacetate

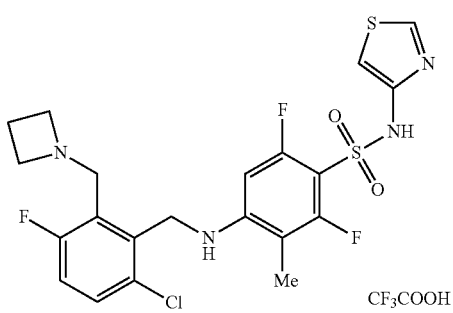 [SMILES: Cc1c(NCc2c(Cl)ccc(F)c2CN2CCC2)cc(F)c(S(=O)(=O)Nc2cscn2)c1F ; "CF3COOH"]

473

Step 1. Preparation of tert-butyl ((4-((2-(azetidin-1-ylmethyl)-6-chloro-3-fluorobenzyl)amino)-2,6-difluoro-3-methylphenyl)sulfonyl)(thiazol-4-yl)carbamate

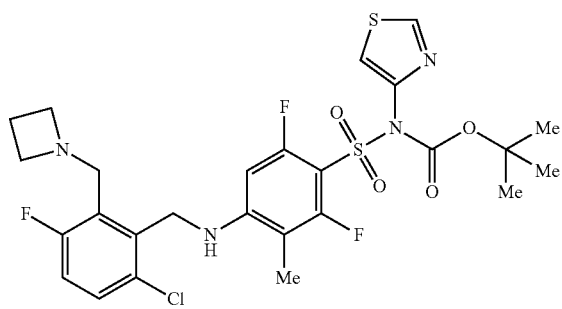 [SMILES: Cc1c(NCc2c(Cl)ccc(F)c2CN2CCC2)cc(F)c(S(=O)(=O)N(C(=O)OC(C)(C)C)c2cscn2)c1F]

Following the procedure as described in EXAMPLE 312, Step 2, and making non-critical modifications as required to replace tert-butyl ((4-((2-(azetidin-1-ylmethyl)benzyl)amino)-6-bromo-2,3-difluorophenyl)sulfonyl)(thiazol-4-yl)carbamate with tert-butyl ((4-((2-(azetidin-1-ylmethyl)-6-chloro-3-fluorobenzyl)amino)-3-bromo-2,6-difluorophenyl)sulfonyl)(thiazol-4-yl)carbamate, the title compound was obtained as a pale oil (0.118 g, 33% yield): $^1$H NMR (300 MHz, CDCl$_3$) δ 8.80 (d, J=2.3 Hz, 1H), 7.51 (d, J=2.4 Hz, 1H), 7.35 (dd, J=8.9, 5.1 Hz, 1H), 7.05-6.99 (m, 1H), 6.53-6.48 (m, 1H), 4.55 (d, J=5.1 Hz, 2H), 3.72 (d, J=2.8 Hz, 2H), 3.31 (t, J=7.1 Hz, 4H), 2.12-2.03 (m, 5H), 1.39 (s, 9H), NH not observed; MS (ES+) m/z 617.4 (M+1), 619.4 (M+1).

Step 2. Preparation of 4-((2-(azetidin-1-ylmethyl)-6-chloro-3-fluorobenzyl)amino)-2,6-difluoro-3-methyl-N-(thiazol-4-yl)benzenesulfonamide 2,2,2-trifluoroacetate

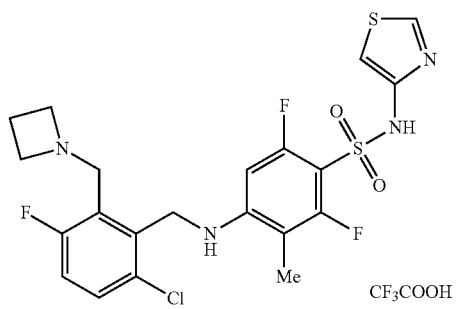 [SMILES: Cc1c(NCc2c(Cl)ccc(F)c2CN2CCC2)cc(F)c(S(=O)(=O)Nc2cscn2)c1F ; "CF3COOH"]

To a solution of tert-butyl ((4-((2-(azetidin-1-ylmethyl)-6-chloro-3-fluorobenzyl)amino)-2,6-difluoro-3-methylphenyl)sulfonyl)(thiazol-4-yl)carbamate (0.113 g, 0.183 mmol) in dichloromethane (4 mL) was added trifluoroacetic acid (2 mL), and the solution was stirred at ambient temperature for 3 h. Concentration in vacuo and trituration of the residue in diethyl ether (20 mL) provided the title compound as a pale solid (0.093 g, 80% yield): $^1$H NMR (300 MHz, DMSO-d$_6$) δ 11.27 (s, 1H), 10.01 (br s, 1H), 8.90 (d, J=2.2 Hz, 1H), 7.70 (dd, J=9.1, 5.4 Hz, 1H), 7.48-7.42 (m, 1H), 6.92 (d, J=2.1 Hz, 1H), 6.48 (d, J=13.6 Hz, 1H), 6.31-6.24 (m, 1H), 4.54-4.44 (m, 4H), 4.23-3.97 (m, 4H), 2.41-2.15 (m, 2H), 1.89 (d, J=1.1 Hz, 3H); MS (ES+) m/z 517.2 (M+1), 519.2 (M+1).

Example 314

Synthesis of 4-((2-((3,3-dimethylazetidin-1-yl)methyl)-6-fluorobenzyl)amino)-2,3-difluoro-6-methyl-N-(thiazol-4-yl)benzenesulfonamide 2,2,2-trifluoroacetate

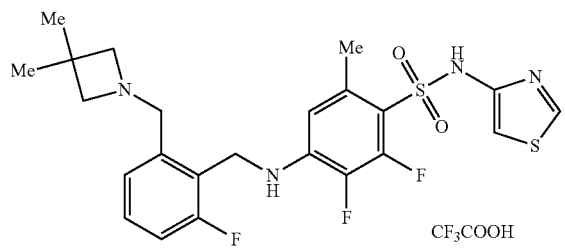 [SMILES: Cc1cc(NCc2c(F)cccc2CN2CC(C)(C)C2)c(F)c(F)c1S(=O)(=O)Nc1cscn1 ; "CF3COOH"]

Step 1. Preparation of 2-((3,3-dimethylazetidin-1-yl)methyl)-6-fluorobenzonitrile

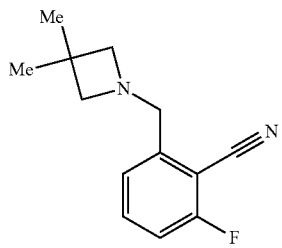 [SMILES: CC1(C)CN(Cc2cccc(F)c2C#N)C1]

A mixture of 2-cyano-3-fluorobenzyl bromide (0.500 g, 2.34 mmol), 3,3-dimethylazetidine hydrochloride (0.305 g, 2.51 mmol), and N,N-diisopropylethylamine (0.52 mL, 3.0 mmol) in dichloromethane (16 mL) was stirred at ambient temperature for 4 h. To it was then added more N,N-diisopropylethylamine (0.52 mL, 2.99 mmol) and the reaction mixture was stirred at ambient temperature for 16 h. The reaction mixture was washed with saturated ammonium chloride (10 mL). The aqueous layer was extracted with dichloromethane (2×10 mL), and the combined organic layers were washed with brine (10 mL), dried over anhydrous magnesium sulfate, and filtered. Concentration of the filtrate in vacuo and purification of the residue by column chromatography, eluting with a gradient of 0 to 30% of ethyl acetate (containing 10% of isopropanol and 10% of triethylamine) in hexanes, afforded the title compound as an orange oil (0.390 g, 76% yield): MS (ES+) m/z 219.4 (M+1).

Step 2. Preparation of (2-((3,3-dimethylazetidin-1-yl)methyl)-6-fluorophenyl)-methanamine

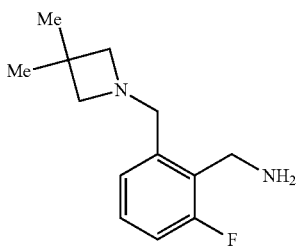 [SMILES: CC1(C)CN(Cc2cccc(F)c2CN)C1]

To a mixture of 2-((3,3-dimethylazetidin-1-yl)methyl)-6-fluorobenzonitrile (0.390 g, 1.79 mmol) in anhydrous tetrahydrofuran (12 mL) was added a 1.0 M solution of lithium aluminum hydride in tetrahydrofuran (2.7 mL, 2.7 mmol) at 0° C., and the mixture was allowed to warm to ambient temperature over 2 h. To it was then added sodium sulfate decahydrate (4.0 g, 12 mmol), and the mixture was stirred at ambient temperature for 16 h. The mixture was filtered, and the filtrate was dried over anhydrous magnesium sulfate. Filtration and concentration of the filtrate in vacuo afforded the title compound as a yellow oil (0.378 g, 95% yield) which was used without further purification: $^1$H NMR (300 MHz, DMSO-d$_6$) δ 7.19 (td, J=7.8, 5.9 Hz, 1H), 7.09-7.01 (m, 2H), 3.69 (m, 2H), 3.63 (s, 2H), 2.86 (s, 4H), 1.87 (br s, 2H), 1.15 (s, 6H); MS (ES+) m/z 223.3 (M+1).

Step 3. Preparation of tert-butyl ((6-bromo-4-((2-((3,3-dimethylazetidin-1-yl)methyl)-6-fluorobenzyl)amino)-2,3-difluorophenyl)sulfonyl)(thiazol-4-yl)carbamate

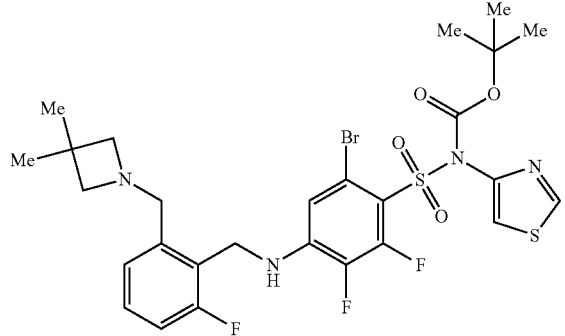 [SMILES: CC1(C)CN(Cc2cccc(F)c2CNc2cc(Br)c(S(=O)(=O)N(C(=O)OC(C)(C)C)c3cscn3)c(F)c2F)C1]

To a mixture of tert-butyl ((6-bromo-2,3,4-trifluorophenyl)sulfonyl)(thiazol-4-yl)carbamate (0.554 g, 1.17 mmol) and potassium carbonate (0.323 g, 2.34 mmol) in anhydrous dimethyl sulfoxide (4 mL) was added a solution of (2-((3,3-dimethylazetidin-1-yl)methyl)-6-fluorophenyl)methanamine (0.260 g, 1.17 mmol) in anhydrous dimethyl sulfoxide (2 mL) and the reaction mixture was stirred at ambient temperature for 2.5 h. The mixture was partitioned between ethyl acetate (50 mL) and ice-water (50 mL). The organic layer was washed with brine (5×15 mL), dried over anhydrous magnesium sulfate and filtered. Concentration of the filtrate in vacuo and purification of the residue by column chromatography, eluting with a gradient of 10 to 30% of ethyl acetate (containing 10% of isopropanol and 10% of triethylamine) in heptane, afforded the title compound as a yellow foam (0.371 g, 47% yield): $^1$H NMR (300 MHz, CDCl$_3$) δ 8.79 (d, J=2.3 Hz, 1H), 7.67 (br s, 1H), 7.54 (d, J=2.3 Hz, 1H), 7.28-7.21 (m, 1H), 7.11-7.03 (m, 3H), 4.45 (s, 2H), 3.65 (s, 2H), 3.02 (s, 4H), 1.38 (s, 9H), 1.24 (s, 6H); MS (ES+) m/z 675.3 (M+1), 677.3 (M+1).

Step 4. Preparation of tert-butyl ((4-((2-((3,3-dimethylazetidin-1-yl)methyl)-6-fluorobenzyl)amino)-2,3-difluoro-6-methylphenyl)sulfonyl)(thiazol-4-yl)carbamate

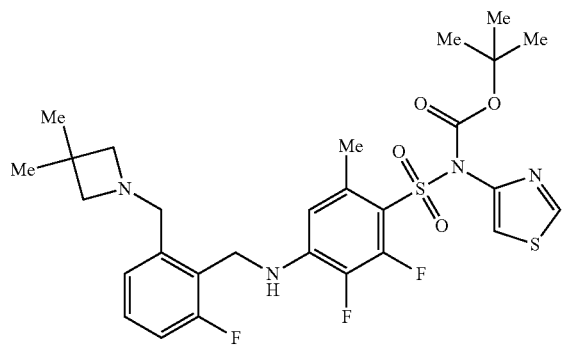 [SMILES: Cc1cc(NCc2c(F)cccc2CN2CC(C)(C)C2)c(F)c(F)c1S(=O)(=O)N(C(=O)OC(C)(C)C)c1cscn1]

Following the procedure as described in EXAMPLE 312, Step 2 and making non-critical variations as required to replace tert-butyl ((4-((2-(azetidin-1-ylmethyl)benzyl)amino)-6-bromo-2,3-difluorophenyl)sulfonyl)(thiazol-4-yl)carbamate with tert-butyl ((6-bromo-4-((2-((3,3-dimethylazetidin-1-yl)methyl)-6-fluorobenzyl)amino)-2,3-difluorophenyl)sulfonyl)(thiazol-4-yl)carbamate, the title compound was obtained as a yellow foam (0.209 g, 64% yield): $^1$H NMR (300 MHz, CDCl$_3$) δ 8.79 (d, J=2.3 Hz, 1H), 7.50 (dd, J=2.3, 0.9 Hz, 1H), 7.27-7.20 (m, 1H), 7.07-7.01 (m, 2H), 6.59-6.56 (m, 1H), 4.46 (s, 2H), 3.65 (s, 2H), 3.02 (s, 4H), 2.68 (s, 3H), 1.33 (s, 9H), 1.24 (s, 6H), NH not observed; MS (ES+) m/z 611.4 (M+1).

Step 5. Preparation of 4-((2-((3,3-dimethylazetidin-1-yl)methyl)-6-fluorobenzyl)amino)-2,3-difluoro-6-methyl-N-(thiazol-4-yl)benzenesulfonamide 2,2,2-trifluoroacetate

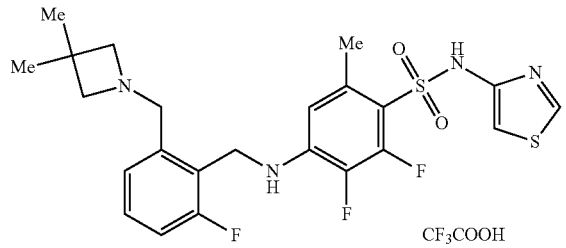 [SMILES: Cc1cc(NCc2c(F)cccc2CN2CC(C)(C)C2)c(F)c(F)c1S(=O)(=O)Nc1cscn1 ; "CF3COOH"]

To a solution of tert-butyl ((4-((2-((3,3-dimethylazetidin-1-yl)methyl)-6-fluorobenzyl)amino)-2,3-difluoro-6-methylphenyl)sulfonyl)(thiazol-4-yl)carbamate (0.193 g, 0.316 mmol) in dichloromethane (4 mL) was added trifluoroacetic acid (2 mL). The reaction mixture was stirred at ambient temperature for 1 h and then concentrated in vacuo. Purification of the residue by preparative reverse-phase HPLC, eluting with a gradient of 15 to 80% of acetonitrile in water containing 0.1% of trifluoroacetic acid, provided the title compound as a pale solid (0.038 g, 19% yield): $^1$H NMR (300 MHz, DMSO-$d_6$) δ 11.12 (s, 1H), 10.25-10.15 (m, 1H), 8.88 (d, J=2.2 Hz, 1H), 7.51-7.44 (m, 1H), 7.35-7.29 (m, 2H), 6.95-6.92 (m, 2H), 6.57 (d, J=8.1 Hz, 1H), 4.53-4.42 (m, 4H), 3.96-3.79 (m, 4H), 2.48 (s, 3H), 1.30 (s, 3H), 1.23 (m, 3H); $^{19}$F NMR (282 MHz, DMSO-$d_6$) δ −74.0 (s, 3F), −115.4 (s, 1F), −135.2 (d, J=21.7 Hz, 1F), −161.2 (d, J=21.7 Hz, 1F); MS (ES+) m/z 511.4 (M+1).

Example 315

Synthesis of 4-((2-(azetidin-1-ylmethyl)-6-fluorobenzyl)amino)-2-fluoro-N-(isoxazol-3-yl)-3-methylbenzenesulfonamide 2,2,2-trifluoroacetate

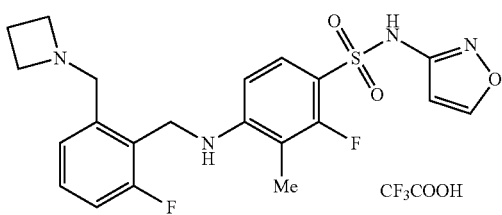 [SMILES: Cc1c(NCc2c(F)cccc2CN2CCC2)ccc(S(=O)(=O)Nc2ccon2)c1F ; "CF3COOH"]

Step 1. Preparation of tert-butyl (2-(azetidin-1-ylmethyl)-6-fluorobenzyl)(2-bromo-4-(N-(tert-butoxycarbonyl)-N-(isoxazol-3-yl)sulfamoyl)-3-fluorophenyl)carbamate

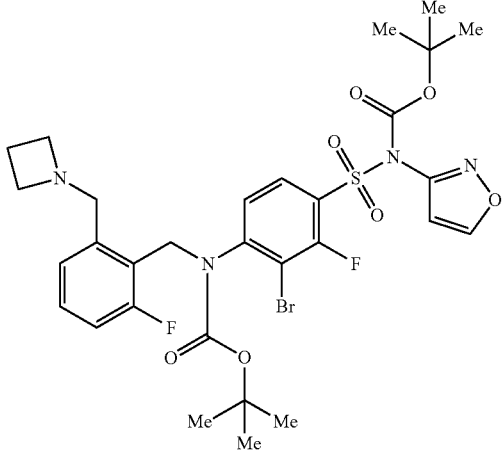 [SMILES: CC(C)(C)OC(=O)N(Cc1c(F)cccc1CN1CCC1)c1ccc(S(=O)(=O)N(C(=O)OC(C)(C)C)c2ccon2)c(F)c1Br]

To a mixture of tert-butyl (2-(azetidin-1-ylmethyl)-6-fluorobenzyl)carbamate (0.336 g, 1.14 mmol) in anhydrous N,N-dimethylformamide (5.5 mL) was added a 60% dispersion of sodium hydride in mineral oil (0.069 g, 1.7 mmol) at 0° C. The mixture was stirred at 0° C. for 30 minutes and then added dropwise to a solution of tert-butyl ((3-bromo-2,4-difluorophenyl)sulfonyl)(isoxazol-3-yl)carbamate (0.502 g, 1.14 mmol) in anhydrous N,N-dimethylformamide (11 mL) at 0° C. The mixture was stirred at 0° C. for 4 h and then diluted with ethyl acetate (100 mL). The organic phase was washed with a 5:1 mixture of water and brine (5×50 mL), brine (15 mL), and dried over anhydrous magnesium sulfate. Filtration and concentration of the filtrate in vacuo provided a residue. Purification of the residue by column chromatography, eluting with a gradient of 0 to 30% of ethyl acetate (containing 10% of isopropanol and 10% of triethylamine) in heptane, afforded the title compound as a pale foam (0.113 g, 14% yield): MS (ES) m/z 713.4 (M+1), 715.4 (M+1).

Step 2. Preparation of 4-((2-(azetidin-1-ylmethyl)-6-fluorobenzyl)amino)-2-fluoro-N-(isoxazol-3-yl)-3-methylbenzenesulfonamide 2,2,2-trifluoroacetate

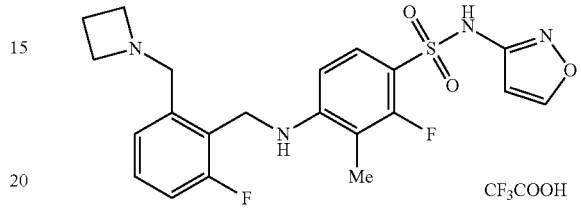

To a mixture of tert-butyl (2-(azetidin-1-ylmethyl)-6-fluorobenzyl)(2-bromo-4-(N-(tert-butoxycarbonyl)-N-(isoxazol-3-yl)sulfamoyl)-3-fluorophenyl)carbamate (0.199 g, 0.279 mmol), methylboronic acid (0.100 g, 1.67 mmol), tetrakis(triphenylphosphine)palladium(0) (0.032 g, 0.028 mmol) in anhydrous 1,4-dioxane (6 mL) was added potassium phosphate tribasic (0.178 g, 0.839 mmol). The mixture was degassed and then heated to 100° C. for 21 h. The mixture was allowed to cool to ambient temperature and partitioned between ethyl acetate (30 mL) and water (10 mL). The mixture was filtered through a pad of Celite, and the organic phase of the filtrate was washed with brine (2×10 mL), dried over anhydrous magnesium sulfate and filtered. Concentration of the filtrate in vacuo afforded a brown foam (0.224 g). To a solution of this residue in dichloromethane (4 mL) was added trifluoroacetic acid (4 mL). The reaction mixture was stirred at ambient temperature for 3 h and then concentrated in vacuo. Purification by preparative reverse-phase HPLC, eluting with a gradient of 15 to 50% of acetonitrile in water containing 0.1% of trifluoroacetic acid, provided the title compound as a yellow solid (0.042 g, 27% yield over 2 steps): $^1$H NMR (300 MHz, DMSO-$d_6$) δ 11.51 (s, 1H), 10.25 (br s, 1H), 8.67 (d, J=1.8 Hz, 1H), 7.59-7.44 (m, 2H), 7.35-7.29 (m, 2H), 6.57 (d, J=8.8 Hz, 1H), 6.36-6.32 (m, 2H), 4.54-4.45 (m, 4H), 4.14-4.03 (m, 4H), 2.45-2.25 (m, 2H), 1.98 (s, 3H); $^{19}$F NMR (282 MHz, DMSO-$d_6$) δ −74.04 (s, 3F), −113.94 (s, 1F), −115.28 (s, 1F); MS (ES+) m/z 449.0 (M+1).

Example 316

Synthesis of (S)-5-chloro-2-fluoro-4-((1-(2-fluorophenyl)propyl)amino)-N-(6-fluoropyridin-2-yl)benzenesulfonamide

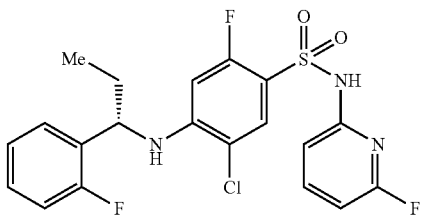 [SMILES: CC[C@H](Nc1cc(F)c(S(=O)(=O)Nc2cccc(F)n2)cc1Cl)c1ccccc1F]

Step 1. Preparation of (S)-5-chloro-N-(2,4-dimethoxybenzyl)-2-fluoro-4-((1-(2-fluorophenyl)propyl)amino)-N-(6-fluoropyridin-2-yl)benzenesulfonamide

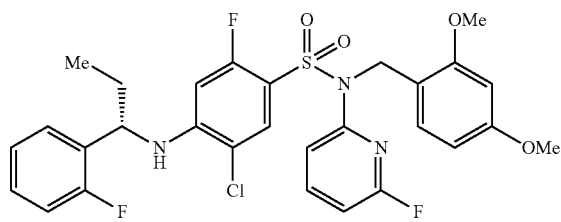 [SMILES: CC[C@H](Nc1cc(F)c(S(=O)(=O)N(Cc2ccc(OC)cc2OC)c2cccc(F)n2)cc1Cl)c1ccccc1F]

A mixture of 5-chloro-N-(2,4-dimethoxybenzyl)-2,4-difluoro-N-(6-fluoropyridin-2-yl)benzenesulfonamide (0.500 g, 1.06 mmol), (S)-1-(2-fluorophenyl)propan-1-amine hydrochloride (0.200 g, 1.06 mmol) and potassium carbonate (0.497 g, 3.60 mmol) in anhydrous dimethyl sulfoxide (5 mL) was stirred at 75° C. for 18 hours. The mixture was diluted with ethyl acetate (10 mL) and water (10 mL). The layers were separated and the aqueous phase was extracted with ethyl acetate (3×10 mL). The combined organic phases were washed with brine (5 mL), dried over anhydrous sodium sulfate, and filtered. Concentration of the filtrate in vacuo and purification of the residue by column chromatography, eluting with a gradient of 5 to 70% of ethyl acetate in hexanes, afforded the title compound as a colorless oil (0.519 g, 81% yield): MS (ES+) m/z 606.0 (M+1), 608.0 (M+1).

Step 2. Preparation of (S)-5-chloro-2-fluoro-4-((1-(2-fluorophenyl)propyl)amino)-N-(6-fluoropyridin-2-yl)benzenesulfonamide

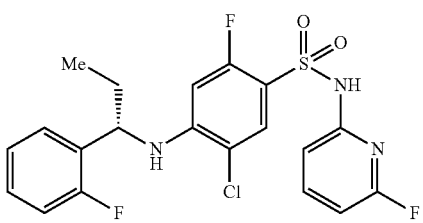 [SMILES: CC[C@H](Nc1cc(F)c(S(=O)(=O)Nc2cccc(F)n2)cc1Cl)c1ccccc1F]

Following the procedure as described for EXAMPLE 222, Step 1 and making non-critical variations as required to replace tert-butyl (S)-((5-chloro-4-((1-(2-chlorophenyl)propyl)amino)-2-fluorophenyl)sulfonyl)(thiazol-4-yl)carbamate with (S)-5-chloro-N-(2,4-dimethoxybenzyl)-2-fluoro-4-((1-(2-fluorophenyl)propyl)amino)-N-(6-fluoropyridin-2-yl)benzenesulfonamide, the title compound was obtained as a colorless solid (0.135 g, 35% yield): $^1$H-NMR (300 MHz, DMSO-$d_6$) δ 11.50 (s, 1H), 7.82 (q, J=8.2 Hz, 1H), 7.75 (d, J=7.5 Hz, 1H), 7.46 (td, J=7.8, 1.7 Hz, 1H), 7.32-7.25 (m, 1H), 7.21-7.18 (m, 1H), 7.16-7.13 (m, 1H), 6.84 (dd, J=7.9, 2.1 Hz, 1H), 6.70 (dd, J=8.0, 2.4 Hz, 2H), 6.37 (d, J=13.4 Hz, 1H), 4.72-4.64 (m, 1H), 2.09-2.00 (m, 1H), 1.87-1.78 (m, 1H), 0.89 (t, J=7.3 Hz, 3H); MS (ES+) m/z 455.9 (M+1), 457.9 (M+1).

Example 317

Synthesis of 2,6-difluoro-4-((2-fluoro-6-(2-methylpyridin-4-yl)benzyl)amino)-N-(thiazol-4-yl)benzenesulfonamide formate

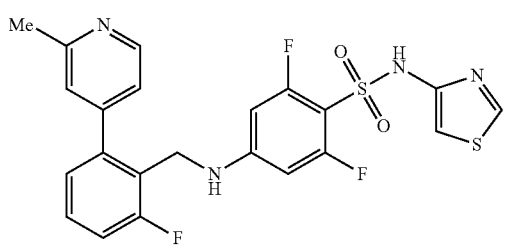 [SMILES: Cc1cc(-c2cccc(F)c2CNc2cc(F)c(S(=O)(=O)Nc3cscn3)c(F)c2)ccn1]

Step 1. Preparation of tert-butyl ((4-((tert-butoxycarbonyl)(2-fluoro-6-(2-methylpyridin-4-yl)benzyl)amino)-2,6-difluorophenyl)sulfonyl)(thiazol-4-yl)carbamate

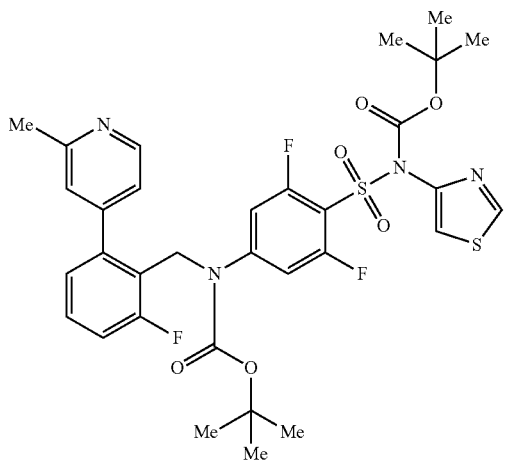 [SMILES: Cc1cc(-c2cccc(F)c2CN(C(=O)OC(C)(C)C)c2cc(F)c(S(=O)(=O)N(C(=O)OC(C)(C)C)c3cscn3)c(F)c2)ccn1]

A mixture of tert-butyl((4-((2-bromo-6-fluorobenzyl)(tert-butoxycarbonyl)amino)-2,6-difluorophenyl)sulfonyl)(thiazol-4-yl)carbamate (0.20 g, 0.29 mmol), (2-methyl-4-pyridyl)boronic acid (0.048 g, 0.35 mmol), sodium carbonate (0.062 g, 0.59 mmol) and [1,1'-bis(diphenylphosphino)ferrocene]dichloropalladium(II) (0.043 g, 0.058 mmol) in anhydrous 1,4-dioxane (5 mL) and water (1.2 mL) was degassed and then heated to 90° C. for 2 h. Water (10 mL) was added, and the resulting mixture was extracted with ethyl acetate (3×20 mL). The combined organic extracts were washed with brine (3×20 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a yellow solid (0.10 g, 49% yield): MS (ES+) m/z 691.4 (M+1).

Step 2. Preparation of 2,6-difluoro-4-((2-fluoro-6-(2-methylpyridin-4-yl)benzyl)amino)-N-(thiazol-4-yl)benzenesulfonamide formate

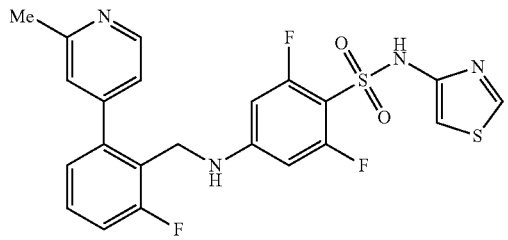 [SMILES: Cc1cc(-c2cccc(F)c2CNc2cc(F)c(S(=O)(=O)Nc3cscn3)c(F)c2)ccn1]

To a solution of tert-butyl ((4-((tert-butoxycarbonyl)(2-fluoro-6-(2-methylpyridin-4-yl)benzyl)amino)-2,6-difluorophenyl)sulfonyl)(thiazol-4-yl)carbamate (0.10 g, 0.15 mmol) in dichloromethane (2 mL) was added trifluoroacetic acid (1.50 g, 13.50 mmol) and the mixture was stirred at ambient temperature for 12 h. The reaction mixture was concentrated in vacuo and the residue was purified by preparative reverse-phase HPLC, eluting with a gradient of acetonitrile in water containing 0.225% formic acid, to afford the title compound as a colorless solid (0.057 g, 72% yield): $^1$H NMR (400 MHz, CD$_3$OD) δ 8.75 (d, J=2.2 Hz, 1H), 8.42 (d, J=5.2 Hz, 1H), 8.25 (br s, 1H), 7.48 (dt, J=8.0, 5.6 Hz, 1H), 7.31-7.24 (m, 2H), 7.24-7.21 (m, 1H), 7.17 (d, J=7.6 Hz, 1H), 6.96 (d, J=2.2 Hz, 1H), 6.07-6.00 (m, 2H), 4.20 (s, 2H), 2.47 (s, 3H), NH not observed; MS (ES+) m/z 491.3 (M+1).

Example 318

Synthesis of 4-((2-(azetidin-1-ylmethyl)-6-fluorobenzyl)amino)-2,6-difluoro-N-(isothiazol-4-yl)benzenesulfonamide

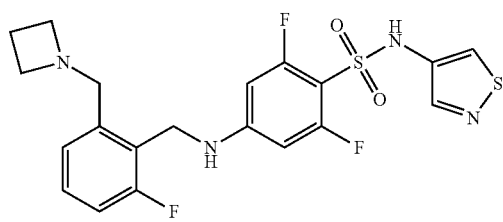 [SMILES: O=S(=O)(Nc1cnsc1)c1c(F)cc(NCc2c(F)cccc2CN2CCC2)cc1F]

Step 1. Preparation of 2,4,6-trifluoro-N-(isothiazol-4-yl)benzenesulfonamide

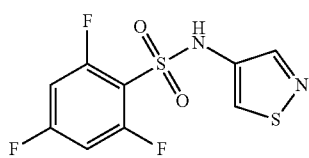 [SMILES: O=S(=O)(Nc1cnsc1)c1c(F)cc(F)cc1F]

To a solution of isothiazol-4-amine (0.40 g, 4.00 mmol) in dichloromethane (2 mL) was added pyridine (0.63 g, 8.00 mmol), and 4,4-dimethylaminopyridine (0.049 g, 0.40 mmol). To it was then added a solution of 2,4,6-trifluorobenzene-1-sulfonyl chloride (1.11 g, 4.80 mmol) in dichloromethane (1 mL), and the mixture was stirred at ambient temperature for 12 h. The mixture was concentrated in vacuo, and the residue was purified by preparative reverse phase HPLC, eluting with a gradient of acetonitrile in water (containing 0.225% formic acid), to afford the title compound as a colorless solid (0.70 g, 59% yield): $^1$H NMR (400 MHz, CD$_3$OD) δ 8.44 (s, 1H), 8.32 (s, 1H), 7.12-7.01 (m, 2H), NH not observed; MS (ES+) m/z 295.1 (M+1).

Step 2. Preparation of 2,4,6-trifluoro-N-(isothiazol-4-yl)-N-((2-(trimethylsilyl)ethoxy)methyl)-benzenesulfonamide

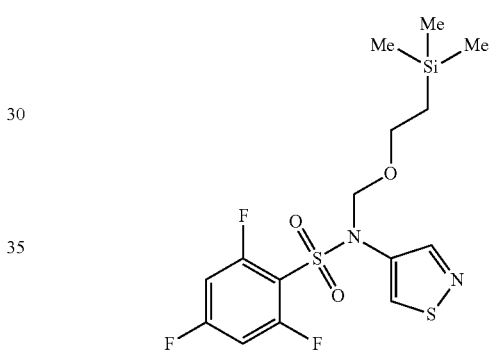

To a mixture of 2,4,6-trifluoro-N-(isothiazol-4-yl)benzenesulfonamide (0.60 g, 2.00 mmol) in anhydrous N,N-dimethylformamide (3 mL) was added potassium carbonate (0.84 g, 6.10 mmol) and the mixture was stirred at ambient temperature for 30 minutes. The mixture was then cooled to 0° C., and 2-(trimethylsilyl)ethoxymethyl chloride (0.68 g, 4.08 mmol) was added to it. The reaction mixture was allowed to warm to ambient temperature and stirred for 12 h. The reaction mixture was diluted with saturated ammonium chloride (20 mL) and extracted with ethyl acetate (3×20 15 mL). The combined organic extracts were washed with brine (3×20 mL), dried over anhydrous sodium sulfate, and filtered. The filtrate was concentrated in vacuo and the residue purified by column chromatography, eluting with a gradient of 10 to 50% of ethyl acetate/petroleum ether, to afford the title compound as yellow oil (0.60 g, 69% yield): $^1$H NMR (400 MHz, CDCl$_3$) δ 8.59 (s, 1H), 8.46 (s, 1H), 6.80-6.71 (m, 2H), 5.15 (s, 2H), 3.70-3.61 (m, 2H), 0.98-0.86 (m, 2H), 0.01 (s, 9H).

Step 3. Preparation of 4-((2-(azetidin-1-ylmethyl)-6-fluorobenzyl)amino)-2,6-difluoro-N-(isothiazol-4-yl)-N-((2-(trimethylsilyl)ethoxy)methyl)benzenesulfonamide

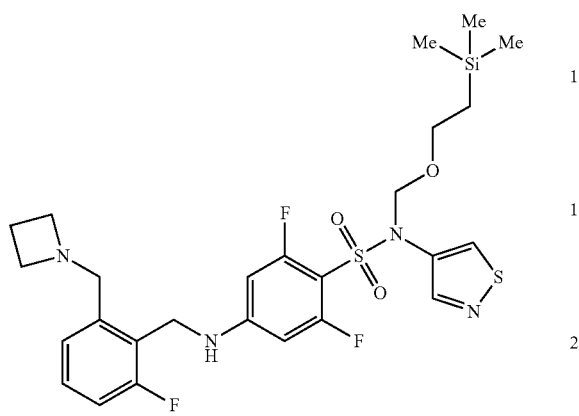

To a solution of 2,4,6-trifluoro-N-(isothiazol-4-yl)-N-((2-trimethylsilyl) ethoxy)methyl)benzenesulfonamide (0.30 g, 0.71 mmol) in anhydrous N,N-dimethylformamide (2 mL) was added (2-(azetidin-1-ylmethyl)-6-fluorophenyl)methanamine (0.14 g, 0.71 mmol) and potassium carbonate (0.20 g, 1.41 mmol), and the mixture was heated to 40° C. for 5 h. After cooling to ambient temperature, the reaction mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography eluting, with a gradient of 10 to 50% of petroleum ether in ethyl acetate, afforded the title compound as yellow oil (0.20 g, 47% yield): MS (ES+) m/z 599.4 (M+1).

Step 4. Preparation of 4-((2-(azetidin-1-ylmethyl)-6-fluorobenzyl)amino)-2,6-difluoro-N-(isothiazol-4-yl)benzenesulfonamide

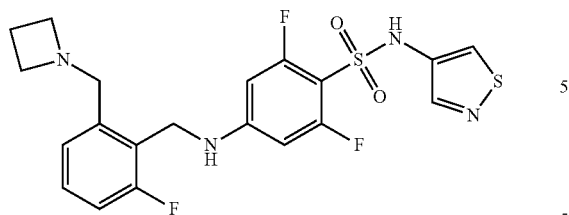

To 4-((2-(azetidin-1-ylmethyl)-6-fluorobenzyl)amino)-2,6-difluoro-N-(isothiazol-4-yl)-N-((2-(trimethylsilyl)ethoxy)methyl)benzenesulfonamide (0.20 g, 0.33 mmol) was added a 4 M solution of hydrogen chloride in 1,4-dioxane (2.00 mL, 8.00 mmol) and the reaction mixture was stirred at ambient temperature for 30 minutes. The mixture was adjusted to pH 7 with triethylamine, and the mixture was then concentrated in vacuo. The residue was purified by preparative reverse-phase HPLC, eluting with a gradient of acetonitrile in water containing 0.225% formic acid, to afford the title compound as a colorless solid (0.044 g, 27% yield): $^1$H NMR (400 MHz, CD$_3$OD) δ 8.40 (s, 1H), 8.32 (s, 1H), 7.28-7.24 (m, 1H), 7.12-7.04 (m, 2H), 6.21 (d, J=12.2 Hz, 2H), 4.35 (s, 2H), 3.68 (s, 2H), 3.32 (t, J=7.2 Hz, 4H), 2.18 (quin, J=7.1 Hz, 3H), NH not observed; MS (ES+) m/z 469.3 (M+1)

Example 319

Synthesis of 4-((2-(2-(3,3-difluoroazetidin-1-yl)ethyl)benzyl)amino)-2,6-difluoro-N-(thiazol-4-yl)benzenesulfonamide

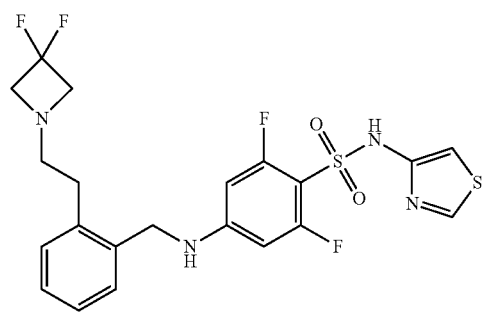 [SMILES: O=S(=O)(Nc1cscn1)c1c(F)cc(NCc2ccccc2CCN2CC(F)(F)C2)cc1F]

Step 1. Preparation of 2-(2-(3,3-difluoroazetidin-1-yl)ethyl)benzonitrile

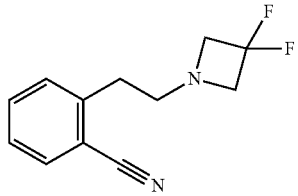 [SMILES: N#Cc1ccccc1CCN1CC(F)(F)C1]

Following the procedure as described for EXAMPLE EXAMPLE 261, Step 3 and making non-critical variations as required to replace azetidine hydrochloride with 3,3-difluoroazetidine, the title compound was obtained as a yellow oil (0.25 g, 36% yield): $^1$H NMR (400 MHz, CDCl$_3$) δ 7.65 (d, J=7.6 Hz, 1H), 7.58-7.52 (m, 1H), 7.39-7.32 (m, 2H), 3.63 (t, J=12.0 Hz, 4H), 2.97-2.85 (m, 4H); MS (ES+) m/z 223.0 (M+1).

Step 2. Preparation of (2-(2-(3,3-difluoroazetidin-1-yl)ethyl)phenyl)methanamine

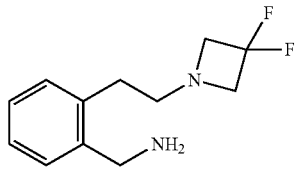 [SMILES: NCc1ccccc1CCN1CC(F)(F)C1]

Following the procedure as described for EXAMPLE EXAMPLE 261, Step 4 and making non-critical variations as required to replace 2-(2-(azetidin-1-yl)ethyl)benzonitrile with 2-(2-(3,3-difluoroazetidin-1-yl)ethyl)benzonitrile, the title compound was obtained as a yellow oil (0.21 g, 83% yield): ¹H NMR (400 MHz, CDCl₃) δ 7.29-7.23 (m, 1H), 7.17-7.06 (m, 3H), 3.82 (s, 2H), 3.49 (t, J=12.0 Hz, 4H), 2.78-2.66 (m, 4H), NH not observed.

Step 3. Preparation of tert-butyl ((4-((2-(2-(3,3-difluoroazetidin-1-yl)ethyl)benzyl)amino)-2,6-difluorophenyl)sulfonyl)(thiazol-4-yl)carbamate

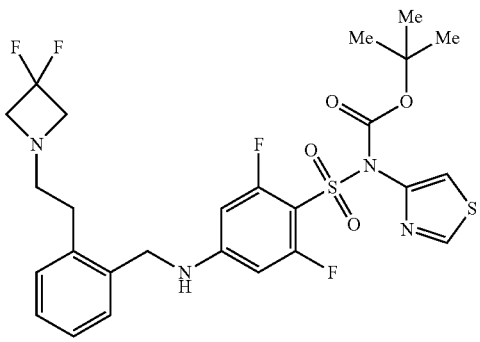 [SMILES: CC(C)(C)OC(=O)N(c1cscn1)S(=O)(=O)c1c(F)cc(NCc2ccccc2CCN2CC(F)(F)C2)cc1F]

Following the procedure as described for EXAMPLE EXAMPLE 261, Step 5 and making non-critical variations as required to replace (2-(2-(azetidin-1-yl) ethyl) phenyl) methanamine with (2-(2-(3,3-difluoroazetidin-1-yl)ethyl) phenyl)methanamine, the title compound was obtained as a colorless oil (0.23 g, 43% yield): ¹H NMR (400 MHz, CDCl₃) δ 8.80 (d, J=2.4 Hz, 1H), 7.51 (d, J=2.4 Hz, 1H), 7.38-7.29 (m, 2H), 7.28-7.23 (m, 2H), 6.53 (br s, 1H), 6.24-6.17 (m, 2H), 4.29 (s, 2H), 3.42 (t, J=12.0 Hz, 4H), 3.01-2.92 (m, 2H), 2.87-2.80 (m, 2H), 1.42 (s, 9H); MS (ES+) m/z 601.3 (M+1).

Step 4. Preparation of 4-((2-(2-(3,3-difluoroazetidin-1-yl)ethyl)benzyl)amino)-2,6-difluoro-N-(thiazol-4-yl)benzenesulfonamide

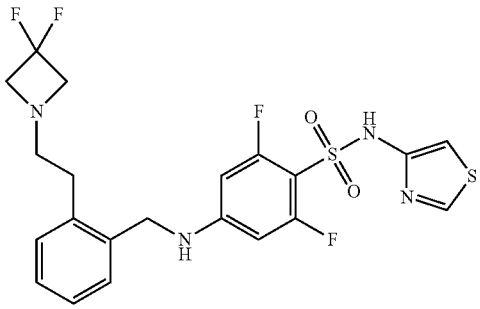 [SMILES: O=S(=O)(Nc1cscn1)c1c(F)cc(NCc2ccccc2CCN2CC(F)(F)C2)cc1F]

Following the procedure as described for EXAMPLE EXAMPLE 261, Step 6 and making non-critical variations as required to replace tert-butyl(4-((2-(2-(azetidin-1-yl) ethyl)benzyl)amino)-5-chloro-2-fluorophenyl)sulfonyl(thiazol-4-yl)carbamate with tert-butyl ((4-((2-(2-(3,3-difluoroazetidin-1-yl)ethyl)benzyl)amino)-2,6-difluorophenyl) sulfonyl)(thiazol-4-yl)carbamate, the title compound was obtained as a colorless solid (0.0235 g, 14% yield): ¹H NMR (400 MHz, CDCl₃) δ 8.71 (d, J=2.0 Hz, 1H), 7.35-7.30 (m, 1H), 7.28-7.21 (m, 3H), 7.05 (d, J=2.0 Hz, 1H), 6.39-6.29 (m, 1H), 6.11 (d, J=11.6 Hz, 2H), 4.21 (d, J=4.4 Hz, 2H), 3.37 (t, J=12.0 Hz, 4H), 2.97-2.89 (m, 2H), 2.83-2.75 (m, 2H), NH not observed; MS (ES+) m/z 501.3 (M+1).

Example 320

Synthesis of 4-((2-(2-(3-fluoroazetidin-1-yl)ethyl) benzyl)amino)-2,6-difluoro-N-(thiazol-4-yl)benzenesulfonamide formate

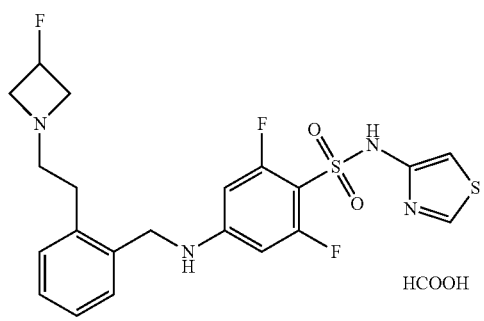 [SMILES: O=S(=O)(Nc1cscn1)c1c(F)cc(NCc2ccccc2CCN2CC(F)C2)cc1F ; "HCOOH"]

Step 1. Preparation of 2-(2-(3-fluoroazetidin-1-yl) ethyl)phenyl)methanamine

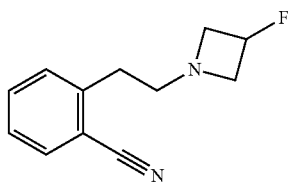 [SMILES: N#Cc1ccccc1CCN1CC(F)C1]

Following the procedure as described for EXAMPLE 261, Step 3 and making non-critical variations as required to replace azetidine hydrochloride with 3-fluoroazetidine, the title compound was obtained as a yellow oil (0.20 g, 35%): ¹H NMR (400 MHz, CDCl₃) δ 7.64 (d, J=7.6 Hz, 1H), 7.54 (td, J=7.6, 1.2 Hz, 1H), 7.39-7.31 (m, 2H), 5.25-5.01 (m, 1H), 3.79-3.65 (m, 2H), 3.28-3.13 (m, 2H), 2.94-2.87 (m, 2H), 2.86-2.79 (m, 2H); MS (ES+) m/z 205.3 (M+1)

Step 2. Preparation of 2-(2-(3-fluoroazetidin-1-yl) ethyl)phenyl)methanamine

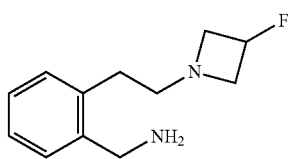 [SMILES: NCc1ccccc1CCN1CC(F)C1]

Following the procedure as described for EXAMPLE 261, Step 4 and making non-critical variations as required to replace 2-(2-azetidin-1-yl)ethyl)phenyl)-methanamine with 2-(2-(3-fluoroazetidin-1-yl)ethyl)phenyl)methanamine, the title compound was obtained as a yellow oil (0.12 g, 59%): ¹H NMR (400 MHz, CDCl₃) δ 7.37-7.32 (m, 1H), 7.26-7.17

(m, 3H), 5.24-5.03 (m, 1H), 3.91 (br s, 2H), 3.78-3.64 (m, 2H), 3.23-3.16 (m, 1H), 3.15-3.10 (m, 1H), 2.75 (s, 4H), NH not observed.

Step 3. Preparation of tert-butyl ((4-((2-(2-(3-fluoroazetidin-1-yl)ethyl)benzyl)amino)-2,6-difluorophenyl)sulfonyl)(thiazol-4-yl)carbamate

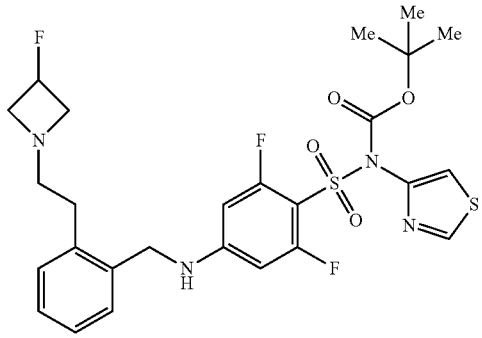 [SMILES: CC(C)(C)OC(=O)N(c1cscn1)S(=O)(=O)c1c(F)cc(NCc2ccccc2CCN2CC(F)C2)cc1F]

Following the procedure as described for EXAMPLE 261, Step 5 and making non-critical variations as required to replace (2-(2-(azetidin-1-yl) ethyl) phenyl)methanamine with (2-(2-(3-fluoroazetidin-1-yl)ethyl)phenyl)methanamine, the title compound was obtained as a colorless oil (0.080 g, 19% yield): $^1$H NMR (400 MHz, CDCl$_3$) δ 8.72 (d, J=2.2 Hz, 1H), 7.43 (d, J=2.0 Hz, 1H), 7.27-7.21 (m, 2H), 7.18-7.13 (m, 2H), 6.87 (br s, 1H), 6.12 (d, J=11.6 Hz, 2H), 5.07-4.83 (m, 1H), 4.19 (d, J=4.4 Hz, 2H), 3.36-3.24 (m, 2H), 3.05-2.93 (m, 2H), 2.81-2.77 (m, 2H), 2.73-2.68 (m, 2H), 1.34 (s, 9H); MS (ES+) m/z 583.4 (M+1).

Step 2. Preparation of 4-((2-(2-(3-fluoroazetidin-1-yl)ethyl)benzyl)amino)-2,6-difluoro-N-(thiazol-4-yl)benzenesulfonamide formate

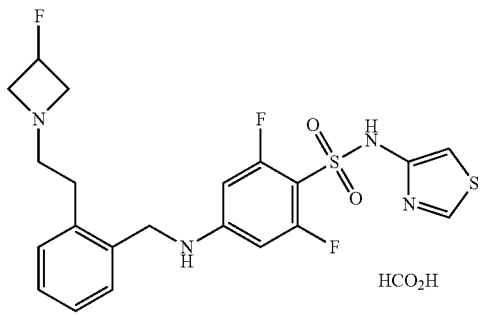 [SMILES: O=S(=O)(Nc1cscn1)c1c(F)cc(NCc2ccccc2CCN2CC(F)C2)cc1F ; "HCO2H"]

Following the procedure as described for EXAMPLE 261, Step 6 and making non-critical variations as required to replace tert-butyl(4-((2-(2-(azetidin-1-yl)ethyl)benzyl)amino)-5-chloro-2-fluorophenyl)sulfonyl(thiazol-4-yl)carbamate with tert-butyl ((4-((2-(2-(3-fluoroazetidin-1-yl)ethyl)benzyl)amino)-2,6-difluorophenyl)sulfonyl)(thiazol-4-yl)carbamate, the title compound was obtained as a colorless solid (0.0376 g, 51% yield): $^1$H NMR (400 MHz, CD$_3$OD) δ 8.75 (d, J=2.2 Hz, 1H), 8.39 (br s, 1H), 7.37-7.21 (m, 4H), 6.96 (d, J=2.2 Hz, 1H), 6.30-6.19 (m, 2H), 5.38-5.13 (m, 1H), 4.33 (s, 2H), 4.13-3.98 (m, 2H), 3.84-3.68 (m, 2H), 3.17-3.08 (m, 2H), 2.90-2.80 (m, 2H), NH and COOH not observed; MS (ES+) m/z 483.3 (M+1).

Example 321

Synthesis of 4-(((1R,3S)-3-(azetidin-1-yl)-2,3-dihydro-1H-inden-1-yl)amino)-5-chloro-2-fluoro-N-(thiazol-4-yl)benzenesulfonamide formate

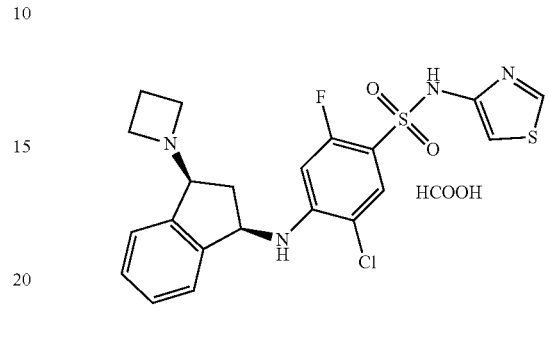

Step 1. Preparation of (R)-3-phenyl-3-(2,2,2-trifluoroacetamido)propanoic acid

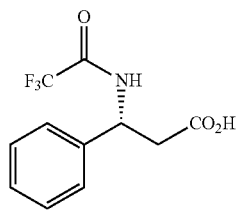 [SMILES: O=C(O)C[C@@H](NC(=O)C(F)(F)F)c1ccccc1]

Following the procedure as described for EXAMPLE 264, Step 1 and making non-critical variations as required to replace (S)-3-amino-3-phenylpropanoic acid with R)-3-amino-3-phenylpropanoic acid, the title compound was obtained as a colorless solid (7.40 g, crude): $^1$H NMR (400 MHz, DMSO-d$_6$) δ 13.31-11.70 (m, 1H), 9.96 (d, J=8.2 Hz, 1H), 7.43-7.33 (m, 5H), 5.29-5.19 (m, 1H), 2.96-2.86 (m, 1H), 2.84-2.74 (m, 1H); MS (ES+) m/z 262.1 (M+1).

Step 2. Preparation of (R)-3-phenyl-3-(2,2,2-trifluoroacetamido)propanoyl chloride

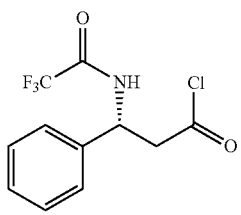 [SMILES: O=C(Cl)C[C@@H](NC(=O)C(F)(F)F)c1ccccc1]

Following the procedure as described for EXAMPLE 264, Step 2 and making non-critical variations as required to replace (R)-3-amino-3-phenylpropanoic acid with tert-butyl ((4-((2-(2-(3-fluoroazetidin-1-yl)ethyl)benzyl)amino)-2,6- difluorophenyl)sulfonyl)(thiazol-4-yl)carbamate, the title compound was obtained as a yellow solid (7.90 g, crude).

Step 3. Preparation of (R)-2,2,2-trifluoro-N-(3-oxo-2,3-dihydro-1H-inden-1-yl)acetamide

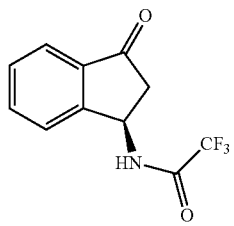 [SMILES: O=C1C[C@@H](NC(=O)C(F)(F)F)c2ccccc21]

Following the procedure as described for EXAMPLE 264, Step 3 and making non-critical variations as required to replace (S)-3-phenyl-3-(2,2,2-trifluoroacetamido)propanoyl chloride with (R)-3-phenyl-3-(2,2,2-trifluoroacetamido)propanoyl chloride, the title compound was obtained as a yellow solid (5.60 g, 82% yield): $^1$H NMR (400 MHz, CDCl$_3$) δ 7.77-7.70 (m, 2H), 7.64 (d, J=7.6 Hz, 1H), 7.54 (t, J=7.2 Hz, 1H), 7.05 (s, 1H), 5.73 (td, J=8.0, 3.2 Hz, 1H), 3.27 (dd, J=19.2, 7.6 Hz, 1H), 2.60 (dd, J=19.2, 3.2 Hz, 1H).

Step 4. Preparation of N-((1R,3S)-3-(azetidin-1-yl)-2,3-dihydro-1H-inden-1-yl)-2,2,2-trifluoroacetamide

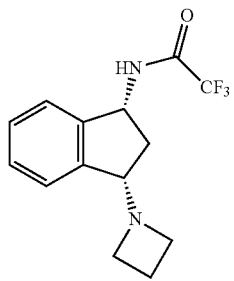 [SMILES: O=C(N[C@@H]1C[C@H](N2CCC2)c2ccccc21)C(F)(F)F]

To a solution of (R)-2,2,2-trifluoro-N-(3-oxo-2,3-dihydro-1H-inden-1-yl)acetamide (5.60 g, 23.03 mmol) and azetidine hydrochloride (4.31 g, 46.06 mmol) in anhydrous tetrahydrofuran (100 mL) was added titanium(iv) isopropoxide (26.18 g, 92.12 mmol) dropwise. The reaction mixture was stirred at 60° C. for 1 h. To it was then added sodium cyanoborohydride (5.79 g, 92.12 mmol), and the mixture was stirred at ambient temperature for 11 h. The mixture was diluted with dichloromethane (50 mL) and saturated ammonium chloride (50 mL). The mixture was filtered and the organic layer was washed with brine (100 mL), dried over anhydrous magnesium sulfate, and filtered. Concentration of the filtrate in vacuo and purification of the residue by preparative reverse phase HPLC, using acetonitrile in water containing 0.05% ammonium hydroxide as eluent, afforded the title compound as a colorless solid (1.00 g, 15% yield): $^1$H NMR (400 MHz, CDCl$_3$) δ 7.53-7.37 (m, 2H), 7.36-7.32 (m, 1H), 7.31-7.29 (m, 1H), 5.44 (br d, J=5.8 Hz, 1H), 4.21-4.03 (m, 1H), 3.74 (d, J=5.4 Hz, 1H), 3.40-3.36 (m, 2H), 3.21 (q, J=6.8 Hz, 2H), 2.45-2.36 (m, 1H), 2.06-2.02 (m, 2H), 1.87 (dd, J=1.2, 13.8 Hz, 1H); MS (ES+) m/z 285.2 (M+1).

Step 5. Preparation of (1R,3S)-3-(azetidin-1-yl)-2,3-dihydro-1H-inden-1-amine

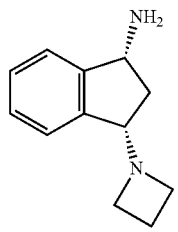 [SMILES: N[C@@H]1C[C@H](N2CCC2)c2ccccc21]

Following the procedure as described for EXAMPLE 264, Step 5 and making non-critical variations as required to replace N-((1S,3S)-3-(azetidin-1-yl)-2,3-dihydro-1H-inden-1-yl)-2,2,2-trifluoroacetamide with N-((1R,3S)-3-(azetidin-1-yl)-2,3-dihydro-1H-inden-1-yl)-2,2,2-trifluoroacetamide, the title compound was obtained as a yellow solid (0.200 g, 50% yield): MS (ES+) m/z 189.3 (M+1).

Step 6. Preparation of tert-butyl (4-(((1R,3S)-3-(azetidin-1-yl)-2,3-dihydro-1H-inden-1-yl)amino)-5-chloro-2-fluorophenyl)sulfonyl(thiazol-4-yl)carbamate

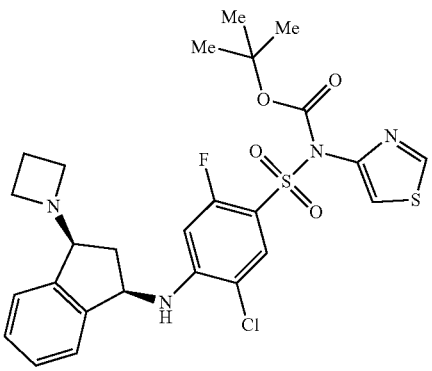 [SMILES: CC(C)(C)OC(=O)N(c1cscn1)S(=O)(=O)c1cc(Cl)c(N[C@@H]2C[C@H](N3CCC3)c3ccccc32)cc1F]

Following the procedure as described for EXAMPLE 264, Step 6 and making non-critical variations as required to replace (1S,3S)-3-(azetidin-1-yl)-2,3-dihydro-1H-inden-1-amine with (1R,3S)-3-(azetidin-1-yl)-2,3-dihydro-1H-inden-1-amine, the title compound was obtained as a yellow oil (0.120 g, 43% yield): MS (ES+) m/z 579.2 (M+1), 581.2 (M+1).

Step 7. Synthesis of 4-(((1R,3S)-3-(azetidin-1-yl)-2,3-dihydro-1H-inden-1-yl)amino)-5-chloro-2-fluoro-N-(thiazol-4-yl)benzenesulfonamide formate

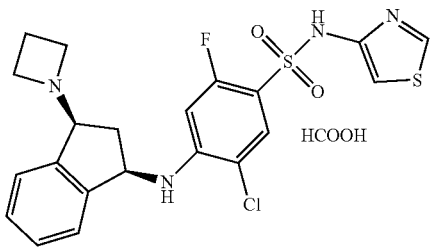 [SMILES: O=S(=O)(Nc1cscn1)c1cc(Cl)c(N[C@@H]2C[C@H](N3CCC3)c3ccccc32)cc1F ; "HCOOH"]

Following the procedure as described for EXAMPLE 264, Step 7 and making non-critical variations as required to replace tert-butyl (4-(((1S,3S)-3-(azetidin-1-yl)-2,3-dihydro-1H-inden-1-yl)amino)-5-chloro-2-fluorophenyl)sulfonyl(thiazol-4-yl)carbamate with (4-(((1R,3S)-3-(azetidin-1-yl)-2,3-dihydro-1H-inden-1-yl)amino)-5-chloro-2-fluorophenyl)sulfonyl(thiazol-4-yl)carbamate, the title compound was obtained as a colorless solid (0.022 g, 20% yield): $^1$H NMR (400 MHz, CDCl$_3$) δ 8.63 (d, J=2.2 Hz, 1H), 8.22 (s, 1H), 7.67 (d, J=7.2 Hz, 1H), 7.35-7.27 (m, 4H), 6.90 (d, J=2.2 Hz, 1H), 6.45 (d, J=12.4 Hz, 1H), 6.17 (br d, J=8.6 Hz, 1H), 4.84-4.78 (m, 1H), 4.20 (dd, J=4.4, 7.2 Hz, 1H), 3.72-3.60 (m, 4H), 2.75-2.66 (m, 1H), 2.24 (quin, J=7.6 Hz, 2H), 1.88 (td, J=13.8, 4.2 Hz, 1H), NH and COOH not observed; MS (ES+) m/z 479.2 (M+1), 481.2 (M+1).

Example 322

Synthesis of 4-((2-(azetidin-1-ylmethyl)-6-fluorobenzyl)amino)-2,6-difluoro-N-(6-fluoropyridin-2-yl)benzenesulfonamide formate

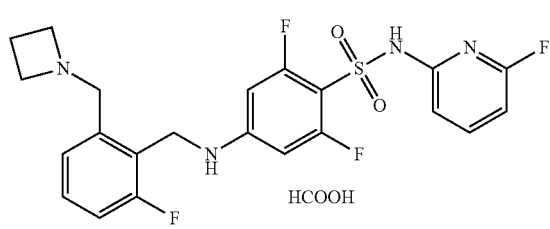 [SMILES: O=S(=O)(Nc1cccc(F)n1)c1c(F)cc(NCc2c(F)cccc2CN2CCC2)cc1F ; "HCOOH"]

Step 1. Synthesis of 4-((2-(azetidin-1-ylmethyl)-6-fluorobenzyl)amino)-N-(2,4-dimethoxybenzyl)-2,6-difluoro-N-(6-fluoropyridin-2-yl)benzenesulfonamide

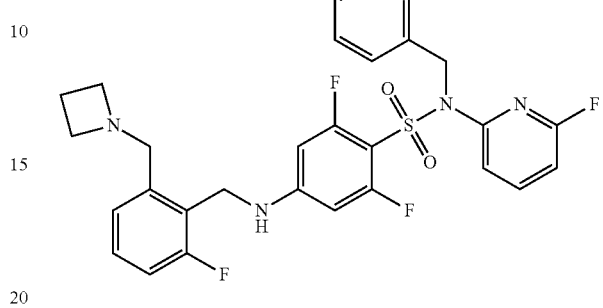

To a solution of N-(2,4-dimethoxybenzyl)-2,4,6-trifluoro-N-(6-fluoropyridin-2-yl)benzenesulfonamide (0.25 g, 0.55 mmol) and (2-(azetidin-1-ylmethyl)-6-fluorophenyl)methanamine (0.138 g, 0.712 mmol) in N,N-dimethylformamide (5 mL) was added potassium carbonate (0.151 g, 1.10 mmol). The mixture was stirred at ambient temperature for 12 h. The mixture was then diluted with water (50 mL) and extracted with ethyl acetate (3×50 mL). The combined organic extracts were washed with brine (20 mL), dried over anhydrous sodium sulfate, and filtered. Concentration in vacuo and purification of the residue by preparative thin layer chromatography, eluting with 33% of ethyl acetate in petroleum ether, to afford the title compound as a yellow solid (0.12 g, 35% yield): $^1$H NMR (400 MHz, CDCl$_3$) δ 7.67 (q, J=8.2 Hz, 1H), 7.37-7.30 (m, 2H), 7.24 (dd, J=7.6, 5.6 Hz, 1H), 7.10-7.03 (m, 2H), 6.62 (dd, J=8.0, 2.8 Hz, 1H), 6.43-6.37 (m, 2H), 6.19 (d, J=12.0 Hz, 2H), 5.16 (s, 2H), 4.34 (s, 2H), 3.77 (d, J=2.8 Hz, 6H), 3.61 (s, 2H), 3.23 (t, J=6.8 Hz, 4H), 2.13 (quin, J=7.2 Hz, 2H), NH not observed.

Step 2. Synthesis of 4-((2-(azetidin-1-ylmethyl)-6-fluorobenzyl)amino)-2,6-difluoro-N-(6-fluoropyridin-2-yl)benzenesulfonamide formate

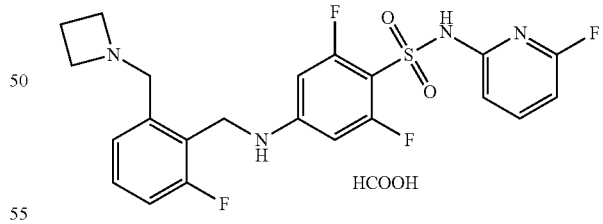

To 4-((2-(azetidin-1-ylmethyl)-6-fluorobenzyl)amino)-N-(2,4-dimethoxybenzyl)-2,6-difluoro-N-(6-fluoropyridin-2-yl)benzenesulfonamide (0.120 g, 0.190 mmol) was added a solution of 4 M hydrogen chloride in ethyl acetate (4 mL) and the mixture was stirred at ambient temperature for 1 h. The mixture was concentrated in vacuo and the residue was purified by preparative reverse phase HPLC, using acetonitrile in water containing 0.225% formic acid as eluent, to afford the title compound as a colorless solid (0.0307 g, 30% yield): $^1$H NMR (400 MHz, CDCl$_3$) δ 8.31 (s, 1H), 7.73 (q, J=8.0 Hz, 1H), 7.33-7.29 (m, 1H), 7.28-7.26 (m, 1H), 7.15-7.06 (m, 2H), 6.61 (dd, J=8.0, 2.4 Hz, 1H), 6.22 (d, J=12.0 Hz, 2H), 4.36 (s, 2H), 3.81 (s, 2H), 3.46 (br t, J=7.2 Hz, 4H), 2.24 (quin, J=7.2 Hz, 2H), NH and COOH not observed; MS (ES+) m/z 481.1 (M+1).

Example 323

Synthesis of 4-((2-(azetidin-1-ylmethyl)benzyl) amino)-2-fluoro-N-(thiazol-4-yl)-5-vinylbenzenesulfonamide formate

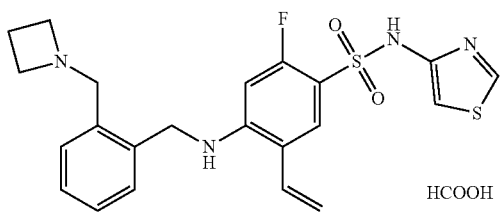 [SMILES: C=Cc1cc(S(=O)(=O)Nc2cscn2)c(F)cc1NCc1ccccc1CN1CCC1 ; "HCOOH"]

Step 1. Preparation of tert-butyl ((5-bromo-2,4-difluorophenyl)sulfonyl)(thiazol-4-yl)carbamate

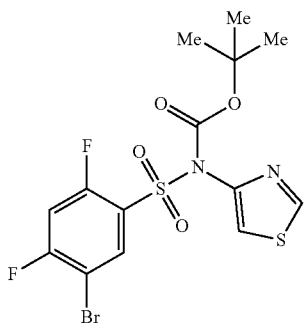 [SMILES: CC(C)(C)OC(=O)N(c1cscn1)S(=O)(=O)c1cc(Br)c(F)cc1F]

To a mixture of tert-butyl thiazol-4-ylcarbamate (2.00 g, 9.99 mmol) in anhydrous N,N-dimethylformamide (20 mL) was added sodium hydride (60% dispersion in mineral oil, 0.799 g, 20.0 mmol) at 0° C. The mixture was allowed to warm to ambient temperature and stirred for 30 minutes. After cooling to 0° C., a solution of 5-bromo-2,4-difluorobenzene-1-sulfonyl chloride (3.79 g, 13.0 mmol) in anhydrous N,N-dimethylformamide (5 mL) was added slowly. The mixture was stirred at 0° C. for 30 minutes and ambient temperature for 1 h. The residue was then poured into ice-water (50 mL) and the aqueous phase was extracted with ethyl acetate (3×50 mL). The combined organic extracts were washed with brine (50 mL), dried over anhydrous sodium sulfate, filtered, and concentrated in vacuo. The residue was purified by column chromatography, eluting with a gradient of 9 to 13% of ethyl acetate in hexanes, to afford the title compound as a yellow solid (3.00 g, 66% yield): $^1$H NMR (400 MHz, CDCl$_3$) δ 8.81 (d, J=2.0 Hz, 1H), 8.38 (t, J=7.2 Hz, 1H), 7.54 (d, J=2.0 Hz, 1H), 7.08 (dd, J=9.2, 8.0 Hz, 1H), 1.39 (s, 9H).

Step 2. Preparation of 4-((2-(azetidin-1-ylmethyl)benzyl)amino)-5-bromo-2-fluoro-N-(thiazol-4-yl)benzenesulfonamide

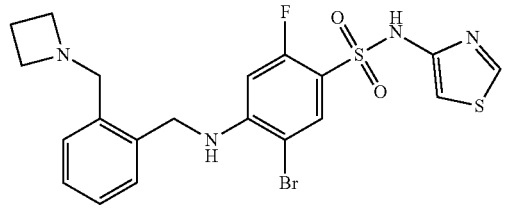 [SMILES: O=S(=O)(Nc1cscn1)c1cc(Br)c(NCc2ccccc2CN2CCC2)cc1F]

To a solution of tert-butyl (5-bromo-2,4-difluorophenyl)sulfonyl(thiazol-4-yl)carbamate (0.60 g, 1.32 mmol) and potassium carbonate (0.36 g, 2.6 mmol) in anhydrous N,N-dimethylformamide (5 mL) was added (2-(azetidin-1-ylmethyl)phenyl)methanamine (0.348 g, 1.98 mmol) dropwise. The mixture was stirred at ambient temperature for 12 h. The mixture was then diluted with water (60 mL) and extracted with ethyl acetate (3×50 mL). The combined organic extracts were washed with brine (50 mL), dried over anhydrous sodium sulfate, filtered, and concentrated in vacuo. The residue was purified by preparative reverse phase HPLC, using acetonitrile in water containing 0.225% formic acid as eluent, to afford the title compound as a colorless solid (0.20 g, 30% yield): $^1$H NMR (400 MHz, CDCl$_3$) δ 8.66 (d, J=2.0 Hz, 1H), 7.90 (d, J=7.6 Hz, 1H), 7.28-7.25 (m, 4H), 6.97 (d, J=2.0 Hz, 1H), 6.53 (d, J=13.2 Hz, 1H), 4.36 (s, 2H), 3.61 (s, 2H), 3.23 (t, J=7.2 Hz, 4H), 2.12-2.08 (m, 2H), NH not observed; MS (ES+) m/z 511.0 (M+1), 513.0 (M+1).

Step 3. Preparation of 4-((2-(azetidin-1-ylmethyl)benzyl)amino)-2-fluoro-N-(thiazol-4-yl)-5-vinylbenzenesulfonamide formate

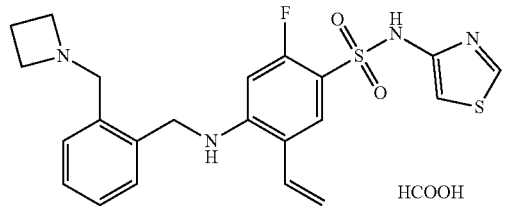 [SMILES: C=Cc1cc(S(=O)(=O)Nc2cscn2)c(F)cc1NCc1ccccc1CN1CCC1 ; "HCOOH"]

To a solution of 4-((2-(azetidin-1-ylmethyl)benzyl) amino)-5-bromo-2-fluoro-N-(thiazol-4-yl) benzenesulfonamide (0.20 g, 0.39 mmol), 4,4,5,5-tetramethyl-2-vinyl-1,3,2-dioxaborolane (0.12 g, 0.78 mmol) and sodium carbonate (0.0829 g, 0.782 mmol) in anhydrous 1,4-dioxane (3 mL) was added [1,1'-bis(diphenylphosphino)ferrocene]dichloropalladium(II) (0.0572 g, 0.0782 mmol) in one portion. The mixture was stirred at 100° C. for 12 h. After cooling to ambient temperature, the mixture was diluted with water (30 mL) and extracted with ethyl acetate (3×30 mL). The combined organic extracts were washed with brine (20 mL), dried over anhydrous sodium sulfate, and filtered. Concentration of the filtrate in vacuo and purification of the residue by preparative reverse phase HPLC, using acetonitrile in water containing 0.225% formic acid as eluent, afforded the title compound as a colorless solid (0.057 g, 31% yield): $^1$H NMR (400 MHz, CDCl₃) δ 8.66 (d, J=2.0 Hz, 1H), 8.39 (s, 1H), 7.73 (d, J=8.2 Hz, 1H), 7.40-7.31 (m, 4H), 6.96 (d, J=2.0 Hz, 1H), 6.72 (dd, J=17.2, 10.8 Hz, 1H), 6.36 (d, J=13.2 Hz, 1H), 5.61 (dd, J=17.2, 0.8 Hz, 1H), 5.40-5.31 (m, 1H), 4.38 (s, 2H), 3.94 (s, 2H), 3.62 (t, J=7.6 Hz, 4H), 2.29 (quin, J=7.6 Hz, 2H), NH and COOH not observed; MS (ES+) m/z 459.2 (M+1).

Example 324

Synthesis of 4-((2-(azetidin-1-ylmethyl)benzyl)amino)-2,6-difluoro-N-(6-fluoropyridin-2-yl)benzenesulfonamide

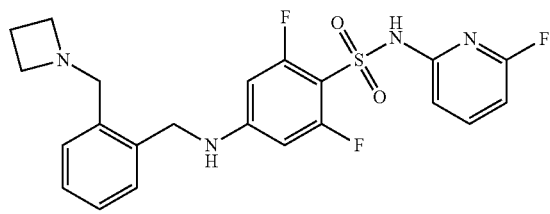 [SMILES: O=S(=O)(Nc1cccc(F)n1)c1c(F)cc(NCc2ccccc2CN2CCC2)cc1F]

Step 1. Preparation of N-(2,4-dimethoxybenzyl)-2,4,6-trifluoro-N-(6-fluoropyridin-2-yl)benzenesulfonamide

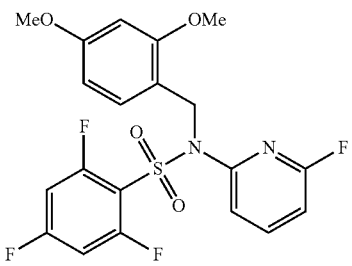 [SMILES: COc1ccc(CN(c2cccc(F)n2)S(=O)(=O)c2c(F)cc(F)cc2F)c(OC)c1]

To a solution of N-(2,4-dimethoxybenzyl)-6-fluoropyridin-2-amine (0.20 g, 0.76 mmol) in anhydrous tetrahydrofuran (10 mL) was added methyllithium (1.6 M, 0.67 mL) dropwise at −78° C. The mixture was warmed to 0° C., stirred for 30 minutes, and then cooled to −78° C. To it was then added a solution of 2,4,6-trifluorobenzene-1-sulfonyl chloride (0.281 g, 1.22 mmol) in anhydrous tetrahydrofuran (3 mL) at −78° C. The mixture was allowed to warm to ambient temperature and stirred for 2 h. The mixture was then diluted with water (50 mL) and extracted with ethyl acetate (3×50 mL). The combined organic extracts were washed with brine (20 mL), dried over anhydrous sodium sulfate, and filtered. Concentration in vacuo and purification of the residue by preparative thin layer chromatography, eluting with 9% of ethyl acetate in petroleum ether, afforded the title compound as a yellow oil (0.14 g, 40% yield): ¹H NMR (400 MHz, CDCl₃) δ 7.69 (q, J=8.0 Hz, 1H), 7.27 (d, J=9.2 Hz, 1H), 7.15 (dd, J=7.6, 1.6 Hz, 1H), 6.81-6.73 (m, 2H), 6.69 (dd, J=8.0, 2.4 Hz, 1H), 6.44-6.39 (m, 2H), 5.13 (s, 2H), 3.79 (s, 3H), 3.76 (s, 3H); MS (ES+) m/z 479.1 (M+23).

Step 2. Preparation of 4-((2-(azetidin-1-ylmethyl)benzyl)amino)-N-(2,4-dimethoxybenzyl)-2,6-difluoro-N-(6-fluoropyridin-2-yl)benzenesulfonamide

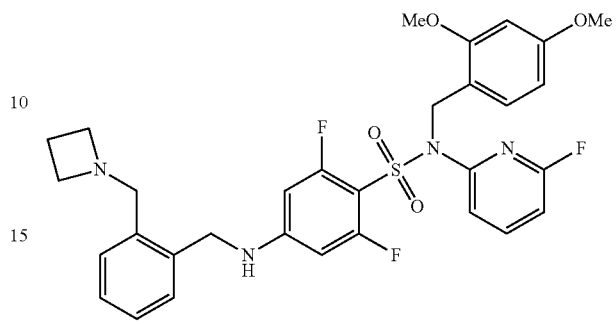

To a solution of N-(2,4-dimethoxybenzyl)-2,4,6-trifluoro-N-(6-fluoropyridin-2-yl)benzenesulfonamide (0.11 g, 0.24 mmol) and (2-(azetidin-1-ylmethyl)phenyl)methanamine (0.0637 g, 0.362 mmol) in anhydrous N,N-dimethylformamide (4 mL) was added potassium carbonate (0.0666 g, 0.482 mmol). The mixture was stirred at ambient temperature for 12 h and was then diluted with water (50 mL) and extracted with ethyl acetate (3×50 mL). The combined organic extracts were washed with brine (20 mL), dried over anhydrous sodium sulfate, and filtered. Concentration of the filtrate in vacuo afforded the title compound as a yellow oil (0.14 g, 95% yield): MS (ES+) m/z 613.2 (M+1).

Step 3. Preparation of 4-((2-(azetidin-1-ylmethyl)benzyl)amino)-2,6-difluoro-N-(6-fluoropyridin-2-yl)benzenesulfonamide

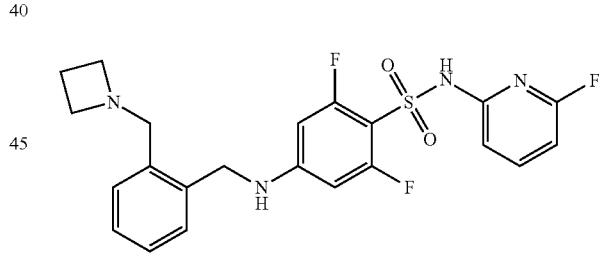

To 4-((2-(azetidin-1-ylmethyl)benzyl)amino)-N-(2,4-dimethoxybenzyl)-2,6-difluoro-N-(6-fluoropyridin-2-yl)benzenesulfonamide (0.10 g, 0.16 mmol) was added a 4 M solution of hydrogen chloride in ethyl acetate (5 mL), and the mixture was stirred at ambient temperature for 1 h. Concentration in vacuo and purification of residue by preparative reverse phase HPLC, using acetonitrile in water containing 0.05% ammonium hydroxide as eluent, afforded the title compound as a colorless solid (0.0269 g, 35% yield): ¹H NMR (400 MHz, DMSO-d₆) δ 7.72 (q, J=8.0 Hz, 1H), 7.52 (br s, 1H), 7.34-7.18 (m, 4H), 6.78 (dd, J=8.0, 2.0 Hz, 1H), 6.54 (br d, J=6.0 Hz, 1H), 6.35 (d, J=12.4 Hz, 2H), 4.38 (s, 2H), 3.60 (s, 2H), 3.16 (t, J=6.8 Hz, 4H), 2.00 (quin, J=6.8 Hz, 2H), NH not observed; MS (ES+) m/z 463.1 (M+1), 464.1 (M+1).

Example 325

Synthesis of (S)-5-chloro-4-((1-(2,5-difluorophenyl)ethyl)amino)-2-fluoro-N-(thiazol-4-yl)benzenesulfonamide

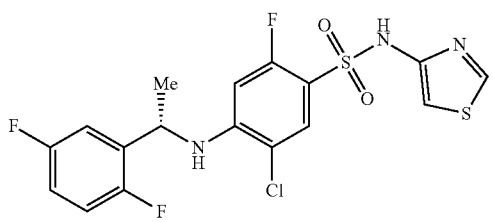 [SMILES: C[C@H](Nc1cc(F)c(S(=O)(=O)Nc2cscn2)cc1Cl)c1cc(F)ccc1F]

Step 1. Preparation of tert-butyl (S)-((5-chloro-4-((1-(2,5-difluorophenyl)ethyl)amino)-2-fluorophenyl)sulfonyl)(thiazol-4-yl)carbamate

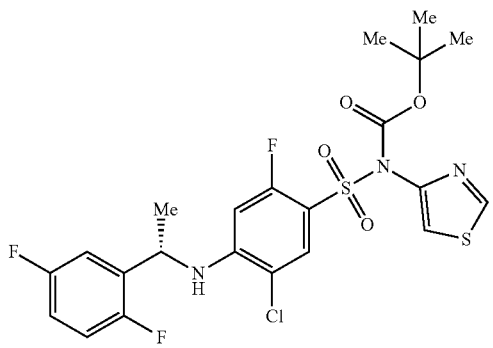 [SMILES: C[C@H](Nc1cc(F)c(S(=O)(=O)N(C(=O)OC(C)(C)C)c2cscn2)cc1Cl)c1cc(F)ccc1F]

Following the procedure as described for EXAMPLE 5, Step 1 and making non-critical variations as required to replace (S)-1-(5-chloro-2-fluorophenyl)ethan-1-amine hydrochloride with (S)-1-(2,5-difluorophenyl)ethan-1-amine hydrochloride, the title compound was obtained as a yellow solid (0.800 g, 50% yield): MS (ES+) m/z 447.9 (M−99).

Step 2. Preparation of (S)-5-chloro-4-((1-(2,5-difluorophenyl)ethyl)amino)-2-fluoro-N-(thiazol-4-yl)benzenesulfonamide

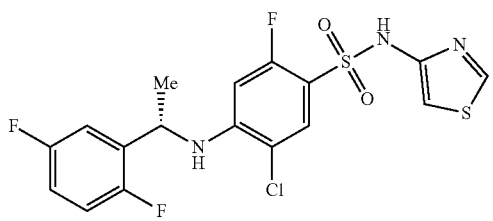 [SMILES: C[C@H](Nc1cc(F)c(S(=O)(=O)Nc2cscn2)cc1Cl)c1cc(F)ccc1F]

Following the procedure as described for EXAMPLE 5, Step 2 and making non-critical variations as required to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl (S)-((5-chloro-4-((1-(2,5-difluorophenyl)ethyl)amino)-2-fluorophenyl)sulfonyl)(thiazol-4-yl)carbamate, the title compound was obtained as a colorless solid (0.153 g, 61% yield): $^1$H NMR (400 MHz, DMSO-$d_6$) δ 8.84 (d, J=2.0 Hz, 1H), 7.62 (d, J=7.4 Hz, 1H), 7.32-7.22 (m, 2H), 7.18-7.10 (m, 1H), 6.90 (br s, 1H), 6.61 (d, J=7.8 Hz, 1H), 6.39 (d, J=13.0 Hz, 1H), 4.93 (quin, J=6.8 Hz, 1H), 1.55 (d, J=6.8 Hz, 3H), NH not observed; MS (ES+) m/z 447.9 (M+1).

Example 326

Synthesis of 2,6-difluoro-4-((2-fluoro-6-((1-methylazetidin-3-yl)oxy)benzyl)amino)-N-(thiazol-4-yl)benzenesulfonamide formate

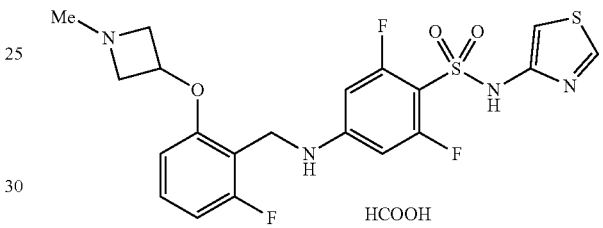

Step 1. Preparation of tert-butyl 3-(2-cyano-3-fluorophenoxy)azetidine-1-carboxylate

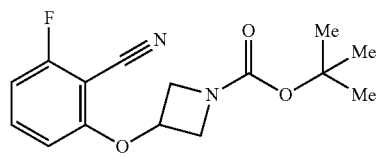 [SMILES: CC(C)(C)OC(=O)N1CC(Oc2cccc(F)c2C#N)C1]

A mixture of 2-fluoro-6-hydroxybenzonitrile (1.50 g, 10.9 mmol), tert-butyl 3-(2-cyano-3-fluorophenoxy)azetidine-1-carboxylate (3.10 g, 10.9 mmol) and potassium carbonate (3.78 g, 27.3 mmol) in anhydrous N,N-dimethylformamide (3 mL) was stirred at 90° C. for 12 h. The reaction mixture was diluted with water (60 mL) and then extracted with ethyl acetate (3×30 mL). The combined organic phase was washed with brine (40 mL), dried over anhydrous sodium sulfate, and filtered. Concentration of the filtrate under reduced pressure and purification of the residue by column chromatography, eluting with a gradient of 18-25% of ethyl acetate in petroleum ether, afforded the title compound as a colorless solid (2.00 g, 63% yield): $^1$H NMR (400 MHz, CDCl$_3$) δ 7.49 (td, J=8.6, 6.6 Hz, 1H), 6.85 (t, J=8.4 Hz, 1H), 6.42 (d, J=8.6 Hz, 1H), 5.02-4.95 (m, 1H), 4.34 (ddd, J=9.8, 6.4, 1.0 Hz, 2H), 4.07-4.14 (m, 2H), 1.46 (s, 9H); MS (ES+) m/z 315.2 (M+23).

Step 2. Preparation of tert-butyl 3-(2-(aminomethyl)-3-fluorophenoxy)azetidine-1-carboxylate

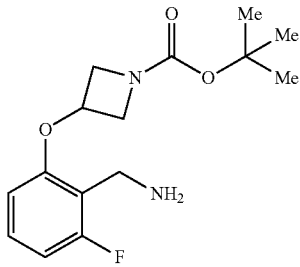 [SMILES: CC(C)(C)OC(=O)N1CC(Oc2cccc(F)c2CN)C1]

To a mixture of tert-butyl 3-(2-cyano-3-fluorophenoxy)azetidine-1-carboxylate (2.00 g, 6.84 mmol) in methanol (100 mL) and concentrated ammonium hydroxide (25 mL) was added Raney nickel (0.58 g, 6.84 mmol), and the mixture was stirred under a hydrogen atmosphere (50 psi) at ambient temperature for 12 h. The reaction mixture was then filtered and the filtrate concentrated under reduced pressure to yield the title compound as a colorless oil (1.00 g, 49% yield): $^1$H NMR (400 MHz, CDCl$_3$) δ 7.10 (br s, 1H), 6.76 (br s, 1H), 6.31 (br d, J=6.1 Hz, 1H), 4.92 (br s, 1H), 4.33 (dd, J=9.4, 6.2 Hz, 2H), 4.17-3.81 (m, 4H), 1.45 (s, 9H), NH not observed; MS (ES+) m/z 297.1 (M+1)

Step 3. Preparation of tert-butyl 3-(2-(((4-(N-(tert-butoxycarbonyl)-N-(thiazol-4-yl)sulfamoyl)-3,5-difluorophenyl)amino)methyl)-3-fluorophenoxy)azetidine-1-carboxylate

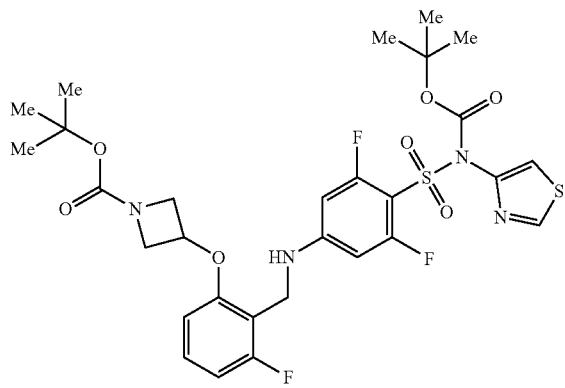 [SMILES: CC(C)(C)OC(=O)N1CC(Oc2cccc(F)c2CNc2cc(F)c(S(=O)(=O)N(C(=O)OC(C)(C)C)c3cscn3)c(F)c2)C1]

To a solution of tert-butyl 3-(2-(aminomethyl)-3-fluorophenoxy)azetidine-1-carboxylate (0.20 g, 0.67 mmol), tert-butyl thiazol-4-yl((2,4,6-trifluorophenyl)sulfonyl)carbamate (0.28 g, 0.70 mmol) in anhydrous N,N-dimethylformamide (15 mL) was added potassium carbonate (0.18 g, 1.3 mmol). The mixture was stirred at ambient temperature for 12 h and then water (100 mL) was added, and the mixture was extracted with ethyl acetate (3×300 mL). The combined organic layers were washed with brine (40 mL), dried over anhydrous sodium sulfate, and filtered. Concentration of the filtrate under reduced pressure and purification of the residue by column chromatography, eluting with a gradient of 20 to 50% of ethyl acetate in petroleum ether, afforded the title compound as a colorless oil (0.23 g, 51% yield): $^1$H NMR (400 MHz, CDCl$_3$) δ 8.79 (d, J=2.3 Hz, 1H), 7.49 (d, J=2.3 Hz, 1H), 7.19-7.26 (m, 1H), 6.78 (t, J=8.6 Hz, 1H), 6.35 (d, J=8.2 Hz, 1H), 6.29 (d, J=11.6 Hz, 2H), 5.03-5.01 (m, 1H), 5.01-4.95 (m, 1H), 4.45 (br d, J=5.8 Hz, 2H), 4.37 (dd, J=9.8, 6.26 Hz, 2H), 4.03 (dd, J=10.4, 3.8 Hz, 2H), 1.47 (s, 9H), 1.37 (s, 9H).

Step 4. Preparation of 4-((2-(azetidin-3-yloxy)-6-fluorobenzyl)amino)-2,6-difluoro-N-(thiazol-4-yl)benzenesulfonamide

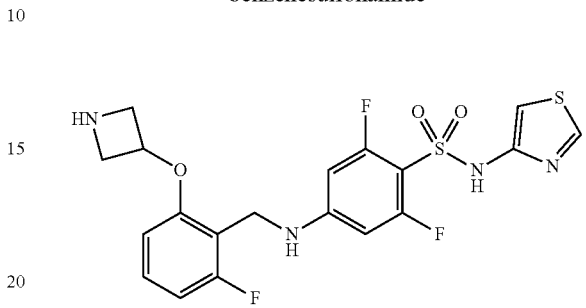

To tert-butyl 3-(2-(((4-(N-(tert-butoxycarbonyl)-N-(thiazol-4-yl)sulfamoyl)-3,5-difluorophenyl)amino)methyl)-3-fluorophenoxy)azetidine-1-carboxylate (0.23 g, 0.34 mmol) was added a 4 M solution of hydrogen chloride in (20 mL) and the mixture was stirred at ambient temperature for 2 h. Concentration in vacuo and purification of the residue by preparative reverse phase HPLC, using acetonitrile in water containing 0.05% ammonium hydroxide as eluent, afforded the title compound as a colorless solid (0.070 g, 43% yield): MS (ES+) m/z 471.1 (M+1).

Step 5. Preparation of 2,6-difluoro-4-((2-fluoro-6-((1-methylazetidin-3-yl)oxy)benzyl)amino)-N-(thiazol-4-yl)benzenesulfonamide formate

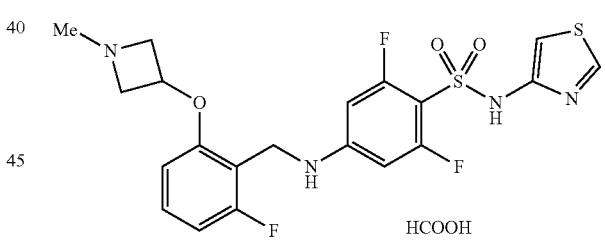

A solution of 4-((2-(azetidin-3-yloxy)-6-fluorobenzyl)amino)-2,6-difluoro-N-(thiazol-4-yl)benzenesulfonamide (0.06 g, 0.1 mmol), paraformaldehyde (0.023 g, 0.26 mmol) and acetic acid (0.00076 g, 0.013 mmol, 0.73 uL) in methanol (2 mL) was stirred at ambient temperature for 30 minutes. To it was then added sodium cyanoborohydride (0.016 g, 0.26 mmol) and the mixture was stirred at ambient temperature for 2.5 h. The reaction mixture was diluted with water (50 ml) and extracted with ethyl acetate (3×30 mL). The combined organic extracts were washed with brine (30 ml), dried over anhydrous sodium sulfate, and filtered. Concentration in vacuo and purification of the residue by preparative thin layer chromatography, eluting with 10% of methanol in dichloromethane, followed by preparative reverse phase HPLC using acetonitrile in water containing 0.225% formic acid as eluent, afford the title compound as a colorless solid (0.0055 g, 9% yield): $^1$H NMR (400 MHz, CD$_3$OD) δ 8.72 (d, J=2.2 Hz, 1H), 8.46 (br s, 1H), 7.28 (dt, J=8.4, 6.8 Hz, 1H), 6.94 (d, J=2.4 Hz, 1H), 6.81 (t, J=8.8 Hz, 1H), 6.55 (d, J=8.4 Hz, 1H), 6.34-6.23 (m, 2H), 5.05-4.98 (m, 1H), 4.37 (s, 2H), 4.24 (dd, J=11.2, 6.2 Hz, 2H), 3.76 (br dd, J=11.0, 4.5 Hz, 2H), 2.71 (s, 3H), NH and COOH not observed.

Example 327

Synthesis of 4-((2-(azetidin-1-ylmethyl)benzyl)amino)-3-chloro-2,6-difluoro-N-(1,2,4-thiadiazol-5-yl)benzenesulfonamide formate

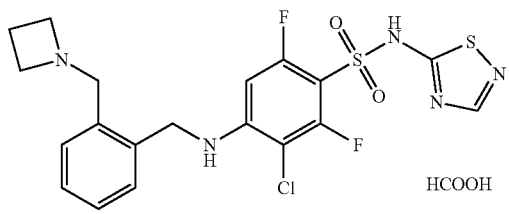 [SMILES: O=S(=O)(Nc1ncns1)c1c(F)cc(NCc2ccccc2CN2CCC2)c(Cl)c1F ; "HCOOH"]

Step 1. Preparation of 4-((2-(azetidin-1-ylmethyl)benzyl)amino)-3-chloro-N-(2,4-dimethoxybenzyl)-2,6-difluoro-N-(1,2,4-thiadiazol-5-yl)benzenesulfonamide

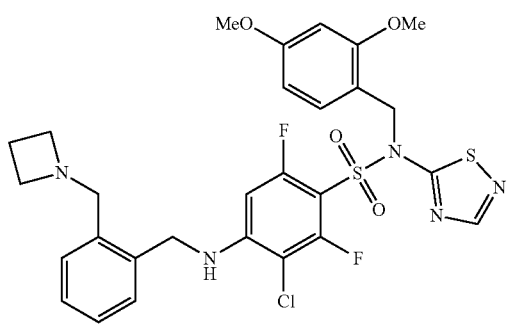 [SMILES: COc1ccc(CN(c2ncns2)S(=O)(=O)c2c(F)cc(NCc3ccccc3CN3CCC3)c(Cl)c2F)c(OC)c1]

To a solution of 3-chloro-N-(2,4-dimethoxybenzyl)-2,4,6-trifluoro-N-(1,2,4-thiadiazol-5-yl)benzenesulfonamide (0.600 g, 1.25 mmol) in anhydrous N,N-dimethylformamide (3 mL) was added cesium carbonate (0.815 g, 2.50 mmol) and the reaction mixture was stirred at ambient temperature for 12 h. The reaction mixture was diluted with ethyl acetate (50 mL) and water (20 mL), and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by column chromatography, eluting with a gradient from 5 to 50% of ethyl acetate in petroleum ether, afforded the title compound as a light brown solid (0.288 g, 36% yield): $^1$H NMR (400 MHz, CDCl$_3$) δ 8.12 (s, 1H), 7.25-7.18 (m, 4H), 7.12 (d, J=8.4 Hz, 1H), 6.29-6.24 (m, 1H), 6.20 (dd, J=13.5, 1.2 Hz, 1H), 6.14 (d, J=2.2 Hz, 1H), 5.28 (s, 2H), 4.24 (s, 2H), 3.61 (s, 6H), 3.53 (s, 2H), 3.15 (t, J=7.2 Hz, 4H), 2.05-1.97 (m, 2H), NH not observed.

Step 2. Preparation of 4-((2-(azetidin-1-ylmethyl)benzyl)amino)-3-chloro-2,6-difluoro-N-(1,2,4-thiadiazol-5-yl)benzenesulfonamide formate

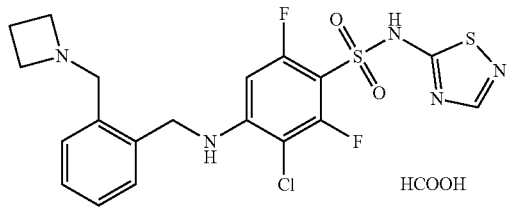 [SMILES: O=S(=O)(Nc1ncns1)c1c(F)cc(NCc2ccccc2CN2CCC2)c(Cl)c1F ; "HCOOH"]

To a mixture of 4-((2-(azetidin-1-ylmethyl)benzyl)amino)-3-chloro-N-(2,4-dimethoxybenzyl)-2,6-difluoro-N-(1,2,4-thiadiazol-5-yl)benzenesulfonamide (0.050 g, 0.079 mmol) in dichloromethane (10 mL) was added trifluoroacetic acid (0.090 g, 0.786 mmol) and the reaction mixture was stirred at ambient temperature for 1 h. Concentration in vacuo and purification of the residue by preparative reverse-phase HPLC, using acetonitrile in water containing 0.225% formic acid as eluent, afforded the title compound as a colorless solid (0.0190 g, 46% yield): $^1$H NMR (400 MHz, CDCl$_3$) δ 7.94 (s, 1H), 7.50-7.32 (m, 4H), 6.11 (d, J=11.6 Hz, 1H), 4.57 (d, J=3.4 Hz, 4H), 4.26 (t, J=8.2 Hz, 4H), 2.53 (quin, J=8.1 Hz, 2H), NH and COOH not observed; $^{19}$F NMR (376.5 MHz, CDCl$_3$) δ −109.1 (s, 1F), −109.2 (s, 1F); MS (ES+) m/z 486.2 (M+1), 488.2 (M+1).

Example 328

Synthesis of 4-((2-(azetidin-1-ylmethyl)-6-fluorobenzyl)amino)-2,6-difluoro-N-(pyridin-2-yl)benzenesulfonamide

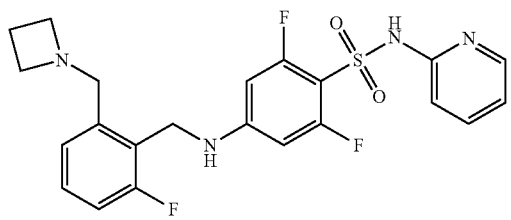 [SMILES: O=S(=O)(Nc1ccccn1)c1c(F)cc(NCc2c(F)cccc2CN2CCC2)cc1F]

Step 1. Preparation of N-(2,4-dimethoxybenzyl)pyridin-2-amine

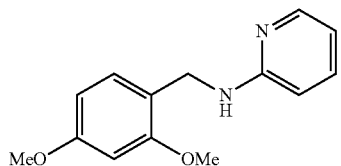 [SMILES: COc1ccc(CNc2ccccn2)c(OC)c1]

A solution of 2-fluoropyridine (1.00 g, 10.3 mmol) in (2,4-dimethoxyphenyl)methanamine (1.72 g, 10.3 mmol) was stirred at 110° C. for 12 h. After cooling to ambient temperature, the mixture was purified by reverse phase column chromatography, eluting with a gradient of 5-60% acetonitrile in water, to afford the title compound as a yellow solid (1.35 g, 52% yield): ¹H NMR (400 MHz, CDCl₃) δ 8.10 (dd, J=5.2, 1.0 Hz, 1H), 7.40 (ddd, J=8.6, 7.0, 1.8 Hz, 1H), 7.23 (d, J=8.2 Hz, 1H), 6.57 (ddd, J=7.2, 5.0, 0.8 Hz, 1H), 6.49 (d, J=2.4 Hz, 1H), 6.46-6.40 (m, 2H), 5.11 (br s, 1H), 4.42 (br d, J=3.4 Hz, 2H), 3.85 (s, 3H), 3.81 (s, 3H); MS (ES+) m/z 245.3 (M+1).

Step 2. Preparation of N-(2,4-dimethoxybenzyl)-2,4,6-trifluoro-N-(pyridin-2-yl)benzenesulfonamide

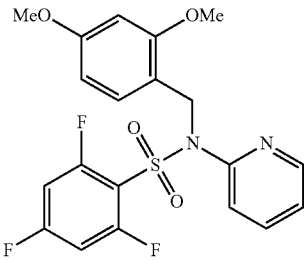 [SMILES: COc1ccc(CN(c2ccccn2)S(=O)(=O)c2c(F)cc(F)cc2F)c(OC)c1]

To a solution of N-(2,4-dimethoxybenzyl)pyridin-2-amine (0.80 g, 3.3 mmol) in anhydrous tetrahydrofuran (10 mL) was added a 1.6 M solution of methyllithium (3.07 mL, 4.9 mmol) at −78° C. The reaction mixture was stirred for 30 minutes at 0° C., and then a solution of 2,4,6-trifluorobenzenesulfonyl chloride (1.06 g, 4.58 mmol) in anhydrous tetrahydrofuran (2 mL) was added at −78° C. The reaction mixture was allowed to warm to ambient temperature ad stirred for 3 h. The reaction mixture was concentrated in vacuo and the residue was purified by column chromatography, eluting with a gradient of 9 to 11% of ethyl acetate in petroleum ether, to afford the title compound as a yellow oil (1.00 g, 48% yield): ¹H NMR (400 MHz, CDCl₃) δ 8.28 (dd, J=4.8, 1.2 Hz, 1H), 7.61 (dt, J=7.8, 1.8 Hz, 1H), 7.26-7.19 (m, 2H), 7.07 (ddd, J=7.4, 4.8, 0.8 Hz, 1H), 6.73 (t, J=8.8 Hz, 2H), 6.41-6.36 (m, 2H), 5.13 (s, 2H), 3.76 (s, 3H), 3.72 (s, 3H); MS (ES+) m/z 461.0 (M+23).

Step 3. Preparation of 4-((2-(azetidin-1-ylmethyl)-6-fluorobenzyl)amino)-N-(2,4-dimethoxybenzyl)-2,6-difluoro-N-(pyridin-2-yl)benzenesulfonamide

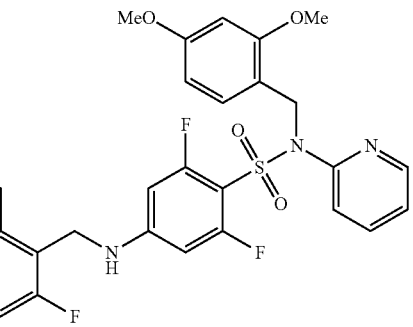

A mixture of (2-(azetidin-1-ylmethyl)-6-fluorophenyl)methanamine (0.31 g, 1.6 mmol), N-(2,4-dimethoxybenzyl)-2,4,6-trifluoro-N-(pyridin-2-yl)benzenesulfonamide (0.70 g, 1.6 mmol) and potassium carbonate (0.442 g, 3.20 mmol) in anhydrous N,N-dimethylformamide (15 mL) was stirred at ambient temperature for 12 h. The reaction mixture was diluted with ethyl acetate (50 mL) and water (20 mL), and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by reverse phase column chromatography, eluting with 5 to 60% of acetonitrile in water, afforded the title compound as a colorless oil (0.10 g, 10% yield): ¹H NMR (400 MHz, CDCl₃) δ 8.30 (dd, J=4.8, 1.4 Hz, 1H), 7.63-7.56 (m, 1H), 7.44 (d, J=8.2 Hz, 1H), 7.27 (s, 2H), 7.25-7.20 (m, 1H), 7.09-7.00 (m, 3H), 6.37 (qd, J=4.4, 2.3 Hz, 2H), 6.18 (d, J=11.9 Hz, 2H), 5.17 (s, 2H), 4.33 (d, J=1.0 Hz, 2H), 3.75 (s, 3H), 3.72 (s, 3H), 3.62 (s, 2H), 3.25 (br s, 4H), 2.13 (quin, J=6.9 Hz, 2H); MS (ES+) m/z 613.2 (M+1).

Step 4. Preparation of 4-((2-(azetidin-1-ylmethyl)-6-fluorobenzyl)amino)-2,6-difluoro-N-(pyridin-2-yl)benzenesulfonamide

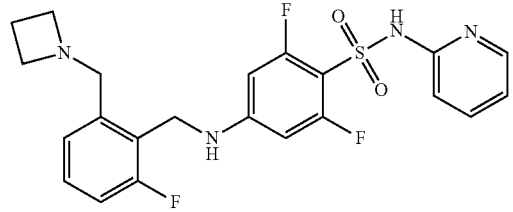 [SMILES: O=S(=O)(Nc1ccccn1)c1c(F)cc(NCc2c(F)cccc2CN2CCC2)cc1F]

To a solution of 4-((2-(azetidin-1-ylmethyl)-6-fluorobenzyl)amino)-N-(2,4-dimethoxybenzyl)-2,6-difluoro-N-(pyridin-2-yl)benzenesulfonamide (0.10 g, 0.16 mmol) in dichloromethane (10 mL) was added trifluoroacetic acid (0.04 g, 0.3 mmol). The mixture was stirred at ambient temperature for 1 h and was then concentrated in vacuo. The residue was purified by preparative reverse phase HPLC, using acetonitrile in water containing 0.225% formic acid as eluent, to afford the title compound as a colorless solid (0.0638 g, 80% yield): ¹H NMR (400 MHz, CDCl₃) δ 8.31 (br d, J=5.8 Hz, 1H), 7.75-7.66 (m, 1H), 7.55 (d, J=8.8 Hz, 1H), 7.27-7.21 (m, 1H), 7.11-7.01 (m, 2H), 6.78 (t, J=6.4 Hz, 1H), 6.19 (br d, J=12.0 Hz, 2H), 4.32 (s, 2H), 3.78 (br s, 2H), 3.42 (br s, 4H), 2.28-2.14 (m, 2H), NH not observed; MS (ES+) m/z 463.0 (M+1).

Example 329

Synthesis of 4-((2-(azetidin-1-ylmethyl)benzyl)amino)-2-fluoro-N-(6-fluoropyridin-2-yl)-5-methyl-benzenesulfonamide

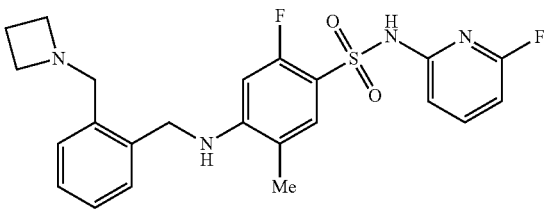 [SMILES: Cc1cc(S(=O)(=O)Nc2cccc(F)n2)c(F)cc1NCc1ccccc1CN1CCC1]

Step 1. Preparation of 4-((2-(azetidin-1-ylmethyl)benzyl)amino)-N-(2,4-dimethoxybenzyl)-2-fluoro-N-(6-fluoropyridin-2-yl)-5-methylbenzenesulfonamide

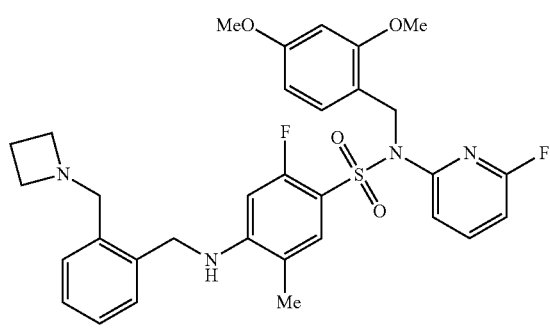 [SMILES: COc1ccc(CN(c2cccc(F)n2)S(=O)(=O)c2cc(C)c(NCc3ccccc3CN3CCC3)cc2F)c(OC)c1]

To a mixture of 4-bromo-N-(2,4-dimethoxybenzyl)-2-fluoro-N-(6-fluoropyridin-2-yl)-5-methylbenzene sulfonamide (0.300 g, 0.584 mmol) in anhydrous 1,4-dioxane (2 mL) was added (2-(azetidin-1-ylmethyl)phenyl)methanamine (0.206 g, 1.17 mmol), cesium carbonate (0.571 g, 1.75 mmol), and chloro(2-dicyclohexylphosphino-2',6'-dimethoxy-1,1'-biphenyl) [2-(2'-amino-1,1'-biphenyl)]palladium(II) (0.042 g, 0.058 mmol). The reaction mixture was heated to 90° C. for 12 h. After cooling to ambient temperature, the reaction mixture was diluted with water (10 mL), and the aqueous phase was extracted with ethyl acetate (3×10 mL). The combined organic extracts were washed with brine (3×10 mL), dried over anhydrous sodium sulfate, and filtered. Concentration of the filtrate in vacuo and purification of the residue by preparative thin layer chromatography, eluting with 50% of ethyl acetate in petroleum ether, afforded the title compound as a yellow oil (0.200 g, 56% yield): $^1$H NMR (400 MHz, CDCl$_3$) δ 7.57 (q, J=8.2 Hz, 1H), 7.41 (d, J=8.0 Hz, 1H), 7.28 (dd, J=7.8, 1.8 Hz, 1H), 7.25-7.19 (m, 4H), 6.71 (br s, 1H), 6.52 (dd, J=7.8, 3.0 Hz, 1H), 6.34-6.28 (m, 3H), 5.00 (s, 2H), 4.21 (s, 2H), 3.67 (d, J=7.2 Hz, 6H), 3.52 (s, 2H), 3.14 (t, J=7.0 Hz, 4H), 2.09 (s, 3H), 2.02-1.98 (m, 2H), NH not observed; MS (ES+) m/z 609.4 (M+1).

Step 2. Preparation of 4-((2-(azetidin-1-ylmethyl)benzyl)amino)-2-fluoro-N-(6-fluoropyridin-2-yl)-5-methylbenzenesulfonamide

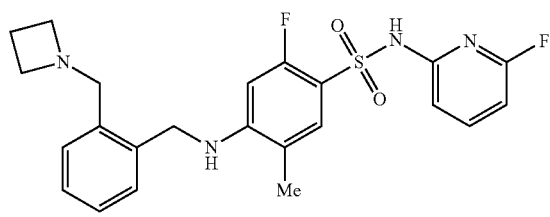 [SMILES: Cc1cc(S(=O)(=O)Nc2cccc(F)n2)c(F)cc1NCc1ccccc1CN1CCC1]

To a solution of 4-((2-(azetidin-1-ylmethyl)benzyl)amino)-N-(2,4-dimethoxybenzyl)-2-fluoro-N-(6-fluoropyridin-2-yl)-5-methylbenzenesulfonamide (0.200 g, 0.329 mmol) in dichloromethane (2 mL) was added trifluoroacetic acid (1.54 g, 13.5 mmol) and the mixture was stirred at ambient temperature for 1 h. The reaction mixture was concentrated in vacuo. The residue was purified by preparative reverse phase HPLC, using acetonitrile in water containing 0.05% ammonium hydroxide as eluent, to afford the title compound as a colorless solid (0.045 g, 29% yield): $^1$H NMR (400 MHz, CDCl$_3$) δ 7.58 (q, J=8.0 Hz, 1H), 7.45 (d, J=8.2 Hz, 1H), 7.21 (dd, J=3.8, 1.4 Hz, 3H), 7.10 (dd, J=7.8, 1.8 Hz, 1H), 7.02-6.63 (m, 1H), 6.48 (dd, J=2.4, 7.8 Hz, 1H), 6.35 (d, J=13.4 Hz, 1H), 4.22 (s, 2H), 3.54 (s, 2H), 3.17 (br s, 4H), 2.10 (s, 3H), 2.00 (td, J=14.0, 6.8 Hz, 2H), NH not observed; $^{19}$F NMR (376.5 MHz, CDCl$_3$) −69.2 (s, 1F), −109.8 (s, 1F); MS (ES+) m/z 459.2 (M+1).

Example 330

Synthesis of 4-((2-(azetidin-1-ylmethyl)benzyl)amino)-2,6-difluoro-3-methyl-N-(1,2,4-thiadiazol-5-yl)benzenesulfonamide

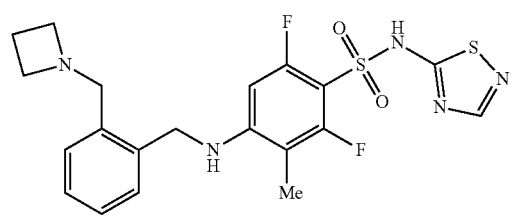 [SMILES: Cc1c(NCc2ccccc2CN2CCC2)cc(F)c(S(=O)(=O)Nc2ncns2)c1F]

Step 1. Preparation of 4-((2-(azetidin-1-ylmethyl)benzyl)amino)-3-bromo-N-(2,4-dimethoxybenzyl)-2,6-difluoro-N-(1,2,4-thiadiazol-5-yl)benzenesulfonamide

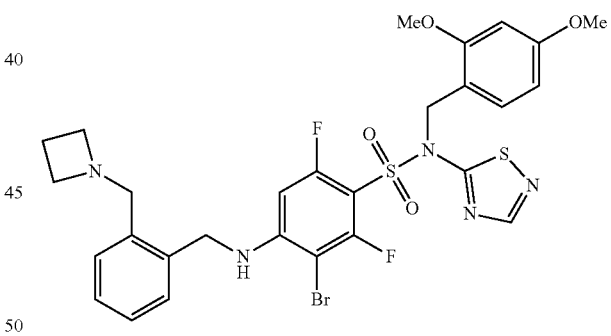

To a solution of 3-bromo-N-(2,4-dimethoxybenzyl)-2,4,6-trifluoro-N-(1,2,4-thiadiazol-5-yl) benzenesulfonamide (1.00 g, 1.91 mmol) in anhydrous N,N-dimethylformamide (20 mL) was added cesium carbonate (1.87 g, 5.73 mmol) and (2-(azetidin-1-ylmethyl)phenyl)methanamine (0.673 g, 3.82 mmol). The mixture was stirred at ambient temperature for 12 h. The reaction mixture was diluted with water (20 mL) and the aqueous phase was extracted with ethyl acetate (2×20 mL). The combined organic extracts were washed with brine (20 mL), dried over anhydrous sodium sulfate, and filtered. Concentration of the filtrate in vacuo and purification of the residue by column chromatography, eluting with a gradient of 9 to 33% of ethyl acetate in petroleum ether, afforded the title compound as a yellow oil (0.600 g, 46% yield): $^1$H NMR (400 MHz, CDCl$_3$) δ 8.21 (s, 1H), 7.33-7.29 (m, 3H), 7.22 (d, J=8.4 Hz, 1H), 6.39-6.30 (m, 2H), 6.30-6.22 (m, 1H), 6.22-6.19 (m, 1H), 4.37 (s, 2H), 3.75 (d, J=7.8 Hz, 2H), 3.71 (s, 3H), 3.67 (s, 3H), 3.65 (s, 2H), 3.28 (t, J=7.2 Hz, 4H), 2.12 (quin, J=7.2 Hz, 2H), NH not observed.

Step 2. Preparation of 4-((2-(azetidin-1-ylmethyl)benzyl)amino)-N-(2,4-dimethoxybenzyl)-2,6-difluoro-3-methyl-N-(1,2,4-thiadiazol-5-yl)benzenesulfonamide

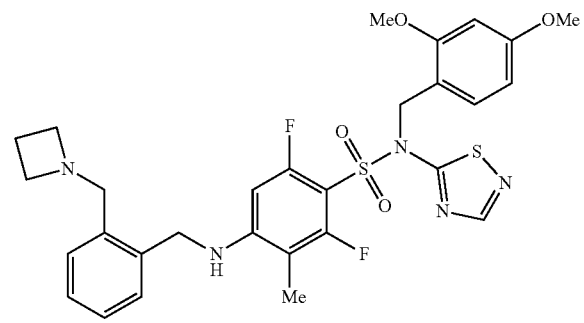 [SMILES: COc1ccc(CN(c2ncns2)S(=O)(=O)c2c(F)cc(NCc3ccccc3CN3CCC3)c(C)c2F)c(OC)c1]

To a mixture of 4-((2-(azetidin-1-ylmethyl)benzyl)amino)-3-bromo-N-(2,4-dimethoxybenzyl)-2,6-difluoro-N-(1,2,4-thiadiazol-5-yl)benzenesulfonamide (0.500 g, 0.734 mmol) in anhydrous toluene (8 mL) was added methylboronic acid (0.087 g, 1.5 mmol), 2-dicyclohexylphosphino-2',6'-dimethoxybiphenyl (0.060 g, 0.15 mmol), potassium phosphate (0.467 g, 2.20 mmol and palladium acetate(II) (0.033 g, 0.147 mmol). The mixture was degassed and heated to 110° C. for 12 h. After cooling to ambient temperature, the reaction mixture was filtered and the filtrate concentrated under reduced pressure. The residue was purified by column chromatography, eluting with a gradient of 9 to 33% of ethyl acetate in petroleum ether, to afford the title compound as a yellow solid (0.300 g, 66% yield): $^1$H NMR (400 MHz, CDCl$_3$) δ 8.18 (s, 1H), 7.35-7.30 (m, 4H), 7.20 (d, J=8.4 Hz, 1H), 6.36 (dd, J=2.4, 8.4 Hz, 1H), 6.30 (d, J=2.4 Hz, 1H), 6.21 (br d, J=13.6 Hz, 1H), 5.33 (s, 2H), 4.40-4.28 (m, 2H), 3.76-3.74 (m, 3H), 3.73 (s, 3H), 3.70 (s, 2H), 3.34 (br s, 4H), 2.14 (br s, 2H), 2.00 (d, J=1.8 Hz, 3H), NH not observed; MS (ES+) m/z 616.4 (M+1).

Step 3. Preparation of 4-((2-(azetidin-1-ylmethyl)benzyl)amino)-2,6-difluoro-3-methyl-N-(1,2,4-thiadiazol-5-yl)benzenesulfonamide

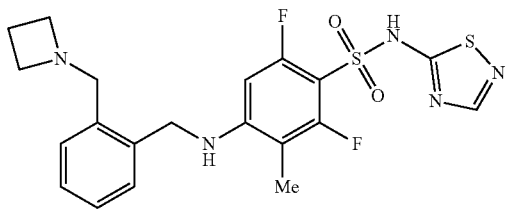 [SMILES: Cc1c(NCc2ccccc2CN2CCC2)cc(F)c(S(=O)(=O)Nc2ncns2)c1F]

To a mixture of 4-((2-(azetidin-1-ylmethyl)benzyl)amino)-N-(2,4-dimethoxybenzyl)-2,6-difluoro-3-methyl-N-(1,2,4-thiadiazol-5-yl)benzenesulfonamide (0.280 g, 0.454 mmol) in dichloromethane (10 mL) was added trifluoroacetic acid (2 mL) and the mixture was stirred at ambient temperature for 30 minutes. The reaction mixture was concentrated in vacuo and the residue was purified by preparative reverse phase HPLC, using acetonitrile in water containing 0.225% formic acid as eluent, to afford the title compound as a colorless solid (0.065 g, 31% yield): $^1$H NMR (400 MHz, DMSO-d$_6$) δ 7.87 (s, 1H), 7.41-7.25 (m, 4H), 6.55 (br s, 1H), 6.04 (d, J=13.4 Hz, 1H), 4.46 (br s, 2H), 4.41 (s, 2H), 4.02 (br t, J=7.8 Hz, 4H), 2.34 (quin, J=7.8 Hz, 2H), 2.00 (d, J=0.8 Hz, 3H), NH signal not observed; MS (ES+) m/z 466.3 (M+1).

Example 331

Synthesis of (S)-5-chloro-2-fluoro-4-((1-(2-fluoro-5-methoxyphenyl)ethyl)amino)-N-(thiazol-4-yl)benzenesulfonamide

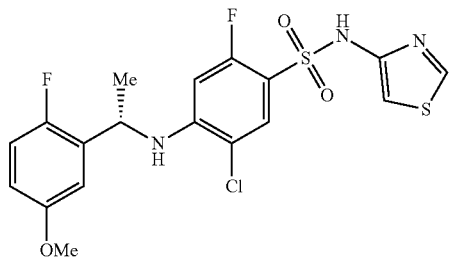 [SMILES: COc1ccc(F)c([C@H](C)Nc2cc(F)c(S(=O)(=O)Nc3cscn3)cc2Cl)c1]

Step 1. Preparation of tert-butyl (S)-((5-chloro-2-fluoro-4-((1-(2-fluoro-5-methoxyphenyl)ethyl)amino)phenyl)sulfonyl)(thiazol-4-yl)carbamate

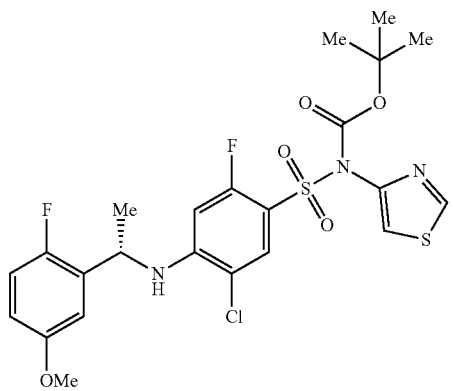 [SMILES: COc1ccc(F)c([C@H](C)Nc2cc(F)c(S(=O)(=O)N(C(=O)OC(C)(C)C)c3cscn3)cc2Cl)c1]

To a solution of tert-butyl (5-chloro-2,4-difluorophenyl)sulfonyl(thiazol-4-yl)carbamate (0.250 g, 0.609 mmol) and (S)-1-(2-fluoro-5-methoxyphenyl) ethanamine (0.124 g, 0.730 mmol) in anhydrous dimethyl sulfoxide (2 mL) was added cesium carbonate (0.397 g, 1.22 mmol) in one portion. The mixture was stirred at ambient temperature for 12 h. The mixture was diluted with water (30 mL) and the aqueous phase was extracted with ethyl acetate (3×20 mL). The combined organic extracts were washed with brine (10 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless oil (0.150 g, 44% yield): $^1$H NMR (400 MHz, CDCl$_3$) δ 8.79 (d, J=2.0 Hz, 1H), 7.97 (d, J=7.2 Hz, 1H), 7.49 (d, J=2.0 Hz, 1H), 7.04 (t, J=8.0 Hz, 1H), 6.81-6.75 (m, 1H), 6.75-6.71 (m, 1H), 6.20 (d, J=12.0 Hz, 1H), 5.32-5.26 (m, 1H), 4.87-4.77 (m, 1H), 3.75 (s, 3H), 1.67 (d, J=6.4 Hz, 3H), 1.37 (s, 9H); MS (ES+) m/z 460.0 (M−99).

Step 2. Preparation of (S)-5-chloro-2-fluoro-4-((1-(2-fluoro-5-methoxyphenyl)ethyl)amino)-N-(thiazol-4-yl)benzenesulfonamide

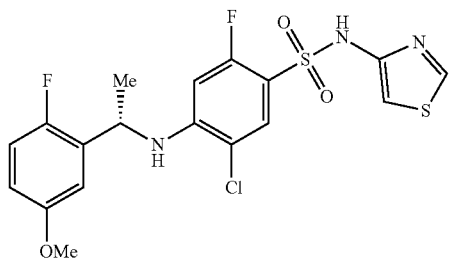 [SMILES: COc1ccc(F)c([C@H](C)Nc2cc(F)c(S(=O)(=O)Nc3cscn3)cc2Cl)c1]

To tert-butyl (S)-((5-chloro-2-fluoro-4-((1-(2-fluoro-5-methoxyphenyl)ethyl)amino)phenyl)-sulfonyl)(thiazol-4-yl)carbamate (0.150 g, 0.268 mmol) was added a 4 M solution of hydrogen chloride in ethyl acetate (5 mL) and the reaction mixture was stirred at ambient temperature for 30 minutes. The mixture was concentrated in vacuo. The residue was purified by preparative reverse phase HPLC, using acetonitrile in water containing 0.225% formic acid as eluent, to afford the title compound as a colorless solid (0.088 g, 66% yield: $^1$H NMR (400 MHz, CDCl$_3$) δ 10.00 (s, 1H), 8.68 (d, J=2.0 Hz, 1H), 7.76 (d, J=7.2 Hz, 1H), 7.02 (t, J=9.2 Hz, 1H), 6.92 (d, J=2.0 Hz, 1H), 6.78-6.73 (m, 1H), 6.71 (dd, J=6.2, 3.2 Hz, 1H), 6.12 (d, J=12.0 Hz, 1H), 5.18 (d, J=5.2 Hz, 1H), 4.74 (q, J=6.4 Hz, 1H), 3.74 (s, 3H), 1.62 (d, J=6.8 Hz, 3H); MS (ES+) m/z 460.1 (M+1).

Example 332

Synthesis of (R)-5-chloro-2-fluoro-N-(thiazol-2-yl)-4-((2,2,2-trifluoro-1-(2-fluorophenyl)ethyl)amino)benzenesulfonamide

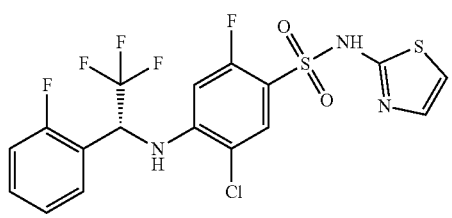 [SMILES: O=S(=O)(Nc1nccs1)c1cc(Cl)c(N[C@H](c2ccccc2F)C(F)(F)F)cc1F]

Step 1. Preparation of (R)-2-methyl-N-(2,2,2-trifluoro-1-(2-fluorophenyl)ethylidene)propane-2-sulfinamide

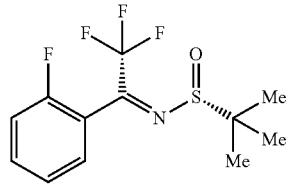

To a solution of 2,2,2-trifluoro-1-(2-fluorophenyl)ethanone (8.0 g, 42 mmol) and (R)-2-methylpropane-2-sulfinamide (6.3 g, 52 mmol) in anhydrous diethyl ether (300 mL) was added titanium(IV) isopropoxide (29.5 g, 104 mmol, 30.8 mL). The mixture was stirred at 50° C. for 24 h and then cooled to ambient temperature. The crude title compound was used without further purification.

Step 2. Preparation of (R)-2-methyl-N—((R)-2,2,2-trifluoro-1-(2-fluorophenyl)ethyl)propane-2-sulfinamide

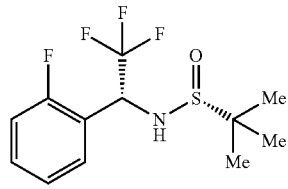 [SMILES: CC(C)(C)[S@@](=O)N[C@H](c1ccccc1F)C(F)(F)F]

To a solution of (R)-2-methyl-N-(2,2,2-trifluoro-1-(2-fluorophenyl)ethylidene)propane-2-sulfinamide (10.0 g, 33.8 mmol) in anhydrous diethyl ether (200 mL) was added sodium borohydride (3.8 g, 101.5 mmol) in portions at −78° C. The mixture was stirred at this temperature for 3 h and then diluted with brine (200 mL) at −78° C. After warming to ambient temperature, the aqueous phase was extracted with ethyl acetate (3×100 mL). The combined organic extracts were concentrated under reduced pressure. The residue was purified by column chromatography, eluting with 25% of ethyl acetate in petroleum ether, to yield the title compound as a colorless solid (6.0 g, 60% yield, 94% de). The diastereomeric excess was determined by $^1$H NMR: $^1$H NMR (400 MHz, CDCl$_3$) δ 7.35-7.50 (m, 2H), 7.18-7.25 (m, 1H), 7.14 (td, J=9.2, 0.8 Hz, 1H), 5.25 (quin, J=6.8 Hz, 1H), 4.00 (d, J=5.2 Hz, 1H), 1.22 (s, 9H); MS (ES+) m/z 298.1 (M+1).

Step 3. Preparation of (R)-2,2,2-trifluoro-1-(2-fluorophenyl)ethan-1-amine

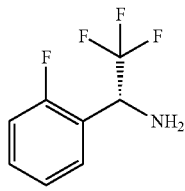 [SMILES: N[C@H](c1ccccc1F)C(F)(F)F]

To (R)-2-methyl-N—((R)-2,2,2-trifluoro-1-(2-fluorophenyl)ethyl)propane-2-sulfinamide (1.5 g, 5.0 mmol) was added to a 4 M solution of hydrogen chloride in methanol (10 mL) and the resulting mixture was stirred at ambient temperature for 4 h. The reaction mixture was concentrated in vacuo. The residue was diluted with methanol (1 mL) and purified by recrystallization from methyl tert-butyl ether (30 mL) to afford the title compound as a colorless solid (0.920 g, 94% yield): $^1$H NMR (400 MHz, CD$_3$OD) δ 7.59-7.77 (m, 2H), 7.28-7.50 (m, 2H), 5.63 (q, J=7.6 Hz, 1H), NH not observed.

Step 4. Preparation of (R)-5-chloro-N-(2,4-dimethoxybenzyl)-2-fluoro-N-(thiazol-2-yl)-4-((2,2,2-trifluoro-1-(2-fluorophenyl)ethyl)amino)benzenesulfonamide

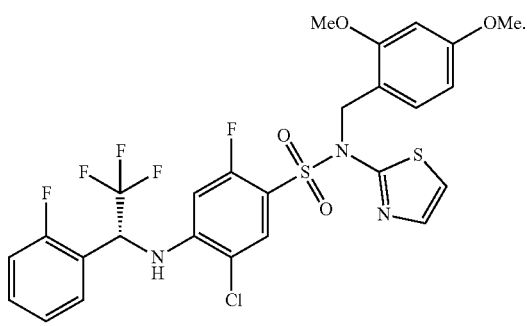 [SMILES: COc1ccc(CN(c2nccs2)S(=O)(=O)c2cc(Cl)c(N[C@H](c3ccccc3F)C(F)(F)F)cc2F)c(OC)c1]

To a mixture of (R)-2,2,2-trifluoro-1-(2-fluorophenyl)ethanamine (0.170 g, 0.880 mmol), and 4-bromo-5-chloro-N-(2,4-dimethoxybenzyl)-2-fluoro-N-(thiazol-2-yl)benzenesulfonamide (0.4592 g, 0.8801 mmol) in anhydrous toluene (2.5 mL) was added potassium tert-butoxide (0.395 g, 3.51 mmol), and (2-dicyclohexylphosphino-2',6'-dimethoxy-1,1'-biphenyl)[2-(2-aminoethylphenyl)]palladium(II) chloride methyl tert-butyl ether adduct (0.067 g, 0.088 mmol). The reaction mixture was degassed heated to 80° C. for 12 h. The mixture was diluted with ethyl acetate (40 mL) and water (30 mL), and the aqueous phase was washed with ethyl acetate (3×40 mL). The combined organic phases were concentrated in vacuo. The residue was purified by preparative thin layer chromatography, eluting with 25% of ethyl acetate in petroleum ether, to afford the title compound as a yellow oil (0.110 g, 20% yield): MS (ES+) m/z 634.1 (M+1), 636.1 (M+1).

Step 5. Preparation of (R)-5-chloro-2-fluoro-N-(thiazol-2-yl)-4-((2,2,2-trifluoro-1-(2-fluorophenyl)ethyl)amino)benzenesulfonamide

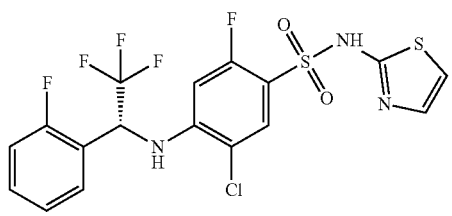 [SMILES: O=S(=O)(Nc1nccs1)c1cc(Cl)c(N[C@H](c2ccccc2F)C(F)(F)F)cc1F]

Following the procedure as described for EXAMPLE 327, Step 2 and making non-critical variations as required to replace 4-((2-(azetidin-1-ylmethyl)benzyl)amino)-3-chloro-N-(2,4-dimethoxybenzyl)-2,6-difluoro-N-(1,2,4-thiadiazol-5-yl)benzenesulfonamide with (R)-5-chloro-N-(2,4-dimethoxybenzyl)-2-fluoro-N-(thiazol-2-yl)-4-((2,2,2-trifluoro-1-(2-fluorophenyl)ethyl)amino)benzenesulfonamide, the title compound was obtained as a colorless solid (0.0369 g, 48% yield): $^1$H NMR (400 MHz, CDCl$_3$) δ 12.93 (br s, 1H), 7.94 (d, J=7.2 Hz, 1H), 7.37-7.50 (m, 2H), 7.13-7.27 (m, 3H), 6.54 (d, J=4.4 Hz, 1H), 6.38 (d, J=11.6 Hz, 1H), 5.57 (d, J=8.3 Hz, 1H), 5.24-5.40 (m, 1H); MS (ES+) m/z 484.1 (M+1), 486.1 (M+1).

Example 333

Synthesis of 4-((2-(azetidin-1-ylmethyl)-6-fluorobenzyl)amino)-2,6-difluoro-N-(pyridazin-3-yl)benzenesulfonamide formate

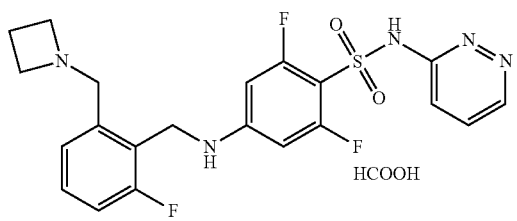 [SMILES: O=S(=O)(Nc1cccnn1)c1c(F)cc(NCc2c(F)cccc2CN2CCC2)cc1F ; "HCOOH"]

Step 1. Preparation of 2,4,6-trifluoro-N-(pyridazin-3-yl)benzenesulfonamide

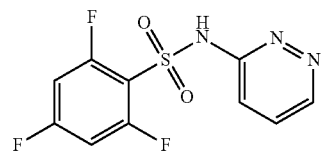 [SMILES: O=S(=O)(Nc1cccnn1)c1c(F)cc(F)cc1F]

To a solution of pyridazin-3-amine (10.0 g, 105 mmol), pyridine (16.6 g, 210 mmol, 17 mL), and 4-dimethylaminopyridine (1.28 g, 10.5 mmol) in dichloromethane (150 mL) was added 2,4,6-trifluorobenzene-1-sulfonyl chloride (29.1 g, 126 mmol) dropwise. The mixture was stirred at ambient temperature for 12 h. The mixture was concentrated in vacuo and the residue was diluted with water (200 mL). The layers were separated and the aqueous phase was extracted with ethyl acetate (3×200 mL). The combined organic extracts were washed with brine (50 mL), dried over anhydrous sodium sulfate, filtered and concentrated in vacuo. Purification of the residue by column chromatography, eluting with a gradient of 17 to 50% of ethyl acetate in petroleum ether, afforded the title compound as a yellow solid (1.50 g, 5% yield): $^1$H NMR (400 MHz, CDCl$_3$) δ 12.99 (br s, 1H), 8.21 (dd, J=4.0, 1.6 Hz, 1H), 7.50-7.45 (m, 1H), 7.43-7.37 (m, 1H), 6.82-6.73 (m, 2H).

Step 2. Preparation of 2,4,6-trifluoro-N-(pyridazin-3-yl)-N-((2-(trimethylsilyl)ethoxy)methyl)benzenesulfonamide

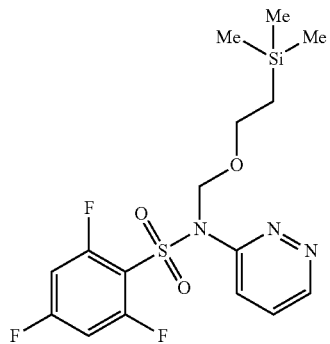 [SMILES: C[Si](C)(C)CCOCN(c1cccnn1)S(=O)(=O)c1c(F)cc(F)cc1F]

To a solution of 2,4,6-trifluoro-N-(pyridazin-3-yl) benzenesulfonamide (1.50 g, 5.19 mmol) and potassium carbonate (1.43 g, 10.4 mmol) in anhydrous N,N-dimethylformamide (20 mL) was added 2-(trimethylsilyl)ethoxymethyl chloride (1.04 g, 6.22 mmol) dropwise at 0° C. The mixture was stirred at ambient temperature for 1 h. The mixture was diluted with water (50 mL) and extracted with ethyl acetate (3×30 mL). The combined organic extracts were washed with brine (30 mL), dried over anhydrous sodium sulfate, filtered and concentrated in vacuo. Purification of the residue by column chromatography, eluting with a gradient of 17 to 25% of ethyl acetate in petroleum ether, afforded the title compound as a yellow solid (1.10 g, 51% yield): $^1$H NMR (400 MHz, CDCl$_3$) δ 8.42 (dd, J=9.6, 1.6 Hz, 1H), 8.14 (dd, J=4.0, 1.6 Hz, 1H), 7.43 (dd, J=9.6, 4.0 Hz, 1H), 6.81-6.72 (m, 2H), 5.69 (s, 2H), 3.78-3.68 (m, 2H), 0.98-0.90 (m, 2H), 0.00 (s, 9H); MS (ES+) m/z 420.3 (M+1).

Step 3. Preparation of 4-((2-(azetidin-1-ylmethyl)-6-fluorobenzyl)amino)-2,6-difluoro-N-(pyridazin-3-yl)-N-((2-(trimethylsilyl)ethoxy)methyl)benzenesulfonamide

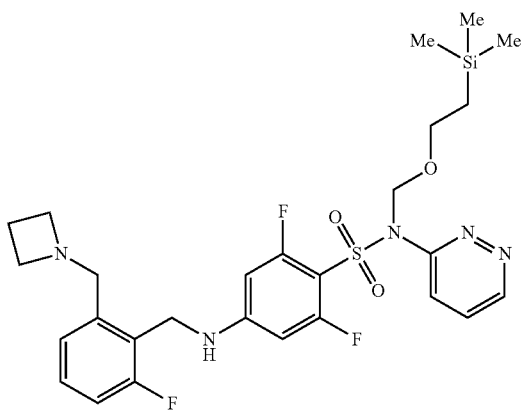 [SMILES: C[Si](C)(C)CCOCN(c1cccnn1)S(=O)(=O)c1c(F)cc(NCc2c(F)cccc2CN2CCC2)cc1F]

To a solution of 2,4,6-trifluoro-N-(pyridazin-3-yl)-N-((2-(trimethylsilyl)ethoxy)methyl)benzenesulfonamide (1.00 g, 2.38 mmol) and (2-(azetidin-1-ylmethyl)-6-fluorophenyl)methanamine (0.74 g, 3.8 mmol) in anhydrous N,N-dimethylformamide (15 mL) was added potassium carbonate (0.66 g, 4.8 mmol) in one portion. The mixture was stirred at ambient temperature for 12 h. The mixture was diluted with water (100 mL) and extracted with ethyl acetate (3×100 mL). The combined organic extracts were washed with brine (30 mL), dried over anhydrous sodium sulfate, filtered and concentrated in vacuo. Purification by preparative reverse phase HPLC using acetonitrile in water containing 0.05% ammonium hydroxide as eluent afforded the title compound as a yellow oil (0.13 g, 9% yield): $^1$H NMR (400 MHz, CDCl$_3$) δ 8.39 (dd, J=9.6, 1.6 Hz, 1H), 8.05 (dd, J=4.0, 1.6 Hz, 1H), 7.92-7.53 (m, 1H), 7.36-7.31 (m, 1H), 7.29-7.22 (m, 1H), 7.11-7.04 (m, 2H), 6.25 (d, J=11.6 Hz, 2H), 5.70 (s, 2H), 4.36 (s, 2H), 3.81-3.73 (m, 2H), 3.63 (br s, 2H), 3.32-3.19 (m, 4H), 2.22-2.11 (m, 2H), 1.02-0.93 (m, 2H), 0.00 (s, 9H); MS (ES+) m/z 594.4 (M+1).

Step 4. Preparation of 4-((2-(azetidin-1-ylmethyl)-6-fluorobenzyl)amino)-2,6-difluoro-N-(pyridazin-3-yl)benzenesulfonamide formate

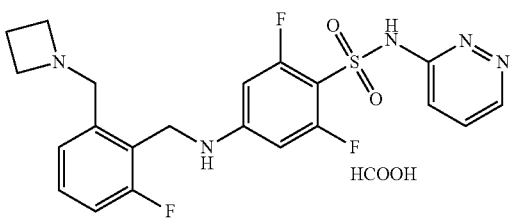

Solid 4-((2-(azetidin-1-ylmethyl)-6-fluorobenzyl)amino)-2,6-difluoro-N-(pyridazin-3-yl)-N-((2-(trimethylsilyl)ethoxy)methyl)benzenesulfonamide (0.12 g, 0.20 mmol) was dissolved in a 4 M solution of hydrogen chloride in methanol (12 mL) and stirred at ambient temperature for 1 h. After concentration in vacuo, purification by preparative reverse phase HPLC using acetonitrile in water containing 0.225% formic acid as eluent, afforded the title compound as a colorless solid (0.0924 g, 90% yield): $^1$H NMR (400 MHz, CDCl$_3$) δ 8.39 (br s, 1H), 8.18 (dd, J=3.6, 1.6 Hz, 1H), 7.42-7.34 (m, 2H), 7.32-7.28 (m, 1H), 7.14-7.07 (m, 2H), 6.22 (d, J=12.0 Hz, 2H), 4.37 (s, 2H), 3.88 (s, 2H), 3.52 (t, J=7.2 Hz, 4H), 2.26 (quin, J=7.2 Hz, 2H), missing 1 COOH and 2 N—H signals; $^{19}$F NMR (376.5 MHz, CDCl$_3$) δ −108.0, −115.1; MS (ES+) m/z 464.1 (M+1).

Example 334

Synthesis of 5-chloro-2-fluoro-4-(((6-fluoro-1H-indazol-7-yl)methyl)amino)-N-(thiazol-4-yl)benzenesulfonamide formate

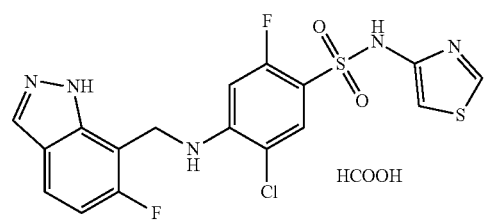 [SMILES: O=S(=O)(Nc1cscn1)c1cc(Cl)c(NCc2c(F)ccc3cn[nH]c23)cc1F ; "HCOOH"]

Step 1. Preparation of 7-bromo-6-fluoro-1H-indazole

To a solution of 3-bromo-2,4-difluorobenzaldehyde (3.00 g, 13.6 mmol) in 1,2-dimethoxyethane (20 mL) was added hydrazine monohydrate (10.3 g, 206 mmol) dropwise. The mixture was stirred at 100° C. for 12 h. After cooling to ambient temperature, the mixture was concentrated in vacuo, diluted with water (100 mL), and extracted with ethyl acetate (3×100 mL). The combined organic extracts were washed with brine (50 mL), dried over anhydrous sodium sulfate, and filtered. Concentration of the filtrate in vacuo and purification of the residue by column chromatography, eluting with a gradient of 9 to 25% of ethyl acetate in petroleum ether, afforded the title compound as a yellow solid (1.50 g, 51% yield): $^1$H NMR (400 MHz, CDCl$_3$) δ 10.14 (br s, 1H), 8.08 (br s, 1H), 7.59 (dd, J=8.8, 4.4 Hz, 1H), 6.96 (t, J=8.8 Hz, 1H); MS (ES+) m/z 215.1 (M+1), 217.1 (M+1).

Step 2. Preparation of 6-fluoro-1H-indazole-7-carbonitrile

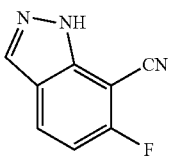 [SMILES: N#Cc1c(F)ccc2cn[nH]c12]

A mixture of 7-bromo-6-fluoro-1H-indazole (1.50 g, 6.98 mmol), tetrakis[triphenylphosphine]palladium(0) (0.40 g, 0.349 mmol) and zinc cyanide (2.46 g, 20.9 mmol, 1.33 mL) in anhydrous N,N-dimethylformamide (10 mL) was heated to 120° C. for 1 h in a microwave reactor. After cooling to ambient temperature, the mixture was diluted with water (100 mL) and extracted with ethyl acetate (3×30 mL). The combined organic extracts were washed with brine (100 mL), dried over anhydrous sodium sulfate, and filtered. Concentration of the filtrate in vacuo and purification of the residue by reverse phase column chromatography, eluting with a gradient of acetonitrile in water containing 0.1% of ammonium hydroxide, to afford the title compound as a yellow solid (0.37 g, 33% yield): $^1$H NMR (400 MHz, CDCl$_3$) δ 8.26 (s, 1H), 8.01 (dd, J=8.8, 4.8 Hz, 1H), 7.09 (t, J=9.2 Hz, 1H), NH not observed; MS (ES+) m/z 162.2 (M+1).

Step 3. Preparation of 6-fluoro-1-((2-(trimethylsilyl)ethoxy)methyl)-1H-indazole-7-carbonitrile To a solution of 6-fluoro-1H-indazole-7-carbonitrile (0.37 g, 2.3 mmol) and potassium carbonate (0.636 g, 4.60 mmol) in anhydrous N,N-dimethylformamide (8 mL) was added 2-(trimethylsilyl)ethoxymethyl chloride (0.575 g, 3.45 mmol) dropwise at 0° C. The mixture was stirred at 0° C. for 1 h and was then diluted with water (100 mL) and extracted with ethyl acetate (3×100 mL). The combined organic extracts were washed with brine (30 mL), dried over anhydrous sodium sulfate, and filtered. Concentration of the filtrate in vacuo and purification of the residue by preparative thin layer chromatography, eluting with 33% of ethyl acetate in petroleum ether, afforded the title compound as a colorless solid (0.27 g, 40% yield): $^1$H NMR (400 MHz, CDCl$_3$) δ8.12 (s, 1H), 7.97 (dd, J=8.8, 4.8 Hz, 1H), 7.11 (t, J=9.2 Hz, 1H), 5.99 (s, 2H), 3.69-3.61 (m, 2H), 0.99-0.92 (m, 2H), 0.03 (s, 9H).

Step 4. Preparation of (6-fluoro-1-((2-(trimethylsilyl)ethoxy)methyl)-1H-indazol-7-yl)methanamine To a solution of 6-fluoro-1-((2-(trimethylsilyl)ethoxy)methyl)-1H-indazole-7-carbonitrile (0.13 g, 0.45 mmol) in methanol (8 mL) and ammonium hydroxide (2 mL) was added Raney-Ni (0.0038 g, 0.045 mmol) in one portion. The mixture was stirred at ambient temperature under an atmosphere of hydrogen (50 psi) for 12 h. The mixture was filtered and the filtrate concentrated in vacuo to yield the title compound as a yellow solid (0.13 g, 98% yield): MS (ES+) m/z 296.3 (M+1).

Step 5. Preparation of tert-butyl ((5-chloro-2-fluoro-4-(((6-fluoro-1-((2-(trimethylsilyl)ethoxy)methyl)-1H-indazol-7-yl)methyl)amino)phenyl)sulfonyl)(thiazol-4-yl)carbamate

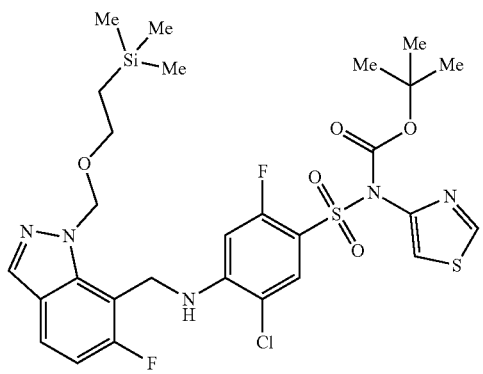 [SMILES: CC(C)(C)OC(=O)N(c1cscn1)S(=O)(=O)c1cc(Cl)c(NCc2c(F)ccc3cnn(COCC[Si](C)(C)C)c23)cc1F]

To a solution of (6-fluoro-1-((2-(trimethylsilyl) ethoxy)methyl)-1H-indazol-7-yl)methanamine (0.11 g, 0.37 mmol) and tert-butyl (5-chloro-2,4-difluorophenyl)sulfonyl(thiazol-4-yl)carbamate (0.153 g, 0.372 mmol) in anhydrous N,N-dimethylformamide (5 mL) was added potassium carbonate (0.103 g, 0.745 mmol) in one portion. The mixture was stirred at ambient temperature for 12 h. The mixture was diluted with water (50 mL) and extracted with ethyl acetate (3×50 mL). The combined organic extracts were washed with brine (20 mL), dried over anhydrous sodium sulfate, filtered, and the filtrate concentrated in vacuo. Purification of the residue by preparative thin layer chromatography, eluting with 33% of ethyl acetate in petroleum ether, afforded the title compound as a colorless oil (0.10 g, 39% yield): $^1$H NMR (400 MHz, CDCl$_3$) δ 8.85 (d, J=2.0 Hz, 1H), 8.06 (s, 1H), 8.02 (d, J=7.2 Hz, 1H), 7.78 (dd, J=8.8, 5.2 Hz, 1H), 7.57 (d, J=2.0 Hz, 1H), 7.16-7.08 (m, 1H), 6.81 (d, J=12.0 Hz, 1H), 5.79 (s, 2H), 5.42 (br s, 1H), 4.91 (br d, J=4.0 Hz, 2H), 3.66-3.60 (m, 2H), 1.44 (s, 9H), 0.99-0.93 (m, 2H), 0.00 (s, 9H); MS (ES+) m/z 686.2 (M+1).

Step 6. Preparation of 5-chloro-2-fluoro-4-(((6-fluoro-1H-indazol-7-yl)methyl)amino)-N-(thiazol-4-yl)benzenesulfonamide formate

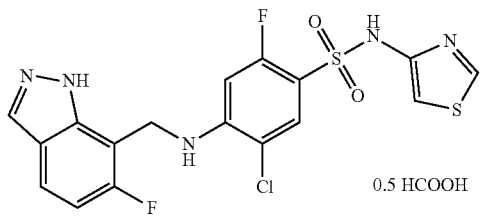 [SMILES: O=S(=O)(Nc1cscn1)c1cc(Cl)c(NCc2c(F)ccc3cn[nH]c23)cc1F]

To tert-butyl ((5-chloro-2-fluoro-4-(((6-fluoro-1-((2-(trimethylsilyl)ethoxy)methyl)-1H-indazol-7-yl)methyl)amino)phenyl)sulfonyl)(thiazol-4-yl)carbamate (0.090 g, 0.13 mmol) was added a 4 M solution of hydrogen chloride in methanol (9 mL), and the mixture was stirred at ambient temperature for 12 h. After concentration in vacuo, the residue was purified by preparative reverse phase HPLC, using acetonitrile in water containing 0.225% formic acid as eluent, to afford the title compound as a colorless solid (0.0326 g, 49% yield): $^1$H NMR (400 MHz, DMSO-d$_6$) δ 13.34 (br s, 1H), 8.76 (s, 1H), 8.30 (br s, 0.5H), 8.11 (s, 1H), 7.74 (dd, J=8.8, 5.2 Hz, 1H), 7.55 (d, J=7.2 Hz, 1H), 7.02 (dd, J=10.0, 8.8 Hz, 1H), 6.97 (br s, 1H), 6.68 (br s, 1H), 6.62 (br d, J=12.8 Hz, 1H), 4.71 (br d, J=6.0 Hz, 2H); MS (ES+) m/z 456.0 (M+1).

Example 335

Synthesis of (R)-5-chloro-4-((1-(2,5-difluorophenyl)-2,2-difluoroethyl)amino)-2-fluoro-N-(thiazol-4-yl)benzenesulfonamide

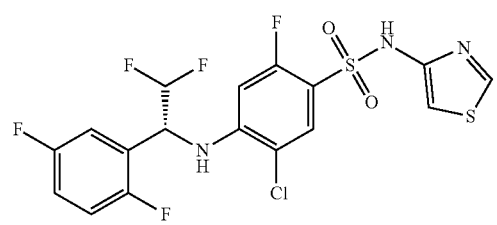 [SMILES: O=S(=O)(Nc1cscn1)c1cc(Cl)c(N[C@H](c2cc(F)ccc2F)C(F)F)cc1F]

Step 1. Preparation of 1-(2,5-difluorophenyl)-2,2-difluoroethane-1-one

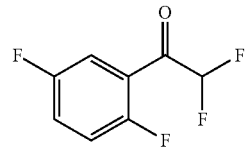 [SMILES: O=C(c1cc(F)ccc1F)C(F)F]

To solution of N,N-diisopropylamine (5.85 g, 57.9 mmol, 8.13 mL) in anhydrous tetrahydrofuran (100 mL) was added n-butyllithium (2.5 M, 23.14 mL, 57.9 mmol) at −70° C. After stirring for 30 minutes, 1,4-difluorobenzene (6.00 g, 52.6 mmol, 5.13 mL) was added to the mixture dropwise at −70° C. After stirring at −70° C. for another 30 minutes, ethyl 2,2-difluoroacetate (7.83 g, 63.11 mmol) was added dropwise. The reaction mixture was allowed to warm to ambient temperature and stirred for 1 h. The mixture was diluted with water (100 mL) and extracted with ethyl acetate (2×100 mL). The organic phase was dried over anhydrous sodium sulfate, filtered, and the filtrate concentrated in vacuo. Purification of the residue by column chromatography, eluting with a gradient of 1 to 5% of ethyl acetate in petroleum ether, afforded the title compound as a colorless oil (5.00 g, 49% yield): $^1$H NMR (400 MHz, CDCl$_3$) δ 7.56 (ddd, J=8.2, 5.2, 3.2 Hz, 1H), 7.29 (tdd, J=8.8, 7.2, 3.6 Hz, 1H), 7.18-7.08 (m, 1H), 6.35 (td, J=53.2, 2.8 Hz, 1H).

Step 2. Preparation of (R)—N—((R)-1-(2,5-difluorophenyl)-2,2-difluoroethyl)-2-methylpropane sulfinamide

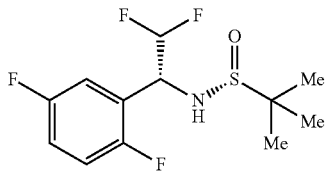 [SMILES: CC(C)(C)[S@@](=O)N[C@H](c1cc(F)ccc1F)C(F)F]

To a solution of (R)-2-methylpropane-2-sulfinamide (4.73 g, 39.1 mmol) and titanium(iv) isopropoxide (14.79 g, 52.06 mmol, 15.41 mL) in anhydrous diethyl ether (100 mL) was added 1-(2,5-difluorophenyl)-2,2-difluoroethanone (5.00 g, 26.0 mmol) at ambient temperature. The reaction mixture was heated to reflux for 1 h. The mixture was then cooled to −70° C. and sodium borohydride (2.36 g, 62.5 mmol) was added in portions. The resulting mixture was stirred at −70° C. for 3 h, diluted with saturated brine solution (20 mL), and allowed to warm to ambient temperature. The resulting suspension was filtered through a plug of Celite and the filter cake was washed with ethyl acetate (20 mL). The combined filtrate was washed with brine (20 mL). The aqueous layer was extracted with ethyl acetate (2×100 mL). The combined organic extracts were dried over anhydrous sodium sulfate, filtered, and the filtrate concentrated in vacuo. Purification of the residue by column chromatography, eluting with a gradient of 9 to 33% of ethyl acetate in petroleum ether, afforded the title compound as a colorless oil (3.00 g, 39% yield): $^1$H NMR (400 MHz, CDCl$_3$) δ 7.14-7.08 (m, 3H), 6.08 (t, J=55.2 Hz, 1H), 4.99 (ddt, J=12.0, 6.0, 3.6 Hz, 1H), 3.94 (br d, J=5.6 Hz, 1H), 1.27 (s, 9H).

Step 3. Preparation of (R)-1-(2,5-difluorophenyl)-2,2-difluoroethane-1-amine

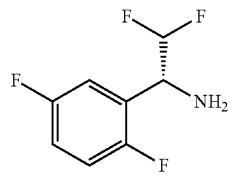 [SMILES: N[C@H](c1cc(F)ccc1F)C(F)F]

To (R)—N—((R)-1-(2,5-difluorophenyl)-2,2-difluoroethyl)-2-methylpropane-2-sulfinamide (1.20 g, 4.04 mmol) was added a 4 M solution of hydrogen chloride in methanol (12.01 mL) and the mixture was stirred at ambient temperature for 1 h. The reaction mixture was concentrated under reduced pressure to afford the title compound as a colorless solid (0.600 g, 77% yield): $^1$H NMR (400 MHz, DMSO-d$_6$) δ 9.52 (br s, 2H), 7.86-7.70 (m, 1H), 7.53-7.34 (m, 2H), 6.61 (t, J=54.0 Hz, 1H), 5.18-4.96 (m, 1H); MS (ES+) m/z 194.0 (M+1).

Step 4. Preparation of tert-butyl (R)-((5-chloro-4-((1-(2,5-difluorophenyl)-2,2-difluoroethyl)amino)-2-fluorophenyl)sulfonyl)(thiazol-4-yl)carbamate

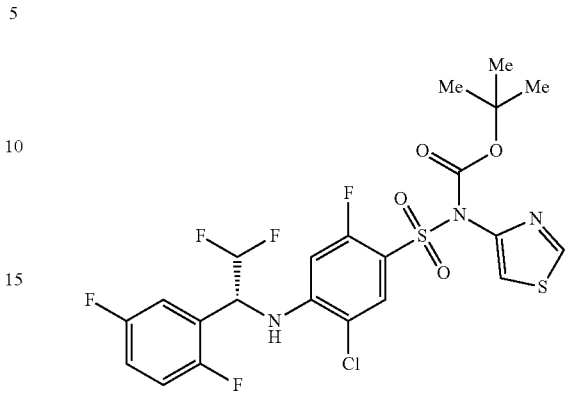

To a solution of tert-butyl (5-chloro-2,4-difluorophenyl)sulfonyl(thiazol-4-yl)carbamate (0.300 g, 0.730 mmol) in anhydrous dimethyl sulfoxide (5 mL) was added N,N-diisopropylethylamine (0.319 mL, 1.83 mmol) and (R)-1-(2,5-difluorophenyl)-2,2-difluoroethanamine (0.423 g, 2.19 mmol). The mixture was then heated to 70° C. for 24 h. The reaction mixture was diluted with water (10 mL) and extracted with ethyl acetate (2×10 mL). The combined organic layers were washed with brine (10 mL), dried over anhydrous sodium sulfate, and filtered. Concentration of the filtrate in vacuo and purification of the residue by preparative thin layer chromatography, eluting with 20% of ethyl acetate in petroleum ether, afforded the title compound as a yellow oil (0.080 g, 19% yield): MS (ES+) m/z 483.9 (M−99), 485.9 (M−99).

Step 5. Preparation of (R)-5-chloro-4-((1-(2,5-difluorophenyl)-2,2-difluoroethyl)amino)-2-fluoro-N-(thiazol-4-yl)benzenesulfonamide

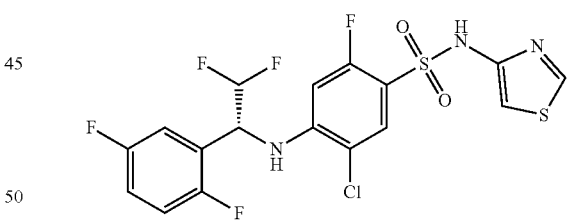

To tert-butyl (R)-((5-chloro-4-((1-(2,5-difluorophenyl)-2,2-difluoroethyl)amino)-2-fluorophenyl)sulfonyl)(thiazol-4-yl)carbamate (0.080 g, 0.137 mmol) was added a 4 M solution of hydrogen chloride in methanol (5 mL) and the reaction mixture was stirred at ambient temperature for 30 minutes. After concentration in vacuo, the residue was purified by preparative reverse phase HPLC using, acetonitrile in water containing 0.225% formic acid as eluent, to afford the title compound as a colorless solid (0.017 g, 26% yield): $^1$H NMR (400 MHz, CD$_3$OD) δ 8.70 (d, J=2.0 Hz, 1H), 8.51 (s, 1H), 7.75 (d, J=7.2 Hz, 1H), 7.31-7.22 (m, 2H), 7.22-7.13 (m, 1H), 6.92 (d, J=1.2 Hz, 1H), 6.55 (d, J=12.4 Hz, 1H), 6.33 (dt, J=55.2, 4.0 Hz, 1H), 5.31 (dt, J=11.8, 4.0 Hz, 1H), NH not observed. MS (ES+) m/z 483.9 (M+1), 485.9 (M+1).

Example 336

Synthesis of (S)-5-chloro-4-((1-(2,5-difluorophenyl)ethyl)amino)-2-fluoro-N-(thiazol-4-yl)benzenesulfonamide

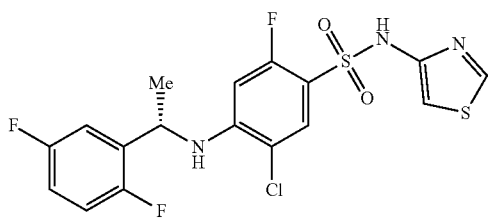 [SMILES: C[C@H](Nc1cc(F)c(S(=O)(=O)Nc2cscn2)cc1Cl)c1cc(F)ccc1F]

Step 1. Preparation of tert-butyl (S)-((5-chloro-4-((1-(2,5-difluorophenyl)ethyl)amino)-2-fluorophenyl)sulfonyl)(thiazol-4-yl)carbamate

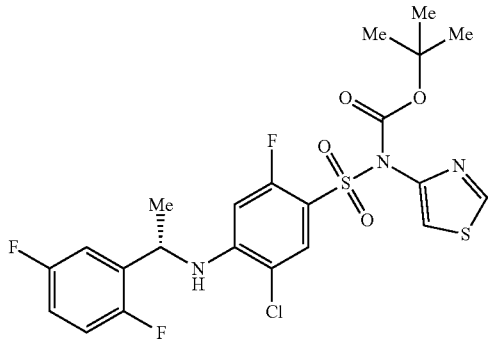 [SMILES: C[C@H](Nc1cc(F)c(S(=O)(=O)N(C(=O)OC(C)(C)C)c2cscn2)cc1Cl)c1cc(F)ccc1F]

Following the procedure as described for EXAMPLE 5, Step 1 and making non-critical variations as required to replace (S)-1-(5-chloro-2-fluorophenyl)ethan-1-amine hydrochloride with (S)-1-(2,5-difluorophenyl)ethan-1-amine hydrochloride, the title compound was obtained as a yellow solid (0.800 mg, 50%): MS (ES+) m/z 447.9 (M−99).

Step 2. Preparation of (S)-5-chloro-4-((1-(2,5-difluorophenyl)ethyl)amino)-2-fluoro-N-(thiazol-4-yl)benzenesulfonamide

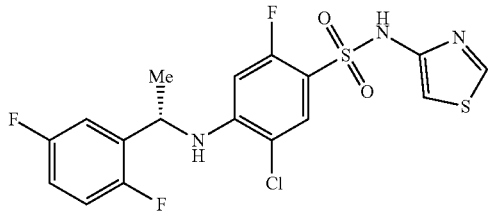 [SMILES: C[C@H](Nc1cc(F)c(S(=O)(=O)Nc2cscn2)cc1Cl)c1cc(F)ccc1F]

Following the procedure as described for EXAMPLE 5, Step 2 and making non-critical variations as required to replace tert-butyl (S)-((5-chloro-4-((1-(5-chloro-2-fluorophenyl)ethyl)amino)-2-fluorophenyl)sulfonyl)(thiazol-4-yl)carbamate with tert-butyl (S)-((5-chloro-4-((1-(2,5-difluorophenyl)ethyl)amino)-2-fluorophenyl)sulfonyl)(thiazol-4-yl)carbamate, the title compound was obtained as a colorless solid (0.153 mg, 61% yield): $^1$H NMR (400 MHz, DMSO-$d_6$) δ 8.84 (d, J=2.0 Hz, 1H), 7.62 (d, J=7.4 Hz, 1H), 7.32-7.22 (m, 2H), 7.18-7.10 (m, 1H), 6.90 (br s, 1H), 6.61 (d, J=7.8 Hz, 1H), 6.39 (d, J=13.0 Hz, 1H), 4.93 (quin, J=6.8 Hz, 1H), 1.55 (d, J=6.8 Hz, 3H), NH not observed; MS (ES+) m/z 447.9 (M+1).

Example 337

Synthesis of 2,6-difluoro-4-((2-fluoro-6-((3-fluoro-3-methylazetidin-1-yl)methyl)benzyl)amino)-N-(isoxazol-3-yl)benzenesulfonamide formate

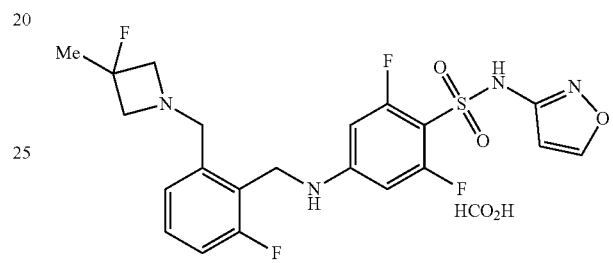

Step 1. Preparation of 2-fluoro-6-((3-fluoro-3-methylazetidin-1-yl)methyl)benzonitrile

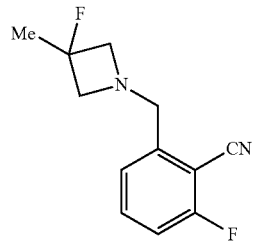 [SMILES: CC1(F)CN(Cc2cccc(F)c2C#N)C1]

To a solution of 2-(bromomethyl)-6-fluorobenzonitrile (0.35 g, 1.64 mmol) and 3-fluoro-3-methylazetidine hydrochloride (0.27 g, 2.13 mmol) in anhydrous N,N-dimethylformamide (10 mL) was added potassium carbonate (0.90 g, 6.54 mmol). The mixture was stirred at ambient temperature for 12 h, and then diluted with water (30 mL) and extracted with ethyl acetate (3×30 mL). The combined organic extracts were washed with brine (20 mL), dried over anhydrous sodium sulfate, and filtered. Concentration of the filtrate in vacuo and purification of the residue by column chromatography, eluting with a gradient of 20 to 35% of ethyl acetate in petroleum ether, provided 2-fluoro-6-((3-fluoro-3-methylazetidin-1-yl)methyl)benzonitrile as a colorless oil (0.36 g, 99% yield): $^1$H NMR (400 MHz, CDCl$_3$) δ 7.48 (td, J=8.2, 5.6 Hz, 1H), 7.24 (d, J=7.6 Hz, 1H), 7.03 (t, J=8.4 Hz, 1H), 3.80 (s, 2H), 3.40-3.23 (m, 4H), 1.64-1.54 (m, 3H); MS (ES+) m/z 223.3 (M+1).

Step 2. Preparation of (2-fluoro-6-((3-fluoro-3-methylazetidin-1-yl)methyl)phenyl)methanamine

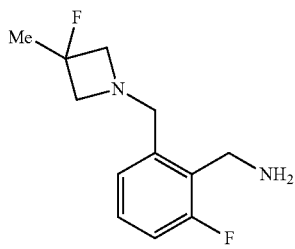 [SMILES: CC1(F)CN(Cc2cccc(F)c2CN)C1]

To a solution of 2-fluoro-6-((3-fluoro-3-methylazetidin-1-yl)methyl)benzonitrile (0.31 g, 1.39 mmol) in methanol (20 mL) and ammonium hydroxide (4 mL) was added Raney-Ni (0.024 g, 0.28 mmol). The mixture was stirred under a hydrogen atmosphere (50 psi) at ambient temperature for 12 h. The mixture was filtered and the filtrate concentrated in vacuo. The residue was purified by preparative reverse-phase HPLC, using a gradient of acetonitrile in water (containing ammonium carbonate, 0.010 M), to provide the title compound as a colorless oil (0.11 g, 35% yield): $^1$H NMR (400 MHz, CDCl$_3$) δ 7.14-7.07 (m, 1H), 6.98-6.91 (m, 2H), 3.84 (d, J=1.6 Hz, 2H), 3.66 (s, 2H), 3.31-3.13 (m, 4H), 1.58-1.48 (m, 3H), NH not observed; MS (ES+) m/z 227.3 (M+1).

Step 3. Preparation of 2,4,6-trifluoro-N-(isoxazol-3-yl)benzenesulfonamide

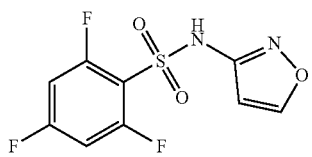 [SMILES: O=S(=O)(Nc1ccon1)c1c(F)cc(F)cc1F]

To a mixture of isoxazol-3-amine (10.00 g, 119 mmol), pyridine (18.80 g, 238 mmol) and N,N-dimethylpyridin-4-amine (1.45 g, 11.9 mmol) in anhydrous dichloromethane (100 mL) was added 2,4,6-trifluorobenzenesulfonyl chloride (32.90 g, 142.70 mmol), and the mixture was stirred at ambient temperature for 3 h. The reaction mixture was quenched with 1 M hydrochloric acid (500 mL) and extracted with dichloromethane (3×800 mL). The combined organic layers were washed with brine (3×100 mL), dried over anhydrous sodium sulfate, and filtered. Concentration of the filtrate in vacuo and purification of the residue by column chromatography, eluting with 10 to 100% of ethyl acetate in petroleum ether, provided the title compound as a yellow solid (13.8 g, 42% yield): $^1$H NMR (400 MHz, CDCl$_3$) δ 8.18 (d, J=1.8 Hz, 1H), 6.71 (t, J=8.4 Hz, 2H), 6.53 (d, J=1.8 Hz, 1H), NH not observed; MS (ES+) m/z 279.0 (M+1).

Step 4. Preparation of 2,4,6-trifluoro-N-(isoxazol-3-yl)-N-(4-methoxybenzyl)-benzenesulfonamide

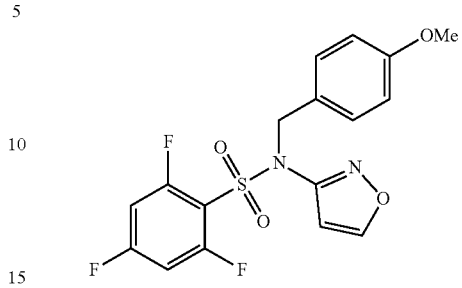

To a solution of 2,4,6-trifluoro-N-(isoxazol-3-yl)benzenesulfonamide (9.00 g, 32.40 mmol) in anhydrous N,N-dimethylformamide (100 mL) was added sodium bicarbonate (13.06 g, 155.48 mmol) and 4-methoxybenzyl chloride (6.59 g, 42.10 mmol). The mixture was heated to 40° C. for 4 h, and then diluted with water (500 mL) and extracted with ethyl acetate (3×500 mL). The combined organic layers were washed with brine (3×100 mL), dried over anhydrous sodium sulfate, and filtered. Concentration of the filtrate under pressure afforded a residue which was purified by column chromatography, eluting with 10 to 33% of ethyl acetate in petroleum ether. Further purification by trituration with methanol (30 mL) provided the title compound as a colorless solid (10.0 g, 77% yield): $^1$H NMR (400 MHz, CDCl$_3$) δ 8.13 (d, J=1.8 Hz, 1H), 7.31 (d, J=8.8 Hz, 2H), 6.81-6.63 (m, 4H), 6.54 (d, J=1.8 Hz, 1H), 5.02 (s, 2H), 3.69 (s, 3H); MS (ES+) m/z 421.0 (M+23).

Step 5. Preparation of 2,6-difluoro-4-((2-fluoro-6-((3-fluoro-3-methylazetidin-1-yl)methyl)benzyl)amino)-N-(isoxazol-3-yl)-N-(4-methoxybenzyl)benzenesulfonamide

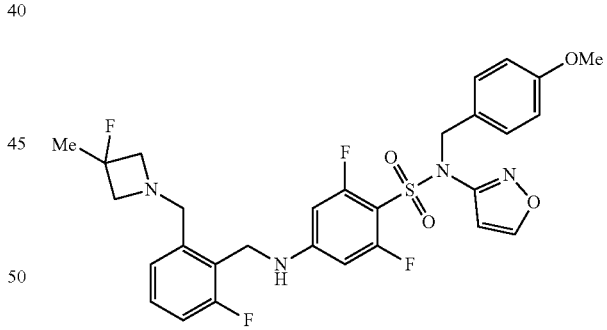

To a solution of (2-fluoro-6-((3-fluoro-3-methylazetidin-1-yl) methyl)phenyl)methanamine (0.090 g, 0.40 mmol) and 2,4,6-trifluoro-N-(isoxazol-3-yl)-N-(4-methoxybenzyl)benzenesulfonamide (0.16 g, 0.40 mmol) in anhydrous N,N-dimethylformamide (5 mL) was added potassium carbonate (0.11 g, 0.80 mmol). The mixture was stirred at ambient temperature for 12 h, then diluted with water (50 mL) and extracted with ethyl acetate (3×40 mL). The combined organic extracts were washed with brine (30 mL), dried over anhydrous sodium sulfate, and filtered. Concentration of the filtrate in vacuo and purification of the residue by preparative thin layer chromatography, eluting with 33% of petroleum ether in ethyl acetate, provided the title compound as a colorless oil (0.11 g, 46% yield): $^1$H NMR (400 MHz, CDCl$_3$) δ 8.15 (d, J=1.6 Hz, 1H), 7.38 (d, J=8.4 Hz, 2H), 7.26-7.18 (m, 1H), 7.11-7.01 (m, 2H), 6.80 (d, J=8.4 Hz, 2H), 6.66 (d, J=1.6 Hz, 1H), 6.18 (d, J=12.2 Hz, 2H), 5.05 (s, 2H), 4.34 (br s, 2H), 3.75 (s, 3H), 3.70 (s, 2H), 3.37-3.17 (m, 4H), 1.63-1.52 (m, 3H), NH not observed; MS (ES+) m/z 605.3 (M+1).

Step 6. Preparation of 2,6-difluoro-4-((2-fluoro-6-((3-fluoro-3-methylazetidin-1-yl)methyl)benzyl)amino)-N-(isoxazol-3-yl)benzenesulfonamide formate

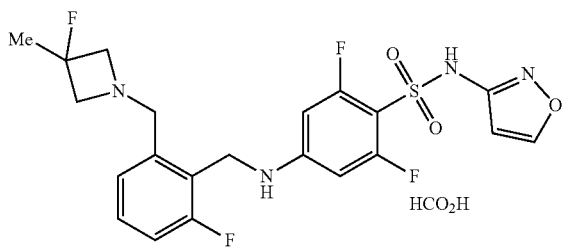 [SMILES: CC1(F)CN(Cc2cccc(F)c2CNc2cc(F)c(S(=O)(=O)Nc3ccon3)c(F)c2)C1 ; "HCO2H"]

To a solution of 2,6-difluoro-4-((2-fluoro-6-((3-fluoro-3-methylazetidin-1-yl)methyl)benzyl)amino)-N-(isoxazol-3-yl)-N-(4-methoxybenzyl)benzenesulfonamide (0.11 g, 0.18 mmol) in dichloromethane (3 mL) was added trifluoroacetic acid (3 mL). The mixture was stirred at ambient temperature for 12 h, and then concentrated in vacuo. The residue was purified by preparative reverse-phase HPLC, eluting with a gradient of acetonitrile in water (containing 0.22% formic acid), to afford the title compound as a colorless solid (0.045 g, 47% yield): $^1$H NMR (400 MHz, CD$_3$OD) δ 8.45 (d, J=1.6 Hz, 1H), 8.14 (br s, 1H), 7.34 (td, J=8.0, 5.6 Hz, 1H), 7.19 (d, J=7.2 Hz, 1H), 7.11 (t, J=9.2 Hz, 1H), 6.43 (d, J=1.6 Hz, 1H), 6.37-6.30 (m, 2H), 4.42 (d, J=1.2 Hz, 2H), 3.83 (s, 2H), 3.40 (s, 2H), 3.37-3.35 (m, 2H), 1.60-1.53 (m, 3H), exchangeable protons not observed; MS (ES+) m/z 485.0 (M+1).

Example 338

Synthesis of (S)-5-chloro-2-fluoro-4-(1-(2-fluorophenyl)propoxy)-N-(thiazol-4-yl)benzenesulfonamide

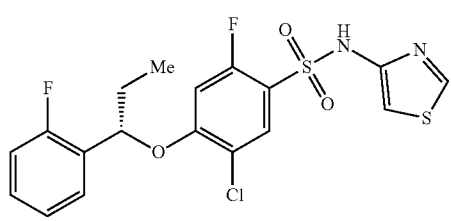 [SMILES: CC[C@H](Oc1cc(F)c(S(=O)(=O)Nc2cscn2)cc1Cl)c1ccccc1F]

Step 1. Preparation of tert-butyl (S)-((5-chloro-2-fluoro-4-(1-(2-fluorophenyl)propoxy)phenyl)sulfonyl)(thiazol-4-yl)carbamate

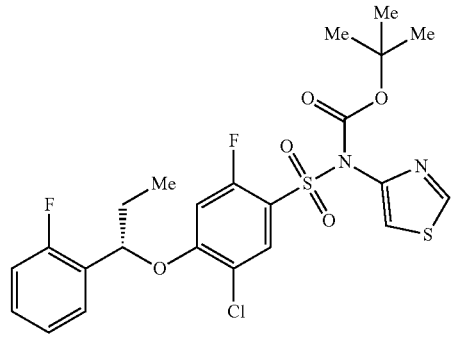 [SMILES: CC[C@H](Oc1cc(F)c(S(=O)(=O)N(C(=O)OC(C)(C)C)c2cscn2)cc1Cl)c1ccccc1F]

To a mixture of (S)-1-(2-fluorophenyl)propan-1-ol (0.070 g, 0.45 mmol) and tert-butyl (5-chloro-2,4-difluorophenyl)sulfonyl(thiazol-4-yl)carbamate (0.22 g, 0.54 mmol) in anhydrous dimethyl sulfoxide (3 mL) was added cesium carbonate (0.30 g, 0.91 mmol). The mixture was stirred at ambient temperature for 4 h, and then poured onto ice water (30 mL). The mixture was extracted with ethyl acetate (3×30 mL). The combined organic extracts were washed with brine (50 mL), dried over anhydrous sodium sulfate, and filtered. Concentration of the filtrate in vacuo afforded the title compound as a yellow oil (0.30 g, quantitative yield): MS (ES+) m/z 545.2 (M+1).

Step 2. Preparation of (S)-5-chloro-2-fluoro-4-(1-(2-fluorophenyl)propoxy)-N-(thiazol-4-yl)benzenesulfonamide

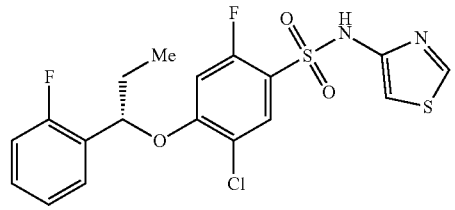 [SMILES: CC[C@H](Oc1cc(F)c(S(=O)(=O)Nc2cscn2)cc1Cl)c1ccccc1F]

Following the procedure as described in EXAMPLE 145, step 5 and making non-critical variations to replace tert-butyl (2-(azetidin-1-ylmethyl)-6-fluorobenzyl)(4-(N-(2,4-dimethoxybenzyl)-N-(pyrimidin-2-yl)sulfamoyl)-3,5-difluorophenyl)carbamate with tert-butyl (S)-((5-chloro-2-fluoro-4-(1-(2-fluorophenyl)propoxy)phenyl)sulfonyl)(thiazol-4-yl)carbamate, and purification preparative reverse phase HPLC, using a gradient of acetonitrile in water (containing 0.225% of formic acid), the title compound was afforded as a colorless solid (0.069 g, 30% yield): $^1$H NMR (400 MHz, CDCl$_3$) δ 9.33 (s, 1H), 8.63 (d, J=2.4 Hz, 1H), 7.87 (d, J=7.6 Hz, 1H), 7.34-7.30 (m, 2H), 7.14 (d, J=7.6 Hz, 2H), 6.98 (d, J=2.0 Hz, 1H), 6.54 (d, J=11.6 Hz, 1H), 5.46 (t, J=6.4 Hz, 1H), 2.16 (q, J=7.2 Hz, 1H), 2.01 (q, J=7.2 Hz, 1H), 1.06 (t, J=7.2 Hz, 3H); MS (ES+) m/z 445.1 (M+1).

BIOLOGICAL ASSAYS

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Electrophysiological Assay (In Vitro Assay)

Patch voltage clamp electrophysiology allows for the direct measurement and quantification of block of voltage-gated sodium channels ($Na_V$'s), and allows the determination of the time- and voltage-dependence of block which has been interpreted as differential binding to the resting, open, and inactivated states of the sodium channel (Hille, B., *Journal of General Physiology* (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% $CO_2$. HEK cells used for the electrophysiology (EP) recordings had a passage number of less than 40 for all studies and were used within three days from the time of plating. $Na_V1.1$, $Na_V1.5$ and $Na_V1.6$ cDNAs (NM_001165964 (SCN1A), NM_000335 (SCN5A) and NM_014191 (SCN8A), respectively) were stably expressed in HEK-293 cells.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM $CaCl_2$, 2 mM $MgCl_2$, 10 mM HEPES, 10 mM EGTA; and adjusted to pH 7.2 with CsOH. The external solution had the following composition: 140 mM NaCl, 5 mM KCl, 2 mM $CaCl_2$, 1 mM $MgCl_2$, 10 mM HEPES; and adjusted to pH 7.4 with NaOH. In some studies, the external sodium was reduced by equimolar replacement with choline. Osmolarity in the CsF internal and NaC external solutions was adjusted to 300 mOsm/kg and 310 mOsm/kg with glucose, respectively. All recordings were performed at ambient temperature in a bath chamber with a volume of 150 µL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete. The voltage is then stepped back to a very negative (Vhold=−150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels.

Representative compounds of the invention, when tested in this assay, demonstrated the $IC_{50}$'s as set forth below in Table 1.

Biological Example 2

Sodium Influx Assay (In Vitro Assay)

This sodium influx assay employs the use of the cell permeable, sodium sensitive dye ANG2 to quantify sodium ion influx through sodium channels which are maintained in an open state by use of sodium channel modulators. This high throughput sodium influx assay allows for rapid profiling and characterization of sodium channel blockers.

In general, Trex HEK293 cells were stably transfected with an inducible expression vector containing the full-length cDNA coding for the desired human sodium channel α-subunit and with an expression vector containing full length cDNA coding for the β1-subunit. Sodium channel expressing cell lines were induced with tetracycline (1 µg/mL) and plated on 384-well PDL-coated plates at a density of 25K-30K cells/well in culture media (DMEM, containing 10% FBS and 1% L-glutamine). After overnight incubation (37° C., 5% $CO_2$), culture media was removed and cells were loaded with 5 uM ANG2 dye for 1-1.5 h in Buffer 1 (155 mM NMDG, 5 mM KCl, 2 mM $CaCl_2$, 1 mM $MgCl_2$, 10 mM HEPES, 10 mM glucose, adjusted with Tris to pH 7.4). Access dye was removed and cells were incubated with test compounds for 1 hr in buffer 1 containing sodium channel modulator(s) at room temperature. Hamamatsu FDSS µCell was used to perform a 1:1 addition of Na/K challenge buffer (140 mM NaCl, 20 mM HEPES, 1 mM $CaCl_2$, 15 mM KCl, 1 mM $MgCl_2$, 10 mM glucose, adjusted with Tris to pH 7.4) and simultaneously read plates at excitation wavelength of 530 nm and emission wavelength set at 558 nm. Percent inhibition of sodium ion influx was calculated for each test compound at each test concentration to determine the $IC_{50}$ values.

Representative compounds of the invention, when tested in this model, demonstrated affinities for the inactivated state of $Na_V1.6$, $Na_V1.5$ and $Na_V1.1$ as set forth below in Table 1.

The Example numbers provided in Table 1 correspond to the Examples herein, "Flux" refers to the Sodium Influx Assay and "EP" refers to the Electrophysiological Assay:

TABLE 1

| | Inhibition of Nav1.1, Nav1.5, and $Na_V1.6$ | | | | | |
|---|---|---|---|---|---|---|
| Ex. No. | Flux $Na_V1.6$ $IC_{50}$ (µM) | EP Nav1.6 $IC_{50}$ (µM) | Flux $Na_V1.5$ $IC_{50}$ (µM) | EP Nav1.5 $IC_{50}$ (µM) | Flux $Na_V1.1$ $IC_{50}$ (µM) | EP Nav1.1 $IC_{50}$ (µM) |
| 1 | 0.120 | | 8.916 | | 0.784 | |
| 2 | 5.021 | | 8.246 | | 15.982 | |
| 3 | 0.679 | | 5.254 | | 3.379 | |
| 4 | 0.794 | 0.041 | 7.010 | | 3.401 | 5.306 |
| 5 | 0.785 | 0.152 | 5.311 | 10.000 | 4.831 | 10.000 |
| 6 | 3.377 | | 5.516 | | 3.758 | |
| 7 | 0.376 | | 9.682 | | 2.995 | |

TABLE 1-continued

Inhibition of Nav1.1, Nav1.5, and Na$_V$1.6

| Ex. No. | Flux Na$_V$1.6 IC$_{50}$ (μM) | EP Nav1.6 IC$_{50}$ (μM) | Flux Na$_V$1.5 IC$_{50}$ (μM) | EP Nav1.5 IC$_{50}$ (μM) | Flux Na$_V$1.1 IC$_{50}$ (μM) | EP Nav1.1 IC$_{50}$ (μM) |
|---|---|---|---|---|---|---|
| 8 | 0.137 | 0.010 | 5.366 | | 1.626 | 0.420 |
| 9 | 0.181 | 0.026 | 4.222 | | 2.363 | 4.335 |
| 10 | 0.461 | 0.128 | 2.349 | | 1.630 | 5.474 |
| 11 | 0.255 | 0.034 | 30.000 | | 30.000 | 10.000 |
| 12 | 1.980 | | 30.000 | | 30.000 | |
| 13 | 5.888 | | 30.000 | | 30.000 | |
| 14 | 1.790 | | 14.431 | | 4.651 | |
| 15 | 7.149 | | 23.642 | | 9.409 | |
| 16 | 0.029 | 0.004 | 23.462 | | 5.408 | 2.189 |
| 17 | 0.308 | | 8.459 | | 0.494 | |
| 18 | 3.351 | | 11.888 | | 8.373 | |
| 19 | 0.425 | 0.130 | 18.511 | | 11.669 | 10.000 |
| 20 | 2.052 | 1.177 | 30.000 | | 30.000 | 10.000 |
| 21 | 3.668 | | 2.888 | | 3.631 | |
| 22 | 1.296 | 0.259 | 4.855 | | 4.291 | 9.000 |
| 23 | 1.519 | | 4.088 | | 5.398 | |
| 24 | 4.092 | | 8.325 | | 5.851 | |
| 25 | 0.175 | 0.057 | 10.297 | | 1.872 | 2.516 |
| 26 | 0.742 | 0.113 | 3.452 | | 4.742 | 6.751 |
| 27 | 0.069 | 0.012 | 8.493 | | 0.476 | 0.112 |
| 28 | 0.876 | 0.406 | 8.254 | | 7.367 | 10.000 |
| 29 | 30.000 | | 24.596 | | 30.000 | |
| 30 | 1.441 | 0.652 | 12.661 | | 10.848 | 10.000 |
| 31 | 0.917 | 0.118 | 16.934 | | 6.168 | 10.000 |
| 32 | 0.092 | 0.023 | 12.788 | | 1.056 | |
| 33 | 0.462 | | 25.817 | | 2.992 | |
| 34 | 1.271 | | 4.910 | | 0.840 | |
| 35 | 0.839 | | 8.691 | | 0.301 | |
| 36 | 1.398 | | 5.117 | | 1.341 | |
| 37 | 2.088 | | 12.346 | | 1.904 | |
| 38 | 0.341 | 0.024 | 9.892 | 10.000 | 2.645 | 0.994 |
| 39 | 0.791 | 0.285 | 6.806 | | 2.350 | 1.846 |
| 40 | 0.123 | 0.024 | 7.898 | | 0.637 | 0.182 |
| 41 | 0.070 | 0.010 | 11.777 | | 0.364 | 0.031 |
| 42 | 3.026 | 0.305 | 14.441 | | 5.646 | 6.768 |
| 43 | 0.191 | 0.028 | 11.122 | | 2.139 | 4.103 |
| 44 | 0.347 | 0.130 | 30.000 | | 1.271 | 2.091 |
| 45 | 0.108 | 0.013 | 6.259 | 5.151 | 1.176 | 0.539 |
| 46 | 1.662 | | 7.040 | | 0.999 | |
| 47 | 0.089 | 0.010 | 6.515 | | 0.816 | 0.114 |
| 48 | 0.716 | 0.230 | 8.656 | | 1.358 | 2.604 |
| 49 | 0.232 | 0.019 | 4.746 | | 0.888 | 0.260 |
| 50 | 0.169 | | 6.073 | | 1.278 | |
| 51 | 10.850 | | 20.603 | | 4.274 | |
| 52 | 0.234 | 0.037 | 10.482 | | 1.545 | 0.590 |
| 53 | 0.741 | | 6.889 | | 0.726 | |
| 54 | 0.265 | 0.025 | 13.516 | | 3.244 | 1.025 |
| 55 | 20.715 | | 21.253 | | 16.083 | |
| 56 | 0.949 | 0.292 | 30.000 | | 4.031 | 1.415 |
| 57 | 2.293 | | 30.000 | | 2.599 | |
| 58 | 0.152 | | 7.086 | | 2.529 | |
| 59 | 0.387 | 0.077 | 30.000 | | 8.394 | 1.718 |
| 60 | 3.341 | | 30.000 | | 1.570 | |
| 61 | 0.021 | 0.004 | 8.910 | 10.000 | 1.129 | 0.283 |
| 62 | 0.138 | 0.052 | 30.000 | | 17.251 | 3.098 |
| 63 | 0.392 | 0.066 | 30.000 | | 14.147 | 10.000 |
| 64 | 0.197 | 0.085 | 30.000 | | 14.476 | 10.000 |
| 65 | 1.019 | 0.087 | 30.000 | | 2.230 | 10.000 |
| 66 | 1.012 | 1.113 | 30.000 | | 0.908 | 10.000 |
| 67 | 0.426 | 0.119 | 30.000 | | 10.568 | 10.000 |
| 68 | 1.808 | | 25.284 | | 5.148 | |
| 69 | 1.591 | | 7.662 | | 3.030 | |
| 70 | 0.181 | 0.036 | 30.000 | | 30.000 | 10.000 |
| 71 | 30.000 | | 30.000 | | 30.000 | |
| 72 | 7.105 | 0.955 | 30.000 | | 30.000 | 10.000 |
| 73 | 3.868 | 1.139 | 30.000 | | 23.119 | 10.000 |
| 74 | 0.521 | 0.052 | 30.000 | | 2.518 | 1.853 |
| 75 | 0.261 | | 21.671 | | 13.646 | |
| 76 | 0.397 | 0.126 | 10.276 | | 3.971 | 10.000 |
| 77 | 8.079 | | 26.085 | | 7.975 | |
| 78 | 0.234 | 0.015 | 7.008 | | 4.169 | 3.103 |
| 79 | 0.237 | 0.039 | 2.548 | | 1.542 | 4.406 |
| 80 | 1.744 | 0.099 | 5.752 | | 11.137 | 10.000 |
| 81 | 0.652 | 0.143 | 30.000 | | 22.468 | 10.000 |
| 82 | 2.155 | | 30.000 | | 28.736 | |
| 83 | 12.338 | | 30.000 | | 11.013 | |
| 84 | 1.169 | 1.773 | 19.337 | | 2.413 | 10.000 |
| 85 | 0.107 | 0.078 | 30.000 | | 0.516 | |
| 86 | 4.060 | 0.558 | 12.743 | | 16.643 | |
| 87 | 8.596 | | 24.672 | | 30.000 | |
| 88 | 1.041 | 0.184 | 18.215 | | 30.000 | 10.000 |
| 89 | 0.948 | 0.239 | 9.090 | | 3.851 | 10.000 |
| 90 | 3.062 | 1.411 | 0.969 | 3.822 | 4.046 | 2.012 |
| 91 | 0.927 | 0.341 | 30.000 | | 10.672 | 10.000 |
| 92 | 2.533 | | 4.431 | | 7.454 | |
| 93 | 0.270 | | 8.468 | | 0.314 | |
| 94 | 0.423 | | 8.620 | | 0.142 | |
| 95 | 0.761 | | 30.000 | | 8.112 | |
| 96 | 0.239 | 0.098 | 15.981 | | 12.647 | 10.000 |
| 97 | 2.974 | | 30.000 | | 4.966 | |
| 98 | 0.299 | | 11.024 | | 0.303 | |
| 99 | 0.373 | | 9.270 | | 1.938 | |
| 100 | 0.216 | | 6.420 | | 0.667 | |
| 101 | 0.814 | 0.462 | 4.655 | | 9.568 | 10.000 |
| 102 | 1.667 | | 5.971 | | 0.941 | |
| 103 | 2.906 | 0.796 | 28.788 | | 16.616 | 10.000 |
| 104 | 0.582 | 0.153 | 6.285 | | 4.432 | 4.510 |
| 105 | 0.564 | 0.027 | 10.564 | | 3.727 | 3.598 |
| 106 | 0.533 | | 10.140 | | 3.701 | |
| 107 | 0.656 | 0.138 | 7.403 | | 10.295 | 8.617 |
| 108 | 14.534 | | 22.353 | | 21.084 | |
| 109 | 0.214 | | 7.861 | | 1.109 | |
| 110 | 1.030 | | 3.152 | | 3.837 | |
| 111 | 0.352 | | 8.334 | | 1.385 | |
| 112 | 0.821 | | 16.079 | | 3.108 | |
| 113 | 0.156 | 0.044 | 25.662 | | 1.886 | 7.967 |
| 114 | 0.977 | 0.255 | 4.638 | | 5.054 | 10.000 |
| 115 | 1.388 | 0.135 | 9.926 | | 17.527 | 10.000 |
| 116 | 0.477 | 0.037 | 4.580 | 14.280 | 5.775 | 9.891 |
| 117 | 0.530 | 0.055 | 6.216 | | 5.892 | 6.782 |
| 118 | 3.181 | | 7.502 | | 15.944 | |
| 119 | 0.310 | 0.023 | 1.825 | | 5.719 | 8.942 |
| 120 | 1.392 | 0.717 | 2.416 | | 24.283 | 10.000 |
| 121 | 2.324 | | 2.154 | | 3.378 | |
| 122 | 1.654 | 0.121 | 30.000 | | 30.000 | 10.000 |
| 123 | 1.169 | 0.716 | 2.147 | | 5.784 | 10.000 |
| 124 | 1.842 | | 1.871 | | 15.897 | |
| 125 | 1.733 | | 3.353 | | 3.257 | |
| 126 | 0.114 | | 11.443 | | 0.147 | |
| 127 | 0.515 | 0.229 | 30.000 | | 30.000 | 10.000 |
| 128 | 0.208 | | 6.715 | | 5.368 | |
| 129 | 0.322 | 0.252 | 30.000 | | 4.244 | 10.000 |
| 130 | 0.307 | 0.100 | 17.669 | | 11.662 | 10.000 |
| 131 | 0.376 | 0.126 | 10.928 | | 8.328 | 10.000 |
| 132 | 5.108 | | 24.684 | | 7.868 | |
| 133 | 0.418 | 0.122 | 9.210 | | 6.357 | 10.000 |
| 134 | 0.643 | | 15.038 | | 10.786 | |
| 135 | 0.444 | | 22.826 | | 7.100 | |
| 136 | 0.384 | 0.041 | 23.699 | | 19.574 | 10.000 |
| 137 | 0.588 | 0.353 | 30.000 | | 30.000 | 10.000 |
| 138 | 0.151 | 0.043 | 9.847 | | 5.758 | 10.000 |
| 139 | 0.107 | 0.038 | 12.879 | 30.000 | 1.292 | |
| 140 | 0.585 | 0.050 | 12.498 | | 5.562 | |
| 141 | 0.479 | 0.031 | 21.015 | | 3.331 | 0.277 |
| 142 | 0.187 | 0.106 | 21.247 | | 3.227 | 10.000 |
| 143 | 0.528 | 0.027 | 7.011 | | 2.492 | 0.159 |
| 144 | 0.214 | 0.034 | 9.674 | | 2.545 | 0.907 |
| 145 | 0.467 | | 30.000 | | 30.000 | |
| 146 | 4.122 | | 9.844 | | 5.574 | |
| 147 | 3.310 | | 2.723 | | 3.430 | |
| 148 | 1.253 | | 4.837 | | 2.954 | |
| 149 | 0.780 | | 6.386 | | 3.358 | |
| 150 | 2.819 | | 8.657 | | 30.000 | |
| 151 | 2.095 | | 30.000 | | 20.505 | |
| 152 | 0.160 | | 18.980 | | 10.284 | |
| 153 | 0.016 | | 30.000 | | 17.465 | |

TABLE 1-continued

Inhibition of Nav1.1, Nav1.5, and Na$_v$1.6

| Ex. No. | Flux Na$_v$1.6 IC$_{50}$ (μM) | EP Nav1.6 IC$_{50}$ (μM) | Flux Na$_v$1.5 IC$_{50}$ (μM) | EP Nav1.5 IC$_{50}$ (μM) | Flux Na$_v$1.1 IC$_{50}$ (μM) | EP Nav1.1 IC$_{50}$ (μM) |
|---|---|---|---|---|---|---|
| 154 | 0.451 | | 30.000 | | 28.833 | |
| 155 | 0.250 | | 30.000 | | 30.000 | |
| 156 | 0.146 | 0.022 | 30.000 | | 24.768 | 10.000 |
| 157 | 2.358 | | 30.000 | | 30.000 | |
| 158 | 0.126 | | 30.000 | | 30.000 | |
| 159 | 0.153 | | 11.806 | | 9.213 | |
| 160 | 0.064 | | 23.003 | | 6.514 | |
| 161 | 0.267 | | 30.000 | | 9.989 | |
| 162 | 0.461 | | 11.035 | | 30.000 | |
| 163 | 0.288 | | 30.000 | | 6.349 | |
| 164 | 0.084 | | 20.313 | | 22.789 | |
| 165 | 0.361 | | 20.768 | | 14.936 | |
| 166 | 0.015 | | 15.174 | | 12.688 | |
| 167 | 0.405 | | 30.000 | | 30.000 | |
| 168 | 0.120 | | 21.667 | | 17.736 | |
| 169 | 0.011 | | 29.045 | | 6.377 | |
| 170 | 0.176 | | 15.153 | | 24.693 | |
| 171 | 0.385 | | 16.752 | | 21.859 | |
| 172 | 0.078 | 0.023 | 30.000 | | 25.815 | |
| 173 | 0.050 | | 19.519 | | 7.221 | |
| 174 | 0.035 | | 30.000 | | 30.000 | |
| 175 | 0.342 | | 14.540 | | 10.709 | |
| 176 | 0.680 | | 16.876 | | 5.747 | |
| 177 | 0.046 | | 22.283 | | 5.396 | |
| 178 | 0.265 | | 30.000 | | 13.433 | |
| 179 | 0.080 | | 6.421 | | 4.596 | |
| 180 | 0.166 | | 24.246 | | 22.075 | |
| 181 | 2.965 | | 30.000 | | 10.586 | |
| 182 | 0.492 | | 22.760 | | 11.922 | |
| 183 | 0.036 | | 27.964 | | 30.000 | |
| 184 | 0.332 | | 30.000 | | 30.000 | |
| 185 | 0.092 | | 30.000 | | 30.000 | |
| 186 | 0.019 | | 9.119 | | 15.548 | |
| 187 | 0.065 | | 30.000 | | 12.353 | |
| 188 | 0.025 | 0.012 | 30.000 | | 9.200 | |
| 189 | 0.522 | | 30.000 | | 30.000 | |
| 190 | 0.571 | 0.055 | 25.833 | 30.000 | 13.360 | 9.705 |
| 191 | 0.244 | 0.112 | 20.003 | | 18.160 | 10.000 |
| 192 | 0.072 | 0.015 | 8.511 | | 16.180 | 10.000 |
| 193 | 7.488 | | 26.713 | | 8.853 | |
| 194 | 0.227 | 0.043 | 30.000 | | 8.539 | 10.000 |
| 195 | 0.688 | | 30.000 | | 27.223 | |
| 196 | 0.187 | | 30.000 | | 25.903 | |
| 197 | 0.023 | | 27.621 | | 11.951 | |
| 198 | 0.391 | | 30.000 | | 25.843 | |
| 199 | 0.213 | | 30.000 | | 4.077 | |
| 200 | 0.496 | | 15.362 | | 4.428 | |
| 201 | 0.561 | | 30.000 | | 30.000 | |
| 202 | 0.534 | | 30.000 | | 30.000 | |
| 203 | 0.225 | | 28.282 | | 26.596 | |
| 204 | 0.187 | 0.081 | 23.107 | | 30.000 | |
| 205 | 0.650 | 0.064 | 22.345 | | 3.638 | 10.000 |
| 206 | 0.448 | 0.076 | 30.000 | | 7.048 | 10.000 |
| 207 | 0.413 | 0.121 | 9.573 | | 4.376 | 8.127 |
| 208 | 0.593 | | 30.000 | | 9.892 | |
| 209 | 0.317 | 0.076 | 30.000 | | 27.304 | 10.000 |
| 210 | 0.416 | | 26.841 | | 3.748 | |
| 211 | 1.757 | | 19.247 | | 3.380 | |
| 212 | 0.226 | 0.041 | 30.000 | 10.000 | 30.000 | 10.000 |
| 213 | 0.156 | 0.021 | 30.000 | | 30.000 | |
| 214 | 0.326 | | 16.170 | | 13.362 | |
| 215 | 0.021 | 0.003 | 21.538 | | 10.337 | |
| 216 | 3.120 | | 30.000 | | 30.000 | |
| 217 | 0.701 | | 11.573 | | 15.301 | |
| 218 | 3.207 | | 20.885 | | 28.398 | |
| 219 | 0.280 | | 30.000 | | 30.000 | |
| 220 | 0.193 | | 3.170 | | 2.115 | |
| 221 | 4.663 | | 19.032 | | 25.374 | |
| 222 | 1.925 | | 8.350 | | 3.987 | |
| 223 | 4.228 | | 12.217 | | 3.736 | |
| 224 | 5.074 | | 30.000 | | 7.757 | |
| 225 | 2.000 | 0.742 | 4.473 | | 9.823 | 10.000 |
| 226 | 8.188 | | 11.318 | | 19.865 | |
| 227 | 1.246 | | 8.602 | | 8.778 | |
| 228 | 1.944 | | 27.494 | | 13.155 | |
| 229 | 0.961 | | 30.000 | | 30.000 | |
| 230 | 0.909 | | 28.707 | | 10.727 | |
| 231 | 4.215 | | 30.000 | | 17.500 | |
| 232 | 1.750 | | 11.221 | | 21.169 | |
| 233 | 0.787 | | 12.433 | | 3.084 | |
| 234 | 0.669 | | 8.666 | | 4.615 | |
| 235 | 3.018 | | 30.000 | | 22.352 | |
| 236 | 3.015 | | 30.000 | | 30.000 | |
| 237 | 3.535 | | 30.000 | | 12.523 | |
| 238 | 0.354 | | 30.000 | | 6.448 | |
| 239 | 1.654 | | 28.886 | | 27.045 | |
| 240 | 3.172 | | 30.000 | | 30.000 | |
| 241 | 2.363 | | 30.000 | | 26.793 | |
| 242 | 1.947 | | 30.000 | | 30.000 | |
| 243 | 8.679 | 6.249 | 30.000 | | 30.000 | 10.000 |
| 244 | 4.277 | | 22.155 | | 30.000 | |
| 245 | 5.383 | | 6.555 | | 10.471 | |
| 246 | 0.200 | 0.033 | 30.000 | | 30.000 | 10.000 |
| 247 | 6.162 | 0.409 | 30.000 | | 25.313 | 10.000 |
| 248 | 0.431 | | 26.490 | | 21.442 | |
| 249 | 0.163 | | 30.000 | | 30.000 | |
| 250 | 9.058 | | 30.000 | | 23.588 | |
| 251 | 3.711 | | 3.348 | | 8.678 | |
| 252 | 0.036 | | 12.569 | | 9.965 | |
| 253 | 2.099 | | 13.101 | | 19.999 | |
| 254 | 9.438 | | 3.617 | | 14.070 | |
| 255 | 0.471 | | 5.980 | | 7.786 | |
| 256 | 1.219 | | 6.972 | | 8.817 | |
| 257 | 0.490 | | 8.386 | | 6.101 | |
| 258 | 3.694 | | 30.000 | | 30.000 | |
| 259 | 1.369 | | 30.000 | | 29.247 | |
| 260 | 1.877 | | 30.000 | | 30.000 | |
| 261 | 0.146 | | 26.323 | | 28.876 | |
| 262 | 1.423 | | 7.321 | | 8.292 | |
| 263 | 1.025 | | 4.781 | | 7.711 | |
| 264 | 30.000 | | 30.000 | | 30.000 | |
| 265 | 0.194 | 0.018 | 12.506 | | 0.794 | 0.050 |
| 266 | 0.117 | 0.015 | 5.440 | | 0.767 | 0.133 |
| 267 | 0.959 | | 6.964 | | 3.577 | |
| 268 | 0.035 | 0.010 | 3.682 | | 0.388 | 0.332 |
| 269 | 0.584 | | 6.718 | | 2.777 | |
| 270 | 0.213 | 0.018 | 11.037 | | 12.513 | 10.000 |
| 271 | 0.448 | | 30.000 | | 30.000 | |
| 272 | 0.163 | 0.031 | 30.000 | 30.000 | 20.668 | 10.000 |
| 273 | 0.896 | 0.122 | 30.000 | | 30.000 | 10.000 |
| 274 | 0.754 | | 4.603 | | 5.251 | |
| 275 | 0.174 | 0.025 | 30.000 | | 5.328 | 4.854 |
| 276 | 0.265 | | 24.260 | | 3.604 | |
| 277 | 0.380 | 0.043 | 9.392 | 10.000 | 3.775 | 5.592 |
| 278 | 0.187 | | 30.000 | | 14.165 | |
| 279 | 0.163 | | 30.000 | | 11.207 | |
| 280 | 1.389 | | 23.926 | | 8.733 | |
| 281 | 1.075 | | 11.015 | | 7.063 | |
| 282 | 0.409 | | 6.580 | | 9.779 | |
| 283 | 0.126 | 0.011 | 28.008 | 30.000 | 14.886 | 14.470 |
| 284 | 1.373 | | 30.000 | | 30.000 | |
| 285 | 0.625 | | 26.611 | | 5.891 | |
| 286 | 3.377 | | 8.782 | | 6.843 | |
| 287 | 1.531 | 0.470 | 30.000 | | 25.150 | 10.000 |
| 288 | 0.180 | 0.036 | 17.948 | | 11.760 | 10.000 |
| 289 | 0.556 | | 30.000 | | 4.266 | |
| 290 | 0.101 | 0.011 | 25.100 | | 6.019 | 10.000 |
| 291 | 0.368 | | 30.000 | | 14.025 | |
| 292 | 0.624 | | 8.402 | | 2.719 | |
| 293 | 0.426 | 0.202 | 30.000 | | 12.729 | 10.000 |
| 294 | 0.688 | | 30.000 | | 30.000 | |
| 295 | 0.383 | 0.042 | 30.000 | | 12.052 | 10.000 |
| 296 | 1.308 | | 30.000 | | 16.890 | |
| 297 | 0.559 | 0.391 | 8.627 | | 2.975 | 10.000 |
| 298 | 0.785 | | 11.257 | | 7.190 | |
| 299 | 3.609 | | 21.644 | | 0.684 | |

TABLE 1-continued

Inhibition of Nav1.1, Nav1.5, and Na$_v$1.6

| Ex. No. | Flux Na$_v$1.6 IC$_{50}$ (μM) | EP Nav1.6 IC$_{50}$ (μM) | Flux Na$_v$1.5 IC$_{50}$ (μM) | EP Nav1.5 IC$_{50}$ (μM) | Flux Na$_v$1.1 IC$_{50}$ (μM) | EP Nav1.1 IC$_{50}$ (μM) |
|---|---|---|---|---|---|---|
| 300 | 0.346 | 0.064 | 30.000 | | 15.949 | 10.000 |
| 301 | 0.493 | | 30.000 | | 30.000 | |
| 302 | 0.049 | | 23.919 | | 9.665 | |
| 303 | 0.007 | | 24.527 | | 5.728 | |
| 304 | 0.008 | 0.002 | 21.180 | | 5.297 | |
| 305 | 0.057 | | 30.000 | | 14.214 | |
| 306 | 0.241 | | 8.104 | | 18.134 | |
| 307 | 0.597 | 0.451 | 21.311 | | 2.285 | 10.000 |
| 308 | 0.605 | | 26.379 | | 25.965 | |
| 309 | 0.085 | | 27.568 | | 6.344 | |
| 310 | 0.010 | 0.011 | 30.000 | | 20.318 | |
| 311 | 0.219 | | 30.000 | | 26.406 | |
| 312 | 0.135 | | 9.590 | | 7.256 | |
| 313 | 0.014 | | 14.313 | | 3.746 | |
| 314 | 0.032 | | 30.000 | | 30.000 | |
| 315 | 0.270 | | 30.000 | | 30.000 | |
| 316 | 0.961 | 0.264 | 5.864 | | 2.497 | 5.654 |
| 317 | 0.328 | 0.982 | 30.000 | | 3.907 | |
| 318 | 6.026 | | 17.287 | | 20.408 | |
| 319 | 2.308 | | 20.016 | | 18.015 | |
| 320 | 0.055 | | 17.906 | | 6.505 | |
| 321 | 0.091 | | 28.138 | | 4.770 | |
| 322 | 0.114 | 0.047 | 30.000 | | 7.753 | |
| 323 | 0.518 | | 15.037 | | 9.380 | |
| 324 | 0.647 | | 30.000 | | 18.892 | |
| 325 | 0.401 | | 30.000 | | 30.000 | |
| 326 | 0.125 | 0.090 | 12.727 | | 7.864 | 10.000 |
| 327 | 0.003 | 0.001 | 30.000 | | 4.443 | |
| 328 | 3.818 | 1.039 | 30.000 | | 30.000 | |
| 329 | 0.214 | | 28.413 | | 8.116 | |
| 330 | 0.001 | 0.001 | 30.000 | | 1.996 | |
| 331 | 0.724 | 0.099 | 11.269 | | 7.883 | 10.000 |
| 332 | 0.275 | | 7.239 | | 0.831 | |
| 333 | 0.257 | 0.186 | 30.000 | | 30.000 | 10.000 |
| 334 | 0.029 | 0.002 | 30.000 | | 4.651 | |
| 335 | 0.385 | 0.085 | 21.221 | | 4.795 | 10.000 |
| 336 | 0.524 | 0.119 | 7.682 | 20.000 | 5.115 | 10.000 |
| 337 | 0.266 | | 30.000 | | 14.328 | |
| 338 | 1.619 | | 2.653 | | 5.710 | |

Biological Example 3

Electrical Stimulation Seizure Assays

Many electric stimulation seizure tests have been used to identify compounds with anti-convulsion activity, i.e., which raise seizure threshold. Two examples of electrical stimulation seizure assays frequently used in the field are the 6 Hz psychomotor seizure assay (6 Hz) and the Maximal Electroshock Seizure (MES). The 6 Hz assay is considered a model of partial seizures observed in humans (Löscher, W. and Schmidt, D., *Epilepsy Res*. (1988), Vol. 2, pp 145-81; Barton, M. E. et al., *Epilepsy Res*. (2001), Vol. 47, pp. 217-27). The MES assay is a model for generalized tonic-clonic seizures in humans and provides an indication of a compound's ability to prevent seizure spread when all neuronal circuits in the brain are maximally active. These seizures are highly reproducible and are electrophysiologically consistent with human seizures (Toman et al., 1946; Piredda et al., 1984; White et al., 1995). Experiments can be performed with healthy animals, or with seizure prone animals that have been genetically modified to model genetic epilepsy syndromes (Piredda, S. G. et al., *J. Pharmacol. Exp. Ther*. (1985), Vol. 232, pp. 741-5; Toman, J. E. et al., *J. Neurophysiol*. (1946), Vol. 9, pp. 231-9; and White, H. S. et al., *Ital. J. Neurol. Sci*. (1995), Vol. 16 (1-2), pp. 73-7).

To facilitate testing mice can be pretreated with the test compound or with the appropriate vehicle prior to the application of the electroshock. Each treatment group (n=4-8 mice/group) is examined for anticonvulsive effects at different time points after administration of the compound and the vehicle. The eyes of mice are first anesthetized with a topical application of Alcaine (proparacaine hydrochloride) 0.5%, one drop in each eye 30 min prior to the stimulation. Seizures are then induced by placing electrodes on the eyes which deliver a transcorneal current.

The 6 Hz Psychomotor Seizure Test:

Following pretreatment, each mouse is challenged with the low-frequency (6 Hz, 0.3 ms pulse width) stimulation for 3 sec. delivered through corneal electrodes at several intensities (12-44 mA). Animals are manually restrained and released immediately following the stimulation and observed for the presence or absence of seizure activity. Typically, the 6 Hz stimulation results in a seizure characterized by a minimal clonic phase that is followed by stereotyped, automatist behaviors, including twitching of the vibrissae, and Straub-tail or by a generalized tonic clonic seizure. The presence, type and latency to seizure (in seconds) after the application of the current are monitored. Animals not displaying a clonic or generalized tonic clonic seizure are considered "protected". All animals are euthanized at the end of assay. Plasma and brain samples are collected.

Maximal Electroshock Test (MES):

Following pretreatment, each mouse is challenged with an alternating current (60 Hz, 0.4-0.6 ms pulse width) for 0.2-0.5 sec. delivered through corneal electrodes at intensities (44-55 mA).

Typically, the MES stimulation results in a generalized tonic seizure that can be followed by a clonic seizure, automatist behaviors and Straub-tail. The presence, type and latency to seizure (in seconds) after the application of the current are monitored. An animal is considered "protected" from MES-induced seizures upon abolition of the hindlimb tonic extensor component of the seizure. After the seizure, mice are expected to resume normal exploratory behaviour within 1 to 4 minutes. Latency to seizure is recorded with a cut-off of 1 minute after which all animals are euthanized.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (Ib2):

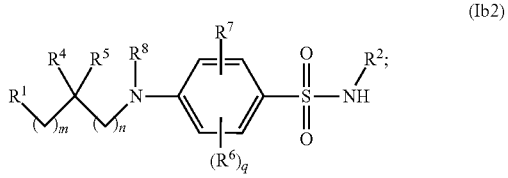

as an individual stereoisomer, enantiomer or tautomer thereof or a mixture thereof;
or a pharmaceutically acceptable salt or solvate thereof, wherein:
m and n are each 0;
q is 1, 2 or 3;
$R^1$ is an optionally substituted aryl, an optionally substituted monocyclic heteroaryl, or an optionally substituted bicyclic heteroaryl;
$R^2$ is an optionally substituted 5-membered N-heteroaryl or an optionally substituted 6-membered N-heteroaryl;
$R^4$ and $R^5$ are each hydrogen;
each $R^6$ is independently alkyl, halo, haloalkyl, cyano, or —$OR^{12}$;
$R^7$ is alkyl, alkenyl, halo, haloalkyl, cyano, or —$OR^{12}$; and
each $R^8$ and $R^{12}$ is independently hydrogen, alkyl, haloalkyl, optionally substituted cycloalkyl, optionally substituted cycloalkylalkyl, optionally substituted heterocyclyl, or optionally substituted heterocyclylalkyl.

2. The compound of claim 1, as an individual stereoisomer, enantiomer or tautomer thereof or a mixture thereof; or a pharmaceutically acceptable salt or solvate thereof, wherein $R^2$ is an optionally substituted 5-membered N-heteroaryl.

3. The compound of claim 1, as an individual stereoisomer, enantiomer or tautomer thereof or a mixture thereof; or a pharmaceutically acceptable salt or solvate thereof, wherein $R^2$ is selected from optionally substituted thiazolyl, optionally substituted thiadiazolyl, optionally substituted isoxazolyl, optionally substituted isothiazolyl or optionally substituted oxazolyl.

4. The compound of claim 1, as an individual stereoisomer, enantiomer or tautomer thereof or a mixture thereof; or a pharmaceutically acceptable salt or solvate thereof, wherein:
$R^1$ is aryl optionally substituted with optionally substituted heterocyclylalkyl and optionally substituted with one or more substituents selected from halo, alkyl, haloalkyl, optionally substituted cycloalkyl, cyano, —$R^9$—$OR^{12}$, —$R^9$—$N(R^{10})R^{11}$, —$R^9$—$N(R^{10})$—$R^{13}$—$OR^{12}$, optionally substituted heterocyclyl, and optionally substituted heteroaryl;
wherein:
each $R^9$ is independently a direct bond or an optionally substituted straight or branched alkylene chain; and
each $R^{10}$, $R^{11}$ and $R^{12}$ is independently hydrogen, alkyl, haloalkyl, optionally substituted cycloalkyl, optionally substituted cycloalkylalkyl, optionally substituted heterocyclyl, or optionally substituted heterocyclylalkyl;
$R^2$ is optionally substituted thiazolyl; and
$R^{13}$ is a branched or straight alkylene chain.

5. The compound of claim 1, as an individual stereoisomer, enantiomer or tautomer thereof or a mixture thereof; or a pharmaceutically acceptable salt or solvate thereof, wherein:
$R^1$ is aryl optionally substituted by one or more substituents selected from halo, alkyl, haloalkyl, optionally substituted cycloalkyl, cyano, —$R^9OR^{12}$, —$R^9$—$N(R^{10})R^{11}$, —$R^9$—$N(R^{10})$—$R^{13}$—$OR^{12}$, optionally substituted heterocyclyl, optionally substituted heterocyclylalkyl, and optionally substituted heteroaryl;
wherein:
each $R^9$ is independently a direct bond or an optionally substituted straight or branched alkylene chain; and
each $R^{10}$, $R^{11}$ and $R^{12}$ is independently hydrogen, alkyl, haloalkyl, optionally substituted cycloalkyl, optionally substituted cycloalkylalkyl, optionally substituted heterocyclyl, or optionally substituted heterocyclylalkyl;
$R^2$ is optionally substituted thiazolyl, optionally substituted isothiazolyl, optionally substituted oxazolyl, or optionally substituted isoxazolyl; and
$R^{13}$ is a branched or straight alkylene chain.

6. The compound of claim 1, as an individual stereoisomer, enantiomer or tautomer thereof or a mixture thereof, or a pharmaceutically acceptable salt or solvate thereof, wherein:
$R^1$ is an optionally aryl; and
$R^2$ is an optionally substituted 6-membered N-heteroaryl.

7. The compound of claim 6, as an individual stereoisomer, enantiomer or tautomer thereof or a mixture thereof, or a pharmaceutically acceptable salt or solvate thereof, wherein $R^2$ is selected from optionally substituted pyridinyl, optionally substituted pyrimidinyl optionally substituted pyridazinyl and optionally substituted pyrazinyl.

8. The compound of claim 1, as an individual stereoisomer, enantiomer or tautomer thereof or a mixture thereof, or a pharmaceutically acceptable salt or solvate thereof, wherein $R^1$ is an optionally substituted monocyclic heteroaryl or an optionally substituted bicyclic heteroaryl.

9. A pharmaceutical composition comprising a pharmaceutically acceptable excipient and a compound of claim 1, as a stereoisomer, enantiomer or tautomer thereof or a mixture thereof; or a pharmaceutically acceptable salt or solvate thereof.

10. A method of treating a disease or a condition associated with $Na_V1.6$ activity in a mammal wherein the disease or condition is epilepsy and/or epileptic seizure disorder and wherein the method comprises administering to the mammal in need thereof a therapeutically effective amount of a compound of claim 1, as a stereoisomer, enantiomer or tautomer thereof or a mixture thereof, or a pharmaceutically acceptable salt or solvate thereof.

11. A method of decreasing ion flux through $Na_V1.6$ in a mammalian cell, wherein the method comprises contacting the cell with a compound of claim 1, as a stereoisomer, enantiomer or tautomer thereof or a mixture thereof, or a pharmaceutically acceptable salt or solvate thereof.

12. A method of selectively inhibiting a first voltage-gated sodium channel over a second voltage-gated sodium channel in a mammal, wherein the method comprises administering to the mammal a modulating amount of a compound of claim 1, as a stereoisomer, enantiomer or tautomer thereof or a mixture thereof; or a pharmaceutically acceptable salt or solvate thereof.

13. The method of claim 12 wherein the first voltage-gated sodium channel is $Na_V1.6$.

14. The method of claim 13 wherein the second voltage-gated sodium channel is $Na_V1.5$.

15. The method of claim 13 wherein the second voltage-gated sodium channel is $Na_V1.1$.

16. The compound of claim 1, which is 4-((2-(azetidin-1-ylmethyl)benzyl)amino)-5-chloro-2-fluoro-N-(thiazol-4-yl)benzenesulfonamide, represented by the formula:

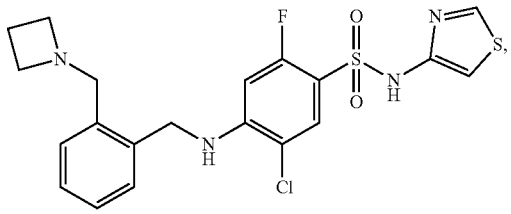 [SMILES: O=S(=O)(Nc1cscn1)c1cc(Cl)c(NCc2ccccc2CN2CCC2)cc1F]

as an individual stereoisomer, enantiomer or tautomer thereof or a mixture thereof; or a pharmaceutically acceptable salt or solvate thereof.

17. The compound of claim 1, which is 4-((2-((2-oxa-6-azaspiro[3.3]heptan-6-yl)methyl)-6-fluorobenzyl)amino)-2,6-difluoro-N-(thiazol-4-yl)benzenesulfonamide, represented by the formula:

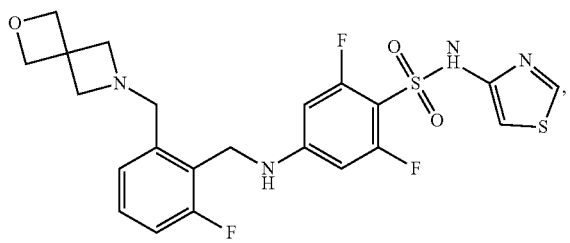 [SMILES: O=S(=O)(Nc1cscn1)c1c(F)cc(NCc2c(F)cccc2CN2CC3(COC3)C2)cc1F]

as an individual stereoisomer, enantiomer or tautomer thereof or a mixture thereof; or a pharmaceutically acceptable salt or solvate thereof.

18. The compound of claim 1, which is 4-((2-((3-azabicyclo[3.1.0]hexan-3-yl)methyl)-6-fluorobenzyl)amino)-2,6-difluoro-N-(thiazol-4-yl)benzenesulfonamide, represented by the formula:

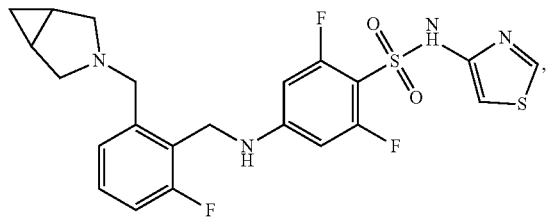 [SMILES: O=S(=O)(Nc1cscn1)c1c(F)cc(NCc2c(F)cccc2CN2CC3CC3C2)cc1F]

as an individual stereoisomer, enantiomer or tautomer thereof or a mixture thereof, or a pharmaceutically acceptable salt or solvate thereof.

19. The compound of claim 1, which is 4-((2-(((tert-butyl(methyl)amino)methyl)-6-fluorobenzyl)amino)-2,6-difluoro-N-(thiazol-4-yl)benzenesulfonamide, represented by the formula:

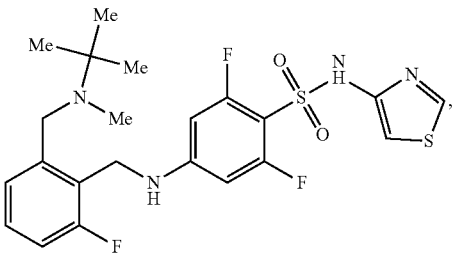 [SMILES: CN(Cc1cccc(F)c1CNc1cc(F)c(S(=O)(=O)Nc2cscn2)c(F)c1)C(C)(C)C]

as an individual stereoisomer, enantiomer or tautomer thereof or a mixture thereof; or a pharmaceutically acceptable salt or solvate thereof.

20. The compound of claim 1, which is 4-((2-(azetidin-1-ylmethyl)benzyl)amino)-2,6-difluoro-N-(thiazol-4-yl)benzenesulfonamide, represented by the formula:

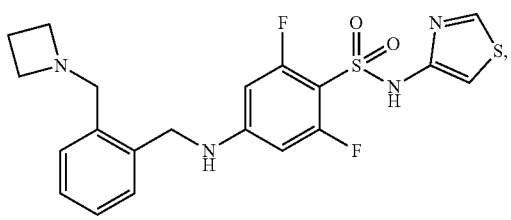 [SMILES: O=S(=O)(Nc1cscn1)c1c(F)cc(NCc2ccccc2CN2CCC2)cc1F]

as an individual stereoisomer, enantiomer or tautomer thereof or a mixture thereof; or a pharmaceutically acceptable salt or solvate thereof.

21. The compound of claim 1, which is (S)-4-((2-(1-(azetidin-1-yl)ethyl)-6-fluorobenzyl)amino)-2,6-difluoro-N-(thiazol-4-yl)benzenesulfonamide, represented by the formula:

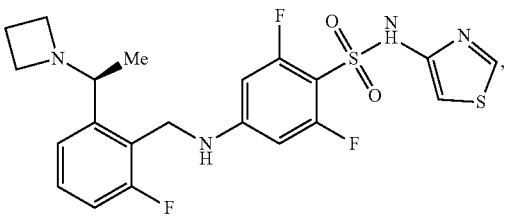 [SMILES: C[C@@H](c1cccc(F)c1CNc1cc(F)c(S(=O)(=O)Nc2cscn2)c(F)c1)N1CCC1]

as an individual stereoisomer, enantiomer or tautomer thereof or a mixture thereof; or a pharmaceutically acceptable salt or solvate thereof.

22. The compound of claim 1, which is 4-((2-(azetidin-1-ylmethyl)-3,6-difluorobenzyl)amino)-2,6-difluoro-N-(thiazol-4-yl)benzenesulfonamide, represented by the formula:

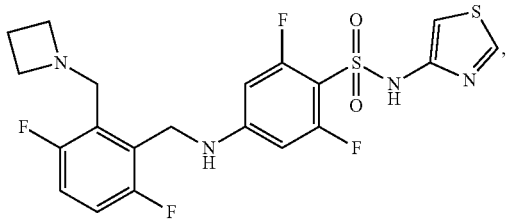 [SMILES: O=S(=O)(Nc1cscn1)c1c(F)cc(NCc2c(F)ccc(F)c2CN2CCC2)cc1F]

as an individual stereoisomer, enantiomer or tautomer thereof or a mixture thereof; or a pharmaceutically acceptable salt or solvate thereof.

23. The compound of claim 1, which is 2,3-difluoro-4-((2-fluoro-6-(pyrrolidin-1-ylmethyl)benzyl)amino)-N-(isoxazol-3-yl)benzenesulfonamide, represented by the formula:

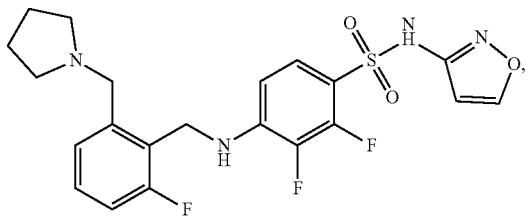 [SMILES: O=S(=O)(Nc1ccon1)c1ccc(NCc2c(F)cccc2CN2CCCC2)c(F)c1F]

as an individual stereoisomer, enantiomer or tautomer thereof or a mixture thereof, or a pharmaceutically acceptable salt or solvate thereof.

24. The compound of claim 1, which is 4-((2-((2,2-dimethylazetidin-1-yl)methyl)benzyl)amino)-2,6-difluoro-3-methyl-N-(thiazol-4-yl)benzenesulfonamide, represented by the formula:

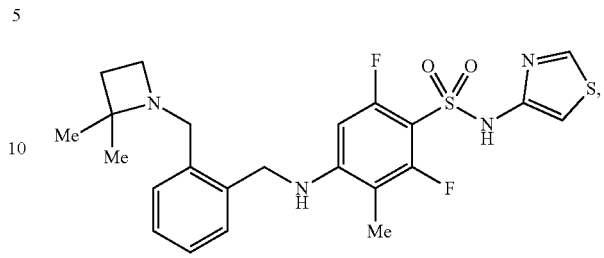

as an individual stereoisomer, enantiomer or tautomer thereof or a mixture thereof; or a pharmaceutically acceptable salt or solvate thereof.

25. The compound of claim 1, which is 2,6-difluoro-4-((2-fluoro-6-((3-fluoro-3-methylazetidin-1-yl)methyl)benzyl)amino)-N-(isoxazol-3-yl)benzenesulfonamide, represented by the formula:

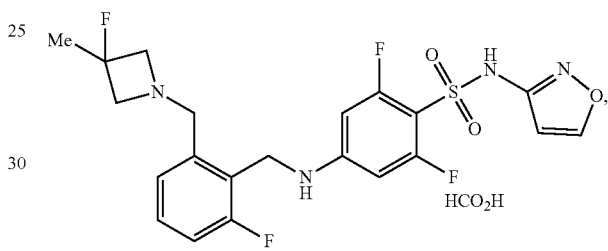

as an individual stereoisomer, enantiomer or tautomer thereof or a mixture thereof; or a pharmaceutically acceptable salt or solvate thereof.

* * * * *